US008293251B2

(12) United States Patent
Scarlato et al.

(10) Patent No.: US 8,293,251 B2
(45) Date of Patent: Oct. 23, 2012

(54) NEISSERIAL ANTIGENS

(75) Inventors: Vincenzo Scarlato, Siena (IT); Vega Masignani, Siena (IT); Rino Rappuoli, Siena (IT); Mariagrazia Pizza, Siena (IT); Guido Grandi, Siena (IT)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 12/653,954

(22) Filed: Dec. 18, 2009

(65) Prior Publication Data

US 2010/0272725 A1 Oct. 28, 2010

Related U.S. Application Data

(60) Division of application No. 10/864,684, filed on Jun. 8, 2004, now Pat. No. 7,655,245, which is a continuation of application No. 09/303,518, filed on Apr. 30, 1999, now Pat. No. 6,914,131, which is a continuation-in-part of application No. PCT/IB98/01665, filed on Oct. 9, 1998.

(30) Foreign Application Priority Data

| Nov. 6, 1997 | (GB) | 9723516.2 |
|---|---|---|
| Nov. 14, 1997 | (GB) | 9724190.5 |
| Nov. 18, 1997 | (GB) | 9724386.9 |
| Nov. 27, 1997 | (GB) | 9725158.1 |
| Dec. 10, 1997 | (GB) | 9726147.3 |
| Jan. 14, 1998 | (GB) | 9800759.4 |
| Sep. 1, 1998 | (GB) | 9819016.8 |

(51) Int. Cl.
*A61K 39/095* (2006.01)
*C07H 21/04* (2006.01)
*C12P 21/04* (2006.01)
*C07K 14/00* (2006.01)

(52) U.S. Cl. ............... 424/250.1; 425/184.1; 425/234.1; 530/350; 435/69.1; 435/69.5; 435/69.7; 536/23.5; 536/23.7

(58) Field of Classification Search ........................ None
See application file for complete search history.

(56) References Cited

U.S. PATENT DOCUMENTS

| 5,288,641 | A | 2/1994 | Roizman |
| 5,422,120 | A | 6/1995 | Kim |
| 5,580,859 | A | 12/1996 | Felgner et al. |
| 5,591,624 | A | 1/1997 | Barber et al. |
| 5,763,188 | A | 6/1998 | Ohno et al. |
| 5,785,974 | A | 7/1998 | Casal Alvarez et al. |
| 6,100,380 | A | 8/2000 | Green et al. |
| 6,127,180 | A | 10/2000 | Narva et al. |
| 6,150,502 | A | 11/2000 | Strachan et al. |
| 6,583,275 | B1 | 6/2003 | Doucette-Stamm et al. |
| 6,914,131 | B1 | 7/2005 | Scarlato et al. |

FOREIGN PATENT DOCUMENTS

| EP | 0176170 | 4/1986 |
| EP | 0334301 | 9/1989 |
| EP | 0345242 | 12/1989 |
| EP | 0415731 | 3/1991 |
| GB | 2200651 A | 8/1988 |
| WO | WO-9011092 | 10/1990 |
| WO | WO-9205266 | 4/1992 |
| WO | WO-9306223 | 4/1993 |
| WO | WO-9307282 | 4/1993 |
| WO | WO-9307283 | 4/1993 |
| WO | WO-9314778 | 8/1993 |
| WO | WO-9318150 | 9/1993 |
| WO | WO-9513796 | 5/1995 |
| WO | WO-9530763 | 11/1995 |
| WO | WO-9605858 | 2/1996 |
| WO | WO-9612020 | 4/1996 |
| WO | WO-9629412 | 9/1996 |
| WO | WO-9631618 | 10/1996 |
| WO | WO-9711181 | 3/1997 |
| WO | WO-9820734 | 5/1998 |
| WO | WO-9924578 | 5/1999 |
| WO | WO-9955873 | 11/1999 |
| WO | WO-9957280 | 11/1999 |

OTHER PUBLICATIONS

Ala'Aldeen et al. Vaccine 12,1994 (Abstract only).*
Houghten et al. (Vaccines, 1986, Edited by Fred Brown: Cold Spring Harbor Laboratory) s.*
Lederman et al (Molecular Immunology 28:1171-1181, 1991.*
Cruse et al., Illustrated Dictionary of Immunology, 2nd Edn., CRC Press, 2003.*
Gomez et al. Vaccine 14: 1340-1346, 1996.*
Malorny et al. J. Bacteriol. 180: 1323-1330, 1998.*
Teerlink et al. J. Exp. Med. 166: 63-76, 1987.*
Forest et al. Gene 192: 165-169, 1997.*
Ala'Aldeen et al. Vaccine 12:535-541, 1994.*
Cruse et al. Illustrated Dictionary of Immunology, 2nd Edn., CRC Press, 2003.*
McGuiness et al, Mol. Microbiol. 7: 505-514, Feb. 1993.*
Fleischmann, R. et al. "Whole-Genome Random Sequencing and Assembly of *Haemophilus influenzae*," Science, vol. 269, 1995, pp. 496-498 and 507-512.
Wolff, K. et al. "Identification and characterizaton of specific encoding pathogenicity associated proteins in the genome of commensal *Neisseria* species," FEMS Microbiology Letters, vol. 125, 1995, pp. 255-264.
Deposit GSP:AAR92766, available at http://ibis.internal.epo.org/IBIS/exam/hitDetails.jsp?id=10247915, 2007.
Deposit GSP:AAY56622, available at http://ibis.internal.epo.org/IBIS.exam/hitDetails.jsp?id=10247833, 2009.
Deposit UNIPROT:O69746, available at http://ibis.internal.epo.org/IBIS/exam/hitDetails.jsp?Id=10247988, 1998.
Accession No. A61824 from PCT Patent Publication No. WO 97/11181. Created Mar. 9, 1998. (2 pages).

(Continued)

*Primary Examiner* — Padma Baskar
(74) *Attorney, Agent, or Firm* — Amy Hessler; Otis Littlefield

(57) ABSTRACT

The invention provides proteins from *Neisseria meningitidis* (strains A & B) and from *Neisseria gonorrhoeae*, including amino acid sequences, the corresponding nucleotide sequences, expression data, and serological data. The proteins are useful antigens for vaccines, immunogenic compositions, and/or diagnostics.

5 Claims, 24 Drawing Sheets

OTHER PUBLICATIONS

Ala'Aldeen et al. (1994). "Vaccine potential of meningococcal FrpB: studies on surface exposure and functional attributes of common epitopes," Vaccine 12(6): 535-541. (Abstract Only).

Ala'Aldeen et al. (1996). "The Meningococcal Transferrin-binding Proteins 1 and 2 are Both Surface Exposed and Generate Bactericidal Antibodies Capable of Killing Homologous and Heterologous Strains," Vaccine 14(1):49-53.

Altschul et al. (1997). "Gapped BLAST and PSI-BLAST: a New Generation of Protein Database Search Programs," Nucleic Acids Research 25:3389-3402.

Berkner. (1988). "Development of Adenovirus Vectors for the Expression of Heterologous Genes," Biotechniques 6: 616-629.

Berzofsky, J. A. (1985). "Intrinsic and Extrinsic Factors in Protein Antigenic Structure," Science 229(4717):932-940.

Connelly et al. (1995). "In vivo Gene Delivery and Expression of Physiological Levels of Functional Human Factor VIII in Mice," Human Gene Therapy 6:185-193.

Costantino et al. (1992). "Development and Phase I Clinical Testing of a Conjugate Vaccine against Meningococcus A and C," Vaccine 10:691-698.

Cruse et al. (2003). Illustrated Dictionary of Immunology, 2nd Edn. CRC Press, 2003. p. 46.

Donnelly et al. (1997). "DNA Vaccines," Annual Review of Immunology 15:617-648.

EBI Accession No. Q9K0G2. Last updated Oct. 1, 2000. (3 pages).

Esposti et al. (1990). "Critical Evaluation of the Hydropathy of Membrane Proteins," European Journal of Biochemistry 190:207-219.

European Search Opinion and Partial European Search Report mailed Feb. 27, 2007, for EP Application 06076711.8 filed May 19, 2000, 16 pages.

Examination Report dated Jun. 23, 2005 for EP application No. 98 946 675.0. 3 pages.

Examination Report dated Nov. 20, 2008 for EP application No. 98 946 675.0. 3 pages.

Forest et al. (1997). "Type-4 pilus structure: outside to inside and top to bottom—a minireview," Gene 192:165-169.

Gao et al. (1989). "Identification and Characterization of T Helper Epitopes in the Nucleoprotein of Influenza A Virus," Journal of Immunology 143:3007-3014.

GenBank Accession No. A61829, last updated Mar. 9, 1998, located at <http://www.ncbi.nlm.nih.gov/entrez/viewer.fcgi?db=nuccore&id=3715998>, last visited on Nov. 20, 2008, 2 pages. (See sequence alignments for SEQ ID Nos. 465, 463.).

GenBank Accession No. AJ001740, last updated May 21, 1998, located at <http://www.ncbi.nlm.nih.gov/entrez/viewer.fcgi?db=nuccore&id=3152399>, last visited on Nov. 20, 2008, 2 pages. (See sequence alignments for SEQ ID Nos. 653, 649, 651).

GenBank Accession No. HIU20229, last updated Feb. 9, 1995, located at <http://www.ncbi.nlm.nih.gov/entrez/viewer.fcgi?db=nuccore&id=644850>, last visited on Nov. 20, 2008, 5 pages. (See sequence alignments for SEQ ID Nos. 131, 127, and 125).

Gomez, J.A. et al., "Antigenicity, cross-reactivity and surface exposure of the Neisseria meningitidis 37 kDa protein (Fbp)," Vaccine 14:1340-1346, Elsevier Science Ltd (1996).

Harlow et al. (1988). Antibodies, A Laboratory Manual. Cold Spring Harbor Laboratory, Chapter 5, p. 76.

Houghten et al. (1986). "Relative Importance of Position and Individual Amino Acid Residues in Peptide Antigen-Antibody Interactions: Implications in the Mechanism of Antigenic Drift and Antigenic Shift," in Vaccines, Edited by Fred Brown, Cold Spring Harbor Laboratory. pp. 21-25.

International Search Report mailed Dec. 8, 1999, for International Application No. PCT/IB98/01665, filed Oct. 9, 1998.

Jolly. (1994). "Viral Vector Systems for Gene Therapy," Cancer Gene Therapy 1:51-64.

Kimura et al. (1994). "Retroviral Delivery of DNA into the Livers of Transgenic Mice Bearing Premalignant and Malignant Hepatocellular Carcinomas," Human Gene Therapy 5:845-852.

Kohler et al. (1975). "Continuous Cultures of Fused Cells Secreting Antibody of Predefined Specificity," Nature 256:495-496.

Lederman et al. (1991). "A single amino acid substitution in a common African allele of the CD4 molecule ablates binding of the monoclonal antibody, OKT4," Molecular Immunology 28(11):1171-1181.

Li et al. (1980). "beta-Endorphin omission analogs: dissociation of immunoreactivity from other biological activities," Proc Natl Acad Sci. USA 77:3211-3214.

Lieberman et al. (1996). "Safety and Immunogenicity of a Serogroups A/C Neisseria meningitidis Oligosaccharide-Protein Conjugate Vaccine in Young Children," Journal of the American Medical Association 275(19):1499-1503.

Martin et al. (1997). "Highly Conserved Neisseria meningitidis Surface Protein Confers Protection against Experimental Infection," J. Exp. Med. 185(7):1173-1183.

Morbidity and Mortality Weekly Report. (1997). "Control and Prevention of Meningococcal Disease: Recommendations of the Advisory Committee on Immunization Practices (ACIP)," vol. 46, No. RR-5. 12 pages.

Morris et al. (1994). "Nucleotide Sequence Analysis and Potential Environmental Distribution of a Ferric Pseudobactin Receptor Gene of Pseudomonas sp. Strain M114," Molecular and General Genetics 242:9-16.

Nassif et al. (1997). "Type-4 pili and meningococcal adhesiveness," Gene 192:149-153.

Opposition to European Patent No. 1194560 B1, granted on Jul. 4, 2007 in the name of Novartis Vaccines and Diagnostics S.r.l.. Opposition filed by GlaxoSmithKline Biologicals S.A. on Apr. 4, 2008.

Paruchuri et al. (Jan. 1990). "Identification and Characterization of a Neisseria gonorrhoea Gene e Encoding a Glycolipid-binding Adhesion," Proceedings of the National Academy of Sciences USA 87:333-337.

Pohlner et al. (1987). "Gene structure and extracellular secretion of Neisseria gonorrhoeae IgA protease," Nature 325(6103):458-462.

Poolman, J.T. (1992). "Development of a Meningococcal Vaccine," Infectious Agents and Disease 4:13-28.

Poulsen et al. (1989). "Cloning and Sequencing of the Immunoglobulin A1 Protease Gene (iga) of Haemophilus influenzae Serotype b," Infection and Immunity 57:3097-3105.

Quakyi et al. (1992). "Development of a Malaria T-cell Vaccine for Blood Stage Immunity," Scandinavian Journal of Immunology Suppl. 11:9-16.

Roberts et al. (1996). "Prediction of HIV Peptide Epitopes by a Novel Algorithm," AIDS Research and Human Retroviruses 12:593-610.

Robinson et al. (1997). "DNA Vaccines," Seminars in Immunology 9:271-283.

Rokbi et al. (1997) "Evaluation of Recombinant Transferrin-Binding Protein B Variants from Neisseria meningitidis for Their Ability to Induce Cross-Reactive and Bactericidal Antibodies against a Genetically Diverse Collection of Serogroup B Strains," Infection and Immunity 65(1):55-63.

Romero et al. (1994). "Current Status of Meningococcal Group B Vaccine Candidates: Capsular or Noncapsular?" Clinical Microbiology Reviews 7(4):559-575.

Rosenfeld et al. (1991)., "Adenovirus-mediated Transfer of a Recombinant ?1-Antitrypsin Gene to the Lung Epithelium In vivo," Science 252:431-434.

Rudel et al. (1995). "Neisseria PiIC protein identified as type-4 pilus tip-located adhesin," Nature 373:357-359.

Schryvers et al. (1999). "Iron Acquisition Systems in the Pathogenic Neisseria," Molecular Microbiology 32(6)1117-1123.

Schuchat et al. (1997). "Bacterial Meningitis in the United States in 1995," New England Journal of Medicine 337(14):970-976.

Sepulvada et al. (1975). "Primary Structure of Porcine Pepsin," Journal of Biological Chemistry, 250(13):5082-5088.

St. Geme III et al. (1994). "A Haemophilus influenzae IgA Protease-like Protein Promotes Intimate Interaction with Human Epithelial Cells," Molecular Microbiology 14(2):217-233.

Sutcliffe et al. (1983). "Antibodies That React with Predetermined Sites on Proteins," Science 219(4585):660-666.

Szoka et al. (1978). "Procedure for Preparation of Liposomes with Large Internal Aqueous Space and High Capture by Reverse-phase Evaporation," Proceedings of the National Academy of Sciences USA.75:4194-4198.

Teerlink et al. (1987). "Antigenic and immunogenic properties of cyanogen bromide peptides from gonococcal outer membrane protein IB. Evidence for the existence of a surface-exposed conserved epitope," J. Exp. Med. 166:63-76, 1987.

Tettelin et al. (2000). "Complete Genome Sequence of *Neisseria meningitidis* Serogroup B Strain MC58," Science 287:1809-1815.

Tettelin et al. (2000). "Hypothetical protein (*Neisseria meningitidis* serogroup B)," Database GENSEQ (Online), Accession No. Q9K0Y5.

Tettelin et al. (2000). "TonB-dependent receptor (*Neisseria meningitidis* serogroup B)," Database GENSEQ (Online), Accession No. Q9JXU3.

UniProtKB/TrEMBL Accession No. Q9X7H1, last updated Feb. 10, 2009, located at <http://www.uniprot.org/uniprot/Q9X7H1.txt> visited on May 12, 2009. (2 pages).

Wedege, E. et al. (Feb. 1986). "Human Antibody Response to a Group B Serotype 2a Meningococcal Vaccine Determined Immunoblotting," Infection and Immunity 51(2):571-578.

Yumoto et al. (1996). "Cloning, sequencing and expression of an *Eikenella corrodens* gene encoding a component protein of the lectin-like adhesin complex," Gene 183(1-2): 115-121.

Zollinger. (1997). "New and Improved Vaccines Against Meningococcal Disease," New Generation Vaccines, 2nd edition, Levine, et al. (eds.), Marcel Dekker, New York 469-488.

\* cited by examiner

FIGURE 1
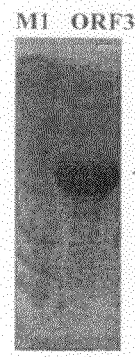
FIG. 1A
FIG. 1B
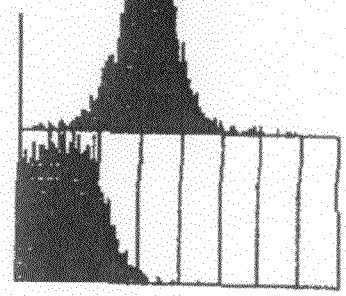
FIG. 1C
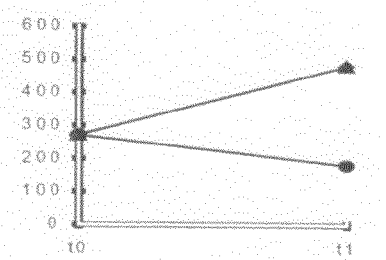
FIG. 1D

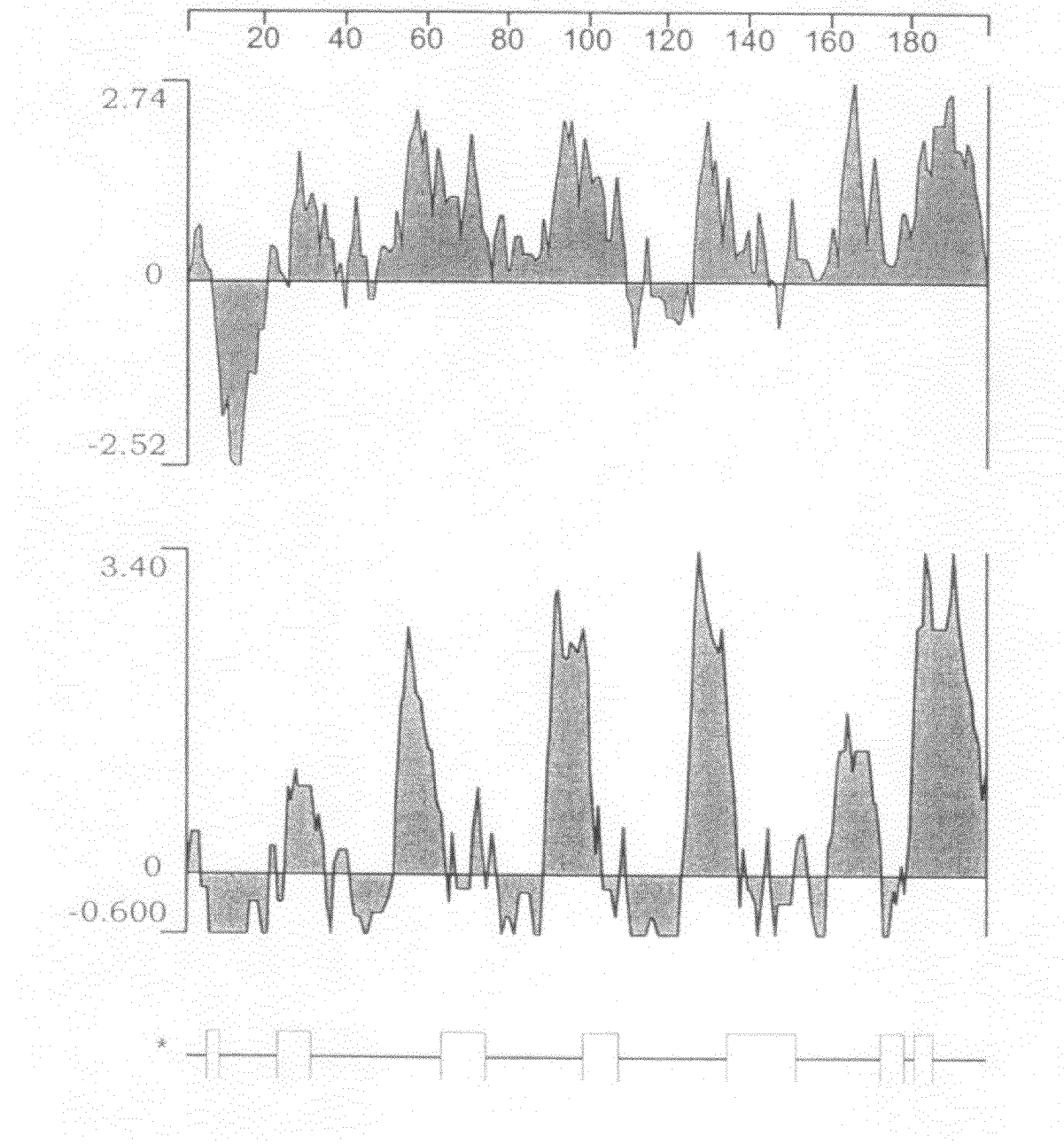

FIGURE 2
FIG. 2A
M1  ORF5
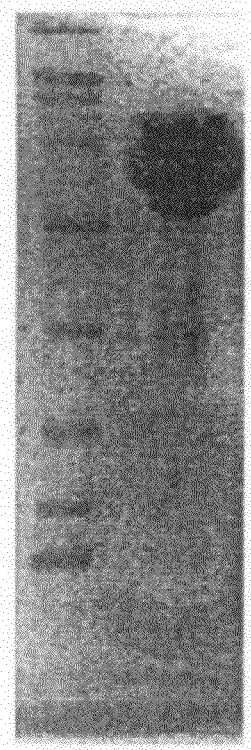
FIG. 2B
TP
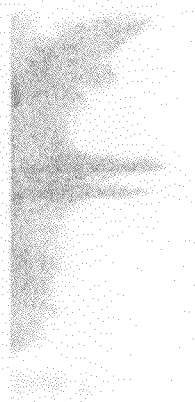

FIGURE 3
FIG. 3A
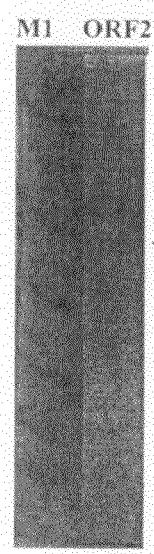
FIG. 3B
FIG. 3C
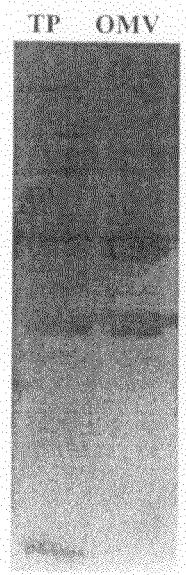
FIG. 3D
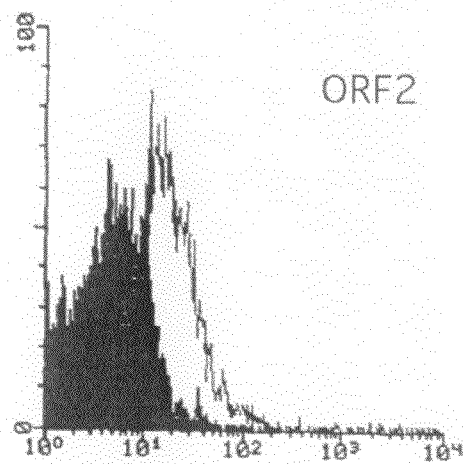

FIGURE 4
FIG. 4A
FIG. 4B
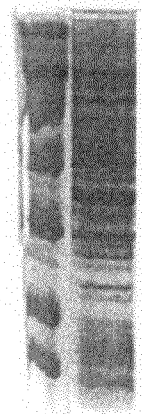
FIG 4C
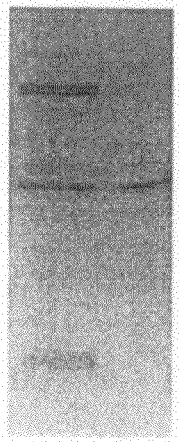

FIGURE 5
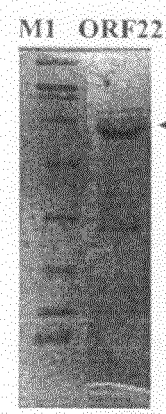
*FIG. 5A*
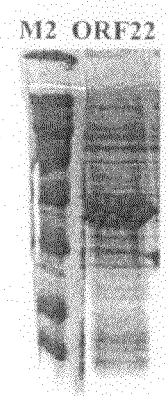
*FIG. 5B*
*FIG. 5C*
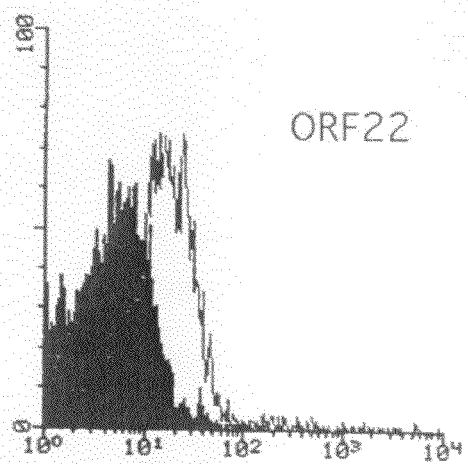

FIGURE 6
FIG. 6A
M1  ORF28
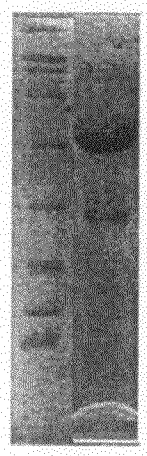
FIG. 6B
M2  ORF28
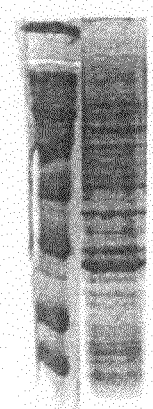
FIGURE 7
FIG. 7A
M1  ORF32
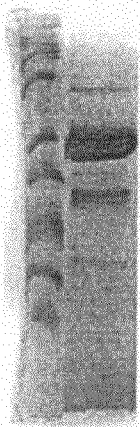
FIG. 7B
M1  ORF32
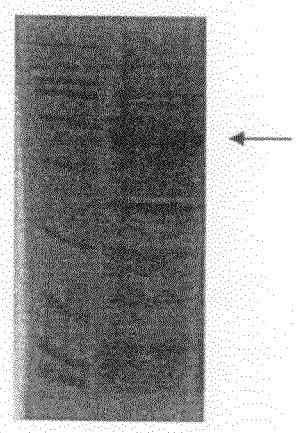

FIGURE 8
FIG. 8A
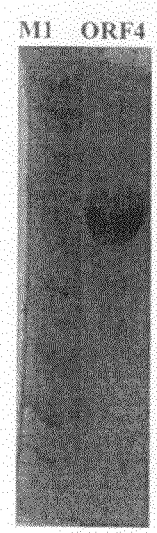
FIG. 8B
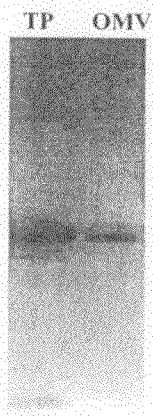
FIG. 8C
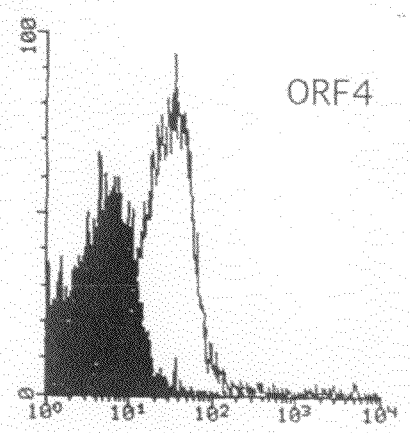
FIG. 8D

FIGURE 10
FIG. 10A
FIG. 10B
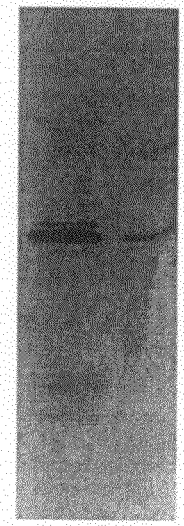
FIG. 10C
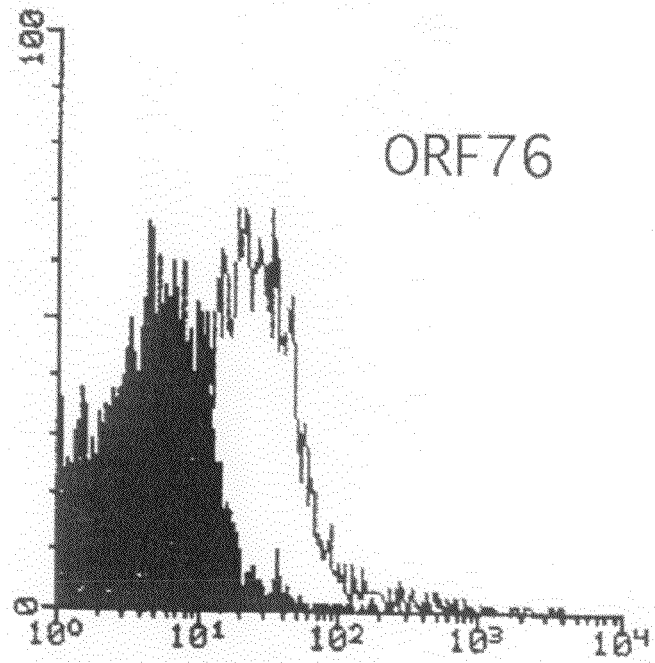

FIGURE 12
FIG. 12A
FIG. 12B
FIG. 12C
FIG. 12D
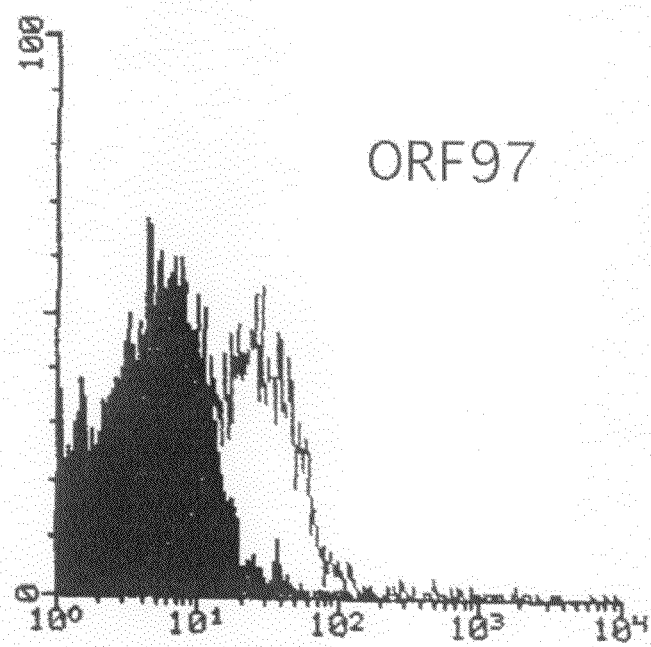

FIGURE 13
FIG. 13A
FIG. 13B
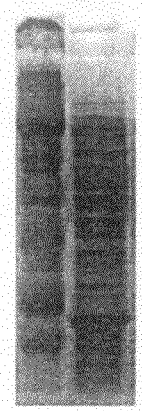
FIG. 13C
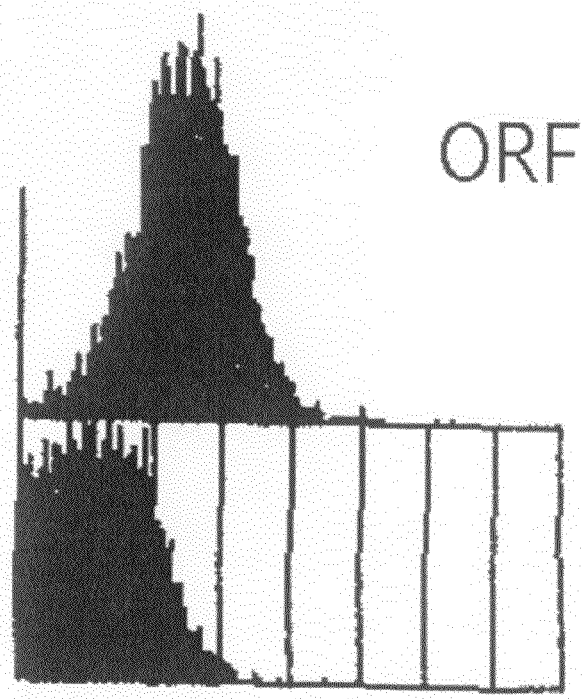
ORF 106

FIGURE 15
FIG. 15A
FIG. 15B
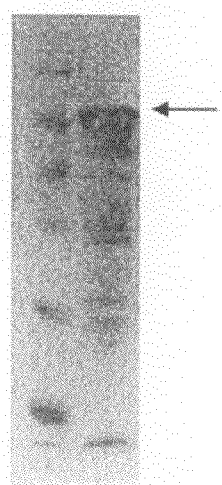
FIG 15C
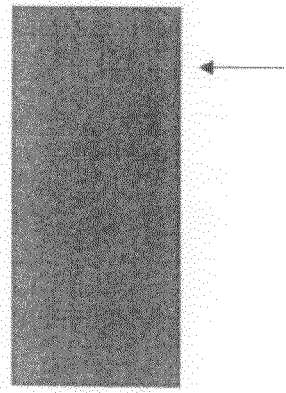

FIGURE 16

FIGURE 17
FIG. 17A
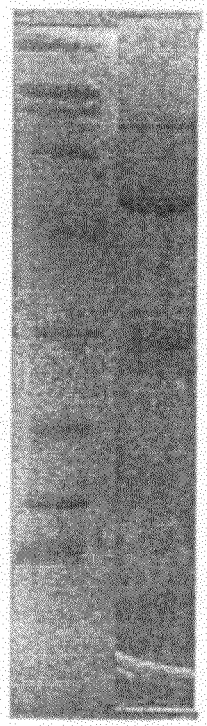
FIG. 17B
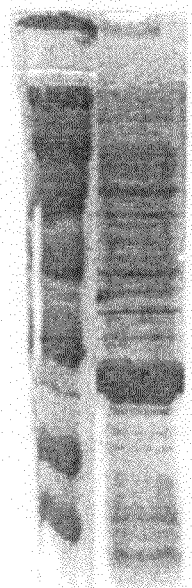

FIGURE 18
FIG. 18A
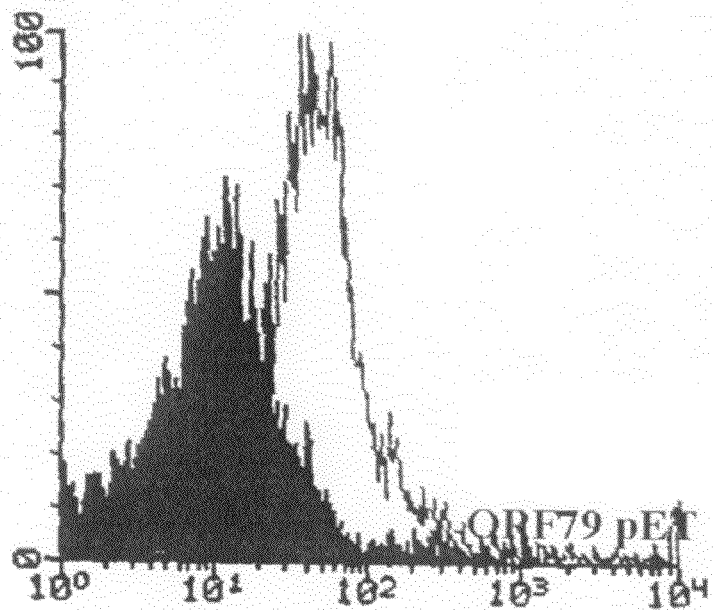
FIG. 18B

FIGURE 19
Fig. 19A
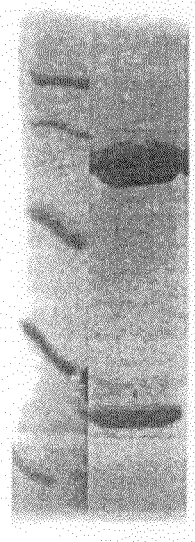
Fig. 19B
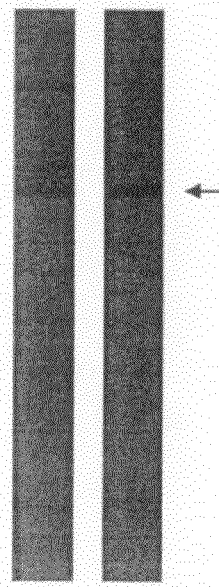
Fig. 19C
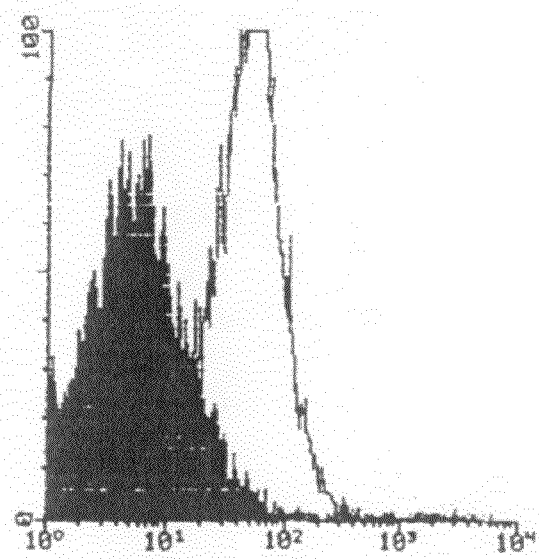

FIGURE 20
FIG. 20A
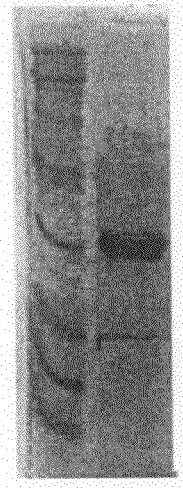
M1  ORF132
FIG. 20B
M2  ORF132
FIG. 20C
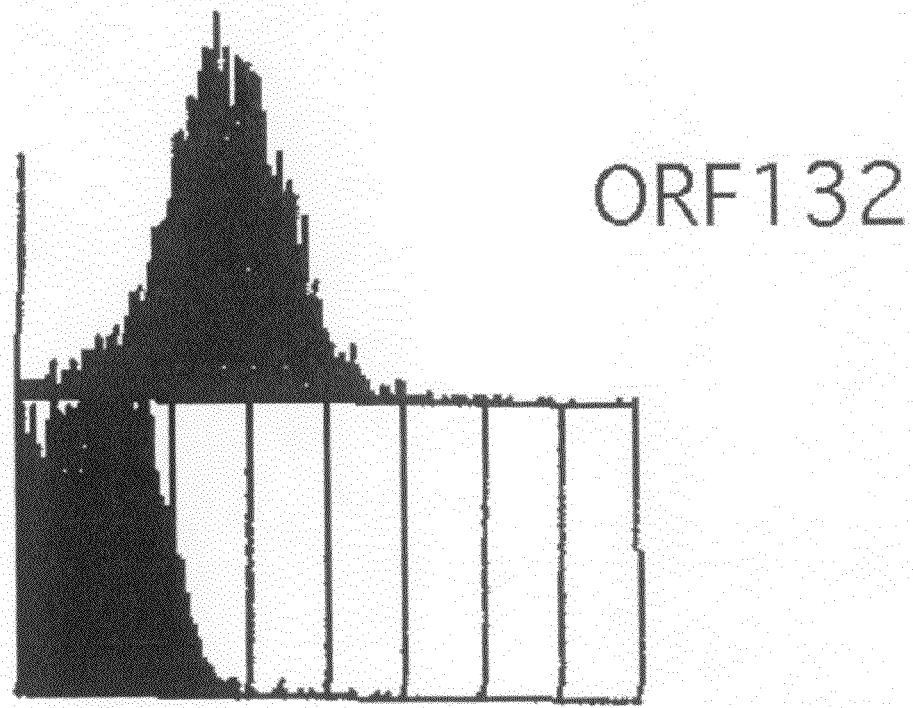
ORF132

NEISSERIAL ANTIGENS

This application is a divisional application of U.S. patent application Ser. No. 10/864,684, filed Jun. 8, 2004, now U.S. Pat. No. 7,655,245, which is a continuation application of U.S. patent application Ser. No. 09/303,518, filed Apr. 30, 1999, now U.S. Pat. No. 6,914,131, which is a continuation-in-part of International Patent Application PCT/IB98/01665, filed Oct. 9, 1998, from which applications priority is claimed pursuant to 35 U.S.C. §120. PCT/IB98/01665 claims priority to Great Britain Patent Applications No. GB19970023516, filed Nov. 6, 1997; No. GB19970024190, filed Nov. 14, 1997; No. GB19970024386, filed Nov. 18, 1997; No. GB19970025158, filed Nov. 27, 1997; No. GB19970026147, filed Dec. 10, 1997; No. GB19980000759, filed Jan. 14, 1998; No. GB19980019016, filed Sep. 1, 1998. All of the above applications are incorporated herein by reference in their entirety.

SUBMISSION ON COMPACT DISC

The content of the following submission on compact discs is incorporated herein by reference in its entirety: A computer readable form (CRF) of the Sequence Listing filed in application Ser. No. 09/303,518, filed Apr. 30, 1999; a duplicate compact disc copy of the Sequence Listing (COPY 1) (file name: complete_seqlist09303518.txt, date recorded: Dec. 16, 2009, size: 2,240 KB); and a duplicate compact disc copy of the Sequence Listing (COPY 2) (file name: complete_seqlist09303518.txt, date recorded: Dec. 16, 2009, size: 2,240 KB).

This invention relates to antigens from *Neisseria* bacteria.

BACKGROUND ART

*Neisseria meningitidis* and *Neisseria gonorrhoeae* are non-motile, gram negative diplococci that are pathogenic in humans. *N. meningitidis* colonises the pharynx and causes meningitis (and, occasionally, septicaemia in the absence of meningitis); *N. gonorrhoeae* colonises the genital tract and causes gonorrhea. Although colonising different areas of the body and causing completely different diseases, the two pathogens are closely related, although one feature that clearly differentiates meningococcus from gonococcus is the presence of a polysaccharide capsule that is present in all pathogenic meningococci.

*N. gonorrhoeae* caused approximately 800,000 cases per year during the period 1983-1990 in the United States alone (chapter by Meitzner & Cohen, "Vaccines Against Gonococcal Infection", In: *New Generation Vaccines*, 2nd edition, ed. Levine, Woodrow, Kaper, & Cobon, Marcel Dekker, New York, 1997, pp. 817-842). The disease causes significant morbidity but limited mortality. Vaccination against *N. gonorrhoeae* would be highly desirable, but repeated attempts have failed. The main candidate antigens for this vaccine are surface-exposed proteins such as pili, porins, opacity-associated proteins (Opas) and other surface-exposed proteins such as the Lip, Laz, IgA1 protease and transferrin-binding proteins. The lipooligosaccharide (LOS) has also been suggested as vaccine (Meitzner & Cohen, supra).

*N. meningitidis* causes both endemic and epidemic disease. In the United States the attack rate is 0.6-1 per 100,000 persons per year, and it can be much greater during outbreaks (see Lieberman et al. (1996) Safety and Immunogenicity of a Serogroups A/C *Neisseria meningitidis* Oligosaccharide-Protein Conjugate Vaccine in Young Children. *JAMA* 275 (19):1499-1503; Schuchat et al (1997) Bacterial Meningitis in the United States in 1995. *N Engl J Med* 337(14):970-976). In developing countries, endemic disease rates are much higher and during epidemics incidence rates can reach 500 cases per 100,000 persons per year. Mortality is extremely high, at 10-20% in the United States, and much higher in developing countries. Following the introduction of the conjugate vaccine against *Haemophilus influenzae*, *N. meningitidis* is the major cause of bacterial meningitis at all ages in the United States (Schuchat et al (1997) supra).

Based on the organism's capsular polysaccharide, 12 serogroups of *N. meningitidis* have been identified. Group A is the pathogen most often implicated in epidemic disease in sub-Saharan Africa. Serogroups B and C are responsible for the vast majority of cases in the United States and in most developed countries. Serogroups W135 and Y are responsible for the rest of the cases in the United States and developed countries. The meningococcal vaccine currently in use is a tetravalent polysaccharide vaccine composed of serogroups A, C, Y and W135. Although efficacious in adolescents and adults, it induces a poor immune response and short duration of protection, and cannot be used in infants [e.g. Morbidity and Mortality weekly report, Vol. 46, No. RR-5 (1997)]. This is because polysaccharides are T-cell independent antigens that induce a weak immune response that cannot be boosted by repeated immunization. Following the success of the vaccination against *H. influenzae*, conjugate vaccines against serogroups A and C have been developed and are at the final stage of clinical testing (Zollinger W D "New and Improved Vaccines Against Meningococcal Disease" in: *New Generation Vaccines*, supra, pp. 469-488; Lieberman et al (1996) supra; Costantino et al (1992) Development and phase I clinical testing of a conjugate vaccine against meningococcus A and C. *Vaccine* 10:691-698).

Meningococcus B remains a problem, however. This serotype currently is responsible for approximately 50% of total meningitis in the United States, Europe, and South America. The polysaccharide approach cannot be used because the menB capsular polysaccharide is a polymer of $\alpha(2-8)$-linked N-acetyl neuraminic acid that is also present in mammalian tissue. This results in tolerance to the antigen; indeed, if an immune response were elicited, it would be anti-self, and therefore undesirable. In order to avoid induction of autoimmunity and to induce a protective immune response, the capsular polysaccharide has, for instance, been chemically modified substituting the N-acetyl groups with N-propionyl groups, leaving the specific antigenicity unaltered (Romero & Outschoorn (1994) Current status of Meningococcal group B vaccine candidates: capsular or non-capsular? *Clin Microbiol Rev* 7(4):559-575).

Alternative approaches to menB vaccines have used complex mixtures of outer membrane proteins (OMPs), containing either the OMPs alone, or OMPs enriched in porins, or deleted of the class 4 OMPs that are believed to induce antibodies that block bactericidal activity. This approach produces vaccines that are not well characterized. They are able to protect against the homologous strain, but are not effective at large where there are many antigenic variants of the outer membrane proteins. To overcome the antigenic variability, multivalent vaccines containing up to nine different porins have been constructed (e.g. Poolman J T (1992) Development of a meningococcal vaccine. *Infect. Agents Dis.* 4:13-28). Additional proteins to be used in outer membrane vaccines have been the opa and opc proteins, but none of these approaches have been able to overcome the antigenic variability (e.g. Ala' Aldeen & Borriello (1996) The meningococcal transferrin-binding proteins 1 and 2 are both surface exposed and generate bactericidal antibodies capable of killing homologous and heterologous strains. *Vaccine* 14(1):49-53).

A certain amount of sequence data is available for meningococcal and gonoccocal genes and proteins (e.g. EP-A-0467714, WO96/29412), but this is by no means complete. The provision of further sequences could provide an opportunity to identify secreted or surface-exposed proteins that are presumed targets for the immune system and which are not antigenically variable. For instance, some of the identified proteins could be components of efficacious vaccines against meningococcus B, some could be components of vaccines against all meningococcal serotypes, and others could be components of vaccines against all pathogenic *Neisseriae*.

THE INVENTION

The invention provides proteins comprising the Neisserial amino acid sequences disclosed in the examples. These sequences relate to *N. meningitidis* or *N. gonorrhoeae*.

It also provides proteins comprising sequences homologous (i.e. having sequence identity) to the Neisserial amino acid sequences disclosed in the examples. Depending on the particular sequence, the degree of identity is preferably greater than 50% (e.g. 65%, 80%, 90%, or more). These homologous proteins include mutants and allelic variants of the sequences disclosed in the examples. Typically, 50% identity or more between two proteins is considered to be an indication of functional equivalence. Identity between the proteins is preferably determined by the Smith-Waterman homology search algorithm as implemented in the MPSRCH program (Oxford Molecular), using an affine gap search with parameters gap open penalty=12 and gap extension penalty=1.

The invention further provides proteins comprising fragments of the Neisserial amino acid sequences disclosed in the examples. The fragments should comprise at least n consecutive amino acids from the sequences and, depending on the particular sequence, n is 7 or more (e.g. 8, 10, 12, 14, 16, 18, 20 or more). Preferably the fragments comprise an epitope from the sequence.

The proteins of the invention can, of course, be prepared by various means (e.g. recombinant expression, purification from cell culture, chemical synthesis etc.) and in various forms (e.g. native, fusions etc.). They are preferably prepared in substantially pure or isolated form (i.e. substantially free from other Neisserial or host cell proteins)

According to a further aspect, the invention provides antibodies which bind to these proteins. These may be polyclonal or monoclonal and may be produced by any suitable means.

According to a further aspect, the invention provides nucleic acid comprising the Neisserial nucleotide sequences disclosed in the examples. In addition, the invention provides nucleic acid comprising sequences homologous (i.e. having sequence identity) to the Neisserial nucleotide sequences disclosed in the examples.

Furthermore, the invention provides nucleic acid which can hybridise to the Neisserial nucleic acid disclosed in the examples, preferably under "high stringency" conditions (e.g. 65° C. in a 0.1×SSC, 0.5% SDS solution).

Nucleic acid comprising fragments of these sequences are also provided. These should comprise at least n consecutive nucleotides from the Neisserial sequences and, depending on the particular sequence, n is 10 or more (eg 12, 14, 15, 18, 20, 25, 30, 35, 40 or more).

According to a further aspect, the invention provides nucleic acid encoding the proteins and protein fragments of the invention.

It should also be appreciated that the invention provides nucleic acid comprising sequences complementary to those described above (e.g. for antisense or probing purposes).

Nucleic acid according to the invention can, of course, be prepared in many ways (e.g. by chemical synthesis, from genomic or cDNA libraries, from the organism itself etc.) and can take various forms (e.g. single stranded, double stranded, vectors, probes etc.).

In addition, the term "nucleic acid" includes DNA and RNA, and also their analogues, such as those containing modified backbones, and also peptide nucleic acids (PNA) etc.

According to a further aspect, the invention provides vectors comprising nucleotide sequences of the invention (e.g. expression vectors) and host cells transformed with such vectors.

According to a further aspect, the invention provides compositions comprising protein, antibody, and/or nucleic acid according to the invention. These compositions may be suitable as vaccines, for instance, or as diagnostic reagents, or as immunogenic compositions.

The invention also provides nucleic acid, protein, or antibody according to the invention for use as medicaments (e.g. as vaccines) or as diagnostic reagents. It also provides the use of nucleic acid, protein, or antibody according to the invention in the manufacture of: (i) a medicament for treating or preventing infection due to Neisserial bacteria; (ii) a diagnostic reagent for detecting the presence of Neisserial bacteria or of antibodies raised against Neisserial bacteria; and/or (iii) a reagent which can raise antibodies against Neisserial bacteria. Said Neisserial bacteria may be any species or strain (such as *N. gonorrhoeae*, or any strain of *N. meningitidis*, such as strain A, strain B or strain C).

The invention also provides a method of treating a patient, comprising administering to the patient a therapeutically effective amount of nucleic acid, protein, and/or antibody according to the invention.

According to further aspects, the invention provides various processes.

A process for producing proteins of the invention is provided, comprising the step of culturing a host cell according to the invention under conditions which induce protein expression.

A process for producing protein or nucleic acid of the invention is provided, wherein the protein or nucleic acid is synthesised in part or in whole using chemical means.

A process for detecting polynucleotides of the invention is provided, comprising the steps of: (a) contacting a nucleic probe according to the invention with a biological sample under hybridizing conditions to form duplexes; and (b) detecting said duplexes.

A process for detecting proteins of the invention is provided, comprising the steps of: (a) contacting an antibody according to the invention with a biological sample under conditions suitable for the formation of an antibody-antigen complexes; and (b) detecting said complexes.

A summary of standard techniques and procedures which may be employed in order to perform the invention (e.g. to utilise the disclosed sequences for vaccination or diagnostic purposes) follows. This summary is not a limitation on the invention but, rather, gives examples that may be used, but are not required.

General

The practice of the present invention will employ, unless otherwise indicated, conventional techniques of molecular biology, microbiology, recombinant DNA, and immunology, which are within the skill of the art. Such techniques are explained fully in the literature e.g. Sambrook *Molecular Cloning, A Laboratory Manual, Second Edition* (1989); *DNA Cloning, Volumes I and ii* (D. N Glover ed. 1985); *Oligonucleotide Synthesis* (M. J. Gait ed, 1984); *Nucleic Acid Hybridization* (B. D. Hames & S. J. Higgins eds. 1984); *Transcription and Translation* (B. D. Hames & S. J. Higgins eds. 1984); *Animal Cell Culture* (R. I. Freshney ed. 1986); *Immobilized Cells and Enzymes* (IRL Press, 1986); B. Perbal, *A Practical Guide to Molecular Cloning* (1984); the *Methods in Enzymology* series (Academic Press, Inc.), especially volumes 154 & 155; *Gene Transfer Vectors for Mammalian Cells* (J. H. Miller and M. P. Calos eds. 1987, Cold Spring Harbor Laboratory); Mayer and Walker, eds. (1987), *Immunochemical Methods in Cell and Molecular Biology* (Academic Press, London); Scopes, (1987) *Protein Purification: Principles and Practice*, Second Edition (Springer-Verlag, N.Y.), and *Handbook of Experimental Immunology, Volumes I-IV* (D. M. Weir and C. C. Blackwell eds 1986).

Standard abbreviations for nucleotides and amino acids are used in this specification.

All publications, patents, and patent applications cited herein are incorporated in full by reference. In particular, the contents of UK patent applications 9723516.2, 9724190.5, 9724386.9, 9725158.1, 9726147.3, 9800759.4, and 9819016.8 are incorporated herein.

Definitions

A composition containing X is "substantially free of" Y when at least 85% by weight of the total X+Y in the composition is X. Preferably, X comprises at least about 90% by weight of the total of X+Y in the composition, more preferably at least about 95% or even 99% by weight.

The term "comprising" means "including" as well as "consisting" e.g. a composition "comprising" X may consist exclusively of X or may include something additional to X, such as X+Y.

The term "heterologous" refers to two biological components that are not found together in nature. The components may be host cells, genes, or regulatory regions, such as promoters. Although the heterologous components are not found together in nature, they can function together, as when a promoter heterologous to a gene is operably linked to the gene. Another example is where a Neisserial sequence is heterologous to a mouse host cell. A further examples would be two epitopes from the same or different proteins which have been assembled in a single protein in an arrangement not found in nature.

An "origin of replication" is a polynucleotide sequence that initiates and regulates replication of polynucleotides, such as an expression vector. The origin of replication behaves as an autonomous unit of polynucleotide replication within a cell, capable of replication under its own control. An origin of replication may be needed for a vector to replicate in a particular host cell. With certain origins of replication, an expression vector can be reproduced at a high copy number in the presence of the appropriate proteins within the cell. Examples of origins are the autonomously replicating sequences, which are effective in yeast; and the viral T-antigen, effective in COS-7 cells.

A "mutant" sequence is defined as DNA, RNA or amino acid sequence differing from but having sequence identity with the native or disclosed sequence. Depending on the particular sequence, the degree of sequence identity between the native or disclosed sequence and the mutant sequence is preferably greater than 50% (e.g. 60%, 70%, 80%, 90%, 95%, 99% or more, calculated using the Smith-Waterman algorithm as described above). As used herein, an "allelic variant" of a nucleic acid molecule, or region, for which nucleic acid sequence is provided herein is a nucleic acid molecule, or region, that occurs essentially at the same locus in the genome of another or second isolate, and that, due to natural variation caused by, for example, mutation or recombination, has a similar but not identical nucleic acid sequence. A coding region allelic variant typically encodes a protein having similar activity to that of the protein encoded by the gene to which it is being compared. An allelic variant can also comprise an alteration in the 5' or 3' untranslated regions of the gene, such as in regulatory control regions (e.g. see U.S. Pat. No. 5,753,235).

Expression Systems

The Neisserial nucleotide sequences can be expressed in a variety of different expression systems; for example those used with mammalian cells, baculoviruses, plants, bacteria, and yeast.

i. Mammalian Systems

Mammalian expression systems are known in the art. A mammalian promoter is any DNA sequence capable of binding mammalian RNA polymerase and initiating the downstream (3') transcription of a coding sequence (e.g. structural gene) into mRNA. A promoter will have a transcription initiating region, which is usually placed proximal to the 5' end of the coding sequence, and a TATA box, usually located 25-30 base pairs (bp) upstream of the transcription initiation site. The TATA box is thought to direct RNA polymerase II to begin RNA synthesis at the correct site. A mammalian promoter will also contain an upstream promoter element, usually located within 100 to 200 bp upstream of the TATA box. An upstream promoter element determines the rate at which transcription is initiated and can act in either orientation [Sambrook et al. (1989) "Expression of Cloned Genes in Mammalian Cells." In *Molecular Cloning: A Laboratory Manual, 2nd ed.*].

Mammalian viral genes are often highly expressed and have a broad host range; therefore sequences encoding mammalian viral genes provide particularly useful promoter sequences. Examples include the SV40 early promoter, mouse mammary tumor virus LTR promoter, adenovirus major late promoter (Ad MLP), and herpes simplex virus promoter. In addition, sequences derived from non-viral genes, such as the murine metallotheionein gene, also provide useful promoter sequences. Expression may be either constitutive or regulated (inducible), depending on the promoter can be induced with glucocorticoid in hormone-responsive cells.

The presence of an enhancer element (enhancer), combined with the promoter elements described above, will usually increase expression levels. An enhancer is a regulatory DNA sequence that can stimulate transcription up to 1000-fold when linked to homologous or heterologous promoters, with synthesis beginning at the normal RNA start site. Enhancers are also active when they are placed upstream or downstream from the transcription initiation site, in either normal or flipped orientation, or at a distance of more than 1000 nucleotides from the promoter [Maniatis et al. (1987) *Science* 236:1237; Alberts et al. (1989) *Molecular Biology of the Cell*, 2nd ed.]. Enhancer elements derived from viruses may be particularly useful, because they usually have a broader host range. Examples include the SV40 early gene enhancer [Dijkema et al (1985) *EMBO J.* 4:761] and the enhancer/promoters derived from the long terminal repeat (LTR) of the Rous Sarcoma Virus [Gorman et al. (1982b)

*Proc. Natl. Acad. Sci.* 79:6777] and from human cytomegalovirus [Boshart et al. (1985) *Cell* 41:521]. Additionally, some enhancers are regulatable and become active only in the presence of an inducer, such as a hormone or metal ion [Sassone-Corsi and Borelli (1986) *Trends Genet.* 2:215; Maniatis et al. (1987) *Science* 236:1237].

A DNA molecule may be expressed intracellularly in mammalian cells. A promoter sequence may be directly linked with the DNA molecule, in which case the first amino acid at the N-terminus of the recombinant protein will always be a methionine, which is encoded by the ATG start codon. If desired, the N-terminus may be cleaved from the protein by in vitro incubation with cyanogen bromide.

Alternatively, foreign proteins can also be secreted from the cell into the growth media by creating chimeric DNA molecules that encode a fusion protein comprised of a leader sequence fragment that provides for secretion of the foreign protein in mammalian cells. Preferably, there are processing sites encoded between the leader fragment and the foreign gene that can be cleaved either in vivo or in vitro. The leader sequence fragment usually encodes a signal peptide comprised of hydrophobic amino acids which direct the secretion of the protein from the cell. The adenovirus triparite leader is an example of a leader sequence that provides for secretion of a foreign protein in mammalian cells.

Usually, transcription termination and polyadenylation sequences recognized by mammalian cells are regulatory regions located 3' to the translation stop codon and thus, together with the promoter elements, flank the coding sequence. The 3' terminus of the mature mRNA is formed by site-specific post-transcriptional cleavage and polyadenylation [Birnstiel et al. (1985) *Cell* 41:349; Proudfoot and Whitelaw (1988) "Termination and 3' end processing of eukaryotic RNA. In *Transcription and splicing* (ed. B. D. Hames and D. M. Glover); Proudfoot (1989) *Trends Biochem. Sci.* 14: 105]. These sequences direct the transcription of an mRNA which can be translated into the polypeptide encoded by the DNA. Examples of transcription terminater/polyadenylation signals include those derived from SV40 [Sambrook et al (1989) "Expression of cloned genes in cultured mammalian cells." In *Molecular Cloning: A Laboratory Manual*].

Usually, the above described components, comprising a promoter, polyadenylation signal, and transcription termination sequence are put together into expression constructs. Enhancers, introns with functional splice donor and acceptor sites, and leader sequences may also be included in an expression construct, if desired. Expression constructs are often maintained in a replicon, such as an extrachromosomal element (e.g. plasmids) capable of stable maintenance in a host, such as mammalian cells or bacteria. Mammalian replication systems include those derived from animal viruses, which require trans-acting factors to replicate. For example, plasmids containing the replication systems of papovaviruses, such as SV40 [Gluzman (1981) *Cell* 23:175] or polyomavirus, replicate to extremely high copy number in the presence of the appropriate viral T antigen. Additional examples of mammalian replicons include those derived from bovine papillomavirus and Epstein-Barr virus. Additionally, the replicon may have two replicaton systems, thus allowing it to be maintained, for example, in mammalian cells for expression and in a prokaryotic host for cloning and amplification. Examples of such mammalian-bacteria shuttle vectors include pMT2 [Kaufman et al. (1989) *Mol. Cell. Biol.* 9:946] and pHEBO [Shimizu et al. (1986) *Mol. Cell. Biol.* 6:1074].

The transformation procedure used depends upon the host to be transformed. Methods for introduction of heterologous polynucleotides into mammalian cells are known in the art and include dextran-mediated transfection, calcium phosphate precipitation, polybrene mediated transfection, protoplast fusion, electroporation, encapsulation of the polynucleotide(s) in liposomes, and direct microinjection of the DNA into nuclei.

Mammalian cell lines available as hosts for expression are known in the art and include many immortalized cell lines available from the American Type Culture Collection (ATCC), including but not limited to, Chinese hamster ovary (CHO) cells, HeLa cells, baby hamster kidney (BHK) cells, monkey kidney cells (COS), human hepatocellular carcinoma cells (e.g. Hep G2), and a number of other cell lines.

ii. Baculovirus Systems

The polynucleotide encoding the protein can also be inserted into a suitable insect expression vector, and is operably linked to the control elements within that vector. Vector construction employs techniques which are known in the art. Generally, the components of the expression system include a transfer vector, usually a bacterial plasmid, which contains both a fragment of the baculovirus genome, and a convenient restriction site for insertion of the heterologous gene or genes to be expressed; a wild type baculovirus with a sequence homologous to the baculovirus-specific fragment in the transfer vector (this allows for the homologous recombination of the heterologous gene in to the baculovirus genome); and appropriate insect host cells and growth media.

After inserting the DNA sequence encoding the protein into the transfer vector, the vector and the wild type viral genome are transfected into an insect host cell where the vector and viral genome are allowed to recombine. The packaged recombinant virus is expressed and recombinant plaques are identified and purified. Materials and methods for baculovirus/insect cell expression systems are commercially available in kit form from, inter alia, Invitrogen, San Diego Calif. ("MaxBac" kit). These techniques are generally known to those skilled in the art and fully described in Summers and Smith, *Texas Agricultural Experiment Station Bulletin No. 1555* (1987) (hereinafter "Summers and Smith").

Prior to inserting the DNA sequence encoding the protein into the baculovirus genome, the above described components, comprising a promoter, leader (if desired), coding sequence of interest, and transcription termination sequence, are usually assembled into an intermediate transplacement construct (transfer vector). This construct may contain a single gene and operably linked regulatory elements; multiple genes, each with its owned set of operably linked regulatory elements; or multiple genes, regulated by the same set of regulatory elements. Intermediate transplacement constructs are often maintained in a replicon, such as an extrachromosomal element (e.g. plasmids) capable of stable maintenance in a host, such as a bacterium. The replicon will have a replication system, thus allowing it to be maintained in a suitable host for cloning and amplification.

Currently, the most commonly used transfer vector for introducing foreign genes into AcNPV is pAc373. Many other vectors, known to those of skill in the art, have also been designed. These include, for example, pVL985 (which alters the polyhedrin start codon from ATG to ATT, and which introduces a BamHI cloning site 32 basepairs downstream from the ATT; see Luckow and Summers, *Virology* (1989) 17:31.

The plasmid usually also contains the polyhedrin polyadenylation signal (Miller et al. (1988) *Ann. Rev. Microbiol.*, 42:177) and a prokaryotic ampicillin-resistance (amp) gene and origin of replication for selection and propagation in *E. coli*.

Baculovirus transfer vectors usually contain a baculovirus promoter. A baculovirus promoter is any DNA sequence capable of binding a baculovirus RNA polymerase and initiating the downstream (5' to 3') transcription of a coding sequence (e.g. structural gene) into mRNA. A promoter will have a transcription initiation region which is usually placed proximal to the 5' end of the coding sequence. This transcription initiation region usually includes an RNA polymerase binding site and a transcription initiation site. A baculovirus transfer vector may also have a second domain called an enhancer, which, if present, is usually distal to the structural gene. Expression may be either regulated or constitutive.

Structural genes, abundantly transcribed at late times in a viral infection cycle, provide particularly useful promoter sequences. Examples include sequences derived from the gene encoding the viral polyhedron protein, Friesen et al., (1986) "The Regulation of Baculovirus Gene Expression," in: *The Molecular Biology of Baculoviruses* (ed. Walter Doerfler); EPO Publ. Nos. 127 839 and 155 476; and the gene encoding the p10 protein, Vlak et al., (1988), *J. Gen. Virol.* 69:765.

DNA encoding suitable signal sequences can be derived from genes for secreted insect or baculovirus proteins, such as the baculovirus polyhedrin gene (Carbonell et al. (1988) *Gene,* 73:409). Alternatively, since the signals for mammalian cell posttranslational modifications (such as signal peptide cleavage, proteolytic cleavage, and phosphorylation) appear to be recognized by insect cells, and the signals required for secretion and nuclear accumulation also appear to be conserved between the invertebrate cells and vertebrate cells, leaders of non-insect origin, such as those derived from genes encoding human α-interferon, Maeda et al., (1985), *Nature* 315:592; human gastrin-releasing peptide, Lebacq-Verheyden et al., (1988), *Molec. Cell. Biol.* 8:3129; human IL-2, Smith et al., (1985) *Proc. Nat'l Acad. Sci. USA,* 82:8404; mouse IL-3, (Miyajima et al., (1987) *Gene* 58:273; and human glucocerebrosidase, Martin et al. (1988) *DNA,* 7:99, can also be used to provide for secretion in insects.

A recombinant polypeptide or polyprotein may be expressed intracellularly or, if it is expressed with the proper regulatory sequences, it can be secreted. Good intracellular expression of nonfused foreign proteins usually requires heterologous genes that ideally have a short leader sequence containing suitable translation initiation signals preceding an ATG start signal. If desired, methionine at the N-terminus may be cleaved from the mature protein by in vitro incubation with cyanogen bromide.

Alternatively, recombinant polyproteins or proteins which are not naturally secreted can be secreted from the insect cell by creating chimeric DNA molecules that encode a fusion protein comprised of a leader sequence fragment that provides for secretion of the foreign protein in insects. The leader sequence fragment usually encodes a signal peptide comprised of hydrophobic amino acids which direct the translocation of the protein into the endoplasmic reticulum.

After insertion of the DNA sequence and/or the gene encoding the expression product precursor of the protein, an insect cell host is co-transformed with the heterologous DNA of the transfer vector and the genomic DNA of wild type baculovirus—usually by co-transfection. The promoter and transcription termination sequence of the construct will usually comprise a 2-5 kb section of the baculovirus genome. Methods for introducing heterologous DNA into the desired site in the baculovirus virus are known in the art. (See Summers and Smith supra; Ju et al. (1987); Smith et al., *Mol. Cell. Biol.* (1983) 3:2156; and Luckow and Summers (1989)). For example, the insertion can be into a gene such as the polyhedrin gene, by homologous double crossover recombination; insertion can also be into a restriction enzyme site engineered into the desired baculovirus gene. Miller et al., (1989), *Bioessays* 4:91. The DNA sequence, when cloned in place of the polyhedrin gene in the expression vector, is flanked both 5' and 3' by polyhedrin-specific sequences and is positioned downstream of the polyhedrin promoter.

The newly formed baculovirus expression vector is subsequently packaged into an infectious recombinant baculovirus. Homologous recombination occurs at low frequency (between about 1% and about 5%); thus, the majority of the virus produced after cotransfection is still wild-type virus. Therefore, a method is necessary to identify recombinant viruses. An advantage of the expression system is a visual screen allowing recombinant viruses to be distinguished. The polyhedrin protein, which is produced by the native virus, is produced at very high levels in the nuclei of infected cells at late times after viral infection. Accumulated polyhedrin protein forms occlusion bodies that also contain embedded particles. These occlusion bodies, up to 15 μm in size, are highly refractile, giving them a bright shiny appearance that is readily visualized under the light microscope. Cells infected with recombinant viruses lack occlusion bodies. To distinguish recombinant virus from wild-type virus, the transfection supernatant is plaqued onto a monolayer of insect cells by techniques known to those skilled in the art. Namely, the plaques are screened under the light microscope for the presence (indicative of wild-type virus) or absence (indicative of recombinant virus) of occlusion bodies. "Current Protocols in Microbiology" Vol. 2 (Ausubel et al. eds) at 16.8 (Supp. 10, 1990); Summers and Smith, supra; Miller et al. (1989).

Recombinant baculovirus expression vectors have been developed for infection into several insect cells. For example, recombinant baculoviruses have been developed for, inter alia: *Aedes aegypti, Autographa californica, Bombyx mori, Drosophila melanogaster, Spodoptera frugiperda,* and *Trichoplusia ni* (WO 89/046699; Carbonell et al., (1985) *J. Virol.* 56:153; Wright (1986) *Nature* 321:718; Smith et al., (1983) *Mol. Cell. Biol.* 3:2156; and see generally, Fraser, et al. (1989) *In Vitro Cell. Dev. Biol.* 25:225).

Cells and cell culture media are commercially available for both direct and fusion expression of heterologous polypeptides in a baculovirus/expression system; cell culture technology is generally known to those skilled in the art. See, eg. Summers and Smith supra.

The modified insect cells may then be grown in an appropriate nutrient medium, which allows for stable maintenance of the plasmid(s) present in the modified insect host. Where the expression product gene is under inducible control, the host may be grown to high density, and expression induced. Alternatively, where expression is constitutive, the product will be continuously expressed into the medium and the nutrient medium must be continuously circulated, while removing the product of interest and augmenting depleted nutrients. The product may be purified by such techniques as chromatography, e.g. HPLC, affinity chromatography, ion exchange chromatography, etc.; electrophoresis; density gradient centrifugation; solvent extraction, or the like. As appropriate, the product may be further purified, as required, so as to remove substantially any insect proteins which are also secreted in the medium or result from lysis of insect cells, so as to provide a product which is at least substantially free of host debris, e.g. proteins, lipids and polysaccharides.

In order to obtain protein expression, recombinant host cells derived from the transformants are incubated under conditions which allow expression of the recombinant protein encoding sequence. These conditions will vary, dependent upon the host cell selected. However, the conditions are readily ascertainable to those of ordinary skill in the art, based upon what is known in the art.

iii. Plant Systems

There are many plant cell culture and whole plant genetic expression systems known in the art. Exemplary plant cellular genetic expression systems include those described in patents, such as: U.S. Pat. Nos. 5,693,506; 5,659,122; and 5,608,143. Additional examples of genetic expression in plant cell culture has been described by Zenk, *Phytochemistry* 30:3861-3863 (1991). Descriptions of plant protein signal peptides may be found in addition to the references described above in Vaulcombe et al., *Mol. Gen. Genet.* 209:33-40 (1987); Chandler et al., *Plant Molecular Biology* 3:407-418 (1984); Rogers, *J. Biol. Chem.* 260:3731-3738 (1985); Rothstein et al., *Gene* 55:353-356 (1987); Whittier et al., Nucleic Acids Research 15:2515-2535 (1987); Wirsel et al., *Molecular Microbiology* 3:3-14 (1989); Yu et al., *Gene* 122:247-253 (1992). A description of the regulation of plant gene expression by the phytohormone, gibberellic acid and secreted enzymes induced by gibberellic acid can be found in R. L. Jones and J. MacMillin, Gibberellins: in: *Advanced Plant Physiology*, Malcolm B. Wilkins, ed., 1984 Pitman Publishing Limited, London, pp. 21-52. References that describe other metabolically-regulated genes: Sheen, *Plant Cell*, 2:1027-1038 (1990); Maas et al., *EMBO J.* 9:3447-3452 (1990); Benkel and Hickey, *Proc. Natl. Acad. Sci.* 84:1337-1339 (1987)

Typically, using techniques known in the art, a desired polynucleotide sequence is inserted into an expression cassette comprising genetic regulatory elements designed for operation in plants. The expression cassette is inserted into a desired expression vector with companion sequences upstream and downstream from the expression cassette suitable for expression in a plant host. The companion sequences will be of plasmid or viral origin and provide necessary characteristics to the vector to permit the vectors to move DNA from an original cloning host, such as bacteria, to the desired plant host. The basic bacterial/plant vector construct will preferably provide a broad host range prokaryote replication origin; a prokaryote selectable marker; and, for *Agrobacterium* transformations, T DNA sequences for *Agrobacterium*-mediated transfer to plant chromosomes. Where the heterologous gene is not readily amenable to detection, the construct will preferably also have a selectable marker gene suitable for determining if a plant cell has been transformed. A general review of suitable markers, for example for the members of the grass family, is found in Wilmink and Dons, 1993, *Plant Mol. Biol. Reptr,* 11(2):165-185.

Sequences suitable for permitting integration of the heterologous sequence into the plant genome are also recommended. These might include transposon sequences and the like for homologous recombination as well as Ti sequences which permit random insertion of a heterologous expression cassette into a plant genome. Suitable prokaryote selectable markers include resistance toward antibiotics such as ampicillin or tetracycline. Other DNA sequences encoding additional functions may also be present in the vector, as is known in the art.

The nucleic acid molecules of the subject invention may be included into an expression cassette for expression of the protein(s) of interest. Usually, there will be only one expression cassette, although two or more are feasible. The recombinant expression cassette will contain in addition to the heterologous protein encoding sequence the following elements, a promoter region, plant 5' untranslated sequences, initiation codon depending upon whether or not the structural gene comes equipped with one, and a transcription and translation termination sequence. Unique restriction enzyme sites at the 5' and 3' ends of the cassette allow for easy insertion into a pre-existing vector.

A heterologous coding sequence may be for any protein relating to the present invention. The sequence encoding the protein of interest will encode a signal peptide which allows processing and translocation of the protein, as appropriate, and will usually lack any sequence which might result in the binding of the desired protein of the invention to a membrane. Since, for the most part, the transcriptional initiation region will be for a gene which is expressed and translocated during germination, by employing the signal peptide which provides for translocation, one may also provide for translocation of the protein of interest. In this way, the protein(s) of interest will be translocated from the cells in which they are expressed and may be efficiently harvested. Typically secretion in seeds are across the aleurone or scutellar epithelium layer into the endosperm of the seed. While it is not required that the protein be secreted from the cells in which the protein is produced, this facilitates the isolation and purification of the recombinant protein.

Since the ultimate expression of the desired gene product will be in a eucaryotic cell it is desirable to determine whether any portion of the cloned gene contains sequences which will be processed out as introns by the host's splicosome machinery. If so, site-directed mutagenesis of the "intron" region may be conducted to prevent losing a portion of the genetic message as a false intron code, Reed and Maniatis, *Cell* 41:95-105, 1985.

The vector can be microinjected directly into plant cells by use of micropipettes to mechanically transfer the recombinant DNA. Crossway, *Mol. Gen. Genet,* 202:179-185, 1985. The genetic material may also be transferred into the plant cell by using polyethylene glycol, Krens, et al., *Nature,* 296, 72-74, 1982. Another method of introduction of nucleic acid segments is high velocity ballistic penetration by small particles with the nucleic acid either within the matrix of small beads or particles, or on the surface, Klein, et al., *Nature,* 327, 70-73, 1987 and Knudsen and Muller, 1991, *Planta,* 185:330-336 teaching particle bombardment of barley endosperm to create transgenic barley. Yet another method of introduction would be fusion of protoplasts with other entities, either minicells, cells, lysosomes or other fusible lipid-surfaced bodies, Fraley, et al., *Proc. Natl. Acad. Sci. USA,* 79, 1859-1863, 1982.

The vector may also be introduced into the plant cells by electroporation. (Fromm et al., *Proc. Natl. Acad. Sci. USA* 82:5824, 1985). In this technique, plant protoplasts are electroporated in the presence of plasmids containing the gene construct. Electrical impulses of high field strength reversibly permeabilize biomembranes allowing the introduction of the plasmids. Electroporated plant protoplasts reform the cell wall, divide, and form plant callus.

All plants from which protoplasts can be isolated and cultured to give whole regenerated plants can be transformed by the present invention so that whole plants are recovered which contain the transferred gene. It is known that practically all plants can be regenerated from cultured cells or tissues, including but not limited to all major species of sugarcane, sugar beet, cotton, fruit and other trees, legumes and vegetables. Some suitable plants include, for example, species from the genera *Fragaria, Lotus, Medicago, Onobrychis, Trifolium, Trigonella, Vigna, Citrus, Linum, Geranium, Manihot, Daucus, Arabidopsis, Brassica, Raphanus, Sinapis, Atropa, Capsicum, Datura, Hyoscyamus, Lycopersion, Nicotiana, Solanum, Petunia, Digitalis, Majorana, Cichorium,*

*Helianthus, Lactuca, Bromus, Asparagus, Antirrhinum, Herocallis, Nemesia, Pelargonium, Panicum, Pennisetum, Ranunculus, Senecio, Salpiglossis, Cucumis, Browaalia, Glycine, Lolium, Zea, Triticum, Sorghum,* and *Datura.*

Means for regeneration vary from species to species of plants, but generally a suspension of transformed protoplasts containing copies of the heterologous gene is first provided. Callus tissue is formed and shoots may be induced from callus and subsequently rooted. Alternatively, embryo formation can be induced from the protoplast suspension. These embryos germinate as natural embryos to form plants. The culture media will generally contain various amino acids and hormones, such as auxin and cytokinins. It is also advantageous to add glutamic acid and proline to the medium, especially for such species as corn and alfalfa. Shoots and roots normally develop simultaneously. Efficient regeneration will depend on the medium, on the genotype, and on the history of the culture. If these three variables are controlled, then regeneration is fully reproducible and repeatable.

In some plant cell culture systems, the desired protein of the invention may be excreted or alternatively, the protein may be extracted from the whole plant. Where the desired protein of the invention is secreted into the medium, it may be collected. Alternatively, the embryos and embryoless-half seeds or other plant tissue may be mechanically disrupted to release any secreted protein between cells and tissues. The mixture may be suspended in a buffer solution to retrieve soluble proteins. Conventional protein isolation and purification methods will be then used to purify the recombinant protein. Parameters of time, temperature pH, oxygen, and volumes will be adjusted through routine methods to optimize expression and recovery of heterologous protein.

iv. Bacterial Systems

Bacterial expression techniques are known in the art. A bacterial promoter is any DNA sequence capable of binding bacterial RNA polymerase and initiating the downstream (3') transcription of a coding sequence (e.g. structural gene) into mRNA. A promoter will have a transcription initiation region which is usually placed proximal to the 5' end of the coding sequence. This transcription initiation region usually includes an RNA polymerase binding site and a transcription initiation site. A bacterial promoter may also have a second domain called an operator, that may overlap an adjacent RNA polymerase binding site at which RNA synthesis begins. The operator permits negative regulated (inducible) transcription, as a gene repressor protein may bind the operator and thereby inhibit transcription of a specific gene. Constitutive expression may occur in the absence of negative regulatory elements, such as the operator. In addition, positive regulation may be achieved by a gene activator protein binding sequence, which, if present is usually proximal (5') to the RNA polymerase binding sequence. An example of a gene activator protein is the catabolite activator protein (CAP), which helps initiate transcription of the lac operon in *Escherichia coli* (*E. coli*) [Raibaud et al. (1984) *Annu. Rev. Genet.* 18:173]. Regulated expression may therefore be either positive or negative, thereby either enhancing or reducing transcription.

Sequences encoding metabolic pathway enzymes provide particularly useful promoter sequences. Examples include promoter sequences derived from sugar metabolizing enzymes, such as galactose, lactose (lac) [Chang et al. (1977) *Nature* 198:1056], and maltose. Additional examples include promoter sequences derived from biosynthetic enzymes such as tryptophan (trp) [Goeddel et al. (1980) *Nuc. Acids Res.* 8:4057; Yelverton et al. (1981) *Nucl. Acids Res.* 9:731; U.S. Pat. No. 4,738,921; EP-A-0036776 and EP-A-0121775]. The g-laotamase (bla) promoter system [Weissmann (1981) "The cloning of interferon and other mistakes." In *Interferon* 3 (ed. I. Gresser)], bacteriophage lambda PL [Shimatake et al. (1981) *Nature* 292:128] and T5 [U.S. Pat. No. 4,689,406] promoter systems also provide useful promoter sequences.

In addition, synthetic promoters which do not occur in nature also function as bacterial promoters. For example, transcription activation sequences of one bacterial or bacteriophage promoter may be joined with the operon sequences of another bacterial or bacteriophage promoter, creating a synthetic hybrid promoter [U.S. Pat. No. 4,551,433]. For example, the tac promoter is a hybrid trp-lac promoter comprised of both trp promoter and lac operon sequences that is regulated by the lac repressor [Amann et al. (1983) *Gene* 25:167; de Boer et al. (1983) *Proc. Natl. Acad. Sci.* 80:21].

Furthermore, a bacterial promoter can include naturally occurring promoters of non-bacterial origin that have the ability to bind bacterial RNA polymerase and initiate transcription. A naturally occurring promoter of non-bacterial origin can also be coupled with a compatible RNA polymerase to produce high levels of expression of some genes in prokaryotes. The bacteriophage T7 RNA polymerase/promoter system is an example of a coupled promoter system [Studier et al. (1986) *J. Mol. Biol.* 189:113; Tabor et al. (1985) *Proc Natl. Acad. Sci.* 82:1074]. In addition, a hybrid promoter can also be comprised of a bacteriophage promoter and an *E. coli* operator region (EPO-A-0 267 851).

In addition to a functioning promoter sequence, an efficient ribosome binding site is also useful for the expression of foreign genes in prokaryotes. In *E. coli*, the ribosome binding site is called the Shine-Dalgarno (SD) sequence and includes an initiation codon (ATG) and a sequence 3-9 nucleotides in length located 3-11 nucleotides upstream of the initiation codon [Shine et al. (1975) *Nature* 254:34]. The SD sequence is thought to promote binding of mRNA to the ribosome by the pairing of bases between the SD sequence and the 3' and of *E. coli* 16S rRNA [Steitz et al. (1979) "Genetic signals and nucleotide sequences in messenger RNA." In *Biological Regulation and Development: Gene Expression* (ed. R. F. Goldberger)]. To express eukaryotic genes and prokaryotic genes with weak ribosome-binding site [Sambrook et al. (1989) "Expression of cloned genes in *Escherichia coli.*" In *Molecular Cloning: A Laboratory Manual*].

A DNA molecule may be expressed intracellularly. A promoter sequence may be directly linked with the DNA molecule, in which case the first amino acid at the N-terminus will always be a methionine, which is encoded by the ATG start codon. If desired, methionine at the N-terminus may be cleaved from the protein by in vitro incubation with cyanogen bromide or by either in vivo on in vitro incubation with a bacterial methionine N-terminal peptidase (EPO-A-0 219 237).

Fusion proteins provide an alternative to direct expression. Usually, a DNA sequence encoding the N-terminal portion of an endogenous bacterial protein, or other stable protein, is fused to the 5' end of heterologous coding sequences. Upon expression, this construct will provide a fusion of the two amino acid sequences. For example, the bacteriophage lambda cell gene can be linked at the 5' terminus of a foreign gene and expressed in bacteria. The resulting fusion protein preferably retains a site for a processing enzyme (factor Xa) to cleave the bacteriophage protein from the foreign gene [Nagai et al. (1984) *Nature* 309:810]. Fusion proteins can also be made with sequences from the lacZ [Jia et al. (1987) *Gene* 60:197], trpE [Allen et al. (1987) *J. Biotechnol.* 5:93; Makoff et al. (1989) *J. Gen. Microbiol.* 135: 11], and *Chey* [EP-A-0 324 647] genes. The DNA sequence at the junction of the two amino acid sequences may or may not encode a cleavable site. Another example is a ubiquitin fusion protein. Such a fusion protein is made with the ubiquitin region that preferably retains a site for a processing enzyme (e.g. ubiquitin specific processing-protease) to cleave the ubiquitin from the foreign protein. Through this method, native foreign protein can be isolated [Miller et al. (1989) *Bio/Technology* 7:698].

Alternatively, foreign proteins can also be secreted from the cell by creating chimeric DNA molecules that encode a fusion protein comprised of a signal peptide sequence fragment that provides for secretion of the foreign protein in bacteria [U.S. Pat. No. 4,336,336]. The signal sequence fragment usually encodes a signal peptide comprised of hydrophobic amino acids which direct the secretion of the protein from the cell. The protein is either secreted into the growth media (gram-positive bacteria) or into the periplasmic space, located between the inner and outer membrane of the cell (gram-negative bacteria). Preferably there are processing sites, which can be cleaved either in vivo or in vitro encoded between the signal peptide fragment and the foreign gene.

DNA encoding suitable signal sequences can be derived from genes for secreted bacterial proteins, such as the *E. coli* outer membrane protein gene (ompA) [Masui et al. (1983), in: *Experimental Manipulation of Gene Expression*; Ghrayeb et al. (1984) *EMBO J.* 3:2437] and the *E. coli* alkaline phosphatase signal sequence (phoA) [Oka et al. (1985) *Proc. Natl. Acad. Sci.* 82:7212]. As an additional example, the signal sequence of the alpha-amylase gene from various *Bacillus* strains can be used to secrete heterologous proteins from *B. subtilis* [Palva et al. (1982) *Proc. Natl. Acad. Sci. USA* 79:5582; EP-A-0 244 042].

Usually, transcription termination sequences recognized by bacteria are regulatory regions located 3' to the translation stop codon, and thus together with the promoter flank the coding sequence. These sequences direct the transcription of an mRNA which can be translated into the polypeptide encoded by the DNA. Transcription termination sequences frequently include DNA sequences of about 50 nucleotides capable of forming stem loop structures that aid in terminating transcription. Examples include transcription termination sequences derived from genes with strong promoters, such as the trp gene in *E. coli* as well as other biosynthetic genes.

Usually, the above described components, comprising a promoter, signal sequence (if desired), coding sequence of interest, and transcription termination sequence, are put together into expression constructs. Expression constructs are often maintained in a replicon, such as an extrachromosomal element (e.g. plasmids) capable of stable maintenance in a host, such as bacteria. The replicon will have a replication system, thus allowing it to be maintained in a prokaryotic host either for expression or for cloning and amplification. In addition, a replicon may be either a high or low copy number plasmid. A high copy number plasmid will generally have a copy number ranging from about 5 to about 200, and usually about 10 to about 150. A host containing a high copy number plasmid will preferably contain at least about 10, and more preferably at least about 20 plasmids. Either a high or low copy number vector may be selected, depending upon the effect of the vector and the foreign protein on the host.

Alternatively, the expression constructs can be integrated into the bacterial genome with an integrating vector. Integrating vectors usually contain at least one sequence homologous to the bacterial chromosome that allows the vector to integrate. Integrations appear to result from recombinations between homologous DNA in the vector and the bacterial chromosome. For example, integrating vectors constructed with DNA from various *Bacillus* strains integrate into the *Bacillus* chromosome (EP-A-0 127 328). Integrating vectors may also be comprised of bacteriophage or transposon sequences.

Usually, extrachromosomal and integrating expression constructs may contain selectable markers to allow for the selection of bacterial strains that have been transformed. Selectable markers can be expressed in the bacterial host and may include genes which render bacteria resistant to drugs such as ampicillin, chloramphenicol, erythromycin, kanamycin (neomycin), and tetracycline [Davies et al. (1978) *Annu. Rev. Microbiol.* 32:469]. Selectable markers may also include biosynthetic genes, such as those in the histidine, tryptophan, and leucine biosynthetic pathways.

Alternatively, some of the above described components can be put together in transformation vectors. Transformation vectors are usually comprised of a selectable market that is either maintained in a replicon or developed into an integrating vector, as described above.

Expression and transformation vectors, either extra-chromosomal replicons or integrating vectors, have been developed for transformation into many bacteria. For example, expression vectors have been developed for, inter alia, the following bacteria: *Bacillus subtilis* [Palva et al. (1982) *Proc. Natl. Acad. Sci. USA* 79:5582; EP-A-0 036 259 and EP-A-0 063 953; WO 84/04541], *Escherichia coli* [Shimatake et al. (1981) *Nature* 292:128; Amann et al. (1985) *Gene* 40:183; Studier et al. (1986) *J. Mol. Biol.* 189:113; EP-A-0 036 776, EP-A-0 136 829 and EP-A-0 136 907], *Streptococcus cremoris* [Powell et al. (1988) *Appl. Environ. Microbiol.* 54:655]; *Streptococcus lividans* [Powell et al. (1988) *Appl. Environ. Microbiol.* 54:655], *Streptomyces lividans* [U.S. Pat. No. 4,745,056].

Methods of introducing exogenous DNA into bacterial hosts are well-known in the art, and usually include either the transformation of bacteria treated with $CaCl_2$ or other agents, such as divalent cations and DMSO. DNA can also be introduced into bacterial cells by electroporation. Transformation procedures usually vary with the bacterial species to be transformed. See e.g. [Masson et al. (1989) *FEMS Microbiol. Lett.* 60:273; Palva et al. (1982) *Proc. Natl. Acad. Sci. USA* 79:5582; EP-A-0 036 259 and EP-A-0 063 953; WO 84/04541, *Bacillus*], [Miller et al. (1988) *Proc. Natl. Acad. Sci.* 85:856; Wang et al. (1990) *J. Bacteriol.* 172:949, *Campylobacter*], [Cohen et al. (1973) *Proc. Natl. Acad. Sci.* 69:2110; Dower et al. (1988) *Nucleic Acids Res.* 16:6127; Kushner (1978) "An improved method for transformation of *Escherichia coli* with ColE1-derived plasmids. In *Genetic Engineering: Proceedings of theInternational Symposium on Genetic Engineering* (eds. H. W. Boyer and S, Nicosia); Mandel et al. (1970) *J. Mol. Biol.* 53:159; Taketo (1988) *Biochim. Biophys. Acta* 949:318; *Escherichia*], [Chassy et al. (1987) *FEMS Microbiol. Lett.* 44:173 *Lactobacillus*]; [Fiedler et al. (1988) *Anal. Biochem* 170:38, *Pseudomonas*]; [Augustin et al. (1990) *FEMS Microbiol. Lett.* 66:203, *Staphylococcus*], [Barany et al. (1980) *J. Bacteriol.* 144:698; Harlander (1987) "Transformation of *Streptococcus* lactis by electroporation, in: *Streptococcal Genetics* (ed. J. Ferretti and R. Curtiss III); Perry et al. (1981) *Infect. Immun.* 32:1295; Powell et al. (1988) *Appl. Environ. Microbiol.* 54:655; Somkuti et al. (1987) *Proc. 4th Evr. Cong. Biotechnology* 1:412, *Streptococcus*].

v. Yeast Expression

Yeast expression systems are also known to one of ordinary skill in the art. A yeast promoter is any DNA sequence capable of binding yeast RNA polymerase and initiating the downstream (3') transcription of a coding sequence (e.g. structural gene) into mRNA. A promoter will have a transcription initiation region which is usually placed proximal to the 5' end of the coding sequence. This transcription initiation region usually includes an RNA polymerase binding site (the "TATA Box") and a transcription initiation site. A yeast promoter may also have a second domain called an upstream activator sequence (UAS), which, if present, is usually distal to the structural gene. The UAS permits regulated (inducible) expression. Constitutive expression occurs in the absence of a UAS. Regulated expression may be either positive or negative, thereby either enhancing or reducing transcription.

Yeast is a fermenting organism with an active metabolic pathway, therefore sequences encoding enzymes in the metabolic pathway provide particularly useful promoter sequences. Examples include alcohol dehydrogenase (ADH) (EP-A-0 284 044), enolase, glucokinase, glucose-6-phosphate isomerase, glyceraldehyde-3-phosphate-dehydrogenase (GAP or GAPDH), hexokinase, phosphofructokinase, 3-phosphoglycerate mutase, and pyruvate kinase (PyK) (EPO-A-0 329 203). The yeast PHO5 gene, encoding acid phosphatase, also provides useful promoter sequences [Myanohara et al. (1983) Proc. Natl. Acad. Sci. USA 80:1].

In addition, synthetic promoters which do not occur in nature also function as yeast promoters. For example, UAS sequences of one yeast promoter may be joined with the transcription activation region of another yeast promoter, creating a synthetic hybrid promoter. Examples of such hybrid promoters include the ADH regulatory sequence linked to the GAP transcription activation region (U.S. Pat. Nos. 4,876, 197 and 4,880,734). Other examples of hybrid promoters include promoters which consist of the regulatory sequences of either the ADH2, GAL4, GAL10, OR PHO5 genes, combined with the transcriptional activation region of a glycolytic enzyme gene such as GAP or PyK (EP-A-0 164 556). Furthermore, a yeast promoter can include naturally occurring promoters of non-yeast origin that have the ability to bind yeast RNA polymerase and initiate transcription. Examples of such promoters include, inter alia, [Cohen et al. (1980) Proc. Natl. Acad. Sci. USA 77:1078; Henikoff et al. (1981) Nature 283:835; Hollenberg et al. (1981) Curr. Topics Microbiol. Immunol. 96:119; Hollenberg et al. (1979) "The Expression of Bacterial Antibiotic Resistance Genes in the Yeast Saccharomyces cerevisiae," in: Plasmids of Medical, Environmental and Commercial Importance (eds. K. N. Timmis and A. Puhler); Mercerau-Puigalon et al. (1980) Gene 11:163; Panthier et al. (1980) Curr. Genet. 2:109;].

A DNA molecule may be expressed intracellularly in yeast. A promoter sequence may be directly linked with the DNA molecule, in which case the first amino acid at the N-terminus of the recombinant protein will always be a methionine, which is encoded by the ATG start codon. If desired, methionine at the N-terminus may be cleaved from the protein by in vitro incubation with cyanogen bromide.

Fusion proteins provide an alternative for yeast expression systems, as well as in mammalian, baculovirus, and bacterial expression systems. Usually, a DNA sequence encoding the N-terminal portion of an endogenous yeast protein, or other stable protein, is fused to the 5' end of heterologous coding sequences. Upon expression, this construct will provide a fusion of the two amino acid sequences. For example, the yeast or human superoxide dismutase (SOD) gene, can be linked at the 5' terminus of a foreign gene and expressed in yeast. The DNA sequence at the junction of the two amino acid sequences may or may not encode a cleavable site. See eg. EP-A-0 196 056. Another example is a ubiquitin fusion protein. Such a fusion protein is made with the ubiquitin region that preferably retains a site for a processing enzyme (e.g. ubiquitin-specific processing protease) to cleave the ubiquitin from the foreign protein. Through this method, therefore, native foreign protein can be isolated (e.g. WO88/024066).

Alternatively, foreign proteins can also be secreted from the cell into the growth media by creating chimeric DNA molecules that encode a fusion protein comprised of a leader sequence fragment that provide for secretion in yeast of the foreign protein. Preferably, there are processing sites encoded between the leader fragment and the foreign gene that can be cleaved either in vivo or in vitro. The leader sequence fragment usually encodes a signal peptide comprised of hydrophobic amino acids which direct the secretion of the protein from the cell.

DNA encoding suitable signal sequences can be derived from genes for secreted yeast proteins, such as the yeast invertase gene (EP-A-0 012 873; JPO. 62,096,086) and the A-factor gene (U.S. Pat. No. 4,588,684). Alternatively, leaders of non-yeast origin, such as an interferon leader, exist that also provide for secretion in yeast (EP-A-0 060 057).

A preferred class of secretion leaders are those that employ a fragment of the yeast alpha-factor gene, which contains both a "pre" signal sequence, and a "pro" region. The types of alpha-factor fragments that can be employed include the full-length pre-pro alpha factor leader (about 83 amino acid residues) as well as truncated alpha-factor leaders (usually about 25 to about 50 amino acid residues) (U.S. Pat. Nos. 4,546,083 and 4,870,008; EP-A-0 324 274). Additional leaders employing an alpha-factor leader fragment that provides for secretion include hybrid alpha-factor leaders made with a presequence of a first yeast, but a pro-region from a second yeast alphafactor. (e.g. see WO 89/02463.)

Usually, transcription termination sequences recognized by yeast are regulatory regions located 3' to the translation stop codon, and thus together with the promoter flank the coding sequence. These sequences direct the transcription of an mRNA which can be translated into the polypeptide encoded by the DNA. Examples of transcription terminator sequence and other yeast-recognized termination sequences, such as those coding for glycolytic enzymes.

Usually, the above described components, comprising a promoter, leader (if desired), coding sequence of interest, and transcription termination sequence, are put together into expression constructs. Expression constructs are often maintained in a replicon, such as an extrachromosomal element (e.g. plasmids) capable of stable maintenance in a host, such as yeast or bacteria. The replicon may have two replication systems, thus allowing it to be maintained, for example, in yeast for expression and in a prokaryotic host for cloning and amplification. Examples of such yeast-bacteria shuttle vectors include YEp24 [Botstein et al. (1979) Gene 8:17-24], pCl/1 [Brake et al. (1984) Proc. Natl. Acad. Sci. USA 81:4642-4646], and YRp17 [Stinchcomb et al. (1982) J. Mol. Biol. 158:157]. In addition, a replicon may be either a high or low copy number plasmid. A high copy number plasmid will generally have a copy number ranging from about 5 to about 200, and usually about 10 to about 150. A host containing a high copy number plasmid will preferably have at least about 10, and more preferably at least about 20. Enter a high or low copy number vector may be selected, depending upon the effect of the vector and the foreign protein on the host. See e.g. Brake et al., supra.

Alternatively, the expression constructs can be integrated into the yeast genome with an integrating vector. Integrating vectors usually contain at least one sequence homologous to a yeast chromosome that allows the vector to integrate, and preferably contain two homologous sequences flanking the expression construct. Integrations appear to result from recombinations between homologous DNA in the vector and the yeast chromosome [Orr-Weaver et al. (1983) *Methods in Enzymol.* 101:228-245]. An integrating vector may be directed to a specific locus in yeast by selecting the appropriate homologous sequence for inclusion in the vector. See Orr-Weaver et al., supra. One or more expression construct may integrate, possibly affecting levels of recombinant protein produced [Rine et al. (1983) *Proc. Natl. Acad. Sci. USA* 80:6750]. The chromosomal sequences included in the vector can occur either as a single segment in the vector, which results in the integration of the entire vector, or two segments homologous to adjacent segments in the chromosome and flanking the expression construct in the vector, which can result in the stable integration of only the expression construct.

Usually, extrachromosomal and integrating expression constructs may contain selectable markers to allow for the selection of yeast strains that have been transformed. Selectable markers may include biosynthetic genes that can be expressed in the yeast host, such as ADE2, HIS4, LEU2, TRP1, and ALG7, and the G418 resistance gene, which confer resistance in yeast cells to tunicamycin and G418, respectively. In addition, a suitable selectable marker may also provide yeast with the ability to grow in the presence of toxic compounds, such as metal. For example, the presence of CUP1 allows yeast to grow in the presence of copper ions [Butt et al. (1987) *Microbiol, Rev.* 51:351].

Alternatively, some of the above described components can be put together into transformation vectors. Transformation vectors are usually comprised of a selectable marker that is either maintained in a replicon or developed into an integrating vector, as described above.

Expression and transformation vectors, either extrachromosomal replicons or integrating vectors, have been developed for transformation into many yeasts. For example, expression vectors have been developed for, inter alia, the following yeasts: *Candida albicans* [Kurtz, et al. (1986) *Mol. Cell. Biol.* 6:142], *Candida maltosa* [Kunze, et al. (1985) *J. Basic Microbiol.* 25:141]. *Hansenula polymorpha* [Gleeson, et al. (1986) *J. Gen. Microbiol.* 132:3459; Roggenkamp et al. (1986) *Mol. Gen. Genet.* 202:302], *Kluyveromyces fragilis* [Das, et al. (1984) *J. Bacteriol.* 158:1165], *Kluyveromyces lactis* [De Louvencourt et al. (1983) *J. Bacteriol.* 154:737; Van den Berg et al. (1990) *Bio/Technology* 8:135], *Pichia guillerimondii* [Kunze, et al. (1985) *J. Basic Microbiol.* 25:141], *Pichia pastoris* [Cregg, et al. (1985) *Mol. Cell. Biol.* 5:3376; U.S. Pat. Nos. 4,837,148 and 4,929,555], *Saccharomyces cerevisiae* [Hinnen et al. (1978) *Proc. Natl. Acad. Sci. USA* 75:1929; Ito et al. (1983) *J. Bacteriol.* 153:163], *Schizosaccharomyces pombe* [Beach and Nurse (1981) *Nature* 300:706], and *Yarrowia lipolytica* [Davidow, et al. (1985) *Curr. Genet.* 10:380471 Gaillardin, et al. (1985) *Curr. Genet.* 10:49].

Methods of introducing exogenous DNA into yeast hosts are well-known in the art, and usually include either the transformation of spheroplasts or of intact yeast cells treated with alkali cations. Transformation procedures usually vary with the yeast species to be transformed. See eg. [Kurtz et al. (1986) *Mol. Cell. Biol.* 6:142; Kunze et al. (1985) *J. Basic Microbiol.* 25:141; *Candida*]; [Gleeson et al. (1986) *J. Gen. Microbiol.* 132:3459; Roggenkamp et al. (1986) *Mol. Gen. Genet.* 202:302; *Hansenula*]; [Das et al. (1984) *J. Bacteriol.* 158:1165; De Louvencourt et al. (1983) *J. Bacteriol.* 154: 1165; Van den Berg et al. (1990) *Bio/Technology* 8:135; *Kluyveromyces*]; [Cregg et al. (1985) *Mol. Cell. Biol.* 5:3376; Kunze et al. (1985) *J. Basic Microbiol.* 25:141; U.S. Pat. Nos. 4,837,148 and 4,929,555; *Pichia*]; [Hinnen et al. (1978) *Proc. Natl. Acad. Sci. USA* 75; 1929; Ito et al. (1983) *J. Bacteriol.* 153:163 *Saccharomyces*]; [Beach and Nurse (1981) *Nature* 300:706; *Schizosaccharomyces*]; [Davidow et al. (1985) *Curr. Genet.* 10:39; Gaillardin et al. (1985) *Curr. Genet.* 10:49; *Yarrowia*].

Antibodies

As used herein, the term "antibody" refers to a polypeptide or group of polypeptides composed of at least one antibody combining site. An "antibody combining site" is the three-dimensional binding space with an internal surface shape and charge distribution complementary to the features of an epitope of an antigen, which allows a binding of the antibody with the antigen. "Antibody" includes, for example, vertebrate antibodies, hybrid antibodies, chimeric antibodies, humanised antibodies, altered antibodies, univalent antibodies, Fab proteins, and single domain antibodies.

Antibodies against the proteins of the invention are useful for affinity chromatography, immunoassays, and distinguishing/identifying Neisserial proteins.

Antibodies to the proteins of the invention, both polyclonal and monoclonal, may be prepared by conventional methods. In general, the protein is first used to immunize a suitable animal, preferably a mouse, rat, rabbit or goat. Rabbits and goats are preferred for the preparation of polyclonal sera due to the volume of serum obtainable, and the availability of labeled anti-rabbit and anti-goat antibodies. Immunization is generally performed by mixing or emulsifying the protein in saline, preferably in an adjuvant such as Freund's complete adjuvant, and injecting the mixture or emulsion parenterally (generally subcutaneously or intramuscularly). A dose of 50-200 µg/injection is typically sufficient. Immunization is generally boosted 2-6 weeks later with one or more injections of the protein in saline, preferably using Freund's incomplete adjuvant. One may alternatively generate antibodies by in vitro immunization using methods known in the art, which for the purposes of this invention is considered equivalent to in vivo immunization. Polyclonal antisera is obtained by bleeding the immunized animal into a glass or plastic container, incubating the blood at 25° C. for one hour, followed by incubating at 4° C. for 2-18 hours. The serum is recovered by centrifugation (e.g. 1,000 g for 10 minutes). About 20-50 ml per bleed may be obtained from rabbits.

Monoclonal antibodies are prepared using the standard method of Kohler & Milstein [*Nature* (1975) 256:495-96], or a modification thereof. Typically, a mouse or rat is immunized as described above. However, rather than bleeding the animal to extract serum, the spleen (and optionally several large lymph nodes) is removed and dissociated into single cells. If desired, the spleen cells may be screened (after removal of nonspecifically adherent cells) by applying a cell suspension to a plate or well coated with the protein antigen. B-cells expressing membrane-bound immunoglobulin specific for the antigen bind to the plate, and are not rinsed away with the rest of the suspension. Resulting B-cells, or all dissociated spleen cells, are then induced to fuse with myeloma cells to form hybridomas, and are cultured in a selective medium (e.g. hypoxanthine, aminopterin, thymidine medium, "HAT"). The resulting hybridomas are plated by limiting dilution, and are assayed for the production of antibodies which bind specifically to the immunizing antigen (and which do not bind to unrelated antigens). The selected MAb-secreting hybridomas are then cultured either in vitro (e.g. in tissue culture bottles or hollow fiber reactors), or in vivo (as ascites in mice).

If desired, the antibodies (whether polyclonal or monoclonal) may be labeled using conventional techniques. Suitable labels include fluorophores, chromophores, radioactive atoms (particularly $^{32}P$ and $^{125}I$), electron-dense reagents, enzymes, and ligands having specific binding partners. Enzymes are typically detected by their activity. For example, horseradish peroxidase is usually detected by its ability to convert 3,3',5,5'-tetramethylbenzidine (TMB) to a blue pigment, quantifiable with a spectrophotometer. "Specific binding partner" refers to a protein capable of binding a ligand molecule with high specificity, as for example in the case of an antigen and a monoclonal antibody specific therefor. Other specific binding partners include biotin and avidin or streptavidin, IgG and protein A, and the numerous receptor-ligand couples known in the art. It should be understood that the above description is not meant to categorize the various labels into distinct classes, as the same label may serve in several different modes. For example, $^{125}$I may serve as a radioactive label or as an electron-dense reagent. HRP may serve as enzyme or as antigen for a MAb. Further, one may combine various labels for desired effect. For example, MAbs and avidin also require labels in the practice of this invention: thus, one might label a MAb with biotin, and detect its presence with avidin labeled with $^{125}$I, or with an anti-biotin MAb labeled with HRP. Other permutations and possibilities will be readily apparent to those of ordinary skill in the art, and are considered as equivalents within the scope of the instant invention.

Pharmaceutical Compositions

Pharmaceutical compositions can comprise either polypeptides, antibodies, or nucleic acid of the invention. The pharmaceutical compositions will comprise a therapeutically effective amount of either polypeptides, antibodies, or polynucleotides of the claimed invention.

The term "therapeutically effective amount" as used herein refers to an amount of a therapeutic agent to treat, ameliorate, or prevent a desired disease or condition, or to exhibit a detectable therapeutic or preventative effect. The effect can be detected by, for example, chemical markers or antigen levels. Therapeutic effects also include reduction in physical symptoms, such as decreased body temperature. The precise effective amount for a subject will depend upon the subject's size and health, the nature and extent of the condition, and the therapeutics or combination of therapeutics selected for administration. Thus, it is not useful to specify an exact effective amount in advance. However, the effective amount for a given situation can be determined by routine experimentation and is within the judgement of the clinician.

For purposes of the present invention, an effective dose will be from about 0.01 mg/kg to 50 mg/kg or 0.05 mg/kg to about 10 mg/kg of the DNA constructs in the individual to which it is administered.

A pharmaceutical composition can also contain a pharmaceutically acceptable carrier. The term "pharmaceutically acceptable carrier" refers to a carrier for administration of a therapeutic agent, such as antibodies or a polypeptide, genes, and other therapeutic agents. The term refers to any pharmaceutical carrier that does not itself induce the production of antibodies harmful to the individual receiving the composition, and which may be administered without undue toxicity. Suitable carriers may be large, slowly metabolized macromolecules such as proteins, polysaccharides, polylactic acids, polyglycolic acids, polymeric amino acids, amino acid copolymers, and inactive virus particles. Such carriers are well known to those of ordinary skill in the art.

Pharmaceutically acceptable salts can be used therein, for example, mineral acid salts such as hydrochlorides, hydrobromides, phosphates, sulfates, and the like; and the salts of organic acids such as acetates, propionates, malonates, benzoates, and the like. A thorough discussion of pharmaceutically acceptable excipients is available in Remington's Pharmaceutical Sciences (Mack Pub. Co., N.J. 1991).

Pharmaceutically acceptable carriers in therapeutic compositions may contain liquids such as water, saline, glycerol and ethanol. Additionally, auxiliary substances, such as wetting or emulsifying agents, pH buffering substances, and the like, may be present in such vehicles. Typically, the therapeutic compositions are prepared as injectables, either as liquid solutions or suspensions; solid forms suitable for solution in, or suspension in, liquid vehicles prior to injection may also be prepared. Liposomes are included within the definition of a pharmaceutically acceptable carrier.

Delivery Methods

Once formulated, the compositions of the invention can be administered directly to the subject. The subjects to be treated can be animals; in particular, human subjects can be treated.

Direct delivery of the compositions will generally be accomplished by injection, either subcutaneously, intraperitoneally, intravenously or intramuscularly or delivered to the interstitial space of a tissue. The compositions can also be administered into a lesion. Other modes of administration include oral and pulmonary administration, suppositories, and transdermal or transcutaneous applications (e.g. see WO98/20734), needles, and gene guns or hyposprays. Dosage treatment may be a single dose schedule or a multiple dose schedule.

Vaccines

Vaccines according to the invention may either be prophylactic (i.e. to prevent infection) or therapeutic (i.e. to treat disease after infection).

Such vaccines comprise immunising antigen(s), immunogen(s), polypeptide(s), protein(s) or nucleic acid, usually in combination with "pharmaceutically acceptable carriers," which include any carrier that does not itself induce the production of antibodies harmful to the individual receiving the composition. Suitable carriers are typically large, slowly metabolized macromolecules such as proteins, polysaccharides, polylactic acids, polyglycolic acids, polymeric amino acids, amino acid copolymers, lipid aggregates (such as oil droplets or liposomes), and inactive virus particles. Such carriers are well known to those of ordinary skill in the art. Additionally, these carriers may function as immunostimulating agents ("adjuvants"). Furthermore, the antigen or immunogen may be conjugated to a bacterial toxoid, such as a toxoid from diphtheria, tetanus, cholera, *H. pylori*, etc. pathogens.

Preferred adjuvants to enhance effectiveness of the composition include, but are not limited to: (1) aluminum salts (alum), such as aluminum hydroxide, aluminum phosphate, aluminum sulfate, etc; (2) oil-in-water emulsion formulations (with or without other specific immunostimulating agents such as muramyl peptides (see below) or bacterial cell wall components), such as for example (a) MF59™ (WO 90/14837; Chapter 10 in *Vaccine design: the subunit and adjuvant approach*, eds. Powell & Newman, Plenum Press 1995), containing 5% Squalene, 0.5% Tween 80, and 0.5% Span 85 (optionally containing various amounts of MTP-PE (see below), although not required) formulated into submicron particles using a microfluidizer such as Model 110Y microfluidizer (Microfluidics, Newton, Mass.), (b) SAF, containing 10% Squalane, 0.4% Tween 80, 5% pluronic-blocked polymer L 121, and thr-MDP (see below) either microfluidized into a submicron emulsion or vortexed to generate a larger particle size emulsion, and (c) Ribi™ adjuvant system (RAS), (Ribi Immunochem, Hamilton, Mont.) containing 2% Squalene, 0.2% Tween 80, and one or more bacterial cell wall components from the group consisting of monophosphorylipid A (MPL), trehalose dimycolate (TDM), and cell wall skeleton (CWS), preferably MPL+CWS (Detox™); (3) saponin adjuvants, such as Stimulon™ (Cambridge Bioscience, Worcester, Mass.) may be used or particles generated therefrom such as ISCOMs (immunostimulating complexes); (4) Complete Freund's Adjuvant (CFA) and Incomplete Freund's Adjuvant (IFA); (5) cytokines, such as interleukins (e.g. IL-1, IL-2, IL-4, IL-5, IL-6, IL-7, IL-12, etc.), interferons (e.g. gamma interferon), macrophage colony stimulating factor (M-CSF), tumor necrosis factor (TNF), etc; and (6) other substances that act as immunostimulating agents to enhance the effectiveness of the composition. Alum and MF59™ are preferred.

As mentioned above, muramyl peptides include, but are not limited to, N-acetyl-muramyl-L-threonyl-D-isoglutamine (thr-MDP), N-acetyl-normuramyl-L-alanyl-D-isoglutamine (nor-MDP), N-acetylmuramyl-L-alanyl-D-isoglutaminyl-L-alanine-2-(1'-2'-dipalmitoyl-sn-glycero-3-hydroxyphosphoryloxy)-ethylamine (MTP-PE), etc.

The immunogenic compositions (e.g. the immunising antigen/immunogen/polypeptide/protein/nucleic acid, pharmaceutically acceptable carrier, and adjuvant) typically will contain diluents, such as water, saline, glycerol, ethanol, etc. Additionally, auxiliary substances, such as wetting or emulsifying agents, pH buffering substances, and the like, may be present in such vehicles.

Typically, the immunogenic compositions are prepared as injectables, either as liquid solutions or suspensions; solid forms suitable for solution in, or suspension in, liquid vehicles prior to injection may also be prepared. The preparation also may be emulsified or encapsulated in liposomes for enhanced adjuvant effect, as discussed above under pharmaceutically acceptable carriers.

Immunogenic compositions used as vaccines comprise an immunologically effective amount of the antigenic or immunogenic polypeptides, as well as any other of the above-mentioned components, as needed. By "immunologically effective amount", it is meant that the administration of that amount to an individual, either in a single dose or as part of a series, is effective for treatment or prevention. This amount varies depending upon the health and physical condition of the individual to be treated, the taxonomic group of individual to be treated (e.g. nonhuman primate, primate, etc.), the capacity of the individual's immune system to synthesize antibodies, the degree of protection desired, the formulation of the vaccine, the treating doctor's assessment of the medical situation, and other relevant factors. It is expected that the amount will fall in a relatively broad range that can be determined through routine trials.

The immunogenic compositions are conventionally administered parenterally, e.g. by injection, either subcutaneously, intramuscularly, or transdermally/transcutaneously (e.g. WO98/20734). Additional formulations suitable for other modes of administration include oral and pulmonary formulations, suppositories, and transdermal applications. Dosage treatment may be a single dose schedule or a multiple dose schedule. The vaccine may be administered in conjunction with other immunoregulatory agents.

As an alternative to protein-based vaccines, DNA vaccination may be employed [e.g. Robinson & Torres (1997) Seminars in Immunology 9:271-283; Donnelly et al. (1997) Annu Rev Immunol 15:617-648; see later herein].

Gene Delivery Vehicles

Gene therapy vehicles for delivery of constructs including a coding sequence of a therapeutic of the invention, to be delivered to the mammal for expression in the mammal, can be administered either locally or systemically. These constructs can utilize viral or non-viral vector approaches in in vivo or ex vivo modality. Expression of such coding sequence can be induced using endogenous mammalian or heterologous promoters. Expression of the coding sequence in vivo can be either constitutive or regulated.

The invention includes gene delivery vehicles capable of expressing the contemplated nucleic acid sequences. The gene delivery vehicle is preferably a viral vector and, more preferably, a retroviral, adenoviral, adeno-associated viral (AAV), herpes viral, or alphavirus vector. The viral vector can also be an astrovirus, coronavirus, orthomyxovirus, papovavirus, paramyxovirus, parvovirus, picornavirus, poxvirus, or togavirus viral vector. See generally, Jolly (1994) Cancer Gene Therapy 1:51-64; Kimura (1994) Human Gene Therapy 5:845-852; Connelly (1995) Human Gene Therapy 6:185-193; and Kaplitt (1994) Nature Genetics 6:148-153.

Retroviral vectors are well known in the art and we contemplate that any retroviral gene therapy vector is employable in the invention, including B, C and D type retroviruses, xenotropic retroviruses (for example, NZB-X1, NZB-X2 and NZB9-1 (see O'Neill (1985) J. Virol. 53:160) polytropic retroviruses e.g. MCF and MCF-M LV (see Kelly (1983) J. Virol. 45:291), spumaviruses and lentiviruses. See RNA Tumor Viruses, Second Edition, Cold Spring Harbor Laboratory, 1985.

Portions of the retroviral gene therapy vector may be derived from different retroviruses. For example, retrovector LTRs may be derived from a Murine Sarcoma Virus, a tRNA binding site from a Rous Sarcoma Virus, a packaging signal from a Murine Leukemia Virus, and an origin of second strand synthesis from an Avian Leukosis Virus.

These recombinant retroviral vectors may be used to generate transduction competent retroviral vector particles by introducing them into appropriate packaging cell lines (see U.S. Pat. No. 5,591,624). Retrovirus vectors can be constructed for site-specific integration into host cell DNA by incorporation of a chimeric integrase enzyme into the retroviral particle (see WO96/37626). It is preferable that the recombinant viral vector is a replication defective recombinant virus.

Packaging cell lines suitable for use with the above-described retrovirus vectors are well known in the art, are readily prepared (see WO95/30763 and WO92/05266), and can be used to create producer cell lines (also termed vector cell lines or "VCLs") for the production of recombinant vector particles. Preferably, the packaging cell lines are made from human parent cells (e.g. HT1080 cells) or mink parent cell lines, which eliminates inactivation in human serum.

Preferred retroviruses for the construction of retroviral gene therapy vectors include Avian Leukosis Virus, Bovine Leukemia, Virus, Murine Leukemia Virus, Mink-Cell Focus-Inducing Virus, Murine Sarcoma Virus, Reticuloendotheliosis Virus and Rous Sarcoma Virus. Particularly preferred Murine Leukemia Viruses include 4070A and 1504A (Hartley and Rowe (1976) J Virol 19:19-25), Abelson (ATCC No. VR-999), Friend (ATCC No. VR-245), Graffi, Gross (ATCC Nol VR-590), Kirsten, Harvey Sarcoma Virus and Rauscher (ATCC No. VR-998) and Moloney Murine Leukemia Virus (ATCC No. VR-190). Such retroviruses may be obtained from depositories or collections such as the American Type Culture Collection ("ATCC") in Rockville, Md. or isolated from known sources using commonly available techniques.

Exemplary known retroviral gene therapy vectors employable in this invention include those described in patent applications GB2200651, EP0415731, EP0345242, EP0334301, WO89/02468; WO89/05349, WO89/09271, WO90/02806, WO90/07936, WO94/03622, WO93/25698, WO93/25234, WO93/11230, WO93/10218, WO91/02805, WO91/02825, WO95/07994, U.S. Pat. No. 5,219,740, U.S. Pat. No. 4,405,712, U.S. Pat. No. 4,861,719, U.S. Pat. No. 4,980,289, U.S. Pat. No. 4,777,127, U.S. Pat. No. 5,591,624. See also Vile (1993) *Cancer Res* 53:3860-3864; Vile (1993) *Cancer Res* 53:962-967; Ram (1993) *Cancer Res* 53 (1993) 83-88; Takamiya (1992) *J Neurosci Res* 33:493-503; Baba (1993) *J Neurosurg* 79:729-735; Mann (1983) *Cell* 33:153; Cane (1984) *Proc Natl Acad Sci* 81:6349; and Miller (1990) *Human Gene Therapy* 1.

Human adenoviral gene therapy vectors are also known in the art and employable in this invention. See, for example, Berkner (1988) *Biotechniques* 6:616 and Rosenfeld (1991) *Science* 252:431, and WO93/07283, WO93/06223, and WO93/07282. Exemplary known adenoviral gene therapy vectors employable in this invention include those described in the above referenced documents and in WO94/12649, WO93/03769, WO93/19191, WO94/28938, WO95/11984, WO95/00655, WO95/27071, WO95/29993, WO95/34671, WO96/05320, WO94/08026, WO94/11506, WO93/06223, WO94/24299, WO95/14102, WO95/24297, WO95/02697, WO94/28152, WO94/24299, WO95/09241, WO95/25807, WO95/05835, WO94/18922 and WO95/09654. Alternatively, administration of DNA linked to killed adenovirus as described in Curiel (1992) *Hum. Gene Ther.* 3:147-154 may be employed. The gene delivery vehicles of the invention also include adenovirus associated virus (AAV) vectors. Leading and preferred examples of such vectors for use in this invention are the AAV-2 based vectors disclosed in Srivastava, WO93/09239. Most preferred AAV vectors comprise the two AAV inverted terminal repeats in which the native D-sequences are modified by substitution of nucleotides, such that at least 5 native nucleotides and up to 18 native nucleotides, preferably at least 10 native nucleotides up to 18 native nucleotides, most preferably 10 native nucleotides are retained and the remaining nucleotides of the D-sequence are deleted or replaced with non-native nucleotides. The native D-sequences of the AAV inverted terminal repeats are sequences of 20 consecutive nucleotides in each AAV inverted terminal repeat (i.e. there is one sequence at each end) which are not involved in HP formation. The non-native replacement nucleotide may be any nucleotide other than the nucleotide found in the native D-sequence in the same position. Other employable exemplary AAV vectors are pWP-19, pWN-1, both of which are disclosed in Nahreini (1993) *Gene* 124:257-262. Another example of such an AAV vector is psub201 (see Samulski (1987) *J. Virol.* 61:3096). Another exemplary AAV vector is the Double-D ITR vector. Construction of the Double-D ITR vector is disclosed in U.S. Pat. No. 5,478,745. Still other vectors are those disclosed in Carter U.S. Pat. No. 4,797,368 and Muzyczka U.S. Pat. No. 5,139,941, Chartejee U.S. Pat. No. 5,474,935, and Kotin WO94/288157. Yet a further example of an AAV vector employable in this invention is SSV9AFABTKneo, which contains the AFP enhancer and albumin promoter and directs expression predominantly in the liver. Its structure and construction are disclosed in Su (1996) *Human Gene Therapy* 7:463-470. Additional AAV gene therapy vectors are described in U.S. Pat. No. 5,354,678, U.S. Pat. No. 5,173,414, U.S. Pat. No. 5,139,941, and U.S. Pat. No. 5,252,479.

The gene therapy vectors of the invention also include herpes vectors. Leading and preferred examples are herpes simplex virus vectors containing a sequence encoding a thymidine kinase polypeptide such as those disclosed in U.S. Pat. No. 5,288,641 and EP0176170 (Roizman). Additional exemplary herpes simplex virus vectors include HFEM/ICP6-LacZ disclosed in WO95/04139 (Wistar Institute), pHSVlac described in Geller (1988) *Science* 241:1667-1669 and in WO90/09441 and WO92/07945, HSV Us3::pgC-lacZ described in Fink (1992) *Human Gene Therapy* 3:11-19 and HSV 7134, 2 RH 105 and GAL4 described in EP 0453242 (Breakefield), and those deposited with the ATCC as accession numbers ATCC VR-977 and ATCC VR-260.

Also contemplated are alpha virus gene therapy vectors that can be employed in this invention. Preferred alpha virus vectors are Sindbis viruses vectors. Togaviruses, Semliki Forest virus (ATCC VR-67; ATCC VR-1247), Middleberg virus (ATCC VR-370), Ross River virus (ATCC VR-373; ATCC VR-1246), Venezuelan equine encephalitis virus (ATCC VR923; ATCC VR-1250; ATCC VR-1249; ATCC VR-532), and those described in U.S. Pat. Nos. 5,091,309, 5, 217,879, and WO92/10578. More particularly, those alpha virus vectors described in U.S. Ser. No. 08/405,627, filed Mar. 15, 1995, WO94/21792, WO92/10578, WO95/07994, U.S. Pat. No. 5,091,309 and U.S. Pat. No. 5,217,879 are employable. Such alpha viruses may be obtained from depositories or collections such as the ATCC in Rockville, Md. or isolated from known sources using commonly available techniques. Preferably, alphavirus vectors with reduced cytotoxicity are used (see U.S. Ser. No. 08/679,640).

DNA vector systems such as eukarytic layered expression systems are also useful for expressing the nucleic acids of the invention. See WO95/07994 for a detailed description of eukaryotic layered expression systems. Preferably, the eukaryotic layered expression systems of the invention are derived from alphavirus vectors and most preferably from Sindbis viral vectors.

Other viral vectors suitable for use in the present invention include those derived from poliovirus, for example ATCC VR-58 and those described in Evans, Nature 339 (1989) 385 and Sabin (1973) *J. Biol. Standardization* 1:115; rhinovirus, for example ATCC VR-1110 and those described in Arnold (1990) *J Cell Biochem* L401; pox viruses such as canary pox virus or vaccinia virus, for example ATCC VR-111 and ATCC VR-2010 and those described in Fisher-Hoch (1989) *Proc Natl Acad Sci* 86:317; Flexner (1989) *Ann NY Acad Sci* 569: 86, Flexner (1990) *Vaccine* 8:17; in U.S. Pat. No. 4,603,112 and U.S. Pat. No. 4,769,330 and WO89/01973; SV40 virus, for example ATCC VR-305 and those described in Mulligan (1979) *Nature* 277:108 and Madzak (1992) *J Gen Virol* 73:1533; influenza virus, for example ATCC VR-797 and recombinant influenza viruses made employing reverse genetics techniques as described in U.S. Pat. No. 5,166,057 and in Enami (1990) *Proc Natl Acad Sci* 87:3802-3805; Enami & Palese (1991) *J Virol* 65:2711-2713 and Luytjes (1989) *Cell* 59:110, (see also McMichael (1983) *NEJ Med* 309:13, and Yap (1978) *Nature* 273:238 and *Nature* (1979) 277:108); human immunodeficiency virus as described in EP-0386882 and in Buchschacher (1992) *J. Virol.* 66:2731; measles virus, for example ATCC VR-67 and VR-1247 and those described in EP-0440219; Aura virus, for example ATCC VR-368; Bebaru virus, for example ATCC VR-600 and ATCC VR-1240; Cabassou virus, for example ATCC VR-922; Chikungunya virus, for example ATCC VR-64 and ATCC VR-1241; Fort Morgan Virus, for example ATCC VR-924; Getah virus, for example ATCC VR-369 and ATCC VR-1243; Kyzylagach virus, for example ATCC VR-927; Mayaro virus, for example ATCC VR-66; Mucambo virus, for example ATCC VR-580 and ATCC VR-1244; Ndumu virus, for example ATCC VR-371; Pixunavirus, for example ATCC VR-372 and ATCC VR-1245; Tonate virus, for example ATCC VR-925; Triniti virus, for example ATCC VR-469; Una virus, for example ATCC VR-374; Whataroa virus, for example ATCC VR-926; Y-62-33 virus, for example ATCC VR-375; O'Nyong virus, Eastern encephalitis virus, for example ATCC VR-65 and ATCC VR-1242; Western encephalitis virus, for example ATCC VR-70, ATCC VR-1251, ATCC VR-622 and ATCC VR-1252; and coronavirus, for example ATCC VR-740 and those described in Hamre (1966) *Proc Soc Exp Biol Med* 121:190.

Delivery of the compositions of this invention into cells is not limited to the above mentioned viral vectors. Other delivery methods and media may be employed such as, for example, nucleic acid expression vectors, polycationic condensed DNA linked or unlinked to killed adenovirus alone, for example see U.S. Ser. No. 08/366,787, filed Dec. 30, 1994 and Curiel (1992) *Hum Gene Ther* 3:147-154 ligand linked DNA, for example see Wu (1989) *J Biol Chem* 264:16985-16987, eucaryotic cell delivery vehicles cells, for example see U.S. Ser. No. 08/240,030, filed May 9, 1994, and U.S. Ser. No. 08/404,796, deposition of photopolymerized hydrogel materials, hand-held gene transfer particle gun, as described in U.S. Pat. No. 5,149,655, ionizing radiation as described in U.S. Pat. No. 5,206,152 and in WO92/11033, nucleic charge neutralization or fusion with cell membranes. Additional approaches are described in Philip (1994) *Mol Cell Biol* 14:2411-2418 and in Woffendin (1994) *Proc Natl Acad Sci* 91:1581-1585.

Particle mediated gene transfer may be employed, for example see U.S. Ser. No. 60/023,867. Briefly, the sequence can be inserted into conventional vectors that contain conventional control sequences for high level expression, and then incubated with synthetic gene transfer molecules such as polymeric DNA-binding cations like polylysine, protamine, and albumin, linked to cell targeting ligands such as asialoorosomucoid, as described in Wu & Wu (1987) *J. Biol. Chem.* 262:4429-4432, insulin as described in Hucked (1990) *Biochem Pharmacol* 40:253-263, galactose as described in Plank (1992) *Bioconjugate Chem* 3:533-539, lactose or transferrin.

Naked DNA may also be employed. Exemplary naked DNA introduction methods are described in WO 90/11092 and U.S. Pat. No. 5,580,859. Uptake efficiency may be improved using biodegradable latex beads. DNA coated latex beads are efficiently transported into cells after endocytosis initiation by the beads. The method may be improved further by treatment of the beads to increase hydrophobicity and thereby facilitate disruption of the endosome and release of the DNA into the cytoplasm.

Liposomes that can act as gene delivery vehicles are described in U.S. Pat. No. 5,422,120, WO95/13796, WO94/23697, WO91/14445 and EP-524,968. As described in U.S. Ser. No. 60/023,867, on non-viral delivery, the nucleic acid sequences encoding a polypeptide can be inserted into conventional vectors that contain conventional control sequences for high level expression, and then be incubated with synthetic gene transfer molecules such as polymeric DNA-binding cations like polylysine, protamine, and albumin, linked to cell targeting ligands such as asialoorosomucoid, insulin, galactose, lactose, or transferrin. Other delivery systems include the use of liposomes to encapsulate DNA comprising the gene under the control of a variety of tissue-specific or ubiquitously-active promoters. Further non-viral delivery suitable for use includes mechanical delivery systems such as the approach described in Woffendin et al (1994) *Proc. Natl. Acad. Sci. USA* 91(24):11581-11585. Moreover, the coding sequence and the product of expression of such can be delivered through deposition of photopolymerized hydrogel materials. Other conventional methods for gene delivery that can be used for delivery of the coding sequence include, for example, use of hand-held gene transfer particle gun, as described in U.S. Pat. No. 5,149,655; use of ionizing radiation for activating transferred gene, as described in U.S. Pat. No. 5,206,152 and WO92/11033

Exemplary liposome and polycationic gene delivery vehicles are those described in U.S. Pat. Nos. 5,422,120 and 4,762,915; in WO 95/13796; WO94/23697; and WO91/14445; in EP-0524968; and in Stryer, Biochemistry, pages 236-240 (1975) W.H. Freeman, San Francisco; Szoka (1980) *Biochem Biophys Acta* 600:1; Bayer (1979) *Biochen Biophys Acta* 550:464; Rivnay (1987) *Meth Enzymol* 149:119; Wang (1987) *Proc Natl Acad Sci* 84:7851; Plant (1989) *Anal Biochem* 176:420.

A polynucleotide composition can comprises therapeutically effective amount of a gene therapy vehicle, as the term is defined above. For purposes of the present invention, an effective dose will be from about 0.01 mg/kg to 50 mg/kg or 0.05 mg/kg to about 10 mg/kg of the DNA constructs in the individual to which it is administered.

Delivery Methods

Once formulated, the polynucleotide compositions of the invention can be administered (1) directly to the subject; (2) delivered ex vivo, to cells derived from the subject; or (3) in vitro for expression of recombinant proteins. The subjects to be treated can be mammals or birds. Also, human subjects can be treated.

Direct delivery of the compositions will generally be accomplished by injection, either subcutaneously, intraperitoneally, intravenously or intramuscularly or delivered to the interstitial space of a tissue. The compositions can also be administered into a lesion. Other modes of administration include oral and pulmonary administration, suppositories, and transdermal or transcutaneous applications (e.g. see WO98/20734), needles, and gene guns or hyposprays. Dosage treatment may be a single dose schedule or a multiple dose schedule.

Methods for the ex vivo delivery and reimplantation of transformed cells into a subject are known in the art and described in e.g. WO93/14778. Examples of cells useful in ex vivo applications include, for example, stem cells, particularly hematopoetic, lymph cells, macrophages, dendritic cells, or tumor cells.

Generally, delivery of nucleic acids for both ex vivo and in vitro applications can be accomplished by the following procedures, for example, dextran-mediated transfection, calcium phosphate precipitation, polybrene mediated transfection, protoplast fusion, electroporation, encapsulation of the polynucleotide(s) in liposomes, and direct microinjection of the DNA into nuclei, all well known in the art.

Polynucleotide and Polypeptide Pharmaceutical Compositions

In addition to the pharmaceutically acceptable carriers and salts described above, the following additional agents can be used with polynucleotide and/or polypeptide compositions.

A. Polypeptides

One example are polypeptides which include, without limitation: asioloorosomucoid (ASOR); transferrin; asialoglycoproteins; antibodies; antibody fragments; ferritin; interleukins; interferons, granulocyte, macrophage colony stimulating factor (GM-CSF), granulocyte colony stimulating factor (G-CSF), macrophage colony stimulating factor (M-CSF), stem cell factor and erythropoietin. Viral antigens, such as envelope proteins, can also be used. Also, proteins from other invasive organisms, such as the 17 amino acid peptide from the circumsporozoite protein of *plasmodium falciparum* known as RII.

B. Hormones, Vitamins, etc.

Other groups that can be included are, for example: hormones, steroids, androgens, estrogens, thyroid hormone, or vitamins, folic acid.

C. Polyalkylenes, Polysaccharides, etc.

Also, polyalkylene glycol can be included with the desired polynucleotides/polypeptides. In a preferred embodiment, the polyalkylene glycol is polyethlylene glycol. In addition, mono-, di-, or polysaccarides can be included. In a preferred embodiment of this aspect, the polysaccharide is dextran or DEAE-dextran. Also, chitosan and poly(lactide-co-glycolide)

D. Lipids, and Liposomes

The desired polynucleotide/polypeptide can also be encapsulated in lipids or packaged in liposomes prior to delivery to the subject or to cells derived therefrom.

Lipid encapsulation is generally accomplished using liposomes which are able to stably bind or entrap and retain nucleic acid. The ratio of condensed polynucleotide to lipid preparation can vary but will generally be around 1:1 (mg DNA: micromoles lipid), or more of lipid. For a review of the use of liposomes as carriers for delivery of nucleic acids, see, Hug and Sleight (1991) *Biochim. Biophys. Acta.* 1097:1-17; Straubinger (1983) *Meth. Enzymol.* 101:512-527.

Liposomal preparations for use in the present invention include cationic (positively charged), anionic (negatively charged) and neutral preparations. Cationic liposomes have been shown to mediate intracellular delivery of plasmid DNA (Felgner (1987) *Proc. Natl. Acad. Sci. USA* 84:7413-7416); mRNA (Malone (1989) *Proc. Natl. Acad. Sci. USA* 86:6077-6081); and purified transcription factors (Debs (1990) *J. Biol. Chem.* 265:10189-10192), in functional form.

Cationic liposomes are readily available. For example, N[1-2,3-dioleyloxy)propyl]-N,N,N-triethylammonium (DOTMA) liposomes are available under the trademark Lipofectin, from GIBCO BRL, Grand Island, N.Y. (See, also, Felgner supra). Other commercially available liposomes include transfectace (DDAB/DOPE) and DOTAP/DOPE (Boerhinger). Other cationic liposomes can be prepared from readily available materials using techniques well known in the art. See, e.g. Szoka (1978) *Proc. Natl. Acad. Sci. USA* 75:4194-4198; WO90/11092 for a description of the synthesis of DOTAP (1,2-bis(oleoyloxy)-3-(trimethylammonio) propane) liposomes.

Similarly, anionic and neutral liposomes are readily available, such as from Avanti Polar Lipids (Biriningham, Ala.), or can be easily prepared using readily available materials. Such materials include phosphatidyl choline, cholesterol, phosphatidyl ethanolamine, dioleoylphosphatidyl choline (DOPC), dioleoylphosphatidyl glycerol (DOPG), dioleoylphoshatidyl ethanolamine (DOPE), among others. These materials can also be mixed with the DOTMA and DOTAP starting materials in appropriate ratios. Methods for making liposomes using these materials are well known in the art.

The liposomes can comprise multilammelar vesicles (MLVs), small unilamellar vesicles (SUVs), or large unilamellar vesicles (LUVs). The various liposome-nucleic acid complexes are prepared using methods known in the art. See eg. Straubinger (1983) *Meth. Immunol.* 101:512-527; Szoka (1978) *Proc. Natl. Acad. Sci. USA* 75:4194-4198; Papahadjopoulos (1975) *Biochim. Biophys. Acta* 394:483; Wilson (1979) *Cell* 17:77); Deamer & Bangham (1976) *Biochim. Biophys. Acta* 443:629; Ostro (1977) *Biochem. Biophys. Res. Commun.* 76:836; Fraley (1979) *Proc. Natl. Acad. Sci. USA* 76:3348); Enoch & Strittmatter (1979) *Proc. Natl. Acad. Sci. USA* 76:145; Fraley (1980) *J. Biol. Chem.* (1980) 255:10431; Szoka & Papahadjopoulos (1978) *Proc. Natl. Acad. Sci. USA* 75:145; and Schaefer-Ridder (1982) *Science* 215:166.

E. Lipoproteins

In addition, lipoproteins can be included with the polynucleotide/polypeptide to be delivered. Examples of lipoproteins to be utilized include: chylomicrons, HDL, IDL, LDL, and VLDL. Mutants, fragments, or fusions of these proteins can also be used. Also, modifications of naturally occurring lipoproteins can be used, such as acetylated LDL. These lipoproteins can target the delivery of polynucleotides to cells expressing lipoprotein receptors. Preferably, if lipoproteins are including with the polynucleotide to be delivered, no other targeting ligand is included in the composition.

Naturally occurring lipoproteins comprise a lipid and a protein portion. The protein portion are known as apoproteins. At the present, apoproteins A, B, C, D, and E have been isolated and identified. At least two of these contain several proteins, designated by Roman numerals, AI, AII, AIV; CI, CII, CIII.

A lipoprotein can comprise more than one apoprotein. For example, naturally occurring chylomicrons comprises of A, B, C, and E, over time these lipoproteins lose A and acquire C and E apoproteins. VLDL comprises A, B, C, and E apoproteins, LDL comprises apoprotein B; and HDL comprises apoproteins A, C, and E.

The amino acid of these apoproteins are known and are described in, for example, Breslow (1985) Annu Rev. Biochem 54:699; Law (1986) Adv. Exp Med. Biol. 151:162; Chen (1986) J Biol Chem 261:12918; Kane (1980) Proc Natl Acad Sci USA 77:2465; and Utennann (1984) Hum Genet. 65:232.

Lipoproteins contain a variety of lipids including, triglycerides, cholesterol (free and esters), and phopholipids. The composition of the lipids varies in naturally occurring lipoproteins. For example, chylomicrons comprise mainly triglycerides. A more detailed description of the lipid content of naturally occurring lipoproteins can be found, for example, in *Meth. Enzymol.* 128 (1986). The composition of the lipids are chosen to aid in conformation of the apoprotein for receptor binding activity. The composition of lipids can also be chosen to facilitate hydrophobic interaction and association with the polynucleotide binding molecule.

Naturally occurring lipoproteins can be isolated from serum by ultracentrifugation, for instance. Such methods are described in *Meth. Enzymol.* (supra); Pitas (1980) *J. Biochem.* 255:5454-5460 and Mahey (1979) *J Clin. Invest* 64:743-750. Lipoproteins can also be produced by in vitro or recombinant methods by expression of the apoprotein genes in a desired host cell. See, for example, Atkinson (1986) *Annu Rev Biophys Chem* 15:403 and Radding (1958) *Biochim Biophys Acta* 30: 443. Lipoproteins can also be purchased from commercial suppliers, such as Biomedical Technologies, Inc., Stoughton, Mass., USA. Further description of lipoproteins can be found in Zuckermann et al. PCT/US97/14465.

F. Polycationic Agents

Polycationic agents can be included, with or without lipoprotein, in a composition with the desired polynucleotide/polypeptide to be delivered.

Polycationic agents, typically, exhibit a net positive charge at physiological relevant pH and are capable of neutralizing the electrical charge of nucleic acids to facilitate delivery to a desired location. These agents have both in vitro, ex vivo, and in vivo applications. Polycationic agents can be used to deliver nucleic acids to a living subject either intramuscularly, subcutaneously, etc.

The following are examples of useful polypeptides as polycationic agents: polylysine, polyarginine, polyornithine, and protamine. Other examples include histones, protamines, human serum albumin, DNA binding proteins, non-histone chromosomal proteins, coat proteins from DNA viruses, such as (X174, transcriptional factors also contain domains that bind DNA and therefore may be useful as nucleic aid condensing agents. Briefly, transcriptional factors such as C/CEBP, c-jun, c-fos, AP-1, AP-2, AP-3, CPF, Prot-1, Sp-1, Oct-1, Oct-2, CREP, and TFIID contain basic domains that bind DNA sequences.

Organic polycationic agents include: spermine, spermidine, and purtrescine.

The dimensions and of the physical properties of a polycationic agent can be extrapolated from the list above, to construct other polypeptide polycationic agents or to produce synthetic polycationic agents.

Synthetic polycationic agents which are useful include, for example, DEAE-dextran, polybrene. Lipofectin™, and lipofectAMINE™ are monomers that form polycationic complexes when combined with polynucleotides/polypeptides.

Immunodiagnostic Assays

Neisserial antigens of the invention can be used in immunoassays to detect antibody levels (or, conversely, anti-Neisserial antibodies can be used to detect antigen levels). Immunoassays based on well defined, recombinant antigens can be developed to replace invasive diagnostics methods. Antibodies to Neisserial proteins within biological samples, including for example, blood or serum samples, can be detected. Design of the immunoassays is subject to a great deal of variation, and a variety of these are known in the art. Protocols for the immunoassay may be based, for example, upon competition, or direct reaction, or sandwich type assays. Protocols may also, for example, use solid supports, or may be by immunoprecipitation. Most assays involve the use of labeled antibody or polypeptide; the labels may be, for example, fluorescent, chemiluminescent, radioactive, or dye molecules. Assays which amplify the signals from the probe are also known; examples of which are assays which utilize biotin and avidin, and enzyme-labeled and mediated immunoassays, such as ELISA assays.

Kits suitable for immunodiagnosis and containing the appropriate labeled reagents are constructed by packaging the appropriate materials, including the compositions of the invention, in suitable containers, along with the remaining reagents and materials (for example, suitable buffers, salt solutions, etc.) required for the conduct of the assay, as well as suitable set of assay instructions.

Nucleic Acid Hybridisation

"Hybridization" refers to the association of two nucleic acid sequences to one another by hydrogen bonding. Typically, one sequence will be fixed to a solid support and the other will be free in solution. Then, the two sequences will be placed in contact with one another under conditions that favor hydrogen bonding. Factors that affect this bonding include: the type and volume of solvent; reaction temperature; time of hybridization; agitation; agents to block the non-specific attachment of the liquid phase sequence to the solid support (Denhardt's reagent or BLOTTO); concentration of the sequences; use of compounds to increase the rate of association of sequences (dextran sulfate or polyethylene glycol); and the stringency of the washing conditions following hybridization. See Sambrook et al. [supra] Volume 2, chapter 9, pages 9.47 to 9.57.

"Stringency" refers to conditions in a hybridization reaction that favor association of very similar sequences over sequences that differ. For example, the combination of temperature and salt concentration should be chosen that is approximately 120 to 200° C. below the calculated Tm of the hybrid under study. The temperature and salt conditions can often be determined empirically in preliminary experiments in which samples of genomic DNA immobilized on filters are hybridized to the sequence of interest and then washed under conditions of different stringencies. See Sambrook et al. at page 9.50.

Variables to consider when performing, for example, a Southern blot are (1) the complexity of the DNA being blotted and (2) the homology between the probe and the sequences being detected. The total amount of the fragment(s) to be studied can vary a magnitude of 10, from 0.1 to 1 µg for a plasmid or phage digest to $10^{-9}$ to $10^{-8}$ g for a single copy gene in a highly complex eukaryotic genome. For lower complexity polynucleotides, substantially shorter blotting, hybridization, and exposure times, a smaller amount of starting polynucleotides, and lower specific activity of probes can be used. For example, a single-copy yeast gene can be detected with an exposure time of only 1 hour starting with 1 µg of yeast DNA, blotting for two hours, and hybridizing for 4-8 hours with a probe of $10^8$ cpm/µg. For a single-copy mammalian gene a conservative approach would start with 10 µg of DNA, blot overnight, and hybridize overnight in the presence of 10% dextran sulfate using a probe of greater than $10^8$ cpm/µg, resulting in an exposure time of ~24 hours.

Several factors can affect the melting temperature (Tm) of a DNA-DNA hybrid between the probe and the fragment of interest, and consequently, the appropriate conditions for hybridization and washing. In many cases the probe is not 100% homologous to the fragment. Other commonly encountered variables include the length and total G+C content of the hybridizing sequences and the ionic strength and formamide content of the hybridization buffer. The effects of all of these factors can be approximated by a single equation:

$$Tm=81+16.6(\log_{10}Ci)+0.4[\%(G+C)]-0.6(\% \text{ formamide})-600/n-1.5(\% \text{ mismatch}).$$

where Ci is the salt concentration (monovalent ions) and n is the length of the hybrid in base pairs (slightly modified from Meinkoth & Wahl (1984) *Anal. Biochem.* 138: 267-284).

In designing a hybridization experiment, some factors affecting nucleic acid hybridization can be conveniently altered. The temperature of the hybridization and washes and the salt concentration during the washes are the simplest to adjust. As the temperature of the hybridization increases (i.e. stringency), it becomes less likely for hybridization to occur between strands that are nonhomologous, and as a result, background decreases. If the radiolabeled probe is not completely homologous with the immobilized fragment (as is frequently the case in gene family and interspecies hybridization experiments), the hybridization temperature must be reduced, and background will increase. The temperature of the washes affects the intensity of the hybridizing band and the degree of background in a similar manner. The stringency of the washes is also increased with decreasing salt concentrations.

In general, convenient hybridization temperatures in the presence of 50% formamide are 42° C. for a probe with is 95% to 100% homologous to the target fragment, 37° C. for 90% to 95% homology, and 32° C. for 85% to 90% homology. For lower homologies, formamide content should be lowered and temperature adjusted accordingly, using the equation above. If the homology between the probe and the target fragment are not known, the simplest approach is to start with both hybridization and wash conditions which are nonstringent. If non-specific bands or high background are observed after autoradiography, the filter can be washed at high stringency and reexposed. If the time required for exposure makes this approach impractical, several hybridization and/or washing stringencies should be tested in parallel.

Nucleic Acid Probe Assays

Methods such as PCR, branched DNA probe assays, or blotting techniques utilizing nucleic acid probes according to the invention can determine the presence of cDNA or mRNA. A probe is said to "hybridize" with a sequence of the invention if it can form a duplex or double stranded complex, which is stable enough to be detected.

The nucleic acid probes will hybridize to the Neisserial nucleotide sequences of the invention (including both sense and antisense strands). Though many different nucleotide sequences will encode the amino acid sequence, the native Neisserial sequence is preferred because it is the actual sequence present in cells. mRNA represents a coding sequence and so a probe should be complementary to the coding sequence; single-stranded cDNA is complementary to mRNA, and so a cDNA probe should be complementary to the non-coding sequence.

The probe sequence need not be identical to the Neisserial sequence (or its complement)—some variation in the sequence and length can lead to increased assay sensitivity if the nucleic acid probe can form a duplex with target nucleotides, which can be detected. Also, the nucleic acid probe can include additional nucleotides to stabilize the formed duplex. Additional Neisserial sequence may also be helpful as a label to detect the formed duplex. For example, a non-complementary nucleotide sequence may be attached to the 5' end of the probe, with the remainder of the probe sequence being complementary to a Neisserial sequence. Alternatively, non-complementary bases or longer sequences can be interspersed into the probe, provided that the probe sequence has sufficient complementarity with the a Neisserial sequence in order to hybridize therewith and thereby form a duplex which can be detected.

The exact length and sequence of the probe will depend on the hybridization conditions, such as temperature, salt condition and the like. For example, for diagnostic applications, depending on the complexity of the analyte sequence, the nucleic acid probe typically contains at least 10-20 nucleotides, preferably 15-25, and more preferably at least 30 nucleotides, although it may be shorter than this. Short primers generally require cooler temperatures to form sufficiently stable hybrid complexes with the template.

Probes may be produced by synthetic procedures, such as the triester method of Matteucci et al. [*J. Am. Chem. Soc.* (1981) 103:3185], or according to Urdea et al. [*Proc. Natl. Acad. Sci. USA* (1983) 80:7461], or using commercially available automated oligonucleotide synthesizers.

The chemical nature of the probe can be selected according to preference. For certain applications, DNA or RNA are appropriate. For other applications, modifications may be incorporated e.g. backbone modifications, such as phosphorothioates or methylphosphonates, can be used to increase in vivo half-life, alter RNA affinity, increase nuclease resistance etc. [e.g. see Agrawal & Iyer (1995) *Curr Opin Biotechnol* 6:12-19; Agrawal (1996) *TIBTECH* 14:376-387]; analogues such as peptide nucleic acids may also be used [e.g. see Corey (1997) *TIBTECH* 15:224-229; Buchardt et al. (1993) *TIBTECH* 11:384-386].

Alternatively, the polymerase chain reaction (PCR) is another well-known means for detecting small amounts of target nucleic acids. The assay is described in: Mullis et al. [*Meth. Enzymol.* (1987) 155: 335-350]; U.S. Pat. Nos. 4,683,195 and 4,683,202. Two "primer" nucleotides hybridize with the target nucleic acids and are used to prime the reaction. The primers can comprise sequence that does not hybridize to the sequence of the amplification target (or its complement) to aid with duplex stability or, for example, to incorporate a convenient restriction site. Typically, such sequence will flank the desired Neisserial sequence.

A thermostable polymerase creates copies of target nucleic acids from the primers using the original target nucleic acids as a template. After a threshold amount of target nucleic acids are generated by the polymerase, they can be detected by more traditional methods, such as Southern blots. When using the Southern blot method, the labelled probe will hybridize to the Neisserial sequence (or its complement).

Also, mRNA or cDNA can be detected by traditional blotting techniques described in Sambrook et al [supra]. mRNA, or cDNA generated from mRNA using a polymerase enzyme, can be purified and separated using gel electrophoresis. The nucleic acids on the gel are then blotted onto a solid support, such as nitrocellulose. The solid support is exposed to a labelled probe and then washed to remove any unhybridized probe. Next, the duplexes containing the labeled probe are detected. Typically, the probe is labelled with a radioactive moiety.

BRIEF DESCRIPTION OF THE DRAWINGS

FIGS. 1-20 show biochemical data obtained in the Examples, and also sequence analysis, for ORFs 37, 5, 2, 15, 22, 28, 32, 4, 61, 76, 89, 97, 106, 138, 23, 25, 27, 79, 85 and 132. M1 and M2 are molecular weight markers. Arrows indicate the position of the main recombinant product or, in Western blots, the position of the main *N. meningitidis* immunoreactive band. TP indicates *N. meningitidis* total protein extract; OMV indicates *N. meningitidis* outer membrane vesicle preparation. In bactericidal assay results: a diamond (♦) shows preimmune data; a triangle (▲) shows GST control data; a circle (●) shows data with recombinant *N. meningitidis* protein. Computer analyses show a hydrophilicity plot (upper), an antigenic index plot (middle), and an AMPHI analysis (lower). The AMPHI program has been used to predict T-cell epitopes [Gao et al. (1989) *J. Immunol.* 143:3007; Roberts et al. (1996) *AIDS Res Hum Retrovir* 12:593; Quakyi et al. (1992) *Scand J Immunol suppl.* 11:9) and is available in the Protean package of DNASTAR, Inc. (1228 South Park Street, Madison, Wis. 53715 USA).

EXAMPLES

Figure 8E:
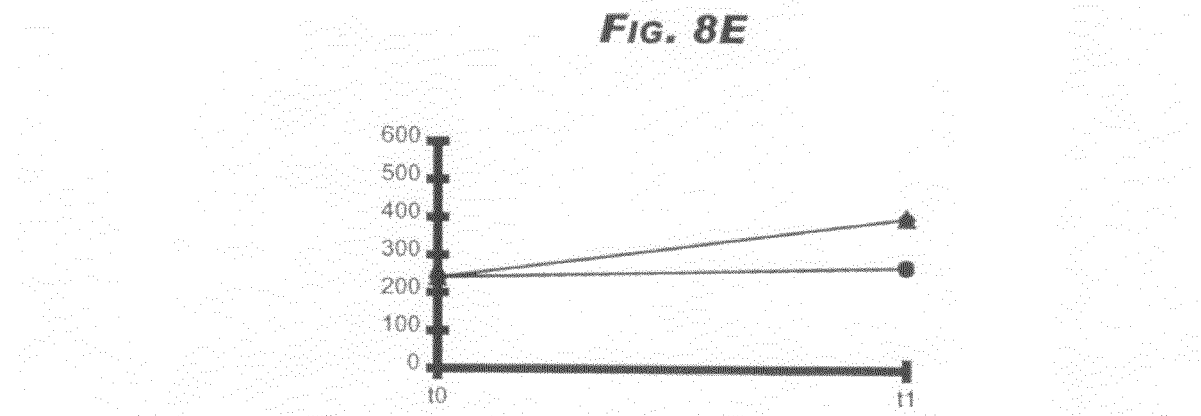

The examples describe nucleic acid sequences which have been identified in *N. meningitidis*, along with their putative translation products, and also those of *N. gonorrhoeae*. Not all of the nucleic acid sequences are complete i.e. they encode less than the full-length wild-type protein.

The examples are generally in the following format:
- a nucleotide sequence which has been identified in *N. meningitidis* (strain B)
- the putative translation product of this sequence
- a computer analysis of the translation product based on database comparisons
- corresponding gene and protein sequences identified in *N. meningitidis* (strain A) and in *N. gonorrhoeae*
- a description of the characteristics of the proteins which indicates that they might be suitably antigenic
- results of biochemical analysis (expression, purification, ELISA, FACS etc.)

The examples typically include details of sequence identity between species and strains. Proteins that are similar in sequence are generally similar in both structure and function, and the sequence identity often indicates a common evolutionary origin. Comparison with sequences of proteins of known function is widely used as a guide for the assignment of putative protein function to a new sequence and has proved particularly useful in whole-genome analyses.

Sequence comparisons were performed at NCBI (http://www.ncbi.nlm.nih.gov) using the algorithms BLAST, BLAST2, BLASTn, BLASTp, tBLASTn, BLASTx, & tBLASTx [e.g. see also Altschul et al. (1997) Gapped BLAST and PSI-BLAST: a new generation of protein database search programs. *Nucleic Acids Research* 25:2289-3402]. Searches were performed against the following databases: non-redundant GenBank+EMBL+DDBJ+PDB sequences and non-redundant GenBank CDS translations+PDB+SwissProt+SP-update+PIR sequences.

To compare Meningococcal and Gonococcal sequences, the tBLASTx algorithm was used, as implemented at http://www.genome.ou.edu/gono_blast.html. The FASTA algorithm was also used to compare the ORFs (from GCG Wisconsin Package, version 9.0).

Dots within nucleotide sequences (e.g. position 495 in SEQ ID 11) represent nucleotides which have been arbitrarily introduced in order to maintain a reading frame. In the same way, double-underlined nucleotides were removed. Lower case letters (e.g. position 496 in SEQ ID 11) represent ambiguities which arose during alignment of independent sequencing reactions (some of the nucleotide sequences in the examples are derived from combining the results of two or more experiments).

Nucleotide sequences were scanned in all six reading frames to predict the presence of hydrophobic domains using an algorithm based on the statistical studies of Esposti et al. [Critical evaluation of the hydropathy of membrane proteins (1990) *Eur J Biochem* 190:207-219]. These domains represent potential transmembrane regions or hydrophobic leader sequences.

Open reading frames were predicted from fragmented nucleotide sequences using the program ORFFINDER (NCBI).

Underlined amino acid sequences indicate possible transmembrane domains or leader sequences in the ORFs, as predicted by the PSORT algorithm (http://www.psort.nibb.acjp). Functional domains were also predicted using the MOTIFS program (GCG Wisconsin & PROSITE).

Various tests can be used to assess the in vivo immunogenicity of the proteins identified in the examples. For example, the proteins can be expressed recombinantly and used to screen patient sera by immunoblot. A positive reaction between the protein and patient serum indicates that the patient has previously mounted an immune response to the protein in question i.e. the protein is an immunogen. This method can also be used to identify immunodominant proteins.

The recombinant protein can also be conveniently used to prepare antibodies e.g. in a mouse. These can be used for direct confirmation that a protein is located on the cell-surface. Labelled antibody (e.g. fluorescent labelling for FACS) can be incubated with intact bacteria and the presence of label on the bacterial surface confirms the location of the protein.

In particular, the following methods (A) to (S) were used to express, purify and biochemically characterise the proteins of the invention:

A) Chromosomal DNA Preparation

*N. meningitidis* strain 2996 was grown to exponential phase in 100 ml of GC medium, harvested by centrifugation, and resuspended in 5 ml buffer (20% Sucrose, 50 mM Tris-HCl, 50 mM EDTA, pH8). After 10 minutes incubation on ice, the bacteria were lysed by adding 10 ml lysis solution (50 mM NaCl, 1% Na-Sarkosyl, 50 µg/ml Proteinase K), and the suspension was incubated at 37° C. for 2 hours. Two phenol extractions (equilibrated to pH 8) and one $CHCl_3$/isoamylalcohol (24:1) extraction were performed. DNA was precipitated by addition of 0.3M sodium acetate and 2 volumes ethanol, and was collected by centrifugation. The pellet was washed once with 70% ethanol and redissolved in 4 ml buffer (10 mM Tris-HCl, 1 mM EDTA, pH 8). The DNA concentration was measured by reading the OD at 260 nm.

B) Oligonucleotide Design

Synthetic oligonucleotide primers were designed on the basis of the coding sequence of each ORF, using (a) the meningococcus B sequence when available, or (b) the gonococcus/meningococcus A sequence, adapted to the codon preference usage of meningococcus as necessary. Any predicted signal peptides were omitted, by deducing the 5'-end amplification primer sequence immediately downstream from the predicted leader sequence.

For most ORFs, the 5' primers included two restriction enzyme recognition sites (BamHI-NdeI, BamHI-NheI, or EcoRI-NheI, depending on the gene's own restriction pattern); the 3' primers included a XhoI restriction site. This procedure was established in order to direct the cloning of each amplification product (corresponding to each ORF) into two different expression systems: pGEX-KG (using either BamHI-XhoI or EcoRI-XhoI), and pET21b+ (using either NdeI-XhoI or NheI-XhoI).

```
5'-end primer tail:                       SEQ ID NO: 1099
CGCGGATCCCATATG      (BamHI-NdeI)

SEQ ID NO: 1100
CGCGGATCCGCTAGC      (BamHI-NheI)

SEQ ID NO: 1101
CCGGAATTCTAGCTAGC    (EcoRI-NheI)

3'-end primer tail:                       SEQ ID NO: 1102
CCCGCTCGAG           (XhoI)
```

For ORFs 5, 15, 17, 19, 20, 22, 27, 28, 65 & 89, two different amplifications were performed to clone each ORF in the two expression systems. Two different 5' primers were used for each ORF; the same 3' XhoI primer was used as before:

```
                                          SEQ ID NO: 1103
5'-end primer tail: GGAATTCCATATGGCCATGG  (NdeI)

5'-end primer tail: CGGGATCC              (BamHI)
```

ORF 76 was cloned in the pTRC expression vector and expressed as an amino-terminus His-tag fusion. In this particular case, the predicted signal peptide was included in the final product. NheI-BamHI restriction sites were incorporated using primers:

```
                                          SEQ ID NO: 1104
5'-end primer tail:    GATCAGCTAGCCATATG  (NheI)

3'-end primer tail:    CGGGATCC           (BamHI)
```

As well as containing the restriction enzyme recognition sequences, the primers included nucleotides which hybridized to the sequence to be amplified. The number of hybridizing nucleotides depended on the melting temperature of the whole primer, and was determined for each primer using the formulae:

$$T_m = 4(G+C) + 2(A+T) \text{ (tail excluded)}$$

$$T_m = 64.9 + 0.41(\% \, GC) - 600/N \text{ (whole primer)}$$

The average melting temperature of the selected oligos were 65-70° C. for the whole oligo and 50-55° C. for the hybridising region alone.

Table I (page 487) shows the forward and reverse primers used for each amplification. In certain cases, it will be noted that the sequence of the primer does not exactly match the sequence in the ORF. When initial amplifications were performed, the complete 5' and/or 3' sequence was not known for some meningococcal ORFs, although the corresponding sequences had been identified in gonococcus. For amplification, the gonococcal sequences could thus be used as the basis for primer design, altered to take account of codon preference. In particular, the following codons were changed: ATA→ATT; TCG→TCT; CAG→CAA; AAG→AAA; GAG→GAA; CGA→CGC; CGG→CGC; GGG→GGC. Italicised nucleotides in Table I indicate such a change. It will be appreciated that, once the complete sequence has been identified, this approach is generally no longer necessary.

Oligos were synthesized by a Perkin Elmer 394 DNA/RNA Synthesizer, eluted from the columns in 2 ml $NH_4OH$, and deprotected by 5 hours incubation at 56° C. The oligos were precipitated by addition of 0.3M Na-Acetate and 2 volumes ethanol. The samples were then centrifuged and the pellets resuspended in either 100 µl or 1 ml of water. $OD_{260}$ was determined using a Perkin Elmer Lambda Bio spectophotometer and the concentration was determined and adjusted to 2-10 pmol/µl.

C) Amplification

The standard PCR protocol was as follows: 50-200ng of genomic DNA were used as a template in the presence of 20-40 µM of each oligo, 400-800 µM dNTPs solution, 1×PCR buffer (including 1.5 mM $MgCl_2$), 2.5 units TaqI DNA polymerase (using Perkin-Elmer AmpliTaQ, GIBCO Platinum, Pwo DNA polymerase, or Tahara Shuzo Taq polymerase).

In some cases, PCR was optimised by the addition of 10 µl DMSO or 50 µl 2M betaine.

After a hot start (adding the polymerase during a preliminary 3 minute incubation of the whole mix at 95° C.), each sample underwent a double-step amplification: the first 5 cycles were performed using as the hybridization temperature the one of the oligos excluding the restriction enzymes tail, followed by 30 cycles performed according to the hybridization temperature of the whole length oligos. The cycles were followed by a final 10 minute extension step at 72° C.

The standard cycles were as follows:

|  | Denaturation | Hybridisation | Elongation |
|---|---|---|---|
| First 5 cycles | 30 seconds 95° C. | 30 seconds 50-55° C. | 30-60 seconds 72° C. |
| Last 30 cycles | 30 seconds 95° C. | 30 seconds 65-70° C. | 30-60 seconds 72° C. |

The elongation time varied according to the length of the ORF to be amplified.

The amplifications were performed using either a 9600 or a 2400 Perkin Elmer GeneAmp PCR System. To check the results, 1/10 of the amplification volume was loaded onto a 1-1.5% agarose gel and the size of each amplified fragment compared with a DNA molecular weight marker.

The amplified DNA was either loaded directly on a 1% agarose gel or first precipitated with ethanol and resuspended in a suitable volume to be loaded on a 1% agarose gel. The DNA fragment corresponding to the right size band was then eluted and purified from gel, using the Qiagen Gel Extraction Kit, following the instructions of the manufacturer. The final volume of the DNA fragment was 30 µl or 50 µl of either water or 10 mM Tris, pH 8.5.

D) Digestion of PCR Fragments

The purified DNA corresponding to the amplified fragment was split into 2 aliquots and double-digested with:

NdeI/XhoI or NheI/XhoI for cloning into pET-21b+ and further expression of the protein as a C-terminus His-tag fusion BamHI/XhoI or EcoRI/XhoI for cloning into pGEX-KG and further expression of the protein as N-terminus GST fusion.

For ORF 76, NheI/BamHI for cloning into pTRC-HisA vector and further expression of the protein as N-terminus His-tag fusion.

EcoRI/PstI, EcoRI/SalI, SalI/PstI for cloning into pGex-His and further expression of the protein as N-terminus His-tag fusion Each purified DNA fragment was incubated (37° C. for 3 hours to overnight) with 20 units of each restriction enzyme (New England Biolabs) in a either 30 or 40 µl final volume in the presence of the appropriate buffer. The digestion product was then purified using the QIAquick PCR purification kit, following the manufacturer's instructions, and eluted in a final volume of 30 or 50 µl of either water or 10 mM Tris-HCl, pH 8.5. The final DNA concentration was determined by 1% agarose gel electrophoresis in the presence of titrated molecular weight marker.

E) Digestion of the Cloning Vectors (pET22B, pGEX-KG, pTRC-His A, and pGex-His)

10 µg plasmid was double-digested with 50 units of each restriction enzyme in 200 µl reaction volume in the presence of appropriate buffer by overnight incubation at 37° C. After loading the whole digestion on a 1% agarose gel, the band corresponding to the digested vector was purified from the gel using the Qiagen QIAquick Gel Extraction Kit and the DNA was eluted in 50 µl of 10 mM Tris-HCl, pH 8.5. The DNA concentration was evaluated by measuring $OD_{260}$ of the sample, and adjusted to 50 µg/µl. 1 µl of plasmid was used for each cloning procedure.

The vector pGEX-His is a modified pGEX-2T vector carrying a region encoding six histidine residues upstream to the thrombin cleavage site and containing the multiple cloning site of the vector pTRC99 (Pharmacia).

F) Cloning

The fragments corresponding to each ORF, previously digested and purified, were ligated in both pET22b and pGEX-KG. In a final volume of 20 µl, a molar ratio of 3:1 fragment/vector was ligated using 0.5 µl of NEB T4 DNA ligase (400 units/µl), in the presence of the buffer supplied by the manufacturer. The reaction was incubated at room temperature for 3 hours. In some experiments, ligation was performed using the Boheringer "Rapid Ligation Kit", following the manufacturer's instructions.

In order to introduce the recombinant plasmid in a suitable strain, 100 µl E. coli DH5 competent cells were incubated with the ligase reaction solution for 40 minutes on ice, then at 37° C. for 3 minutes, then, after adding 800 µl LB broth, again at 37° C. for 20 minutes. The cells were then centrifuged at maximum speed in an Eppendorf microfuge and resuspended in approximately 200 µl of the supernatant. The suspension was then plated on LB ampicillin (100 mg/ml).

The screening of the recombinant clones was performed by growing 5 randomly-chosen colonies overnight at 37° C. in either 2 ml (pGEX or pTC clones) or 5 ml (pET clones) LB broth+100 µg/ml ampicillin. The cells were then pelletted and the DNA extracted using the Qiagen QIAprep Spin Miniprep Kit, following the manufacturer's instructions, to a final volume of 30 µl. 5 µl of each individual miniprep (approximately 1 g) were digested with either NdeI/XhoI or BamHI/XhoI and the whole digestion loaded onto a 1-1.5% agarose gel (depending on the expected insert size), in parallel with the molecular weight marker 1Kb DNA Ladder, GIBCO). The screening of the positive clones was made on the base of the correct insert size.

For the cloning of ORFs 110, 111, 113, 115, 119, 122, 125 & 130, the double-digested PCR product was ligated into double-digested vector using EcoRI-PstI cloning sites or, for ORFs 115 & 127, EcoRI-SalI or, for ORF 122, SalI-PstI. After cloning, the recombinant plasmids were introduced in the E. coli host W3110. Individual clones were grown overnight at 37° C. in L-broth with 50 µl/ml ampicillin.

G) Expression

Each ORF cloned into the expression vector was transformed into the strain suitable for expression of the recombinant protein product. 1 µl of each construct was used to transform 30 µl of E. coli BL21 (pGEX vector), E. coli TOP 10 (PTRC vector) or E. coli BL21-DE3 (PET vector), as described above. In the case of the pGEX-His vector, the same E. coli strain (W3110) was used for initial cloning and expression. Single recombinant colonies were inoculated into 2 ml LB+Amp (100 µg/ml), incubated at 37° C. overnight, then diluted 1:30 in 20 ml of LB+Amp (100 µg/ml) in 100 ml flasks, making sure that the $OD_{600}$ ranged between 0.1 and 0.15. The flasks were incubated at 30° C. into gyratory water bath shakers until OD indicated exponential growth suitable for induction of expression (0.4-0.8 OD for pET and pTRC vectors; 0.8-1 OD for pGEX and pGEX-His vectors). For the pET, pTRC and pGEX-His vectors, the protein expression was induced by addition of 1 mM IPTG, whereas in the case of pGEX system the final concentration of IPTG was 0.2 mM. After 3 hours incubation at 30° C., the final concentration of the sample was checked by OD. In order to check expression, 1 ml of each sample was removed, centrifuged in a microfuge, the pellet resuspended in PBS, and analysed by 12% SDS-PAGE with Coomassie Blue staining. The whole sample was centrifuged at 6000 g and the pellet resuspended in PBS for further use.

H) GST-fusion Proteins Large-scale Purification.

A single colony was grown overnight at 37° C. on LB+Amp agar plate. The bacteria were inoculated into 20 ml of LB+Amp liquid culture in a water bath shaker and grown overnight. Bacteria were diluted 1:30 into 600 ml of fresh medium and allowed to grow at the optimal temperature (20-37° C.) to $OD_{550}$ 0.8-1. Protein expression was induced with 0.2 mM IPTG followed by three hours incubation. The culture was centrifuged at 8000 rpm at 4° C. The supernatant was discarded and the bacterial pellet was resuspended in 7.5 ml cold PBS. The cells were disrupted by sonication on ice for 30 sec at 40 W using a Branson sonifier B-15, frozen and thawed twice and centrifuged again. The supernatant was collected and mixed with 150 µl Glutatione-Sepharose 4B resin (Pharmacia) (previously washed with PBS) and incubated at room temperature for 30 minutes. The sample was centrifuged at 700 g for 5 minutes at 4° C. The resin was washed twice with 10 ml cold PBS for 10 minutes, resuspended in 1 ml cold PBS, and loaded on a disposable column. The resin was washed twice with 2 ml cold PBS until the flow-through reached $OD_{280}$ of 0.02-0.06. The GST-fusion protein was eluted by addition of 700 µl cold Glutathione elution buffer (10 mM reduced glutathione, 50 mM Tris-HCl) and fractions collected until the $OD_{280}$ was 0.1. 21 µl of each fraction were loaded on a 12% SDS gel using either Biorad SDS-PAGE Molecular weight standard broad range (M1) (200, 116.25, 97.4, 66.2, 45,31, 21.5, 14.4, 6.5 kDa) or Amersham Rainbow Marker (M2) (220, 66, 46, 30, 21.5, 14.3 kDa) as standards. As the MW of GST is 26 kDa, this value must be added to the MW of each GST-fusion protein.

I) His-fusion Solubility Analysis (ORFs 111-129)

To analyse the solubility of the His-fusion expression products, pellets of 3 ml cultures were resuspended in buffer M1 [500 µl PBS pH 7.2]. 25 µl lysozyme (10 mg/ml) was added and the bacteria were incubated for 15 min at 4° C. The pellets were sonicated for 30 sec at 40 W using a Branson sonifier B-15, frozen and thawed twice and then separated again into pellet and supernatant by a centrifugation step. The supernatant was collected and the pellet was resuspended in buffer M2 [8M urea, 0.5M NaCl, 20 mM imidazole and 0.1 M $NaH_2PO_4$] and incubated for 3 to 4 hours at 4° C. After centrifugation, the supernatant was collected and the pellet was resuspended in buffer M3 [6M guanidinium-HCl, 0.5M NaCl, 20 mM imidazole and 0.1 M $NaH_2PO_4$] overnight at 4° C. The supernatants from all steps were analysed by SDS-PAGE.

The proteins expressed from ORFs 113, 119 and 120 were found to be soluble in PBS, whereas ORFs 111, 122, 126 and 129 need urea and ORFs 125 and 127 need guanidium-HCl for their solubilization.

J) His-fusion Large-scale Purification.

A single colony was grown overnight at 37° C. on a LB+Amp agar plate. The bacteria were inoculated into 20 ml of LB+Amp liquid culture and incubated overnight in a water bath shaker. Bacteria were diluted 1:30 into 600 ml fresh medium and allowed to grow at the optimal temperature (20-37° C.) to $OD_{550}$ 0.6-0.8. Protein expression was induced by addition of 1 mM IPTG and the culture further incubated for three hours. The culture was centrifuged at 800 rpm at 4° C., the supernatant was discarded and the bacterial pellet was resuspended in 7.5 ml of either (i) cold buffer A (300 mM NaCl, 50 mM phosphate buffer, 10 mM imidazole, pH 8) for soluble proteins or (ii) buffer B (urea 8M, 10 mM Tris-HCl, 100 mM phosphate buffer, pH 8.8) for insoluble proteins. The cells were disrupted by sonication on ice for 30 sec at 40 W using a Branson sonifier B-15, frozen and thawed two times and centrifuged again.

For insoluble proteins, the supernatant was stored at −20° C., while the pellets were resuspended in 2 ml buffer C (6M guanidine hydrochloride, 100 mM phosphate buffer, 10 mM Tris-HCl, pH 7.5) and treated in a homogenizer for 10 cycles. The product was centrifuged at 13000 rpm for 40 minutes.

Supernatants were collected and mixed with 150 µl $Ni^{2+}$-resin (Pharmacia) (previously washed with either buffer A or buffer B, as appropriate) and incubated at room temperature with gentle agitation for 30 minutes. The sample was centrifuged at 700 g for 5 minutes at 4° C. The resin was washed twice with 10 ml buffer A or B for 10 minutes, resuspended in 1 ml buffer A or B and loaded on a disposable column. The resin was washed at either (i) 4° C. with 2 ml cold buffer A or (ii) room temperature with 2 ml buffer B, until the flow-through reached $OD_{280}$ of 0.02-0.06.

The resin was washed with either (i) 2 ml cold 20 mM imidazole buffer (300 mM NaCl, 50 mM phosphate buffer, 20 mM imidazole, pH 8) or (ii) buffer D (urea 8M, 10 mM Tris-HCl, 100 mM phosphate buffer, pH 6.3) until the flow-through reached the $O.D._{280}$ of 0.02-0.06. The His-fusion protein was eluted by addition of 700 µl of either (i) cold elution buffer A (300 mM NaCl, 50 mM phosphate buffer, 250 mM imidazole, pH 8) or (ii) elution buffer B (urea 8M, 10 mM Tris-HCl, 100 mM phosphate buffer, pH 4.5) and fractions collected until the O.D$_{280}$ was 0.1. 21 µl of each fraction were loaded on a 12% SDS gel.

K) His-fusion Proteins Renaturation

10% glycerol was added to the denatured proteins. The proteins were then diluted to 20 µg/ml using dialysis buffer I (10% glycerol, 0.5M arginine, 50 mM phosphate buffer, 5 mM reduced glutathione, 0.5 mM oxidised glutathione, 2M urea, pH 8.8) and dialysed against the same buffer at 4° C. for 12-14 hours. The protein was further dialysed against dialysis buffer II (10% glycerol, 0.5M arginine, 50 mM phosphate buffer, 5 mM reduced glutathione, 0.5 mM oxidised glutathione, pH 8.8) for 12-14 hours at 4° C. Protein concentration was evaluated using the formula:

$$\text{Protein (mg/ml)} = (1.55 \times OD_{280}) - (0.76 \times OD_{260})$$

L) His-fusion Large-scale Purification (ORFs 111-129)

500 ml of bacterial cultures were induced and the fusion proteins were obtained soluble in buffer M1, M2 or M3 using the procedure described above. The crude extract of the bacteria was loaded onto a Ni-NTA superflow column (Quiagen) equilibrated with buffer M1, M2 or M3 depending on the solubilization buffer of the fusion proteins. Unbound material was eluted by washing the column with the same buffer. The specific protein was eluted with the corresponding buffer containing 500 mM imidazole and dialysed against the corresponding buffer without imidazole. After each run the columns were sanitized by washing with at least two column volumes of 0.5 M sodium hydroxide and reequilibrated before the next use.

M) Mice Immunisations

20 µg of each purified protein were used to immunise mice intraperitoneally. In the case of ORFs 2, 4, 15, 22, 27, 28, 37, 76, 89 and 97, Balb-C mice were immunised with Al(OH)$_3$ as adjuvant on days 1, 21 and 42, and immune response was monitored in samples taken on day 56. For ORFs 44, 106 and 132, CD1 mice were immunised using the same protocol. For ORFs 25 and 40, CD1 mice were immunised using Freund's adjuvant, rather than AL(OH)$_3$, and the same immunisation protocol was used, except that the immune response was measured on day 42, rather than 56. Similarly, for ORFs 23, 32,38 and 79, CD1 mice were immunised with Freund's adjuvant, but the immune response was measured on day 49.

N) ELISA Assay (Sera Analysis)

The acapsulated MenB M7 strain was plated on chocolate agar plates and incubated overnight at 37° C. Bacterial colonies were collected from the agar plates using a sterile dracon swab and inoculated into 7 ml of Mueller-Hinton Broth (Difco) containing 0.25% Glucose. Bacterial growth was monitored every 30 minutes by following OD$_{620}$. The bacteria were let to grow until the OD reached the value of 0.3-0.4. The culture was centrifuged for 10 minutes at 10000 rpm. The supernatant was discarded and bacteria were washed once with PBS, resuspended in PBS containing 0.025% formaldehyde, and incubated for 2 hours at room temperature and then overnight at 4° C. with stirring. 100 µl bacterial cells were added to each well of a 96 well Greiner plate and incubated overnight at 4° C. The wells were then washed three times with PBT washing buffer (0.1% Tween-20 in PBS). 200 µl of saturation buffer (2.7% Polyvinylpyrrolidone 10 in water) was added to each well and the plates incubated for 2 hours at 37° C. Wells were washed three times with PBT. 200 µl of diluted sera (Dilution buffer: 1% BSA, 0.1% Tween-20, 0.1% NaN$_3$ in PBS) were added to each well and the plates incubated for 90 minutes at 37° C. Wells washed three times with PBT. 100 µl of HRP-conjugated rabbit anti-mouse (Dako) serum diluted 1:2000 in dilution buffer were added to each well and the plates were incubated for 90 minutes at 37° C. Wells were washed three times with PBT buffer. 100 µl of substrate buffer for HRP (25 ml of citrate buffer pH5, 10 mg of O-phenildiamine and 10 µl of H$_2$O) were added to each well and the plates were left at room temperature for 20 minutes. 100 µl H$_2$SO$_4$ was added to each well and OD$_{490}$ was followed. The ELISA was considered positive when OD$_{490}$ was 2.5 times the respective pre-immune sera.

O) FACScan Bacteria Binding Assay Procedure.

The acapsulated MenB M7 strain was plated on chocolate agar plates and incubated overnight at 37° C. Bacterial colonies were collected from the agar plates using a sterile dracon swab and inoculated into 4 tubes containing 8 ml each Mueller-Hinton Broth (Difco) containing 0.25% glucose. Bacterial growth was monitored every 30 minutes by following OD$_{620}$. The bacteria were let to grow until the OD reached the value of 0.35-0.5. The culture was centrifuged for 10 minutes at 4000 rpm. The supernatant was discarded and the pellet was resuspended in blocking buffer (1% BSA, 0.4% NaN$_3$) and centrifuged for 5 minutes at 400 rpm. Cells were resuspended in blocking buffer to reach OD$_{620}$ of 0.07. 100 µl bacterial cells were added to each well of a Costar 96 well plate. 100 µl of diluted (1:200) sera (in blocking buffer) were added to each well and plates incubated for 2 hours at 4° C. Cells were centrifuged for 5 minutes at 400 rpm, the supernatant aspirated and cells washed by addition of 200 µl/well of blocking buffer in each well. 100 µl of R-Phicoerytrin conjugated F(ab)$_2$ goat anti-mouse, diluted 1:100, was added to each well and plates incubated for 1 hour at 4° C. Cells were spun down by centrifugation at 400 rpm for 5 minutes and washed by addition of 200 µl/well of blocking buffer. The supernatant was aspirated and cells resuspended in 200 µl/well of PBS, 0.25% formaldehyde. Samples were transferred to FACScan tubes and read. The condition for FACScan setting were: FL1 on, FL2 and FL3 off; FSC-H threshold:92; FSC PMT Voltage: E 02; SSC PMT: 474; Amp. Gains 7.1; FL-2 PMT: 539; compensation values: 0.

P) OMV Preparations

Bacteria were grown overnight on 5 GC plates, harvested with a loop and resuspended in 10 ml 20 mM Tris-HCl. Heat inactivation was performed at 56° C. for 30 minutes and the bacteria disrupted by sonication for 10 minutes on ice (50% duty cycle, 50% output). Unbroken cells were removed by centrifugation at 5000 g for 10 minutes and the total cell envelope fraction recovered by centrifugation at 50000 g at 4° C. for 75 minutes. To extract cytoplasmic membrane proteins from the crude outer membranes, the whole fraction was resuspended in 2% sarkosyl (Sigma) and incubated at room temperature for 20 minutes. The suspension was centrifuged at 10000 g for 10 minutes to remove aggregates, and the supernatant further ultracentrifuged at 50000 g for 75 minutes to pellet the outer membranes. The outer membranes were resuspended in 10 mM Tris-HCl, pH8 and the protein concentration measured by the Bio-Rad Protein assay, using BSA as a standard.

Q) Whole Extracts Preparation

Bacteria were grown overnight on a GC plate, harvested with a loop and resuspended in 1 ml of 20 mM Tris-HCl. Heat inactivation was performed at 56° C. for 30 minutes.

R) Western Blotting

Purified proteins (500ng/lane), outer membrane vesicles (5 µg) and total cell extracts (25 µg) derived from MenB strain 2996 were loaded on 15% SDS-PAGE and transferred to a nitrocellulose membrane. The transfer was performed for 2 hours at 150 mA at 4° C., in transferring buffer (0.3% Tris base, 1.44% glycine, 20% methanol). The membrane was saturated by overnight incubation at 4° C. in saturation buffer (10% skimmed milk, 0.1% Triton X100 in PBS). The membrane was washed twice with washing buffer (3% skimmed milk, 0.1% Triton X100 in PBS) and incubated for 2 hours at 37° C. with mice sera diluted 1:200 in washing buffer. The membrane was washed twice and incubated for 90 minutes with a 1:2000 dilution of horseradish peroxidase labelled anti-mouse Ig. The membrane was washed twice with 0.1% Triton X100 in PBS and developed with the Opti-4CN Substrate Kit (Bio-Rad). The reaction was stopped by adding water.

S) Bactericidal Assay

MC58 strain was grown overnight at 37° C. on chocolate agar plates. 5-7 colonies were collected and used to inoculate 7 ml Mueller-Hinton broth. The suspension was incubated at 37° C. on a nutator and let to grow until $OD_{620}$ was 0.5-0.8. The culture was aliquoted into sterile 1.5 ml Eppendorf tubes and centrifuged for 20 minutes at maximum speed in a microfuge. The pellet was washed once in Gey's buffer (Gibco) and resuspended in the same buffer to an $OD_{620}$ of 0.5, diluted 1:20000 in Gey's buffer and stored at 25° C.

50 μl of Gey's buffer/1% BSA was added to each well of a 96-well tissue culture plate. 25 μl of diluted mice sera (1:100 in Gey's buffer/0.2% BSA) were added to each well and the plate incubated at 4° C. 25 μl of the previously described bacterial suspension were added to each well. 25 μl of either heat-inactivated (56° C. waterbath for 30 minutes) or normal baby rabbit complement were added to each well. Immediately after the addition of the baby rabbit complement, 22 μl of each sample/well were plated on Mueller-Hinton agar plates (time 0). The 96-well plate was incubated for 1 hour at 37° C. with rotation and then 22 μl of each sample/well were plated on Mueller-Hinton agar plates (time 1). After overnight incubation the colonies corresponding to time 0 and time 1 hour were counted.

Table II (page 493) gives a summary of the cloning, expression and purification results.

Example 1

The following partial DNA sequence was identified in *N. meningitidis* <SEQ ID 1>:

```
  1 ATGAAACAGA CAGTCAA.AT GCTTGCCGCC GCCCTGATTG CCTTGGGCTT
 51 GAACCGACCG GTGTGGNCGG ATGACGTATC GGATTTTCGG GAAAACTTGC
101 A.GCGGCAGC ACAGGGAAAT GCAGCAGCCC AATACAATTT GGGCGCAATG
151 TAT.TACAAA GGACGCGCGT GCGCCGGGAT GATGCTGAAG CGGTCAGATG
201 GTATCGGCAG CCGGCGGAAC AGGGGTTAGC CCAAGCCCAA TACAATTTGG
251 GCTGGATGTA TGCCAACGGG CGCGC.GTGC GCCAAGATGA TACCGAAGCG
301 GTCAGATGGT ATCGGCAGGC GGCAGCGCAG GGGGTTGTCC AAGCCCAATA
351 CAATTTGGGC GTGATATATG CCGAAGGACG TGGAGTGCGC CAAGACGATG
401 TCGAAGCGGT CAGATGGTTT CGGCAGGCGG CAGCGCAGGG GGTAGCCCAA
451 GCCCAAAACA ATTTGGGCGT GATGTATGCC GAAAGANCGC GCGTGCGCCA
501 AGACCG...
```

This corresponds to the amino acid sequence <SEQ ID 2; ORF37>:

```
  1 MKQTVXMLAA ALIALGLNRP VWXDDVSDFR ENLXAAAQGN AAAQYNLGAM
 51 YXQRTRVRRD DAEAVRWYRQ PAEQGLAQAQ YNLGWMYANG RXVRQDDTEA
101 VRWYRQAAAQ GVVQAQYNLG VIYAEGRGVR QDDVEAVRWF RQAAAQGVAQ
151 AQNNLGVMYA ERXRVRQD...
```

Further work revealed the complete nucleotide sequence <SEQ ID 3>:

```
  1 ATGAAACAGA CAGTCAAATG GCTTGCCGCC GCCCTGATTG CCTTGGGCTT
 51 GAACCGAGCG GTGTGGGCGG ATGACGTATC GGATTTTCGG GAAAACTTGC
101 AGGCGGCAGC ACAGGGAAAT GCAGCAGCCC AATACAATTT GGGCGCAATG
151 TATTACAAAG GACGCGGCGT GCGCCGGGAT GATGCTGAAG CGGTCAGATG
201 GTATCGGCAG GCGGCGGAAC AGGGGTTAGC CCAAGCCCAA TACAATTTGG
251 GCTGGATGTA TGCCAACGGG CGCGGCGTGC GCCAAGATGA TACCGAAGCG
301 GTCAGATGGT ATCGGCAGGC GGCAGCGCAG GGGGTTGTCC AAGCCCAATA
```

```
351 CAATTTGGGC GTGATATATG CCGAAGGACG TGGAGTGCGC CAAGACGATG

401 TCGAAGCGGT CAGATGGTTT CGGCAGGCGG CAGCGCAGGG GGTAGCCCAA

451 GCCCAAAACA ATTTGGGCGT GATGTATGCC GAAAGACGCG GCGTGCGCCA

501 AGACCGCGCC CTTGCACAAG AATGGTTTGG CAAGGCTTGT CAAACGGAG

551 ACCAAGACGG CTGCGACAAT GACCAACGCC TGAAGGCGGG TTATTGA
```

This corresponds to the amino acid sequence <SEQ ID 4; ORF37-1>:

```
  1 MKQTVKWLAA ALIALGLNRA VWADDVSDFR ENLQAAAQGN AAAQYNLGAM

51 YYKGRGVRRD DAEAVRWYRQ AAEQGLAQAQ YNLGWMYANG RGVRQDDTEA

101 VRWYRQAAAQ GVVQAQYNLG VIYAEGRGVR QDDVEAVRWF RQAAAQGVAQ

151 AQNNLGVMYA ERRGVRQDRA LAQEWFGKAC QNGDQDGCDN DQRLKAGY*
```

Further work identified the corresponding gene in strain A of *N. meningitidis* <SEQ ID 5>:

```
  1 ATGAAACAGA CAGTCAAATG GCTTGCCGCC GCCCTGATTG CCTTGGGCTT

51 GAACCAAGCG GTGTGGGCGG ATGACGTATC GGATTTTCGG GAAAACTTGC

101 AGGCGGCAGC ACAGGGAAAT GCAGCAGCCC AAAACAATTT GGGCGTGATG

151 TATGCCGAAA GACGCGGCGT GCGCCAAGAC CGCGCCCTTG CACAAGAATG

201 GCTTGGCAAG GCTTGTCAAA ACGGATACCA AGACAGCTGC GACAATGACC

251 AACGCCTGAA AGCGGGTTAT TGA
```

This encodes a protein having amino acid sequence <SEQ ID 6; ORF37a>:

```
 1 MKQTVKWLAA ALIALGLNQA VWADDVSDFR ENLQAAAQGN AAAQNNLGVM

51 YAERRGVRQD RALAQEWLGK ACQNGYQDSC DNDQRLKAGY *
```

The originally-identified partial strain B sequence (ORF37) shows 68.0% identity over a 75aa overlap with ORF37a:

```
                    10        20        30        40        50        60
orf37.pep   MKQTVXMLAAALIALGLNRPVWXDDVSDFRENLXAAAQGNAAAQYNLGAMYXQRTRVRRD
            |||||  |||||||||||: || |||||||||| |||||||||| |||:|| :|  ||:|
orf37a      MKQTVKWLAAALIALGLNQAVWADDVSDFRENLQAAAQGNAAAQNNLGVMYAERRGVRQD
                    10        20        30        40        50        60

70        80        90       100       110       120
orf37.pep   DAEAVRWYRQPAEQGLAQAQYNLGWMYANGRXVRQDDTEAVRWYRQAAAQGVVQAQYNLG
             | | :|  :  ::|
orf37a      RALAQEWLGKACQNGYQDSCDNDQRLKAGYX
                    70        80        90
```

Further work identified the corresponding gene in *N. gonorrhoeae* <SEQ ID 7>:

```
  1 ATGAAACAGA CAGTCAAATG GCTTGCCGCC GCCCTGATTG CCTTGGGCTT

51 GAACCAAGCG GTGTGGGCGG GTGACGTATC GGATTTTCGG GAAAACTTGC

101 AGgcggcaGA ACaggGAAAT GCAGCAGCCC AATTCAATTT GGGCGTGATG
```

```
-continued
151 TATGAAAATG GACAAGGAGT TCGTCAAGAT TATGTACAGG CAGTGCAGTG

201 GTATCGCAAG GCTTCAGAAC AAGGGGATGC CCAAGCCCAA TACAATTTGG

251 GCTTGATGTA TTACGATGGA CGCGGCGTGC GCCAAGACCT TGCGCTCGCT

301 CAACAATGGC TTGGCAAGGC TTGTCAAAAC GGAGACCAAA ACAGCTGCGA

351 CAATGACCAA CGCCTGAAGG CGGGTTATTA A
```

This encodes a protein having amino acid sequence <SEQ ID 8; ORF37ng>:

```
  1 MKQTVKWLAA ALIALGLNQA VWAGDVSDFR ENLQAAEQGN AAAQFNLGVM

51 YENGQGVRQD YVQAVQWYRK ASEQGDAQAQ YNLGLMYYDG RGVRQDLALA

101 QQWLGKACQN GDQNSCDNDQ RLKAGY*
```

The originally-identified partial strain B sequence (ORF37) shows 64.9% identity over a 111aa overlap with ORF37ng:

```
orf37.pep   MKQTVXMLAAALIALGLNRPVWXDDVSDFRENLXAAAQGNAAAQYNLGAMYXQRTRVRRD    60
            ||||  |||||||||||:  ||  ||||||||| || |||||||:||:|| :    ||:|
orf37ng     MKQTVKWLAAALIALGLNQAVWAGDVSDFRENLQAAEQGNAAAQFNLGVMYENGQGVRQD    60 orf37.pep   DAEAVRWYRQPAEQGLAQAQYNLGWMYANGRXVRQDDTEAVRWYRQAAAQGVVQAQYNLG   120
             ::||:|||: :||| |||||||| || :|| |||| : |:|| : |  :|   :|
 orf37ng    YVQAVQWYRKASEQGDAQAQYNLGLMYYDGRGVRQDLALAQQWLGKACQNGDQNSCDNDQ    12 orf37.pep   VIYAEGRGVRQDDVEAVRWFRQAAAQGVAQAQNNLGVMYAERXRVRQD             168 orf37ng     RLKAGY                                                        126
```

The complete strain B sequence (ORF37-1) and ORF37ng show 51.5% identity in 198 aa overlap:

```
                         10        20        30        40        50        60
      orf37-1.pep  MKQTVKWLAAALIALGLNRAVWADDVSDFRENLQAAAQGNAAAQYNLGAMYYKGRGVRRD
                   ||||||||||||||||||| ||||  ||||||||||| ||||||||   |: :||| |:|
      orf37ng      MKQTVKWLAAALIALGLNQAVWAGDVSDFRENLQAAEQGNAAAQFNLGVMYENGQGVRQD
                         10        20        30        40        50        60

70        80        90       100       110       120
      orf37-1.pep  DAEAVRWYRQAAEQGLAQAQYNLGWMYANGRGVRQDDTEAVRWYRQAAAQGVVQAQYNLG
                   ::||:|||:|:||| |||||||| ||  :||||||
      orf37ng      YVQAVQWYRKASEQGDAQAQYNLGLMYYDGRGVRQD------------------------
                         70        80        90

130       140       150       160       170       180
      orf37-1.pep  VIYAEGRGVRQDDVEAVRWFRQAAAQGVAQAQNNLGVMYAERRGVRQDRALAQEWFGKAC
                                                                   ||||:|:||||
      orf37ng      -----------------------------------------------LALAQQWLGKAC
                                                                          100

190      199
      orf37-1.pep  QNGDQDGCDNDQRLKAGYX
                   |||||::||||||||||||
      orf37ng      QNGDQNSCDNDQRLKAGYX
                        110       120
```

Computer analysis of these amino acid sequences indicates a putative leader sequence, and it was predicted that the proteins from N. meningitidis and N. gonorrhoeae, and their epitopes, could be useful antigens for vaccines or diagnostics, or for raising antibodies.

ORF37-1 (11 kDa) was cloned in pET and pGex vectors and expressed in E. coli, as described above. The products of protein expression and purification were analyzed by SDS-PAGE. FIG. 1A shows the results of affinity purification of the GST-fusion protein, and FIG. 1B shows the results of expression of the His-fusion in E. coli. Purified GST-fusion protein was used to immunise mice, whose sera were used for ELISA (positive result), FACS analysis (FIG. 1C), and a bactericidal assay (FIG. 1D). These experiments confirm that ORF37-1 is a surface-exposed protein, and that it is a useful immunogen.

FIG. 1E shows plots of hydrophilicity, antigenic index, and AMPHI regions for ORF37-1.

Example 2

The following partial DNA sequence was identified in N. meningitidis <SEQ ID 9>:

```
TTCGGCGA CATCGGCGGT TTGAAGGTCA ATGCCCCCGT
CAAATCCGCA GGCGTATTGG TCGGGCGCGT CGGCGCTATC
GGACTTGACC CGAAATCCTA TCAGGCGAGG GTGCGCCTCG
ATTTGGACGG CAAGTATCAG TTCAGCAGCG ACGTTTCCGC
GCAAATCCTG ACTTCsGGAC TTTTGGGCGA GCAGTACATC
GGGCTGCAGC AGGGCGGCGA CACGGAAAAC CTTGCTGCCG
GCGACACCAT CTCCGTAACC AGTTCTGCAA TGGTTCTGGA
AAACCTTATC GGCAAATTCA TGACGAGTTT TGCCGAGAAA
AATGCCGACG GCGGCAATGC GGAAAAAGCC GCCGAATAA
```

This corresponds to the amino acid sequence <SEQ ID 10>:

```
  1 FGDIGGLKVN APVKSAGVLV GRVGAIGLDP KSYQARVRLD LDGKYQFSSD
 51 VSAQILTSGL LGEQYIGLQQ GGDTENLAAG DTISVTSSAM VLENLIGKFM
101 TSFAEKNADG GNAEKAAE*
```

Computer analysis of this amino acid sequence gave the following results:

Homology with a Hypothetical H. influenzae Protein (ybrd.haein; Accession Number p45029)

SEQ ID 9 and ybrd.haein show 48.4% aa identity in 122 aa overlap:

```
                20         30         40         50         60         70
yrbd.h   LGIGALVFLGLRVANVQGFAETKSYTVTATFDNIGGLKVRAPLKIGGVVIGRVSAITLDE
             |::|||||:||:| :||::|||:||:||
N.m                                 FGDIGGLKVNAPVKSAGVLVGRVGAIGLDP
                                        10         20         30
                80         90        100        110        120        130
yrbd.h   KSYLPKVSIAINQEYNEIPENSSLSIKTSGLLGEQYIALTMGFDDGDTAMLKNGSQIQDT
         |||  ::|:::::  :|  :::::  |   |  |||||||||:|   |   |||: | :|: |   |
N.m      KSYQARVRLDLDGKY-QFSSDVSAQILTSGLLGEQYIGLQQG---GDTENLAAGDTISVT
                40         50         60         70         80
               140        150        160
yrbd.h   TSAMVLEDLIGQFL--YGSKKSDGNEKSESTEQ
         :|||||||:|||:|:  :::|::||::  ::::|:
N.m      SSAMVLENLIGKFMTSFAEKNADGGNAEKAAEX
                90        100        110        120
```

Homology with a Predicted ORF from N. gonorrhoeae

SEQ ID 9 shows 99.2% identity over a 118aa overlap with a predicted ORF from N. gonorrhoeae.

```
                20         30         40         50         60         70
yrbd     GAAAVAFLAFRVAGGAAFGGSDKTYAVYADFGDIGGLKVNAPVKSAGVLVGRVGAIGLDP
                                       ||||||||||||||||||||||||||||||
N.m                                    FGDIGGLKVNAPVKSAGVLVGRVGAIGLDP
                                           10         20         30
                80         90        100        110        120        130
yrbd     KSYQARVRLDLDGKYQFSSDVSAQILTSGLLGEQYIGLQQGGDTENLAAGDTISVTSSAM
         ||||||||||||||||||||||||||||||||||||||||||||||||||||||||||||
N.m      KSYQARVRLDLDGKYQFSSDVSAQILTSGLLGEQYIGLQQGGDTENLAAGDTISVTSSAM
                40         50         60         70         80         90
```

```
              140        150        160
    yrbd  VLENLIGKFMTSFAEKNAEGGNAEKAAEX
          ||||||||||||||||||:||||||||||
    N.m   VLENLIGKFMTSFAEKNADGGNAEKAAEX
                   100        110        120
```

The complete yrbd *H. influenzae* sequence has a leader sequence and it is expected that the full-length homologous *N. meningitidis* protein will also have one. This suggests that it is either a membrane protein, a secreted protein, or a surface protein and that the protein, or one of its epitopes, could be a useful antigen for vaccines or diagnostics.

Example 3

The following partial DNA sequence was identified in *N. meningitidis* <SEQ ID 11>:

```
  1..ATTTTGATAT ACCTCATCCG CAAGAATCTA GGTTCGCCCG TCTTCTTCTT

51  TCAGGAACGC CCCGGAAAGG ACGGAAAACC TTTTAAAATG GTCAAATTCC

101  GTTCCATGCG CGACGGCTTG TATTCAGACG GCATTCCGCT GCCCGACGGA

151  GAACGCCTGA CACCGTTCGG CAAAAAACTG CGTGCCGcCA GTwTGGACGA

201  ACTGCCTGAA TTATGGAATA TCTTAAAAGG CGAGATGAGC CTGGTCGGCC

251  CCCGCCCGCT GCTGATGCAA TATCTGCCGC TGTACGACAA CTTCCAAAAC

301  CGCCGCCACG AAATGAAACC CGGCATTACC GGCTGGGCGC AGGTCAACGG

351  GCGCAACGCg CTTTCGTGGG ACGAAAAATT CGCCTGCGAT GTTTGGTATA

401  TCGACCACTT CAGCCTGTGC CTCGACATCA AAATCCTACT GCTGACGGTT

451  AAAAAGTAT TAATCAAGGA AGGGATTTCC GCACAGGGCG AACA.aCCAT

501  GCCCCCTTTC ACAGGAAAAC GCAAACTCGC CGTCGTCGGT GCGGGCGGAC

551  ACGGAAAAGT CGTTGCCGAC CTTGCCGCCG CACTCGGCCG GTACAGGGAA

601  ATCGTTTTTC TGGACGACCG CGCACAAGGC AGCGTCAACG GCTTTTCCGT

651  CATCGGCACG ACGCTGCTGC TTGAAAACAG TTTATCGCCC GAACAATACG

701  ACGTCGCCGT CGCCGTCGGC AACAACCGCA TCCGCCGCCA AATCGCCGAA

751  AAAGCCGCCG CGCTCGGCTT CGCCCTGCCC GTACTGGTTC ATCCGGACGC

801  GACCGTCTCG CCTTCTGCAA CAGTCGGACA AGGCAGCGTC GTTATGGCGA

851  AAGCGGTCG..
```

This corresponds to the amino acid sequence <SEQ ID 12; ORF3>:

```
  1..ILIYLIRKNL GSPVFFFQER PGKDGKPFKM VKFRSMRDGL YSDGIPLPDG

51  ERLTPFGKKL RAASXDELPE LWNILKGEMS LVGPRPLLMQ YLPLYDNFQN

101  RRHEMKPGIT GWAQVNGRNA LSWDEKFACD VWYIDHFSLC LDIKILLLTV

151  KKVLIKEGIS AQGEXTMPPF TGKRKLAVVG AGGHGKVVAD LAAALGRYRE

201  IVFLDDRAQG SVNGFSVIGT TLLLENSLSP EQYDVAVAVG NNRIRRQIAE

251  KAAALGFALP VLVHPDATVS PSATVGQGSV VMAKAV..
```

Further sequence analysis revealed the complete nucleotide sequence <SEQ ID 13>:

```
   1 ATGAGTAAAT TCTTCAAACG CCTGTTTGAC ATTGTTGCCT CCGCCTCGGG
  51 ACTGATTTTC CTCTCGCCAG TATTTTTGAT TTTGATATAC CTCATCCGCA
 101 AGAATCTAGG TTCGCCCGTC TTCTTCTTTC AGGAACGCCC CGGAAAGGAC
 151 GGAAAACCTT TTAAAATGGT CAAATTCCGT TCCATGCGCG ACGCGCTTGA
 201 TTCAGACGGC ATTCCGCTGC CCGACGGAGA ACGCCTGACA CCGTTCGGCA
 251 AAAAACTGCG TGCCGCCAGT TTGGACGAAC TGCCTGAATT ATGGAATATC
 301 TTAAAAGGCG AGATGAGCCT GGTCGGCCCC CGCCCGCTGC TGATGCAATA
 351 TCTGCCGCTG TACGACAACT TCCAAAACCG CCGCCACGAA ATGAAACCCG
 401 GCATTACCGG CTGGGCGCAG GTCAACGGGC GCAACGCGCT TTCGTGGGAC
 451 GAAAAATTCG CCTGCGATGT TTGGTATATC GACCACTTCA GCCTGTGCCT
 501 CGACATCAAA ATCCTACTGC TGACGGTTAA AAAAGTATTA ATCAAGGAAG
 551 GGATTTCCGC ACAGGGCGAA GCCACCATGC CCCCTTTCAC AGGAAAACGC
 601 AAACTCGCCG TCGTCGGTGC GGGCGGACAC GGAAAAGTCG TTGCCGACCT
 651 TGCCGCCGCA CTCGGCCGGT ACAGGGAAAT CGTTTTTCTG GACGACCGCG
 701 CACAAGGCAG CGTCAACGGC TTTTCCGTCA TCGGCACGAC GCTGCTGCTT
 751 GAAAACAGTT TATCGCCCGA ACAATACGAC GTCGCCGTCG CCGTCGGCAA
 801 CAACCGCATC CGCCGCCAAA TCGCCGAAAA AGCCGCCGCG CTCGGCTTCG
 851 CCCTGCCCGT TCTGGTTCAT CCGGACGCGA CCGTCTCGCC TTCTGCAACA
 901 GTCGGACAAG GCAGCGTCGT TATGGCGAAA GCCGTCGTAC AGGCAGGCAG
 951 CGTATTGAAA GACGGCGTGA TTGTGAACAC TGCCGCCACC GTCGATCACG
1001 ACTGCCTGCT TAACGCTTTC GTCCACATCA GCCCAGGCGC GCACCTGTCG
1051 GGCAACACGC ATATCGGCGA AGAAAGCTGG ATAGGCACGG GCGCGTGCAG
1101 CCGCCAGCAG ATCCGTATCG GCAGCCGCGC AACCATTGGA GCGGGCGCAG
1151 TCGTCGTACG CGACGTTTCA GACGGCATGA CCGTCGCGGG CAATCCGGCA
1201 AAGCCGCTGC CGCGCAAAAA CCCCGAGACC TCGACAGCAT AA
```

This corresponds to the amino acid sequence <SEQ ID 14; ORF3-1>:

```
   1 MSKFFKRLFD IVASASGLIF LSPVFLILIY LIRKNLGSPV FFFQERPGKD

51 GKPFKMVKFR SMRDALDSDG IPLPDGERLT PFGKKLRAAS LDELPELWNI

101 LKGEMSLVGP RPLLMQYLPL YDNFQNRRHE MKPGITWAQ VNGRNALSWD

151 EKFACDVWYI DHFSLCLDIK ILLLTVKKVL IKEGISAQGE ATMPPFTGKR

201 KLAVVGAGGH GKVVADLAAA LGRYREIVFL DDRAQGSVNG FSVIGTTLLL

251 ENSLSPEQYD VAVAVGNNRI RRQIAEKAAA DGFALPVLVH PDATVSPSAT

301 VGQGSVVMAK AVVQAGSVLK DGIVVNTAAT VDHDCLLNAF VHISPGAHLS

351 GNTHIGEESW IGTGACSRQQ IRIGSRATIG AGAVVVRDVS DGMTVAGNPA

401 KPLPRKNPET STA*
```

Computer analysis of this amino acid sequence gave the following results:

Homology with a Predicted ORF from *N. meningitidis* (Strain A)

ORF3 shows 93.0% identity over a 286aa overlap with an ORF (ORF3a) from strain A of *N. meningitidis*.

```
                                10        20        30
orf3.pep                ILIYLIRKNLGSPVFFFQERPGKDGKPFKMVKFR
                        |||||||||||||||||||||||||||||||||
orf3a    MSKFFKRLFDIVASASGLIFLSPVFLILIYLIRKNLGSPVFFFQERPGKDGKPFKMVKFR
             10        20        30        40        50        60
              40        50        60        70        80        90
orf3.pep SMRDGLYSDGIPLPDGERLTPFGKKLRAASXDELPELWNILKGEMSLVGPRPLLMQYLPL
         ||:|:|  ||||  ||||||||||||||| ||||||::||| ||||||||||||||||
orf3a    SMHDALDSDGILLPDGERLTPFGKKLRAASLDELPELWNVLKGDMSLVGPRPLLMQYLPL
              70        80        90       100       110       120
             100       110       120       130       140       150
orf3.pep YDNFQNRRHEMKPGITGWAQVNGRNALSWDEKFACDVWYIDHFSLCLDIKILLLTVKKVL
         ||||||||||||| |||||||||||||||||:|||||||||||||||||||||||||||
orf3a    YDNFQNRRHEMKPBITGWAQVNGRNALSWDERFACDIWYIDHFSLCLDIKILLLTVKKVL
             130       140       150       160       170       180
             160       170       180       190       200       210
orf3.pep IKEGISAQGEXTMPPFTGKRKLAVVGAGGHGKVVADLAAALGRYREIVFLDDRAQGSVNG
         |||||||||| |||||||||||||||||||||||:||||||| | |||||||||:||||
orf3a    IKEGISAQGEATMPPFTGKRKLAVVGAGGHGKVVAELAAALGTYGEIVFLDDRVQGSVNG
             190       200       210       220       230       240
             220       230       240       250       260       270
orf3.pep FSVIGTTLLLENSLSPEQYDVAVAVGNNRIRRQIAEKAAALGFALPVLVHPDATVSPSAT
         | |||||||||||||||:|:|||||||||||||| |||||||||||:|||:||||||||
orf3a    FPVIGTTLLLENSLSPEQFDIAVAVGNNRIRRQIAWKAAALGFALPVLIHPDSTVSPSAT
             250       260       270       280       290       300
             280
orf3.pep VGQGSVVMAKAV
         ||||:|||||||
orf3a    VGQGGVVMAKAVVQADSVLKDGVIVNTAATVDHDCLLDAFVHISPGAHLSGNTRIGEESW
             310       320       330       340       350       360
```

The complete length ORF3a nucleotide sequence <SEQ ID 15> is:

```
  1 ATGAGTAAAT TCTTCAAACG CCTGTTTGAC ATTGTTGCCT CCGCCTCGGG

51 ACTGATTTTC CTCTCGCCAG TATTTTTGAT TTTGATATAC CTCATCCGCA

101 AGAATCTGGG TTCGCCCGTC TTCTTCTTTC AGGAACGCCC CGGAAAGGAC

151 GGAAAACCTT TTAAAATGGT CAAATTCCGT TCCATGCACG ACGCGCTTGA

201 TTCAGACGGC ATTCTGCTGC CCGACGGAGA ACGCCTGACA CCGTTCGGCA

251 AAAAACTGCG TGCCGCCAGT TTGGACGAAC TGCCCGAACT GTGGAACGTC

301 CTCAAAGGCG ACATGAGCCT GGTCGGCCCC CGCCCGCTGC TGATGCAATA

351 TCTGCCGCTG TACGACAACT TCCAAAACCG CCGCCACGAA ATGAAACCGG

401 GCATTACCGG CTGGGCGCAG GTCAACGGGC GCAACGCGCT TTCGTGGGAC

451 GAACGCTTCG CATGCGACAT CTGGTATATC GACCACTTCA GCCTGTGCCT

501 CGAGATCAAA ATCCTACTGC TGACGGTTAA AAAAGTATTA ATCAAAGAAG

551 GGATTTCCGC ACAGGGCGAA GCCACCATGC CCCCTTTCAC AGGAAAACGC

601 AAACTTGCCG TCGTCGGTGC GGGCGGACAC GGCAAAGTCG TTGCCGAGCT

651 TGCCGCCGCA CTCGGCACAT ACGGCGAAAT CGTTTTTCTG GACGACCGCG

701 TCCAAGGCAG CGTCAACGGC TTCCCCGTCA TCGGCACGAC GCTGCTGCTT

751 GAAAACAGTT TATCGCCCGA ACAATTCGAC ATCGCCGTCG CCGTCGGCAA

801 CAACCGCATC CGCCGCCAAA TCGCCGAAAA AGCCGCCGCG CTCGGCTTCG

851 CCCTGCCCGT CCTGATTCAT CCGGACTCGA CCGTCTCGCC TTCTGCAACA
```

```
 901 GTCGGACAAG GCGGCGTCGT TATGGCGAAA GCCGTCGTAC AGGCTGACAG

951 CGTATTGAAA GACGGCGTAA TTGTGAACAC TGCCGCCACC GTCGATCACG

1001 ATTGCCTGCT TGATGCTTTC GTCCACATCA GCCCGGGCGC GCACCTGTCG

1051 GGCAACACGC GTATCGGCGA AGAAAGCTGG ATAGGCACAG GCGCGTGCAG

1101 CCGCCAGCAG ATCCGTATCG GCAGCCGCGC AACCATTGGA GCGGGCGCAG

1151 TCGTCGTGCG CGACGTTTCA GACGGCATGA CCGTCGCGGG CAACCCGGCA

1201 AAACCATTGG CAGGCAAAAA TACCGAGACC CTGCGGTCGT AA
```

This is predicted to encode a protein having amino acid sequence <SEQ ID 16>:

```
  1 MSKFFKRLFD IVASASGLIF LSPVFLILIY LIRKNLGSPV FFFQERPGKD

51 GKPFKMVKFR SMHDALDSDG ILLPDGERLT PFGKKLRAAS LDELPELWNV

101 LKGDMSLVGP RPLLMQYLPL YDNFQNRRHE MKPGITGWAQ VNGRNALSWD

151 ERFACDIWYI DHFSLCLDIK ILLLTVKKVL IKEGISAQGE ATMPPFTGKR

201 KLAVVGAGGH GKVVAELAAA LGTYGEIVFL DDRVQGSVNG FPVIGTTLLL

251 ENSLSPEQFD IAVAVGNNRI RRQIAEKAAA LGFALPVLIH PDSTVSPSAT

301 VGQGGVVMAK AVVQADSVLK DGVIVNTAAT VDHDCLLDAF VHISPGAHLS

351 GNTRIGEESW IGTGACSRQQ IRIGSRATIG AGAVVVRDVS DGMTVAGNPA

401 KPLAGKNTET LRS*
```

Two transmembrane domains are underlined.
ORF3-1 shows 94.6% identity in 410 aa overlap with ORF3a:

```
                  10         20         30         40         50         60
     orf3a.pep  MSKFFKRLFDIVASASGLIFLSPVFLILIYLIRKNLGSPVFFFQERPGKDGKPFKMVKFR
                ||||||||||||||||||||||||||||||||||||||||||||||||||||||||||||
       orf3-1  MSKFFKRLFDIVASASGLIFLSPVFLILIYLIRKNLGSPVFFFQERPGKDGKPFKMVKFR
                  10         20         30         40         50         60

70         80         90        100        110        120
     orf3a.pep  SMHDALDSDGILLPDGERLTPFGKKLRAASLDELPELWNVLKGDMSLVGPRPLLMQYLPL
                ||:|||||||| |||||||||||||||||||||||||||| |||:|||||||||||||||
       orf3-1  SMRDALDSDGIPLPDGERLTPFGKKLRAASLDELPELWNILKGEMSLVGPRPLLMQYLPL
                  70         80         90        100        110        120

130        140        150        160        170        180
     orf3a.pep  YDNFQNRRHEMKPGITGWAQVNGRNALSWDERFACDIWYIDHFSLCLDIKILLLTVKKVL
                |||||||||||||||||||||||||||||||:||||:|||||||||||||||||||||||
       orf3-1  YDNFQNRRHEMKPGITGWAQVNGRNALSWDEKFACDVWYIDHFSLCLDIKILLLTVKKVL
                 130        140        150        160        170        180

190        200        210        220        230        240
     orf3a.pep  IKEGISAQGEATMPPFTGKRKLAVVGAGGHGKVVAELAAALGTYGEIVFLDDRVQGSVNG
                |||||||||||||||||||||||||||||||||||:|||||| | |||||||||:|||||
       orf3-1  IKEGISAQGEATMPPFTGKRKLAVVGAGGHGKVVADLAAALGRYREIVFLDDRAQGSVNG
                 190        200        210        220        230        240

250        260        270        280        290        300
     orf3a.pep  FPVIGTTLLLENSLSPEQFDIAVAVGNNRIRRQIAEKAAALGFALPVLIHPDSTVSPSAT
                | ||||||||||||||||::||||||||||||||||||||||||||||| |||||||||
       orf3-1  FSVIGTTLLLENSLSPEQYDVAVAVGNNRIRRQIAEKAAALGFALPVLVHPDATVSPSAT
                 250        260        270        280        290        300

310        320        330        340        350        360
     orf3a.pep  VGQGGVVMAKAVVQADSVLKDGVIVNTAATVDHDCLLDAFVHISPGAHLSGNTRIGEESW
                ||||:|||||||||| ||||||||||||||||||||:|||||||||||||||| ||||||
       orf3-1  VGQGSVVMAKAVVQAGSVLKDGVIVNTAATVDHDCLLNAFVHISPGAHLSGNTHIGEESW
                 310        320        330        340        350        360

370        380        390        400        410
     orf3a.pep  IGTGACSRQQIRIGSRATIGAGAVVVRDVSDGMTVAGNPAKPLAGKNTETLRSX
                |||||||||||||||||||||||||||||||||||||||||||  || ||
       orf3-1  IGTGACSRQQIRIGSRATIGAGAVVVRDVSDGMTVAGNPAKPLPRKNPETSTAX
                 370        380        390        400        410
```

Homology with Hypothetical Protein Encoded by yvfc Gene
(Accession Z71928) of *B. subtilis*

ORF3 and YVFC proteins show 55% aa identity in 170 aa overlap (BLASTp):

```
ORF3    3   IYLIRKNLGSPVFFFQERPGKDGKPFKMVKFRSMRDGLYSDGIPLPDGERLTPFGKKLRA  62
            I ++R  +GSPVFF Q RPG  GKPF + KFR+M D    S G  LPD  RLT  G+ +R
yvfc   27   IAVVRLKIGSPVFFKQVRPGLHGKPFTLYKFRTMTDERDSKGNLLPDEVRLTKTGRLIRK  86

ORF3   63   ASXDELPELWNILKGEMSLVGPRPLLMQYLPLYDNFQNRRHEMKPGITGWAQVNGRNALS 122
            S DELP+L N+LKG++SLVGPRPLLM YLPLY   Q RRHE+KPGITGWAQ+NGRNA+S
yvfc   87   LSIDELPQLLNVLKGDLSLVGPRPLLMDYLPLYTEKQARRHEVKPGITGWAQINGRNAIS 146

ORF3  123   WDEKFACDVWYIDHFSLCLDXXXXXXXXXXXXXXXXEGISAQGEXTMPPFTG         172
            W++KF  DVWY+D++S  LD                EGI    T  FTG
yvfc  147   WEKKFELDVWYVDNWSFFLDLKILCLTVRKVLVSEGIQQTNHVTAERFTG          196
```

Homology with a Predicted ORF from *N. gonorrhoeae*
ORF3 shows 86.3% identity over a 286aa overlap with a predicted ORF (ORF3.ng) from *N. gonorrhoeae*:

```
orf3                    ILIYLIRKNLGSPVFFFQERPGKDGKPFKMVKFR   34
                         :||||||||  |||||| ::|||||||||||||||
orf3ng  MSKAVKRLFDIIASASGLIVLSPVFLVLIYLIRKNKGSPVFFIRERPGKDGKPFKMVKFR   60
orf3    SMRDGLYSDGIPLPDGERLTPFGKKLRAASXDELPELWNILKGEMSLVGPRPLLMQYLPL   94
        ||||:| ||||||||| |||| :|||||||:| ||||||||:||||||||||||||||||
orf3ng  SMRDALDSDGIPLPDSERLTDFGKKLRATSLDELPELWNVLKGEMSLVGPRPLLMQYLPL  120
orf3    YDNFQNRRHEMKPGITGWAQVNGRNALSWDEKFACDVWYIDHFSLCLDIKILLLTVKKVL  154
        |::|||||||||||||||||||||||||||||:|||||  :|||  :|||  :|||||||
orf3ng  YNKFQNRRHEMKPGITGWAQVNGRNALSWDEKFSCDVWYTDNFSFWLDMKILFLTVKKVL  180
orf3    IKEGISAQGEXTMPPFTGKRKLAVVGAGGHGKVVADLAAALGRYREIVFLDDRAQGSVNG  214
        ||||||||||| ||||:|:|||||:||||||||||:|||||| | |||||||:|||||
orf3ng  IKEGISAQGEATMPPFAGNRKLAVIGAGGHGKVVAELAAALGTYGEIVFLDDRTQGSVNG  240
orf3    FSVIGTTLLLENSLSPEQYDVAVAVGNNRIRRQIAEKAAALGFALPVLVHPDATVSPSAT  274
        | ||||||||||||||||:|::|:||||||||||:||||||||:|||||||||||||||
orf3ng  FPVIGTTLLLENSLSPEQFDITVAVGNNRIRRQITENAAALGFKLPVLIHPDATVSPSAI  300
orf3    VGQGSVVMAKAV                                                 286
        :|||||||||||
orf3ng  IGQGSVVMAKAVVQAGSVLKDGVIVNTAATVDHDCLLDAFVHISPGAHLSGNTRIGEESR  360
```

The complete length ORF3ng nucleotide sequence <SEQ ID 17> is:

```
  1 ATGAGTAAAG CCGTCAAACG CCTGTTCGAC ATCATCGCAT CCGCATCGGG
 51 GCTGATTGTC CTGTCGCCCG TGTTTTTGGT TTTAATATAC CTCATCCGCA
101 AAAACTTAGG TTCGCCCGTC TTCTTCattC GGGAACGCCc cgGAAAGGAc
151 ggaaaacCTT TTAAAATGGT CAAATTCCGT TCCAtgcgcg acgcgcttGA
201 TTCAGACGGC ATTCCGCTGC CCGATAGCGA ACGCCTGACC GATTTCGGCA
251 AAAAATTACG CGCCACCAGT TTGGACGAAC TTCCTGAATT ATGGAATGTC
301 CTCAAAGGCG AGATGAGCCT GGTCGGCCCC CGCCCGCTTT TGATGCAGTA
351 TCTGCCGCTT TACAACAAAT TCAAAACCG CCGCCACGAA ATGAAACCGG
401 GCATTACCGG CTGGGCGCAG GTCAACGGGC GCAACGCGCT TTCGTGGGAC
451 GAAAAGTTCT CCTGCGATGT TTGGTACACC GACAATTTCA GCTTTTGGCT
501 GGATATGAAA ATCCTGTTTC TGACAGTCAA AAAGTCTTG ATTAAAGAAG
551 GCATTTCGGC GCAAGGGGAA GCCACCATGC CCCCTTTCGC GGGGAATCGC
601 AAACTCGCCG TTATCGGCGC GGGCGGACAC GGCAAAGTCG TTGCCGAGCT
651 TGCCGCCGCA CTCGGCACAT ACGGCGAAAT CGTTTTTCTG GACGACCGCA
701 CCCAAGGCAG CGTCAACGGC TTCCCCGTCA TCGGCACGAC GCTGCTGCTT
```

```
 751 GAAAACAGTT TATCGCCCGA ACAATTCGAC ATCACCGTCG CCGTCGGCAA

801 CAACCGCATC CGCCGCCAAA TCACCGAAAA CGCCGCCGCG CTCGGCTTCA

851 AACTGCCCGT TCTGATTCAT CCCGACGCGA CCGTCTCGCC TTCTGCAATA

901 ATCGGACAAG GCAGCGTCGT AATGGCGAAA GCCGTCGTAC AGGCCGGCAG

951 CGTATTGAAA GACGGCGTGA TTGTGAACAC TGCCGCCACC GTCGATCACG

1001 ACTGCCTGCT TGACGCTTTC GtccaCATCA GCCCGGGCGC GCACCTGTCG

1051 GGCAACACGC GTATCGGCGA AGAAAGCCGG ATAGGCACGG GCGCGTGCAG

1101 CCGCCAGCAG ACAACCGTCG GCAGCGGGGT TACCgccgGT GCAGGGgcGG

1151 TTATCGTATG CGACATCCCG GACGGCATGA CCGTCGCGGG CAACCCGGCA

1201 AAGCCCCTTA CGGGCAAAAA CCCCAAGACC GGGACGGCAT AA
```

This encodes a protein having amino acid sequence <SEQ ID 18>:

```
  1 MSKAVKRLFD IIASASGLIV LSPVFLVLIY LIRKNLGSPV FFIRERPGKD

51 GKPFKMVKFR SMRDALDSDG IPLPDSERLT DFGKKLRATS LDELPELWNV

101 LKGEMSLVGP RPLLMQYLPL YNKFQNRRHE MKPGITGWAQ VNGRNALSWD

151 EKFSCDVWYT DNFSFWLDMK ILFLTVKKVL IKEGISAQGE ATMPPFAGNR

201 KLAVIGAGGH GKVVAELAAA LGTYGEIVFL DDRTQGSVNG FPVIGTTLLL

251 ENSLSPEQFD ITVAVGNNRI RRQITENAAA LGFKLPVLIH PDATVSPSAI

301 IGQGSVVMAK AVVQAGSVLK DGVIVNTAAT VDHDCLLDAF VHISPGAHLS

351 GNTRIGEESR IGTGACSRQQ TTVGSGVTAG AGAVIVCDIP DGMTVAGNPA

401 KPLTGKNPKT GTA*
```

This protein shows 86.9% identity in 413 aa overlap with ORF3-1:

```
                  10         20         30         40         50         60
   orf3-1.pep  MSKFFKRLFDIVASASGLIFLSPVFLILIYLIRKNLGSPVFFFQERPGKDGKPFKMVKFR
               |||  ||||||:||||||| ||||||:||||:|||||||||  :||||||||||||||||
   orf3ng      MSKAVKRLFDIIASASGLIVLSPVFLVLIYLIRKNKGSPVFFIRERPGKDGKPFKMVKFR
                  10         20         30         40         50         60

70         80         90        100        110        120
   orf3-1.pep  SMRDALDSDGIPLPDGERLTPFGKKLRAASLDELPELWNILKGEMSLVGPRPLLMQYLPL
               |||||||||||||||| |||| ||||||:|||||||||||:|||||||||||||||||||
   orf3ng      SMRDALDSDGIPLPDSERLTPFGKKLRATSLDELPELWNVLKGEMSLVGPRPLLMQYLPL
                  70         80         90        100        110        120

130        140        150        160        170        180
   orf3-1.pep  YDNFQNRRHEMKPGITGWAQVNGRNALSWDEKFACDVWYIDHFSLCLDIKILLLTVKKVL
               |::||||||||||||||||||||||||||||||:||||||: ||::||  ||:||||||
   orf3ng      YNKFQNRRHEMKPGITGWAQVNGRNALSWDEKFSCDVWYTDNFSFWLDMKILFLTVKKVL
                 130        140        150        160        170        180

190        200        210        220        230        240
   orf3-1.pep  IKEGISAQGEATMPPFTGKRKLAVVGAGGHGKVVADLAAALGRYREIVFLDDRAQGSVNG
               ||||||||||||||||::|:||||:||||||||||:||||||  :|||||||| |||||
   orf3ng      IKEGISAQGEATMPPFAGNRKLAVIGAGGHGKVVAELAAALGTYGEIVFLDDRTQGSVNG
                 190        200        210        220        230        240

250        260        270        280        290        300
   orf3-1.pep  FSVIGTTLLLENSLSPEQYDVAVAVGNNRIRRQIAEKAAALGFALPVLVHPDATVSPSAT
               | ||||||||||||||||::: |||||||||||| :||||||| ||||:||||||||||
   orf3ng      FPVIGTTLLLENSLSPEQFDITVAVGNNRIRRQITENAAALGFKLPVLIHPDATVSPSAI
                 250        260        270        280        290        300

310        320        330        340        350        360
   orf3-1.pep  VGQGSVVMAKAVVQAGSVLKDGVIVNTAATVDHDCLLNAFVHISPGAHLSGNTHIGEESW
               :|||||||||||||||||||||||||||||||||||:|||||||||||||||| |||||
   orf3ng      IGQGSVVMAKAVVQAGSVLKDGVIVNTAATVDHDCLLDAFVHISPGAHLSGNTRIGEESR
                 310        320        330        340        350        360
```

```
                        370       380       390       400       410
orf3-1.pep   IGTGACSRQQIRIGSRATIGAGAVVVRDVSDGMTVAGNPAKPLPRKNPETSTAX
             ||||||||||  :||  :|  ||||||:|  |:  |||||||||||||  |||:|:|||
orf3ng       IGTGACSRQQTTVGSGVTAGAGAVIVCDIPDGMTVAGNPAKPLTGKNPKTGTAX
                        370       380       390       400       410
```

In addition, ORF3ng shows significant homology with a hypothetical protein from *B. subtilis*:

```
gnl|PID|e238668 (Z71928) hypothetical protein [Bacillus subtilis]
>gi|1945702|gnl|PID|e313004 (Z94043) hypothetical protein [Bacillus subtilis]
>gi|2635938|gnl|PID|e1186113 (Z99121) similar to capsular polysaccharide
biosynthesis [Bacillus subtilis]Length = 202
Score = 235 bits (594), Expect = 3e-61
Identities = 114/195 (58%), Positives = 142/195 (72%)

Query:    5  VKRLFDIIASASGLIVLSPVFLVLIYLIRKNLGSPVFFIRERPGKDGKPFKMVKFRSMRD    64
             +KRLFD+ A+    L    S + L  I ++R  +GSPVFF + RPG  GKPF + KFR+M D
Sbjct:    3  LKRLFDLTAAIFLLCCTSVIILFTIAVVRLKIGSPVFFKQVRPGLHGKPFTLYKFRTMTD    62

Query:   65  ALDSDGIPLPDSERLTDFGKKLRATSLDELPELWNVLKGEMSLVGPRPLLMQYLPLYNKF   124
               DS G  LPD  RLT  G+ +R   S+DELP+L NVLKG++SLVGPRPLLM YLPLY +
Sbjct:   63  ERDSKGNLLPDEVRLTKTGRLIRKLSIDELPQLLNVLKGDLSLVGPRPLLMDYLPLYTEK   122

Query:  125  QNRRHEMKPGITGWAQVNGRNALSWDEKFSCDVWYTDNFSFWLDMKILFLTVKKVLIKEG   184
             Q RRHE+KPGITGWAQ+NGRNA+SW++KF   DVWY DN+SF+LD+KIL LTV+KVL+ EG
Sbjct:  123  QARRHEVKPGITGWAQINGRNAISWEKKFELDVWYVDNWSFFLDLKILCLTVRKVLVSEG   182

Query:  185  ISAQGEATMPPFAGN                                              199
             I      T   F G+
Sbjct:  183  IQQTNHVTAERFTGS                                              197
```

The hypothetical product of yvfc gene shows similarity to EXOY of *R. meliloti*, an exopolysaccharide production protein. Based on this and on the two predicted transmembrane regions in the homologous *N. gonorrhoeae* sequence, it is predicted that these proteins, or their epitopes, could be useful antigens for vaccines or diagnostics, or for raising antibodies.

Example 4

The following partial DNA sequence was identified in *N. meningitidis* <SEQ ID 19>:

```
  1..AACCATATGG CGATTGTCAT CGACGAATAC GGCGGCACAT CCGGCTTGGT

51   CACCTTTGAA GACATCATCG AGCAAATCGT CGGCGAAATC GAAGACGAGT

101   TTGACGAAGA CGATAGCGCC GACAATATCC ATGCCGTTTC TTCAGACACG

151   TGGCGCATCC ATGCAGCTAC CGAAATCGAA GACATCAACA CCTTCTTCGG

201   CACGGAATAC AGCATCGAAG AAGCCGACAC CATT.GGCGG CCTGGTCATT

251   CAAGAGTTGG GACATCTGCC CGTGCGCGGC GAAAAGTCC TTATCGGCGG

301   TTTGCAGTTC ACCGTCGCAC GCGCCGACAA CCGCCGCCTG CATACGCTGA

351   TGGCGACCCG CGTGAAGTAA GC........ .....ACCGC CGTTTCTGCA

401   CAGTTTAG
```

This corresponds to amino acid sequence <SEQ ID 20; ORF5>:

```
  1 ..NHMAIVIDEY GGTSGLVTFE DIIEQIVGEI EDEFDEDDSA DNIHAVSSDT
 51   WRIHAATEIE DINTFFGTEY SIEEADTIXR PGHSRVGTSA RARRKSPYRR
101   FAVHRRTRRQ PPPAYADGDP REVS....XR RFCTV*
```

Further sequence analysis revealed the complete DNA sequence to be <SEQ ID 21>:

```
  1 ATGGACGGCG CACAACCGAA AACGAATTTT TTTGAACGCC TGATTGCCCG
 51 ACTCGCCCGC GAACCCGATT CCGCCGAAGA CGTATTAAAC CTGCTTCGGC
101 AGGCGCACGA GCAGGAAGTT TTTGATGCGG ATACGCTTTT AAGATTGGAA
151 AAAGTCCTCG ATTTTTCCGA TTTGGAAGTG CGCGACGCGA TGATTACGCG
201 CAGCCGTATG AACGTTTTAA AGAAAACGA CAGCATCGAG CGCATCACCG
251 CCTACGTTAT CGATACCGCC CATTCGCGCT TCCCCGTCAT CGGCGAAGAC
301 AAAGACGAAG TTTTGGGCAT TTTGCACGCC AAAGACCTGC TCAAATATAT
351 GTTTAACCCC GAGCAGTTCC ACCTCAAATC CATTCTCCGC CCCGCCGTCT
401 TCGTCCCCGA AGGCAAATCG CTGACCGCCC TTTTAAAAGA GTTCCGCGAA
451 CAGCGCAACC ATATGGCGAT TGTCATCGAC GAATACGGCG GCACATCCGG
501 CTTGGTCACC TTTGAAGACA TCATCGAGCA AATCGTCGGC GAAATCGAAG
551 ACGAGTTTGA CGAAGACGAT AGCGCCGACA ATATCCATGC CGTTTCTTCC
601 GAACGCTGGC GCATCCATGC AGCTACCGAA ATCGAAGACA TCAACACCTT
651 CTTCGGCACG GAATACAGCA GCGAAGAAGC CGACACCATT CGGCCTGGTC
701 ATTCAAGAGT TGGGACATCT GCCCGTGCGC GGCGAAAAAG TCCTTATCGG
751 CGGTTTGCAG TTCACCGTCG CACGCGCCGA CAACCGCCGC CTGCATACGC
801 TGATGGCGAC CCGCGTGAAG TAAGCACCGC CGTTTCTGCA CAGTTTAGGA
851 TGACGGTACG GGCGTTTTCT GTTTCAATCC GCCCCATCCG CCAAACATAA
```

This corresponds to amino acid sequence <SEQ ID 22; ORF5-1>:

```
  1 MDGAQPKTNF FERLIARLAR EPDSAEDVLN LLRQAHEQEV FDADTLLRLE
 51 KVLDFSDLEV RDAMITRSRM NVLKENDSIE RITAYVIDTA HSRFPVIGED
101 KDEVLGILHA KDLLKYMFNP EQFHLKSILR PAVFVPEGKS LTALLKEFRE
151 QRNHMAIVID EYGGTSGLVT FEDIIEQIVG EIEDEFDEDD SADNIHAVSS
201 ERWRIHAATE IEDINTFFGT EYSSEEADTI RPGHSRVGTS ARARRKSPYR
251 RFAVHRRTRR QPPPAYADGD PREVSTAVSA QFRMTVRAFS VSIRPIRQT*
```

Further work identified the corresponding gene in strain A of *N. meningitidis* <SEQ ID 23>:

```
  1 ATGGACGGCG CACAACCGAA AACAAATTTT TTNNAACGCC TGATTGCCCG
 51 ACTCGCCCGC GAACCCGATT CCGCCGAAGA CGTATTGACC CTGTTGCGCC
101 AAGCGCACGA ACAGGAAGTA TTTGATGCGG ATACGCTTTT AAGATTGGAA
151 AAAGTCCTCG ATTTTTCTGA TTTGGAAGTG CGCGACGCGA TGATTACGCG
```

-continued

201 CAGCCGTATG AACGTTTTAA AAGAAAACGA CAGCATCGAA CGCATCACCG

251 CCTACGTTAT CGATACCGCC CATTCGCGCT TCCCCGTCAT CGGTGAAGAC

301 AAAGACGAAG TTTTGGGTAT TTTGCACGCC AAAGACCTGC TCAAATATAT

351 GTTCAACCCC GAGCAGTTCC ACCTCAAATC GATATTGCGC CCTGCCGTCT

401 TCGTCCCCGA AGGCAAATCG CTGACCGCCC TTTTAAAAGA GTTCCGCGAA

451 CAGCGCAACC ATATGGCAAT CGTCATCGAC GAATACGGCG GCACGTCGGG

501 TTTGGTAACT TTTGAAGACA TCATCGAGCA AATCGTCGGC GACATCGAAG

551 ATGAGTTTGA CGAAGACGAA AGCGCGGACA ACATCCACGC CGTTTCCGCC

601 GAACGCTGGC GCATCCACGC GGCTACCGAA ATCGAAGACA TCAACGCCTT

651 TTTCGGCACG GAATACAGCA GCGAAGAAGC CGACACCATC GGCGGCCNTG

701 GTCATTCAGG AATTGGNACA CCTGCCCGTG CGCGGCGAAA AAGTCNTTAT

751 CGGCGNNTTG CANTTCACNG TCGCCNGCGC NGACAACCGC CGCCTGCATA

801 CGCTGATGGC GACCCGCGTG AAGTAAGCTC CGCCGTTTCT GTACAGTTTA

851 GGATGACGGT ACGGGCGTTT TCTGTTTCAA TCCGCCCCAT CCGCCANACA

901 TAA

This encodes a protein having amino acid sequence <SEQ ID 24; ORF5a>:

1 MDGAQPKTNF XXRLIARLAR EPDSAEDVLT LLRQAHEQEV FDADTLLRLE

51 KVLDFSDLEV RDAMITRSRM NVLKENDSIE RITAYVIDTA HSRFPVIGED

101 KDEVLGILHA KDLLKYMFNP EQFHLKSILR PAVFVPEGKS LTALLKEFRE

151 QRNHMAIVID EYGGTSGLVT FEDIIEQIVG DIEDEFDEDE SADNIHAVSA

201 ERWRIHAATE IEDINAFFGT EYSSEEADTI GGXGHSGIGT PARARRKSXY

251 RRXAXHXRXR XQPPPAYADG DPREVSSAVS VQFRMTVRAF SVSIRPIRXT

301 *

The originally-identified partial strain B sequence (ORF5) shows 54.7% identity over a 124aa overlap with ORF5a:

```
                                                  10        20        30
orf5.pep                                NHMAIVIDEYGGTSGLVTFEDIIEQIVGEI
                                        ||||||||||||||||||||||||||||:|
orf5a       FHLKSILRPAVFVPEGKSLTALLKEFREQRNHMAIVIDEYGGTSGLVTFEDIIEQIVGDI
                 130       140       150       160       170       180

40        50        60        70        80        90
orf5.pep    EDEFDEDDSADNIHAVSSDTWRIHAATEIEDINTFFGTEYSIEEADTIXRPGHSRVGTSA
            |||||||:|||||||||:: |||||||||||||:||||||| ||||||   ||| :|| |
orf5a       EDEFDEDESADNIHAVSAERWRIHAATEIEDINAFFGTEYSSEEADTIGGXGHSGIGTPA
                 190       200       210       220       230       240

100       110       120       130
orf5.pep    RARRKSPYRRFAVHRRTRRQPPPAYADGDPREVSXXXXXRRFCTV
            |||||| ||| | | |:| |||||||||||||||
orf5a       RARRKSXYRRXAXHXRXRXQPPPAYADGDPREVSSAVSVQFRMTVRAFSVSIRPIRXTX
                 250       260       270       280       290       300
```

The complete strain B sequence (ORF5-1) and ORF5a show 92.7% identity in 300 aa overlap:

```
                        10        20        30        40        50        60
orf5a.pep      MDGAQPKTNFXXRLIARLAREPDSAEDVLTLLRQAHEQEVFDADTLLRLEKVLDFSDLEV
               ||||||||||  |||||||||||||||||:||||||||||||||||||||||||||||||
orf5-1         MDGAQPKTNFFERLIARLAREPDSAEDVLNLLRQAHEQEVFDADTLLRLEKVLDFSDLEV
                        10        20        30        40        50        60

70        80        90       100       110       120
orf5a.pep      RDAMITRSRMNVLKENDSIERITAYVIDTAHSRFPVIGEDKDEVLGILHAKDLLKYMFNP
               ||||||||||||||||||||||||||||||||||||||||||||||||||||||||||||
orf5-1         RDAMITRSRMNVLKENDSIERITAYVIDTAHSRFPVIGEDKDEVLGILHAKDLLKYMFNP
                        70        80        90       100       110       120

130       140       150       160       170       180
orf5a.pep      EQFHLKSILRPAVFVPEGKSLTALLKEFREQRNHMAIVIDEYGGTSGLVTFEDIIEQIVG
               ||||||||||||||||||||||||||||||||||||||||||||||||||||||||||||
orf5-1         EQFHLKSILRPAVFVPEGKSLTALLKEFREQRNHMAIVIDEYGGTSGLVTFEDIIEQIVG
                       130       140       150       160       170       180

190       200       210       220       230       240
orf5a.pep      DIEDEFDEDESADNIHAVSAERWRIHAATEIEDINAFFGTEYSSEEADTIGGXGHSGIGT
               :||||||||:|||||||||:|||||||||||||||:||||||||||||||   ||| :||
orf5-1         EIEDEFDEDDSADNIHAVSSERWRIHAATEIEDINTFFGTEYSSEEADTIRP-GHSRVGT
                       190       200       210       220       230

250       260       270       280       290       300
orf5a.pep      PARARRKSXYRRXAXHXRXRXQPPPAYADGDPREVSSAVSVQFRMTVRAFSVSIRPIRXT
                ||||||| ||| | | |:| |||||||||||||||:|||:||||||||||||||||| |
orf5-1         SARARRKSPYRRFAVHRRTRRQPPPAYADGDPREVSTAVSAQFRMTVRAFSVSIRPIRQT
             240       250       260       270       280       290
```

Further work identified the a partial DNA sequence in *N. gonorrhoeae* <SEQ ID 25> which encodes a protein having amino acid sequence <SEQ ID 26; ORF5ng>:

```
  1 MDGAQPKTNF FERLIARLAR EPDSAEDVLN LLRQAHEQEV FDADTLTRLE

51 KVLDFAELEV RDAMITRSRM NVLKENDSIE RITAYVIDTA HSRFPVIGED

101 KDEVLGILHA KDLLKYMFNP EQFHLKSVLR PAVFVPEGKS LTALLKEFRE

151 QRNHMAIVID EYGGTSGLVT FEDIIEQIVG DIEDEFDEDE SADDIHSVSA

201 ERWRIHAATE IEDINAFFGT EYGSEEADTI RRLGHSGIGT PARARRKSPY

251 RRFAVHRRPR RQPPPAHADG DPREVSRACP HRRFCTV*
```

Further analysis revealed the complete gonococcal nucleotide sequence <SEQ ID 27> to be:

```
  1 ATGGACGGCG CACAACCGAA AACAAATTTT TTTGAACGCC TGATTGCCCG

51 ACTCGCCCGC GAACCCGATT CCGCCGAAGA CGTATTAAAC CTGCTTCGGC

101 AGGCGCACGA ACAGGAAGTT TTTGATGCCG ACACACTGAC CCGGCTGGAA

151 AAAGTATTGG ACTTTGCCGA GCTGGAAGTG CGCGATGCGA TGATTACGCG

201 CAGCCGCATG AACGTATTGA AAGAAAACGA CAGCATCGAA CGCATCACCG

251 CCTACGTCAT CGATACCGCC CATTCGCGCT TCCCCGTCAT CGGCGAAGAC

301 AAAGACGAAG TTTTGGGCAT TTTGCACGCC AAAGACCTGC TCAAATATAT

351 GTTCAACCCC GAGCAGTTCC ACCTGAAATC CGTCTTGCGC CCTGCCGTTT

401 TCGTGCCCGA AGGCAAATCT TTGACCGCCC TTTTAAAAGA GTTCCGCGAA

451 CAGCGCAACC ATATGGCAAT CGTCATCGAC GAATACGGCG GCACGTCGGG

501 TTTGGTCACC TTTGAAGACA TCATCGAGCA AATCGTCGGT GACATCGAAG

551 ACGAGTTTGA CGAAGACGAA AGCGccgacg acatCCACTC cgTTTccgCC

601 GAACGCTGGC GCATCCacgc ggctaCCGAA ATCGAAGaca TCAACGCCTT

651 TTTCGGTACG GAatacggca gcgaagaagc cgacaccatc cggcggctTG
```

-continued
```
701 GTCATTCAGG AATTGGGACA CCTGCCCGTG CGCGGCGAAA AAGTCCTTAt
751 cggcgGTTTG Cagttcaccg tCGCCCGCGC CGACAACCGC CGCCTGCACA
801 CGCTGATGGC GACCCGCGTG AAGTAAGCAG AGCCTGCCcg AccgccgttT
851 CTGCacAGTT TAGGatgACG gtaCGGTCGT TTTCTGTTTC AATCCGCCCC
901 ATCCGCCAAA CATAA
```

This encodes a protein having amino acid sequence <SEQ ID 28; ORF5ng-1>:

```
  1 MDGAQPKTNF FERLIARLAR EPDSAEDVLN LLRQAHEQEV FDADTLTRLE
 51 KVLDFAELEV RDAMITRSRM NVLKENDSIE RITAYVIDTA HSRFPVIGED
101 KDEVLGILHA KDLLKYMFNP EQFHLKSVLR PAVFVPEGKS LTALLKEFRE
151 QRNHMAIVID EYGGTSGLVT FEDIIEQIVG DIEDEFDEDE SADDIHSVSA
201 ERWRIHAATE IEDINAFFGT EYGSEEADTI RRLGHSGIGT PARARRKSPY
251 RRFAVHRRPR RQPPPAHADG DPREVSRACP TAVSAQFRMT VRSFSVSIRP
301 IRQT*
```

The originally-identified partial strain B sequence (ORF5) shows 83.1% identity over a 135aa overlap with the partial gonococcal sequence (ORF5ng):

```
orf5                       NHMAIVIDEYGGTSGLVTFEDIIEQIVGEI   30
                           ||||||||||||||||||||||||||||:|
orf5ng  FHLKSVLRPAVFVPEGKSLTALLKEFREQRNHMAIVIDEYGGTSGLVTFEDIIEQIVGDI  182
orf5    EDEFDEDDSADNIHAVSSDTWRIHAATEIEDINTFFGTEYSIEEADTIXRPGHSRVGTSA   90
        ||||||| :|||:||::|: ||||||||||||:||||||: |||||| | |||  :||| 
orf5ng  EDEFDEDESADDIHSVSAERWRIHAATEIEDINAFFGTEYGSEEADTIRRLGHSGIGTPA  242
orf5    RARRKSPYRRFAVHRRTRRQPPPAYADGDPREVSX----RRFCTV                 131
        ||||||||||||||||| |||||:|||||||||      ||||||
orf5ng  RARRKSPYRRFAVHRRPRRQPPPAHADGDPREVSRACPHRRFCTV                 287
```

The complete strain B and gonococcal sequences (ORF5-1 & ORF5ng-1) show 92.4% identity in 304 aa overlap:

```
                        10         20         30         40         50         60
orf5ng-1.pep    MDGAQPKTNFFERLIARLAREPDSAEDVLNLLRQAHEQEVFDADTLTRLEKVLDFAELEV
                ||||||||||||||||||||||||||||||||||||||||||||||||||||::|||
orf5-1          MDGAQPKTNFFERLIARLAREPDSAEDVLNLLRQAHEQEVFDADTLLRLEKVLDFSDLEV
                        10         20         30         40         50         60
                        70         80         90        100        110        120
orf5ng-1.pep    RDAMITRSRMNVLKENDSIERITAYVIDTAHSRFPVIGEDKDEVLGILHAKDLLKYMFNP
                ||||||||||||||||||||||||||||||||||||||||||||||||||||||||||||
orf5-1          RDAMITRSRMNVLKENDSIERITAYVIDTAHSRFPVIGEDKDEVLGILHAKDLLKYMFNP
                        70         80         90        100        110        120
                       130        140        150        160        170        180
orf5ng-1.pep    EQFHLKSVLRPAVFVPEGKSLTALLKEFREQRNHMAIVIDEYGGTSGLVTFEDIIEQIVG
                ||||||:|||||||||||||||||||||||||||||||||||||||||||||||||||||
orf5-1          EQFHLKSILRPAVFVPEGKSLTALLKEFREQRNHMAIVIDEYGGTSGLVTFEDIIEQIVG
                        130        140        150        160        170        180
                       190        200        210        220        230        240
orf5ng-1.pep    DIEDEFDEDESADDIHSVSAERWRIHAATEIEDINAFFGTEYGSEEADTIRRLGHSGIGT
                :|||||||| :|||:||::|: |||||||||||||:|||||| :|||||||| ||| |||
orf5-1          EIEDEFDEDDSADNIHAVSSERWRIHAATEIEDINTFFGTEYSSEEADTIRP-GHSRVGT
                        190        200        210        220        230
                       250        260        270        280        290        300
orf5ng-1.pep    PARARRKSPYRRFAVHRRPRRQPPPAHADGDPREVSRACPTAVSAQFRMTVRSFSVSIRP
                 ||||||||||||||||| |||||:|||||||||||    ||||||||||||:||||||
orf5-1           SARARRKSPYRRFAVHRRTRRQPPPAYADGDPREVS----TAVSAQFRMTVRAFSVSIRP
                        240        250        260        270        280        290
orf5ng-1.pep    IRQTX
                |||||
orf5-1          IRQTX
                  300
```

Computer analysis of these amino acid sequences indicates a putative leader sequence, and identified the following homologies:

Homology with Hemolysin Homolog TlyC (Accession U32716) of *H. influenzae*

ORF5 and TlyC proteins show 58% aa identity in 77 aa overlap (BLASTp).

```
ORF5    2 HMAIVIDEYGGTSGLVTFEDIIEQIVGEIEDEFDEDDSADNIHAVSSDTWRIHAATEIED    61
          HMAIV+DE+G  SGLVT EDI+EQIVG+IEDEFDE++ AD I  +S  T+ + A T+I+D
TlyC  166 HMAIVVDEFGAVSGLVTIEDILEQIVGDIEDEFDEEEIAD-IRQLSRHTYAVRALTDIDD   224

ORF5   62 INTFFGTEYSIEEADTI                                             78
          N   F T++   EE DTI
TlyC  225 FNAQFNTDFDDEEVDTI                                            241
```

ORF5ng-1 also shows significant homology with TlyC:

```
        SCORES Init1: 301  Initn: 419  Opt: 668
        Smith-Waterman score: 668; 45.9% identity in 242 aa overlap 10         20         30         40         50
        orf5ng-1.pep        MDGAQPKTNFFERLIARLAR-EPDSAEDVLNLLRQAHEQEVFDADTLTRLEK
                              ||: |::|: :  |    : |:::::|:::::::::|  :|   :|
        tlyc_haein          MNDEQQNSNQSENTKKPFFQSLFGRFFQGELKNREELVEVIRDSEQNDLIDQNTREMIEG
                            10         20         30         40         50         60

60         70         80         90        100       109
        orf5ng-1.pep        VLDFAELEVRDAMITRSRMNVLKENDSIERITAYVIDTAHSRFPVIGE--DKDEVLGILH
                            |:::|||:|||  ||  ||::   ::::::::    :|::|||||||::  |::::|||
        tlyc_haein          VMEIAELRVRDIMIPRSQIIFIEDQQDLNTCLNTIIESAHSRFPVIADADDRDNIVGILH
                            70         80         90        100       110       120

110        120        130        140        150        160
        orf5ng-1.pep        AKDLLKYMF-NPEQFHLKSVLRPAVFVPEGKSLTALLKEFREQRNHMAIVIDEYGGTSGL
                            ||||||::   :  |:|:|||:|||||: :  :||:||  :||||||||:|:|::|||
        tlyc_haein          AKDLLKFLREDAEVFDLSSLLRPVVIVPESKRVDRMLKDFRSERFHMAIVVDEFGAVSGL
                            130        140        150        160        170        180

170        180        190        200        210        220
        orf5ng-1.pep        VTFEDIIEQIVGDIEDEFDEDESADDIHSVSAERWRIHAATEIEDINAFFGTEYGSEEAD
                            ||:|||:|||||||||||||||:|  ||  |:::| :  :::|  |:|:|:||  :||:|
        tlyc_haein          VTIEDILEQIVGDIEDEFDEEEIAD-IRQLSRHTYAVRALTDIDDFNAQFNTDFDDEEVD
                            190        200        210        220        230

230        240        250        260        270        280
        orf5ng-1.pep        TIRRLGHSGIG-TPARARRKSPYRRFAVHRRPRRQPPPAHADGDPREVSRACPTAVSAQF
                            ||  |  : :|   ||   |:
        tlyc_haein          TIGGLIMQTFGYLPKRGEEIILKNLQFKVTSADSRRLIQLRVTVPDEHLAEMNNVDEKSE
                            240        250        260        270        280        290
```

Homology with a Hypothetical Secreted Protein from *E. coli*:

ORF5a shows homology to a hypothetical secreted protein from *E. coli*:

```
sp|P77392|YBEX_ECOLI HYPOTHETICAL 33.3 KD PROTEIN IN CUTE-ASNB INTERGENIC REGION
>gi|1778577 (U82598) similar to H. influenzae [Escherichia coli] >gi|1786879
(AE000170) f292; This 292 aa ORF is 23% identical (9 gaps) to 272 residues of an
approx. 440 aa protein YTFL_HAEIN SW: P44717 [Escherichia coli] Length = 292
Score = 212 bits (533), Expect = 3e-54
Identities = 112/230 (48%), Positives = 149/230 (64%), Gaps = 3/230 (1%)

Query:    2 DGAQPKTNFXXRLIARLAR-EPDSAEDVLTLLRQAHEQEVFDADTLLRLEKVLDFSDLEV   60
            D   K F  L+++L    EP + +++L L+R + + ++  D DT   LE V+D +D  V
Sbjct:   10 DTISNKKGFFSLLLSQLFHGEPKNRDELLALIRDSGQNDLIDEDTRDMLEGVMDIADQRV   69

Query:   61 RDAMITRSRMNVLKENDSIERITAYVIDTAHSRFPVIGEDKDEVLGILHAKDLLKYM-FN  119
            RD MI RS+M  LK N +++    +I++AHSRFPVI  EDKD + GIL AKDLL +M  +
Sbjct:   70 RDIMIPRSQMITLKRNQTLDECLDVIIESAHSRFPVISEDKDHIEGILMAKDLLPFMRSD  129

Query:  120 PEQFHLKSILRPAVFVPEGKSLTALLKEFREQRNHMAIVIDEYGGTSGLVTFEDIIEQIV  179
              E F +  +LR AV VPE K  +LKEFR QR HMAIVIDE+GG SGLVT EDI+E IV
Sbjct:  130 AEAFSMDKVLRQAVVVPESKRVDRMLKEFRSQRYHMAIVIDEFGGVSGLVTIEDILELIV  189

Query:  180 GDIEDEFDEDESADNIHAVSAERWRIHAATEIEDINAFFGTEYSSEEADT            229
            G+IEDE+DE++   D    +S    W  + A    IED N  FGT +S EE DT
Sbjct:  190 GEIEDEYDEEDDID-FRQLSRHTWTVRALASIEDFNEAFGTHFSDEEVDT            238
```

Based on this analysis, including the amino acid homology to the TlyC hemolysin-homologue from *H. influenzae* (hemolysins are secreted proteins), it was predicted that the proteins from *N. meningitidis* and *N. gonorrhoeae* are secreted and could thus be useful antigens for vaccines or diagnostics.

ORF5-1 (30.7 kDa) was cloned in the pGex vector and expressed in *E. coli*, as described above. The products of protein expression and purification were analyzed by SDS-PAGE. FIG. 2A shows the results of affinity purification of the GST-fusion protein. Purified GST-fusion protein was used to immunise mice, whose sera were used for Western blot analysis (FIG. 1B). These experiments confirm that ORF5-1 is a surface-exposed protein, and that it is a useful immunogen.

Example 5

The following partial DNA sequence was identified in *N. meningitidis* <SEQ ID 29>:

```
  1 ATGCGCGGCG GCAGGCCGGA TTCCGTTACC GTGCAGATTA TCGAAGGTTC
 51 GCGTTTTTCG CATATGAGGA AAGTCATCGA CGCAACGCCC GACATCGGAC
101 ACGACACCAA AGGCTGGAGC AATGAAAAAC TGATGGCGGA AGTTGCGCCC
151 GATGCCTTCA GCGGCAATCC TGAAgGGCAG TTTTTCCCCG ACAGCTACGA
201 AATCGATGCG GCGGCAGTG ATTTGCAGAT TTACCAAACC GCCTACAAgG
251 GCGATGCAAC GCCGCCTGAA TGAgGGCATG GGAAAGCAGG CAGGACGGGC
301 TGCCTTATAA AAACCCTTAT GAAATGCTGA TTATGGCGAr CCTGGTCGAA
351 AAGGAAACAG GCATGAAGC CGAsCsCGAC CATGTcGCTT CCGTCTTCGT
401 CAACCGCCTG AAAATCGGTA TGCGCCTGCA AACCgAssCG TCCGTGATTT
451 ACGGCATGGG TGCGGCATAC AAGGGCAAAA TCCGTAAAGC CGACCTGCGC
501 CGCGACACGC CGTACAACAC CTACACGCGC GGCGGTCTGC CGCCAACCCC
551 GATTGCGCTG CCC..
```

This corresponds to the amino acid sequence <SEQ ID 30; ORF7>:

```
  1 MRGGRPDSVT VQIIEGSRFS HMRKVIDATP DIGHDTKGWS NEKLMAEVAP
 51 DAFSGNPEGQ FFPDSYEIDA GGSDLQIYQT AYKAMQRRLN EAWESRQDGL
101 PYKNPYEMLI MAXLVEKETG HEAXXDHVAS VFVNRLKIGM RLQTXXSVIY
151 GMGAAYKGKI RKADLRRDTP YNTYTRGGLP PTPIALP..
```

Further sequence analysis revealed the complete DNA sequence <SEQ ID 31>:

```
  1 ATGTTGAGAA AATTGTTGAA ATGGTCTGCC GTTTTTTTGA CCGTGTCGGC
 51 AGCCGTTTTC GCCGCGCTGC TTTTTGTTCC TAAGGATAAC GGCAGGGCAT
101 ACCGAATCAA AATTGCCAAA AACCAGGGTA TTTCGTCGGT CGGCAGGAAA
151 CTTGCCGAAG ACCGCATCGT GTTCAGCAGG CATGTTTTGA CGGCGGCGGC
201 CTACGTTTTG GGTGTGCACA ACAGGCTGCA TACGGGACG TACAGATTGC
251 CTTCGGAAGT GTCTGCTTGG GATATCTTGC AGAAAATGCG CGGCGGCAGG
301 CCGGATTCCG TTACCGTGCA GATTATCGAA GGTTCGCGTT TTTCGCATAT
351 GAGGAAAGTC ATCGACGCAA CGCCCGACAT CGGACACGAC ACCAAAGGCT
401 GGAGCAATGA AAAACTGATG GCGGAAGTTG CGCCCGATGC CTTCAGCGGC
451 AATCCTGAAG GCAGTTTTT CCCCGACAGC TACGAAATCG ATGCGGGCGG
501 CAGTGATTTG CAGATTTACC AAACCGCCTA CAAGGCGATG CAACGCCGCC
551 TGAATGAGGC ATGGGAAAGC AGGCAGGACG GGCTGCCTTA TAAAAACCCT
601 TATGAAATGC TGATTATGGC GAGCCTGGTC GAAAAGGAAA CAGGGCATGA
```

```
651 AGCCGACCGC GACCATGTCG CTTCCGTCTT CGTCAACCGC CTGAAAATCG

701 GTATGCGCCT GCAAACCGAC CCGTCCGTGA TTTACGGCAT GGGTGCGGCA

751 TACAAGGGCA AAATCCGTAA AGCCGACCTG CGCCGCGACA CGCCGTACAA

801 CACCTACACG CGCGGCGGTC TGCCGCCAAC CCCGATTGCG CTGCCCGGCA

851 AGGCGGCACT CGATGCCGCC GCCCATCCGT CCGGCGAAAA ATACCTGTAT

901 TTCGTGTCCA AAATGGACGG CACGGGCTTG AGCCAGTTCA GCCATGATTT

951 GACCGAACAC AATGCCGCCG TCCGCAAATA TATTTTGAAA AAATAA
```

This corresponds to the amino acid sequence <SEQ ID 32; ORF7-1>:

```
  1 MLRKLLKWSA VFLTVSAAVF AALLFVPKDN GRAYRIKIAK NQGISSVGRK

51 LAEDRIVFSR HVLTAAAYVL GVHNRLHTGT YRLPSEVSAW DILQKMRGGR

101 PDSVTVQIIE GSRFSHMRKV IDATPDIGHD TKGWSNEKLM AEVAPDAFSG

151 NPEGQFFPDS YEIDAGGSDL QIYQTAYKAM QRRLNEAWES RQDGLPYKNP

201 YEMLIMASLV EKETGHEADR DHVASVFVNR LKIGMRLQTD PSVIYGMGAA

251 YKGKIRKADL RRDTPYNTYT RGGLPPTPIA LPGKAALDAA AHPSGEKYLY

301 FVSKMDGTGL SQFSHDLTEH NAAVRKYILK K*
```

Computer analysis of this amino acid sequence gave the following results:

Homology with Hypothetical Protein Encoded by yceg Gene (Accession P44270) of *H. influenzae*

ORF7 and yceg proteins show 44% aa identity in 192 aa overlap:

```
ORF7    1 MRGGRPDSVTVQIIEGSRFSHMRKVIDATPDIGHDTKGWSNEKLMA-----EVAPDAFSG    55
            + G+     V+ IEG  F  RK ++ P +    K  SNE++ A          ++ +
yceg  102 LNSGKEVQFNVKWIEGKTFKDWRKDLENAPHLVQTLKDKSNEEIFALLDLPDIGQNLELK   161

ORF7   56 NPEGQFFPDSYEIDAGGSDLQIYQTAYKAMQRRLNEAWESRQDGLPYKNPYEMLIMAXLV   115
            N EG  +PD+Y       +DL++ + + + M++ LN+AW  R + LP  NPYEMLI+A +V
yceg  162 NVEGWLYPDTYNYTPKSTDLELLKRSAERMKKALNKAWNERDEDLPLANPYEMLILASIV   221

ORF7  116 EKETGHEAXXDHVASVFVNRLKIGMRLQTXXSVIYGMGAAYKGKIRKADLRRDTPYNTYT   175
            EKETG       VASVF+NRLK  M+LQT  +VIYGMG  Y G IRK DL     TPYNTY
yceg  222 EKETGIANERAKVASVFINRLKAKMKLQTDPTVIYGMGENYNGNIRKKDLETKTPYNTYV   281

ORF7  176 RGGLPPTPIALP                                                  187
            GLPPTPIA+P
yceg  282 IDGLPPTPIAMP                                                  293
```

The complete length YCEG protein has sequence:

```
  1 MKKFLIAILL LILILAGVAS FSYYKMTEFV KTPVNVQADE LLTIERGTTS

51 SKLATLFEQE KLIADGKLLP YLLKLKPELN KIKAGTYSLE NVKTVQDLLD

101 LLNSGKEVQF NVKWIEGKTF KDWRKDLENA PHLVQTLKDK SNEEIFALLD

151 LPDIGQNLEL KNVEGWLYPD TYNYTPKSTD LELLKRSAER MKKALNKAWN

201 ERDEDLPLAN PYEMLILASI VEKETGIANE RAKVASVFIN RLKAKMKLQT

251 DPTVIYGMGE NYNGNIRKKD LETKTPYNTY VIDGLPPTPI AMPSESSLQA

301 VANPEKTDFY YFVADGSGGH KFTRNLNEHN KAVQEYLRWY RSQKNAK
```

Homology with a Predicted ORF from *N. meningitidis* (Strain A)

ORF7 shows 95.2% identity over a 187aa overlap with an ORF (ORF7a) from strain A of *N. meningitidis*:

```
                          10         20         30
orf7.pep                  MRGGRPDSVTVQIIEGSRFSMHRKVIDATP
                          |||||||||||||||||||||||||||||
orf7a     AAYVLGVHNRLHTGYTRLPSEVSAWDILQKMRGGRPDSVTVQIIEGSRFSHMRKVIDATP
                70        80        90       100       110       120
                   40         50         60         70         80         90
orf7.pep   DIGHDTKGWSNEKLMAEVAPDAFSGNPEGQFFPDSYEIDAGGSDLQIYQTAYKAMQRRLN
           || ||||||||||||||||||||||||||||||||||||||||| |||:||| ||||||
orf7a      DIEHDTKGWSNEKLMAEVAPDAFSGNPEGQFFPDSYEIDAGGSDLRIYQIAYKAMQRRLN
              130       140       150       160       170       180
                  100       110        120       130       140       150
orf7.pep   EAWESRQDGLPYKNPYEMLIMAXLVEKETGHEAXXDHVASVFVNRLKIGMRLQTXXSVIY
           |||||||||||||||||||||||:||||||||||   |||||||||||||||||||  ||||
orf7a      EAWESRQDGLPYKNPYEMLIMASLIEKETGHEADRDHVASVFVNRLKIGMRLQTDPSVIY
              190       200       210       220       230       240
                   160       170        180
orf7.pep   GMGAAYKGKIRKADLRRDTPYNTYTRGGLPPTPIALP
           ||||||||||||||||||||||||||||||||||||
orf7a      GMGAAYKGKIRKADLRRDTPYNTYTRGGLPPTPIALPGKAALDAAAHPSGEKYLYFVSKM
              250       260       270       280       290       300
orf7a      DGTGLSQFSHDLTEHNAAVRKYILKKX
              310       320       330
```

The complete length ORF7a nucleotide sequence <SEQ ID 33> is:

```
  1 ATGTTGAGAA AATTGTTGAA ATGGTCTGCC GTTTTTTTGA CCGTATCGGC

51 AGCCGTTTTC GCCGCGCTGC TTTTCGTCCC TAAAGACAAC GGCAGGGCAT

101 ACAGGATTAA AATTGCCAAA AACCAGGGTA TTTCGTCGGT CGGCAGGAAA

151 CTTGCCGAAG ACCGCATCGT GTTCAGCAGG CATGTTTTGA CGGCGGCGGC

201 CTACGTTTTG GGTGTGCACA ACAGGCTGCA TACGGGGACG TACAGACTGC

251 CTTCGGAAGT GTCTGCTTGG GATATCTTGC AGAAAATGCG CGGCGGCAGG

301 CCGGATTCCG TTACCGTGCA GATTATCGAA GGTTCGCGTT TTTCGCATAT

351 GAGGAAAGTC ATCGACGCAA CGCCCGACAT CGAACACGAC ACCAAAGGCT

401 GGAGCAATGA AAAACTGATG GCGGAAGTTG CCCCTGATGC CTTCAGCGGC

451 AATCCTGAAG GGCAGTTTTT CCCCGACAGC TACGAAATCG ATGCGGGCGG

501 CAGCGATTTA CGGATTTACC AAATCGCCTA CAAGGCGATG CAACGCCGAC

551 TGAATGAGGC ATGGGAAAGC AGGCAGGACG GGCTGCCTTA TAAAAACCCT

601 TATGAAATGC TGATTATGGC GAGCCTGATC GAAAAGGAAA CAGGGCATGA

651 AGCCGACCGC GACCATGTCG CTTCCGTCTT CGTCAACCGC CTGAAAATCG

701 GTATGCGCCT GCAAACCGAC CCGTCCGTGA TTTACGGCAT GGGTGCGGCA

751 TACAAGGGCA AAATCCGTAA AGCCGACCTG CGCCGCGACA CGCCGTACAA

801 CACCTACACG CGCGGCGGTC TGCCGCCAAC CCCGATCGCG CTGCCCGGCA

851 AGGCGGCACT CGATGCCGCC GCCCATCCGT CCGGTGAAAA ATACCTGTAT

901 TTCGTGTCCA AAATGGACGG TACGGGCTTG AGCCAGTTCA GCCATGATTT

951 GACCGAACAC AACGCCGCCG TTCGCAAATA TATTTTGAAA AAATAA
```

This is predicted to encode a protein having amino acid sequence <SEQ ID 34>:

```
  1 MLRKLLKWSA VFLTVSAAVF AALLFVPKDN GRAYRIKIAK NQGISSVGRK

51 LAEDRIVFSR HVLTAAAYVL GVHNRLHTGT YRLPSEVSAW DILQKMRGGR

101 PDSVTVQIIE GSRFSHMRKV IDATPDIEHD TKGWSNEKLM AEVAPDAFSG

151 NPEGQFFPDS YEIDAGGSDL RIYQIAYKAM QRRLNEAWES RQDGLPYKNP

201 YEMLIMASLI EKETGHEADR DHVASVFVNR LKIGMRLQTD PSVIYGMGAA

251 YKGKIRKADL RRDTPYNTYT RGGLPPTPIA LPGKAALDAA AHPSGEKYLY

301 FVSKMDGTGL SQFSHDLTEH NAAVRKYILK K*
```

A leader peptide is underlined.
ORF7a and ORF7-1 show 98.8% identity in 331 aa overlap:

```
                   10        20        30        40        50        60
    orf7a.pep  MLRKLLKWSAVFLTVSAAVFAALLFVPKDNGRAYRIKIAKNQGISSVGRKALEDRIVFSR
               ||||||||||||||||||||||||||||||||||||||||||||||||||||||||||||
    orf7-1     MLRKLLKWSAVFLTVSAAVFAALLFVPKDNGRAYRIKIAKNQGISSVGRKALEDRIVFSR
                   10        20        30        40        50        60

70        80        90       100       110       120
    orf7a.pep  HVLTAAAYVLGVHNRLHTGTYRLPSEVSAWDILQKMRGGRPDSVTVQIIEGSRFSHMRKV
               ||||||||||||||||||||||||||||||||||||||||||||||||||||||||||||
    orf7-1     HVLTAAAYVLGVHNRLHTGTYRLPSEVSAWDILQKMRGGRPDSVTVQIIEGSRFSHMRKV
                   70        80        90       100       110       120

130       140       150       160       170       180
    orf7a.pep  IDATPDIEHDTKGWSNEKLMAEVAPDAFSGNPEGQFFPDSYEIDAGGSDLRIYQIAYKAM
               ||||||| |||||||||||||||||||||||||||||||||||||||||:|||  |||||
    orf7-1     IDATPDIGHDTKGWSNEKLMAEVAPDAFSGNPEGQFFPDSYEIDAGGSDLQIYQTAYKAM
                  130       140       150       160       170       180

190       200       210       220       230       240
    orf7a.pep  QRRLNEAWESRQDGLPYKNPYEMLIMASLIEKETGHEADRDHVASVFVNRLKIGMRLQTD
               |||||||||||||||||||||||||||||||:||||||||||||||||||||||||||||
    orf7-1     QRRLNEAWESRQDGLPYKNPYEMLIMASLVEKETGHEADRDHVASVFVNRLKIGMRLQTD
                  190       200       210       220       230       240

250       260       270       280       290       300
    orf7a.pep  PSVIYGMGAAYKGKIRKADLRRDTPYNTYTRGGLPPTPIALPGKAALDAAAHPSGEKYLY
               ||||||||||||||||||||||||||||||||||||||||||||||||||||||||||||
    orf7-1     PSVIYGMGAAYKGKIRKADLRRDTPYNTYTRGGLPPTPIALPGKAALDAAAHPSGEKYLY
                  250       260       270       280       290       300

310       320       330
    orf7a.pep  FVSKMDGTGLSQFSHDLTEHNAAVRKYILKKX
               |||||||||||||||||||||||||||||||
    orf7-1     FVSKMDGTGLSQFSHDLTEHNAAVRKYILKKX
                  310       320       330
```

Homology with a Predicted ORF from *N. gonorrhoeae*
ORF7 shows 94.7% identity over a 187aa overlap with a predicted ORF (ORF7.ng) from *N. gonorrhoeae*:

```
    orf7    MRGGRPDSVTVQIIEGSRFSHMRKVIDATPDIGHDTKGQSNEKLMAEVAPDAFSGNPEGQ    60
            ||||||||||||||||||||||||||||||||||||||||||||||||||||||||||||
    orf7ng  MRGGRPDSVTVQIIEGSRFSHMRKVIDATPDIGHDTKGQSNEKLMAEVAPDAFSGNPEGQ    60 orf7    FFPDSYEIDAGGSDLQIYQTAYKAMQRRMNEAWESRQDGLPYKNPYEMLIMAXLVEKETG   120
            |||||||||||||||||||||||||||||||||| :||||||||||||||||||| :||||
    orf7ng  FFPDSYEIDAGGSDLQIYQTAYKAMQRRMNEAWAGRQDGLPYKNPYEMLIMASLIEKETG   120 orf7    HEAXXDHVASVFVNRLKIGMRLQTXXSVIYGMGAAYKGKIRKADLRRDTPYNTYTRGGLP   180
            |||   ||||||||||||||||||||  ||||||||||||||||||||||||||||||||
    orf7ng  HEADRDHVASVFVNRLKIGMRLQTDPSVIYGMGAAYKGKIRKADLRRDTPYNTYTGGGLP   180 orf7    PTPIALP                                                        187
            || ||||
    orf7ng  PTRIALPGKAAMDAAAHPSGEKYLYFVSKMDGTGLSQFSHDLTEHNAAVRKYILKK       236
```

An ORF7ng nucleotide sequence <SEQ ID 35> is predicted to encode a protein having amino acid sequence <SEQ ID 36>:

```
  1 MRGGRPDSVT VQIIEGSRFS HMRKVIDATP DIGHDTKGWS NEKLMAEVAP

51 DAFSGNPEGQ FFPDSYEIDA GGSDLQIYQT AYKAMQRRLN EAWAGRQDGL

101 PYKNPYEMLI MASLIEKETG HEADRDHVAS VFVNRLKIGM RLQTDPSVIY

151 GMGAAYKGKI RKADLRRDTP YNTYTGGGLP PTRIALPGKA AMDAAAHPSG

201 EKYLYFVSKM DGTGLSQFSH DLTEHNAAVR KYILKK*
```

Further sequence analysis revealed a partial DNA sequence of ORF7ng <SEQ ID 37>:

```
  1..taccgaatca AGATTGCCAA AAATCAGGGT ATTTCGTCGG TCGGCAGGAA

51 ACTTGCcgaA GACCGCATCG TGTTCAGCAG GCATGTTTTG ACAGCGGCGG

101 CCTACGTTTT GGGTGTGCAC AACAGGCTGC ATACGGGGAC gTACAGATTG

151 CCTTCGGAAG TGTCTGCTTG GGATATCTTG CAGAAAATGC GCGGCGGCAG

201 GCCGGATTCC GTTACCGTGC AGATTATCGA AGGTTCGCGT TTTTCGCATA

251 TGAGGAAAGT CATCGACGCA ACGCCCGACA TCGGACACGA CACCAAAGGC

301 TGGAGCAATG AAAAACTGAT GGCGGAAGTT GCGCCCGATG CCTTCAGCGG

351 CAATCCTGAA GGGCAGTTTT TTCCCGACAG CTACGAAATC GATGCGGGCG

401 GCAGCGATTT GCAGATTTAC CAAACCGCCT ACAAGGCGAT GCAACGCCGC

451 CTGAACGAGG CATGGGCAGG CAGGCAGGAC GGGCTGCCTT ATAAAAACCC

501 TTATGAAATG CTGATTATGG CGAGCCTGAT CGAAAAGGAA ACGGGGCATG

551 AGGCCGACCG CGACCATGTC GCTTCCGTCT TCGTCAACCG CCTGAAAATC

601 GGTATGCGCC TGCAAACCGA CCCGTCCGTG ATTTACGGCA TGGGTGCGGC

651 ATACAAGGGC AAAATCCGTA AAGCCGACCT GCGCCGCGAC ACGCCGTACA 701 aCAccTAtac gggcgggggc ttgccgccaa cccggattgc gctgcccggC 751 Aaggcggcaa tggatgccgc cgcccacccg tccggcgaAa aatacctgTa 801 tttcgtgtcC AAAATGGACG GCACGGGCTT GAGCCAGTTC AGCCATGATT 851 TGACCGAACA CAACGCCGCc gTcCGCAAAT ATATTTTGAA AAAATAA
```

This corresponds to the amino acid sequence <SEQ ID 38; ORF7ng-1>:

```
  1..YRIKIAKNQG ISSVGRKLAE DRIVFSRHVL TAAAYVLGVH NRLHTGTYRL

51 PSEVSAWDIL QKMRGGRPDS VTVQIIEGSR FSHMRKVIDA TPDIGHDTKG

101 WSNEKLMAEV APDAFSGNPE GQFFPDSYEI DAGGSDLQIY QTAYKAMQRR

151 LNEAWAGRQD GLPYKNPYEM LIMASLIEKE TGHEADRDHV ASVFVNALKI

201 GMRLQTDPSV IYGMGAAYKG KIRKADLRRD TPYNTYTGGG LPPTRIALPG

251 KAAMDAAAHP SGEKYLYFVS KMDGTGLSQF SHDLTEHNAA VRKYILKK*
```

ORF7ng-1 and ORF7-1 show 98.0% identity in 298 aa overlap:

```
                    10        20        30        40        50        60
orf7-1.pep  KLLKWSAVFLTVSAAVFAALLFVPKDNGRAYRIKIAKNQGISSVGRKLAEDRIVFSRHVL
                                         ||||||||||||||||||||||||||||||
orf7ng-1                                 YRIKIAKNQGISSVGRKLAEDRIVFSRHVL
                                                 10        20        30
                    70        80        90       100       110       120
orf7-1.pep  TAAAYVLGVHNRLHTGTYRLPSEVSAWDILQKMRGGRPDSVTVQIIEGSRFSHMRLVIDA
            ||||||||||||||||||||||||||||||||||||||||||||||||||||||||||||
orf7ng-1    TAAAYVLGVHNRLHTGTYRLPSEVSAWDILQKMRGGRPDSVTVQIIEGSRFSHMRLVIDA
                    40        50        60        70        80        90
                   130       140       150       160       170       180
orf7-1.pep  TPDIGHDTKGQSNEKLMAEVAPDAFSGNPEGQFFPDSYEIDAGGSDLQIYQTAYKAMQRR
            ||||||||||||||||||||||||||||||||||||||||||||||||||||||||||||
orf7ng-1    TPDIGHDTKGQSNEKLMAEVAPDAFSGNPEGQFFPDSYEIDAGGSDLQIYQTAYKAMQRR
                   100       110       120       130       140       150
                   190       200       210       220       230       240
orf7-1.pep  LNEAWESRQDGLPYKNPYEMLIMASLVEKETGHEADRDHVASVFVNRLKIGMRLQTDPSV
            |||||:||||||||||||||||||||:|||||||||||||||||||||||||||||||||
orf7ng-1    LNEAWAGRQDGLPYKNPYEMLIMASLIEKETGHEADRDHVASVFVNRLKIGMRLQTDPSV
                   160       170       180       190       200       210
                   250       260       270       280       290       300
orf7-1.pep  IYGMGAAYKGKIRKADLRRDTPYNTYTRGGLPPTPIALPGKAALDAAAHPSGEKYLYFVS
            |||||||||||||||||||||||||||| ||||||||||||||:||||||||||||||||
orf7ng-1    IYGMGAAYKGKIRKADLRRDTPYNTYTGGGLPPTRIALPGKAAMDAAAHPSGEKYLYFVS
                   220       230       240       250       260       270
                   310       320       330
orf7-1.pep  KMDGTGLSQFSHDLTEHNAAVRKYILKKX
            |||||||||||||||||||||||||||||
orf7ng-1    KMDGTGLSQFSHDLTEHNAAVRKYILKKX
                   280       290
```

In addition, ORF7ng-1 shows significant homology with a hypothetical *E. coli* protein:

```
sp|P28306|YCEG_ECOLI HYPOTHETICAL 38.2 KD PROTEIN IN PABC-HOLB
INTERGENIC REGION
gi|1787339 (AE000210) o340; 100% identical to fragment YCEG_ECOLI SW:
P28306 but has 97 additional C-terminal residues [Escherichia coli]
Length = 340
Score = 79 (36.2 bits), Expect = 5.0e-57, Sum P(2) = 5.0e-57
Identities = 20/87 (22%), Positives = 40/87 (45%)

Query:  10 GISSVGRKLAEDRIVFSRHVLTAAAYVLGVHNRLHTGTYRLPSEVSAWDILQKMRGGRPD  69
           G  ++G +L  D+I+     V    +     GTYR    +++ ++L+ +   G+
Sbjct:  49 GRLALGEQLYADKIINRPRVFQWLLRIEPDLSHFKAGTYRFTPQMTVREMLKLLESGKEA 108

Query:  70 SVTVQIIEGSRFSHMRKVIDATPDIGH  96
              ++++EG R S   K +    P I H
Sbjct: 109 QFPLRLVEGMRLSDYLKQLREAPYIKH 135

Score = 438 (200.7 bits), Expect = 5.0e-57, Sum P(2) = 5.0e-57
Identities = 84/155 (54%), Positives = 111/155 (71%)

Query: 120 EGQFFPDSYEIDAGGSDLQIYQTAYKAMQRRLNEAWAGRQDGLPYKNPYEMLIMASLIEK 179
           EG F+PD++    A  +D+ +  +A+K M  ++  AW GR DGLPYK+   +++ MAS+IEK
Sbjct: 158 EGWFWPDTWMYTANTTDVALLKRAHKKMVKAVDSAWEGRADGLPYKDKNQLVTMASIIEK 217

Query: 180 ETGHEADRDHVASVFVNRLKIGMRLQTDPSVIYGMGAAYKGKIRKADLRRDTPYNTYTGG 239
           ET   ++RD VASVF+NRL+IGMRLQTDP+VIYGMG  Y GK+ +ADL   T YNTYT
Sbjct: 218 ETAVASERDKVASVFINRLRIGMRLQTDPTVIYGMGERYNGKLSRADLETPTAYNTYTIT 277

Query: 240 GLPPTRIALPGKAAMDAAAHPSGEKYLYFVSKMDG 274
           GLPP  IA PG  ++ AAAHP+   YLYFV+   G
Sbjct: 278 GLPPGAIATPGADSLKAAAHPAKTPYLYFVADGKG 312
```

Based on this analysis, including the fact that the *H. influenzae* YCEG protein possesses a possible leader sequence, it is predicted that the proteins from *N. meningitidis* and *N. gonorrhoeae*, and their epitopes, could be useful antigens for vaccines or diagnostics, or for raising antibodies.

Example 6

The following partial DNA sequence was identified in *N. meningitidis* <SEQ ID 39>:

```
  1 CGTTTCAAAA TGTTAACTGT GTTGACGGCA ACCTTGATTG CCGGACAGGT
 51 ATCTGCCGCC GGAGGCGGTG CGGGGGATAT GAAACAGCCG AAGGAAGTCG
101 GAAAGGTTTT CAGAAAGCAG CAGCGTTACA GCGAGGAAGA AATCAAAAAC
151 GAACGCGCAC GGCTTGCGGC AGTGGGCGAG CGGGTTAATC AGATATTTAC
201 GTTGCTGGGA GGGGAAACCG CCTTGCAAAA GGGGCAGGCG GAACGGCTC
251 TGGCAACCTA TATGCTGATG TTGGAACGCA CAAAATCCCC CGAAGTCGCC
301 GAACGCGCCT TGGAAATGGC CGTGTCGCTG AACGCGTTTG AACAGGCGGA
351 AATGATTTAT CAGAAATGGC GGCAGATTGA GCCTATACCG GGTAAGGCGC
401 AAAAACGGGC GGGGTGGCTG CGGAACGTGC TGAGGGAAAG AGGAAATCAG
451 CATCTGGACG GACGGGAAGA AGTGCTGGCT CAGGCGGACG AAGGACAG
```

This corresponds to the amino acid sequence <SEQ ID 40; ORF9>:

```
  1 ..RFKMLTVLTA TLIAGQVSAA GGGAGDMKQP KEVGKVFRKQ QRYSEEEIKN
 51   ERARLAAVGE RVNQIFTLLG GETALQKGQA GTALATYMLM LERTKSPEVA
101   ERALEMAVSL NAFEQAEMIY QKWRQIEPIP GKAQKRAGWL RNVLRERGNQ
151   HLDGREEVLA QADEGQ
```

Further sequence analysis revealed the complete DNA sequence <SEQ ID 41>:

```
  1 ATGTTACCTA ACCGTTTCAA AATGTTAACT GTGTTGACGG CAACCTTGAT
 51 TGCCGGACAG GTATCTGCCG CCGGAGGCGG TGCGGGGGAT ATGAAACAGC
101 CGAAGGAAGT CGGAAAGGTT TTCAGAAAGC AGCAGCGTTA CAGCGAGGAA
151 GAAATCAAAA ACGAACGCGC ACGGCTTGCG GCAGTGGGCG AGCGGGTTAA
201 TCAGATATTT ACGTTGCTGG GAGGGGAAAC CGCCTTGCAA AAGGGGCAGG
251 CGGGAACGGC TCTGGCAACC TATATGCTGA TGTTGGAACG CACAAAATCC
301 CCCGAAGTCG CCGAACGCGC CTTGGAAATG GCCGTGTCGC TGAACGCGTT
351 TGAACAGGCG GAAATGATTT ATCAGAAATG GCGGCAGATT GAGCCTATAC
101 CGGGTAAGGC GCAAAAACGG GCGGGGTGGC TGCGGAACGT GCTGAGGGAA
451 AGAGGAAATC AGCATCTGGA CGGACTGGAA GAAGTGCTGG CTCAGGCGGA
501 CGAAGGACAG AACCGCAGGG TGTTTTTATT GTTGGCACAA GCCGCCGTGC
551 AACAGGACGG GTTGGCGCAA AAAGCATCGA AAGCGGTTCG CCGCGCGGCG
601 TTGAAATATG AACATCTGCC CGAAGCGGCG GTTGCCGATG TGGTGTTCAG
651 CGTACAGGGA CGCGAAAAGG AAAAGGCAAT CGGAGCTTTG CAGCGTTTGG
701 CGAAGCTCGA TACGGAAATA TTGCCCCCCA CTTTAATGAC GTTGCGTCTG
751 ACTGCACGCA AATATCCCGA AATACTCGAC GGCTTTTTCG AGCAGACAGA
801 CACCCAAAAC CTTTCGGCCG TCTGGCAGGA AATGGAAATT ATGAATCTGG
851 TTTCCCTGCA CAGGCTGGAT GATGCCTATG CGCGTTTGAA CGTGCTGTTG
901 GAACGCAATC CGAATGCAGA CCTGTATATT CAGGCAGCGA TATTGGCGGC
```

```
 951 AAACCGAAAA GAAGGTGCTT CCGTTATCGA CGGCTACGCC GAAAAGGCAT

1001 ACGGCAGGGG GACGGAGGAA CAGCGGAGCA GGGCGGCGCT AACGGCGGCG

1051 ATGATGTATG CCGACCGCAG GGATTACGCC AAAGTCAGGC AGTGGCTGAA

1101 AAAAGTATCC GCGCCGGAAT ACCTGTTCGA CAAAGGTGTG CTGGCGGCTG

1151 CGGCGGCTGT CGAGTTGGAC GGCGGCAGGG CGGCTTTGCG GCAGATCGGC

1201 AGGGTGCGGA AACTTCCCGA ACAGCAGGGG CGGTATTTTA CGGCAGACAA

1251 TTTGTCCAAA ATACAGATGC TCGCCCTGTC GAAGCTGCCC GATAAACGGG

1301 AGGCTTTGAG GGGGTTGGAC AAGATTATCG AAAAACCGCC TGCCGGCAGT

1351 AATACAGAGT TACAGGCAGA GGCATTGGTA CAGCGGTCAG TTGTTTACGA

1401 TCGGCTTGGC AAGCGGAAAA AAATGATTTC AGATCTTGAA AGGGCGTTCA

1451 GGCTTGCACC CGATAACGCT CAGATTATGA ATAATCTGGG CTACAGCCTG

1501 CTGACCGATT CCAAACGTTT GGACGAAGGT TTCGCCCTGC TTCAGACGGC

1551 ATACCAAATC AACCCGGACG ATACCGCTGT CAACGACAGC ATAGGCTGGG

1601 CGTATTACCT GAAAGGCGAC GCGGAAAGCG CGCTGCCGTA TCTGCGGTAT

1651 TCGTTTGAAA ACGACCCCGA GCCCGAAGTT GCCGCCCATT TGGGCGAAGT

1701 GTTGTGGGCA TTGGGCGAAC GCGATCAGGC GGTTGACGTA TGGACGCAGG

1751 CGGCACACCT TACGGGAGAC AAGAAAATAT GGCGGGAAAC GCTCAAACGT

1801 CACGGCATCG CATTGCCCCA ACCTTCCCGA AAACCTCGGA AATAA
```

This corresponds to the amino acid sequence <SEQ ID 42; ORF9-1>:

```
  1 MLPNRFKMLT VLTATLIAGQ VSAAGGGAGD MKQPKEVGKV FRKQQRYSEE

51 EIKNERARLA AVGERVNQIF TLLGGETALQ KGQAGTALAT YMLMLERTKS

101 PEVAERALEM AVSLNAFEQA EMIYQKWRQI EPIPGKAQKR AGWLRNVLRE

151 RGNQHLDGLE EVLAQADEGQ NRRVFLLLAQ AAVQQDGLAQ KASKAVRRAA

201 LKYEHLPEAA VADVVFSVQG REKEKAIGAL QRLAKLDTEI LPPTLMTLRL

251 TARKYPEILD GFFEQTDTQN LSAVWQEMEI MNLVSLHRLD DAYARLNVLL

301 ERNPNADLYI QAAILAANRK EGASVIDGYA EKAYGRGTEE QRSRAALTAA

351 MMYADRRDYA KVRQWLKKVS APEYLFDKGV LAAAAAVELD GGRAALRQIG

401 RVRKLPEQQG RYFTADNLSK IQMLALSKLP DKREALRGLD KIIEKPPAGS

451 NTELQAEALV QRSVVYDRLG KRKKMISDLE RAFRLAPDNA QIMNNLGYSL

501 LTDSKRLDEG FALLQTAYQI NPDDTAVNDS IGWAYYLKGD AESALPYLRY

551 SFENDPEPEV AAHLGEVLWA LGERDQAVDV WTQAAHLTGD KKIWRETLKR

601 HGIALPQPSR KPRK*
```

Computer analysis of this amino acid sequence gave the following results:

Homology with a Predicted ORF from *N. meningitidis* (Strain A)

ORF9 shows 89.8% identity over a 166aa overlap with an ORF (ORF9a) from strain A of *N. meningitidis*.

```
                   10        20        30        40        50
    orf9.pep       RFKMLTVLTATLIAGQVSAAGGGAGDMKQPKEVGKVFRKQQRYSEEEIKNERARLA
                   || :|:||:|:|:|||: ||   ||:| | |||||||||||||||||||||||||
    orf9a          MLPARFTILSVLAAALLAGQAYAA--GAADAKPPKEVGKVFRKQQRYSEEEIKNERARLA
                        10        20        30        40        50

60        70        80        90       100       110
    orf9.pep       AVGERVNQIFTLLGGETALQKGQAGTALATYMLMLERTKSPEVAERALEMAVSLNAFEQA
                   ||||||||||||||| |||||||||||||||||||||||||||||||||||||||||||
    orf9a          AVGERVNQIFTLLGXETALQKGQAGTALATYMLMLERTKSPEVAERALEMAVSLNAFEQA
                        60        70        80        90       100       110

120       130       140       150       160
    orf9.pep       EMIYQKWRQIEPIPGKAQKRAGWLRNVLRERGMQHLDGREEVLAQADEGQ
                   |||||||||||||||||||||||||||||||||||||| || |||||| |
    orf9a          EMIYQKWRQIEPIPGKAQKRAGWLRNVLRERGMQHLDGLEEXLAQADEXQNRRVFLLLAQ
                       120       130       140       150       160       170
```

The complete length ORF9a nucleotide sequence <SEQ ID 43> is:

```
   1 ATGTTACCCG CCCGTTTCAC CATTTTATCT GTGCTCGCGG CAGCCCTGCT
  51 TGCCGGGCAG GCGTATGCCG CCGGCGCGGC GGATGCGAAG CCGCCGAAGG
 101 AAGTCGGAAA GGTTTTCAGA AAGCAGCAGC GTTACAGCGA GGAAGAAATC
 151 AAAAACGAAC GCGCACGGCT TGCGGCAGTG GGCGAGCGGG TTAATCAGAT
 201 ATTTACGTTG CTGGGANGGG AAACCGCCTT GCAAAAGGGG CAGGCGGGAA
 251 CGGCTCTGGC AACCTATATG CTGATGTTGG AACGCACAAA ATCCCCCGAA
 301 GTCGCCGAAC GCGCCTTGGA AATGGCCGTG TCNCTGAACG CGTTTGAACA
 351 GGCGGAAATG ATTTATCAGA AATGGCGGCA GATTGAGCCT ATACCGGGTA
 401 AGGCGCAAAA ACGGGCGGGG TGGCTGCGGA ACGTGCTGAG GGAAAGAGGA
 451 AATCAGCATC TAGACGGACT GGAAGAANTG CTGGCTCAGG CGGACGAANG
 501 ACAGAACCGC AGGGTGTTTT TATTGTTGGC ACAAGCCGCC GTGCAACAGG
 551 ACGGGTTGGC GCAAAAAGCA TCGAAAGCGG TTCGCCGCGC GGCGTTGAGA
 601 TATGAACATC TGCCCGAAGC GGCGGTTGCC GATGTGGTGT TCAGCGTACA
 651 GGNACGCGAA AAGGAAAAGG CAATCGGAGC TTTGCAGCGT TTGGCGAAGC
 701 TCGATACGGA AATATTGCCC CCCACTTTAA TGACGTTGCG TCTGACTGCA
 751 CGCAAATATC CCGAAATACT CGACGGCTTT TTCGAGCAGA CAGACACCCA
 801 AAACCTTTCG GCCGTCTGGC AGGAAATGGA AATTATGAAT CTGGTTTCCC
 851 TGCACAGGCT GGATGATGCC TATGCGCGTT TGAACGTGCT GTTGGAACGC
 901 AATCCGAATG CAGACCTGTA TATTCAGGCA GCGATATTGG CGGCAAACCG
 951 AAAAGAANGT GCTTCCGTTA TCGACGGCTA CGCCGAAAAG GCATACGGCA
1001 GGGGGACGGG GGAACAGCGG GGCAGGGCGG CAATGACGGC GGCGATGATA
1051 TATGCCGACC GAAGGGATTA CACCAAAGTC AGGCAGTGGT TGAAAAAAGT
1101 GTCCGCGCCG GAATACCTGT TCGACAAAGG TGTGCTGGCG GCTGCGGCGG
1151 CTGTCGAGTT GGACNGCGGC AGGGCGGCTT TGCGGCAGAT CGGCAGGGTG
1201 CGGAAACTTC CCGAACAGCA GGGGCGGTAT TTTACGGCAG ACAATTTGTC
```

```
1251 CAAAATACAG ATGTTCGCCC TGTCGAAGCT GCCCGACAAA CGGGAGGCTT

1301 TGAGGGGGTT GGACAAGATT ATCGAAAAAC CGCCTGCCGG CAGTAATACA

1351 GAGTTACAGG CAGAGGCATT GGTACAGCGG TCAGTTGTTT ACGATCGGCT

1401 TGGCAAGCGG AAAAAAATGA TTTCAGATCT TGAAAGGGCG TTCAGGCTTG

1451 CACCCGATAA CGCTCAGATT ATGAATAATC TGGGCTACAG CCTGCTTTCC

1501 GATTCCAAAC GTTTGGACGA AGGCTTCGCC CTGCTTCAGA CGGCATACCA

1551 AATCAACCCG GACGATACCG CTGTCAACGA CAGCATAGGC TGGGCGTATT

1601 ACCTGAAAAG CGACGCGGAA AGCGCGCTGC CGTATCTGCG GTATTCGTTT

1651 GAAAACGACC CCGAGCCCGA AGTTGCCGCC CATTTGGGCG AAGTGTTGTG

1701 GGCATTGGGC GAACGCGATC AGGCGGTTGA CGTATGGACG CAGGCGGCAC

1751 ACCTTACGGG AGACAAGAAA ATATGGCGGG AAACGCTCAA ACGTCACGGC

1801 ATCGCATTGC CCCAACCTTC CCGAAAACCT CGGAAATAA
```

This encodes a protein having amino acid sequence <SEQ ID 44>:

```
  1 MLPARFTILS VLAAALLAGQ AYAAGAADAK PPKEVGKVFR KQQRYSEEEI

51 KNERARLAAV GERVNQIFTL LGXETALQKG QAGTALATYM LMLERTKSPE

101 VAERALEMAV SLNAFEQAEM IYQKWRQIEP IPGKAQKRAG WLRNVLRERG

151 NQHLDGLEEX LAQADEXQNR RVFLLLAQAA VQQDGLAQKA SKAVRRAALR

201 YEHLPEAAVA DVVFSVQXRE KEKAIGALQR LAKLDTEILP PTLMTLRLTA

251 RKYPEILDGF FEQTDTQNLS AVWQEMEIMN LVSLHRLDDA YARLNVLLER

301 NPNADLYIQA AILAANRKEX ASVIDGYAEK AYGRGTGEQR GRAAMTAAMI

351 YADRRDYTKV RQWLKKVSAP EYLFDKGVLA AAAAVELDXG RAALRQIGRV

401 RKLPEQQGRY FTADNLSKIQ MFALSKLPDK REALRGLDKI IEKPPAGSNT

451 ELQAEALVQR SVVYDRLGKR KKMISDLERA FRLAPDNAQI MNNLGYSLLS

501 DSKRLDEGFA LLQTAYQINP DDTAVNDSIG WAYYLKXDAE SALPYLRYSF

551 ENDPEPEVAA HLGEVLWALG ERDQAVDVWT QAAHLTGDKK IWRETLKRHG

601 IALPQPSRKP RK*
```

ORF9a and ORF9-1 show 95.3% identity in 614 aa overlap:

```
                 10        20        30        40        50
     orf9a.pep  MLPARFTILSVLAAALLAGQAYAAG--AADAKPPKEVGKVFRKQQRYSEEEIKNERARLA
                ||| || :|:||:|:||| ||| |:| ||||||||||||||||||||||||||
     orf9-1     MLPNRFKMLTVLTATLIAGQVSAAGGGAGDMKQPKEVGKVFRKQQRYSEEEIKNERARLA
                        10        20        30        40        50        60

60        70        80        90       100       110
     orf9a.pep  AVGERVNQIFTLLGXETALQKGQAGTALATYMLMLERTKSPEVAERALEMAVSLNAFEQA
                ||||||||||||||| |||||||||||||||||||||||||||||||||||||||||||
     orf9-1     AVGERVNQIFTLLGGETALQKGQAGTALATYMLMLERTKSPEVAERALEMAVSLNAFEQA
                        70        80        90       100       110       120

120       130       140       150       160       170
     orf9a.pep  EMIYQKWRQIEPIPGKAQKRAGWLRNVLRERGNQHLDGLEEXLAQADEXQNRRVFLLLAQ
                |||||||||||||||||||||||||||||||||||||||||| |||||| ||||||||||
     orf9-1     EMIYQKWRQIEPIPGKAQKRAGWLRNVLRERGNQHLDGLEEVLAQADEGQNRRVFLLLAQ
                       130       140       150       160       170       180

180       190       200       210       220       230
     orf9a.pep  AAVQQDGLAQKASKAVRRAALRYEHLPEAAVADVVFSVQXREKEKAIGALQRLAKLDTEI
                |||||||||||||||||||||||:|||||||||||||||| ||||||||||||||||||
     orf9-1     AAVQQDGLAQKASKAVRRAALKYEHLPEAAVADVVFSVQGREKEKAIGALQRLAKLDTEI
                       190       200       210       220       230       240
```

```
             240       250       260       270       280       290
orf9a.pep    LPPTLMTLRLTARKYPEILDGFFEQTDTQNLSAVWQEMEIMNLVSLHRLDDAYARLNVLL
             ||||||||||||||||||||||||||||||||||||||||||||||||||||||||||||
orf9-1       LPPTLMTLRLTARKYPEILDGFFEQTDTQNLSAVWQEMEIMNLVSLHRLDDAYARLNVLL
               250       260       270       280       290       300

300       310       320       330       340       350
orf9a.pep    ERNPNADLYIQAAILAANRKEXASVIDGYAEKAYGRGTGEQRGRAAMTAAMIYADRRDYT
             ||||||||||||||||||||| ||||||||||||||||||  |:|||| :||||||||:
orf9-1       ERNPNADLYIQAAILAANRKEGASVIDGYAEKAYGRGTEEQRSRAALTAAMMYADRRDYA
               310       320       330       340       350       360

360       370       380       390       400       410
orf9a.pep    KVRQWLKKVSAPEYLFDKGVLAAAAAVELDXGRAALRQIGRVRKLPEQQGRYFTADNLSK
             |||||||||||||||||||||||||||||| |||||||||||||||||||||||||||||
orf9-1       KVRQWLKKVSAPEYLFDKGVLAAAAAVELDGGRAALRQIGRVRKLPEQQGRYFTADNLSK
               370       380       390       400       410       420

420       430       440       450       460       470
orf9a.pep    IQMFALSKLPDKREALRGLDKIIEKPPAGSNTELQAEALVQRSVVYDRLGKRKKMISDLE
             |||:||||||||||||||||||||||||||||||||||||||||||||||||||||||
orf9-1       IQMLALSKLPDKREALRGLDKIIEKPPAGSNTELQAEALVQRSVVYDRLGKRKKMISDLE
               430       440       450       460       470       480

480       490       500       510       520       530
orf9a.pep    RAFRLAPDNAQIMNNLGYSLLSDSKRLDEGFALLQTAYQINPDDTAVNDSIGWAYYLKXD
             ||||||||||||||||||||||:|||||||||||||||||||||||||||||||||| |
orf9-1       RAFRLAPDNAQIMNNLGYSLLTDSKRLDEGFALLQTAYQINPDDTAVNDSIGWAYYLKGD
               490       500       510       520       530       540

540       550       560       570       580       590
orf9a.pep    AESALPYLRYSFENDPEPEVAAKLGEVLWALGERDQAVDVWTQAAHLTGDKKIWRETLKR
             ||||||||||||||||||||||||||||||||||||||||||||||||||||||||||||
orf9-1       AESALPYLRYSFENDPEPEVAAKLGEVLWALGERDQAVDVWTQAAHLTGDKKIWRETLKR
               550       560       570       580       590       600

600       610
orf9a.pep    HGIALPQPSRKPRKX
             |||||||||||||||
orf9-1       HGIALPQPSRKPRKX
               610
```

Homology with a Predicted ORF from *N. gonorrhoeae*

ORF9 shows 82.8% identity over a 163aa overlap with a predicted ORF (ORF9.ng) from *N. gonorrhoeae*.

```
Orf9          RFKMLTVLTATLIAGQVSAAGGGAGDMKQPKEVGKVFRKQQRYSEEEIKNERAR    54
              || :|:||:|:|||:  ||   ||:|:: |||||||:||::|||||||||||||
orf9ng   MIMLPARFTILSVLAAALLAGQAYAA--GAADVELPKEVGKVLRKHRRYSEEEIKNERAR    58 orf9          LAAVGERVNQIFTLLGGETALQKGQAGTALATYMLMLERTKSPEVAERALEMAVSLNAFE   114
              ||||||||||:::||||||||||||||||||||||||||||||||||||||||||||||
orf9ng        LAAVGERVNRVFTLLGGETALQKGQAGTALATYMLMLERTKSPEVAERALEMAVSLNAFE   118 orf9          QAEMIYQKWRQIEPIPGKAQKRAGWLRNVLRERGNQHLDGREEVLAQADEGQ          166
              |||||||||||||||||||:|||||||||||||:|||||:|||:|||||:|
orf9ng        QAEMIYQKWRQIEPIPGEAQKPAGWLRNVLKEGGNPHLDRLEEVPAQSDYVHQPMIFLLL  178
```

The ORF9ng nucleotide sequence <SEQ ID 45> was predicted to encode a protein having including acid sequence <SEQ ID 46>:

```
  1 MIMLPARFTI LSVLAAALLA GQAYAAGAAD VELPKEVGKV LRKHRRYSEE

51 EIKNERARLA AVGERVNRVF TLLGGETALQ KGQAGTALAT YMLMLERTKS

101 PEVAERALEM AVSLNAFEQA EMIYQKWRQI EPIPGEAQKP AGWLRNVLKE

151 GGNPHLDRLE EVPAQSDYVH QPMIFLLLVQ AAVQHGGVAQ KPSKAVRPAA

201 YNYEVLPETA GADAVFCVQG PQYEKAIQSF PPCGRNPQTE NIAPPFNELF

251 RPTARPISPK LLQRFFRTEP NLAKPFRPPG PEMETYQTGF PRPLTRNNPT
```

Amino acids 1-28 are a putative leader sequence, and 173-189 are predicted to be a transmembrane domain.

Further sequence analysis revealed the complete length ORF9ng DNA sequence <SEQ ID 47>:

```
   1 ATGTTACCCG CCCGTTTCAC TATTTTATCT GTCCTCGCAG CAGCCCTGCT
  51 TGCCGGACAG GCGTATGCTG CCGGCGCGGC GGATGTGGAG CTGCCGAAGG
 101 AAGTCGGAAA GGTTTTAAGG AAACATCGGC GTTACAGCGA GGAAGAAATC
 151 AAAAACGAAC GCGCACGGCT TGCGGCAGTG GGCGAACGGG TCAACAGGGT
 201 GTTTACGCTG TTGGGCGGTG AAACGGCTTT GCAGAAAGGG CAGGCGGGAA
 251 CGGCTCTGGC AACCTATATG CTGATGTTGG AACGCACAAA ATCCCCCGAA
 301 GTCGCCGAAC GCGCCTTGGA AATGGCCGTG TCGCTGAACG CGTTTGAACA
 351 GGCGGAAATG ATTTATCAGA AATGgcggca gatcgagcct ataCcggtg
 401 aggcgcaaaa accgGcgggG tggctgcgga acgtattgaa ggaagggGGa
 451 aaTCAGCATC TGGAcgggtt gaaagaggTG CtggcgcaAT cggacgatGT
 501 GCAAAAAcgc aggaTATTTT TGCTGCTGGT GCAAGCCGCC GTGCagcagg
 551 gTGGGGTGGC TCAAAAAGCA TCGAAAGCGG TTCGCcgtgc GGcgttgaAG
 601 TATGAACATC TGCCcgaagc ggcggTTGCC GATGcggTGT TCGGCGTACA
 651 GGGACGCGAA AAGGAAAagg caaTCGAAGC TTTGCAGCGT TTGGCGAAGC
 701 TCGATACGGA AATATTGCCC CCCACTTTAA TGACGTTGCG TCTGACTGCA
 751 CGCAAATATC CCGAAATACT CGACGGCTTT TTCGAGCAGA CAGACACCCA
 801 AAACCTTTCG GCCGTCTGGC AGGAAATGGA AATTATGAAT CTGGTTTCCC
 851 TGCGTAAGCC GGATGATGCC TATGCGCGTT TGAACGTGCT GTTGGAACAC
 901 AACCCGAATG CAAACCTGTA TATTCAGGCG GCGATATTGG CGGCAAACCG
 951 AAAAGAAGGT GCGTCCGTTA TCGACGGCTA CGCCGAAAAG GCATACGGCA
1001 GGGGGACGGG GGAACAGCGG GGCagggcgg cAATgacggc GGCGATGATA
1051 TATGCCGACC GCAGGGATTA CGCCAAAGTC AGGCAGTGGT TGAAAAAAGT
1101 GTCCGCGCCG GAATACCTGT TCGACAAAGG CGTGCTGGCG GCTGCGGCGG
1151 CTGCCGAATT GGACGGAGGC CGGGCGGCTT TGCGGCAGAT CGGCAGGGTG
1201 CGGAAACTTC CCGAACAGCA GGGGCGGTAT TTTACGGCAG ACAATTTGTC
1251 CAAAATACAG ATGCTCGCCC TGTCGAAGCT GCCCGACAAA CGGGAAGCCC
1301 TGATCGGGCT GAACAACATC ATCGCCAAAC TTTCGGCGGC GGGAAGCACG
1351 GAACCTTTGG CGGAAGCATT GGCACAGCGT TCCATTATTT ACGaacAGTT
1401 cggCAAACGG GGAAAAATGA TTGCCGACCT tgaAACcgcg CTCAAACTTA
1451 CGCCCGATAA TGCACAAATT ATGAATAATC TGGGCTACAG CCTGCTTTCC
1501 GATTCCAAAC GTTTGGACGA GGGTTTCGCC CTGCTTCAGA CGGCATACCA
1551 AATCAACCCG GACGATACCG CCGTTAACGA CAGCATAGGC TGGGCGTATT
1601 ACCTGAAAGG CGACgcggaA AGCGCGCTGC CGTATCTGcg gtattcgttt
1651 gAAAACGACC CCGAGCCCGA AGTTGCCGCC CATTTGGGCG AAGTGTTGTG
1701 GGCATTGGGC GAACGCGATC AGGCGGTTGA CGTATGGACG CAGGCGGCAC
1751 ACCTTAGGGG AGACAAGAAA ATATGGCGGG AGACGCTCAA ACGCTACGGA
1801 ATCGCCTTGC CCGAGCCTTC CCGAAAACCC CGGAAATAA
```

This encodes a protein having amino acid sequence <SEQ ID 48>:

```
  1 MLPARFTILS VLAAALLAGQ AYAAGAADVE LPKEVGKVLR KHRRYSEEEI
 51 KNERARLAAV GERVNRVFTL LGGETALQKG QAGTALATYM LMLERTKSPE
101 VAERALEMAV SLNAFEQAEM IYQKWRQIEP IPGEAQKPAG WLRNVLKEGG
151 NQHLDGLKEV LAQSDDVQKR RIFLLLVQAA VQQGGVAQKA SKAVRRAALK
201 YEHLPEAAVA DAVFGVQGRE KEKAIEALQR LAKLDTEILP PTLMTLRLTA
251 RKYPEILDGF FEQTDTQNLS AVWQEMEIMN LVSLRKPDDA YARLNVLLEH
301 NPNANLYIQA AILAANRKEG ASVIDGYAEK AYGRGTGEQR GRAAMTAAMI
351 YADRRDYAKV RQWLKKVSAP EYLFDKGVLA AAAAAELDGG RAALRQIGRV
401 RKLPEQQGRY FTADNLSKIQ MLALSKLPDK REALIGLNNI IAKLSAAGST
451 EPLAEALAQR SIIYEQFGKR GKMIADLETA LKLTPDNAQI MNNLGYSLLS
501 DSKRLDEGFA LLQTAYQINP DDTAVNDSIG WAYYLKGDAE SALPYLRYSF
551 ENDPEPEVAA HLGEVLWALG ERDQAVDVWT QAAHLRGDKK IWRETLKRYG
601 IALPEPSRKP RK*
```

ORF9ng and ORF9-1 show 88.1% identity in 614 aa overlap:

```
                   10         20         30         40         50         60
    orf9-1.pep  MLPNRFKMLTVLTATLIAGQVSAAGGGAGDMKQPKEVGKVFRKQQRYSEEEIKNERARLA
                |||  || :|:||:|:|||: |||    |:|:: |||||||||||:||||||::||||||
    orf9ng-1    MLPARFTILSVLAAALLAGQAYAAG--AADVELPKEVGKVLRKHRRYSEEEIKNERARLA
                         10         20          30        40         50

70         80         90        100        110        120
    orf9-1.pep  AVGERVNQIFTLLGGETALQKGQAGTALATYMLMLERTKSPEVAERALEMAVSLNAFEQA
                ||||||| :|:|||||||||||||||||||||||||||||||||||||||||||||||||
    orf9ng-1    AVGERVNRVFTLLGGETALQKGQAGTALATYMLMLERTKSPEVAERALEMAVSLNAFEQA
                         60         70         80         90        100        110

130        140        150        160        170        180
    orf9-1.pep  EMIYQKWRQIEPIPGKAQKRAGWLRNVLRERGNQHLDGLEEVLAQADEGQNRRVFLLLAQ
                ||||||||||||||| :||| ||||||||:|:|||||||| |||| ||||:| :|:|||||:|
    orf9ng-1    EMIYQKWRQIEPIPGEAQKPAGWLRNVLKEGGNQHLDGLKEVLAQSDDVQKRRIFLLLVQ
                        120        130        140        150        160        170

190        200        210        220        230        240
    orf9-1.pep  AAVQQDGLAQKASKAVRRAALKYEHLPEAAVADVVFSVQGREKEKAIGALQRLAKLDTEI
                |||||  :||||||||||||||||||||||||| :|:|||||||||||| ||||||||||
    orf9ng-1    AAVQQGGVAQKASKAVRRAALKYEHLPEAAVADAVFGVQGREKEKAIEALQRLAKLDTEI
                        180        190        200        210        220        230

250        260        270        280        290        300
    orf9-1.pep  LPPTLMTLRLTARKYPEILDGFFEQTDTQNLSAVWQEMEIMNLVSLDDAYARLNVLL
                |||||||||||||||||||||||||||||||||||||||||||||:: ||||||||||
    orf9ng-1    LPPTLMTLRLTARKYPEILDGFFEQTDTQNLSAVWQEMEIMNLVSLRKPDDAYARLNVLL
                        240        250        260        270        280        290

310        320        330        340        350        360
    orf9-1.pep  ERNPNADLYIQAAILAANRKEGASVIDGYAEKAYGRGTEEQRSRAALTAAMMYADRRDYA
                |:||||:||||||||||||||||||||||||||||||||| ||:|||:|||:||||||||
    orf9ng-1    EHNPNANLYIQAAILAANRKEGASVIDGYAEKAYGRGTGEQRGRAAMTAAMIYADRRDYA
                        300        310        320        330        340        350

370        380        390        400        410        420
    orf9-1.pep  KVRQWLKKVSAPEYLFDKGVLAAAAAVELDGGRAALRQIGRVRKLPEQQGRYFTADNLSK
                |||||||||||||||||||||||||||:|||||||||||||||||||||||||||||||
    orf9ng-1    KVRQWLKKVSAPEYLFDKGVLAAAAAAELDGGRAALRQIGRVRKLPEQQGRYFTADNLSK
                        360        370        380        390        400        410

430        440        450        460        470        480
    orf9-1.pep  IQMLALSKLPDKREALRGLDKIIEKPPAGSNTELQAEALVQRSVVYDRLGKRKKMISDLE
                |||||||||||||||| ::||| |    |:::|| ||||:|::::|||  ||| |||:|||
    orf9ng-1    IQMLALSKLPDKREALIGLNNIIAKLSAAGSTEPLAEALAQRSIIYEQFGKRGKMIADLE
                        420        430        440        450        460        470

490        500        510        520        530        540
    orf9-1.pep  RAFRLAPDNAQIMNNLGYSLLTDSKRLDEGFALLQTAYQINPDDTAVNDSIGWAYYLKGD
                |::|| |||||||||||||||||:|||||||||||||||||||||||||||||||||||
    orf9ng-1    TALKLTPDNAQIMNNLGYSLLSDSKRLDEGFALLQTAYQINPDDTAVNDSIGWAYYLKGD
                        480        490        500        510        520        530
```

```
                 550        560        570        580        590        600
orf9-1.pep   AESALPYLRYSFENDPEPEVAAHLGEVLWALGERDQAVDVWTQAAHLTGDKKIWRETLKR
             |||||||||||||||||||||||||||||||||||||||||||||| ||||||||||||
orf9ng-1     AESALPYLRYSFENDPEPEVAAHLGEVLWALGERDQAVDVWTQAAHLRGDKKIWRETLKR
             540        550        560        570        580        590

610
orf9-1.pep   HGIALPQPSRKPRKX
             :||||| :|||||||
orf9ng-1     YGIALPEPSRKPRKX
             600        610
```

In addition, ORF9ng shows significant homology with a hypothetical protein from *P. aeruginosa*:

```
sp|P42810|YHE3_PSEAE HYPOTHETICAL 64.8 KD PROTEIN IN HEMM-HEMA
INTERGENIC REGION (ORF3)
>gi|1072999|pir||S49376 hypothetical protein 3 - Pseudomonas aeruginosa
>gi|557259
(X82071) orf3 [Pseudomonas aeruginosa] Length = 576
Score = 128 bits (318), Expect = 1e-28
Identities = 138/587 (23%), Positives = 228/587 (38%), Gaps = 125/587 (21%)

Query:  67 VFTLLGGETALQKGQAGTALATYMLMLERTKSPEVAERALEMAVSLNAFEQAEMIYQKWR 126
            +++LL  E A Q+ +   AL+ Y++  ++T+ P V+ERA   +A   L A ++A       W
Sbjct:  53 LYSLLVAELAGQRNRFDIALSNYVVQAQKTRDPGVSERAFRIAEYLGADQEALDTSLLWA 112

Query: 127 QIEPIPGEAQKPAG--------------WLRNVLKEGGNQHLDGLKEVLAQSDDVQKRRI 172
           + P  +AQ+ A              ++ VL   G+ H DL   A++D  +  +
Sbjct: 113 RSAPDNLDAQRAAAIQLARAGRYEESMVYMEKVLNGQGDTHFDFLALSAAETDPDTRAGL 172

Query: 173 FXXXXXXXXXXXXXXXXXKASKAVRRAALKYEHLPEAAVADAVFGVQGREKEKAIEALQRLA 232
                              ++      KY +  +    A+   Q   ++A+  L+  +
Sbjct: 173 L-----------------QSFDHLLKKYPNNGQLLFGKALLLQQDGRPDEALTLLEDNS 214

Query: 233 KLDTEILPPTLMTLRLTARK-----YPEILDGFFEQTDTQNLSAVWQEMEIMNLVSLRKP 287
            E+ P L+ L +K      P + G  E D + + + +     LV  +
Sbjct: 215 ASRHEVAPLLLRSLLQSMKRSDEALPLLKAGIKEHPDDKRVRLAYARL----LVEQNRL 270

Query: 288 DDAYARLNVLLEHNPN--------------------ANLYIQAAI-------------- 312
           DDA  A    L++  P+                    A +Y++  +
Sbjct: 271 DDAKAEFAGLVQQFPDDDDDLRFSLALVCLEAQAWDEARIYLEELVERDSHVDAAHFNLG 330

Query: 313 -LAANRKEGASVIDGYAEKAYGRGTGEQRGRAAMTAAMIYADRRDYAKVRQWLKKVSAPE 371
            LA +K+ A  +D YA+   G G       +  T  ++ A R D A R     +  P+
Sbjct: 331 RLAEEQKDTARALDEYAQ--VGPGNDFLPAQLRQTDVLLKAGRVDEAAQRLDKARSEQPD 388

Query: 372 YLFDKXXXXXXXXXXXXXXXXXXXXRQIGRVRKLPEQQGRYFTADNLSKIQMLALSKLPDKR 431
           Y                                         A  L  I+  ALS    +
Sbjct: 389 Y----------------------------------------AIQLYLIEAEALSNNDQQE 408

Query: 432 EALIGLNNIIAKLSAAGSTEPLAEALAQRSIIYEQFGKRGKMIADLETALKLTPDNAQIM 491
            +A  +   ++    E L   L RS++ E+    +M DL  +  PDNA +
Sbjct: 409 KAWQAIQEGLKQYP-----EDL-NLLYTRSMLAEKRNDLAQMEKDLRFVIAREPDNAMAL 462

Query: 492 NNLGYSLLSDSKRLDEGFALLQTAYQINPDDTAVNDSIGWAYYLKGDAESALPYLRYSFE 551
           N LGY+L    + R  E  L+   A+++NPDD A+ DS+GW  Y +G    A  YLR + +
Sbjct: 463 NALGYTLADRTTRYGEARELILKAHKLNPDDPAILDSMGWINYRQGKLADAERYLRQALQ 522

Query: 552 NDPEPEVAAHLGEVLWALGERDQAVDVWTQAAHLRGDKKIWRETLKR             598
            P+ EVAAHLGEVLWA G + A  +W +      + D +R T+KR
Sbjct: 523 RYPDHEVAAHLGEVLWAQGRQGDARAIWREYLDKQPDSDVLRRTIKR             569 gi|2983399 (AE000710) hypothetical protein [Aquifex aeolicus] Length = 545
Score = 81.5 bits (198), Expect = 1e-14
Identities = 61/198 (30%), Positives = 98/198 (48%), Gaps = 19/198 (9%)

Query: 408 GRYFTADNL-SKIQMLALSKLPDKREALIGLNNIIAKLSAAGSTEPLAEALAQ------- 459
           G   +  +L  ++ LA   PDK+E L    +K    + + +L +
Sbjct: 335 GNYEDAKRLIEKAKVLA----PDKKEILFLEADYYSKTKQYDKALEILKKLEKDYPNDSR 390

Query: 460 ----RSIIYEQFGKRGKMIADLETALKLTPDNAQIMNNLGYSLLS--DSKRLDEGFALLQ 513
               +I+Y+   G       L  A++L P+N  N LGYSLL   +R++E  L++
Sbjct: 391 VYFMEAIVYDNLGDIKNAEKALRKAIELDPENPDYYNYLGYSLLLWYGKERVEEAEELIK 450

Query: 514 TAYQINPDDTAVNDSIGWAYYLKGDAESALPYLRYSF-ENDPEPEVAAHLGEVLWALGER 572
            A +  +P++  A   DS+GW YYLKGD E A+ YL  +  E  +P V  H+G+VL  +G +
Sbjct: 451 KALEKDPENPAYIDSMGWVYYLKGDYERAMQYLLKALREAYDDPVVNEHVGDVLLKMGYK 510
```

```
Query:  573 DQAVDVWTQAAHLRGDKK                                  590
            ++A + + +A   L   + K
Sbjct:  511 EEARNYYERALKLLEEGK                                  528
```

Based on this analysis, it is predicted that the proteins from *N. meningitidis* and *N. gonorrhoeae*, and their epitopes, could be useful antigens for vaccines or diagnostics, or for raising antibodies.

Example 7

The following partial DNA sequence was identified in *N. meningitidis* <SEQ ID 49>:

```
  1 AACCTCTACG CCGGCCCGCA GACCACATCC GTCATCGCAA ACATCGCCGA
 51 CAACCTGCAA CTGGCCAAAG ACTACGGCAA AGTACACTGG TTCGCCTCCC
101 CGCTCTTCTG GCTCCTGAAC CAACTGCACA ACATCATCGG CAACTGGGGC
151 TGGGCGATTA TCGTTTTAAC CATCATCGTC AAAGCCGTAC TGTATCCATT
201 GACCAACGCC TCTTACCGCT CTATGGCGAA AATGCGTGCC GCCGCACCCA
251 AACTGCAAGC CATCAAAGAG AAATACGGCG ACGACCGTAT GGCGCAACAA
301 CAGGCGATGA TGCAGCTTTA CACAGACGAG AAAATCAACC CGaCTGGGCG
351 GCTGCCTGCC TATGCTGTTG CAAATCCCCG TCTTCATCGG ATTGTATTGG
401 GCATTGTTCG CCTCCGTAGA ATTGCGCCAG GCACCTTGGC TGGGTTGGAT
451 TACCGACCTC AGCCGCGCCG ACCCCTACTA CATCCTGCCC ATCATTATGG
501 CGGCAACGAT GTTCGCCCAA ACTTATCTGA ACCCGCCGCC GAcCGACCCG
551 ATGCagGCGA AAATGATGAA AATCATGCCG TTGGTTTTCT CsGwCrTGTT
601 CTTCTTCTTC CCTGCCGGks TGGTATTGTA CTGGGTAGTC AACAACCTCC
651 TGACCATCGC CCAGCAATGG CACATCAACC GCAGCATCGA AAAACAACGC
701 GCCCAAGGCG AAGTCGTTTC CTAA
```

This corresponds to the amino acid sequence <SEQ ID 50; ORF11>:

```
  1 ..NLYAGPQTTS VIANIADNLQ LAKDYGKVHW FASPLFWLLN QLHNIIGNWG
 51 WAIIVLTIIV KAVLYPLTNA SYRSMAKMRA AAPKLQAIKE KYGDDRMAQQ
101 QAMMQLYTDE KINPLGGCLP MLLQIPVFIG LYWALFASVE LRQAPWLGWI
151 TDLSRADPYY ILPIIMAATM FAQTYLNPPP TDPMQAKMMK IMPLVFSXXF
201 FFFPAGXVLY WVVNNLLTIA QQWHINRSIE KQRAQGEVVS *
```

Further sequence analysis revealed the complete DNA sequence <SEQ ID 51>:

```
  1 ATGGATTTTA AAAGACTCAC GGCGTTTTTC GCCATCGCGC TGGTGATTAT
 51 GATCGGCTGG GAAAAGATGT TCCCCACTCC GAAGCCAGTC CCCGCGCCCC
101 AACAGGCAGC ACAACAACAG GCCGTAACCG CTTCCGCCGA AGCCGCGCTC
151 GCGCCCGCAA CGCCGATTAC CGTAACGACC GACACGGTTC AAGCCGTCAT
201 TGATGAAAAA AGCGGCGACC TGCGCCGGCT GACCCTGCTC AAATACAAAG
```

```
 251 CAACCGGCGA CGAAAATAAA CCGTTCATCC TGTTTGGCGA CGGCAAAGAA

301 TACACCTACG TCGCCCAATC CGAACTTTTG GACGCGCAGG GCAACAACAT

351 TCTAAAAGGC ATCGGCTTTA GCGCACCGAA AAACAGTAC AGCTTGGAAG

401 GCGACAAAGT TGAAGTCCGC CTGAGCGCGC TGAAACACG CGGTCTGAAA

451 ATCGACAAAG TTTATACTTT CACCAAAGGC AGCTATCTGG TCAACGTCCG

501 CTTCGACATC GCCAACGGCA GCGGTCAAAC CGCCAACCTG AGCGCGGACT

551 ACCGCATCGT CCGCGACCAC AGCGAACCCG AGGGTCAAGG TTACTTTACC

601 CACTCTTACG TCGGCCCTGT TGTTTATACC CCTGAAGGCA ACTTCCAAAA

651 AGTCAGCTTT TCCGACTTGG ACGACGATGC CAAATCCGGC AAATCCGAGG

701 CCGAATACAT CCGCAAAACC CCGACCGGCT GGCTCGGCAT GATTGAACAC

751 CACTTCATGT CCACCTGGAT TCTCCAACCT AAAGGCAGAC AAAGCGTTTG

801 CGCCGCAGGC GAGTGCAACA TCGACATCAA ACGCCGCAAC GACAAGCTGT

851 ACAGCACCAG CGTCAGCGTG CCTTTAGCCG CCATCCAAAA CGGCGCGAAA

901 GCCGAAGCCT CCATCAACCT CTACGCCGGC CGCAGACCA CATCCGTCAT

951 CGCAAACATC GCCGACAACC TGCAACTGGC CAAAGACTAC GGCAAAGTAC

1001 ACTGGTTCGC CTCCCCGCTC TTCTGGCTCC TGAACCAACT GCACAACATC

1051 ATCGGCAACT GGGGCTGGGC GATTATCGTT TTAACCATCA TCGTCAAAGC

1101 CGTACTGTAT CCATTGACCA ACGCCTCTTA CCGCTCTATG GCGAAAATGC

1151 GTGCCGCCGC ACCCAAACTG CAAGCCATCA AGAGAAATA CGGCGACGAC

1201 CGTATGGCGC AACAACAGGC GATGATGCAG CTTTACACAG ACGAGAAAAT

1251 CAACCCGCTG GGCGGCTGCC TGCCTATGCT GTTGCAAATC CCCGTCTTCA

1301 TCGGATTGTA TTGGGCATTG TTCGCCTCCG TAGAATTGCG CCAGGCACCT

1351 TGGCTGGGTT GGATTACCGA CCTCAGCCGC GCCGACCCCT ACTACATCCT

1401 GCCCATCATT ATGGCGGCAA CGATGTTCGC CCAAACTTAT CTGAACCCGC

1451 CGCCGACCGA CCCGATGCAG GCGAAAATGA TGAAAATCAT GCCGTTGGTT

1501 TTCTCCGTCA TGTTCTTCTT CTTCCCTGCC GGTCTGGTAT TGTACTGGGT

1551 AGTCAACAAC CTCCTGACCA TCGCCCAGCA ATGGCACATC AACCGCAGCA

1601 TCGAAAAACA ACGCGCCCAA GGCGAAGTCG TTTCCTAA
```

This corresponds to the amino acid sequence <SEQ ID 52; ORF11-1>:

```
  1 MDFKRLTAFF AIALVIMIGW EKMFPTPKPV PAPQQAAQQQ AVTASAEAAL

51 APATPITVTT DTVQAVIDEK SGDLRRLTLL KYKATGDENK PFILFGDGKE

101 YTYVAQSELL DAQGNNILKG IGFSAPKKQY SLEGDKVEVR LSAPETRGLK

151 IDKVYTFTKG SYLVNVRFDI ANGSGQTANL SADYRIVRDH SEPEGQGYFT

201 HSYVGPVVYT PEGNFQKVSF SDLDDDAKSG KSEAEYIRKT PTGWLGMIEH

251 HFMSTWILQP KGRQSVCAAG ECNIDIKRRN DKLYSTSVSV PLAAIQNGAK

301 AEASINLYAG PQTTSVIANI ADNLQLAKDY GKVHWFASPL FWLLNQLHNI

351 IGNWGWAIIV LTIIVKAVLY PLTNASYRSM AKMRAAAPKL QAIKEKYGDD

401 RMAQQQAMMQ LYTDEKINPL GGCLPMLLQI PVFIGLYWAL FASVELRQAP
```

```
451 WLGWITDLSR ADPYYILPII MAATMFAQTY LNPPPTDPMQ AKMMKIMPLV

501 FSVMFFFFPA GLVLYWVVNN LLTIAQQWHI NRSIEKQRAQ GEVVS*
```

Computer analysis of this amino acid sequence gave the following results:

Homology with a 60 kDa Inner-Membrane Protein (Accession P25754) of *Pseudomonas putida*

ORF11 and the 60 kDa protein show 58% aa identity in 229 aa overlap (BLASTp).

```
ORF11    2 LYAGPQTTSVIANIADNLQLAKDYGKVHWFASPLFWLLNQLHNIIGNWGWAIIVLTIIVK   61
           LYAGP+  S +  ++  L+L  DYG + + A P+FWLL   +H+++GNWGW+IIVLT+++K
60K    324 LYAGPKIQSKLKELSPGLELTVDYGFLWFIAQPIFWLLQHIHSLLGNWGWSIIVLTMLIK  383

ORF11   62 AVLYPLTNASYRSMAKMRAAAPKLQAIKEKYGDDRXXXXXXXXXXLYTDEKINPLGGCLPM  121
           + +PL+ ASYRSMA+MRA APKL A+KE++GDDR         LY EKINPLGGCLP+
60K    384 GLFFPLSAASYRSMARMRAVAPKLAALKERFGDDRQKMSQAMMELYKKEKINPLGGCLPI  443

ORF11  122 LLQIPVFIGLYWALFASVELRQAPWLGWITDLSRADPYYILPIIMAATMFAQTYLNPPPT  181
           L+Q+PVF+ LYW L  SVE+RQAPW+ WITDLS  DP++ILPIIM ATMF Q  LNP P
60K    444 LVQMPVFLALYWVLLESVEMRQAPWILWITDLSIKDPFFILPIIMGATMFIQQRLNPTPP  503

ORF11  182 DPMQAKMMKIMPLVXXXXXXXXXPAGXVLYWVVNNLLTIAQQWHINRSIE           230
           DPMQAK+MK+MP++         PAG VLYWVVNN L+I+QQW+I R IE
60K    504 DPMQAKVMKMMPIIFTFFFLWFPAGLVLYWVVNNCLSISQQWYITRRIE           552
```

Homology with a Predicted ORF from *N. meningitidis* (Strain A)

ORF11 shows 97.9% identity over a 240aa overlap with an ORF (ORF11a) from strain A of *N. meningitidis*.

```
                                           10        20        30
    orf11.pep                     NLYAGPQTTSVIANIADNLQLAKDYGKVHW
                                  |||||||||||||||||| ||||||||
    orf711a   IKRRNDKLYSTSVSVPLAAIQNGAKSXASINLYAGPQTTSVIANIADNLQLXKDYGKVHW
                280       290       300       310       320       330
                   40        50        60        70        80        90
    orf11.pep  FASPLFWLLNQLHNIIGNWGWAIIVLTIIVLAVLYPLTNASYRSMAKMRAAAPKLQAIKE
               ||||||||||||||||||||||||||||||||||||||||||||||||||||||||||
    orf711a   FASPLFWLLNQLHNIIGNWGWAIIVLTIIVLAVLYPLTNASYRSMAKMRAAAPKLQAIKE
                340       350       360       370       380       390
                  100       110       120       130       140       150
    orf11.pep  KYGDDRMAQQQAMMQLYTDEKINPLGGCLPMLLQIPVFIGLYWALFASVELRQAPWLGWI
               ||||||||||||||||||||||||||||||||||||||||||||||||||||||||||
    orf711a   KYGDDRMAQQQAMMQLYTDEKINPLGGCLPMLLQIPVFIGLYWALFASVELRQAPWLGWI
                400       410       420       430       440       450
                  160       170       180       190       200       210
    orf11.pep  TDLSRADPYYILPIIMAATMFAQTYLNPPPTDPMQAKMMKIMPLVFSXXFFFFPAGXVLY
               ||||||||||||||||||||||||||||||||||||||||||||| |||| ||||  |||
    orf711a   TDLSRADPYYILPIIMAATMFAQTYLNPPPTDPMQAKMMKIMPLVXSXXFFXFPAGLVLY
                460       470       480       490       500       510
                  220       230       240
    orf11.pep  WVVNNLLTIAQQWHINRSIEKQRAQGEVVSX
               || :|||||||||||||||||||||||||||
    orf711a   WVINNLLTIAQQWHINRSIEKQRAQGEVVSX
                520       530       540
```

The complete length ORF11a nucleotide sequence <SEQ ID 53> is:

```
  1 ANGGATTTTA AAAGACTCAC NGNGTTTTTC GCCATCGCAC TGGTGATTAT

51 GATCGGATNG NAAANGATGT TCCCCACTCC GAAGCCCGTC CCCGCGCCCC

101 AACAGACGGC ACAACAACAG GCCGTAANCG CTTCCGCCGA AGCCGCGCTC

151 GCGCCCGNAN CGCCGATTAC CGTAACGACC GACACGGTTC AAGCCGTCAT

201 TGATGAAAAA AGCGGCGACC TGCGCCGGCT GACCCTGCTC AAATACAAAG
```

-continued

```
 251 CAACCGGCGA CNAAAATAAA CCGTTCATCC TGTTTGGCGA CGGCAAANAA
 301 TACACCTACN TCGCCCANTC CGAACTTTTG GACGCGCAGG GCAACAACAT
 351 TCTAAAAGGC ATCGGCTTTA GCGCACCGAA AAAACAGTAC AGCTTGGAAG
 401 GCGACAAAGT TGAAGTCCGC CTGAGCGCAC CTGAAACACG CGGTCTGAAA
 451 ATCGACAAAG TTTATACTTT CACCAAAGGC AGCTATCTGG TCAACGTCCG
 501 CTTCGACATC GCCAACGGCA GCGGTCAAAC CGCCAACCTG AGCGCGGACT
 551 ACCGCATCGT CCGCGACCAC AGCGAACCCG AGGGTCAAGG CTACTTTACC
 601 CACTCTTACG TCGGCCCTGT TGTTTATACC CCTGAAGGCA ACTTCCAAAA
 651 AGTCAGCTTC TCCGACTTGG ACGACGATGC CAANTCCGGN AAATCCGAGG
 701 CCGAATACAT CCGCAAAACC CNGACCGGCT GGCTCGGCAT GATTGAACAC
 751 CACTTCATGT CCACCTGGAT CCTCCAACCC AAAGGCGGAC AAAGCGTTTG
 801 CGCCGCTGGC GACTGCNGTA TNGACATCAA ACGCCGCAAC GACAAGCTGT
 851 ACAGCACCAG CGTCAGCGTG CCTTTAGCCG CTATCCAAAA CGGTGCGAAA
 901 TCCNAAGCCT CCATCAACCT CTACGCCGGC CCACAGACCA CATCNGTTAT
 951 CGCAAACATC GCCGACAACC TGCAACTGGN CAAAGACTAC GGCAAAGTAC
1001 ACTGGTTCGC CTCCCCCCTC TTTTGGCTTT TGAACCAACT GCACAACATC
1051 ATCGGCAACT GGGGCTGGGC GATTATCGTT TTAACCATCA TCGTCAAAGC
1101 CGTACTGTAT CCATTGACCA ACGCCTCTTA CCGTTCGATG GCGAAAATGC
1151 GTGCCGCCGC GCCCAAACTG CAAGCCATCA AGAGAAATA CGGCGACGAC
1201 CGTATGGCGC AGCAACAAGC CATGATGCAG CTTTACACAG ACGAGAAAAT
1251 CAACCCGCTG GGCGGCTGCC TGCCTATGCT GTTGCAAATC CCCGTCTTCA
1301 TCGGATTGTA TTGGGCATTG TTCGCCTCCG TAGAATTGCG CCAGGCACCT
1351 TGGCTGGGTT GGATTACCGA CCTCAGCCGC GCCGACCCNT ACTACATCCT
1401 GCCCATCATT ATGGCGGCAA CGATGTTCGC CCAAACCTAT CTGAACCCGC
1451 CGCCGACCGA CCCGATGCAG GCGAAAATGA TGAAAATCAT GCCTTTGGTT
1501 NTNTCNNNNA NGTTCTTCNN CTTCCCTGCC GGTCTGGTAT TGTACTGGGT
1551 GATCAACAAC CTCCTGACCA TCGCCCAGCA ATGGCACATC AACCGCAGCA
1601 TCGAAAAACA ACGCGCCCAA GGCGAAGTCG TTTCCTAA
```

This encodes a protein having amino acid sequence <SEQ ID 54>:

```
  1 XDFKRLTXFF AIALVIMIGX XXMFPTPKPV PAPQQTAQQQ AVXASAEAAL
 51 APXXPITVTT DTVQAVIDEK SGDLRRLTLL KYKATGDXNK PFILFGDGKX
101 YTYXAXSELL DAQGNNILKG IGFSAPKKQY SLEGDKVEVR LSAPETRGLK
151 IDKVYTFTKG SYLVNVRFDI ANGSGQTANL SADYRIVRDH SEPEGQGYFT
201 HSYVGPVVYT PEGNFQKVSF SDLDDDAXSG KSEAEYIRKT XTGWLGMIEH
251 HFMSTWILQP KGGQSVCAAG DCXXDIKRRN DKLYSTSVSV PLAAIQNGAK
301 SXASINLYAG PQTTSVIANI ADNLQLXKDY GKVHWFASPL FWLLNQLHNI
351 IGNWGWAIIV LTIIVKAVLY PLTNASYRSM AKMRAAAPKL QAIKEKYGDD
401 RMAQQQAMMQ LYTDEKINPL GGCLPMLLQI PVFIGLYWAL FASVELRQAP
```

```
451 WLGWITDLSR ADPYYILPII MAATMFAQTY LNPPPTDPMQ AKMMKIMPLV

501 XSXXFFXFPA GLVLYWVINN LLTIAQQWHI NRSIEKQRAQ GEVVS*
```

ORF11a and ORF11-1 show 95.2% identity in 544 aa overlap:

```
                 10         20         30         40         50         60
orf11a.pep  XDFKRLTXFFAIALVIMIGXXXMFPTPKPVPAPQQTAQQQAVXASAEAALAPXXPITVTT
            |||||| |||||||||||| |||||||||||||||| |||| :|||||||||| :||||||
orf11-1     MDFKRLTAFFAIALVIMIGWEKMFPTPKPVPAPQQAAQQQAVTASAEAALAPATPITVTT
                 10         20         30         40         50         60

70         80         90        100        110        120
orf11a.pep  DTVQAVIDEKSGDLRRLTLLKYKATGDXNKPFILFGDGKXYTYXAXSELLDAQGNNILKG
            ||||||||||||||||||||||||||||| ||||||||||| ||| ||| ||||||||||||
orf11-1     DTVQAVIDEKSGDLRRLTLLKYKATGDENKPFILFGDGKEYTYVAGSELLDAQGNNILKG
                 70         80         90        100        110        120

130        140        150        160        170        180
orf11a.pep  IGFSAPKKQYSLEGDKVEVRLSAPETRGLKIDKVYTFTKGSYLVNVRFDIANGSGQTANL
            ||||||||||||||||||||||||||||||||||||||||||||||||||||||||||||
orf11-1     IGFSAPKKQYSLEGDKVEVRLSAPETRGLKIDKVYTFTKGSYLVNVRFDIANGSGQTANL
                130        140        150        160        170        180

190        200        210        220        230        240
orf11a.pep  SADYRIVRDHSEPEGQGYFTHSYVGPVVYTPEGNFQKVSFSDLDDDAXSGKSEAEYIRKT
            |||||||||||||||||||||||||||||||||||||||||||||| |||||||||||||
orf11-1     SADYRIVRDHSEPEGQGYFTHSYVGPVVYTPEGNFQKVSFSDLDDDAKSGKSEAEYIRKT
                190        200        210        220        230        240

250        260        270        280        290        300
orf11a.pep  XTGWLGMIEHHFMSTWILQPKGGQSVCAAGDCXXDIKRRNDKLYSTSVSVPLAAIQNGAK
             ||||||||||||||||||||||| |||||| ||||||||||||||||||||||||||||
orf11-1     PTGWLGMIEHHFMSTWILQPKGRQSVCAAGECNIDIKRRNDKLYSTSVSVPLAAIQNGAK
                250        260        270        280        290        300

310        320        330        340        350        360
orf11a.pep  SXASINLYAGPQTTSVIANIADNLQLXKDYGKVHWFASPLFWLLNQLHNIIGNWGWAIIV
            : |||||||||||||||||||||||| |||||||||||||||||||||||||||||||||
orf11-1     AEASINLYAGPQTTSVIANIADNLQLAKDYGKVHWFASPLFWLLNQLHNIIGNWGWAIIV
                310        320        330        340        350        360

370        380        390        400        410        420
orf11a.pep  LTIIVKAVLYPLTNASYRSMAKMRAAAPKLQAIKEKYGDDRMAQQQAMMQLYTDEKINPL
            ||||||||||||||||||||||||||||||||||||||||||||||||||||||||||||
orf11-1     LTIIVKAVLYPLTNASYRSMAKMRAAAPKLQAIKEKYGDDRMAQQQAMMQLYTDEKINPL
                370        380        390        400        410        420

430        440        450        460        470        480
orf11a.pep  GGCLPMLLQIPVFIGLYWALFASVELRQAPWLGWITDLSRADPYYILPIIMAATMFAQTY
            ||||||||||||||||||||||||||||||||||||||||||||||||||||||||||||
orf11-1     GGCLPMLLQIPVFIGLYWALFASVELRQAPWLGWITDLSRADPYYILPIIMAATMFAQTY
                430        440        450        460        470        480

490        500        510        520        530        540
orf11a.pep  LNPPPTDPMQAKMMKIMPLVXSXXFFXFPAGLVLYWVINNLLTIAQQWHINRSIEKQRAQ
            |||||||||||||||||||| |  || ||||||:||||||||||||||||||||||||||
orf11-1     LNPPPTDPMQAKMMKIMPLVFSVMFFFFPAGLVLYWVVNNLLTIAQQWHINRSIEKQRAQ
                490        500        510        520        530        540 orf11a.pep  GEVVSX
            ||||||
orf11-1     GEVVSX
```

Homology with a Predicted ORF from *N. gonorrhoeae*

ORF11 shows 96.3% identity over a 240aa overlap with a predicted ORF (ORF11.ng) from *N. gonorrhoeae*:

```
Orf11     NLYAGPQTTSVIANIADNLQLAKDYGKVHWFASPLFWLLNQLHNIIGNWGWAIIVLT   57
          |||||||||||||||||||||||||||||||||||||||||||||||||||||:|||
orf11ng  MAVNLYAGPQTTSVIANIADNLQLAKDYGKVHWFASPLFWLLNQLHNIIGNWGWAIVVLT   60

Orf11     IIVKAVLYPLTNASYRSMAKMRAAAPKLQAIKEKYGDDRMAQQQAMMQLYTDEKINPLGG  117
          ||||||||||||||||||||||||||:||| :||||||||||||||||||:| :||||||
orf11ng   IIVKAVLYPLTNASYRSMAKMRAAAPELQTIKEKYGDDRMAQQQAMMQLFEDEEINPLGG  120

Orf11     CLPMLLQIPVGIGLYWALFASVELRQAPWLGWITDLSRADPYYILPIIMAATMFAQTYLN  177
          ||||||||||||||||||||||||||||||||||||||||||||||||||||||||||||
orf11ng   CLPMLLQIPVGIGLYWALFASVELRQAPWLGWITDLSRADPYYILPIIMAATMFAQTYLN  180

Orf11     PPPTDPMQAKMMKIMPLVFSXXFFFFPAGXVLYWVNNLLTAIQQWHINRSIEKQRAQGE   237
          ||||||||||||||||||||| ||||||| ||||||||||||||||||||||||||||
orf11ng   PPPTDPMQAKMMKIMPLVFSVMFFFFPAGLVLYWVNNLLTAIQQWHINRSIEKQRAQGE   240

Orf11     VVS                                                          240
          |||
orf11ng   VVS                                                          243
```

An ORF11ng nucleotide sequence <SEQ ID 55> was predicted to encode a protein having amino acid sequence <SEQ ID 56>:

```
  1 MAVNLYAGPQ TTSVIANIAD NLQLAKDYGK VHWFASPLFW LLNQLHNIIG

51 NWGWAIVVLT IIVKAVLYPL TNASYRSMAK MRAAAPELQT IKEKYGDDRM

101 AQQQAMMQLF EDEEINPLGG CLPMLLQIPV FIGLYWALFA SVELRQAPWL

151 GWITDLSRAD PYYILPIIMA ATMFAQTYLN PPPTDPMQAK MMKIMPLVFS

201 VMFFFFPAGL VLYWVVNNLL TIAQQWHINR SIEKQRAQGE VVS*
```

Further sequence analysis revealed the complete gonococcal DNA sequence <SEQ ID 57> to be:

```
   1 ATGGATTTTA AAAGACTCAC GGCGTTTTTC GCCATCGCGC TGGTGATTAT

51 GATCGGCTGG GAAAAAATGT TCCCCACCCC GAAACCCGTC CCCGCGCCCC

101 AACAGGCGGC ACAAAAACAG GCAGCAACCG CTTCCGCCGA AGCCGCGCTC

151 GCGCCCGCAA CGCCGATTAC CGTAACGACC GACACGGTTC AAGCCGTTAT

201 TGATGAAAAA AGTGGCGACC TGCGCCGGCT GACCCTGCTC AAATACAAAG

251 CAACCGGCGA CGAAAACAAA CCGTTCGTCC TGTTTGGCGA CGGCAAAGAA

301 TACACCTACG TCGCCCAATC CGAACTTTTG GACGCGCAGG GCAACAACAT

351 TCTGAAAGGC ATCGGCTTTA GCGCACCGAA AAACAGTAC ACCCTCAACG

401 GCGACACAGT CGAAGTCCGC CTGAGCGCGC CCGAAACCAA CGGACTGAAA

451 ATCGACAAAG TCTATACCTT TACCAAAGAC AGCTATCTGG TCAACGTCCG

501 CTTCGACATC GCCAACGGCA GCGGTCAAAC CGCCAACCTG AGCGCGGACT

551 ACCGCATCGT CCGCGACCAC AGCGAACCCG AGGGTCAAGG CTACTTTACC

601 CACTCTTACG TCGGCCCTGT TGTTTATACC CCTGAAGGCA ACTTCCAAAA

651 AGTCAGCTTC TCCgacTTgg acgACGATGC gaaaTccggc aaATccgagg 701 ccgaatacaT CCGCAAAACC ccgaccggtt ggctcggcat gattgaacac 751 cacttcatgt ccacctggat cctccAAcct aaaggcggcc aaaacgtttg 801 cgcccaggga gactgccgta tcgacattaa aCgccgcaac gacaagctgt 851 acagcgcaag cgtcagcgtg cctttaaccg ctatcccaac ccgggggcca 901 aaaccgaaaa tggcggTCAA CCTGTATGCC GGTCCGCAAA CCACATCCGT 951 TATCGCAAAC ATCGCcgacA ACCTGCAACT GGCAAAAGAC TACGGTAAAG

1001 TACACTGGTT CGCATCGCCG CTCTTCTGGC TCCTGAACCA ACTGCACAAC

1051 ATTATCGGCA ACTGGGGCTG GGCAATCGTC GTTTTGACCA TCATCGTCAA

1101 AGCCGTACTG TATCCATTGA CCAACGcctc ctACCGTTCG ATGGCGAAAA

1151 TGCGTGccgc cgcacCcaaA CTGCAGACCA TCAAAGAAAA ATAcgGCGAC

1201 GACCGTATGG CGCAACAGCA AGCGATGATG CAGCTTTACA AAgacgAGAA

1251 AATCAACCCG CTGGGCGGCT GTctgcctat gctgttgCAA ATCCCCGTCT

1301 TCATCGGCTT GTACTGGGCA TTGTTCGCCT CCGTAGAATT GCGCCAGGCA

1351 CCTTGGCTGG GCTGGATTAC CGACCTCAGC CGCGCCGACC CTACTACAT

1401 CCTGCCCATC ATTATGGCGG CAACGATGTT CGCCCAAACC TATCTGAACC

1451 CGCCGCCGAC CGACCCGATG CAGGCGAAAA TGATGAAAAT CATGCCGTTG

1501 GTTTTCTCCG TCATGTTCTT CTTCTTCCCT GCCGGTTTGG TTCTCTACTG
```

```
1551 GGTGGTCAAC AACCTCCTGA CCATCGCCCA GCAGTGGCAC ATCAACCGCA

1601 GCATCGAAAA ACAACGCGCC CAAGGCGAAG TCGTTTCCTA A
```

This encodes a protein having amino acid sequence <SEQ ID 58; ORF11ng-1>:

```
  1 MDFKRLTAFF AIALVIMIGW EKMFPTPKPV PAPQQAAQKQ AATASAEAAL

51 APATPITVTT DTVQAVIDEK SGDLRRLTLL KYKATGDENK PFVLFGDGKE

101 YTYVAQSELL DAQGNNILKG IGFSAPKKQY TLNGDTVEVR LSAPETNGLK

151 IDKVYTFTKD SYLVNVRFDI ANGSGQTANL SADYRIVRDH SEPEGQGYFT

201 HSYVGPVVYT PEGNFQKVSF SDLDDDAKSG KSEAEYIRKT PTGWLGMIEH

251 HFMSTWILQP KGGQNVCAQG DCRIDIKRRN DKLYSASVSV PLTAIPTRGP

301 KPKMAVNLYA GPQTTSVIAN IADNLQLAKD YGKVHWFASP LFWLLNQLHN

351 IIGNWGWAIV VLTIIVKAVL YPLTNASYRS MAKMRAAAPK LQTIKEKYGD

401 DRMAQQQAMM QLYKDEKINP LGGCLPMLLQ IPVFIGLYWA LFASVELRQA

451 PWLGWITDLS RADPYYILPI IMAATMFAQT YLNPPPTDPM QAKMMKIMPL

501 VFSVMFFFFP AGLVLYWVVN NLLTIAQQWH INRSIEKQRA QGEVVS*
```

ORF11ng-1 and ORF11-1 shown 95.1% identity in 546 aa overlap:

```
                       10         20         30         40         50         60
orf11ng-1.pep  MDFKRLTAFFAIALVIMIGWEKMFPTPKPVPAPQQAAQKQAATASAEAALAPATPITVTT
               ||||||||||||||||||||||||||||||||||||::||:|||||||||||||||||||
orf11-1        MDFKRLTAFFAIALVIMIGWEKMFPTPKPVPAPQQAAQQQAVTASAEAALAPATPITVTT
                       10         20         30         40         50         60

70         80         90        100        110        120
orf11ng-1.pep  DTVQAVIDEKSGDLRRLTLLKYKATGDENKPFVLFGDGKEYTYVAQSELLDAQGNNILKG
               ||||||||||||||||||||||||||||||||:|||||||||||||:|||||||||||||
orf11-1        DTVQAVIDEKSGDLRRLTLLKYKATGDENKPFILFGDGKEYTYVAGSELLDAQGNNILKG
                       70         80         90        100        110        120

130        140        150        160        170        180
orf11ng-1.pep  IGFSAPKKQYTLNGDTVEVRLSAPETNGLKIDKVYTFTKDSYLVNVRFDIANGSGQTANL
               ||||||||||:|:||||||||||||||:|||||||||||:||||||||||||||||||||
orf11-1        IGFSAPKKQYSLEGDKVEVRLSAPETRGLKIDKVYTFTKGSYLVNVRFDIANGSGQTANL
                      130        140        150        160        170        180

190        200        210        220        230        240
orf11ng-1.pep  SADYRIVRDHSEPEGQGYFTHSYVGPVVYTPEGNFQKVSFSDLDDDAKSGKSEAEYIRKT
               ||||||||||||||||||||||||||||||||||||||||||||||||||||||||||||
orf11-1        SADYRIVRDHSEPEGQGYFTHSYVGPVVYTPEGNFQKVSFSDLDDDAKSGKSEAEYIRKT
                      190        200        210        220        230        240

250        260        270        280        290        300
orf11ng-1.pep  PTGWLGMIEHHFMSTWILQPKGGQNVCAQGDCRIDIKRRNDKLYSASVSVPLTAIPTRGP
               |||||||||||||||||||||||:|||:||:|||||||||||||:||||||:||:::|:|
orf11-1        PTGWLGMIEHHFMSTWILQPKGRQSVCAAGECNIDIKRRNDKLYSTSVSVPLAAIQN-GA
                      250        260        270        280        290

310        320        330        340        350        360
orf11ng-1.pep  KPKMAVNLYAGPQTTSVIANIADNLQLAKDYGKVHWFASPLFWLLNQLHNIIGNWGWAIV
               |:::::||||||||||||||||||||||||||||||||||||||||||||||||||||:
orf11-1        KAEASINLYAGPQTTSVIANIADNLQLAKDYGKVHWFASPLFWLLNQLHNIIGNWGWAII
               300        310        320        330        340        350

370        380        390        400        410        420
orf11ng-1.pep  VLTIIVKAVLYPLTNASYRSMAKMRAAAPKLQTIKEKYGDDRMAQQQAMMQLYKDEKINP
               ||||||||||||||||||||||||||||||||:|||||||||||||||||||:|||||||
orf11-1        VLTIIVKAVLYPLTNASYRSMAKMRAAAPKLQAIKEKYGDDRMAQQQAMMQLYTDEKINP
                      360        370        380        390        400        410

430        440        450        460        470        480
orf11ng-1.pep  LGGCLPMLLQIPVFIGLYWALFASVELRQAPWLGWITDLSRADPYYILPIIMAATMFAQT
               ||||||||||||||||||||||||||||||||||||||||||||||||||||||||||||
orf11-1        LGGCLPMLLQIPVFIGLYWALFASVELRQAPWLGWITDLSRADPYYILPIIMAATMFAQT
               420        430        440        450        460        470

490        500        510        520        530        540
orf11ng-1.pep  YLNPPPTDPMQAKMMKIMPLVFSVMFFFFPAGLVLYWVVNNLLTIAQQWHINRSIEKQRA
               ||||||||||||||||||||||||||||||||||||||||||||||||||||||||||||
orf11-1        YLNPPPTDPMQAKMMKIMPLVFSVMFFFFPAGLVLYWVVNNLLTIAQQWHINRSIEKQRA
                      480        490        500        510        520        530
```

```
orf11ng-1.pep    GEVVSX
                 ||||||
orf11-1          GEVVSX
              540
```

In addition, ORF11ng-1 shows significant homology with an inner-membrane protein from the database (accession number p25754):

```
ID    60IM_PSEPU  STANDARD; PRT; 560 AA.
AC    P25754;
DT    01-MAY-1992 (REL. 22, CREATED)
DT    01-MAY-1992 (REL. 22, LAST SEQUENCE UPDATE)
DT    01-NOV-1995 (REL. 32, LAST ANNOTATION UPDATE)
DE    60 KD INNER-MEMBRANE PROTEIN....

SCORES Init1: 1074 Initn: 1293 Opt: 1103
Smith-Waterman score: 1406; 41.5% identity in 574 aa overlap 10         20              30        40
orf11ng-1.pep    MDFKR---LTAFFAIALVIMIGW-----EKMFPT-----------PKPVPAPQQAAQKQ
                 ||:||   ::|: ::: |::: |     : :||           | ||| :::|: :
p25754           MDIKRTILIAALAVVSYVMVLKWNDDYGQAALPTQNTAASTVAPGLPDGVPAGNNGASAD
                      10        20        30        40        50        60

50        60        70        80        90
orf11ng-1.pep    AATASAEAALAPATPIT-------VTTDTVQAVIDEKSGDLRRLTLLKYKATGDE-NKPF
                 : :|:||:: |   :|::        | ||:: :||  :||: :|:| ||     |: ||
p25754           VPSANAESSPAELAPVALSKDLIRVKTDVLELAIDPVGGDIVQLNLPKYRRRQDHPNIPF
                      70        80        90       100       110       120

100       110       120       130       140
orf11ng-1.pep    VLFGDKEYTYVAQSELLDAQGNNILKGIG---FSAPKKQYTL-NGD---TVEVRLSAPE
                 || :|  :|:|||    |:|::  :: :    :|::| | |::::|
p25754           QLFDNGGERVYLAQSGLTGTDGPDA-RASGRPLYAAEQKSYQLADGQEQLVVDLKFS---
                      130       140       150       160       170

150       160       170       180       190       200
orf11ng-1.pep    TNGLKIDKVYTFTKDSYLVNVRFDIANGSGQTANLSADYRIVRDHS-EPEGQGYF-THSY
                 ||::  |  ::|  :  |  :||  :  | |   |||: |:  ::   ||  |  :|  :|
p25754           DNGVNYIKRFSFKRGEYDLNVSYLIDNQSGQAWNGNMFAQLKRDASGDPSSSTATGTATY
                      180       190       200       210       220       230

210       220       230       240       250       260
orf11ng-1.pep    VGPVVYTPEGNFQKVSFSDLDDDAKSGKSEAEYIRKTPTGWLGMIEHHFMSTWILQPKGG
                 :|  :::|   ::|||::|:|   |::  :|    ::  ||  :::|::::||   |:
p25754           LGAALWTASEPYKKVSMKDID---KGSLKE-----NVSGGWVAWLQHYFVTAWI-PAKSD
                      240       250       260       270       280

270       280       290       300       310       320
orf11ng-1.pep    QNVCAQGDCRIDIKRRNDKLYSASVSVPLTAIPTRGPKPKMAVNLYAGPQTTSVIANIAD
                 :||         :: :: :: |  :  : : :|: | |  : ::  ||||||:  |  : :::
p25754           NNV-------VQTRKDSQGNYIIGYTGPVISVPA-GGKVETSALLYAGPKIQSKLKELSP
                      290       300       310       320       330

330       340       350       360       370       380
orf11ng-1.pep    NLQLAKDYGKVHWF-ASPLFWLLNQLHNIIGNWGWAIVVLTIIVKAVLYPLTNASYRSMA
                 :|:|: ||| : || |::| ||||:|:::||||||||:  ||:|||||  |   ||||||
p25754           GLELTVDYGFL-WFIAQPIFWLLQHIHSLLGNWGWSIIVLTMLIKGLFFPLSAASYRSMA
                 340       350       360       370       380       390

390       400       410       420       430       440
orf11ng-1.pep    KMRAAAPKLQTIKEKYGDDRMAQQQAMMQLYKDEKINPLGGLCPMLLQIPVFIGLYWALF
                 :||| ||||  :: ||::||||  ::||||:|| ||||||||| :|:|:|||:|||:|:
p25754           RMRAVAPKLAALKERFGCCRQKMSQAMMELYKKEKINPLGGCLPILVQMPVFLALYWVLL
                 400       410       420       430       440       450

450       460       470       480       490       500
orf11ng-1.pep    ASVELRQAPWLGWITDLSRADPYYILPIIMAATMFAQTYLNPPPTDPMQAKMMKIMPLVF
                 |||:|||||| |||||||:||  |:::|||||:||||   ||| ||||||||:|::|||::|
p25754           ESVEMRQAPWILWITDLSIKDPFFILPIIMGATMFIQQRLNPTPPDPMQAKVMKMMPIIF
                 460       470       480       490       500       510

510       520       530       540
orf11ng-1.pep    SVMFFFFPAGLVLYWVVNNLLTIAQQWHINRSIEKQRAQGEVVSX
                 : :|::||||||||||||||  |:|:|||:|:| ||
p25754           TFFFLWFPAGLVLYWVVNNCLSISQQWYITRRIEAATKKAAA
                 520       530       540       550       560
```

Based on this analysis, including the homology to an inner-membrane protein from *P. putida* and the predicted transmembrane domains (seen in both the meningococcal and gonococcal proteins), it is predicted that the proteins from *N. meningitidis* and *N. gonorrhoeae*, and their epitopes, could be useful antigens for vaccines or diagnostics, or for raising antibodies.

Example 8

The following partial DNA sequence was identified in *N. meningitidis* <SEQ ID 59>:

```
  1..GCCGTCTTAA TCATCGAATT ATTGACGGGA ACGGTTTATC TTTTGGTTGT

51   NAGCGCGGCT TTGGCGGGTT CGGGCATTGC TTACGGGCTG ACCGGCAGTA

101   CGCCTGCCGC CGTCTTGACC GNCGCTCTGC TTTCCGCGCT GGGTATTTNG

151   TTCGTACACG CCAAAACCGC CGTTAGAAAA GTTGAAACGG ATTCATATCA

201   GGATTTGGAT GCCGGACAAT ATGTCGAAAT CCTCCGNCAC ACAGGCGGCA

251   ACCGTTACGA AGTT.TTTAT CGCGGTACG. ACTGGCAGGC TCAAAATACG

301   GGGCAAGAAG AGCTTGAACC AGGAACTCGC GCCCTCATTG TCCGCAAGGA

351   AGGCAACCTT CTTATTATCA CACACCCTTA A
```

This corresponds to the amino acid sequence <SEQ ID 60; ORF13>:

```
  1..AVLIIELLTG TVYLLVVSAA LAGSGIAYGL TGSTPAAVLT XALLSALGIX

51   FVHAKTAVRK VETDSYQDLD AGQYVEILRH TGGNRYEVXY RGTXWQAQNT

101   GQEELEPGTR ALIVRKEGNL LIITHP*
```

Further sequence analysis elaborated the DNA sequence slightly <SEQ ID 61>:

```
  1..GCCGTCTTAA TCATCGAATT ATTGACGGGA ACGGTTTATC TTTTGGTTGT 51   nAGCGCGGCT TTGGCGGGTT CGGGCATTGC TTACGGGCTG ACCGGCAGTA

101   CGCCTGCCGC CGTCTTGACC GnCGCTCTGC TTTCCGCGCT GGGTATTTnG

151   TTCGTACACG CCAAAACCGC CGTTAGAAAA GTTGAAACGG ATTCATATCA

201   GGATTTGGAT GCCGGACAAT ATGTCGAAAT CCTCCGACAC ACAGGCGGCA

251   ACCGTTACGA AGTTTTtTAT CGCGGTACGc ACTGGCAGGC TCAAAATACG

301   GGGCAAGAAG AGCTTGAACC AGGAACTCGC GCCCTCATTG TCCGCAAGGA

351   AGGCAACCTT CTTATTATCA CACACCCTTA A
```

This corresponds to the amino acid sequence <SEQ ID 62; ORF13-1>:

```
  1..AVLIIELLTG TVYLLVVSAA LAGSGIAYGL TGSTPAAVLT XALLSALGIX

51   FVHAKTAVRK VETDSYQDLD AGQYVEILRH TGGNRYEVFY RGTHWQAQNT

101   GQEELEPGTR ALIVRKEGNL LIITHP*
```

Computer analysis of this amino acid sequence gave the following results:

Homology with a Predicted ORF from *N. meningitidis* (Strain A)

ORF13 shows 92.9% identity over a 126aa overlap with an ORF (ORF13a) from strain A of *N. meningitidis*:

```
                        10        20        30        40        50
    orf13.pep           AVLIIELLTGTVYLLVVSAALAGSGIAYGLTGSTPAAVLTXALLSALGIXF
                        ||||||||||||||||||||||||||||||||||||| |||||||| |
    orf13a     MTVWFVAAVAVLIIELLTGTVYLLVVSAALAGSGIAYGLTGSTPAAVLTAALLSALGIWF
               10        20        30        40        50        60

60        70        80        90       100       110
    orf13.pep  VHAKTAVRKVETDSYQDLDAGQYVEILRHTGGNRYEVXYRGTXWQAQNTGQEELEPGTRA
               |||||||  ||||||||||||||||:||||| ||||||  |||| |||||||||||||||
    orf13a     VHAKTAVGKVETDSYQDLDAGQYAEILRHAGGNRYEVFYRGTHWQAQNTGQEELEPGTRA
                        70        80        90       100       110       120

120
    orf13.pep  LIVRKEGNLLIITHPX
               ||||||||||||::||
    orf13a     LIVRKEGNLLIIAKPX
                       130
```

The complete length ORF13a nucleotide sequence <SEQ ID 63> is:

```
  1 ATGACTGTAT GGTTTGTTGC CGCTGTTGCC GTCTTAATCA TCGAATTATT
 51 GACGGGAACG GTTTATCTTT TGGTTGTCAG CGCGGCTTTG GCGGGTTCGG
101 GCATTGCTTA CGGGCTGACC GGCAGCACGC CTGCCGCCGT CTTGACCGCC
151 GCTCTGCTTT CCGCGCTGGG TATTTGGTTC GTACACGCCA AAACCGCCGT
201 GGGAAAAGTT GAAACGGATT CATATCAGGA TTTGGATGCC GGGCAATATG
251 CCGAAATCCT CCGGCACGCA GGCGGCAACC GTTACGAAGT TTTTTATCGC
301 GGTACGCACT GGCAGGCTCA AAATACGGGG CAAGAAGAGC TTGAACCAGG
351 AACGCGCGCC CTAATCGTCC GCAAGGAAGG CAACCTTCTT ATCATCGCAA
401 AACCTTAA
```

This encodes a protein having amino acid sequence <SEQ ID 64>:

```
  1 MTVWFVAAVA VLIIELLTGT VYLLVVSAAL AGSGIAYGLT GSTPAAVLTA
 51 ALLSALGIWF VHAKTAVGKV ETDSYQDLDA GQYAEILRHA GGNRYEVFYR
101 GTHWQAQNTG QEELEPGTRA LIVRKEGNLL IIAKP*
```

ORF13a and ORF13-1 show 94.4% identity in 126 aa overlap

```
                        10        20        30        40        50        60
    orf13a.pep MTVWFVAAVAVLIIELLTGTVYLLVVSAALAGSGIAYGLTGSTPAAVLTAALLSALGIWF
                        |||||||||||||||||||||||||||||||||||||| |||||||| |
    orf13-1             AVLIIELLTGTVYLLVVSAALAGSGIAYGLTGSTPAAVLTXALLSALGIXF
                        10        20        30        40        50

70        80        90       100       110       120
    orf13a.pep VHAKTAVGKVETDSYQDLDAGQYAEILRHAGGNRYEVFYRGTHWQAQNTGQEELEPGTRA
               |||||||  ||||||||||||||||:||||| ||||||||||||||||||||||||||||
    orf13-1    VHAKTAVRKVETDSYQDLDAGQYVEILRHTGGNRYEVFYRGTHWQAQNTGQEELEPGTRA
                        60        70        80        90       100       110

130
    orf13a.pep LIVRKEGNLLIIAKPX
               ||||||||||||::||
    orf13-1    LIVRKEGNLLIITHPX
                       120
```

Homology with a Predicted ORF from *N. gonorrhoeae*
ORF13 shows 89.7% identity over a 126aa overlap with a predicted ORF (ORF13.ng) from *N. gonorrhoeae*:

```
orf13              AVLIIELLTGTVYLLVVSAALAGSGIAYGLTGSTPAAVLTXALLSALGIXF   51
                   ||||||||||||||||||||||||||||||||||||||||| ||||||| |
orf13ng  MTVWFVAAVAVLIIELLTGTVYLLVVSAALAGSGIAYGLTGSTPAAVLTAALLSALGIWF   60
orf13    VHAKTAVRKVETDSYQDLDAGQYVEILRHTGGNRYEVXYRGTXWQAQNTGQEELEPGTRA  111
         ||||||| |||||||||||:|:|:||||:||||||||| |||| ||||||||| :||||||
orf13ng  VHAKTAVGKVETDSYQDLDTGKYAEILRYTGGNRYEVFYRGTHWQAQNTGQEVFEPGTRA  120
orf13    LIVRKEGNLLIITHP                                               126
         |||||||||||||::|
orf13ng  LIVRKEGNLLIIANP                                               135
```

The complete length ORF13ng nucleotide sequence <SEQ ID 65> is:

```
  1 ATGACTGTAT GGTTTGTTGC CGCTGTTGCC GTCTTAATCA TCGAATTATT

51 GACGGGAACG GTTTATCTTT TGGTTGTCAG CGCGGCTTTG GCGGGTTCGG

101 GCATTGCCTA CGGGCTGACT GGCAGCACGC CTGCCGCCGT CTTGACCGCC

151 GCACTGCTTT CCGCGCTGGG CATTTGGTTC GTACATGCCA AAACCGCCGT

201 GGGAAAAGTT GAAACGGATT CATATCAGGA TTTGGATACC GGAAAATATG

251 CCGAAATCCT CCGATACACA GGCGGCAACC GTTACGAAGT TTTTTATCGC

301 GGTACGCACT GGCAGGCGCA AAATACGGGG CAGGAAGTGT TTGAACCGGG

351 AACGCGCGCC CTCATCGTCC GCAAAGAAGG TAACCTTCTT ATCATCGCAA

401 ACCCTTAA
```

This encodes a protein having amino acid sequence <SEQ ID 66>:

```
  1 MTVWFVAAVA VLIIELLTGT VYLLVVSAAL AGSGIAYGLT GSTPAAVLTA

51 ALLSALGIWF VHAKTAVGKV ETDSYQDLDT GKYAEILRYT GGNRYEVFYR

101 GTHWQAQNTG QEVFEPGTRA LIVRKEGNLL IIANP*
```

ORF13ng shows 91.3% identity in 126 aa overlap with ORF13-1:

```
                          10         20         30         40         50
orf13-1.pep            AVLIIELLTGTVYLLVVSAALAGSGIAYGLTGSTPAAVLTXALLSALGIXF
                       ||||||||||||||||||||||||||||||||||||||||| ||||||| |
orf13ng      MTVWFVAAVAVLIIELLTGTVYLLVVSAALAGSGIAYGLTGSTPAAVLTAALLSALGIWF
                     10         20         30         40         50         60

60         70         80         90        100        110
orf13-1.pep  VHAKTAVRKVETDSYQDLDAGQYVEILRHTGGNRYEVFYRGTHWQAQNTGQEELEPGTRA
             ||||||| |||||||||||:|:|:||||:|||||||||||||||||||||||  :|||||
orf13ng      VHAKTAVGKVETDSYQDLDTGKYAEILRYTGGNRYEVFYRGTHWQAQNTGQEVFEPGTRA
                     70         80         90        100        110        120

120
orf13-1.pep  LIVRKEGNLLIITHPX
             |||||||||||||::||
orf13ng      LIVRKEGNLLIIANPX
                    130
```

Based on this analysis, including the extensive leader sequence in this protein, it is predicted that ORF13 and ORF13ng are likely to be outer membrane proteins. It is thus predicted that the proteins from *N. meningitidis* and *N. gonorrhoeae*, and their epitopes, could be useful antigens for vaccines or diagnostics, or for raising antibodies.

Example 9

The following DNA sequence was identified in *N. meningitidis* <SEQ ID 67>:

```
  1 ATGTwTGATT TCGGTTTrGG CGArCTGGTT TTTGTCGGCA TTATCGCCCT
 51 GATwGtCCTC GGCCCCGAAC GCsTGCCCGA GGCCGCCCGC AyCGCCGGAC
101 GGcTCATCGG CAGGCTGCAA CGCTTTGTCG GcAGCGTCAA ACAGGAATTT
151 GACACTCAAA TCGAACTGGA AGAACTGAGG AAGGCAAAGC AGGAATTTGA
201 AGCTGCCGcC GCTCAGGTTC GAGACAGCCT CAAAGAAACC GGTACGGATA
251 TGGAAGGCAA TCTGCACGAC ATTTCCGACG GTCTGAAGCC TTGGGAAAAA
301 CTGCCCGAAC AGCGGACACC TGCCGATTTC GGTGTCGATG AAAACGGCAA
351 TCCGCT.TCC CGATGCGGCA ACACCCTAT CAGACGGCAT TTCCGACGTT
401 ATGCCGTC..
```

This corresponds to the amino acid sequence <SEQ ID 68; ORF2>:

```
  1 MXDFGLGELV FVGIIALIVL GPERXPEAAR XAGRLIGRLQ RFVGSVKQEF
 51 DTQIELEELR KAKQEFEAAA AQVRDSLKET GTDMEGNLHD ISDGLKPWEK
101 LPEQRTPADF GVDENGNPXS RCGKHPIRRH FRRYAV..
```

Further work revealed the complete nucleotide sequence <SEQ ID 69>:

```
  1 ATGTTTGATT TCGGTTTGGG CGAGCTGGTT TTTGTCGGCA TTATCGCCCT
 51 GATTGTCCTC GGCCCCGAAC GCCTGCCCGA GGCCGCCCGC ACCGCCGGAC
101 GGCTCATCGG CAGGCTGCAA CGCTTTGTCG GCAGCGTCAA ACAGGAATTT
151 GACACTCAAA TCGAACTGGA AGAACTGAGG AAGGCAAAGC AGGAATTTGA
201 AGCTGCCGCC GCTCAGGTTC GAGACAGCCT CAAAGAAACC GGTACGGATA
251 TGGAAGGCAA TCTGCACGAC ATTTCCGACG GTCTGAAGCC TTGGGAAAAA
301 CTGCCCGAAC AGCGGACACC TGCCGATTTC GGTGTCGATG AAAACGGCAA
351 TCCGCTTCCC GATGCGGCAA ACACCCTATC AGACGGCATT TCCGACGTTA
401 TGCCGTCCGA ACGTTCCTAC GCTTCCGCCG AAACCCTTGG GGACAGCGGG
451 CAAACCGGCA GTACAGCCGA ACCCGCGGAA ACCGACCAAG ACCGCGCATG
501 GCGGGAATAC CTGACTGCTT CTGCCGCCGC ACCCGTCGTA CAGACCGTCG
551 AAGTCAGCTA TATCGATACT GCTGTTGAAA CGCCTGTTCC GCACACCACT
601 TCCCTGCGCA ACAGGCAAT AAGCCGCAAA CGCGATTTTC GTCCGAAACA
651 CCGCGCCAAA CCTAAATTGC GCGTCCGTAA ATCATAA
```

This corresponds to the amino acid sequence <SEQ ID 70; ORF2-1>:

```
  1 MFDFGLGELV FVGIIALIVL GPERLPEAAR TAGRLIGRLQ RFVGSVKQEF
 51 DTQIELEELR KAKQEFEAAA AQVRDSLKET GTDMEGNLHD ISDGLKPWEK
101 LPEQRTPADF GVDENGNPLP DAANTLSDGI SDVMPSERSY ASAETLGDSG
```

```
151 QTGSTAEPAE TDQDRAWREY LTASAAAPVV QTVEVSYIDT AVETPVPHTT

201 SLRKQAISRK RDFRPKHRAK PKLRVRKS*
```

Further work identified the corresponding gene in strain A of *N. meningitidis* <SEQ ID 71>:

```
  1 ATGTTTGATT TCGGTTTGGG CGAGCTGGTT TTTGTCGGCA TTATCGCCCT

51 GATTGTCCTC GGCCCCGAAC GCCTGCCCGA GGCCGCCCGC ACCGCCGGAC

101 GGCTCATCGG CAGGCTGCAA CGCTTTGTCG GCAGCGTCAA ACAGGAATTT

151 GACACGCAAA TCGAACTGGA AGAACTAAGG AAGGCAAAGC AGGAATTTGA

201 AGCTGCCGCT GCTCAGGTTC GAGACAGCCT CAAAGAAACC GGTACGGATA

251 TGGAGGGTAA TCTGCACGAC ATTTCCGACG GTCTGAAGCC TTGGGAAAAA

301 CTGCCCGAAC AGCGCACGCC TGCTGATTTC GGTGTCGATG AAAACGGCAA

351 TCCCTTTCCC GATGCGGCAA ACACCCTATT AGACGGCATT TCCGACGTTA

401 TGCCGTCCGA ACGTTCCTAC GCTTCCGCCG AAACCCTTGG GGACAGCGGG

451 CAAACCGGCA GTACAGCCGA ACCCGCGGAA ACCGACCAAG ACCGTGCATG

501 GCGGGAATAC CTGACTGCTT CTGCCGCCGC ACCCGTCGTA CAGACCGTCG

551 AAGTCAGCTA TATCGATACC GCTGTTGAAA CCCCTGTTCC GCATACCACT

601 TCGCTGCGTA AACAGGCAAT AAGCCGCAAA CGCGATTTGC GTCCTAAATC

651 CCGCGCCAAA CCTAAATTGC GCGTCCGTAA ATCATAA
```

This encodes a protein having amino acid sequence <SEQ ID 72; ORF2a>:

```
  1 MFDFGLGELV FVGIIALIVL GPERLPEAAR TAGRLIGRLQ RFVGSVKQEF

51 DTQIELEELR KAKQEFEAAA AQVRDSLKET GTDMEGNLHD ISDGLKPWEK

101 LPEQRTPADF GVDENGNPFP DAANTLLDGI SDVMPSERSY ASAETLGDSG

151 QTGSTAEPAE TDQDRAWREY LTASAAAPVV QTVEVSYIDT AVETPVPHTT

201 SLRKQAISRK RDLRPKSRAK PKLRVRKS*
```

The originally-identified partial strain B sequence (ORF2) shows 97.5% identity over a 118aa overlap with ORF2a:

```
                    10         20         30         40         50         60
     orf2.pep  MXDFGLGELVFVGIIALIVLGPERXPEAARXAGRLIGRLQRFVGSVKQEFDTQIELEELR
               | |||||||||||||||||||| ||||| |||||||||||||||||||||||||||||||
     orf2a     MFDFGLGELVFVGIIALIVLGPERLPEAARTAGRLIGRLQRFVGSVKQEFDTQIELEELR
                    10         20         30         40         50         60

70         80         90        100        110        120
     orf2.pep  KAKQEFEAAAAQVRDSLKETGTDMEGNLHDISDGLKPWEKLPEQRTPADFGVDENGNPXS
               |||||||||||||||||||||||||||||||||||||||||||||||||||||||||| 
     orf2a     KAKQEFEAAAAQVRDSLKETGTDMEGNLHDISDGLKPWEKLPEQRTPADFGVDENGNPFP
                    70         80         90        100        110        120

130
     orf2.pep  RCGKHPIRRHFRRYAV orf2a     DAANTLLDGISDVMPSERSYASAETLGDSGQTGSTAEPAETDQDRAWREYLTASAAAPVV
                   130        140        150        160        170        180
```

The complete strain B sequence (ORF2-1) and ORF2a show 98.2% identity in 228 aa overlap:

```
orf2a.pep   MFDFGLGELVFVGIIALIVLGPERLPEAARTAGRLIGRLQRFVGSVKQEFDTQIELEELR   60
            ||||||||||||||||||||||||||||||||||||||||||||||||||||||||||||
orf2-1      MFDFGLGELVFVGIIALIVLGPERLPEAARTAGRLIGRLQRFVGSVKQEFDTQIELEELR   60
orf2a.pep   KAKQEFEAAAAQVRDSLKETFTDMEGNLHDISDGLKPWEKLPEQRTPADFGVDENGNPFP  120
            ||||||||||||||||||||||||||||||||||||||||||||||||||||||||||:|
orf2-1      KAKQEFEAAAAQVRDSLKETFTDMEGNLHDISDGLKPWEKLPEQRTPADFGVDENGNPLP  120
orf2a.pep   DAANTLLDGISDVMPSERSYASAETLGDSGQTGSTAEPAETDQDRAWREYLTASAAAPVV  180
            ||||||| ||||||||||||||||||||||||||||||||||||||||||||||||||||
orf2-1      DAANTLLDGISDVMPSERSYASAETLGDSGQTGSTAEPAETDQDRAWREYLTASAAAPVV  180
orf2a.pep   QTVEVSYIDTAVETPVPHTTSLRKQAISRKRDLRPKSRAKPKLRVRKSX             229
            |||||||||||||||||||||||||||||||:|||  ||||||||||||
orf2-1      QTVEVSYIDTAVETPVPHTTSLRKQAISRKRDFRPKHRAKPKLRVRKSX             229
```

Further work identified a partial DNA sequence <SEQ ID 73> in *N. gonorrhoeae* encoding the following amino acid sequence <SEQ ID 74; ORF2ng>:

```
  1 MFDFGLGELI FVGIIALIVL GPERLPEAAR TAGRLIGRLQ RFVGSVKQEL

51 DTQIELEELR KVKQAFEAAA AQVRDSLKET DTDMQNSLHD ISDGLKPWEK

101 LPEQRTPADF GVDEKGNSLS RYGKHRIRRH FRRYAV*
```

Further work identified the complete gonococcal gene sequence <SEQ ID 75>:

```
  1 ATGTTTGATT TCGGTTTGGG CGAGCTGATT TTTGTCGGCA TTATCGCCCT

51 GATTGTCCTT GGTCCAGAAC GCCTGCCCGA AGCCGCCCGC ACTGCCGGAC

101 GGCTTATCGG CAGGCTGCAA CGCTTTGTAG GAAGCGTCAA ACAAGAACTT

151 GACACTCAAA TCGAACTGGA AGAGCTGAGG AAGGTCAAGC AGGCATTCGA

201 AGCTGCCGCC GCTCAGGTTC GAGACAGCCT CAAAGAAACC GATACGGATA

251 TGCAGAACAG TCTGCACGAC ATTTCCGACG GTCTGAAGCC TTGGGAAAAA

301 CTGCCCGAAC AGCGCACGCc tgccgatttc gGTGTCGATg AAAacggcaa 351 tccccttccc gATACGGCAA ACACCGTATC AGACGGCATT TCCGACGTTA 401 TGCCGTCTGA ACGTTCCGAT ACTtccgcCG AAACCCTTGG GGACGACAGG

451 CAAACCGGCA GTACAGCCGA ACCTGCGGAA ACCGACAAAG ACCGCGCATG

501 GCGGGAATAC CTGactgctt ctgccgccgc acctgtcgta Cagagggccg 551 tcgaagtcag ctaTATCGAT ACTGCTGTTG AAacgcctgT tccgcaCacc 601 acttccctgc gcaAACAGGC AATAAACCGC AAACGCGATT TttgtccgaA 651 ACACCGCGCc aAACCGAAat tgcgcgtcCG TAAATCATAA
```

This encodes a protein having the amino acid sequence <SEQ ID 76; ORF2ng-1>:

```
  1 MFDFGLGELI FVGIIALIVL GPERLPEAAR TAGRLIGRLQ RFVGSVKQEL

51 DTQIELEELR KVKQAFEAAA AQVRDSLKET DTDMQNSLHD ISDGLKPWEK

101 LPEQRTPADF GVDENGNPLP DTANTVSDGI SDVMPSERSD TSAETLGDDR

151 QTGSTAEPAE TDKDRAWREY LTASAAAPVV QRAVEVSYID TAVETPVPHT

201 TSLRKQAINR KRDFCPKHRA KPKLRVRKS*
```

The originally-identified partial strain B sequence (ORF2) shows 87.5% identity over a 136aa overlap with ORF2ng:

```
orf2.pep   MXDFGLGELVFVGIIALIVLGPERXPEAARXAGRLIGRLQRFVGSVKQEFDTQIELEELR    60
           | |||||| :||||||||||||| |||||| |||||||||||||||||||:|||||||||
orf2ng     MFDFGLGELIFVGIIALIVLGPERLPEAARTAGRLIGRLQRFVGSVKQELDTQIELEELR    60
orf2.pep   KAKQEFEAAAAQVRDSLKETGTDMEGNLHDISDGLKPWEKLPEQRTPADFGVDENGNPXS   120
           |:|| ||||||||||||||||| |||:::|||||||||||||||||||||||||||| ||
orf2ng     KVKQAFEAAAAQVRDSLKETDTDMQNSLHDISDGLKPWEKLPEQRTPADFGVDEKGNSLP   120
orf2.pep   RCGKHPIRRHFRRYAV                                               136
           | ||| ||||||||||
orf2ng     RYGKHRIRRHFRRYAV                                               136
```

The complete strain B and gonococcal sequences (ORF2-1 & ORF2ng-1) show 91.7% identity in 229 aa overlap:

```
                   10        20        30        40        50        60
orf2-1.pep MFDFGLGELVFVGIIALIVLGPERLPEAARTAGRLIGRLQRFVFSVKQEFDTQIELEELR
           |||||||||:|||||||||||||||||||||||||||||||||||||||:||||||||||
orf2ng-1   MFDFGLGELIFVGIIALIVLGPERLPEAARTAGRLIGRLQRFVFSVKQELDTQIELEELR
                   10        20        30        40        50        60

70        80        90       100       110       120
orf2-1.pep KAKQEFEAAAAQVRDSLKETGTDMEGNLHDISDGLKPWEKLPEQRTPADFGVDENGNPLP
           |:|| ||||||||||||||||| |||:::|||||||||||||||||||||||||||||||
orf2ng-1   KVKQAFEAAAAQVRDSLKETDTDMQNSLHDISDGLKPWEKLPEQRTPADFGVDENGNPLP
                   70        80        90       100       110       120

130       140       150       160       170       180
orf2-1.pep DAANTLSDGISDVMPSERSYASAETLGDSGQTGSTAEPAETDQDRAWREYLTASAAAPVV
           :|||:|||||||||||||| :||||||: ||||||||||||:||||||||||||||||||
orf2ng-1   DTANTVSDGISDVMPSERSDTSAETLGDDRQTGSTAEPAETDKDRAWREYLTASAAAPVV
                  130       140       150       160       170       180

190       200       210       220       229
orf2-1.pep Q-TVEVSYIDTAVETPVPHTTSLRKQAISRKRDFRPKHRAKPKLRVRKSX
           | :|||||||||||||||||||||||||:||||| ||||||||||||||
orf2ng-1   QRAVEVSYIDTAVETPVPHTTSLRKQAINRKRDFCPKHRAKPKLRVRKSX
                  190       200       210       220       230
```

Computer analysis of these amino acid sequences indicates a transmembrane region (underlined), and also revealed homology (59% identity) between the gonococcal sequence and the TatB protein of *E. coli*:

```
gnl|PID|e1292181 (AJ005830) TatB protein [Escherichia coli] Length = 171
Score = 56.6 bits (134), Expect = 1e-07
Identities = 30/88 (34%), Positives = 52/88 (59%), Gaps = 1/88 (1%)

Query:  1 MFDFGLGELIFVGIIALIVLGPERLPEAARTAGRLIGRLQRFVGSVKQELDTQIELEELR   60
          MFD G  EL+ V II L+VLGP+RLP A +T    I  L+    +V+ EL  +++L+E +
Sbjct:  1 MFDIGFSELLLVFIIGLVVGPQRLPVAVKTVAGWIRALRSLATTVQNELTQELKLQEFQ    60

Query: 61 -KVKQAFEAAAAQVRDSLKETDTDMQNS                                  87
           +K+ +A+   +  LK +  +++ +
Sbjct: 61 DSLKKVEKASLTNLTPELKASMDELRQA                                  88
```

Based on this analysis, it was predicted that ORF2, ORF2a and ORF2ng are likely to be membrane proteins and so the proteins from *N. meningitidis* and *N. gonorrhoeae*, and their epitopes, could be useful antigens for vaccines or diagnostics, or for raising antibodies.

ORF2-1 (16 kDa) was cloned in pET and pGex vectors and expressed in *E. coli*, as described above. The products of protein expression and purification were analyzed by SDS-PAGE. FIG. 3A shows the results of affinity purification of the GST-fusion protein, and FIG. 3B shows the results of expression of the His-fusion in *E. coli*. Purified GST-fusion protein was used to immunise mice, whose sera were used for Western blots (FIG. 3C), ELISA (positive result), and FACS analysis (FIG. 3D). These experiments confirm that ORF37-1 is a surface-exposed protein, and that it is a useful immunogen.

Example 10

The following partial DNA sequence was identified in *N. meningitidis* <SEQ ID 77>:

```
  1 ATGCAAGCAC GGCTGCTGAT ACCTATTCTT TTTTCAGTTT TTATTTTATC
 51 CGC.TGCGGG ACACTGACAG GTATTCCATC GCATGGCGgA GkTAAACgCT
101 TTgCGGTCGA ACAAGAACTT GTGGCCGCTT CTGCCAGAGC TGCCGTTAAA
151 GACATGGATT TACAGGCATT ACACGGACGA AAAGTTGCAT TGTACATTGC
201 CACTATGGGC GACCAAGGTT CAGGcAGTTT GACAGGGGGG TCGCTACTCC
251 ATTGATGCAC kGrTwCsTGG CGAATACATA AACAGCCCTG CCGTCCGTAC
301 CGATTACACC TATCCACGTT ACGAAACCAC CGCTGAAACA ACATCAGGCG
351 GTTTGACAGG TTTAACCACT TCTTTATCTA CACTTAATGC CCCTGCACTC
401 TCTCGCACCC AATCAGACGG TAGCGGAAGT AAAAGCAGTC TGGGCTTAAA
451 TATTGGCGGG ATGGGGGATT ATCGAAATGA AACCTTGACG ACTAACCCGC
501 GCGACACTGC CTTTCTTTCC CACTTGGTAC AGACCGTATT TTTCCTGCGC
551 GGCATAGACG TTGTTTCTCC TGCCAATGCC GATACAGATG TGTTTATTAA
601 CATCGACGTA TTCGGAACGA TACGCAACAG AACCGAAATG..
```

This corresponds to the amino acid sequence <SEQ ID 78; ORF15>:

```
  1 MQARLLIPIL FSVFILSACG TLTGIPSHGG XKRFAVEQEL VAASARAAVK
 51 DMDLQALHGR KVALYIATMG DQGSGSLTGG RYSIDAXXXG EYINSPAVRT
101 DYTYPRYETT AETTSGGLTG LTTSLSTLNA PALSRTQSDG SGSKSSLGLN
151 IGGMGDYRNE TLTTNPRDTA FLSHLVQTVF FLRGIDVVSP ANADTDVFIN
201 IDVFGTIRNR TEM..
```

Further work revealed the complete nucleotide sequence <SEQ ID 79>:

```
  1 ATGCAAGCAC GGCTGCTGAT ACCTATTCTT TTTTCAGTTT TTATTTTATC
 51 CGCCTGCGGG ACACTGACAG GTATTCCATC GCATGGCGGA GGTAAACGCT
101 TTGCGGTCGA ACAAGAACTT GTGGCCGCTT CTGCCAGAGC TGCCGTTAAA
151 GACATGGATT TACAGGCATT ACACGGACGA AAAGTTGCAT TGTACATTGC
201 CACTATGGGC GACCAAGGTT CAGGCAGTTT GACAGGGGGT CGCTACTCCA
251 TTGATGCACT GATTCGTGGC GAATACATAA ACAGCCCTGC CGTCCGTACC
301 GATTACACCT ATCCACGTTA CGAAACCACC GCTGAAACAA CATCAGGCGG
351 TTTGACAGGT TTAACCACTT CTTTATCTAC ACTTAATGCC CCTGCACTCT
401 CTCGCACCCA ATCAGACGGT AGCGGAAGTA AAAGCAGTCT GGGCTTAAAT
451 ATTGGCGGGA TGGGGGATTA TCGAAATGAA ACCTTGACGA CTAACCCGCG
501 CGACACTGCC TTTCTTTCCC ACTTGGTACA GACCGTATTT TTCCTGCGCG
551 GCATAGACGT TGTTTCTCCT GCCAATGCCG ATACAGATGT GTTTATTAAC
601 ATCGACGTAT TCGGAACGAT ACGCAACAGA ACCGAAATGC ACCTATACAA
651 TGCCGAAACA CTGAAAGCCC AAACAAAACT GGAATATTTC GCAGTAGACA
701 GAACCAATAA AAAATTGCTC ATCAAACCAA AACCAATGC GTTTGAAGCT
```

```
751 GCCTATAAAG AAAATTACGC ATTGTGGATG GGGCCGTATA AAGTAAGCAA

801 AGGAATTAAA CCGACGGAAG GATTAATGGT CGATTTCTCC GATATCCGAC

851 CATACGGCAA TCATACGGGT AACTCCGCCC CATCCGTAGA GGCTGATAAC

901 AGTCATGAGG GGTATGGATA CAGCGATGAA GTAGTGCGAC AACATAGACA

951 AGGACAACCT TGA
```

This corresponds to the amino acid sequence <SEQ ID 80; ORF15-1>:

```
  1 MQARLLIPIL FSVFILSACG TLTGIPSHGG GKRFAVEQEL VAASARAAVK

51 DMDLQALHGR KVALYIATMG DQGSGSLTGG RYSIDALIRG EYINSPAVRT

101 DYTYPRYETT AETTSGGLTG LTTSLSTLNA PALSRTQSDG SGSKSSLGLN

151 IGGMGDYRNE TLTTNPRDTA FLSHLVQTVF FLRGIDVVSP ANADTDVFIN

201 IDVFGTIRNR TEMHLYNAET LKAQTKLEYF AVDRTNKKLL IKPKTNAFEA

251 AYKENYALWM GPYKVSKGIK PTEGLMVDFS DIRPYGNHTG NSAPSVEADN

301 SHEGYGYSDE VVRQHRQGQP *
```

Further work identified the corresponding gene in strain A of *N. meningitidis* <SEQ ID 81>:

```
  1 ATGCAAGCAC GGCTGCTGAT ACCTATTCTT TTTTCAGTTT TTATTTTATC
 51 CGCCTGCGGG ACACTGACAG GTATTCCATC GCATGGCGGA GGTAAACGCT
101 TTGCGGTCGA ACAAGAACTT GTGGCCGCTT CTGCCAGAGC TGCCGTTAAA
151 GACATGGATT TACAGGCATT ACACGGACGA AAAGTTGCAT TGTACATTGC
201 AACTATGGGC GACCAAGGTT CAGGCAGTTT GACAGGGGGT CGCTACTCCA
251 TTGATGCACT GATTCGTGGC GAATACATAA ACAGCCCTGC CGTCCGTACC
301 GATTACACCT ATCCACGTTA CGAAACCACC GCTGAAACAA CATCAGGCGG
351 TTTGACAGGT TTAACCACTT CTTTATCTAC ACTTAATGCC CCTGCACTCT
401 CGCGCACCCA ATCAGACGGT AGCGGAAGTA AAAGCAGTCT GGGCTTAAAT
451 ATTGGCGGGA TGGGGGATTA TCGAAATGAA ACCTTGACGA CTAACCCGCG
501 CGACACTGCC TTTCTTTCCC ACTTGGTACA GACCGTATTT TTCCTGCGCG
551 GCATAGACGT TGTTTCTCCT GCCAATGCCG ATACGGATGT GTTTATTAAC
601 ATCGACGTAT TCGGAACGAT ACGCAACAGA ACCGAAATGC ACCTATACAA
651 TGCCGAAACA CTGAAAGCCC AAACAAAACT GGAATATTTC GCAGTAGACA
701 GAACCAATAA AAAATTGCTC ATCAAACCAA AAACCAATGC GTTTGAAGCT
751 GCCTATAAAG AAAATTACGC ATTGTGGATG GGACCGTATA AAGTAAGCAA
801 AGGAATTAAA CCGACAGAAG GATTAATGGT CGATTTCTCC GATATCCAAC
851 CATACGGCAA TCATATGGGT AACTCTGCCC CATCCGTAGA GGCTGATAAC
901 AGTCATGAGG GGTATGGATA CAGCGATGAA GCAGTGCGAC GACATAGACA
951 AGGGCAACCT TGA
```

This encodes a protein having amino acid sequence <SEQ ID 82; ORF15a>:

```
  1 MQARLLIPIL FSVFILSACG TLTGIPSHGG GKRFAVEQEL VAASARAAVK

51 DMDLQALHGR KVALYIATMG DQGSGSLTGG RYSIDALIRG EYINSPAVRT

101 DYTYPRYETT AETTSGGLTG LTTSLSTLNA PALSRTQSDG SGSKSSLGLN

151 IGGMGDYRNE TLTTNPRDTA FLSHLVQTVF FLRGIDVVSP ANADTDVFIN

201 IDVFGTIRNR TEMHLYNAET LKAQTKLEYF AVDRTNKKLL IKPKTNAFEA

251 AYKENYALWM GPYKVSKGIK PTEGLMVDFS DIQPYGNHMG NSAPSVEADN

301 SHEGYGYSDE AVRRHRQGQP *
```

15

The originally-identified partial strain B sequence (ORF15) shows 98.1% identity over a 213aa overlap with ORF15a:

```
                      10         20         30         40         50         60
    orf15.pep  MQARLLIPILFSVFILSACGTLTGIPSHGGXKRFAVEQELVAASARAAVKDMDLQALHGR
               ||||||||||||||||||||||||||||||| |||||||||||||||||||||||||||
    orf15a     MQARLLIPILFSVFILSACGTLTGIPSHGGGKRFAVEQELVAASARAAVKDMDLQALHGR
                      10         20         30         40         50         60

70         80         90        100        110        120
    orf15.pep  KVALYIATMGDQGSGSLTGGRYSIDAXXXGEYINSPAVRTDYTYPRYETTAETTSGGLTG
               |||||||||||||||||||||||||||   ||||||||||||||||||||||||||||||
    orf15a     KVALYIATMGDQGSGSLTGGRYSIDALIRGEYINSPAVRTDYTYPRYETTAETTSGGLTG
                      70         80         90        100        110        120

130        140        150        160        170        180
    orf15.pep  LTTSLSTLNAPALSRTQSDGSGSKSSLGLNIGGMGDYRNETLTTNPRDTAFLSHLVQTVF
               ||||||||||||||||||||||||||||||||||||||||||||||||||||||||||||
    orf15a     LTTSLSTLNAPALSRTQSDGSGSKSSLGLNIGGMGDYRNETLTTNPRDTAFLSHLVQTVF
                     130        140        150        160        170        180

190        200        210
    orf15.pep  FLRGIDVVSPANADTDVFINIDVFGTIRNRTEM
               |||||||||||||||||||||||||||||||||
    orf15a     FLRGIDVVSPANADTDVFINIDVFGTIRNRTEMHLYNAETLKAQTKLEYFAVDRTNKKLL
                     190        200        210        220        230        240
```

The complete strain B sequence (ORF15-1) and ORF15a show a 98.8% identity in 320 aa overlap:

```
                       10         20         30         40         50         60
    orf15a.pep  MQARLLIPILFSVFILSACGTLTGIPSHGGGKRFAVEQELVAASARAAVKDMDLQALHGR
                ||||||||||||||||||||||||||||||||||||||||||||||||||||||||||||
    orf15-1     MQARLLIPILFSVFILSACGTLTGIPSHGGGKRFAVEQELVAASARAAVKDMDLQALHGR
                       10         20         30         40         50         60

70         80         90        100        110        120
    orf15a.pep  KVALYIATMGDQGSGSLTGGRYSIDALIRGEYINSPAVRTDYTYPRYETTAETTSGGLTG
                ||||||||||||||||||||||||||||||||||||||||||||||||||||||||||||
    orf15-1     KVALYIATMGDQGSGSLTGGRYSIDALIRGEYINSPAVRTDYTYPRYETTAETTSGGLTG
                       70         80         90        100        110        120

130        140        150        160        170        180
    orf15a.pep  LTTSLSTLNAPALSRTQSDGSGSKSSLGLNIGGMGDYRNETLTTNPRDTAFLSHLVQTVF
                ||||||||||||||||||||||||||||||||||||||||||||||||||||||||||||
    orf15-1     LTTSLSTLNAPALSRTQSDGSGSKSSLGLNIGGMGDYRNETLTTNPRDTAFLSHLVQTVF
                      130        140        150        160        170        180

190        200        210        220        230        240
    orf15a.pep  FLRGIDVVSPANADTDVFINIDVFGTIRNRTEMHLYNAETLKAQTKLEYFAVDRTNKKLL
                ||||||||||||||||||||||||||||||||||||||||||||||||||||||||||||
    orf15-1     FLRGIDVVSPANADTDVFINIDVFGTIRNRTEMHLYNAETLKAQTKLEYFAVDRTNKKLL
                      190        200        210        220        230        240

250        260        270        280        290        300
    orf15a.pep  IKPKTNAFEAAYKENYALWMGPYKVSKGIKPTEGLMVDFSDIQPYGNHMGNSAPSVEADN
                |||||||||||||||||||||||||||||||||||||||||:|||||:||||||||||||
    orf15-1     IKPKTNAFEAAYKENYALWMGPYKVSKGIKPTEGLMVDFSDIRPYGNHTGNSAPSVEADN
                      250        260        270        280        290        300

310        320
    orf15a.pep  SHEGYGYSDEAVRRHRQRQPX
                ||||||||||:||:|||||||
    orf15-1     SHEGYGYSDEVVRQHRQRQPX
                      310        320
```

Further work identified the corresponding gene in *N. gonorrhoeae* <SEQ ID 83>:

```
  1 ATGCGGGCAC GGCTGCTGAT ACCTATTCTT TTTTCAGTTT TTATTTTATC

51 CGCCTGCGGG ACACTGACAG GTATTCCATC GCATGGCGGA GGCAAACGCT

101 TCGCGGTCGA ACAAGAACTT GTGGCCGCTT CTGCCAGAGC TGCCGTTAAA

151 GACATGGATT TACAGGCATT ACACGGACGA AAAGTTGCAT TGTACATTGC

201 AACTATGGGC GACCAAGGTT CAGGCAGTTT GACAGGGGGT CGCTACTCCA

251 TTGATGCACT GATTCGCGGC GAATACATAA ACAGCCCTGC CGTCCGCACC

301 GATTACACCT ATCCGCGTTA CGAAACCACC GCTGAAACAA CATCAGGCGG

351 TTTGACGGGT TTAACCACTT CTTTATCTAC ACTTAATGCC CCTGCACTCT

401 CGCGCACCCA ATCAGACGGT AGCGGAAGTA GGAGCAGTCT GGGCTTAAAT

451 ATTGGCGGGA TGGGGGATTA TCGAAATGAA ACCTTGACGA CCAACCCGCG

501 CGACACTGCC TTTCTTTCCC ACTTGGTGCA GACCGTATTT TTCCTGCGCG

551 GCATAGACGT TGTTTCTCCT GCCAATGCCG ATACAGATGT GTTTATTAAC

601 ATCGACGTAT TCGGAACGAT ACGCAACAGA ACCGAAATGC ACCTATACAA

651 TGCCGAAACA CTGAAAGCCC AAACAAAACT GGAATATTTC GCAGTAGACA

701 GAACCAATAA AAAATTGCTC ATCAAACCCA AAACCAATGC GTTTGAAGCT

751 GCCTATAAAG AAAATTACGC ATTGTGGATG GGGCCGTATA AAGTAAGCAA

801 AGGAATCAAA CCGACGGAAG GATTGATGGT CGATTTCTCC GATATCCAAC

851 CATACGGCAA TCATACGGGT AACTCCGCCC CATCCGTAGA GGCTGATAAC

901 AGTCATGAGG GGTATGGATA CAGCGATGAA GCAGTGCGAC AACATAGACA

951 AGGGCAACCT TGA
```

This encodes a protein having amino acid sequence <SEQ ID 84; ORF15ng>:

```
  1 MRARLLIPIL FSVFILSACG TLTGIPSHGG GKRFAVEQEL VAASARAAVK

51 DMDLQALHGR KVALYIATMG DQGSGSLTGG RYSIDALIRG EYINSPAVRT

101 DYTYPRYETT AETTSGGLTG LTTSLSTLNA PALSRTQSDG SGSRSSLGLN

151 IGGMGDYRNE TLTTNPRDTA FLSHLVQTVF FLRGIDVVSP ANADTDVFIN

201 IDVFGTIRNR TEMHLYNAET LKAQTKLEYF AVDRTNKKLL IKPKTNAFEA

251 AYKENYALWM GPYKVSKGIK PTEGLMVDFS DIQPYGNHTG NSAPSVEADN

301 SHEGYGYSDE AVRQHRQGQP *
```

The originally-identified partial strain B sequence (ORF 15) shows 97.2% identity over a 213aa overlap with ORF15ng:

```
orf15.pep   MQARLLIPILFSVFILSACGTLTGIPSHGGXKRFAVEQELVAASARAAVKDMDLQALHGR   60
            |:||||||||||||||||||||||||||||| ||||||||||||||||||||||||||||
orf15ng     MRARLLIPILFSVFILSACGTLTGIPSHGGGKRFAVEQELVAASARAAVKDMDLQALHGR   60 orf15.pep   KVALYIATMGDQGSGSLTGGRYSIDAXXXGEYINSPAVRTDYTYPRYETTAETTSGGLTG  120
            ||||||||||||||||||||||||||   |||||||||||||||||||||||||||||||
orf15ng     KVALYIATMGDQGSGSLTGGRYSIDALIRGEYINSPAVRTDYTYPRYETTAETTSGGLTG  120 orf15.pep   LTTSISTLNAPALSRTQSDGSGSKSSLGLNIGGMGDYRNETLTTNPRDTAFLSHLVQTVF  180
            ||||||||||||||||||||||||:|||||||||||||||||||||||||||||||||||
orf15ng     LTTSISTLNAPALSRTQSDGSGSRSSLGLNIGGMGDYRNETLTTNPRDTAFLSHLVQTVF  120
```

```
                                                                       -continued
orf15.pep      FLRGIDVVSPANADTDVFINIDVFGTIRNRTEM                                      213
               ||||||||||||||||||||||||||||||||
orf15ng        FLRGIDVVSPANADTDVFINIDVFGTIRNRTEMHLYNAETLKAQTKLEYFAVDRTNKKLL           240
```

The complete strain B sequence (ORF15-1) and ORF15ng show 98.8% identity in 320 aa overlap:

```
                        10         20         30         40         50         60
orf15-1.pep    MQARLLIPILFSVFILSACGTLTGIPSHGGGKRFAVEQELVAASARAAVKDMDLQALHGR
               |:||||||||||||||||||||||||||||||||||||||||||||||||||||||||
orf15ng        MRARLLIPILFSVFILSACGTLTGIPSHGGGKRFAVEQELVAASARAAVKDMDLQALHGR
                        10         20         30         40         50         60
                        70         80         90        100        110        120
orf15-1.pep    KVALYIATMGDQGSGSLTGGRYSIDALIRGEYINSPAVRTDYTYPRYETTAETTSGGLTG
               ||||||||||||||||||||||||||||||||||||||||||||||||||||||||||||
orf15ng        KVALYIATMGDQGSGSLTGGRYSIDALIRGEYINSPAVRTDYTYPRYETTAETTSGGLTG
                        70         80         90        100        110        120
                       130        140        150        160        170        180
orf15-1.pep    LTTSLSTLNAPALSRTQSDGSGSKSSLGLNIGGMGDYRNETLTTNPRDTAFLSHLVQTVF
               |||||||||||||||||||||||||:||||||||||||||||||||||||||||||||||
orf15ng        LTTSLSTLNAPALSRTQSDGSGSRSSLGLNIGGMGDYRNETLTTNPRDTAFLSHLVQTVF
                       130        140        150        160        170        180
                       190        200        210        220        230        240
orf15-1.pep    FLRGIDVVSPANADTDVFINIDVFGTIRNRTEMHLYNAETLKAQTKLEYFAVDRTNKKLL
               ||||||||||||||||||||||||||||||||||||||||||||||||||||||||||||
orf15ng        FLRGIDVVSPANADTDVFINIDVFGTIRNRTEMHLYNAETLKAQTKLEYFAVDRTNKKLL
                       190        200        210        220        230        240
                       250        260        270        280        290        300
orf15-1.pep    IKPKTNAFEAAYKENYALWMGPYKVSKGIKPTEGLMVDFSDIRPTGNHTGNSAPSVEADN
               |||||||||||||||||||||||||||||||||||||||||:||||||||||||||||||
orf15ng        IKPKTNAFEAAYKENYALWMGPYKVSKGIKPTEGLMVDFSDIQPTGNHTGNSAPSVEADN
                       250        260        270        280        290        300
                       310        320
orf15-1.pep    SHEGYGYSDEVVRQHRQGQPX
               |||||||||:|||||||||||
orf15ng        SHEGYGYSDEAVRQHRQGQPX
                       310        320
```

Computer analysis of these amino acid sequences reveals an ILSAC motif (putative membrane lipoprotein lipid attachment site, as predicted by the MOTIFS program). indicates a putative leader sequence, and it was predicted that the proteins from *N. meningitidis* and *N. gonorrhoeae*, and their epitopes, could be useful antigens for vaccines or diagnostics, or for raising antibodies.

ORF15-1 (31.7 kDa) was cloned in pET and pgex vectors and expressed in *E. coli*, as described above. The products of protein expression and purification were analyzed by SDS-PAGE. FIG. 4A shows the results of affinity purification of the GST-fusion protein, and FIG. 4B shows the results of expression of the His-fusion in *E. coli*. Purified GST-fusion protein was used to immunise mice, whose sera were used for Western blot (FIG. 4C) and ELISA (positive result). These experiments confirm that ORFX-1 is a surface-exposed protein, and that it is a useful immunogen.

Example 11

The following partial DNA sequence was identified in *N. meningitidis* <SEQ ID 85>:

```
  1 ..GG.CAGCACA AAAAACAGGC GGTTGAACGG AAAAACCGTA TTTACGATGA

51    TGCCGGGTAT GATATTCGGC GTATTCACGG GCGCATTCTC CGCAAAATAT
```

```
101  ATCCCCGCGT TCGGGCTTCA AATTTTCTTC ATCCTGTTTT TAACCGCCGT

151  CGCATTCAAA ACACTGCATA CCGACCCTCA GACGGCATCC CGCCCGCTGC

201  CCGGACTGCC CrGACTGACT GCGGTTTCCA CACTGTTCGG CACAATGTCG

251  AGCTGGGTCG GCATAGGCGG CGGTTCACTT TCCGTCCCCT TCTTAATCCA

301  CTGCGGCTTC CCCGCCCATA AAGCCATCGG CACATCATCC GGCCTTGCCT

351  GGCCGATTGC ACTCTCCGGC GCAATATCGT ATCTGCTCAA CGGCCTGAAT

401  ATTGCAGGAT GCCCGAAGG GTCACTGGGC TTCCTTTACC TGCCCGCCGT

451  CGCCGTCCTC AGCGCGGCAA CCATTGCCTT TGCCCCGCTC GGTGTCAAAA

501  CCGCCCACAA ACTTTCTTCT GCCAAACTCA AAAAATC.TT CGGCATTATG

551  TTGCTTTTGA TTGCCGGAAA AATGCTGTAC AACCTGCTTT AA
```

This corresponds to the amino acid sequence <SEQ ID 86; ORF17>:

```
  1..GQHKKQAVNG KTVFTMMPGM IFGVFTGAFS AKYIPAFGLQ IFFILFLTAV

51  AFKTLHTDPQ TASRPLPGLP XLTAVSTLFG TMSSWVGIGG GSLSVPFLIH

101  CGFPAHKAIG TSSGLAWPIA LSGAISYLLN GLNIAGLPEG SLGFLYLPAV

151  AVLSAATIAF APLGVKTAHK LSSAKLKKSF GIMLLLIAGK MLYNLL*
```

Further work revealed the complete nucleotide sequence <SEQ ID 87>:

```
  1  ATGTGGCATT GGGACATTAT CTTAATCCTG CTTGCCGTAG GCAGTGCGGC

51  AGGTTTTATT GCCGGCCTGT TCGGCGTAGG CGGCGGCACG CTGATTGTCC

101  CTGTCGTTTT ATGGGTGCTT GATTTGCAGG GTTTGGCACA ACATCCTTAC

151  GCGCAACACC TCGCCGTCGG CACATCCTTC GCCGTCATGG TCTTCACCGC

201  CTTTTCCAGT ATGCTGGGGC AGCACAAAAA ACAGGCGGTC GACTGGAAAA

251  CCGTATTTAC GATGATGCCG GGTATGATAT TCGGCGTATT CACGGGCGCA

301  CTCTCCGCAA AATATATCCC CGCGTTCGGG CTTCAAATTT TCTTCATCCT

351  GTTTTTAACC GCCGTCGCAT TCAAAACACT GCATACCGAC CCTCAGACGG

401  CATCCCGCCC GCTGCCCGGA CTGCCCGGAC TGACTGCGGT TTCCACACTG

451  TTCGGCACAA TGTCGAGCTG GGTCGGCATA GGCGGCGGTT CACTTTCCGT

501  CCCCTTCTTA ATCCACTGCG GCTTCCCCGC CCATAAAGCC ATCGGCACAT

551  CATCCGGCCT TGCCTGGCCG ATTGCACTCT CCGGCGCAAT ATCGTATCTG

601  CTCAACGGCC TGAATATTGC AGGATTGCCC GAAGGGTCAC TGGGCTTCCT

651  TTACCTGCCC GCCGTCGCCG TCCTCAGCGC GGCAACCATT GCCTTTGCCC

701  CGCTCGGTGT CAAAACCGCC CACAAACTTT CTTCTGCCAA ACTCAAAAAA

751  Tc.TTCGGCA TTATGTTGCT TTTGATTGCC GGAAAAATGC TGTACAACCT

801  GCTTTAA
```

This corresponds to the amino acid sequence <SEQ ID 88; ORF17-1>:

```
  1  MWHWDIILIL LAVGSAAGFI AGLFGVGGGT LIVPVVLWVL DLQGLAQHPY

51  AQHLAVGTSF AVMVFTAFSS MLGQHKKQAV DWKTVFTMMP GMIFGVFTGA
```

```
101 LSAKYIPAFG LQIFFILFLT AVAFKTLHTD PQTASRPLPG LPGLTAVSTL

151 FGTMSSWVGI GGGSLSVPFL IHCGFPAHKA IGTSSGLAWP IALSGAISYL

201 LNGLNIAGLP EGSLGFLYLP AVAVLSAATI AFAPLGVKTA HKLSSAKLKK

251 XFGIMLLLIA GKMLYNLL*
```

Computer analysis of this amino acid sequence gave the following results:

Homology with Hypothetical *H. influenzae* Transmembrane Protein HI0902 (Accession Number P44070)

ORF17 and HI0902 proteins show 28% aa identity in 192 aa overlap:

```
ORF17    3 HKKQAVNGKTVFTMMPGMIFGVFT-GAFSAKYIPAFGLQIF--FILFLTAVAFKTLHTDP   59
           HK   +  + V  + P ++  VF  G F  +       +IF   +++L     ++  D
HI0902  72 HKLGNIVWQAVRILAPVIMLSVFICGLFIGRLDREISAKIFACLVVYLATKMVLSIKKD-  130

ORF17   60 QTASRPLPGLPXLTAVSTLFGTMSSWVGIGGGSLSVPFLIHCGFPAHKAIGTSSGLAWPI  119
           Q   ++ L  L +      L G  SS  GIGGG   VPFL  G    +AIG+S+    +
HI0902 131 QVTTKSLTPLSSVIG-GILIGMASSAAGIGGGGFIVPFLTARGINIKQAIGSSAFCGMLL  189

ORF17  120 ALSGAISYLLNGLNIAGLPEGSLGFLYLPAVAVLSAATIAFAPLGVXXXXXXXXXXXXXX  179
           +SG   S++++G     +PE SLG++YLPAV  ++A +    + LG
HI0902 190 GISGMFSFIVSGWGNPLMPEYSLGYIYLPAVLGITATSFFTSKLGASATAKLPVSTLKKG  249

ORF17  180 FGIMLLLIAGKM                                                 191
           F + L+++A  M
HI0902 250 FALFLIVVAINM                                                 261
```

Homology with a Predicted ORF from *N. meningitidis* (Strain A)

ORF17 shows 96.9% identity over a 196aa overlap with an ORF (ORF17a) from strain A of *N. meningitidis*:

```
                                               10        20         30
orf17.pep                            GQHKKQAVNGKTVFTMMPGMIFGVFTGAFS
                                     ||||||||: |||||||||||:||||:||:|
orf17a    QGLAQHPYAQHLAVGTSFAVMVFTAFSSMLGQHKKQAVDWKTVFTMMPGMVFGVFAGALS
                50        60        70        80        90        100

40        50        60        70        80        90
orf17.pep AKYIPAFGLQIFFILFLTAVAFKTLHTDPQTASRPLPGLPXLTAVSTLFGTMSSWVGIGG
          ||||||||||||||||||||||||||||||||||||||||| ||||||||||||||||||
orf17a    AKYIPAFGLQIFFILFLTAVAFKTLHTDPQTASRPLPGLPGLTAVSTLFGTMSSWVGIGG
                 110       120       130       140       150       160

100       110       120       130       140       150
orf17.pep GSLSVPFLIHCGFPAHKAIGTSSGLAWPIALSGAISYLLNGLNIAGLPEGSLGFLYLPAV
          ||||||||||||||||||||||||||||||||||||||||||||||||||||||||||||
orf17a    GSLSVPFLIHCGFPAHKAIGTSSGLAWPIALSGAISYLLNGLNIAGLPEGSLGFLYLPAV
                170       180       190       200       210       220

160       170       180       190
orf17.pep AVLSAATIAFAPLGVKTAHKLSSAKLKKSFGIMLLLIAGKMLYNLLX
          |||||||||||||||||||||||||||||||||||||||||||||||
orf17a    AVLSAATIAFAPLGVKTAHKLSSAKLKKSFGIMLLLIAGKMLYNLLX
                230       240       250       260
```

The complete length ORF17a nucleotide sequence <SEQ ID 89> is:

```
  1 ATGTGGCATT GGGACATTAT CTTAATCCTG CTTGCCGTAG GCAGTGCGGC

51 AGGTTTTATT GCCGGCCTGT TCGGCGTAGG CGGCGGCACG CTGATTGTCC

101 CTGTCGTTTT ATGGGTGCTT GATTTGCAGG GTTTGGCACA ACATCCTTAC

151 GCGCAACACC TCGCCGTCGG CACATCCTTC GCCGTCATGG TCTTCACCGC
```

-continued
```
201 CTTTTCCAGT ATGCTGGGGC AGCACAAAAA ACAGGCGGTC GACTGGAAAA

251 CCGTATTTAC GATGATGCCG GGTATGGTAT TCGGCGTATT CGCTGGCGCA

301 CTCTCCGCAA AATATATCCC AGCGTTCGGG CTTCAAATTT TCTTCATCCT

351 GTTTTTAACC GCCGTCGCAT TCAAAACACT GCATACCGAC CCTCAGACGG

401 CATCCCGCCC GCTGCCCGGA CTGCCCGGAC TGACTGCGGT TTCCACACTG

451 TTCGGCACAA TGTCGAGCTG GGTCGGCATA GGCGGCGGTT CACTTTCCGT

501 CCCCTTCTTA ATCCACTGCG GCTTCCCCGC CCATAAAGCC ATCGGCACAT

551 CATCCGGCCT TGCCTGGCCG ATTGCACTCT CCGGCGCAAT ATCGTATCTG

601 CTCAACGGCC TGAATATTGC AGGATTGCCC GAAGGGTCAC TGGGCTTCCT

651 TTACCTGCCC GCCGTCGCCG TCCTCAGCGC GGCAACCATT GCCTTTGCCC

701 CGCTCGGTGT CAAAACCGCC CACAAACTTT CTTCTGCCAA ACTCAAAAAA

751 TCCTTCGGCA TTATGTTGCT TTTGATTGCC GGAAAAATGC TGTACAACCT

801 GCTTTAA
```

This encodes a protein having amino acid sequence <SEQ ID 90>:

```
  1 MWHWDIILIL LAVGSAAGFI AGLFGVGGGT LIVPVVLWVL DLQGLAQHPY

51 AQHLAVGTSF AVMVFTAFSS MLGQHKKQAV DWKTVFTMMP GMVFGVFAGA

101 LSAKYIPAFG LQIFFILFLT AVAFKTLHTD PQTASRPLPG LPGLTAVSTL

151 FGTMSSWVGI GGGSLSVPFL IHCGFPAHKA IGTSSGLAWP IALSGAISYL

201 LNGLNIAGLP EGSLGFLYLP AVAVLSAATI AFAPLGVKTA HKLSSAKLKK

251 SFGIMLLLIA GKMLYNLL*
```

ORF17a and ORF17-1 show 98.9% identity in 268 aa overlap:

```
                10         20         30         40         50         60
orf17a.pep  MWHWDIILILLAVGSAAGFIAGLFGVGGGTLIVPVVLWVLDLQGLAQHPYAQHLAVGTSF
            ||||||||||||||||||||||||||||||||||||||||||||||||||||||||||||
orf17-1     MWHWDIILILLAVGSAAGFIAGLFGVGGGTLIVPVVLWVLDLQGLAQHPYAQHLAVGTSF
                10         20         30         40         50         60

70         80         90        100        110        120
orf17a.pep  AVMVFTAFSSMLGQHKKQAVDWKTVFTMMPGMVFGVFAGALSAKYIPAFGLQIFFILFLT
            ||||||||||||||||||||||||||||||||||:||||:||||||||||||||||||||
orf17-1     AVMVFTAFSSMLGQHKKQAVDWKTVFTMMPGMIFGVFTGALSAKYIPAFGLQIFFILFLT
                70         80         90        100        110        120

130        140        150        160        170        180
orf17a.pep  AVAFKTLHTDPQTASRPLPGLPGLTAVSTLFGTMSSWVGIGGGSLSVPFLIHCGFPAHKA
            ||||||||||||||||||||||||||||||||||||||||||||||||||||||||||||
orf17-1     AVAFKTLHTDPQTASRPLPGLPGLTAVSTLFGTMSSWVGIGGGSLSVPFLIHCGFPAHKA
               130        140        150        160        170        180

190        200        210        220        230        240
orf17a.pep  IGTSSGLAWPIALSGAISYLLNGLNIAGLPEGSLGFLYLPAVAVLSAATIAFAPLGVKTA
            ||||||||||||||||||||||||||||||||||||||||||||||||||||||||||||
orf17-1     IGTSSGLAWPIALSGAISYLLNGLNIAGLPEGSLGFLYLPAVAVLSAATIAFAPLGVKTA
               190        200        210        220        230        240

250        260        269
orf17a.pep  HKLSSAKLKKSFGIMLLLIAGKMLYNLLX
            ||||||||||:||||||||||||||||||
orf17-1     HKLSSAKLKKXFGIMLLLIAGKMLYNLLX
               250        260
```

Homology with a Predicted ORF from *N. gonorrhoeae*

ORF17 shows 93.9% identity over a 196aa overlap with a predicted ORF (ORF17.ng) from *N. gonorrhoeae*:

```
orf17.pep           GQHKKQAVNGKTVFTMMPGMIFGVFTGAFS  30
                    ||||||:||:|:|||||||||||:||:|
orf17ng   QGLAQHPYAQHLAVGTSFAVMVFTAFSSMLGQHKKQAVDWKTIFAMMPGMIFGVFAGALS  102 orf17.pep AKYIPAFGLQIFFILFLTAVAFKTLHTDPQTASRPLPGLPXLTAVSTLFGTMSSWVGIGG  90
          ||||||||||||||||||||||||||||:|||||||||||:||||||||:||||||||
orf17ng   AKYIPAFGLQIFFILFLTAVAFKTLHTGRQTASRPLPGLPGLTAVSTLFGAMSSWVGIGG  162 orf17.pep GSLSVPFLIHCGFPAHKAIGTSSGLAWPIALSGAISYLLNGLNIAGLPEGSLGFLYLPAV  150
          |||||||||||||||||||||||||||||||||||||:||||||||||||||||||||
orf17ng   GSLSVPFLIHCGFPAHKAIGTSSGLAWPIALSGAISYLVNGLNIAGLPEGSLGFLYLPAV  202 orf17.pep AVLSAATIAFAPLGVKTAHKLSSAKLKKSFGIMLLLIAGKMLYNLL  196
          |||||||||||||||||||||||||||:||||||||||||||||
orf17ng   AVLSAATIAFAPLGVKTAHKLSSAKLKESFGIMLLLIAGKMLYNLL  268
```

An ORF17ng nucleotide sequence <SEQ ID 91> is predicted to encode a protein having amino acid sequence <SEQ ID 92>:

```
  1 MWHWDIILIL LAVGSAAGFI AGLFGVGGGT LIVPVVLWVL DLQGLAQHPY

51 AQHLAVGTSF AVMVFTAFSS MLGQHKKQAV DWKTIFAMMP GMIFGVFAGA

101 LSAKYIPAFG LQIFFILFLT AVAFKTLHTG RQTASRPLPG LPGLTAVSTL

151 FGAMSSWVGI GGGSLSVPFL IHCGFPAHKA IGTSSGLAWP IALSGAISYL

201 VNGLNIAGLP EGSLGFLYLP AVAVLSAATI AFAPLGVKTA HKLSSAKLKE

251 SFGIMLLLIA GKMLYNLL*
```

Further work revealed the complete gonococcal DNA sequence <SEQ ID 93>:

```
  1 ATGTGGCATT GGGACATTAT CTTAATCCTG CTTGCcgtag gcAGTGCGGC

51 AGGTTTTATT GCCGGCCTGT Tcggtgtagg cggcgGTACG CTGATTGTCC

101 CTGTCGTTTT ATGGGTGCTT GATTTGCAGG GTTTGGCACA ACATCCTTAC

151 GCGCAACACC TCGCCGTCGG CAcaTccttc gcCGTCATGG TCTTCACCGC

201 CTTTTCCAGT ATGTTGGGGC AGCACAAAAA ACAGGCGGTC GACTGGAAAA

251 CCATATTTGC GATGATGCCG GGTATGATAT TCGGCGTATT CGCTGGCGCA

301 CTCTCCGCAA AATATATCCC CGCGTTCGGG CTTCAAATTT TCTTCATCCT

351 GTTTTTAACC GCCGTCGCAT TCAAAACACT GCATACCGGT CGTCAGACGG

401 CATCCCGCCC GCTGCCCGGG CTGCCCGGAC TGACTGCGGT TTCCACACTG

451 TTCGGCGCAA TGTCGAGCTG GGTCGGCATA GGCGGCGGTT CACTTTCCGT

501 CCCCTTCTTA ATCCACTGCG GCTTCCCCGC CCATAAAGCC ATCGGCACAT

551 CATCCGGCCT TGCCTGGCCG ATTGCACTCT CCGGCGCAAT ATCGTATCTG

601 GTCAACGGTC TGAATATTGC AGGATTGCCC GAAGGGTCGC TGGGCTTCCT

651 TTACCTGCCC GCCGTCGCCG TCCTCAGCGC GGCAACCATT GCCTTTGCCC

701 CGCTCGGTGT CAAAACCGCC CACAAACTTT CTTCTGCCAA ACTCAAAGAA

751 TCCTTCGGCA TTATGTTGCT TTTGATTGCC GGAAAAATGC TGTACAACCT

801 GCTTTAA
```

This corresponds to the amino acid sequence <SEQ ID 94; ORF17ng-1>:

```
  1 MWHWDIILIL LAVGSAAGFI AGLFGVGGGT LIVPVVLWVL DLQGLAQHPY

51 AQHLAVGTSF AVMVFTAFSS MLGQHKKQAV DWKTIFAMMP GMIFGVFAGA
```

```
101 LSAKYIPAFG LQIFFILFLT AVAFKTLHTG RQTASRPLPG LPGLTAVSTL

151 FGAMSSWVGI GGGSLSVPFL IHCGFPAHKA IGTSSGLAWP IALSGAISYL

201 VNGLNIAGLP EGSLGFLYLP AVAVLSAATI AFAPLGVKTA HKLSSAKLKE

251 SFGIMLLLIA GKMLYNLL*
```

ORF17ng-1 and ORF17-1 show 96.6% identity in 268 aa overlap:

```
                    10         20         30         40         50         60
    orf17-1.pep  MWHWDIILILLAVGSAAGFIAGLFGVGGGTLIVPVVLWVLDLQGLAQHPYAQHLAVGTSF
                 ||||||||||||||||||||||||||||||||||||||||||||||||||||||||||||
    orf17ng-1    MWHWDIILILLAVGSAAGFIAGLFGVGGGTLIVPVVLWVLDLQGLAQHPYAQHLAVGTSF
                    10         20         30         40         50         60

70         80         90        100        110        120
    orf17-1.pep  AVMVFTAFSSMLGQHKKQAVDWKTVFTMMPGMIFGVFTGALSAKYIPAFGLQIFFILFLT
                 ||:|||||||||||||||||||||||:|:|||||||||:|||||||||||||||||||||
    orf17ng-1    AVMVFTAFSSMLGQHKKQAVDWKTIFAMMPGMIFGVFAGALSAKYIPAFGLQIFFILFLT
                    70         80         90        100        110        120

130        140        150        160        170        180
    orf17-1.pep  AVAFKTLHTDPQTASRPLPGLPGLTAVSTLFGTMSSWVGIGGGSLSVPFLIHCGFPAHKA
                 ||||||||||:|||||||||||||||||||||:|||||||||||||||||||||||||||
    orf17ng-1    AVAFKTLHTGRQTASRPLPGLPGLTAVSTLFGAMSSWVGIGGGSLSVPFLIHCGFPAHKA
                   130        140        150        160        170        180

190        200        210        220        230        240
    orf17-1.pep  IGTSSGLAWPIALSGAISYLLNGLNIAGLPEGSLGFLYLPAVAVLSAATIAFAPLGVKTA
                 |||||||||||||||||||||:||||||||||||||||||||||||||||||||||||||
    orf17ng-1    IGTSSGLAWPIALSGAISYLVNGLNIAGLPEGSLGFLYLPAVAVLSAATIAFAPLGVKTA
                   190        200        210        220        230        240

250        260     269
    orf17-1.pep  HKLSSAKLKKXFGIMLLLIAGKMLYNLLX
                 |||||||||:||||||||||||||||||
    orf17ng-1    HKLSSAKLKESFGIMLLLIAGKMLYNLLX
                   250        260
```

In addition, ORF17ng-1 shows significant homology with a hypothetical *H. influenzae* protein:

```
sp|P44070|Y902_HAEIN HYPOTHETICAL PROTEIN HI0902 pir||G64015
hypothetical protein HI0902 - Haemophilus influenzae (strain Rd KW20)
gi|1573922 (U32772) H. influenzae predicted coding region HI0902
[Haemophilus influenzae] Length = 264
Score = 74 (34.9 bits), Expect = 1.6e-23, Sum P(2) = 1.6e-23
Identities = 15/43 (34%), Positives = 23/43 (53%)

Query:   55 AVGTSFAVMVFTAFSSMLGQHKKQAVDWKTIFAMMPGMIFGVF             97
            A+GTSFA +V T  S    HK   + W+ +  + P ++  VF
Sbjct:   52 ALGTSFATIVITGIGSAQRHHKLGNIVWQAVRILAPVIMLSVF             94

Score = 195 (91.9 bits), Expect = 1.6e-23, Sum P(2) = 1.6e-23
Identities = 44/114 (38%), Positives = 65/114 (57%)

Query:  150 LFGAMSSWVGIGGGSLSVPFLIHCGFPAHKAIGTSSGLAWPIALSGAISYLVNGLNIAGL  209
            L G  SS  GIGGG   VPFL  G   +AIG+S+    + +SG   S++V+G    +
Sbjct:  148 LIGMASSAAGIGGGGFIVPFLTARGINIKQAIGSSAFCGMLLGISGMFSFIVSGWGNPLM  207

Query:  210 PEGSLGFLYLPAVAVLSAATIAFAPLGVKTAFIKLSSAKLKESFGIMLLLIAGKM       263
            PE SLG++YLPAV  +A +   + LG      KL   LK+ F + L+++A  M
Sbjct:  208 PEYSLGYIYLPAVLGITATSFFTSKLGASATAKLPVSTLKKGFALFLIVVAINM       261
```

This analysis, including the homology with the hypothetical *H. influenzae* transmembrane protein, suggests that the proteins from *N. meningitidis* and *N. gonorrhoeae*, and their epitopes, could be useful antigens for vaccines or diagnostics, or for raising antibodies.

Example 12

The following partial DNA sequence was identified in *N. meningitidis* <SEQ ID 95>:

```
  1..GGAAACGGAT GGCAGGCAGA CCCCGAACAT CCGCTGCTCG GGCTTTTTGC
 51  CGTCAGTAAT GTATCGATGA CGCTTGCTTT TGTCGGAATA TGTGCGTTGG
101  TGCATTATTG CTTTTCGGGA ACGGTTCAAG TGTTTGTGTT TGCGGCACTG
151  CTCAAACTTT ATGCGCTGAA GCCGGTTTAT TGGTTCGTGT TGCAGTTTGT
201  GCTGATGGCG GTTGCCTATG TCCACCGCTG CGGTATAGAC CGGCAGCCGC
251  CGTCAACGTT CGGCGGCTCG CAGCTGCGAC TCGGCGGGTT GACGGCAGCG
301  TTGATGCAGG TCTCGGTACT GGTGCTGCTG CTTTCAGAAA TTGGAAGATA
351  A
```

This corresponds to the amino acid sequence <SEQ ID 96; ORF18>:

```
  1 ..GNGWQADPEH PLLGLFAVSN VSMTLAFVGI CALVHYCFSG TVQVFVFAAL
 51   LKLYALKPVY WFVLQFVLMA VAYVHRCGID RQPPSTFGGS QLRLGGLTAA
101   LMQVSVLVLL LSEIGR*
```

Further work revealed the complete nucleotide sequence <SEQ ID 97>:

```
  1 ATGATTTTGC TGCATTTGGA TTTTTTGTCT GCCTTACTGT ATGCGGCGGT
 51 TTTTCTGTTT CTGATATTCC GCGCAGGAAT GTTGCAATGG TTTTGGGCGA
101 GTATTATGCT GTGGCTGGGC ATATCGGTTT TGGGGGCAAA GCTGATGCCC
151 GGCATATGGG GAATGACCCG CGCCGCGCCC TTGTTCATCC CCCATTTTTA
201 CCTGACTTTG GGCAGCATAT TTTTTTTCAT CGGGCATTGG AACCGGAAAA
251 CAGATGGAAA CGGATGGCAG GCAGACCCCG AACATCCGCT GCTCGGGCTT
301 TTTGCCGTCA GTAATGTATC GATGACGCTT GCTTTTGTCG GAATATGTGC
351 GTTGGTGCAT TATTGCTTTT CGGGAACGGT TCAAGTGTTT GTGTTTGCGG
401 CACTGCTCAA ACTTTATGCG CTGAAGCCGG TTTATTGGTT CGTGTTGCAG
451 TTTGTGCTGA TGGCGGTTGC CTATGTCCAC CGCTGCGGTA TAGACCGGCA
501 GCCGCCGTCA ACGTTCGGCG GCTCGCAGCT GCGACTCGGC GGGTTGACGG
551 CAGCGTTGAT GCAGGTCTCG GTACTGGTGC TGCTGCTTTC AGAAATTGGA
601 AGATAA
```

This corresponds to the amino acid sequence <SEQ ID 98; ORF18-1>:

```
  1 MILLHLDFLS ALLYAAVFLF LIFRAGMLQW FWASIMLWLG ISVLGAKLMP
 51 GIWGMTRAAP LFIPHFYLTL GSIFFFIGHW NRKTDGNGWQ ADPEHPLLGL
101 FAVSNVSMTL AFVGICALVH YCFSGTVQVF VFAALLKLYA LKPVYWFVLQ
151 FVLMAVAYVH RCGIDRQPPS TFGGSQLRLG GLTAALMQVS VLVLLLSEIG
201 R*
```

Computer analysis of this amino acid sequence gave the following results:

Homology with a Predicted ORF from *N. meningitidis* (Strain A)

ORF18 shows 98.3% identity over a 116aa overlap with an ORF (ORF18a) from strain A of *N. meningitidis*:

```
                                    10        20        30
orf18.pep                     GNGWQADPEHPLLGLFAVSNVSMTLAFVGI
                              ||||||||||||||||||||||||||||||
orf18a      TRAAPLFIPHFYLTLGSIFFFIGHWNRKTDGNGWQADPEHPLLGLFAVSNVSMTLAFVGI
              60        70        80        90       100       110

40        50        60        70        80        90
orf18.pep   CALVHYCFSGTVQVFVFAALLKLYALKPVYWFVLQFVLMAVAYVHRCGIDRQPPSTFGGS
            ||||||||  ||||||||||||||||||||||||||||||  ||||||||||||||||||
orf18a      CALVHYCFSXTVQVFVFAALLKLYALKPVYWFVLQFVLMAVAYVHRCGIDRQPPSTFGGS
              120       130       140       150       160       170

100       110
orf18.pep   QLRLGGLTAALMQVSVLVLLLSEIGRX
            |||||||||||||| ||||||||||||
orf18a      QLRLGGLTAALMQXSVLVLLLSEIGRX
              180       190       200
```

The complete length ORF18a nucleotide sequence <SEQ ID 99> is:

```
  1 ATGATTTTGC TGCATTTGGA TTTTTTGTCT GCCTTACTGT ATGCGGCGGT

51 TTTTCTGTTT CTGATATTCC GCGCAGGAAT GTTGCAATGG TTTTGGGCGA

101 GTATTATGCT GTGGCTGGGC ATATCGGTTT TGGGGGCAAA GCTGATGCCC

151 GGCATATGGG GAATGACCCG CGCCGCGCCC TTGTTCATCC CCCATTTTTA

201 CCTGACTTTG GGCAGCATAT TTTTTTTCAT CGGGCATTGG AACCGGAAAA

251 CGGATGGAAA CGGATGGCAG GCAGACCCCG AACATCCTCT GCTCGGGCTG

301 TTTGCCGTCA GTAATGTATC GATGACGCTT GCTTTTGTCG AAATATGTGC

351 GTTGGTGCAT TATTGCTTTT CGNGAACGGT TCAAGTGTTT GTGTTTGCGG

401 CACTGCTCAA ACTTTATGCG CTGAAGCCGG TTTATTGGTT CGTGTTGCAG

451 TTTGTGCTGA TGGCGGTTGC CTATGTCCAC CGCTGCGGTA TAGACCGGCA

501 GCCGCCGTCA ACGTTCGGCG GNTCGCAGCT GCGACTCGGC GGGTTGACGG

551 CAGCGTTGAT GCAGNTCTCG GTACTGGTGC TGCTGCTTTC AGAAATTGGA

601 AGATAA
```

This encodes a protein having amino acid sequence <SEQ ID 100>:

```
  1 MILLHLDFLS ALLYAAVFLF LIFRAGMLQW FWASIMLWLG ISVLGAKLMP

51 GIWGMTRAAP LFIPHFYLTL GSIFFFIGHW NRKTDGNGWQ ADPEHPLLGL

101 FAVSNVSMTL AFVGICALVH YCFSXTVQVF VFAALLKLYA LKPVYWFVLQ

151 FVLMAVAYVH RCGIDRQPPS TFGGSQLRLG GLTAALMQXS VLVLLLSEIG

201 R*
```

ORF18a and ORF18-1 show 99.0% identity in 201 aa overlap:

```
                  10        20        30        40        50        60
orf18a.pep  MILLHLDFLSALLYAAVFLFLIFRAGMLQWFWASIMLWLGISVLGAKLMPGIWGMTRAAP
            ||||||||||||||||||||||||||||||||||||||||||||||||||||||||||||
orf18-1     MILLHLDFLSALLYAAVFLFLIFRAGMLQWFWASIMLWLGISVLGAKLMPGIWGMTRAAP
                  10        20        30        40        50        60
                  70        80        90       100       110       120
orf18a.pep  LFIPHFYLTLGSIFFFIGHWNRKTDGNGWQADPEHPLLGLFAVSNVSMTLAFVGICALVH
            ||||||||||||||||||||||||||||||||||||||||||||||||||||||||||||
orf18-1     LFIPHFYLTLGSIFFFIGHWNRKTDGNGWQADPEHPLLGLFAVSNVSMTLAFVGICALVH
                  70        80        90       100       110       120
                 130       140       150       160       170       180
orf18a.pep  YCFSXTVQVFVFAALLKLYALKPVYWFVLQFVLMAVAYVHRCGIDRQPPSTFGGSQLRLG
            ||||| ||||||||||||||||||||||||||||||||||||||||||||||||||||||
orf18-1     YCFSGTVQVFVFAALLKLYALKPVYWFVLQFVLMAVAYVHRCGIDRQPPSTFGGSQLRLG
                 130       140       150       160       170       180
                 190       200
orf18a.pep  GLTAALMQXSVLVLLLSEIGRX
            |||||||| |||||||||||||
orf18-1     GLTAALMQVSVLVLLLSEIGRX
                 190       200
```

Homology with a Predicted ORF from *N. gonorrhoeae*

ORF18 shows 93.1% identity over a 116aa overlap with a predicted ORF (ORF18.ng) from *N. gonorrhoeae*.

```
orf18.pep                            GNGWQADPEHPLLGLFAVSNVSMTLAFVGI    30
                                     ||||||||||||||||||||||||||||||
orf18ng    TRAAPLFIPHFYLTLGSIFFFIGYWNRKTDGNGWQADPEHPLLGLFAVSNVSMTLAFVGI   115
orf18.pep  CALVHYCFSGTVQVFVFAALLKLYALKPVYWFVLQFVLMAVAYVHRCGIDRQPPSTFGGS    90
           ||||||||||||||||||||||||||||||||||||||||||||||||||||||||||||
orf18ng    CALVHYCFSGTVQVFVFAALLKLYALKPVYWFVLQFVLMAVAYVHRCGIDRQPPSTFGGS   175
orf18.pep  QLRLGGLTAALMQVSVLVLLLSEIGR                                     116
           ||||| |:| ||||:| ::||:||||
orf18ng    QLRLGVLAAMLMQVAVTAMLLAEIGR                                     201
```

The complete length ORF18ng nucleotide sequence is <SEQ ID 101>:

```
  1 ATGATTTTGC TGCATTTGGA TTTTTTGTCT GCCTTACTGt aTGCGGcggt 51 tttTctgTTT CTGATATTCC GCGCAGGAAT GTTGCAATGG TTTTGGGCGA

101 GTATTGCGTT GTGGCTCGGC ATCTCGGTTT TAGGGGTAAA GCTGATGCCG

151 GGGATGTGGG GAATGACCCG CGCCGCGCCT TTGTTCATCC CCCATTTTTA

201 CCTGACTTTG GGCAGCATAT TTTTTTTCAT CGGGTATTGG AACCGGAAAA

251 CAGATGGAAA CGGATGGCAG GCAGACCCCG AACATCCGCT GCTCGGGCTT

301 TTTGCCGTCA GTAATGTATC GATGACGCTT GCTTTTGTCG GAATATGTGC

351 GTTGGTGCAT TATTGCTTTT CGGGAACGGT TCAAGTGTTT GTGTTTGCGG

401 CATTGCTCAA ACTTTATGCG CTGAAGCCGG TTTATTGGTT CGTGTTGCAG

451 TTTGTATTGA TGGCGGttgC CTATGTCCAC CGCTGCGGTA TAGACCGGCA

501 GCCGCCGTCA ACGTTCGGCG GTTCGCAGCT GCGACTCGGC GTGTTGGCGG

551 CGATGTTGAT GCAGGTTGCG GTAACGGCGA TGCTGCTTGC CGAAATCGGC

601 AGATGA
```

This encodes a protein having amino acid sequence <SEQ ID 102>:

```
  1 MILLHLDFLS ALLYAAVFLF LIFRAGMLQW FWASIALWLG ISVLGVKLMP

51 GMWGMTRAAP LFIPHFYLTL GSIFFFIGYW NRKTDGNGWQ ADPEHPLLGL
```

```
101 FAVSNVSMTL AFVGICALVH YCFSGTVQVF VFAALLKLYA LKPV YWFVLQ

151 FVLMAVAYVH RCGIDRQPPS TFGGSQLRLG VLAAMLMQVA VTAMLLAEIG

201 R*
```

This ORF18ng protein sequence shows 94.0% identity in 201 aa overlap with ORF18-1:

```
                        10        20        30        40        50        60
     orf18-1.pep  MILLHLDFLSALLYAAVFLFLIFRAGMLQWFWASIMLWLGISVLGAKLMPGIWGMTRAAP
                  |||||||||||||||||||||||||||||||||||:||||||||:||||||:|||||||
     orf18ng      MILLHLDFLSALLYAAVFLFLIFRAGMLQWFWASIALWLGISVLGVKLMPGMWGMTRAAP
                        10        20        30        40        50        60

70        80        90       100       110       120
     orf18-1.pep  LFIPHFYLTLGSIFFFIGHWNRKTDGNGWQADPEHPLLGLFAVSNVSMTLAFVGICALVH
                  |||||||||||||||||:||||||||||||||||||||||||||||||||||||||||||
     orf18ng      LFIPHFYLTLGSIFFFIGYWNRKTDGNGWQADPEHPLLGLFAVSNVSMTLAFVGICALVH
                        70        80        90       100       110       120

130       140       150       160       170       180
     orf18-1.pep  YCFSGTVQVFVFAALLKLYALKPVYWFVLQFVLMAVAYVHRCGIDRQPPSTFGGSQLRLG
                  ||||||||||||||||||||||||||||||||||||||||||||||||||||||||||||
     orf18ng      YCFSGTVQVFVFAALLKLYALKPVYWFVLQFVLMAVAYVHRCGIDRQPPSTFGGSQLRLG
                       130       140       150       160       170       180

190       200
     orf18-1.pep  GLTAALMQVSVLVLLLSEIGRX
                  |:| ||||:| ::||:||||||
     orf18ng      VLAAMLMQVAVTAMLLAEIGRX
                       190       200
```

Based on this analysis, including the presence of several putative transmembrane domains in the gonococcal protein, it is predicted that the proteins from *N. meningitidis* and *N. gonorrhoeae*, and their epitopes, could be useful antigens for vaccines or diagnostics, or for raising antibodies.

Example 13

The following partial DNA sequence was identified in *N. meningitidis* <SEQ ID 103>:

```
  1 ATGAAAACCC CACTCCTCAA GCCTCTGCTN ATTACCTCGC TTCCCGTTTT

51 CGCCAGTGTT TTTACCGCCG CCTCCATCGT CTGGCAGCTA GGCGAACCCA

101 AGCTCGCCAT GCCCTTCGTA CTCGGCATCA TCGCCGGCGG CCTTGTCGAT

151 TTGGACAACC NCNTGACCGG ACGGCTNAAA AACATCATCA CCACCGTCGC

201 CCTGTTCACC CTCTCCTCGC TCACGGCACA AAGCACCCTC GGCACAGGGC

251 TGCCCTTCAT CCTCGCCATG ACCCTGATGA CTT.CG.CTT CACCATTTTA

301 GGCGCGGNCG ...
```

This corresponds to the amino acid sequence <SEQ ID 104; ORF19>:

```
  1 MKTPLLKPLL ITSLPVFASV FTAASIVWQL GEPKLAMPFV LGIIAGGLVD

51 LDNXXTGRLK NIITTVALFT LSSLTAQSTL GTGLPFILAM TLMTXXFTIL

101 GAX...
```

Further work revealed the complete nucleotide sequence
<SEQ ID 105>:

```
   1 ATGAAAACCC CACTCCTCAA GCCTCTGCTC ATTACCTCGC TTCCCGTTTT
  51 CGCCAGTGTT TTTACCGCCG CCTCCATCGT CTGGCAGCTA GGCGAACCCA
 101 AGCTCGCCAT GCCCTTCGTA CTCGGCATCA TCGCCGGCGG CCTTGTCGAT
 151 TTGGACAACC GCCTGACCGG ACGGCTGAAA ACATCATCA CCACCGTCGC
 201 CCTGTTCACC CTCTCCTCGC TCACGGCACA AAGCACCCTC GGCACAGGGC
 251 TGCCCTTCAT CCTCGCCATG ACCCTGATGA CCTTCGGCTT CACCATTTTA
 301 GGCGCGGTCG GGCTCAAATA CCGCACCTTC GCCTTCGGTG CACTCGCCGT
 351 CGCCACCTAC ACCACACTTA CCTACACCCC CGAAACCTAC TGGCTGACCA
 401 ACCCCTTCAT GATTTTATGC GGCACCGTAC TGTACAGCAC CGCCATCCTC
 451 CTGTTCCAAA TCGTCCTGCC CCACCGCCCC GTCCAAGAAA GCGTCGCCAA
 501 CGCCTACGAC GCACTCGGCG GCTACCTCGA AGCCAAAGCC GACTTCTTCG
 551 ACCCCGATGA GGCAGCCTGG ATAGGCAACC GCCACATCGA CCTCGCCATG
 601 AGCAACACCG GCGTCATCAC CGCCTTCAAC CAATGCCGTT CCGCCCTGTT
 651 TTACCGCCTT CGCGGCAAAC ACCGCCACCC GCGCACCGCC AAAATGCTGC
 701 GTTACTACTT TGCCGCCCAA GACATACACG AACGCATCAG CTCCGCCCAC
 751 GTCGATTATC AGGAAATGTC CGAAAAATTC AAAAACACCG ACATCATCTT
 801 CCGCATCCAC CGCCTGCTCG AAATGCAGGG ACAAGCCTGC CGCAACACCG
 851 CCCAAGCCCT GCGCGCAAGC AAAGACTACG TTTACAGCAA ACGCCTCGGC
 901 CGCGCCATCG AAGGCTGCCG CCAATCGCTG CGCCTCCTTT CAGACAGCAA
 951 CGACAGTCCC GACATCCGCC ACCTGCGCCG CCTTCTCGAC AACCTCGGCA
1001 GCGTCGACCA GCAGTTCCGC CAACTCCAGC ACAACGGCCT GCAGGCAGAA
1051 AACGACCGCA TGGGCGACAC CCGCATCGCC GCCCTCGAAA CCAGCAGCCT
1101 CAAAAACACC TGGCAGGCAA TCCGTCCGCA GCTAAACCTC GAATCAGGCG
1151 TATTCCGCCA TGCCGTCCGC CTGTCCCTCG TCGTTGCCGC CGCCTGCACC
1201 ATCGTCGAAG CCCTCAACCT CAACCTCGGC TACTGGATAC TACTGACCGC
1251 CCTTTTCGTC TGCCAACCCA ACTACACCGC CACCAAAAGC CGCGTCCGCC
1301 AGCGCATCGC CGGCACCGTA CTCGGCGTAA TCGTCGGCTC GCTCGTCCCC
1351 TACTTCACCC CGTCTGTCGA AACCAAACTC TGGATTGTCA TCGCCAGTAC
1401 CACCCTCTTT TTCATGACCC GCACCTACAA ATACAGTTTC TCCACCTTCT
1451 TCATTACCAT TCAAGCCCTG ACCAGCCTCT CCCTCGCAGG TTTGGACGTA
1501 TACGCCGCCA TGCCCGTACG CATCATCGAC ACCATTATCG GCGCATCCCT
1551 TGCCTGGGCG GCAGTCAGCT ACCTGTGGCC AGACTGGAAA TACCTCACGC
1601 TCGAACGCAC CGCCGCCCTT GCCGTATGCA GCAACGGTGC CTATCTCGAA
1651 AAAATCACCG AACGCCTCAA AAGCGGCGAA ACCGGCGACG ACGTCGAATA
1701 CCGCGCCACC CGCCGCCGCG CCCACGAACA CACCGCCGCC CTCAGCAGCA
1751 CCCTTTCCGA CATGAGCAGC GAACCCGCAA AATTCGCCGA CAGCCTGCAA
1801 CCCGGCTTTA CCCTGCTCAA AACCGGCTAC GCCCTGACCG GCTACATCTC
1851 CGCCCTCGGC GCATACCGCA GCGAAATGCA CGAAGAATGC AGCCCCGACT
1901 TTACCGCACA GTTCCACCTC GCCGCCGAAC ACACCGCCCA CATCTTCCAA
```

```
1951 CACCTGCCCG AAACCGAACC CGACGACTTT CAGACAGCAC TGGATACACT

2001 GCGCGGCGAA CTCGACACCC TCCGCACCCA CAGCAGCGGA ACACAAAGCC

2051 ACATCCTCCT CCAACAGCTC CAACTCATCG CCCGACAGCT CGAACCCTAC

2101 TACCGCGCCT ACCGCCAAAT TCCGCACAGG CAGCCCCAAA ATGCAGCCTG

2151 A
```

This corresponds to the amino acid sequence <SEQ ID 106; ORF19-1>:

```
  1 MKTPLLKPLL ITSLPVFASV FTAASIVWQL GEPKLAMPFV LGIIAGGLVD
 51 LDNRLTGRLK NIITTVALFT LSSLTAQSTL GTGLPFILAM TLMTFGFTIL
101 GAVGLKYRTF AFGALAVATY TTLTYTPETY WLTNPFMILC GTVLYSTAIL
151 LFQIVLPHRP VQESVANAYD ALGGYLEAKA DFFDPDEAAW IGNRHIDLAM
201 SNTGVITAFN QCRSALFYRL RGKHRHPRTA KMLRYYFAAQ DIHERISSAH
251 VDYQEMSEKF KNTDIIFRIH RLLEMQGQAC RNTAQALRAS KDYVYSKRLG
301 RAIEGCRQSL RLLSDSNDSP DIRHLRRLLD NLGSVDQQFR QLQHNGLQAE
351 NDRMGDTRIA ALETSSLKNT WQAIRPQLNL ESGVFRHAVR LSLVVAAACT
401 IVEALNLNLG YWILLTALFV CQPNYTATKS RVRQRIAGTV LGVIVGSLVP
451 YFTPSVETKL WIVIASTTLF FMTRTYKYSF STFFITIQAL TSLSLAGLDV
501 YAAMPVRIID TIIGASLAWA AVSYLWPDWK YLTLERTAAL AVCSNGAYLE
551 KITERLKSGE TGDDVEYRAT RRRAHEHTAA LSSTLSDMSS EPAKFADSLQ
601 PGFTLLKTGY ALTGYISALG AYRSEMHEEC SPDFTAQFHL AAEHTAHIFQ
651 HLPETEPDDF QTALDTLRGE LDTLRTHSSG TQSHILLQQL QLIARQLEPY
701 YRAYRQIPHR QPQNAA*
```

Computer analysis of this amino acid sequence gave the following results:

Homology with Predicted Transmembrane Protein YHFK of *H. influenzae* (Accession Number P44289)

ORF19 and YHFK proteins show 45% aa identity in 97 aa overlap:

```
orf19    6 LKPLLITSLPVFASVFTAASIVWQLGEPKLAMPFVLGIIAGGLVDLDNXXTGRLKNIITT   65
             L   +I+++PVF +V AA  +W       +MP +LGIIAGGLVDLDN  TGRLKN+  T
YHFK     5 LNAKVISTIPVFIAVNIAAVGIWFFDISSQSMPLILGIIAGGLVDLDNRLTGRLKNVFFT   64 orf19   66 VALFTLSSLTAQSTLGTGLPFILAMTLMTXXFTILGA                          102
             +  F++SS  Q  +G  +  +I+ MT++T  FT++GA
YHFK    65 LIAFSISSFIVQLHIGKPIQYIVLMTVLTFIFTMIGA                          101
```

Homology with a Predicted ORF from *N. meningitidis* (Strain A)

ORF19 shows 92.2% identity over a 102aa overlap with an ORF (ORF19a) from strain A of *N. meningitidis*.

```
                    10         20         30         40         50         60
orf19.pep  MKTPLLKPLLITSLPVFASVFTAASIVWQLGEPKLAMPFVLGIIAGGLVDLDNXXTGRLK
           ||||  ||||||||||||||||||||||||||||||||||||||||||||||||  |||||
orf19a     MKTPPLKPLLITSLPVFASVFTAASIVWQLGEPKLAMPFVLGIIAGGLVDLDNRLTGRLK
                    10         20         30         40         50         60
```

```
                      70           80          90         100
orf19.pep  NIITTVALFTLSSLTAQSTLGTGLPFILAMTLMTXXFTILGAX
           |||:||||||||||:|||||||||||||||||   |:||
orf19a     NIIATVALFTLSSLVAQSTLGTGLPFILAMTLMTFGFTIMGAXGLKYRTFAFGALAVATY
                      70           80          90         100        110       120
orf19a     TTLTYTPETYWLTNPFMILCGTVLYSTAIILFQIILPHRPVQENVANAYEALGSYLEAKA
                    130          140         150         160       170       180
```

The complete length ORF19a nucleotide sequence <SEQ ID 107> is:

```
   1 ATGAAAACCC CACCCCTCAA GCCTCTGCTC ATTACCTCGC TTCCCGTTTT
  51 CGCCAGTGTC TTTACCGCCG CCTCCATCGT CTGGCAGCTG GGCGAACCCA
 101 AGCTCGCCAT GCCCTTCGTA CTCGGCATCA TCGCTGGCGG CCTGGTCGAT
 151 TTGGACAACC GCCTGACCGG ACGGCTGAAA ACATCATCG CCACCGTCGC
 201 CCTGTTCACC CTCTCCTCAC TTGTCGCGCA AGCACCCTC GGCACAGGTT
 251 TGCCATTCAT CCTCGCCATG ACCCTGATGA CTTTCGGCTT TACCATCATG
 301 GGCGCGGTCG GGCTGAAATA CCGCACCTTC GCCTTCGGCG CACTCGCCGT
 351 CGCCACCTAC ACCACACTTA CCTACACCCC CGAAACCTAC TGGCTGACCA
 401 ACCCCTTTAT GATTCTGTGC GGAACCGTAC TGTACAGCAC CGCCATCATC
 451 CTGTTCCAAA TCATCCTGCC CCACCGCCCC GTTCAAGAAA ACGTCGCCAA
 501 CGCCTACGAA GCACTCGGCA GCTACCTCGA AGCCAAAGCC GACTTTTTCG
 551 ATCCCGACGA AGCCGAATGG ATAGGCAACC GCCACATCGA CCTCGCCATG
 601 AGCAACACCG GCGTCATCAC CGCCTTCAAC CAATGCCGTT CCGCCCTGTT
 651 TTACCGCCTT CGCGGCAAAC ACCGCCACCC GCGCACCGCC AAAATGCTGC
 701 GCTACTACTT CGCCGCCCAA GACATACACG AACGCATCAG CTCCGCCCAC
 751 GTCGACTACC AAGAGATGTC CGAAAAATTC AAAAACACCG ACATCATCTT
 801 CCGCATCCAC CGCCTGCTCG AAATGCAGGG ACAAGCCTGC CGCAACACCG
 851 CCCAAGCCCT GCGCGCAAGC AAAGACTACG TTTACAGCAA ACGCCTCGGC
 901 CGCGCCATCG AAGGCTGCCG CCAATCGCTG CGCCTCCTTT CAGACAGCAA
 951 CGACAATCCC GACATCCGCC ACCTGCGCCG CCTTCTCGAC AACCTCGGCA
1001 GCGTCGACCA GCAGTTCCGC CAACTCCAGC ACAACGGCCT GCAGGCAGAA
1051 AACGACCGCA TGGGCGACAC CCGCATCGCC GCCCTCGAAA CCGGCAGCCT
1101 CAAAAACACC TGGCAGGCAA TCCGTCCGCA GCTAAACCTC GAATCAGGCG
1151 TATTCCGCCA TGCCGTCCGC CTGTCCCTTG TCGTTGCCGC CGCCTGCACC
1201 ATCGTCGAAG CCCTCAACCT CAACCTCGGC TACTGGATAC TACTGACCGC
1251 CCTTTTCGTC TGCCAACCCA ACTACACCGC CACCAAAAGC CGCGTCCGCC
1301 AGCGCATCGC CGGCACCGTA CTCGGCGTAA TCGTCGGCTC GCTCGTCCCC
1351 TACTTTACCC CCTCCGTCGA AACCAAACTC TGGATCGTCA TCGCCAGTAC
1401 CACCCTCTTT TTCATGACCC GCACCTACAA ATACAGCTTC TCGACATTTT
1451 TCATCACCAT TCAAGCCCTG ACCAGCCTCT CCCTCGCAGG GTTGGACGTA
1501 TACGCCGCCA TGCCCGTACG CATCATCGAC ACCATTATCG GCGCATCCCT
1551 TGCCTGGGCG GCAGTCAGCT ACCTGTGGCC AGACTGGAAA TACCTCACGC
1601 TCGAACGCAC CGCCGCCCTT GCCGTATGCA GCAACGGCGC CTATCTCGAA
```

```
1651 AAAATCACCG AACGCCTCAA AAGCGGCGAA ACCGGCGACG ACGTCGAATA

1701 CCGCGCCACC CGCCGCCGCG CCCACGAACA CACCGCCGCC CTCAGCAGCA

1751 CCCTTTCCGA CATGAGCAGC GAACCCGCAA AATTCGCCGA CAGCCTGCAA

1801 CCCGGCTTTA CCCTGCTCAA AACCGGCTAC GCCCTGACCG GCTACATCTC

1851 CGCCCTCGGC GCATACCGCA GCGAAATGCA CGAAGAATGC AGCCCCGACT

1901 TTACCGCACA GTTCCACCTC GCCGCCGAAC ACACCGCCCA CATCTTCCAA

1951 CACCTGCCCG AAACCGAACC CGACGACTTT CAGACAGCAC TGGATACACT

2001 GCGCGGCGAA CTCGACACCC TCCGCACCCA CAGCAGCGGA ACACAAAGCC

2051 ACATCCTCCT CCAACAGCTC CAACTCATCG CCCGGCAGCT CGAACCCTAC

2101 TACCGCGCCT ACCGACAAAT TCCGCACAGG CAGCCCCAAA ACGCAGCCTG

2151 A
```

This encodes a protein having amino acid sequence <SEQ ID 108>:

```
  1 MKTPPLKPLL ITSLPVFASV FTAASIVWQL GEPKLAMPFV LGIIAGGLVD

51 LDNRLTGRLK NIIATVALFT LSSLVAQSTL GTGLPFILAM TLMTFGFTIM

101 GAVGLKYRTF AFGALAVATY TTLTYTPETY WLTNPFMILC GTVLYSTAII

151 LFQIILPHRP VQENVANAYE ALGSYLEAKA DFFDPDEAEW IGNRHIDLAM

201 SNTGVITAFN QCRSALFYRL RGKHRHPRTA KMLRYYFAAQ DIHERISSAH

251 VDYQEMSEKF KNTDIIFRIH RLLEMQGQAC RNTAQALRAS KDYVYSKRLG

301 RAIEGCRQSL RLLSDSNDNP DIRHLRRLLD NLGSVDQQFR QLQHNGLQAE

351 NDRMGDTRIA ALETGSLKNT WQAIRPQLNL ESGVFRHAVR LSLVVAAACT

401 IVEALNLNLG YWILLTALFV CQPNYTATKS RVRQRIAGTV LGVIVGSLVP

451 YFTPSVETKL WIVIASTTLF FMTRTYKYSF STFFITIQAL TSLSLAGLDV

501 YAAMPVRIID TIIGASLAWA AVSYLWPDWK YLTLERTAAL AVCSNGAYLE

551 KITERLKSGE TGDDVEYRAT RRRAHEHTAA LSSTLSDMSS EPAKFADSLQ

601 PGFTLLKTGY ALTGYISALG AYRSEMHEEC SPDFTAQFHL AAEHTAHIFQ

651 HLPETEPDDF QTALDTLRGE LDTLRTHSSG TQSHILLQQL QLIARQLEPY

701 YRAYRQIPHR QPQNAA*
```

ORF19a and ORF19-1 show 98.3% identity in 716 aa overlap:

```
                   10         20         30         40         50         60
orf19a.pep  MKTPPLKPLLITSLPVFASVFTAASIVWQLGEPKLAMPFVLGIIAGGLVDLDNRLTGRLK
            ||||:|||||||||||||||||||||||||||||||||||||||||||||||||||||||
orf19-1     MKTPLLKPLLITSLPVFASVFTAASIVWQLGEPKLAMPFVLGIIAGGLVDLDNRLTGRLK
                   10         20         30         40         50         60

70         80         90        100        110        120
orf19a.pep  NIIATVALFTLSSLVAQSTLGTGLPFILAMTLMTFGFTIMGAVGLKYRTFAFGALAVATY
            |||:||||||||||:||||||||||||||||||||||||:||||||||||||||||||||
orf19-1     NIITTVALFTLSSLTAQSTLGTGLPFILAMTLMTFGFTILGAVGLKYRTFAFGALAVATY
                   70         80         90        100        110        120

130        140        150        160        170        180
orf19a.pep  TTLTYTPETYWLTNPFMILCGTVLYSTAIILFQIILPHRPVQENVANAYEALGSYLEAKA
            |||||||||||||||||||||||||||||||||||:|||||||:|||:||:|||||||||
orf19-1     TTLTYTPETYWLTNPFMILCGTVLYSTAILLFQIVLPHRPVQESVANAYDALGGYLEAKA
                  130        140        150        160        170        180

190        200        210        220        230        240
orf19a.pep  DFFDPDEAEWIGNRHIDLAMSNTGVITAFNQCRSALFYRLRGKHRHPRTAKMLRYYFAAQ
            ||||||||:|||||||||||||||||||||||||||||||||||||||||||||||||||
orf19-1     DFFDPDEAAWIGNRHIDLAMSNTGVITAFNQCRSALFYRLRGKHRHPRTAKMLRYYFAAQ
                  190        200        210        220        230        240
```

```
                 250        260        270        280        290        300
orf19a.pep  DIHERISSAHVDYQEMSEKFKNTDIIFRIHRLLEMQGQACRNTAQALRASKDYVYSKRLG
            ||||||||||||||||||||||||||||||||||||||||||||||||||||||||||||
orf19-1     DIHERISSAHVDYQEMSEKFKNTDIIFRIHRLLEMQGQACRNTAQALRASKDYVYSKRLG
                 250        260        270        280        290        300

310        320        330        340        350        360
orf19a.pep  RAIEGCRQSLRLLSDSNDNPDIRHLRRLLDNLGSVDQQFRQLQHNGLQAENDRMGDTRIA
            |||||||||||||||||||:||||||||||||||||||||||||:|||||||||||||||
orf19-1     RAIEGCRQSLRLLSDSNDSPDIRHLRRLLDNLGSVDQQFRQLQHNGLQAENDRMGDTRIA
                 310        320        330        340        350        360

370        380        390        400        410        420
orf19a.pep  ALETGSLKNTWQAIRPQLNLESGVFRHAVRLSLVVAAACTIVEALNLNGYWILLTALFV
            ||||:||||||||||||||||||||||||||||||||||||||||||||||||||||||
orf19-1     ALETSSLKNTWQAIRPQLNLESGVFRHAVRLSLVVAAACTIVEALNLNGYWILLTALFV
                 370        380        390        400        410        420

430        440        450        460        470        480
orf19a.pep  CQPNYTATKSRVRQRIAGTVLGVIVGSLVPYFTPSVETKLWIVIASTTLFFMTRTYKYSF
            ||||||||||||||||||||||||||||||||||||||||||||||||||||||||||||
orf19-1     CQPNYTATKSRVRQRIAGTVLGVIVGSLVPYFTPSVETKLWIVIASTTLFFMTRTYKYSF
                 430        440        450        460        470        480

490        500        510        520        530        540
orf19a.pep  STFFITIQALTSLSLAGLDVYAAMPVRIIDTIIGASLAWAAVSYLWPDWKYLTLERTAAL
            ||||||||||||||||||||||||||||||||||||||||||||||||||||||||||||
orf19-1     STFFITIQALTSLSLAGLDVYAAMPVRIIDTIIGASLAWAAVSYLWPDWKYLTLERTAAL
                 490        500        510        520        530        540

550        560        570        580        590        600
orf19a.pep  AVCSNGAYLEKITERLKSGETGDDVEYRATRRRAHEHTAALSSTLSDMSSEPAKFADSLQ
            ||||||||||||||||||||||||||||||||||||||||||||||||||||||||||||
orf19-1     AVCSNGAYLEKITERLKSGETGDDVEYRATRRRAHEHTAALSSTLSDMSSEPAKFADSLQ
                 550        560        570        580        590        600

610        620        630        640        650        660
orf19a.pep  PGFTLLKTGYALTGYISALGAYRSEMHEECSPDFTAQFHLAAEHTAHIFQHLPETEPDDF
            ||||||||||||||||||||||||||||||||||||||||||||||||||||||||||||
orf19-1     PGFTLLKTGYALTGYISALGAYRSEMHEECSPDFTAQFHLAAEHTAHIFQHLPETEPDDF
                 610        620        630        640        650        660

670        680        690        700        710
orf19a.pep  QTALDTLRGELDTLRTHSSGTQSHILLQQLQLIARQLEPYYRAYRQIPHRQPQNAAX
            ||||||||||||||||||||||||||||||||||||||||||||||||||||||||
orf19-1     QTALDTLRGELDTLRTHSSGTQSHILLQQLQLIARQLEPYYRAYRQIPHRQPQNAAX
                 670        680        690        700        710
```

Homology with a Predicted ORF from *N. gonorrhoeae*

ORF19 shows 95.1% identity over a 102aa overlap with a predicted ORF (ORF19.ng) from *N. gonorrhoeae*:

```
orf19.pep   MKTPLLKPLLITSLPVFASVFTAASIVWQLGEPKLAMPFVLGIIAGGLVDLDNXXTGRLK    60
            |||||||||||||||||||||||||||||||||||||||||||||||||||||  |||||
orf19ng     MKTPLLKPLLITSLPVFASVFTAASIVWQLGEPKLAMPFVLGIIAGGLVDLDNRLTGRLK    60 orf19.pep   NIITTVALFTLSSLTAQSTLGTGLPFILAMTLMTXXFTILGAX                   103
            ||||:|||||||||||||||||||||||||||||||  ||||||
orf19ng     NIIATVALFTLSSLTAQSTLGTGLPFILAMTLMTFGFTILGAVGLKYRTFAFGALAVATY  175
```

An ORF19ng nucleotide sequence <SEQ ID 109> is predicted to encode a protein having amino acid sequence <SEQ ID 110>:

```
  1 MKTPLLKPLL ITSLPVFASV FTAASIVWQL GEPKLAMPFV LGIIAGGLVD

51 LDNRLTGRLK NIIATVALFT LSSLTAQSTL GTGLPFILAM TLMTFGFTIL

101 GAVGLKYRTF AFGALAVATY TTLTYTPETY WLTNPFMILC GTVLYSTAII

151 LFQIILPHRP VQESVANAYE ALGGYLEAKA DFFDPDEAAW IGNRHIDLAM

201 SNTGVITAFN QCRSALFYRL RGKHRHPRTA KMLRYYFAAQ DIHERISSAH

251 VDYQEMSEKF KNTDIIFRIR RLLEMQGQAC RNTAQAIRSG KDYVYSKRLG

301 RAIEGCRQSL RLLSDGNDSP DIRHLSRLLD NLGSVDQQFR QLRHSDSPAE

351 NDRMGDTRIA ALETGSFKNT *
```

Further work revealed the complete nucleotide sequence
<SEQ ID 111>:

```
   1 ATGAAAACCC CACTCCTCAA GCCTCTGCTC ATTACCTCGC TTCCCGTTTT
  51 CGCCAGTGTC TTTACCGCCG CCTCCATCGT CTGGCAGCTA GGCGAACCCA
 101 AGCTCGCCAT GCCCTTCGTA CTCGGCATCA TCGCCGGCGG CCTGGTCGAT
 151 TTGGACAACC GCCTGACCGG ACGGCTGAAA AACATCATCG CCACCGTCGC
 201 CCTGTTTACC CTCTCCTCGC TCACGGCGCA AAGCACCCTC GGCACAGGGC
 251 TGCCCTTCAT CCTCGCCATG ACCCTGATGA CCTTCGGCTT TACCATTTTA
 301 GGCGCGGTCG GGCTGAAATA CCGCACCTTC GCCTTCGGCG CACTCGCCGT
 351 CGCCACCTAC ACCACGCTTA CCTACACCCC CGAAACCTAC TGGCTGACCA
 401 ACCCCTTCAT GATTTTATGC GGCACCGTAC TGTACAGCAC CGCCATCATC
 451 CTGTTCCAAA TCATCCTGCC CCACCGCCCC GTCCAAGAAA GCGTCGCCAA
 501 TGCCTACGAA GCACTCGGCG GCTACCTCGA AGCCAAAGCC GACTTCTTCG
 551 ACCCCGATGA GGCAGCCTGG ATAGGCAACC GCCACATCGA CCTCGCCATG
 601 AGCAACACCG GCGTCATCAC CGCCTTCAAC CAATGCCGTT CCGCCCTGTT
 651 TTACCGTTTG CGCGGCAAAC ACCGCCACCC GCGCACCGCC AAAATGCTGC
 701 GCTACTACTT CGCCGCCCAA GACATCCACG AACGCATCAG CTCCGCCCAC
 751 GTCGACTACC AAGAGATGTC CGAAAAATTC AAAAACACCG ACATCATCTT
 801 CCGCATCCGC CGCCTGCTCG AAATGCAGGG GCAGGCGTGC CGCAACACCG
 851 CCCAAGCCAT CCGGTCGGGC AAAGACTAcg tTTACAGCAA ACGCCTCGGA
 901 CGCGCCATCg aaggctgCCG CCAGTCGCtg cgcctCCTTt cagacggcaA
 951 CGACAGTCCC GACATCCGCC ACCTGAGccg CCTTCTCGAC AACCTCGgca
1001 GCGTCgacca gcagtTCcgc caactCCGAC ACAgcgactC CCCCGCcgaa
1051 Aacgaccgca tgggcgacaC CCGCATCGCC GCCCtcgaaa ccggcagctT
1101 caaaaaCAcc tggcaggCAA TCCGTCCGCa gctgaaCCTC GAATCatgCG
1151 TATTCCGCCA TGCCGTCCGC CTGTCCCTCG TCGTTGCCGC CGCCTGCACC
1201 ATCGTCgaag cCCTCAACCT CAACCTCGGC TACTGGATAC TGCTGACCGC
1251 CCTTTTCGTC TGCCAACCCA ACTACACCGC CACCAAAAGC CGCGTGTACC
1301 AACGCATCGC CGGCACCGTA CTCGGCGTAA TCGTCGGCTC GCTCGTCCCC
1351 TACTTCACCC CCTCCGTCGA AACCAAACTC TGGATTGTCA TCGCCGGTAC
1401 CACCCTGTTC TTCATGACCC GCACCTACAA ATACAGTTTC TCCACCTTCT
1451 TCATCACCAT TCAGGCACTG ACCAGCCTCT CCCTCGCAGG TTTGGACGTA
1501 TACGCCGCCA TGCCCGTGCG CATCATcgaC ACCATTATCG GCGCATCCCT
1551 TGCCTGGGCG GCGGTCAGCT ACCTGTGGCC AGACTGGAAA TACCTCACGC
1601 TCGAACGCAC CGCCGCCCTT GCCGTATGCA GCAGCGGCAC ATACCTCCAA
1651 AAAATTGCCG AACGCCTCAA AACCGGCGAA ACCGGCGACG ACATAGAATA
1701 CCGCATCACC CGCCGCCGCG CCCACGAACA CACCGCCGCC CTCAGCAGCA
1751 CCCTTTCCGA CATGAGCAGC GAACCCGCAA AATTCGCCGA CAGCCTGCAA
1801 CCCGGCTTTA CCCTGCTCAA AACCGGCTAC GCCCTGACCG GCTACATCTC
1851 CGCCCTCGGC GCATACCGCA GCGAAATGCA CGAAGAATGC AGCCCCGACT
1901 TTACCGCACA GTTCCACCTT GCCGCCGAAC ACACCGCCCA CATCTTCCAA
```

```
1951 CACCTGCCCG ACATGGGACC CGACGACTTT CAGACGGCAT GGATACACT

2001 GCGCGGCGAA CTCGGCACCC TCCGCACCCG CAGCAGCGGA ACACAAAGCC

2051 ACATCCTCCT CCAACAGCTC CAACTCATCG CccgGCAACT CGAACCCTAC

2101 TACCGCGCCT ACCGACAAAT TCCGCACAGG CAGCCCCAAA ACGCAGCCTG

2151 A
```

This corresponds to the amino acid sequence <SEQ ID 10 112; ORF19ng-1>:

```
  1 MKTPLLKPLL ITSLPVFASV FTAASIVWQL GEPKLAMPFV LGIIAGGLVD

51 LDNRLTGRLK NIIATVALFT LSSLTAQSTL GTGLPFILAM TLMTFGFTIL

101 GAVGLKYRTF AFGALAVATY TTLTYTPETY WLTNPFMILC GTVLYSTAII

151 LFQIILPHRP VQESVANAYE ALGGYLEAKA DFFDPDEAAW IGNRHIDLAM

201 SNTGVITAFN QCRSALFYRL RGKHRHPRTA KMLRYYFAAQ DIHERISSAH

251 VDYQEMSEKF KNTDIIFRIR RLLEMQGQAC RNTAQAIRSG KDYVYSKRLG

301 RAIEGCRQSL RLLSDGNDSP DIRHLSRLLD NLGSVDQQFR QLRHSDSPAE

351 NDRMGDTRIA ALETGSFKNT WQAIRPQLNL ESCVFRHAVR LSLVVAAACT

401 IVEALNLNLG YWILLTALFV CQPNYTATKS RVYQRIAGTV LGVIVGSLVP

451 YFTPSVETKL WIVIAGTTLF FMTRTYKYSF STFFITIQAL TSLSLAGLDV

501 YAAMPVRIID TIIGASLAWA AVSYLWPDWK YLTLERTAAL AVCSSGTYLQ

551 KIAERLKTGE TGDDIEYRIT RRRAHEHTAA LSSTLSDMSS EPAKFADSLQ

601 PGFTLLKTGY ALTGYISALG AYRSEMHEEC SPDFTAQFHL AAEHTAHIFQ

651 HLPDMGPDDF QTALDTLRGE LGTLRTRSSG TQSHILLQQL QLIARQLEPY

701 YRAYRQIPHR QPQNAA*
```

ORF19ng-1 and ORF19-1 show 95.5% identity in 716 aa overlap:

```
                    10         20         30         40         50         60
orf19-1.pep MKTPLLKPLLITSLPVFASVFTAASIVWQLGEPKLAMPFVLGIIAGGLVDLDNRLTGRLK
            ||||||||||||||||||||||||||||||||||||||||||||||||||||||||||||
orf19ng-1   MKTPLLKPLLITSLPVFASVFTAASIVWQLGEPKLAMPFVLGIIAGGLVDLDNRLTGRLK
                    10         20         30         40         50         60

70         80         90        100        110        120
orf19-1.pep NIITTVALFTLSSLTAQSTLGTGLPFILAMTLMTFGFTILGAVGLKYRTFAFGALAVATY
            |||:||||||||||||||||||||||||||||||||||||||||||||||||||||||||
orf19ng-1   NIIATVALFTLSSLTAQSTLGTGLPFILAMTLMTFGFTILGAVGLKYRTFAFGALAVATY
                    70         80         90        100        110        120

130        140        150        160        170        180
orf19-1.pep TTLTYTPETYWLTNPFMILCGTVLYSTAILLFQIVLPHRPVQESVANAYDALGGYLEAKA
            ||||||||||||||||||||||||||||||:||||:|||||||||||||||:||||||||
orf19ng-1   TTLTYTPETYWLTNPFMILCGTVLYSTAIILFQIILPHRPVQESVANAYEALGGYLEAKA
                   130        140        150        160        170        180

190        200        210        220        230        240
orf19-1.pep DFFDPDEAAWIGNRHIDLAMSNTGVITAFNQCRSALFYRLRGKHRHPRTAKMLRYYFAAQ
            ||||||||||||||||||||||||||||||||||||||||||||||||||||||||||||
orf19ng-1   DFFDPDEAAWIGNRHIDLAMSNTGVITAFNQCRSALFYRLRGKHRHPRTAKMLRYYFAAQ
                   190        200        210        220        230        240

250        260        270        280        290        300
orf19-1.pep DIHERISSAHVDYQEMSEKFKNTDIIFRIHRLLEMQGQACRNTAQALRASKDYVYSKRLG
            ||||||||||||||||||||||||||||||:|||||||||||||||||:::|||||||||
orf19ng-1   DIHERISSAHVDYQEMSEKFKNTDIIFRIRRLLEMQGQACRNTAQAIRSGKDYVYSKRLG
                   250        260        270        280        290        300

310        320        330        340        350        360
orf19-1.pep RAIEGCRQSLRLLSDSNDSPDIRHLRRLLDNLGSVDQQFRQLHQNGLQAENDRMGDTRIA
            |||||||||||||||:||||||||||:|||||||||||||||:|:||:||||||||||||
orf19ng-1   RAIEGCRQSLRLLSDGNDSPDIRHLSRLLDNLGSVDQQFRQLRHSDSPAENDRMGDTRIA
                   310        320        330        340        350        360
```

```
                  370        380        390        400        410        420
orf19-1.pep  ALETSSLKNTWQAIRPQLNLESGVFRHAVRLSLVVAAACTIVEALNLNLGYWILLTALFV
             ||||:|||||||||||||||:|||||||||||||||||||||||||||||||||||||
orf19ng-1    ALETGSFKNTWQAIRPQLNLESCVFRHAVRLSLVVAAACTIVEALNLNLGYWILLTALFV
                  370        380        390        400        410        420

430        440        450        460        470        480
orf19-1.pep  CQPNYTATKSRVRQRIAGTVLGVIVGSLVPYFTPSVETKLWIVIASTTLFFMTRTYKYSF
             |||||||||||||:||||||||||||||||||||||||||||||:||||||||||||||
orf19ng-1    CQPNYTATKSRVYQRIAGTVLGVIVGSLVPYFTPSVETKLWIVIAGTTLFFMTRTYKYSF
                  430        440        450        460        470        480

490        500        510        520        530        540
orf19-1.pep  STFFITIQALTSLSLAGLDVYAAMPVRIIDTIIGASLAWAAVSYLWPDWKYLTLERTAAL
             ||||||||||||||||||||||||||||||||||||||||||||||||||||||||||||
orf19ng-1    STFFITIQALTSLSLAGLDVYAAMPVRIIDTIIGASLAWAAVSYLWPDWKYLTLERTAAL
                  490        500        510        520        530        540

550        560        570        580        590        600
orf19-1.pep  AVCSNGAYLEKITERLKSGETGDDVEYRATRRRAHEHTAALSSTLSDMSSEPAKFADSLQ
             ||||:|:|||:||||:||||||||:||:|||||||||||||||||||||||||||||||
orf19ng-1    AVCSSGTYLQKIAERLKTGETGDDIEYRITRRRAHEHTAALSSTLSDMSSEPAKFADSLQ
                  550        560        570        580        590        600

610        620        630        640        650        660
orf19-1.pep  PGFTLLKTGYALTGYISALGAYRSEMHEECSPDFTAQFHLAAEHTAHIFQHLPETEPDDF
             |||||||||||||||||||||||||||||||||||||||||||||||||||||:|||||
orf19ng-1    PGFTLLKTGYALTGYISALGAYRSEMHEECSPDFTAQFHLAAEHTAHIFQHLPDMGPDDF
                  610        620        630        640        650        660

670        680        690        700        710
orf19-1.pep  QTALDTLRGELDTLRTHSSGTQSHILLQQLQLIARQLEPYYRAYRQIPHRQPQNAAX
             |||||||||||:||||:|||||||||||||||||||||||||||||||||||||||
orf19ng-1    QTALDTLRGELGTLRTRSSGTQSHILLQQLQLIARQLEPYYRAYRQIPHRQPQNAAX
                  670        680        690        700        710
```

In addition, ORF19ng-1 shows significant homology to a hypothetical gonococcal protein previously entered in the databases:

```
sp|O33369|YOR2_NEIGO HYPOTHETICAL 45.5 KD PROTEIN (ORF2) gnl|PID|e1154438
(AJ002423) hypothetical protein [Neisseria gonorrh] Length = 417
Score = 1512 (705.6 bits), Expect = 5.3e-203, P = 5.3e-203
Identities = 301/326 (92%), Positives = 306/326 (93%)

Query:  307 RQSLRLLSDGNDSPDIRHLSRLLDNLGSVDQQFRQLRHSDSPAENDRMGDTRIAALETGS  366
            RQSLRLLSDGNDS DIRHLSRLLDNLGSVDQQFRQLRHSDSPAENDRMGDTRIAALETGS
Sbjct:    1 RQSLRLLSDGNDSXDIRHLSRLLDNLGSVDQQFRQLRHSDSPAENDRMGDTRIAALETGS   60

Query:  367 FKNTWQAIRPQLNLESCVFRHAVRLSLVVAAACTIVEALNLNLGYWILLTALFVCQPNYT  426
            FKNTWQAIRPQLNLES VFRHAVRLSLVVAAACTIVEALNLNLGYWILLT LFVCQPNYT
Sbjct:   61 FKNTWQAIRPQLNLESGVFRHAVRLSLVVAAACTIVEALNLNLGYWILLTRLFVCQPNYT  120

Query:  427 ATKSRVYQRIAGTVLGVIVGSLVPYFTPSVETKLWIVIAGTTLFFMTRTYKYSFSTFFIT  486
            ATKSRVYQRIAGTVLGVIVGSLVPYFTPSVETKLWIVIAGTTLFFMTRTYKYSFSTFFIT
Sbjct:  121 ATKSRVYQRIAGTVLGVIVGSLVPYFTPSVETKLWIVIAGTTLFFMTRTYKYSFSTFFIT  180

Query:  487 IQALTSLSLAGLDVYAAMPVRIIDTIIGASLAWAAVSYLWPDWKYLTLERTAALAVCSSG  546
            IQALTSLSLAGLDVYAAMPVRIIDTIIGASLAWAAVSYLWPDWKYLTLERTAALAVCSSG
Sbjct:  181 IQALTSLSLAGLDVYAAMPVRIIDTIIGASLAWAAVSYLWPDWKYLTLERTAALAVCSSG  240

Query:  547 TYLQKIAERLKTGETGDDIEYRITRRRAHEHTAALSSTLSDMSSEPAKFADSLQPGFTLL  606
            TYLQKIAERLKTGETGDDIEYRITRRRAHEHTAALSSTLSDMSSEPAKFAD+  P
Sbjct:  241 TYLQKIAERLKTGETGDDIEYRITRRRAHEHTAALSSTLSDMSSEPAKFADTCNPALPCS  300

Query:  607 KTGYALTGYISALGAYRSEMHEECSP                                    632
            K   ALTGYISALG  ++ +  +P
Sbjct:  301 KPATALTGYISALGHTAAKCTKNAAP                                    326
```

Based on this analysis, including the presence of several putative transmembrane domains in the gonococcal protein (the first of which is also seen in the meningococcal protein), and on homology with the YHFK protein, it is predicted that the proteins from N. meningitidis and N. gonorrhoeae, and their epitopes, could be useful antigens for vaccines or diagnostics, or for raising antibodies.

Example 14

The following DNA sequence, believed to be complete, was identified in *N. meningitidis* <SEQ ID 113>.

```
   1 ATGAATATGC TGGGAGCTTT GGCAAAAGTC GGCAGCCTGA CGATGGTGTC
  51 GCGCGTTTTG GGATTTGTGC GCGATACGGT CATTGCGCGG GCATTCGGCG
 101 CGGGTATGGC GACGGATGCG TTTTTTGTCG CGTTCAAACT GCCCAACCTG
 151 CTTCGCCGCG TGTTTGCGGA GGGGGCGTTT GCCCAAGCGT TTGTGCCGAT
 201 TTTGGCGGAA TACAAGGAAA CGCGTTCAAA AGAGGCGG.C GAAGCCTTTA
 251 TCCGCCATGT GGCGGGGATG CTGTCGTTTG TACTGGTTAT CGTTACCGCG
 301 CTGGGCATAC TTGCCGCGCC TTGGGTGATT TATGTTTCCG CACCCGAGTT
 351 TGCCCAAGA TGCCGACAAA TTTCAGCTCT CCATCGATTT GCTGCGGATT
 401 ACGTTTCCTT ATATATTATT GATTTCCCTG TCTTCATTTG TCGGCTCGGT
 451 ACTCAATTCT TATCATAAGT TCGGCATTCC GGCGTTTACG CCAC.GTTTC
 501 TGAACGTGTC GTTTATCGTA TTCGCGCTGT TTTTCGTGCC GTATTTCGAT
 551 CCGCCCGTTA CCGCGCyGGC GTGGGCGGTC TTTGTCGGCG GCATTTTGCA
 601 ACTCGrmTTC CAACTGCCCT GGCTGGCGAA ACTGGGCTTT TTGAAACTGC
 651 CCAAACtGAG TTTCAAAGAT GCGGCGGTCA ACCGCGTGAT GAAACAGATG
 701 GCGCCTGCgA TTTTgGGCGT GAgCGTGGCG CAGGTTTCTT TGGTGATCAA
 751 CACGATTTTc GCGTCTTATC TGCAATCGGG CAGCGTTTCA TGGATGTATT
 801 ACGCCGACCG CATGATGGAG CTGCCCAGCG GCGTGCTGGG GGCGGCACTC
 851 GGTACGATTT TGCTGCCGAC TTTGTCCAAA CACTCGGCAA ACCaAGATAC
 901 GGaACAGTTT TCCGCCCTGC TCGACTGGGG TTTGCGCCTG TGCATGCtgc
 951 TGACGCTGCC GGCGgcGGTC GGACTGGCGG TGTTGTCGTT cCCgCtGGTG
1001 GCGACGCTGT TTATGTACCG CGwATTTACG CTGTTTGACG CGCAGATGAC
1051 GCAACACGCG CTGATTGCCT ATTCTTTCGG TTTAATCGGC TTAATCATGA
1101 TTAAAGTGTT GGCACCCGGC TTCTATGCGC GGCAAAACAT CAAwAmGCCC
1151 GTCAAAATCG CCATCTTCAC GCTCATCTGC mCGCAGTTGA TGAACCTTGs
1201 CTTTAyCGGC CCACTrrAAC rCasTCGGAC TTTCGCTTGC CATCGGTCTG
1251 GGCGCGTGTA TCAATGCCGG ATTGTTGTTT TACCTGTTGC GCAGACACGG
1301 TATTTACCAA CCTGG.CAAG GGTTGGGCAG CGTTCTT.AG CAAAAATGCT
1351 GcTCTCGCTC GCCGTGA
```

This corresponds to the amino acid sequence <SEQ ID 114; ORF20>:

```
  1 MNMLGALAKV GSLTMVSRVL GFVRDTVIAR AFGAGMATDA FFVAFKLPNL
 51 LRRVFAEGAF AQAFVPILAE YKETRSKEAX EAFIRHVAGM LSFVLVIVTA
101 LGILAAPWVI YVSAPSFAQD ADKFQLSIDL LRITFPYILL ISLSSFVGSV
151 LNSYHKFGIP AFTPXFLNVS FIVFALFFVP YFDPPVTAXA WAVFVGGILQ
201 LXFQLPWLAK LGFLKLPKLS FKDAAVNRVM KQMAPAILGV SVAQVSLVIN
251 TIFASYLQSG SVSWMYYADR MMELPSGVLG AALGTILLPT LSKHSANQDT
301 EQFSALLDWG LRLCMLLTLP AAVGLAVLSF PLVATLFMYR XFTLFDAQMT
```

```
351 QHALIAYSFG LIGLIMIKVL APGFYARQNI XXPVKIAIFT LICXQLMNLX

401 FXGPLXXIGL SLAIGLGACI NAGLLFYLLR RHGIYQPXQG LGSVLXQKCC

451 SRSP*
```

These sequences were elaborated, and the complete DNA sequence <SEQ ID 115> is:

```
   1 ATGAATATGC TGGGAGCTTT GGCAAAAGTC GGCAGCCTGA CGATGGTGTC

51 GCGCGTTTTG GGATTTGTGC GCGATACGGT CATTGCGCGG GCATTCGGCG

101 CGGGTATGGC GACGGATGCG TTTTTTGTCG CGTTCAAACT GCCCAACCTG

151 CTTCGCCGCG TGTTTGCGGA GGGGGCGTTT GCCCAAGCGT TTGTGCCGAT

201 TTTGGCGGAA TACAAGGAAA CGCGTTCAAA AGAGGCGGCG GAGGCTTTTA

251 TCCGCCATGT GGCGGGGATG CTGTCGTTTG TACTGGTTAT CGTTACCGCG

301 CTGGGCATAC TTGCCGCGCC TTGGGTGATT TATGTTTCCG CACCCGGTTT

351 TGCCCAAGAT GCCGACAAAT TCAGCTCTC CATCGATTTG CTGCGGATTA

401 CGTTTCCTTA TATATTATTG ATTTCCCTGT CTTCATTTGT CGGCTCGGTA

451 CTCAATTCTT ATCATAAGTT CGGCATTCCG GCGTTTACGC CCACGTTTCT

501 GAACGTGTCG TTTATCGTAT TCGCGCTGTT TTTCGTGCCG TATTTCGATC

551 CGCCCGTTAC CGCGCTGGCG TGGGCGGTCT TTGTCGGCGG CATTTTGCAA

601 CTCGGCTTCC AACTGCCCTG GCTGGCGAAA CTGGGCTTTT TGAAACTGCC

651 CAAACTGAGT TTCAAAGATG CGGCGGTCAA CCGCGTGATG AAACAGATGG

701 CGCCTGCGAT TTTGGGCGTG AGCGTGGCGC AGGTTTCTTT GGTGATCAAC

751 ACGATTTTCG CGTCTTATCT GCAATCGGGC AGCGTTTCAT GGATGTATTA

801 CGCCGACCGC ATGATGGAGC TGCCCAGCGG CGTGCTGGGG CGGCACTCG

851 GTACGATTTT GCTGCCGACT TTGTCCAAAC ACTCGGCAAA CCAAGATACG

901 GAACAGTTTT CCGCCCTGCT CGACTGGGGT TGCGCCTGT GCATGCTGCT

951 GACGCTGCCG GCGGCGGTCG GACTGGCGGT GTTGTCGTTC CCGCTGGTGG

1001 CGACGCTGTT TATGTACCGC GAATTTACGC TGTTTGACGC GCAGATGACG

1051 CAACACGCGC TGATTGCCTA TTCTTTCGGT TTAATCGGCT TAATCATGAT

1101 TAAAGTGTTG GCACCCGGCT TCTATGCGCG GCAAAACATC AAAACGCCCG

1151 TCAAAATCGC CATCTTCACG CTCATCTGCA CGCAGTTGAT GAACCTTGCC

1201 TTTATCGGCC CACTGAAACA CGTCGGACTT TCGCTTGCCA TCGGTCTGGG

1251 CGCGTGTATC AATGCCGGAT TGTTGTTTTA CCTGTTGCGC AGACACGGTA

1301 TTTACCAACC TGGCAAGGGT TGGGCAGCGT TCTTAGCAAA AATGCTGCTC

1351 TCGCTCGCCG TGATGTGCGG CGGACTGTGG GCAGCGCAGG CTTACCTGCC

1401 GTTTGAATGG GCGCACGCCG GCGGAATGCG GAAAGCGGGG CAGCTCTGCA

1451 TCCTGATTGC CGTCGGCGGC GGACTGTATT TCGCATCACT GGCGGCTTTG

1501 GGCTTCCGTC CGCGCCATTT CAAACGCGTG GAAAACTGA
```

This corresponds to the amino acid sequence <SEQ ID 116; ORF20-1>:

```
  1 MNMLGALAKV GSLTMVSRVL GFVRDTVIAR AFGAGMATDA FFVAFKLPNL
 51 LRRVFAEGAF AQAFVPILAE YKETRSKEAA EAFIRHVAGM LSFVLVIVTA
101 LGILAAPWVI YVSAPGFAQD ADKFQLSIDL LRITFPYILL ISLSSFVGSV
151 LNSYHKFGIP AFTPTFLNVS FIVFALFFVP YFDPPVTALA WAVFVGGILQ
201 LGFQLPWLAK LGFLKLPKLS FKDAAVNRVM KQMAPAILGV SVAQVSLVIN
251 TIFASYLQSG SVSWMYYADR MMELPSGVLG AALGTILLPT LSKHSANQDT
301 EQFSALLDWG LRLCMLLTLP AAVGLAVLSF PLVATLFMYR EFTLFDAQMT
351 QHALIAYSFG LIGLIMIKVL APGFYARQNI KTPVKIAIFT LICTQLMNLA
401 FIGPLKHVGL SLAIGLGACI NAGLLFYLLR RHGIYQPGKG WAAFLAKMLL
451 SLAVMCGGLW AAQAYLPFEW AHAGGMRKAG QLCILIAVGG GLYFASLAAL
501 GFRPRHFKRV EN*
```

Computer analysis of this amino acid sequence gave the following results:

Homology with the MviN Virulence Factor of *S. typhimurium* (Accession Number P37169)

ORF20 and MviN proteins show 63% aa identity in 440aa overlap:

```
Orf20    1 MNMLGALAKVGSLTMVSRVLGFVRDTVIARAFGAMATDAFFVAFKLPNLLRRVFAEGAF   60
           MN+L +LA V S+TM SRVLGF RD ++AR FGAGMATDAFFVAFKLPNLLRR+FAEGAF
MviN    14 MNLLKSLAAVSSMTMFSRVLGFARDAIVARIFGAGMATDAFFVAFKLPNLLRRIFAEGAF   73

Orf20   61 AQAFVPILAEYKETRSKEAXEAFIRHVAGMLSFVLVIVTALGILAAPWVIYVSAPSFAQD  120
           +QAFVPILAEYK   + +EA    F+ +V+G+L+   L  +VT   G+LAAPWVI V+AP    FA
MviN    74 SQAFVPILAEYKSKQGEEATRIFVAYVSGLLTLALAVVTVAGMLAAPWVIMVTAPGFADT  133

Orf20  121 ADKFQLSIDLLRITFPYILLISLSSFVGSVLNSYHKFGIPAFTPXFLNVSFIVFALFFVP  180
              ADKF L+  LLRITFPYILLISL+S  VG++LN++++F  IPAF P  FLN+S I  FALF   P
MviN   134 ADKFALTTQLLRITFPYILLISLASLVGAILNTWNRFSIPAFAPTFLNISMIGFALFAAP  193

Orf20  181 YFDPPVTAXAWAVFVGGILQLXFQLPWLAKLGFLKLPKLSFKDAAVNRVMKOMAPAILGV  240
             YF+PPV A AWAV VGG+LQL +QLP+L  K+G L  LP+++F+D     RV+KQM PAILGV
MviN   194 YFNPPVLALAWAVTVGGVLQLVYQLPYLKKIGMLVLPRINFRDTGAMRVVKQMGPAILGV  253

Orf20  241 SVAQVSLVINTIFASYLQSGSVSWMYYADRMMELPSGVLGAALGTILLPTLSKHSANQDT  300
            SV+Q+SL+INTIFAS+L  SGSVSWMYYADR+ME PSGVLG ALGTILLP+LSK   A+ +
MviN   254 SVSQISLIINTIFASFLASGSVSWMYYADRLMEFPSGVLGVALGTILLPSLSKSFASGNH  313

Orf20  301 EQFSALLDWGLRLCMLLTLPAAVGLAVLSFPLVATLFMYRXFTLFDAQMWHALIMSFG    360
           +++  L+DWGLRLC LL LP+AV L +L+ PL  +LF Y  FT FDA MTQ ALIAYS G
MviN   314 DEYCRLMDWGLRLCFLLALPSAVALGILAKPLTVSLFQYGKFTAFDAAMTQRALIAYSVG  373

Orf20  361 LIGLIMIKVLAPGFYARQNIXXPVKIAIFTLICXQLMNLXFXXXXXXXXXXXXXXXXXCI  420
           LIGLI++KVLAPGFY+RQ+I   PVKIAI TLI  QLMNL F                 C+
MviN   374 LIGLIVVKVLAPGFYSRQDIKTPVKIAIVTLIMTQLMNLAFIGPLKHAGLSLSIGLAACL  433

Orf20  421 NAGLLFYLLRRHGIYQPXQG                                         440
           NA LL++ LR+  I+ P  G
MviN   434 NASLLYWQLRKQNIFTPQPG                                         453
```

Homology with a Predicted ORF from *N. meningitidis* (Strain A)

ORF20 shows 93.5% identity over a 447aa overlap with an ORF (ORF20a) from strain A of *N. meningitidis*.

```
                  10         20         30         40         50         60
orf20.pep  MNMLGALAKVGSLTMVSRVLGFVRDTVIARAFGAGMATDAFFVAFKLPNLLRRVFAEGAF
           ||||||:|||||||||||||||||||||||||||||||||||||||||||||||||||||
orf20a     MNMLGALVKVGSLTMVSRVLGFVRDTVIARAFGAGMATDAFFVAFKLPNLLRRVFAEGAF
                  10         20         30         40         50         60

70         80         90        100        110        120
orf20.pep  AQAFVPILAEYKETRSKEAXEAFIRHVAGMLSFVLVIVTALGILAAPWVIYVSAPSFAQD
           ||||||||||||||||||||:|||||||||||||||||||||||||||||||||:||:|
orf20a     AQAFVPILAEYKETRSKEATEAFIRHVAGMLSFVLVIVTALGILAAPWVIYVSAPGFAKD
                  70         80         90        100        110        120

130        140        150        160        170        180
orf20.pep  ADKFQLSIDLLRITFPYILLISLSSFVGSVLNSYHKFGIPAFTPXFLNVSFIVFALFFVP
           |||||||||||||||||||||||||||||||||||||:|||||||:||||||||||||||
orf20a     ADKFQLSIDLLRITFPYILLISLSSFVGSVLNSYHKFSIPAFTPTFLNVSFIVFALFFVP
                 130        140        150        160        170        180

190        200        210        220        230        240
orf20.pep  YFDPPVTAXAWAVFVGGILQLXFQLPWLAKLGFLKLPKLSFKDAAVNRVMKQMAPAILGV
           |||||||| ||||||||||||| |||||||||||||||||||||||||||||||||||||
orf20a     YFDPPVTALAWAVFVGGILQLGFQLPWLAKLGFLKLPKLSFKDAAVNRVMKQMAPAILGV
                 190        200        210        220        230        240

250        260        270        280        290        300
orf20.pep  SVAQVSLVINTIFASYLQSGSVSWMYYADRMMELPSGVLGAALGTILLPTLSKHSANQDT
           ||||:|||||||||||||||||||||||||||||||:|||||||||||||||||||||||
orf20a     SVAQISLVINTIFASYLQSGSVSWMYYADRMMELPGGVLGAALGTILLPTLSKHSANQDT
                 250        260        270        280        290        300

310        320        330        340        350        360
orf20.pep  EQFSALLDWGLRLCMLLTLPAAVGLAVLSFPLVATLFMYRXFTLFDAQMTQHALIAYSFG
           |||||||||||| |||||||||||:|||||||||||||||| |||||||||||||||||
orf20a     EQFSALLDWGLRXCMLLTLPAAVGLMVLSFPLVATLFMYREFTLFDAQMTQHALIAYSFG
                 310        320        330        340        350        360

370        380        390        400        410        420
orf20.pep  LIGLIMIKVLAPGFYARQNIXXPVKIAIFTLICXQLMNLXFXGPLXXIGLSLAIGLGACI
           |||||||||||||||||||| ||||||||||||:|||| |  |||  :|||||||||||
orf20a     LIGLIMIKVLAPGFYARQNIKTPVKIAIFTLICTQLMNLAFIGPLKHVGLSLAIGLGACI
                 370        380        390        400        410        420

430        440        450
orf20.pep  NAGLLFYLLRRHGIYQPXQGLGSVLXQKCCSRSPX
           |||||||||||||||||  :|  ::  |  :
orf20a     NAGLLFYLLRRHGIYQPGKGWAAFLAKMLLSLAVMGGGLYAAQIWLPFDWAHAGGMQKAA
                 430        440        450        460        470        480
```

The complete length ORF20a nucleotide sequence <SEQ ID 117> is:

```
  1  ATGAATATGC TGGGAGCTTT GGTAAAAGTC GGCAGCCTGA CGATGGTGTC

51  GCGCGTTTTG GGATTTGTGC GCGATACGGT CATTGCGCGC GCATTCGGCG

101  CAGGCATGGC GACGGATGCG TTCTTTGTCG CGTTCAAACT GCCCAACCTG

151  CTTCGCCGCG TGTTTGCGGA GGGGGCGTTT GCCCAAGCGT TTGTGCCGAT

201  TTTGGCGGAA TATAAGGAAA CGCGTTCTAA AGAGGCGACG GAGGCTTTTA

251  TCCGCCATGT GGCGGGGATG CTGTCGTTTG TACTGGTCAT CGTTACCGCG

301  CTGGGCATAC TTGCCGCGCC TTGGGTGATT TATGTTTCCG CACCCGGTTT

351  TGCCAAAGAT GCCGACAAAT TCAGCTCTC TATCGATTTG CTGCGGATTA

401  CGTTTCCTTA TATCTTATTG ATTTCACTTT CCTCTTTTGT CGGCTCGGTA

451  CTCAATTCCT ATCATAAATT CAGCATTCCT GCGTTTACGC CCACGTTCCT

501  GAACGTGTCG TTTATCGTAT TCGCGCTGTT TTTCGTGCCG TATTTCGATC

551  CTCCCGTTAC CGCGCTGGCT TGGGCGGTTT TTGTCGGCGG CATTTTGCAA

601  CTCGGCTTCC AACTGCCCTG GCTGGCGAAA CTGGGTTTTT TGAAACTGCC

651  CAAACTGAGT TTCAAAGATG CGGCGGTCAA CCGCGTGATG AAACAGATGG
```

```
 701 CGCCTGCGAT TTTGGGCGTG AGCGTGGCGC AGATTTCTTT GGTGATCAAC

751 ACGATTTTCG CGTCTTATCT GCAATCGGGC AGCGTTTCAT GGATGTATTA

801 CGCCGACCGC ATGATGGAAC TGCCCGGCGG CGTGCTGGGG GCGGCACTCG

851 GTACGATTTT GCTGCCGACT TTGTCCAAAC ACTCGGCAAA CCAAGATACG

901 GAACAGTTTT CCGCCCTGCT CGACTGGGGT TTGCGCNTGT GCATGCTGCT

951 GACGCTGCCG GCGGCGGTCG GAATGGCGGT GTTGTCGTTC CCGCTGGTGG

1001 CAACCTTGTT TATGTACCGA GAATTCACGC TGTTTGACGC GCAGATGACG

1051 CAACACGCGC TGATTGCCTA TTCTTTCGGT TTAATCGGTT TAATCATGAT

1101 TAAAGTGTTG GCGCCCGGCT TTTATGCGCG GCAAACATC AAAACGCCCG

1151 TCAAAATCGC CATCTTCACG CTCATTTGCA CGCAGTTGAT GAACCTTGCC

1201 TTTATCGGCC CACTGAAACA CGTCGGACTT TCGCTTGCCA TCGGTCTGGG

1251 CGCGTGTATC AATGCCGGAT TGTTGTTTTA CCTGTTGCGC AGACACGGTA

1301 TTTACCAACC TGGCAAGGGT TGGGCAGCGT TCTTGGCAAA AATGCTGCTC

1351 TCGCTCGCCG TGATGGGAGG CGGCCTGTAT GCCGCCCAAA TCTGGCTGCC

1401 GTTCGACTGG GCACACGCCG GCGGAATGCA AAAGGCCGCC CGGCTCTTCA

1451 TCCTGATTGC CGTCGGCGGC GGACTGTATT TCGCATCACT GGCGGCTTTG

1501 GGCTTCCGTC CGCGCCATTT CAAACGCGTG GAAAGCTGA
```

This encodes a protein having amino acid sequence <SEQ ID 118>:

```
  1 MNMLGALVKV GSLTMVSRVL GFVRDTVIAR AFGAGMATDA FFVAFKLPNL

51 LRRVFAEGAF AQAFVPILAE YKETRSKEAT EAFIRHVAGM LSFVLVIVTA

101 LGILAAPWVI YVSAPGFAKD ADKFQLSIDL LRITFPYILL ISLSSFVGSV

151 LNSYHKFSIP AFTPTFLNVS FIVFALFFVP YFDPPVTALA WAVFVGGILQ

201 LGFQLPWLAK LGFLKLPKLS FKDAAVNRVM KQMAPAILGV SVAQISLVIN

251 TIFASYLQSG SVSWMYYADR MMELPGGVLG AALGTILLPT LSKHSANQDT

301 EQFSALLDWG LRXCMLLTLP AAVGMAVLSF PLVATLFMYR EFTLFDAQMT

351 QHALIAYSFG LIGLIMIKVL APGFYARQNI KTPVKIAIFT LICTQLMNLA

401 FIGPLKHVGL SLAIGLGACI NAGLLFYLLR RHGIYQPGKG WAAFLAKMLL

451 SLAVMGGGLY AAQIWLPFDW AHAGGMQKAA RLFILIAVGG GLYFASLAAL

501 GFRPRHFKRV ES*
```

ORF20a and ORF20-1 show 96.5% identity in 512 aa overlap:

```
                    10         20         30         40         50         60
    orf20a.pep  MNMLGALVKVGSLTMVSRVLGFVRDTVIARAFGAGMATDAFFVAFKLPNLLRRVFAEGAF
                ||||||:|||||||||||||||||||||||||||||||||||||||||||||||||||||
    orf20-1     MNMLGALAKVGSLTMVSRVLGFVRDTVIARAFGAGMATDAFFVAFKLPNLLRRVFAEGAF
                    10         20         30         40         50         60
                    70         80         90        100        110        120
    orf20a.pep  AQAFVPILAEYKETRSKEATEAFIRHVAGMLSFVLVIVTALGILAAPWVIYVSAPGFAKD
                ||||||||||||||||||:|||||||||||||||||||||||||||||||||||||||:|
    orf20-1     AQAFVPILAEYKETRSKEAAEAFIRHVAGMLSFVLVIVTALGILAAPWVIYVSAPGFAQD
                    70         80         90        100        110        120
                   130        140        150        160        170        180
    orf20a.pep  ADKFQLSIDLLRITFPYILLISLSSFVGSVLNSYHKFSIPAFTPTFLNVSFIVFALFFVP
                ||||||||||||||||||||||||||||||||||||||||:|||||||||||||||||||
    orf20-1     ADKFQLSIDLLRITFPYILLISLSSFVGSVLNSYHKFSIPAFTPTFLNVSFIVFALFFVP
                   130        140        150        160        170        180
```

```
                      190       200       210       220       230       240
orf20a.pep  YFDPPVTALAWAVFVGGILQLGFQLPWLAKLGFLKLPKLSFKDAAVNRVMKQMAPAILGV
            ||||||||||||||||||||||||||||||||||||||||||||||||||||||||||||
orf20-1     YFDPPVTALAWAVFVGGILQLGFQLPWLAKLGFLKLPKLSFKDAAVNRVMKQMAPAILGV
                      190       200       210       220       230       240

250       260       270       280       290       300
orf20a.pep  SVAQISLVINTIFASYLQSGSVSWMYYADRMMELPGGVLGAALGTILLPTLSKHSANQDT
            ||||:|||||||||||||||||||||||||||||||||:|||||||||||||||||||||
orf20-1     SVAQVSLVINTIFASYLQSGSVSWMYYADRMMELPSGVLGAALGTILLPTLSKHSANQDT
                      250       260       270       280       290       300

310       320       330       340       350       360
orf20a.pep  EQFSALLDWGLRXCMLLTLPAAVGMAVLSFPLVATLFMYREFTLFDAQMTQHALIAYSFG
            |||||||||||||:|||||||||||:||||||||||||||||||||||||||||||||||
orf20-1     EQFSALLDWGLRLCMLLTLPAAVGLAVLSFPLVATLFMYREFTLFDAQMTQHALIAYSFG
                      310       320       330       340       350       360

370       380       390       400       410       420
orf20a.pep  LIGLIMIKVLAPGFYARQNIKTPVKIAIFTLICTQLMNLAFIGPLKHVGLSLAIGLGACI
            ||||||||||||||||||||||||||||||||||||||||||||||||||||||||||||
orf20-1     LIGLIMIKVLAPGFYARQNIKTPVKIAIFTLICTQLMNLAFIGPLKHVGLSLAIGLGACI
                      370       380       390       400       410       420

430       440       450       460       470       480
orf20a.pep  NAGLLFYLLRRHGIYQPGKGWAAFLAKMLLSLAVMGGGLYAAQIWLPFDWAHAGGMQKAA
            ||||||||||||||||||||||||||||||||||||||| ||| ||:|| |||||:|:|
orf20-1     NAGLLFYLLRRHGIYQPGKGWAAFLAKMLLSLAVMCGGLWAAQAYLPFEWAHAGGMRKAG
                      430       440       450       460       470       480

490       500       510
orf20a.pep  RLFILIAVGGGLYFASLAALGFRPRHFKRVESX
            :|||||||||||||||||||||||||||||:|
orf20-1     QLCILIAVGGGLYFASLAALGFRPRHFKRVENX
                      490       500       510
```

Homology with a Predicted ORF from *N. gonorrhoeae*

ORF20 shows 92.1% identity over a 454aa overlap with a predicted ORF (ORF20ng) from *N. gonorrhoeae*.

```
orf20.pep  MNMLGALAKVGSLTMVSRVLGFVRDTVIARAFGAGMATDAFFVAFKLPNLLRRVFAEGAF   60
           ||||||||||||||||||||||||||||||||||||||||||||||||||||||||||||
orf20ng    MNMLGALAKVGSLTMVSRVLGFVRDTVIARAFGAGMATDAFFVAFKLPNLLRRVFAEGAF   60 orf20.pep  AQAFVPILAEYKETRSKEAXEAFIRHVAGMLSFVLIVTALGILAAPWVIYVSAPSFAQD   120
           |||||||||||||||||||:|||||||||||||||:||||||||||||||||||:|::|
orf20ng    AQAFVPILAEYKETRSKEATEAFIRHVAGMLSFVLIVVTALGILAAPWVIYVSAPGFTKD   120 orf20.pep  ADKFQLSIDLLRITFPYILLISLSSFVGSVLNSYHKFGIPAFTPXFLNVSFIVFALFFVP   180
           ||||||||:||||||||||||||||||:||||||||||||||||:|||:||||||||||
orf20ng    ADKFQLSISLLRITFPYILLISLSSFIGSVLNSYHKFGIPAFTPTFLNISFIVFALFFVP   180 orf20.pep  YFDPPVTAXAWAVFVGGILQLXFQLPWLAKLGFLKLPKLSFKDAAVNRVMKQMAPAILGV   240
           |||||||| ||||||||||||:|||||||||||||||||:||||||||||||||||||||
orf20ng    YFDPPVTALAWAVFVGGILQLGFQLPWLAKLGFLKLPKLNFKDAAVNRVMKQMAPAILGV   240 orf20.pep  SVAQVSLVINTIFASYLQSGSVSWMYYADRMMELPSGVLGAALGTILLPTLSKHSANQDT   300
           ||||:|||||||||||||||||||||||||||||||:|||||||||||||||||||||||
orf20ng    SVAQISLVINTIFASYLQSGSVSWMYYADRMMELPGGVLGAALGTILLPTLSKHSANQDT   300 orf20.pep  EQFSALLDWGLRLCMLLTLPAAVGLAVLSFPLVATLFMYRXFTLFDAQMTQHALIAYSFG   360
           ||||||||||||||||||||||:|||||||||||||||| ||||||||||||||||||||
orf20ng    EQFSALLDWGLRLCMLLTLPAAAGLAVLSFPLVATLFMYREFTLFDAQMTQHALIAYSFG   360 orf20.pep  LIGLIMIKVLAPGFYARQNIXXPVKIAIFTLICXQLMNLXFXGPLXXIGLSLAIGLGACI   420
           ||||||||||||:|||||||||||||||||||||||||:||| |||||||||||||||
orf20ng    LIGLIMIKVLASGFYARQNIKTPVKIAIFTLICXQLMNLAFIGPLKHAGLSLAIGLGACI   420 orf20.pep  NAGLLFYLLRRHGIYQPXQGLGSVLXQKCCSRSP   454
           ||||||:|:|:|||||:| ||||:   :||||||||
orf20ng    NAGLLFFLFRKHGIYRPGQGLGQPSWRKCCSRSP   454
```

An ORF20ng nucleotide sequence <SEQ ID 119> was predicted to encode a protein having amino acid sequence <SEQ ID 120>:

```
  1 MNMLGALAKV GSLTMVSRVL GFVRDTVIAR AFGAGMATDA FFVAFKLPNL

51 LRRVFAEGAF AQAFVPILAE YKETRSKEAT EAFIRHVAGM LSFVLIVVTA

101 LGILAAPWVI YVSAPGFTKD ADKFQLSISL LRITFPYILL ISLSSFVGSI

151 LNSYHKFGIP AFTPTFLNIS FIVFALFFVP YFDPPVTALA WAVFVGGILQ

201 LGFQLPWLAK LGFLKLPKLN FKDAAVNRVM KQMAPAILGV SVAQISLVIN

251 TIFASYLQSG SVSWMYYADR MMELPGGVLG AALGTILLPT LSKHSANQDT
```

```
301 EQFSALLDWG LRLCMLLTLP AAAGLAVLSF PLVATLFMYR EFTLFDAQMT

351 QHALIAYSFG LIGLIMIKVL ASGFYARQNI KTPVKIAIFT LICTQLMNLA

401 FIGPLKHAGL SLAIGLGACI NAGLLFFLFR KHGIYRPGQG LGQPSWRKCC

451 SRSP*
```

Further DNA sequence analysis revealed the following DNA sequence <SEQ ID 121>:

```
   1 ATGAATATGC TTGGAGCTTT GGCAAAAGTC GGCAGCCTGA CGATGGTGTC

51 GCGCGTTTTG GGATTTGTGC GCGATACGGT CATTGCGCGG GCATTCGGCG

101 CGGGTATGGC GACGGATGCG TTTTTTGTCG CGTTCAAACT GCCCAACCTG

151 CTTCGCCGCG TGTTTGCGGA GGGGGCGTTT GCCCAAGCGT TTGTGCCGAT

201 TTTGGCGGAA TATAAGGAAA CGCGTTCTAA AGAGGCGAcg gAGGCTTTTA

251 TCCGCCACGt tgcgggAatg CTGTCGTTTG TGCTGATcgt cGttacCGCG

301 CTGGGCATAC TTGCCGCgcc tTGGGTGATT TATGTTtccg CgcccGGCTT

351 TACCAAAGAC GCGGACAAGT TCCAACTTTC CATCAGCCTG CTGCGGATTA

401 CGTTTCCTTA TATATTATTG ATTTCTTTGT CTTCTTTTGT CGGCTCGATA

451 CTCAATTCCT ACCATAAGTT CGGCATTCCC GCGTTTACGC CCACGTTTTT

501 AAACATCTCT TTTATCGTAT TCGCACTGTT TTTCGTGCCG TATTTCGATC

551 CGCCCGTTAC CGCGCTGGCG TGGGCGGTTT TTGTCGGCGG TATTTTGCAG

601 CTCGGTTTCC AACTGCCGTG GCTGGCGAAA CTGGGCTTTT TGAAACTGCC

651 CAAACTGAAT TCAAAGATG CGGCGGTCAA CCGCGTCATG AAACAGATGG

701 CGCCTGCGAT TTTGGGCGTG agcgTGGCGC AAATTTCTTT GgttATCAAC

751 ACGATTTTCG CGTCTTATCT GCAATCGGGC AGCGTTTCAT GGATGTatta 801 cgCCGACCGC ATGATGGAGc tgcgccGGGG CGTGCTGGGG GCTGCACTCG

851 GTACAATTTT GCTGCCGACT TTGTCCAAAC ACTCGGCAAA CCAAGATACG

901 GAACAGTTTT CCGCCCTGCT CGACTGGGGT TTGCGCCTGT GCATGCTGCT

951 GACGCTGCCG GCGGCGGccg GACTGGCGGT ATTGTCGTTC CCGCTGGTGG

1001 CGACGCTGTT TATGTACCGA GAATTCACGC TGTTTGACGC ACAAATGACG

1051 CAACACGCGC TGATTGCCTA TTCTTTCGGT TTAATCGGTT TAATTATGAT

1101 TAAAGTGTTG GCATCCGGCT TTTATGCGCG GCAAAACATC AAAACGCCCG

1151 TCAAAATCGC CATCTTCACG CTCATCTGCA CGCAGTTGAT GAACCTCGCC

1201 TTTATCGGTC CGTTGAAACA CGCCGGGCTT TCGCTCGCCA TCGGCCTGGG

1251 CGCGTGCATC AACGCCGGAT TGTTGTTCTT CCTGTTGCGC AAACACGGTA

1301 TTTACCGGCC cggcaggggt tgggcggcgt TCTTGGCGAA AATGCTGCTC

1351 GCGCTCGCCG TGATGTGCGG CGGACTGTGG GCGGCGCAGG CTTGCCTGCC

1401 GTTCGAATGG GCGCACGCCG GCGGAATGCG GAAAGCGGGG CAGCTCTGCA

1451 TCCTGATTGC CGTCGGCGGC GGACTGTATT TCGCATCTCT GGCGGCTTTG

1501 GGCTTCCGTC CGCGCCATTT CAAACGCGTG GAAAGCTGA
```

This encodes the following amino acid sequence <SEQ ID 122; ORF20ng-1>:

```
  1 MNMLGALAKV GSLTMVSRVL GFVRDTVIAR AFGAGMATDA FFVAFKLPNL

51 LRRVFAEGAF AQAFVPILAE YKETRSKEAT EAFIRHVAGM LSFVLIVVTA

101 LGILAAPWVI YVSAPGFTKD ADKFQLSISL LRITFPYILL ISLSSFVGSI

151 LNSYHKFGIP AFTPTFLNIS FIVFALFFVP YFDPPVTALA WAVFVGGILQ

201 LGFQLPWLAK LGFLKLPKLN FKDAAVNRVM KQMAPAILGV SVAQISLVIN

251 TIFASYLQSG SVSWMYYADR MMELRRGVLG AALGTILLPT LSKHSANQDT

301 EQFSALLDWG LRLCMLLTLP AAAGLAVLSF PLVATLFMYR EFTLFDAQMT

351 QHALIAYSFG LIGLIMIKVL ASGFYARQNI KTPVKIAIFT LICTQLMNLA

401 FIGPLKHAGL SLAIGLGACI NAGLLFFLLR KHGIYRPGRG WAAFLAKMLL

451 ALAVMCGGLW AAQACLPFEW AHAGGMRKAG QLCILIAVGG GLYFASLAAL

501 GFRPRHFKRV ES*
```

ORF20ng-1 and ORF20-1 show 95.7% identity in 512 aa overlap:

```
                    10         20         30         40         50         60
orf20-1a.pep  MNMLGALAKVGSLTMVSRVLGFVRDTVIARAFGAGMATDAFFVAFKLPNLLRRVFAEGAF
              ||||||||||||||||||||||||||||||||||||||||||||||||||||||||||||
orf20ng-1     MNMLGALAKVGSLTMVSRVLGFVRDTVIARAFGAGMATDAFFVAFKLPNLLRRVFAEGAF
                    10         20         30         40         50         60

70         80         90        100        110        120
orf20-1.pep   AQAFVPILAEYKETRSKEAAEAFIRHVAGMLSFVLVIVTALGILAAPWVIYVSAPGFAQD
              |||||||||||||||||||| ||||||||||||||| ||||||||||||||||||||| |
orf20ng-1     AQAFVPILAEYKETRSKEATEAFIRHVAGMLSFVLIVVTALGILAAPWVIYVSAPGFTKD
                    70         80         90        100        110        120

130        140        150        160        170        180
orf20-1.pep   ADKFQLSIDLLRITFPYILLISLSSFVGSVLNSYHKFGIPAFTPTFLNVSFIVFALFFVP
              ||||||||| ||||||||||||||||||| |||||||||||||||||||| |||||||||
orf20ng-1     ADKFQLSISLLRITFPYILLISLSSFVGSILNSYHKFGIPAFTPTFLNISFIVFALFFVP
                   130        140        150        160        170        180

190        200        210        220        230        240
orf20-1.pep   YFDPPVTALAWAVFVGGILQLGFQLPWLAKLGFLKLPKLSFKDAAVNRVMKQMAPAILGV
              ||||||||||||||||||||||||||||||||||||||||.|||||||||||||||||||
orf20ng-1     YFDPPVTALAWAVFVGGILQLGFQLPWLAKLGFLKLPKLNFKDAAVNRVMKQMAPAILGV
                   190        200        210        220        230        240

250        260        270        280        290        300
orf20-1.pep   SVAQVSLVINTIFASYLQSGSVSWMYYADRMMELPSGVLGAALGTILLPTLSKHSANQDT
              ||||:|||||||||||||||||||||||||||||| ||||||||||||||||||||||||
orf20ng-1     SVAQISLVINTIFASYLQSGSVSWMYYADRMMELRRGVLGAALGTILLPTLSKHSANQDT
                   250        260        270        280        290        300

310        320        330        340        350        360
orf20-1.pep   EQFSALLDWGLRLCMLLTLPAAVGLAVLSFPLVATLFMYREFTLFDAQMTQHALIAYSFG
              |||||||||||||||||||||| |||||||||||||||||||||||||||||||||||||
orf20ng-1     EQFSALLDWGLRLCMLLTLPAAAGLAVLSFPLVATLFMYREFTLFDAQMTQHALIAYSFG
                   310        320        330        340        350        360

370        380        390        400        410        420
orf20-1.pep   LIGLIMIKVLAPGFYARQNIKTPVKIAIFTLICTQLMNLAFIGPLKHVGLSLAIGLGACI
              |||||||||||:||||||||||||||||||||||||||||||||||| ||||||||||||
orf20ng-1     LIGLIMIKVLASGFYARQNIKTPVKIAIFTLICTQLMNLAFIGPLKHAGLSLAIGLGACI
                   370        380        390        400        410        420

430        440        450        460        470        480
orf20-1.pep   NAGLLFYLLRRHGIYQPGKGWAAFLAKMLLSLAVMCGGLWAAQAYLPFEWAHAGGMRKAG
              ||||||:|||:|||||:|:|||||||||||:|||||||||||| ||||||||||||||||
orf20ng-1     NAGLLFFLLRKHGIYRPGRGWAAFLAKMLLALAVMCGGLWAAQACLPFEWAHAGGMRKAG
                   430        440        450        460        470        480

490        500        510
orf20-1.pep   QLCILIAVGGGLYFASLAALGFRPRHFKRVENX
              ||||||||||||||||||||||||||||||| |
orf20ng-1     QLCILIAVGGGLYFASLAALGFRPRHFKRVESX
                   490        500        510
```

In addition, ORF20ng-1 shows significant homology with
a virulence factor of *S. typhimurium*:

```
sp|P37169|MVIN_SALTY VIRULENCE FACTOR MVIN pir||S40271 mviN protein -
Salmonella typhimurium gi|438252 (Z26133) mviB gene product
[Salmonella typhimurium] gnl|PID|d1005521 (D25292) ORF2
[Salmonella typhimurium] Length = 524
Score = 1573 (750.1 bits), Expect = 1.1e-220, Sum P(2) = 1.1e-220
Identities = 309/467 (66%), Positives = 368/467 (78%)

Query:    1 MNMLGALAKVGSLTMVSRVLGFVRDTVIARAFGAGMATDAFFVAFKLPNLLRRVFAEGAF    60
            MN+L +LA V S+TM SRVLGF RD ++AR FGAGMATDAFFVAFKLPNLLRR+FAEGAF
Sbjct:   14 MNLLKSLAAVSSMTMFSRVLGFARDAIVARIFGAGMATDAFFVAFKLPNLLRRIFAEGAF    73

Query:   61 AQAFVPILAEYKETRSKEATEAFIRHVAGMLSFVLIVVTALGILAAPWVIYVSAPGFTKD   120
            +QAFVPILAEYK  + +EAT  F+ +V+G+L+   L VVT   G+LAAPWVI V+APGF
Sbjct:   74 SQAFVPILAEYKSKQGEEATRIFVAYVSGLLTLALAVVTVAGMLAAPWVIMVTAPGFADT   133

Query:  121 ADKFQLSISLLRITFPYILLISLSSFVGSILNSYHKFGIPAFTPTFLNISFIVFALFFVP   180
            ADKF L+   LLRITFPYILLISL+S VG+ILN++++F IPAF PTFLNIS I FALF  P
Sbjct:  134 ADKFALTTQLLRITFPYILLISLASLVGAILNTWNRFSIPAFAPTFLNISMIGFALFAAP   193

Query:  181 YFDPPVTALAWAVFVGGILQLGFQLPWLAKLGFLKLPKLNFKDAAVNRVMKQMAPAILGV   240
            YF+PPV ALAWAV VGG+LQL +QLP+L K+G L LP++NF+D    RV+KQM PAILGV
Sbjct:  194 YFNPPVLALAWAVTVGGVLQLVYQLPYLKKIGMLVLPRINFRDTGAMRVVKQMGPAILGV   253

Query:  241 SVAQISLVINTIFASYLQSGSVSWMYYADRMMELRRGVLGAALGTILLPTLSKHSANQDT   300
            SV+QISL+INTIFAS+L SGSVSWMYYADR+ME   GVLG ALGTILLP+LSK  A+  +
Sbjct:  254 SVSQISLIINTIFASFLASGSVSWMYYADRLMEFPSGVLGVALGTILLPSLSKSFASGNH   313

Query:  301 EQFSALLDWGLRLCMLLTLPAAAGLAVLSFPLVATLFMYREFTLFDAQMTQHALIAYSFG   360
            +++  L+DWGLRLC LL LP+A  L +L+ PL  +LF Y +FT FDA MTQ ALIAYS G
Sbjct:  314 DEYCRLMDWGLRLCFLLALPSAVALGILAKPLTVSLFQYGKFTAFDAAMTQRALIAYSVG   373

Query:  361 LIGLIMIKVLASGFYARQNIKTPVKIAIFTLICTQLMNLAFIGPLKHAGLSLAIGLGACI   420
            LIGLI++KVLA GFY+RQ+IKTPVKIAI TLI TQLMNLAFIGPLKHAGLSL+IGL AC+
Sbjct:  374 LIGLIVVKVLAPGFYSRQDIKTPVKIAIVTLIMTQLMNLAFIGPLKHAGLSLSIGLAACL   433

Query:  421 NAGLLFFLLRKHGIYRPGRGWXXXXXXXXXXXXVMCGGLWAAQACLP              467
            NA LL++ LRK  I+ P  GW            VM   L+     +P
Sbjct:  434 NASLLYWQLRKQNIFTPQPGWMWFLMRLIISVLVMAAVLFGVLHIMP              480

Score = 70 (33.4 bits), Expect = 1.1e-220, Sum P(2) = 1.1e-220
Identities = 14/41 (34%), Positives = 23/41 (56%)

Query:  469 EWAHAGGMRKAGQLCILIAVGGGLYFASLAALGFRPRHFKR                    509
            EW+    + +  +L ++  G    YFA+LA LGF+ + F R
Sbjct:  481 EWSQGSMLWRLLRLMAVVIAGIAAYFAALAVLGFKVKEFVR                    521
```

Based on this analysis, including the homology with a virulence factor from *S. typhimurium*, it is predicted that these proteins from *N. meningitidis* and *N. gonorrhoeae*, and their epitopes, could be useful antigens for vaccines or diagnostics, or for raising antibodies.

Example 15

The following partial DNA sequence was identified in *N. meningitidis* <SEQ ID 123>:

```
  1 atGATTAAAA TCAAAAAAGG TCTAAACCTG CCCATCGCGG GCAGACCGGA

51 GCAAGCCGTT tACGACGGCC CGGCCaTTAC CGAAGtCGCG TTGCTTGGCG

101 AAGAATATGC CGGTATGCGC CCCTCGATGA AAGTCAAGGA AGGCGATGCC

151 GTcAAAAAAG GCCAAGTGCT GTTTGAAGAC AAAAAGAATC CGGGCGTGGT

201 GTTTACTGCG CCGGCTTCAG GcAAAATCGC CGCGATTCAC CGTGGCGAAA

251 AGCGCGTACT TCAGTCAGTC GTGATTGCCG TTGAArGCAA CGACGAAATC

301 GAGTTTGAAC GCTACGCACC TGAAGCGCTG GCAAACTTAA GCGGCGAAGA

351 AGTGCGCCGC AACCTGATCC AATCCGGTTT GTGGACTGCG CTGCGCACCC
```

```
401 GTCCGTTCAG CAAAATTCCT GCCGTCGATG CCGAGCCGTT CGCCATCTTC

451 GTCAATGCGA tGGACACCAA TCCG..
```

This corresponds to the amino acid sequence <SEQ ID 124; ORF22>:

```
  1 MIKIKKGLNL PIAGRPEQAV YDGPAITEVA LLGEEYAGMR PSMKVKEGDA

51 VKKGQVLFED KKNPGVVFTA PASGKIAAIH RGEKRVLQSV VIAVEXNDEI

101 EFERYAPEAL ANLSGEEVRR NLIQSGLWTA LRTRPFSKIP AVDAEPFAIF

151 VNAMDTNP..
```

Further work revealed the complete nucleotide sequence <SEQ ID 125>:

```
   1 ATGATTAAAA TCAAAAAGG TCTAAACCTG CCCATCGCGG GCAGACCGGA

51 GCAAGCCGTT TACGACGGCC CGGCCATTAC CGAAGTCGCG TTGCTTGGCG

101 AAGAATATGC CGGTATGCGC CCCTCGATGA AGTCAAGGA AGGCGATGCC

151 GTCAAAAAAG GCCAAGTGCT GTTTGAAGAC AAAAAGAATC CGGGCGTGGT

201 GTTTACTGCG CCGGCTTCAG GCAAAATCGC CGCGATTCAC CGTGGCGAAA

251 AGCGCGTACT TCAGTCAGTC GTGATTGCCG TTGAAGGCAA CGACGAAATC

301 GAGTTTGAAC GCTACGCACC TGAAGCGCTG GCAAACTTAA GCGGCGAAGA

351 AGTGCGCCGC AACCTGATCC AATCCGGTTT GTGGACTGCG CTGCGCACCC

401 GTCCGTTCAG CAAAATTCCT GCCGTCGATG CCGAGCCGTT CGCCATCTTC

451 GTCAATGCGA TGGACACCAA TCCGCTGGCT GCCGACCCTA CGGTCATTAT

501 CAAAGAAGCC GCCGAGGATT TCAAACGCGG CCTGTTGGTA TTGAGCCGTT

551 TGACCGAACG CAAAATCCAT GTTTGTAAGG CAGCTGGCGC AGACGTGCCG

601 TCTGAAAATG CTGCCAACAT CGAAACACAT GAATTCGGCG GCCCGCATCC

651 TGCCGGTTTG AGTGGCACGC ACATTCATTT CATCGAGCCG GTCGGCGCGA

701 ATAAAACCGT GTGGACCATC AATTATCAAG ATGTAATTAC CATTGGCCGT

751 TTGTTTGCAA CAGGCCGTCT GAACACCGAG CGCGTGATTG CCCTAGGTGG

801 TTCTCAAGTC AACAAACCGC GCCTCTTGCG TACCGTTTTG GGTGCGAAAG

851 TATCGCAAAT TACTGCGGGC GAATTGGTTG ACACAGACAA CCGCGTGATT

901 TCCGGTTCGG TATTGAACGG CGCGATTACA CAAGGCGCGC ACGATTATTT

951 GGGACGCTAC CACAATCAGA TTTCCGTTAT CGAAGAAGGC CGCAGCAAAG

1001 AGCTGTTCGG CTGGGTTGCG CCGCAGCCGG ACAAATACTC CATCACGCGT

1051 ACAACCCTCG GCCATTTCCT GAAAAACAAA CTCTTCAAGT CAACACAGC

1101 CGTCAACGGC GGCGACCGCG CCATGGTGCC GATTGGTACT TACGAGCGCG

1151 TGATGCCCTT GGATATCCTG CCCACCCTGC TTTTGCGCGA TTTAATCGTC

1201 GGCGATACCG ACAGCGCGCA GGCATTGGGT TGCTTGGAAT TGGACGAAGA

1251 AGACCTCGCT TTGTGCAGCT TCGTCTGCCC GGGCAAATAC GAATACGGCC

1301 CGCTGTTGCG CAAAGTGCTG GAAACCATTG AGAAGGAAGG CTGA
```

This corresponds to the amino acid sequence <SEQ ID 126; ORF22-1>:

```
  1 MIKIKKGLNL PIAGRPEQAV YDGPAITEVA LLGEEYAGMR PSMKVKEGDA
 51 VKKGQVLFED KKNPGVVFTA PASGKIAAIH RGEKRVLQSV VIAVEGNDEI
101 EFERYAPEAL ANLSGEEVRR NLIQSGLWTA LRTRPFSKIP AVDAEPFAIF

151 VNAMDTNPLA ADPTVIIKEA AEDFKRGLLV LSRLTERKIH VCKAAGADVP

201 SENAANIETH EFGGPHPAGL SGTHIHFIEP VGANKTVWTI NYQDVITIGR

251 LFATGRLNTE RVIALGGSQV NKPRLLRTVL GAKVSQITAG ELVDTDNRVI

301 SGSVLNGAIT QGAHDYLGRY HNQISVIEEG RSKELFGWVA PQPDKYSITR

351 TTLGHFLKNK LFKFNTAVNG GDRAMVPIGT YERVMPLDIL PTLLLRDLIV

401 GDTDSAQALG CLELDEEDLA LCSFVCPGKY EYGPLLRKVL ETIEKEG*
```

Further work identified the corresponding gene in strain A of *N. meningitidis* <SEQ ID 127>:

```
   1 ATGATTAAAA TCAAAAAAGG TCTAAACCTG CCCATCGCGG GCAGACCGGA
  51 GCAAGTCATT TATGACGGGC CCGTCATTAC CGAAGTCGCG TTGCTTGGCG
 101 AAGAATATGC CGGTATGCGC CCCTNGATGA AAGTCAAGGA AGGCGATGCC
 151 GTCAAAAAAG GCCAAGTGCT GTTTGAAGAC AAAAAGNATC CGGGCGTGGT
 201 GTTTACCGCG CCNGTTTCAG GCAAAATCGC CGCCATCCAT CGCGGCGAAA
 251 AGCGCGTACT TCAGTCGGTC GTGATTGCCG TTGAAGGCAA CGACGAAATC
 301 GAGTTCGAAC GCTACGCGCC CGAAGCGTTG GCAAACTTAA GCGGCGANGA
 351 ANTNNGNNGC AATCTGATCC AATCCGGTTT GTGGACTGCG CTGCGTANCC
 401 GTCCGTTCAG CAAAATCCCT GCCGTCGATG CCGAGCCGTT CGCCATCTTC
 451 GTCAATGCGA TGGACACCAA TCCGCTNGCG GCAGACCCTG TGGTTGTGAT
 501 CAAAGAAGCC GNCGANGATT TCAGACGANG TNTGCTGGTA TTGAGCCGTT
 551 TGACCGAGCG TAAAATCCAT GTGTGTAAGG CAGCTGGCGC AGACGTGCCG
 601 TCTGAAAATG CTGCCAACAT CGAAACACAT GAATTCGGCG GCCCGCATCC
 651 GGCCGGTTTG AGTGGCACGC ACATTCATTT CATTGAGCCG GTCGGTGCAA
 701 ACAAAACCGT TTGGACCATC AATTATCAAG ATGTAATTGC CATCGGACGT
 751 TTGTTTGCAA CAGGCCGTCT GAACACCGAG CGCGTGATTG CTTTGGGTGG
 801 TTCTCAAGTC AACAAACCAC GCCTCTTGCG TACCGTTTTG GGTGCGAAAG
 851 TATCGCAAAT TACTGCGGGC GAATTGGTTG ACGCAGACAA CCGCGTGATT
 901 TCCGGTTCGG TATTGAACGG CGCGATTACA CAAGGCGCGC ACGATTATTT
 951 GGGACGCTAC CACAATCAGA TTTCCGTTAT CGAAGAAGGC CGCAGCAAAG
1001 AGCTGTTCGG CTGGGTTGCG CCGCAGCCGG ACAAATACTC CATCACGCGT
1051 ACGACCCTCG GCCATTTCCT GAAAAACAAA CTCTTCAAGT TCACGACAGC
1101 CGTCAACGGT GGCGACCGCG CCATGGTGCC GATTGGTACT TACGAGCGCG
1151 TAATGCCGCT AGACATCCTG CCTACCCTGC TTTTGCGCGA TTTAATCGTC
1201 GGCGATACCG ACAGCGCGCA AGCATTGGGT TGCTTGGAAT TGGACGAAGA
1251 AGACCTCGCT TTGTGCAGCT TCGTCTGCCC GGGCAAATAC GAATANGGCC
1301 CGCTGTTGCG TAAGGTGCTG GAAACCNTTG AGAAGGAAGG CTGA
```

This encodes a protein having amino acid sequence <SEQ ID 128; ORF22a>:

```
  1 MIKIKKGLNL PIAGRPEQVI YDGPVITEVA LLGEEYAGMR PXMKVKEGDA

51 VKKGQVLFED KKXPGVVFTA PVSGKIAAIH RGEKRVLQSV VIAVEGNDEI

101 EFERYAPEAL ANLSGXEXXX NLIQSGLWTA LRXRPFSKIP AVDAEPFAIF

151 VNAMDTNPLA ADPVVVIKEA XXDFRRXXLV LSRLTERKIH VCKAAGADVP

201 SENAANIETH EFGGPHPAGL SGTHIHFIEP VGANKTVWTI NYQDVIAIGR

251 LFATGRLNTE RVIALGGSQV NKPRLLRTVL GAKVSQITAG ELVDADNRVI

301 SGSVLNGAIT QGAHDYLGRY HNQISVIEEG RSKELFGWVA PQPDKYSITR

351 TTLGHFLKNK LFKFTTAVNG GDRAMVPIGT YERVMPLDIL PTLLLRDLIV

401 GDTDSAQALG CLELDEEDLA LCSFVCPGKY EXGPLLRKVL ETXEKEG*
```

The originally-identified partial strain B sequence (ORF22) shows 94.2% identity over a 158aa overlap with ORF22a:

```
                  10         20         30         40         50         60
orf22.pep   MIKIKKGLNLPIAGRPEQAVYDGPAITEVALLGEEYAGMRPSMKVKEGDAVKKGQVLFED
            ||||||||||||||||||::||||:|||||||||||||||| ||||||||||||||||||
orf22a      MIKIKKGLNLPIAGRPEQVIYDGPVITEVALLGEEYAGMRPXMKVKEGDAVKKGQVLFED
                  10         20         30         40         50         60
                  70         80         90        100        110        120
orf22.pep   KKNPGVVFTAPASGKIAAIHRGEKRVLQSVVIAVEXNDEIEFERYAPEALANLSGEEVRR
            || |||||||:|||||||||||||||||||||||| ||||||||||||||||||||| |
orf22a      KKXPGVVFTAPVSGKIAAIHRGEKRVLQSVVIAVEGNDEIEFERYAPEALANLSGXEXXX
                  70         80         90        100        110        120
                 130        140        150
orf22.pep   NLIQSGLWTALRTRPFSKIPAVDAEPFAIFVNAMDTNP
            ||||||||||||:||||||||||||||||||||||||
orf22a      NLIQSGLWTALRXRPFSKIPAVDAEPFAIFVNAMDTNPLAADPVVVIKEAXXDFRRXXLV
                 130        140        150        160        170        180
```

The complete strain B sequence (ORF22-1) and ORF22a show 94.9% identity in 447 aa overlap:

```
                     10         20         30         40         50         60
orf22a.pep    MIKIKKGLNLPIAGRPEQVIYDGPVITEVALLGEEYAGMRPXMKVKEGDAVKKGQVLFED
              ||||||||||||||||||::||||:||||||||||||||| |||||||||||||||||||
orf20-1       MIKIKKGLNLPIAGRPEQAVYDGPAITEVALLGEEYAGMRPSMKVKEGDAVKKGQVLFED
                     10         20         30         40         50         60
                     70         80         90        100        110        120
orf22a.pep    KKXPGVVFTAPVSGKIAAIHRGEKRVLQSVVIAVEGNDEIEFERYAPEALANLSGXEXXX
              || ||||||||:||||||||||||||||||||||||||||||||||||||||||| |
orf22-1       KKNPGVVFTAPASGKIAAIHRGEKRVLQSVVIAVEGNDEIEFERYAPEALANLSGEEVRR
                     70         80         90        100        110        120
                    130        140        150        160        170        180
orf22a.pep    NLIQSGLWTALRXRPFSKIPAVDAEPFAIFVNAMDTNPLAADPVVVIKEAXXDFRRXXLV
              ||||||||||||:||||||||||||||||||||||||||||||:: |||| ||| ||
orf22-1       NLIQSGLWTALRTRPFSKIPAVDAEPFAIFVNAMDTNPLAADPTVIIKEAAEDFKRGLLV
                    130        140        150        160        170        180
                    190        200        210        220        230        240
orf22a.pep    LSRLTERKIHVCKAAGADVPSENAANIETHEFGGPHPAGLSGTHIHFIEPVGANKTVWTI
              ||||||||||||||||||||||||||||||||||||||||||||||||||||||||||||
orf22-1       LSRLTERKIHVCKAAGADVPSENAANIETHEFGGPHPAGLSGTHIHFIEPVGANKTVWTI
                    190        200        210        220        230        240
                    250        260        270        280        290        300
orf22a.pep    NYQDVIAIGRLFATGRLNTERVIALGGSQVNKPRLLRTVLGAKVSQITAGELVDADNRVI
              |||||| |||||||||||||||||||||||||||||||||||||||||||||||: ||||
orf22-1       NYQDVITIGRLFATGRLNTERVIALGGSQVNKPRLLRTVLGAKVSQITAGELVDTDNRVI
                    250        260        270        280        290        300
                    310        320        330        340        350        360
orf22a.pep    SGSVLNGAITQGAHDYLGRYHNQISVIEEGRSKELFGWVAPQPDKYSITRTTLGHFLKNK
              ||||||||||||||||||||||||||||||||||||||||||||||||||||||||||||
orf22-1       SGSVLNGAITQGAHDYLGRYHNQISVIEEGRSKELFGWVAPQPDKYSITRTTLGHFLKNK
                    310        320        330        340        350        360
```

```
                      370        380        390        400        410        420
orf22a.pep    LFKFTTAVNGGDRAMVPIGTYERVMPLDILPTLLLRDLIVGDTDSAQALGCLELDEEDLA
              ||||:|||||||||||||||||||||||||||||||||||||||||||||||||||||||
orf22-1       LFKFNTAVNGGDRAMVPIGTYERVMPLDILPTLLLRDLIVGDTDSAQALGCLELDEEDLA
                      370        380        390        400        410        420
                      430        440
orf22a.pep    LCSFVCPGKYEXGPLLRKVLETXEKEGX
              ||||||||||||:|||||||||||:|||
orf22-1       LCSFVCPGKYEYGPLLRKVLETIEKEGX
                      430        440
```

Further work identified a partial gene sequence <SEQ ID 129> from *N. gonorrhoeae*, which encodes the following amino acid sequence <SEQ ID 130; ORF22ng>:

```
  1 MIKIKKGLNL PIAGRPEQVI YDGPAITEVA LLGEEYVGMR PSMKIKEGEA
 51 VKKGQVLFED KKNPGVVFTA PASGKIAAIH RGEKRVLQSV VIAVEGNDEI
101 EFERYVPEAL AKLSSEKVRR NLIQSGLWTA LRTRPFSKIP AVDAEPFAIF
151 VNAMDTNPLA ADPTVIIKEA AEDFKRGLLV LSRLTERKIH VCKAAGADVP
201 SENAANIETH EFGGPHPAGL SGTHIHFIEP VGANKTVWTI NYQDVIAIGR
251 LFVTGRLNTE RVVALGGLQV NKPRLLRTVL GAKVSQLTAG ELVDADNRVI
301 SGSVLNGAIA QGAHDYLGRY HN*
```

Further work identified complete gonococcal gene <SEQ ID 131>:

```
   1 ATGATTAAAA TCAAAAAAGG TCTAAATCTG CCCATCGCGG GCAGACCGGA
  51 GCAAGTCATT TATGACGGCC CGGCCATTAC CGAAGTCGCG TTGCTTGGCG
 101 AAGAATATGT CGGCATGCGC CCCTCGATGA AAATCAAGGA AGGTGAAGCC
 151 GTCAAAAAAG GCCAAGTGCT GTTTGAAGAC AAAAAGAATC CGGGCGTAGT
 201 ATTTACTGCG CCGGCTTCAG GCAAAATCGC CGCTATTCAC CGTGGCGAAA
 251 AGCGCGTACT TCAGTCAGTC GTGATTGCCG TTGAAGGCAA CGACGAAATC
 301 GAGTTCGAAC GCTACGTACC TGAAGCGCTG GCAAAATTGA GCAGCGAAAA
 351 AGTGCGCCGC AACCTGATTC AATCAGGCTT ATGGACTGCG CTTCGCACCC
 401 GTCCGTTCAG CAAAATCCCT GCCGTAGATG CCGAGCCGTT CGCCATCTTC
 451 GTCAATGCGA TGGACACCAA TCCGCTGGCT GCCGACCCTA CGGTCATCAT
 501 CAAAGAAGCC GCCGAAGACT TCAAACGCGG CCTGTTGGTA TTGAGCCGCC
 551 TGACCGAACG TAAAATCCAT GTGTGTAAAG CAGCAGGCGC AGACGTGCCG
 601 TCTGAAAATG CTGCCAATAT CGAAACACAT GAATTTGGCG GCCCGCATCC
 651 TGCCGGCTTG AGTGGCACGC ACATTCATTT CATCGAGCCA GTCGGCGCGA
 701 ATAAAACCGT GTGGACCATC AATTATCAAG ACGTGATTGC TATCGGACGT
 751 TTGTTCGTAA CAGGCCGTCT GAATACCGAG CGCGTGGTTG CCTTGGGCGG
 801 CCTGCAAGTC AACAAACCGC GCCTCTTGCG TACCGTTTTG GGTGCGAAGG
 851 TGTCTCAACT TACCGCCGGC GAATTGGTTG ACGCGGACAA CCGCGTGATT
 901 TCCGGTTCGG TATTGAACGG TGCGATTGCA CAAGGCGCGC ATGATTATTT
 951 GGGACGCTAC CACAATCAGA TTTCCGTTAT CGAAGAAGGC CGCAGCAAAG
1001 AGCTGTTCGG CTGGGTTGCG CCGCAGCCGG ACAAATACTC CATCACGCGC
1051 ACCACTCTCG GCCATTTCCT AAAAAACAAA CTCTTCAAGT TCACGACAGC
```

```
-continued
1101 CGTCAACGGC GGCGACCGCG CCATGGTACC GATCGGCACT TATGAGCGCG

1151 TAATGCCGTT GGACATCCTG CCTACCTTGC TTTTGCGCGA TTTAATCGTC

1201 GGCGATACCG ACAGCGCGCA GGCTTTGGGT TGCTTGGAAT TGGACGAAGA

1251 AGACCTCGCT TTGTGCAGCT TCGTCTGCCC GGGCAAATAC GAATACGGCC

1301 CGCTGTTGCG CAAAGTGCTG GAAACCATTG AGAAGGAAGG CTGA
```

This encodes a protein having amino acid sequence <SEQ ID 132; ORF22ng-1>:

```
  1 MIKIKKGLNL PIAGRPEQVI YDGPAITEVA LLGEEYVGMR PSMKIKEGEA

51 VKKGQVLFED KKNPGVVFTA PASGKIAAIH RGEKRVLQSV VIAVEGNDEI

101 EFERYVPEAL AKLSSEKVRR NLIQSGLWTA LRTRPFSKIP AVDAEPFAIF

151 VNAMDTNPLA ADPTVIIKEA AEDFKRGLLV LSRLTERKIH VCKAAGADVP

201 SENAANIETH EFGGPHPAGL SGTHIHFIEP VGANKTVWTI NYQDVIAIGR

251 LFVTGRLNTE RVVALGGLQV NKPRLLRTVL GAKVSQLTAG ELVDADNRVI

301 SGSVLNGAIA QGAHDYLGRY HNQISVIEEG RSKELFGWVA PQPDKYSITR

351 TTLGHFLKNK LFKFTTAVNG GDRAMVPIGT YERVMPLDIL PTLLLRDLIV

401 GDTDSAQALG CLELDEEDLA LCSFVCPGKY EYGPLLRKVL ETIEKEG*
```

The originally-identified partial strain B sequence (ORF22) shows 93.7% identity over a 158aa overlap with ORF22ng:

```
orf22.pep  MIKIKKGLNLPIAGRPEQAVYDGPAITEVALLGEEYAGMRPSMKVKEGDAVKKGQVLFED   60
           ||||||||||||||||||::||||||||||||||||:||||||:|||:||||||||||||
orf22ng    MIKIKKGLNLPIAGRPEQVIYDGPAITEVALLGEEYVGMRPSMKIKEGEAVKKGQVLFED   60
orf22.pep  KKNPGVVFTAPASGKIAAIHRGEKRVLQSVVIAVEXNDEIEFERYAPEALANLSGEEVRR  120
           ||||||||||||||||||||||||||||||||||| |||||||||:||||:||:|:|||
orf22ng    KKNPGVVFTAPASGKIAAIHRGEKRVLQSVVIAVEGNDEIEFERYVPEALAKLSSEKVRR  120
orf22.pep  NLIQSGLWTALRTRPFSKIPAVDAEPFAIFVNAMDTNP                        120
           ||||||||||||||||||||||||||||||||||||||
orf22ng    NLIQSGLWTALRTRPFSKIPAVDAEPFAIFVNAMDTNPLAADPTVIIKEAAEDFKRGLLV  120
```

The complete sequences from strain B (ORF22-1) and gonococcus (ORF22ng) show 96.2% identity in 447 aa overlap:

```
                     10         20         30         40         50         60
orf22-1.pep  MIKIKKGLNLPIAGRPEQAVYDGPAITEVALLGEEYAGMRPSMKVKEGDAVKKGQVLFED
             ||||||||||||||||||::||||||||||||||||:||||||:|||:||||||||||||
orf22ng-1    MIKIKKGLNLPIAGRPEQVIYDGPAITEVALLGEEYVGMRPSMKIKEGEAVKKGQVLFED
                     10         20         30         40         50         60
                     70         80         90        100        110        120
orf22-1.pep  KKNPGVVFTAPASGKIAAIHRGEKRVLQSVVIAVEGNDEIEFERYAPEALANLSGEEVRR
             |||||||||||||||||||||||||||||||||||||||||||||:||||:||:|:|||
orf22ng-1    KKNPGVVFTAPASGKIAAIHRGEKRVLQSVVIAVEGNDEIEFERYVPEALAKLSSEKVRR
                     70         80         90        100        110        120
                    130        140        150        160        170        180
orf22-1.pep  NLIQSGLWTALRTRPFSKIPAVDAEPFAIFVNAMDTNPLAADPTVIIKEAAEDFKRGLLV
             ||||||||||||||||||||||||||||||||||||||||||||||||||||||||||||
orf22ng-1    NLIQSGLWTALRTRPFSKIPAVDAEPFAIFVNAMDTNPLAADPTVIIKEAAEDFKRGLLV
                    130        140        150        160        170        180
                    190        200        210        220        230        240
orf22-1.pep  LSRLTERKIHVCKAAGADVPSENAANIETHEFGGPHPAGLSGTHIHFIEPVGANKTVWTI
             ||||||||||||||||||||||||||||||||||||||||||||||||||||||||||||
orf22ng-1    LSRLTERKIHVCKAAGADVPSENAANIETHEFGGPHPAGLSGTHIHFIEPVGANKTVWTI
                    190        200        210        220        230        240
                    250        260        270        280        290        300
orf22-1.pep  NYQDVITIGRLFATGRLNTERVIALGGSQVNKPRLLRTVLGAKVSQITAGELVDTDNRVI
             ||||||:||||||||||||||||:|||:||||||||||||||||||:||||||||:||||
orf22ng-1    NYQDVIAIGRLFVTGRLNTERVVALGGLQVNKPRLLRTVLGAKVSQLTAGELVDADNRVI
                    250        260        270        280        290        300
```

```
                       310        320        330        340        350        360
orf22-1.pep  SGSVLNGAITQGAHDYLGRYHNQISVIEEGRSKELFGWVAPQPDKYSITRTTLGHFLKNK
             ||||||||:||||||||||||||||||||||||||||||||||||||||||||||||||
orf22ng-1    SGSVLNGAIAQGAHDYLGRYHNQISVIEEGRSKELFGWVAPQPDKYSITRTTLGHFLKNK
                       310        320        330        340        350        360

370        380        390        400        410        420
orf22-1.pep  LFKFNTAVNGGDRAMVPIGTYERVMPLDILPTLLLRDLIVGDTDSAQALGCLELDEEDLA
             ||||:|||||||||||||||||||||||||||||||||||||||||||||||||||||||
orf22ng-1    LFKFTTAVNGGDRAMVPIGTYERVMPLDILPTLLLRDLIVGDTDSAQALGCLELDEEDLA
                       370        380        390        400        410        420

430        440
orf22-1.pep  LCSFVCPGKYEYGPLLRKVLETIEKEGX
             ||||||||||||||||||||||||||||
orf22ng-1    LCSFVCPGKYEYGPLLRKVLETIEKEGX
                       430        440
```

Computer analysis of these sequences gave the following results:

Homology with 48 kDa Outer Membrane Protein of *Actinobacillus pleuropneumoniae* (Accession Number U24492).

ORF22 and this 48 kDa protein show 72% aa identity in 158aa overlap:

```
Orf22     1 MIKIKKGLNLPIAGRPEQAVYDGPAITEVALLGEEYAGMRPSMKVKEGDAVKKGQVLFED    60
            MI IKKGL+LPIAG P Q +++G  + EVA+LGEEY GMRPSMKV+EGD VKKGQVLFED
48 kDa    1 MITIKKGLDLPIAGTPAQVIHNGNTVNEVAMLGEEYVGMRPSMKVREGDVVKKGQVLFED    60 orf22    61 KKNPGVVFTAPASGKIAAIHRGEKRVLQSVVIAVEXNDEIEFERYAPEALANLSGEEVRR   120
            KKNPGVVFTAPASG +  I+RGEKRVLQSVVI VE +++I F RY    LA+LS E+V++
48 kDa   61 KKNPGVVFTAPASGTVVTINRGEKRVLQSVVIKVEGDEQITFTRYEAAQLASLSAEQVKQ   120 orf22   121 NLIQSGLWTALRTRPFSKIPAVDAEPFAIFVNAMDTNP                         158
            NLI+SGLWTA RTRPFSK+PA+DA P +IFVNAMDTNP
48 kDa  121 NLIESGLWTAFRTRPFSKVPALDAIPSSIFVNAMDTNP                         158
```

ORF22a also shows homology to the 48 kDa *Actinobacillus pleuropneumoniae* protein:

```
gi|1185395 (U24492) 48 kDa outer membrane protein
[Actinobacillus pleuropneumoniae]
Length = 449

Score = 530 bits (1351), Expect = e-150
 Identities = 274/450 (60%), Positives = 323/450 (70%), Gaps = 4/450 (0%)

Query:    1 MIKIKKGLNLPIAGRPEQVIYDGPVITEVALLGEEYAGMRPXMKVKEGDAVKKGQVLFED    60
            MI IKKGL+LPIAG P QVI++G  + EVA+LGEEY GMRP MKV+EGD VKKGQVLFED
Sbjct:    1 MITIKKGLDLPIAGTPAQVIHNGNTVNEVAMLGEEYVGMRPSMKVREGDVVKKGQVLFED    60

Query:   61 KKXPGVVFTAPVSGKIAAIHRGEKRVLQSVVIAVEGNDEIEFERYAPEALANLSGXEXXX   120
            KK PGVVFTAP SG +  I+RGEKRVLQSVVI VEG+++I F RY    LA+LS  +
Sbjct:   61 KKNPGVVFTAPASGTVVTINRGEKRVLQSVVIKVEGDEQITFTRYEAAQLASLSAEQVKQ   120

Query:  121 NLIQSGLWTALRXRPFSKIPAVDAEPFAIFVNAMDTNPLAADPVVVIKEAXXDFRRXXLV   180
            NLI+SGLWTA R RPFSK+PA+DA P +IFVNAMDTNPLAADP VV+KE    DF+    V
Sbjct:  121 NLIESGLWTAFRTRPFSKVPALDAIPSSIFVNAMDTNPLAADPEVVLKEYETDFKDGLTV   180

Query:  181 LSRL--TERKIHVCKAAGADVP-SENAANIETHEFGGPHPAGLSGTHIHFIEPVGANKTV   237
            L+RL    ++ +++CK A +++P S    I    F G HPAGL GTHIHF++PVGA K V
Sbjct:  181 LTRLFNGQKPVYLCKDADSNIPLSPAIEGITIKSFSGVHPAGLVGTHIHFVDPVGATKQV   240

Query:  238 WTINYQDVIAIGRLFATGRLNTERVIALGGSQVNKPRLLRTVLGAKVSQITAGELVDADN   297
            W +NYQDVIAIG+LF  TG L T+R+I+L G QV  PRL+RT LGA +SQ+TA EL   +N
Sbjct:  241 WHLNYQDVIAIGKLFTTGELFTDRIISLAGPQVKNPRLVRTRLGANLSQLTANELNAGEN   300

Query:  298 RVISGSVLNGAITQGAHDYLGRYHNQISVIEEGRSKELFGWVAPQPDKYSITRTTLGHFL   357
            RVISGSVL+GA   G  DYLGRY  Q+SV+  EGR KELFGW+ P  DK SITRT LGHF
Sbjct:  301 RVISGSVLSGATAAGPVDYLGRYALQVSVLAEGREKELFGWIMPGSDKFSITRTVLGHFG   360

Query:  358 KNKLFKFTTAVNGGDRAMVPIGTYERVMXXXXXXXXXXXXXXXVGDTDSAQXXXXXXXXXX   417
            K KLF FTTAV+GG+RAMVPIG YERVM               GDTDSAQ
Sbjct:  361 K-KLFNFTTAVHGGERAMVPIGAYERVMPLDIIPTLLLRDLAAGDTDSAQNLGCLELDEE   419

Query:  418 XXXXXSFVCPGKYEXGPLLRKVLETXEKEG                                 447
                 +VCPGK   GP+LR LE  EKEG
```

ORF22ng-1 also shows homology with the OMP from *A. pleuropneumoniae*:

```
gi|1185395 (U24492) 48 kDa outer membrane protein [Actinobacillus
pleuropneumoniae] Length = 449
Score = 555 bits (1414), Expect = e-157
Identities = 284/450 (63%), Positives = 337/450 (74%), Gaps = 4/450 (0%)

Query:  27 MIKIKKGLNLPIAGRPEQVIYDGPAITEVALLGEEYVGMRPSMKIKEGEAVKKGQVLFED    86
           MI IKKGL+LPIAG P QVI++G  + EVA+LGEEYVGMRPSMK++EG+ VKKGQVLFED
Sbjct:   1 MITIKKGLDLPIAGTPAQVIHNGNTVNEVAMLGEEYVGMRPSMKVREGDVVKKGQVLFED    60

Query:  87 KKNPGVVFTAPASGKIAAIHRGEKRVLQSVVIAVEGNDEIEFERYVPEALAKLSSEKVRR   146
           KKNPGVVFTAPASG +  I+RGEKRVLQSVVI VEG+++I F RY    LA LS+E+V++
Sbjct:  61 KKNPGVVFTAPASGTVVTINRGEKRVLOSVVIKVEGDEQITFTRYEAAQLASLSAEQVKQ   120

Query: 147 NLIQSGLWTALRTRPFSKIPAVDAEPFAIFVNAMDTNPLAADPTVIIKEAAEDFKRGLLV   206
           NLI+SGLWTA RTRPFSK+PA+DA P +IFVNAMDTNPLAADP V++KE    DFK GL V
Sbjct: 121 NLIESGLWTAFRTRPFSKVPALDAIPSSIFVNAMDTNPLAADPEVVLKEYETDFKDGLTV   180

Query: 207 LSRL--TERKIHVCKAAGADVP-SENAANIETHEFGGPHPAGLSGTHIHFIEPVGANKTV   263
           L+RL    ++ +++CK A +++P S     I    F G HPAGL GTHIHF++PVGA K V
Sbjct: 181 LTRLFNGQKPVYLCKDADSNIPLSPAIEGITIKSFSGVHPAGLVGTHIHFVDPVGATKQV   240

Query: 264 WTINYQDVIAIGRLFVTGRLNTERVVALGGLQVNKPRLLRTVLGAKVSQLTAGELVDADN   323
           W +NYQDVIAIG+LF TG L T+R+++L G QV  PRL+RT LGA +SQLTA EL   +N
Sbjct: 241 WHLNYQDVIAIGKLFTTGELFTDRIISLAGPQVKNPRLVRTRLGANLSQLTANELNAGEN   300

Query: 324 RVISGSVLNGAIAQGAHDYLGRYHNQISVIEEGRSKELFGWVAPQPDKYSITRTTLGHFL   383
           RVISGSVL+GA A G  DYLGRY  Q+SV+EGR KELFGW+ P  DK+SITRT LGHF
Sbjct: 301 RVISGSVLSGATAAGPVDYLGRYALQVSVLAEGREKELFGWIMPGSDKFSITRTVLGHFG   360

Query: 384 KNKLFKFTTAVNGGDRAMVPIGTYERVMXXXXXXXXXXXXXXXXVGDIDSAQXXXXXXXXXX   443
           K KLF FTTAV+GG+RAMVPIG YERVM                GDTDSAQ
Sbjct: 361 K-KLFNFTTAVHGGERAMVPIGAYERVMPLDIIPTLLLRDLAAGDIDSAQNLGCLELDEE   419

Query: 444 XXXXXSFVCPGKYEYGPLLRKVLETIEKEG                              473
                 ++VCPGK  YGP+LR  LE IEKEG
Sbjct: 420 DLALCTYVCPGKNNYGPMLRAALEKIEKEG                              449
```

Based on this analysis, including the homology with the outer membrane protein of *Actinobacillus pleuropneumoniae*, it was predicted that these proteins from *N. meningitidis* and *N. gonorrhoeae*, and their epitopes, could be useful antigens for vaccines or diagnostics, or for raising antibodies.

ORF22-1 (35.4 kDa) was cloned in pET and pGex vectors and expressed in *E. coli*, as described above. The products of protein expression and purification were analyzed by SDS-PAGE. FIG. 5A shows the results of affinity purification of the GST-fusion protein, and FIG. 5B shows the results of expression of the His-fusion in *E. coli*. Purified GST-fusion protein was used to immunise mice, whose sera were used for ELISA (positive result) and FACS analysis (FIG. 5C). These experiments confirm that ORF22-1 is a surface-exposed protein, and that it is a useful immunogen.

Example 16

The following partial DNA sequence was identified in *N. meningitidis* <SEQ ID 133>:

```
  1 ..GCGnCGnAAA TCATCCATCC CC..nACGTC GTAGGCCCTG AAGCCAACTG

51 GTTTTTTATG GTAGCCAGTA CGTTTGTGAT TGCTTTGATT GGTTATTTTG

101 TTACTGAAAA AATCGTCGAA CCGCAATTGG GCCCTTATCA ATCAGATTTG

151 TCACAAGAAG AAAAAGACAT TCGGCATTCC AATGAAATCA CGCCTTTGGA

201 ATATAAAGGA TTAATTTGGG CTGGCGTGGT GTTTGTTGCC TTATCCGCCC
```

-continued

```
251 TATTGGCTTG GAGCATCGTC CCTGCCGACG GTATTTTGCG TCATCCTGAA

301 ACAGGATTGG TTTCCGGTTC GCCGTTTTTA AAATCGATTG TTGTTTTTAT

351 TTTCTTGTTG TTTGCACTGC CGGGCATTGT TTATGGCCGG GTAACCCGAA

401 GTTTGCGCGG CGAACAGGAA GTCGTTAATG CGmyGGCCGA ATCGATGAGT

451 ACTCTGGsGC TTTmTTTGsw CAkcATCTTT TTTGCCGCAC AGTTTGTCGC

501 ATTTTTTAAT TGGACGAATA TTGGGCAATA TATTGCCGTT AAAGGGGCGA

551 CGTTCTTAAA AGAAGTCGGC TTGGGCGGCA GCGTGTTGTT TATCGGTTTT

601 ATTTTAATTT GTGCTTTTAT CAATCTGATG ATAGGCTCCG CCTCCGCGCA

651 ATGGGCGGTA ACTGCGCCGA TTTTCGTCCC TATGCTGATG TTGGCCGGCT

701 ACGCGCCCGA AGTCATTCAA GCCGCTTACC GCATCGGTGA TTCCGTTACC

751 AATATTATTA CGCCGATGAT GAGTTATTTC GGGCTGATTA TGGCGACGGT

801 GrkCmmmTAC AAAAAGATG CGGGCGTGGG TaCGcTGATT wCTATGATGT

851 TGCCGTATTC CGCTTTCTTC TTGATTGCgT GGATTGCCTT ATTCTGCATT

901 TGGGTATTTg TTTTGGGCCT GCCCGTCGGT CCCGGCGCGC CCACATTCTA

951 TCCCGCACCT TAA
```

This corresponds to the amino acid sequence <SEQ ID 134; ORF12>:

```
  1..AXXIIHPXXVVGPEANWFFM VASTFVIALI GYFVTEKIVEPQLGPYQSDL

51 SQEEKDIRHS NEITPLEYKG LIWAGVVFVA LSALLAWSIV PADGILRHPE

101 TGLVSGSPFL KSIVVFIFLL FALPGIVYGR VTRSLRGEQEVVNAXAESMS

151 TLXLXLXXIF FAAQFVAFFN WTNIGQYIAV KGATFLKEVG LGGSVLFIGF

201 ILICAFINLM IGSASAQWAV TAPIFVPMLM LAGYAPEVIQ AAYRIGDSVT

251 NIITPMMSYF GLIMATVXXY KKDAGVGTLI XMMLPYSAFF LIAWIALFCI

301 WVFVLGLPVG PGAPTFYPAP *
```

Further sequence analysis revealed the complete DNA sequence <SEQ ID 135> to be:

```
  1 ATGAGTCAAA CCGATACGCA ACGGGACGGA CGATTTTTAC GCACAGTCGA

51 ATGGCTGGGC AATATGTTGC CGCATCCGGT TACGCTTTTT ATTATTTTCA

101 TTGTGTTATT GCTGATTGCC TCTGCCGTCG GTGCGTATTT CGGACTATCC

151 GTCCCCGATC CGCGCCCTGT TGGTGCGAAA GGACGTGCCG ATGACGGTTT

201 GATTTACATT GTCAGCCTGC TCAATGCCGA CGGTTTTATC AAAATCCTGA

251 CGCATACCGT TAAAAATTTC ACCGGTTTCG CGCCGTTGGG AACGGTGTTG

301 GTTTCTTTAT TGGGCGTGGG GATTGCGGAA AAATCGGGCT GATTTCCGC

351 ATTAATGCGC TTATTGCTCA CAAAATCGCC ACGCAAACTC ACTACTTTTA

401 TGGTTGTTTT TACAGGGATT TTATCTAATA CCGCTTCTGA ATTGGGCTAT

451 GTCGTCCTAA TCCCTTTGTC CGCCATCATC TTTCATTCCC TCGGCCGCCA

501 TCCGCTTGCC GGTCTGGCTG CGGCTTTCGC GGCGTTTCG GGCGGTTATT

551 CGGCCAATCT GTTCTTAGGC ACAATCGATC CGCTCTTGGC AGGCATCACC

601 CAACAGGCGG CGCAAATCAT CCATCCCGAC TACGTCGTAG GCCCTGAAGC
```

```
 651 CAACTGGTTT TTTATGGTAG CCAGTACGTT TGTGATTGCT TTGATTGGTT

701 ATTTTGTTAC TGAAAAAATC GTCGAACCGC AATTGGGCCC TTATCAATCA

751 GATTTGTCAC AAGAAGAAAA AGACATTCGG CATTCCAATG AAATCACGCC

801 TTTGGAATAT AAAGGATTAA TTTGGGCTGG CGTGGTGTTT GTTGCCTTAT

851 CCGCCCTATT GGCTTGGAGC ATCGTCCCTG CCGACGGTAT TTTGCGTCAT

901 CCTGAAACAG GATTGGTTTC CGGTTCGCCG TTTTTAAAAT CGATTGTTGT

951 TTTTATTTTC TTGTTGTTTG CACTGCCGGG CATTGTTTAT GGCCGGGTAA

1001 CCCGAAGTTT GCGCGGCGAA CAGGAAGTCG TTAATGCGAT GGCCGAATCG

1051 ATGAGTACTC TGGGGCTTTA TTTGGTCATC ATCTTTTTTG CCGCACAGTT

1101 TGTCGCATTT TTTAATTGGA CGAATATTGG GCAATATATT GCCGTTAAAG

1151 GGGCGACGTT CTTAAAAGAA GTCGGCTTGG GCGGCAGCGT GTTGTTTATC

1201 GGTTTTATTT TAATTTGTGC TTTTATCAAT CTGATGATAG GCTCCGCCTC

1251 CGCGCAATGG GCGGTAACTG CGCCGATTTT CGTCCCTATG CTGATGTTGG

1301 CCGGCTACGC GCCCGAAGTC ATTCAAGCCG CTTACCGCAT CGGTGATTCC

1351 GTTACCAATA TTATTACGCC GATGATGAGT TATTTCGGGC TGATTATGGC

1401 GACGGTGATC AAATACAAAA AAGATGCGGG CGTGGGTACG CTGATTTCTA

1451 TGATGTTGCC GTATTCCGCT TTCTTCTTGA TTGCGTGGAT TGCCTTATTC

1501 TGCATTTGGG TATTTGTTTT GGGCCTGCCC GTCGGTCCCG GCGCGCCCAC

1551 ATTCTATCCC GCACCTTAA
```

This corresponds to the amino acid sequence <SEQ ID 136; ORF12-1>:

```
  1 MSQTDTQRDG RFLRTVEWLG NMLPHPVTLF IIFIVLLLIA SAVGAYFGLS

51 VPDPRPVGAK GRADDGLIYI VSLLNADGFI KILTHTVKNF TGFAPLGTVL

101 VSLLGVGIAE KSGLISALMR LLLTKSPRKL TTFMVVFTGI LSNTASELGY

151 VVLIPLSAII FHSLGRHPLA GLAAAFAGVS GGYSANLFLG TIDPLLAGIT

201 QQAAQIIHPD YVVGPEANWF FMVASTFVIA LIGYFVTEKI VEPQLGPYQS

251 DLSQEEKDIR HSNEITPLEY KGLIWAGVVF VALSALLAWS IVPADGILRH

301 PETGLVSGSP FLKSIVVFIF LLFALPGIVY GRVTRSLRGE QEVVNAMAES

351 MSTLGLYLVI IFFAAQFVAF FNWTNIGQYI AVKGATFLKE VGLGGSVLFI

401 GFILICAFIN LMIGSASAQW AVTAPIFVPM LMLAGYAPEV IQAAYRIGDS

451 VTNIITPMMS YFGLIMATVIKYKKDAGVGT LISMMLPYSA FFLIAWIALF

501 CIWVFVLGLP VGPGAPTFYP AP*
```

Computer analysis of this amino acid sequence gave the following results:

Homology with a Predicted ORF from *N. meningitidis* (Strain A)

ORF12 shows 96.3% identity over a 320aa overlap with an ORF (ORF12a) from strain A of *N. meningitidis*.

```
                            10         20         30
orf12.pep          AXXIIHPXXVVGPEANWFFMVASTFVIALI
                   |  ||||  ||||||||||||||||||||||
orf12a  AAAFAGVSGGYSANLFLGTIDPLLAGITQQAAQIIHPDYVVGPEANWFFMVASTFVIALI
              180        190        200        210        220        230
```

```
                  40         50         60         70         80         90
orf12.pep  GYFVTEKIVEPQLGPYQSDLSQEEKDIRHSNEITPLEYKGLIWAGVVFVALSALLAWSIV
           ||||||||||||||||||||||||||||||||||||||||||||||||||||||||||||
orf12a     GYFVTEKIVEPQLGPYQSDLSQEEKDIRHSNEITPLEYKGLIWAGVVFVALSALLAWSIV
                  240        250        260        270        280        290

100        110        120        130        140        150
orf12.pep  PADGILRHPETGLVSGSPFLKSIVVFIFLLFALPGIVYGRVTRSLRGEQEVVNAXAESMS
           |||||||||||||||||||||||||||||||||||||||||||||||||||||| ||||
orf12a     PADGILRHPETGLVSGSPFLKSIVVFIFLLFALPGIVYGRVTRSLRGEQEVVNAMAESMS
                  300        310        320        330        340        350

160        170        180        190        200        210
orf12.pep  TLXLXLXXIFFAAQFVAFFNWTNIGQYIAVKGATFLKEVGLGGSVLFIGFILICAFINLM
           ||  |  | ||||||||||||||||||||||||||||||||||||||||||||||||||
orf12a     TLGLYLVIIFFAAQFVAFFNWTNIGQYIAVKGATFLKEVGLGGSVLFIGFILICAFINLM
                  360        370        380        390        400        410

220        230        240        250        260        270
orf12.pep  IGSASAQWAVTAPIFVPMLMLAGYAPEVIQAAYRIGDSVTNIITPMMSYFGLIMATVXXY
           |||||||||||||||||||||||||||||||||||||||||||||||||||||||||  |
orf12a     IGSASAQWAVTAPIFVPMLMLAGYAPEVIQAAYRIGDSVTNIITPMMSYFGLIMATVIKY
                  420        430        440        450        460        470

280        290        300        310        320
orf12.pep  KKDAGVGTLIXMMLPYSAFFLIAWIALFCIWVFVLGLPVGPGAPTFYPAPX
           |||||||||| |||||||||||||||||||||||||||||||||||||||
orf12a     KKDAGVGTLISMMLPYSAFFLIAWIALFCIWVFVLGLPVGPGAPTFYPAPX
                  480        490        500        510        520
```

The complete length ORF12a nucleotide sequence <SEQ ID 137> is:

```
   1 ATGAGTCAAA CCGATACGCA ACGGGACGGA CGATTTTTAC GCACAGTCGA
  51 ATGGCTGGGC AATATGTTGC CGCACCCGGT TACGCTTTTT ATTATTTTCA
 101 TTGTGTTATT GCTGATTGCC TCTGCCGCCG GTGCGTATTT CGGACTATCC
 151 GTCCCCGATC CGCGCCCTGT TGGTGCGAAA GGACGTGCCG ATGACGGTTT
 201 GATTCACGTT GTCAGCCTGC TCGATGCTGA CGGTTTGATC AAAATCCTGA
 251 CGCATACCGT TAAAAATTTC ACCGGTTTCG CGCCGTTGGG AACGGTGTTG
 301 GTTTCTTTAT TGGGCGTGGG GATTGCGGAA AAATCGGGCT TGATTTCCGC
 351 ATTAATGCGC TTATTGCTCA CAAAATCTCC ACGCAAACTC ACTACTTTTA
 401 TGGTTGTTTT TACAGGGATT TTATCTAATA CCGCTTCTGA ATTGGGCTAT
 451 GTCGTCCTAA TCCCTTTGTC CGCCATCATC TTTCATTCCC TCGGCCGCCA
 501 TCCGCTTGCC GGTCTGGCTG CGGCTTTCGC GGCGTTTCG GCGGTTATT
 551 CGGCCAATCT GTTCTTAGGC ACAATCGATC CGCTCTTGGC AGGCATCACC
 601 CAACAGGCGG CGCAAATCAT CCATCCCGAC TACGTCGTAG CCCTGAAGC
 651 CAACTGGTTT TTTATGGTAG CCAGTACGTT TGTGATTGCT TGATTGGTT
 701 ATTTTGTTAC TGAAAAAATC GTCGAACCGC AATTGGGCCC TTATCAATCA
 751 GATTTGTCAC AAGAAGAAAA AGACATTCGA CATTCCAATG AAATCACGCC
 801 TTTGGAATAT AAAGGATTAA TTTGGGCTGG CGTGGTGTTT GTTGCCTTAT
 851 CCGCCCTATT GGCTTGGAGC ATCGTCCCTG CCGACGGTAT TTTGCGTCAT
 901 CCTGAAACAG GATTGGTTTC CGGTTCGCCG TTTTTAAAAT CAATTGTTGT
 951 TTTTATTTTC TTGTTGTTTG CACTGCCGGG CATTGTTTAT GGCCGGGTAA
1001 CCCGAAGTTT GCGCGGCGAA CAGGAAGTCG TTAATGCGAT GGCCGAATCG
1051 ATGAGTACTC TGGGGCTTTA TTTGGTCATC ATCTTTTTTG CCGCACAGTT
1101 TGTCGCATTT TTTAATTGGA CGAATATTGG GCAATATATT GCCGTTAAAG
1151 GGGCGACGTT CTTAAAAGAA GTCGGCTTGG GCGGCAGCGT GTTGTTTATC
```

-continued
```
1201 GGTTTTATTT TAATTTGTGC TTTTATCAAT CTGATGATAG GCTCCGCCTC

1251 CGCGCAATGG GCGGTAACTG CGCCGATTTT CGTCCCTATG CTGATGTTGG

1301 CCGGCTACGC GCCCGAAGTC ATTCAAGCCG CTTACCGCAT CGGTGATTCC

1351 GTTACCAATA TTATTACGCC GATGATGAGT TATTTCGGGC TGATTATGGC

1401 GACGGTGATC AAATACAAAA AAGATGCGGG CGTGGGTACG CTGATTTCTA

1451 TGATGTTGCC GTATTCCGCT TTCTTCTTGA TTGCGTGGAT TGCCTTATTC

1501 TGCATTTGGG TATTTGTTTT GGGCCTGCCC GTCGGTCCCG GCGCGCCCAC

1551 ATTCTATCCC GCACCTTAA
```

This encodes a protein having amino acid sequence <SEQ ID 138>:

```
  1 MSQTDTQRDG RFLRTVEWLG NMLPHPVTLF IIFIVLLLIA SAAGAYFGLS

51 VPDPRPVGAK GRADDGLIHV VSLLDADGLI KILTHTVKNF TGFAPLGTVL

101 VSLLGVGIAE KSGLISALMR LLLTKSPRKL TTFMVVFTGI LSNTASELGY

151 VVLIPLSAII FHSLGRHPLA GLAAAFAGVS GGYSANLFLG TIDPLLAGIT

201 QQAAQIIHPD YVVGPEANWF FMVASTFVIA LIGYFVTEKI VEPQLGPYQS

251 DLSQEEKDIR HSNEITPLEY KGLIWAGVVF VALSALLAWS IVPADGILRH

301 PETGLVSGSP FLKSIVVFIF LLFALPGIVY GRVTRSLRGE QEVVNAMAES

351 MSTLGLYLVI IFFAAQFVAF FNWTNIGQYI AVKGATFLKE VGLGGSVLFI

401 GFILICAFIN LMIGSASAQW AVTAPIFVPM LMLAGYAPEV IQAAYRIGDS

451 VTNIITPMMS YFGLIMATVI KYKKDAGVGT LISMMLPYSA FFLIAWIALF

501 CIWVFVLGLP VGPGAPTFYP AP*
```

ORF12a and ORF12-1 show 99.0% identity in 522 aa overlap:

```
                    10         20         30         40         50         60
   orf12a.pep  MSQTDTQRDGRFLRTVEWLGNMLPHPVTLFIIFIVLLLIASAAGAYFGLSVPDPRPVGAK
               ||||||||||||||||||||||||||||||||||||||||:|||||||||||||||||||
   orf12-1     MSQTDTQRDGRFLRTVEWLGNMLPHPVTLFIIFIVLLLIASAVGAYFGLSVPDPRPVGAK
                    10         20         30         40         50         60

70         80         90        100        110        120
   orf12a.pep  GRADDGLIHVVSLLDADGLIKILTHTVKNFTGFAPLGTVLVSLLGVGIAEKSGLISALMR
               |||||||||::||||:|||:|||||||||||||||||||||||||||||||||||||||
   orf12-1     GRADDGLIYIVSLLNADGFIKILTHTVKNFTGFAPLGTVLVSLLGVGIAEKSGLISALMR
                    70         80         90        100        110        120

130        140        150        160        170        180
   orf12a.pep  LLLTKSPRKLTTFMVVFTGILSNTASELGYVVLIPLSAIIFHSLGRHPLAGLAAAFAGVS
               ||||||||||||||||||||||||||||||||||||||||||||||||||||||||||||
   orf12-1     LLLTKSPRKLTTFMVVFTGILSNTASELGYVVLIPLSAIIFHSLGRHPLAGLAAAFAGVS
                   130        140        150        160        170        180

190        200        210        220        230        240
   orf12a.pep  GGYSANLFLGTIDPLLAGITQQAAQIIHPDYVVGPEANWFFMVASTFVIALIGYFVTEKI
               ||||||||||||||||||||||||||||||||||||||||||||||||||||||||||||
   orf12-1     GGYSANLFLGTIDPLLAGITQQAAQIIHPDYVVGPEANWFFMVASTFVIALIGYFVTEKI
                   190        200        210        220        230        240

250        260        270        280        290        300
   orf12a.pep  VEPQLGPYQSDLSQEEKDIRHSNEITPLEYKGLIWAGVVFVALSALLAWSIVPADGILRH
               ||||||||||||||||||||||||||||||||||||||||||||||||||||||||||||
   orf12-1     VEPQLGPYQSDLSQEEKDIRHSNEITPLEYKGLIWAGVVFVALSALLAWSIVPADGILRH
                   250        260        270        280        290        300

310        320        330        340        350        360
   orf12a.pep  PETGLVSGSPFLKSIVVFIFLLFALPGIVYGRVTRSLRGEQEVVNAMAESMSTLGLYLVI
               ||||||||||||||||||||||||||||||||||||||||||||||||||||||||||||
   orf12-1     PETGLVSGSPFLKSIVVFIFLLFALPGIVYGRVTRSLRGEQEVVNAMAESMSTLGLYLVI
                   310        320        330        340        350        360

370        380        390        400        410        420
   orf12a.pep  IFFAAQFVAFFNWTNIGQYIAVKGATFLKEVGLGGSVLFIGFILICAFINLMIGSASAQW
               ||||||||||||||||||||||||||||||||||||||||||||||||||||||||||||
   orf12-1     IFFAAQFVAFFNWTNIGQYIAVKGATFLKEVGLGGSVLFIGFILICAFINLMIGSASAQW
                   370        380        390        400        410        420
```

```
             430       440       450       460       470       480
orf12a.pep   AVTAPIFVPMLMLAGYAPEVIQAAYRIGDSVTNIITPMMSYFGLIMATVIKYKKDAGVGT
             ||||||||||||||||||||||||||||||||||||||||||||||||||||||||||||
orf12-1      AVTAPIFVPMLMLAGYAPEVIQAAYRIGDSVTNIITPMMSYFGLIMATVIKYKKDAGVGT
             430       440       450       460       470       480

490       500       510       520
orf12a.pep   LISMMLPYSAFFLIAWIALFCIWVFVLGLPVGPGAPTFYPAPX
             ||||||||||||||||||||||||||||||||||||||||||
orf12-1      LISMMLPYSAFFLIAWIALFCIWVFVLGLPVGPGAPTFYPAPX
             490       500       510       520
```

Homology with a Predicted ORF from *N. gonorrhoeae*

ORF12 shows 92.5% identity over a 320aa overlap with a predicted ORF (ORF12.ng) from *N. gonorrhoeae*.

```
orf12.pep                              AXXIIHPXXVVGPEANWFFMVASTFVIALI     30
                                       |   ||||  |||||||||||||:||||||||||
orf12ng      AAAFAGVSGGYSANLFLGTIDPLLAGITQQAAQIIHPDYVVGPEANWFFMAASTFVIALI    232
orf12.pep    GYFVTEKIVEPQLGPYQSDLSQEEKDIRHSNEITPLEYKGLIWAGVVFVALSALLAWSIV     90
             ||||||||||||||||||||||||||||||||||||||||||||||||||||||||||||
orf12ng      GYFVTEKIVEPQLGPYQSDLSQEEKDIRHSNEITPLEYKGLIWAGVVFVALSALLAWSIV    292
orf12.pep    PADGILRHPETGLVSGSPFLKSIVVFIFLLFALPGIVYGRVTRSLRGEQEVVNAXAESMS    150
             ||||||||||||||:|||||||||||||||||||||||||:||||||||||:|||||||
orf12ng      PADGILRHPETGLVAGSPFLKSIVVFIFLLFALPGIVYGRITRSLRGEREVVNAMAESMS    352
orf12.pep    TLXLXLXXIFFAAQFVAFFNWTNIGQYIAVKGATFLKEVGLGGSVLFIGFILICAFINLM    210
             ||  |   ||||||||||||||||||||||||:|||:  ||||||||||||||||||||
orf12ng      TLGLYLVIIFFAAQFVAFFNWTNIGQYIAVKGAVFLKKFRLGGSVLFIGFILICAFINLM    412
orf12.pep    IGSASAQWAVTAPIFVPMLMLAGYAPEVIQAAYRIGDSVTNIITPMMSYFGLIMATVXXY    270
             |||||||||||||||||||||||:|||||||||||||||||||||||||||||||||  |
orf12ng      IGSASAQWAVTAPIFVPMLMLAGNAPQVIQAAYRIGDSVTNIITPMMSYFGLIMATVIKY    472
orf12.pep    KKDAGVGTLIXMMLPYSAFFLIAWIALFCIWVFVLGLPVGPGAPTFYPAPX           320
             ||||||||||| |||||||||||||||||||||||||||||||:||||||:|
orf12ng      KKDAGVGTLISMMLPYSAFFLIAWIALFCIWVFVLGLPVGPGTPTFYPAVX           522
```

The complete length ORF12ng nucleotide sequence <SEQ ID 139> is:

```
  1  ATGAGTCAAA CCGACGCGCG TCGTAGCGGA CGATTTTTAC GCACAGTCGA
 51  ATGGCTGGGC AATATGTTGC CGCACCCGGT TACGCTTTTT ATTATTTTCA
101  TTGTGTTATT GCTGATTGcc tctgCCGTCG GTGCGTATTT CGGACTATCC
151  GTCCCCGATC CGCGTCCTGT TGGGGCGAAA GGACGTGCCG ATGACGGTTT
201  GATTCACGTT GTCAGCCTGC TCGATGCCGA CGGTTTGATC AAAATCCTGA
251  CGCATACCGT TAAAAATTTC ACCGGTTTCG CGCCGTTGGG AACGGTGTTG
301  GTTTCTTTAT TGGGCGTGGG GATTGCGGAA AAATCGGGCT TGATTTCCGC
351  ATTAATGCGC TTATTGCTCA CAAAATCCCC ACGCAAACTC ACTACTTTTA
401  TGGTTGTTTT TACAGGGATT TTATCCAATA CGGCTTCTGA ATTGGGCTAT
451  GTCGTCCTAA TCCCTTTGTC CGCCGTCATC TTTCATTCGC TCGGCCGCCA
501  TCCGCTTGCC GGTTTGGCTG CGGCTTTCGC GGCGTTTCG GCGGTTATT
551  CGGCCAATCT GTTCTTAGGC ACAATCGATC CGCTCTTGGC AGGCATCACC
601  CAACAGGCGG CGCAAATCAT CCATCCCGAC TACGTCGTAG CCCTGAAGC
651  CAACTGGTTT TTTATGGCAG CCAGTACGTT TGTGATTGCT TTGATTGGTT
701  ATTTTGTTAC TGAAAAAATC GTCGAACCGC AATTGGGCCC TTATCAATCA
751  GATTTGTCAC AAGAAGAAAA AGACATTCGG CATTCCAATG AAATCACGCC
801  TTTGGAATAT AAAGGATTAA TTTGGGCAGG CGTGGTGTTT GTTGCCTTAT
851  CCGCCCTATT GGCTTGGAGC ATCGTCCCTG CCGACGGTAT TTTGCGTCAT
```

-continued

```
 901 CCTGAAACAG GATTGGTTGC CGGTTCGCCG TTTTTAAAAT CGATTGTTGT
 951 TTTTATTTTC TTGTTGTTTG CGCTGCCGGG CATTGTTTAT GGCCGGATAA
1001 CCCGAAGTTT GCGCGGCGAA CGGGAAGTCG TTAATGCGAT GGCCGAATCG
1051 ATGAGTACTT TGGGACTTTA TTTGGTCATC ATCTTTTTTG CCGCACAGTT
1101 TGTCGCATTT TTTAATTGGA CGAATATTGG GCAATATATT GCCGTTAAAG
1151 GGGCGGTGTT CTTAAAAGAA GTCGGCTTGG GCGGCAGTGT GTTGTTTATC
1201 GGTTTTATTT TAATTTGTGC TTTTATCAAT CTGATGATAG GCTCCGCCTC
1251 CGCGCAATGG GCGGTAACTG CGCCGATTTT CGTCCCTATG CTGATGTTGG
1301 CCGGCTACGC GCCCGAAGTC ATTCAAGCCG CTTACCGCAT CGGTGATTCC
1351 GTTACCAATA TTATTACGCC GATGATGAGT TATTTCGGGC TGATTATGGC
1401 GACGGTAATC AAATACAAAA AAGATGCGGG CGTAGGCACG CTGATTTCTA
1451 TGATGTTGCC GTATTCCGCT TTCTTCTTAA TTGCATGGAT CGCCTTATTC
1501 TGCATTTGGG TATTTGTTTT GGGTCTGCCC GTCGGTCCCG GCACACCCAC
1551 ATTCTATCCG GTGCCTTAA
```

This encodes a protein having amino acid sequence <SEQ ID 140>:

```
  1 MSQTDARRSG RFLRTVEWLG NMLPHPVTLF IIFIVLLLIA SAVGAYFGLS
 51 VPDPRPVGAK GRADDGLIHV VSLLDADGLI KILTHTVKNF TGFAPLGTVL
101 VSLLGVGIAE KSGLISALMR LLLTKSPRKL TTFMVVFTGI LSNTASELGY
151 VVLIPLSAVI FHSLGRHPLA GLAAAFAGVS GGYSANLFLG TIDPLLAGIT
201 QQAAQIIHPD YVVGPEANWF FMAASTFVIA LIGYFVTEKI VEPQLGPYQS
251 DLSQEEKDIR HSNEITPLEY KGLIWAGVVF VALSALLAWS IVPADGILRH
301 PETGLVAGSP FLKSIVVFIF LLFALPGIVY GRITRSLRGE REVVNAMAES
351 MSTLGLYLVI IFFAAQFVAF FNWTNIGQYI AVKGAVFLKK FRLGGSVLFI
401 GFILICAFIN LMIGSASAQW AVTAPIFVPM LMLAGNAPQV IQAAYRIGDS
451 VTNIITPMMS YFGLIMATVI KYKKDAGVGT LISMMLPYSA FFLIAWIALF
501 CIWVFVLGLP VGPGTPTFYP VP*
```

ORF12ng shows 97.1% identity in 522 aa overlap with ORF12-1:

```
                    10         20         30         40         50         60
    orf12-1.pep MSQTDTQRDGRFLRTVEWLGNMLPHPVTLFIIFIVLLLIASAVGAYFGLSVPDPRPVGAK
                ||||::|:|||||||||||||||||||||||||||||||||||||||||||||||||||
    orf12ng     MSQTDARRSGRFLRTVEWLGNMLPHPVTLFIIFIVLLLIASAVGAYFGLSVPDPRPVGAK
                    10         20         30         40         50         60

70         80         90        100        110        120
    orf12-1.pep GRADDGLIYIVSLLNADGFIKILTHTVKNFTGFAPLGTVLVSLLGVGIAEKSGLISALMR
                ||||||||::|||:|||:||||||||||||||||||||||||||||||||||||||||
    orf12ng     GRADDGLIHVVSLLDADGLIKILTHTVKNFTGFAPLGTVLVSLLGVGIAEKSGLISALMR
                    70         80         90        100        110        120

130        140        150        160        170        180
    orf12-1.pep LLLTKSPRKLTTFMVVFTGILSNTASELGYVVLIPLSAIIFHSLGRHPLAGLAAAFAGVS
                |||||||||||||||||||||||||||||||||||||:|||||||||||||||||||||
    orf12ng     LLLTKSPRKLTTFMVVFTGILSNTASELGYVVLIPLSAVIFHSLGRHPLAGLAAAFAGVS
                   130        140        150        160        170        180

190        200        210        220        230        240
    orf12-1.pep GGYSANLFLGTIDPLLAGITQQAAQIIHPDYVVGPEANWFFMVASTFVIALIGYFVTEKI
                ||||||||||||||||||||||||||||||||||||||||||||||||||||||||||||
    orf12ng     GGYSANLFLGTIDPLLAGITQQAAQIIHPDYVVGPEANWFFMAASTFVIALIGYFVTEKI
                   190        200        210        220        230        240
```

```
                     250        260        270        280        290        300
orf12-1.pep  VEPQLGPYQSDLSQEEKDIRHSNEITPLEYKGLIWAGVVFVALSALLAWSIVPADGILRH
             ||||||||||||||||||||||||||||||||||||||||||||||||||||||||||||
orf12ng      VEPQLGPYQSDLSQEEKDIRHSNEITPLEYKGLIWAGVVFVALSALLAWSIVPADGILRH
                     250        260        270        280        290        300

310        320        330        340        350        360
orf12-1.pep  PETGLVSGSPFLKSIVVFIFLLFALPGIVYGRVTRSLRGEQEVVNAMAESMSTLGLYLVI
             ||||||:|||||||||||||||||||||||||:||||||||:||||||||||||||||||
orf12ng      PETGLVAGSPFLKSIVVFIFLLFALPGIVYGRITRSLRGEREVVNAMAESMSTLGLYLVI
                     310        320        330        340        350        360

370        380        390        400        410        420
orf12-1.pep  IFFAAQFVAFFNWTNIGQYIAVKGATPLKEVGLGGSVLFIGFILICAFINLMIGSASAQW
             ||||||||||||||||||||||||||:|||||||||||||||||||||||||||||||||
orf12ng      IFFAAQFVAFFNWTNIGQYIAVKGAVPLKEVGLGGSVLFIGFILICAFINLMIGSASAQW
                     370        380        390        400        410        420

430        440        450        460        470        480
orf12-1.pep  AVTAPIFVPMLMLAGYAPEVIQAAYRIGDSVTNIITPMMSYFGLIMATVIKYKKDAGVGT
             ||||||||||||||||||||||||||||||||||||||||||||||||||||||||||||
orf12ng      AVTAPIFVPMLMLAGYAPEVIQAAYRIGDSVTNIITPMMSYFGLIMATVIKYKKDAGVGT
                     430        440        450        460        470        480

490        500        510        520
orf12-1.pep  LISMMLPYSAFFLIAWIALFCIWVFVLGLPVGPGAPTFYPAPX
             ||||||||||||||||||||||||||||||||||||:|||||:||
orf12ng      LISMMLPYSAFFLIAWIALFCIWVFVLGLPVGPGTPTFYPVPX
                     490        500        510        520
```

In addition, ORF12ng shows significant homology with a hypotehtical protein from E. coli:

```
sp|P46133|YDAH_ECOLI HYPOTHETICAL 55.1 KD PROTEIN IN OGT-DBPA
INTERGENIC REGION
>gi|1787597 (AE000231) hypothetical protein in ogt 5'region
[Escherichia coli]
Length = 510
Score = 329 bits (835), Expect = 2e-89
Identities = 178/507 (35%), Positives = 281/507 (55%), Gaps = 15/507 (2%)

Query:    8 RSGRFLRTVEWLGNMLPHPVTXXXXXXXXXXXXASAVGAYFGLSVPDPRPVGAKGRADDGL  67
            +SG+    VE +GN +PHP              +A+ + FG+S  +P           D
Sbjct:   13 QSGKLYGWVERIGNKVPHPFLLFIYLIIVLMVTTAILSAFGVSAKNP--------TDGTP  64

Query:   68 IHVVSLLDADGLIKILTHTVKNFTGFAPXXXXXXXXXXXXXIAEKSGLISALMRLLLTKSP 127
            + V +LL +GL   L + +KNF+GFAP             +AE+ GL+ ALM   +
Sbjct:   65 VVVKNLLSVEGLHWFLPNVIKNFSGFAPLGAILALVLGAGLAERVGLLPALMVKMASHVN 124

Query:  128 RKLTTFMVVFTGILSNTASELGYVVLIPLSAVIFHSLGRHPLAGLAAAFAGVSGGYSANL 187
              + ++MV+F     S+ +S+   V++ P+ A+IF ++GRHP+AGL AA AGV  G++ANL
Sbjct:  125 ARYASYMVLFIAFFSHISSDAALVIMPPMGALIFLAVGRHPVAGLLAAIAGVGCGFTANL 184

Query:  188 FLGTIDPLLAGITQQAAQIIHPDYVVGPEANWFFMAASTFVIALIGYFVTEKIVEPQLGP 247
            + T D LL+GI+ +AA   +P V    NW+FMA+S V+ ++G  +T+KI+EP+LG
Sbjct:  185 LIVTTDVLLSGISTEAAAAFNPQMHVSVIDNWYFMASSVVVLTIVGGLITDKIIEPRLGQ 244

Query:  248 YQSDLSQEEKDIRHSNEITPLEYKGLIWAGVVFVALSALLAWSIVPADGILRHPETGLVA 307
            +Q +  ++ + + S          GL  AGVV +   A +A  ++P +GILR P    V
Sbjct:  245 WQGNSDEKLQTLTESQRF------GLRIAGVVSLLFIAAIALMVIPQNGILRDPINHTVM 298

Query:  308 GSPFLKSIVVFIFLLFALPGIVYGRITRSLRGEREVVNAMAESMSTLGLYLXXXXXXXXX 367
             SPF+K IV   I L F +   + YG  TR++R  + ++ + M E M    +     ++
Sbjct:  299 PSPFIKGIVPLIILFFFVVSLAYGIATRTIRRQADLPHLMIEPMKEMAGFIVMVFPLAQF 358

Query:  368 XXXXNWTNIGQYIAVKGAVFLKEVGLGGSVLFIGFILICAFINLMIGSASAQWAVTAPIF 427
                NW+N+G++IAV     L+ GL G   F+G L+ +F+ +I S SA W++ APIF
Sbjct:  359 VAMFNWSNMGKFIAVGLTDILESSGLSGIPAFVGLALLSSFLCMFIASGSAIWSILAPIF 418

Query:  428 VPMLMLAGYAPEVIQAAYRIGDSVTNIITPMMSYFGLIMATVIKYKKDAGVGTLISMMLP 487
            VPM ML G+ P  Q  +RI DS    + P+    L    + +YK DA +GT S++LP
Sbjct:  419 VPMFMLLGFHPAFAQILFRIADSSVLPLAPVSPFVPLFLGFLQRYKPDAKLGTYYSLVLP 478

Query:  488 YSAFFLIAWIALFCIWVFVLGLPVGPG                                  514
            Y    FL+ W+ +    W   +++GLP+GPG
Sbjct:  479 YPLIFLVVWLLMLLAW-YLVGLPIGPG                                  504
```

Based on this analysis, including the presence of several putative transmembrane domains and the predicted actinin-type actin-binding domain signature (shown in bold) in the gonococcal protein, it is predicted that the proteins from N. meningitidis and N. gonorrhoeae, and their epitopes, could be useful antigens for vaccines or diagnostics, or for raising antibodies.

Example 17

The following partial DNA sequence was identified in *N. meningitidis* <SEQ ID 141>:

```
  1 ..ACAGCCGGCG CAGCAGGTTn CnCGGTCTTC GTTTTCGTAA CGGACAGTCA

51   GGTGGAGGTG TTCGGGAACA TCCAGACCGC AGTGGAAACA GGTTTTTTTC

101   ATGGCATTTC GGTTTCGTCT GTGTTTGGTG CGGCGGCACA AGACTCGGCA

151   ATgGCTTCGC GCAGTGCGTC TATACCGGTA TTTTCAGCAA CGGAAATGCG

201   GACGGcGgCA ATTTTTCCCG CAGCGTCGCG CCATATGCCC GTGTTTTgTT

251   CTTCAGACGG CAGCAGGTCG GTTTTGTTGT ACACCTTgAT GCACGGAaTA

301   TCGCCGGCAT GGATTTCTTG CAGTACGTTT TCCACGTCTT CAATCTGCTG

351   TCCGCTGTTC GGAGCGGCGG CATCGACGAC GTGCAGCAGC ACATCgGcTT 401   gCGCGGTTTC TTCCAGCGTG GCgGAAAAGG CGGAAATCAG TTTgTGCGGC 451   agATyGCTnA CGAATCCGAC GGTATCGGTC AGGATAATGC TGCATTCGGG

501   ACT..
```

This corresponds to the amino acid sequence <SEQ ID 142; ORF14>:

```
  1 ..TAGAAGXXVF VFVTDSQVEV FGNIQTAVET GFFHGISVSS VFGAAAQDSA

51   MASRSASIPV FSATEMRTAA IFPAASRHMP VFCSSDGSRS VLLYTLMHGI

101   SPAWISCSTF STSSICCPLF GAAASTTCSS TSACAVSSSV AEKAEISLCG

151   RXLTNPTVSV RIMLHSG..
```

Computer analysis of this amino acid sequence gave the following results:

Homology with a Predicted ORF from *N. meningitidis* (Strain A)

ORF14 shows 94.0% identity over a 167aa overlap with an ORF (ORF14a) from strain A of *N. meningitidis*.

```
                                        10         20         30
orf14.pep                        TAGAAGXXVFVFVTDSQVEVFGNIQTAVET
                                 |:||||  ||||||:|::|||:|  ||||
orf14a    GRQLGFLRVGGALFVITAQARVNNALCDCLTTGAAGFAVFVFVTDGQMQVFGNVQPAVET
                  150       160       170       180       190       200
                   40         50         60         70         80         90
orf14.pep GFFHGISVSSVFGAAAQDSAMASRSASIPVFSATEMRTAAIFPAASRHMPVFCSSDGSRS
          ||||||||||||||||| ||||||||||||||||||||||||||||||||||||||||||
orf14a    GFFHGISVSSVFGAAAQYSAMASRSASIPVFSATEMRTAAIFPAASRHMPVFCSSDGSRS
                  210       220       230       240       250       260
                  100       110       120       130       140       150
orf14.pep VLLYTLMHGISPAWISCSTFSTSSICCPLFGAAASTTCSSTSACAVSSSVAEKAEISLCG
          ||||||||||||||||||||||||||||||||||||||||||||||||||||||||||||
orf14a    VLLYTLMHGISPAWISCSTFSTSSICCPLFGAAASTTCSSTSACAVSSSVAEKAEISLCG
                  270       280       290       300       310       320
                  160
orf14.pep RXLTNPTVSVRIMLHSG
          |||||||||||||||||
orf14a    RSLTNPTVSVRIMLHSGLMYSRRAVVSSVAKSWSFAYMPDLVSRLNRLDLPTLVX
                  330       340       350       360       370       380
```

The complete length ORF14a nucleotide sequence <SEQ ID 143> is:

```
   1 ATGGAGGATT TGCAGGAAAT CGGGTTCGAT GTCGCCGCCG TAAAGGTAGG

51 TCGGCAGCGC GAACATCATC GTCTGCATCA TCCCCAGCCC GGCAACGGCG

101 AGGCGGACGA TGTATTGTTT GCGTTCTTTT TGGTTGGCGG CTTCGATTTT

151 TTGCGCGTCA TAGGGTGCGG CGGTGTAGCC TATCTGCCTG ATTTTCAACA

201 GAATGTCGGA AAGGCGGATT TTGCCGTCGT CCCAGACGAC GCGGCAGCGG

251 TGCGTGCTGT AATTGAGGTC GATGCGGACG ATGCCGTCTG TACGCAAAAG

301 CTGCTGTTCG ATCAGCCAGA CGCAGGCGGC GCAGGTGATG CCGCCGAGCA

351 TTAAAACCGC CTCGCGCGTG CCGCCGTGGG TTTCCACAAA GTCGGACTGG

401 ACTTCGGGCA GGTCGTACAG GCGGATTTGG TCGAGGATTT CTTGGGGCGG

451 CAGCTCGGTT TTTTGCGCGT CGGCGGTGCG TTGTTTGTAA TAACTGCCCA

501 AGCCCGCGTC AATAATGCTT TGTGCGACTG CCTGACAACC GGCGCAGCAG

551 GTTTCGCGGT CTTCGTTTTC GTAACGGACG GTCAGATGCA GGTTTTCGGG

601 AACGTCCAGC CCGCAGTGGA AACAGGTTTT TTTCATGGCA TTTCGGTTTC

651 GTCTGTGTTT GGTGCGGCGG CACAATACTC GGCAATGGCT TCGCGCAGTG

701 CGTCTATACC GGTATTTTCA GCAACGGAAA TGCGGACGGC GGCAATTTTT

751 CCCGCAGCGT CGCGCCATAT GCCCGTGTTT TGTTCTTCAG ACGGCAGCAG

801 GTCGGTTTTG TTGTACACCT TGATGCACGG AATATCGCCG GCATGGATTT

851 CTTGCAGTAC GTTTTCCACG TCTTCAATCT GCTGTCCGCT GTTCGGAGCG

901 GCGGCATCGA CGACGTGCAG CAGCACATCG GCTTGCGCGG TTTCTTCCAG

951 CGTGGCGGAA AAGGCGGAAA TCAGTTTGTG CGGCAGATCG CTGACGAATC

1001 CGACGGTATC GGTCAGGATA ATGCTGCATT CGGGACTGAT GTACAGCCGC

1051 CGCGCCGTCG TGTCGAGTGT GGCGAAAAGC TGGTCTTTCG CATATATGCC

1101 CGACTTGGTC AGCCGGTTGA ACAGACTGGA TTTGCCGACA TTGGTATAG
```

This encodes a protein having amino acid sequence <SEQ ID 144>:

```
   1 MEDLQEIGFD VAAVKVGRQR EHHRLHHPQP GNGEADDVLF AFFLVGGFDF

51 LRVIGCGGVA YLPDFQQNVG KADFAVVPDD AAAVRAVIEV DADDAVCTQK

101 LLFDQPDAGG AGDAAEH*NR LARAAVGFHK VGLDFGQVVQ ADLVEDFLGR

151 QLGFLRVGGA LFVITAQARV NNALCDCLTT GAAGFAVFVF VTDGQMQVFG

201 NVQPAVETGF FHGISVSSVF GAAAQYSAMA SRSASIPVFS ATEMRTAAIF

251 PAASRHMPVF CSSDGSRSVL LYTLMHGISP AWISCSTFST SSICCPLFGA

301 AASTTCSSTS ACAVSSSVAE KAEISLCGRS LTNPTVSVRI MLHSGLMYSR

351 RAVVSSVAKS WSFAYMPDLV SRLNRLDLPT LV*
```

It should be noted that this sequence includes a stop codon at position 118.

Homology with a Predicted ORF from *N. gonorrhoeae*

ORF14 shows 89.8% identity over a 167aa overlap with a predicted ORF (ORF14.ng) from *N. gonorrhoeae*:

```
orf14.pep                         TAGAAGXXVFVFVTDSQVEVFGNIQTAVET  30
                                  || |||  ||:||:|:|::||||:| ||||
orf14ng   GRQFGFFRVGGASFVITAQAGIDDALCDCLTADAAGFAVAVFVADGQMQVFGNVQPAVET 208
orf14.pep GFFHGISVSSVFGAAAQDSAMASRSASIPVFSATEMRTAAIFPAASRHMPVFCSSDGSRS  90
          |||||||||||||||| |||||||||||||||||||||||||||||||||||||||||||
orf14ng   GFFHGISVSSVFGAAAQYSAMASRSASIPVFSATEMRTAAIFPAASRHMPVFCSSDGSRS 268
orf14.pep VLLYTLMHGISPAWISCSTFSTSSICCPLFGAAASTTCSSTSACAVSSSVAEKAEISLCG 150
          |||||||||||| |||||||||||||||||| |||||||||||||:|||:|||||||||
orf14ng   VLLYTLMHGISWAWISCSTFSTSSICCPLFRAAASTTCSSTSACTVSSKVAEKAEISLCG 328
orf14.pep RXLTNPTVSVRIMLHSG                                            167
          | |||||||||||||:|
orf14ng   RSLTNPTVSVRIMLHAGLMYSRRAVVSRVAKSWSFAYMPDLVSRLNRLDLPTLV       382
```

The complete length ORF14ng nucleotide sequence <SEQ ID 145> is predicted to encode a protein having amino acid sequence <SEQ ID 146>:

```
  1 MEDLQEIGFD VAAVKVGRQR EHHRLHHTQS GNGKADDVLF AFFLVGGFDF
 51 LRVIGCGGVA CLPDFQQNVG EADFAVVPDD AAAVRAVIEV DADDAVCAQK
101 LLFDQPDAGG AGNAAEHQHC FVRAIMGFHK VGLDFGQVVQ ADLVEDFLGR
151 QFGFFRVGGA SFVITAQAGI DDALCDCLTA DAAGFAVFAF VADGQMQVFG
201 NVQPAVETGF FHGISVSSVF GAAAQYSAMA SRSASIPVFS ATEMRTAAIF
251 PAASRHMPVF CSSDGSRSVL LYTLMHGISW AWISCSTFST SSICCPLFRA
301 AASTTCSSTS ACTVSSKVAE KAEISLCGRS LTNPTVSVRI MLHAGLMYSR
351 RAVVSRVAKS WSFAYMPDLV SRLNRLDLPT LV*
```

Based on the putative transmembrane domain in the gonococcal protein, it is predicted that the proteins from *N. meningitidis* and *N. gonorrhoeae*, and their epitopes, could be useful antigens for vaccines or diagnostics, or for raising antibodies.

Example 18

The following partial DNA sequence was identified in *N. meningitidis* <SEQ ID 147>:

```
  1 ..GGCCATTACT CCGACCGCAC TTGGAAGCCG CGTTTGGNCG GCCGCCGTCT
 51   GCCGTATCTG CTTTATGGCA CGCTGATTGC GGTTATTGTG ATGATTTTGA
101   TGCCGAACTC GGGCAGCTTC GGTTTCGGCT ATGCGTCGCT GGCGGCTTTG
151   TCGTTCGGCG CGCTGATGAT TGCGCTGTTA GACGTGTCGT CAAATATGGC
201   GATGCAGCCG TTTAAGATGA TGGTCGGCGA CATGGTCAAC GAGGAGCAGA
251   AAA.NTACGC CTACGGGATT CAAAGTTTCT TAGCAAATAC GGGCGCGGTC
301   GTGGCGGCGA TTCTGCCGTT TGTGTTTGCG TATATCGGTT TGGCGAACAC
351   CGCCGANAAA GGCGTTGTGC CGCAGACCGT GGTCGTGGCG TTTTATGTGG
401   GTGCGGCGTT GCTGGTGATT ACCAGCGCGT TCACGATTTT CAAAGTGAAG
451   GAATACGANC CGGAAACCTA CGCCCGTTAC CACGGCATCG ATGTCGCCGC
501   GAATCAGGAA AAAGCCAACT GGATCGCACT CTTAAAA.CC GCGC..
```

This corresponds to the amino acid sequence <SEQ ID 148; ORF16>:

```
  1 ..GHYSDRTWKP RLXGRRLPYL LYGTLIAVIV MILMPNSGSF GFGYASLAAL

51   SFGALMIALL DVSSNMAMQP FKMMVGDMVN EEQKXYAYGI QSFLANTGAV

101   VAAILPFVFA YIGLANTAXK GVVPQTVVVA FYVGAALLVI TSAFTIFKVK

151   EYXPETYARY HGIDVAANQE KANWIALLKX A..
```

Further work revealed the complete nucleotide sequence <SEQ ID 149>:

```
   1 ATGTCGGAAT ATACGCCTCA AACAGCAAAA CAAGGTTTGC CCGCGCTGGC

51 AAAAAGCACG ATTTGGATGC TCAGTTTCGG CTTTCTCGGC GTTCAGACGG

101 CCTTTACCCT GCAAAGCTCG CAAATGAGCC GCATTTTTCA AACGCTAGGC

151 GCAGACCCGC ACAATTTGGG CTGGTTTTTC ATCCTGCCGC CGCTGGCGGG

201 GATGCTGGTG CAGCCGATTG TCGGCCATTA CTCCGACCGC ACTTGGAAGC

251 CGCGTTTGGG CGGCCGCCGT CTGCCGTATC TGCTTTATGG CACGCTGATT

301 GCGGTTATTG TGATGATTTT GATGCCGAAC TCGGGCAGCT TCGGTTTCGG

351 CTATGCGTCG CTGGCGGCTT TGTCGTTCGG CGCGCTGATG ATTGCGCTGT

401 TAGACGTGTC GTCAAATATG GCGATGCAGC CGTTTAAGAT GATGGTCGGC

451 GACATGGTCA ACGAGGAGCA GAAAGGCTAC GCCTACGGGA TTCAAAGTTT

501 CTTAGCAAAT ACGGGCGCGG TCGTGGCGGC GATTCTGCCG TTTGTGTTTG

551 CGTATATCGG TTTGGCGAAC ACCGCCGAGA AAGGCGTTGT GCCGCAGACC

601 GTGGTCGTGG CGTTTTATGT GGGTGCGGCG TTGCTGGTGA TTACCAGCGC

651 GTTCACGATT TTCAAAGTGA AGGAATACGA TCCGGAAACC TACGCCCGTT

701 ACCACGGCAT CGATGTCGCC GCGAATCAGG AAAAAGCCAA CTGGATCGAA

751 CTCTTGAAAA CCGCGCCTAA GGCGTTTTGG ACGGTTACTT TGGTGCAATT

801 CTTCTGCTGG TTCGCCTTCC AATATATGTG GACTTACTCG GCAGGCGCGA

851 TTGCGGAAAA CGTCTGGCAC ACCACCGATG CGTCTTCCGT AGGTTATCAG

901 GAGGCGGGTA ACTGGTACGG CGTTTTGGCG GCGGTGCAGT CGGTTGCGGC

951 GGTGATTTGT TCGTTTGTAT TGGCGAAAGT GCCGAATAAA TACCATAAGG

1001 CGGGTTATTT CGGCTGTTTG GCTTTGGGCG CGCTCGGCTT TTTCTCCGTT

1051 TTCTTCATCG GCAACCAATA CGCGCTGGTG TTGTCTTATA CCTTAATCGG

1101 CATCGCTTGG GCGGGCATTA TCACTTATCC GCTGACGATT GTGACCAACG

1151 CCTTGTCGGG CAAGCATATG GGCACTTACT TGGGCTTGTT TAACGGCTCT

1201 ATCTGTATGC CTCAAATCGT CGCTTCGCTG TTGAGTTTCG TGCTTTTCCC

1251 TATGCTGGGC GGCTTGCAGG CCACTATGTT CTTGGTAGGG GGCGTCGTCC

1301 TGCTGCTGGG CGCGTTTTCC GTGTTCCTGA TTAAAGAAAC ACACGGCGGG

1351 GTTTGA
```

This corresponds to the amino acid sequence <SEQ ID 150; ORF16-1>:

```
  1 MSEYTPQTAK QGLPALAKST IWMLSFGFLG VQTAFTLQSS QMSRIFQTLG

51 ADPHNLGWFF ILPPLAGMLV QPIVGHYSDR TWKPRLGGRR LPYLLYGTLI
```

-continued

```
101  AVIVMILMPN SGSFGFGYAS LAALSFGALM IALLDVSSNM AMQPFKMMVG

151  DMVNEEQKGY AYGIQSFLAN TGAVVAAILP FVFAYIGLAN TAEKGVVPQT

201  VVVAFYVGAA LLVITSAFTI FKVKEYDPET YARYHGIDVA ANQEKANWIE

251  LLKTAPKAFW TVTLVQFFCW FAFQYMWTYS AGAIAENVWH TTDASSVGYQ

301  EAGNWYGVLA AVQSVAAVIC SFVLAKVPNK YHKAGYFGCL ALGALGFFSV

351  FFIGNQYALV LSYTLIGIAW AGIITYPLTI VTNALSGKHM GTYLGLFNGS

401  ICMPQIVASL LSFVLFPMLG GLQATMFLVG GVVLLLGAFS VFLIKETHGG

451  V*
```

Computer analysis of this amino acid sequence gave the following results:

Homology with a Predicted ORF from *N. meningitidis* (Strain A)

ORF16 shows 96.7% identity over a 181aa overlap with an ORF (ORF16a) from strain A of *N. meningitidis*:

```
                                       10         20         30
    orf16.pep                    GHYSDRTWKPRLXGRRLPYLLYGTLIAVIV
                                 ||||||||||||| ||||||||||||||||
    orf16a    IFQTLGADPHSLGWFFILPPLAGMLVQPIVGHYSDRTWKPRLGGRRLPYLLYGTLIAVIV
                    50        60        70        80        90       100
                    40        50        60        70        80        90
    orf16.pep MILMPNSGSFGFGYASLAALSFGALMIALLDVSSNMAMQPFKMMVGDMVNEEQKXYAYGI
              |||||||||||||||||||||||||||||||||||||||||||||||||||||| |||||
    orf16a    MILMPNSGSFGFGYASLAALSFGALMIALLDVSSNMAMQPFKMMVGDMVNEEQKGYAYGI
                   110       120       130       140       150       160
                   100       110       120       130       140       150
    orf16.pep QSFLANTGAVVAAILPFVFAYIGLANTAXKGVVPQTVVVAFYVGAALLVITSAFTIFKVK
              |||||||||||||||||||||||||||||| |||||||||||||||||||||||||||||
    orf16a    QSFLANTGAVVAAILPFVFAYIGLANTAEKGVVPQTVVVAFYVGAALLVITSAFTIFKVK
                   170       180       190       200       210       220
                   160       170       180
    orf16.pep EYXPETYARYHGIDVAANQEKANWIALLKXA
              || ||||||||||||||||||||||| :|
    orf16a    EYNPETYARYHGIDVAANQEKANWIELLKTAPKAFWTVTLVQFFCWFAFQYMWTYSAGAI
                   230       240       250       260       270       280
    orf16a    AENVWHTTDASSVGYQEAGNWYGVLAAVQSVAAVICSFVLAKVPNKYHKAGYFGCLALGA
                   290       300       310       320       330       340
```

The complete length ORF16a nucleotide sequence <SEQ ID 151> is:

```
  1  ATGTCGGAAT ATACGCCTCA AACAGCAAAA CAAGGTTTGC CCGCGCTGGC

51  AAAAAGCACG ATTTGGATGC TCAGTTTCGG CTTTCTCGGC GTTCAGACGG

101  CCTTTACCCT GCAAAGCTCG CAGATGAGCC GCATCTTCCA GACGCTCGGT

151  GCCGATCCGC ACAGCCTCGG CTGGTTCTTT ATCCTGCCGC CGCTGGCGGG

201  GATGCTGGTG CAGCCGATTG TCGGCCATTA CTCCGACCGC ACTTGGAAGC

251  CGCGTTTGGG CGGCCGCCGT CTGCCGTATC TGCTTTATGG CACGCTGATT

301  GCGGTTATTG TGATGATTTT GATGCCGAAC TCGGGCAGCT TCGGTTTCGG

351  CTATGCGTCG CTGGCGGCTT TGTCGTTCGG CGCGCTGATG ATTGCGCTGT

401  TAGACGTGTC GTCAAATATG GCGATGCAGC CGTTTAAGAT GATGGTCGGC

451  GACATGGTCA ACGAGGAGCA GAAAGGCTAC GCCTACGGGA TTCAAAGTTT

501  CTTAGCGAAT ACGGGCGCGG TCGTGGCGGC GATTCTGCCG TTTGTGTTTG

551  CGTATATCGG TTTGGCGAAC ACCGCCGAGA AAGGCGTTGT GCCGCAGACC
```

-continued

```
 601 GTGGTCGTGG CGTTTTATGT GGGTGCGGCG TTGCTGGTGA TTACCAGCGC

651 GTTCACGATT TTCAAAGTGA AGGAATACAA TCCGGAAACC TACGCCCGTT

701 ACCACGGCAT CGATGTCGCC GCGAATCAGG AAAAAGCCAA CTGGATCGAA

751 CTCTTGAAAA CCGCGCCTAA GGCGTTTTGG ACGGTTACTT TGGTGCAATT

801 CTTCTGCTGG TTCGCCTTCC AATATATGTG GACTTACTCG GCAGGCGCGA

851 TTGCGGAAAA CGTCTGGCAC ACCACCGATG CGTCTTCCGT AGGTTATCAG

901 GAGGCGGGTA ACTGGTACGG CGTTTTGGCG GCGGTGCAGT CGGTTGCGGC

951 GGTGATTTGT TCGTTTGTAT TGGCGAAAGT GCCGAATAAA TACCATAAGG

1001 CGGGTTATTT CGGCTGTTTG GCTTTGGGCG CGCTCGGCTT TTTCTCCGTT

1051 TTCTTCATCG GCAACCAATA CGCGCTGGTG TTGTCTTATA CCTTAATCGG

1101 CATCGCTTGG GCGGGCATTA TCACTTATCC GCTGACGATT GTGACCAACG

1151 CCTTGTCGGG CAAGCATATG GGCACTTACT TGGGCCTGTT TAACGGCTCT

1201 ATCTGTATGC CGCAAATCGT CGCTTCGCTG TTGAGTTTCG TGCTTTTCCC

1251 TATGCTGGGC GGCTTGCAGG CCACTATGTT CTTGGTAGGG GGCGTCGTCC

1301 TGCTGCTGGG CGCGTTTTCC GTGTTCCTGA TTAAAGAAAC ACACGGCGGG

1351 GTTTGA
```

This encodes a protein having amino acid sequence <SEQ ID 152>:

```
  1 MSEYTPQTAK QGLPALAKST IWMLSFGFLG VQTAFTLQSS QMSRIFQTLG

51 ADPHSLGWFF ILPPLAGMLV QPIVGHYSDR TWKPRLGGRR LPYLLYGTLI

101 AVIVMILMPN SGSFGFGYAS LAALSFGALM IALLDVSSNM AMQPFKMMVG

151 DMVNEEQKGY AYGIQSFLAN TGAVVAAILP FVFAYIGLAN TAEKGVVPQT

201 VVVAFYVGAA LLVITSAFTI FKVKEYNPET YARYHGIDVA ANQEKANWIE

251 LLKTAPKAFW TVTLVQFFCW FAFQYMWTYS AGAIAENVWH TTDASSVGYQ

301 EAGNWYGVLA AVQSVAAVIC SFVLAKVPNK YHKAGYFGCL ALGALGFFSV

351 FFIGNQYALV LSYTLIGIAW AGIITYPLTI VTNALSGKHM GTYLGLFNGS

401 ICMPQIVASL LSFVLFPMLG GLQATMFLVG GVVLLLGAFS VFLIKETHGG

451 V*
```

ORF16a and ORF16-1 show 99.6% identity in 451 aa overlap:

```
                   10         20         30         40         50         60
orf16a.pep MSEYTPQTAKQGLPALAKSTIWMLSFGFLGVQTAFTLQSSQMSRIFQTLGADPHSLGWFF
           ||||||||||||||||||||||||||||||||||||||||||||||||||||:|||||
orf16-1    MSEYTPQTAKQGLPALAKSTIWMLSFGFLGVQTAFTLQSSQMSRIFQTLGADPHNLGWFF
                   10         20         30         40         50         60

70         80         90        100        110        120
orf16a.pep ILPPLAGMLVQPIVGHYSDRTWKPRLGGRRLPYLLYGTLIAVIVMILMPNSGSFGFGYAS
           ||||||||||||||||||||||||||||||||||||||||||||||||||||||||||||
orf16-1    ILPPLAGMLVQPIVGHYSDRTWKPRLGGRRLPYLLYGTLIAVIVMILMPNSGSFGFGYAS
                   70         80         90        100        110        120

130        140        150        160        170        180
orf16a.pep LAALSFGALMIALLDVSSNMAMQPFKMMVGDMVNEEQKGYAYGIQSFLANTGAVVAAILP
           ||||||||||||||||||||||||||||||||||||||||||||||||||||||||||||
orf16-1    LAALSFGALMIALLDVSSNMAMQPFKMMVGDMVNEEQKGYAYGIQSFLANTGAVVAAILP
                  130        140        150        160        170        180
```

```
                        190       200       210       220       230       240
   orf16a.pep  FVFAYIGLANTAEKGVVPQTVVVAFYVGAALLVITSAFTIFKVKEYNPETYARYHGIDVA
               ||||||||||||||||||||||||||||||||||||||||||||:||||||||||||||
   orf16-1     FVFAYIGLANTAEKGVVPQTVVVAFYVGAALLVITSAFTIFKVKEYDPETYARYHGIDVA
                        190       200       210       220       230       240
                        250       260       270       280       290       300
   orf16a.pep  ANQEKANWIELLKTAPKAFWTVTLVQFFCWFAFQYMWTYSAGAIAENVWHTTDASSVGYQ
               ||||||||||||||||||||||||||||||||||||||||||||||||||||||||||||
   orf16-1     ANQEKANWIELLKTAPKAFWTVTLVQFFCWFAFQYMWTYSAGAIAENVWHTTDASSVGYQ
                        250       260       270       280       290       300
                        310       320       330       340       350       360
   orf16a.pep  EAGNWYGVLAAVQSVAAVICSFVLAKVPNKYHKAGYFGCLALGALGFFSVFFIGNQYALV
               ||||||||||||||||||||||||||||||||||||||||||||||||||||||||||||
   orf16-1     EAGNWYGVLAAVQSVAAVICSFVLAKVPNKYHKAGYFGCLALGALGFFSVFFIGNQYALV
                        310       320       330       340       350       360
                        370       380       390       400       410       420
   orf16a.pep  LSYTLIGIAWAGIITYPLTIVTNALSGKHMGTYLGLFNGSICMPQIVASLLSFVLFPMLG
               ||||||||||||||||||||||||||||||||||||||||||||||||||||||||||||
   orf16-1     LSYTLIGIAWAGIITYPLTIVTNALSGKHMGTYLGLFNGSICMPQIVASLLSFVLFPMLG
                        370       380       390       400       410       420
                        430       440       450
   orf16a.pep  GLQATMFLVGGVVLLLGAFSVFLIKETHGGVX
               ||||||||||||||||||||||||||||||||
   orf16-1     GLQATMFLVGGVVLLLGAFSVFLIKETHGGVX
                        430       440       450
```

Homology with a Predicted ORF from *N. gonorrhoeae*

ORF16 shows 93.9% identity over a 181aa overlap with a predicted ORF (ORF16.ng) from *N. gonorrhoeae*.

```
   orf16.pep                                           GHYSDRTWKPRLXGRRLPYLLYGTLIAVIV    30
                                                       |:|||||||||  |||||||||||||||||
   orf16ng    HFSNARRRPAQFGLVFHPAAAGGDAGSADSGYYSDRTWKPRLGGRRLPYLLYGTLIAVIV   131 orf16.pep  MILMPNSGSFGFGYASLAALSFGALMIALLDVSSNMAMQPFKMMVGDMVNEEQKXYAYGI    90
              ||||||||||||||||||||||||||||||||||||||||||||||||||||||| ||||
   orf16ng    MILMPNSGSFGFGYASLAALSFGALMIALLDVSSNMAMQPFKMMVGDMVNEEQKSYAYGI   191 orf16.pep  QSFLANTGAVVAAILPFVFAYIGLANTAXKGVVPQTVVVAFYVGAALLVITSAFTIFKVK   150
              |||||| ||||||||||||||||||||| |||||||||||||||||||:|||||  |||
   orf16ng    QSFLANTDAVVAAILPFVFAYIGLANTAEKGVVPQTVVVAFYVGAALLIITSAFTISKVK   251 orf16.pep  EYXPETYARYHGIDVAANQEKANWIALLKXA                                181
              ||  ||||||||||||||||||||||||:  |||:|
   orf16ng    EYDPETYARYHGIDVAANQEKANWFELLKTAPKVFWTVTPVQFFCWFAFRYMWTYSAGAI   311
```

The complete length ORF16ng nucleotide sequence <SEQ ID 153> is:

```
   1  ATGATAGGGG ATCGCCGCGC CGGCAACCAT TTCGGATTTT CCAAAGCAAA

51  TACTTTTCAA ATCAAAAAAA AGGATTTACT TTATGTCGGA ATATACGCCT

101  CAAACAGCAA AACAAGGTTT GCCCGCGCCG GCAAAAAGCA CGATTTGGAT

151  GTTGAGCTTC GGCTATCTCG GCGTTCAGAC GGCCTTTACC CTGCAAAGCT

201  CGCAGATGAG CCGCATTTTT CAAACGCTAG GCGCAGACCC GCACAATTTG

251  GGCTGGTTTT TCATCCTGCC GCCGCTGGCG GGGATGCTGG TTCAGCCGAT

301  AGTGGCTACT ACTCAGACCG CACTTGGAAG CCGCGCTTGG GCGGCCGCCG

351  CCTGCCGTAT CTGCTTTACG GCACGCTGAT TGCGGTCATC GTGATGATTT

401  TGATGCCGAA CTCGGGCAGC TTCGGTTTCG GCTATGCGTC GCTGGCGGCC

451  TTGTCGTTCG GCGCGCTGAT GATTGCGCTG TTGGACGTGT CGTCGAATAT

501  GGCGATGCAG CCGTTTAAGA TGATGGTCGG CGATATGGTC AACGAGGAGC

551  AGAAAAGCTA CGCCTACGGG ATTCAAAGTT TCTTAGCGAA TACGGACGCG

601  GTTGTGGCAG CGATTCTGCC GTTTGTGTTC GCGTATATCG GTTTGGCGAA

651  CACTGCCGAG AAAGGCGTTG TGCCACAAAC CGTGGTCGTA GCATTCTATG
```

```
 701 TGGGTGCGGC GTTACTGATT ATTACCAGTG CGTTCACAAT CTCCAAAGTC

751 AAAGAATACG ACCCGGAAAC CTACGCCCGT TACCACGGCA TCGATGTCGC

801 CGCGAATCAG GAAAAAGCCA ACTGGTTCGA ACTCTTAAAA ACCGCGCCTA

851 AAGTGTTTTG GACGGTTACT CCGGTACAGT TTTTCTGCTG GTTCGCCTTC

901 CGGTATATGT GGACTTACTC GGCAGGCGCG ATTGCAGAAA ACGTCTGGCA

951 CACTACCGAT GCGTCTTCCG TAGGCCATCA GGAGGCGGGC AACCGGTACG

1001 GCGTTTTGGC GGCGGTGTAG
```

This encodes a protein having amino acid sequence <SEQ ID 154>:

```
  1 MIGDRRAGNH FGFSKANTFQ IKKKDLLYVG IYASNSKTRF ARAGKKHDLD

51 VELRLSRRSD GLYPAKLADE PHFSNARRRP AQFGLVFHPA AAGGDAGSAD

101 SGYYSDRTWK PRLGGRRLPY LLYGTLIAVI VMILMPNSGS FIGFGYASLAA

151 LSFGALMIAL LDVSSNMAMQ PFKMMVGDMV NEEQKSYAYG IQSFLANTDA

201 VVAAILPFVF AYIGLANTAE KGVVPQTVVV AFYVGAALLI ITSAFTISKV

251 KEYDPETYAR YHGIDVAANQ EKANWFELLK TAPKVFWTVT PVQFFCWFAF

301 RYMWTYSAGA IAENVWHTTD ASSVGHQEAG NRYGVLAAV*
```

ORF16ng and ORF16-1 show 89.3% identity in 261 aa overlap:

```
                      30        40        50        60        70        80
   orf16-1.pep  MLSFGFLGVQTAFTLQSSQMSRIFQTLGADPHNLGWFFILPPLAGMLVQPI-VGHYSDRT
                              |::|  |   |   ||   :    |:|||||
   orf16ng           DVELRLSRRSDGLYPAKLADEPHFSNARRRPAQFGLVF-HPAAAGGDAGSADSGYYSDRT
                    50        60        70        80        90       100

90       100       110       120       130       140
   orf16-1.pep  WKPRLGGRRLPYLLYGTLIAVIVMILMPNSGSFGFGYASLAALSFGALMIALLDVSSNMA
                ||||||||||||||||||||||||||||||||||||||||||||||||||||||||||||
   orf16ng      WKPRLGGRRLPYLLYGTLIAVIVMILMPNSGSFGFGYASLAALSFGALMIALLDVSSNMA
                   110       120       130       140       150       160

150       160       170       180       190       200
   orf16-1.pep  MQPFKMMVGDMVNEEQKGYAYGIQSFLANTGAVVAAILPFVFAYIGLANTAEKGVVPQTV
                ||||||||||||||||| :|||||||||||  ||||||||||||||||||||||||||||
   orf16ng      MQPFKMMVGDMVNEEQKSYAYGIQSFLANTDAVVAAILPFVFAYIGLANTAEKGVVPQTV
                   170       180       190       200       210       220

210       220       230       240       250       260
   orf16-1.pep  VVAFYVGAALLVITSAFTIFKVKEYDPETYARYHGIDVAANQEKANWIELLKTAPKAFWT
                |||||||||||:||||||| |||||||||||||||||||||||||||| ||||||:|||
   orf16ng      VVAFYVGAALLIITSAFTISKVKEYDPETYARYHGIDVAANQEKANWFELLKTAPKVFWT
                   230       240       250       260       270       280

270       280       290       300       310       320
   orf16-1.pep  VTLVQFFCWFAFQYMWTYSAGAIAENVWHTTDASSVGYQEAGNWYGVLAAVQSVAAVICS
                || ||||||||||:|||||||||||||||||||||||:||||| |||||||
   orf16ng      VTPVQFFCWFAFRYMWTYSAGAIAENVWHTTDASSVGHQEAGNRYGVLAAVX
                   290       300       310       320       330       340
```

Based on this analysis, including the presence of several putative transmembrane domains in the gonococcal protein, it is predicted that the proteins from *N. meningitidis* and *N. gonorrhoeae*, and their epitopes, could be useful antigens for vaccines or diagnostics, or for raising antibodies.

Example 19

The following partial DNA sequence was identified in *N. meningitidis* <SEQ ID 155>:

```
  1 ATGTTGTTCC GTAAAACGAC CGCCGCCGTT TTGGCGCATA CCTTGATGCT
 51 GAACGGCTGT ACGTTGATGT TGTGGGGAAT GAACAACCCG GTCAGCGAAA
101 CAATCACCCG NAAACACGTT GNCAAAGACC AAATCCGNGN CTTCGGTGTG
151 GTTGCCGAAG ACAATGCCCA ATTGGAAAAG GGCAGCCTGG TGATGATGGG
201 CGGAAAATAC TGGTTCGTCG TCAATCCCGA AGATTCGGCG AA.NTGACGG
251 GNATTTTGAN GGCAGGGCTG GACAAACCCT TCCAAATAGT TNAGGATACC
301 CCGAGCTATG C.TGCCACCA AGCCCTGCCG GTCAAACTCG GATCGNCTGG
351 CAGCCAGAAT...
```

This corresponds to the amino acid sequence <SEQ ID 156; ORF28>:

```
  1 MLFRKTTAAV LAHTLMLNGC TLMLWGMNNP VSETITRKHV XKDQIRXFGV
 51 VAEDNAQLEK GSLVMMGGKY WFVVNPEDSA XXTGILXAGL DKPFQIVXDT
101 PSYXCHQALP VKLGSXGSQN...
```

Further work revealed the complete nucleotide sequence <SEQ ID 157>:

```
  1 ATGTTGTTCC GTAAAACGAC CGCCGCCGTT TTGGCGGCAA CCTTGATGCT
 51 GAACGGCTGT ACGTTGATGT TGTGGGGAAT GAACAACCCG GTCAGCGAAA
101 CAATCACCCG CAAACACGTT GACAAAGACC AAATCCGCGC CTTCGGTGTG
151 GTTGCCGAAG ACAATGCCCA ATTGGAAAAG GGCAGCCTGG TGATGATGGG
201 CGGAAAATAC TGGTTCGTCG TCAATCCCGA AGATTCGGCG AAGCTGACGG
251 GCATTTTGAA GGCAGGGCTG GACAAACCCT TCCAAATAGT TGAGGATACC
301 CCGAGCTATG CTCGCCACCA AGCCCTGCCG GTCAAACTCG AATCGCCTGG
351 CAGCCAGAAT TTCAGTACCG AAGGCCTTTG CCTGCGCTAC GATACCGACA
401 AGCCTGCCGA CATCGCCAAG CTGAAACAGC TCGGGTTTGA AGCGGTCAAA
451 CTCGACAATC GGACCATTTA CACGCGCTGC GTATCCGCCA AAGGCAAATA
501 CTACGCCACA CCGCAAAAAC TGAACGCCGA TTACCATTTT GAGCAAAGTG
551 TGCCTGCCGA TATTTATTAC ACGGTTACTG AAGAACATAC CGACAAATCC
601 AAGCTGTTTG CAAATATCTT ATATACGCCC CCCTTTTTGA TACTGGATGC
651 GGCGGGCGCG GTACTGGCCT TGCCTGCGGC GGCTCTGGGT GCGGTCGTGG
701 ATGCCGCCCG CAAATGA
```

This corresponds to the amino acid sequence <SEQ ID 158; ORF28-1>:

```
  1 MLFRKTTAAV LAATLMLNGC TLMLWGMNNP VSETITRKHV DKDQIRAFGV
 51 VAEDNAQLEK GSLVMMGGKY WFVVNPEDSA KLTGILKAGL DKPFQIVEDT
101 PSYARHQALP VKLESPGSQN FSTEGLCLRY DTDKPADIAK LKQLGFEAVK
```

```
151 LDNRTIYTRC VSAKGKYYAT PQKLNADYHF EQSVPADIYY TVTEEHTDKS

201 KLFANILYTP PFLILDAAGA VLALPAAALG AVVDAARK*
```

Computer analysis of this amino acid sequence gave the following results:

Homology with a Predicted ORF from *N. meningitidis* (Strain A)

ORF28 shows 79.2% identity over a 120aa overlap with an ORF (ORF28a) from strain A of *N. meningitidis*:

```
                     10         20         30         40         50         60
orf28.pep    MLFRKTTAAVLAHTLMLNGCTLMWGMNNPVSETITRKHVXKDQIRXFGVVAEDNAQLEK
             |||||||||||| ||||||||:|:|||||| ||| :|||||||||| ||||||||||||
orf28a       MLFRKTTAAVLAATLMLNGCTVMMWGMNSPFSETTARKHVDKDQIRAFGVVAEDNAQLEK
                     10         20         30         40         50         60

70         80         90        100        110        120
orf28.pep    GSLVMMGGKYWFVVNPEDSAXXTGILXAGLDKPFQIVXDTPSYXCHQALPVKLGSXGSQN
             |||||||||||||||||||| |||| ||||||| ||:|  :|:   : :||||||| :||
orf28a       GSLVMMGGKYWFVVNPEDSAKLTGILKAGLDKQFQMVEPNPRFA-YQALPVKLESPASQN
                     70         80         90        100        110 orf28a       FSTEGLCLRYDTDRPADIAKLKQLEFEAVELDNRTIYTRCVSAKGKYYATPQKLNADYHF
                    120        130        140        150        160        170
```

The complete length ORF28a nucleotide sequence <SEQ ID 159> is:

```
  1 ATGTTGTTCC GTAAAACGAC CGCCGCCGTT TTGGCGGCAA CCTTGATGTT

51 GAACGGCTGT ACGGTAATGA TGTGGGGTAT GAACAGCCCG TTCAGCGAAA

101 CGACCGCCCG CAAACACGTT GACAAGGACC AAATCCGCGC CTTCGGTGTG

151 GTTGCCGAAG ACAATGCCCA ATTGGAAAAG GGCAGCCTGG TGATGATGGG

201 CGGGAAATAC TGGTTCGTCG TCAATCCTGA AGATTCGGCG AAGCTGACGG

251 GCATTTTGAA GGCCGGGTTG GACAAGCAGT TCAAATGGT TGAGCCCAAC

301 CCGCGCTTTG CCTACCAAGC CCTGCCGGTC AAACTCGAAT CGCCCGCCAG

351 CCAGAATTTC AGTACCGAAG GCCTTTGCCT GCGCTACGAT ACCGACAGAC

401 CTGCCGACAT CGCCAAGCTG AAACAGCTTG AGTTTGAAGC GGTCGAACTC

451 GACAATCGGA CCATTTACAC GCGCTGCGTC TCCGCCAAAG GCAAATACTA

501 CGCCACACCG CAAAAACTGA ACGCCGATTA TCATTTTGAG CAAAGTGTGC

551 CTGCCGATAT TTATTACACG GTTACGAAAA AACATACCGA CAAATCCAAG

601 TTGTTTGAAA ATATTGCATA TACGCCCACC ACGTTGATAC TGGATGCGGT

651 GGGCGCGGTG CTGGCCTTGC CTGTCGCGGC GTTGATTGCA GCCACGAATT

701 CCTCAGACAA ATGA
```

This encodes a protein having amino acid sequence <SEQ ID 160>:

```
  1 MLFRKTTAAV LAATLMLNGC TVMMWGMNSP FSETTARKHV DKDQIRAFGV

51 VAEDNAQLEK GSLVMMGGKY WFVVNPEDSA KLTGILKAGL DKQFQMVEPN

101 PRFAYQALPV KLESPASQNF STEGLCLRYD TDRPADIAKL KQLEFEAVEL

151 DNRTIYTRCV SAKGKYYATP QKLNADYHFE QSVPADIYYT VTKKHTDKSK

201 LFENIAYTPT TLILDAVGAV LALPVAALIA ATNSSDK*
```

ORF28a and ORF28-1 show 86.1% identity in 238 aa overlap:

```
                 10        20        30        40        50        60
orf28a.pep  MLFRKTTAAVLAATLMLNGCTVMMWGMNSPFSETTARKHVDKDQIRAFGVVAEDNAQLEK
            ||||||||||||||||||||||:|:||||:|  |||  :||||||||||||||||||||||
orf28-1     MLFRKTTAAVLAATLMLNGCTLMLWGMNNPVSETITRKHVDKDQIRAFGVVAEDNAQLEK
                 10        20        30        40        50        60

70        80        90       100       110       119
orf28a.pep  GSLVMMGGKYWFVVNPEDSAKLTGILKAGLDKQFQMVEPNPRFA-YQALPVKLESPASQN
            |||||||||||||||||||||||||||||||| ||:|| :| :|:||||||||||:|||
orf28-1     GSLVMMGGKYWFVVNPEDSAKLTGILKAGLDKPFQIVEDTPSYARHQALPVKLESPGSQN
                 70        80        90       100       110       120

120       130       140       150       160       170       179
orf28a.pep  FSTEGLCLRYDTDRPADIAKLKQLEFEAVELDNRTIYTRCVSAKGKYYATPQKLNADYHF
            |||||||||||||:|||||||||||||:||||||||||||||||||||||||||||||||
orf28-1     FSTEGLCLRYDTDKPADIAKLKQLGFEAVKLDNRTIYTRCVSAKGKYYATPQKLNADYHF
                130       140       150       160       170       180

180       190       200       210       220       230
orf28a.pep  EQSVPADIYYTVTKKHTDKSKLFENIAYTPTTLILDAVGAVLALPVAALIAATNSSDKX
            ||||||||||||||::||||||||||:|| |||  |||||||||||::::::||
orf28-1     EQSVPADIYYTVTEEHTDKSKLFANILYTPPPLILDAAGAVLALPAAALGAVVDAARKX
                190       200       210       220       230
```

Homology with a Predicted ORF from *N. gonorrhoeae*

ORF28 shows 84.2% identity over a 120aa overlap with a predicted ORF (ORF28.ng) from *N. gonorrhoeae*:

```
orf28.pep   MLFRKTTAAVLAHTLMLNGCTLMLWGMNNPVSETITRKHVXKDQIRXFGVVAEDNAQLEK 60
            |||||||||||| ||:||||:||  |||||||:|||||| |||| ||||||||||||||
orf28ng     MLFRKTTAAVLAATLILNGCTMMLRGMNNPVSQTITRKHVDKDQIRAFGVVAEDNAQLEK 60 orf28.pep   GSLVMMGGKYWFVVNPEDSAXXTGILXAGLDKPFQIVXDTPSYXCHQALPVKLGSXGSQN 120
            |||||||||||||:|||||||  ||:| |||||||||| |||||  |||||||: : |||
orf28ng     GSLVMMGGKYWFAVNPEDSAKLTGLLKAGLDKPFQIVEDTPSYARHQALPVKFEAPGSQN 120
```

The complete length ORF28ng nucleotide sequence <SEQ ID 161> is

```
  1 ATGTTGTTCC GTAAAACGAC CGCCGCCGTT TTGGCGGCAA CCTTGATACT

51 GAACGGCTGT ACGATGATGT TGCGGGGGAT GAACAACCCG GTCAGCCAAA

101 CAATCACCCG CAAACACGTT GACAAAGACC AAATCCGCGC CTTCGGTGTG

151 GTTGCCGAAG ACAATGCCCA ATTGGAAAAG GGCAGCCTGG TGATGATGGG

201 CGGGAAATAC TGGTTCGCCG TCAATCCCGA AGATTCGGCG AAGCTGACGG

251 GCCTTTTGAA GGCCGGGTTG GACAAGCCCT TCCAAATAGT TGAGGATACC

301 CCGAGCTATG CCCGCCACCA AGCCCTGCCG GTCAAATTCG AAGCGCCCGG

351 CAGCCAGAAT TTCAGTACCG GAGGTCTTTG CCTGCGCTAT GATACCGGCA

401 GACCTGACGA CATCGCCAAG CTGAAACAGC TTGAGTTTAA AGCGGTCAAA

451 CTCGACAATC GGACCATTTA CACGCGCTGC GTATCCGCCA AAGGCAAATA

501 CTACGCCACG CCGCAAAAAC TGAACGCCGA TTATCATTTT GAGCAAAGTG

551 TGCCCGCCGA TATTTATTAT ACGGTTACTG AAAAACATAC CGACAAATCC

601 AAGCTGTTTG AAATATCTT ATATACGCCC CCCTTGTTGA TATTGGATGC

651 GGCGGCCGCG GTGCTGGTCT TGCCTATGGC TCTGATTGCA GCCGCGAATT

701 CCTCAGACAA ATGA
```

This encodes a protein having amino acid sequence <SEQ ID 162>:

```
  1 MLFRKTTAAV LAATLILNGC TMMLRGMNNP VSQTITRKHV DKDQIRAFGV

51 VAEDNAQLEK GSLVMMGGKY WFAVNPEDSA KLTGLLKAGL DKPFQIVEDT

101 PSYARHQALP VKFEAPGSQN FSTGGLCLRY DTGRPDDIAK LKQLEFKAVK

151 LDNRTIYTRC VSAKGKYYAT PQKLNADYHF EQSVPADIYY TVTEKHTDKS

201 KLFGNILYTP PLLILDAAAA VLVLPMALIA AANSSDK*
```

ORF28ng and ORF28-1 share 90.0% identity in 231 aa overlap:

```
                   10         20         30         40         50         60
     orf28-1.pep  MLFRKTTAAVLAATLMLNGCTLMLWGMNNPVSETITRKHVDKDQIRAFGVVAEDNAQLEK
                  ||||||||||||||||:|||||:|| ||||||||:||||||||||||||||||||||||
     orf28ng      MLFRKTTAAVLAATLILNGCTMMLRGMNNPVSQTITRKHVDKDQIRAFGVVAEDNAQLEK
                   10         20         30         40         50         60
                   70         80         90        100        110        120
     orf28-1.pep  GSLVMMGGKYWFVVNPEDSAKLTGILKAGLDKPFQIVEDTPSYARHQALPVKLESPGSQN
                  ||||||||||||:||||||||||||:||||||||||||||||||||||||||||||||||
     orf28ng      GSLVMMGGKYWFAVNPEDSAKLTGLLKAGLDKPFQIVEDTPSYARHQALPVKFEAPGSQN
                   70         80         90        100        110        120
                  130        140        150        160        170        180
     orf28-1.pep  FSTEGLCLRYDTDKPADIAKLKQLGFEAVKLDNRTIYTRCVSAKGKYYATPQKLNADYHF
                  ||| |||||||| :| ||||||||| |:|||||||||||||||||||||||||||||||
     orf28ng      FSTGGLCLRYDTGRPDDIAKLKQLEFKAVKLDNRTIYTRCVSAKGKYYATPQKLNADYHF
                  130        140        150        160        170        180
                  190        200        210        220        230        239
     orf28-1.pep  EQSVPADIYYTVTEEHTDKSKLFANILYTPPFLILDAAGAVLALPAAALGAVVDAARKX
                  ||||||||||||||:||||||||| :||||||:||||||:|||||:|| |  ::|:
     orf28ng      EQSVPADIYYTVTEKHTDKSKLFGNILYTPPLLILDAAAAVLVLPMALIAAANSSDKX
                  190        200        210        220        230
```

Based on this analysis, including the presence of a putative transmembrane domain in the gonococcal protein, it was predicted that the proteins from *N. meningitidis* and *N. gonorrhoeae*, and their epitopes, could be useful antigens for vaccines or diagnostics, or for raising antibodies.

ORF28-1 (24 kDa) was cloned in pET and pGex vectors and expressed in *E. coli*, as described above. The products of protein expression and purification were analyzed by SDS-PAGE. FIG. 6A shows the results of affinity purification of the GST-fusion protein, and FIG. 6B shows the results of expression of the His-fusion in *E. coli*. Purified GST-fusion protein was used to immunise mice, whose sera were used for ELISA, which gave a positive result. These experiments confirm that ORF28-1 is a surface-exposed protein, and that it may be a useful immunogen.

Example 20

The following partial DNA sequence was identified in *N. meningitidis* <SEQ ID 163>:

```
  1 ..GTCAGTCCTG TACTGCCTAT TACACACGAA CGGACAGGGT TTGAAGGTGT

51 TATCGGTTAT GAAACCCATT TTTCAGGGCA CGGACATGAA GTACACAGTC

101 CGTTCGATCA TCATGATTCA AAAAGCACTT CTGATTTCAG CGGCGGTGTA

151 GACGGCGGTT TTACTGTTTA CCAACTTCAT CGAACATGGT CGGAAATCCA

201 TCCGGAGGAT GAATATGACG GGCCGCAAGC AGCG.ATTAT CCGCCCCCCG
```

-continued
```
251  GAGGAGCAAG GGATATATAC AGCTATTATG TCAAAGGAAC TTCAACAAAA

301  ACAAAGACTA GTATTGTCCC TCAAGCCCCA TTTTCAGACC GTTGGCTAGA

351  AGAAAATGCC GGTGCCGCCT CTGGT..
```

This corresponds to the amino acid sequence <SEQ ID 164; ORF29>:

```
  1..VSPVLPITHE RTGFEGVIGY ETHFSGHGHE VHSPFDHHDS KSTSDFSGGV

51  DGGFTVYQLH RTWSEIHPED EYDGPQAAXY PPPGGARDIY SYYVKGTSTK

101  TKTSIVPQAP FSDRWLEENA GAASG..
```

Further work revealed the complete nucleotide sequence <SEQ ID 165>:

```
   1 ATGAATTTGC CTATTCAAAA ATTCATGATG CTGTTTGCAG CAGCAATATC

51 GTTGCTGCAA ATCCCCATTA GTCATGCGAA CGGTTTGGAT GCCCGTTTGC

101 GCGATGATAT GCAGGCAAAA CACTACGAAC CGGGTGGTAA ATACCATCTG

151 TTTGGTAATG CTCGCGGCAG TGTTAAAAAG CGGGTTTACG CCGTCCAGAC

201 ATTTGATGCA ACTGCGGTCA GTCCTGTACT GCCTATTACA CACGAACGGA

251 CAGGGTTTGA AGGTGTTATC GGTTATGAAA CCCATTTTTC AGGGCACGGA

301 CATGAAGTAC ACAGTCCGTT CGATCATCAT GATTCAAAAA GCACTTCTGA

351 TTTCAGCGGC GGTGTAGACG GCGGTTTTAC TGTTTACCAA CTTCATCGAA

401 CAGGGTCGGA AATCCATCCG GAGGATGGAT ATGACGGGCC GCAAGGCAGC

451 GATTATCCGC CCCCCGGAGG AGCAAGGGAT ATATACAGCT ATTATGTCAA

501 AGGAACTTCA ACAAAAACAA AGACTAATAT TGTCCCTCAA GCCCCATTTT

551 CAGACCGTTG GCTAAAAGAA AATGCCGGTG CCGCCTCTGG TTTTTTCAGC

601 CGTGCGGATG AAGCAGGAAA ACTGATATGG GAAAGCGACC CCAATAAAAA

651 TTGGTGGGCT AACCGTATGG ATGATGTTCG CGGCATCGTC CAAGGTGCGG

701 TTAATCCTTT TTTAATGGGT TTTCAAGGAG TAGGGATTGG GGCAATTACA

751 GACAGTGCAG TAAGCCCGGT CACAGATACA GCCGCGCAGC AGACTCTACA

801 AGGTATTAAT GATTTAGGAA AATTAAGTCC GGAAGCACAA CTTGCTGCCG

851 CGAGCCTATT ACAGGACAGT GCTTTTGCGG TAAAAGACGG TATCAACTCT

901 GCCAAACAAT GGGCTGATGC CCATCCAAAT ATAACAGCTA CTGCCCAAAC

951 TGCCCTTTCC GCAGCAGAGG CCGCAGGTAC GGTTTGGAGA GGTAAAAAAG

1001 TAGAACTTAA CCCGACTAAA TGGGATTGGG TTAAAAATAC CGGTTATAAA

1051 AAACCTGCTG CCCGCCATAT GCAGACTTTA GATGGGGAGA TGGCAGGTGG

1101 GAATAAACCT ATTAAATCTT TACCAAACAG TGCCGCTGAA AAAGAAAAC

1151 AAAATTTTGA GAAGTTTAAT AGTAACTGGA GTTCAGCAAG TTTTGATTCA

1201 GTGCACAAAA CACTAACTCC CAATGCACCT GGTATTTTAA GTCCTGATAA

1251 AGTTAAAACT CGATACACTA GTTTAGATGG AAAAATTACA ATTATAAAAG

1301 ATAACGAAAA CAACTATTTT AGAATCCATG ATAATTCACG AAAACAGTAT

1351 CTTGATTCAA ATGGTAATGC TGTGAAAACC GGTAATTTAC AAGGTAAGCA
```

```
1401 AGCAAAAGAT TATTTACAAC AACAAACTCA TATCAGGAAC TTAGACAAAT

1451 GA
```

This corresponds to the amino acid sequence <SEQ ID 166; ORF29-1>:

```
  1 MNLPIQKFMM LFAAAISLLQ IPISHANGLD ARLRDDMQAK HYEPGGKYHL

51 FGNARGSVKK RVYAVQTFDA TAVSPVLPIT HERTGFEGVI GYETHFSGHG

101 HEVHSPFDHH DSKSTSDFSG GVDGGFTVYQ LHRTGSEIHP EDGYDGPQGS

151 DYPPPGGARD IYSYYVKGTS TKTKTNIVPQ APFSDRWLKE NAGAASGFFS

201 RADEAGKLIW ESDPNKNWWA NRMDDVRGIV QGAVNPFLMG FQGVGIGAIT

251 DSAVSPVTDT AAQQTLQGIN DLGKLSPEAQ LAAASLLQDS AFAVKDGINS

301 AKQWADAHPN ITATAQTALS AAEAAGTVWR GKKVELNPTK WDWVKNTGYK

351 KPAARHMQTL DGEMAGGNKP IKSLPNSAAE KRKQNFEKFN SNWSSASFDS

401 VHKTLTPNAP GILSPDKVKT RYTSLDGKIT IIKDNENNYF RIHDNSRKQY

451 LDSNGNAVKT GNLQGKQAKD YLQQQTHIRN LDK*
```

Computer analysis of this amino acid sequence gave the following results:

Homology with a Predicted ORF from *N. meningitidis* (Strain A)

ORF29 shows 88.0% identity over a 125aa overlap with an ORF (ORF29a) from strain A of *N. meningitidis*.

```
                              10         20         30
    orf29.pep                 VSPVLPITHERTGFEGVIGYETHFSGHGHE
                              |:|||||||||||||:||||||||||||
    orf29a    EPGGKYHLFGNARGSVKNRVYAVQTFDATAVGPILPITHERTGFEGIIGYETHFSGHGHE
                   50         60         70         80         90        100
                 40         50         60         70         80         90
    orf29.pep VHSPFDHHDSKSTSDFSGGVDGGFTVYQLHRTWSEIHPEDEYDGPQAAXYPPPGGARDIY
              ||||||:||||||||||||||||||||||||||||| |||||| |||::||||||||||
    orf29a    VHSPFDNHDSKSTSDFSGGVDGGFTVYQLHRTGSEIHPEDGYDGPQGSDYPPPGGARDIY
                   110        120        130        140        150        160
                 100        110        120
    orf29.pep SYYVKGTSTKTKTSIVPQAPFSDRWLEENAGAASG
              |||||||||||||::||||||||||||:|||||||
    orf29a    XXYVKGTSTKTKSNIVPRAPFSDRWLKENAGAASGFFSRADEAGKLIWESDPNKNWWANR
                   170        180        190        200        210        220
    orf29a    MDDIRGIVQGAVNPFLMGFQGVAIGAITDSAVSPVTDTAAQQTLQGXNHLGXLSPEAQLA
                   230        240        250        260        270        280
```

The complete length ORF29a nucleotide sequence <SEQ ID 167> is:

```
  1 ATGAATTNGC CTATTCAAAA ATTCATGATG CTGTTTGCAG CAGCAATATC

51 GTNGCTGCAA ATCCCNATTA GTCATGCGAA CGGTTTGGAT GCCCGTTTGC

101 GCGATGATAT GCAGGCAAAA CACTACGAAC CGGGTGGTAA ATACCATCTG

151 TTTGGTAATG CTCGCGGCAG TGTTAAAAAT CGGGTTTACG CCGTCCAAAC

201 ATTTGATGCA ACTGCGGTCG GCCCCATACT GCCTATTACA CACGAACGGA

251 CAGGATTTGA AGGCATTATC GGTTATGAAA CCCATTTTTC AGGACATGGA

301 CATGAAGTAC ACAGTCCGTT CGATAATCAT GATTCAAAAA GCACTTCTGA
```

```
 351 TTTCAGCGGC GGCGTAGACG GTGGTTTTAC CGTTTACCAA CTTCATCGGA

401 CAGGGTCGGA AATCCATCCG GAGGATGGAT ATGACGGGCC GCAAGGCAGC

451 GATTATCCGC CCCCCGGAGG AGCAAGGGAT ATATACANNT ANTATGTCAA

501 AGGAACTTCA ACAAAAACAA AGAGTAATAT TGTTCCCCGA GCCCCATTTT

551 CAGACCGCTG GCTAAAAGAA AATGCCGGTG CCGCCTCTGG TTTTTTCAGC

601 CGTGCTGATG AAGCAGGAAA ACTGATATGG GAAAGCGACC CCAATAAAAA

651 TTGGTGGGCT AACCGTATGG ATGATATTCG CGGCATCGTC CAAGGTGCGG

701 TTAATCCTTT TTTAATGGGT TTTCAAGGAG TAGGGATTGG GGCAATTACA

751 GACAGTGCAG TAAGCCCGGT CACAGATACA GCCGCGCAGC AGACTCTACA

801 AGGTATNAAT CATTTAGGAA ANTTAAGTCC CGAAGCACAA CTTGCGGCTG

851 CAACCGCATT ACAAGACAGT GCTTTTGCGG TAAAAGACGG TATCAATTCC

901 GCCAGACAAT GGGCTGATGC CCATCCGAAT ATAACTGCAA CAGCCCAAAC

951 TGCCCTTGCC GTAGCAGANG CCGCAACTAC GGTTTGGGGC GGTAAAAAAG

1001 TAGAACTTAA CCCGACCAAA TGGGATTGGG TTAAAAATAC NGGCTATAAN

1051 ACACCTGCTG TTCGCACCAT GCATACTTTG GATGGGGAAA TGGCCGGTGG

1101 GAATAGACCG CCTAAATCTA TAACGTCCAA CAGCAAAGCA GATGCTTCCA

1151 CACAACCGTC TTTACAAGCG CAACTAATTG GAGAACAAAT TANNNNNGGG

1201 CATGCTTATA ACAAGCATGT CATAAGACAA CAAGAATTTA CGGATTTAAA

1251 TATCAATTCA CCAGCAGATT TTGCTCGGCA TATTGAAAAT ATTGTTAGCC

1301 ATCCANCAAA TATGAAAGAG TTACCTCGCG GTAGAACTGC GTATTGGGAT

1351 NATAAAACAG GGACNATAGT TATCCGAGAT AAAAATTCTG ACGATGGAGG

1401 TACAGCATTT AGACCAACAT CAGGTAAAAA ATATTATGAT GATTTATAG
```

This encodes a protein having amino acid sequence <SEQ ID 168>:

```
  1 MNXPIQKFMM LFAAAISXLQ IPISHANGLD ARLRDDMQAK HYEPGGKYHL

51 FGNARGSVKN RVYAVQTFDA TAVGPILPIT HERTGFEGII GYETHFSGHG

101 HEVHSPFDNH DSKSTSDFSG GVDGGFTVYQ LHRTGSEIHP EDGYDGPQGS

151 DYPPPGGARD IYXXYVKGTS TKTKSNIVPR APFSDRWLKE NAGAASGFFS

201 RADEAGKLIW ESDPNKNWWA NRMDDIRGIV QGAVNPFLMG FQGVGIGAIT

251 DSAVSPVTDT AAQQTLQGXN HLGXLSPEAQ LAAATALQDS AFAVKDGINS

301 ARQWADAHPN ITATAQTALA VAXAATTVWG GKKVELNPTK WDWVKNTGYX

351 TPAVRTMHTL DGEMAGGNRP PKSITSNSKA DASTQPSLQA QLIGEQIXXG

401 HAYNKHVIRQ QEFTDLNINS PADFARHIEN IVSHPXNMKE LPRGRTAYWD

451 XKTGTIVIRD KNSDDGGTAF RPTSGKKYYD DL*
```

ORF29a and ORF29-1 show 90.1% identity in 385 aa overlap:

```
                  10        20        30        40        50        60
    orf29a.pep  MNXPIQKFMMLFAAAISXLQIPISHANGLDARLRDDMQAKHYEPGGKYHLFGNARGSVKN
                || |||||||||||| |||||||||||||||||||||||||||||||||||||||||||:
    orf29-1     MNLPIQKFMMLFAAAISLLQIPISHANGLDARLRDDMQAKHYEPGGKYHLFGNARGSVKK
                  10        20        30        40        50        60
```

```
                      70        80        90       100       110       120
    orf29a.pep RVYAVQTFDATAVGPILPITHERTGFEGIIGYETHFSGHGHEVHSPFDNHDSKSTSDFSG
               ||||||||||||||:|:||||||||||||:||||||||||||||||||:|||||||||||
    orf29-1    RVYAVQTFDATAVSPVLPITHERTGFEGVIGYETHFSGHGHEVHSPFDHHDSKSTSDFSG
                      70        80        90       100       110       120

130       140       150       160       170       180
    orf29a.pep GVDGGFTVYQLHRTGSEIHPEDGYDGPQGSDYPPPGGARDIYXXYVKGTSTKTKSNIVPR
               |||||||||||||||||||||||||||||||||||||||||   ||||||||||:||||:
    orf29-1    GVDGGFTVYQLHRTGSEIHPEDGYDGPQGSDYPPPGGARDIYSYYVKGTSTKTKTNIVPQ
                     130       140       150       160       170       180

190       200       210       220       230       240
    orf29a.pep APFSDRWLKENAGAASGFFSRADEAGKLIWESDPNKNWWANRMDDIRGIVQGAVNPFLMG
               |||||||||||||||||||||||||||||||||||||||||||:||||||||||||||||
    orf29-1    APFSDRWLKENAGAASGFFSRADEAGKLIWESDPNKNWWANRMDDVRGIVQGAVNPFLMG
                     190       200       210       220       230       240

250       260       270       280       290       300
    orf29a.pep FQGVGIGAITDSAVSPVTDTAAQQTLQGXNHLGXLSPEAQLAAATALQDSAFAVKDGINS
               ||||||||||||||||||||||||||||  |  ||||||||||:|||||||||||||||
    orf29-1    FQGVGIGAITDSAVSPVTDTAAQQTLQGINDLGKLSPEAQLAAASLLQDSAFAVKDGINS
                     250       260       270       280       290       300

310       320       330       340       350       360
    orf29a.pep ARQWADAHPNITATAQTALAVAXAATTVWGGKKVELNPTKWDWVKNTGYXTPAVRTMHTL
               |:||||||||||||||||||::| |||  |||||||||||||||||||   ||:|::||
    orf29-1    AKQWADAHPNITATAQTALSAAEEAAGTVWRGKKVELNPTKWDWVKNTGYKKPAARHMQTL
                     310       320       330       340       350       360

370       380       390       400       410       420
    orf29a.pep DGEMAGGNRPPKSITSNSKADASTQPSLQAQLIGEQIXXGHAYNKHVIRQQEFTDLNINS
               ||||||||:| ||:   || |:      |
    orf29-1    DGEMAGGNKPIKSLP-NSAAEKRKQNFEKFNSNWSSASFDSVHKTLTPNAPGILSPDKVK
                     370       380       390       400       410
```

Homology with a Predicted ORF from *N. gonorrhoeae*
ORF29 shows 88.8% identity over a 125aa overlap with a predicted ORF (ORF29.ng) from *N. gonorrhoeae*:

```
    orf29.pep                            VSPVLPITHERTGFEGVIGYETHFSGHGHE    30
                                         |:|:||||||||||||||||||||||||||
    orf29ng   EPGGKYHLFGNARGSVKNRVCAVQTFDATAVGPILPITHERTGFEGVIGYETHFSGHGHE  102 orf29.pep VHSPFDHHDSKSTSDFSGGVDGGFTVYQLHRTWSEIHPEDEYDGPQAAXYPPPGGARDIY   90
              ||||||:|||||||||||||||||||||:||||||||||||:||||:  ||||||||||||
    orf29ng   VHSPFDNHDSKSTSDFSGGVDGGFRVYQLHRTGSEIHPEDGYDGPQGGGYPPPGGARDIY  162 orf29.pep SYYVKGTSTKTKTSIVPQAPFSDRWLEENAGAASG                            125
              ||::|||||||||:||||||||||||||:||||||
    orf29ng   SYHIKGTSTKTKINTVPQAPFSDRWLKENAGAASGFLSRADEAGKLIWENDPDKNWRANR   222
```

The complete length ORF29ng nucleotide sequence <SEQ ID 169> is predicted to encode a protein having amino acid sequence <SEQ ID 170>:

```
  1 MNLPIQKFMM LFAAAISLLQ IPISHANGLD ARLRDDMQAK HYEPGGKYHL

51 FGNARGSVKN RVCAVQTFDA TAVGPILPIT HERTGFEGVI GYETHFSGHG

101 HEVHSPFDNH DSKSTSDFSG GVDGGFTVYQ LHRTGSEIHP EDGYDGPQGG

151 GYPPPGGARD IYSYHIKGTS TKTKINTVPQ APFSDRWLKE NAGAASGFLS

201 RADEAGKLIW ENDPDKNWRA NRMDDIRGIV QGAVNPFLTG FQGLGVGAIT

251 DSAVSPVTYA AARKTLQGIH NLGNLSPEAQ LAAATALQDS AFAVKDSINS

301 ARQWADAHPN ITATAQTALA VTEAATTVWG GKKVELNPAK WDWVKNTGYK

351 KPAARHMQTV DGEMAGGNKP LESKNTVTTN NFFENTGYTE KVLRQASNGD

401 YHGFPQSVDA FSENGTVIQI VGGDNIVRHK LYIPGSYKGK DGNFEYIREA

451 DGKINHRLFV PNQQLPEK*
```

In a second experiment, the following DNA sequence <SEQ ID 171> was identified:

```
   1 atgAATTTGC CTATTCAAAA ATTCATGATG ctgttggcAg cggcaatatc
  51 gatgctGCat ATCCCCATTA GTCATGCGAA CGGTTTGGAT GCCCGTTTGC
 101 GCGATGATAT GCAGGCAAAA CACTACGAAC CGGGTGGCAA ATACCATCTG
 151 TTTGGTAATG CTCGCGGCAG TGTTAAAAAT CGGGTTTGCG CCGTCCAAAC
 201 ATTTGATGCA ACTGCGGTCG GCCCCATACT GCCTATTACA CACGAACGGA
 251 CAGGATTTGA AGGTGTTATC GGCTATGAAA CCCATTTTTC AGGACACGGA
 301 CACGAAGTAC ACAGTCCGTT CGATAATCAT GATTCAAAAA GCACTTCTGA
 351 TTTCAGCGGC GGCGTAGACG GCGGTTTTAC CGTTTACCAA CTTCATCGGA
 401 CAGGGTCGGA AATACATCCC GCAGACGGAT ATGACGGGCC TCAAGGCGGC
 451 GGTTATCCGG AACCACAAGG GGCAAGGGAT ATATACAGCT ACCATATCAA
 501 AGGAACTTCA ACCAAAACAA AGATAAACAC TGTTCCGCAA GCCCCTTTTT
 551 CAGACCGCTG GCTAAAAGAA AATGCCGGTG CCGCTTCCGG TTTTCTCAGC
 601 CGTGCGGATG AAGCAGGAAA ACTGATATGG GAAAACGACC CCGATAAAAA
 651 TTGGCGGGCT AACCGTATGG ATGATATTCG CGGCATCGTC CAAGGTGCGG
 701 TTAATCCTTT TTTAACGGGT TTTCAAGGGG TAGGGATTGG GGCAATTACA
 751 GACAGTGCGG TAAGCCCGGT CACAGATACA GCCGCTCAGC AGACTCTACA
 801 AGGTATTAAT GATTTAGGAA ATTTAAGTCC GGAAGCACAA CTTGCCGCCG
 851 CGAGCCTATT ACAGGACAGT GCCTTTGCGG TAAAAGACGG CATCAATTCC
 901 GCCAGACAAT GGGCTGATGC CCATCCGAAT ATAACAGCAA CAGCCCAAAC
 951 TGCCCTTGCC GTAGCAGAGG CCGCAGGTAC GGTTTGGCGC GGTAAAAAAG
1001 TAGAACTTAA CCCGACCAAA TGGGATTGGG TTAAAAATAC CGGCTATAAA
1051 AAACCTGCTG CCCGCCATAT GCAGACTGTA GATGGGGAGA TGGCAGGGGG
1101 GAATAGACCG CCTAAATCTA TAACGTCGGA AGGAAAAGCT AATGCTGCAA
1151 CCTATCCTAA GTTGGTTAAT CAGCTAAATG AGCAAACTT AAATAACATT
1201 GCGGCTCAAG ATCCAAGATT GAGTCTAGCT ATTCATGAGG GTAAAAAAAA
1251 TTTTCCAATA GGAACTGCAA CTTATGAAGA GGCAGATAGA CTAGGTAAAA
1301 TTTGGGTTGG TGAGGGTGCA AGACAAACTA GTGGAGGCGG ATGGTTAAGT
1351 AGAGATGGCA CTCGACAATA TCGGCCACCA ACAGAAAAAA AATCACAATT
1401 TGCAACTACA GGTATTCAAG CAAATTTTGA AACTTATACT ATTGATTCAA
1451 ATGAAAAAAG AAATAAAATT AAAAATGGAC ATTTAAATAT TAGGTAA
```

This encodes a protein having amino acid sequence <SEQ ID 172; ORF29ng-1>:

```
  1 MNLPIQKFMM LLAAAISMLH IPISHANGLD ARLRDDMQAK HYEPGGKYHL
 51 FGNARGSVKN RVCAVQTFDA TAVGPILPIT HERTGFEGVI GYETHFSGHG
101 HEVHSPFDNH DSKSTSDFSG GVDGGFTVYQ LHRTGSEIHP ADGYDGPQGG
151 GYPEPQGARD IYSYHIKGTS TKTKINTVPQ APFSDRWLKE NAGAASGFLS
201 RADEAGKLIW ENDPDKNWRA NRMDDIRGIV QGAVNPFLTG FQGVGIGAIT
251 DSAVSPVTDT AAQQTLQGIN DLGNLSPEAQ LAAASLLQDS AFAVKDGINS
```

```
301 ARQWADAHPN ITATAQTALA VAEAAGTVWR GKKVELNPTK WDWVKNTGYK

351 KPAARHMQTV DGEMAGGNRP PKSITSEGKA NAATYPKLVN QLNEQNLNNI

401 AAQDPRLSLA IHEGKKNFPI GTATYEEADR LGKIWVGEGA RQTSGGGWLS

451 RDGTRQYRPP TEKKSQFATT GIQANFETYT IDSNEKRNKI KNGHLNIR*
```

ORF29ng-1 and ORF29-1 show 86.0% identity in 401 aa overlap:

```
                   10         20         30         40         50         60
   orf29ng-1.pep  MNLPIQKFMMLLAAAISMLHIPISHANGLDARLRDDMQAKHYEPGGKYHLFGNARGSVKN
                  ||||||||||:|||||:|:||||||||||||||||||||||||||||||||||||||:
        orf29-1  MNLPIQKFMMLFAAAISLLQIPISHANGLDARLRDDMQAKHYEPGGKYHLFGNARGSVKK
                          10         20         30         40         50         60

70         80         90        100        110        120
   orf29ng-1.pep  RVCAVQTFDATAVGPILPITHERTGFEGVIGYETHFSGHGHEVHSPFDNHDSKSTSDFSG
                  ||  |||||||||:|:|||||||||||||||||||||||||||||||:||||||||||
        orf29-1  RVYAVQTFDATAVSPVLPITHERTGFEGVIGYETHFSGHGHEVHSPFDHHDSKSTSDFSG
                          70         80         90        100        110        120

130        140        150        160        170        180
   orf29ng-1.pep  GVDGGFTVYQLHRTGSEIHPADGYDGPQGGGYPEPQGARDIYSYHIKGTSTKTKINTVPQ
                  |||||||||||||||||||| ||||||||:  || |||||||||::|||||||| |||
        orf29-1  GVDGGFTVYQLHRTGSEIHPEDGYDGPQGSDYPPPGGARDIYSYYVKGTSTKTKTNIVPQ
                         130        140        150        160        170        180

190        200        210        220        230        240
   orf29ng-1.pep  APFSDRWLKENAGAASGFLSRADEAGKLIWENDPDKNWRANRMDDIRGIVQGAVNPPLTG
                  ||||||||||||||||||:|||||||||||||:||||| ||||||:||||||||||| |
        orf29-1  APFSDRWLKENAGAASGFFSRADEAGKLIWESDPNKNWWANRMDDVRGIVQGAVNPPLMG
                         190        200        210        220        230        240

250        260        270        280        290        300
   orf29ng-1.pep  FQGVGIGAITDSAVSPVTDTAAQQTLQGINDLGNLSPEAQLAAASLLQDSAFAVKDGINS
                  |||||||||||||||||||||||||||||||||:||||||||||||||||||||||||
        orf29-1  FQGVGIGAITDSAVSPVTDTAAQQTLQGINDLGKLSPEAQLAAASLLQDSAFAVKDGINS
                         250        260        270        280        290        300

310        320        330        340        350        360
   orf29ng-1.pep  ARQWADAHPNITATAQTALAVAEAAGTVWRGKKVELNPTKWDWVKNTGYKKPAARHMQTV
                  |:||||||||||||||||||::||||||||||||||||||||||||||||||||||||:
        orf29-1  AKQWADAHPNITATAQTALSAAEAAGTVWRGKKVELNPTKWDWVKNTGYKKPAARHMQTL
                         310        320        330        340        350        360

370        380        390        400        410        419
   orf29ng-1.pep  DGEMAGGNRPPKSI-TSEGKANAATYPKLVNQLNEQNLNNIAAQDPRLSLAIHEGKKNFP
                  ||||||||:| ||: :|  ::    |: :: :  :::::
        orf29-1  DGEMAGGNKPIKSLPNSAAEKRKQNFEKFNSNWSSASFDSVHKTLTPNAPGILSPDKVKT
                         370        380        390        400        410        420

420        430        440        450        460        470        479
   orf29ng-1.pep  IGTATYEEADRLGKIWVGEGARQTSGGGWLSRDGTRQYRPPTEKKSQFATTGIGANFETY orf29-1  RYTSLDGKITIIKDNENNYFRIHDNSRKQYLDSNGNAVKTGNLQGKQAKDYLQQQTHIRN
                         430        440        450        460        470        480
```

Based on this analysis, including the presence of a putative leader sequence in the gonococcal protein, it is predicted that the proteins from *N. meningitidis* and *N. gonorrhoeae*, and their epitopes, could be useful antigens for vaccines or diagnostics, or for raising antibodies.

Example 21

The following partial DNA sequence was identified in *N. meningitidis* <SEQ ID 173>:

```
  1 ATGAAAAAAC AAATCACCGC AGCCGTAATG ATGCTGTCTA TGATTGCCCC

51 CGCAATGGCA AACGGCTTGG ACAATCAGGC ATTTGAAGAC CAAATGT

This corresponds to the amino acid sequence <SEQ ID 174; ORF30>:

```
  1 MKKQITAAVM MLSMIAPAMA NGLDNQAFED QMFHTRADAP MQ..
```

Further work revealed the complete nucleotide sequence <SEQ ID 175>:

```
  1 ATGAAAAAAC AAATCACCGC AGCCGTAATG ATGCTGTCTA TGATTGCCCC
 51 CGCAATGGCA AACGGCTTGG ACAATCAGGC ATTTGAAGAC CAAGTGTTCC
101 ACACGCGGGC AGATGCACCG ATGCAGTTGG CGGAGCTTTC TCAAAAGGAG
151 ATGAAGGAGA CAGAGGGGGC GTTTCTTCCA TTGGCTATCT TGGGTGGTGC
201 TGCCATTGGT ATGTGGACAC AGCATGGTTT TAGTTATGCA ACGACAGGCA
251 GACCAGCTTC TGTTAGAGAT GTTGCTATTG CTGGCGGATT AGGCGCAATT
301 CCTGGTGGTG TAGGCGCCGC AGGAAAGGTT GTTTCCTTTG CTAAATATGG
351 ACGTGAGATT AAAATCGGCA ATAATATGCG GATAGCCCCT TTCGGTAATA
401 GAACAGGTCA TCCTATTGGA AAATTTCCCC ATTATCATCG TCGAGTTACG
451 GATAATACGG GCAAGACTTT GCCTGGACAG GGAATTGGTC GTCATCGCCC
501 TTGGGAATCA AAATCTACGG ACAGATCATG GAAAAACCGC TTCTAA
```

This corresponds to the amino acid sequence <SEQ ID 176; ORF30-1>:

```
  1 MKKQITAAVM MLSMIAPAMA NGLDNQAFED QVFHTRADAP MQLAELSQKE
 51 MKETEGAFLP LAILGGAAIG MWTQHGFSYA TTGRPASVRD VAIAGGLGAI
101 PGGVGAAGKV VSFAKYGREI KIGNNMRIAP FGNRTGHPIG KFPHYHRRVT
151 DNTGKTLPGQ GIGRHRPWES KSTDRSWKNR F*
```

Computer analysis of this amino acid sequence gave the following results:

Homology with a Predicted ORF from *N. meningitidis* (Strain A)

ORF30 shows 97.6% identity over a 42aa overlap with an ORF (ORF30a) from strain A of *N. meningitidis*.

```
                   10        20        30        40
orf30.pep  MKKQITAAVMMLSMIAPAMANGLDNQAFEDQMFHTRADAPMQ
           |||||||||||||||||||||||||||||:|||||||||||
orf30a     MKKQITAAVMMLSMIAPAMANGLDNQAFEDQVFHTRADAPMQLAELSQKEMKXTXGAFLP
                   10        20        30        40        50        60
orf30a     LXILGGAAIGMWTQHGFSYATTGRPASVRDVAIAGGLGAIPGXVGAAGKVVSFAKYFREI
                   70        80        90       100       110       120
```

The complete length ORF30a nucleotide sequence <SEQ ID 177> is:

```
  1 ATGAAAAAAC AAATCACCGC AGCCGTAATG ATGCTGTCTA TGATTGCCCC
 51 CGCAATGGCA AACGGCTTGG ACAATCAGGC ATTTGAAGAC CAAGTGTTCC
101 ACACGCGGGC AGATGCACCG ATGCAGTTGG CGGAGCTTTC TCAAAAGGAG
151 ATGAAGGANA CAGNGGGGGC GTTTCTTCCA TTGGNTATCT TGGGTGGTGC
```

```
201 TGCCATTGGT ATGTGGACAC AGCATGGTTT TAGTTATGCA ACGACAGGCA

251 GACCAGCTTC TGTTAGAGAT GTTGCTATTG CTGGCGGATT AGGCGCAATT

301 CCTGGTGNTG TAGGCGCCGC AGGAAAGGTT GTTTCCTTTG CTAAATATGG

351 ACGTGAGATT AAAATCGGCA ATAATATGCG GATAGCCCCT TTCGGTAATA

401 GAACAGGTCA TCCTATTGGN AAATTTCCCC ATTATCATCG TCGAGTTACG

451 GATAATACGG GCAAGACTTT GCCTGGACAG GGAATTGGTC GTCATCGCCC

501 TTGGGAATCA AAATCTACGG ACAGATCATG GAAAAACCGC TTCTAA
```

This encodes a protein having amino acid sequence <SEQ ID 178>:

```
  1 MKKQITAAVM MLSMIAPAMA NGLDNQAFED QVFHTRADAP MQLAELSQKE

51 MKXTXGAFLP LXILGGAAIG MWTQHGFSYA TTGRPASVRD VAIAGGLGAI

101 PGXVGAAGKV VSFAKYGREI KIGNNMRIAP FGNRTGHPIG KFPHYHRRVT

151 DNTGKTLPGQ GIGRHRPWES KSTDRSWKNR F*
```

ORF30a and ORF30-1 show 97.8% identity in 181 aa overlap:

```
orf30a.pep MKKQITAAVMMLSMIAPAMANGLDNQAFEDQVFHTRADAPMQLAELSQKEMKXTXGAFLP  60
           |||||||||||||||||||||||||||||||||||||||||||||||||| | |||||
orf30-1    MKKQITAAVMMLSMIAPAMANGLDNQAFEDQVFHTRADAPMQLAELSQKEMKETEGAFLP  60
orf30a.pep LXILGGAAIGMWTQHGFSYATTGRPASVRDVAIAGGLGAIPGXVGAAGKVVSFAKYGREI 120
           | ||||||||||||||||||||||||||||||||||||||| |||||||||||||||||
orf30-1    LAILGGAAIGMWTQHGFSYATTGRPASVRDVAIAGGLGAIPGGVGAAGKVVSFAKYGREI 120
orf30a.pep KIGNNMRIAPFGNRTGHPIGKFPHYHRRVTDNTGKTLPGQGIGRHRPWESKSTDRSWKNR 180
           ||||||||||||||||||||||||||||||||||||||||||||||||||||||||||||
orf30-1    KIGNNMRIAPFGNRTGHPIGKFPHYHRRVTDNTGKTLPGQGIGRHRPWESKSTDRSWKNR 180
orf30a.pep FX
           ||
orf30-1    FX
```

Homology with a Predicted ORF from *N. gonorrhoeae*

ORF30 shows 97.6% identity over a 42aa overlap with a predicted ORF (ORF30.ng) from *N. gonorrhoeae*.

```
orf30.pep MKKQITAAVMMLSMIAPAMANGLDNQAFEDQMFHTRADAPMQ                   42
          ||||||||||||||||||||||||||||||:||||||||||
orf30ng   MKKQITAAVMMLSMIAPAMANGLDNQAFEDQVFHTRADAPMQLAELSQKEMKETEGAFLP 60
```

The complete length ORF30ng nucleotide sequence <SEQ ID 179> is

```
  1 ATGAAAAAAC AAATCACCGC AGCCGTAATG ATGCTGTCTA TGATCGCCCC

51 CGCAATGGCA AACGGATTGG ACAATCAGGC ATTTGAAGAC CAAGTGTTCC

101 ACACGCGGGC AGATGCGCCG ATGCAGTTGG CGGAGCTTTC TCAGAAGGAG

151 ATGAAGGAGA CTGAAGGGGC TTTTCTTCCA TTGGCTATCT TGGGTGGTGC

201 TGCCATTGGT ATGTGGACAC AGCATGGTTT TAGTTATGCA ACGACAGGCA

251 GACCAGCTTC TGTTAGAGAT GTTGCTGGCG GATTAGGCGC AATTCCTGGT

301 GATGTAGGTG CTGCAGGAAA GGTTGTTTCC TTTGCTAAAT ATGGACGTGA

351 GATTAAAATC GGCAATAATA TGCGGATAGC CCCTTTCGGT AATAGAACAG

401 GTCATCCTAT TGGAAAATTT CCCCATTATC ATCGTCGAGT TACGGATAAT
```

```
451 ACGGGCAAGA CTTTGCCTGG ACAGGGAATT GGTCGTCATC GCCCTTGGGA

501 ATCAAAATCT ACGGACAGAT CATGGAAAAA CCGCTTCTAA
```

This encodes a protein having amino acid sequence <SEQ ID 180>:

```
  1 MKKQITAAVM MLSMIAPAMA NGLDNQAFED QVFHTRADAP MQLAELSQKE

51 MKETEGAFLP LAILGGAAIG MWTQHGFSYA TTGRPASVRD VAGGLGAIPG

101 DVGAAGKVVS FAKYGREIKI GNNMRIAPFG NRTGHPIGKF PHYHRRVTDN

151 TGKTLPGQGI GRHRPWESKS TDRSWKNRF*
```

ORF30ng and ORF30-1 show 98.3% identity in 181 aa overlap:

```
                    10        20        30        40        50        60
    orf30ng.pep  MKKQITAAVMMLSMIAPAMANGLDNQAFEDQVFHTRADAPMQLAELSQKEMKETEGAFLP
                 ||||||||||||||||||||||||||||||||||||||||||||||||||||||||||||
    orf30-1      MKKQITAAVMMLSMIAPAMANGLDNQAFEDQVFHTRADAPMQLAELSQKEMKETEGAFLP
                    10        20        30        40        50        60

70        80        90       100       100
    orf30ng.pep  LAILGGAAIGMWTQHGFSYATTGRPASVRDVA--GGLGAIPGDVGAAGKVVSFAKYGREI
                 |||||||||||||||||||||||||||||||||  |||||||| ||||||||||||||||
    orf30-1      LAILGGAAIGMWTQHGFSYATTGRPASVRDVAIAGGLGAIPGGVGAAGKVVSFAKYGREI
                    70        80        90       100       110       120

120       130       140       150       160       170
    orf30ng.pep  KIGNNMRIAPFGNRTGHPIGKFPHYHRRVTDNTGKTLPGQGIGRHRPWESKSTDRSWKNR
                 ||||||||||||||||||||||||||||||||||||||||||||||||||||||||||||
    orf30-1      KIGNNMRIAPFGNRTGHPIGKFPHYHRRVTDNTGKTLPGQGIGRHRPWESKSTDRSWKNR
                   130       140       150       160       170       180

180
    orf30ng.pep  FX
                 ||
    orf30-1      FX
```

Based on this analysis, including the presence of a putative leader sequence in the gonococcal protein, it is predicted that the proteins from *N. meningitidis* and *N. gonorrhoeae*, and their epitopes, could be useful antigens for vaccines or diagnostics, or for raising antibodies.

Example 22

The following partial DNA sequence was identified in *N. meningitidis* <SEQ ID 181>:

```
  1 ATGAATAAAA CTCTCTATCG TGTAATTTTC AACCGCAAAC GTGGGGCTGT

51 GrTAGCCGTT GCTGAAACTA CCAAGCGCGA AGGTAAAAGC TGTGCCGATA

101 GTGATTCAGG CAGCGCTCAT GTGAAATCTG TTCCTTTTGG TACTACTCAT

151 GCACCTGTTT GTg.CGTTaC AAATATCTTT TCTTTTTCTT TATTGGGCTT

201 TTCTTTATGT TTGGCTGTAG GtacGGyCAA TATTGCTTTT GCTGATGGCA

251 TT..
```

This corresponds to the amino acid sequence <SEQ ID 182; ORF31>:

```
  1 MNKTLYRVIF NRKRGAVXAV AETTKREGKS CADSDSGSAH VKSVPFGTTH
 51 APVCXVTNIF SFSLLGFSLC LAVGTXNIAF ADGI..
```

Further work revealed a further partial nucleotide sequence <SEQ ID 183>:

```
  1 ATGAATAAAA CTCTCTATCG TGTAATTTTC AACCGCAAAC GTGGGGCTGT
 51 GGTAGCCGTT GCTGAAACTA CCAAGCGCGA AGGTAAAAGC TGTGCCGATA
101 GTGATTCAGG CAGCGCTCAT GTGAAATCTG TTCCTTTTGG TACTACTCAT
151 GCACCTGTTT GTCGTTCAAA TATCTTTTCT TTTTCTTTAT TGGGCTTTTC
201 TTTATGTTTG GCTGTAGGTA CGGCCAATAT TGCTTTTGCT GATGGCATT..
```

This corresponds to the amino acid sequence <SEQ ID 184; ORF31-1>:

```
  1 MNKTLYRVIF NRKRGAVVAV AETTKREGKS CADSDSGSAH VKSVPFGTTH
 51 APVCRSNIFS FSLLGFSLCL AVGTANIAFA DGI..
```

Computer analysis of this amino acid sequence gave the following results:

Homology with a Predicted ORF from *N. gonorrhoeae*

ORF31 shows 76.2% identity over a 84aa overlap with a predicted ORF (ORF31.ng) from *N. gonorrhoeae*:

```
orf31.pep  MNKTLYRVIFNRKRGAVXAVAETTKREGKSCADSDSGSAHVKSVPFGTTHAPVCXVTNIF  60
           ||||||||||||||||| |||||||||||||| |||:|||| |  ||      :: |
orf31ng    MNKTLYRVIFNRKRGAVVAVAETTKREGKSCADSGSGSVYVKSVSFIPTH------SKAF  54 orf31.pep  SFSLLGFSLCLAVGTXNIAFADGI                                      84
           || ||||||||:|| ||||||||
orf31ng    CFSALFGSLCLALGTVNIAFADGIITDKAAPKTQQATILQTGNGIPQVNIQTPTSAGVSV 114
```

The complete length ORF31ng nucleotide sequence <SEQ ID 185> is:

```
  1 ATGAACAAAA CCCTCTATCG TGTGATTTTC AACCGCAAAC GCGGTGCTGT
 51 GGTAGCTGTT GCCGAAACCA CCAAGCGCGA AGGTAAAAGC TGTGCCGATA
101 GTGGTTCGGG CAGCGTTTAT GTGAAATCCG TTTCTTTCAT TCCTACTCAT
151 TCCAAAGCCT TTTGTTTTTC TGCATTAGGC TTTTCTTTAT GTTTGGCTTT
201 GGGTACGGTC AATATTGCTT TTGCTGACGG CATTATTACT GATAAAGCTG
251 CTCCTAAAAC CCAACAAGCC ACGATTCTGC AAACAGGTaa cGGCATACCG
301 CAAGTCAATA TTCAAACCCC TACTTCGGCA GGGGTTTCTG TTAATCAATA
351 TGCCCAGTTT GATGTGGGTA ATCGCGGGGC GATTTTAAAC AACAGTCGCA
401 GCAACACCCA AACACAGCTA GGCGGTTGGA TTCAAGGCAA TCCTTGGTTG
451 ACAAGGGGCG AAGCACGTGT GGTTGTAAAC CAAATCAACA GCAGCCATCC
501 TTCACAACTG AATGGCTATA TTGAAGTGGG TGGACGACGT GCAGAAGTCG
551 TTATTGCCAA TCCGGCAGGG ATTGCAGTCA ATGGTGGTGG TTTTATCAAT
601 GCTTCCCGTG CCACTTTGAC GACAGGCCAA CCGCAATATC AAGCAGGAGA
```

```
651 CTTTAGCGGC TTTAAGATAA GGCAAGGCAA TGCTGTAATC GCCGGACACG

701 GTTTGGATGC CCGTGATACC GATTTCACAC GTATTCTTGT ATGCCAACAA

751 AATCACCTTG ATCAGTACGG CCGAACAAGC AGGCATTCGT AA
```

This encodes a protein having amino acid sequence <SEQ ID 186>:

```
  1 MNKTLYRVIF NRKRGAVVAV AETTKREGKS CADSGSGSVY VKSVSFIPTH

51 SKAFCFSALG FSLCLALGTV NIAFADGIIT DKAAPKTQQA TILQTGNGIP

101 QVNIQTPTSA GVSVNQYAQF DVGNRGAILN NSRSNTQTQL GGWIQGNPWL

151 TRGEARVVVN QINSSHPSQL NGYIEVGGRR AEVVIANPAG IAVNGGGFIN

201 ASRATLTTGQ PQYQAGDFSG FKIRQGNAVI AGHGLDARDT DFTRILVCQQ

251 NHLDQYGRTS RHS*
```

This gonococcal protein shares 50% identity over a 149aa overlap with the pore-forming hemolysins-like HecA protein from *Erwinia chrysanthemi* (accession number L39897):

```
orf31ng   96 GNGIPQVNIQTPTSAGVSVNQYAQFDVGNRGAILNNSRSN-TQTQLGGWIQGNPWLTRGE 154
             GNG+P VNI TP ++G+S N+Y  F+V NRG ILNN  +   T +QLGG IQ NP L
HecA      45 GNGVPVVNIATPDASGLSHNRYHDFNVDNRGLILNNGTARLTPSQLGGLIQNNPNLNGRA 104

Orf31ng  155 ARVVVNQINSSHPSQLNGYIEVGGRRAEVVIANPAGIAVNGGGFINASRATLTTGQPQYQ 214
             A   ++N++ S + S+L GY+EV G+ A VV+ANP GI   +G GF+N   R TLTTG PQ+
HecA     105 AAAILNEVVSPNRSRLAGYLEVAGQAANVVVANPYGITCSGCGFLNTPRLTLTTGTPQFD 164

Orf31ng  215 -AGDFSGFKIRQGNAVIAGHGLDARDTDF                                242
              AG  SG  +R G+ +I G GLDA  +D+
HecA     165 AAGGLSGLDVRGGDILIDGAGLDASRSDY                                193
```

Furthermore, ORF31ng and ORF31-1 show 79.5% identity in 83 aa overlap:

```
                      10         20         30         40         50         60
    orf31-1.pep MNKTLYRVIFNRKRGAVVAVAETTKREGKSCADSDSGSAHVKSVPFGTTHAPVCRSNIFS
                |||||||||||||||||||||||||||||||||||:||||  |||::||||  ||   |:  |
        orf31ng MNKTLYRVIFNRKRGAVVAVAETTKREGKSCADSGSGSVYVKSVSFIPTH-----SKAFC
                      10         20         30         40         50
                      70         80
    orf31-1.pep FSLLGFSLCLAVGTANIAFADGI
                ||  ||||||||:||:|||||||
        orf31ng FSALGFSLCLALGTVNIAFADGIITDKAAPKTQQATILQTGNGIPQVNIQTPTSAGVSVN
                      60         70         80         90        100        110
```

On this basis, including the homology with hemolysins, and also with adhesins, it is predicted that the proteins from *N. meningitidis* and *N. gonorrhoeae*, and their epitopes, could be useful antigens for vaccines or diagnostics, or for raising antibodies.

Example 23

The following partial DNA sequence was identified in *N. meningitidis* <SEQ ID 187>:

```
  1  ATGAATACTC CTCCTTTTGT CTGTTGGATT TTTTGCAAGG TCATCGACAA

51  TTTCGGCGAC ATCGGCGTTT CGTGGCGGCT CGCCCGTGTT TTGCACCGCG
```

```
101 AACTCGGTTG GCAGGTGCAT TTGTGGACGG ACGATGTGTC CGCCTTGCGT

151 GCGCTTTGCC CTGATTTGCC CGATGTTCCC TGCGTTCATC AGGATATTCA

201 TGTCCGCACT TGGCATTCCG ATGCGGCAGA TATTGATACC GCG..
```

This corresponds to the amino acid sequence <SEQ ID 188; ORF32>:

```
  1 MNTPPFVCWI FCKVIDNFGD IGVSWRLARV LHRELGWQVH LWTDDVSALR

51 ALCPDLPDVP CVHQDIHVRT WHSDAADIDT A..
```

Further work revealed the complete nucleotide sequence <SEQ ID 189>:

```
   1 ATGAATACTC CTCCTTTTGT CTGTTGGATT TTTTGCAAGG TCATCGACAA

51 TTTCGGCGAC ATCGGCGTTT CGTGGCGGCT CGCCCGTGTT TTGCACCGCG

101 AACTCGGTTG GCAGGTGCAT TTGTGGACGG ACGATGTGTC CGCCTTGCGT

151 GCGCTTTGCC CTGATTTGCC CGATGTTCCC TGCGTTCATC AGGATATTCA

201 TGTCCGCACT TGGCATTCCG ATGCGGCAGA TATTGATACC GCGCCTGTTC

251 CCGATGTCGT CATCGAAACT TTTGCCTGCG ACCTGCCCGA AAATGTGCTG

301 CACATTATCC GCCGACACAA GCCGCTTTGG CTGAATTGGG AATATTTGAG

351 CGCGGAGGAA AGCAATGAAA GGCTGCATCT GATGCCTTCG CCGCAGGAGG

401 GTGTTCAAAA ATATTTTTGG TTTATGGGTT TCAGCGAAAA AAGCGGCGGG

451 TTGATACGCG AACGTGATTA CTGCGAAGCC GTCCGTTTCG ATACTGAAGC

501 CCTGCGAGAG CGGCTGATGC TGCCCGAAAA AAACGCCTCC GAATGGCTGC

551 TTTTCGGCTA TCGGAGCGAT GTTTGGGCAA AGTGGCTGGA AATGTGGCGA

601 CAGGCAGGCA GCCCGATGAC ACTGTTGCTG GCGGGGACGC AAATCATCGA

651 CAGCCTCAAA CAAAGCGGCG TTATTCCGCA AGATGCCCTG CAAAACGACG

701 GCGATGTTTT TCAGACGGCA TCCGTCCGCC TCGTCAAAAT CCCTTTCGTG

751 CCGCAACAGG ACTTCGACCA ACTGCTGCAC CTTGCCGACT GCGCCGTCAT

801 CCGCGGCGAA GACAGTTTCG TGCGCGCCCA GCTTGCGGGC AAACCCTTCT

851 TTTGGCACAT CTACCCGCAA GACGAGAATG TCCATCTCGA CAAACTCCAC

901 GCCTTTTGGG ATAAGGCACA CGGTTTCTAC ACGCCCGAAA CCGTGTCGGC

951 ACACCGCCGT CTTTCGGACG ACCTCAACGG CGGAGAGGCT TTATCCGCAA

1001 CACAACGCCT CGAATGTTGG CAAACCCTGC AACAACATCA AAACGGCTGG

1051 CGGCAAGGCG CGGAGGATTG GAGCCGTTAT CTTTTCGGGC AGCCGTCAGC

1101 TCCTGAAAAA CTCGCTGCCT TTGTTTCAAA GCATCAAAAA ATACGCTAG
```

This corresponds to the amino acid sequence <SEQ ID 190; ORF32-1>:

```
  1 MNTPPFVCWI FCKVIDNFGD IGVSWRLARV LHRELGWQVH LWTDDVSALR

51 ALCPDLPDVP CVHQDIHVRT WHSDAADIDT APVPDVVIET FACDLPENVL

101 HIIRRHKPLW LNWEYLSAEE SNERLHLMPS PQEGVQKYFW FMGFSEKSGG

151 LIRERDYCEA VRFDTEALRE RLMLPEKNAS EWLLFGYRSD VWAKWLEMWR

201 QAGSPMTLLL AGTQIIDSLK QSGVIPQDAL QNDGDVFQTA SVRLVKIPFV
```

```
251  PQQDFDQLLH LADCAVIRGE DSFVRAQLAG KPFFWHIYPQ DENVHLDKLH

301  AFWDKAHGFY TPETVSAHRR LSDDLNGGEA LSATQRLECW QTLQQHQNGW

351  RQGAEDWSRY LFGQPSAPEK LAAFVSKHQK IR*w
```

Computer analysis of this amino acid sequence gave the following results:

Homology with a Predicted ORF from *N. meningitidis* (Strain A)

ORF32 shows 93.8% identity over a 81aa overlap with an ORF (ORF32a) from strain A of *N. meningitidis*.

```
                    10         20         30         40         50         60
    orf32.pep  MNTPPFVCWIFCKVIDNFGDIGVSWRLARVLHRELGWQVHLWTDDVSALRALCPDLPDVP
               ||||||    |||||||||||||||||||||||||||||||||||||||||||||||||
      orf32a  MNTPPFSAGXFCKVIDNFGDIGVSWRLARVLHRELGWQVHLWTDDVSALRALCPDLPDVP
                    10         20         30         40         50         60
                    70         80
    orf32.pep  CVHQDIHVRTWHSDAADIDTA
               |||||||||||||||||||||
      orf32a  CVHQDIHVRTWHSDAADIDTAPVXDVVIETFACDLPENVLHIIRRHKPLWLXWEYLSAEX
                    70         80         90        100        110        120
```

The complete length ORF32a nucleotide sequence <SEQ ID 191> is:

```
   1  ATGAATACTC CTCCTTTTTC TGCTGGANTT TTTTGCAAGG TCATCGACAA

51  TTTCGGCGAC ATCGGCGTTT CGTGGCGGCT TGCCCGTGTT TTGCACCGCG

101  AACTCGGTTG GCAGGTGCAT TTGTGGACGG ACGATGTGTC CGCCTTGCGT

151  GCGCTTTGCC CTGATTTGCC CGATGTTCNC TGCGTTCATC AGGATATTCA

201  TGTCCGCACT TGGCATTCCG ATGCGGCAGA TATTGATACC GCGCCTGTTC

251  NCGATGTCGT CATCGAAACT TTTGCCTGCG ACCTGCCCGA AAATGTGCTG

301  CACATCATCC GCCGACACAA GCCGCTTTGG CTGAANTGGG AATATTTGAG

351  CGCGGAGGAN AGCAATGAAA GGCTGCACNT GATGCCTTCG CCGCAGGAGA

401  GTGTTCNAAA ATANTTTTGG TTTATGGGTT TCAGCGAANN NAGCGGCGGA

451  CTGATACGCG AACGCGATTA CTGCGAAGCC GTCCGTTTCG ATAGCGGAGC

501  CTTGCGCAAG AGGCTGATGC TTCCCGAAAA AAACGNCCCC GAATGGCTGC

551  TTTTCGGCTA TCGGAGCGAT GTTTGGGCAA AGTGGCTGGA AATGTGGCGA

601  CAGGCAGGCA GTCCGTTGAC ACTTTTGCTG GCNGGGGCGC ANATTATCGA

651  CAGCCTCAAA CAAAACGGCG TTATTCCGCA AGATGCCCTG CAAAACGACG

701  GCGATGTTTT TCAGACGGCA TCCGTCCGCC TCGTCAAAAT CCCTTTCGTG

751  CCGCAACAGG ACTTCGACAA ACTGCTGCAC CTTGCCGACT GCGCCGTCAT

801  CCGCGGCGAA GACAGTTTCG TGCGCGCCCA GCTTGCGGGC AAACCCTTCT

851  TTTGGCACAT CTACCCGCAA GATGAGAATG TCCATCTCGA CAAACTCCAC

901  GCCTTTTGGG ATAAGGCACA CGGTTTCTAC ACGCCCGAAA CCGCATCGGC

951  ACACCGCCGC CTTTCAGACG ACCTCAACGG CGGAGAGGCT TTATCCGCAA

1001  CACAACGCCT CGAATGTTGG CAAATCCTGC AACAACATCA AACGGCTGG

1051  CGGCAAGGCG CGGAGGATTG GAGCCGTTAT CTTTTTGGGC AGCCTTCCGC

1101  ATCCGAAAAA CTCGCCGCCT TTGTTTCAAA GCATCAAAAA ATACGCTAG
```

This encodes a protein having amino acid sequence <SEQ ID 192>:

```
  1 MNTPPFSAGX FCKVIDNFGD IGVSWRLARV LHRELGWQVH LWTDDVSALR

51 ALCPDLPDVX CVHQDIHVRT WHSDAADIDT APVXDVVIET FACDLPENVL

101 HIIRRHKPLW LXWEYLSAEX SNERLHXMPS PQESVXKXFW FMGFSEXSGG

151 LIRERDYCEA VRFDSGALRK RLMLPEKNXP EWLLFGYRSD VWAKWLEMWR

201 QAGSPLTLLL AGAXIIDSLK QNGVIPQDAL QNDGDVFQTA SVRLVKIPFV

251 PQQDFDKLLH LADCAVIRGE DSFVRAQLAG KPFFWHIYPQ DENVHLDKLH

301 AFWDKAHGFY TPETASAHRR LSDDLNGGEA LSATQRLECW QILQQHQNGW

351 RQGAEDWSRY LFGQPSASEK LAAFVSKHQK IR*
```

ORF32a and ORF32-1 show 93.2% identity in 382 aa overlap:

```
                    10         20         30         40         50         60
orf32-1.pep MNTPPFVCWIFCKVIDNFGDIGVSWRLARVLHRELGWQVHLWTDDVSALRALCPDLPDVP
            ||||||  ||||||||||||||||||||||||||||||||||||||||||||||||||||
    orf32a  MNTPPFSAGXFCKVIDNFGDIGVSWRLARVLHRELGWQVHLWTDDVSALRALCPDLPDVP
                    10         20         30         40         50         60

70         80         90        100        110        120
orf32-1.pep CVHQDIHVRTWHSDAADIDTAPVPDVVIETFACDLPENVLHIIRRHKPLWLNWEYLSAEE
            |||||||||||||||||||||||| |||||||||||||||||||||||||||| ||||| 
    orf32a  CVHQDIHVRTWHSDAADIDTAPVXDVVIETFACDLPENVLHIIRRHKPLWLXWEYLSAEX
                    70         80         90        100        110        120

130        140        150        160        170        180
orf32-1.pep SNERLHLMPSPQEGVQKYFWFMGFSEKSGGLIRERDYCEAVRFDTEALRERLMLPEKNAS
            ||||||  ||:||||  :  |||||| ||||||||||||||||| :|||||||||||| 
    orf32a  SNERLHXMPSPQESVXKXFWFMGFSEXSGGLIRERDYCEAVRFDSGALRKRLMLPEKNXP
                   130        140        150        160        170        180

190        200        210        220        230        240
orf32-1.pep EWLLFGYRSDVWAKWLEMWRQAGSPMTLLLAGTQIIDSLKQSGVIPQDALQNDGDVFQTA
            |||||||||||||||||||||||||:|||||:||||||||||:|||||||||||||||||
    orf32a  EWLLFGYRSDVWAKWLEMWRQAGSPLTLLLAGAXIIDSLKQNGVIPQDALQNDGDVFQTA
                   190        200        210        220        230        240

250        260        270        280        290        300
orf32-1.pep SVRLVKIPFVPQQDFDQLLHLADCAVIRGEDSFVRAQLAGKPFFWHIYPQDENVHLDKLH
            |||||||||||||||||:||||||||||||||||||||||||||||||||||||||||||
    orf32a  SVRLVKIPFVPQQDFDKLLHLADCAVIRGEDSFVRAQLAGKPFFWHIYPQDENVHLDKLH
                   250        260        270        280        290        300

310        320        330        340        350        360
orf32-1.pep AFWDKAHGFYTPETVSAHRRLSDDLNGGEALSATQRLECWQTLQQHQNGWRQGAEDWSRY
            ||||||||||||||:|||||||||||||||||||||||||| ||||||||||||||||||
    orf32a  AFWDKAHGFYTPETASAHRRLSDDLNGGEALSATQRLECWQILQQHQNGWRQGAEDWSRY
                   310        320        330        340        350        360

370        380
orf32-1.pep LFGQPSAPEKLAAFVSKHQKIRX
            ||||||| |||||||||||||||
    orf32a  LFGQPSASEKLAAFVSKHQKIRX
                   370        380
```

Homology with a Predicted ORF from *N. gonorrhoeae*

ORF32 shows 95.1% identity over a 82aa overlap with a predicted ORF (ORF32.ng) from *N. gonorrhoeae*:

```
orf32.pep   MNTPPF-VCWIFCKVIDNFGDIGVSWRLARVLHRELGWQVHLWTDDVSALRALCPDLP   57
            |||  | ||||||||||||||||||||||||||||||||||||||||||||||||||
orf32ng     MVMNTYAFPVCWIFCKVIDNFGDIGVSWRLARVLHRELGWQVHLWTDDVSALRALCPDLP   60 orf32.pep   DVPCVHQDIHVRTWHSDAADIDTA                                     81
            ||| ||||||||||||||||||||
orf32ng     DVPFVHQDIHVRTWHSDAADIDTAPVPDAVIETFACDLPENVLNIIRRHKPLWLNWEYLS  120
```

An ORF32ng nucleotide sequence <SEQ ID 193> was predicted to encode a protein having amino acid sequence <SEQ ID 194>:

```
  1  MVMNTYAFPV CWIFCKVIDN FGDIGVSWRL ARVLHRELGW QVHLWTDDVS
 51  ALRALCPDLP DVPFVHQDIH VRTWHSDAAD IDTAPVPDAV IETFACDLPE
101  NVLNIIRRHK PLWLNWEYLS AEESNERLHL MPSPQEGVQK YFWFMGFSEK
151  SGGLIRERDY REAVRFDTEA LRRRLVLPEK NAPEWLLFGY RGDVWAKWLD
201  MWQQAGSLMT LLLAGAQIID SLKQSGVIPQ NALQNEGGVF QTASVRLVKI
251  PFVPQQDFDK LLHLADCAVI RGEDSFVRTQ LAGKPFFWHI YPQDENVHLD
301  KLHAFWDKAY GFYTPETASV HRLLSDDLNG GEALSATQRL ECGVL*
```

Further sequencing revealed the following DNA sequence <SEQ ID 195>:

```
   1  ATGAATACAT ACGCTTTTCC TGTCTGTTGG ATTTTTTGCA AGGTCATCGA
  51  CAATTTCGGC GACATCGGCG TTTCGTGGCG GCTCGCCCGT GTTTTGCACC
 101  GCGAACTCGG TTGGCAGGTG CATTTGTGGA CGGACGACGT GTCCGCCTTG
 151  CGCGCGCTTT GTCCCGATTT GCCCGATGTT CCCTTCGTTC ATCAGGATAT
 201  TCATGTCCGC ACTTGGCATT CCGATGCGGC AGACATTGAT ACCGCGCCCG
 251  TTCCCGATGC CGTTATCGAA ACTTTTGCCT GCGACCTGCC CGAAAATGTG
 301  CTGAACATCA TCCGCCGACA CAAACCGCTT TGGCTGAATT GGGAATATTT
 351  GAGCGCGGAG GAAAGCAATG AAAGGCTGCA CCTGATGCCT TCGCCGCAGG
 401  AGGGCGTTCA AAAATATTTT TGGTTTATGG GTTTCAGCGA AAAAAGCGGC
 451  GGGTTGATAC GCGAACGCGA TTACCGCGAA GCCGTCCGTT TCGATACCGA
 501  AGCCCTGCGC CGGCGGCTGG TGCTGCCCGA AAAAAACGCC CCGAATGGC
 551  TGCTTTTCGG CTATCGGGGC GATGTTTGGG CAAAGTGGCT GGACATGTGG
 601  CAACAGGCAG GCAGCCTGAT GACCCTACTG CTGGCGGGGG CGCAAATTAT
 651  CGACAGCCTC AAACAAAGCG GCGTTATTCC GCAAAACGCC CTGCAAAAtg
 701  aaggcgGTGT CTTTCagacG gcatccgTcC gccttGTCAA AAtcCCGTTC
 751  GTGCcGCAAC AGGAcTTCGA CAAATTGCTG CAcctcgcCG ACTGCGCCGT
 801  GATACGCGGC GAAGACAGTT TCGTGCGTAC CCAGCTTGCC GGAAAACCCT
 851  TTTTTTGGCA CATCTACCCG CAAGACGAGA ATGTCCATCT CGACAAACTC
 901  CACGCCTTTT GGGATAAGGC ATACGGCTTC TACACGCCCG AAACCGCATC
 951  GGTGCACCGC CTCCTTTCGG ACGACCTCAA CGGCGGAGAG GCTTTATCCG
1001  CAACACAACG CCTCGAATGT TGGCAAACCC TGCAACAACA TCAAAACGGC
1051  TGGCGGCAAG GCGCGGAGGA TTGGAGCCGT TATCTTTTCG GGCAGCCTTC
1101  CGCATCCGAA AAACTCGCCG CCTTTGTTTC AAAGCATCAA AAAATACGCT
1151  AG
```

This encodes a protein having amino acid sequence <SEQ ID 196; ORF32ng-1>:

```
  1  MNTYAFPVCW IFCKVIDNFG DIGVSWRLAR VLHRELGWQV HLWTDDVSAL
 51  RALCPDLPDV PFVHQDIHVR TWHSDAADID TAPVPDAVIE TFACDLPENV
```

```
101  LNIIRRHKPL  WLNWEYLSAE  ESNERLHLMP  SPQEGVQKYF  WFMGFSEKSG

151  GLIRERDYRE  AVRFDTEALR  RRLVLPEKNA  PEWLLFGYRG  DVWAKWLDMW

201  QQAGSLMTLL  LAGAQIIDSL  KQSGVIPQNA  LQNEGGVFQT  ASVRLVKIPF

251  VPQQDFDKLL  HLADCAVIRG  EDSFVRTQLA  GKPFFWHIYP  QDENVHLDKL

301  HAFWDKAYGF  YTPETASVHR  LLSDDLNGGE  ALSATQRLEC  WQTLQQHQNG

351  WRQGAEDWSR  YLFGQPSASE  KLAAFVSKHQ  KIR*
```

ORF32ng-1 and ORF32-1 show 93.5% identity in 383 aa overlap:

```
                    10         20         30         40         50         59
orf32-1.pep    MNTPPF-VCWIFCKVIDNFGDIGVSWRLARVLHRELGWQVHLWTDDVSALRALCPDLPDV
               |||   ||||||||||||||||||||||||||||||||||||||||||||||||||||||
orf32ng-1      MNTYAFPVCWIFCKVIDNFGDIGVSWRLARVLHRELGWQVHLWTDDVSALRALCPDLPDV
                    10         20         30         40         50         60

60         70         80         90        100        110        119
orf32-1.pep    PCVHQDIHVRTWHSDAADIDTAPVPDVVIETFACDLPENVLHIIRRHKPLWLNWEYLSAE
               | ||||||||||||||||||||||||||:|||||||||||||:|||||||||||||||||
orf32ng-1      PFVHQDIHVRTWHSDAADIDTAPVPDAVIETFACDLPENVLNIIRRHKPLWLNWEYLSAE
                    70         80         90        100        110        120

120        130        140        150        160        170        179
orf32-1.pep    ESNERLHLMPSPQEGVQKYFWFMGFSEKSGGLIRETDYCEAVRFDTEALRETLMLPEKNA
               |||||||||||||||||||||||||||||||||||||||:||:|||||||||::||||||
orf32ng-1      ESNERLHLMPSPQEGVQKYFWFMGFSEKSGGLIRETDYREAVRFDTEALRRRLVLPEKNA
                   130        140        150        160        170        180

180        190        200        210        220        230        239
orf32-1.pep    SEWLLFGYRSDVWAKWLEMWRQAGSPMTLLLAGTQIIDSLKQSGVIPQDALQNDGDVFQT
               ::|||||||:||||||||:||:||||:||||||:||||||||||||||::||::|:||||
orf32ng-1      PEWLLFGYRGDVWAKWLDMWQQAGSLMTLLLAGAQIIDSLKQSGVIPQNALQNEGGVFQT
                   190        200        210        220        230        240

240        250        260        270        280        290        299
orf32-1.pep    ASVRLVKIPFVPQQDFDQLLHLADCAVIRGEDSFVRAQLAGKPFFWHIYPQDENVHLDKL
               |||||||||||||||||:|||||||||||||||||:|||||||||||||||||||||||
orf32ng-1      ASVRLVKIPFVPQQDFDKLLHLADCAVIRGEDSFVRTQLAGKPFFWHIYPQDENVHLDKL
                   250        260        270        280        290        300

300        310        320        330        340        350        359
orf32-1.pep    HAFWDKAHGFYTPETVSAHRRLSDDLNGGEALSATQRLECWQTLQQHQNGWRQGAEDWSR
               |||||||:||||||:|:|:||||||||||||||||||||||||||||||||||||||||
orf32ng-1      HAFWDKAYGFYTPETASVHRLLSDDLNGGEALSATQRLECWQTLQQHQNGWRQGAEDWSR
                   310        320        330        340        350        360

360        370        380
orf32-1.pep    YLFGQPSAPEKLAAFVSKHQKIRX
               ||||||||| ||||||||||||||
orf32ng-1      YLFGQPSASEKLAAFVSKHQKIRX
                   370        380
```

On this basis, including the RGD sequence in the gonococcal protein, characteristic of adhesins, it is predicted that the proteins from *N. meningitidis* and *N. gonorrhoeae*, and their epitopes, could be useful antigens for vaccines or diagnostics, or for raising antibodies.

ORF32-1 (42 kDa) was cloned in pET and pGex vectors and expressed in *E. coli*, as described above. The products of protein expression and purification were analyzed by SDS-PAGE. FIG. 7A shows the results of affinity purification of the His-fusion protein, and FIG. 7B shows the results of expression of the GST-fusion in *E. coli*. Purified His-fusion protein was used to immunise mice, whose sera were used for ELISA, giving a positive result. These experiments confirm that ORF32-1 is a surface-exposed protein, and that it is a useful immunogen.

Example 24

The following partial DNA sequence was identified in *N. meningitidis* <SEQ ID 197>:

```
  1  ..TTGTTCCTGC GTGTNAAAGT GGGGCGTTTT TTCAGCAGTC CGGCGACGTG

51  GTTTCGGGNC AAAGACCCTG TAAATCAGGC GGTGTTGCGG CTGTATNCGG

101  ACGAGTGGCG GCA.ACTTCG GTACGTTGGA AAATAGNCGC AACGTCGCAC

151  AGCCTGTGGC TCTGCACGCT GCTCGGAATG CTGGTGTCGG TATTGTTGCT

201  GCTTTTGGTG CGGCAATATA CGTTCAACTG GGAAAGCACG CTGTTGAGCA

251  ATGCCGCTTC GGTACGCGCG GTGGAAATGT TGGCATGGCT GCCGTCGAAA

301  CTCGGTTTCC CTGTCCCCGA TGCGCGGTCG GTCATCGAAG GCCGTCTGAA
```

-continued

```
351 CGGCAATATT GCCGATGCGC GGGCTTGGTC GGGGCTGCTG GTCGNCAGTA

401 TCGCCTGCTA NGGCATCCTG CCGCGCCTG..
```

This corresponds to the amino acid sequence <SEQ ID 198; ORF33>:

```
  1 ..LFLRVKVGRF FSSPATWFRX KDPVNQAVLR LYXDEWRXTS VRWKIXATSH

51   SLWLCTLLGM LVSVLLLLLV RQYTFNWEST LLSNAASVRA VEMLAWLPSK

101   LGFPVPDARS VIEGRLNGNI ADARAWSGLL VXSIACXGIL PRL..
```

Further work revealed the complete nucleotide sequence <SEQ ID 199>:

```
   1 ATGTTGAATC CATCCCGAAA ACTGGTTGAG CTGGTCCGTA TTTTGGACGA

51 AGGCGGTTTT ATTTTCAGCG GCGATCCCGT ACAGGCGACG GAGGCTTTGC

101 GCCGCGTGGA CGGCAGTACG GAGGAAAAAA TCATCCGTCG GGCGGAGATG

151 ATTGACAGGA ACCGTATGCT GCGGGAGACG TTGGAACGTG TGCGTGCGGG

201 GTCGTTCTGG TTGTGGGTGG TGGCGGCGAC GTTTGCATTT TTTACCGGTT

251 TTTCAGTCAC TTATCTTCTA ATGGACAATC AGGGTCTGAA TTTCTTTTTG

301 GTTTTGGCGG GCGTGTTGGG CATGAATACG CTGATGCTGG CAGTATGGTT

351 GGCAATGTTG TTCCTGCGTG TGAAAGTGGG GCGTTTTTTC AGCAGTCCGG

401 CGACGTGGTT TCGGGGCAAA GACCCTGTAA ATCAGGCGGT GTTGCGGCTG

451 TATGCGGACG AGTGGCGGCA ACCTTCGGTA CGTTGGAAAA TAGGCGCAAC

501 GTCGCACAGC CTGTGGCTCT GCACGCTGCT CGGAATGCTG GTGTCGGTAT

551 TGTTGCTGCT TTTGGTGCGG CAATATACGT TCAACTGGGA AAGCACGCTG

601 TTGAGCAATG CCGCTTCGGT ACGCGCGGTG GAAATGTTGG CATGGCTGCC

651 GTCGAAACTC GGTTTCCCTG TCCCCGATGC GCGGGCGGTC ATCGAAGGCC

701 GTCTGAACGG CAATATTGCC GATGCGCGGG CTTGGTCGGG GCTGCTGGTC

751 GGCAGTATCG CCTGCTACGG CATCCTGCCG CGCCTGCTGG CTTGGGTAGT

801 GTGTAAAATC CTTTTGAAAA CAAGCGAAAA CGGATTGGAT TTGGAAAAGC

851 CCTATTATCA GGCGGTCATC CGCCGCTGGC AGAACAAAAT CACCGATGCG

901 GATACGCGTC GGGAAACCGT GTCCGCCGTT TCACCGAAAA TCATCTTGAA

951 CGATGCGCCG AAATGGGCGG TCATGCTGGA GACCGAGTGG CAGGACGGCG

1001 AATGGTTCGA GGGCAGGCTG GCGCAGGAAT GGCTGGATAA GGGCGTTGCC

1051 ACCAATCGGG AACAGGTTGC CGCGCTGGAG ACAGAGCTGA AGCAGAAACC

1101 GGCGCAACTG CTTATCGGCG TGCGCGCCCA AACTGTGCCG GACCGCGGCG

1151 TGTTGCGGCA GATTGTCCGA CTCTCGGAAG CGGCGCAGGG CGGCGCGGTG

1201 GTGCAGCTTT TGGCGGAACA GGGGCTTTCA GACGACCTTT CGGAAAAGCT

1251 GGAACATTGG CGTAACGCGC TGGCCGAATG CGGCGCGGCG TGGCTTGAGC

1301 CTGACAGGGC GGCGCAGGAA GGGCGTTTGA AAGACCAATA A
```

This corresponds to the amino acid sequence <SEQ ID 200; ORF33-1>:

```
  1  MLNPSRKLVE LVRILDEGGF IFSGDPVQAT EALRRVDGST EEKIIRRAEM

51  IDRNRMLRET LERVRAGSFW LWVVAATFAF FTGFSVTYLL MDNQGLNFFL

101  VLAGVLGMNT LMLAVWLAML FLRVKVGRFF SSPATWFRGK DPVNQAVLRL

151  YADEWRQPSV RWKIGATSHS LWLCTLLGML VSVLLLLLVR QYTFNWESTL

201  LSNAASVRAV EMLAWLPSKL GFPVPDARAV IEGRLNGNIA DARAWSGLLV

251  GSIACYGILP RLLAWVVCKI LLKTSENGLD LEKPYYQAVI RRWQNKITDA

301  DTRRETVSAV SPKIILNDAP KWAVMLETEW QDGEWFEGRL AQEWLDKGVA

351  TNREQVAALE TELKQKPAQL LIGVRAQTVP DRGVLRQIVR LSEAAQGGAV

401  VQLLAEQGLS DDLSEKLEHW RNALAECGAA WLEPDRAAQE GRLKDQ*
```

Computer analysis of this amino acid sequence gave the following results:

Homology with a Predicted ORF from *N. meningitidis* (Strain A)

ORF33 shows 90.9% identity over a 143aa overlap with an ORF (ORF33a) from strain A of *N. meningitidis*.

```
                                              10         20         30
    orf33.pep                        LFLRVKVGRFFSSPATWFRXKDPVNQAVLR
                                     |||||||||||||||||| ||||||||||
    orf33a   LMDNQGLNFFLVLAGVXGMNTLMLAVWLAMLFLRVKVGRFFSSPATWFRGKDPVNQAVLR
             90       100       110       120       130       140
                      40         50         60         70         80         90
    orf33.pep    LYXDEWRXTSVRWKIXATSHSLWLCTLLGMLVSVLLLLLVRQYTFNWESTLLSNAASVRA
                 || |||||  |||||| ||||||||||||||||||||||||||||||||||::::|||
    orf33a       LYADEWRXPSVRWKIGATSHSLWLCTLLGMLVSVLLLLLVRQYTFNWESTLLGDSSSVRL
              150       160       170       180       190       200
                      100       110       120       130       140
    orf33.pep    VEMLAWLPSKLGFPVPDARSVIEGRLNGNIADARAWSGLLVXSIACXGILPRL
                 ||||||||:||||||||||:||||||||||||||||||||||  ||| |||||
    orf33a       VEMLAWLPAKLGFPVPDARAVIEGRLNGNIADARAWSGLLVGSIACYGILPRLLAWAVCK
              210       220       230       240       250       260
    orf33a       ILXXTSENGLDLEKXXXXXXIRRWQNKITDADTRRETVSAVSPKIVLNDAPKWAVMLETE
              270       280       290       300       310       320
```

The complete length ORF33a nucleotide sequence <SEQ ID 201> is:

```
  1  ATGTTGAATC CATCCCGAAA ACTGGTTGAG CTGGTCCGTA TTTTGGAAGA

51  AGGCGGCTTT ATTTTCAGCG GCGATCCCGT GCAGGCGACG GAGGCTTTGC

101  GCCGCGTGGA CGGCAGTACG GAGGAAAAAA TCATCCGTCG GGCGAAGATG

151  ATCGACAGGA ACCGTATGCT GCGGGAGACG TTGGAACGTG TGCGTGCGGG

201  GTCGTTCTGG TTGTGGGTGG CGGCGGCGAC GTTTGCGTTT NTTACCGNTT

251  TTTCAGTTAC TTATCTTCTA ATGGACAATC AGGGTCTGAA TTTCTTTTTG

301  GTTTTGGCGG GCGTGNTGGG CATGAATACG CTGATGCTGG CAGTATGGTT

351  GGCAATGTTG TTCCTGCGCG TGAAAGTGGG GCGTTTTTTC AGCAGTCCGG

401  CGACGTGGTT TCGGGGCAAA GACCCTGTCA ATCAGGCGGT GTTGCGGCTG

451  TATGCGGACG AGTGGCGGCN ACCTTCGGTA CGTTGGAAAA TAGGCGCAAC

501  GTCGCACAGC CTGTGGCTCT GCACGCTGCT CGGAATGCTG GTGTCGGTAT

551  TGTTGCTGCT TTTGGTGCGG CAATATACGT TCAACTGGGA AAGCACGCTG
```

```
 601  TTGGGCGATT CGTCTTCGGT ACGGCTGGTG GAAATGTTGG CATGGCTGCC
 651  TGCGAAACTG GGTTTTCCCG TGCCTGATGC GCGGGCGGTC ATCGAAGGTC
 701  GTCTGAACGG CAATATTGCC GATGCGCGGG CTTGGTCGGG GCTGCTGGTC
 751  GGCAGTATCG CCTGCTACGG CATCCTGCCG CGCCTCTTGG CTTGGGCGGT
 801  ATGCAAAATC CTTNTGNAAA CAAGCGAAAA CGGCTTGGAT TTGGAAAAGC
 851  NCNNNNNTCN NNCGNTCATC CGCCGCTGGC AGAACAAAAT CACCGATGCG
 901  GATACGCGTC GGGAAACCGT GTCCGCCGTT TCGCCGAAAA TCGTCTTGAA
 951  CGATGCGCCG AAATGGGCGG TCATGCTGGA GACCGAATGG CAGGACGGCG
1001  AATGGTTCGA GGGCAGGCTG GCGCAGGAAT GGCTGGATAA GGGCGTTGCC
1051  GCCAATCGGG AACAGGTTGC CGCGCTGGAG ACAGAGCTGA AGCAGAAACC
1101  GGCGCAACTG CTTATCGGCG TGCGCGCCCA AACTGTGCCC GACCGCGGCG
1151  TGTTGCGGCA GATCGTCCGA CTTTCGGAAG CGGCGCAGGG CGGCGCGGTG
1201  GTGCANCTTT TGGCGGAACA GGGGCTTTCA GACGACCTTT CGGAAAAGCT
1251  GGAACATTGG CGTAACGCGC TGACCGAATG CGGCGCGGCC TGGCTGGAAC
1301  CCGACAGAGC GGCGCAGGAA GGCCGTCTGA AAACCAACGA CCGCACTTGA
```

This encodes a protein having amino acid sequence <SEQ ID 202>:

```
  1  MLNPSRKLVE LVRILEEGGF IFSGDPVQAT EALRRVDGST EEKIIRRAKM
 51  IDRNRMLRET LERVRAGSFW LWVAAATFAF XTXFSVTYLL MDNQGLNFFL
101  VLAGVXGMNT LMLAVWLAML FLRVKVGRFF SSPATWFRGK DPVNQAVLRL
151  YADEWRXPSV RWKIGATSHS LWLCTLLGML VSVLLLLLVR QYTFNWESTL
201  LGDSSSVRLV EMLAWLPAKL GFPVPDARAV IEGRLNGNIA DARAWSGLLV
251  GSIACYGILP RLLAWAVCKI LXXTSENGLD LEKXXXXXXI RRWQNKITDA
301  DTRRETVSAV SPKIVLNDAP KWAVMLETEW QDGEWFEGRL AQEWLDKGVA
351  ANREQVAALE TELKQKPAQL LIGVRAQTVP DRGVLRQIVR LSEAAQGGAV
401  VXLLAEQGLS DDLSEKLEHW RNALTECGAA WLEPDRAAQE GRLKTNDRT*
```

45

ORF33a and ORF33-1 show 94.1% identity in 444 aa overlap:

```
                    10         20         30         40         50         60
orf33a.pep  MLNPSRKLVELVRILEEGGFIFSGDPVQATEALRRVDGSTEEKIIRRAKMIDRNRMLRET
            |||||||||||||||:||||||||||||||||||||||||||||||||:|||||||||||
orf33-1     MLNPSRKLVELVRILDEGGFIFSGDPVQATEALRRVDGSTEEKIIRRAEMIDRNRMLRET
                    10         20         30         40         50         60

70         80         90        100        110        120
orf33a.pep  LERVRAGSFWLWVAAATFAFXTXFSVTYLLMDNQGLNFFLVLAGVXGMNTLMLAVWLAML
            ||||||||||||||:||||| | ||||||||||||||||||||||| |||||||||||||
orf33-1     LERVRAGSFWLWVVAATFAFFTGFSVTYLLMDNQGLNFFLVLAGVLGMNTLMLAVWLAML
                    70         80         90        100        110        120

130        140        150        160        170        180
orf33a.pep  FLRVKVGRFFSSPATWFRGKDPVNQAVLRLYADEWRXPSVRWKIGATSHSLWLCTLLGML
            ||||||||||||||||||||||||||||||||||||| ||||||||||||||||||||||
orf33-1     FLRVKVGRFFSSPATWFRGKDPVNQAVLRLYADEWRQPSVRWKIGATSHSLWLCTLLGML
                   130        140        150        160        170        180

190        200        210        220        230        240
orf33a.pep  VSVLLLLLVRQYTFNWESTLLGDSSSVRLVEMLAWLPAKLGFPVPDARAVIEGRLNGNIA
            |||||||||||||||||||||:::::|||||||||||:||||||||||||||||||||||
orf33-1     VSVLLLLLVRQYTFNWESTLLSNAASVRAVEMLAWLPSKLGFPVPDARAVIEGRLNGNIA
                   190        200        210        220        230        240
```

```
                   250         260        270        280        290        300
orf33a.pep DARAWSGLLVGSIACYGILPRLLAWAVCKILXXTSENGLDLEKXXXXXXXIRRWQNKITDA
           ||||||||||||||||||||||||||||:|||||  |||||||||||   ||||||||||||
orf33-1    DARAWSGLLVGSIACYGILPRLLAWVVCKILLKTSENGLDLEKPYYQAVIRRWQNKITDA
                   250         260        270        280        290        300
                   310        320        330        340        350        360
orf33a.pep DTRRETVSAVSPKIVLNDAPKWAVMLETEWQDGEWFEGRLAQEWLDKGVAANREQVAALE
           |||||||||||||:|||||||||||||||||||||||||||||||||||||:||||||||
orf33-1    DTRRETVSAVSPKIILNDAPKWAVMLETEWQDGEWFEGRLAQEWLDKGVATNREQVAALE
                   310        320        330        340        350        360
                   370        380        390        400        410        420
orf33a.pep TELKQKPAQLLIGVRAQTVPDRGVLRQIVRLSEAAQGGAVVXLLAEQGLSDDLSEKLEHW
           |||||||||||||||||||||||||||||||||||||||||| |||||||||||||||||
orf33-1    TELKQKPAQLLIGVRAQTVPDRGVLRQIVRLSEAAQGGAVVQLLAEQGLSDDLSEKLEHW
                   370        380        390        400        410        420
                   430        440        450
orf33a.pep RNALTECGAAWLEPDRAAQEGRLKTNDRTX
           ||||:|||||||||||||||||||||
orf33-1    RNALAECGAAWLEPDRAAQEGRLKDQX
                   430        440
```

Homology with a Predicted ORF from *N. gonorrhoeae*
ORF33 shows 91.6% identity over a 143aa overlap with a predicted ORF (ORF33.ng) from *N. gonorrhoeae*:

```
orf33.pep                                LFLRVKVGRFFSSPATWFRXKDPVNQAVLR  30
                                         |||||||||||||||||||||||| ||||||
   orf33ng LMDNQGLNFFLVLAGVLGMNTLMLAVWLATLFLRVKVGRFFSSPATWFRXKGPVNQAVLR 100
orf33.pep  LYXDEWRXTSVRWKIXATSHSLWLCTLLGMLVSVLLLLLVRQYTFNWESTLLSNAASVRA  90
           || :||  |||||| ||:|||||||||||||||||||||||||||||||||||||||||||
   orf33ng LYADQWRQPSVRWKIGATAHSLWLCTLLGMLVSVLLLLLVRQYTFNWESTLLSNAASVRA 160
orf33.pep  VEMLAWLPSKLGFPVPDARSVIEGRLNGNIADARAWSGLLVXSIACXGILPRL         143
           ||||||||||||||||||||||||:|||||||||||||||| ||:|||||||||
   orf33ng VEMLAWLPSKLGFPVPDARSVIEGRLNGNIADARAWSGLLVXSIACXGILPRLLAWVVCK 220
```

An ORF33ng nucleotide sequence <SEQ ID 203> was predicted to encode a protein having amino acid sequence <SEQ ID 204>:

```
  1 MIDRDRMLRD TLERVRAGSF WLWVVVASMM FTAGFSGTYL LMDNQGLNFF

51 LVLAGVLGMN TLMLAVWLAT LFLRVKVGRF FSSPATWFRG KGPVNQAVLR

101 LYADQWRQPS VRWKIGATAH SLWLCTLLGM LVSVLLLLLV RQYTFNWEST

151 LLSNAASVRA VEMLAWLPSK LGFPVPDARA VIEGRLNGNI ADARAWSGLL

201 VGSIVCYGIL PRLLAWVVCK ILLKTSENGL DLEKTYYQAV IRRWQNKITD

251 ADTRRETVSA VSPKIVLNDA PKWALMLETE WQDGQWFEGR LAQEWLDKGV

301 AANREQVAAL ETELKQKPAQ LLIGVRAQTV PDRGVLRQIV RLSEAAQGGA

351 VVQLLAEQGL SDDLSEKLEH WRNALTECGA AWLEPDRVAQ EGRLKDQ*
```

Further sequence analysis revealed the following DNA sequence <SEQ ID 205>:

```
  1 ATGTTGaatC CATCCCgaAA ACTGgttgag ctGgTCCgtA Ttttgaataa 51 aggggggtTTT attttcagcg gcgatcctgt gcaggcgacg gaggctttgc 101 gccgcgtgga cggcAGTACG GAggAaaaaa tcttccgtcg GGCGGAGAtg 151 atcgACAGGg accgtatgtt gcgggACaCg TtggaacGTG TGCGTGCggg 201 gtcgtTctgG TTATGGGTGG TggtggCAtC gATGATGTtt aCCGCCGGAT 251 TTTCAGgcac ttatCttCTG ATGGACaatC AGGGGCtGAA TtTCTTTTTA 301 GTTTTggcgG GAGTGTtggG CATGaatacG ctgATGCTGG CAGTATGGtt
```

```
 351 gGCAACGTTG TTCCTGCGCG TGAAAGTGGG ACGGTTTTTC AGCAGTCCGG

401 CGACGTGGTT TCGGGGCAAA GGCCCTGTAA ATCAGGCGGT GTTGCGGCTG

451 TATGCGGACC AGTGGCGGCA ACCTTCGGTA CGATGGAAAA TAGGCGCAAC

501 GGCGCACAGC TTGTGGCTCT GCACGCTGCT CGGAATGCTG GTGTCGGTAT

551 TGCTGCTGCT TTTGGTGCGG CAATATACGT TCAACTGGGA AAGCACGCTG

601 TTGAGCAATG CCGCTTCGGT ACGCGCGGTG GAAATGTTGG CATGGCTGCC

651 GTCGAAACTC GGTTTCCCTG TCCCCGATGC GCGGGCGGTC ATCGAAGGTC

701 GTCTGAACGG CAATATTGCC GATGCGCGGG CTTGGTCGGG GCTGCTGGTC

751 GGCAGTATCG TCTGCTACGG CATCCTGCCG CGCCTCTTGG CTTGGGTAGT

801 GTGTAAAATC CTTTTGAAAA CAAGCGAAAA CGGattgGAT TTGGAAAAAA

851 CCTATTATCA GGCGGTCATC CGCCGCTGGC AGAACAAAAT CACCGATGCG

901 GATACGCGTC GGGAAACCGT GTCCGCCGTT TCGCcgaAAA TCGTCTTGAA

951 CGATGCGCCG AAATGGGCGC TCATGCTGGA GACCGAGTGG CAGGACGGCC

1001 AATGGTTCGA GGGCAGGCTG GCGCAGGAAT GGCTGGATAA GGGCGTTGCC

1051 GCCAATCGGG AACAGGTTGC CGCGCTGGAG ACAGAGCTGA AGCAGAAACC

1101 GGCGCAACTG CTTATCGGCG TACGCGCCCA AACTGTGCCG GACCGGGGCG

1151 TGCTGCGGCA GATTGTGCGG CTTTCGGAAG CGGCGCAGGG CGGCGCGGTG

1201 GTGCAGCTTT TGGCGGAACA GGGGCTTTCA GACGACCTTT CGGAAAAGCT

1251 GGAACATTGG CGTAACGCGC TGACCGAATG CGGCGCGGCG TGGCTTGAGC

1301 CTGACAGGGT GGCGCAGGAA GGCCGTTTGA AGACCAATA A
```

This encodes a protein having amino acid sequence <SEQ ID 206; ORF33ng-1>:

```
  1 MLNPSRKLVE LVRILNKGGF IFSGDPVQAT EALRRVDGST EEKIFRRAEM

51 IDRDRMLRDT LERVRAGSFW LWVVVASMMF TAGFSGTYLL MDNQGLNFFL

101 VLAGVLGMNT LMLAVWLATL FLRVKVGRFF SSPATWFRGK GPVNQAVLRL

151 YADQWRQPSV RWKIGATAHS LWLCTLLGML VSVLLLLLVR QYTFNWESTL

201 LSNAASVRAV EMLAWLPSKL GFPVPDARAV IEGRLNGNIA DARAWSGLLV

251 GSIVCYGILP RLLAWVVCKI LLKTSENGLD LEKTYYQAVI RRWQNKITDA

301 DTRRETVSAV SPKIVLNDAP KWALMLETEW QDGQWFEGRL AQEWLDKGVA

351 ANREQVAALE TELKQKPAQL LIGVRAQTVP DRGVLRQIVR LSEAAQGGAV

401 VQLLAEQGLS DDLSEKLEHW RNALTECGAA WLEPDRVAQE GRLKDQ*
```

ORF33ng-1 and ORF33-1 show 94.6% identity in 446 aa overlap:

```
                    10         20         30         40         50         60
       orf33-1.pep MLNPSRKLVELVRILDEGGFIFSGDPVQATEALRRVDGSTEEKIIRRAEMIDRNRMLRET
                   ||||||||||||||||::||||||||||||||||||||||||||:||||||||:||||:|
       orf33ng-1   MLNPSRKLVELVRILNKGGFIFSGDPVQATEALRRVDGSTEEKIFRRAEMIDRDRMLRDT
                    10         20         30         40         50         60

70         80         90        100        110        120
       orf33-1.pep LERVRAGSFWLWVVAATPAFFTGFSVTYLLMDNQGLNFFLVLAGVLGMNTLMLAVWLAML
                   ||||||||||||||||::|  :  :|||||||||||||||||||||||||||||||||:|
       orf33ng-1   LERVRAGSFWLWVVVASMMFTAGFSGTYLLMDNQGLNFFLVLAGVLGMNTLMLAVWLATL
                    70         80         90        100        110        120
```

```
             130        140        150        160        170        180
orf33-1.pep  FLRVKVGRFFSSPATWFRGKDPVNQAVLRLYADEWRQPSVRWKIGATSHSLWLCTLLGML
             ||||||||||||||||||| |||||||||||||||||:|||||||||||:|||||||||||
orf33ng-1    FLRVKVGRFFSSPATWFRGKGPVNQAVLRLYADQWRQPSVRWKIGATAHSLWLCTLLGML
             130        140        150        160        170        180

190        200        210        220        230        240
orf33-1.pep  VSVLLLLLVRQYTFNWESTLLSNAASVRAVEMLAWLPSKLGFPVPDARAVIEGRLNGNIA
             ||||||||||||||||||||||||||||||||||||||||||||||||||||||||||||
orf33ng-1    VSVLLLLLVRQYTFNWESTLLSNAASVRAVEMLAWLPSKLGFPVPDARAVIEGRLNGNIA
             190        200        210        220        230        240

250        260        270        280        290        300
orf33-1.pep  DARAWSGLLVGSIACYGILPRLLAWVVCKILLKTSENGLDLEKPYYQAVIRRWQNKITDA
             |||||||||||:||||||||||||||||||||||||||||||:|||||||||||||||
orf33ng-1    DARAWSGLLVGSIVCYGILPRLLAWVVCKILLKTSENGLDLEKTYYQAVIRRWQNKITDA
             250        260        270        280        290        300

310        320        330        340        350        360
orf33-1.pep  DTRRETVSAVSPKIILNDAPKWAVMLETEWQDGEWFEGRLAQEWLDKGVATNREQVAALE
             ||||||||||||||:|||||||||:|||||||||:|||||||||||||||:||||||||
orf33ng-1    DTRRETVSAVSPKIVLNDAPKWALMLETEWQDGQWFEGRLAQEWLDKGVAANREQVAALE
             310        320        330        340        350        360

370        380        390        400        410        420
orf33-1.pep  TELKQKPAQLLIGVRAQTVPDRGVLRQIVRLSEAAQGGAVVQLLAEQGLSDDLSEKLEHW
             ||||||||||||||||||||||||||||||||||||||||||||||||||||||||||||
orf33ng-1    TELKQKPAQLLIGVRAQTVPDRGVLRQIVRLSEAAQGGAVVQLLAEQGLSDDLSEKLEHW
             370        380        390        400        410        420

430        440
orf33-1.pep  RNALAECGAAWLEPDRAAQEGRLKDQX
             ||||:|||||||||||:||||||||||
orf33ng-1    RNALTECGAAWLEPDRVAQEGRLKDQX
             430        440
```

Based on the presence of several putative transmembrane domains in the gonococcal protein, it is predicted that the proteins from *N. meningitidis* and *N. gonorrhoeae*, and their epitopes, could be useful antigens for vaccines or diagnostics, or for raising antibodies.

Example 25

The following partial DNA sequence was identified in *N. meningitidis* <SEQ ID 207>:

```
  1..CAGAAGAGTT TGTCGAGAAT TCTTTATGG GGTTTGGGCG GCGTGTTTTT

51  CGGGGTGTCC GGTCTGGTAT GGTTTTCTTT GGGCGTTTCT TT.GAGTGCG

101  CCTGTTTTTC GGGTGTTTCT TTTCGGGGTT CGGGACGGGG GACGTTTGTG

151  GGCAGTACGG GGGTTTCTTT GAGTGTGTTT TCAGCTTGTG TTCC.GGCGT

201  CGTCCGGCTG CCTGTCGGTT TGAGCTGTGT CGGCAGGTTG CG..GTTTGA

251  CCCGGTTTTT CTTGGGTGCG GCAGGGGACG TCATTCTCCT GCCGCTTTCG

301  TCTGTGCCGT CCGGCTGTGC GGGTTCGGAT GAGGCGGCGT GGTGGTGTTC

351  GGGTTGGGCG GCATCTTGTT CCGACTACGC CGTTTGGCAG CCAGAATTCG

401  GTTTCGCGGG GGCTGTCGGT GTGTTGCGGT TCGGCTTGAA GGGTTTTGTC

451  GTCC..
```

This corresponds to the amino acid sequence <SEQ ID 208; ORF34>:

```
  1..QKSLSRISLW GLGGVFFGVS GLVWFSLGVS XECACFSGVS FRGSGRGTFV

51  GSTGVSLSVF SACVXGVVRL PVGLSCVGRL XXLTRFFLGA AGDVILLPLS
```

```
101 SVPSGCAGSD EAAWWCSGWA ASCPTTPFGS QNSVSRGLSV CCGSA*RVLS

151 S..
```

Further work revealed the complete nucleotide sequence <SEQ ID 209>:

```
   1 ATGATGATGC CGTTCATAAT GCTTCCTTGG ATTGCkGGTG TGCCTGCCGT

51 GCCGGGTCAG AATAGGTTGT CCAGAATTTC TTTATGGGGT TGGGCGGCG

101 TGTTTTTCGG GGTGTCCGGT TTGGTATGGT TTTCTTTGGG CGTTTCTTTG

151 GGCTGCGCCT GTTTTTCGGG TGTTTCTTTT CGGGGTTCGG GACGGGGGAC

201 GTTTGTGGGC AGTACGGGGG TTTCTTTGAG TGTGTTTTCA GCTTGTGTTC

251 CGGCGTCGTC CGGCTGCCTG TCGGTTTGAG CTGTGTCGGC AGGTTGCGGT

301 TTGACCCGGT TTTTCTTGGG TGCGGCAGGG GACGGCAGTC CGCTGCCGCT

351 TTCGTCTGTG CCGTCCGGCT GTGCGGGTTC GGATGAGGCG GCGTGGTGGT

401 GTTCGGGTTG GGCGGCATCT TGTCCGACTA CGCCGTTTGG CAGCCAGAAT

451 TCGGTTTCGC GGGGCTGTC GGTGTGTTGC GGTTCGGCTT GAAGGGTTTT

501 GTCGCCGTTC GGGTTGAATG TGCTGACGAT GCCTATTGCC AATGCGCCGA

551 TGGCGGCGAT ACAGATGAGC AATACGGCGC GTATCAGGAG TTTGGGGGTC

601 AGCCTGAAGG GTTTGTTCGG TTTTTTTGCC ATTTTGATTG TGCTTTTGGG

651 GTGTCGGGCA ATGCCGTCTG AAGGCGGTTC AGACGGCATT GCCGAGTCAG

701 CGTTGGACGT AGTTTTGGTA GAGGGTGATG ACTTTTTGTA CGCCGACGGT

751 GGTGCTGACT TTTTGGGTAA TCTGCGCCTG TTCTTCGGGG GTGAGGATGC

801 CCATAACGTA GGTTACGTTG CCGTAGGTAA CGATTTTGAC GCGCGCCTGT

851 GTGGCGGGGC TGATGCCCAA CAGCGTGGCG CGGACTTTGG ATGTGTTCCA

901 AGTGTCGCCG GCGATGTCGC CGGCAGTGCG CGGCAGGGAG GCGACGGTAA

951 TATAGTTGTA CACGCCTTCG GCGGCCTGTT CGGAACGTGC AATCTGACCG

1001 ACGAACTGTT TTTCGCCTTC GGTGGCGACT TGTCCGAGCA GCAGCAGGTG

1051 GCGGTTGTAG CCGACGACGG AGATTTGGGG CGTGTAGCCT TTGGTTTGGT

1101 TGTTTTGGCG CAGATAGGAA CGGGCGGTGG TTTCGATACG CAACGCCATA

1151 ACGTTGTCGT CGGTTTGCGC GCCGGTGGTT CGGCGGTCGA CGGCGGATTT

1201 CGCGCCGACG GCGGCGCTTC CGATTACTGC GCTGACGCAG CCGCTAAGGG

1251 CAAGGCTGAA AATGGCGGCA ATCAGGGTGC GGACGGTGTG CGGTTTGGGT

1301 TTCATCGGGT GCTTCCTTTC TTGGGCGTTT CAGACGGCAT TGCTTTGCGC

1351 CATGCCGTCT GA
```

This corresponds to the amino acid sequence <SEQ ID 210; ORF34-1>:

```
  1 MMMPFIMLPW IAGVPAVPGQ NRLSRISLWG LGGVFFGVSG LVWFSLGVSL

51 GCACFSGVSF RGSGRGTFVG STGVSLSVFS ACVPASSGCL SV*AVSAGCG

101 LTRFFLGAAG DGSPLPLSSV PSGCAGSDEA AWWCSGWAAS CPTTPFGSQN

151 SVSRGLSVCC GSA*RVLSPF GLNVLTMPIA NAPMAAIQMS NTARIRSLGV

201 SLKGLFGFFA ILIVLLGCRA MPSEGGSDGI AESALDVVLV EGDDFLYADG
```

-continued
```
251 GADFLGNLRL FFGGEDAHNV GYVAVGNDFD ARLCGGADAQ QRGADFGCVP

301 SVAGDVAGSA RQGGDGNIVV HAFGGLFGTC NLTDELFFAF GGDLSEQQQV

351 AVVADDGDLG RVAFGLVVLA QIGTGGGFDT QRHNVVVGLR AGGSAVDGGF

401 RADGGASDYC ADAAAKGKAE NGGNQGADGV RFGFHRVLPF LGVSDGIALR

451 HAV*
```

Computer analysis of this amino acid sequence gave the following results:

Homology with a Predicted ORF from *N. meningitidis* (Strain A)

ORF34 shows 73.3% identity over a 161aa overlap with an ORF (ORF34a) from strain A of *N. meningitidis*:

```
                           10        20        30
orf34.pep              QKSLSRISLWGLGGVFFGVSGLVWFSLGVSXE------CAC
                             ||||| ||||||||||||||||||||||||      |||
   orf34a MMXPXIMLPWIAGVPAVPGQKRLSRXSLWGLGGXFFGVSGLVWFSLGVSXSLGVSXGCAC
              10        20        30        40        50        60
                 40        50        60        70        80        90
orf34.pep  FSGVSFRGSGRGTFVGSTGVSLSVFSACVXGVVRLPVGLSCVGRLXX-----LTRFFLGA
           ||||||||||||||||||||||||||||:       |::  :|::        ||| |||
   orf34a  FSGVSFRGSGRGTFVGSTGVSLSVFSACA------PASSGCLSVXAVSAGCGLTRXFXGA
              70        80        90       100       110
                100       110       120       130       140       150
orf34.pep  AGDVILLPLSSVPSGCAGSDEAAWWCSGWAASCPTTPFGSQNSVSRGLSVCCGSAXRVLS
           |||  ||||||||||||||| :||    ||||||||||||||||||||||||||:  |||
   orf34a  AGDGSPLPLSSVPSGCAGADEEAXXCSGWAASCPTTPFGSQNSVSRGLSVCCGSVWRVLS
              120       130       140       150       160       170
orf34.pep  S orf34a  PFGXNVLTMPIANAPMAVIQMSNTARIRSLGVSLKGLFXFFAILIVLLGCRAMPSEGGSD
              180       190       200       210       220       230
```

The complete length ORF34a nucleotide sequence <SEQ ID 211> is:

```
  1 ATGATGATNC CGTTNATAAT GCTTCCTTGG ATTGCGGGTG TGCCTGCCGT

51 GCCGGGTCAG AAGAGGTTGT CGAGAANTTC TTTATGGGGT TTAGGCGGCN

101 TGTTTTTCGG GGTGTCCGGT TTGGTATGGT TTTCTTTGGG CGTTTCTNTT

151 TCTTTGGGTG TTTCTNTGGG CTGTGCCTGT TTTTCGGGTG TTTCTTTTCG

201 GGGTTCGGGA CGGGGGACGT TTGTGGGCAG TACNGGGGTT TCTTTGAGTG

251 TGTTTTCAGC TTGTGCTCCG GCGTCGTCCG GCTGCCTGTC GGTTTNAGCT

301 GTGTCGGCAG GTTGCGGTTT GACCCGGNTT TTCTTNGGTG CGGCAGGGGA

351 CGGCAGTCCG CTGCCGCTTT CGTCTGTGCC GTCCGGCTGT GCGGGTGCGG

401 ATGAGGAGGC GTNGTNGTGT TCGGGTTGGG CGGCATCTTG TCCGACTACG

451 CCGTTTGGCA GCCAGAATTC GGTTTCGCGG GGGCTGTCGG TGTGTTGCGG

501 TTCGGTNTGG AGGGTTTTGT CNCCGTTCGG GTNGAATGTG CTGACGATGC

551 CTATTGCCAA TGCGCCGATG GCGGTGATAC AGATGAGCAA TACGGCGCGT

601 ATCAGGAGTT TGGGGGTCAG CCTGAAGGGT TTGTTCNGTT TTTTTGCCAT

651 TTTGATTGTG CTTTTGGGGT GTCGGGCAAT GCCGTCTGAA GGCGGTTCAG

701 ACGGCATTGC CGAGTCAGCG TTGGACGTAG TTTNGGTAGA GGGTGATGAC

751 TTTTTGTACG CCGACGGTGG TGCTGACTTT TTGGGTAATC TGCGCCTGTT

801 CTTCGGGGGT GAGGATGCCC ATAACGTAGG TTACGTTGCC GTAGGTAACG
```

```
 851 ATTTTGACGC GCGCCTGTGT GGCGGGGCTG ATGCCCAACA GCGTGGCGCG

901 GACTTTGGAT GTGTTCCAAG TGTCGCCGGC GATGTCGCCG GCAGTGCGCG

951 GCAGGGAGGC GACGGTAATG TANTTGTACA CGCCTTCGGC GGCCTGTTCG

1001 GAACGTGCAA TCTGACCGAC GAACTGTTTC TCGCCTTCGG TGGCGACTTG

1051 TCCGAGCAGC AGCAGGTGGC GGTTGTAGCC GACAACGGAG ATTTGGGGCG

1101 TGTANCCTTT GGTTTGGTTG TTTTGGCGCA GATAGGAGCG GGCGGTGGTT

1151 TCGATACGCA GCGCCATTAC GTTGTCGTCG GTTNGCGCGC CGGTGGTTCG

1201 GCGGTCGACG GCGGATTTCG CGCCGACCGC CGCGCCGCCG ACGACTGCGC

1251 TGACGCAGCC GCCGAGGGCA AGGCTGAGGA CGGCGGCAGT CAGGGTGCGG

1301 ACGGTGTGCG GTTTGGGTTT CATCGGGTGC TTCCTTTCTT GGGCGTTTCA

1351 GACGGCATTG CTTTGCGCCA TGCCGTCTGA
```

This encodes a protein having amino acid sequence <SEQ ID 212>:

```
  1 MMXPXIMLPW IAGVPAVPGQ KRLSRXSLWG LGGXFFGVSG LVWFSLGVSX
 51 SLGVSXGCAC FSGVSFRGSG RGTFVGSTGV SLSVFSACAP ASSGCLSVXA
101 VSAGCGLTRX FXGAAGDGSP LPLSSVPSGC AGADEEAXXC SGWAASCPTT
151 PFGSQNSVSR GLSVCCGSVW RVLSPFGXNV LTMPIANAPM AVIQMSNTAR
201 IRSLGVSLKG LFXFFAILIV LLGCRAMPSE GGSDGIAESA LDVVXVEGDD
251 FLYADGGADF LGNLRLFFGG EDAHNVGYVA VGNDFDARLC GGADAQQRGA
301 DFGCVPSVAG DVAGSARQGG DGNVXVHAFG GLFGTCNLTD ELFLAFGGDL
351 SEQQQVAVVA DNGDLGRVXF GLVVLAQIGA GGGFDTQRHY VVVGXRAGGS
401 AVDGGFRADR RAADDCADAA AEGKAEDGGS QGADGVRFGF HRVLPFLGVS
451 DGIALRHAV*
```

ORF34a and ORF34-1 show 91.3% identity in 459 aa overlap:

```
                    10         20         30         40         50         60
    orf34a.pep  MMXPXIMLPWIAGVPAVPGQKRLSRXSLWGLGGXFFGVSGLVWFSLGVSXSLGVSXGCAC
                || | |||||||||||||||:||||  ||||||| |||||||||||||||      ||||
     orf34-1   MMMPFIMLPWIAGVPAVPGQNRLSRISLWGLGGVFFGVSGLVWFSLGVSL------GCAC
                    10         20         30         40         50

70         80         90        100        110        120
    orf34a.pep  FSGVSFRGSGRGTFVGSTGVSLSVFSACAPASSGCLSVXAVSAGCGLTRXFXGAAGDGSP
                ||||||||||||||||||||||||||||:|||||||||| ||||||||| | ||||||||
     orf34-1   FSGVSFRGSGRGTFVGSTGVSLSVFSACVPASSGCLSVXAVSAGCGLTRFFLGAAGDGSP
                    60         70         80         90        100        110

130        140        150        160        170        180
    orf34a.pep  LPLSSVPSGCAGADEEAXXCSGWAASCPTTPFGSQNSVSRGLSVCCGSVWRVLSPFGXNV
                ||||||||||||:|| || |||||||||||||||||||||||||||||: ||||||| ||
     orf34-1   LPLSSVPSGCAGSDEAAWWCSGWAASCPTTPFGSQNSVSRGLSVCCGSAXRVLSPFGLNV
                   120        130        140        150        160        170

190        200        210        220        230        240
    orf34a.pep  LTMPIANAPMAVIQMSNTARIRSLGVSLKGLFXFFAILIVLLGCRAMPSEGGSDGIAESA
                ||||||||||:|||||||||||||||||||||| |||||||||||||||||||||||||
     orf34-1   LTMPIANAPMAAIQMSNTARIRSLGVSLKGLFGFFAILIVLLGCRAMPSEGGSDGIAESA
                   180        190        200        210        220        230

250        260        270        280        290        300
    orf34a.pep  LDVVXVEGDDFLYADGGADFLGNLRLFFGGEDAHNVGYVAVGNDFDARLCGGADAQQRGA
                |||| |||||||||||||||||||||||||||||||||||||||||||||||||||||||
     orf34-1   LDVVLVEGDDFLYADGGADFLGNLRLFFGGEDAHNVGYVAVGNDFDARLCGGADAQQRGA
                   240        250        260        270        280        290
```

```
                    310       320       330       340       350       360
orf34a.pep  DFGCVPSVAGDVAGSARQGGDGNVXVHAFGGLFGTCNLTDELFLAFGGDLSEQQQVAVVA
            ||||||||||||||||||||||| ||||||||||||||||| ||||||||||||||||||
orf34-1     DFGCVPSVAGDVAGSARQGGDGNIVVHAFGGLFGTCNLTDELFFAFGGDLSEQQQVAVVA
                  300       310       320       330       340       350

370       380       390       400       410       420
orf34a.pep  DNGDLGRVXFGLVVLAQIGAGGGFDTQRHYVVVGXRAGGSAVDGGFRADRRAADDCADAA
            : ||||||  ||||||||| :|||||||||| |||| |||||||||||||| :| |||||
orf34-1     DDGDLGRVAFGLVVLAQIGTGGGFDTQRHNVVVGLRAGGSAVDGGFRADGGAADYCADAA
                  360       370       380       390       400       410

430       440       450       460
orf34a.pep  AEGKAEDGGSQGADGVRFGFHRVLPFLGVSDGIALRHAVX
            |:||||:||:||||||||||||||||||||||||||||||
orf34-1     AKGKAENGGNQGADGVRFGFHRVLPFLGVSDGIALRHAVX
                  420       430       440       450
```

Homology with a Predicted ORF from *N. gonorrhoeae*
ORF34 shows 77.6% identity over a 161aa overlap with a predicted ORF (ORF34.ng) from *N. gonorrhoeae*.

```
orf34.pep                         QKSLSRISLWGLGGVFFGVSGLVWFSLGVSXE------CAC  35
                                  || |||||||||||:|||||||||||||||| :      |||
orf34ng     MMMPFIMLPWIAGVPAVPGQKRLSRISLWGLAGVFFGVSGLVWFSLGVSFSLGVSLGCAC  60
orf34.pep   FSGVSFRGSGRGTFVGSTGVSLSVFSACVXGVVRLPVGLSCV-----GRLXXLTRFFLGA  90
            ||||||||||   |:|||||||||||||||        :||:   | :      ||||||||||
orf34ng     FSGVSFRGSGWGAFVGSTGVSLSVFSACVP----VPVNESAARAASEGR--GLTRFFLGA 114
orf34.pep   AGDVILLPLSSVPSGCAGSDEAAWWCSGWAASCPTTPFGSQNSVSRGLSVCCGSAXRVLS 150
            ||| ||||||||||||||||||||||||||||||:|||||||||||||||||||:  ||||
orf34ng     AGDGSPLPLSSVPSGCAGSDEAAWWCSGWAASCPTAPFGSQNSVSRGLSVCCGSVWRVLS 174
orf34.pep   S                                                            175 orf34ng     PFGLNVLTMPTANAPMAVIQMSNTARIRSLGVSLKGLFGFFAILIVLLGCRAMPSEGGSD 234
```

The complete length ORF34ng nucleotide sequence <SEQ ID 213> is:

```
  1  ATGATGATGC CGTTCATAAT GCTTCCTTGG ATTGCGGGTG TGCCTGCCGT

51  GCCGGGTCAA AAGAGGTTGT CGAGAATCTC TTTATGGGGT TGGCCGGCG

101  TGTTTTTCGG GGTGTCCGGT TTGGTATGGT TTTCTTTGGG CGTTTCTTTT

151  TCTTTGGGTG TTTCTTTGGG CTGCGCCTGT TTTTCGGGTG TTTCTTTTCG

201  GGGTTCGGGA TGGGGGGCGT TTGTGGGCAG TACGGGGGTT TCTTTGAGTG

251  TGTTTTCAGC TTGTGTTCCG GTGCCGGTTA ACGAATCGGC TGCCCGGGCC

301  GCATCCGAAG GGCGCGGTTT gACCCGGTTT TTCTTGGGTG CGGCAGGGGA

351  CGGCAGTCCG CTGCCGCTTT CTTCTGTGCC GTCCGGCTGT GCGGGTTCGG

401  ATGAGGCGGC GTGGTGGTGT TCGGGTTGGG CGGCATCTTG TCCGACGGCG

451  CCGTTTGGCA GCCAGAATTC GGTTTCGCGG GGGCTGTCGG TGTGTTGCGG

501  TTCGGTTTGG AGGGTTTTGT CGCCGTTCGG GTTGAATGTG CTGACGATGC

551  CTACTGCCAA TGCGCCGATG GCGGTGATAC AGATGAGCAA TACGGCGCGT

601  ATCAGGAGTT TGGGGGTCAG CCTGAAGGGT TGTTCGGTT TTTTTGCCAT

651  TTTGATTGTG CTTTTGGGGT GTCGGGCAAT GCCGTCTGAA GGCGGTTCAG

701  ACGGCATTGC CGAGTCAGCG TTGGACGTAG TTTTGGTAGA GGGTAATGAC

751  TTTTTGTACG CCGAcggTGG TGCTGACTTT TTGGGTAATC TGCGCCTGTT

801  CTTCGGGGGT GAGGATGCCC ATAACGTAGG TTACATTGCC GTAGGTAATG

851  ATTTTGACGC GCGCCTGTGT AGCGGGGCTG ATGCCCAGCA GcgtgGCGCG

901  GACTTTGGAC GTGTTCCAAG TGTCGCCGGC GATGTCGCCC GCAGTGCGCG
```

```
 951 GCAGGGAGGC GACGGTAATG TAGTTGTATA CGCCTTCGGC GGCCTGTTCG

1001 GAACGTGCAA TCTGACCGAC GAACTGTTTT TCGCCTTCGG TGGCGACTTG

1051 TCCGAGCAGC AGCAGGTGGC GGTTGTAGCC GACGACGGAG ATTTGGGGCG

1101 TGTAGCCTTT GGTTTGGTTG TTTTGGCGCA GGTAGGAACG GGCGGTGGTT

1151 TCGATACGCA ACGCCATAAC GTtgtCATCG GTTtgcgcgc CGGTGGTTcg 1201 gCGGTCGATG ACGGATTTTG CGCCGACGGC GGCCCCGCCG ACGACTGCGC

1251 TGAAGCAGCC GCCGAGGGCA AGGCTGAGGA CGGCGGCAAT CAGGGTGCGG

1301 ACGGTGTGTG GTTTGGGTTT CATCGGGGAC TTCCTTTCTT GGGCGTTTCA

1351 GACGGCATTG CTTTGCGCCA TGCCGTCTGA
```

This encodes a protein having amino acid sequence <SEQ ID 214>:

```
  1 MMMPFIMLPW IAGVPAVPGQ KRLSRISLWG LAGVFFGVSG LVWFSLGVSF

51 SLGVSLGCAC FSGVSFRGSG WGAFVGSTGV SLSVFSACVP VPVNESAARA

101 ASEGRGLTRF FLGAAGDGSP LPLSSVPSGC AGSDEAAWWC SGWAASCPTA

151 PFGSQNSVSR GLSVCCGSVW RVLSPFGLNV LTMPTANAPM AVIQMSNTAR

201 IRSLGVSLKG LFGFFAILIV LLGCRAMPSE GGSDGIAESA LDVVLVEGND

251 FLYADGGADF LGNLRLFFGG EDAHNVGYIA VGNDFDARLC SGADAQQRGA

301 DFGRVPSVAG DVARSARQGG DGNVVVYAFG GLFGTCNLTD ELFFAFGGDL

351 SEQQQVAVVA DDGDLGRVAF GLVVLAQVGT GGGFDTQRHN VVIGLRAGGS

401 AVDDGFCADG GPADDCAEAA AEGKAEDGGN QGADGVWFGF HRGLPFLGVS

451 DGIALRHAV*
```

ORF34ng and ORF34-1 show 90.0% identity in 459 aa overlap:

```
                     10         20         30         40          4         50
   orf34-1.pep  MMMPFIMLPWIAGVPAVPGQNRLSRISLWGLGGVFFGVSGLVWFSLGVS------LGCAC
                |||||||||||||||||||| |||||||||||:|||||||||||||||||      |||||
   orf34ng      MMMPFIMLPWIAGVPAVPGQKRLSRISLWGLAGVFFGVSGLVWFSLGVSFSLGVSLGCAC
                         10         20         30         40         50         60

60         70         80         90        100        110
   orf34-1.pep  FSGVSFRGSGRGTFVGSTGVSLSVFSACVPASSGCLSVXAVSAGCGLTRFFLGAAGDGSP
                ||||||||||   : |||||||||||||||||:    :  :: |:|  |||||||||||||
   orf34ng      FSGVSFRGSGWGAFVGSTGVSLSVFSACVPVPVNESAARAASEGRGLTRFFLGAAGDGSP
                         70         80         90        100        110        120

120        130        140        150        160        170
   orf34-1.pep  LPLSSVPSGCAGSDEAAWWCSGWAASCPTTPFGSQNSVSRGLSVCCGSAXRVLSPFGLNV
                |||||||||||||||||||||||||||||: |||||||||||||||||:  |||||||||
   orf34ng      LPLSSVPSGCAGSDEAAWWCSGWAASCPTAPFGSQNSVSRGLSVCCGSVWRVLSPFGLNV
                        130        140        150        160        170        180

180        190        200        210        220        230
   orf34-1.pep  LTMPIANAPMAAIQMSNTARIRSLGVSLKGLFGFFAILIVLLGCRAMPSEGGSDGIAESA
                |||| |||||||:|||||||||||||||||||||||||||||||||||||||||||||||
   orf34ng      LTMPTANAPMAVIQMSNTARIRSLGVSLKGLFGFFAILIVLLGCRAMPSEGGSDGIAESA
                        190        200        210        220        230        240

240        250        260        270        280        290
   orf34-1.pep  LDVVLVEGDDFLYADGGADFLGNLRLFFGGEDAHNVGYVAVGNDFDARLCGGADAQQRGA
                ||||||||:|||||||||||||||||||||||||||||:||||||||||| :|||||||
   orf34ng      LDVVLVEGNDFLYADGGADFLGNLRLFFGGEDAHNVGYIAVGNDFDARLCSGADAQQRGA
                        250        260        270        280        290        300

300        310        320        330        340        350
   orf34-1.pep  DFGCVPSVAGDVAGSARQGGDGNIVVHAFGGLFGTCNLTDELFFAFGGDLSEQQQVAVVA
                ||| ||||||||| ||||||||||:||:|||||||||||||||||||||||||||||||
   orf34ng      DFGRVPSVAGDVARSARQGGDGNVVVYAFGGLFGTCNLTDELFFAFGGDLSEQQQVAVVA
                        310        320        330        340        350        360
```

```
                 360        370        380        390        400        410
orf34-1.pep DDGDLGRVAFGLVVLAQIGTGGGFDTQRHNVVVGLRAGGSAVDGGFRADGGASDYCADAA
            ||||||||||||||||:||||||||||||||:|||||||||| || |||| :| ||:||
orf34ng     DDGDLGRVAFGLVVLAQVGTGGGFDTQRHNVVIGLRAGGSAVDDGFCADGGPADDCAEAA
                 370        380        390        400        410        420

420        430        440        450
orf34-1.pep AKGKAENGGNQGADGVRFGFHRVLPFLGVSDGIALRHAVX
            |:||||:|||||||||| ||||| ||||||||||||||||
orf34ng     AEGKAEDGGNQGADGVWFGFHRGLPFLGVSDGIALRHAVX
                 430        440        450        460
```

Based on this analysis, including the presence of a putative leader sequence (double-underlined) and several putative transmembrane domains (single-underlined) in the gonococcal protein, it is predicted that the proteins from *N. meningitidis* and *N. gonorrhoeae*, and their epitopes, could be useful antigens for vaccines or diagnostics, or for raising antibodies.

Example 26

The following partial DNA sequence was identified in *N. meningitidis* <SEQ ID 215>:

```
  1 ATGAAAACCT TCTTCAAAAC CCTTTCCGCC GCCGCACTCG CGCTCATCCT

51 CGCCGCCTGC GGATT.CAAA AAGACAGCGC GCCCGCCGCA TCCGCTTCTG

101 CCGCCGCCGA CAACGGCGCG GCGTAAAAAA GAAATCGTCT TCGGCACGAC

151 CGTCGGCGAC TTCGGCGATA TGGTCAAAGA ACAAATCCAA GCCGAGCTGG

201 AGAAAAAAGG CTACACCGTC AAACTGGTCG AGTTTACCGA CTATGTACGC

251 CCGAATCTGG CATTGGCTGA GGGCGAGTTG
```

This corresponds to the amino acid sequence <SEQ ID 216; ORF4>:

```
  1 MKTFFKTLSA AALALILAAC G.QKDSAPAA SASAAADNGA AKKEIVFGTT

51 VGDFGDMVKE QIQAELEKKG YTVKLVEFTD YVRPNLALAE GEL
```

Further sequence analysis revealed the complete nucleotide sequence <SEQ ID 217>:

```
  1 ATGAAAACCT TCTTCAAAAC CCTTTCCGCC GCCGCACTCG CGCTCATCCT

51 CGCCGCCTGC GGCGGTCAAA AAGACAGCGC GCCCGCCGCA TCCGCTTCTG

101 CCGCCGCCGA CAACGGCGCG GCGAAAAAAG AAATCGTCTT CGGCACGACC

151 GTCGGCGACT TCGGCGATAT GGTCAAAGAA CAAATCCAAG CCGAGCTGGA

201 GAAAAAGGC TACACCGTCA AACTGGTCGA GTTTACCGAC TATGTACGCC

251 CGAATCTGGC ATTGGCTGAG GGCGAGTTGG ACATCAACGT CTTCCAACAC

301 AAACCCTATC TTGACGACTT CAAAAAAGAA CACAATCTGG ACATCACCGA

351 AGTCTTCCAA GTGCCGACCG CGCCTTTGGG ACTGTACCCG GGCAAGCTGA

401 AATCGCTGGA AGAAGTCAAA GACGGCAGCA CCGTATCCGC GCCCAACGAC

451 CCGTCCAACT TCGCCCGCGT CTTGGTGATG CTCGACGAAC TGGGTTGGAT

501 CAAACTCAAA GACGGCATCA ATCCGTTGAC CGCATCCAAA GCGGACATCG

551 CCGAGAACCT GAAAACATC AAAATCGTCG AGCTTGAAGC CGCGCAACTG
```

-continued

```
601 CCGCGTAGCC GCGCCGACGT GGATTTTGCC GTCGTCAACG GCAACTACGC

651 CATAAGCAGC GGCATGAAGC TGACCGAAGC CCTGTTCCAA GAACCGAGCT

701 TTGCCTATGT CAACTGGTCT GCCGTCAAAA CCGCCGACAA AGACAGCCAA

751 TGGCTTAAAG ACGTAACCGA GGCCTATAAC TCCGACGCGT TCAAAGCCTA

801 CGCGCACAAA CGCTTCGAGG GCTACAAATC CCCTGCCGCA TGGAATGAAG

851 GCGCAGCCAA ATAA
```

This corresponds to the amino acid sequence <SEQ ID 218; ORF4-1>:

```
  1 MKTFFKTLSA AALALILAAC GGQKDSAPAA SASAAADNGA AKKEIVFGTT

51 VGDFGDMVKE QIQAELEKKG YTVKLVEFTD YVRPNLALAE GELDINVFQH

101 KPYLDDFKKE HNLDITEVFQ VPTAPLGLYP GKLKSLEEVK DGSTVSAPND

151 PSNFARVLVM LDELGWIKLK DGINPLTASK ADIAENLKNI KIVELEAAQL

201 PRSRADVDFA VVNGNYAISS GMKLTEALFQ EPSFAYVNWS AVKTADKDSQ

251 WLKDVTEAYN SDAFKAYAHK RFEGYKSPAA WNEGAAK*
```

Computer analysis of this amino acid sequence gave the following results:

Homology with a Predicted ORF from *N. meningitidis* (Strain A)

ORF4 shows 93.5% identity over a 93aa overlap with an ORF (ORF4a) from strain A of *N. meningitidis*:

```
                 10        20        30        40        50        59
    orf4.pep MKTFFKTLSAAALALILAACG-QKDSAPAASASAAADNGAAKKEIVFGTTVGDFGDMVKE
             ||||||||||||||||||| ||||||||||||||||||| |||||||||||||||||||
      orf4a MKTFFKTLSAAALALILAACGGQKDSAPAASASAAADNGAAXKEIVFGTTVGDFGDMVKE
                 10        20        30        40        50        60

60        70        80        90
    orf4.pep QIQAELEKKGYTVKLVEFTDYVRPNLALAEGEL
             || |||||||||||||| |||||| ||||||||
      orf4a XIQPELEKKGYTVKLVEXTDYVRXNLALAEGELDINVXQHXXYLDDXKKXHNLDITXVXQ
                 70        80        90       100       110       120 orf4a VPTAPLGLYPGKLKSLXXVKXGSTVSAPNDPXXFXRVLVMLDELGXIKLKDXIXXXXXXX
                130       140       150       160       170       180
```

The complete length ORF4a nucleotide sequence <SEQ ID 219> is:

```
  1 ATGAAAACCT TCTTCAAAAC CCTTTCCGCC GCCGCACTCG CGCTCATCCT

51 CGCCGCCTGC GGCGGTCAAA AGATAGCGC GCCCGCCGCA TCCGCTTCTG

101 CCGCCGCCGA CAACGGCGCG GCGAANAAAG AAATCGTCTT CGGCACGACC

151 GTCGGCGACT TCGGCGATAT GGTCAAAGAA CANATCCAAC CCGAGCTGGA

201 GAAAAAGGC TACACCGTCA AACTGGTCGA GTNTACCGAC TATGTGCGCN

251 CGAATCTGGC ATTGGCTGAG GCGAGTTGG ACATCAACGT CTTNCAACAC

301 ANACNCTATC TTGACGACTN CAAAAAANAA CACAATCTGG ACATCACCNN

351 AGTCTTNCAA GTGCCGACCG CGCCTTTGGG ACTGTACCCG GGCAAGCTGA

401 AATCGCTGGA NNAAGTCAAA GANGGCAGCA CCGTATCCGC GCCCAACGAC

451 CCGTNNNACT TCGNCCGCGT CTTGGTGATG CTCGACGAAC TGGGGTTNGAT
```

```
501 CAAACTCAAA GACNGCATCA NNNNGNNGNN NNNANCNANA NNNGANANNN

551 NNNNANNNNT NNNNNNNNNN NNNNNCNNCG NNNNNNNANN NNNNNNNNNN

601 NCGNNTNNNN NNGCNNNNNT NNANNNTNNN NNCNNCNNNN NNNNNTNNNN

651 NANNANNAGC GGCATGAAGC TGACCGAAGC CCTGTTCCAA GAACCGAGCT

701 TTGCCTATGT CAACTGGTCT GCCGTCAAAA CCGCCGACAA AGACAGCCAA

751 TGGCTTAAAG ACGTAACCGA GGCCTATAAC TCCGACGCGT TCAAAGCCTA

801 CGCGCACAAA CGCTTCGAGG GCTACAAATC CCCTGCCGCA TGGAATGAAG

851 GCGCAGCCAA ATAA
```

This is predicted to encode a protein having amino acid sequence <SEQ ID 220>:

```
  1 MKTFFKTLSA AALALILAAC GGQKDSAPAA SASAAADNGA AXKEIVFGTT

51 VGDFGDMVKE XIQPELEKKG YTVKLVEXTD YVRXNLALAE GELDINVXQH

101 XXYLDDXKKX HNLDITXVXQ VPTAPLGLYP GKLKSLXXVK XGSTVSAPND

151 PXXFXRVLVM LDELGXIKLK DXIXXXXXXX XXXXXXXXXX XXXXXXXXXX

201 XXXXAXXXXX XXXXXXXXXS GMKLTEALFQ EPSFAYVNWS AVKTADKDSQ

251 WLKDVTEAYN SDAFKAYAHK RFEGYKSPAA WNEGAAK*
```

A leader peptide is underlined.
Further analysis of these strain A sequences revealed the complete DNA sequence <SEQ ID 221>:

```
  1 ATGAAAACCT TCTTCAAAAC CCTTTCCGCC GCCGCACTCG CGCTCATCCT

51 CGCCGCCTGC GGCGGTCAAA AGATAGCGC GCCCGCCGCA TCCGCTTCTG

101 CCGCCGCCGA CAACGGCGCG GCGAAAAAAG AAATCGTCTT CGGCACGACC

151 GTCGGCGACT TCGGCGATAT GGTCAAAGAA CAAATCCAAC CCGAGCTGGA

201 GAAAAAGGC TACACCGTCA AACTGGTCGA GTTTACCGAC TATGTGCGCC

251 CGAATCTGGC ATTGGCTGAG GGCGAGTTGG ACATCAACGT CTTCCAACAC

301 AAACCCTATC TTGACGACTT CAAAAAAGAA CACAATCTGG ACATCACCGA

351 AGTCTTCCAA GTGCCGACCG CGCCTTTGGG ACTGTACCCG GGCAAGCTGA

401 AATCGCTGGA AGAAGTCAAA GACGGCAGCA CCGTATCCGC GCCCAACGAC

451 CCGTCCAACT TCGCCCGCGT CTTGGTGATG CTCGACGAAC TGGGTTGGAT

501 CAAACTCAAA GACGGCATCA ATCCGCTGAC CGCATCCAAA GCGGACATTG

551 CCGAAAACCT GAAAACATC AAAATCGTCG AGCTTGAAGC CGCGCAACTG

601 CCGCGTAGCC GCGCCGACGT GGATTTTGCC GTCGTCAACG GCAACTACGC

651 CATAAGCAGC GGCATGAAGC TGACCGAAGC CCTGTTCCAA GAACCGAGCT

701 TTGCCTATGT CAACTGGTCT GCCGTCAAAA CCGCCGACAA AGACAGCCAA

751 TGGCTTAAAG ACGTAACCGA GGCCTATAAC TCCGACGCGT TCAAAGCCTA

801 CGCGCACAAA CGCTTCGAGG GCTACAAATC CCCTGCCGCA TGGAATGAAG

851 GCGCAGCCAA ATAA
```

This encodes a protein having amino acid sequence <SEQ ID 222; ORF4a-1>:

```
  1 MKTFFKTLSA AALALILAAC GGQKDSAPAA SASAAADNGA AKKEIVFGTT

51 VGDFGDMVKE QIQPELEKKG YTVKLVEFTD YVRPNLALAE GELDINVFQH

101 KPYLDDFKKE HNLDITEVFQ VPTAPLGLYP GKLKSLEEVK DGSTVSAPND

151 PSNFARVLVM LDELGWIKLK DGINPLTASK ADIAENLKNI KIVELEAAQL

201 PRSRADVDFA VVNGNYAISS GMKLTEALFQ EPSFAYVNWS AVKTADKDSQ

251 WLKDVTEAYN SDAFKAYAHK RFEGYKSPAA WNEGAAK*
```

ORF4a-1 and ORF4-1 show 99.7% identity in 287 aa overlap:

```
                10        20        30        40        50        60
   orf4a-1 MKTFFKTLSAAALALILAACGGQKDSAPAASASAAADNGAAKKEIVFGTTVGDFGDMVKE
           ||||||||||||||||||||||||||||||||||||||||||||||||||||||||||||
   orf4-1  MKTFFKTLSAAALALILAACGGQKDSAPAASASAAADNGAAKKEIVFGTTVGDFGDMVKE
                10        20        30        40        50        60

70        80        90       100       110       120
   orf4a-1 QIQPELEKKGYTVKLVEFTDYVRPNLALAEGELDINVFQHKPYLDDFKKEHNLDITEVFQ
           ||| ||||||||||||||||||||||||||||||||||||||||||||||||||||||||
   orf4-1  QIQAELEKKGYTVKLVEFTDYVRPNLALAEGELDINVFQHKPYLDDFKKEHNLDITEVFQ
                70        80        90       100       110       120

130       140       150       160       170       180
   orf4a-1 VPTAPLGLYPGKLKSLEEVKDGSTVSAPNDPSNFARVLVMLDELGWIKLKDGINPLTASK
           ||||||||||||||||||||||||||||||||||||||||||||||||||||||||||||
   orf4-1  VPTAPLGLYPGKLKSLEEVKDGSTVSAPNDPSNFARVLVMLDELGWIKLKDGINPLTASK
               130       140       150       160       170       180

190       200       210       220       230       240
   orf4a-1 ADIAENLKNIKIVELEAAQLPRSRADVDFAVVNGNYAISSGMKLTEALFQEPSFAYVNWS
           ||||||||||||||||||||||||||||||||||||||||||||||||||||||||||||
   orf4-1  ADIAENLKNIKIVELEAAQLPRSRADVDFAVVNGNYAISSGMKLTEALFQEPSFAYVNWS
               190       200       210       220       230       240

250       260       270       280
   orf4a-1 AVKTADKDSQWLKDVTEAYNSDAFKAYAHKRFEGYKSPAAWNEGAAKX
           ||||||||||||||||||||||||||||||||||||||||||||||||
   orf4-1  AVKTADKDSQWLKDVTEAYNSDAFKAYAHKRFEGYKSPAAWNEGAAKX
               250       260       270       280
```

Homology with an Outer Membrane Protein of *Pasteurella haemolitica* (Accession q08869).

ORF4 and this outer membrane protein show 33% aa identity in 91aa overlap:

```
                                              10        20
   lip2.pasha                         MNFKKLLGVALVSALALTACKDEKAQAP----
                                      ||| ::||  || |:||  :|: |
   ORF4    VXTPNPDGRTPCPSFLFETATTSGENMKTFFKTLSAAAL--ALILAACGFKKTARPPHPL
                 110       120       130       140         150

30        40        50        60        70        80
   lip2.pasha -ATTAKTENKAPLKVGVMTGPEAQMTEVAVKIAKEKYGLDVELVQFTEYTQPNAALHSKD
              : :: |   : :|  |  |  ::|:: |    || |   |:||:|:|::|| ||   :
   ORF4       LPPPTTARRKKEIVFGTTVGDFGDMVKEQIQAELEKKGYTVKLVEFTDYVRPNLALAEGE
                160       170       180       190       200       210

90       100       110       120       130       140
   lip2.pasha LDANAFQTVPYLEQEVKDRGYKLAIIGNTLVWPIAAYSKKIKNISELKDGATVAIPNNAS
              |
   ORF4       L.....
```

Homology with a Predicted ORF from *N. gonorrhoeae*

ORF4 shows 93.6% identity over a 94aa overlap with a predicted ORF (ORF4.ng) from *N. gonorrhoeae*:

```
                                          10        20        30
orf4nm.pep                        MKTFFKTLSAAALALILAACGXQKDSAPAA
                                  ||||||||||:|:||||||||| ||||||||
    orf4ng RANAVXTPNPDGRTPCLSFLFETATTSGENMKTFFKTLSTASLALILAACGGQKDSAPAA
              200       210       220       230       240       250
                  40        50        60        70        80        89
orf4nm.pep SASA-AADNGAAKKEIVFGTTVGDFGDMVKEQIQAELEKKGYTVKLVEFTDYVRPNLALA
           ||:| :||||||||||||||||||||||||||||||||||||||||||||||||||||||
    orf4ng SAAAPSADNGAAKKEIVFGTTVGDFGDMVKEQIQAELEKKGYTVKLVEFTDYVRPNLALA
              260       270       280       290       300       310
           90
orf4nm.pep EGEL
           ||||
    orf4ng EGELDINVFQHKPYLDDFKKEHNLDITEAFQVPTAPLGLYPGKLKSLEEVKDGSTVSAPN
              320       330       340       350       360       370
```

The complete length ORF4ng nucleotide sequence <SEQ ID 223> was predicted to encode a protein having amino acid sequence <SEQ ID 224>:

```
  1  MKTFFKTLST ASLALILAAC GGQKDSAPAA SAAAPSADNG AAKKEIVFGT
 51  TVGDFGDMVK EQIQAELEKK GYTVKLVEFT DYVRPNLALA EGELDINVFQ
101  HKPYLDDFKK EHNLDITEAF QVPTAPLGLY PGKLKSLEEV KDGSTVSAPN
151  DPSNFARALV MLNELGWIKL KDGINPLTAS KADIAENLKN IKIVELEAAQ
201  LPRSRADVDF AVVNGNYAIS SGMKLTEALF QEPSFAYVNW SAVKTADKDS
251  QWLKDVTEAY NSDAFKAYAH KRFEGYKYPA AWNEGAAK*
```

Further analysis revealed the complete length ORF4ng DNA sequence <SEQ ID 225> to be:

```
  1  atgAAAACCT TCTTCAAAAC cctttccgcc gccgcaCTCG CGCTCATCCT
 51  CGCAGCCTGc ggCggtcaAA AAGACAGCGC GCCCgcagcc tctgcCGCCG
101  CCCCTTCTGC CGATAACGgc gCgGCGAAAA AAGAAAtcgt ctTCGGCACG
151  Accgtgggcg acttcggcgA TAtggTCAAA GAACAAATCC AagcCGAgct
201  gGAGAAAAAA GgctACACcg tcAAattggt cgaatttacc gactatgtGC
251  gCCCGAATCT GGCATTGGCG GAGGGCGAGT TGGACATCAA CGTCTTCCAA
301  CACAAACCCT ATCTTGACGA TTTCAAAAAA GAACACAACC TGGACATCAC
351  CGAAGCCTTC CAAGTGCCGA CCGCGCCTTT GGGACTGTAT CCGGGCAAAC
401  TGAAATCGCT GGAAGAAGTC AAAGACGGCA GCACCGTATC CGCGCCCAac
451  gACccgTCCA ACTTCGCACG CGCCTTGGTG ATGCTGAACG AACTGGGTTG
501  GATCAAACTC AAAGACGGCA TCAATCCGCT GACCGCATCC AAAGCCGACA
551  TCGCGGAAAA CCTGAAAAAC ATCAAAATCG TCGAGCTTGA AGCCGCACAA
601  CTGCCGCGCA GCCGCGCCGA CGTGGATTTT GCCGTCGTCA ACGGCAACTA
651  CGCCATAAGC AGCGGCATGA AGCTGACCGA AGCCCTGTTC CAAGAGCCGA
701  GCTTTGCCTA TGTCAACTGG TCTGCCgtcA AAACCGCCGA CAAAGACAGC
751  CAATGGCTTA AGACGTAAC CGAGGCCTAT AACTCCGACG CGTTCAAAGC
801  CTACGCGCAC AAACGCTTCG AGGGCTACAA ATACCCTGCC GCATGGAATG
851  AAGGCGCAGC CAAATAA
```

This encodes a protein having amino acid sequence <SEQ ID 226; ORF4ng-1>:

```
  1 MKTFFKTLSA AALALILAAC GGQKDSAPAA SAAAPSADNG AAKKEIVFGT

51 TVGDFGDMVK EQIQAELEKK GYTVKLVEFT DYVRPNLALA EGELDINVFQ

101 HKPYLDDFKK EHNLDITEAF QVPTAPLGLY PGKLKSLEEV KDGSTVSAPN

151 DPSNFARALV MLNELGWIKL KDGINPLTAS KADIAENLKN IKIVELEAAQ

201 LPRSRADVDF AVVNGNYAIS SGMKLTEALF QEPSFAYVNW SAVKTADKDS

251 QWLKDVTEAY NSDAFKAYAH KRFEGYKYPA AWNEGAAK*
```

This shows 97.6% identity in 288 aa overlap with ORF4-1:

```
                   10         20         30         40         50        59
orf4-1.pep  MKTFFKTLSAAALALILAACGGQKDSAPAASASA-AADNGAAKKEIVFGTTVGDFGDMVK
            ||||||||||||||||||||||||||||||:| :||||||||||||||||||||||||||
orf4ng-1    MKTFFKTLSAAALALILAACGGQKDSAPAASAAAPSADNGAAKKEIVFGTTVGDFGDMVK
                   10         20         30         40         50        60

60         70         80         90        100        110       119
orf4-1.pep  EQIQAELEKKGYTVKLVEFTDYVRPNLALAEGELDINVFQHKPYLDDFKKEHNLDITEVF
            ||||||||||||||||||||||||||||||||||||||||||||||||||||||||||:|
orf4ng-1    EQIQAELEKKGYTVKLVEFTDYVRPNLALAEGELDINVFQHKPYLDDFKKEHNLDITEAF
                   70         80         90        100        110        120

120        130        140        150        160        170       179
orf4-1.pep  QVPTAPLGLYPGKLKSLEEVKDGSTVSAPNDPSNFARVLMLDELGWIKLKDGINPLTAS
            |||||||||||||||||||||||||||||||||||||:|||:||||||||||||||||||
orf4ng-1    QVPTAPLGLYPGKLKSLEEVKDGSTVSAPNDPSNFARALVMLNELGWIKLKDGINPLTAS
                  130        140        150        160        170        180

180        190        200        210        220        230       239
orf4-1.pep  KADIAENLKNIKIVELEAAQLPRSRADVDFAVVNGNYAISSGMKLTEALFQEPSFAYVNW
            ||||||||||||||||||||||||||||||||||||||||||||||||||||||||||||
orf4ng-1    KADIAENLKNIKIVELEAAQLPRSRADVDFAVVNGNYAISSGMKLTEALFQEPSFAYVNW
                  190        200        210        220        230        240

240        250        260        270        280
orf4-1.pep  SAVKTADKDSQWLKDVTEAYNSDAFKAYAHKRFEGYKSPAAWNEGAAKX
            ||||||||||||||||||||||||||||||||||||||| |||||||||
orf4ng-1    SAVKTADKDSQWLKDVTEAYNSDAFKAYAHKRFEGYKYPAAWNEGAAKX
                  250        260        270        280
```

In addition, ORF4ng-1 shows significant homology with an outer membrane protein from the database:

```
ID LIP2_PASHA STANDARD; PRT; 276 AA.
AC Q08869;
DT 01-NOV-1995 (REL. 32, CREATED)
DT 01-NOV-1995 (REL. 32, LAST SEQUENCE UPDATE)
DT 01-NOV-1995 (REL. 32, LAST ANNOTATION UPDATE)
DE 28.2 KD OUTER MEMBRANE PROTEIN PRECURSOR. . .
SCORES Init1; 279 Initn: 416 Opt: 494
Smith-Waterman score: 494; 36.0% identity in 275 aa overlap 10        20        30        40        50
orf4ng-1.pep  MKTFFKTLSAAAL--ALILAACGGQKDSAPAASAAAPSADNGAAKKEIVFGTTVGDFGDM
              ||| |   ::||   || |:||   :|:|||:|    :::|| |   |: |  |  |  |
lip2_pashs    MNFKKLLGVALVSALALTACKDEKAQAPATTA---KTENKAPLK---VGVMTGPEAQM
                      10        20        30           40           50

60        70        80        90       100       110
orf4ng-1.pep  VKEQIQAELEKKGYTVKLVEFTDYVRPNLALAEGELDINVFQHKPYLDDFKKEHNLDITE
              ::   ::    || |    |:||:|:::|| ||   :||  :||  |:||   |::: :
lip2_pashs    TEVAVKIAKEKYGLDVELVQFTEYTQPNAALHSKDLDANAFQTVPYLEQEVKDRGYKLAI
                      60        70        80        90       100       110

120       130       140       150       160       170
orf4ng-1.pep  AFQVPTAPLGLYPGKLKSLEEVKDGSTVSAPNDPSNFARALVMLNELGWIKLKDGINPLT
              :: : |:: |   |:|:: |:|||:||: ||  ||||||::|:   |:|||| |:
lip2_pashs    IGNTLVWPIAAYSKKKIKNISELKDGATVAIPNNASNTARALLLLQAHGLLKLKDPKN-VF
                     120       130       140       150       160       170

180       190       200       210       220       230
orf4ng-1.pep  ASKADIAENLKNIKIVELEAAQLPRSRADVDFAVVNGNYAISSGMKLTE--ALFQEPSFA
              |::   ||   ||||||||:  :::  ||   ||:::|:|:::||  ::|:    :   :
lip2_pashs    ATENDIIENPKNIKIVQDTSLLTRMLDDVELAVINNTYAGQAGLSPDKDGIIVESKDSP
                     180       190       200       210       220       230
```

```
                  240         250         260         270         280        289
orf4ng-1.pep  YVNWSAVKTADKDSQWLKDVTEAYNSDAFKAYAHKRFEGYKYPAAWNEGAAKX
              |||   :   :||:   |:   :::::::      |   |   |:|
lip2_pashs    YVNLVVSREDNKDDPRLQTFVKSFQTEEVFQEALKLFNGGVVKGW
                  240         250         260         270
```

Based on this analysis, including the homology with the outer membrane protein of *Pasteurella haemolitica*, and on the presence of a putative prokaryotic membrane lipoprotein lipid attachment site in the gonococcal protein, it was predicted that these proteins from *N. meningitidis* and *N. gonorrhoeae*, and their epitopes, could be useful antigens for vaccines or diagnostics, or for raising antibodies.

ORF4-1 (30 kDa) was cloned in pET and pGex vectors and expressed in *E. coli*, as described above. The products of protein expression and purification were analyzed by SDS-PAGE. FIGS. 8A and 8B show, respectively, the results of affinity purification of the His-fusion and GST-fusion proteins. Purified His-fusion protein was used to immunise mice, whose sera were used for ELISA (positive result), Western blot (FIG. 8C), FACS analysis (FIG. 8D), and a bactericidal assay (FIG. 8E). These experiments confirm that ORF4-1 is a surface-exposed protein, and that it is a useful immunogen.

Figure 8F:
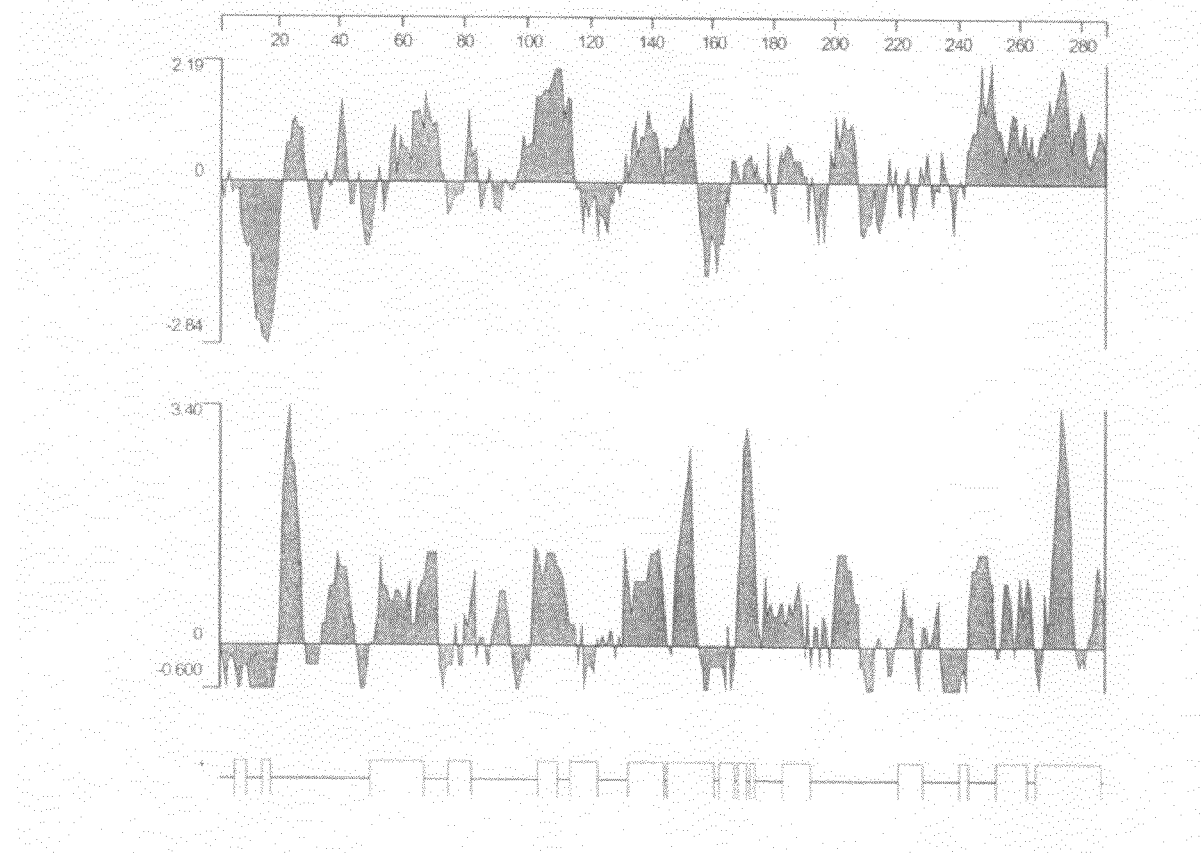

FIG. 8F shows plots of hydrophilicity, antigenic index, and AMPHI regions for ORF4-1.

Example 27

The following partial DNA sequence was identified in *N. meningitidis* <SEQ ID 227>:

```
  1  CCTCGTCGTC CTCGGCATGC TCCAGTTTCA AGGGGCGATT TACTCCAAGG

51  CGGTGGAACG TATGCTCGGC ACGGTCATCG GGCTGGGCGC GGGTTTGGGC

101  GTTTTATGGC TGAACCAGCA TTATTTCCAC GGCAACCTCC TCTTCTACCT

151  CACCGTCGGC ACGGCAAGCG CACTGGCCGG CTGGGCGGCG GTCGGCAAAA

201  ACGGCTACGT CCCTmTGCTG GCAGGGCTGA CGATGTGTAT GCTCATCGGC

251  GACAACGGCA GCGAATGGCT CGACAGCGGA CTCATGCGCG CCATGAACGT

301  CCTCATCGGC GyGGCCATCG CCATCGCCGC CGCCAAACTG CTGCCGCTGA

351  AATCCACACT GATGTGGCGT TTCATGCTTG CCGACAACCT GGCCGACTGC

401  AGCAAAATGA TTGCCGAAAT CAGCAACGGC AGGCGCATGA CCCGCGAACG

451  CCTCGAGGAG AACATGGCGA AAATGCGCCA AATCAACGCA CGCATGGTCA

501  AAAGCCGCAG CCATCTCGCC GCCACATCGG GCGAAAGCTG CATCAGCCCC

551  GCCATGATGG AAGCCATGCA GCACGCCCAC CGTAAAATCG TCAACACCAC

601  CGAGCTGCTC CTGACCACCG CCGCCAAGCT GCAATCTCCC AAACTCAACG

651  GCAGCGAAAT CCGGCTGCTT GACCGCCACT TCACACTGCT CCAAAC....

701  ............................ GC AGACACGCCC GCCGCATCCG

751  CATCGACACC GCCATCAACC CCGAACTGGA AGCCCTCGCC GAACACCTCC

801  ACTACCAATG GCAGGGCTTC CTCTGGCTCA GCACCGATAT GCGTCAGGAA

851  ATTTCCGCCC TCGTCATCCT GCTGCAACGC ACCCGCCGCA AATGGCTGGA

901  TGCCCACGAA CGCCAACACC TGCGCCAAAG CCTGCTTGA
```

This corresponds to the amino acid sequence <SEQ ID 228; ORF8>:

```
  1 ......PRRP RHAPVSRGDL LQGGGTYARH GHRAGRGFGR FMAEPALFPR

51 QPPLLPHRRH GKRTGRLGGG RQKRLRPXAG RADDVYAHRR QRQRMARQRT

101 HARHERPHRR GHRHRRRQTA AAEIHTDVAF HACRQPGRLQ QNDCRNQQRQ

151 AHDPRTPRGE HGENAPNQRT HGQKPQPSRR HIGRKLHQPR HDGSHAARPP

201 XNRQHHRAAP DHRRQAAISQ TQRQRNPAAX PPLHTAPN.. .........Q

251 TRPPHPHRHR HQPRTGSPRR TPPLPMAGLP LAQHRYASGN FRPRHPAATH

301 PPQMAGCPRT PTPAPKPA*
```

Computer analysis of this amino acid sequence gave the following results:

Sequence Motifs

ORF8 is proline-rich and has a distribution of proline residues consistent with a surface localization. Furthermore the presence of an RGD motif may indicate a possible role in bacterial adhesion events.

Homology with a Predicted ORF from N. gonorrhoeae

ORF8 shows 86.5% identity over a 312aa overlap with a predicted ORF (ORF8.ng) from N. gonorrhoeae.

```
orf8ng      1 MDRDDRLRRPRHAPVPRRDLLQRGGTYARYGHRAGRGFGRFMAEPALFPR  50
              |||||||  ||||  ||||| :|||||||||||||||||||||
orf8.pep    1 .......PRPRHAPVSRGDLLQGGGTYARHGHRAGRGFGRFMAEPALFPR  44 orf8ng     51 QPPLLPDHRHGKRTGRLGGGRQKRLRPYVGGADDVHAHRRQRQRMARQRP 100
              ||||||  |||||||||||||||||||  |  ||||:|||||||||||||
orf8.pep   45 QPPLLPHRRHGKRTGRLGGGRQKRLRPXAGGADDVYAHRRQRQRMARQRP  94 orf8ng    101 DARDERPHRRRHRHCRRQTAAAEIHTDVAFHACRQPGRLQQNDCRNQQRQ 150
              ||  ||||||| ||||||||||||||||||||||||||||  |||||||||
orf8.pep   45 HARHERPHRRGHRHRRRQTAAAEIHTDVAFHACRQPGRMQQNDCRNQQRQ 144 orf8ng    151 AYDARTFGAEYGQNAPNQRTHGQKPQPPRRHIGRKPHQPLHDGSHAARPP 200
              |:| ||   |:|:|||||||||||||| |||||||| ||| |||||||||
orf8.pep  145 AHDPRTPRGEHGENAPNQRTHGQKPQPSRRHIGRKLHQPRHDGSHAARPP 194 orf8ng    201 QNRQHHRAAPDHRRQAAISQTQRQRNPAARPPLHTAPNRPATNRRPHQRQ 250
              |||||||||||||||||||||||||||||  |||||||||       |
orf8.pep  195 XNRQHHRAAPDHRRQAAISQTQRQRNPAAXPPLHTAPN...........Q 244 orf8ng    251 TRPPHPHRHRHQPRTGSPRRTPPLPMAGFPLAQHQYASGNFRPHHPPATH 300
              |||||||||||||||||||||||||||||||| |||.|||||||||||||   |||
orf8.pep  245 TRPPHPHRHRHQPRTGSPRRTPPLPMAGLPLAQHRYASGNFRPRHPAATH 294 orf8ng    301 PPQMAGCPRTPTPAPKA*                                 319
              ||||||||||||||||||
orf8.pep  295 PPQMAGCPRTPTPAPKA*                                 313
```

The complete length ORF8ng nucleotide sequence <SEQ ID 229> is predicted to encode a protein having amino acid sequence <SEQ ID 230>:

```
  1 MDRDDRLRRP RHAPVPRRDL LQRGGTYARY GHRAGRGFGR FMAEPALFPR

51 QPPLLPDHRH GKRTGRLGGG RQKRLRPYVG GADDVHAHRR QRQRMARQRP

101 DARDERPHRR RHRHCRRQTA AAEIHTDVAF HACRQPGRLQ QNDCRNQQRQ

151 AYDARTFGAE YGQNAPNQRT HGQKPQPPRR HIGRKPHQPL HDGSHAARPP

201 QNRQHHRAAP DHRRQAAISQ TQRQRNPAAR PPLHTAPNRP ATNRRPHQRQ

251 TRPPHPHRHR HQPRTGSPRR TPPLPMAGFP LAQHQYASGN FRPRHPPATH

301 PPQMAGCPRT PTPAPKPA*
```

Based on the sequence motifs in these proteins, it is predicted that the proteins from *N. meningitidis* and *N. gonorrhoeae*, and their epitopes, could be useful antigens for vaccines or diagnostics, or for raising antibodies.

Example 28

The following partial DNA sequence was identified in *N. meningitidis* <SEQ ID 231>:

```
  1 ..GAAATCAGCC TGCGGTCCGA CNACAGGCCG GTTTCCGTGN CGAAGCGGCG
 51   GGATTCGGAA CGTTTTCTGC TGTTGGACGG CGGCAACAGC CGGCTCAAGT
101   GGGCGTGGGT GGAAAACGGC ACGTTCGCAA CCGTCGGTAG CGCGCCGTAC
151   CGCGATTTGT CGCCTTTGGG CGCGGAGTGG GCGGAAAAGG CGGATGGAAA
201   TGTCCGCATC GTCGGTTGCG CTGTGTGCGG AGAATTCAAA AAGGCACAAG
251   TGCAGGAACA GCTCGCCCGA AAAATCGAGT GGCTGCCGTC TTCCGCACAG
301   GCTTT.GGCA TACGCAACCA CTACCGCCAC CCCGAAGAAC ACGGTTCCGA
351   CCGCTGGTTC AACGCCTTGG GCAGCCGCCG CTTCAGCCGC AACGCCTGCG
401   TCGTCGTCAG TTGCGGCACG GCGGTAACGG TTGACGCGCT CACCGATGAC
451   GGACATTATC TCGGAGA.GG AACCATCATG CCCGGTTTCC ACCTGATGAA
501   AGAATCGCTC GCCGTCCGAA CCGCCAACCT CAACCGGCAC GCCGGTAAGC
551   GTTATCCTTT CCCGACCGG..
```

This corresponds to the amino acid sequence <SEQ ID 232; ORF61>:

```
  1 ..EISLRSDXRP VSVXKRRDSE RFLLLDGGNS RLKWAWVENG TFATVGSAPY
 51   RDLSPLGAEW AEKADGNVRI VGCAVCGEFK KAQVQEQLAR KIEWLPSSAQ
101   AXGIRNHYRH PEEHGSDRWF NALGSRRFSR NACVVVSCGT AVTVDALTDD
151   GHYLGXGTIM PGFHLMKESL AVRTANLNRH AGKRYPFPT..
```

Further work revealed the complete nucleotide sequence <SEQ ID 233>:

```
  1   ATGACGGTTT TGAAGCTTTC GCACTGGCGG GTGTTGGCGG AGCTTGCCGA
 51   CGGTTTGCCG CAACACGTCT CGCAACTGGC GCGTATGGCG GATATGAAGC
101   CGCAGCAGCT CAACGGTTTT TGGCAGCAGA TGCCGGCGCA CATACGCGGG
151   CTGTTGCGCC AACACGACGG CTATTGGCGG CTGGTGCGCC CATTGGCGGT
201   TTTCGATGCC GAAGGTTTGC GCGAGCTGGG GGAAAGGTCG GGTTTTCAGA
251   CGGCATTGAA GCACGAGTGC GCGTCCAGCA ACGACGAGAT ACTGGAATTG
301   GCGCGGATTG CGCCGGACAA GGCGCACAAA ACCATATGCG TGACCCACCT
351   GCAAAGTAAG GGCAGGGGGC GGCAGGGGCG GAAGTGGTCG CACCGTTTGG
401   GCGAGTGTCT GATGTTCAGT TTTGGCTGGG TGTTTGACCG GCCGCAGTAT
451   GAGTTGGGTT CGCTGTCGCC TGTTGCGGCA GTGGCGTGTC GGCGCGCCTT
501   GTCGCGTTTA GGTTTGGATG TGCAGATTAA GTGGCCCAAT GATTTGGTTG
551   TCGGACGCGA CAAATTGGGC GGCATTCTGA TTGAAACGGT CAGGACGGGC
601   GGCAAAACGG TTGCCGTGGT CGGTATCGGC ATCAATTTTG TCCTGCCCAA
```

```
 651  GGAAGTAGAA AATGCCGCTT CCGTGCAATC GCTGTTTCAG ACGGCATCGC

701  GGCGGGGCAA TGCCGATGCC GCCGTGCTGC TGGAAACGCT GTTGGTGGAA

751  CTGGACGCGG TGTTGTTGCA ATATGCGCGG GACGGATTTG CGCCTTTTGT

801  GGCGGAATAT CAGGCTGCCA ACCGCGACCA CGGCAAGGCG GTATTGCTGT

851  TGCGCGACGG CGAAACCGTG TTCGAAGGCA CGGTTAAAGG CGTGGACGGA

901  CAAGGCGTTT TGCACTTGGA AACGGCAGAG GGCAAACAGA CGGTCGTCAG

951  CGGCGAAATC AGCCTGCGGT CCGACGACAG GCCGGTTTCC GTGCCGAAGC

1001  GGCGGGATTC GGAACGTTTT CTGCTGTTGG ACGGCGGCAA CAGCCGGCTC

1051  AAGTGGGCGT GGGTGGAAAA CGGCACGTTC GCAACCGTCG GTAGCGCGCC

1101  GTACCGCGAT TTGTCGCCTT TGGGCGCGGA GTGGGCGGAA AAGGCGGATG

1151  GAAATGTCCG CATCGTCGGT TGCGCTGTGT GCGGAGAATT CAAAAAGGCA

1201  CAAGTGCAGG AACAGCTCGC CCGAAAAATC GAGTGGCTGC CGTCTTCCGC

1251  ACAGGCTTTG GCATACGCA ACCACTACCG CCACCCCGAA GAACACGGTT

1301  CCGACCGCTG GTTCAACGCC TTGGGCAGCC GCCGCTTCAG CCGCAACGCC

1351  TGCGTCGTCG TCAGTTGCGG CACGGCGGTA ACGGTTGACG CGCTCACCGA

1401  TGACGGACAT TATCTCGGGG GAACCATCAT GCCCGGTTTC CACCTGATGA

1451  AAGAATCGCT CGCCGTCCGA ACCGCCAACC TCAACCGGCA CGCCGGTAAG

1501  CGTTATCCTT TCCCGACCAC AACGGGCAAT GCCGTCGCCA GCGGCATGAT

1551  GGATGCGGTT TGCGGCTCGG TTATGATGAT GCACGGGCGT TTGAAAGAAA

1601  AAACCGGGGC GGGCAAGCCT GTCGATGTCA TCATTACCGG CGGCGGCGCG

1651  GCAAAAGTTG CCGAAGCCCT GCCGCCTGCA TTTTTGGCGG AAAATACCGT

1701  GCGCGTGGCG GACAACCTCG TCATTTACGG GTTGTTGAAC ATGATTGCCG

1751  CCGAAGGCAG GGAATATGAA CATATTTAA
```

This corresponds to the amino acid sequence <SEQ ID 234; ORF61-1>:

```
  1  MTVLKLSHWR VLAELADGLP QHVSQLARMA DMKPQQLNGF WQQMPAHIRG

51  LLRQHDGYWR LVRPLAVFDA EGLRELGERS GFQTALKHEC ASSNDEILEL

101  ARIAPDKAHK TICVTHLQSK GRGRQGRKWS HRLGECLMFS FGWVFDRPQY

151  ELGSLSPVAA VACRRALSRL GLDVQIKWPN DLVVGRDKLG GILIETVRTG

201  GKTVAVVGIG INFVLPKEVE NAASVQSLFQ TASRRGNADA AVLLETLLVE

251  LDAVLLQYAR DGFAPFVAEY QAANRDHGKA VLLLRDGETV FEGTVKGVDG

301  QGVLHLETAE GKQTVVSGEI SLRSDDRPVS VPKRRDSERF LLLDGGNSRL

351  KWAWVENGTF ATVGSAPYRD LSPLGAEWAE KADGNVRIVG CAVCGEFKKA

401  QVQEQLARKI EWLPSSAQAL GIRNHYRHPE EHGSDRWFNA LGSRRFSRNA

451  CVVVSCGTAV TVDALTDDGH YLGGTIMPGF HLMKESLAVR TANLNRHAGK

501  RYPFPTTTGN AVASGMMDAV CGSVMMMHGR LKEKTGAGKP VDVIITGGGA

551  AKVAEALPPA FLAENTVRVA DNLVIYGLLN MIAAEGREYE HI*
```

Figure 9:
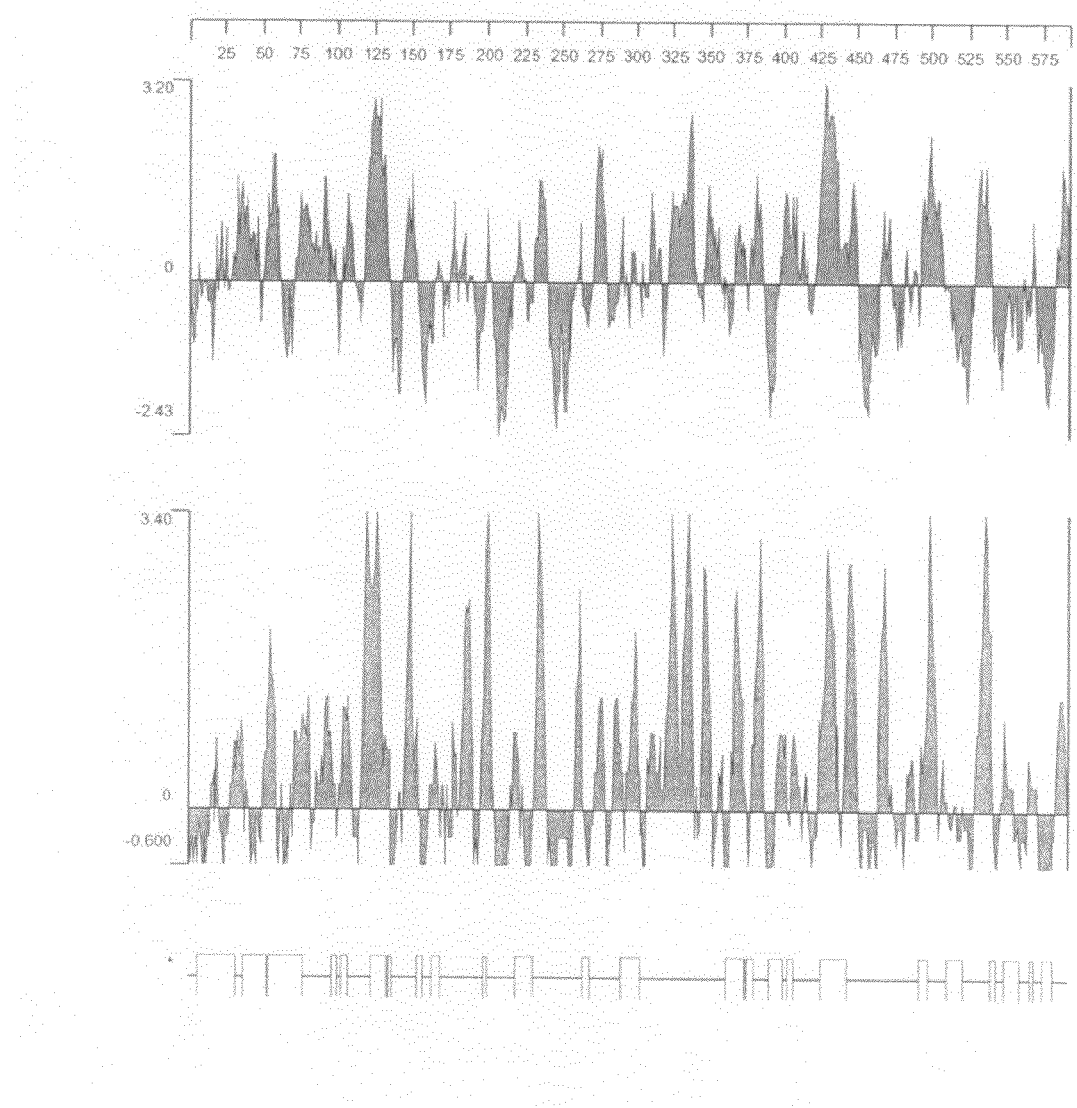

FIG. 9 shows plots of hydrophilicity, antigenic index, and AMPHI regions for ORF61-1. Further computer analysis of this amino acid sequence gave the following results:

Homology with the baf Protein of *B. pertussis* (Accession Number U12020).

ORF61 and baf protein show 33% aa identity in 166aa overlap:

```
orf61    23 LLLDGGNSRLKWAWVE-NGTFATVGSAPYR----DLSPLGAEWAEKADGNVRIVGCAVCG   77
            +L+D GNSRLK W + +   A   AP      DL  LG  A      R +G  V G
baf       3 ILIDSGNSRLKVGWFDPDAPQAAREPAPVAFDNLDLDALGRWLATLPRRPQRALGVNVAG   62 orf61    78 EFKKAQVQEQLAR---KIEWLPSSAQAXGIRNHYRHPEEHGSDRW---FNALGSRRFSRN  131
            +  +  L      I WL +   A G+RN YR+P++ G+DRW        L  +
baf      63 LARGEAIAATLRAGGCDIRWLRAQPLAMGLRNGYRNPDQLGADRWACMVGVLARQPSVHP  122 orf61   132 ACVVVSCGTAVTVDALTDDGHYLGXGTIMPGFHLMKESLAVRTANL               177
            +V S GTA T+D +  D   + G G I+PG  +M+ +LA  TA+L
baf     123 PLLVASFGTATTLDTIGPDNVFPG-GLILPGPAMMRGALAYGTAHL               167
```

Homology with a Predicted ORF from *N. meningitidis* (Strain A)

ORF61 shows 97.4% identity over a 189aa overlap with an ORF (ORF61a) from strain A of *N. meningitidis*.

```
                                          10        20        30
        orf61.pep                   EISLRSDXRPVSVXKRRDSERFLLLDGGNS
                                    ||||||| |||||  |||||||||||||||
        orf61a    TVFEGTVKGVDGQGVLHLETAEGKQTVVSGEISLRSDDRPVSVPKRRDSERFLLLDGGNS
                  290       300       310       320       330       340
                          40        50        60        70        80        90
        orf61.pep RLKWAWVENGTFATVGSAPYRDLSPLGAEWAEKADGNVRIVGCAVCGEFKKAQVQEQLAR
                  ||||||||||||||||||||||||||||||||||| ||||||||||||||||||||||||
        orf61a    RLKWAWVENGTFATVGSAPYRDLSPLGAEWAEKVDGNVRIVGCAVCGEFKKAQVQEQLAR
                  350       360       370       380       390       400
                          100       110       120       130       140       150
        orf61.pep KIEWLPSSAQAXGIRNHYRHPEEHGSDRWFNALGSRRFSRNACVVVSCGTAVTVDALTDD
                  |||||||||||| |||||||||||||||||||||||||||||||||||||||||||||||
        orf61a    KIEWLPSSAQALGIRNHYRHPEEHGSDRWFNALGSRRFSRNACVVVSCGTAVTVDALTDD
                  410       420       430       440       450       460
                          160       170       180    189
        orf61.pep GHYLGXGTIMPGFHLMKESLAVRTANLNRHAGKRYPFPT
                  ||||| |||||||||||||||||||||||||||||||||
        orf61a    GHYLG-GTIMPGFHLMKESLAVRTANLNRHAGKRYPFPTTTGNAVASGMMDAVCGSVMMM
                  470       480       490       500       510       520
        orf61a    HGRLKEKTGAGKPVDVIITGGGAAKVAEALPPAFLAENTVRADNLVIHGLLNLIAAEGG
                  530       540       550       560       570       580
```

The complete length ORF61a nucleotide sequence <SEQ ID 235> is:

```
  1 ATGACGGTTT TGAAGCCTTC GCACTGGCGG GTGTTGGCGG AGCTTGCCGA
 51 CGGTTTGCCG CAACACGTCT CGCAACTGGC GCGTATGGCG GATATGAAGC
101 CGCAGCAGCT CAACGGTTTT TGGCAGCAGA TGCCGGCGCA CATACGCGGG
151 CTGTTGCGCC AACACGACGG CTATTGGCGG CTGGTGCGCC CATTGGCGGT
201 TTTCGATGCC GAAGGTTTGC GCGAGCTGGG GGAAAGGTCG GGTTTTCAGA
251 CGGCATTGAA GCACGAGTGC GCGTCCAGCA ACGACGAGAT ACTGGAATTG
301 GCGCGGATTG CGCCGGACAA GGCGCACAAA ACCATATGTG TGACCCACCT
351 GCAAAGTAAG GGCAGGGGGC GGCAGGGGCG GAAGTGGTCG CACCGTTTGG
401 GCGAGTGTCT GATGTTCAGT TTTGGCTGGG TGTTTGACCG GCCGCAGTAT
451 GAGTTGGGTT CGCTGTCGCC TGTTGCGGCA GTGGCGTGCC GGCGCGCCTT
501 GTCGCGTTTG GGTTTGAAAA CGCAAATCAA GTGGCCAAAC GATTTGGTCG
551 TCGGACGCGA CAAATTGGGC GGCATTCTGA TTGAAACGGT CAGGACGGGC
601 GGCAAAACGG TTGCCGTGGT CGGTATCGGC ATCAATTTCG TGCTGCCCAA
```

```
 651 GGAAGTGGAA AACGCCGCTT CCGTGCAATC GCTGTTTCAG ACGGCATCGC

701 GGCGGGGAAA TGCCGATGCC GCCGTGTTGC TGGAAACGCT GTTGGCGGAA

751 CTTGATGCGG TGTTGTTGCA ATATGCGCGG GACGGATTTG CGCCTTTTGT

801 GGCGGAATAT CAGGCTGCCA ACCGCGACCA CGGCAAGGCG GTATTGCTGT

851 TGCGCGACGG CGAAACCGTG TTCGAAGGCA CGGTTAAAGG CGTGGACGGA

901 CAAGGCGTTC TGCACTTGGA AACGGCAGAG GGCAAACAGA CGGTCGTCAG

951 CGGCGAAATC AGCCTGCGGT CCGACGACAG GCCGGTTTCC GTGCCGAAGC

1001 GGCGGGATTC GGAACGTTTT CTGCTGTTGG ACGGCGGCAA CAGCCGGCTC

1051 AAGTGGGCGT GGGTGGAAAA CGGCACGTTC GCAACCGTCG GTAGCGCGCC

1101 GTACCGCGAT TTGTCGCCTT TGGGCGCGGA GTGGGCGGAA AAGGTGGATG

1151 GAAATGTCCG CATCGTCGGT TGCGCCGTGT GCGGAGAATT CAAAAAGGCA

1201 CAAGTGCAGG AACAGCTCGC CCGAAAAATC GAGTGGCTGC CGTCTTCCGC

1251 ACAGGCTTTG GGCATACGCA ACCACTACCG CCACCCCGAA GAACACGGTT

1301 CCGACCGCTG GTTCAACGCC TTGGGCAGCC GCCGCTTCAG CCGCAACGCC

1351 TGCGTCGTCG TCAGTTGCGG CACGGCGGTA ACGGTTGACG CGCTCACCGA

1401 TGACGGACAT TATCTCGGGG GAACCATCAT GCCCGGTTTC CACCTGATGA

1451 AAGAATCGCT CGCCGTCCGA ACCGCCAACC TCAACCGGCA CGCCGGTAAG

1501 CGTTATCCTT TCCCGACCAC AACGGGCAAT GCCGTCGCCA GCGGCATGAT

1551 GGATGCGGTT TGCGGCTCGG TTATGATGAT GCACGGGCGT TTGAAAGAAA

1601 AAACCGGGGC GGGCAAGCCT GTCGATGTCA TCATTACCGG CGGCGGCGCG

1651 GCAAAAGTTG CCGAAGCCCT GCCGCCTGCA TTTTTGGCGG AAAATACCGT

1701 GCGCGTGGCG GACAACCTCG TCATTCACGG GCTGCTGAAC CTGATTGCCG

1751 CCGAAGGCGG GGAATCGGAA CATACTTAA
```

This encodes a protein having amino acid sequence <SEQ ID 236>:

```
  1 MTVLKPSHWR VLAELADGLP QHVSQLARMA DMKPQQLNGF WQQMPAHIRG

51 LLRQHDGYWR LVRPLAVFDA EGLRELGERS GFQTALKHEC ASSNDEILEL

101 ARIAPDKAHK TICVTHLQSK GRGRQGRKWS HRLGECLMFS FGWVFDRPQY

151 ELGSLSPVAA VACRRALSRL GLKTQIKWPN DLVVGRDKLG GILIETVRTG

201 GKTVAVVGIG INFVLPKEVE NAASVQSLFQ TASRRGNADA AVLLETLLAE

251 LDAVLLQYAR DGFAPFVAEY QAANRDHGKA VLLLRDGETV FEGTVKGVDG

301 QGVLHLETAE GKQTVVSGEI SLRSDDRPVS VPKRRDSERF LLLDGGNSRL

351 KWAWVENGTF ATVGSAPYRD LSPLGAEWAE KVDGNVRIVG CAVCGEFKKA

401 QVQEQLARKI EWLPSSAQAL GIRNHYRHPE EHGSDRWFNA LGSRRFSRNA

451 CVVVSCGTAV TVDALTDDGH YLGGTIMPGF HLMKESLAVR TANLNRHAGK

501 RYPFPTTTGN AVASGMMDAV CGSVMMMHGR LKEKTGAGKP VDVIITGGGA

551 AKVAEALPPA FLAENTVRVA DNLVIHGLLN LIAAEGGESE HT*
```

ORF61a and ORF61-1 show 98.5% identity in 591 aa overlap:

```
                10         20         30         40         50         60
orf61a.pep  MTVLKPSHWRVLAELADGLPQHVSQLARMADMKPQQLNGFWQQMPAHIRGLLRQHDGYWR
            ||||| |||||||||||||||||||||||||||||||||||||||||||||||||||||
orf61-1     MTVLKLSHWRVLAELADGLPQHVSQLARMADMKPQQLNGFWQQMPAHIRGLLRQHDGYWR
                10         20         30         40         50         60

70         80         90        100        110        120
orf61a.pep  LVRPLAVFDAEGLRELGERSGFQTALKHECASSNDEILELARIAPDKAHKTICVTHLQSK
            ||||||||||||||||||||||||||||||||||||||||||||||||||||||||||||
orf61-1     LVRPLAVFDAEGLRELGERSGFQTALKHECASSNDEILELARIAPDKAHKTICVTHLQSK
                70         80         90        100        110        120

130        140        150        160        170        180
orf61a.pep  GRGRQGRKWSHRLGECLMFSFGWVFDRPQYELGSLSPVAAVACRRALSRLGLKTQIKWPN
            |||||||||||||||||||||||||||||||||||||||||||||||||||| :||||||
orf61-1     GRGRQGRKWSHRLGECLMFSFGWVFDRPQYELGSLSPVAAVACRRALSRLGLDVQIKWPN
               130        140        150        160        170        180

190        200        210        220        230        240
orf61a.pep  DLVVGRDKLGGILIETVRTGGKTVAVVGIGINFVLPKEVENAASVQSLFQTASRRGNADA
            ||||||||||||||||||||||||||||||||||||||||||||||||||||||||||||
orf61-1     DLVVGRDKLGGILIETVRTGGKTVAVVGIGINFVLPKEVENAASVQSLFQTASRRGNADA
               190        200        210        220        230        240

250        260        270        280        290        300
orf61a.pep  AVLLETLLAELDAVLLQYARDGFAPFVAEYQAANRDHGKAVLLLRDGETVFEGTVKGVDG
            |||||||| :||||||||||||||||||||||||||||||||||||||||||||||||||
orf61-1     AVLLETLLVELDAVLLQYARDGFAPFVAEYQAANRDHGKAVLLLRDGETVFEGTVKGVDG
               250        260        270        280        290        300

310        320        330        340        350        360
orf61a.pep  QGVLHLETAEGKQTVVSGEISLRSDDRPVSVPKRRDSERFLLLDGGNSRLKWAWVENGTF
            ||||||||||||||||||||||||||||||||||||||||||||||||||||||||||||
orf61-1     QGVLHLETAEGKQTVVSGEISLRSDDRPVSVPKRRDSERFLLLDGGNSRLKWAWVENGTF
               310        320        330        340        350        360

370        380        390        400        410        420
orf61a.pep  ATVGSAPYRDLSPLGAEWAEKVDGNVRIVGCAVCGEFKKAQVQEQLARKIEWLPSSAQAL
            |||||||||||||||||||||| :||||||||||||||||||||||||||||||||||||
orf61-1     ATVGSAPYRDLSPLGAEWAEKADGNVRIVGCAVCGEFKKAQVQEQLARKIEWLPSSAQAL
               370        380        390        400        410        420

430        440        450        460        470        480
orf61a.pep  GIRNHYRHPEEHGSDRWFNALGSRRFSRNACVVVSCGTAVTVDALTDDGHYLGGTIMPGF
            ||||||||||||||||||||||||||||||||||||||||||||||||||||||||||||
orf61-1     GIRNHYRHPEEHGSDRWFNALGSRRFSRNACVVVSCGTAVTVDALTDDGHYLGGTIMPGF
               430        440        450        460        470        480

490        500        510        520        530        540
orf61a.pep  HLMKESLAVRTANLNRHAGKRYPFPTTTGNAVASGMMDAVCGSVMMMHGRLKEKTGAGKP
            ||||||||||||||||||||||||||||||||||||||||||||||||||||||||||||
orf61-1     HLMKESLAVRTANLNRHAGKRYPFPTTTGNAVASGMMDAVCGSVMMMHGRLKEKTGAGKP
               490        500        510        520        530        540

550        560        570        580        590
orf61a.pep  VDVIITGGGAAKVAEALPPAFLAENTVRVADNLVIHGLLNLIAAEGGESEHTX
            |||||||||||||||||||||||||||||||||||||| :||||:||||| ||
orf61-1     VDVIITGGGAAKVAEALPPAFLAENTVRVADNLVIYGLLNMIAAEGREYEHIX
               550        560        570        580        590
```

Homology with a Predicted ORF from *N. gonorrhoeae*
ORF61 shows 94.2% identity over a 189aa overlap with a predicted ORF (ORF61.ng) from *N. gonorrhoeae*.

```
orf61.pep                                EISLRSDXRPVSVXKRRDSERFLLLDGGNS    30
                                         ||||| | ||| ||  ||||:||||||||
orf61ng   TVCEGTVKGVDGRGVLHLETAEGEQTVVSGEISLRPDNRSVSVPKRPDSERFLLLEGGNS   211 orf61.pep  RLKWAWVENGTFATVGSAPYRDLSPLGAEWAEKADGNVRIVGCAVCGEFKKAQVQEQLAR    90
           ||||||||||||||||||||||||||||||||||||||||||||||||| ||||:|||||
orf61ng    RLKWAWVENGTFATVGSAPYRDLSPLGAEWAEKADGNVRIVGCAVCGESKKAQVKEQLAR   271 orf61.pep  KIEWLPSSAQAXGIRNHYRHPEEHGSDRWFNALGSRRFSRNACVVVSCGTAVTVDALTDD   150
           ||||||||||| ||||||||||||||||||||||||||||||||||||||||||||||||
orf61ng    KIEWLPSSAQALGIRNHYRHPEEHGSDRWFNALGSRRFSRNACVVVSCGTAVTVDALTDD   331 orf61.pep  GHYLGXGTIMPGFHLMKESLAVRTANLNRHAGKRYPFPT                        189
           |||||  ||||||||||||||||||||||| ||||||||
orf61ng    GHYLG-GTIMPGFHLMKESLAVRTANLNRPAGKRYPFPTTTGNAVASGMMDAVCGSIMMM   390
```

An ORF61ng nucleotide sequence <SEQ ID 237> was predicted to encode a protein having amino acid sequence <SEQ ID 238>:

```
  1 MFSFGWAFDR PQYELGSLSP VAALACRRAL GCLGLETQIK WPNDLVVGRD

51 KLGGILIETV RAGGKTVAVV GIGINFVLPK EVENAASVQS LFQTASRRGN

101 ADAAVLLETL LAELGAVLEQ YAEEGFAPFL NEYETANRDH GKAVLLLRDG

151 ETVCEGTVKG VDGRGVLHLE TAEGEQTVVS GEISLRPDNR SVSVPKRPDS

201 ERFLLLEGGN SRLKWAWVEN GTFATVGSAP YRDLSPLGAE WAEKADGNVR

251 IVGCAVCGES KKAQVKEQLA RKIEWLPSSA QALGIRNHYR HPEEHGSDRW

301 FNALGSRRFS RNACVVVSCG TAVTVDALTD DGHYLGGTIM PGFHLMKESL

351 AVRTANLNRP AGKRYPFPTT TGNAVASGMM DAVCGSIMMM HGRLKEKNGA

401 GKPVDVIITG GGAAKVAEAL PPAFLAENTV RVADNLVIHG LLNLIAAEGG

451 ESEHA*
```

Further analysis revealed the complete gonococcal DNA sequence <SEQ ID 239> to be:

```
   1 ATGACGGTTT TGAAGCCTTC GCATTGGCGG GTGTTGGCGG AGCTTGCCGA

51 CGGTTTGCCG CAACACGTAT CGCAATTGGC GCGTGAGGCG GACATGAAGC

101 CGCAGCAGCT CAACGGTTTT TGGCAGCAGA TGCCGGCGCA TATACGCGGG

151 CTGTTGCGCC AACACGACGG CTATTGGCGG CTGGTGCGCC CCTTGGCGGT

201 TTTCGATGCC GAAGGTTTGC GCGATCTGGG GGAAAGGTCG GGTTTTCAGA

251 CGGCATTGAA GCACGAGTGC GCGTCCAGCA ACGACGAGAT ACTGGAATTG

301 GCGCGGATTG CGCCGGACAA GGCGCACAAA ACCATATGCG TGACCCACCT

351 GCAAAGTAAG GGCAGGGGGC GGCAGGGGCG GAAGTGGTCG CACCGTTTGG

401 GCGAGTGCCT GATGTTCAGT TTCGGCTGGG CGTTTGACCG GCCGCAGTAT

451 GAGTTGGGTT CGCTGTCGCC TGTTGCGGCA CTTGCGTGCC GGCGCGCTTT

501 GGGGTGTTTG GGTTTGGAAA CGCAAATCAA GTGGCCAAAC GATTTGGTCG

551 TCGGACGCGA CAAATTGGGC GGCATTCTGA TTGAAACAGT CAGGGCGGGC

601 GGTAAAACGG TTGCCGTGGT CGGTATCGGC ATCAATTTCG TGCTGCCCAA

651 GGAAGTGGAA AACGCCGCTT CCGTGCAGTC GCTGTTTCAG ACGGCATCGC

701 GGCGGGGCAA TGCCGATGCC GCCGTATTGC TGGAAACATT GCTTGCGGAA

751 CTGGGCGCGG TGTTGGAACA ATATGCGGAA GAAGGGTTCG CGCCATTTTT

801 AAATGAGTAT GAAACGGCCA ACCGCGACCA CGGCAAGGCG GTATTGCTGT

851 TGCGCGACGG CGAAACCGTG TGCGAAGGCA CGGTTAAAGG CGTGGACGGA

901 CGAGGCGTTC TGCACTTGGA AACGGCAgaa ggcgaACAGa cggtcgtcag 951 cggcgaaaTC AGcctGCggc ccgacaacaG GTCGGtttcc gtgccgaagc 1001 ggccggatTC Ggaacgt TTT tTGCtgttgg aaggcgggaa cagccgGCTC 1051 AAGTGGGCGT GggtggAAAa cggcacgttc gcaaccgtgg gcagcgcgCc 1101 gtaCCGCGAT TTGTCGCCTT TGGGCGCGGA GTGGGCGGAA AAGGCGGATG

1151 GAAATGTCCG CATCGTCGGT TGCGCCGTGT GCGGAGAATC CAAAAAGGCA

1201 CAAGTGAAGG AACAGCTCGC CCGAAAAATC GAGTGGCTGC CGTCTTCCGC

1251 ACAGGCTTTG GGCATACGCA ACCACTACCG CCACCCCGAA GAACACGGTT
```

```
1301 CCGACCGTTG GTTCAACGCC TTGGGCAGCC GCCGCTTCAG CCGCAACGCC

1351 TGCGTCGTCG TCAGTTGCGG CACGGCGGTA ACGGTTGACG CGCTCACCGA

1401 TGACGGACAT TATCTCGGCG AACCATCAT GCCCGGCTTC CACCTGATGA

1451 AAGAATCGCT CGCCGTCCGA ACCGCCAACC TCAACCGCCC CGCCGGCAAA

1501 CGTTACCCTT TCCCGACCAC AACGGGCAAC GCCGTCGCAA GCGGCATGAT

1551 GGACGCGGTT TGCGGCTCGA TAATGATGAT GCACGGCCGT TTGAAAGAAA

1601 AAAACGGCGC GGGCAAGCCT GTCGATGTCA TCATTACCGG CGGCGGCGCG

1651 GCGAAAGTCG CCGAAGCCCT GCCGCCTGCA TTTTTGGCGG AAAATACCGT

1701 GCGCGTGGCG GACAACCTCG TCATCCACGG GCTGCTGAAC CTGATTGCCG

1751 CCGAAGGCGG GGAATCGGAA CACGCTTAA
```

This corresponds to the amino acid sequence <SEQ ID 240; ORF61ng-1>:

```
  1 MTVLKPSHWR VLAELADGLP QHVSQLAREA DMKPQQLNGF WQQMPAHIRG

51 LLRQHDGYWR LVRPLAVFDA EGLRDLGERS GFQTALKHEC ASSNDEILEL

101 ARIAPDKAHK TICVTHLQSK GRGRQGRKWS HRLGECLMFS FGWAFDRPQY

151 ELGSLSPVAA LACRRALGCL GLETQIKWPN DLVVGRDKLG GILIETVRAG

201 GKTVAVVGIG INFVLPKEVE NAASVQSLFQ TASRRGNADA AVLLETLLAE

251 LGAVLEQYAE EGFAPFLNEY ETANRDHGKA VLLLRDGETV CEGTVKGVDG

301 RGVLHLETAE GEQTVVSGEI SLRPDNRSVS VPKRPDSERF LLLEGGNSRL

351 KWAWVENGTF ATVGSAPYRD LSPLGAEWAE KADGNVRIVG CAVCGESKKA

401 QVKEQLARKI EWLPSSAQAL GIRNHYRHPE EHGSDRWFNA LGSRRFSRNA

451 CVVVSCGTAV TVDALTDDGH YLGGTIMPGF HLMKESLAVR TANLNRPAGK

501 RYPFPTTTGN AVASGMMDAV CGSIMMMHGR LKEKNGAGKP VDVIITGGGA

551 AKVAEALPPA FLAENTVRVA DNLVIHGLLN LIAAEGGESE HA*
```

ORF61ng-1 and ORF61-1 show 93.9% identity in 591 aa overlap:

```
orf61ng-1.pep  MTVLKPSHWRVLAELADGLPQHVSQLAREADMKPQQLNGFWQQMPAHIRGLLRQHDGYWR   60
               ||||| ||||||||||||||||||||||| ||||||||||||||||||||||||||||||
orf61-1        MTVLKLSHWRVLAELADGLPQHVSQLARMADMKPQQLNGFWQQMPAHIRGLLRQHDGYWR   60 orf61ng-1.pep  LVRPLAVFDAEGLRDLGERSGFQTALKHECASSNDEILELARIAPDKAHKTICVTHLQSK  120
               |||||||||||||:||||||||||||||||||||||||||||||||||||||||||||||
orf61-1        LVRPLAVFDAEGLRELGERSGFQTALKHECASSNDEILELARIAPDKAHKTICVTHLQSK  120 orf61ng-1.pep  GRGRQGRKWSHRLGECLMFSFGWAFDRPQYELGSLSPVAALACRRALGCLGLETQIKWPN  180
               |||||||||||||||||||||||:|||||||||||||||||||:|||||:|||:||||||
orf61-1        GRGRQGRKWSHRLGECLMFSFGWVFDRPQYELGSLSPVAAVACRRALSRLGLDVQIKWPN  180 orf61ng-1.pep  DLVVGRDKLGGILIETVRAGGKTVAVVGIGINFVLPKEVENAASVQSLFQTASRRGNADA  240
               ||||||||||||||||||||:|||||||||||||||||||||||||||||||||||||||
orf61-1        DLVVGRDKLGGILIETVRTGGKTVAVVGIGINFVLPKEVENAASVQSLFQTASRRGNADA  240 orf61ng-1.pep  AVLLETLLAELGAVLEQYAEEGFAPFLNEYETANRDHGKAVLLLRDGETVCEGTVKGVDG  300
               ||||||||:||  ||:|||:  ||||: ||: ||||||||||||||||| ||||||||||
orf61-1        AVLLETLLVELDAVLLQYARDGFAPFVAEYQAANRDHGKAVLLLRDGETVFEGTVKGVDG  300 orf61ng-1.pep  RGVLHLETAEGEQTVVSGEISLRPDNRSVSVPKRPDSERFLLLEGGNSRLKWAWVENGTF  360
               :|||||||||| |||||||||||: |||| |||||||||:||||||||||||||||||||
orf61-1        QGVLHLETAEGKQTVVSGEISLRSDDRPVSVPKRRDSERFLLLDGGNSRLKWAWVENGTF  360 orf61ng-1.pep  ATVGSAPYRDLSPLGAEWAEKADGNVRIVGCAVCGESKKAQVKEQLARKIEWLPSSAQAL  420
               ||||||||||||||||||||||||||||||||||||| ||||:|||||||||||||||||
orf61-1        ATVGSAPYRDLSPLGAEWAEKADGNVRIVGCAVCGEFKKAQVQEQLARKIEWLPSSAQAL  420 orf61ng-1.pep  GIRNHYRHPEEHGSDRWFNALGSRRFSRNACVVVSCGTAVTVDALTDDGHYLGGTIMPGF  480
               ||||||||||||||||||||||||||||||||||||||||||||||||||||||||||||
orf61-1        GIRNHYRHPEEHGSDRWFNALGSRRFSRNACVVVSCGTAVTVDALTDDGHYLGGTIMPGF  480
```

```
orf61ng-1.pep   HLMKESLAVRTANLNRPAGKRYPFPTTTGNAVASGMMDAVCGSIMMMHGRLKEKNGAGKP  540
                ||||||||||||||| ||||||||||||||||||||||||||:|||||||||:|||||
orf61-1         HLMKESLAVRTANLNRHAGKRYPFPTTTGNAVASGMMDAVCGSVMMMHGRLKEKTGAGKP  540 orf61ng-1.pep   VDVIITGGGAAKVAEALPPAFLAENTVRVADNLVIHGLLNLIAAEGGESEHAX         593
                ||||||||||||||||||||||||||||||||||||:||||:||||| | ||
orf61-1         VDVIITGGGAAKVAEALPPAFLAENTVRVADNLVIYGLLNMIAAEGREYEHIX         593
```

Based on this analysis, including the homology with the baf protein of *B. pertussis* and the presence of a putative prokaryotic membrane lipoprotein lipid attachment site, it is predicted that these proteins from *N. meningitidis* and *N. gonorrhoeae*, and their epitopes, could be useful antigens for vaccines or diagnostics, or for raising antibodies.

Example 29

The following partial DNA sequence was identified in *N. meningitidis* <SEQ ID 241>:

```
  1 ATGTTTTACC AAATCCTTGC CCTGATTATC TGGAGCAGCT CGTTTATTGC
 51 CGCCAAATAT GTCTATGGCG GCATCGATCC CGCATTGATG GTCGGCGTGC
101 GCCTGCTAAT TGCCGCGCTG CCTGCACTGC CCGCCTGCCG CCGTCATGTC
151 GGCAAGATTC CGCGTGAGGA ATGGAAGCCG TTGCTGATTG TGTCGTTCGT
201 CAACTATGTG CTGACCCTGC TGCTTCAGTT TGTCGGGTTG AAATACACTT
251 CCGCCGCCAG CGCATCGGTC ATTGTCGGAC TCGAGCCGCT GCTGATGGTG
301 TTTGTCGGAC ACTTTTTCTT CAACGACAAA GCGCGTGCCT ACCACTGGAT
351 ATGCGGCGCG GCGGCATTTG CCGGTGTCGC GCTGCTGATG GCGGGCGGTG
401 CGGaAGAGGG CGGCGaAGTC GGCTGGTTCG GCTGCCTGCT GGTGTTGTTG
451 GCGGGCGCGG GCTTTTGTGC CGCTATGCGT CCGACGCAAA GGCTGATTGC
501 ACGCATCGGC GCACCGGCAT TCACATCTGT TTCCATTGCC GCCGCATCGT
551 TGATGTGCCT GCCGTTTTCG CTTGCTTTGG CGCAAAGTTA TACCGTGGAC
601 TGGAGCGTCG GGATGGTATT GTCGCTGCTG TATTTGGGTT TGGGGTGC..
```

This corresponds to the amino acid sequence <SEQ ID 242; ORF62>:

```
  1 MFYQILALII WSSSFIAAKY VYGGIDPALM VGVRLLIAAL PALPACRRHV
 51 GKIPREEWKP LLIVSFVNYV LTLLLQFVGL KYTSAASASV IVGLEPLLMV
101 FVGHFFFNDK ARAYHWICGA AAFAGVALLM AGGAEEGGEV GWFGCLLVLL
151 AGAGFCAAMR PTQRLIARIG APAFTSVSIA AASLMCLPFS LALAQSYTVD
201 WSVGMVLSLL YLGLGC..
```

Further work revealed the complete nucleotide sequence <SEQ ID 243>:

```
  1 ATGTTTTACC AAATCCTTGC CCTGATTATC TGGAGCAGCT CGTTTATTGC
 51 CGCCAAATAT GTCTATGGCG GCATCGATCC CGCATTGATG GTCGGCGTGC
101 GCCTGCTAAT TGCCGCGCTG CCTGCACTGC CCGCCTGCCG CCGTCATGTC
151 GGCAAGATTC CGCGTGAGGA ATGGAAGCCG TTGCTGATTG TGTCGTTCGT
```

```
201 CAACTATGTG CTGACCCTGC TGCTTCAGTT TGTCGGGTTG AAATACACTT

251 CCGCCGCCAG CGCATCGGTC ATTGTCGGAC TCGAGCCGCT GCTGATGGTG

301 TTTGTCGGAC ACTTTTTCTT CAACGACAAA GCGCGTGCCT ACCACTGGAT

351 ATGCGGCGCG GCGGCATTTG CCGGTGTCGC GCTGCTGATG GCGGGCGGTG

401 CGGAAGAGGG CGGCGAAGTC GGCTGGTTCG GCTGCCTGCT GGTGTTGTTG

451 GCGGGCGCGG GCTTTTGTGC CGCTATGCGT CCGACGCAAA GGCTGATTGC

501 ACGCATCGGC GCACCGGCAT TCACATCTGT TTCCATTGCC GCCGCATCGT

551 TGATGTGCCT GCCGTTTTCG CTTGCTTTGG CGCAAAGTTA TACCGTGGAC

601 TGGAGCGTCG GGATGGTATT GTCGCTGCTG TATTTGGGTT TGGGGTGCGG

651 CTGGTACGCC TATTGGCTGT GGAACAAGGG GATGAGCCGT GTTCCTGCCA

701 ATGTTTCGGG ACTGTTGATT TCGCTCGAAC CCGTCGTCGG CGTGCTGCTG

751 GCGGTTTTGA TTTTGGGCGA ACACCTGTCG CCCGTGTCCG CCTTGGGCGT

801 GTTTGTCGTC ATCGCCGCCA CCTTGGTTGC CGGCCGGCTG TCGCATCAAA

851 AATAA
```

This corresponds to the amino acid sequence <SEQ ID 244; ORF62-1>:

```
  1 MFYQILALII WSSSFIAAKY VYGGIDPALM VGVRLLIAAL PALPACRRHV

51 GKIPREEWKP LLIVSFVNYV LTLLLQFVGL KYTSAASASV IVGLEPLLMV

101 FVGHFFFNDK ARAYHWICGA AAFAGVALLM AGGAEEGGEV GWFGCLLVLL

151 AGAGFCAAMR PTQRLIARIG APAFTSVSIA AASLMCLPFS LALAQSYTVD

201 WSVGMVLSLL YLGLGCGWYA YWLWNKGMSR VPANVSGLLI SLEPVVGVLL

251 AVLILGEHLS PVSALGVFVV IAATLVAGRL SHQK*
```

Computer analysis of this amino acid sequence gave the following results:

Homology with Hypothetical Transmembrane Protein HI0976 of *H. influenzae* (Accession Number Q57147)

ORF62 and HI0976 show 50% aa identity in 114aa overlap:

```
Orf62    1 MFYQILALIIWSSSFIAAKYVYGGIDPALMVGVRXXXXXXXXXXXCRRHVGKIPREEWKP   60
           M YQILAL+IWSSS I  K  Y  +DP L+V VR           R   KI +     K
HI0976   1 MYQILALLIWSSSLIVGKLTYSMMDPVLVVQVRLIIAMIIVMPLFLRRWKKIDKPMRKQ   60

Orf62   61 LLIVSFVNYVLTLLLQFVGLKYTSAASASVIVGLEPLLMVFVGHFFFNDKARAY      114
           L ++F NY    LLQF+GLKYTSA+SA ++GLEPLL+VFVGHFFF K +
HI0976  61 LWWLAFFNYTAVFLLQFIGLKYTSASSAVTMIGLEPLLVVFVGHFFFKTKQNGF      114
```

Homology with a Predicted ORF from *N. meningitidis* (Strain A)

ORF62 shows 99.5% identity over a 216aa overlap with an ORF (ORF62a) from strain A of *N. meningitidis*.

```
                  10        20        30        40        50        60
   orf62.pep MFYQILALIIWSSSFIAAKYVYGGIDPALMVGVRLLIAALPALPACRRHVGKIPREEWDP
             ||||||||||||||||||||||||||||||||||||||||||||||||||||||||||
     orf62a  MFYQILALIIWSSSFIAAKYVYGGIDPALMVGVRLLIAALPALPACRRHVGKIPREEWKP
                  10        20        30        40        50        60
```

```
              70         80         90        100        110        120
orf62.pep  LLIVSFVNYVLTLLLQFVGLKYTSAASASVIVGLEPLLMVFVGHFFFNDKARAYHWICGA
           ||||||||||||||||||||||||||||||||||||||||||||||||||||||||||||
orf62a     LLIVSFVNYVLTLLLQFVGLKYTSAASASVIVGLEPLLMVFVGHFFFNDKARAYHWICGA
              70         80         90        100        110        120
             130        140        150        160        170        180
orf62.pep  AAFAGVALLMAGGAEEGGEVGWFGCLLVLLAGAGFCAAMRPTQRLIARIGAPAFTSVSIA
           ||||||||||||||||||||||||||||||||||||||||||||||||||||||||||||
orf62a     AAFAGVALLMAGGAEEGGEVGWFGCLLVLLAGAGFCAAMRPTQRLIARIGAPAFTSVSIA
             130        140        150        160        170        180
             190        200        210
orf62.pep  AASLMCLPFSLALAQSYTVDWSVGMVLSLLYLGLGC
           |||||||||||||||||||||||||||||||||:||
orf62a     AASLMCLPFSLALAQSYTVDWSVGMVLSLLYLGVGCSWYAYWLWNKGMSRVPANVSGLLI
             190        200        210        220        230        240 orf62a     SLEPVVGVLLAVLILGEHLSPVSVLGVFVVIAATLVAGRLSHQKX
             250        260        270        280
```

The complete length ORF62a nucleotide sequence <SEQ ID 245> is:

```
  1 ATGTTTTACC AAATCCTTGC CCTGATTATC TGGAGCAGCT CGTTTATTGC

51 CGCCAAATAT GTCTATGGCG GCATCGATCC CGCATTGATG GTCGGCGTGC

101 GCCTGCTGAT TGCTGCGCTG CCTGCACTGC CCGCCTGCCG CCGTCATGTC

151 GGCAAGATTC CGCGTGAGGA ATGGAAGCCG TTGCTGATTG TGTCGTTCGT

201 CAACTATGTG CTGACCCTGC TACTTCAGTT TGTCGGGTTG AAATACACTT

251 CCGCCGCCAG CGCATCGGTC ATTGTCGGAC TCGAGCCACT GCTGATGGTG

301 TTTGTCGGAC ACTTTTTCTT CAACGACAAA GCGCGTGCCT ACCACTGGAT

351 ATGCGGCGCG GCGGCATTTG CCGGTGTCGC GCTGCTGATG GCGGGCGGTG

401 CGGAAGAGGG CGGCGAAGTC GGCTGGTTCG GCTGCCTGCT GGTGTTGTTG

451 GCGGGCGCGG GCTTTTGTGC CGCTATGCGT CCGACGCAAA GGCTGATTGC

501 ACGCATCGGC GCACCGGCAT TCACATCTGT TTCCATTGCC GCCGCATCGT

551 TGATGTGCCT GCCGTTTTCG CTTGCTTTGG CGCAAAGTTA TACCGTGGAC

601 TGGAGCGTCG GAATGGTATT GTCGCTGCTG TATTTGGGCG TGGGGTGCAG

651 CTGGTACGCC TATTGGCTGT GGAACAAGGG GATGAGCCGT GTTCCTGCCA

701 ACGTTTCGGG ACTGTTGATT TCGCTCGAAC CCGTCGTCGG CGTGCTGCTG

751 GCGGTTTTGA TTTTGGGCGA ACACCTGTCG CCCGTGTCCG TCTTGGGCGT

801 GTTTGTCGTC ATCGCCGCCA CCTTGGTTGC CGGCCGGCTG TCGCATCAAA

851 AATAA
```
                                                          50

This encodes a protein having amino acid sequence <SEQ ID 246>:

```
  1 MFYQILALII WSSSFIAAKY VYGGIDPALM VGVRLLIAAL PALPACRRHV

51 GKIPREEWKP LLIVSFVNYV LTLLLQFVGL KYTSAASASV IVGLEPLLMV

101 FVGHFFFNDK ARAYHWICGA AAFAGVALLM AGGAEEGGEV GWFGCLLVLL

151 AGAGFCAAMR PTQRLIARIG APAFTSVSIA AASLMCLPFS LALAQSYTVD

201 WSVGMVLSLL YLGVGCSWYA YWLWNKGMSR VPANVSGLLI SLEPVVGVLL

251 AVLILGEHLS PVSVLGVFVV IAATLVAGRL SHQK*
```

ORF62a and ORF62-1 show 98.9% identity in 284 aa overlap:

```
orf62a.pep    MFYQILALIIWSSSFIAAKYVYGGIDPALMVGVRLLIAALPALPACRRHVGKIPREEWKP    60
              ||||||||||||||||||||||||||||||||||||||||||||||||||||||||||||
orf62-1       MFYQILALIIWSSSFIAAKYVYGGIDPALMVGVRLLIAALPALPACRRHVGKIPREEWKP    60
orf62a.pep    LLIVSFVNYVLTLLLQFVGLKYTSAASASVIVGLEPLLMVFVGHFFFNDKARAYHWICGA   120
              ||||||||||||||||||||||||||||||||||||||||||||||||||||||||||||
orf62-1       LLIVSFVNYVLTLLLQFVGLKYTSAASASVIVGLEPLLMVFVGHFFFNDKARAYHWICGA   120
orf62a.pep    AAFAGVALLMAGGAEEGGEVGWFGCLLVLLAGAGFCAAMRPTQRLIARIGAPAFTSVSIA   180
              ||||||||||||||||||||||||||||||||||||||||||||||||||||||||||||
orf62-1       AAFAGVALLMAGGAEEGGEVGWFGCLLVLLAGAGFCAAMRPTQRLIARIGAPAFTSVSIA   180
orf62a.pep    AASLMCLPFSLALAQSYTVDWSVGMVLSLLYLGVGCSWYAYWLWNKGMSRVPANVSGLLI   240
              |||||||||||||||||||||||||||||||:||:|||||||||||||||||||||||||
orf62-1       AASLMCLPFSLALAQSYTVDWSVGMVLSLLYLGLGCGWYAYWLWNKGMSRVPANVSGLLI   240
orf62a.pep    SLEPVVGVLLAVLILGEHLSPVSVLGVFVVIAATLVAGRLSHQKX                 285
              |||||||||||||||||||||||||:||||||||||||||||||
orf62-1       SLEPVVGVLLAVLILGEHLSPVSALGVFVVIAATLVAGRLSHQKX                 285
```

Homology with a Predicted ORF from *N. gonorrhoeae*

ORF62 shows 99.5% identity over a 216aa overlap with a predicted ORF (ORF62.ng) from *N. gonorrhoeae*.

```
orf62.pep     MFYQILALIIWSSSFIAAKYVYGGIDPALMVGVRLLIAALPALPACRRHVGKIPREEWKP    60
              |||||||||:||||||||||||||||||||||||||||||||||||||||||||||||||
orf62ng       MFYQILALIIWGSSFIAAKYVYGGIDPALMVGVRLLIAALPALPACRRHVGKIPREEWKP    60
orf62.pep     LLIVSFVNYVLTLLLQFVGLKYTSAASASVIVGLEPLLMVFVGHFFFNDKARAYHWICGA   120
              ||||||||||||||||||||||||||||||||||||||||||||||||||||||||||||
orf62ng       LLIVSFVNYVLTLLLQFVGLKYTSAASASVIVGLEPLLMVFVGHFFFNDKARAYHWICGA   120
orf62.pep     AAFAGVALLMAGGAEEGGEVGWFGCLLVLLAGAGFCAAMRPTQRLIARIGAPAFTSVSIA   180
              ||||||||||||||||||||||||||||||||||||||||||||||||||||||||||||
orf62ng       AAFAGVALLMAGGAEEGGEVGWFGCLLVLLAGAGFCAAMRPTQRLIARIGAPAFTSVSIA   180
orf62.pep     AASLMCLPFSLALAQSYTVDWSVGMVLSLLYLGLGC                          216
              |||||||||||||||||||||||||||||||||||
orf62ng       AASLMCLPFSLALAQSYTVDWSVGMVLSLLYLGLGCGWYAYWLWNKGMSRVPANASGLLI   240
```

The complete length ORF62ng nucleotide sequence <SEQ ID 247> is:

```
  1 ATGTTTTACC AAATCCTTGC CCTGATTATC TGGGGCAGCT CGTTTATTGC
 51 CGCCAAATAT GTCTATGGCG GCATCGATCC CGCATTGATG GTCGGCGTGC
101 GCCTGCTGAT TGCCGCGCTG CCTGCACTGC CCGCCTGCCG CCGTCATGTC
151 GGCAAGATTC CGCGTGAGGA ATGGAAGCCG TTGCTGATTG TGTCGTTCGT
201 CAACTATGTG CTGACCCTGC TGCTTCAGTT TGTCGGGTTG AAATACACTT
251 CCGCCGCCAG CGCATCGGTC ATTGTCGGAC TCGAGCCGCT GCTGATGGTG
301 TTTGTCGGAC ACTTTTTCTT CAACGACAAA GCGCGTGCCT ACCACTGGAT
351 ATGCGGCGCG GCGGCATTTG CCGGTGTCGC GCTGCTGATG GCGGGCGGTG
401 CGGAAGAGGG CGGCGAAGTC GGCTGGTTCG GCTGCCTGCT GGTGTTGTTG
451 GCGGGCGCGG GCTTTTGTGC CGCTATGCGT CCGACGCAAA GGCTGATTGC
501 CCGCATCGGC GCACCGGCAT TCACATCTGT TTCCATTGCC GCCGCATCGT
551 TGATGTGCCT GCCGTTTTCG CTTGCTTTGG CGCAAAGTTA TACCGTGGAC
601 TGGAGCGTCG GGATGGTATT GTCGCTGTTG TATTTGGGTT TGGGGTGCGG
651 CTGGTACGCC TATTGGCTGT GGAACAAGGG GATGAGCCGT GTTCCTGCCA
701 ACGCGTCGGG ACTGTTGATT TCGCTCGAAC CCGTCGTCGG CGTGCTGTTG
751 GCGGTTTTGA TTTTGGGCGA ACATTTATCG CCCGTGTCCG CCTTGGGCGT
```

```
801 GTTTGTCGTC ATCGCCGCCA CTTTCGCCGC CGGCCGGCTG TCGCGCAGGG

851 ACGCGCAAAA CGGCAATGCC GTCTGA
```

This encodes a protein having amino acid sequence <SEQ ID 248>:

```
  1 MFYQILALII WGSSFIAAKY VYGGIDPALM VGVRLLIAAL PALPACRRHV

51 GKIPREEWKP LLIVSFVNYV LTLLLQFVGL KYTSAASASV IVGLEPLLMV

101 FVGHFFFNDK ARAYHWICGA AAFAGVALLM AGGAEEGGEV GWFGCLLVLL

151 AGAGFCAAMR PTQRLIARIG APAFTSVSIA AASLMCLPFS LALAQSYTVD

201 WSVGMVLSLL YLGLGCGWYA YWLWNKGMSR VPANASGLLI SLEPVVGVLL

251 AVLILGEHLS PVSALGVFVV IAATFAAGRL SRRDAQNGNA V*
```

ORF62ng and ORF62-1 show 97.9% identity in 283 aa overlap:

```
                    10         20         30         40         50         60
    orf62ng.pep  MFYQILALIIWGSSFIAAKYVYGGIDPALMVGVRLLIAALPALPACRRHVGKIPREEWKP
                 ||||||||||:|||||||||||||||||||||||||||||||||||||||||||||||||
    orf62-1      MFYQILALIIWSSSFIAAKYVYGGIDPALMVGVRLLIAALPALPACRRHVGKIPREEWKP
                    10         20         30         40         50         60

70         80         90        100        110        120
    orf62ng.pep  LLIVSFVNYVLTLLLQFVGLKYTSAASASVIVGLEPLLMVFVGHFFFNDKARAYHWICGA
                 ||||||||||||||||||||||||||||||||||||||||||||||||||||||||||||
    orf62-1      LLIVSFVNYVLTLLLQFVGLKYTSAASASVIVGLEPLLMVFVGHFFFNDKARAYHWICGA
                    70         80         90        100        110        120

130        140        150        160        170        180
    orf62ng.pep  AAFAGVALLMAGGAEEGGEVGWFGCLLVLLAGAGFCAAMRPTQRLIARIGAPAFTSVSIA
                 ||||||||||||||||||||||||||||||||||||||||||||||||||||||||||||
    orf62-1      AAFAGVALLMAGGAEEGGEVGWFGCLLVLLAGAGFCAAMRPTQRLIARIGAPAFTSVSIA
                   130        140        150        160        170        180

190        200        210        220        230        240
    orf62ng.pep  AASLMCLPFSLALAQSYTVDWSVGMVLSLLYLGLGCGWYAYWLWNKGMSRVPANASGLLI
                 |||||||||||||||||||||||||||||||||||||||||||||||||||||||:||||
    orf62-1      AASLMCLPFSLALAQSYTVDWSVGMVLSLLYLGLGCGWYAYWLWNKGMSRVPANVSGLLI
                   190        200        210        220        230        240

250        260        270        280        290
    orf62ng.pep  SLEPVVGVLLAVLILGEHLSPVSALGVFVVIAATFAAGRLSRRDAQNGNAVX
                 ||||||||||||||||||||||||||||||||::||||::
    orf62-1      SLEPVVGVLLAVLILGEHLSPVSALGVFVVIAATLVAGRLSHQKX
                   250        260        270        280
```

Furthermore, ORF62ng shows significant homology to a hypothetical *H. influenzae* protein:

```
sp|Q57147|Y976_HAEIN HYPOTHETICAL PROTEIN HI0976 >gi|1074589|pir||B64163
hypothetical protein HI0976 - Haemophilus influenzae (strain Rd KW20)
>gi|1574004 (U32778) hypothetical [Haemophilus influenzae] Length = 128
Score = 106 bits (262), Expect = 2e-22
Identities = 56/114 (49%), Positives = 68/114 (59%)

Query:   1 MFYQILALIIWGSSFIAAKYVYGGIDPALMVGVRXXXXXXXXXXXCRRHVGKIPREEWKP    60
           M YQILAL+IW SS I   K Y +DP L+V VR           R  KI +    K
Sbjct:   1 MLYQILALLIWSSSLIVGKLTYSMMDPVLVVQVRLIIAMIIVMPLFLRRWKKIDKPMRKQ   60

Query:  61 LLIVSFVNYVLTLLLQFVGLKYTSAASASVIVGLEPLLMVFVGHFFFNDKARAY        114
           L  ++F NY     LLQF+GLKYTSA+SA  +GLEPLL+VFVGHFFF  K   +
Sbjct:  61 LWWLAFFNYTAVFLLQFIGLKYTSASSAVTMIGLEPLLVVFVGHFFFKTKQNGF        114
```

Based on this analysis, including the homology with the transmembrane protein of *H. influenzae* and the putative leader sequence and several transmembrane domains in the gonococcal protein, it is predicted that these proteins from *N. meningitidis* and *N. gonorrhoeae*, and their epitopes, could be useful antigens for vaccines or diagnostics, or for raising antibodies.

Example 30

The following partial DNA sequence was identified in *N. meningitidis* <SEQ ID 249>:

```
   1 ATGCGCCGTT TTCTACCGAT CGCAGCCATA TGCGCmGwms TCCTGkkGTA
  51 sGGACTGACG GCGGCAACCG GCAGCACCAG TTCGCTGGCG GATTATTTCT
 101 GGTGGATTGT TGCGTTCAGC GCAATGCTGC TGCTGGTGTT GTCCGCCGTT
 151 TTGGCACGTT ATGTCATATT GCTGTTGAAA GACAGGCGCG ACGGCGTATT
 201 CGGTTCGCtA srTyGCCAAA gsGCCTgkks TGGG.ATGTT TACGCTGGTT
 251 GCCGkACTGC CCGGCGTGTT TCTGTTCGGC TTTCCCGCAC AGTTCATCAA
 301 CGGCACGATT AATTCGTGGT TCGGCAACGA TACCCACGAG GCGCTTGAAC
 351 GCAGCCTCAA TTTGAGCAAG TCCGCATTGA ATTTGGCGGC AGACAACGCC
 401 CTCGGCAACG CCGTCCCCGT GCAGATAGAC CTCATCGGCG CGGCTTCCCT
 451 GCCCGGGGAT ATGGGCAGGG TGCTGGAACA TTACGCCGGC AGCGGTTTTG
 501 CCCAGCTTGC CCTGTACAAy ksCGCAAGCG GCAAAATCGA AAAAAGCATC
 551 AACCCGCACA AGCTCGATCA GCCGTTTCCA GGTAAGGCGC GTTGGGAaAa
 601 AATCCaACGG GCGGGTTCGG TCAGGGATTT GGAAAGCATA GGCGGCGTAT
 651 TGTaCGCGCA GGGCTGGCTG TCGGCGGGTA CGCACwACGG GCGCGATTAC
 701 GCCTTGTTTT TCCGTCAGCC GGTTCCCAAA GGCGTGGCAG AGGATGCCGT
 751 yTTAATCGAA AAGGCAAGGG CGAAATATGC TGAGTTGAGT TACAGCAAAA
 801 AAGGTTTGCA GACCTTTTTC CTGGCAACCC TGCTGATTGC CTCGCTGCTG
 851 TCGATTTTTC TTGCACTGGT CATGGCACTG TATTTCGCCC GCCGTTTCGT
 901 CGAACCCGTC CTATCGCTTG CCGAGGGGGC GAAGGCGGTG GCGCAAGGCG
 951 ATTTCAGCCA GACGCGCCCC GTGTTGCGCA ACGACGAGTT CGGACGCTTG
1001 ACCArGTTGT TCAACCACAT GACCGAGCAG CTTTCCATCG CCAAAGATGC
1051 AGACGAGCGC AACCGCCGGC GCGAGGAAGC CGCCAGGCAT TATCTTGAAT
1101 GCGTGTTGGA GGGGCTGACC ACGGGCGTGG TGGTGTTTGA CGAACAAGGC
1151 TGTCTGAAAA CCTTCAACAA AGCGGCGGGT ACC..
```

This corresponds to the amino acid sequence <SEQ ID 250; ORF64>:

```
   1 MRRFLPIAAI CAXXLXXGLT AATGSTSSLA DYFWWIVAFS AMLLLVLSAV
  51 LARYVILLLK DRRDGVFGSX XAKXPXXXMF TLVAXLPGVF LFGFPAQFIN
 101 GTINSWFGND THEALERSLN LSKSALNLAA DNALGNAVPV QIDLIGAASL
 151 PGDMGRVLEH YAGSGFAQLA LYNXASGKIE KSINPHKLDQ PFPGKARWEK
 201 IQRAGSVRDL ESIGGVLYAQ GWLSAGTHXG RDYALFFRQP VPKGVAEDAV
 251 LIEKARAKYA ELSYSKKGLQ TFFLATLLIA SLLSIFLALV MALYFARRFV
 301 EPVLSLAEGA KAVAQGDFSQ TRPVLRNDEF GRLTXLFNHM TEQLSIAKDA
 351 DERNRRREEA ARHYLECVLE GLTTGVVVFD EQGCLKTFNK AAGT..

Further work revealed the complete nucleotide sequence <SEQ ID 251>:

```
   1 ATGCGCCGTT TTCTACCGAT CGCAGCCATA TGCGCCGTCG TCCTGTTGTA
  51 CGGACTGACG GCGGCAACCG GCAGCACCAG TTCGCTGGCG GATTATTTCT
 101 GGTGGATTGT TGCGTTCAGC GCAATGCTGC TGCTGGTGTT GTCCGCCGTT
 151 TTGGCACGTT ATGTCATATT GCTGTTGAAA GACAGGCGCG ACGGCGTATT
 201 CGGTTCGCAG ATTGCCAAAC GCCTTTCTGG GATGTTTACG CTGGTTGCCG
 251 TACTGCCCGG CGTGTTTCTG TTCGGCGTTT CCGCACAGTT CATCAACGGC
 301 ACGATTAATT CGTGGTTCGG CAACGATACC CACGAGGCGC TTGAACGCAG
 351 CCTCAATTTG AGCAAGTCCG CATTGAATTT GGCGGCAGAC AACGCCCTCG
 401 GCAACGCCGT CCCCGTGCAG ATAGACCTCA TCGGCGCGGC TTCCCTGCCC
 451 GGGGATATGG GCAGGGTGCT GGAACATTAC GCCGGCAGCG GTTTTGCCCA
 501 GCTTGCCCTG TACAATGCCG CAAGCGGCAA AATCGAAAAA AGCATCAACC
 551 CGCACAAGCT CGATCAGCCG TTTCCAGGTA AGGCGCGTTG GGAAAAAATC
 601 CAACGGGCGG GTTCGGTCAG GGATTTGGAA AGCATAGGCG GCGTATTGTA
 651 CGCGCAGGGC TGGCTGTCGG CGGGTACGCA CAACGGGCGC GATTACGCCT
 701 TGTTTTTCCG TCAGCCGGTT CCCAAAGGCG TGGCAGAGGA TGCCGTCTTA
 751 ATCGAAAAGG CAAGGGCGAA ATATGCTGAG TTGAGTTACA GCAAAAAAGG
 801 TTTGCAGACC TTTTTCCTGG CAACCCTGCT GATTGCCTCG CTGCTGTCGA
 851 TTTTTCTTGC ACTGGTCATG GCACTGTATT TCGCCCGCCG TTTCGTCGAA
 901 CCCGTCCTAT CGCTTGCCGA GGGGGCGAAG GCGGTGGCGC AAGGCGATTT
 951 CAGCCAGACG CGCCCCGTGT TGCGCAACGA CGAGTTCGGA CGCTTGACCA
1001 AGTTGTTCAA CCACATGACC GAGCAGCTTT CCATCGCCAA AGAAGCAGAC
1051 GAGCGCAACC GCCGGCGCGA GGAAGCCGCC AGGCATTATC TTGAATGCGT
1101 GTTGGAGGGG CTGACCACGG GCGTGGTGGT GTTTGACGAA CAAGGCTGTC
1151 TGAAAACCTT CAACAAAGCG GCGGAACAGA TTTTGGGGAT GCCGCTTACC
1201 CCCCTGTGGG GCAGCAGCCG GCACGGTTGG CACGGCGTTT CGGCGCAGCA
1251 GTCCCTGCTT GCCGAAGTGT TTGCCGCCAT CGGCGCGGCG GCAGGTACGG
1301 ACAAACCGGT CCATGTGAAA TATGCCGCGC CGGACGATGC CAAAATCCTG
1351 CTGGGCAAGG CAACCGTCCT GCCCGAAGAC AACGGCAACG GCGTGGTAAT
1401 GGTGATTGAC GACATCACCG TTTTGATACA CGCGCAAAAA GAAGCCGCGT
1451 GGGGCGAAGT GGCGAAGCGG CTGGCACACG AAATCCGCAA TCCGCTCACG
1501 CCCATCCAGC TTTCCGCCGA ACGGCTGGCG TGGAAATTGG GCGGGAAGCT
1551 GGATGAGCAG GATGCGCAAA TCCTGACGCG TTCGACCGAC ACCATCGTCA
1601 AACAGGTGGC GGCATTGAAG GAAATGGTCG AAGCATTCCG CAATTATGCG
1651 CGTTCCCCTT CGCTCAAATT GGAAAATCAG GATTTGAACG CCTTAATCGG
1701 CGATGTGTTG GCATTGTATG AAGCCGGTCC GTGCCGGTTT GCGGCGGAGC
1751 TTGCCGGCGA ACCGCTGACG GTGGCGGCGG ATACGACCGC CATGCGGCAG
1801 GTGCTGCACA ATATTTTCAA AAATGCCGCC GAAGCGGCGG AAGAAGCCGA
1851 TGTGCCCGAA GTCAGGGTAA AATCGGAAAC AGGGCAGGAC GGTCGGATTG
1901 TCCTGACGGT TTGCGACAAC GGCAAAGGGT TCGGCAGGGA AATGCTGCAC
```

```
-continued
1951 AACGCCTTCG AGCCGTATGT AACGGACAAA CCGGCGGGAA CGGGATTGGG

2001 TCTGCCTGTG GTGAAAAAAA TCATTGAAGA ACACGGCGGC CGCATCAGCC

2051 TGAGCAATCA GGATGCGGGT GGCGCGTGTG TCAGAATCAT CTTGCCAAAA

2101 ACGGTAAAAA CTTATGCGTA G
```

This corresponds to the amino acid sequence <SEQ ID 252; ORF64-1>:

```
  1  MRRFLPIAAI CAVVLLYGLT AATGSTSSLA DYFWWIVAFS AMLLLVLSAV

51  LARYVILLLK DRRDGVFGSQ IAKRLSGMFT LVAVLPGVFL FGVSAQFING

101  TINSWFGNDT HEALERSLNL SKSALNLAAD NALGNAVPVQ IDLIGAASLP

151  GDMGRVLEHY AGSGFAQLAL YNAASGKIEK SINPHKLDQP FPGKARWEKI

201  QRAGSVRDLE SIGGVLYAQG WLSAGTHNGR DYALFFRQPV PKGVAEDAVL

251  IEKARAKYAE LSYSKKGLQT FFLATLLIAS LLSIFLALVM ALYFARRFVE

301  PVLSLAEGAK AVAQGDFSQT RPVLRNDEFG RLTKLFNHMT EQLSIAKEAD

351  ERNRRREEAA RHYLECVLEG LTTGVVVFDE QGCLKTFNKA AEQILGMPLT

401  PLWGSSRHGW HGVSAQQSLL AEVFAAIGAA AGTDKPVHVK YAAPDDAKIL

451  LGKATVLPED NGNGVVMVID DITVLIHAQK EAAWGEVAKR LAHEIRNPLT

501  PIQLSAERLA WKLGGKLDEQ DAQILTRSTD TIVKQVAALK EMVEAFRNYA

551  RSPSLKLENQ DLNALIGDVL ALYEAGPCRF AAELAGEPLT VAADTTAMRQ

601  VLHNIFKNAA EAAEEADVPE VRVKSETGQD GRIVLTVCDN GKGFGREMLH

651  NAFEPYVTDK PAGTGLGLPV VKKIIEEHGG RISLSNQDAG GACVRIILPK

701  TVKTYA*
```

Computer analysis of this amino acid sequence gave the following results:

Homology with a Predicted ORF from *N. meningitidis* (Strain A)

ORF64 shows 92.6% identity over a 392aa overlap with an ORF (ORF64a) from strain A of *N. meningitidis*:

```
                      10         20         30         40         50         60
    orf64.pep  MRRFLPIAAICAXXLXXGLTAATGSTSSLADYFWWIVAFSAMLLLVLSAVLARYVILLLK
               ||||||||||   |  ||||||||||||||||||||||||||||||||||||||||||||
    orf64a     MRRFLPIAAICAVVLLYGLTAATGSTSSLADYFWWIVAFSAMLLLVLSAVLARYVILLLK
                      10         20         30         40         50         60

70         80         90        100        110        120
    orf64.pep  DRRDGVFGSXXAKXPXXXMFTLVAXLPGVFLFGFPAQFINGTINSWFGNDTHEALERSLN
               |||||||||  ||  || |||||| |||||||| ||||||||||||||||||||||||||
    orf64a     DRRDGVFGSQIAKR-LSGMFTLVAVLPGVFLFGVSAQFINGTINSWFGNDTHEALERSLN
                      70         80         90        100        110

130        140        150        160        170        180
    orf64.pep  LSKSALNLAADNALGNAVPVQIDLIGAASLPGDMGRVLEHYAGSGFAQLALYNXASGKIE
               ||||||||||||||| |||||| ||||||||| |||||||||||||||||||| |||||
    orf64a     LSKSALNLAADNALGNAIPVQIDXIGAASLPXDMGRVLEHYAGSGFAQLALYNAASGKIE
                     120        130        140        150        160        170

190        200        210        220        230        240
    orf64.pep  KSINPHKLDQPFPGKARWEKIQRAGSVRDLESIGGVLYAQGWLSAGTHXGRDYALFFRQP
               ||||||||||||||||||||| |||||||| ||||||| |||||  | |||||||||||
    orf64a     KSINPHKLDQPFPGKARWEKIQQAGSVRDXESIGGVLYAXGWLSAXTHNGRDYALFFRQP
                  180        190        200        210        220        230

250        260        270        280        290        300
    orf64.pep  VPKGVAEDAVLIEKARAKYAELSYSKKGLQTFFLATLLIASLLSIFLALVMALYFARRFV
               |||||||||||||||||   |||||||||||||||||||||||||||||||||||||||
    orf64a     VPKGVAEDAVLIEKARAXXXLSYSKKGLQTFFLATLLIASLLSIFLALVMALYFARRFV
                     240        250        260        270        280        290
```

```
                   310        320        330        340        350        360
orf64.pep  EPVLSLAEGAKAVAQGDFSQTRPVLRNDEFGRLTXLFNHMTEQLSIAKDADERNRRREEA
           ||||||||||||||||||||||||||||||||| |||||||||||||:|||||||||||
orf64a     EPVLSLAEGAKAVAQGDFSQTRPVLRNDEFGRLTKLFNHMTEQLSIAKEADERNRRREEA
           300        310        320        330        340        350

370        380        390
orf64.pep  ARHYLECVLEGLTTGVVVFDEQGCLKTFNKAAGT
           |||||||||||||||||||||||||||||||
orf64a     ARHYLECVLEGLTTGVVVFDEQGCLKTFNKAAEQILGMPLTPLWGSSRHGWHGVSAQQSL
           360        370        380        390        400        410 orf64a     LAEVFAAIGAAAGTDKPVHVKYAAPDDAKILLGKATVLPEDNXNGVVMVIDDITVLIHAQ
           420        430        440        450        460        470
```

The complete length ORF64a nucleotide sequence <SEQ ID 253> is:

```
   1 ATGCGCCGTT TTCTACCGAT CGCAGCCATA TGCGCCGTCG TCCTGTTGTA

51 CGGACTGACG GCGGCAACCG GCAGCACCAG TTCGCTGGCG GATTATTTCT

101 GGTGGATTGT TGCGTTCAGC GCAATGCTGC TGCTGGTGTT GTCCGCCGTT

151 TTGGCACGTT ATGTCATATT GCTGTTGAAA GACAGGCGCG ACGGCGTATT

201 CGGTTCGCAG ATTGCCAAAC GCCTTTCCGG GATGTTTACG CTGGTTGCCG

251 TACTGCCCGG CGTGTTTCTG TTCGGCGTTT CCGCACAGTT TATCAACGGC

301 ACGATTAATT CGTGGTTCGG CAACGATACC CACGAGGCGC TTGAACGCAG

351 CCTCAATTTG AGCAAGTCCG CATTGAATCT GGCGGCAGAC AACGCCCTTG

401 GCAACGCCAT CCCCGTGCAG ATAGACNTCA TCGGCGCGGC TTCCCTGCCC

451 NGGGATATGG GCAGGGTGCT GGAACATTAC GCCGGCAGCG GTTTTGCCCA

501 GCTTGCCCTG TACAATGCCG CAAGCGGCAA AATCGAAAAA AGCATCAACC

551 CGCACAAGCT CGATCAGCCG TTTCCAGGTA AGGCGCGTTG GGAAAAAATC

601 CAACAGGCGG GTTCGGTCAG GGATNNGGAA AGCATAGGCG GCGTATTGTA

651 CGCGCANGGC TGGCTGTCGG CAGNNACGCA CAACGGGCGC GATTACGCCT

701 TGTTTTTCCG TCAGCCGGTT CCCAAAGGCG TGGCAGAGGA TGCCGTCTTA

751 ATCGAAAAGG CAAGGGCGNA ANANNNTNAG TTGAGTTACA GCAAAAAAGG

801 TTTGCAGACC TTTTTCCTNG CAACCCTGCT GATTGCCTCN CTGCTGTCGA

851 TTTTTCTTGC ACTGGTCATG GCACTGTATT TCGCCCGCCG TTTCGTCGAA

901 CCCGTCCTAT CGCTTGCCGA GGGGGCGAAG GCGGTGGCGC AAGGCGATTT

951 CAGCCAGACG CGCCCCGTGT TGCGCAACGA CGAGTTCGGA CGCTTGACCA

1001 AGTTGTTCAA CCACATGACC GAGCAGCTTT CCATCGCCAA AGAAGCAGAC

1051 GAGCGCAACC GCCGGCGCGA GGAAGCCGCC AGACATTATC TCGAATGCGT

1101 GTTGGAGGGG CTGACCACGG GCGTGGTGGT GTTTGACGAA CAAGGCTGTC

1151 TGAAAACCTT CAACAAAGCG GCGAACAGA TTTTGGGGAT GCCGCTTACC

1201 CCCCTGTGGG GCAGCAGCCG GCACGGTTGG CACGGCGTTT CGGCGCAGCA

1251 GTCCCTGCTT GCCGAAGTGT TTGCCGCCAT CGGCGCGGCG GCAGGTACGG

1301 ACAAACCGGT CCATGTGAAA TATGCCGCGC CGGACGATGC CAAAATCCTG

1351 CTGGGCAAGG CAACCGTCCT GCCCGAAGAC AACNGCAACG GCGTGGTAAT

1401 GGTGATTGAC GACATCACCG TTTTGATACA CGCGCAAAAA GAAGCCGCGT

1451 GGGGCGAAGT GGCAAAACGG CTGGCACACG AAATCCGCAA TCCGCTCACG

1501 CCCATCCAGC TTTCTGCCGA ACGGCTGGCG TGGAAATTGG GCGGGAAGCT
```

```
-continued
1551 GGACGAGCAN GACGCGCAAA TCCTGACACG TTCGACCGAC ACCATCATCA

1601 AACAAGTGGC GGCATTAAAA GAAATGGTCG AGGCATTCCG CAATTACNCG

1651 CGTTCCCCTT CGNCTCAATT GGAAAATCAG GATTTGAACG CCTTAATCGG

1701 CGATGTGTTG GCATTGTACG AAGCTGGTCC GTGCCGGTTT GCGGCGGAAC

1751 TTGCCGGCGA ACCGCTGATG ATGGCGGCGG ATACGACCGC CATGCGGCAG

1801 GTGCTGCACA ATATTTTCAA AAATGCCGCC GAAGCGGCGG AAGAAGCCGA

1851 TGTGCCCGAA GTCAGGGTAA AATCGGAAGC GGGGCAGGAC GGACGGATTG

1901 TCCTGACAGT TTGCGACAAC GGCAAGGGGT TCGGCAGGGA AATGCTGCAC

1951 AATGCCTTCG AGCCGTATGT AACGGACAAA CCGGCTGGAA CGGGATTGNG

2001 ACTGCCCGTG GTGAAAAAAA TCATTGAAGA ACACGGCGGC CNCATCAGCC

2051 TGAGCAATCA GGATGCGGGC GGCGCGTNTG TCAGAATCAT CTTGCCAAAA

2101 ACGGTAGAAA CTTATGCGTA G
```

This encodes a protein having amino acid sequence <SEQ ID 254>:

```
  1 MRRFLPIAAI CAVVLLYGLT AATGSTSSLA DYFWWIVAFS AMLLLVLSAV

51 LARYVILLLK DRRDGVFGSQ IAKRLSGMFT LVAVLPGVFL FGVSAQFING

101 TINSWFGNDT HEALERSLNL SKSALNLAAD NALGNAIPVQ IDXIGAASLP

151 XDMGRVLEHY AGSGFAQLAL YNAASGKIEK SINPHKLDQP FPGKARWEKI

201 QQAGSVRDXE SIGGVLYAXG WLSAXTHNGR DYALFFRQPV PKGVAEDAVL

251 IEKARAXXXX LSYSKKGLQT FFLATLLIAS LLSIFLALVM ALYFARRFVE

301 PVLSLAEGAK AVAQGDFSQT RPVLRNDEFG RLTKLFNHMT EQLSIAKEAD

351 ERNRRREEAA RHYLECVLEG LTTGVVVFDE QGCLKTFNKA AEQILGMPLT

401 PLWGSSRHGW HGVSAQQSLL AEVFAAIGAA AGTDKPVHVK YAAPDDAKIL

451 LGKATVLPED NXNGVVMVID DITVLIHAQK EAAWGEVAKR LAHEIRNPLT

501 PIQLSAERLA WKLGGKLDEX DAQILTRSTD TIIKQVAALK EMVEAFRNYX

551 RSPSXQLENQ DLNALIGDVL ALYEAGPCRF AAELAGEPLM MAADTTAMRQ

601 VLHNIFKNAA EAAEEADVPE VRVKSEAGQD GRIVLTVCDN GKGFGREMLH

651 NAFEPYVTDK PAGTGLXLPV VKKIIEEHGG XISLSNQDAG GAXVRIILPK

701 TVETYA*
```

ORF64a and ORF64-1 show 96.6% identity in 706 aa overlap:

```
                 10        20        30        40        50        60
  orf64a.pep MRRFLPIAAICAVVLLYGLTAATGSTSSLADYFWWIVAFSAMLLLVLSAVLARYVILLLK
             ||||| ||||||||||||||||||||||||||||||||||||||||||||||||||||||
  orf64-1    MRRFLPIAAICAVVLLYGLTAATGSTSSLADYFWWIVAFSAMLLLVLSAVLARYVILLLK
                 10        20        30        40        50        60

70        80        90       100       110       120
  orf64a.pep DRRDGVFGSQIAKRLSGMFTLVAVLPGVFLFGVSAQFINGTINSWFGNDTHEALERSLNL
             ||||| ||||||||||||||||||||||||||||||||||||||||||||||||||||||
  orf64-1    DRRDGVFGSQIAKRLSGMFTLVAVLPGVFLFGVSAQFINGTINSWFGNDTHEALERSLNL
                 70        80        90       100       110       120

130       140       150       160       170       180
  orf64a.pep SKSALNLAADNALGNAIPVQIDXIGAASLPXDMGRVLEHYAGSGFAQLALYNAASGKIEK
             ||||||||||||||| |||||| |||||| ||||||||||||||||||||||||||||||
  orf64-1    SKSALNLAADNALGNAVPVQIDLIGAASLPGDMGRVLEHYAGSGFAQLALYNAASGKIEK
                130       140       150       160       170       180
```

-continued

```
              190       200       210       220       230       240
orf64a.pep  SINPHKLDQPFPGKARWEKIQQAGSVRDXESIGGVLYAXGWLSAXTHNGRDYALFFRQPV
            |||||  |||||||||||||| :||||| |||||||||| |||||:|||||||||||||
orf64-1     SINPHKLDQPFPGKARWEKIQRAGSVRDLESIGGVLYAQGWLSAGTHNGRDYALFFRQPV
              190       200       210       220       230       240

250       260       270       280       290       300
orf64a.pep  PKGVAEDAVLIEKARAXXXXLSYSKKGLQTFFLATLLIASLLSIFLALVMALYFARRFVE
            ||||||||||||||||    ||||||||||||||||||||||||||||||||||||||||
orf64-1     PKGVAEDAVLIEKARAKYAELSYSKKGLQTFFLATLLIASLLSIFLALVMALYFARRFVE
              250       260       270       280       290       300

310       320       330       340       350       360
orf64a.pep  PVLSLAEGAKAVAQGDFSQTRPVLRNDEFGRLTKLFNHMTEQLSIAKEADERNRRREEAA
            ||||||||||||||||||||||||||||||||||||||||||||||||||||||||||||
orf64-1     PVLSLAEGAKAVAQGDFSQTRPVLRNDEFGRLTKLFNHMTEQLSIAKEADERNRRREEAA
              310       320       330       340       350       360

370       380       390       400       410       420
orf64a.pep  RHYLECVLEGLTTGVVVFDEQGCLKTFNKAAEQILGMPLTPLWGSSRHGWHGVSAQQSLL
            ||||||||||||||||||||||||||||||||||||||||||||||||||||||||||||
orf64-1     RHYLECVLEGLTTGVVVFDEQGCLKTFNKAAEQILGMPLTPLWGSSRHGWHGVSAQQSLL
              370       380       390       400       410       420

430       440       450       460       470       480
orf64a.pep  AEVFAAIGAAAGTDKPVHVKYAAPDDAKILLGKATVLPEDNXNGVVMVIDDITVLIHAQK
            ||||||||||||||||||||||||||||||||||||||||||| ||||||||||||||||
orf64-1     AEVFAAIGAAAGTDKPVHVKYAAPDDAKILLGKATVLPEDNGNGVVMVIDDITVLIHAQK
              430       440       450       460       470       480

490       500       510       520       530       540
orf64a.pep  EAAWGEVAKRLAHEIRNPLTPIQLSAERLAWKLGGKLDEXDAQILTRSTDTIIKQVAALK
            |||||||||||||||||||||||||||||||||||||| |||||||||||||:|||||||
orf64-1     EAAWGEVAKRLAHEIRNPLTPIQLSAERLAWKLGGKLDEQDAQILTRSTDTIVKQVAALK
              490       500       510       520       530       540

550       560       570       580       590       600
orf64a.pep  EMVEAFRNYXRSPSXQLENQDLNALIGDVLALYEAGPCRFAAELAGEPLMMAADTTAMRQ
            |||||||||  ||| :||||||||||||||||||||||||||||||||| :||||||||
orf64-1     EMVEAFRNYARSPSLKLENQDLNALIGDVLALYEAGPCRFAAELAGEPLTVAADTTAMRQ
              550       560       570       580       590       600

610       620       630       640       650       660
orf64a.pep  VLHNIFKNAAEAAEEADVPEVRVSEAGQDGRIVLTVCDNGKGFGREMLHNAFEPYVTTDK
            ||||||||||||||||||||||||::| ||||||||||||||||||||||||||||||||
orf64-1     VLHNIFKNAAEAAEEADVPEVRVKSETGQDGRIVLTVCDNGKGFGREMLHNAFEPYVTTDK
              610       620       630       640       650       660

670       680       690       700
orf64a.pep  PAGTGLXLPVVKKIIEEHGGXISLSNQDAGGAXVRIILPKTVETYAX
            ||||||  ||||||||||||| |||||||||| |||||||||:||||
orf64-1     PAGTGLGLPVVKKIIEEHGGRISLSNQDAGGACVRIILPKTVKTYAX
              670       680       690       700
```

Homology with a Predicted ORF from *N. gonorrhoeae*
ORF64 shows 86.6% identity over a 387aa overlap with a predicted ORF (ORF64.ng) from *N. gonorrhoeae*:

```
orf64.pep  MRRFLPIAAICAXXLXXGLTAATGSTSSLADYFWWIVAFSAMLLLVLSAVLARYVILLLK  60
           |||||||||||   |  ||||||||||||||||||:||||||||||||||||||||||||
orf64ng    MRRFLPIAAICAVVLLYGLTAATGSTSSLADYFWWIVSFSAMLLLVLSAVLARYVILLLK  60 orf64.pep  DRRDGVFGSXXAKXPXXXMFTLVAXLPGVFLFGFPAQFINGTINSWFGNDTHEALERSLN  120
           |||:||||| ||  ||||||:|||| |||||||||||||||||||||||
orf64ng    DRRNGVFGSQIAKR-LSGMFTLVAVLPGLFLFGISAQFINGTINSWFGNDTHEALERSLN  119 orf64.pep  LSKSALNLAADNALGNAVPVQIDLIGAASLPGDMGRVLEHYAGSGFAQLALYNXASGKIE  180
           ||||||:|||||||::|||||||||||:|| | ||||||||||||||||||| ||||||
orf64ng    LSKSALDLAADNAVSNAVPVQIDLIGTASLSGNMGSVLEHYAGSGFAQLALYNAASGKIE  179 orf64.pep  KSINPHKLDQPFPGKARWEKIQRAGSVRDLESIGGVLYAQGWLSAGTHXGRDYALFFRQP  240
           |||||:|||:|  :|| :||||:||||||||||||||||||||||||| |||||||||||
orf64ng    KSINPHQFDQPLPDKEHWEQIQQTGSVRSLESIGGVLYAQGWLSAGTHNGRDYALFFRQP  239 orf64.pep  VPKGVAEDAVLIEKARAKYAELSYSKKGLQTFFLATLLIASLLSIFLALVMALYFARRFV  300
           :|:::|||||||||||||||||||||||||||||:|||||||||||||||||||||||||
orf64ng    IPENVAQDAVLIEKARAKYAELSYSKKGLQTFFLVTLLIASLLSIFLALVMALYFARRFV  299 orf64.pep  EPVLSLAEGAKAVAQGDFSQTRPVLRNDEFGRLTXLFNHMTEQLSIAKDADERNRRREEA  360
           ||:|||||||||||||||||||||||||||||||||||||||||||:||||||||||||
orf64ng    EPILSLAEGAKAVAQGDFSQTRPVLRNDEFGRLTKLFNHMTEQLSIAKEADERNRRREEA  359 orf64.pep  ARHYLECVLEGLTTGVVVFDEQGCLKTFNKAAGT                            394
           |||||||||:|||||||||     :|  :|
orf64ng    ARHYLECVLDGLTTGVVVSYPLSCCRTAVFSTCHSSPLSYF                    400
```

An ORF64ng nucleotide sequence <SEQ ID 255> was predicted to encode a protein having amino acid sequence <SEQ ID 256>:

```
  1 MRRFLPIAAI CAVVLLYGLT AATGSTSSLA DYFWWIVSFS AMLLLVLSAV

51 LARYVILLLK DRRNGVFGSQ IAKRLSGMFT LVAVLPGLFL FGISAQFING

101 TINSWFGNDT HEALERSLNL SKSALDLAAD NAVSNAVPVQ IDLIGTASLS

151 GNMGSVLEHY AGSGFAQLAL YNAASGKIEK SINPHQFDQP LPDKEHWEQI

201 QQTGSVRSLE SIGGVLYAQG WLSAGTHNGR DYALFFRQPI PENVAQDAVL

251 IEKARAKYAE LSYSKKGLQT FFLVTLLIAS LLSIFLALVM ALYFARRFVE

301 PILSLAEGAK AVAQGDFSQT RPVLRNDEFG RLTKLFNHMT EQLSIAKEAD

351 ERNRRREEAA RHYLECVLDG LTTGVVVSYP LSCCRTAVFS TCHSSPLSYF*
```

Further work revealed the complete gonococcal DNA sequence <SEQ ID 257>:

```
   1 ATGCGCCGCT TCCTACCGAT CGCAGCCATA TGCGCCGTCG TCCTGCTGTA

51 CGGATTGACG GCGGCGACCG GCAGCACCAG TTCGCTGGCG GATTATTTCT

101 GGTGGATAGT CTCGTTCAGC GCAATGCTGC TGCTGGTGTT GTCCGCCGTT

151 TTGGCACGTT ATGTCATATT GCTGTTGAAA GACAGGCGCA ACGGCGTGTT

201 CGGTTCGCAG ATTGCCAAAC GCCTTTCCGG GATGTTCACG CTGGTCGCCG

251 TACTGCCCGG CTTGTTCCTG TTCGGCATTT CCGCGCAGTT TATCAACGGC

301 ACGATTAATT CGTGGTTCGG CAACGACACC CACGAAGCCC TCGAACGCAG

351 CCTTAATTTG AGCAAGTCCG CACTGGATTT GGCGGCAGAC AATGCCGTCA

401 GCAACGCCGT TCCCGTACAG ATAGACCTCA TCGGCACCGC CTCCCTGTCG

451 GGCAATATGG GCAGTGTGCT GGAACACTAC GCCGGCAGCG GTTTTGCCCA

501 GCTTGCCCTG TACAATGCCG CAAGCGGGAA AATCGAAAAA AGCATCAATC

551 CGCACCAATT CGACCAGCCG CTTCCCGACA AGAACATTG GAACAGATT

601 CAGCAGACCG GTTCGGTTCG GAGTTTGGAA AGCATAGGCG GCGTATTGTA

651 CGCGCAGGGA TGGTTGTCGG CAGGTACGCA CAACGGGCGC GATTACGCGC

701 TGTTCTTCCG CCAGCCGATT CCCGAAAATG TCGCACAGGA TGCCGTTCTG

751 ATTGAAAAGG CGCGGGCGAA ATATGCCGAA TTGAGTTACA GCAAAAAAGG

801 TTTGCAGACC TTTTTTCTGG TAACCCTGCT GATTGCCTCG CTGCTGTCGA

851 TTTTTCTTGC GCTGGTAATG GCACTGTATT TTGCCCGCCG TTTCGTCGAA

901 CCCATTCTGT CGCTTGCCGA GGGCGCAAAG GCGGTGGCGC AGGGTGATTT

951 CAGCCAGACG CGCCCCGTAT TGCGCAACGA CGAGTTCGGA CGTTTGACCA

1001 AGCTGTTCAA CCATATGACC GAGCAGCTTT CCATCGCCAA AGAAGCAGAC

1051 GAACGCAACC GCCGGCGCGA GGAAGCCGCC CGTCACTACC TCGAGTGCGT

1101 GTTGGATGGG TTGACTACCG GTGTGGTGGT GTTTGACGAA AAAGGCCGTT

1151 TGAAAACCTT CAACAAGGCG GCGGAACAGA TTTTGGGGAT GCCGCTCGCC

1201 CCCCTGTGGG GCAGCAGCCG GCACGGTTGG CACGGCGTTT CGGCGCAGCA

1251 GTCCCTGCTT GCCGAAGTGT TtgccgccAT CGGTGCGGCG GCAGGTACGG

1301 ACAAACCGGT CCAGGTGGAA TATGCCGCGC CGGACGATGC CAAAATCCTG

1351 CTGGGCAAGG CGACGGTATT GCCCGAAGAC AACGGCAACG GCGTGGTGAT
```

-continued

```
1401 GGTGATTGAC GACATCACCG TGCTGATACG CGCGCAAAAA GAAGCCGCGT

1451 GGGGTGAAGT GGCGAAGCGG CTGGCACACG AAATCCGCAA TCCGCTCACG

1501 CCCATCCAGC TTTCCGCCGA ACGGCTGGCG TGGAAATTGG GCGGGAAGCT

1551 GGACGATCAG GACGCGCAAA TCCTGACGCG TtcgACCGAC ACCATCATCA

1601 AACAGgtggc gGCGTTAAAA GAAATGGTCG AGGCATTCCG CAATTACGCG

1651 CGCGCCCCTT CGCTCAAACT GGAAAATCAG GATTTGAACG CCTTAATCGG

1701 CGATGTTTTG GCCCTGTACG AAGCCGGCCC GTGCCGGTTT GAGGCGGAAC

1751 TTGCCGGCGA ACCGCTGATG ATGGCGGCGG ATACGACCGC CATGCGGCAG

1801 GTGCTGCACA ATATTTTCAA AAATGCCGCC GAAGCGGCGG AAGAAGCCGA

1851 TATGCCCGAA GTCAGGGTAA AATCGGAAAC GGGGCAGGAC GGACGGATTG

1901 TCCTGACGGT TTGCGACAAC GGCAAGGGAT TCGGCAAGGA AATGCTGCAC

1951 AATGCTTTCG AGCCGTATGT GACGGATAAG CCGGCGGGAA CGGGACTGGG

2001 TCTGCCTGTA GTGAAAAAAA TCATTGGAGA ACACGGCGGC CGCATCAGCC

2051 TGAGCAATCA GGATGCGGGT GGGGCGTGTG TCAGAATCAT CTTGCCAAAA

2101 ACGGTAGAAA CTTATGCGTA G
```

This corresponds to the amino acid sequence <SEQ ID 258; ORF64ng-1>:

```
  1 MRRFLPIAAI CAVVLLYGLT AATGSTSSLA DYFWWIVSFS AMLLLVLSAV

51 LARYVILLLK DRRNGVFGSQ IAKRLSGMFT LVAVLPGLFL FGISAQFING

101 TINSWFGNDT HEALERSLNL SKSALDLAAD NAVSNAVPVQ IDLIGTASLS

151 GNMGSVLEHY AGSGFAQLAL YNAASGKIEK SINPHQFDQP LPDKEHWEQI

201 QQTGSVRSLE SIGGVLYAQG WLSAGTHNGR DYALFFRQPI PENVAQDAVL

251 IEKARAKYAE LSYSKKGLQT FFLVTLLIAS LLSIFLALVM ALYFARRFVE

301 PILSLAEGAK AVAQGDFSQT RPVLRNDEFG RLTKLFNHMT EQLSIAKEAD

351 ERNRRREEAA RHYLECVLDG LTTGVVVFDE KGRLKTFNKA AEQILGMPLA

401 PLWGSSRHGW HGVSAQQSLL AEVFAAIGAA AGTDKPVQVE YAAPDDAKIL

451 LGKATVLPED NGNGVVMVID DITVLIRAQK EAAWGEVAKR LAHEIRNPLT

501 PIQLSAERLA WKLGGKLDDQ DAQILTRSTD TIIKQVAALK EMVEAFRNYA

551 RAPSLKLENQ DLNALIGDVL ALYEAGPCRF EAELAGEPLM MAADTTAMRQ

601 VLHNIFKNAA EAAEEADMPE VRVKSETGQD GRIVLTVCDN GKGFGKEMLH

651 NAFEPYVTDK PAGTGLGLPV VKKIIGEHGG RISLSNQDAG GACVRIILPK

701 TVETYA*
```

ORF64ng-1 and ORF64-1 show 93.8% identity in 706 aa overlap:

```
                       10        20        30        40        50        60
   orf64ng-1.pep  MRRFLPIAAICAVVLLYGLTAATGSTSSLADYFWWIVSFSAMLLLVLSAVLARYVILLLK
                  ||||||||||||||||||||||||||||||||||||||:|||||||||||||||||||||
   orf64-1        MRRFLPIAAICAVVLLYGLTAATGSTSSLADYFWWIVAFSAMLLLVLSAVLARYVILLLK
                       10        20        30        40        50        60
```

```
              70         80         90        100        110        120
orf64ng-1.pep DRRNGVFGSQIAKRLSGMFTLVAVLPGLFLFGISAQFINGTINSWFGNDTHEALERSLNL
              |||:||||||||||||||||||||:||||:|||||||||||||||||||||||||||||
orf64-1       DRRDGVFGSQIAKRLSGMFTLVAVLPGVFLFGVSAQFINGTINSWFGNDTHEALERSLNL
              70         80         90        100        110        120

130        140        150        160        170        180
orf64ng-1.pep SKSALDLAADNAVSNAVPVQIDLIGTASLSGNMGSVLEHYAGSGFAQLALYNAASGKIEK
              |||||:||||::|||||||||||||||:||:|:||||||||||||||||||||||||||
orf64-1       SKSALNLAADNALGNAVPVQIDLIGAASLPGDMGRVLEHYAGSGFAQLALYNAASGKIEK
             130        140        150        160        170        180

190        200        210        220        230        240
orf64ng-1.pep SINPHQFDQPLPDKEHWEQIQQTGSVRSLESIGGVLYAQGWLSAGTHNGRDYALFFRQPI
              ||||:::|||:|:|  |||:|::|||||:|||||||||||||||||||||||||||||:
orf64-1       SINPHKLDQPFPGKARWEKIQRAGSVRDLESIGGVLYAQGWLSAGTHNGRDYALFFRQPV
             190        200        210        220        230        240

250        260        270        280        290        300
orf64ng-1.pep PENVAQDAVLIEKARAKYAELSYSKKGLQTFFLVTLLIASLLSIFLALVMALYFARRFVE
              |::||:|||||||||||||||||||||||||||:||||||||||||||||||||||||||
orf64-1       PKGVAEDAVLIEKARAKYAELSYSKKGLQTFFLATLLIASLLSIFLALVMALYFARRFVE
             250        260        270        280        290        300

310        320        330        340        350        360
orf64ng-1.pep PILSLAEGAKAVAQGDFSQTRPVLRNDEFGRLTKLFNHMTEQLSIAKEADERNRREEAA
              |:|||||||||||||||||||||||||||||||||||||||||||||||||||||||||
orf64-1       PVLSLAEGAKAVAQGDFSQTRPVLRNDEFGRLTKLFNHMTEQLSIAKEADERNRREEAA
             310        320        330        340        350        360

370        380        390        400        410        420
orf64ng-1.pep RHYLECVLDGLTTGVVVFDEKGRLKTFNKAAEQILGMPLAPLWGSSRHGWHGVSAQQSLL
              ||||||||:|||||||||||:|:|:||||||||||||||:|||||||||||||||||||
orf64-1       RHYLECVLEGLTTGVVVFDEQGCLKTFNKAAEQILGMPLTPLWGSSRHGWHGVSAQQSLL
             370        380        390        400        410        420

430        440        450        460        470        480
orf64ng-1.pep AEVFAAIGAAAGTDKPVQVEYAAPDDAKILLGKATVLPEDNGNGVVMVIDDITVLIRAQK
              ||||||||||||||||:|:|||||||||||||||||||||||||||||||||||||:|||
orf64-1       AEVFAAIGAAAGTDKPVHVKYAAPDDAKILLGKATVLPEDNGNGVVMVIDDITVLIHAQK
             430        440        450        460        470        480

490        500        510        520        530        540
orf64ng-1.pep EAAWGEVAKRLAHEIRNPLTPIQLSAERLAWKLGGKLDDQDAQILTRSTDTIIKQVAALK
              |||||||||||||||||||||||||||||||||||||:|||||||||||||:|||||||
orf64-1       EAAWGEVAKRLAHEIRNPLTPIQLSAERLAWKLGGKLDEQDAQILTRSTDTIVKQVAALK
             490        500        510        520        530        540

550        560        570        580        590        600
orf64ng-1.pep EMVEAFRNYARAPSLKLENQDLNALIGDVLALYEAGPCRFEAELAGEPLMMAADTTAMRQ
              |||||||||| ||||||||||||||||||||||||||||||||||||||:||||||||
orf64-1       EMVEAFRNYARSPSLKLENQDLNALIGDVLALYEAGPCRFAAELAGEPLTVAADTTAMRQ
             550        560        570        580        590        600

610        620        630        640        650        660
orf64ng-1.pep VLHNIFKNAAEAAEEADMPEVRVKSETGQDGRIVLTVCDNGKGFGKEMLHNAFEPYVTDK
              ||||||||||||||||:|||||||||||||||||||||||||||:||||||||||||||
orf64-1       VLHNIFKNAAEAAEEADVPEVRVKSETGQDGRIVLTVCDNGKGFGREMLHNAFEPYVTDK
             610        620        630        640        650        660

670        680        690        700
orf64ng-1.pep PAGTGLGLPVVKKIIGEHGGRISLSNQDAGGACVRIILPKTVETYAX
              |||||||||||||||:|||||||||||||||||||||||||:||||
orf64-1       PAGTGLGLPVVKKIIEEHGGRISLSNQDAGGACVRIILPKTVKTYAX
             670        680        690        700
```

Furthermore, ORF64ng-1 shows significant homology to a protein from *A. caulinodans*:

```
sp|Q04850|NTRY_AZOCA NITROGEN REGULATION PROTEIN NTRY >gi|77479|pir||S18624 ntrY
protein —Azorhizobium caulinodans >gi|38737 (X63841) NtrY gene product
[Azorhizobium caulinodans] Length = 771
Score = 218 bits (550), Expect = 7e-56
Identities = 195/720 (27%), Positives = 320/720 (44%), Gaps = 58/720 (8%)

Query:     7 IAAICAVVLLYGLTAATGSTSSLADYFWWIXXXXXXXXXXXXXXXXXRYVILLLKDRRNGV    66
             I+A+  ++L GLT  +       +         +            R+   + KR  G
Sbjct:    35 ISALATFLILMGLTPVVPTHQVVIS----VLLVNAAAVLILSAMVGREIWRIAKARARGR    90

Query:    67 FGSQIAKRLSGMFTLVAVLPGLFLFGISAQFINGTINSWFGNDTHEALERSLNLSKSALD   126
             +++   R+ G+F +V+V+P + +   +++   ++ ++ WF   T E +  S++++++ +
Sbjct:    91 AAARLHIRIVGLFAVVSVVPAILVAVVASLTLDRGLDRWFSMRTQEIVASSVSVAQTYVR   150

Query:   127 LAADNAVSNAVPVQIDLIGTASLSGNMGSVLEHYAG--SGFAQLALYNAASGKIEKSINP   184
                A N    +   + DL     S+          YG  SF Q+   AA    +  ++
Sbjct:   151 EHALNIRGDILAMSADLTRLKSV---------YEGDRSRFNQILTAQAALRNLPGAMLI   200
```

```
Query:    185 HQFDQPLPDKEHWEQIQQTGSVRSLESIGGVLYAQGWLSAGTHNGRDYA----------  233
              + D  ++ +   I +   V + +IG     Q +     N  DY
Sbjct:    201 RR-DLSVVERAN-VNIGREFIVPANLAIGDATPDQPVIYLP--NDADYVAAVVPLKDYDD  256

Query:    234 --LFFRQPIPENVAQDAVLIEKARAKYAELSYSKKGLQTFFLVTXXXXXXXXXXXXXVMA  291
                L+  + I   V         ++  A Y  L   + G+Q  F +                +
Sbjct:    257 LYLYVARLIDPRVIGYLKTTQETLADYRSLEERRFGVQVAFALMYAVITLIVLLSAVWLG  316

Query:    292 LYFARRFVEPILSLAEGAKAVAQGDFSQTRPVLRND-EFGRLTKLFNHMTEQLSIXXXXX  350
              L F++  V PI   L    A   VA+G+        P+ R + +    L + FN MT +L
Sbjct:    317 LNFSKWLVAPIRRLMSAADHVAEGNLDVRVPIYRAEGDLASLAETFNKMTHELRSQREAI  376

Query:    351 XXXXXXXXXXXHYLECVLDGLTTGVVVFDEKGRLKTFNKAAEQILGMPLAPLWGSSRHGW  410
                         + E VL G+   GV+  D + R+    N++AE++LG  L+ +       RH
Sbjct:    377 LTARDQIDSRRRFTEAVLSGVGAGVIGLDSQERITILNRSAERLLG--LSEVEALHRHLA  434

Query:    411 HGVSAQQSLLAEVFXXXXXXXXXTDKPVQVEYAAPDDAKILLGKATVLPEDNG---NGVVM  467
                V     LL E            + VQ        D +   V  E +     +G V+
Sbjct:    435 EVVPETAGLLEEA------EHARQRSVQGNITLTRDGRERVFAVRVTTEQSPEAEHGWVV  488

Query:    468 VIDDITVLIRAQKEAAWGEVAKRLAHEIRNPLTPIQLSAERLAWKLGGKLDDQDAQILTR  527
              +DDIT LI AQ+ +AW +VA+R+AHEI+NPLTPIQLSAERL   K G +   QD +I  +
Sbjct:    489 TLDDITELISAQRTSAWADVARRIAHEIKNPLTPIQLSAERLKRKFGRHV-TQDREIFDQ  547

Query:    528 STDTIIKQVAALKEMVEAFRNYARAPSLKLENQDLNALIGDVLALYEAGPCRFEAELAGE  587
              +TDTII+QV +   MV+ F ++AR P    +++QD++ +I  + L    G           +
Sbjct:    548 CTDTIIRQVGDIGRMVDEFSSFARMPKPVVDSQDMSEIIRQTVFLMRVGHPEVVFDSEVP  607

Query:    588 PLMMAA-DTTAMRQVLHNIFKNXXXXXXXXXDMPEVRVK-------SETGQDGRIVLTVCD  639
              P M  A  D   + Q L NI KN                P+VR +         + G+D  +V+ + D
Sbjct:    608 PAMPARFDRRLVSQALTNILKNAAEAIEAVP-PDVRGQGRIRVSANRVGED--LVIDIID  664

Query:    640 NGKGFGKEMLHNAFEPYVTDKPAGTGLGLPVVKKIIGEHGGRISLSNQDAG-GACVRIIL  698
              NG G  +E  +    EPYVT  +  GTGLGL +V KI+ EHGG I L++     G GA +R+ L
Sbjct:    665 NGTGLPQESRNRLLEPYVTTREKGTGLGLAIVGKIMEEHGGGIELNDAPEGRGAWIRLTL  724
```

Based on this analysis, including the presence of a putative leader sequence (double-underlined) and several putative transmembrane domains (single-underlined) in the gonococcal protein, it is predicted that the proteins from *N. meningitidis* and *N. gonorrhoeae*, and their epitopes, could be useful antigens for vaccines or diagnostics, or for raising antibodies.

Example 31

The following partial DNA sequence was identified in *N. meningitidis* <SEQ ID 259>:

```
  1 ATGTACGCAT TTACCGCCGC ACAGCAACAG AAGGCACTCT TCCGGCTGGT

51 GCTTTTTCAT ATCCTCATCA TCGCCGCCAG CAACTATCTG GTGCAGTTCC

101 CTTTCCAAAT TTTCGGCATC CACACCACTT GGGGCGCATT TTCCTTTCCC

151 TTCATCTTCC TTGCCACCGA CCTGACCGTC CGCATTTTCG GTTCTCACTT

201 GGCACGGCGG ATTATCTTTT GGGTGATGTT CCCCGCCCTT TTGCTTTCCT

251 ACGTCTTTTC CGTTTTGTTC CACAACGGCA GTTGGACAGG CTTGGGCGCG

301 CTGTCCGAAT TCAACACCTT TGTCGGACGC ATCGCCTTAG CCAGCTTTGC

351 CGCCTACGCG ATCGGACAAA TCCTTGATAT TTTTGTATTC AACAAATTAC

401 GCCGTCTGAA AGCGTGGTGG ATTGCACCGA ACGCATCAAC CGTCATCGGG

451 CACGCGTTGG ATACG...
```

This corresponds to the amino acid sequence <SEQ ID 260; ORF66>:

```
  1  MYAFTAAQQQ KALFRLVLFH ILIIAASNYL VQFPFQIFGI HTTWGAFSFP

51  FIFLATDLTV RIFGSHLARR IIFWVMFPAL LLSYVFSVLF HNGSWTGLGA

101  LSEFNTFVGR IALASFAAYA IGQILDIFVF NKLRRLKAWW IAPNASTVIG

151  HALDT...
```

Further work revealed the complete nucleotide sequence <SEQ ID 261>:

```
  1  ATGTACGCAT TACCGCCGC ACAGCAACAG AAGGCACTCT TCCGGCTGGT

51  GCTTTTTCAT ATCCTCATCA TCGCCGCCAG CAACTATCTG GTGCAGTTCC

101  CTTTCCAAAT TTTCGGCATC CACACCACTT GGGGCGCATT TTCCTTTCCC

151  TTCATCTTCC TTGCCACCGA CCTGACCGTC CGCATTTTCG GTTCTCACTT

201  GGCACGGCGG ATTATCTTTT GGGTGATGTT CCCCGCCCTT TTGCTTTCCT

251  ACGTCTTTTC CGTTTTGTTC CACAACGGCA GTTGGACAGG CTTGGGCGCG

301  CTGTCCGAAT TCAACACCTT TGTCGGACGC ATCGCCTTAG CCAGCTTTGC

351  CGCCTACGCG ATCGGACAAA TCCTTGATAT TTTTGTATTC AACAAATTAC

401  GCCGTCTGAA AGCGTGGTGG ATTGCACCGA CCGCATCAAC CGTCATCGGC

451  AACGCCTTGG ATACGCTGGT ATTTTTCGCC GTTGCCTTCT ACGCAAGCAG

501  CGATGGATTT ATGGCGGCAA ACTGGCAGGG CATCGCTTTT GTCGATTACC

551  TGTTCAAACT TACCGTCTGC ACCCTCTTCT TCCTGCCCGC CTACGGCGTG

601  ATACTGAATC TGCTGACGAA AAAACTGACA ACCCTGCAAA CCAAACAGGC

651  GCAAGACCGC CCCGCGCCCT CGCTGCAAAA TCCGTAA
```

This corresponds to the amino acid sequence <SEQ ID 262; ORF66-1>:

```
  1  MYAFTAAQQQ KALFRLVLFH ILIIAASNYL VQFPFQIFGI HTTWGAFSFP

51  FIFLATDLTV RIFGSHLARR IIFWVMFPAL LLSYVFSVLF HNGSWTGLGA

101  LSEFNTFVGR IALASFAAYA IGQILDIFVF NKLRRLKAWW IAPTASTVIG

151  NALDTLVFFA VAFYASSDGF MAANWQGIAF VDYLFKLTVC TLFFLPAYGV

201  ILNLLTKKLT TLQTKQAQDR PAPSLQNP*
```

Computer analysis of this amino acid sequence gave the following results:

Homology with the Hypothetical Protein o221 of *E. Coli* (Accession Number P37619)

ORF66 and o221 protein show 67% aa identity in 155aa overlap:

```
orf66    1  MYAFTAAQQQKALFRLVLFHILIIAASNYLVQPFQIFGIHTTWGAFSFPFIFLATDLTV   60
            M   F+  Q+ KALF L LFH+L+I +SNYLVQ P  I G HTTWGAFSFPFIFLATDLTV
o221     1  MNVFSQTQRYKALFWLSLFHLLVITSSNYLVQLPVSILGFHTTWGAFSFPFIFLATDLTV   60 orf66   61  RIFGSHLARRIIFWVMFPALLLSYVFSVLFHNGSWTGLGALSEFNTFVGRIALASFAAYA  120
            RIFG+ LARRIIF VM PALL+SYV S LF+ GSW G GAL+ FN FV RIA ASF AYA
o221    61  RIFGAPLARRIIFAVMIPALLISYVISSLFYMGSWQGFGALAHFNLFVARIATASFMAYA  120
```

```
orf66   121 IGQILDIFVFNKLRRLKAWWIAPNASTVIGHALDT                        155
            +GQILD+ VFN+LR+ + WW+AP AST+ G+   DT
o221    121 LGQILDVHVFNRLRQSRRWWLAPTASTLFGNVSDT                        155
```

Homology with a Predicted ORF from *N. meningitidis* (Strain A)

ORF66 shows 96.1% identity over a 155aa overlap with an ORF (ORF66a) from strain A of *N. meningitidis*:

```
                    10        20        30        40        50        60
orf66.pep  MYAFTAAQQQKALFRLVLFHILIIAASNYLVQFPFQIFGIHTTWGAFSFPFIFLATDLTV
           ||||||||||||| ||||||||||||||||||||||| ||||||||||||||||||||||
orf66a     MYAFTAAQQQKALFWLVLFHILIIAASNYLVQFPFQISGIHTTWGAFSFPFIFLATDLTV
                    10        20        30        40        50        60

70        80        90       100       110       120
orf66.pep  RIFGSHLARRIIFWVMFPALLLSYVFSVLFHNGSWTGLGALSEFNTFVGRIALASFAAYA
           ||||||||||||||||||||||||||||||||||||||||||||||||||||||||||||
orf66a     RIFGSHLARRIIFWVMFPALLLSYVFSVLFHNGSWTGLGALSEFNTFVGRIALASFAAYA
                    70        80        90       100       110       120

130       140       150
orf66.pep  IGQILDIFVFNKLRRLKAWWIAPNASTVIGHALDT
           :||||||||||||||||||:||:|||||| :||||
orf66a     LGQILDIFVFNKLRRLKAWWVAPTASTVIGNALDTLVFFAVAFYASSDGFMAANWQGIAF
                   130       140       150       160       170       180 orf66a     VDYLFKLTVCGLFFLPAYGVILNLLTKKLTTLQTKQAQDRPAPSLQNPX
                   190       200       210       220
```

The complete length ORF66a nucleotide sequence <SEQ ID 263> is:

```
  1  ATGTACGCAT TTACCGCCGC ACAGCAACAG AAGGCACTCT TCTGGCTGGT
 51  GCTTTTTCAT ATCCTCATCA TCGCCGCCAG CAACTATCTG GTGCAGTTCC
101  CCTTCCAAAT TTCCGGCATC CACACCACTT GGGGCGCGTT TTCCTTTCCC
151  TTCATCTTCC TCGCCACCGA CCTGACCGTC CGCATTTTCG GTTCGCACTT
201  GGCACGGCGG ATTATCTTTT GGGTCATGTT CCCCGCCCTT TTGCTTTCCT
251  ACGTCTTTTC CGTTTTGTTC CACAACGGCA GTTGGACGGG CTTGGGCGCG
301  CTGTCCGAAT TCAACACCTT TGTCGGACGC ATCGCGCTGG CAAGTTTTGC
351  CGCCTACGCG CTCGGACAAA TCCTTGATAT TTTTGTGTTC AACAAATTAC
401  GCCGTCTGAA AGCGTGGTGG GTTGCCCCGA CTGCATCAAC CGTCATCGGC
451  AACGCCTTAG ATACGTTGGT ATTTTTCGCC GTTGCCTTCT ACGCAAGCAG
501  CGATGGATTT ATGGCGGCAA ACTGGCAGGG CATCGCTTTT GTCGATTACC
551  TGTTCAAACT CACCGTCTGC GGTCTGTTTT TCCTGCCCGC CTACGGCGTG
601  ATTCTGAATC TGCTGACGAA AAAACTGACG ACCCTGCAAA CCAAACAGGC
651  GCAAGACCGC CCCGCGCCCT CGCTGCAAAA TCCGTAA
```

This encodes a protein having amino acid sequence <SEQ ID 264>:

```
  1  MYAFTAAQQQ KALFWLVLFH ILIIAASNYL VQFPFQISGI HTTWGAFSFP

51  FIFLATDLTV RIFGSHLARR IIFWVMFPAL LLSYVFSVLF HNGSWTGLGA

101  LSEFNTFVGR IALASFAAYA LGQILDIFVF NKLRRLKAWW VAPTASTVIG

151  NALDTLVFFA VAFYASSDGF MAANWQGIAF VDYLFKLTVC GLFFLPAYGV

201  ILNLLTKKLT TLQTKQAQDR PAPSLQNP*
```

ORF66a and ORF66-1 show 97.8% identity in 228 aa overlap:

```
                 10        20        30        40        50        60
orf66a.pep  MYAFTAAQQQKALFWLVLFHILIIAASNYLVQFPFQISGIHTTWGAFSFPFIFLATDLTV
            |||||||||||||:|||||||||||||||||||||||:||||||||||||||||||||||
orf66-1     MYAFTAAQQQKALFRLVLFHILIIAASNYLVQFPFQIFGIHTTWGAFSFPFIFLATDLTV
                 10        20        30        40        50        60

70        80        90       100       110       120
orf66a.pep  RIFGSHLARRIIFWVMFPALLLSYVFSVLFHNGSWTGLGALSEFNTFVGRIALASFAAYA
            ||||||||||||||||||||||||||||||||||||||||||||||||||||||||||||
orf66-1     RIFGSHLARRIIFWVMFPALLLSYVFSVLFHNGSWTGLGALSEFNTFVGRIALASFAAYA
                 70        80        90       100       110       120

130       140       150       160       170       180
orf66a.pep  LGQILDIFVFNKLRRLKAWWVAPTASTVIGNALDTLVFFAVAFYASSDGFMAANWQGIAF
            :||||||||||||||||||||:||||||||||||||||||||||||||||||||||||||
orf66-1     IGQILDIFVFNKLRRLKAWWIAPTASTVIGNALDTLVFFAVAFYASSDGFMAANWQGIAF
                130       140       150       160       170       180

190       200       210       220     229
orf66a.pep  VDYLFKLTVCGLFFLPAYGVILNLLTKKLTTLQTKQAQDRPAPSLQNPX
            |||||||||| :|||||||||||||||||||||||||||||||||||||
orf66-1     VDYLFKLTVCTLFFLPAYGVILNLLTKKLTTLQTKQAQDRPAPSLQNPX
                190       200       210       220
```

Homology with a Predicted ORF from *N. gonorrhoeae*
ORF66 shows 94.2% identity over a 155aa overlap with a predicted ORF (ORF66.ng) from *N. gonorrhoeae*.

```
orf66.pep   MYAFTAAQQQKALFRLVLFHILIIAASNYLVQFPFQIFGIHTTWGAFSFPFIFLATDLTV   60
            |||:||||||||||||||||||||||||||||||||:|||||||||||||||||||||||
orf66ng     MYALTAAQQQKALFRLVLFHILIIAASNYLVQPPFRIFGIHTTWGAFSFPFIFLATDLTV   60 orf66.pep   RIFGSHLARRIIFWVMFPALLLSYVFSVLFHNGSWTGLGALSEFNTFVGRIALASFAAYA  120
            |||||||||||||||||||||| |||||||||||||||||| :|||||||||||||||||
orf66ng     RIFGSHLARRIIFWVMFPALSLSYVFSVLFHNGSWTGLGAPSQFNTFVGRIALASFAAYA  120 orf66.PEP   IGQILDIFVFNKLRRLKAWWIAPNASTVIGHALDT                           155
            :|||||||||:|||||||||| |||||||| ||||
orf66ng     LGQILDIFVFDKLRRLKAWWIAPAASTVIGNALDTLVFFAVAFYASSDEFMAANWQGIAF  180
```

The complete length ORF66ng nucleotide sequence <SEQ ID 265> is:

```
  1 ATGTACGCAT TGACCGCCGC ACAGCAACAG AAGGCACTCT TCCGGCTGGT

51 GCTTTTCCAT ATCCTCATCA TCGCCGCCAG CAACTATCTG GTGCAGTTCC

101 CCTTCCGGAT TTTCGGCATC CACACCACTT GGGGCGCGTT TTCCTTTCCC

151 TTCATCTTCC TCGCCACCGA CCTGACCGTC CGCATTTTCG GTTCGCACTT

201 GGCGCGGCGG ATTATCTTTT GGGTGATGTT CCCCGCCCTT ttgCTTTcat 251 aCGTCTTTTC CGTTTTGTTC CACAACGGCA GTTGGACGGG CTTGGGCGCG 301 ctgTCCCAAT TCAACACCTT TGTCGGACGC ATCGCGCTGG CAAGTTTTGC

351 CGCCTACGCG CTCGGACAAA TCCTTGATAT TTTCGTATTC GACAAATTAC

401 GCCGTCTGAA AGCGTGGTGG ATTGCCCCGG CCGCATCAAC CGTCATCGGC

451 AATGCACTGG ACACGTTAGT ATTTTTTGCC GTTGCCTTTT ACGCAAGCAG

501 CGATGAATTT ATGGCGGCAA ACTGGCAGGG CATCGCTTTT GTCGATTACC

551 TGTTCAAACT TACCGTCTGC ACCCTCTTCT TCCTGCCCGC CTACGGCGTG

601 ATACTGAATC TGCTGACGAA AAAACTGACG GCCCTGCAAA CCAAACAGGC

651 GCAAGACCGC CCCGTGCCCT CGCTGCAAAA TCCGTAA
```

This encodes a protein having amino acid sequence <SEQ ID 266>:

```
  1 MYALTAAQQQ KALFRLVLFH ILIIAASNYL VQFPFRIFGI HTTWGAFSFP

51 FIFLATDLTV RIFGSHLARR IIFWVMFPAL SLSYVFSVLF HNGSWTGLGA

101 PSQFNTFVGR IALASFAAYA LGQILDIFVF DKLRRLKAWW IAPAASTVIG

151 NALDTLVFFA VAFYASSDEF MAANWQGIAF VDYLFKLTVC TLFFLPAYGV

201 ILNLLTKKLT ALQTKQAQDR PVPSLQNP*
```

An alternative annotated sequence is:

```
  1 MYALTAAQQQ KALFRLVLFH ILIIAASNYL VQFPFRIFGI HTTWGAFSFP

51 FIFLATDLTV RIFGSHLARR IIFWVMFPAL LLSYVFSVLF HNGSWTGLGA

101 LSQFNTFVGR IALASFAAYA LGQILDIFVF DKLRRLKAWW IAPAASTVIG

151 NALDTLVFFA VAFYASSDEF MAANWQGIAF VDYLFKLTVC TLFFLPAYGV

201 ILNLLTKKLT ALQTKQAQDR PVPSLQNP*
```

ORF66ng and ORF66-1 show 96.1% identity in 228 aa overlap:

```
orf66-1.pep   MYAFTAAQQQKALFRLVLFHILIIAASNYLVQPFQIFGIHTTWGAFSFPFIFLATDLTV    60
              |||:||||||||||||||||||||||||||||||:|||||||||||||||||||||||
orf66ng       MYALTAAQQQKALFRLVLFHILIIAASNYLVQPFRIFGIHTTWGAFSFPFIFLATDLTV    60 orf66-1.pep   RIFGSHLARRIIFWVMFPALLLSYVFSVLFHNGSWTGLGALSEFNTFVGRIALASFAAYA   120
              ||||||||||||||||||||||||||||||||||||||||||:|||||||||||||||||
orf66ng       RIFGSHLARRIIFWVMFPALLLSYVFSVLFHNGSWTGLGALSQFNTFVGRIALASFAAYA   120 orf66-1.pep   IGQILDIFVFNKLRRLKAWWIAPTASTVIGNALDTLVFFAVAFYASSDGFMAANWQGIAF   180
              :||||||||||:|||||||||||||:||||||||||||||||||||||:|||||||||||
orf66ng       LGQILDIFVFDKLRRLKAWWIAPAASTVIGNALDTLVFFAVAFYASSDEFMAANWQGIAF   180 orf66-1.pep   VDYLFKLTVCTLFFLPAYGVILNLLTKKLTTLQTKQAQDRPAPSLQNPX             229
              |||||||||||||||||||||||||||||||:|||||||||:|||||||
orf66ng       VDYLFKLTVCTLFFLPAYGVILNLLTKKLTALQTKQAQDRPVPSLQNPX             229
```

Furthermore, ORF66ng shows significant homology with an *E. coli* ORF:

```
sp|P37619|YHHQ_ECOLI HYPOTHETICAL 25.3 KD PROTEIN IN FTSY-NIKA INTERGENIC
REGION (O221)
>gi|1073495|pir||S47690 hypothetical protein o221 -
Escherichia coli >gi|466607 (U00039) No definition line found
[Escherichia coli] >gi|1789882 (AE000423) hypothetical 25.3 kD protein in
ftsY-nikA intergenic region [Escherichia coli]
Length = 221
Score = 273 bits (692), Expect = 5e-73
Identities = 132/203 (65%), Positives = 155/203 (76%)

Query:   1MYALTAAQQQKALFRLVLFHILIIAASNYLVQPFRIFGIHTTWGAFSFPFIFLATDLTV   60
          M   + Q+ KALF L LFH+L+I +SNYLVQ P   I G HTTWGAFSFPFIFLATDLTV
Sbjct:   1MNVFSQTQRYKALFWLSLFHLLVITSSNYLVQLPVSILGFHTTWGAFSFPFIFLATDLTV   60

Query:  61RIFGSHLARRIIFWVMFPALLLSYVFSVLFHNGSWTGLGALSQFNTFVGRIALASFAAYA  120
           RIFG+ LARRIIF VM PALL+SYV S LF+ GSW G GAL+ FN FV RIA ASF AYA
Sbjct:  61RIFGAPLARRIIFAVMIPALLISYVISSLFYMGSWQGFGALAHFNLFVARIATASFMAYA  120

Query: 121LGQILDIFVFDKLRRLKAWWIAPAASTVIGNALDTLVFFAVAFYASSDEFMAANWQGIAF  180
           LGQILD+ VF++LR+ + WW+AP AST+ GN  DTL FF +AF+ S D FMA +W  IA
Sbjct: 121LGQILDVHVFNRLRQSRRWWLAPTASTLFGNVSDTLAFFFIAFWRSPDAFMAEHWMEIAL  180

Query: 181VDYLFKLTVCTLFFLPAYGVILN                                      203
           VDY FK+ +  +FFLP YGV+LN
Sbjct: 181VDYCFKVLISIVFFLPMYGVLLN                                      203
```

Based on this analysis, including the homology with the *E. coli* protein and the presence of several putative transmembrane domains in the gonococcal protein, it is predicted that these proteins from *N. meningitidis* and *N. gonorrhoeae*, and their epitopes, could be useful antigens for vaccines or diagnostics, or for raising antibodies.

Example 32

The following partial DNA sequence was identified in *N. meningitidis* <SEQ ID 267>:

```
  1 ATGGTCATAA AATATACAAA TTTGAATTTT GCGAAATTGT CGATAATTGC

51 AATTTTGATG ATGTATTCGT TGAAGCGAA TGCAAAyGCA GTmwrAATAT

101 CTGAAACTGT TTCAGTTGAT ACCGGACAAG GTGCGAAAAT TCATAAGTTT

151 GTACCTAAAA ATAGTAAAAC TTATTCATCT GATTTAATAA AAACGGTAGA

201 TTTAACACAC AyyCCTACGG GCGCAAAAGC CCGAATCAAC GCCAAAATAA

251 CCGCCAGCGT ATCCCGCGCC GGCGTATTGG CGGGGGTCGG CAAACTTGCC

301 CGCTTAGgCG CGAAATTCAG CACAAGGGCG GTtCCCTATG TCGGAACAGC

351 CcTTTTAGCC CACGACGTAT ACGAAAcTTT CAAAGAAGAC ATACAGGCAC

401 GAGGCTACCA ATACGACCCC GAAACCGACA AATTTGTAAA AGGCTACGAA

451 TATAGTAATT GCCTTTGGTA CGAAGACAAA AGACGTATTA ATAGAACCTA

501 TGGCTGCTAC GGCGTTGAT..
```

This corresponds to the amino acid sequence <SEQ ID 268; ORF72>:

```
  1 MVIKYTNLNF AKLSIIAILM MYSFEANANA VXISETVSVD TGQGAKIHKF

51 VPKNSKTYSS DLIKTVDLTH XPTGAKARIN AKITASVSRA GVLAGVGKLA

101 RLGAKFSTRA VPYVGTALLA HDVYETFKED IQARGYQYDP ETDKFVKGYE

151 YSNCLWYEDK RRINRTYGCY GVD..
```

Further work revealed the complete nucleotide sequence <SEQ ID 269>:

```
  1 ATGGTCATAA AATATACAAA TTTGAATTTT GCGAAATTGT CGATAATTGC

51 AATTTTGATG ATGTATTCGT TGAAGCGAA TGCAAATGCA GTAAAAATAT

101 CTGAAACTGT TTCAGTTGAT ACCGGACAAG GTGCGAAAAT TCATAAGTTT

151 GTACCTAAAA ATAGTAAAAC TTATTCATCT GATTTAATAA AAACGGTAGA

201 TTTAACACAC ATCCCTACGG GCGCAAAAGC CCGAATCAAC GCCAAAATAA

251 CCGCCAGCGT ATCCCGCGCC GGCGTATTGG CGGGGGTCGG CAAACTTGCC

301 CGCTTAGGCG CGAAATTCAG CACAAGGGCG GTTCCCTATG TCGGAACAGC

351 CCTTTTAGCC CACGACGTAT ACGAAACTTT CAAAGAAGAC ATACAGGCAC

401 GAGGCTACCA ATACGACCCC GAAACCGACA AATTTGCAAA GGTCTCAGGC

451 TAA
```

This corresponds to the amino acid sequence <SEQ ID 270; ORF72-1>:

```
  1 MVIKYTNLNF AKLSIIAILM MYSFEANANA VKISETVSVD TGQGAKIHKF

51 VPKNSKTYSS DLIKTVDLTH IPTGAKARIN AKITASVSRA GVLAGVGKLA

101 RLGAKFSTRA VPYVGTALLA HDVYETFKED IQARGYQYDP ETDKFAKVSG

151 *
```

Computer analysis of this amino acid sequence gave the following results:

Homology with a Predicted ORF from *N. meningitidis* (Strain A)

ORF72 shows 98.0% identity over a 147aa overlap with an ORF (ORF72a) from strain A of *N. meningitidis*.

```
                      10         20         30         40         50         60
        orf72.pep  MVIKYTNLNFAKLSIIAILMMYSFEANANAVXISETVSVDTGQGAKIHKFVPKNSKTYSS
                   |||||||||||||||||||||||||||||| |||||||||||||||||||||||||||||
        orf72a     MVIKYTNLNFAKLSIIAILMMYSFEANANAVKISETVSVDTGQGAKIHKFVPKNSKTYSS
                      10         20         30         40         50         60
                      70         80         90        100        110        120
        orf72.pep  DLIKTVDLTHXPTGAKARINAKITASVSRAGVLAGVGKLARLGAKFSTRAVPYVGTALLA
                   |||||||||| |||||||||||||||||||||||||||||||||||||||||||||||||
        orf72a     DLIKTVDLTHIPTGAKARINAKITASVSRAGVLAGVGKLARLGAKFSTRAVPYVGTALLA
                      70         80         90        100        110        120
                     130        140        150        160        170
        orf72.pep  HDVYETFKEDIQARGYQYDPETDKFVKGYEYSNCLWYEDKRRINRTYGCYGVD
                   ||||||||||||||||||||||||||| :|
        orf72a     HDVYETFKEDIQARGYQYDPETDKFAKVSGX
                     130        140        150
```

The complete length ORF72a nucleotide sequence <SEQ ID 271> is:

```
  1 ATGGTCATAA AATATACAAA TTTGAATTTT GCGAAATTGT CGATAATTGC

51 AATTTTGATG ATGTATTCGT TTGAAGCGAA TGCAAATGCA GTAAAAATAT

101 CTGAAACTGT TTCAGTTGAT ACCGGACAAG GTGCGAAAAT TCATAAGTTT

151 GTACCTAAAA ATAGTAAAAC TTATTCATCT GATTTAATAA AAACGGTAGA

201 TTTAACACAC ATCCCTACGG GCGCAAAAGC CCGAATCAAC GCCAAAATAA

251 CCGCCAGCGT ATCCCGCGCC GGCGTATTGG CGGGGGTCGG CAAACTTGCC

301 CGCTTAGGCG CGAAATTCAG CACAAGGGCG GTTCCCTATG TCGGAACAGC

351 CCTTTTAGCC CACGACGTAT ACGAAACTTT CAAAGAAGAC ATACAGGCAC

401 GAGGCTACCA ATACGACCCC GAAACCGACA AATTTGCAAA GGTCTCAGGC

451 TAA
```

This encodes a protein having amino acid sequence <SEQ ID 272>:

```
  1 MVIKYTNLNF AKLSIIAILM MYSFEANANA VKISETVSVD TGQGAKIHKF

51 VPKNSKTYSS DLIKTVDLTH IPTGAKARIN AKITASVSRA GVLAGVGKLA

101 RLGAKFSTRA VPYVGTALLA HDVYETFKED IQARGYQYDP ETDKFAKVSG

151 *
```

ORF72a and ORF72-1 show 100.0% identity in 150 aa overlap:

```
                    10         20         30         40         50         60
    orf72a.pep  MVIKYTNLNFAKLSIIAILMMYSFEANANAVKISETVSVDTGQGAKIHKFVPKNSKTYSS
                ||||||||||||||||||||||||||||||||||||||||||||||||||||||||||||
    orf72-1     MVIKYTNLNFAKLSIIAILMMYSFEANANAVKISETVSVDTGQGAKIHKFVPKNSKTYSS
                    10         20         30         40         50         60

70         80         90        100        110        120
    orf72a.pep  DLIKTVDLTHIPTGAKARINAKITASVSRAGVLAGVGKLARLGAKFSTRAVPYVGTALLA
                ||||||||||||||||||||||||||||||||||||||||||||||||||||||||||||
    orf72-1     DLIKTVDLTHIPTGAKARINAKITASVSRAGVLAGVGKLARLGAKFSTRAVPYVGTALLA
                    70         80         90        100        110        120

130        140        150
    orf72a.pep  HDVYETFKEDIQARGYQYDPETDKFAKVSGX
                ||||||||||||||||||||||||||||||
    orf72-1     HDVYETFKEDIQARGYQYDPETDKFAKVSGX
                   130        140        150
```

Homology with a Predicted ORF from *N. gonorrhoeae*

ORF72 shows 89% identity over a 173aa overlap with a predicted ORF (ORF72.ng) from *N. gonorrhoeae*:

```
    orf72.pep   MVIKYTNLNFAKLSIIAILMMYSFEANANAVXISETVSVDTGQGAKIHKFVPKNSKTYSS   60
                || :||||||||||||||||||||||||||| |||:|||||||||:||||||:|: |||
    orf72ng     MVTKHTNLNFAKLSIIAILMMYSFEANANAVKISETLSVDTGQGAKVHKFVPKSSNIYSS   60
    orf72.pep   DLIKTVDLTHXPTGAKARINAKITASVSRAGVLAGVGKLARLGAKFSTRAVPYVGTALLA  120
                || :|||||  |||||||||||||||||||||:||||||:|||| ||||:|||||||||
    orf72ng     DLTKAVDLTHIPTGAKARINAKITASVSRAGVLSGVGKLVRQGAKFGTRAVPYVGTALLA  120
    orf72.pep   HDVYETFKEDIQARGYQYDPETDKFVKGYEYSNCLWYEDKRRINRTYGCYGVD         173
                |||||||||||||||:||||||||||||||||:|||||||:|||||||||||||
    orf72ng     HDVYETFKEDIQARGCRYDPETDKFVKGYEYANCLWYEDERRINRTYGCYGVDSSIMRLM  180
```

An ORF72ng nucleotide sequence <SEQ ID 273> was predicted to encode a protein having amino acid sequence <SEQ ID 274>:

```
  1 MVTKHTNLNF AKLSIIAILM MYSFEANANA VKISETLSVD TGQGAKVHKF

51 VPKSSNIYSS DLTKAVDLTH IPTGAKARIN AKITASVSRA GVLSGVGKLV

101 RQGAKFGTRA VPYVGTALLA HDVYETFKED IQARGCRYDP ETDKFVKGYE

151 YANCLWYEDE RRINRTYGCY GVDSSIMRLM PDRSRFPEVK QLMESQMYRL

201 ARPFWNWRKE ELNKLSSLDW NNFVLNRCTF DWNGGGCAVN KGDDFRAGAS

251 FSLGRNPKYK EEMDAKKPEE ILSLKVDADP DKYIEATGYP GYSEKVEVAP

301 GTKVNMGPVT DRNGNPVQVA ATFGRDAQGN TTADVQVIPR PDLTPASAEA

351 PHAQPLPEVS PAENPANNPD PDENPGTRPN PEPDPDLNPD ANPDTDGQPG

401 TSPDSPAVPD RPNGRHRKER KEGEDGGLSC DYFPEILACQ EMGKPSDRMF

451 HDISIPQVTD DKTWSSHNFL PSNGVCPQPK TFHVFGRQYR ASYEPLCVFA

501 EKIRFAVLLA FIIMSAFVVF GSLGGE*
```

After further analysis, the following gonococcal DNA sequence <SEQ ID 275> was identified:

```
  1 ATGGTCACAA AACATACAAA TTTGAATTTT GCGAAATTGT CGATAATTGC

51 AATTTTGATG ATGTATTCGT TTGAAGCGAA TGCAAATGCA GTAAAAATAT

101 CTGAAACTCT TTCGGTTGAT ACCGGACAAG GCGCGAAAGT TCATAAGTTC

151 GTTCCTAAAT CAAGTAATAT TTATTCATCT GATTTAACAA AAGCGGTAGA

201 TTTAACGCAT ATCCCCACGG GCGCAAAAGC CCGAATCAAC GCCAAAATAA
```

```
251 CCGCCAGCGT ATCCCGCGCC GGCGTATTGT CGGGGGTCGG CAAACTTGTC

301 CGCCAAGGCG CGAAATTCGG CACAAGGGCG GTTCCCTATG TCGGAACAGC

351 CCTTTTAGCC CACGACGTAT ACGAAACTTT CAAAGAAGAC ATACAGGCAC

401 GAGGCTGCCG ATACGATCCC GAAACCGACA AATTT
```

This corresponds to the amino acid sequence <SEQ ID 276; ORF72ng-1>:

```
  1 MVTKHTNLNF AKLSIIAILM MYSFEANANA VKISETLSVD TGQGAKVHKF

51 VPKSSNIYSS DLTKAVDLTH IPTGAKARIN AKITASVSRA GVLSGVGKLV

101 RQGAKFGTRA VPYVGTALLA HDVYETFKED IQARGCRYDP ETDKF
```

ORF72ng-1 and ORF721-1 show 89.7% identity in 145 aa overlap:

```
                   10         20         30         40         50         60
    orf72ng-1.pe   MVTKHTNLNFAKLSIIAILMMYSFEANANAVKISETLSVDTGQGAKVHKFVPKSSNIYSS
                   || :||||||||||||||||||||||||||||:||||||||:||||||:|:    |||
    orf72-1        MVIKYTNLNFAKLSIIAILMMYSFEANANAVKISETVSVDTGQGAKIHKFVPKNSKTYSS
                   10         20         30         40         50         60

70         80         90        100        110        120
    orf72ng-1.pe   DLTKAVDLTHIPTGAKARINAKITASVSRAGVLSGVGKLVRQGAKFGTRAVPYVGTALLA
                   || :|||||||||||||||||||||||||||:|||||:||||:|||||:||||||||||
    orf72-1        DLIKTVDLTHIPTGAKARINAKITASVSRAGVLAGVGKLARLGAKFSTRAVPYVGTALLA
                   70         80         90        100        110        120

130        140
    orf72ng-1.pe   HDVYETFKEDIQARGCRYDPETDKF
                   |||||||||||||||:|||||||||
    orf72-1        HDVYETFKEDIQARGYQYDPETDKFAKVSGX
                  130        140        150
```

Based on this analysis, including the presence of a putative leader sequence and transmembrane domains in the gonococcal protein, it is predicted that the proteins from *N. meningitidis* and *N. gonorrhoeae*, and their epitopes, could be useful antigens for vaccines or diagnostics, or for raising antibodies.

Example 33

The following partial DNA sequence was identified in *N. meningitidis* <SEQ ID 277>:

```
  1 ATGAGATTTT TCGGTATCGG TTTTTTGGTG CTGCTGTTTT TGGAGATTAT

51 GTCGATTGTG TGGGTTGCCG ATTGGCTGGG CGGCGGCTGG ACGTTGTTTT

101 TGATGGCGGC AGGTTTTGCC GCCGGCGTGC TGATGCTCAG GCAAACCGGG

151 GCTGACCGGT CTTTTATTGG CGGGCGCGGC AATGAGAAGC GGCGGGAAGG

201 TATCCGTTTA TCAGATGTTG TGGCCTATC..
```

This corresponds to the amino acid sequence <SEQ ID 278; ORF73>:

```
  1 MRFFGIGFLV LLFLEIMSIV WVADWLGGGW TLFLMAAGFA AGVLMLRQTG

51 LTGLLLAGAA MRSGGKVSVY QMLWPI..
```

Further work revealed the complete nucleotide sequence <SEQ ID 279>:

```
  1 ATGAGATTTT TCGGTATCGG TTTTTTGGTG CTGCTGTTTT TGGAGATTAT

51 GTCGATTGTG TGGGTTGCCG ATTGGCTGGG CGGCGGCTGG ACGTTGTTTT

101 TGATGGCGGC AGGTTTTGCC GCCGGCGTGC TGATGCTCAG GCATACGGGG

151 CTGTCCGGTC TTTTATTGGC GGGCGCGGCA ATGAGAAGCG GCGGGAGGGT

201 ATCCGTTTAT CAGATGTTGT GGCCTATCCG TTATACGGTG GCGGCTGTGT

251 GTCTGATGAG TCCGGGATTC GTATCCTCGG TGTTGGCGGT ATTGCTGCTG

301 CTGCCGTTTA AGGGAGGGGC AGTGTTGCAG GCAGGAGGTG CGGAAAATTT

351 TTTCAACATG AACCAATCGG GCAGAAAAGA GGGCTTTTCC CGCGATGACG

401 ATATTATCGA GGGAGAATAT ACGGTTGAAG AGCCTTACGG CGGCAATCGT

451 TCCCGAAACG CCATCGAACA CAAAAAAGAC GAATAA
```

This corresponds to the amino acid sequence <SEQ ID 280; ORF73-1>:

```
  1 MRFFGIGFLV LLFLEIMSIV WVADWLGGGW TLFLMAAGFA AGVLMLRHTG

51 LSGLLLAGAA MRSGGRVSVY QMLWPIRYTV AAVCLMSPGF VSSVLAVLLL

101 LPFKGGAVLQ AGGAENFFNM NQSGRKEGFS RDDDIIEGEY TVEEPYGGNR

151 SRNAIEHKKD E*
```

Computer analysis of this amino acid sequence gave the following results:

Homology with a Predicted ORF from *N. meningitidis* (Strain A)

ORF73 shows 90.8% identity over a 76aa overlap with an ORF (ORF73a) from strain A of *N. meningitidis*.

```
                  10        20        30        40        50        60
    orf73.pep  MRFFGIGFLVLLFLEIMSIVWVADWLGGGWTLFLMAAGFAAGVLMLRQTGLTGLLLAGAA
               ||||||||||||||||||||||||||||||||||||||||  :|||:|||:||||||||
    orf73a     MRFFGIGFLVLLFLEIMSIVWVADWLGGGWTLFLMAATFAAGVVMLRHTGLSGLLLAGAA
                  10        20        30        40        50        60
                  70
    orf73.pep  MRSGGKVSVYQMLWPI
               |||||:||||  ||| |
    orf73a     MRSGGRVSVYXMLWXIRYTVAAVCXMSPGFVSSVXAVLLXLPFKGGAVLQAGGAENFFNM
```

The complete length ORF73a nucleotide sequence <SEQ ID 281> is:

```
  1 ATGAGATTTT TCGGTATCGG TTTTTTGGTG CTGCTGTTTT TGGAGATTAT

51 GTCGATTGTG TGGGTTGCCG ATTGGTTGGG CGGCGGTTGG ACGCTGTTTC

101 TAATGGCGGC AACCTTTGCC GCCGGCGTGG TGATGCTCAG GCATACGGGG

151 CTGTCCGGTC TTTTATTGGC GGGCGCGGCA ATGAGAAGCG GCGGGAGGGT

201 ATCCGTTTAT CANATGTTGT GGCNTATCCG TTATACGGTG GCGGCGGTGT

251 GTCNGATGAG TCCGGGATTC GTATCCTCGG TGTNGGCGGT ATTGCTGNTG

301 CTNCCGTTTA AGGGAGGTGC AGTGTTGCAG GCAGGAGGTG CGGAAAATTT

351 TTTCAACATG AACCANTCGG GCAGAAAAGA NGGCNTTTCC CGCGATGACG
```

```
401 ATATTATCGA GGGGGAATAT ACGGTTGAAG ANCCTTACGG CGGCANTCGT

451 TTCCGAAACG CCNTNGAACA CAAAAAGAC GAATAA
```

This encodes a protein having amino acid sequence <SEQ ID 282>:

```
  1 MRFFGIGFLV LLFLEIMSIV WVADWLGGGW TLFLMAATFA AGVVMLRHTG

51 LSGLLLAGAA MRSGGRVSVY XMLWXIRYTV AAVCXMSPGF VSSVXAVLLX

101 LPFKGGAVLQ AGGAENFFNM NXSGRKXGXS RDDDIIEGEY TVEXPYGGXR

151 FRNAXEHKKD E*
```

ORF73a and ORF73-1 show 91.3% identity in 161 aa overlap

```
                    10         20         30         40         50         60
   orf73a.pep  MRFFGIGFLVLLFLEIMSIVWVADWLGGGWTLFLMAATFAAGVVMLRHTGLSGLLLAGAA
               ||||||||||||||||||||||||||||||||||||| |||||:||||||||||||||||
   orf73-1     MRFFGIGFLVLLFLEIMSIVWVADWLGGGWTLFLMAAGFAAGVMLRHTGLSGLLLAGAA
                    10         20         30         40         50         60
                    70         80         90        100        110        120
   orf73a.pep  MRSGGRVSVYXMLWXIRYTVAAVCXMSPGFVSSVXAVLLXLPFKGGAVLQAGGAENFFNM
               ||||||||||  ||| ||||||||||| |||||||| ||||| |||||||||||||||||
   orf73-1     MRSGGRVSVYQMLWPIRYTVAAVCLMSPGFVSSVLAVLLLLPFKGGAVLQAGGAENFFNM
                    70         80         90        100        110        120
                   130        140        150        160
   orf73a.pep  NXSGRKXGXSRDDDIIEGEYTVEXPYGGXRFRNAXEHKKDEX
               | ||||  | ||||||||||||| |||| |||  |||||||||
   orf73-1     NQSGRKEGFSRDDDIIEGEYTVEEPYGGNRSRNAIEHKKDEX
                   130        140        150        160
```

Homology with a Predicted ORF from *N. gonorrhoeae*

ORF73 shows 92.1% identity over a 76aa overlap with a predicted ORF (ORF73.ng) from *N. gonorrhoeae*:

```
   orf73.pep  MRFFGIGFLVLLFLEIMSIVWVADWLGGGWTLFLMAAGFAAGVMLRQTGLTGLLLAGAA  60
              |||||||||||||||||||||||||||||||||||| |||| :|||:|||:|||||||||
   orf73ng    MRFFGIGFLVLLFLEIMSIVWVADWLGGGWTLFLMAATFAAGVVMLRHTGLSGLLLAGAA  60
   orf73.pep  MRSGGKVSVYQMLWPI                                              76
              ::|:||||||||||||
   orf73ng    VKSSGKVSVYQMLWPIRYTVAAVCLMSPGFVSSVLAVLLLLPFKGGAVLQAGGAENFFNM 120
```

The complete length ORF73ng nucleotide sequence <SEQ ID 283> is:

```
  1 ATGAGATTTT TCGGTATCGG TTTTTTGGTG CTGCTGTTTT TGGAAATTAT

51 GTCGATTGTG TGGGTTGCCG ATTGGCTGGG CGGCGGTTGG AcgcTGTTTC

101 TAATGGCGGC AACCTTTGCC GCCGGTGTGC TGATGCTCAG GCATAcggGG

151 CTGTCCGGTC TTTTATTGGC TGGCGCGGCG GTAAAAagta gtgGGAAGGT

201 ATCTGTTTAT CagatgtTGT GGCCTATCCG TTATAcggtg gcggcggtgT

251 GTCTGatgag tCcggGATTC GTATCCTccg tgttggCGGT ATTGCTGCTG

301 CTGCcgttta aggGaggGgc agtgttgcag gcaggaggtg cggaaaATTT

351 TTTCAACATg aaCcaatcgg gcagaaAaga gggattttc cacgatgacg 401 atattatcga gggagaatat acggttgaaa aacctgacgg cggcaatcgt 451 tcccgaAAcg ccatcgaaca cgaaaAagac gaataA
```

This encodes a protein having amino acid sequence <SEQ ID 284>:

```
  1 MRFFGIGFLV LLFLEIMSIV WVADWLGGGW TLFLMAATFA AGVLMLRHTG

51 LSGLLLAGAA VKSSGKVSVY QMLWPIRYTV AAVCLMSPGF VSSVLAVLLL

101 LPFKGGAVLQ AGGAENFFNM NQSGRKEGFF HDDDIIEGEY TVEKPDGGNR

151 SRNAIEHEKD E*
```

ORF73ng and ORG73-1 show 93.8% identity in 161 aa overlap

```
                  10        20        30        40        50        60
   orf73-1.pep MRFFGIGFLVLLFLEIMSIVWVADWLGGGWTLFLMAAGFAAGVLMLRHTGLSGLLLAGAA
               ||||||||||||||||||||||||||||||||||||| ||||||||||||||||||||||
   orf73ng     MRFFGIGFLVLLFLEIMSIVWVADWLGGGWTLFLMAATFAAGVLMLRHTGLSGLLLAGAA
                  10        20        30        40        50        60
                  70        80        90       100       110       120
   orf73-1.pep MRSGGRVSVYQMLWPIRYTVAAVCLMSPGFVSSVLAVLLLLPFKGGAVLQAGGAENFFNM
               ::|:|:||||||||||||||||||||||||||||||||| ||||||||||||||||||||
   orf73ng     VKSSGKVSVYQMLWPIRYTVAAVCLMSPGFVSSVLAVLLLLPFKGGAVLQAGGAENFFNM
                  70        80        90       100       110       120
                 130       140       150       160
   orf73-1.pep NQSGRKEGFSRDDDIIEGEYTVEEPYGGNRSRNAIEHKKDEX
               ||||||||| :||||||||||||| :| ||||||||||:|||
   orf73ng     NQSGRKEGFFHDDDIIEGEYTVEKPDGGNRSRNAIEHEKDEX
                 130       140       150       160
```

Based on this analysis, including the presence of a putative leader sequence and putative transmembrane domain in the gonococcal protein, it is predicted that the proteins from *N. meningitidis* and *N. gonorrhoeae*, and their epitopes, could be useful antigens for vaccines or diagnostics, or for raising antibodies.

Example 34

The following partial DNA sequence was identified in *N. meningitidis* <SEQ ID 285>:

```
  1 ATGTTTGTTT TTCAGACGGC ATTCTT.ATG TTTCAGAAAC ATTTGCAGAA

51 AGCCTCCGAC AGCGTCGTCG GAGGGACATT ATACGTGGTT GCCACGCCCA

101 TCGGCAATTT GGCGGACATT ACCCTGCGCG CTTTGGCGGT ATTGCAAAAG

151 GCG....... .....GCCGA AGACACGCGC GTTACCGCAC AGCTTTTGAG

201 CGCGTACGGC ATTCAGGGCA AACTCGTCAG TGTGCGCGAA CACAACGAAC

251 GGCAGATGGC GGACAAGATT GTCGGCTATC TTTCAGACGG CATGGTTGTG

301 GCACAGGTTT CCGATGCGGG TACGCCGGCC GTGTGCGACC CGGGCGCGAA

351 ACTCGCCCGC CGCGTGCGTG AGGCCGGGTT TAAAGTCGTT CCCGTCGTGG

401 GCGCAAC.GC GGTGATGGCG GCTTTGAGCG TGGCCGGTGT GGAAGGATCC

451 GATTTTTATT TCAACGGTTT TGTACCGCCG AAATCGGGAG AACGCAGGAA

501 ACTGTTTGCC AAATGGGTGC GGGCGGCGTT TCCTATCGTC ATGTTTGAAA

551 CGCCGCACCG CATCGGTGCA GCGCTTGCCG ATATGGCGGA ACTGTTCCCC

601 GAACGCCGAT TAATGCTGGC GCGCGAAATT ACGAAAACGT TTGAAACGTT

651 CTTAAGCGGC ACGGTTGGGG AAATTCAGAC GGCATTGTCT GCCGACGGCG

701 ACCAATCGCG CGGCGAGATG GTGTTGGTGC TTTATCCGGC GCAGGATGAA
```

-continued
```
751 AAACACGAAG GCTTGTCCGA GTCCGCGCAA AACATCATGA AAATCCTCAC

801 AGCCGAGCTG CCGACCAAAC AGGCGGCGGA GCTTGCTGCC AAAATCACGG

851 GCGAGGGAAA GAAAGCTTTG TACGAT..
```

This corresponds to the amino acid sequence <SEQ ID 286; ORF75>:

```
  1 MFVFQTAFXM FQKHLQKASD SVVGGTLYVV ATPIGNLADI TLRALAVLQK

51 A....AEDTR VTAQLLSAYG IQGKLVSVRE HNERQMADKI VGYLSDGMVV

101 AQVSDAGTPA VCDPGAKLAR RVREAGFKVV PVVGAXAVMA ALSVAGVEGS

151 DFYFNGFVPP KSGERRKLFA KWVRAAFPIV MFETPHRIGA ALADMAELFP

201 ERRLMLAREI TKTFETFLSG TVGEIQTALS ADGDQSRGEM VLVLYPAQDE

251 KHEGLSESAQ NIMKILTAEL PTKQAAELAA KITGEGKKAL YD..
                                                    20
```

Further work revealed the complete nucleotide sequence <SEQ ID 287>:

```
  1 ATGTTTCAGA AACATTTGCA GAAAGCCTCC GACAGCGTCG TCGGAGGGAC

51 ATTATACGTG GTTGCCACGC CCATCGGCAA TTTGGCGGAC ATTACCCTGC

101 GCGCTTTGGC GGTATTGCAA AAGGCGGACA TCATCTGTGC CGAAGACACG

151 CGCGTTACCG CACAGCTTTT GAGCGCGTAC GGCATTCAGG GCAAACTCGT

201 CAGTGTGCGC GAACACAACG AACGGCAGAT GGCGGACAAG ATTGTCGGCT

251 ATCTTTCAGA CGGCATGGTT GTGGCACAGG TTTCCGATGC GGGTACGCCG

301 GCCGTGTGCG ACCCGGGCGC GAAACTCGCC CGCCGCGTGC GTGAGGCCGG

351 GTTTAAAGTC GTTCCCGTCG TGGGCGCAAG CGCGGTGATG GCGGCTTTGA

401 GCGTGGCCGG TGTGGAAGGA TCCGATTTTT ATTTCAACGG TTTTGTACCG

451 CCGAAATCGG GAGAACGCAG GAAACTGTTT GCCAAATGGG TGCGGGCGGC

501 GTTTCCTATC GTCATGTTTG AAACGCCGCA CCGCATCGGT GCGACGCTTG

551 CCGATATGGC GGAACTGTTC CCCGAACGCC GATTAATGCT GGCGCGCGAA

601 ATTACGAAAA CGTTTGAAAC GTTCTTAAGC GGCACGGTTG GGGAAATTCA

651 GACGGCATTG TCTGCCGACG GCAACCAATC GCGCGGCGAG ATGGTGTTGG

701 TGCTTTATCC GGCGCAGGAT GAAAAACACG AAGGCTTGTC CGAGTCCGCG

751 CAAAACATCA TGAAAATCCT CACAGCCGAG CTGCCGACCA AACAGGCGGC

801 GGAGCTTGCT GCCAAAATCA CGGGCGAGGG AAAGAAAGCT TTGTACGATC

851 TGGCTCTGTC TTGGAAAAAC AAATAG
```

This corresponds to the amino acid sequence <SEQ ID 288; ORF75-1>:

```
  1MFQKHLQKAS DSVVGGTLYV VATPIGNLAD ITLRALAVLQ KADIICAEDT

51RVTAQLLSAY GIQGKLVSVR EHNERQMADK IVGYLSDGMV VAQVSDAGTP

101AVCDPGAKLA RRVREAGFKV VPVVGASAVM AALSVAGVEG SDFYFNGFVP

151PKSGERRKLF AKWVRAAFPI VMFETPHRIG ATLADMAELF PERRLMLARE

201ITKTFETFLS GTVGEIQTAL SADGNQSRGE MVLVLYPAQD EKHEGLSESA

251QNIMKILTAE LPTKQAAELA AKITGEGKKA LYDLALSWKN K*
```

Computer analysis of this amino acid sequence gave the following results:

Homology with a Predicted ORF from *N. meningitidis* (Strain A)

ORF75 shows 95.8% identity over a 283aa overlap with an ORF (ORF75a) from strain A of *N. meningitidis*.

```
                    10        20        30        40        50        60
    orf75.pep  MFVFQTAFXMFQKHLQKASDSVVGGTLYVVATPIGNLADITLRALAVLQKAXXXXAEDTR
                        ||||||||||||||||||||||||||||||||||||||||    ||||
    orf75a            MFQKHLQKASDSVVGGTLYVVATPIGNLADITLRALAVLQKADIICAEDTR
                              10        20        30        40        50
                    70        80        90       100       110       120
    orf75.pep  VTAQLLSAYGIQGKLVSVREHNERQMADKIVGYLSDGMVVAQVSDAGTPAVCDPGAKLAR
               ||||||||||||||||||||||||||||||||||||||||||||||||||||||||||||
    orf75a     VTAQLLSAYGIQGKLVSVREHNERQMADKIVGYLSDGMVVAQVSDAGTPAVCDPGAKLAR
                         60        70        80        90       100       110
                   130       140       150       160       170       180
    orf75.pep  RVREAGFKVVPVVGAXAVMAALSVAGVEGSDFYFNGFVPPKSGERRKLFAKWVRAAFPIV
               ||||:|||||||||| |||||||||| ||||||||||||||||||||||||||:|||:|
    orf75a     RVREVGFKVVPVVGASAVMAALSVAGVAGSDFYFNGFVPPKSGERRKLFAKWVRVAFPVV
                        120       130       140       150       160       170
                   190       200       210       220       230       240
    orf75.pep  MFETPHRIGAALADMAELFPERRLMLAREITKTFETFLSGTVGEIQTALSADGDQSRGEM
               ||||||||||:|||||||||||||||||||||||||||||||||||||||:|||:|||||
    orf75a     MFETPHRIGATLADMAELFPERRLMLAREITKTFETFLSGTVGEIQTALAADGNQSRGEM
                        180       190       200       210       220       230
                   250       260       270       280       290
    orf75.pep  VLVLYPAQDEKHEGLSESAQNIMKILTAELPTKQAAELAAKITGEGKKALYD
               ||||||||||||||||||||||||||||||||||||||||||||||||||||
    orf75a     VLVLYPAQDEKHEGLSESAQNIMKILTAELPTKQAAELAAKITGEGKKALYDLALSWKNK
                        240       250       260       270       280       290
    orf75a     X
```

The complete length ORF75a nucleotide sequence <SEQ ID 289> is:

```
  1 ATGTTTCAGA AACATTTGCA GAAAGCCTCC GACAGCGTCG TCGGAGGGAC

51 ATTATACGTG GTTGCCACGC CCATCGGCAA TTTGGCGGAC ATTACCCTGC

101 GCGCTTTGGC GGTATTGCAA AAGGCGGACA TCATCTGTGC CGAAGACACG

151 CGCGTTACCG CGCAGCTTTT GAGCGCGTAC GGCATTCAGG GCAAACTCGT

201 CAGCGTGCGC GAACACAACG AACGGCAGAT GGCGGACAAG ATTGTCGGCT

251 ATCTTTCAGA CGGCATGGTT GTGGCACAGG TTTCCGATGC GGGTACGCCG

301 GCCGTGTGCG ACCCGGGCGC GAAACTCGCC CGCCGCGTGC GTGAGGTCGG

351 GTTTAAAGTT GTCCCTGTTG TCGGCGCAAG CGCGGTGATG GCGGCTTTGA

401 GTGTGGCTGG TGTGGCGGGA TCCGATTTTT ATTTCAACGG TTTTGTACCG

451 CCGAAATCGG GCGAACGTAG GAAATTGTTT GCCAAATGGG TGCGGGTGGC

501 GTTTCCCGTC GTGATGTTTG AAACGCCGCA CCGCATCGGG GCGACGCTTG

551 CCGATATGGC GGAACTGTTC CCCGAACGCC GATTAATGCT GGCGCGCGAA

601 ATCACGAAAA CGTTTGAAAC GTTCTTAAGC GGCACGGTTG GGGAAATTCA

651 GACGGCATTG GCGGCGGACG GCAACCAATC GCGCGGCGAG ATGGTGTTGG

701 TGCTTTATCC GGCGCAGGAT GAAAAACACG AAGGCTTGTC CGAGTCCGCG

751 CAAAACATCA TGAAAATCCT CACAGCCGAG CTGCCGACCA AACAGGCGGC

801 GGAGCTTGCC GCCAAAATCA CGGGCGAGGG AAAAAAAGCT TTGTACGATC

851 TGGCACTGTC TTGGAAAAAC AAATGA
```

This encodes a protein having amino acid sequence <SEQ ID 290>:

```
  1 MFQKHLQKAS DSVVGGTLYV VATPIGNLAD ITLRALAVLQ KADIICAEDT

51 RVTAQLLSAY GIQGKLVSVR EHNERQMADK IVGYLSDGMV VAQVSDAGTP

101 AVCDPGAKLA RRVREVGFKV VPVVGASAVM AALSVAGVAG SDFYFNGFVP

151 PKSGERRKLF AKWVRVAFPV VMFETPHRIG ATLADMAELF PERRLMLARE

201 ITKTFETFLS GTVGEIQTAL AADGNQSRGE MVLVLYPAQD EKHEGLSESA

251 QNIMKILTAE LPTKQAAELA AKITGEGKKA LYDLALSWKN K*
```

ORF75a and ORF75-1 show 98.3% identity in 291 aa overlap:

```
                 10         20         30         40         50         60
    orf75a.pep   MFQKHLQKASDSVVGGTLYVVATPIGNLADITLRALAVLQKADIICAEDTRVTAQLLSAY
                 ||||||||||||||||||||||||||||||||||||||||||||||||||||||||||||
    orf75-1      MFQKHLQKASDSVVGGTLYVVATPIGNLADITLRALAVLQKADIICAEDTRVTAQLLSAY
                 10         20         30         40         50         60

70         80         90        100        110        120
    orf75a.pep   GIQGKLVSVREHNERQMADKIVGYLSDGMVVAQVSDAGTPAVCDPGAKLARRVREVGFKV
                 |||||||||||||||||||||||||||||||||||||||||||||||||||||:||||
    orf75-1      GIQGKLVSVREHNERQMADKIVGYLSDGMVVAQVSDAGTPAVCDPGAKLARRVREAGFKV
                 70         80         90        100        110        120

130        140        150        160        170        180
    orf75a.pep   VPVVGASAVMAALSVAGVAGSDFYFNGFVPPKSGERRKLFAKWVRVAFPVVMFETPHRIG
                 |||||||||||||||||||:|||:||||||||||||||||||||||:|||:|||||||||
    orf75-1      VPVVGASAVMAALSVEGVEGSDFYFNGFVPPKSGERRKLFAKWVRAAFPIVMFETPHRIG
                130        140        150        160        170        180

190        200        210        220        230        240
    orf75a.pep m ATLADMAELFPERRLMLAREITKTFETFLSGTVGEIQTALAADGNQSRGEMVLVLYPAQD
                 |||||||||||||||||||||||||||||||||||||||:||||||||||||||||||||
    orf75-1      ATLADMAELFPERRLMLAREITKTFETFLSGTVGEIQTALSADGNQSRGEMVLVLYPAQD
                190        200        210        220        230        240

250        260        270        280        290
    orf75a.pep   EKHEGLSESAQNIMKILTAELPTKQAAELAAKITGEGKKALYDLALSWKNKX
                 ||||||||||||||||||||||||||||||||||||||||||||||||||||
    orf75-1      EKHEGLSESAQNIMKILTAELPTKQAAELAAKITGEGKKALYDLALSWKNKX
                250        260        270        280        290
```

Homology with a Predicted ORF from *N. gonorrhoeae*

ORF75 shows 93.2% identity over a 292aa overlap with a predicted ORF (ORF75.ng) from *N. gonorrhoeae*:

```
orf75.pep  MFVFQTAFXMFQKHLQKASDSVVGGTLYVVATPIGNLADITLRALAVLQKA----AEDTR   56
           | |||||| |||||||||||||||||||||||||||||||||||||||||||    |||||
orf75ng    MSVFQTAFFMFQKHLQKASDSVVGGTLYVVATPIGNLADITLRALAVLQKADIICAEDTR   60 orf75.pep  VTAQLLSAYGIQGKLVSVREHNERQMADKIVGYLSDGMVVAQVSDAGTPAVCDPGAKLAR  116
           ||||||||||||| |||||||||||||||::|:||||:||||||||||||||||||||||
orf75ng    VTAQLLSAYGIQGRLVSVREHNERQMADKVIGFLSDGLVVAQVSDAGTPAVCDPGAKLAR  120 orf75.pep  RVREAGFKVVPVVGAXAVMAALSVAGVEGSDFYFNGFVPPKSGERRKLFAKWVRAAFPIV  176
           |||||||||||||||  ||||||||||| |||||||||||||||||||||||||||||:|
orf75ng    RVREAGFKVVPVVGASAVMAALSVAGVAESDFYFNGFVPPKSGERRKLFAKWVRAAFPVV  180
                          .

orf75.pep  MFETPHRIGAALADMAELFPERRLMLAREITKTFETFLSGTVGEIQTALSADGDQSRGEM  236
           |||||||||  |||||||||||||||||||||||||||||||||||||||:|||:|||||
orf75ng    MFETPHRIGATLADMAELFPERRLMLAREITKTFETFLSGTVGEIQTALAADGNQSRGEM  240 orf75.pep  VLVLYPAQDEKHEGLSESAQNIMKILTAELPTKQAAELAAKITGEGKKALYD          288
           ||||||||||||||||||||| ||||:|||||||||||||||||||||||||
orf75ng    VLVLYPAQDEKHEGLSESAQNAMKILAAELPTKQAAELAAKITGEGKKALYDLALSWKNK  300
```

An ORF75ng nucleotide sequence <SEQ ID 291> was predicted to encode a protein having amino acid sequence <SEQ ID 292>:

```
  1 MSVFQTAFFM FQKHLQKASD SVVGGTLYVV ATPIGNLADI TLRALAVLQK

51 ADIICAEDTR VTAQLLSAYG IQGRLVSVRE HNERQMADKV IGFLSDGLVV
```

-continued

```
101 AQVSDAGTPA VCDPGAKLAR RVREAGFKVV PVVGASAVMA ALSVAGVAES

151 DFYFNGFVPP KSGERRKLFA KWVRAAFPVV MFETPHRIGA TLADMAELFP

201 ERRLMLAREI TKTFETFLSG TVGEIQTALA ADGNQSRGEM VLVLYPAQDE

251 KHEGLSESAQ NAMKILAAEL PTKQAAELAA KITGEGKKAL YDLALSWKNK

301 *
```

After further analysis, the following gonococcal DNA sequence <SEQ ID 293> was identified:

```
  1 ATGTTTCAGA AACACTTGCA GAAAGCCTCC GACAGCGTCG TCGGAGGGAC

51 ATTATACGTG GTTGCCACGC CCATCGGCAA TTTGGCAGAC ATTACCCTGC

101 GCGCTTTGGC GGTATTGCAA AAGGCGGACA TCATTTGTGC CGAAGACACG

151 CGCGTTACTG CGCAGCTTTT GAGCGCGTAC GGCATTCAGG GCAGGTTGGT

201 CAGTGTGCGC GAACACAACG AGCGGCAGAT GGCGGACAAG GTAATCGGTT

251 TCCTTTCAGA CGGCCTGGTT GTGGCGCAGG TTTCCGATGC GGGTACGCCG

301 GCCGTGTGCG ACCCGGGCGC GAAACTCGCC CGCCGCGTGC GCGAAGCAGG

351 GTTCAAAGTC GTTCCCGTCG TGGGCGCAAG CGCGGTAATG GCGGCGTTGA

401 GTGTGGCCGG TGTGGCGGAA TCCGATTTTT ATTTCAACGG TTTTGTACCG

451 CCGAAATCGG GCGAACGTAG GAAATTGTTT GCCAAATGGG TGCGGGCGGC

501 ATTTCCTGTC GTCATGTTTG AAACGCCGCA CCGAATCGGG GCAACGCTTG

551 CCGATATGGC GGAATTGTTC CCCGAACGCC GTCTGATGCT GGCGCGCGAA

601 ATCACGAAAA CGTTTGAAAC GTTCTTAAGC GGCACGGTTG GGGAAATTCA

651 GACGGCATTG GCGGCGGACG GCAACCAATC GCGCGGCGAG ATGGTGTTGG

701 TGCTTTATCC GGCGCAGGAT GAAAAACACG AAGGCTTGTC CGAGTCTGCG

751 CAAAATGCGA TGAAAATCCT TGCGGCCGAG CTGCCGACCA AGCAGGCGGC

801 GGAGCTTGCC GCCAAGATTA CAGGTGAGGG CAAAAAGGCT TTGTACGATT

851 TGGCACTGTC GTGGAAAAAC AAATGA
```

This corresponds to the amino acid sequence <SEQ ID 294; ORF75ng-1>:

```
  1 MFQKHLQKAS DSVVGGTLYV VATPIGNLAD ITLRALAVLQ KADIICAEDT

51 RVTAQLLSAY GIQGRLVSVR EHNERQMADK VIGFLSDGLV VAQVSDAGTP

101 AVCDPGAKLA RRVREAGFKV VPVVGASAVM AALSVAGVAE SDFYFNGFVP

151 PKSGERRKLF AKWVRAAFPV VMFETPHRIG ATLADMAELF PERRLMLARE

201 ITKTFETFLS GTVGEIQTAL AADGNQSRGE MVLVLYPAQD EKHEGLSESA

251 QNAMKILAAE LPTKQAAELA AKITGEGKKA LYDLALSWKN K*
```

ORF75ng-1 and ORF75-1 show 96.2% identity in 291 aa overlap:

```
                    10         20         30         40         50         60
    orf75-1.pep MFQKHLQKASDSVVGGTLYVVATPIGNLADITLRALAVLQKADIICAEDTRVTAQLLSAY
                ||||||||||||||||||||||||||||||||||||||||||||||||||||||||||||
    orf75ng-1   MFQKHLQKASDSVVGGTLYVVATPIGNLADITLRALAVLQKADIICAEDTRVTAQLLSAY
                    10         20         30         40         50         60
```

-continued

```
                       70         80         90        100        110        120
orf75-1.pep   GIQGKLVSVREHNERQMADKIVGYLSDGMVVAQVSDAGTPAVCDPGAKLARRVREAGFKV
              ||||:||||||||||||||||||::|:||||:||||||||||||||||||||||||||||
orf75ng-1     GIQGRLVSVREHNERQMADKVIGFLSDGLVVAQVSDAGTPAVCDPGAKLARRVREAGFKV
                       70         80         90        100        110        120

130        140        150        160        170        180
orf75-1.pep   VPVVGASAVMAALSVAGVEGSDFYFNGFVPPKSGERRKLFAKWVRAAFPIVMFETPHRIG
              ||||||||||||||||||||:||||||||||||||||||||||||||||:|||||||||
orf75ng-1     VPVVGASAVMAALSVAGVAESDFYFNGFVPPKSGERRKLFAKWVRAAFPVVMFETPHRIG
                      130        140        150        160        170        180

190        200        210        220        230        240
orf75-1.pep   ATLADMAELFPERRLMLAREITKTFETFLSGTVGEIQTALSADGNQSRGEMVLVLYPAQD
              ||||||||||||||||||||||||||||||||||||||||:|||||||||||||||||||
orf75ng-1     ATLADMAELFPERRLMLAREITKTFETFLSGTVGEIQTALAADGNQSRGEMVLVLYPAQD
                      190        200        210        220        230        240

250        260        270        280        290
orf75-1.pep   EKHEGLSESAQNIMKILTAELPTKQAAELAAKITGEGKKALYDLALSWKNKX
              ||||||||||||:||||:||||||||||||||||||||||||||||||||||
orf75ng-1     EKHEGLSESAQNAMKILAAELPTKQAAELAAKITGEGKKALYDLALSWKNKX
                      250        260        270        280        290
```

Furthermore, ORG75ng-1 shows significant homology to a hypothetical *E. coli* protein:

```
sp|P45528|YRAL_ECOLI HYPOTHETICAL 31.3 KD PROTEIN IN
AGAI-MTR INTERGENIC REGION (F286)
>gi|606086 (U18997) ORF_f286 [Escherichia coli]
>gi|1789535 (AE000395) hypothetical 31.3 kD protein in agai-mtr intergenic
region [Escherichia coli] Length = 286
Score = 218 bits (550), Expect = 3e-56
Identities = 128/284 (45%), Positives = 171/284 (60%), Gaps = 4/284 (1%)

Query:    4 KHLQKASDSVVGGTLYVVATPIGNLADITLRALAVLQKADIICAEDTRVTAQLLSAYGIQ   63
            K  Q A +S    G LY+V TPIGNLADIT RAL VLQ  D+I AEDTR T  LL  +GI
Sbjct:    2 KQHQSADNSQ--GQLYIVPTPIGNLADITQRALEVLQAVDLIAAEDTRHTGLLLQHFGIN   59

Query:   64 GRLVSVREHNERQMADKVIGFLSDGLVVAQVSDAGTPAVCDPGAKLARRVREAGFKVVPV  123
             RL ++ +HNE+Q A+ ++   L +G  +A VSDAGTP + DPG  L R  REA +VVP+
Sbjct:   60 ARLFALHDHNEQQKAETLLAKLQEGQNIALVSDAGTPLINDPGYHLVRTCREAGIRVVPL  119

Query:  124 VGASAVMAALSVAGVAESDFYFNGFVPPKSGERRKLFAKWVRAAFPVVMFETPHRIGATL  183
              G A + ALS AG+    F + GF+P KS  RR            ++ +E+ HR+  +L
Sbjct:  120 PGPCAAITALSAAGLPSDRFCYEGFLPAKSKGRRDALKAIEAEPRTLIFYESTHRLLDSL  179

Query:  184 ADMAELFPERR-LMLAREITKTFETFLSGTVGEIQTALAADGNQSRGEMVLVLYPAQDEK  242
             D+  + E R ++LARE+TKT+ET    VGE+    D N+ +GEMVL++          +
Sbjct:  180 EDIVAVLGESRYVVLARELTKTWETIHGAPVGELLAWVKEDENRRKGEMVLIV-EGHKAQ  238

Query:  243 HEGLSESAQNMKILAAELPTKQAAELAAKITGEGKKALYDLAL                  286
              E L  A   +L AELP K+AA LAA+I G  K ALY  AL
Sbjct:  239 EEDLPADALRTLALLQAELPLKKAAALAAEIHGVKKNALYKYAL                 282
```

Based on this analysis, including the presence of a putative transmembrane domain in the gonococcal protein, it is predicted that the proteins from *N. meningitidis* and *N. gonorrhoeae*, and their epitopes, could be useful antigens for vaccines or diagnostics, or for raising antibodies.

Example 35

The following partial DNA sequence was identified in *N. meningitidis* <SEQ ID 295>:

```
  1 ATGAAACAGA AAAAAACCGA TGCCGCAGTT ATTGCTGCAA TFTTGGCAGG
 51 TTTTGCGGCA GC.AAAGCAC CCGAAATCGA CCCGGCTTTG ..........
                              //
651 .......... ...GAGTTGG TCAGAAACCA GTTGGAGCAG GGTTTGAGAC
701 AGGAAAAAGC CCGCTTGAAA ATCGATGCCC TTTTGGAAGA AAACGGTGTC
751 AAACCGTAA
```

This corresponds to the amino acid sequence <SEQ ID 296; ORF76>:

```
  1 MKQKKTAAAV IAAMLAGFAA XKAPEIDPAL .......... ..........
                                //
201 .......... .......... ELVRNQLEQG LRQEKARLKI DALLEENGVK
251 P*
```

Further work revealed the complete nucleotide sequence <SEQ ID 297>:

```
  1 ATGAAACAGA AAAAAACCGC TGCCGCAGTT ATTGCTGCAA TGTTGGCAGG

51 TTTTGCGGCA GCCAAAGCAC CCGAAATCGA CCCGGCTTTG GTGGATACGC

101 TGGTGGCGCA GATCATGCAG CAGGCAGACC GGCATGCGGA GCAGTCCCAA

151 AAACCGGACG GCCAGGCAAT CCGAAACGAT GCCGTCCGCC GGCTACAAAC

201 TTTGGAAGTT TTGAAAAACA GGGCATTGAA GGAAGGTTTG GATAAGGATA

251 AGGATGTCCA AAACCGCTTT AAAATCGCCG AAGCGTCTTT TTATGCCGAG

301 GAGTACGTCC GTTTTCTGGA ACGTTCGGAA ACGGTTTCCG AAGACGAGCT

351 GCACAAGTTT TACGAACAGC AAATCCGCAT GATCAAATTG CAGCAGGTCA

401 GCTTCGCAAC CGAAGAGGAG GCGCGTCAGG CGCAGCAGCT CCTGCTCAAA

451 GGGCTGTCTT TTGAAGGGCT GATGAAGCGT TATCCGAACG ACGAGCAGGC

501 TTTTGACGGT TTCATTATGG CGCAGCAGCT TCCCGAGCCG CTGGCTTCGC

551 AGTTTGCCGC GATGAATCGG GGCGACGTTA CCCGCGATCC GGTCAAATTG

601 GGCGAACGCT ATTATCTGTT CAAACTCAGC GAGGTCGGGA AAAACCCCGA

651 CGCGCAGCCT TTCGAGTTGG TCAGAAACCA GTTGGAGCAG GGTTTGAGAC

701 AGGAAAAAGC CCGCTTGAAA ATCGATGCCC TTTTGGAAGA AAACGGTGTC

751 AAACCGTAA
```

This corresponds to the amino acid sequence <SEQ ID 298; ORF76-1>:

```
  1 MKQKKTAAAV IAAMLAGFAA AKAPEIDPAL VDTLVAQIMQ QADRHAEQSQ

51 KPDGQAIRND AVRRLQTLEV LKNRALKEGL DKDKDVQNRF KIAEASFYAE

101 EYVRFLERSE TVSEDELHKF YEQQIRMIKL QQVSFATEEE ARQAQQLLLK

151 GLSFEGLMKR YPNDEQAFDG FIMAQQLPEP LASQFAAMNR GDVTRDPVKL

201 GERYYLFKLS EVGKNPDAQP FELVRNQLEQ GLRQEKARLK IDALLEENGV

251 KP*
```

Computer analysis of this amino acid sequence gave the following results:
Homology with a Predicted ORF from *N. meningitidis* (Strain A)
ORF76 shows 96.7% identity over a 30aa overlap and 96.8% identity over a 31 aa overlap with an ORF (ORF76a) from strain A of *N. meningitidis*.

```
                  10        20        30
orf76.pep  MKQKKTAAAVIAAMLAGFAAXKAPEIDPAL
           ||||||||||||||||||| |||||||||
orf76a     MKQKKTAAAVIAAMLAGFAAAKAPEIDPALVDTLVAQIMQQADRHAEQSQKPDGQAIRND
                  10        20        30        40        50        60
                            //
                                      70        80        90
orf76.pep                            XELVRNQLEQGLRQEKARLKIDALLEENGVKPX
                                     |||||||||||||||||||||:||||||||||
orf76a     DVTRDPVKLGERYYLFKLSEVGKNPDAQPFELVRNQLEQGLRQEKARLKIDAILEENGVKPX
                 200       210       220       230       240       250
```

The complete length ORF76a nucleotide sequence <SEQ ID 299> is:

```
  1 ATGAAACAGA AAAAAACCGC TGCCGCAGTT ATTGCTGCAA TGTTGGCAGG
 51 TTTTGCGGCA GCCAAAGCAC CCGAAATCGA CCCGGCTTTG GTGGATACGC
101 TGGTGGCGCA GATCATGCAG CAGGCAGACC GGCATGCGGA GCAGTCCCAA
151 AAACCGGACG GCAGGCAAT CCGAAACGAT GCCGTCCGTC GGCTGCAAAC
201 TTTGGAAGTT TTGAAAAACA GGGCATTGAA GGAAGGTTTG ATAAGGATA
251 AGGATGTCCA AACCGCTTT AAAATCGCCG AAGCGTCTTT TTATGCCGAG
301 GAGTACGTCC GTTTTCTGGA ACGTTCGGAA ACGGTTTCCG AAAGCGCACT
351 GCGTCAGTTT TATGAGCGGC AAATCCGCAT GATCAAATTG CAGCAGGTCA
401 GCTTCGCAAC CGAAGAGGAG GCGCGTCAGG CGCAGCAGCT CCTGCTCAAA
451 GGGCTGTCTT TTGAAGGGCT GATGAAGCGT TATCCGAACG ACGAGCAGGC
501 TTTTGACGGT TTCATTATGG CGCAGCAGCT TCCCGAGCCG CTGGCTTCGC
551 AGTTTGCAGC GATGAATCGG GGCGACGTTA CCCGCGATCC GGTCAAATTG
601 GGCGAACGCT ATTATCTGTT CAAACTCAGC GAGGTCGGGA AAAACCCCGA
651 CGCGCAGCCT TTCGAGTTGG TCAGAAACCA GTTGGAACAA GGTTTGAGAC
701 AGGAAAAAGC CCGCTTGAAA ATCGATGCCA TTTTGGAAGA AAACGGTGTC
751 AAACCGTAA
```

This encodes a protein having amino acid sequence <SEQ ID 300>:

```
  1 MKQKKTAAAV IAAMLAGFAA AKAPEIDPAL VDTLVAQIMQ QADRHAEQSQ
 51 KPDGQAIRND AVRRLQTLEV LKNRALKEGL DKDKDVQNRF KIAEASFYAE
101 EYVRFLERSE TVSESALRQF YERQIRMIKL QQVSFATEEE ARQAQQLLLK
151 GLSFEGLMKR YPNDEQAFDG FIMAQQLPEP LASQFAAMNR GDVTRDPVKL
201 GERYYLFKLS EVGKNPDAQP FELVRNQLEQ GLRQEKARLK IDAILEENGV
251 KP*
```

ORF76a and ORF76-1 show 97.6% identity in 252 aa overlap:

```
                  10        20        30        40        50        60
orf76a.pep MKQKKTAAAVIAAMLAGFAAAKAPEIDPALVDTLVAQIMQQADRHAEQSQKPDGQAIRND
           ||||||||||||||||||||||||||||||||||||||||||||||||||||||||||||
orf76-1    MKQKKTAAAVIAAMLAGFAAAKAPEIDPALVDTLVAQIMQQADRHAEQSQKPDGQAIRND
                  10        20        30        40        50        60
```

```
                     70        80        90        100       110       120
orf76a.pep  AVRRLQTLEVLKNRALKEGLDKDKDVQNRFKIAEASFYAEEYVRFLERSERVSESALRQF
            ||||||||||||||||||||||||||||||||||||||||||||||||||||||:::|
orf76-1     AVRRLQTLEVLKNRALKEGLDKDKDVQNRFKIAEASFYAEEYVRFLERSERVSEDELHKF
                     70        80        90        100       110       120

130       140       150       160       170       180
orf76a.pep  YERQIRMIKLQQVSFATEEEARQAQQLLLKGLSFEGLMKRYPNDEQAFDGFIMAQQLPEP
            ||:|||||||||||||||||||||||||||||||||||||||||||||||||||||||
orf76-1     YEQQIRMIKLQQVSFATEEEARQAQQLLLKGLSFEGLMKRYPNDEQAFDGFIMAQQLPEP
                     130       140       150       160       170       180

190       200       210       220       230       240
orf76a.pep  LASQFAAMNRGDVTRDPVKLGERYYLFKLSEVGKNPDAQPFELVRNQLEQFLRQEKARLK
            ||||||||||||||||||||||||||||||||||||||||||||||||||||||||||||
orf76-1     LASQFAAMNRGDVTRDPVKLGERYYLFKLSEVGKNPDAQPFELVRNQLEQFLRQEKARLK
                     190       200       210       220       230       240

250
orf76a.pep  IDAILEENGVKPX
            |||:|||||||||
orf76-1     IDALLEENGVKPX
                     250
```

Homology with a Predicted ORF from N. gonorrhoeae

The aligned aa sequences of ORF76 and a predicted ORF (ORF76.ng) from N. gonorrhoeae of the N- and C-termini show 96.7% and 100% identity in 30 and 31 overlap, respectively:

```
orf76.pep  MKQKKTAAAVIAAMLAGRAAXKAPEIDPAL                                30
           ||||||||||||||||||||| |||||||||
orf76ng    MKQKKTAAAVIAAMLAGFAAAKAPEIDPALVDTLVAQIMQQADRHAEQSQRPDGQAIRND  60
                                        //
orf76.pep                        ELVRNQLEQGLRQEKARLKIDALLEENGVKP 251
                                 |||||||||||||||||||||||||||||||
orf76ng    VTRNPVKLGERYYLFKLGAVGKNPDAQPFELVRNQLEQGLRQEKARLKIDALLEENGVKP 251
```

The complete length ORF76ng nucleotide sequence <SEQ ID 301> is:

```
  1 ATGAAACAGA AAAAGACCGC TGCCGCAGTT ATTGCTGCAA TGTTGGCAGG

51 TTTTGCGGCA GCCAAAGCAC CCGAAATCGA CCCGGCTTTG GTGGATACGC

101 TGGTGGCGCA GATCATGCAG CAGGCAGACC GGCATGCGGA GCAGTCCCAA

151 AGACCGGACG GGCAGGCAAT CCGAAACGAT GCCGTCCGCC GGCTGCAAAC

201 TTTGGAAGTT TTGAAAAACA GGGCATTGAA GGAAGGTTTG GATAAGGATA

251 AGGATGTCCA AAACCGCTTT AAAATCGCCG AAGCGTCTTT TTATGCCGAG

301 GAGTACGTCC GTTTTCTGGA ACGTTCGGAA ACGGTTTCCG AAAGCGCACT

351 GCGTCAGTTT TATGAGCGGC AAATCCGCAT GATCAAATTG CAGCAGGTCA

401 GCTTCGCAAC CGAAGAGGAG GCGCGTCAGG CGCAGCAGCT CCTGCTCAAA

451 GGGCTGTCTT TTGAAGGGCT GATGAAGCGT TATCCGAACG ACGAGCAGGC

501 GTTCGACGGT TTCATTATGG CGCAGCAGCT TCCCGAGCCG CTGGCTTcgc 551 agtttgCCGG TATGAACCGT GGCGACGTTA CCCGCAATCC GGTCAAATTG

601 GGCGAACGCT ATTACCTGTT CAAACTCGGC GCGGTCGGGA AAACCCCGA

651 CGCGCAGCCT TTCGAGTTGG TCAGAAACCA GTTGGAACAA GGTTTGAGGC

701 AGGAAAAAGC CCGCTTGAAA ATCGATGCCC TTTTGGAaga Aaacggtgtc

751 AaacCGTAA
```

This encodes a protein having amino acid sequence <SEQ ID 302>:

```
  1 MKQKKTAAAV IAAMLAGFAA AKAPEIDPAL VDTLVAQIMQ QADRHAEQSQ

51 RPDGQAIRND AVRRLQTLEV LKNRALKEGL DKDKDVQNRF KIAEASFYAE

101 EYVRFLERSE TVSESALRQF YERQIRMIKL QQVSFATEEE ARQAQQLLLK

151 GLSFEGLMKR YPNDEQAFDG FIMAQQLPEP LASQFAGMNR GDVTRNPVKL

201 GERYYLFKLG AVGKNPDAQP FELVRNQLEQ GLRQEKARLK IDALLEENGV

251 KP*
```

ORF76ng and ORF76-1 show 96.0% identity in 252 aa overlap

```
                   10         20         30         40         50         60
    orf76a.pep MKQKKTAAAVIAAMLAGFAAAKAPEIDPALVDTLVAQIMQQADRHAEQSQKPDGQAIRND
               ||||||||||||||||||||||||||||||||||||||||||||||||||||||||||||
    orf76-1    MKQKKTAAAVIAAMLAGFAAAKAPEIDPALVDTLVAQIMQQADRHAEQSQKPDGQAIRND
                   10         20         30         40         50         60

70         80         90        100        110        120
    orf76a.pep AVRRLQTLEVLKNRALKEGLDKDKDVQNRFKIAEASFYAEEYVRFLERSETVSEDELHKF
               |||||||||||||||||||||||||||||||||||||||||||||||||||||:|::|
    orf76-1    AVRRLQTLEVLKNRALKEGLDKDKDVQNRFKIAEASFYAEEYVRFLERSETVSESALRQF
                   70         80         90        100        110        120

130        140        150        160        170        180
    orf76a.pep YEQQIRMIKLQQVSFATEEEARQAQQLLLKGLSFEGLMKRYPNDEQAFDGFIMAQQLPEP
               ||:|||||||||||||||||||||||||||||||||||||||||||||||||||||||||
    orf76-1    YERQIRMIKLQQVSFATEEEARQAQQLLLKGLSFEGLMKRYPNDEQAFDGFIMAQQLPEP
                  130        140        150        160        170        180

190        200        210        220        230        240
    orf76a.pep LASQFAAMNRGDVTRDPVKLGERYYLFKLSEVGKNPDAQPFELVRNQEQGLRQEKARLK
               ||||||:||||||||:|||||||||||||:|||||||||||||||||||:||||||||||
    orf76-1    LASQFAGMNRGDVTRNPVKLGERYYLFKLGAVGKNPDAQPFELVRNQLEQFLRQEKARLK
                  190        200        210        220        230        240

250
    orf76a.pep IDALLEENGVKPX
               |||||||||||||
    orf76-1    IDALLEENGVKPX
                  250
```

Furthermore, ORF76ng shows significant homology to a *B. subtilis* export protein precursor:

```
sp|P24327|PRSA_BACSU PROTEIN EXPORT PROTEIN PRSA
PRECURSOR >gi|98227|pir||S15269
33K lipoprotein - Bacillus subtilis >gi|39782 (X57271) 33 kDa lipoprotein
[Bacillus subtilis]
>gi|2226124|gnl|PID|e325181 (Y14077) 33 kDa lipoprotein [Bacillus subtilis]
>gi|2633331|gnl|PID|e1182997 (Z99109) molecular chaperonin
[Bacillus subtilis]
Length = 292
Score = 50.4 bits (118), Expect = 1e-05
Identities = 48/199 (24%), Positives = 82/199 (41%), Gaps = 32/199 (16%)

Query:  70 VLKNRALKEGLDK-----DKDVQNRFKIAEASF----------YAEEYVRFLERSETVSE  114
           VL    ++ LDK     DK++ N+ K   +            Y ++Y++   + E +++

Sbjct:  53 VLTQLVQEKVLDKKYKVSDKEIDNKLKEYKTQLGDQYTALEKQYGKDYLKEQVKYELLTQ  112

Query: 115 SA-----------LRQFYERQIRMIKLQQVSFATEEEARQAQQLLLKGLSFEGLMKRYPN  163
           A            +++++E    I+   + A ++ A + ++ L  KG   FE  L  K Y Sbjct: 113 KAAKDNIKVTDADIKEYWEGLKGKIRASHILVADKKTAEEVEKKLKKGEKFEDLAKEYST  172

Query: 164 DEQAFDG-----FIMAQQLPEPLASQFAAMNRGDVTRDPVKLGERYYLFKLSEVGKNPDA  218
             D  A  G        F  Q+ E +      + G+V+ DPVK   Y++  K  +E      D Sbjct: 173 DSSASKGGDLGWFAKEGQMDETFSKAAFKLKTGEVS-DPVKTQYGYHIIKKTEERGKYDD  231
```

```
Query: 219 QPFELVRNQLEQGLRQEKA                                         237
           EL    LEQ L    A
Sbjct: 232 MKKELKSEVLEQKLNDNAA                                         250
```

Based on this analysis, including the presence of a putative leader sequence and a RGD motif in the gonococcal protein, it was predicted that the proteins from *N. meningitidis* and *N. gonorrhoeae*, and their epitopes, could be useful antigens for vaccines or diagnostics, or for raising antibodies.

ORF76-1 (27.8 kDa) was cloned in the pET vector and expressed in *E. coli*, as described above. The products of protein expression and purification were analyzed by SDS-PAGE. FIG. 10A shows the results of affinity purification of the His-fusion protein, Purified His-fusion protein was used to immunise mice, whose sera were used for Western blot (FIG. 10B), ELISA (positive result), and FACS analysis (FIG. 10C). These experiments confirm that ORF76-1 is a surface-exposed protein, and that it is a useful immunogen.

Example 36

The following partial DNA sequence was identified in *N. meningitidis* <SEQ ID 303>:

```
   1 ATGAAAAAAT CTTTCCTTAC GCTTGTTCTG TATTCGTCTT TACTTACCGC
  51 CAGCGAAATT GCCTTACCCC TTGGAATTGG GGATTGAAAC CTTACCGGCG
 101 GCAAAAATTG CGGAAACGTT TGCGCTGACA TTTGTGATTG CTGCGCTGTA
 151 TCTGTTTGCG CGTAATAAGG TGACGCGTTT GTTGATTGCG GTGTTTTTTG
 201 CGTTCAGCAT TATTCGGAAC AATGTGCATT ACGCGGATTA TCAAAGCTGG
 251 ATGACG....  .......... ..........  .......... ..........
                                   //
1201 ..........  CAAACCGTAT TCGAGCAGCT GCAAAAGACT CCTGACGGCA
1251 ACTGGCTGTT TGCCTATACC TCCGATCATG GCCAGTATGT TCGCCAAGAT
1301 ATCTACAATC AAGGCACGGT GCAGCCCGAC AGCTATCTCG TGCCGCTAGT
1351 GTTGTACAGC CCGGATAAGG CCGTGCAACA GGCTGCCAAC CAGGCTTTTG
1401 CGCCTTGCGA GATTGCCTTC CATCAGCAGC TTTCAACGTT CCTGATTCAC
1451 ACGTTGGGCT ACGATATGCC GGTTTCAGGT TGTCGCGAAG GCTCGGTAAC
1501 GGGCAACCTG ATTACGGGTG ATGCAGGCAG CTTGAACATT CGCGACGGCA
1551 AGGCGGAATA TGTTTATCCG CAATGA
```

This corresponds to the amino acid sequence <SEQ ID 304; ORF81>:

```
  1 MKKSFLTLVL YSSLLTASEI AYPLELGIET LPAAKIAETF ALTFVIAALY
 51 LFARNKVTRL LIAVFFAFSI IANNVHYADY QSWMT.....  ..........
                                 //
401 ...QTVFEQL QKTPDGNWLF AYTSDHGQYV RQDIYNQGTV QPDSYLVPLV
451 LYSPDKAVQQ AANQAFAPCE IAFHQQLSTF LIHTLGYDMP VSGCREGSVT
501 GNLITGDAGS LNIRDGKAEY VYPQ*
```

Further work revealed the complete nucleotide sequence <SEQ ID 305>:

```
  1 ATGAAAAAAT CTTTCCTTAC GCTTGTTCTG TATTCGTCTT TACTTACCGC

51 CAGCGAAATT GCCTATCGCT TTGTATTTGG GATTGAAACC TTACCGGCGG

101 CAAAAATTGC GGAAACGTTT GCGCTGACAT TTGTGATTGC TGCGCTGTAT

151 CTGTTTGCGC GTTATAAGGT GACGCGTTTG TTGATTGCGG TGTTTTTTGC

201 GTTCAGCATT ATTGCCAACA ATGTGCATTA CGCGGTTTAT CAAAGCTGGA

251 TGACGGGCAT CAATTATTGG CTGATGCTGA AGAGGTTAC CGAAGTCGGC
```

-continued

```
 301 AGCGCGGGTG CGTCGATGTT GGATAAGTTG TGGCTGCCTG TGTTGTGGGG
 351 CGTGTTGGAA GTCATGTTGT TTTGCAGCCT TGCCAAGTTC CGCCGTAAGA
 401 CGCATTTTTC TGCCGATATA CTGTTTGCCT TCCTAATGCT GATGATTTTC
 451 GTGCGTTCGT TCGACACGAA ACAAGAGCAC GGTATTTCGC CCAAACCGAC
 501 ATACAGCCGC ATCAAAGCCA ATTATTTCAG CTTCGGTTAT TTTGTCGGAC
 551 GCGTGTTGCC GTATCAGTTG TTTGATTTAA GCAGGATTCC CGCCTTTAAG
 601 CAGCCTGCTC CAAGCAAAAT CGGGCAGGGC AGTGTTCAAA ATATCGTCCT
 651 GATTATGGGC GAAAGCGAAA GCGCGGCGCA TTTGAAGCTG TTTGGCTACG
 701 GACGCGAAAC TTCGCCGTTT TTAACCCGGC TGTCGCAAGC CGATTTTAAG
 751 CCGATTGTGA AACAAAGTTA TTCCGCAGGC TTTATGACTG CAGTGTCCCT
 801 GCCCAGTTTT TTCAATGCGA TACCGCACGC CAACGGCTTG AACAAATCA
 851 GCGGCGGCGA TACCAATATG TTCCGCCTCG CCAAAGAGCA GGGCTATGAA
 901 ACGTATTTTT ACAGCGCGCA GGCGGAAAAC GAGATGGCGA TTTTGAACTT
 951 AATCGGTAAG AAATGGATAG ACCATCTGAT TCAGCCGACG CAACTTGGCT
1001 ACGGCAACGG CGACAATATG CCCGATGAGA AGCTGCTGCC GTTGTTCGAC
1051 AAAATCAATT TGCAGCAGGG CAAGCATTTT ATCGTGTTGC ACCAACGCGG
1101 TTCGCACGCC CCATACGGCG CATTGTTGCA GCCTCAAGAT AAAGTATTCG
1151 GCGAAGCCGA TATTGTGGAT AAGTACGACA ACACCATCCA CAAAACCGAC
1201 CAAATGATTC AAACCGTATT CGAGCAGCTG CAAAAGCAGC CTGACGGCAA
1251 CTGGCTGTTT GCCTATACCT CCGATCATGG CCAGTATGTT CGCCAAGATA
1301 TCTACAATCA AGGCACGGTG CAGCCCGACA GCTATCTCGT GCCGCTAGTG
1351 TTGTACAGCC CGGATAAGGC CGTGCAACAG CTGCCAACC AGGCTTTTGC
1401 GCCTTGCGAG ATTGCCTTCC ATCAGCAGCT TTCAACGTTC CTGATTCACA
1451 CGTTGGGCTA CGATATGCCG GTTTCAGGTT GTCGCGAAGG CTCGGTAACG
1501 GGCAACCTGA TTACGGGTGA TGCAGGCAGC TTGAACATTC GCGACGGCAA
1551 GGCGGAATAT GTTTATCCGC AATGA
```

This corresponds to the amino acid sequence <SEQ ID 306; ORF81-1>:

```
  1 MKKSFLTLVL YSSLLTASEI AYRFVFGIET LPAAKIAETF ALTFVIAALY
 51 LFARYKVTRL LIAVFFAFSI IANNVHYAVY QSWMTGINYW LMLKEVTEVG
101 SAGASMLDKL WLPVLWGVLE VMLFCSLAKF RRKTHFSADI LFAFLMLMIF
151 VRSFDTKQEH GISPKPTYSR IKANYFSFGY FVGRVLPYQL FDLSRIPAFK
201 QPAPSKIGQG SVQNIVLIMG ESESAAHLKL FGYGRETSPF LTRLSQADFK
251 PIVKQSYSAG FMTAVSLPSF FNAIPHANGL EQISGGDTNM FRLAKEQGYE
301 TYFYSAQAEN EMAILNLIGK KWIDHLIQPT QLGYGNGDNM PDEKLLPLFD
351 KINLQQGKHF IVLHQRGSHA PYGALLQPQD KVFGEADIVD KYDNTIHKTD
401 QMIQTVFEQL QKQPDGNWLF AYTSDHGQYV RQDIYNQGTV QPDSYLVPLV
451 LYSPDKAVQQ AANQAFAPCE IAFHQQLSTF LIHTLGYDMP VSGCREGSVT
501 GNLITGDAGS LNIRDGKAEY VYPQ*
```

Computer analysis of this amino acid sequence gave the following results:

Homology with a Predicted ORF from *N. meningitidis* (Strain A)

ORF81 shows 84.7% identity over a 85aa overlap and 99.2% identity over a 121aa overlap with an ORF (ORF81a) from strain A of *N. meningitidis*:

```
                  10         20         30         40         50         60
orf81.pep  MKKSFLTLVLYSSLLTASEIAYPLELGIETLPAAKIAETFALTFVIAALYLFARNKVTRL
           ||||:::| ||||||||||||| : :||||||||||:|||||||||||||||| |:|||
orf81a     MKKSLFVLFLYSSLLTASEIAYRFVFGIETLPAAKMAETFALTFVIAALYLFARYKATRL
                  10         20         30         40         50         60

70         80         90        100        110        120
orf81.pep  LIAVFFAFSIIANNVHYADYQSWMT
           ||||||||||||||||||| ||||:|
orf81a     LIAVFFAFSIIANNVHYAVYQSWITGINYWLMLKEITEVGGAGASMLDKLWLPALWGVLE
                  70         80         90        100        110        120
                                //
                                               120        130        140
orf81.pep                                  QTVFEQLQKTPDGNWLFAYTSDHGQYVRQD
                                           ||||||||| ||||||||||||||||||||
orf81a     IPHANGLEQISGGDIVDKYDNTIHKTDQMIQTVFEQLQKQPDGNWLFAYTSDHGQYVRQD
                 280        290        300        310        320        330

150        160        170        180        190        200
orf81.pep  IYNQGTVQPDSYLVPLVLYSPDKAVQQAANQAFAPCEIAFHQQLSTFLIHTLGYDMPVSG
           ||||||||||||||||||||||||||||||||||||||||||||||||||||||||||||
orf81a     IYNQGTVQPDSYLVPLVLYSPDKAVQQAANQAFAPCEIAFHQQLSTFLIHTLGYDMPVSG
                 340        350        360        370        380        390

210        220        230
orf81.pep  CREGSVTGNLITGDAGSLNIRDGKAEYVYPQX
           |||||||||||||||||||||||||||||||
orf81a     CREGSVTGNLITGDAGSLNIRDGKAEYVYPQX
                 400        410        420
```

The complete length ORF81a nucleotide sequence <SEQ ID 307> is:

```
  1  ATGAAAAAAT CCCTTTTCGT TCTCTTTCTG TATTCGTCCC TACTTACTGC
 51  CAGCGAAATT GCTTATCGCT TTGTATTCGG AATTGAAACC TTACCGGCTG
101  CAAAAATGGC AGAAACGTTT GCGCTGACAT TTGTGATTGC TGCGCTGTAT
151  CTGTTTGCGC GTTATAAGGC AACGCGTTTG TTGATTGCGG TGTTTTTCGC
201  GTTCAGCATT ATTGCCAACA ATGTGCATTA CGCGGTTTAT CAAAGCTGGA
251  TAACGGGCAT TAATTATTGG CTGATGCTGA AAGAGATTAC CGAAGTTGGC
301  GGCGCAGGGG CGTCGATGTT GGATAAGTTG TGGCTGCCTG CGTTGTGGGG
351  CGTGTTGGAA GTCATGTTGT TTTGCAGCCT TGCCAAGTTC CGCCGTAAGA
401  CGCATTTTTC TGCCGATATA CTGTTTGCCT TCCTAATGCT GATGATTTTC
451  GTGCGTTCGT TCGACACGAA ACAAGAACAC GGTATTTCGC CCAAACCGAC
501  ATACAGCCGC ATCAAAGCCA ATTATTTCAG CTTCGGTTAT TTTGTCGGAC
551  GCGTGTTGCC GTATCAGTTG TTTGATTTAA GCAAGATTCC TGTGTTCAAA
601  CAGCCTGCTC CAAGCAGAAT CGGGCAAGGC AGTATTCAAA ATATCGTCCT
651  GATTATGGGC GAAAGCGAAA GCGCGGCGCA TTTGAAATTG TTTGGCTACG
701  GGCGCGAAAC TTCGCCGTTT TTGACCCAGC TTTCGCAAGC CGATTTTAAG
751  CCGATTGTGA AACAAAGTTA TTCCGCAGGC TTTATGACGG CAGTATCCCT
801  GCCCAGTTTC TTTAACGTCA TACCGCATGC CAACGGCTTG GAACAAATCA
851  GCGGCGGCGA TATTGTGGAT AAGTACGACA ACACCATCCA CAAAACCGAC
901  CAAATGATTC AAACCGTATT CGAGCAGCTG CAAAAGCAGC CTGACGGCAA
```

-continued

```
 951 CTGGCTGTTT GCCTATACCT CCGATCATGG CCAGTATGTT CGCCAAGATA
1001 TCTACAATCA AGGCACGGTG CAGCCCGACA GCTATCTCGT GCCGCTGGTG
1051 TTGTACAGCC CGGATAAGGC CGTGCAACAG GCTGCCAACC AGGCTTTTGC
1101 GCCTTGCGAG ATTGCCTTCC ATCAGCAGCT TTCAACGTTC CTGATTCACA
1151 CGTTGGGCTA CGATATGCCG GTTTCAGGTT GTCGCGAAGG CTCGGTAACG
1201 GGCAACCTGA TTACGGGTGA TGCAGGCAGC TTGAACATTC GCGACGGCAA
1251 GGCGGAATAT GTTTATCCGC AATGA
```

This encodes a protein having amino acid sequence <SEQ ID 308>:

```
  1 MKKSLFVLFL YSSLLTASEI AYRFVFGIET LPAAKMAETF ALTFVIAALY
 51 LFARYKATRL LIAVFFAFSI IANNVHYAVY QSWITGINYW LMLKEITEVG
101 GAGASMLDKL WLPALWGVLE VMLFCSLAKF RRKTHFSADI LFAFLMLMIF
151 VRSFDTKQEH GISPKPTYSR IKANYFSFGY FVGRVLPYQL FDLSKIPVFK
201 QPAPSRIGQG SIQNIVLIMG ESESAAHLKL FGYGRETSPF LTQLSQADFK
251 PIVKQSYSAG FMTAVSLPSF FNVIPHANGL EQISGGDIVD KYDNTIHKTD
301 QMIQTVFEQL QKQPDGNWLF AYTSDHGQYV RQDIYNQGTV QPDSYLVPLV
351 LYSPDKAVQQ AANQAFAPCE IAFHQQLSTF LIHTLGYDMP VSGCREGSVT
401 GNLITGDAGS LNIRDGKAEY VYPQ*
```

ORF81a and ORF81-1 show 77.9% identity in 524 aa overlap:

```
                   10         20         30         40         50         60
orf81a.pep MKKSLFVLFLYSSLLTASEIAYRFVFGIETLPAAKMAETFALTFVIAALYLFARYKATRL
           ||||:::| |||||||||||||||||||||||||:||||||||||||||||||||:|||
orf81-1    MKKSFLTLVLYSSLLTASEIAYRFVFGIETLPAAKIAETFALTFVIAALYLFARYKVTRL
                   10         20         30         40         50         60

70         80         90        100        110        120
orf81a.pep LIAVFFAFSIIANNVHYAVYQSWITGINYWLMLKEITEVGGAGASMLDKLWLPALWGVLE
           |||||||||||||||||||||||:|||||||||||:||||:||||||||||||:|||||
orf81-1    LIAVFFAFSIIANNVHYAVYQSWMTGINYWLMLKEVTEVGSAGASMLDKLWLPVLWGVLE
                   70         80         90        100        110        120

130        140        150        160        170        180
orf81a.pep VMLFCSLAKFRRKTHFSADILFAFLMLMIFVRSFDTKQEHGISPKPTYSRIKANYFSFGY
           ||||||||||||||||||||||||||||||||||||||||||||||||||||||||||||
orf81-1    VMLFCSLAKFRRKTHFSADILFAFLMLMIFVRSFDTKQEHGISPKPTYSRIKANYFSFGY
                  130        140        150        160        170        180

190        200        210        220        230        240
orf81a.pep FVGRVLPYQLFDLSKIPVFKQPAPSRIGQGSIQNIVLIMGESESAAHLKLFGYGRETSPF
           |||||||||||||:|:|||||||||||:|||:||||||||||||||||||||||||||
orf81-1    FVGRVLPYQLFDLSRIPAFKQPAPSKIGQGSVQNIVLIMGESESAAHLKLFGYGRETSPF
                  190        200        210        220        230        240

250        260        270        280
orf81a.pep LTQLSQADFKPIVKQSYSAGFMTAVSLPSFFNVIPHANGLEQISGGD-------------
           ||:||||||||||||||||||||||||||||:|||||||||||||||
orf81-1    LTRLSQADFKPIVKQSYSAGFMTAVSLPSFFNAIPHANGLEQISGGDTNMFRLAKEQGYE
                  250        260        270        280        290        300 orf81a.pep ------------------------------------------------------------
orf81-1    TYFYSAQAENEMAILNLIGKKWIDHLIQPTQLGYGNGDNMPDEKLLPLFDKINLQQGKHF
                  310        320        330        340        350        360

290        300        310        320
orf81a.pep ------------------------IVDKYDNTIHKTDQMIQTVFEQLQKQPDGNWLF
                                   ||||||||||||||||||||||||||||||||
orf81-1    IVLHQRGSHAPYGALLQPDKVFGEADIVDKYDNTIHKTDQMIQTVFEQLQKQPDGNWLF
                  370        380        390        400        410        420

330        340        350        360        370        380
orf81a.pep AYTSDHGQYVRQDIYNQGTVQPDSYLVPLVLYSPDKAVQQAANQAFAPCEIAFHQQLSTF
           ||||||||||||||||||||||||||||||||||||||||||||||||||||||||||||
orf81-1    AYTSDHGQYVRQDIYNQGTVQPDSYLVPLVLYSPDKAVQQAANQAFAPCEIAFHQQLSTF
                  430        440        450        460        470        480
```

```
          390       400       410       420
orf81a.pep LIHTLGYDMPVSGCREGSVTGNLITGDAGSLNIRDGKAEYVYPQX
           ||||||||||||||||||||||||||||||||||||||||||||
orf81-1    LIHTLGYDMPVSGCREGSVTGNLITGDAGSLNIRDGKAEYVYPQX
          490       500       510       420
```

Homology with a Predicted ORF from *N. gonorrhoeae*

The aligned aa sequences of ORF81 and a predicted ORF (ORF81.ng) from *N. gonorrhoeae* of the N- and C-termini show 82.4% and 97.5% identity in 85 and 121 overlap, respectively:

```
orf81.pep MKKSFLTLVLYSSLLTASEIAYPLELGIETLPAAKIAETFALTFVIAALYLFARNKVTRL  60
          ||||:::| ||||||||||||| : :|||||||||:|||||||:||||||||| |::||
orf81ng   MKKSLFVLFLYSSLLTASEIAYRFVFGIETLPAAKMAETFALTFMIAALYLFARYKASRL  60 orf81.pep LIAVFFAFSIIANNVHYADYQSWMT                                    85
          ||||||||||:|||||||| ||||||
orf81ng   LIAVFFAFSMIANNVHYAVYQSWMTGINYWLMLKEVTEVGSAGASMLDKLWLPALWGVAE 120
                                   // orf81.pep                                 QTVFEQLQKTPDGNWLFAYTSDHGQYVRQD 433
                                          |||||||||| ||||||||||||||||||
orf81ng   ALLQPQDKVFGEADIVDKYDNTIHKTDQMIQTVFEQLQKQPDGNWLFAYTSDHGQYVRQD 433 orf81.pep IYNQGTVQPDSYLVPLVLYSPDKAVQQAANQAFAPCEIAFHQQLSTFLIHTLGYDMPVSG 493
          ||||||||||||:|||||||||||||||||||||||||||||||||||||||||||||||
orf81ng   IYNQGTVQPDSYIVPLVLYSPDKAVQQAANQAFAPCEIAFHQQLSTFLIHTLGYDMPVSG 493 orf81.pep CREGSVTGNLITGDAGSLNIRDGKAEYVYPQ                              524
          ||||||||||||||||||||||:||||||||
orf81ng   CREGSVTGNLITGDAGSLNIRNGKAEYVYPQ                              524
```

The complete length ORF81ng nucleotide sequence <SEQ ID 309> is:

```
   1 ATGAAAAAAT CCCTTTTCGT TCTCTTTCTG TATTCATCCC TACTTACCGC
  51 CAGCGAAATC GCCTATCGCT TTGTATTCGG AATTGAAACC TTACCGGCTG
 101 CAAAAATGGC GGAAACGTTT GCGCTGACAT TTATGATTGC TGCGCTGTAT
 151 CTGTTTGCGC GTTATAAGGC TTCGCGGCTG CTGATTGCGG TGTTTTTCGC
 201 GTTCAGCATG ATTGCCAACA ATGTGCATTA CGCGGTTTAT CAAAGCTGGA
 251 TGACGGGTAT TAACTATTGG CTGATGCTGA AAGAGGTTAC CGAAGTCGGC
 301 AGCGCGGGCG CGTCGATGTT GGATAAGTTG TGGCTGCCTG CTTTGTGGGG
 351 CGTGGCGGAA GTCATGTTGT TTTGCAGCCT TGCCAAGTTC CGCCGTAAGA
 401 CGCATTTTTC TGCCGATATA CTGTTTGCCT TCCTAATGCT GATGATTTTC
 451 GTGCGTTCGT TCGACACGAA ACAAGAGCAC GGTATTTCGC CCAAACCGAC
 501 ATACAGCCGC ATCAAAGCCA ATTATTTCAG CTTCGGTTAT TTTGTCGGGC
 551 GCGTGTTGCC GTATCAGTTG TTTGATTTAA GCAAGATCCC TGTGTTCAAA
 601 CAGCCTGCTC CAAGCAAAAT CGGGCAAGGC AGTATTCAAA ATATCGTCCT
 651 GATTATGGGC GAAAGCGAAA GCGCGGCGCA TTTGAAATTG TTTGGTTACG
 701 GGCGCGAAAC TTCGCCGTTT TTAACCCGGC TGTCGCAAGC CGATTTTAAG
 751 CCGATTGTGA AACAAAGTTA TTCCGCAGGC TTTATGACGG CAGTATCCCT
 801 GCCCAGTTTC TTTAACGTCA TACCGCACGC CAACGGCTTG AACAAATCA
 851 GCGGCGGCGA TACCAATATG TTCCGCCTCG CCAAAGAGCA GGGCTATGAA
 901 ACGTATTTTT ACAGTGCCCA GGCTGAAAAC CAAATGGCAA TTTTGAACTT
 951 AATCGGTAAG AAATGGATAG ACCATCTGAT TCAGCCGACG CAACTTGGCT
1001 ACGGCAACGG CGACAATATG CCCGATGAGA AGCTGCTGCC GTTGTTCGAC
```

-continued

```
1051 AAAATCAATT TGCAGCAGGG CAGGCATTTT ATCGTGTTGC ACCAACGCGG

1101 TTCGCACGCC CCATACGGCG CATTGTTGCA GCCTCAAGAT AAAGTATTCG

1151 GCGAAGCCGA TATTGTGGAT AAGTACGACA ACACCATCCA CAAAACCGAC

1201 CAAATGATTC AAACCGTATT CGAGCAGCTG CAAAAGCAGC CTGACGGCAA

1251 CTGGCTGTTT GCCTATACCT CCGATCATGG CCAGTATGTG CGCCAAGATA

1301 TCTACAATCA AGGCACGGTG CAGCCCGACA GCTATATTGT GCCTCTGGTT

1351 TTGTACAGCC CGGATAAGGC CGTGCAACAG CTGCCAACC AGGCTTTTGC

1401 GCCTTGCGAG ATTGCCTTCC ATCAGCAGCT TTCAACGTTC CTGATTCACA

1451 CGTTGGGCTA CGATATGCCG GTTTCAGGTT GTCGCGAAGG CTCGGTAACA

1501 GGCAACCTGA TTACGGGCGA TGCAGGCAGC TTGAACATTC GCAACGGCAA

1551 GGCGGAATAT GTTTATCCGC AATAA
```

This encodes a protein having amino acid sequence <SEQ ID 310>:

```
  1 MKKSLFVLFL YSSLLTASEIAYRFVFGIET LPAAKMAETF ALTFMIAALY

51 LFARYKASRL LIAVFFAFSM IANNVHYAVY QSWMTGINYW LMLKEVTEVG

101 SAGASMLDKL WLPALWGVAE VMLFCSLAKF RRKTHFSADI LFAFLMLMIF

151 VRSFDTKQEH GISPKPTYSR IKANYFSFGY FVGRVLPYQL FDLSKIPVFK

201 QPAPSKIGQG SIQNIVLIMG ESESAAHLKL FGYGRETSPF LTRLSQADFK

251 PIVKQSYSAG FMTAVSLPSF FNVIPHANGL EQISGGDTNM FRLAKEQGYE

301 TYFYSAQAEN QMAILNLIGK KWIDHLIQPT QLGYGNGDNM PDEKLLPLFD

351 KINLQQGRHF IVLHQRGSHA PYGALLQPQD KVFGEADIVD KYDNTIHKTD

401 QMIQTVFEQL QKQPDGNWLF AYTSDHGQYV RQDIYNQGTV QPDSYIVPLV

451 LYSPDKAVQQ AANQAFAPCE IAFHQQLSTF LIHTLGYDMP VSGCREGSVT

501 GNLITGDAGS LNIRNGKAEY VYPQ*
```

ORF81ng and ORF81-1 show 96.4% identity in 524 aa overlap:

```
                    10         20         30         40         50         60
orf81ng-1.pep  MKKSLFVLFLYSSLLTASEIAYRFVFGIETLPAAKMAETFALTFMIAALYLFARYKASRL
               ||||:::|  ||||||||||||||||||||||||||:||||||:|||||||||||:||
orf81-1        MKKSFLTLVLYSSLLTASEIAYRFVFGIETLPAAKIAETFALTFVIAALYLFARYKVTRL
                    10         20         30         40         50         60

70         80         90        100        110        120
orf81ng-1.pep  LIAVFFAFSMIANNVHYAVYQSWMTGINYWLMLKEVTEVGSAGASMLDKLWLPALWGVAE
               ||||||||||:|||||||||||||||||||||||||||||||||||||||||:||| |
orf81-1        LIAVFFAFSIIANNVHYAVYQSWMTGINYWLMLKEVTEVGSAGASMLDKLWLPVLWGVLE
                    70         80         90        100        110        120

130        140        150        160        170        180
orf81ng-1.pep  VMLFCSLAKFRRKTHFSADILFAFLMLMIFVRSFDTKQEHGISPKPTYSRIKANYFSFGY
               ||||||||||||||||||||||||||||||||||||||||||||||||||||||||||||
orf81-1        VMLFCSLAKFRRKTHFSADILFAFLMLMIFVRSFDTKQEHGISPKPTYSRIKANYFSFGY
                   130        140        150        160        170        180

190        200        210        220        230        240
orf81ng-1.pep  FVGRVLPYQLFDLSKIPVFKQPAPSKIGQGSIQNIVLIMGESESAAHLKLFGYGRETSPF
               ||||||||||||||:||:||||||||||||||:|||||||||||||||||||||||||||
orf81-1        FVGRVLPYQLFDLSRIPAFKQPAPSKIGQGSVQNIVLIMGESESAAHLKLFGYGRETSPF
                   190        200        210        220        230        240

250        260        270        280        290        300
orf81ng-1.pep  LTRLSQADFKPIVKQSYSAGFMTAVSLPSFFNVIPHANGLEQISGGDTNMFRLAKEQGYE
               ||||||||||||||||||||||||||||||||:|||||||||||||||||||||||||||
orf81-1        LTRLSQADFKPIVKQSYSAGFMTAVSLPSFFNAIPHANGLEQISGGDTNMFRLAKEQGYE
                   250        260        270        280        290        300
```

```
             310        320        330        340        350        360
orf81ng-1.pep TYFYSAQAENQMAILNLIGKKWIDHLIQPTQLGYGNGDNMPDEKLLPLFDKINLQQGRHF
              ||||||||||:|||||||||||||||||||||||||||||||||||||||||||||:||
orf81-1       TYFYSAQAENEMAILNLIGKKWIDHLIQPTQLGYGNGDNMPDEKLLPLFDKINLQQGKHF
             310        320        330        340        350        360

370        380        390        400        410        420
orf81ng-1.pep IVLHQRGSHAPYGALLQPQDKVFGEADIVDKYDNTIHKTDQMIQTVFEQLQKQPDGNWLF
              ||||||||||||||||||||||||||||||||||||||||||||||||||||||||||||
orf81-1       IVLHQRGSHAPYGALLQPQDKVFGEADIVDKYDNTIHKTDQMIQTVFEQLQKQPDGNWLF
             370        380        390        400        410        420

430        440        450        460        470        480
orf81ng-1.pep AYTSDHGQYVRQDIYNQGTVQPDSYIVPLVLYSPDKAVQQAANQAFAPCEIAFHQQLSTF
              |||||||||||||||||||||||||||:||||||||||||||||||||||||||||||||
orf81-1       AYTSDHGQYVRQDIYNQGTVQPDSYLVPLVLYSPDKAVQQAANQAFAPCEIAFHQQLSTF
             430        440        450        460        470        480

490        500        510        520
orf81ng-1.pep LIHTLGYDMPVSGCREGSVTGNLITGDAGSLNIRNGKAEYVYPQX
              |||||||||||||||||||||||||||||||||:|||||||||||
orf81-1       LIHTLGYDMPVSGCREGSVTGNLITGDAGSLNIRDGKAEYVYPQX
             490        500        510        520
```

Furthermore, ORF81ng shows significant homology to an *E. coli* OMP:

```
gi|1256380 (050906) outer membrane adherence protein-associated
protein [E. coli] Length = 547
Score = 87.4 bits (213), Expect = 2e-16
Identities = 122/468 (26%), Positives = 198/468 (42%),
Gaps = 70/468 (14%)

Query:  25 VFGIETLPAAKMAETFA-LTFMIAALYLFARYKAS--RLLIAVFFAFSMIANNVHYAVYQ   81
           VFGI  L A+   A    L F +  + +  R +    RLL+A F    + A ++  ++Y
Sbjct:  29 VFGITNLVASSGAHMVQRLLFFVLTILVVKRISSLPLRLLVAAPFVL-LTAADMSISLY-  86

Query:  82 SWMT-------GINYWLMLKEVTEVGSAGASMLDKLWLPALWGVAEVMLFCSLAKFRRKT  134
           SW T       G    ++  + EV    A ML ++ P L   A + L          +
Sbjct:  87 SWCTFGTTFNDGFAISVLQSDPDEV----AKMLG-MYSPYLCAFAFLSLLFLAVIIKYDV  141

Query: 135 HFSADILFAFLMLMIFVRSF         DTKQEHGISPKPTYSRIKAN--YFSFGYFVG  183
                +   L+L++     S         D K  ++  SP       SR     +F+    YF
Sbjct: 142 SLPTKKVTGILLLIVISGSLFSACQFAYKDAKNKNAFSPYILASRFATYTPFFNLNYFAL  201

Query: 184 RVLPYQ--LFDLSKIPVFKQPAPSKIGQGSIQNIVLIMGESESAAHLKLFGYGRETSPFL  241
                +Q   L   + +P F+         +    I   VLI+GES    ++ L+GY R T+P +
Sbjct: 202 AAKEHQRLLSIANTVPYFQL----SVRDTGIDTYVLIVGESVRVDNMSLYGYTRSTTPQV  257

Query: 242 TRLSQADFKPIVKQSYSAGFMTAVSLP---SFFNVIPHANGLEQISGGDTNMFRLAKEQG  298
           +Q     + Q+ S   TA+S+P    +V+ H       I         N+ +A +  G
Sbjct: 258 E--AQRKQIKLFNQAISGAPYTALSVPLSLTADSVLSH-----DIHNYPDNIINMANQAG  310

Query: 299 YETYFYSAQA---ENQMAILNLIGKKWIDHLIQPTQLGYGNGDNMPDEKLLPLFDKINLQ  355
           ++T++ S+Q+   +N  A+  ++             ++   +  Y  G    DE LLP     +           Q
Sbjct: 311 FQTFWLSSQSAFRQNGTAVTSI--------AMRAMETVYVRGF---DELLLPHLSQALQQ  359

Query: 356 --QGRHFIVLHQRGSHAPYGALLQPQDKVFGEADIVDK-YDNTIHKTDQMIQTVFEQLQK  412
             Q +   IVLH  GSH P +         VF   D  D    YDN+IH  TD ++     VFE L+
Sbjct: 360 NTQQKKLIVLHLNGSHEPACSAYPQSSAVFQPQDDQACYDNSIHYTDSLLGQVFELLK-   418

Query: 413 QPDGNWLFAYTSDHG---QYVRQDIYNQG--TVQPDSYIVPL-VLYSP            454
              D       Y +DHG    ++++Y  G          +Y VP+ +  YSP
Sbjct: 419 --DRRASVMYFADHGLERDPTKKNVYFHGGREASQQAYHVPMFIWYSP            464
```

Based on this analysis, including the presence of a putative leader sequence (double-underlined) and several putative transmembrane domains (single-underlined) in the gonococcal protein, it is predicted that the proteins from *N. meningitidis* and *N. gonorrhoeae*, and their epitopes, could be useful antigens for vaccines or diagnostics, or for raising antibodies.

Example 37

The following partial DNA sequence was identified in *N. meningitidis* <SEQ ID 311>:

```
  1...ACCCTGCTCC TCTTCATCCC CCTCGTCCTC ACAC.GTGCG GCACACTGAC

51   CGGCATACTC GCCCaCGGCG GCGGCAAACG CTTTGCCGTC GAACAAGAAC

101   TCGTCGCCGC ATCGTCCCGC GCCGCCGTCA AGAAATGGA TTTGTCCGCC 151   yTAAAAGGAC GCAAAGCCGC CyTTTACGTC TCCGTTATGG GCGACCAAGG

201   TTCGGGCAAC ATAAGCGGCG GACGCTACTC TATCGACGCA CTGATACGCG

251   GCGGCTACCA CAACAACCCC GAAAGTGCCA CCCAATACAG CTACCCCGCC

301   TACGACACTA CCGCCACCAC CAAATCCGAC GCGCTCTCCA GCGTAACCAC

351   TTCCACATCG CTTTTGAACG CCCCCGCCGC CGyCyTGACG AAAAACAGCG

401   GACGCAAAGG CGAACGcTCC GCCGGACTGT CCGTCAACGG CACGGGCGAC

451   TACCGCAACG AAACCCTGCT CGCCAACCCC CGCGACGTTT CCTTCCTGAC

501   CAACCTCATC CAAACCGTCT TCTACCTGCG CGGCATCGAA GTCgTACCGC

551   CCGrATACGC CGACACCGAC GTATTCGTAA CCGTCGACGT A...
                                                         25
```

This corresponds to the amino acid sequence <SEQ ID 312; ORF83>:

```
  1..TLLLFIPLVL TXCGTLTGIL AHGGGKRFAV EQELVAASSR AAVKEMDLSA

51   LKGRKAAXYV SVMGDQGSGN ISGGRYSIDA LIRGGYHNNP ESATQYSYPA

101   YDTTATTKSD ALSSVTTSTS LLNAPAAXLT KNSGRKGERS AGLSVNGTGD

151   YRNETLLANP RDVSFLTNLI QTVFYLRGIE VVPPXYADTD VFVTVDV..
```

Further work revealed the complete nucleotide sequence <SEQ ID 313>:

```
  1 ATGAAAACCC TGCTCCTCCT CATCCCCCTC GTCCTCACAG CCTGCGGCAC

51 ACTGACCGGC ATACCCGCCC ACGGCGGCGG CAAACGCTTT GCCGTCGAAC

101 AAGAACTCGT CGCCGCATCG TCCCGCGCCG CCGTCAAAGA AATGGATTTG

151 TCCGCCCTAA AAGGACGCAA AGCCGCCCTT TACGTCTCCG TTATGGGCGA

201 CCAAGGTTCG GGCAACATAA GCGGCGGACG CTACTCTATC GACGCACTGA

251 TACGCGGCGG CTACCACAAC AACCCCGAAA GTGCCACCCA ATACAGCTAC

301 CCCGCCTACG ACACTACCGC CACCACCAAA TCCGACGCGC TCTCCAGCGT

351 AACCACTTCC ACATCGCTTT TGAACGCCCC CGCCGCCGCC CTGACGAAAA

401 ACAGCGGACG CAAAGGCGAA CGCTCCGCCG GACTGTCCGT CAACGGCACG

451 GGCGACTACC GCAACGAAAC CCTGCTCGCC AACCCCCGCG ACGTTTCCTT

501 CCTGACCAAC CTCATCCAAA CCGTCTTCTA CCTGCGCGGC ATCGAAGTCG

551 TACCGCCCGA ATACGCCGAC ACCGACGTAT TCGTAACCGT CGACGTATTC

601 GGCACCGTCC GCAGCCGTAC CGAACTGCAC CTCTACAACG CCGAAACCCT

651 TAAAGCCCAA ACCAAGCTCG AATATTTCGC CGTTGACCGC GACAGCCGGA

701 AACTGCTGAT TACCCCTAAA ACCGCCGCCT ACGAATCCCA ATACCAAGAA

751 CAATACGCCC TTTGGACCGG CCCTTACAAA GTCAGCAAAA CCGTCAAAGC

801 CTCAGACCGC CTGATGGTCG ATTTCTCCGA CATTACCCCC TACGGCGACA
```

```
851 CAACCGCCCA AAACCGTCCC GACTTCAAAC AAAACAACGG TAAAAAACCC

901 GATGTCGGCA ACGAAGTCAT CCGCCGCCGC AAAGGAGGAT AA
```

This corresponds to the amino acid sequence <SEQ ID 314; ORF83-1>:

```
  1 MKTLLLLIPL VLTACGTLTG IPAHGGGKRF AVEQELVAAS SRAAVKEMDL

51 SALKGRKAAL YVSVMGDQGS GNISGGRYSI DALIRGGYHN NPESATQYSY

101 PAYDTTATTK SDALSSVTTS TSLLNAPAAA LTKNSGRKGE RSAGLSVNGT

151 GDYRNETLLA NPRDVSFLTN LIQTVFYLRG IEVVPPEYAD TDVFVTVDVF

201 GTVRSRTELH LYNAETLKAQ TKLEYFAVDR DSRKLLITPK TAAYESQYQE

251 QYALWTGPYK VSKTVKASDR LMVDFSDITP YGDTTAQNRP DFKQNNGKKP

301 DVGNEVIRRR KGG*
```

Computer analysis of this amino acid sequence gave the following results:

Homology with a Predicted ORF from *N. meningitidis* (Strain A)

ORF83 shows 96.4% identity over a 197aa overlap with an ORF (ORF83a) from strain A of *N. meningitidis*:

```
                    10         20         30         40         50
    orf83.pep   TLLLFIPLVLTXCGTLTGILAHGGGKRFAVEQELVAASSRAAVKEMDLSALKGRKAAX
                ||| :|||||| |||||| |||||||||||||||||||||||||||||||||||||||
    orf83a      MKTLLXLIPLVLTACGTLTGIPAHGGGKRFAVEQELVAASSRAAVKEMDLSALKGRKAAL
                    10         20         30         40         50         60
                   60         70         80         90        100        110
    orf83.pep   YVSVMGDQGSGNISGGRYSIDALIRGGYHNNPESATQYSYPAYDTTATTKSDALSSVTTS
                ||||||||||||||||||||||||||||||||||||||||||||||||||||||||||||
    orf83a      YVSVMGDQGSGNISGGRYSIDALIRGGYHNNPESATQYSYPAYDTTATTKSDALSSVTTS
                       70         80         90        100        110        120
                  120        130        140        150        160        170
    orf83.pep   TSLLNAPAAXLTKNSGRKGERSAGLSVNGTGDYRNETLLANPRDVSFLTNLIQTVFYLRG
                ||||||||| ||||||||||||||||||||||||||||||||||||||||||||||||||
    orf83a      TSLLNAPAAALTKNSGRKGERSAGLSVNGTGDYRNETLLANPRDVSFLTNLIQTVFYLRG
                       130        140        150        160        170        180
                  180        190
    orf83.pep   IEVVPPXYADTDVFVTVDV
                |||||| |||||||||||||
    orf83a      IEVVPPEYADTDVFVTVDVFGTVRSRTELHLYNAETLKAQTKLEYFAVDRDSRKLLIAPK
                       190        200        210        220        230        240
```

The complete length ORF83a nucleotide sequence <SEQ ID 315> is:

```
  1 ATGAAAACCC TGCTCNTCCT CATCCCCCTC GTCCTCACAG CCTGCGGCAC

51 ACTGACCGGC ATACCCGCCC ACGGCGGCGG CAAACGCTTT GCCGTCGAAC

101 AAGAACTCGT CGCCGCATCG TCCCGCGCCG CCGTCAAAGA AATGGACTTG

151 TCCGCCCTGA AAGGACGCAA AGCCGCCCTT TACGTCTCCG TTATGGGCGA

201 CCAAGGTTCG GGCAACATAA GCGGCGGACG CTACTCTATC GACGCACTGA

251 TACGCGGCGG CTACCACAAC AACCCCGAAA GTGCCACCCA ATACAGCTAC

301 CCCGCCTACG ACACTACCGC CACCACCAAA TCCGACGCGC TCTCCAGCGT

351 AACCACTTCC ACATCGCTTT TGAACGCCCC CGCCGCCGCC CTGACGAAAA

401 ACAGCGGACG CAAAGGCGAA CGCTCCGCCG GACTGTCCGT CAACGGCACG
```

```
451 GGCGACTACC GCAACGAAAC CCTGCTCGCC AACCCCCGCG ACGTTTCCTT

501 CCTGACCAAC CTCATCCAAA CCGTCTTCTA CCTGCGCGGC ATCGAAGTCG

551 TACCGCCCGA ATACGCCGAC ACCGACGTAT TCGTAACCGT CGACGTATTC

601 GGCACCGTCC GCAGCCGCAC CGAACTGCAC CTCTACAACG CCGAAACCCT

651 TAAAGCCCAA ACCAAGCTCG AATATTTCGC CGTTGACCGC GACAGCCGGA

701 AACTGCTGAT TGCCCCTAAA ACCGCCGCCT ACGAATCCCA ATACCAAGAA

751 CAATACGCCC TCTGGATGGG ACCTTACAGC GTCGGCAAAA CCGTCAAAGC

801 CTCAGACCGC CTGATGGTCG ATTTCTCCGA CATCACCCCC TACGGCGACA

851 CAACCGCCCA AAACCGTCCC GACTTCAAAC AAAACAACGG TAAAAAACCC

901 GATGTCGGCA ACGAAGTCAT CCGCCGCCGC AAAGGAGGAT AA
```

This encodes a protein having amino acid sequence <SEQ ID 316>:

```
  1 MKTLLXLIPL VLTACGTLTG IPAHGGGKRF AVEQELVAAS SRAAVKEMDL

51 SALKGRKAAL YVSVMGDQGS GNISGGRYSI DALIRGGYHN NPESATQYSY

101 PAYDTTATTK SDALSSVTTS TSLLNAPAAA LTKNSGRKGE RSAGLSVNGT

151 GDYRNETLLA NPRDVSFLTN LIQTVFYLRG IEVVPPEYAD TDVFVTVDVF

201 GTVRSRTELH LYNAETLKAQ TKLEYFAVDR DSRKLLIAPK TAAYESQYQE

251 QYALWMGPYS VGKTVKASDR LMVDFSDITP YGDTTAQNRP DFKQNNGKKP

301 DVGNEVIRRR KGG*
```

ORF83a and ORF83-1 show 98.4% identity in 313 aa overlap:

```
                    10         20         30         40         50         60
    orf83a.pep MKTLLXLIPLVLTACGTLTGIPAHGGGKRFAVEQELVAASSRAAVKEMDLSALKGRKAAL
               |||||  |||||||||||||||||||||||||||||||||||||||||||||||||||||
    orf83-1    MKTLLLLIPLVLTACGTLTGIPAHGGGKRFAVEQELVAASSRAAVKEMDLSALKGRKAAL
                    10         20         30         40         50         60

70         80         90        100        110        120
    orf83a.pep YVSVMGDQGSGNISGGRYSIDALIRGGYHNNPESATQYSYPAYDTTATTKSDALSSVTTS
               ||||||||||||||||||||||||||||||||||||||||||||||||||||||||||||
    orf83-1    YVSVMGDQGSGNISGGRYSIDALIRGGYHNNPESATQYSYPAYDTTATTKSDALSSVTTS
                    70         80         90        100        110        120

130        140        150        160        170        180
    orf83a.pep TSLLNAPAAALTKNSGRKGERSAGLSVNGTGDYRNETLLANPRDVSFLTNLIQTVFYLRG
               ||||||||||||||||||||||||||||||||||||||||||||||||||||||||||||
    orf83-1    TSLLNAPAAALTKNSGRKGERSAGLSVNGTGDYRNETLLANPRDVSFLTNLIQTVFYLRG
                   130        140        150        160        170        180

190        200        210        220        230        240
    orf83a.pep IEVVPPEYADTDVFVTVDVFGTVRSRTELHLYNAETLKAQTKLEYFAVDRDSRKLLIAPK
               |||||||||||||||||||||||||||||||||||||||||||||||||||||||||:||
    orf83-1    IEVVPPEYADTDVFVTVDVFGTVRSRTELHLYNAETLKAQTKLEYFAVDRDSRKLLITPK
                   190        200        210        220        230        240

250        260        270        280        290        300
    orf83a.pep TAAYESQYQEQYALWMGPYSVGKTVKASDRLMVDFSDITPYGDTTAQNRPDFKQNNGKKP
               |||||||||||||||:|:||||||||||||||||||||||||||||||||||||||||||
    orf83-1    TAAYESQYQEQYALWTGPYKVSKTVKASDRLMVDFSDITPYGDTTAQNRPDFKQNNGKKP
                   250        260        270        280        290        300

310
    orf83a.pep DVGNEVIRRRKGGX
               ||||||||||||||
    orf83-1    DVGNEVIRRRKGGX
                   310
```

Homology with a Predicted ORF from *N. gonorrhoeae*

ORF83 shows 94.9% identity over a 197aa overlap with a predicted ORF (ORF83.ng) from *N. gonorrhoeae*:

```
orf83.pep  TLLLFIPLVLTXCGTLTGILAHGGGKRFAVEQELVAASSRAAVKEMDLSALKGRKAAX  58
           ||||:|||||| |||||||| |||||||||||||||||||||||||||||||||||||
orf83ng    MKTLLLLIPLVLTACGTLTGIPAHGGGKRFAVEQELVAASSRAAVKEMDLSALKGRKAAL  60 orf83.pep  YVSVMGDQGSGNISGGRYSIDALIRGGYHNNPESATQYSYPAYDTTATTKSDALSSVTTS 118
           ||||||||||||||||||||||||||||||||:|||:||||||||||||||||||:|||
orf83ng    YVSVMGDQGSGNISGGRYSIDALIRGGYHNNPDSATRYSYPAYDTTATTKSDALSGVTTS 120 orf83.pep  TSLLNAPAAXLTKNSGRKGERSAGLSVNGTGDYRNETLLANPRDVSFLTNLIQTVFYLRG 178
           |||||||||: ||||:||||||||||||||||||||||||||||||||||||||||||
orf83ng    TSLLNAPAAALTKNNGRKGERSAGLSVNGTGDYRNETLLANPRDVSFLTNLIQTVFYLRG 180 orf83.pep  IEVVPPXYADTDVFVTVDV                                          197
           |||||| ||||||||||||
orf83ng    IEVVPPEYADTDVFVTVDVFGTVRSRTELHLYNAETLKAQTKLEYFAVDRDSRKLLIAPK 240
```

The complete length ORF83ng nucleotide sequence <SEQ ID 317> is:

```
  1 ATGAAAACCC TGCTCCTCCT CATCCCCCTC GTACTCACCG CCTGCGGCAC
 51 ACTGACCGGC ATACCCGCCC ACGGCGGCGG CAAACGCTTT GCCGTCGAAC
101 AGGAACTCGT CGCCGCATCG TCCCGCGCCG CCGTCAAAGA AATGGACTTG
151 TCCGCCCTGA AAGGACGCAA AGCCGCCCTT TACGTCTCCG TTATGGGCGA
201 CCAAGGTTCG GGCAACATAA GCGGCGGACG CTACTCCATC GACGCACTGA
251 TACGCGGCGG CTACCACAAC AACCCCGACA GCGCCACCCG ATACAGCTAC
301 CCCGCCTATG ACACTACCGC CACCACCAAA TCCGACGCGC TCTCCGGCGT
351 AACCACTTCC ACATCGCTTT TGAACGCCCC CGCCGCCGCC CTGACGAAAA
401 ACAACGGACG CAAAGGCGAA CGCTCCGCCG GACTGTCCGT CAACGGCACG
451 GGCGACTACC GCAACGAAAC CCTGCTCGCC AACCCCCGCG ACGTTTCCTT
501 CCTGACCAAC CTCATCCAAA CCGTCTTCTA CCTGCGCGGC ATCGAAGTCG
551 TACCGCCCGA ATACGCCGAC ACCGACGTAT TCGTAACCGT CGACGTATTC
601 GGCACCGTCC GCAGCCGTAC CGAACTGCAC CTCTACAACG CCGAAACCCT
651 TAAAGCCCAA ACCAAGCTCG AATATTTCGC CGTCGACCGC GACAGCCGGA
701 AACTGCTGAT TGCCCCTAAA ACCGCCGCCT ACGAATCCCA ATACCAAGAA
751 CAATACGCCC TCTGGATGGG ACCTTACAGC GTCGGCAAAA CCGTCAAAGC
801 CTCAGACCGC CTGATGGTCG ATTTCTCCGA CATCACCCCC TACGGCGACA
851 CAACCGCCCA AAACCGTCCC GACTTCAAAC AAAACAACGG TAAAAACCCC
901 GATGTCGGCA ACGAAGTCAT CCGCCGCCGC AAAGGAGGAT AA
```

This encodes a protein having amino acid sequence <SEQ ID 318>:

```
  1 MKTLLLLIPL VLTACGTLTG IPAHGGGKRF AVEQELVAAS SRAAVKEMDL
 51 SALKGRKAAL YVSVMGDQGS GNISGGRYSI DALIRGGYHN NPDSATRYSY
101 PAYDTTATTK SDALSGVTTS TSLLNAPAAA LTKNNGRKGE RSAGLSVNGT
151 GDYRNETLLA NPRDVSFLTN LIQTVFYLRG IEVVPPEYAD TDVFVTVDVF
201 GTVRSRTELH LYNAETLKAQ TKLEYFAVDR DSRKLLIAPK TAAYESQYQE
251 QYALWMGPYS VGKTVKASDR LMVDFSDITP YGDTTAQNRP DFKQNNGKNP
301 DVGNEVIRRR KGG*
```

ORF83ng and ORF83-1 show 97.1% identity in 313 aa overlap

```
                10         20         30         40         50         60
orf83-1.pep MKTLLLLIPLVLTACGTLTGIPAHGGGKRFAVEQELVAASSRAAVKEMDLSALKGRKAAL
            ||||||||||||||||||||||||||||||||||||||||||||||||||||||||||||
orf83ng     MKTLLLLIPLVLTACGTLTGIPAHGGGKRFAVEQELVAASSRAAVKEMDLSALKGRKAAL
                10         20         30         40         50         60

70         80         90        100        110        120
orf83-1.pep YVSVMGDQGSGNISGGRYSIDALIRGGYHNNPESATQYSYPAYDTTATTKSDALSSVTTS
            |||||||||||||||||||||||||||||||:|||:||||||||||||||||||:||||
orf83ng     YVSVMGDQGSGNISGGRYSIDALIRGGYHNNPDSATRYSYPAYDTTATTKSDALSGVTTS
                70         80         90        100        110        120

130        140        150        160        170        180
orf83-1.pep TSLLNAPAAALTKNSGRKGERSAGLSVNGTGDYRNETLLANPRDVSFLTNLIQTVFYLRG
            |||||||||||||:||||||||||||||||||||||||||||||||||||||||||||||
orf83ng     TSLLNAPAAALTKNNGRKGERSAGLSVNGTGDYRNETLLANPRDVSFLTNLIQTVFYLRG
               130        140        150        160        170        180

190        200        210        220        230        240
orf83-1.pep IEVVPPEYADTDVFVTVDVFGTVRSRTELHLYNAETLKAQTKLEYFAVDRDSRKLLITPK
            ||||||||||||||||||||||||||||||||||||||||||||||||||||||||:||
orf83ng     IEVVPPEYADTDVFVTVDVFGTVRSRTELHLYNAETLKAQTKLEYFAVDRDSRKLLIAPK
               190        200        210        220        230        240

250        260        270        280        290        300
orf83-1.pep TAAYESQYQEQYALWTGPYKVSKTVKASDRLMVDFSDITPYGDTTAQNRPDFKQNNGKKP
            ||||||||||||||||:|:|||||||||||||||||||||||||||||||||||||:|
orf83ng     TAAYESQYQEQYALWMGPYSVGKTVKASDRLMVDFSDITPYGDTTAQNRPDFKQNGKKP
               250        260        270        280        290        300

310
orf83-1.pep DVGNEVIRRRKGGX
            ||||||||||||||
orf83ng     DVGNEVIRRRKGGX
               310
```

Based on this analysis, including the presence of a putative ATP/GTP-binding site motif A (P-loop) in the gonococcal protein (double-underlined) and a putative prokaryotic membrane lipoprotein lipid attachment site (single-underlined), it is predicted that the proteins from *N. meningitidis* and *N. gonorrhoeae*, and their epitopes, could be useful antigens for vaccines or diagnostics, or for raising antibodies.

Example 38

The following DNA sequence, believed to be complete, was identified in *N. meningitidis* <SEQ ID 319>:

```
  1 ATGGCAGAGA TCTGTTTGAT AACCGGCACG CCCGGTTCAG GGAAAACATT
 51 AAAAATGGTT TCCATGATGG CGAATGATGA AATGTTTAAG CCTGATGAAA
101 AAGCCATACG CCGTAAAGTA TTTACGAACA TAAAAGGCTT GAAAATACCG
151 CACACCTACA TAGAAACGGA CGCAAAAAAG CTGCCGAAAT CGACAGATGA
201 GCAGCTTTCG GCGCATGATA TGTACGAATG GATAAAGAAG CCCGAAAATA
251 TCGGGTCTAT TGTCATTGTA GATGAAGCTC AAGACGTATG GCCGGCACGC
301 TCGGCAGGTT CAAAAATCCC TGAAAATGTC CAATGGCTGA ATACGCACAG
351 ACATCAGGGC ATTGATATAT TTGTTTTGAC TCAAGGTCCT AAGCTTCTAG
401 ATCAAAATCT TAGAACGCTT GTACGGAAAC ATTACCACAT CGCTTCAAAC
451 AAGATGGGTA TGCGTACGCT TTTAGAATGG AAAATATGCG CGGACGATCC
501 CGTAAAAATG GCATCAAGCG CATTCTCCAG TATCTATACA CTGGATAAAA
551 AAGTTTATGA CTTGTAysrr TmmGCGGAAG TTCATACCGT AAATAAGGTC
601 AAGCGGTCAA AGTGGTTTTA CACTCTGCCa GTAATAGTAT TGCTGATTCC
651 CGTGTTTGTC GGCCTGTCCT ATAAAATGTT GagCaGTTAC GGAAAAAAAC
```

-continued

```
 701 aGGAAGAACC CGCAGCACAA GAATCGGCGG CAACAGAACA GCAGGCAGTA
 751 CTTCCGGATA AAACAGAAGG CGAGCCGGTA AATAACGGCA ACCTTACCGC
 801 AGATATGTTT GTTCCGACAT TGTCCGAaAA ACCCGrAAGC AAGCcgaTTT
 851 ATAACGGTGT AAGGCAGGTA AGAACCTTTG AATATATAGC AGGCTGTATA
 901 GAAGGCGGAA GAACCGGATG CGCCTGCTAT TCGCaTCAAG GGACGGCATt
 951 gaAAGAAGTG ACGGaGTTGA TGTGccaAgG aCTATGTaAA AAacGGCTTG
1001 CCGTTTAACC CaTACAAAGA AGAAAGCCAA GGGCAGGAAG TTCAGCAAAG
1051 CGCGCAgCAA CATTCGGACA GGGCGcCAAG TTGCCACATT GGGCGGAAAA
1101 CCGTAGCAGA ACCTAATGTA CGATAATTGG GAAGAACGCG GGAAACCGTT
1151 TGAAGGAATC GGaCGGGGGC GTGGTCGGAT CGGCAAACTG A
```

This corresponds to the amino acid sequence <SEQ ID 320; ORF84>:

```
  1 MAEICLITGT PGSGKTLKMV SMMANDEMFK PDEKAIRRKV FTNIKGLKIP
 51 HTYIETDAKK LPKSTDEQLS AHDMYEWIKK PENIGSIVIV DEAQDVWPAR
101 SAGSKIPENV QWLNTHRHQG IDIFVLTQGP KLLDQNLRTL VRKHYHIASN
151 KMGMRTLLEW KICADDPVKM ASSAFSSIYT LDKKVYDLYX XAEVHTVNKV
201 KRSKWFYTLP VIVLLIPVFV GLSYKMLSSY GKKQEEPAAQ ESAATEQQAV
251 LPDKTEGEPV NNGNLTADMF VPTLSEKPXS KPIYNGVRQV RTFEYIAGCI
301 EGGRTGCACY SHQGTALKEV TELMCKDYVK NGLPFNPYKE ESQGQEVQQS
351 AQQHSDRAQV ATLGGKPXQN LMYDNWEERG KPFEGIGGGV VGSAN*
```

Further work revealed the complete nucleotide sequence <SEQ ID 321>:

```
  1 ATGGCAGAGA TCTGTTTGAT AACCGGCACG CCCGGTTCAG GGAAAACATT
 51 AAAAATGGTT TCCATGATGG CGAATGATGA AATGTTTAAG CCTGATGAAA
101 ACGGCATACG CCGTAAAGTA TTTACGAACA TAAAAGGCTT GAAAATACCG
151 CACACCTACA TAGAAACGGA CGCAAAAAAG CTGCCGAAAT CGACAGATGA
201 GCAGCTTTCG GCGCATGATA TGTACGAATG GATAAAGAAG CCCGAAAATA
251 TCGGGTCTAT TGTCATTGTA GATGAAGCTC AAGACGTATG GCCGGCACGC
301 TCGGCAGGTT CAAAAATCCC TGAAAATGTC CAATGGCTGA ATACGCACAG
351 ACATCAGGGC ATTGATATAT TTGTTTTGAC TCAAGGTCCT AAGCTTCTAG
401 ATCAAAATCT TAGAACGCTT GTACGGAAAC ATTACCACAT CGCTTCAAAC
451 AAGATGGGTA TGCGTACGCT TTTAGAATGG AAAATATGCG CGGACGATCC
501 CGTAAAAATG GCATCAAGCG CATTCTCCAG TATCTATACA CTGGATAAAA
551 AAGTTTATGA CTTGTACGAA TCAGCGGAAG TTCATACCGT AAATAAGGTC
601 AAGCGGTCAA AGTGGTTTTA CACTCTGCCA GTAATAGTAT TGCTGATTCC
651 CGTGTTTGTC GGCCTGTCCT ATAAAATGTT GAGCAGTTAC GGAAAAAAAC
701 AGGAAGAACC CGCAGCACAA GAATCGGCGG CAACAGAACA GCAGGCAGTA
751 CTTCCGGATA AAACAGAAGG CGAGCCGGTA AATAACGGCA ACCTTACCGC
801 AGATATGTTT GTTCCGACAT TGTCCGAAAA ACCCGAAAGC AAGCCGATTT
```

-continued

```
 851 ATAACGGTGT AAGGCAGGTA AGAACCTTTG AATATATAGC AGGCTGTATA

901 GAAGGCGGAA GAACCGGATG CGCCTGCTAT TCGCATCAAG GGACGGCATT

951 GAAAGAAGTG ACGGAGTTGA TGTGCAAGGA CTATGTAAAA AACGGCTTGC

1001 CGTTTAACCC ATACAAAGAA GAAAGCCAAG GGCAGGAAGT TCAGCAAAGC

1051 GCGCAGCAAC ATTCGGACAG GGCGCAAGTT GCCACATTGG GCGGAAAACC

1101 GTAGCAGAAC CTAATGTACG ATAATTGGGA AGAACGCGGG AAACCGTTTG

1151 AAGGAATCGG CGGGGGCGTG GTCGGATCGG CAAACTGA
```

This corresponds to the amino acid sequence <SEQ ID 322; ORF84-1>:

```
  1 MAEICLITGT PGSGKTLKMV SMMANDEMFK PDENGIRRKV FTNIKGLKIP

51 HTYIETDAKK LPKSTDEQLS AHDMYEWIKK PENIGSIVIV DEAQDVWPAR

101 SAGSKIPENV QWLNTHRHQG IDIFVLTQGP KLLDQNLRTL VRKHYHIASN

151 KMGMRTLLEW KICADDPVKM ASSAFSSIYT LDKKVYDLYE SAEVHTVNKV

201 KRSKWFYTLP VIVLLIPVFV GLSYKMLSSY GKKQEEPAAQ ESAATEQQAV

251 LPDKTEGEPV NNGNLTADMF VPTLSEKPES KPIYNGVRQV RTFEYIAGCI

301 EGGRTGCACY SHQGTALKEV TELMCKDYVK NGLPFNPYKE ESQGQEVQQS

351 AQQHSDRAQV ATLGGKP*QN LMYDNWEERG KPFEGIGGGV VGSAN*
```

Computer analysis of this amino acid sequence gave the following results:

Homology with a Predicted ORF from *N. meningitidis* (Strain A)

ORF84 shows 93.9% identity over a 395aa overlap with an ORF (ORF84a) from strain A of *N. meningitidis*:

```
                    10         20         30         40         50         60
    orf84.pep MAEICLITGTPGSGKTLKMVSMMANDEMFKPDEKAIRRKVFTNIKGLKIPHTYIETDAKK
              |||||||||||||||||||||||||||||||||::|||||||||||||||||||||||||
    orf84ng   MAEICLITGTPGSGKTLKMVSMMANDEMFKPDENGIRRKVFTNIKGLKIPHTYIETDAKK
                    10         20         30         40         50         60

70         80         90        100        110        120
    orf84.pep LPKSTDEQLSAHDMYEWIKKPENIGSIVIVDEAQDVWPARSAGSKIPENVQWLNTHRHQG
              ||||||||||||||||||||||||||||||||||||||||||||||||||||||||||||
    orf83ng   LPKSTDEQLSAHDMYEWIKKPENIGSIVIVDEAQDVWPARSAGSKIPENVQWLNTHRHQG
                    70         80         90        100        110        120

130        140        150        160        170        180
    orf84.pep IDIFVLTQGPKLLDQNLRTLVRKHYHIASNKMGMRTLLEWKICADDPVKMASSAFSSIYT
              ||||||||| ||||||||||||||||||||||||||||||||||||||||||||||||||
    orf83ng   IDIFVLTQGSKLLDQNLRTLVRKHYHIASNKMGMRTLLEWKICADDPVKMASSAFSSIYT
                   130        140        150        160        170        180

190        200        210        220        230        240
    orf84.pep LDKKVYDLYXXAEVHTVNKVKRSKWFYTLPVIVLLIPVFVGLSYKMLSSYGKKQEEPAAQ
              ||||||||||   |||||||||||||||||||||| ||||||||||||||||||||||||
    orf83ng   LDKKVYDLYESAEVHTVNKVKRSKWFYTLPVIILLIPVFVGLSYKMLSSYGKKQEEPAAQ
                   190        200        210        220        230        240

250        260        270        280        290        300
    orf84.pep ESAATEQQAVLPDKTEGEPVNNGNLTADMFVPTLSEKPXSKPIYNGVRQVRTFEYIAGCI
              ||||||:|||:|||||||||||||||||||||||||||:|||||||||||||||||||:
    orf83ng   ESAATEHQAVFQDKTEGEPVNNGNLTADMFVPTLSEKPESKPIYNGVRQVRTFEYIAGCV
                   250        260        270        280        290        300

310        320        330        340        350        360
    orf84.pep EGGRTGCACYSHQGTALKEVTELMCKDYVKNGLPFNPYKEESQGQEVQQSAQQHSDRAQV
              |||||||:|||||||||||:|: |||||:|||||||||||||||::|||| :|||||:||
    orf83ng   EGGRTGCTCYSHQGTALKEITKEMCKDYARNGLPFNPYKEESQGRDVQQSEQHHSDRPQV
                   310        320        330        340        350        360

370        380        390
    orf84.pep ATLGGKPXQNLMYDNWEERGKPFEGIGGGVVGSANX
              ||||||| ||||||||:|||||||||||||||||||
    orf83ng   ATLGGKPWQNLMYDNWQERGKPFEGIGGGVVGSANX
                   370        380        390
```

The complete length ORF84a nucleotide sequence <SEQ ID 323> is:

```
   1 ATGGCAGAGA TCTGTTTGAT AACCGGCACG CCCGGTTCAG GGAAAACATT
  51 AAAAATGGTT TCCATGATGG CAAACGATGA AATGTTTAAG CCGGATGAAA
 101 ACGGCATACG CCGTAAAGTA TTTACGAACA TCAAAGGCTT GAAGATACCG
 151 CACACCTACA TAGAAACGGA CGCGAAAAAG CTGCCGAAAT CGACAGATGA
 201 GCAGCTTTCG GCGCATGATA TGTACGAATG GATAAAGAAG CCCGAAAATA
 251 TCGGGTCTAT TGTCATTGTA GATGAAGCTC AAGACGTATG GCCGGCACGC
 301 TCGGCAGGTT CAAAAATCCC TGAAAATGTC CAATGGCTGA ATACGCACAG
 351 ACATCAGGGC ATTGATATAT TTGTTTTGAC TCAAGGCTCT AAGCTTCTAG
 401 ATCAAAATCT TAGAACGCTT GTACGAAAC ATTACCACAT CGCTTCAAAC
 451 AAGATGGGTA TGCGTACGCT TTTAGAATGG AAAATATGCG CGGACGATCC
 501 CGTAAAAATG GCATCAAGCG CATTCTCCAG TATCTATACA CTGGATAAAA
 551 AAGTTTATGA CTTGTACGAA TCAGCGGAAG TTCATACCGT AAATAAGGTC
 601 AAGCGGTCAA ATGGTTTTA TACTCTGCCA GTAATAATAT TGCTGATTCC
 651 CGTTTTTGTC GGCCTGTCCT ATAAAATGTT AAGTAGTTAT GGAAAAAAAC
 701 AGGAAGAACC CGCAGCACAA GAATCGGCGG CAACAGAACA TCAGGCAGTA
 751 TTTCAGGATA AAACAGAAGG CGAGCCGGTA ACAACGGTA ACCTTACCGC
 801 AGATATGTTT GTTCCGACAT TGTCCGAAAA ACCCGAAAGC AAGCCGATTT
 851 ATAACGGTGT AAGGCAGGTA AGAACCTTTG AATATATAGC AGGCTGTGTA
 901 GAAGGCGGAA GAACCGGATG CACATGCTAT TCGCATCAAG GACGGCATT
 951 GAAAGAAATT ACAAAGGAAA TGTGCAAGGA TTACGCAAGA AACGGATTGC
1001 CGTTTAACCC ATATAAAGAA GAAAGCCAAG GGCGGGATGT CCAGCAAAGT
1051 GAGCAGCACC ATTCGGACAG ACCGCAAGTT GCCACGTTGG GCGGAAAGCC
1101 GTGGCAAAAT CTTATGTATG ATAATTGGCA GGAGCGCGGA AAACCGTTTG
1151 AAGGAATCGG CGGGGGCGTG GTCGGATCGG CAAACTGA
```

This encodes a protein having amino acid sequence <SEQ ID 324>:

```
  1 MAEICLITGT PGSGKTLKMV SMMANDEMFK PDENGIRRKV FTNIKGLKIP

51 HTYIETDAKK LPKSTDEQLS AHDMYEWIKK PENIGSIVIV DEAQDVWPAR

101 SAGSKIPENV QWLNTHRHQG IDIFVLTQGS KLLDQNLRTL VRKHYHIASN

151 KMGMRTLLEW KICADDPVKM ASSAFSSIYT LDKKVYDLYE SAEVHTVNKV

201 KRSKWFYTLP VIILLIPVFV GLSYKMLSSY GKKQEEPAAQ ESAATEHQAV

251 FQDKTEGEPV NNGNLTADMF VPTLSEKPES KPIYNGVRQV RTFEYIAGCV

301 EGGRTGCTCY SHQGTALKEI TKEMCKDYAR NGLPFNPYKE ESQGRDVQQS

351 EQHHSDRPQV ATLGGKPWQN LMYDNWQERG KPFEGIGGGV VGSAN*
```

ORF84a and ORF84-1 show 95.2% identity in 395 aa overlap:

```
                 10        20        30        40        50        60
orf84a.pep  MAEICLITGTPGSGKTLKMVSMMANDEMFKPDENGIRRKVFTNIKGLKIPHTYIETKAKK
            ||||||||||||||||||||||||||||||||||||||||||||||||||||||||||||
orf84-1     MAEICLITGTPGSGKTLKMVSMMANDEMFKPDENGIRRKVFTNIKGLKIPHTYIETKAKK
                 10        20        30        40        50        60
                 70        80        90       100       110       120
orf84a.pep  LPKSTDEQLSAHDMYEWIKKPENIGSIVIVDEAQDVWPARSAGSKIPENVQWLNTHRHQG
            ||||||||||||||||||||||||||||||||||||||||||||||||||||||||||||
orf84-1     LPKSTDEQLSAHDMYEWIKKPENIGSIVIVDEAQDVWPARSAGSKIPENVQWLNTHRHQG
                 70        80        90       100       110       120
                130       140       150       160       170       180
orf84a.pep  IDIFVLTQGSKLLDQNLRTLVRKHYHIASNKMGMRTLLEWKICADDPVKMASSAFSSIYT
            |||||||||:||||||||||||||||||||||||||||||||||||||||||||||||||
orf84-1     IDIFVLTQGPKLLDQNLRTLVRKHYHIASNKMGMRTLLEWKICADDPVKMASSAFSSIYT
                130       140       150       160       170       180
                250       260       270       280       290       300
orf84a.pep  ESAATEHQAVFQDKTEGEPVNNGNLTADMFVPTLSEKPESKPIYNGVRQVRTFEYIAGCV
            ||||||:|||:|||||||||||||||||||||||||||||||||||||||||||||||:
orf84-1     ESAATEQQAVLPDKTEGEPVNNGNLTADMFVPTLSEKPESKPIYNGVRQVRTFEYIAGCI
                250       260       270       280       290       300
                310       320       330       340       350       360
orf84a.pep  EGGRTGCTCYSHQGTALKEITKEMCKDYARNGLPFNPYKEESQGRDVQQSEQHHSDRPQV
            |||||||:|||||||||||::|:||||||::||||||||||||||::|||:|:||||:||
orf84-1     EGGRTGCACYSHQGTALKEVTELMCKDYVKNGLPFNPYKEESQGQEVQQSAQQHSDRAQV
                310       320       330       340       350       360
                370       380       390
orf84a.pep  ATLGGKPWQNLMYDNWQERGKPFEGIGGGVVGSANX
            |||||||:|||||||||:|||||||||||||||||
orf84-1     ATLGGKPXQNLMYDNWEERGKPFEGIGGGVVGSANX
                370       380       390
```

Homology with a Predicted ORF from *N. gonorrhoeae*

ORF84 shows 94.2% identity over a 395aa overlap with a predicted ORF (ORF84.ng) from *N. gonorrhoeae*.

```
orf84.pep  MAEICLITGTPGSGKTLKMVSMMANDEMFKPDEKAITTKVFTNIKGLKIPHTYIETDAKK   60
           |||||||||||||||||||||||||||||||||:::|||||||||||||||||:||||||
orf84ng    MAEICLITGTPGSGKTLKMVSMMANDEMFKPDENGVTTKVFTNIKGLKIPHTHIETDAKK   60
orf84.pep  LPKSTDEQLSAHDMYEWIKKPENIGSIVIVDEAQDVWPARSAGSKIPENVQWLNTHRHQG  120
           |||||||||||||||||||||||||:|||||||||||||||||||||||||||||||||
orf84ng    LPKSTDEQLSAHDMYEWIKKPENVGAIVIVDEAQDVWPARSAGSKIPENVQWLNTHRHQG  120
orf84.pep  IDIFVLTQGPKLLDQNLRTLVRKHYHIASNKMGMRTLLEWKICADDPVKMASSAFSSIYT  180
           |||||||||||||||||||||||||::|||||:||:|||||||:|||||||||||||||
orf84ng    IDIFVLTQGPKLLDQNLRTLVRKHYHIAANKMGLRTLLEWKVCADDPVKMASSAFSSIYT  180
orf84.pep  LDKKVYDLYXXAEVHTVNKVKRSKWFYTLPVIVLLIPVFVGLSYKMLSSYGKKQEEPAAQ  240
           |||||||||  :|||||||||||||||:||||:||||:|||||||||||:|||||||||
orf84ng    LDKKVYDLYESAEIHTVNKVKRSKWFYALPVIILLIPLFVGLSYKMLGSYGKKQEEPAAQ  240
orf84.pep  ESAATEQQAVLPDKTEGEPVNNGNLTADMFVPTLSEKPXSKPIYNGVRQVRTFEYIAGCI  300
           |||||||||||||||||||:|||||||||||||||:||||||||||||||||||||||||
orf84ng    ESAATEQQAVLPDKTEGESVNNGNLTADMFVPTLPEKPESKPIYNGVRQVRTFEYIAGCI  300
orf84.pep  EGGRTGCACYSHQGTALKEVTELMCKDYVKNGLPFNPYKEESQGQEVQQSAQQHSDRAQV  360
           ||||||:|||||||||||||||||||||||||||||||||||||||||||||||||||||
orf84ng    EGGRTGCTCYSHQGTALKEVTELMCKDYVKNGLPFNPYKEESQGQEVQQSAQQHSDRAQV  360
orf84.pep  ATLGGKPXQNLMYDNWEERGKPFEGIGGGVVGSAN  395
           |||||||:|||||||||||||||||||||||||||
orf84ng    ATLGGKPQQNLMYDNWEERGKPFEGIGGGVVGSAN  395
```

The complete length ORF84ng nucleotide sequence <SEQ ID 325> is:

```
  1 ATGGCAGAAA TCTGTTTGAT AACCGGCACG CCCGGTTCAG GGAAAACATT

51 AAAAATGGTT TCCATGATGG CAAACGATGA AATGTTTAAG CCAGATGAAA

101 ACGGCGTACG CCGTAAAGTA TTTACGAACA TCAAAGGTTT GAAGATACCG

151 CACACCCACA TAGAAACAGA CGCAAAGAAG CTGCCGAAAT CAACCGATGA

201 ACAGCTTTCG GCGCATGATA TGTATGAATG GATCAAGAAG CCTGAAAacg 251 tcggcgCAAT CGTTATTGTC GATGAGGCGC AAGACGTATG GCCCGCACGC
```

-continued

```
 301 TccgCAGGTT CGAAAATCCC CGAAAACGTC CAATGGCTGA ACACACACAG

351 GCATCAGGGC ATAGATATAT TTGTATTGAC ACAAGGTCCT AAACTCTTAG

401 ATCAGAACTT GCGAACATTG GTTAAAAGAC ATTACCACAT TGCGGCCAAC

451 AAAATGGGTT TGCGTACCCT GCTTGAATGG AAAGTATGCG CGGATGACCC

501 GGTAAAAATG GCATCAAGTG CATTTTCCAG TATCTACACA CTGGATAAAA

551 AAGTTTATGA CTTGTACGAA TCCGCAGAAA TTCACACGGT AAACAAAGTC

601 AAGCGTTCAA AATGGTTTTA TGCATTGCCC GTCATCATAT TATTGATTCC

651 GCTATTTGTC GGTTTGTCTT ACAAAATGTT GGGCAGTTAC GGAAAAAAAC

701 AGGAAGAACC CGCAGCACAA GAATCGGCGG CAACAGAACA GCAGGCAGTA

751 CTTCCGGATA AACAGAAGG AGAATCGGTG AATAACGAA ACCTTACGGC

801 AGATATGTTT GTTCCGACAT TGCCCGAAAA ACCCGAAAGC AAGCCGATTT

851 ATAACGGTGT AAGGCAGGTA AGGACCTTTG AATATATAGC AGGCTGTATA

901 GAAGGCGGAA GAACCGGATG CACCTGCTAT TCGCATCAAG GGACGGCATT

951 GAAAGAAGTG ACGGAGTTGA TGTGCAAGGA CTATGTAAAA AACGGCTTGC

1001 CGTTTAACCC ATACAAAGAA GAAAGCCAAG GGCAGGAAGT TCAGCAAAGC

1051 GCGCAGCAAC ATTCGGACAG GGCGCAAGTT GCCACCTTGG GCGGAAAACC

1101 GCAGCAGAAC CTAATGTACG ACAATTGGGA AGAACGCGGG AAACCGTTTG

1151 AAGGAATCGG CGGGGGCGTG GTCGGATCGG CAAACTGA
```

This encodes a protein having amino acid sequence <SEQ ID 326>:

```
  1 MAEICLITGT PGSGKTLKMV SMMANDEMFK PDENGVRRKV FTNIKGLKIP

51 HTHIETDAKK LPKSTDEQLS AHDMYEWIKK PENVGAIVIV DEAQDVWPAR

101 SAGSKIPENV QWLNTHRHQG IDIFVLTQGP KLLDQNLRTL VKRHYHIAAN

151 KMGLRTLLEW KVCADDPVKM ASSAFSSIYT LDKKVYDLYE SAEIHTVNKV

201 KRSKWFYALP VIILLIPLFV GLSYKMLGSY GKKQEEPAAQ ESAATEQQAV

251 LPDKTEGESV NNGNLTADMF VPTLPEKPES KPIYNGVRQV RTFEYIAGCI

301 EGGRTGCTCY SHQGTALKEV TELMCKDYVK NGLPFNPYKE ESQGQEVQQS

351 AQQHSDRAQV ATLGGKPQQN LMYDNWEERG KPFEGIGGGV VGSAN*
```

ORF84ng and ORF84-1 show 95.4% identity in 395 aa overlap:

```
                     10         20         30         40         50         60
orf84-1.pep  MAEICLITGTPGSGKTLKMVSMMANDEMFKPDENGIRRKVFTNIKGLKIPHTYIETDAKK
             ||||||||||||||||||||||||||||||||||||:|||||||||||||||:|||||||
orf84ng      MAEICLITGTPGSGKTLKMVSMMANDEMFKPDENGVRRKVFTNIKGLKIPHTHIETDAKK
                     10         20         30         40         50         60

70         80         90        100        110        120
orf84-1.pep  LPKSTDEQLSAHDMYEWIKKPENIGSIVIVDEAQDVWPARSAGSKIPENVQWLNTHRHQG
             ||||||||||||||||||||||||:|:|||||||||||||||||||||||||||||||||
orf84ng      LPKSTDEQLSAHDMYEWIKKPENVGAIVIVDEAQDVWPARSAGSKIPENVQWLNTHRHQG
                     70         80         90        100        110        120

130        140        150        160        170        180
orf84-1.pep  IDIFVLTQGPKLLDQNLRTLVRKHYHIASNKMGMRTLLEWKICADDPVKMASSAFSSIYT
             |||||||||||||||||||||||||||||:|||:|||||||:||||||||||||||||||
orf84ng      IDIFVLTQGPKLLDQNLRTLVKRHYHIAANKMGLRTLLEWKVCADDPVKMASSAFSSIYT
                    130        140        150        160        170        180

190        200        210        220        230        240
orf84-1.pep  LDKKVYDLYESAEVHTVNKVKRSKWFYTLPVIVLLIPVFVGLSYKMLSSYGKKQEEPAAQ
             |||||||||||||:|||||||||||||:|||||:||||:|||||||||:|||||||||||
orf84ng      LDKKVYDLYESAEIHTVNKVKRSKWFYALPVIILLIPLFVGLSYKMLGSYGKKQEEPAAQ
                    190        200        210        220        230        240
```

```
                   250        260        270        280        290        300
orf84-1.pep ESAATEQQAVLPDKTEGEPVNNGNLTADMFVPTLSEKPESKPIYNGVRQVRTFEYIAGCI
            ||||||||||||||||||| |||||||||||||||| |||||||||||||||||||||||
orf84ng     ESAATEQQAVLPDKTEGESVNNGNLTADMFVPTLPEKPESKPIYNGVRQVRTFEYIAGCI
                   250        260        270        280        290        300

310        320        330        340        350        360
orf84-1.pep EGGRTGCACYSHQGTALKEVTELMCKDYVKNGLPFNPYKEESQGQEVQQSAQQHSDRAQV
            ||||||:||||||||||||||||||||||||||||||||||||||||||||||||||||
orf84ng     EGGRTGCTCYSHQGTALKEVTELMCKDYVKNGLPFNPYKEESQGQEVQQSAQQHSDRAQV
                   310        320        330        340        350        360

370        380        390
orf84-1.pep ATLGGKPXQNLMYDNWEERGKPFEGIGGGVVGSANX
            ||||||| |||||||||||||||||||||||||||
orf84ng     ATLGGKPQQNLMYDNWEERGKPFEGIGGGVVGSANX.
                   370        380        390
```

Based on this analysis, including the presence of a putative transmembrane domain (single-underlined) in the gonococcal protein, and a putative ATP/GTP-binding site motif A (P-loop, double-underlined), it is predicted that the proteins from *N. meningitidis* and *N. gonorrhoeae*, and their epitopes, could be useful antigens for vaccines or diagnostics, or for raising antibodies.

Example 39

The following partial DNA sequence was identified in *N. meningitidis* <SEQ ID 327>:

```
   1 GTGGTTTTCC TGAATGCCGA CAACGGGATA TTGGTTCAGG ACTTGCCTTT

51 TGAAGTCAAA CTGAAAAAAT TCCATATCGA TTTTTACAAT ACGGGTATGC

101 CGCGTGATTT CGCCAGCGAT ATTGAAGTGA CGGACAAGGC AACCGGTGAG

151 AAACTCGAGC GCACCATCCG CGTGAACCAT CCTTTGACCT TGCACGGCAT

201 CACGATTTAT CAGGCGAGTT TTGCCGACGG CGGTTCGGAT TTGACATTCA

251 AGGCGTGGAA TTTGGGTGAT GCTTCGCGCG AGCCTGTCGT GTTGAAGGCA

301 ACATCCATAC ACCAGTTTCC GTTGGAAATT GGCAAACACA AATATCGTCT

351 TGAGTTCGAT CAGTTCACTT CTATGAATGT GGAGGACATG AGCGAGGGCG

401 CGGAACGGGA AAAAAGCCTG AAATCCACGC TGCCCGATGT CCGCGCCGTT

451 ACTCAGGAAG GTCACAAATA CACCAAT... .......... .....TACCG

501 TATCCGTGAT GCGCCAGGCC AGGCGGTCGA ATATAAAAAC TATATGCTGC

551 CGGTTTTGCA GGAACAGGAT TATTTTTGGA TTACCGGCAC GCGCAGCGC.

601 TTGCAGCAGC AATACCGCTG GCTGCGTATC CCCTTGGACA AGCAGTTGAA

651 AGCGGACACC TTTATGGCAT TGCGTGAGTT TTTGAAAGAT GGGGAAGGGC

701 GCAAACGTCT .GTTGCCGAC GCAACCAAAG GCGCACCTGC CGAAATCCGC

751 GAACAATTCA TGCTGGCTGC GGAAAACACG CTGAACATCT TTGCACAAAA

801 AGGCTATTTG GGATTGGACG AATTTATTAC GTCCAATATC CCGAAAGAGC

851 AGCAGGATAA GATGCAGGGC TATTTCTACG AAATGCTTTA CGGCGTGATG

901 AACGCTGCTT TGGATGAAAC CAT.ACCCGG TACGGCTTGC CCGAATGGCA

951 GCAGGATGAA GCGCGGAATC GTTTCCTGCT GCACAGTATG GATGCGTACA

1001 CGGGTTTGAC CGAATATCCC GCGCCTATGC TGCTGCAACT TGATGGGTTT

1051 TCCGAGGTGC GTTCGTCGGG TTTGCAGATG ACCCGTTCCC C.GGTCCGCT

1101 TTTGGTCTAT CTC...
```

This corresponds to the amino acid sequence <SEQ ID 328; ORF88>:

```
  1 MVFLNADNGI LVQDLPFEVK LKKFHIDFYN TGMPRDFASD IEVTDKATGE

51 KLERTIRVNH PLTLHGITIY QASFADGGSD LTFKAWNLGD ASREPVVLKA

101 TSIHQFPLEI GKHKYRLEFD QFTSMNVEDM SEGAEREKSL KSTLPDVRAV

151 TQEGHKYTNX XXXXXYRIRD APGQAVEYKN YMLPVLQEQD YFWITGTRSX

201 LQQQYRWLRI PLDKQLKADT FMALREFLKD GEGRKRXVAD ATKGAPAEIR

251 EQFMLAAENT LNIFAQKGYL GLDEFITSNI PKEQQDKMQG YFYEMLYGVM

301 NAALDETXTR YGLPEWQQDE ARNRFLLHSM DAYTGLTEYP APMLLQLDGF

351 SEVRSSGLQM TRSXGPLLVY L...
```

Further work revealed the complete nucleotide sequence <SEQ ID 329>:

```
   1 ATGAGTAAAT CCCGTAGATC TCCCCCACTT CTTTCCCGTC CGTGGTTCGC

51 TTTTTTCAGC TCCATGCGCT TTGCAGTCGC TTTGCTCAGT CTGCTGGGTA

101 TTGCATCGGT TATCGGTACG GTGTTGCAGC AAAACCAGCC GCAGACGGAT

151 TATTTGGTCA AATTCGGATC GTTTTGGGCG CAGATTTTTG GTTTTCTGGG

201 ACTGTATGAC GTCTATGCTT CGGCATGGTT TGTCGTTATC ATGATGTTTT

251 TGGTGGTTTC TACCAGTTTG TGCCTGATTC GCAATGTGCC GCCGTTCTGG

301 CGCGAAATGA AGTCTTTTCG GGAAAAGGTT AAAGAAAAAT CTCTGGCGGC

351 GATGCGCCAT TCTTCGCTGT TGGATGTAAA AATTGCGCCC GAGGTTGCCA

401 AACGTTATCT GGAAGTACAA GGTTTTCAGG AAAAACCAT TAACCGTGAA

451 GACGGGTCGG TTCTGATTGC CGCCAAAAAA GGCACAATGA ACAAATGGGG

501 CTATATCTTT GCCCATGTTG CTTTGATTGT CATTTGCCTG GGCGGGTTGA

551 TAGACAGTAA CCTGCTGTTG AAACTGGGTA TGCTGACCGG TCGGATTGTT

601 CCGGACAATC AGGCGGTTTA TGCCAAGGAT TTCAAGCCCG AAAGTATTTT

651 GGGTGCGTCC AATCTCTCAT TTAGGGGCAA CGTCAATATT TCCGAGGGGC

701 AGAGTGCGGA TGTGGTTTTC CTGAATGCCG ACAACGGGAT ATTGGTTCAG

751 GACTTGCCTT TTGAAGTCAA ACTGAAAAAA TTCCATATCG ATTTTTACAA

801 TACGGGTATG CCGCGTGATT TCGCCAGCGA TATTGAAGTG ACGGACAAGG

851 CAACCGGTGA GAAACTCGAG CGCACCATCC GCGTGAACCA TCCTTTGACC

901 TTGCACGGCA TCACGATTTA TCAGGCGAGT TTTGCCGACG GCGGTTCGGA

951 TTTGACATTC AAGGCGTGGA ATTTGGGTGA TGCTTCGCGC GAGCCTGTCG

1001 TGTTGAAGGC AACATCCATA CACCAGTTTC CGTTGGAAAT TGGCAAACAC

1051 AAATATCGTC TTGAGTTCGA TCAGTTCACT TCTATGAATG TGGAGGACAT

1101 GAGCGAGGGC GCGGAACGGG AAAAAAGCCT GAAATCCACG CTGAACGATG

1151 TCCGCGCCGT TACTCAGGAA GGTAAAAAAT ACACCAATAT CGGCCCTTCC

1201 ATTGTTTACC GTATCCGTGA TGCGGCAGGG CAGGCGGTCG AATATAAAAA

1251 CTATATGCTG CCGGTTTTGC AGGAACAGGA TTATTTTTGG ATTACCGGCA

1301 CGCGCAGCGG CTTGCAGCAG CAATACCGCT GGCTGCGTAT CCCCTTGGAC

1351 AAGCAGTTGA AAGCGGACAC CTTTATGGCA TTGCGTGAGT TTTTGAAAGA
```

```
1401 TGGGGAAGGG CGCAAACGTC TGGTTGCCGA CGCAACCAAA GGCGCACCTG

1451 CCGAAATCCG CGAACAATTC ATGCTGGCTG CGGAAAACAC GCTGAACATC

1501 TTTGCACAAA AAGGCTATTT GGGATTGGAC GAATTTATTA CGTCCAATAT

1551 CCCGAAAGAG CAGCAGGATA AGATGCAGGG CTATTTCTAC GAAATGCTTT

1601 ACGGCGTGAT GAACGCTGCT TTGGATGAAA CCATACGCCG GTACGGCTTG

1651 CCCGAATGGC AGCAGGATGA AGCGCGGAAT CGTTTCCTGC TGCACAGTAT

1701 GGATGCGTAC ACGGGTTTGA CCGAATATCC CGCGCCTATG CTGCTGCAAC

1751 TTGATGGGTT TTCCGAGGTG CGTTCGTCGG GTTTGCAGAT GACCCGTTCC

1801 CCGGGTGCGC TTTTGGTCTA TCTCGGCTCG GTGCTGTTGG TATTGGGTAC

1851 GGTATTGATG TTTTATGTGC GCGAAAAACG GGCGTGGGTA TTGTTTTCAG

1901 ACGGCAAAAT CCGTTTTGCC ATGTCTTCGG CCCGCAGCGA ACGGGATTTG

1951 CAGAAGGAAT TTCCAAAACA CGTCGAGAGT CTGCAACGGC TCGGCAAGGA

2001 CTTGAATCAT GACTGA
```

This corresponds to the amino acid sequence <SEQ ID 330; ORF88-1>:

```
  1 MSKSRRSPPL LSRPWFAFFS SMRFAVALLS LLGIASVIGT VLQQNPQTD

51 YLVKFGSFWA QIFGFLGLYD VYASAWFVVI MMFLVVSTSL CLIRNVPPFW

101 REMKSFREKV KEKSLAAMRH SSLLDVKIAP EVAKRYLEVQ GFQGKTINRE

151 DGSVLIAAKK GTMNKWGYIF AHVALIVICL GGLIDSNLLL KLGMLTGRIV

201 PDNQAVYAKD FKPESILGAS NLSFRGNVNI SEGQSADVVF LNADNGILVQ

251 DLPFEVKLKK FHIDFYNTGM PRDFASDIEV TDKATGEKLE RTIRVNHPLT

301 LHGITIYQAS FADGGSDLTF KAWNLGDASR EPVVLKATSI HQFPLEIGKH

351 KYRLEFDQFT SMNVEDMSEG AEREKSLKST LNDVRAVTQE GKKYTNIGPS

401 IVYRIRDAAG QAVEYKNYML PVLQEQDYFW ITGTRSGLQQ QYRWLRIPLD

451 KQLKADTFMA LREFLKDGEG RKRLVADATK GAPAEIREQF MLAAENTLNI

501 FAQKGYLGLD EFITSNIPKE QQDKMQGYFY EMLYGVMNAA LDETIRRYGL

551 PEWQQDEARN RFLLHSMDAY TGLTEYPAPM LLQLDGFSEV RSSGLQMTRS

601 PGALLVYLGS VLLVLGTVLM FYVREKRAWV LFSDGKIRFA MSSARSERDL

651 QKEFPKHVES LQRLGKDLNH D*
```

Computer analysis of this amino acid sequence gave the following results:

Homology with a Predicted ORF from *N. meningitidis* (Strain A)

ORF88 shows 95.7% identity over a 371aa overlap with an ORF (ORF88a) from strain A of *N. meningitidis*.

```
                                    10         20         30
orf88.pep               MVFLNADNGILVQDLPFEVKLKKFHIDFYN
                        :|||||||||||||||||||||||||||||
orf88a      AKDFKPESILGASNLSFRGNVNISEGQSADVVFLNADNGILVQDLPFEVKLKKFHIDFYN
            210       220       230       240       250       260

40         50         60         70         80         90
orf88.pep   TGMPRDFASDIEVTDKATGEKLERTIRVNHPLTLHGITIYQASFADGGSDLTFKAWNLGD
            ||||||||||||||||||||||||||||||||||||||||||||||||||||||||||||
orf88a      TGMPRDFASDIEVTDKATGEKLERTIRVNHPLTLHGITIYQASFADGGSDLTFKAWNLGD
            270       280       290       300       310       320
```

```
                  100        110        120        130        140        150
orf88.pep  ASREPVVLKATSIHQFPLEIGKHKYRLEFDQFTSMNVEDMSEGAEREKSLKSTLPDVRAV
           |||||||||||||||||||||||||||||||||||||||||||||||||||| |||||
orf88a     ASREPVVLKATSIHQFPLEIGKHKYRLEFDQFTSMNVEDMSEGAEREKSLKSTLNDVRAV
                  330        340        350        360        370        380
                  160        170        180        190        200        210
orf88.pep  TQEGHKYTNXXXXXXYRIRDAPGQAVEYKNYMLPVLQEQDYFWITGTRSXLQQQYRWLRI
           |||| :||||      |||||||  |||||||||||||||||||||||| |||||||||
orf88a     TQEGKKYTNIGPSIVYRIRDAAGQAVEYKNYMLPVLQEQDYFWITGTRSGLQQQYRWLRI
                  390        400        410        420        430        440
                  220        230        240        250        260        270
orf88.pep  PLDKQLKADTFMALREFLKDGEGRKRXVADATKGAPAEIREQFMLAAENTLNIFAQKGYL
           |||||||||||||||||||||||||| |||||||||||||||||||||||||||||||||
orf88a     PLDKQLKADTFMALREFLKDGEGRKRLVADATKGAPAEIREQFMLAAENTLNIFAQKGYL
                  450        460        470        480        490        500
                  220        230        240        250        260        270
orf88.pep  PLDKQLKADTFMALREFLKDGEGRKRXVADATKGAPAEIREQFMLAAENTLNIFAQKGYL
           ||||||||||||||||||||||||||| ||||||||||||||||||||||||||||||||
orf88a     PLDKQLKADTFMALREFLKDGEGRKRLVADATKGAPAEIREQFMLAAENTLNIFAQKGYL
                  450        460        470        480        490        500
                  280        290        300        310        320        330
orf88.pep  GLDEFITSNIPKEQQDKMQGYFYEMLYGVMNAALDETXTRYGLPEWQQDEARNRFLLHSM
           ||||||||||||||||||||||||||||||||||||| |||||||||||||||||||||
orf88a     GLDEFITSNIPKEQQDKMQGYFYEMLYGVMNAALDETIRRYGLPEWQQDEARNRFLLHSM
                  510        520        530        540        550        560
                  340        350        360        370
orf88.pep  DAYTGLTEYPAPMLLQLDGFSEVRSSGLQMTRSXGPLLVYL
           |||||||||||||||||||||||||||||||| ||||||||
orf88a     DAYTGLTEYPAPMLLQLDGFSEVRSSGLQMTRSPGALLVYLGSVLLVLGTVLMFYVREKR
                  570        580        590        600        610        620
orf88a     AWVLFSDGKIRFAMSSARSERDLQKEFPKHVESLQRLGKDLNHDX
                  630        640        650        660        670
```

The complete length ORF88a nucleotide sequence <SEQ ID 331> is:

```
   1 ATGAGTAAAT CCCGTAGATC TCCCCCACTT CTTTCCCGTC CGTGGTTCGC
  51 TTTTTTCAGC TCCATGCGCT TTGCGGTCGC TTTGCTCAGT CTGCTGGGTA
 101 TTGCATCGGT TATCGGTACG GTGTTGCAGC AAAACCAGCC GCAGACGGAT
 151 TATTTGGTCA AATTCGGATC GTTTTGGGCG CAGATTTTTG GTTTTCTGGG
 201 ACTGTATGAC GTCTATGCTT CGGCATGGTT TGTCGTTATC ATGATGTTTT
 251 TGGTGGTTTC TACCAGTTTG TGCCTGATTC GCAATGTGCC GCCGTTCTGG
 301 CGCGAAATGA AGTCTTTTCG GGAAAAGGTT AAAGAAAAAT CTCTGGCGGC
 351 GATGCGCCAT TCTTCGCTGT TGGATGTAAA AATTGCGCCC GAGGTTGCCA
 401 AACGTTATCT GGAAGTACAA GGTTTTCAGG GAAAAACCAT TAACCGTGAA
 451 GACGGGTCGG TTCTGATTGC CGCCAAAAAA GGCACAATGA ACAAATGGGG
 501 CTATATCTTT GCCCATGTTG CTTTGATTGT CATTTGCCTG GGCGGGTTGA
 551 TAGACAGTAA CCTGCTGTTG AAACTGGGTA TGCTGACCGG TCGGATTGTT
 601 CCGGACAATC AGGCGGTTTA TGCCAAGGAT TTCAAGCCCG AAAGTATTTT
 651 GGGTGCGTCC AATCTCTCAT TTAGGGGCAA CGTCAATATT TCCGAGGGGC
 701 AGAGTGCGGA TGTGGTTTTC CTGAATGCCG ACAACGGGAT ATTGGTTCAG
 751 GACTTGCCTT TTGAAGTCAA ACTGAAAAAA TTCCATATCG ATTTTTACAA
 801 TACGGGTATG CCGCGCGATT TGCCAGTGA TATTGAAGTA ACGGATAAGG
 851 CAACCGGTGA GAAACTCGAG CGCACCATCC GCGTGAACCA TCCTTTGACC
 901 TTGCACGGCA TCACGATTTA TCAGGCGAGT TTTGCCGACG GCGGTTCGGA
 951 TTTGACATTC AAGGCGTGGA ATTTGGGTGA TGCTTCGCGC GAGCCTGTCG
1001 TGTTGAAGGC AACATCCATA CACCAGTTTC CGTTGGAAAT TGGCAAACAC
1051 AAATATCGTC TTGAGTTCGA TCAGTTTACT TCTATGAATG TGGAGGACAT
```

```
-continued
1101 GAGCGAGGGC GCGGAACGGG AAAAAAGCCT GAAATCCACG CTGAACGATG

1151 TCCGCGCCGT TACTCAGGAA GGTAAAAAAT ACACCAATAT CGGCCCTTCC

1201 ATTGTTTACC GTATCCGTGA TGCGGCAGGG CAGGCGGTCG AATATAAAAA

1251 CTATATGCTG CCGGTTTTGC AGGAACAGGA TTATTTTTGG ATTACCGGCA

1301 CGCGCAGCGG CTTGCAGCAG CAATACCGCT GGCTGCGTAT CCCCTTGGAC

1351 AAGCAGTTGA AAGCGGACAC CTTTATGGCA TTGCGTGAGT TTTTGAAAGA

1401 TGGGGAAGGG CGCAAACGTC TGGTTGCCGA CGCAACCAAA GGCGCACCTG

1451 CCGAAATCCG CGAACAATTC ATGCTGGCTG CGGAAAACAC GCTGAACATC

1501 TTTGCACAAA AAGGCTATTT GGGATTGGAC GAATTTATTA CGTCCAATAT

1551 CCCGAAAGAG CAGCAGGATA AGATGCAGGG CTATTTCTAC GAAATGCTTT

1601 ACGGCGTGAT GAACGCTGCT TTGGATGAAA CCATACGCCG GTACGGCTTG

1651 CCCGAATGGC AGCAGGATGA AGCGCGGAAT CGTTCCTGC TGCACAGTAT

1701 GGATGCGTAC ACGGGTTTGA CCGAATATCC CGCGCCTATG CTGCTGCAAC

1751 TTGATGGGTT TTCCGAGGTG CGTTCGTCGG GTTTGCAGAT GACCCGTTCC

1801 CCGGGTGCGC TTTTGGTCTA TCTCGGCTCG GTGCTGTTGG TATTGGGTAC

1851 GGTATTGATG TTTTATGTGC GCGAAAAACG GGCGTGGGTA TTGTTTTCAG

1901 ACGGCAAAAT CCGTTTTGCC ATGTCTTCGG CCCGCAGCGA ACGGGATTTG

1951 CAGAAGGAAT TCCAAAACA CGTCGAGAGT CTGCAACGGC TCGGCAAGGA

2001 CTTGAATCAT GACTGA
```

This encodes a protein having amino acid sequence <SEQ ID 332>:

```
  1 MSKSRRSPPL LSRPWFAFFS SMRFAVALLS LLGIASVIGT VLQQNQPQTD

51 YLVKFGSFWA QIFGFLGLYD VYASAWFVVI MMFLVVSTSL CLIRNVPPFW

101 REMKSFREKV KEKSLAAMRH SSLLDVKIAP EVAKRYLEVQ GFQGKTINRE

151 DGSVLIAAKK GTMNKWGYIF AHVALIVICL GGLIDSNLLL KLGMLTGRIV

201 PDNQAVYAKD FKPESILGAS NLSFRGNVNI SEGQSADVVF LNADNGILVQ

251 DLPFEVKLKK FHIDFYNTGM PRDFASDIEV TDKATGEKLE RTIRVNHPLT

301 LHGITIYQAS FADGGSDLTF KAWNLGDASR EPVVLKATSI HQFPLEIGKH

351 KYRLEFDQFT SMNVEDMSEG AEREKSLKST LNDVRAVTQE GKKYTNIGPS

401 IVYRIRDAAG QAVEYKNYML PVLQEQDYFW ITGTRSGLQQ QYRWLRIPLD

451 KQLKADTFMA LREFLKDGEG RKRLVADATK GAPAEIREQF MLAAENTLNI

501 FAQKGYLGLD EFITSNIPKE QQDKMQGYFY EMLYGVMNAA LDETIRRYGL

551 PEWQQDEARN RFLLHSMDAY TGLTEYPAPM LLQLDGFSEV RSSGLQMTRS

601 PGALLVYLGS VLLVLGTVLM FYVREKRAWV LFSDGKIRFA MSSARSERDL

651 QKEFPKHVES LQRLGKDLNH D*
```

ORF88a and ORF88-1 100.0% identity in 671 aa overlap:

```
orf88a.pep  MSKSRRSPPLLSRPWFAFFSSMRFAVALLSLLGIASVIGTVLQQNQPQTDYLVKFGSFWA  60
            ||||||||||||||||||||||||||||||||||||||||||||||||||||||||||||
orf88-1     MSKSRRSPPLLSRPWFAFFSSMRFAVALLSLLGIASVIGTVLQQNQPQTDYLVKFGSFWA  60
```

```
orf88a.pep  QIFGFLGLYDVYASAWFVVIMMFLVVSTSLCLIRNVPPFWREMKSFREKVKEKSLAAMRH  120
            ||||||||||||||||||||||||||||||||||||||||||||||||||||||||||||
orf88-1     QIFGFLGLYDVYASAWFVVIMMFLVVSTSLCLIRNVPPFWREMKSFREKVKEKSLAAMRH  120 orf88a.pep  SSLLDVKIAPEVAKRYLEVQGFQGKTINREDGSVLIAAKKGTMNKWGYIFAHVALIVICL  180
            ||||||||||||||||||||||||||||||||||||||||||||||||||||||||||||
orf88-1     SSLLDVKIAPEVAKRYLEVQGFQGKTINREDGSVLIAAKKGTMNKWGYIFAHVALIVICL  180 orf88a.pep  GGLIDSNLLLKLGMLTGRIVPDNQAVYAKDFKPESILGASNLSFRGNVNISEGQSADVVF  240
            ||||||||||||||||||||||||||||||||||||||||||||||||||||||||||||
orf88-1     GGLIDSNLLLKLGMLTGRIVPDNQAVYAKDFKPESILGASNLSFRGNVNISEGQSADVVF  240 orf88a.pep  LNADNGILVQDLPFEVKLKKFHIDFYNTGMPRDFASDIEVTDKATGEKLERTIRVNHPLT  300
            ||||||||||||||||||||||||||||||||||||||||||||||||||||||||||||
orf88-1     LNADNGILVQDLPFEVKLKKFHIDFYNTGMPRDFASDIEVTDKATGEKLERTIRVNHPLT  300 orf88a.pep  LHGITIYQASFADGGSDLTFKAWNLGDASREPVVLKATSIHQFPLEIGKHKYRLEFDQFT  360
            ||||||||||||||||||||||||||||||||||||||||||||||||||||||||||||
orf88-1     LHGITIYQASFADGGSDLTFKAWNLGDASREPVVLKATSIHQFPLEIGKHKYRLEFDQFT  360 orf88a.pep  SMNVEDMSEGAEREKSLKSTLNDVRAVTQEGKKYTNIGPSIVYRIRDAAGQAVEYKNYML  420
            ||||||||||||||||||||||||||||||||||||||||||||||||||||||||||||
orf88-1     SMNVEDMSEGAEREKSLKSTLNDVRAVTQEGKKYTNIGPSIVYRIRDAAGQAVEYKNYML  420 orf88a.pep  PVLQEQDYFWITGTRSGLQQQYRWLRIPLDKQLKADTFMALREFLKDGEGRKRLVADATK  480
            ||||||||||||||||||||||||||||||||||||||||||||||||||||||||||||
orf88-1     PVLQEQDYFWITGTRSGLQQQYRWLRIPLDKQLKADTFMALREFLKDGEGRKRLVADATK  480 orf88a.pep  GAPAEIREQFMLAAENTLNIFAQKGYLGLDEFITSNIPKEQQDKMQGYFYEMLYGVMNAA  540
            ||||||||||||||||||||||||||||||||||||||||||||||||||||||||||||
orf88-1     GAPAEIREQFMLAAENTLNIFAQKGYLGLDEFITSNIPKEQQDKMQGYFYEMLYGVMNAA  540 orf88a.pep  LDETIRRYGLPEWQQDEARNRFLLHSMDAYTGLTEYPAPMLLQLDGFSEVRSSGLQMTRS  600
            ||||||||||||||||||||||||||||||||||||||||||||||||||||||||||||
orf88-1     LDETIRRYGLPEWQQDEARNRFLLHSMDAYTGLTEYPAPMLLQLDGFSEVRSSGLQMTRS  600 orf88a.pep  PGALLVYLGSVLLVLGTVLMFYVREKRAWVLFSDGKIRFAMSSARSERDLQKEFPKHVES  660
            ||||||||||||||||||||||||||||||||||||||||||||||||||||||||||||
orf88-1     PGALLVYLGSVLLVLGTVLMFYVREKRAWVLFSDGKIRFAMSSARSERDLQKEFPKHVES  660 orf88a.pep  LQRLGKDLNHD                                                  672
            |||||||||||
orf88-1     LQRLGKDLNHD                                                  672
```

Homology with a Predicted ORF from *N. gonorrhoeae*

ORF88 shows 93.8% identity over a 371aa overlap with a predicted ORF (ORF88.ng) from *N. gonorrhoeae*:

```
orf88.pep   MVFLNADNGILVQDLPFEVKLKKFHIDFYNTGMPRDFASDIEVTDKATGEKLERTIRVNH   60
            |||||||||:||||||||||||||||||||||||||||||||||||||||||||||||||
orf88ng     MVFLNADNGMLVQDLPFEVKLKKFHIDFYNTGMPRDFASDIEVTDKATGEKLERTIRVNH   60 orf88.pep   PLTLHGITIYQASFADGGSDLTFKAWNLGDASREPVVLKATSIHQFPLEIGKHKYRLEFD  120
            |||||||||||||||||||||||||||||||:||||||||||||||||||||||||||||
orf88ng     PLTLHGITIYQASFADGGSDLTFKAWNLRDASREPVVLKATSIHQFPLEIGKHKYRLEFD  120 orf88.pep   QFTSMNVEDMSEGAEREKSLKSTLPDVRAVTQEGHKYTNXXXXXXYRIRDAPGQAVEYKN  180
            ||||||||||||||||||||||||:|||||||||:||||       |||||:||||||||
orf88ng     QFTSMNVEDMSEGAEREKSLKSTLNDVRAVTQEGKKYTNIGPSIVYRIRDAAGQAVEYKN  180 orf88.pep   YMLPVLQEQDYFWITGTRSXLQQQYRWLRIPLDKQLKADTFMALREFLKDGEGRKRXVAD  240
            ||||::||:||||||||||| |||||||||||||||||||||||||||||||||||:|||
orf88ng     YMLPILQDKDYFWLTGTRSGLQQQYRWLRIPLDKQLKADTFMALREFLKDGEGRKRLVAD  240 orf88.pep   ATKGAPAEIREQFMLAAENTLNIFAQKGYLGLDEFITSNIPKEQQDKMQGYFYEMLYGVM  300
            |||:||||||||||||||||||||||||||||||||||||||:|||||||||||||||||
orf88ng     ATKDAPAEIREQFMLAAENTLNIFAQKGYLGLDEFITSNIPKGQQDKMQGYFYEMLYGVM  300 orf88.pep   NAALDETXTRYGLPEWQQDEARNRFLLHSMDAYTGLTEYPAPMLLQLDGFSEVRSSGLQM  360
            |||||||  |||||||||||||||||||||||||||||||||||||||||||||||||||
orf88ng     NAALDETIRRYGLPEWQQDEARNRFLLHSMDAYTGLTEYPAPMLLQLDGFSEVRSSGLQM  360 orf88.pep   TRSXGPLLVYL                                                  371
            |||||||||||
orf88ng     TRSPGALLVYLGSVLLVLGTVFMFYVPKKRAWVLFSNXKIRFAMSSARSERDLQKEFPKH  420
```

An ORF88ng nucleotide sequence <SEQ ID 333> was predicted to encode a protein having amino acid sequence <SEQ ID 334>:

```
  1 MVFLNADNGM LVQDLPFEVK LKKFHIDFYN TGMPRDFASD IEVTDKATGE

51 KLERTIRVNH PLTLHGITIY QASFADGGSD LTFKAWNLRD ASREPVVLKA

101 TSIHQFPLEI GKHKYRLEFD QFTSMNVEDM SEGAEREKSL KSTLNDVRAV

151 TQEGKKYTNI GPSIVYRIRD AAGQAVEYKN YMLPILQDKD YFWLTGTRSG

201 LQQQYRWLRI PLDKQLKADT FMALREFLKD GEGRKRLVAD ATKDAPAEIR
```

```
251 EQFMLAAENT LNIFAQKGYL GLDEFITSNI PKGQQDKMQG YFYEMLYGVM

301 NAALDETIRR YGLPEWQQDE ARNRFLLHSM DAYTGLTEYP APMLLQLDGF

351 SEVRSSGLQM TRSPGALLVY LGSVLLVLGT VFMFYVPKKR AWVLFSNXKI

401 RFAMSSARSE RDLQKEFPKH VESLQRLGKD LNHD*
```

Further work revealed the complete gonococcal DNA sequence <SEQ ID 335>:

```
   1 ATGAGTAAAT CCCGTATATC TCCCACACTT CTTTCCCGTC CGTGGTTCGC

51 TTTTTTCAGC TCCATGCGCT TGCGGTCGC TTTGCTCAGT CTGCTGGGTA

101 TTGCATCGGT TATCGGCACG GTGTTACAGC AAAACCAGCC GCAGACGGAT

151 TATTTGGTCA AATTCGGACC GTTTTGGACT CGGATTTTTG ATTTTTTGGG

201 TTTGTATGAT GTCTATGCTT CGGCATGGTT TGTCGTTATC ATGATGTTTC

251 TGGTGGTTTC TACCAGTTTG TGTTTAATCC GTAACGTTCC GCCGTTTTGG

301 CGCGAAATGA AGTCTTTCCG GGAAAAGGTT AAAGAAAAAT CTCTGGCGGC

351 GATGCGCCAT TCTTCGCTGT TGGATGTAAA AATTGCCCCC GAAGTTGCCA

401 AACGTTATCT GGAGGTGCGG GGTTTTCAGG GAAAAACCGT CAGCCGTGAG

451 GACGGGTCGG TTCTGATTGC CGCCAAAAAA GGCAcaatga acaaATGGGG

501 CTATATCTTT GCccaagtag ctTTGATTGT CATTTGCCTG GGCGGGTTGA

551 TAGACAGTAA CCTGCTGCTG AAGCTGGGTA TGCTGGCCGG TCGGATTGTT

601 CCGGACAATC AGGCGGTTTA TGCCAAGGAT TTCAAGCCCG AAAGTATTTT

651 GGGTGCGTCC AATCTCTCAT TTAGGGGCAA CGTCAATATT TCCGAGGGGC

701 AAAGTGCGGA TGTGGTTTTC CTGAATGCCG ACAACGGGAT GTTGGTTCAG

751 GACTTGCCTT TGAAGTCAA ACTGAAAAAA TTCCATATCG ATTTTTACAA

801 TACGGGTATG CCGCGCGATT TGCCAGCGA TATTGAAGTA ACGGACAAGG

851 CAACCGGTGA GAAACTCGAG CGCACCATCC GCGTGAACCA TCCTTTGACC

901 TTGCACGGCA TCACGATTTA TCAGGCGAGT TTTGCCGACG GCGGTTCGGA

951 TTTGACATTC AAGGCGTGGA ATTTGAGGGA TGCTTCGCGC GAACCTGTCG

1001 TGTTGAAGGC AACCTCCATA CACCAGTTTC CGTTGGAAAT CGGCAAACAC

1051 AAATATCGTC TTGAGTTCGA TCAGTTCACT TCTATGAATG TGGAGGACAT

1101 GAGCGAGGGT GCGGAACGGG AAAAAAGCCT GAAATCCACT CTGAACGATG

1151 TCCGCGCCGT TACTCAGGAA GGTAAAAAAT ACACCAATAT CGGCCCTTCC

1201 ATCGTGTACC GCATCCGTGA TGcggCAGGG CAGGCGGTCG AATATAAAAA

1251 CTATATGCTG CCGATTTTGC AGGACAAAGA TTATTTTTGG CTGACCGGCA

1301 CGCGCAGCGG CTTGCAGCAG CAATACCGCT GGCTGCGTAT CCCCTTGGAC

1351 AAGCAGTTGA AAGCGGACAC CTTTATGGCA TTGCGTGAGT TTTTGAAAGA

1401 TGGGGAAGGG CGCAAACGTC TGGTTGCCGA CGCAACCAAA GACGCACCTG

1451 CCGAAATCCG CGAACAATTC ATGCTGGCTG CGGAAAACAC GCTGAATATC

1501 TTTGCGCAAA AAGGCTATTT GGGATTGGAC GAATTTATTA CGTCCAATAT

1551 CCCGAAAGGG CAGCAGGATA AGATGCAGGG CTATTTCTAC GAAATGCTTT

1601 ACGGCGTGAT GAACGCTGCT TTGGATGAAA CCATACGCCG GTACGGCTTG

1651 CCCGAATGGC AGCAGGATGA AGCGCGGAAC CGTTTCCTGC TGCACAGTAT
```

-continued

```
1701 GGATGCCTAT ACGGGGCTGA CGGAATATCC CGCGCCTATG CTGCTCCAGC

1751 TTGACGGGTT TTCCGAGGTG CGTTCCTCAG GTTTGCAGAT GACCCGTTCG

1801 CCGGGTGCGC TTTTGGTCTA TCtcggctcg gtattgttgg TTTTGGgtac 1851 ggtaTtttatg tTTTATGTGC GCGAAAAACG GGCGTGGgta tTGTTTTCag 1901 aCGGCAAAAT CCGTTTTGCT ATGtCTTcgg CCcgcagcga ACGGGATTTG 1951 cAGAaggaaT TTCCAAAACA CGtcgAGAGC CTGCAACggc tcggcaaggA 2001 CttgaaTCAT GACTga
```

This corresponds to the amino acid sequence <SEQ ID 336; ORF88ng-1>:

```
  1 MSKSRISPTL LSRPWFAFFS SMRFAVALLS LLGIASVIGT VLQQNQPQTD

51 YLVKFGPFWT RIFDFLGLYD VYASAWFVVI MMFLVVSTSL CLIRNVPPFW

101 REMKSFREKV KEKSLAAMRH SSLLDVKIAP EVAKRYLEVR GFQGKTVSRE

151 DGSVLIAAKK GTMNKWGYIF AQVALIVICL GGLIDSNLLL KLGMLAGRIV

201 PDNQAVYAKD FKPESILGAS NLSFRGNVNI SEGQSADVVF LNADNGMLVQ

251 DLPFEVKLKK FHIDFYNTGM PRDFASDIEV TDKATGEKLE RTIRVNHPLT

301 LHGITIYQAS FADGGSDLTF KAWNLRDASR EPVVLKATSI HQFPLEIGKH

351 KYRLEFDQFT SMNVEDMSEG AEREKSLKST LNDVRAVTQE GKKYTNIGPS

401 IVYRIRDAAG QAVEYKNYML PILQDKDYFW LTGTRSGLQQ QYRWLRIPLD

451 KQLKADTFMA LREFLKDGEG RKRLVADATK DAPAEIREQF MLAAENTLNI

501 FAQKGYLGLD EFITSNIPKG QQDKMQGYFY EMLYGVMNAA LDETIRRYGL

551 PEWQQDEARN RFLLHSMDAY TGLTEYPAPM LLQLDGFSEV RSSGLQMTRS

601 PGALLVYLGS VLLVLGTVFM FYVREKRAWV LFSDGKIRFA MSSARSERDL

651 QKEFPKHVES LQRLGKDLNH D*
                                                       40
```

ORF88ng-1 and ORF88-1 show 97.0% identity in 671 aa overlap:

```
orf88-1.pep  MSKSRRSPPLLSRPWFAFFSSMRFAVALLSLLGIASVIGTVLQQNQPQTDYLVKFGSFWA  60
             |||||  || |||||||||||||||||||||||||||||||||||||||||||||| ||
orf88ng-1    MSKSRISPTLLSRPWFAFFSSMRFAVALLSLLGIASVIGTVLQQNQPQTDYLVKFGPFWT  60 orf88-1.pep  QIFGFLGLYDVYASAWFVVIMMFLVVSTSLCLIRNVPPFWREMKSFREKVKEKSLAAMRH  120
              ||||||||||||||||||||||||||||||||||||||||||||||||||||||||||
orf88ng-1    RIFDFLGLYDVYASAWFVVIMMFLVVSTSLCLIRNVPPFWREMKSFREKVKEKSLAAMRH  120 orf88-1.pep  SSLLDVKIAPEVAKRYLEVQGFQGKTINREDGSVLIAAKKGTMNKWGYIFAHVALIVICL  180
             ||||||||||||||||||||:|||||||::||||||||||||||||||||||:|||||||
orf88ng-1    SSLLDVKIAPEVAKRYLEVRGFQGKTVSREDGSVLIAAKKGTMNKWGYIFAQVALIVICL  180 orf88-1.pep  GGLIDSNLLLKLGMLTGRIVPDNQAVYAKDFKPESILGASNLSFRGNVNISEGQSADVVF  240
             ||||||||||||||| :|||||||||||||||||||||||||||||||||||||||||||
orf88ng-1    GGLIDSNLLLKLGMLAGRIVPDNQAVYAKDFKPESILGASNLSFRGNVNISEGQSADVVF  240 orf88-1.pep  LNADNGILVQDLPFEVKLKKFHIDFYNTGMPRDFASDIEVTDKATGEKLERTIRVNHPLT  300
             ||||||:|||||||||||||||||||||||||||||||||||||||||||||||||||
orf88ng-1    LNADNGMLVQDLPFEVKLKKFHIDFYNTGMPRDFASDIEVTDKATGEKLERTIRVNHPLT  300 orf88-1.pep  LHGITIYQASFADGGSDLTFKAWNLGDASREPVVLKATSIHQFPLEIGKHKYRLEFDQFT  360
             |||||||||||||||||||||||||| ||||||||||||||||||||||||||||||||
orf88ng-1    LHGITIYQASFADGGSDLTFKAWNLRDASREPVVLKATSIHQFPLEIGKHKYRLEFDQFT  360 orf88-1.pep  SMNVEDMSEGAEREKSLKSTLNDVRAVTQEGKKYTNIGPSIVYRIRDAAGQAVEYKNYML  420
             ||||||||||||||||||||||||||||||||||||||||||||||||||||||||||
orf88ng-1    SMNVEDMSEGAEREKSLKSTLNDVRAVTQEGKKYTNIGPSIVYRIRDAAGQAVEYKNYML  420 orf88-1.pep  PVLQEDYFWITGTRSGLQQQYRWLRIPLDKQLKADTFMALREFLKDGEGRKRLVADATK  480
             |:||:::||||||||||||||||||||||||||||||||||||||||||||||||||||
orf88ng-1    PILQDKDYFWLTGTRSGLQQQYRWLRIPLDKQLKADTFMALREFLKDGEGRKRLVADATK  480 orf88-1.pep  GAPAEIREQFMLAAENTLNIFAQKGYLGLDEFITSNIPKEQQDKMQGYFYEMLYGVMNAA  480
              |||||||||||||||||||||||||||||||||||||:|||||||||||||||||||
orf88ng-1    DAPAEIREQFMLAAENTLNIFAQKGYLGLDEFITSNIPKGQQDKMQGYFYEMLYGVMNAA  480
```

-continued

```
orf88-1.pep    LDETIRRYGLPEWQQDEARNRFLLHSMDAYTGLTEYPAPMLLQLDGFSEVRSSGLQMTRS   600
               ||||||||||||||||||||||||||||||||||||||||||||||||||||||||||||
orf88ng-1      LDETIRRYGLPEWQQDEARNRFLLHSMDAYTGLTEYPAPMLLQLDGFSEVRSSGLQMTRS   600 orf88-1.pep    PGALLVYLGSVLLVLGTVLMFYVREKRAWVLFSDGKIRFAMSSARSERDLQKEFPKHVES   660
               ||||||||||||||||:|||||||||||||||||||||||||||||||||||||||||||
orf88ng-1      PGALLVYLGSVLLVLGTVFMFYVREKRAWVLFSDGKIRFAMSSARSERDLQKEFPKHVES   660 orf88-1.pep    LQRLGKDLNHD                                                    671
               |||||||||||
orf88ng-1      LQRLGKDLNHD                                                    671
```

Furthermore, ORG88ng-1 shows homology with a hypothetical protein from *Aquifex aeolicus*:

```
gi|2984296 (AE000771) hypothetical protein [Aquifex aeolicus]
Length = 537
Score = 94.4 bits (231), Expect = 2e-18.
Identities = 91/334 (27%), Positives = 159/334 (47%),
Gaps = 59/334 (17%)

Query:   16 FAFFSSMRFAVALLSLLGIASVIG-TVLQQNQPQTDYLVKFGPFWTRIFDFLGLYDVYAS    74
            + F +S++ A+ ++ +LGI S++G T ++QNQ      YL +FG       L L DV+ S
Sbjct:   80 YDFLASLKLAIFIMLVLGILSMLGSTYIKQNQSFEWYLDQFGYDVGIWIWKLWLNDVFHS   139

Query:   75 AWFVVIMMFLVVSTSLCLIRNVPPFWREMKSFREKVKEKSLAAMRHSSLLDVKIAPEVAK   134
            ++++ ++ L V+    C I+ +P  W++  S +E++ +     A  +H    + VKI P+  K
Sbjct:  140 WYYILFIVLLAVNLIFCSIKRLPRVWKQAFS-KERILKLDEHAEKHLKPITVKI-PDKDK   197

Query:  135 --RYLEVRGFQGKTVSREDGSVLIAAKKGTMNKWGYIFAQVALIVICLGGLIDSNLLLKL   192
              ++L +GF+    V E   + + A+KG ++ G      +AL+VI   G LID
Sbjct:  198 VLKFLLKKGFK-VFVEEEGNKLYVFAEKGRFSRLGVYITHIALLVIMAGALID-------   249

Query:  193 GMLAGRIVPDNQAVYAKDFKPESILGASNLSFRGNVNISEGQSADVVFLNADNGMLVQDL   252
                                 +I+G         RG++ ++EG + DV+ + A+      L
Sbjct:  250 ----------------------AIVGV-----RGSLIVAEGDTNDVMLVGAE--QKPYKL   280

Query:  253 PFEVKLKKFHIDFY---NTGMPRDFA-------SDIEVTDKATGEKLER--TIRVNHPLT   300
            PF V L  F I Y    N + + FA         SDIE+ +   G K+E    T++VN P
Sbjct:  281 PFAVHLIDFRIKTYAEENPNVDKRFAQAVSSYESDIEIIN---GGKVEAKGTVKVNEPFD   337

Query:  301 LHGITIYQASFA--DGGSDLTFKAWNLRDASREP                             332
             ++QA++    DG S +    + + A  +P
Sbjct:  338 FGRYRLFQATYGILDGTSGMGVIVVDRKKAHEDP                             371
```

Based on this analysis, including the putative transmembrane domain in the gonococcal protein, it is predicted that the proteins from *N. meningitidis* and *N. gonorrhoeae*, and their epitopes, could be useful antigens for vaccines or diagnostics, or for raising antibodies.

Example 40

The following DNA sequence, believed to be complete, was identified in *N. meningitidis* <SEQ ID 337>:

```
  1 ATGATGAGTA ATAmAATGGm ACAAAAAGGG TTTACATTGA TTGmGmTGAT

51 GATAGTCGTC GCGATACTCG GCATTATCAG CGTCATTGCC ATACCTTCTT

101 ATCmAAGTTA TATTGAAAAA GGCTATCAGT CCCAGCTTTA TACGGAGATG

151 GyCGGTATCA ACAATATTTC CAAACAGTTT ATTTTGAAAA ATCCCCTGGA

201 CGATAATCAG ACCATCGAGA ACAAACTGGA AATATTTGTC TCAGGCTATA

251 AGATGAATCC GAAAATTGCC AAAAAaTATA GTGTTTCGGT AAAGTTTGTC

301 GATAAGGAAA AATCAAGGGC ATACAGGTTG GTCGGCGTTC CGAAGGCGGG

351 GACGGGTTAT ACTTTGTCGG TATGGATGAA CAGCGTGGGC GACGGATACA
```

```
401 AATGCCGTGA TGCCGCTTCT GCCCAAGCCC ATTTGGAGAC CTTGTCCTCA

451 GATGTCGGCT GTGAAGCCTT CTCTAATCGT AAAAAATAA
```

This corresponds to the amino acid sequence <SEQ ID 338; ORF89>:

```
  1 MMSNXMXQKG FTLIXXMIVV AILGIISVIA IPSYXSYIEK GYQSQLYTEM

51 XGINNISKQF ILKNPLDDNQ TIENKLEIFV SGYKMNPKIA KKYSVSVKFV

101 DKEKSRAYRL VGVPKAGTGY TLSVWMNSVG DGYKCRDAAS AQAHLETLSS

151 DVGCEAFSNR KK*
```

Further work revealed the complete nucleotide sequence <SEQ ID 339>:

```
  1 ATGATGAGTA ATAAAATGGA ACAAAAAGGG TTTACATTGA TTGAGATGAT

51 GATAGTCGTC GCGATACTCG GCATTATCAG CGTCATTGCC ATACCTTCTT

101 ATCAAAGTTA TATTGAAAAA GGCTATCAGT CCCAGCTTTA TACGGAGATG

151 GTCGGTATCA ACAATATTTC CAAACAGTTT ATTTTGAAAA ATCCCCTGGA

201 CGATAATCAG ACCATCGAGA ACAAACTGGA ATATTTGTC TCAGGCTATA

251 AGATGAATCC GAAAATTGCC AAAAAATATA GTGTTTCGGT AAAGTTTGTC

301 GATAAGGAAA AATCAAGGGC ATACAGGTTG GTCGGCGTTC CGAAGGCGGG

351 GACGGGTTAT ACTTTGTCGG TATGGATGAA CAGCGTGGGC GACGGATACA

401 AATGCCGTGA TGCCGCTTCT GCCCAAGCCC ATTTGGAGAC CTTGTCCTCA

451 GATGTCGGCT GTGAAGCCTT CTCTAATCGT AAAAAATAA
```

This corresponds to the amino acid sequence <SEQ ID 340; ORF89-1>:

```
  1 MMSNKMEQKG FTLIEMMIVV AILGIISVIA IPSYQSYIEK GYQSQLYTEM

51 VGINNISKQF ILKNPLDDNQ TIENKLEIFV SGYKMNPKIA KKYSVSVKFV

101 DKEKSRAYRL VGVPKAGTGY TLSVWMNSVG DGYKCRDAAS AQAHLETLSS

151 DVGCEAFSNR KK*
```

Computer analysis of this amino acid sequence gave the following results:
Homology with PilE of *N. gonorrhoeae* (Accession Number Z69260).

ORF89 and PilE protein show 30% aa identity in 120a overlap:

```
orf89   8 QKGFTLIXXMIVVAILGIISVIAIPSYXSYIEKGYQSQLYTEMXGINNISKQFILKNPL-   66
          QKGFTLI  MIV+AI+GI++ +A+P+Y  Y + S+      G +   ++ L + +
PilE    5 QKGFTLIELMIVIAIVGILAAVALPAYQDYTARAQVSEAILLAEGQKSAVTEYYLNHGIW   64 orf89  67 -DDNQTIENKLEIFVSGYKMNPKIAKKYSVSVKFVDKEKSRAYRLVGVPKAGTGYTLSVW  125
            DN +      +G + KI  KY SV      +         GV K    G  LS+W
PilE   65 PKDNTS---------AGVASSDKIKGKYVQSVTVAKGVVTAEMASTGVNKEIQGKKLSLW  115
```

Homology with a Predicted ORF from *N. meningitidis* (Strain A)

ORF89 shows 83.3% identity over a 162aa overlap with an ORF (ORF89a) from strain A of *N. meningitidis*

```
                  10         20         30         40         50         60
orf89.pep  MMSNXMXQKGFTLIXXMIVVAILGIISVIAIPSYXSYIEKGYQSQLYTEMXGINNISKQF
           ||||  | |||||||||        ||   |||  ||||||||||||||||| ||||||||
orf88a     MMSNKMEQKGFTLIXXXXXXAIXXXXSVIXXXXYXSYIEKGYQSQLYTEMVGINNISKQX
                  10         20         30         40         50         60

70         80         90        100        110        120
orf89.pep  ILKNPLDDNQTIENKLEIFVSGYKMNPKIAKKYSVSVKFVDKEKSRAYRLVGVPKAGTY
           ||||  | |||||::|||||||||||||||||:||:|||:::|| ||| ||||||:|||
orf88a     ILKNPLDDNQTIKSKLEIFVSGYKMNPKIAEKYNVSVHFVNEEKPRAYSLVGVPKTGTGY
                  70         80         90        100        110        120

130        140        150        160
orf89.pep  TLSVWMNSVGDGYKCRDAASAQAHLETLSSDVGCEAFSNRKKX
           |||||||||||||||||||||:|||||||||||||||||||||
orf88a     TLSVWMNSVGDGYKCRDAASARAHLETLSSDVGCEAFSNRKKX
                 130        140        150        160
```

The complete length ORF89a nucleotide sequence <SEQ ID 341> is:

```
  1 ATGATGAGTA ATAAAATGGA ACAAAAAGGG TTTACATTGA TTGNGANGNT

51 NATNGNCNTC GCGATACNCN GCNTTANCAG CGTCATTNCN ATNNNTNCNT

101 ATCNNAGTTA TATTGAAAAA GGCTATCAGT CCCAGCTTTA TACGGAGATG

151 GTCGGTATCA ACAATATTTC CAAACAGTNT ATTTTGAAAA ATCCCCTGGA

201 CGATAATCAG ACCATCAAGA GCAAACTGGA AATATTTGTC TCAGGCTATA

251 AGATGAATCC GAAAATTGCC GAAAAATATA ATGTTTCGGT GCATTTTGTC

301 AATGAGGAAA AACCNAGGGC ATACAGCTTG GTCGGCGTTC CAAAGACGGG

351 GACGGGTTAT ACTTTGTCGG TATGGATGAA CAGCGTGGGC GACGGATACA

401 AATGCCGTGA TGCCGCTTCT GCCCGAGCCC ATTTGGAGAC CTTGTCCTCA

451 GATGTCGGCT GTGAAGCCTT CTCTAATCGT AAAAAATAG
```

This encodes a protein having amino acid sequence <SEQ ID 342>:

```
  1 MMSNKMEQKG FTLIXXXXXX AIXXXXSVIX XXXYXSYIEK GYQSQLYTEM

51 VGINNISKQX ILKNPLDDNQ TIKSKLEIFV SGYKMNPKIA EKYNVSVHFV

101 NEEKPRAYSL VGVPKTGTGY TLSVWMNSVG DGYKCRDAAS ARAHLETLSS

151 DVGCEAFSNR KK*
```

ORF89a and ORF89-1 show 83.3% identity in 162 aa overlap:

```
                   10         20         30         40         50         60
orf89a.pep  MMSNKMEQKGFTLIXXXXXXAIXXXXSVIXXXXYXSYIEKGYQSQLYTEMVGINNISKQX
            |||||||||||||||      ||   |||  ||||||||||||||||||| ||||||||
orf89-1     MMSNKMEQKGFTLIEMMIVVAILGIISVIAIPSYQSYIEKGYQSQLYTEMVGINNISKQF
                   10         20         30         40         50         60

70         80         90        100        110        120
orf89a.pep  ILKNPLDDNQTIKSKLEIFVSGYKMNPKIAEKYNVSVHFVNEEKPRAYSLVGVPKTGTGY
            ||||||||||||::|||||||||||||||||:||:|||:::||  |||  ||||||:|||
orf89-1     ILKNPLDDNQTIENKLEIFVSGYKMNPKIAKKYSVSVKFVDKEKSRAYRLVGVPKAGTGY
                   70         80         90        100        110        120
```

```
               130       140       150       160
orf89a.pep  TLSVWMNSVGDGYKCRDAASARAHLETLSSDVGCEAFSNRKKX
            ||||||||||||||||||||||:||||||||||||||||||
orf89-1     TLSVWMNSVGDGYKCRDAASAQAHLETLSSDVGCEAFSNRKKX
               130       140       150       160
```

Homology with a Predicted ORF from *N. gonorrhoeae*

ORF89 shows 84.6% identity over a 162aa overlap with a predicted ORF (ORF89.ng) from *N. gonorrhoeae*.

```
orf89     MMSNXMXQKGFTLIXXMIVVAILGIISVIAIPSYXSYIEKGYQSQLYTEMXGINNISKQF   60
          ||||:||:|||||||:||:||||:|||||||||||:||||||||||||||||||:|||
orf89ng   MMSNKMEQKGFTLIEMMIVVTILGIISVIAIPSYQSYIEKGYQSQLYTEMVGINNVLKQF   60
orf89     ILKNPLDDNQTIENKLEIFVSGYKMNPKIAKKYSVSVKFVDKEKSRAYRLVGVPKAGTGY  120
          |||||:|||:::||:|||||||||||||||||||||||||:||||:|||||||||:||||
orf89ng   ILKNPQDDNDTLKSKLKIFVSGYKMNPKIAKKYSVSVRFVDAEKPRAYRLVGVPNAGTGY  120
orf89     TLSVWMNSVGDGYKCRDAASAQAHLETLSSDVGCEAFSNRKK                    162
          ||||||||||||||||||||:|||::|||:|||||||||||
orf89ng   TLSVWMNSVGDGYKCRDATSAQAYSDTLSADSGCEAFSNRKK                   162
```

The complete length ORF89ng nucleotide sequence <SEQ ID 343> is:

```
  1 aTGATGAGCA ATAAAATGGA ACAAAAAGGG TTTACATTGA TTGAGATGAT

51 GATAGTTGTC ACGATACTCG GCATCATCAG CGTCATTGCC ATACCTTCTT

101 ATCAGAGTTA TATTGAAAAA GGCTATCAGT CCCAGCTTTA TACGGAGATG

151 GTCGGTATCA ACAATGTTCT CAAACAGTTT ATTTTGAAAA ATCCCCAGGA

201 CGATAATGAT ACCCTCAAGA GCAAACTGAA AATATTTGTC TCAGGCTATA

251 AGATGAATCC GAAAAttgCC AAAAAATATA GTGTTTCGGt aaggtttGTC 301 gatGCGGAAA AACCAAGGGC ATACAGGTTG GTCGGCGTTC CGAACGCGGG

351 GACGGGTTAT ACTTTGTCGG TATGGATGAA CAGCGTGGGC GACGGATACA

401 AATGCCGTGA TGCCACTTCT GCCCAGGCCT ATTCGGACAC CTTGTCCGCA

451 GATAGCGGCT GTGAAGCTTT CTCTAATCGT AAAAAATAG
```

This encodes a protein having amino acid sequence <SEQ ID 344>:

```
  1 MMSNKMEQKG FTLIEMMIVV TILGIISVIA IPSYQSYIEK GYQSQLYTEM

51 VGINNVLKQF ILKNPQDDND TLKSKLKIFV SGYKMNPKIA KKYSVSVRFV

101 DAEKPRAYRL VGVPNAGTGY TLSVWMNSVG DGYKCRDATS AQAYSDTLSA

151 DSGCEAFSNR KK*
```

This gonococcal protein has a putative leader peptide (underlined) and N-terminal methylation site (NMePhe or type-4 pili, double-underlined). In addition, ORF89ng and ORF89-1 show 88.3% identity in 162 aa overlap:

```
                     10        20        30        40        50        60
orf89-1.pep  MMSNKMEQKGFTLIEMMIVVAILGIISVIAIPSYQSYIEKGYQSQLYTEMVGINNISKQF
             |||||||||||||||||||| :|||||||||||||||||||||||||||||||||: |||
orf89ng      MMSNKMEQKGFTLIEMMIVVTILGIISVIAIPSYQSYIEKGYQSQLYTEMVGINNVLKQF
                     10        20        30        40        50        60

70        80        90       100       110       120
orf89-1.pep  ILKNPLDDNQTIENKLEIFVSGYKMNPKIAKKYSVSVKFVDKEKSRAYRLVGVPKAGTGY
             |||||:|||:::||:||||||||||||||||||||||:|||| || ||||||||| ||||
orf89ng      ILKNPQDDNDTLKSKLKIFVSGYKMNPKIAKKYSVSVRFVDAEKPRAYRLVGVPNAGTGY
                     70        80        90       100       110       120
```

```
                         -continued
                   130        140        150       160
    orf89-1.pep  TLSVWMNSVGDGYKCRDAASAQAHLETLSSDVGCEAFSNRKKX
                 ||||||||||||||||:||||: :|||:| |||||||||||||
    orf89ng      TLSVWMNSVGDGYKCRDATSAQAYSDTLSADSGCEAFSNRKKX
                   130        140        150       160
```

Based on this analysis, including the gonococcal motifs and the homology with the known PilE protein, it was predicted that these proteins from *N. meningitidis* and *N. gonorrhoeae*, and their epitopes, could be useful antigens for vaccines or diagnostics, or for raising antibodies.

Figure 11:
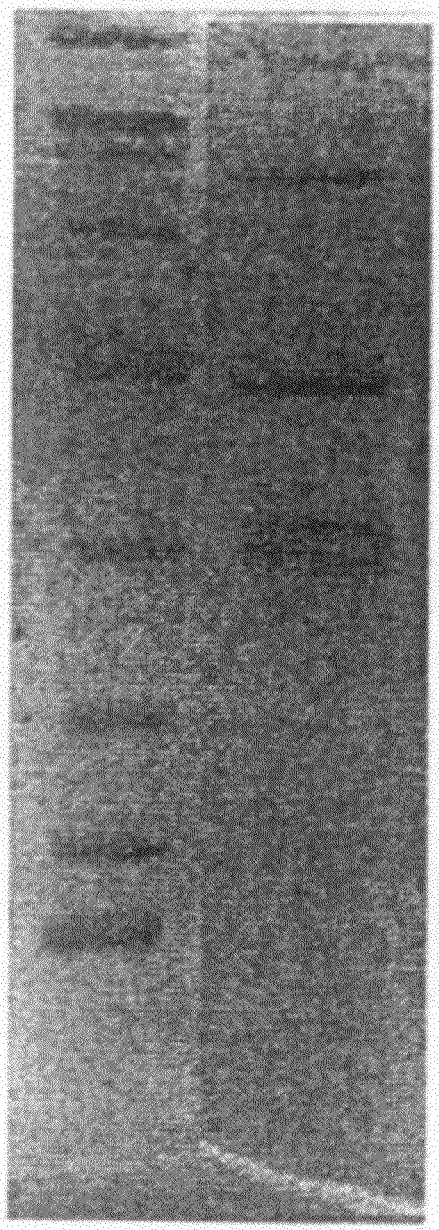

ORF89-1 (13.6 kDa) was cloned in the pGex vector and expressed in *E. coli*, as described above. The products of protein expression and purification were analyzed by SDS-PAGE. FIG. 11A shows the results of affinity purification of the GST-fusion protein. Purified GST-fusion protein was used to immunise mice, whose sera gave a positive result in the ELISA test, confirming that ORF89-1 is a surface-exposed protein, and that it is a useful immunogen.

Example 41

The following partial DNA sequence was identified in *N. meningitidis* <SEQ ID 345>:

```
  1 ATGAAAAAAT CCTCCCTCAT CAGCGCATTG GGCATCGGTA TTTTGAGCAT

51 CGGCATGGCA TTTGCCGCCC CTGCCGACGC GGTAAGCCAA ATCCGTCAAA

101 ACGCCACTCA AGTATTGAGC ATCTTAAAAA ACGGCGATGC CAACACCGCT

151 CGCCAAAAAG CCGAAGCCTA TGCGATTCCC TATTTCGATT TCCAACGTAT

201 GACCGCATTG GCGGTCGGCA ACCCTTGGsG CACCG.GTCC GACG.GCAAA

251 AACAAGCGTT GGCCn.AGAA TTTCAACCC...
```

This corresponds to the amino acid sequence <SEQ ID 346; ORF91>:

```
  1 MKKSSLISAL GIGILSIGMA FAAPADAVSQ IRQNATQVLS ILKNGDANTA

51 RQKAEAYAIP YFDFQRMTAL AVGNPWXTXS DXQKQALAXE FQP...
```

Further work revealed the complete nucleotide sequence <SEQ ID 347>:

```
  1 ATGAAAAAAT CCTCCCTCAT CAGCGCATTG GGCATCGGTA TTTTGAGCAT

51 CGGCATGGCA TTTGCCGCCC CTGCCGACGC GGTAAGCCAA ATCCGTCAAA

101 ACGCCACTCA AGTATTGAGC ATCTTAAAAA ACGGCGATGC CAACACCGCT

151 CGCCAAAAAG CCGAAGCCTA TGCGATTCCC TATTTCGATT TCCAACGTAT

201 GACCGCATTG GCGGTCGGCA ACCCTTGGCG CACCGCGTCC GACGCGCAAA

251 AACAAGCGTT GGCCAAAGAA TTTCAAACCC TGCTGATCCG CACCTATTCC

301 GGCACGATGC TGAAATTAAA AAACGCCAAC GTCAACGTCA AGACAATCC

351 CATCGTCAAT AAAGGCGGCA AAGAAATCAT CGTCCGCGCC GAAGTCGGCG

401 TACCCGGGCA AAACCCGTC AACATGGACT TCACCACCTA CCAAAGCGGC

451 GGTAAATACC GTACCTACAA CGTCGCCATC GAAGGCGCGA GCCTGGTTAC
```

```
501 CGTGTACCGC AACCAATTCG GCGAAATTAT CAAAGCGAAA GGCGTGGACG

551 GACTGATTGC CGAGTTGAAA GCCAAAAACG GCGGCAAATA A
```

This corresponds to the amino acid sequence <SEQ ID 348; ORF91-1>:

```
  1 MKKSSLISAL GIGILSIGMA FAAPADAVSQ IRQNATQVLS ILKNGDANTA

51 RQKAEAYAIP YFDFQRMTAL AVGNPWRTAS DAQKQALAKE FQTLLIRTYS

101 GTMLKLKNAN VNVKDNPIVN KGGKEIIVRA EVGVPGQKPV NMDFTTYQSG

151 GKYRTYNVAI EGASLVTVYR NQFGEIIKAK GVDGLIAELK AKNGGK*
```

Computer analysis of this amino acid sequence gave the following results:

Homology with a Predicted ORF from *N. meningitidis* (Strain A)

ORF91 shows 92.4% identity over a 92aa overlap with an ORF (ORF91a) from strain A of *N. meningitidis*:

```
                   10         20         30         40         50         60
    orf91.pep  MKKSSLISALGIGILSIGMAFAAPADAVSQIRQNATQVLSILKNGDANTARQKAEAYAIP
               |||||:||||||||||||||||||||||||:|||||||||||:|||||||||||||||||
    orf91a     MKKSSFISALGIGILSIGMAFAAPADAVNQIRQNATQVLSILKSGDANTARQKAEAYAIP
                   10         20         30         40         50         60
                   70         80         90
    orf91.pep  YFDFQRMTALAVGNPWXTXSDXQKQALAXEFQP
               |||||||||||||||| || ||||| |||| ||
    orf91a     YFDFQRMTALAVGNPWRTASDAQKQALAKEFQTLLIRTYSGTMLKLKNANVNVKDNPIVN
                   70         80         90        100        110        120
    orf91a     KGGKEIIVRAEVGVPGQKPVNMDFTTYQSGGKYRTYNVAIEGASLVTVYRNQFGEIIKAK
                  130        140        150        160        170        180
```

The complete length ORF91a nucleotide sequence <SEQ ID 349> is:

```
  1 ATGAAAAAAT CCTCCTTCAT CAGCGCATTG GGCATCGGTA TTTTGAGCAT

51 CGGCATGGCA TTTGCCGCCC TGCCGACGC GGTAAACCAA ATCCGTCAAA

101 ACGCCACTCA AGTATTGAGC ATCTTAAAAA GCGGTGATGC CAACACCGCC

151 CGCCAAAAAG CCGAAGCCTA TGCGATTCCC TATTTCGATT TCCAACGTAT

201 GACCGCATTG GCGGTCGGCA ACCCTTGGCG CACCGCGTCC GACGCGCAAA

251 AACAAGCGTT GGCCAAAGAA TTTCAAACCC TGCTGATCCG CACCTATTCC

301 GGCACGATGC TGAAATTAAA AAACGCCAAC GTCAACGTCA AGACAATCC

351 CATCGTCAAT AAAGGCGGCA AAGAAATCAT CGTCCGCGCC GAAGTCGGCG

401 TACCCGGGCA AAAACCCGTC AACATGGACT TCACCACCTA CCAAAGCGGC

451 GGTAAATACC GTACCTACAA CGTCGCCATC GAAGGCGCGA GCCTGGTTAC

501 CGTGTACCGC AACCAATTCG GCGAAATTAT CAAAGCGAAA GGCGTGGACG

551 GACTGATTGC CGAGTTGAAG GCTAAAAACG GCAGCAAGTA A
```

This encodes a protein having amino acid sequence <SEQ ID 350>:

```
  1 MKKSSFISAL GIGILSIGMA FAAPADAVNQ IRQNATQVLS ILKSGDANTA

51 RQKAEAYAIP YFDFQRMTAL AVGNPWRTAS DAQKQALAKE FQTLLIRTYS
```

```
101 GTMLKLKNAN VNVKDNPIVN KGGKEIIVRA EVGVPGQKPV NMDFTTYQSG

151 GKYRTYNVAI EGASLVTVYR NQFGEIIKAK GVDGLIAELK AKNGSK*
```

ORF91a and ORF91-1 show 98.0% identity in 196 aa overlap:

```
                10         20         30         40         50         60
  orf91a.pep  MKKSSFISALGIGILSIGMAFAAPADAVNQIRQNATQVLSILKSGDANTARQKAEAYAIP
              ||||:|||||||||||||||||||||||:||||||||||||:||||||||||||||||||
  orf91-1     MKKSSLISALGIGILSIGMAFAAPADAVSQIRQNATQVLSILKNGDANTARQKAEAYAIP
                10         20         30         40         50         60

70         80         90        100        110        120
  orf91a.pep  YFDFQRMTALAVGNPWRTASDAQKQALAKEFQTLLIRTYSGTMLKLKNANVNVKDNPIVN
              ||||||||||||||||||||||||||||||||||||||||||||||||||||||||||||
  orf91-1     YFDFQRMTALAVGNPWRTASDAQKQALAKEFQTLLIRTYSGTMLKLKNANVNVKDNPIVN
                70         80         90        100        110        120

130        140        150        160        170        180
  orf91a.pep  KGGKEIIVRAEVGVPGQKPVNMDFTTYQSGGKYRTYNVAIEGASLVTVYRNQFGEIIKAK
              ||||||||||||||||||||||||||||||||||||||||||||||||||||||||||||
  orf91-1     KGGKEIIVRAEVGVPGQKPVNMDFTTYQSGGKYRTYNVAIEGASLVTVYRNQFGEIIKAK
               130        140        150        160        170        180

190
  orf91a.pep  GVDGLIAELKAKNGSKX
              |||||||||||||:||
  orf91-1     GVDGLIAELKAKNGGKX
               190
```

Homology with a Predicted ORF from *N. gonorrhoeae*

ORF91 shows 84.8% identity over a 92aa overlap with a predicted ORF (ORF91.ng) from *N. gonorrhoeae*:

```
  orf91.pep   MKKSSLISALGIGILSIGMAFAAPADAVSQIRQNATQVLSILKNGDANTARQKAEAYAIP    60
              :||||:||||||||||||||||:||||:||||||||||:|||:|||  :||  ||||||:|
  orf91g      VKKSSFISALGIGILSIGMAFASPADAVGQIRQNATQVLTILKSGDAASARPKAEAYAVP    60 orf91.pep   YFDFQRMTALAVGNPWXTXSDXQKQALAXEFQP
              ||||||||||||||||||||||||||||||||
  orf91ng     YFDFQRMTALAVGNPWRTASDAQKQALAKEFQTLLIRTYSGTMLKFKNATVNVKDNPIVN    93
                                                                           120
```

The complete length ORF91ng nucleotide sequence <SEQ ID 351> is predicted to encode a protein having amino acid sequence <SEQ ID 352>:

```
  1 VKKSSFISAL GIGILSIGMA FASPADAVGQ IRQNATQVLT ILKSGDAASA

51 RPKAEAYAVP YFDFQRMTAL AVGNPWRTAS DAQKQALAKE FQTLLIRTYS

101 GTMLKFKNAT VNVKDNPIVN KGGKEIVVRA EVGIPGQKPV NMDFTTYQSG

151 GKYRTYNVAI EGTSLVTVYR NQFGEIIKAK GIDGLIAELK AKNGGK*
```

Further work revealed the complete nucleotide sequence <SEQ ID 353>:

```
  1 ATGAAAAAAT CCTCCTTCAT CAGCGCATTG GGCATCGGTA TTTTGAGCAT

51 CGGCATGGCA TTTGCCTCCC CGGCCGACGC AGTGGGACAA ATCCGCCAAA

101 ACGCCACACA GGTTTTGACC ATCCTCAAAA GCGGCGACGC GGCTTCTGCA

151 CGCCCAAAAG CCGAAGCCTA TGCGGTTCCC TATTTCGATT CCAACGTAT

201 GACCGCATTG GCGGTCGGCA ACCCTTGGCG TACCGCGTCC GACGCGCAAA

251 AACAAGCGTT GGCCAAAGAA TTTCAAACCC TGCTGATCCG CACCTATTCC

301 GGCACGATGC TGAAATTCAA AAACGCGACC GTCAACGTCA AGACAATCC

351 CATCGTCAAT AAGGGCGGCA AGGAAATCGT CGTCCGTGCC GAAGTCGGCA
```

```
401 TCCCCGGTCA GAAGCCCGTC AATATGGACT TTACCACCTA CCAAAGCGGC

451 GGCAAATACC GTACCTACAA CGTCGCCATC GAAGGCACGA GCCTGGTTAC

501 CGTGTACCGC AACCAATTCG GCGAAATCAT CAAAGCCAAA GGCATCGACG

551 GGCTGATTGC CGAGTTGAAA GCCAAAAACG GCGGCAAATA A
```

This corresponds to the amino acid sequence <SEQ ID 354; ORF91ng-1>:

```
  1 MKKSSFISAL GIGILSIGMA FASPADAVGQ IRQNATQVLT ILKSGDAASA

51 RPKAEAYAVP YFDFQRMTAL AVGNPWRTAS DAQKQALAKE FQTLLIRTYS

101 GTMLKFKNAT VNVKDNPIVN KGGKEIVVRA EVGIPGQKPV NMDFTTYQSG

151 GKYRTYNVAI EGTSLVTVYR NQFGEIIKAK GIDGLIAELK AKNGGK*
```

ORF91ng-1 and ORF91-1 show 92.3% identity in 196 aa overlap:

```
                    10         20         30         40         50         60
orf91-1.pep MKKSSLISALGIGILSIGMAFAAPADAVSQIRQNATQVLSILKNGDANTARQKAEAYAIP
            |||||:||||||||||||||||:||||||:|||||||||||:||:|||  :||||||||:|
orf91ng-1   MKKSSFISALGIGILSIGMAFASPADAVGQIRQNATQVLTILKSGDAASARPKAEAYAVP
                    10         20         30         40         50         60

70         80         90        100        110        120
orf91-1.pep YFDFQRMTALAVGNPWRTASDAQKQALAKEFQTLLIRTYSGTMLKLKNANVNVKDNPIVN
            |||||||||||||||||||||||||||||||||||||||||||||:|||||||||||||
orf91ng-1   YFDFQRMTALAVGNPWRTASDAQKQALAKEFQTLLIRTYSGTMLKFKNATVNVKDNPIVN
                    70         80         90        100        110        120

130        140        150        160        170        180
orf91-1.pep KGGKEIIVRAEVGVPGQKPVNMDFTTYQSGGKYRTYNVAIEGASLVTVYRNQFGEIIKAK
            ||||||:|||||:|||||||||||||||||||||||||||||:|||||||||||||||||
orf91ng-1   KGGKEIVVRAEVGIPGQKPVNMDFTTYQSGGKYRTYNVAIEGTSLVTVYRNQFGEIIKAK
                   130        140        150        160        170        180

190
orf91-1.pep GVDGLIAELKAKNGGKX
            |:|||||||||||||||
orf91ng-1   GIDGLIAELKAKNGGKX
                   190
```

In addition, ORF91ng-1 shows homology to a hypothetical E. Coli protein:

```
sp|P45390|YRBC_ECOLI HYPOTHETICAL 24.0 KD PROTEIN IN MURA-RPON INTERGENIC
REGION PRECURSOR (F211) >gi|606130 (U18997) ORF_f211 [Escherichia coli]
>gi|1789583 (AE000399) hypothetical 24.0 kD protein in murZ-rpoN intergenic
region [Escherichia coli]Length = 211
Score = 70.6 bits (170), Expect = 6e-12
Identities = 42/137 (30%), Positives = 76/137 (54%), Gaps = 6/137 (4%)

Query:  59 VPYFDFQRMTALAVGNPWRTASDAQKQALAKEFQTLLIRTYSGTMLKFKNATVNVKDNPI 118
            +PY   +   AL +G  +++A+ AQ++A     F+  L + Y   +   T   +   P
Sbjct:  65 LPYVQVKYAGALVLGQYYKSATPAQREAYFAAFREYLKQAYGQALAMYHGQTYQIA--PE 122

Query: 119 VNKGGKEIV-VRAEVGIP-GQKPVNMDFTTYQSG--GKYRTYNVAIEGTSLVTVYRNQFG 174
              G K IV +R  + P G+ PV +DF   ++     G ++ Y++  EG S++T  +N++G
Sbjct: 123 QPLGDKTIVPIRVTIIDPNGRPPVRLDFQWRKNSQTGNWQAYDMIAEGVSMITTKQNEWG 182

Query: 175 EIIKAKGIDGLIAELKA                                            191
              +++ KGIDGL A+LK+
Sbjct: 183 TLLRTKGIDGLTAQLKS                                            199
```

Based on this analysis, including the presence of a putative leader sequence in the gonococcal protein, it is predicted that the proteins from *N. meningitidis* and *N. gonorrhoeae*, and their epitopes, could be useful antigens for vaccines or diagnostics, or for raising antibodies.

Example 42

The following DNA sequence was identified in *N. meningitidis* <SEQ ID 355>:

```
  1 ATGAAACACA TACTCCCCCT GATTGCCGCA TCCGCACTCT GCATTTCAAC
 51 CGCTTCGGCA CATCCTGCCA GCGAACCGTC CACTCAAAAC GAAACCGCTA
101 TGATCACGCA TACCCTCATC TCAAAATACA GTTTTGGnnn nnnnnnnnnn
151 nnnnnnnnnn nnGCCATAAA AGCAAAGGG ATGGACATTT TGCCGTCAT
201 CGACCATCAG GAAGCCGCAC GCCGAAACGG CTTAACGATG CAGCCGGCAA
251 AAGTCATCGT CTTCGGCACG CCCAAAGCCG GCACGCCGCT GATGGTCAAA
301 GACCCCGCCT TCGCCCTGCA ACTGCCCCTA CGCGTCCTCG TTACCGAAAC
351 GGACGGCAAA GTACGCGCCG CCTATACCGA TACGCGCGCC CTCATCGCCG
401 GCAGCCGCAT CGGTTTCGAC GAAGTGGCAA ACACTTTGGC AAACGCCGAA
451 AAACTGATAC AAAAAACCGT AGGCGAATAA
```

This corresponds to the amino acid sequence <SEQ ID 356; ORF97>:

```
  1 MKHILPLIAA SALCISTASA HPASEPSTQN ETAMITHTLI SKYSFGXXXX
 51 XXXXAIKSKG MDIFAVIDHQ EAARRNGLTM QPAKVIVFGT PKAGTPLMVK
101 DPAFALQLPL RVLVTETDGK VRAAYTDTRA LIAGSRIGFD EVANTLANAE
151 KLIQKTVGE*
```

Further work revealed the complete nucleotide sequence <SEQ ID 357>:

```
  1 ATGAAACACA TACTCCCCCT GATTGCCGCA TCCGCACTCT GCATTTCAAC
 51 CGCTTCGGCA CATCCTGCCA GCGAACCGTC CACCCAAAAC GAAACCGCTA
101 TGACCACGCA TACCCTCACC TCAAAATACA GTTTTGACGA AACCGTCAGC
151 CGCCTTGAAA CCGCCATAAA AGCAAAGGG ATGGACATTT TGCCGTCAT
201 CGACCATCAG GAAGCCGCCC GCCGAAACGG CTTAACGATG CAGCCGGCAA
251 AAGTCATCGT CTTCGGCACG CCCAAAGCCG GCACGCCGCT GATGGTCAAA
301 GACCCCGCCT TCGCCCTGCA ACTGCCCCTA CGCGTCCTCG TTACCGAAAC
351 GGACGGCAAA GTACGCGCCG CCTATACCGA TACGCGCGCC CTCATCGCCG
401 GCAGCCGCAT CGGTTTCGAC GAAGTGGCAA ACACTTTGGC AAACGCCGAA
451 AAACTGATAC AAAAAACCGT AGGCGAATAA
```

This corresponds to the amino acid sequence <SEQ ID 358; ORF97-1>:

```
  1 MKHILPLIAA SALCISTASA HPASEPSTQN ETAMTTHTLT SKYSFDETVS
 51 RLETAIKSKG MDIFAVIDHQ EAARRNGLTM QPAKVIVFGT PKAGTPLMVK
101 DPAFALQLPL RVLVTETDGK VRAAYTDTRA LIAGSRIGFD EVANTLANAE
151 KLIQKTVGE*
```

ORF97 shows 88.7% identity over a 159aa overlap with an ORF (ORF97a) from strain A of *N. meningitidis*:

```
                 10         20         30         40         50         60
orf97.pep  MKHILPLIAASALCISTASAHPASEPSTQNETAMITHTLISKYSFGXXXXXXXXAIKSKG
           | ||||| ||||||||||| ||||||:|||||| |||| ||||| :       :||||||
orf97a     MXHILPLXXASALCISTASXHPASEPQTQNETAMTTHTLTSKYSFDETVSRLETAIKSKG
                 10         20         30         40         50         60

70         80         90        100        110        120
orf97.pep  MDIFAVIDHQEAARRNGLTMQPAKVIVFGTPKAGTPLMVKDPAFALQLPLRVLVTETDGK
           ||||||||||||||||||||||||||||||||||||||||||||||||||||| ||||||
orf97a     MDIFAVIDHQEAARRNGLTMQPAKVIVFGTPKAGTPLMVKDPAFALQLPLRVXVTETDGK
                 70         80         90        100        110        120

130        140        150        160
orf97.pep  VRAAYTDTRALIAGSRIGFDEVANTLANAEKLIQKTVGEX
           |||||||||||||||||||||||||||||||||||:|||
orf97a     VRAAYTDTRALIAGSRIGFDEVANTLANAEKLIQKTIGEX
                130        140        150        160
```

The complete length ORF97a nucleotide sequence <SEQ ID 359> is:

```
  1 ATGANACACA TACTCCCCCT GANTGNCGCA TCCGCACTCT GCATTTCAAC

51 CGCTTCGGNN CATCCTGCCA GCGAACCGCA AACCCAAAAC GAAACCGCTA

101 TGACCACGCA TACCCTCACC TCAAAATACA GTTTTGACGA AACCGTCAGC

151 CGCCTTGAAA CCGCCATAAA AAGCAAAGGG ATGGACATTT TTGCCGTCAT

201 CGACCATCAG GAAGCCGCCC GCCGAAACGG CTTAACGATG CAGCCGGCAA

251 AAGTCATCGT CTTCGGCACG CCCAAAGCCG GTACGCCGCT GATGGTCAAA

301 GACCCCGCCT TCGCCCTGCA ACTGCCCCTG CGCGTCNTCG TTACCGAAAC

351 GGACGGCAAA GTACGCGCCG CCTATACCGA TACGCGCGCC CTCATCGCCG

401 GCAGCCGCAT CGGTTTCGAC GAAGTGGCAA ACACTTTGGC AAACGCCGAA

451 AAACTGATAC AAAAAACCAT AGGCGAATAA
```

This encodes a protein having amino acid sequence <SEQ ID 360>:

```
  1 MXHILPLXXA SALCISTASX HPASEPQTQN ETAMTTHTLT SKYSFDETVS

51 RLETAIKSKG MDIFAVIDHQ EAARRNGLTM QPAKVIVFGT PKAGTPLMVK

101 DPAFALQLPL RVXVTETDGK VRAAYTDTRA LIAGSRIGFD EVANTLANAE

151 KLIQKTIGE*
```

ORF97a and ORF97-1 show 95.6% identity in 159 aa overlap:

```
                  10         20         30         40         50         60
orf97a.pep  MXHILPLXXASALCISTASXHPASEPQTQNETAMTTHTLTSKYSFDETVSRLETAIKSKG
            | ||||   ||||||||||  |||||:||||||| |||| |||||||||||||||||||
orf97-1     MKHILPLIAASALCISTASAHPASEPSTQNETAMTTHTLTSKYSFDETVSRLETAIKSKG
                  10         20         30         40         50         60

70         80         90        100        110        120
orf97a.pep  MDIFAVIDHQEAARRNGLTMQPAKVIVFGTPKAGTPLMVKDPAFALQLPLRVXVTETDGK
            ||||||||||||||||||||||||||||||||||||||||||||||||||||| ||||||
orf97-1     MDIFAVIDHQEAARRNGLTMQPAKVIVFGTPKAGTPLMVKDPAFALQLPLRVLVTETDGK
                  70         80         90        100        110        120

130        140        150        160
orf97a.pep  VRAAYTDTRALIAGSRIGFDEVANTLANAEKLIQKTIGEX
            |||||||||||||||||||||||||||||||||||:|||
orf97-1     VRAAYTDTRALIAGSRIGFDEVANTLANAEKLIQKTVGEX
                 130        140        150        160
```

Homology with a Predicted ORF from *N. gonorrhoeae*

ORF97 shows 88.1% identity over a 159aa overlap with a predicted ORF (ORF97.ng) from *N. gonorrhoeae*.

```
orf97.pep    MKHILPLIAASALCISTASAHPASEPSTQNETAMITHTLISKYSFGXXXXXXXXXAIKSKG    60
             ||||| :||||| :|||||||||| :|||||||||| ||||| :          :|||||
orf97ng      MKHILPPIAASAFCISTASAHPAGKPPTQNETAMTTHTLTSKYSFDETVSRLETAIKSKG    60 orf97.pep    MDIFAVIDHQEAARRNGLTMQPAKVIVFGTPKAGTPLMVKDPAFALQLPLRVLVTETDGK   120
             ||||||||||||||||||||||||||||||||||||||||||||||||||||||||||||
orf97ng      MDIFAVIDHQEAARRNGLTMQPAKVIVFGTPKAGTPLMVKDPAFALQLPLRVLVTETDGK   120 orf97.pep    VRAAYTDTRALIAGSRIGFDEVANTLANAEKLIQKTVGE                       159
             ||:|||||||||:||||:|||||||||||||||||||||
orf97ng      VRTAYTDTRALIVGSRISFDEVANTLANAEKLIQKTVGE                       159
```

The complete length ORF97ng nucleotide sequence <SEQ ID 361> is predicted to encode a protein having amino acid sequence <SEQ ID 362>:

```
  1 MKHILPPIAA SAFCISTASA HPAGKPPTQN ETAMTTHTLT SKYSFDETVS

51 RLETAIKSKG MDIFAVIDHQ EAARRNGLTM QPAKVIVFGT PKAGTPLMVK

101 DPAFALQLPL RVLVTETDGK VRTAYTDTRA LIVGSRISFD EVANTLANAE

151 KLIQKTVGE*
```

Further work revealed the complete nucleotide sequence <SEQ ID 363>:

```
  1 ATGAAACACA TACTCCCcct gatcgccgca TccgcactCT GCATTTCAAC

51 CGCTTCGGCA CACCCTGCCG GCAAACCGCC CACCCAAAAC GAAACCGCTA

101 TGACCACGCA CACCCTCACC TCGAAATACA GTTTTGACGA AACCGTCAGC

151 CGCCTTGAAA CCGCCATAAA AAGCAAAGGG ATGGACATTT TTGCCGTCAT

201 CGACCATCAG GAAGCGGCAC GCCGAAACGG CCTGACCATG CAGCCGGCAA

251 AAGTCATCGT CTTCGGCACG CCCAAGGCCG GTACGCCgct GATGGTCAAA

301 GACCCCGCCT TCGCCCTGCA ACTGCCCCTG CGCGTCCTCG TTACCGAAAC

351 GGACGGCAAA GTACGCACCG CCTATACCGA TACGCGCGCC CTCATCGTCG

401 GCAGCCGCAT CAGTTTCGAC GAAGTGGCAA ACACTTTGGC AAACGCCGAA

451 AAACTGATAC AAAAAACCGT AGGCGAATAA
```

This corresponds to the amino acid sequence <SEQ ID 364; ORF97ng-1>:

```
  1 MKHILPLIAA SALCISTASA HPAGKPPTQN ETAMTTHTLT SKYSFDETVS

51 RLETAIKSKG MDIFAVIDHQ EAARRNGLTM QPAKVIVFGT PKAGTPLMVK

101 DPAFALQLPL RVLVTETDGK VRTAYTDTRA LIVGSRISFD EVANTLANAE

151 KLIQKTVGE*
```

ORF97ng-1 and ORF97-1 show 96.2% identity in 159 aa overlap:

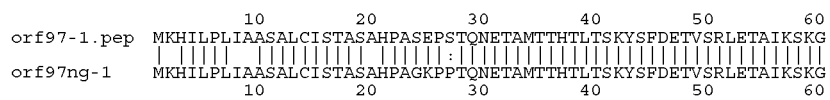

```
                  70         80         90        100        110        120
orf97-1.pep  MDIFAVIDHQEAARRNGLTMQPAKVIVFGTPKAGTPLMVKDPAFALQLPLRVLVTETDGK
             ||||||||||||||||||||||||||||||||||||||||||||||||||||||||||||
orf97ng-1    MDIFAVIDHQEAARRNGLTMQPAKVIVFGTPKAGTPLMVKDPAFALQLPLRVLVTETDGK
                  70         80         90        100        110        120

130        140        150        160
orf97-1.pep  VRAAYTDTRALIAGSRIGFDEVANTLANAEKLIQKTVGEX
             ||:||||||||:||||:|||||||||||||||||||||||
orf97ng-1    VRTAYTDTRALIVGSRISFDEVANTLANAEKLIQKTVGEX
                 130        140        150        160
```

Based on this analysis, including the presence of a putative leader sequence in the gonococcal protein, it was predicted that the proteins from *N. meningitidis* and *N. gonorrhoeae*, and their epitopes, could be useful antigens for vaccines or diagnostics, or for raising antibodies.

Figure 12E:
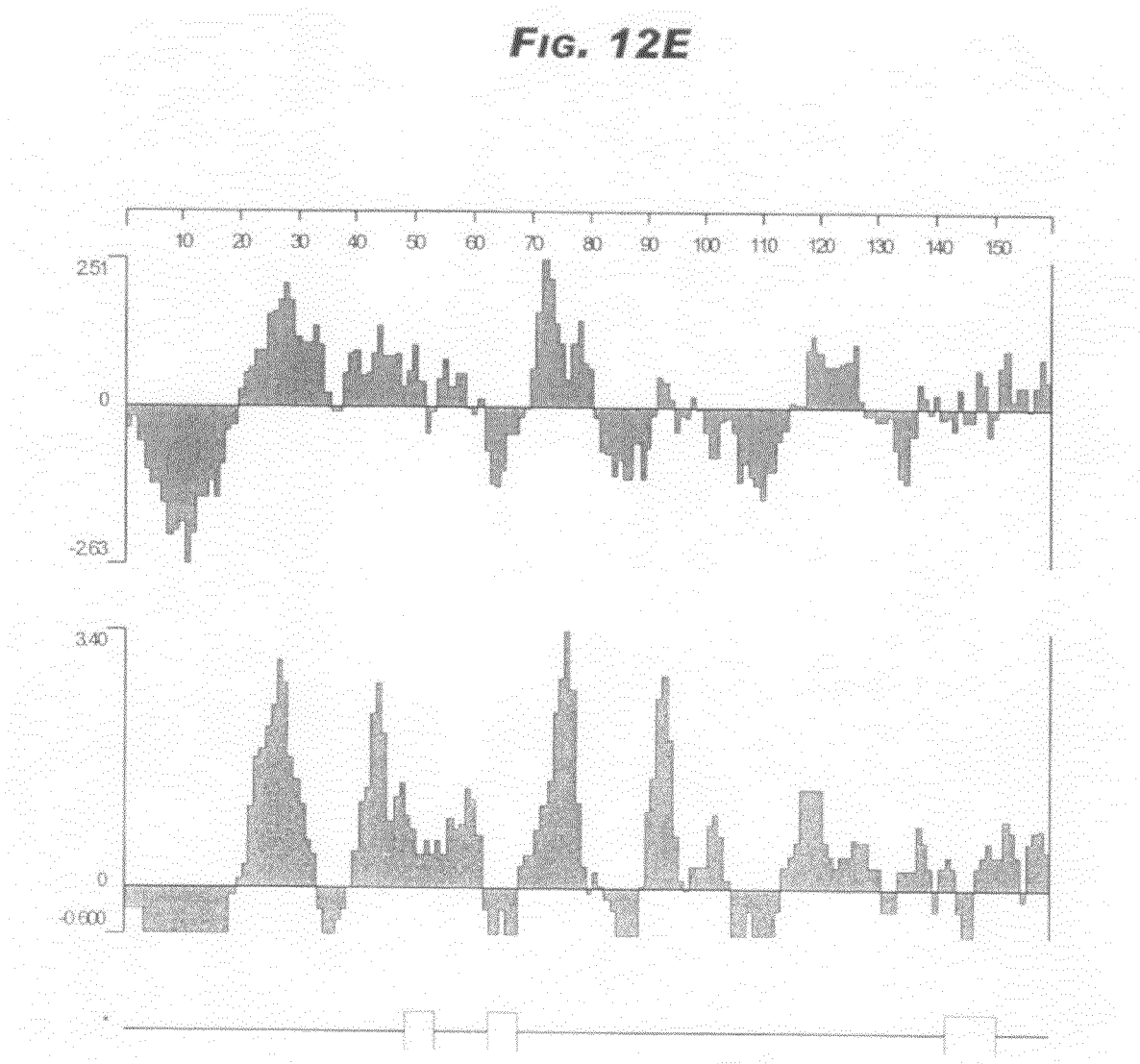

ORF97-1 (15.3 kDa) was cloned in pET and pGex vectors and expressed in *E. coli*, as described above. The products of protein expression and purification were analyzed by SDS-PAGE. FIGS. 12A & 12B show, respectively, the results of affinity purification of the GST-fusion and His-fusion proteins. Purified GST-fusion protein was used to immunise mice, whose sera were used for Western Blot (FIG. 12C), ELISA (positive result), and FACS analysis (FIG. 12D). These experiments confirm that ORF97-1 is a surface-exposed protein, and that it is a useful immunogen. FIG. 12E shows plots of hydrophilicity, antigenic index, and AMPHI regions for ORF97-1.

Example 43

The following DNA, believed to be complete, sequence was identified in *N. meningitidis* <SEQ ID 365>:

```
  1 ATGGCTTTTA TTACGCGCTT ATTCAAAAGC AGTAAATGGC TGATTGTGCC

51 GCTGATGCTC CCCGCCTTTC AGAATGTGGC GGCGGAGGGG ATAGATGTGA

101 GCCGTGCCGA AGCGAGGATA ACCGACGGCG GGCAGCTTTC CATCAGCAGC

151 CGCTTCCAAA CCGAGCTGCC CGACCAGCTC AACAGGCGT  TGCGCCGGGg

201 CGTGCCGCTC AACTTTACCT TAAGCTGGCA GCTTTCCGCC CCGATAATCG

251 CTTCTTATCG GTTTAAATTG GGGCAACTGA TTGGCGATGA CGACaATATT

301 GACTACAAAC TGAGTTTCCA TCCGCTGACc AaACGCTACC GCGTTACCgT

351 CGgCGCGTTT TCGACAGACT ACGACACCTT GGATGCGGCA TTGCGCGCGA

401 CCGGCGCGGT TGCCAACTGG AAAGTCCTGA ACAAAGGCGC GCTGTCCGGT

451 GCGGAAGCAG GGGAAACCAA GGCGGAAATC CGCCTGACGC TGTCCACTTC

501 AAAACTGCCC AAGCCTTTTC AAATCAATGC ATTGACTTCT CAAAACTGGC

551 ATTTGGATTC GGGTTGGAAA CCTCTAAACA TCATCGGGAA CAAATAA
```

This corresponds to the amino acid sequence <SEQ ID 366; ORF106>:

```
  1 MAFITRLFKS SKWLIVPLML PAFQNVAAEG IDVSRAEARI TDGGQLSISS

51 RFQTELPDQL QQALRRGVPL NFTLSWQLSA PIIASYRFKL GQLIGDDDNI

101 DYKLSFHPLT KRYRVTVGAF STDYDTLDAA LRATGAVANW KVLNKGALSG

151 AEAGETKAEI RLTLSTSKLP KPFQINALTS QNWHLDSGWK PLNIIGNK*
```

Further work revealed the following DNA sequence <SEQ ID 367>:

```
  1 ATGGCTTTTA TTACGCGCTT ATTCAAAAGC AGTAAATGGC TGATTGTGCC

51 GCTGATGCTC CCCGCCTTTC AGAATGTGGC GGCGGAGGGG ATAGATGTGA

101 GCCGTGCCGA AGCGAGGATA ACCGACGGCG GGCAGCTTTC CATCAGCAGC

151 CGCTTCCAAA CCGAGCTGCC CGACCAGCTC AACAGGCGT TGCGCCGGGG

201 CGTGCCGCTC AACTTTACCT TAAGCTGGCA GCTTTCCGCC CCGATAATCG

251 CTTCTTATCG GTTTAAATTG GGCAACTGA TTGGCGATGA CGACAATATT

301 GACTACAAAC TGAGTTTCCA TCCGCTGACC AACCGCTACC GCGTTACCGT

351 CGGCGCGTTT TCGACAGACT ACGACACCTT GGATGCGGCA TTGCGCGCGA

401 CCGGCGCGGT TGCCAACTGG AAAGTCCTGA ACAAAGGCGC GCTGTCCGGT

451 GCGGAAGCAG GGGAAACCAA GGCGGAAATC CGCCTGACGC TGTCCACTTC

501 AAAACTGCCC AAGCCTTTTC AAATCAATGC ATTGACTTCT CAAAACTGGC

551 ATTTGGATTC GGGTTGGAAA CCTCTAAACA TCATCGGGAA CAAATAA
```

This corresponds to the amino acid sequence <SEQ ID 368; ORF106-1>:

```
  1 MAFITRLFKS SKWLIVPLML PAFQNVAAEG IDVSRAEARI TDGGQLSISS

51 RFQTELPDQL QQALRRGVPL NFTLSWQLSA PIIASYRFKL GQLIGDDDNI

101 DYKLSFHPLT NRYRVTVGAF STDYDTLDAA LRATGAVANW KVLNKGALSG

151 AEAGETKAEI RLTLSTSKLP KPFQINALTS QNWHLDSGWK PLNIIGNK*
```

Computer analysis of this amino acid sequence gave the following results:

Homology with a Predicted ORF from *N. meningitidis* (Strain A)

ORF106 shows 87.4% identity over a 199aa overlap with an ORF (ORF106a) from strain A of *N. meningitidis*:

```
                  10         20         30         40         50        59
orf106.pep   MAFITRLFKSSK-WLIVPLMLPAFQNVAAEGIDVSRAEARITDGGQLSISSRFQTELPDQ
             |||||||||| | ||::  ||  :: ::|||||||||||||:||||| ||||||||||
orf106a      MAFITRLFKSIKQWLVLLPMLSVLPDAAAEGIDVSRAEARIXDGGQLSXXSRFQTELPDQ
                  10         20         30         40         50        60

60         70         80         90        100        110       119
orf106.pep   LQQALRRGVPLNFTLSWQLSAPIIASYRFKLGQLIGDDDNIDYKLSFHPLTKRYRVTVGA
             ||| ||| || || |||||||||||||||| |||||||| ||||||||||:||||||||
orf106a      LQXAXXRGVXLNXTLXWQLSAPIIASYRFXLGQLIGDDDXIDYKLSFHPLTNRYRVTVGA
                  70         80         90        100        110        120

120        130        140        150        160        170       179
orf106.pep   FSTDYDTLDAALRATGAVANWKVLNKGALSGAEAGETKAEIRLTLSTSKLPKPFQINALT
             ||| ||||||||||||||||||||||||||||||||||||||||||||||||||||||||
orf106a      FSTXYDTLDAALRATGAVANWKVLNKGALSGAEAGETKAEIRLTLSTSKLPKPFQINALT
                 130        140        150        160        170        180

180        190        199
orf106.pep   SQNWHLDSGWKPLNIIGNKX
             |||  ||||||||||||||
orf106a      SQNWHLDSGWKPLNIIGNKX
                 190        200
```

Due to the K→N substitution at residue 111, the homology between ORF106a and ORF106-1 is 87.9% over the same 199 aa overlap.

The complete length ORF106a nucleotide sequence <SEQ ID 369> is:

```
  1 ATGGCTTTTA TTACGCGCTT ATTCAAAAGC ATTAAACAAT GGCTTGTGCT

51 GCTGCCGATG CTTTCCGTTT TGCCGGACGC GGCGGCGGAG GGGATAGATG

101 TGAGCCGCGC CGAAGCGAGG ATAANCGACG GCGGGCAGCT TTCCATNAGN

151 AGCCGCTTCC AAACCGAGCT GCCCGACCAG CTCCAANNNG CGNNGNGCCG

201 GGGCGTGNCG CTCAACTNTA CCTTAAGNTG GCAGCTTTCC GCCCCGATAA

251 TCGCTTCTTA TCGGTTTNAA TTGGGGCAAC TGATTGGCGA TGACGACNAT

301 ATTGACTACA AACTGAGTTT CCATCCGCTG ACCAACCGCT ACCGCGTTAC

351 CGTCGGCGCG TTTTCGACAG ANTACGACAC CTTGGATGCG GCATTGCGCG

401 CGACCGGCGC GGTTGCCAAC TGGAAAGTCC TGAACAAAGG CGCGCTGTCC

451 GGTGCGGAAG CAGGGGAAAC CAAGGCGGAA ATCCGCCTGA CGCTGTCCAC

501 TTCAAAACTG CCCAAGCCTT TTCAAATCAA TGCATTGACT TCTCAAAACT

551 GGCATTTGGA TTCGGGTTGG AAACCTCTAA ACATCATCGG GAACAAATAA
```

This encodes a protein having amino acid sequence <SEQ ID 370>:

```
  1 MAFITRLFKS IKQWLVLLPM LSVLPDAAAE GIDVSRAEAR IXDGGQLSXX

51 SRFQTELPDQ LQXAXXRGVX LNXTLXWQLS APIIASYRFX LGQLIGDDDX

101 IDYKLSFHPL TNRYRVTVGA FSTXYDTLDA ALRATGAVAN WKVLNKGALS

151 GAEAGETKAE IRLTLSTSKL PKPFQINALT SQNWHLDSGW KPLNIIGNK*
```

35

Homology with a Predicted ORF from *N. gonorrhoeae*

ORF106 shows 90.5% identity over a 199aa overlap with a predicted ORF (ORF106.ng) from *N. gonorrhoeae*:

```
orf106.pep  MAFITRLFKSSK-WLIVPLMLPAFQNVAAEGIDVSRAEARITDGGQLSISSRFQTELPDQ   59
            |||||||||| | ||::  :| ::  ::||||  ::|||||||||:||||||||||||||
orf106ng    MAFITRLFKSIKQWLVLLPILSVLPDAAAEGIAATRAEARITDGGRLSISSRFQTELPDQ   60 orf106.pep  LQQALRRGVPLNFTLSWQLSAPIIASYRFKLGQLIGDDDNIDYKLSFHPLTKRYRVTVGA  119
            ||||||||||||||||||||||:|||||||||||||||||||||||||||:|||||||
orf106ng    LQQALRRGVPLNFTLSWQLSAPTIASYRFKLGQLIGDDDNIDYKLSFHPLTNRYRVTVGA  120 orf106.pep  FSTDYDTLDAALRATGAVANWKVLNKGALSGAEAGETKAEIRLTLSTSKLPKPFQINALT  179
            ||||||||||||||||||||||||||||||||||||||||||||||||||||||||||||
orf106ng    FSTDYDTLDAALRATGAVANWKVLNKGALSGAEAGETKAEIRLTLSTSKLPKPFQINALT  180 orf106.pep  SQNWHLDSGWKPLNIIGNK  198
            |||||||||||||||||||
orf106ng    SQNWHLDSGWKPLNIIGNK  199
```

Due to the K→N substitution at residue 111, the homology between ORF106ng and ORF106-1 is 91.0% over the same 199 aa overlap.

The complete length ORF106ng nucleotide sequence <SEQ ID 371> is:

55

```
  1 ATGGCTTTTA TTACGCGCTT ATTCAAAAGC ATTAAACAAT GGCTTGTGCT

51 GTTGCCGATA CTCTCCGTTT TGCCGGACGC GGCGGCGGAG GGCATTGCCG

101 CGACCCGCGC CGAAGCGAGG ATAACCGACG GCGGGCGGCT TTCCATCAGC

151 AGCCGCTTCC AAACCGAGCT GCCCGACCAG CTCCAACAGG CGTTGCGCCG

201 GGGCGTACCG CTCAACTTTA CCTTAAGCTG GCAGCTTTCC GCCCCGACAA
```

```
251  TCGCTTCTTA TCGGTTTAAA TTGGGGCAAC TGATTGGCGA TGACGACAAT

301  ATTGACTACA AACTAAGTTT CCATCCGCTG ACCAACCGCT ACCGCGTTAC

351  CGTCGGCGCA TTTTCCACCG ATTACGACAC TTTGGATGCG GCATTGCGCG

401  CGACCGGCGC GGTTGCCAAC TGGAAAGTCC TGAACAAAGG CGCGTTGTCC

451  GGTGCGGAAG CAGGGGAAAC CAAGGCGGAA ATCCGCCTGA CGCTGTCCAC

501  TTCAAAACTG CCCAAGCCTT TCCAAATCAA CGCATTGACT TCTCAAAACT

551  GGCATTTGGA TTCGGGTTGG AAACCTCTAA ACATCATCGG GAACAAATAA
```

This encodes a protein having amino acid sequence <SEQ ID 372>:

```
  1  MAFITRLFKS IKQWLVLLPI LSVLPDAAAE GIAATRAEAR ITDGGRLSIS

51  SRFQTELPDQ LQQALRRGVP LNFTLSWQLS APTIASYRFK LGQLIGDDDN

101  IDYKLSFHPL TNRYRVTVGA FSTDYDTLDA ALRATGAVAN WKVLNKGALS

151  GAEAGETKAE IRLTLSTSKL PKPFQINALT SQNWHLDSGW KPLNIIGNK*
```

Based on this analysis, including the presence of a putative leader sequence in the gonococcal protein, it was predicted that the proteins from *N. meningitidis* and *N. gonorrhoeae*, and their epitopes, could be useful antigens for vaccines or diagnostics, or for raising antibodies.

ORF106-1 (18 kDa) was cloned in pET and pGex vectors and expressed in *E. coli*, as described above. The products of protein expression and purification were analyzed by SDS-PAGE. FIG. 13A shows the results of affinity purification of the His-fusion protein, and FIG. 13B shows the results of expression of the GST-fusion in *E. coli*. Purified His-fusion protein was used to immunise mice, whose sera were used for FACS analysis (FIG. 13C) These experiments confirm that ORF106-1 is a surface-exposed protein, and that it is a useful immunogen.

Example 44

The following DNA sequence, believed to be complete, was identified in *N. meningitidis* <SEQ ID 373>:

```
  1  ATGGACACAA AAGAAATCCT CGG.TACGCG GcAGGcTCGA TCGGCAGCGC

51  GGTTTTAGCC GTCATCATCc TGCCGCTGCT GTCGTGGTAT TTCCCCGCCG

101  ACGACATCGG GCGCATCGTG CTGATGCAGA CGGCGGCGGG GCTgACGGTG

151  TCGGTGTTGT GCCTCGGGCT GGATCAGGCA TACGTCCGCG AATACTATGC

201  CACCGCCGAC AAAGACAcCT TGTTCAAAAC CCTGTTCCTG CCGCCGCTGC

251  TGTCTGCCGC CGCGATAGCC GCCCTGCTGC TTTCCCGCCC GTCCCTGCCG

301  TCTGAAATCC TGTTTTCACT CGACGATGCC gCCGCCGGCa TCGGGCTGGT

351  GCTGTTTGAA CtGAGCTTCC TGCCCATCCG cTTTCTCTTA CTGGTTTTGC

401  GTATGGAAGG ACGCGCCcTT GCCTTTTCGT CCGCGCAACT CGTGCcCAAG

451  CTCGCCATCC TGCTGCTG.T GCCGCTGACG GTCGGGCTGC TGCACTTTCC

501  AGCGAACACC GCCGTCCTGA CCGCCGTTTA CGCGCTGGCA AACCTTGCCG
```

```
551 CCGCCGCCTT TTTGCTGTTT CAAAACCGAT GCCGTCTGAA GGCCGTCCGG

601 CACGCACCGT TTTCGCCCGC CGTCCTGCAC CGGGGG.TGC GCTACGGCAT

651 ACCGATCGCA CTGAGCAGCA TCGCCTATTG GGGGCTGGCA TCCGCCGACC

701 GTTTGTTCCT GAAAAAATAT GCCGGCCTGG AACAGCTCGG CGTTTATTCG

751 ATGGGTATTT CGTTCGGCGG GGCGGCATTA TTGTTCCAAA GCATCTTTTC

801 AACGGTCTGG ACACCGTATA TTTTCCGCGC AATCGAAGAA AACGCCCCGC

851 CCGCTCGCCT CTCGGCAACG GCAGAATCCG CCGCCGCCCT GCTTGCCTCC

901 GCCCTCTGC. TGACCGGCAT TTTCTCGCCC CTTGCCTCCC TCCTGCTGCC

951 GGAAAACTAC GCCGCCGTCC GGTTTATCGT CGTATCGTGT ATG.TGCCGC

1001 CGCTGTTTTG CACGCTGGCG GAAATCAGCG GCATCGGTTT GAACGTCGTT

1051 CGCAAAACGC GCCCGATCGC GCTCGCCACC TTGGGCGCGC TGGCGGCAAA

1101 CCTGCTGCTG CTGGGGCTTG ACCGTGCCGT ACCGGCGAGG CCGCC.GGCG

1151 CGGCGGTTGC CTGTGCCGCC TCATTCTGGC TGTTTTTTGC CTTCAAGACC

1201 GAAAGCTCyT GCCGCCTGTG GCAGCCGCTC AAACGCCTGC CGCTTTATCT

1251 GCACACATTG TTCTGCCTGA CCTCCTCGGC GGCCTACACC TGCTTCGGCA

1301 CGCCGGCAAA CTATCCCCTG TTTGCCGGCG TATGGGCGGC ATATCTGGCA

1351 GGCTGCATCC TGCGCCACCG GAAAGATTTG CACAAACTGT TCATTATTT

1401 GAAAAAACAA GGTTTCCCAT TATGA
```

This corresponds to the amino acid sequence <SEQ ID 374; ORF10>:

```
  1 MDTKEILXYA AGSIGSAVLA VIILPLLSWY FPADDIGRIV LMQTAAGLTV

51 SVLCLGLDQA YVREYYATAD KDTLFKTLFL PPLLSAAAIA ALLLSRPSLP

101 SEILFSLDDA AAGIGLVLFE LSFLPIRFLL LVLRMEGRAL AFSSAQLVPK

151 LAILLLXPLT VGLLHFPANT AVLTAVYALA NLAAAAFLLF QNRCRLKAVR

201 HAPFSPAVLH RGXRYGIPIA LSSIAYWGLA SADRLFLKKY AGLEQLGVYS

251 MGISFGGAAL LFQSIFSTVW TPYIFRAIEE NAPPARLSAT AESAAALLAS

301 ALCXTGIFSP LASLLLPENY AAVRFIVVSC MXPPLFCTLA EISGIGLNVV

351 RKTRPIALAT LGALAANLLL LGLDRAVPAR PXGAAVACAA SFWLFFAFKT

401 ESSCRLWQPL KRLPLYLHTL FCLTSSAAYT CFGTPANYPL FAGVWAAYLA

451 GCILRHRKDL HKLFHYLKKQ GFPL*
```

Further sequence analysis revealed the complete DNA sequence <SEQ ID 375> to be:

```
  1 ATGGACACAA AAGAAATCCT CGGCTACGCG GCAGGCTCGA TCGGCAGCGC

51 GGTTTTAGCC GTCATCATCC TGCCGCTGCT GTCGTGGTAT TTCCCCGCCG

101 ACGACATCGG GCGCATCGTG CTGATGCAGA CGGCGGCGGG GCTGACGGTG

151 TCGGTGTTGT GCCTCGGGCT GGATCAGGCA TACGTCCGCG AATACTATGC

201 CACCGCCGAC AAAGACACCT TGTTCAAAAC CCTGTTCCTG CCGCCGCTGC

251 TGTCTGCCGC CGCGATAGCC GCCCTGCTGC TTTCCCGCCC GTCCCTGCCG

301 TCTGAAATCC TGTTTTCACT CGACGATGCC GCCGCCGGCA TCGGGCTGGT
```

```
 351 GCTGTTTGAA CTGAGCTTCC TGCCCATCCG CTTTCTCTTA CTGGTTTTGC

401 GTATGGAAGG ACGCGCCCTT GCCTTTTCGT CCGCGCAACT CGTGCCCAAG

451 CTCGCCATCC TGCTGCTGCT GCCGCTGACG GTCGGGCTGC TGCACTTTCC

501 AGCGAACACC GCCGTCCTGA CCGCCGTTTA CGCGCTGGCA AACCTTGCCG

551 CCGCCGCCTT TTTGCTGTTT CAAAACCGAT GCCGTCTGAA GGCCGTCCGG

601 CACGCACCGT TTTCGCCCGC CGTCCTGCAC CGGGGGCTGC GCTACGGCAT

651 ACCGATCGCA CTGAGCAGCA TCGCCTATTG GGGGCTGGCA TCCGCCGACC

701 GTTTGTTCCT GAAAAAATAT GCCGGCCTGG AACAGCTCGG CGTTTATTCG

751 ATGGGTATTT CGTTCGGCGG GGCGGCATTA TTGTTCCAAA GCATCTTTTC

801 AACGGTCTGG ACACCGTATA TTTTCCGCGC AATCGAAGAA AACGCCCCGC

851 CCGCCCGCCT CTCGGCAACG GCAGAATCCG CCGCCGCCCT GCTTGCCTCC

901 GCCCTCTGCC TGACCGGCAT TTTCTCGCCC CTTGCCTCCC TCCTGCTGCC

951 GGAAAACTAC GCCGCCGTCC GGTTTATCGT CGTATCGTGT ATGCTGCCGC

1001 CGCTGTTTTG CACGCTGGCG GAAATCAGCG GCATCGGTTT GAACGTCGTC

1051 CGCAAAACGC GCCCGATCGC GCTCGCCACC TTGGGCGCGC TGGCGGCAAA

1101 CCTGCTGCTG CTGGGGCTTG CCGTGCCGTC CGGCGGCGCG CGCGGCGCGG

1151 CGGTTGCCTG TGCCGCCTCA TTCTGGCTGT TTTTTGCCTT CAAGACCGAA

1201 AGCTCCTGCC GCCTGTGGCA GCCGCTCAAA CGCCTGCCGC TTTATCTGCA

1251 CACATTGTTC TGCCTGACCT CCTCGGCGGC CTACACCTGC TTCGGCACGC

1301 CGGCAAACTA TCCCCTGTTT GCCGGCGTAT GGGCGGCATA TCTGGCAGGC

1351 TGCATCCTGC GCCACCGGAA AGATTTGCAC AAACTGTTTC ATTATTTGAA

1401 AAAACAAGGT TTCCCATTAT GA
```

This corresponds to the amino acid sequence <SEQ ID 376; ORF10-1>:

```
  1 MDTKEILGYA AGSIGSAVLA VIILPLLSWY FPADDIGRIV LMQTAAGLTV

51 SVLCLGLDQA YVREYYATAD KDTLFKTLFL PPLLSAAAIA ALLLSRPSLP

101 SEILFSLDDA AAGIGLVLFE LSFLPIRFLL LVLRMEGRAL AFSSAQLVPK

151 LAILLLLPLT VGLLHFPANT AVLTAVYALA NLAAAAFLLF QNRCRLKAVR

201 HAPFSPAVLH RGLRYGIPIA LSSIAYWGLA SADRLFLKKY AGLEQLGVYS

251 MGISFGGAAL LFQSIFSTVW TPYIFRAIEE NAPPARLSAT AESAAALLAS

301 ALCLTGIFSP LASLLLPENY AAVRFIVVSC MLPPLFCTLA EISGIGLNVV

351 RKTRPIALAT LGALAANLLL LGLAVPSGGA RGAAVACAAS FWLFFAFKTE

401 SSCRLWQPLK RLPLYLHTLF CLTSSAAYTC FGTPANYPLF AGVWAAYLAG

451 CILRHRKDLH KLFHYLKKQG FPL*
```

Computer analysis of this amino acid sequence gave the following results:
Prediction
ORF10-1 is predicted to be the precursor of an integral membrane protein, since it comprises several (12-13) potential transmembrane segments, and a probable cleavable signal peptide- Homology with EpsM from *Streptococcus* thermophilus (Accession Number U40830).

ORF10 shows homology with the epsM gene of *S. thermophilus*, which encodes a protein of a size similar to ORF10 and is involved in expolysaccharide synthesis. Other homologies are with prokaryotic membrane proteins:

```
Identities = (25%)
Query:  213 LRYGIPLALSSLAYWGLASADRLFLKKYAGLEQLGVYSMGISFGGAALLLQSIFSTVW    270
            L Y +PL  SS+ +W L ++ R F+  + G     G+ ++        +  +IF+  W
Sbjct:  210 LYYALPLIPSSILWWLLNASSRYFVLFFLGAGANGLLAVATKIPSIISIFNTIFTQAW    267

Identities = 15/57 (26%), Positives = 31/57 (54%)

Query:    7 LGYAAGSIGSAVLAVIILPLLSWYFPADDIGRIVLMQTAAGLTVSVLCLGLDQAYVR     63
            L +   G++GS +L   +++PL ++      + G   L QT A L + ++ + +  A +R
Sbjct:   12 LVFTIGNLGSKLLVFLLVPLYTYAMTPQEYGMADLYQTTANLLLPLITMNVFDATLR     68

Identities = 16/96 (16%), Positives = 36/96 (37%)

Query:  307 IFSPLASLLLPENYAAVRFTVVSCMLPPLFYTLTEISGIGLNVVRKTRPIXXXXXXXXXX   366
              + P+   ++    +YA+      V   ML  LF + ++    G      ++T+ +
Sbjct:  305 VLKPIVEKVVSSDYASSWQYVPFFMLSMLFSSFSDFFGTNYIAAKQTKGVFMTSIYGTIV   364
```

Homology with a Predicted ORF from *N. meningitidis* (Strain A)

ORF10 shows 95.4% identity over a 475aa overlap with an ORF (ORF10a) from strain A of *N. meningitidis*:

```
                      10         20         30         40         50         60
    orf10.pep MDTKEILXYAAGSIGSAVLAVIILPLLSWYFPADDIGRIVLMQTAAGLTVSVLCLGLDQA
              ||||||| ||||||||||||||||||||||||||||||||||||||||||||||||||||
    orf10a    MDTKEILGYAAGSIGSAVLAVIILPLLSWYFPADDIGRIVLMQTAAGLTVSVLCLGLDQA
                      10         20         30         40         50         60

70         80         90        100        110        120
    orf10.pep YVREYYATADKDTLFKTLFLPPLLSAAAIAALLLSRPSLPSEILFSLDDAAAGIGLVLFE
              ||||||:|||||||||||||||||||||||||||||||||||||||||||||||||||||
    orf10a    YVREYYAAADKDTLFKTLFLPPLLSAAAIAALLLSRPSLPSEILFSLDDAAAGIGLVLFE
                      70         80         90        100        110        120

130        140        150        160        170        180
    orf10.pep LSFLPIRFLLLVLRMEGRALAFSSAQLVPKLAILLLXPLTVGLLHFPANTAVLTAVYALA
              |||||||||||||||||||||||||||||: ||||| ||||||||||||||||||||||
    orf10a    LSFLPIRFLLLVLRMEGRALAFSSAQLVSKLAILLLLPLTVGLLHFPANTAVLTAVYALA
                     130        140        150        160        170        180

190        200        210        220        230        240
    orf10.pep NLAAAAFLLFQNRCRLKAVRHAPFSPAVLHRGXRYGIPIALSSIAYWGLASADRLFLKKY
              |||||||||||||||||||||:||||  ||||| |||||||||||||||||||||||||
    orf10a    NLAAAAFLLFQNRCRLKAVRRAPFSSAVLHRGLRYGIPIALSSIAYWGLASADRLFLKKY
                     190        200        210        220        230        240

250        260        270        280        290        300
    orf10.pep AGLEQLGVYSMGISFGGAALLFQSIFSTVWTPYIFRAIEENAPPARLSATAESAAALLAS
              |||||||||||||||||||||||||||||||||||||||:||||||||||||||||||||
    orf10a    AGLEQLGVYSMGISFGGAALLFQSIFSTVWTPYIFRAIEANAPPARLSATAESAAALLAS
                     250        260        270        280        290        300

310        320        330        340        350        360
    orf10.pep ALCXTGIFSPLASLLLPENYAAVRFIVVSCMXPPLFCTLAEISGIGLNVVRKTRPIALAT
              ||| |||||||||||||||||||||||||||:|||||||:||||||||||||||||||||
    orf10a    ALCLTGIFSPLASLLLPENYAAVRFIVVSCMLPPLFCTLVEISGIGLNVVRKTRPIALAT
                     310        320        330        340        350        360

370        380        390        400        410       419
    orf10.pep LGALAANLLLLGLDRAVPAR-PXGAAVACAASFWLFFAFKTESSCRLWQPLKRLPLYLHT
              |||||||||||| |||:       |||||||||||||:||||||||||||||||||:||
    orf10a    LGALAANLLLLGL--AVPSGGARGAAVACAASFWLFFVFKTESSCRLWQPLKRLPLYMHT
                     370        380        390        400        410

420        430        440        450        460        470
    orf10.pep LFCLTSSAAYTCFGTPANYPLFAGVWAAYLAGCILRHRKDLHKLFHYLKKQGFPLX
              ||||:|||||||||||||||||||||||:||||||||||||||||||||||||||
    orf10a    LFCLASSAAYTCFGTPANYPLFAGVWAVYLAGCILRHRKDLHKLFHYLKKQGFPLX
                420        430        440        450        460        470
```

The complete length ORFLOa nucleotide sequence <SEQ ID 377> is:

```
   1 ATGGACACAA AAGAAATCCT CGGCTACGCG GCAGGCTCGA TCGGCAGCGC
  51 GGTTTTAGCC GTCATCATCC TGCCGCTGCT GTCGTGGTAT TTCCCTGCCG
 101 ACGACATCGG ACGCATCGTG CTGATGCAGA CGGCGGCGGG GCTGACGGTG
 151 TCGGTGTTGT GCCTCGGGCT GGATCAGGCA TACGTCCGCG AATACTATGC
 201 CGCCGCCGAC AAAGACACTT TGTTCAAAAC CCTGTTCCTG CCGCCGCTGC
 251 TGTCTGCCGC CGCGATAGCC GCCCTGCTGC TTTCCCGCCC ATCCCTGCCG
 301 TCTGAAATCC TGTTTTCGCT CGACGATGCC GCCGCCGGCA TCGGGCTGGT
 351 GCTGTTTGAA CTGAGCTTCC TGCCCATCCG CTTTCTCTTA CTGGTTTTGC
 401 GTATGGAAGG ACGCGCCCTT GCCTTTTCGT CCGCGCAACT CGTGTCCAAG
 451 CTCGCCATCC TGCTGCTGCT GCCGCTGACG GTCGGGCTGC TGCACTTTCC
 501 GGCGAACACC GCCGTCCTGA CCGCCGTTTA CGCGCTGGCA AACCTTGCCG
 551 CCGCCGCCTT TTTGCTGTTT CAAAACCGAT GCCGTCTGAA GGCCGTCCGG
 601 CGCGCACCGT TTTCATCCGC CGTCCTGCAT CGCGGCCTGC GCTACGGCAT
 651 ACCGATCGCA CTAAGCAGCA TCGCCTATTG GGGGCTGGCA TCCGCCGACC
 701 GTTTGTTCCT GAAAAAATAT GCCGGCCTAG AACAGCTCGG CGTTTATTCG
 751 ATGGGTATTT CGTTCGGCGG AGCGGCATTA TTGTTCCAAA GCATCTTTTC
 801 AACGGTCTGG ACACCGTATA TTTTCCGCGC AATCGAAGCA AACGCCCCGC
 851 CCGCCCGCCT CTCGGCAACG GCAGAATCCG CCGCCGCCCT GCTTGCCTCC
 901 GCCCTCTGCC TGACCGGCAT TTTCTCGCCC CTCGCCTCCC TCCTGCTGCC
 951 GGAAAACTAC GCCGCCGTCC GGTTTATCGT CGTATCGTGT ATGCTGCCTC
1001 CGCTGTTTTG CACGCTGGTA GAAATCAGCG GCATCGGTTT GAACGTCGTC
1051 CGAAAAACAC GCCCGATCGC GCTCGCCACC TTGGGCGCGC TGGCGGCAAA
1101 CCTGCTGCTG CTGGGGCTTG CCGTACCGTC CGGCGGCGCG CGCGGCGCGG
1151 CGGTTGCCTG TGCCGCCTCA TTTTGGCTGT TTTTTGTTTT CAAGACCGAA
1201 AGCTCCTGCC GCCTGTGGCA GCCGCTCAAA CGCCTGCCGC TTTATATGCA
1251 CACATTGTTC TGCCTGGCCT CCTCGGCGGC CTACACCTGC TTCGGCACTC
1301 CGGCAAACTA CCCCCTGTTT GCCGGCGTAT GGGCGGTATA TCTGGCAGGC
1351 TGCATCCTGC GCCACCGGAA AGATTTGCAC AAACTGTTTC ATTATTTGAA
1401 AAAACAAGGT TTCCCATTAT GA
```

This encodes a protein having amino acid sequence <SEQ ID 378>:

```
  1 MDTKEILGYA AGSIGSAVLA VIILPLLSWY FPADDIGRIV LMQTAAGLTV
 51 SVLCLGLDQA YVREYYAAAD KDTLFKTLFL PPLLSAAAIA ALLLSRPSLP
101 SEILFSLDDA AAGIGLVLFE LSFLPIRFLL LVLRMEGRAL AFSSAQLVSK
151 LAILLLLPLT VGLLHFPANT AVLTAVYALA NLAAAAFLLF QNRCRLKAVR
201 RAPFSSAVLH RGLRYGIPIA LSSIAYWGLA SADRLFLKKY AGLEQLGVYS
251 MGISFGGAAL LFQSIFSTVW TPYIFRAIEA NAPPARLSAT AESAAALLAS
301 ALCLTGIFSP LASLLLPENY AAVRFIVVSC MLPPLFCTLV EISGIGLNVV
```

351 RKTRPIALAT LGALAANLLL LGLAVPSGGA RGAAVACAAS FWLFFVFKTE

401 SSCRLWQPLK RLPLYMHTLF CLASSAAYTC FGTPANYPLF AGVWAVYLAG

451 CILRHRKDLH KLFHYLKKQG FPL*

ORF10a and ORF10-1 show 95.4% identity in 475 aa overlap:

```
                  10         20         30         40         50         60
orf10-1.pep   MDTKEILXYAAGSIGSAVLAVIILPLLSWYFPADDIGRIVLMQTAAGLTVSVLCLGLDQA
              ||||||| |||||||||||||||||||||||||||||||||||||||||||||||||||
orf10a        MDTKEILGYAAGSIGSAVLAVIILPLLSWYFPADDIGRIVLMQTAAGLTVSVLCLGLDQA
                  10         20         30         40         50         60

70         80         90        100        110        120
orf10-1.pep   YVREYYATADKDTLFKTLFLPPLLSAAAIAALLLSRPSLPSEILFSLDDAAAGIGLVLFE
              |||||||:||||||||||||||||||||||||||||||||||||||||||||||||||
orf10a        YVREYYAAADKDTLFKTLFLPPLLSAAAIAALLLSRPSLPSEILFSLDDAAAGIGLVLFE
                  70         80         90        100        110        120

130        140        150        160        170        180
orf10-1.pep   LSFLPIRFLLLVLRMEGRALAFSSAQLVPKLAILLLXPLTVGLLHFPANTAVLTAVYALA
              |||||||||||||||||||||||||||||||| ||||||| |||||||||||||||||||
orf10a        LSFLPIRFLLLVLRMEGRALAFSSAQLVSKLAILLLLPLTVGLLHFPANTAVLTAVYALA
                 130        140        150        160        170        180

190        200        210        220        230        240
orf10-1.pep   NLAAAAFLLFQNRCRLKAVRHAPFSPAVLHRGXRYGIPIALSSIAYWGLASADRLFLKKY
              ||||||||||||||||||||||:||||||||| |||||||||||||||||||||||||
orf10a        NLAAAAFLLFQNRCRLKAVRRAPFSSAVLHRGLRYGIPIALSSIAYWGLASADRLFLKKY
                 190        200        210        220        230        240

250        260        270        280        290        300
orf10-1.pep   AGLEQLGVYSMGISFGGAALLFQSIFSTVWTPYIFRAIEENAPPARLSATAESAAALLAS
              ||||||||||||||||||||||||||||||||||||||||||||||||||||||||||||
orf10a        AGLEQLGVYSMGISFGGAALLFQSIFSTVWTPYIFRAIEENAPPARLSATAESAAALLAS
                 250        260        270        280        290        300

310        320        330        340        350        360
orf10-1.pep   ALCXTGIFSPLASLLLPENYAAVRFIVVSCMXPPLFCTLAEISGIGLNVVRKTRPIALAT
              ||| |||||||||||||||||||||||||| |||||||:||||||||||||||||||||
orf10a        ALCLTGIFSPLASLLLPENYAAVRFIVVSCMLPPLFCTLVEISGIGLNVVRKTRPIALAT
                 310        320        330        340        350        360

370        380        390        400        410        419
orf10-1.pep   LGALAANLLLLGLDRAVPAR-PXGAAVACAASFWLFFAFKTESSCRLWQPLKRLPLYLHT
              ||||||||||||| |||: |||||||||||||:||||||||||||||||||:||
orf10a        LGALAANLLLLGL--AVPSGGARGAAVACAASFWLFFVFKTESSCRLWQPLKRLPLYMHT
                 370        380        390        400        410

420        430        440        450        460        470
orf10-1.pep   LFCLTSSAAYTCFGTPANYPLFAGVWAAYLAGCILRHRKDLHKLFHYLKKQGFPLX
              ||||:|||||||||||||||||||||:|||||||||||||||||||||||||||||
orf10a        LFCLASSAAYTCFGTPANYPLFAGVWAVYLAGCILRHRKDLHKLFHYLKKQGFPLX
              420        430        440        450        460        470
```

Homology with a Predicted ORF from *N. gonorrhoeae*

ORF10 shows 94.1% identity over a 475aa overlap with a predicted ORF (ORF10.ng) from *N. gonorrhoeae*:

```
orf10ng.pep   MDTKEILGYAAGSIGSAVLAVIILPLLSWYFPADDIGRIVLMQTAAGLTVSVLCLGLDQA   60
              ||||||| ||||||||||||||||||||||||||||||||||||||||||||||||||||
orf10nm       MDTKEILXYAAGSIGSAVLAVIILPLLSWYFPADDIGRIVLMQTAAGLTVSVLCLGLDQA   60 orf10ng.pep   YVREYYAAADKDTLFKTLFLPPLLFSAAIAALLLSRPSLPSEILFSLDDAAAGIGLVLFE  120
              |||||||:||||||||||||||||  :|||||||||||||||||||||||||||||||||
orf10nm       YVREYYATADKDTLFKTLFLPPLLSAAAIAALLLSRPSLPSEILFSLDDAAAGIGLVLFE  120 orf10ng.pep   LSFLPIRFLLLVLRMEGRALAFSSAQLVPKLAILLLLPLTVGLLHFPANTSVLTAVYALA  180
              |||||||||||||||||||||||||||||||||||| :||||||||||||||||||||||
orf10nm       LSFLPIRFLLLVLRMEGRALAFSSAQLVPKLAILLLXPLTVGLLHFPANTAVLTAVYALA  180 orf10ng.pep   NLAAAAFLLFQNRCRLKAVRRAPFSPAVLHRGLRYGIPLALSSLAYWGLASADRLFLKKY  240
              ||||||||||||||||||||:|||||||||||| |||| :|||: |||||||||||||||
orf10nm       NLAAAAFLLFQNRCRLKAVRHAPFSPAVLHRGXRYGIPIALSSIAYWGLASADRLFLKKY  240 orf10ng.pep   AGLEQLGVYSMGISFGGAALLLQSIFSTVWTPYIFRAIEENATPARLSATAESAAALLAS  300
              ||||||||||||||||||||| :|||||||||||||||||||:|||||||||||||||||
orf10nm       AGLEQLGVYSMGISFGGAALLFQSIFSTVWTPYIFRAIEENAPPARLSATAESAAALLAS  300 orf10ng.pep   ALCLTGIFSPLASLLLPENYAAVRFTVVSCMLPPLFYTLTEISGIGLNVVRKTRPIALAT  360
              ||| ||||||||||||||||||||| |||||||||| |||:||||||||||||||||||
orf10nm       ALCXTGIFSPLASLLLPENYAAVRFIVVSCMXPPLFCTLAEISGIGLNVVRKTRPIALAT  360 orf10ng.pep   ALCLTGIFSPLASLLLPENYAAVRFTVVSCMLPPLFYTLTEISGIGLNVVRKTRPIALAT  360
              ||| |||||||||||||||||||||| ||||| |||| :|||||||||||||||||||
orf10nm       ALCXTGIFSPLASLLLPENYAAVRFIVVSCMXPPLFCTLAEISGIGLNVVRKTRPIALAT  360
```

```
                   370         380         390         400         410
orf10ng.pep  LGALAANLLLLGL--AVPSGGTRGAAVACAASFWLFFVFKTESSCRLWQPLKRLPLYMHT
             ||||||||||||  |||:  ||||||||||||||:|||||||||||||||||||||||:||
orf10nm      LGALAANLLLLGLDRAVPAR-PXGAAVACAASFWLFFAFKTESSCRLWQPLKRLPLYLHT
                   370         380         390         400         410

420         430         440         450         460         470
orf10ng.pep  LFCLASSAAYTCFGTPANYPLFAGVWAAYLAGCILRHRKNLHKLFHYLKKQGFPLX
             ||||:|||||||||||||||||||||||||||||||||:||||||||||||||||
orf10nm      LFCLTSSAAYTCFGTPANYPLFAGVWAAYLAGCILRHRKDLHKLFHYLKKQGFPLX
             420         430         440         450         460         470
```

The complete length ORF10ng nucleotide sequence <SEQ ID 379> is:

```
   1 ATGGACACAA AAGAAATCCT CGGCTACGCG GCAGGCTCGA TCGGCAGCGC
  51 GGTTTTAGCC GTCATCATCC TGCCGCTGCT GTCGTGGTAT TTCcccgCCG
 101 ACGACATCGG GCGCATCGTG CTGATGCAGA CGGCGGCGGG ACTGACGGTG
 151 TCGGTATTGT GCCTCGGGCT GGATCAGGCA TACGTCCGCG AATACTATGC
 201 CGCCGCCGAC AAAGACACTT TGTTCAAAAC CCTGTTCCTG CCGCCGCTGC
 251 TGTTTTCCGC CGCGATAGCC GCCCTGCTGC TTTCCCGCCC GTCCCTGCCG
 301 TCTGAAATCC TGTTTTCGCT CGACGATGCC GCCGCCGGCA TCGGGCTGGT
 351 GCTGTTTGAA CTGAGCTTCC TGCCCATCCG CTTTCTCTTA CTGGTTTTGC
 401 GTATGGAAGG GCGCGCCCTT GCCTTTTCGT CCGCGCAACT CGTGCCCAAA
 451 CTCGCCATTC TGCTGCTGTT GCCGCTGACG GTCGGGCTGC TGCACTTTCC
 501 GGCGAACACC TCCGTCCTGA CCGCCGTTTA CGCGCTGGCA AACCTTGCCG
 551 CCGCCGCCTT TTTGCTGTTT CAAAACCGAT GCCGTCTGAA GGCCGTCCGG
 601 CGCGCGCCGT TTCGCCCGC CGTCCTGCAC CGGGGGCTGC GCTACGGCAT
 651 ACCGCTCGCA CTGAGCAGCC TTGCCTATTG GGGGCTGGCA TCCGCCGACC
 701 GTTTGTTCCT GAAAAAATAT GCGGGCCTGG AACAGCTCGG CGTTTATTCG
 751 ATGGGTATTT CGTTCGGCGG GGCGGCATTA TTGCTCCAAA GCATCTTTTC
 801 AACGGTCTGG ACACCGTATA TTTTCCGTGC AATCGAAGAA AACGCCACGC
 851 CCGCCCGCCT CTCGGCAACG GCAGAATCCG CCGCCGCCCT GCTTGCCTCC
 901 GCCCTCTGCC TGACCGGAAT TTTCTCGCCC CTCGCCTCCC TCCTGCTGCC
 951 GGAAAACTAC GCCGCCGTCC GGTTTACCGT CGTATCGTGT ATGCTGccgc
1001 cgctGTTTTA CACGCTGACC GAAATCAGCG GCATCGGTTT GAACGTCGTC
1051 CGCAAAACGC GTCCGATCGC GCTTGCCACC TTGGGCGCGC TGGCGGCAAA
1101 CCTGCTGCTG CTGGGGCTTG CCGTACCGTC CGGCGGCACG CGCGGCGCGG
1151 CGGTTGCCTG TGCCGCCTCA TTCTGGTTGT TTTTTGTTTT CAAGACAGAA
1201 AGCTCCTGCC GCCTGTGGCA GCCGCTCAAA CGCCTGCCGC TTTATATGCA
1251 CACATTGTTC TGCCTgGCCT CCTCGGCGGC CTACACCTGC TTCGGCACAC
1301 CGGCAAACTA CCCcctgttt gccggcgtAT GGGCGGCATA TCTGGCAGGC
1351 TGCATCCTGC GCCACCGGAA AAATTTGCAC AAACTGTTTC ATTATTTGAA
1401 AAAACAAGGT TTCCCATTAT GA
```

This encodes a protein having amino acid sequence <SEQ ID 380>:

```
  1  MDTKEILGYA AGSIGSAVLA VIILPLLSWY FPADDIGRIV LMQTAAGLTV

51  SVLCLGLDQA YVREYYAAAD KDTLFKTLFL PPLLFSAAIA ALLLSRPSLP

101  SEILFSLDDA AAGIGLVLFE LSFLPIRFLL LVLRMEGRAL AFSSAQLVPK

151  LAILLLLPLT VGLLHFPANT SVLTAVYALA NLAAAAFLLF QNRCRLKAVR

201  RAPFSPAVLH RGLRYGIPLA LSSLAYWGLA SADRLFLKKY AGLEQLGVYS

251  MGISFGGAAL LLQSIFSTVW TPYIFRAIEE NATPARLSAT AESAAALLAS

301  ALCLTGIFSP LASLLLPENY AAVRFTVVSC MLPPLFYTLT EISGIGLNVV

351  RKTRPIALAT LGALAANLLL LGLAVPSGGT RGAAVACAAS FWLFFVFKTE

401  SSCRLWQPLK RLPLYMHTLF CLASSAAYTC FGTPANYPLF AGVWAAYLAG

451  CILRHRKNLH KLFHYLKKQG FPL*
```

ORF10ng and ORF10-1 show 96.4% identity in 473 aa overlap:

```
                    10         20         30         40         50         60
    orf10-1.pep  MDTKEILGYAAGSIGSAVLAVIILPLLSWYFPADDIGRIVLMQTAAGLTVSVLCLGLDQA
                 ||||||||||||||||||||||||||||||||||||||||||||||||||||||||||||
    orf10ng-1    MDTKEILGYAAGSIGSAVLAVIILPLLSWYFPADDIGRIVLMQTAAGLTVSVLCLGLDQA
                    10         20         30         40         50         60

70         80         90        100        110        120
    orf10-1.pep  YVREYYATADKDTLFKTLFLPPLLSAAAIAALLLSRPSLPSEILFSLDDAAAGIGLVLFE
                 ||||||| :|||||||||||||||||| :||||||||||||||||||||||||||||||
    orf10ng-1    YVREYYAAADKDTLFKTLFLPPLLFSAAIAALLLSRPSLPSEILFSLDDAAAGIGLVLFE
                    70         80         90        100        110        120

130        140        150        160        170        180
    orf10-1.pep  LSFLPIRFLLLVLRMEGRALAFSSAQLVPKLAILLLLPLTVGLLHFPANTAVLTAVYALA
                 |||||||||||||||||||||||||||||||||||||||||||||||||||:||||||||
    orf10ng-1    LSFLPIRFLLLVLRMEGRALAFSSAQLVPKLAILLLLPLTVGLLHFPANTSVLTAVYALA
                   130        140        150        160        170        180

190        200        210        220        230        240
    orf10-1.pep  NLAAAAFLLFQNRCRLKAVRHAPFSPAVLHRGLRYGIPIALSSIAYWGLASADRLFLKKY
                 ||||||||||||||||||||:||||||||||||||||||||||:||||||||||||||||
    orf10ng-1    NLAAAAFLLFQNRCRLKAVRRAPFSPAVLHRGLRYGIPIALSSLAYWGLASADRLFLKKY
                   190        200        210        220        230        240

250        260        270        280        290        300
    orf10-1.pep  AGLEQLGVYSMGISFGGAALLFQSIFSTVWTPYIFRAIEENAPPARLSATAESAAALLAS
                 |||||||||||||||||||||:||||||||||||||||||||:|||||||||||||||||
    orf10ng-1    AGLEQLGVYSMGISFGGAALLLQSIFSTVWTPYIFRAIEENATPARLSATAESAAALLAS
                   250        260        270        280        290        300

310        320        330        340        350        360
    orf10-1.pep  ALCLTGIFSPLASLLLPENYAAVRFIVVSCMLPPLFCTLAEISGIGLNVVRKTRPIALAT
                 |||||||||||||||||||||||||:||||||||||||: ||| ||||||||||||||||
    orf10ng-1    ALCLTGIFSPLASLLLPENYAAVRFTVVSCMLPPLFYTLTEISGIGLNVVRKTRPIALAT
                   310        320        330        340        350        360

370        380        390        400        410        420
    orf10-1.pep  LGALAANLLLLGLAVPSGGARGAAVACAASFWLFFAFKTESSCRLWQPLKRLPLYLHTLF
                 |||||||||||||||||||:||||||||||||||:|||||||||||||||||||:||||
    orf10ng-1    LGALAANLLLLGLAVPSGGTRGAAVACAASFWLFFVFKTESSCRLWQPLKRLPLYMHTLF
                   370        380        390        400        410        420

430        440        450        460        470
    orf10-1.pep  CLTSSAAYTCFGTPANYPLFAGVWAAYLAGCILRHRKDLHKLFHYLKKQGFPLX
                 ||:|||||||||||||||||||||||||||||||||:|||||||||||||||||
    orf10ng-1    CLASSAAYTCFGTPANYPLFAGVWAAYLAGCILRHRKNLHKLFHYLKKQGFPLX
                   430        440        450        460        470
```

Based on this analysis, including the presence of a putative leader peptide and several transmembrane segments and the presence of a leucine-zipper motif (4 Leu residues spaced by 6 aa, shown in bold), it is predicted that these proteins from *N. meningitidis* and *N. gonorrhoeae*, and their epitopes, could be useful antigens for vaccines or diagnostics, or for raising ant Example 45

The following partial DNA sequence was identified in *N. meningitidis* <SEQ ID 381>:

```
  1 ..ATCCTGAAAC CGCATAACCA GCTTAAGGAA GACATCCAAC CTGATCCGGC

51   CGATCAAAAC GCCTTGTCCG AACCGGATGC TGCGACAGAG GCAGAGCAGT

101   CGGATGCGGA AAATGCTGCC GACAAGCAGC CCGTTGCCGA TAAAGCCGAC

151   GAGGTTGAAG AAAAGGCGGG CGAGCCGGAA CGGGAAGAGC CGGACGGACA

201   GGCAGTGCGT AAGAAAGCGC TGACGGAAGA GCGTGAACAA ACCGTCAGGG

251   AAAAAGCGCA GAAGAAAGAT GCCGAAACGG TTAAAATACA AGCGGTAAAA

301   CCGTCTAAAG AAACAGAGAA AAAAGCTTCA AAAGAAGAGA AAAAGGCGGC

351   GAAGGAAAAA GTTGCACCCA AACCAACCCC GGAACAAATC CTCAACAGCG

401   GCAgCATCGA AAAmGCGCGC AgTGCCGCCG CCAAAGAAGT GCAGAAAATG

451   AA.AACGTCC GACAAGGCGG AAGC.AACGC ATTATCTGCA AATGGGCGCG

501   TATGCCGACC GTCAGAGCGC GGAAGGGCAG CGTGCCAAAC TGGCAATCTT

551   GGGCATATCT TCCAAGGTGG TCGGTTATCA GGCGGGACAT AAAACGCTTT

601   ACCGGGTGCA AAGCGGCAAT ATGTCTGCCG ATGCGGTGA
```

This corresponds to the amino acid sequence <SEQ ID 382; ORF65>:

```
  1 ..ILKPHNQLKE DIQPDPADQN ALSEPDAATE AEQSDAENAA DKQPVADKAD

51   EVEEKAGEPE REEPDGQAVR KKALTEEREQ TVREKAQKKD AETVKIQAVK

101   PSKETEKKAS KEEKKAAKEK VAPKPTPEQI LNSGSIEXAR SAAAKEVQKM

151   XNVRQGGSXR IICKWARMPT VRARKGSVPN WQSWAYLPRW SVIRRDIKRF

201   TGCKAAICLP MR*
```

Further work revealed the complete nucleotide sequence <SEQ ID 383>:

```
  1   ATGTTTATGA ACAAATTTTC CCAATCCGGA AAAGGTCTGT CCGGTTTTTT

51   CTTCGGTTTG ATACTGGCGA CGGTCATTAT TGCCGGTATT TTGTTTTATC

101   TGAACCAGAG CGGTCAAAAT GCGTTCAAAA TCCCGGCTTC GTCGAAGCAG

151   CCTGCAGAAA CGGAAATCCT GAAACCGAAA AACCAGCCTA AGGAAGACAT

201   CCAACCTGAA CCGGCCGATC AAAACGCCTT GTCCGAACCG GATGCTGCGA

251   CAGAGGCAGA GCAGTCGGAT GCGGAAAAAG CTGCCGACAA GCAGCCCGTT

301   GCCGATAAAG CCGACGAGGT TGAAGAAAAG GCGGGCGAGC CGGAACGGGA

351   AGAGCCGGAC GGACAGGCAG TGCGTAAGAA AGCGCTGACG GAAGAGCGTG

401   AACAAACCGT CAGGGAAAAA GCGCAGAAGA AGATGCCGA AACGGTTAAA

451   AAACAAGCGG TAAAACCGTC TAAAGAAACA GAGAAAAAAG CTTCAAAAGA

501   AGAGAAAAAG GCGGCGAAGG AAAAAGTTGC ACCCAAACCA ACCCCGGAAC

551   AAATCCTCAA CAGCGGCAGC ATCGAAAAAG CGCGCAGTGC CGCCGCCAAA

601   GAAGTGCAGA AAATGAAAAC GTCCGACAAG GCGGAAGCAA CGCATTATCT

651   GCAAATGGGC GCGTATGCCG ACCGTCAGAG CGCGGAAGGG CAGCGTGCCA

701   AACTGGCAAT CTTGGGCATA TCTTCCAAGG TGGTCGGTTA TCAGGCGGGA
```

-continued

```
751 CATAAAACGC TTTACCGGGT GCAAAGCGGC AATATGTCTG CCGATGCGGT

801 GAAAAAAATG CAGGACGAGT TGAAAAAACA TGAAGTCGCC AGCCTGATCC

851 GTTCTATCGA AAGCAAATAA
```

This corresponds to the amino acid sequence <SEQ ID 384; ORF65-1>:

```
  1 MFMNKFSQSG KGLSGFFFGL ILATVIIAGI LFYLNQSGQN AFKIPASSKQ

51 PAETEILKPK NQPKEDIQPE PADQNALSEP DAATEAEQSD AEKAADKQPV

101 ADKADEVEEK AGEPEREEPD GQAVRKKALT EEREQTVREK AQKKDAETVK

151 KQAVKPSKET EKKASKEEKK AAKEKVAPKP TPEQILNSGS IEKARSAAAK

201 EVQKMKTSDK AEATHYLQMG AYADRQSAEG QRAKLAILGI SSKVVGYQAG

251 HKTLYRVQSG NMSADAVKKM QDELKKHEVA SLIRSIESK*
```

Computer analysis of this amino acid sequence gave the following results:

Homology with a Predicted ORF from *N. meningitidis* (Strain A)

ORF65 shows 92.0% identity over a 150aa overlap with an ORF (ORF65a) from strain A of *N. meningitidis*.

```
                                              10         20         30
   orf65.pep                            ILKPHNQLKEDIQPDPADQNALSEPDAATE
                                        ||||:|| |||||:||||||||||||| |
   orf65a    IIAGILFYLNQSGQNAFKIPVPSKQPAETEILKPKNQPKEDIQPEPADQNALSEPDAAKE
                    30         40         50         60         70         80
                    40         50         60         70         80         90
   orf65.pep AEQSDAENAADKQPVADKADEVEEKAGEPEREEPDGQAVRKKALTEEREQTVREKAQKKD
             ||||||:|||||||||||||||||||||| |||| : ||||||||||||||||| ||||||
   orf65a    AEQSDAEKAADKQPVADKADEVEEKADEPEREKSDGQAVRKKALTEEREQTVGEKAQKKD
                    90        100        110        120        130        140
                   100        110        120        130        140        150
   orf65.pep AETVKIQAVKPSKETEKKASKEEKKAAKEKVAPKPTPEQILNSGSIEXARSAAAKEVQKM
             ||||| ||||||||||||||||||||| ||||||||||||||||||||| |||||||||||
   orf65a    AETVKKQAVKPSKETEKKASKEEKKAEKEKVAPKPTPEQILNSGSIEKARSAAAKEVQKM
                   150        160        170        180        190        200
                   160        170        180        190        200        210
   orf65.pep XNVRQGGSXRIICKWARMPTVRARKGSVPNWQSWAYLPRWSVIRRDIKRFTGCKAAICLP orf65a    KTPDKAEATHYLQMGAYADRRSAEGQRAKLAILGISSKVVGYQAGHKTLYRVQSGNMSAD
                   210        220        230        240        250        260
```

The complete length ORF65a nucleotide sequence <SEQ ID 385> is:

```
  1 ATGTTTATGA ACAAATTTTC CCAATCCGGA AAAGGTCTGT CCGGTTTTTT

51 CTTCGGTTTG ATACTGGCGA CGGTCATTAT TGCCGGTATT TTGTTTTATC

101 TGAACCAGAG CGGTCAAAAT GCGTTCAAAA TCCCGGTTCC GTCGAAGCAG

151 CCTGCAGAAA CGGAAATCCT GAAACCGAAA AACCAGCCTA AGGAAGACAT

201 CCAACCTGAA CCGGCCGATC AAAACGCCTT GTCCGAACCG GATGCTGCGA

251 AAGAGGCAGA GCAGTCGGAT GCGGAAAAAG CTGCCGACAA GCAGCCCGTT

301 GCCGACAAAG CCGACGAGGT TGAGGAAAAG GCGGACGAGC CGGAGCGGGA

351 AAAGTCGGAC GGACAGGCAG TGCGCAAGAA AGCACTGACG GAAGAGCGTG

401 AACAAACCGT CGGGGAAAAA GCGCAGAAGA AGATGCCGAA ACGGTTAAA

451 AAACAAGCGG TAAAACCATC TAAAGAAACA GAGAAAAAAG CTTCAAAGA
```

```
501 AGAGAAAAAG GCGGAGAAGG AAAAAGTTGC ACCCAAACCG ACCCCGGAAC

551 AAATCCTCAA CAGCGGCAGC ATCGAAAAAG CGCGCAGTGC CGCTGCCAAA

601 GAAGTGCAGA AAATGAAAAC GCCCGACAAG GCGGAAGCAA CGCATTATCT

651 GCAAATGGGC GCGTATGCCG ACCGCCGGAG CGCGGAAGGG CAGCGTGCCA

701 AACTGGCAAT CTTGGGCATA TCTTCCAAGG TGGTCGGTTA TCAGGCGGGA

751 CATAAAACGC TTTACCGGGT GCAAAGCGGC AATATGTCTG CCGATGCGGT

801 GAAAAAAATG CAGGACGAGT TGAAAAAACA TGAAGTCGCC AGCCTGATCC

851 GTTCTATCGA AAGCAAATAA
```

This encodes a protein having amino acid sequence <SEQ ID 386>:

```
  1 MFMNKFSQSG KGLSGFFFGL ILATVIIAGI LFYLNQSGQN AFKIPVPSKQ

51 PAETEILKPK NQPKEDIQPE PADQNALSEP DAAKEAEQSD AEKAADKQPV

101 ADKADEVEEK ADEPEREKSD GQAVRKKALT EEREQTVGEK AQKKDAETVK

151 KQAVKPSKET EKKASKEEKK AEKEKVAPKP TPEQILNSGS IEKARSAAAK

201 EVQKMKTPDK AEATHYLQMG AYADRRSAEG QRAKLAILGI SSKVVGYQAG

251 HKTLYRVQSG NMSADAVKKM QDELKKHEVA SLIRSIESK*
```

ORF65a and ORF65-1 show 96.5% identity in 289 aa overlap:

```
                      10         20         30         40         50         60
    orf65a.pep  MFMNKFSQSGKGLSGFFFGLILATVIIAGILFYLNQSGQNAFKIPVPSKQPAETEILKPK
                ||||||||||||||||||||||||||||||||||||||||||:||||||||||||||||
    orf65-1     MFMNKFSQSGKGLSGFFFGLILATVIIAGILFYLNQSGQNAFKIPASSKQPAETEILKPK
                      10         20         30         40         50         60

70         80         90        100        110        120
    orf65a.pep  NQPKEDIQPEPADQNALSEPDAAKEAEQSDAEKAADKQPVADKADEVEEKADEPEREKSD
                ||||||||||||||||||||||||:|||||||||||||||||||||||||||:|||||:|
    orf65-1     NQPKEDIQPEPADQNALSEPDAATEAEQSDAEKAADKQPVADKADEVEEKAGEPEREEPD
                      70         80         90        100        110        120

130        140        150        160        170        180
    orf65a.pep  GQAVRKKALTEEREQTVGEKAQKKDAETVKKQAVKPSKETEKKASKEEKKAEKEKVAPKP
                ||||||||||||||||||:|||||||||||||||||||||||||||||||||||||||||
    orf65-1     GQAVRKKALTEEREQTVREKAQKKDAETVKKQAVKPSKETEKKASKEEKKAAKEKVAPKP
                     130        140        150        160        170        180

190        200        210        220        230        240
    orf65a.pep  TPEQILNSGSIEKARSAAAKEVQKMKTPDKAEATHYLQMGAYADRRSAEGQRAKLAILGI
                ||||||||||||||||||||||||||||:|||||||||||||||:|||||||||||||||
    orf65-1     TPEQILNSGSIEKARSAAAKEVQKMKTSDKAEATHYLQMGAYADRQSAEGQRAKLAILGI
                     190        200        210        220        230        240

250        260        270        280        290
    orf65a.pep  SSKVVGYQAGHKTLYRVQSGNMSADAVKKMQDELKKHEVASLIRSIESKX
                ||||||||||||||||||||||||||||||||||||||||||||||||||
    orf65-1     SSKVVGYQAGHKTLYRVQSGNMSADAVKKMQDELKKHEVASLIRSIESKX
                     250        260        270        280        290
```

Homology with a Predicted ORF from *N. gonorrhoeae*

ORF65 shows 89.6% identity over a 212aa overlap with a predicted ORF (ORF65.ng) from *N. gonorrhoeae*:

```
                 30         40         50         60         70         80
    ORF65ng   IIAGILLYLNQGGQNAFKIPAPSKQPAETEILKLKNQPKEDIQPEPADQNALSEPDVAKE
              |||:||  ||||||:|||||||||||:|  |
    ORF65                              ILKPHNQLKEDIQPDPADQNALSEPDAATE
                                             10         20         30
```

-continued

```
                90        100       110       120       130       140
ORF65ng  AEQSDAEKAADKQPVADKADEVEEKAGEPEREEPDGQAVRKKALTEEREQTVREKAQKKD
         ||||||:||||||||||||||||||||||||||||||||||||||||||||||||||||
ORF65    AEQSDAENAADKQPVADKADEVEEKAGEPEREEPDGQAVRKKALTEEREQTVREKAQKKD
                40        50        60        70        80        90

150       160       170       180       190       200
ORF65ng  AETVKKKAVKPSKETEKKASKEEKKAAKEKVAPKPTPEQILNSRSIEKARSAAAKEVQKM
         ||||| :|||||||||||||||||||||||||||||||||||||  ||||||||||||||
ORF65    AETVKIQAVKPSKETEKKASKEEKKAAKEKVAPKPTPEQILNSGSIEXARSAAAKEVQKM
                100       110       120       130       140       150

210       220       230       240       250       260
ORF65ng  KNFGQGGSQRIICKWARMPNPGARKGSVPNWQSWAYLPKWSAIRRDIKRFTACKAAICPP
         | |||| |||||||||||: |||||||||||||||||||:|| |||||||||:|||||| |
ORF65    XNVRQGGSXRIICKWARMPTVRARKGSVPNWQSWAYLPRWSVIRRDIKRFTGCKAAICLP
                160       170       180       190       200       210

ORF65ng  MR
         ||
ORF65    MR
```

An ORF65ng nucleotide sequence <SEQ ID 387> was predicted to encode a protein having amino acid sequence <SEQ ID 388>:

```
  1 MFMNKFSQSG KGLSGFFFGL ILATVIIAGI LLYLNQGGQN AFKIPAPSKQ

51 PAETEILKLK NQPKEDIQPE PADQNALSEP DVAKEAEQSD AEKAADKQPV

101 ADKADEVEEK AGEPEREEPD GQAVRKKALT EEREQTVREK AQKKDAETVK

151 KKAVKPSKET EKKASKEEKK AAKEKVAPKP TPEQILNSRS IEKARSAAAK

201 EVQKMKNFGQ GGSQRIICKW ARMPNPGARK GSVPNWQSWA YLPKWSAIRR

251 DIKRFTACKA AICPPMR*
```

After further analysis, the complete gonococcal DNA sequence <SEQ ID 389> was found to be:

```
  1 ATGTTTATGA ACAAATTTTC CCAATCCGGA AAAGGTCTGT CCGGTTTCTT

51 CTTCGGTTTG ATACTGGCAA CGGTCATTAT TGCCGGTATT TTGCTTTATC

101 TGAACCAGGG CGGTCAAAAT GCGTTCAAAA TCCCGGCTCC GTCGAAGCAG

151 CCTGCAGAAA CGGAAATCCT GAAACTGAAA AACCAGCCTA AGGAAGACAT

201 CCAACCTGAA CCGGCCGATC AAAACGCCTT GTCCGAACCG GATGTTGCGA

251 AAGAGGCAGA GCAGTCGGAT GCGGAAAAAG CTGCCGACAA GCAGCCCGTT

301 GCCGACAAag ccgacgAGGT TGAAGAAag GcGGgcgAgc cggaACGGga 351 aGAGCCGGAC ggACAGGCAG TGCGCAAGAA AGCACTGAcg gAAGAgcGTG 401 AACAAACcgt cagggAAAAA GCGCagaaga AAGATGCCGA AACGgTTAAA 451 AAacaaGCgg tAaaaccgtc tAAAGAAACa gagaaaaaag cTtcaaaaga 501 agagaaaaag gcggcgaaag aaaAAGttgc acccaaaccg accccggaaC 551 aaatcctcaa cagccgCagc atcgaaaaag cgcgtagtgc cgctgccaaa 601 gaAgtgcaGA AAatgaaaaa ctTtgggcaa ggcgGaagcc aacgcattaT 651 CTGcaaatgg gcgcgtatgc cgaccgtccg gagcgcggaA gggcagcgtg 701 ccaaACtggc aAtcttgGgc atatctTccg aagtggtcgG CTATCAGGCG 751 GGACATAAAA CGCTTTACCG CGTGCAAagc GGCAatatgt ccgccgatgc 801 gGTGAAAAAA ATGCAGGACG AGTTGAAAAA GCATGGGGtt gcCAGCCTGA 851 TCCGTGcgAT TGAAGGCAAA TAA
```

This encodes the following amino acid sequence <SEQ ID 390>:

```
  1 MFMNKFSQSG KGLSGFFFGL ILATVIIAGI LLYLNQGGQN AFKIPAPSKQ

51 PAETEILKLK NQPKEDIQPE PADQNALSEP DVAKEAEQSD AEKAADKQPV

101 ADKADEVEEK AGEPEREEPD GQAVRKKALT EEREQTVREK AQKKDAETVK

151 KQAVKPSKET EKKASKEEKK AAKEKVAPKP TPEQILNSRS IEKARSAAAK

201 EVQKMKNFGQ GGSQRIICKW ARMPTVRSAE GQRAKLAILG ISSEVVGYQA

251 GHKTLYRVQS GNMSADAVKK MQDELKKHGV ASLIRAIEGK *
```

ORF65ng-1 and ORF65-1 show 89.0% identity in 290 aa overlap:

```
                    10         20         30         40         50         60
     orf65-1.pep    MFMNKFSQSGKGLSGFFFGLILATVIIAGILFYLNQSGQNAFKIPASSKQPAETEILKPK
                    ||||||||||||||||||||||||||||||:||||:|||||||||| ||||||||||:|
     orf65ng-1      MFMNKFSQSGKGLSGFFFGLILATVIIAGILLYLNQGGQNAFKIPAPSKQPAETEILKLK
                    10         20         30         40         50         60

70         80         90        100        110        120
     orf65-1.pep    NQPKEDIQPEPADQNALSEPDAATEAEQSDAEKAADKQPVADKADEVEEKAGEPEREEPD
                    ||||||||||||||||||||| :|||||||||||||||||||||||||||||||||||||
     orf65ng-1      NQPKEDIQPEPADQNALSEPDVAKEAEQSDAEKAADKQPVADKADEVEEKAGEPEREEPD
                    70         80         90        100        110        120

130        140        150        160        170        180
     orf65-1.pep    GQAVRKKALTEEREQTVREKAQKKDAETVKKQAVKPSKETEKKASKEEKKAAKEKVAPKP
                    ||||||||||||||||||||||||||||||||||||||||||||||||||||||||||||
     orf65ng-1      GQAVRKKALTEEREQTVREKAQKKDAETVKKQAVKPSKETEKKASKEEKKAAKEKVAPKP
                    130        140        150        160        170        180

190        200        210        220        230        239
     orf65-1.pep    TPEQILNSGSIEKARSAAAKEVQKMKTSDKAEATHYL-QMGAYADRQSAEGQRAKLAILG
                    ||||||||  ||||||||||||||||:   ::  : :  :    :||||||||||||||
     orf65ng-1      TPEQILNSRSIEKARSAAAKEVQKMKNFGQGGSQRIICKWARMPTVRSAEGQRAKLAILG
                    190        200        210        220        230        240

240        250        260        270        280        290
     orf65-1.pep    ISSKVVGYQAGHKTLYRVQSGNMSADAVKKMQDELKKHEVASLIRSIESKX
                    |||:|||||||||||||||||||||||||||||||||| ||||||:||:||
     orf65ng-1      ISSEVVGYQAGHKTLYRVQSGNMSADAVKKMQDELKKHGVASLIRAIEGKX
                    250        260        270        280        290
```

On this basis, including the presence of a putative transmembrane domain in the gonococcal protein, it is predicted that the proteins from *N. meningitidis* and *N. gonorrhoeae*, and their epitopes, could be useful antigens for vaccines or diagnostics, or for raising antibodies.

Example 46

The following DNA sequence, believed to be complete, was identified in *N. meningitidis* <SEQ ID 391>:

```
  1 ATGAACCACG ACATCACTTT CCTCACCCTG TTCCTACTCG GTkTCTTCGG

51 CGGAAcGCAC TGCATCGGTA TGTGCGGCGG ATTAAGCAGC GcGTTTGs.s

101 TCCAACTCCC CCCGCATATC AACCGCTTTT GGCTGATCCT GCTGCTTAAC

151 ACAGGACGGG TAAGCAGCTA TACGGCAAtC GGCCTGATAC TCGGATTAAT

201 CGGACAGGTC GGCGTTTCAC TCGAcCAaAC CCGCGTCCTG CAGAATATTT

251 TATACACGGC CGCCAACCTC CTGCTGCTCT TTTTAGGCTT ATACTTGAGC

301 GGTATTTCTT CCTTGGCGGC AAAAATCGAG AAaATCGGCA AACCGATATG

351 GCGGAACCTG AACCCGATAC TCAACCGGCT GTTACCCATA AAATCCATAC

401 CCGCCTGCCT tGCGgTCGGA ATATTATGGG GCTGGCTGCC GTGCGGACTG
```

-continued

```
451 GTTTACAGCG CGTCGCTTTA CGCGCTGGGA AgCGGTAGTG CGGCAACGGG

501 CGGGTTATAT ATGCTTGCCT TTGCACTGGG TACGCTGCCC AATCTTtTAG

551 CAATCGGCAT TTTtTCCCTG CAACTGAAwA AAATCATGCA AAACCGATAT

601 ATCCGCCTGT GTACGGGATT ATCCGTATCA TTATGGGCAT TATGGAAACT

651 TGCCGTCCTG TGGCTGTAA
```

This corresponds to the amino acid sequence <SEQ ID 392; ORF103>:

```
  1 MNHDITFLTL FLLGXFGGTH CIGMCGGLSS AFXXQLPPHI NRFWLILLLN

51 TGRVSSYTAI GLILGLIGQV GVSLDQTRVL QNILYTAANL LLLFLGLYLS

101 GISSLAAKIE KIGKPIWRNL NPILNRLLPI KSIPACLAVG ILWGWLPCGL

151 VYSASLYALG SGSAATGGLY MLAFALGTLP NLLAIGIFSL QLXKIMQNRY

201 IRLCTGLSVS LWALWKLAVL WL*
```

Further work elaborated the DNA sequence <SEQ ID 393> as:

```
  1 ATGAACCACG ACATCACTTT CCTCACCCTG TTCCTACTCG GTTTCTTCGG

51 CGGAACGCAC TGCATCGGTA TGTGCGGCGG ATTAAGCAGC GCGTTTGCGC

101 TCCAACTCCC CCCGCATATC AACCGCTTTT GGCTGATCCT GCTGCTTAAC

151 ACAGGACGGG TAAGCAGCTA TACGGCAATC GGCCTGATAC TCGGATTAAT

201 CGGACAGGTC GGCGTTTCAC TCGACCAAAC CCGCGTCCTG CAGAATATTT

251 TATACACGGC CGCCAACCTC CTGCTGCTCT TTTTAGGCTT ATACTTGAGC

301 GGTATTTCTT CCTTGGCGGC AAAAATCGAG AAAATCGGCA AACCGATATG

351 GCGGAACCTG AACCCGATAC TCAACCGGCT GTTACCCATA AAATCCATAC

401 CCGCCTGCCT TGCGGTCGGA ATATTATGGG GCTGGCTGCC GTGCGGACTG

451 GTTTACAGCG CGTCGCTTTA CGCGCTGGGA AGCGGTAGTG CGGCAACGGG

501 CGGGTTATAT ATGCTTGCCT TTGCACTGGG TACGCTGCCC AATCTTTTAG

551 CAATCGGCAT TTTTTCCCTG CAACTGAAAA AAATCATGCA AAACCGATAT

601 ATCCGCCTGT GTACGGGATT ATCCGTATCA TTATGGGCAT TATGGAAACT

651 TGCCGTCCTG TGGCTGTAA
```

This corresponds to the amino acid sequence <SEQ ID 394; ORF103-1>:

```
  1 MNHDITFLTL FLLGFFGGTH CIGMCGGLSS AFALQLPPHI NRFWLILLLN

51 TGRVSSYTAI GLILGLIGQV GVSLDQTRVL QNILYTAANL LLLFLGLYLS

101 GISSLAAKIE KIGKPIWRNL NPILNRLLPI KSIPACLAVG ILWGWLPCGL

151 VYSASLYALG SGSAATGGLY MLAFALGTLP NLLAIGIFSL QLKKIMQNRY

201 IRLCTGLSVS LWALWKLAVL WL*
```

Computer analysis of this amino acid sequence gave the following results:

Homology with a Predicted ORF from *N. meningitidis* (Strain A)

ORF103 shows 93.8% identity over a 222aa overlap with an ORF (ORF103a) from strain A of *N. meningitidis*:

```
                    10        20        30        40        50        60
    orf103.pep  MNHDITFLTLFLLGXFGGTHCIGMCGGLSSAFXXQLPPHINRFWLILLLNTGRVSSYTAI
                || |||||||||| |||||||||||||| |||||||| ||||||||||||||||||
    orf103a    MNXDITFLTLFLLGFFGGTHCIGMCGGLSSAFALQLPPHINRXWLILLLNTGRVSSYTAI
                    10        20        30        40        50        60
                    70        80        90       100       110       120
    orf103.pep  GLILGLIGQVGVSLDQTRVLQNILYTAANLLLLFLGLYLSGISSLAAKIEKIGKPIWRNL
                |||||||||||||||||||| |||||||||||||||||||||||||||||||||||||||
    orf103a    GLILGLIGQVGVSLDQTRVXQNILYTAANLLLLFLGLYLSGISSLAAKIEKIGKPIWRNL
                    70        80        90       100       110       120
                   130       140       150       160       170       180
    orf103.pep  NPILNRLLPIKSIPACLAVGILWGWLPCGLVYSASLYALGSGSAATGGLYMLAFALGTLP
                ||||||||||||||||||||||||||||||||||||||||||||||||||||||||||||
    orf103a    NPILNRLLPIKSIPACLAVGILWGWLPCGLVYSASLYALGSGSAATGGLYMLAFALGTLP
                   130       140       150       160       170       180
                   190       200       210       220
    orF103.pep  NLLAIGIFSLQLXKIMQNRYIRLCTGLSVSLWALWKLAVLWLX
                || |||||||||||||||||||||||||||||||||||||||
    orf103a    NLXAIGIFSLQLXKIMQNRYIRLCTGLSVSLWALWKLAVLWLX
                   190       200       210       220
```

The complete length ORF103a nucleotide sequence <SEQ ID 395> is:

```
  1 ATGAACCANG ACATCACTTT CCTCACCCTG TTCCTACTCG GTTTCTTCGG

51 CGGAACGCAC TGCATCGGTA TGTGCGGCGG ATTAAGCAGC GCGTTTGCGC

101 TCCAACTCCC CCCGCATATC AACCGCTTNT GGCTGATCCT GCTGCTTAAC

151 ACAGGACGGG TAAGCAGCTA TACGGCAATC GGCCTGATAC TCGGATTAAT

201 CGGACAGGTC GGCGTTTCAC TCGACCAAAC CCGCGTCNTG CAGAATATTT

251 TATACACGGC CGCCAACCTC CTGCTGCTCT TTTTAGGCTT ATACTTGAGC

301 GGTATTTCTT CCTTGGCGGC AAAAATCGAG AAAATCGGCA AACCGATATG

351 GCGGAACCTG AACCCGATAC TCAACCGGCT GTTACCCATA AAATCCATAC

401 CCGCCTGCCT TGCGGTCGGA ATATTATGGG CTGGCTGCC GTGCGGACTA

451 GTTTACAGCG CGTCGCTTTA CGCGCTGGGA AGCGGTAGTG CGGCAACGGG

501 CGGGTTATAT ATGCTTGCCT TTGCACTGGG TACGCTGCCC AATCTTTNGG

551 CAATCGGCAT TTTTTCCCTG CAACTGNAAA AAATCATGCA AAACCGATAT

601 ATCCGCCTGT GTACGGGATT ATCCGTATCA TTATGGGCAT TATGGAAACT

651 TGCCGTCCTG TGGCTGTAA
```

This encodes a protein having amino acid sequence <SEQ ID 396>:

```
  1 MNXDITFLTL FLLGFFGGTH CIGMCGGLSS AFALQLPPHI NRXWLILLLN

51 TGRVSSYTAI GLILGLIGQV GVSLDQTRVX QNILYTAANL LLLFLGLYLS

101 GISSLAAKIE KIGKPIWRNL NPILNRLLPI KSIPACLAVG ILWGWLPCGL

151 VYSASLYALG SGSAATGGLY MLAFALGTLP NLXAIGIFSL QLXKIMQNRY

201 IRLCTGLSVS LWALWKLAVL WL*
```

ORF103a and ORF103-1 show 97.7% identity in 222 aa overlap:

```
                       10        20        30        40        50        60
    orf103a.pep  MNXDITFLTLFLLGFFGGTHCIGMCGGLSSAFALQLPPHINRXWLILLLNTGRVSSYTAI
                 ||  ||||||||||||||||||||||||||||||||||||||| ||||||||||| ||||
    orf103-1     MNHDITFLTLFLLGFFGGTHCIGMCGGLSSAFALQLPPHINRFWLILLLNTGRVSSYTAI
                       10        20        30        40        50        60

70        80        90       100       110       120
    orf103a.pep  GLILGLIGQVGVSLDQTRVXQNILYTAANLLLLFLGLYLSGISSLAAKIEKIGKPIWRNL
                 |||||||||||||||||||| |||||||||||||||||||||||||||||||||||||||
    orf103-1     GLILGLIGQVGVSLDQTRVLQNILYTAANLLLLFLGLYLSGISSLAAKIEKIGKPIWRNL
                       70        80        90       100       110       120

130       140       150       160       170       180
    orf103a.pep  NPILNRLLPIKSIPACLAVGILWGWLPCGLVYSASLYALGSGSAATGGLYMLAFALGTLP
                 ||||||||||||||||||||||||||||||||||||||||||||||||||||||||||||
    orf103-1     NPILNRLLPIKSIPACLAVGILWGWLPCGLVYSASLYALGSGSAATGGLYMLAFALGTLP
                      130       140       150       160       170       180

190       200       210       220
    orf103a.pep  NLXAIGIFSLQLXKIMQNRYIRLCTGLSVSLWALWKLAVLWLX
                 || |||||||||| ||||||||||||||||||||||||||||
    orf103-1     NLLAIGIFSLQLKKIMQNRYIRLCTGLSVSLWALWKLAVLWLX
                      190       200       210       220
```

Homology with a Predicted ORF from *N. gonorrhoeae*

ORF103 shows 95.5% identity over a 222aa overlap with a predicted ORF (ORF103.ng) from *N. gonorrhoeae*:

```
    orf103.pep   MNHDITFLTLFLLGXFGGTHCIGMCGGLSSAFXXQLPPHINRFWLILLLNTGRVSSYTAI 60
                 |||||||||||||| |||||||||||||||||  |||||||||||||||||||:||||||
    orf103ng     MNHDITFLTLFLLGFFGGTHCIGMCGGLSSAFALQLPPHINRFWLILLLNTGRISSYTAI 60
    orf103.pep   GLILGLIGQVGVSLDQTRVLQNILYTAANLLLLFLGLYLSGISSLAAKIEKIGKPIWRNL 120
                 ||:||||| |:|||||||||||||||||:|||||||||||||||||||||||||||||||
    orf103ng     GLMLGLIGQLGISLDQTRVLQNILYTADNLLLLFLGLYLSGISSLAAKIEKIGKPIWRNL 120
    orf103.pep   NPILNRLLPIKSIPACLAVGILWGWLPCGLVYSASLYALGSGSAATGGLYMLAFALGTLP 180
                 ||||||||||||||||||||||||||||||||||||||||||||||:|||||||||||||
    orF103ng     NPILNRLLPIKSIPACLAVGILWGWLPCGLVYSASLYALGSGSATTGGLYMLAFALGTLP 180
    orF103.pep   NLLAIGIFSLQLXKIMQNRYIRLCTGLSVSLWALWKLAVLWL 222
                 |||||||||||| ||||||||||||||||||||||||||||
    orf103ng     NLLAIGIFSLQLKKIMQNRYIRLCTGLSVSLWALWKLAVLWL 222
```

The complete length ORF103ng nucleotide sequence <SEQ ID 397> is:

```
  1 ATGAACCACG ACATCACTTT CCTCACCCTG TTCCTGCTCG GTTTCTTCGG

51 CGGAACTCAC TGCATCGGTA TGTGCGGCGG ATTAAGCAGC GCGTTTGCGC

101 TCCAACTCCC CCCGCATATC AACCGCTTTT GGCTGATTCT GCTGCTTAAC

151 ACAGGACGGA TAAGCAGCTA TACGGCAATC GGCCTGATGC TCGGATTAAT

201 CGGACAACTC GGCATTTCAC TCGACCAAAc ccgcgTCCTG CAAAATATTT 251 tatacacagc ctccaaCCTC CTGCTGCTCT TTTTAGGCTT ATACTTGAGC

301 GGTATTTCTT CCTTGGCGGC AAAAATCGAG AAAATCGGCA AACCGATATG

351 GCGCAACCTG AACCCGATAC TCAACCGGCT GCTGCCCATA AAATCCATAC

401 CCGCCTGCCT TGCTGTCGGA ATATTATGGG GCTGGCTGCC GTGCGGACTG

451 GTTTACAGCG CATCACTTTA CGCGCTGGGA AGCGGTAGTG CGACAACCGG

501 CGGACTGTAT ATGCTTGCCT TTGCACTGGG TACGCTGCCC AATCTTTTGG

551 CAATCGGCAT TTTTTCCCTG CAACTGAAAA AAATCATGCA AAACCGATAT

601 ATCCGCCTGT GTACAGGATT ATCCGTATCA TTATGGGCAT TATGGAAGCT

651 TGCCGTCCTG TGGCTGTAA
```

This encodes a protein having amino acid sequence <SEQ ID 398>:

```
  1 MNHDITFLTL FLLGFFGGTH CIGMCGGLSS AFALQLPPHI NRFWLILLLN

51 TGRISSYTAI GLMLGLIGQL GISLDQTRVL QNILYTASNL LLLFLGLYLS

101 GISSLAAKIE KIGKPIWRNL NPILNRLLPI KSIPACLAVG ILWGWLPCGL

151 VYSASLYALG SGSATTGGLY MLAFALGTLP NLLAIGIFSL QLKKIMQNRY

201 IRLCTGLSVS LWALWKLAVL WL*
```

In addition, ORF103ng and ORF103-1 show 97.3% identity in 222 aa overlap:

```
                    10         20         30         40         50         60
      orf103-1.pep MNHDITFLTLFLLGFFGGTHCIGMCGGLSSAFALQLPPHINRFWLILLLNTGRVSSYTAI
                   |||||||||||||||||||||||||||||||||||||||||||||||||||:||||||
         orf103ng MNHDITFLTLFLLGFFGGTHCIGMCGGLSSAFALQLPPHINRFWLILLLNTGRISSYTAI
                    10         20         30         40         50         60

70         80         90        100        110        120
      orF103-1.pep GLILGLIGQVGVSLDQTRVLQNILYTAANLLLLFLGLYLSGISSLAAKIEKIGKPIWRNL
                   ||:||||||:|:||||||||||||||||:|||||||||||||||||||||||||||||||
         orF103ng GLMLGLIGQLGISLDQTRVLQNILYTASNLLLLFLGLYLSGISSLAAKIEKIGKPIWRNL
                    70         80         90        100        110        120

130        140        150        160        170        180
      orf103-1.pep NPILNRLLPIKSIPACLAVGILWGWLPCGLVYSASLYALGSGSAATGGLYMLAFALGTLP
                   |||||||||||||||||||||||||||||||||||||||||||:||||||||||||||||
         orf103ng NPILNRLLPIKSIPACLAVGILWGWLPCGLVYSASLYALGSGSATTGGLYMLAFALGTLP
                   130        140        150        160        170        180

190        200        210        220
      orf103-1.pep NLLAIGIFSLQLKKIMQNRYIRLCTGLSVSLWALWKLAVLWLX
                   ||||||||||||||||||||||||||||||||||||||||||
         orf103ng NLLAIGIFSLQLKKIMQNRYIRLCTGLSVSLWALWKLAVLWLX
                   190        200        210        220
```

Based on this analysis, including the presence of a putative leader sequence (double-underlined) and several putative transmembrane domains (single-underlined) in the gonococcal protein, it is predicted that the proteins from *N. meningitidis* and *N. gonorrhoeae*, and their epitopes, could be useful antigens for vaccines or diagnostics, or for raising antibodies.

Example 47

The following partial DNA sequence was identified in *N. meningitidis* <SEQ ID 399>:

```
  1 ATGGAAAACC AAAGGCCGCT CCTAGGCTTT CGCTTGGCAC TTTTGGCGGC

51 GATGACGTGG GGAACGCTGC CGAT.TCCGT GCGGCAGGTA TTGAAGTTTG

101 TCGATGCGCC GACGCTGGTG TGGGTGCGTT TTACCGTGGC GGCGGCGGTA

151 TTGTTTGTTT TGCTGGCACT GGGCGGGCGG CTGCcGAAGC GGCGaGGATT

201 TTTCTTGGTG CTCATTCAGG CTGCTGCTGC TCGGCGTGGC GGGCATTTCG

251 GCAAACTTTG TGCTGATTGC CCAAGGGCTG CATTATATTT CGCCGACCAC

301 GACGCAGGTT TTGTGGCAGA TTTCGCCGTT TACGATGATT GTwGTCGGTG

351 TGTTGGTGTT TAAAGACCGG ATGACTGCCG CTCAGAAAAT CGGCTTGGTT

401 TTGCTGCTTG CCGGTTTGCT TATGTATTTT AACGATAAAT TCGGCGAGTT

451 GTCGGGTTTG GGCGCGTATG C.AAGGGCGT GTTGCTGTGT GCGGCAGGCA

501 GTATGGCATG GGTGTGTAAT GCCGTGGCGC AAAAGCTGCT GTCGGCGCAA
```

```
551 TTCGGGCCGC AACAGATTCT GCTGTTGATT TATGCGGCAA GTGCCGCCGT

601 GTTCCTGCCG TTTGCCGAAC CGGCACACAT CGGAAGTATG GACGGTACGT

651 TGGCGTGGGT ATGTATTGCG TATTGCTGCT TGAATACGTT AATCGGTTAC

701 GGCTCGTTCG GCGAGGCGTT GAAACATTGG GAGGCTTCCA AAGTCAGCGC

751 GGTAACAACC TTGCTCCCCG TGTTTACCGT AATAAATACT TTGCTCGGGC

801 ATTATGTGAT GCCTGAAACT TTTGCCGCGC CGGA..
```

This corresponds to the amino acid sequence <SEQ ID 400; ORF104>:

```
  1 MENQRPLLGF RLALLAAMTW GTLPXSVRQV LKFVDAPTLV WVRFTVAAAV

51 LFVLLALGGR LPKRRDFSWC SFRLLLLGVA GISANFVLIA QGLHYISPTT

101 TQVLWQISPF TMIVVGVLVF KDRMTAAQKI GLVLLLAGLL MYFNDKFGEL

151 SGLGAYXKGV LLCAAGSMAW VCNAVAQKLL SAQFGPQQIL LLIYAASAAV

201 FLPFAEPAHI GSMDGTLAWV CIAYCCLNTL IGYGSFGEAL KHWEASKVSA

251 VTTLLPVFTV INTLLGHYVM PETFAAP...
```

Further work revealed further partial DNA sequence <SEQ ID 401>:

```
  1 ATGGAAAACC AAAGGCCGCT CCTAGGCTTC GCGTTGGCAC TTTTGGCGGC

51 GATGACGTGG GGAACGCTGC CGATTGCCGT GCGGCAGGTA TTGAAGTTTG

101 TCGATGCGCC GACGCTGGTG TGGGTGCGTT TTACCGTGGC GGCGGCGGTA

151 TTGTTTGTTT TGCTGGCACT GGGCGGGCGG CTGCCGAAGC GGCGGGATTT

201 TTCTTGGTGC TCATTCAGGC TGCTGCTGCT CGGCGTGGCG GGCATTTCGG

251 CAAACTTTGT GCTGATTGCC CAAGGGCTGC ATTATATTTC GCCGACCACG

301 ACGCAGGTTT TGTGGCAGAT TTCGCCGTTT ACGATGATTG TTGTCGGTGT

351 GTTGGTGTTT AAAGACCGGA TGACTGCCGC TCAGAAAATC GGCTTGGTTT

401 TGCTGCTTGC CGGTTTGCTT ATGTTTTTTA ACGATAAATT CGGCGAGTTG

451 TCGGGTTTGG GCGCGTATGC GAAGGGCGTG TTGCTGTGTG CGGCAGGCAG

501 TATGGCATGG GTGTGTTATG CCGTGGCGCA AAAGCTGCTG TCGGCGCAAT

551 TCGGGCCGCA ACAGATTCTG CTGTTGATTT ATGCGGCAAG TGCCGCCGTG

601 TTCCTGCCGT TTGCCGAACC GGCACACATC GGAAGTTTGG ACGGTACGTT

651 GGCGTGGGTT TGTTTTGCGT ATTGCTGCTT GAATACGTTA ATCGGTTACG

701 GCTCGTTCGG CGAGGCGTTG AAACATTGGG AGGCTTCCAA AGTCAGCGCG

751 GTAACAACCT TGCTCCCCGT GTTTACCGTA ATAwTwwCTT TGCTCGGGCA

801 TTATGTGATG CCTGAAACTT TTGCCGCGCC GGA...
```

This corresponds to the amino acid sequence <SEQ ID 402; ORF104-1>:

```
  1 MENQRPLLG ALALLAAMTW GTLPIAVRQV LKFVDAPTLV WVRFTVAAAV

51 LFVLLALGGR LPKRRDFSWC SFRLLLLGVA GISANFVLIA QGLHYISPTT

101 TQVLWQISPF TMIVVGVLVF KDRMTAAQKI GLVLLLAGLL MFFNDKFGEL

151 SGLGAYAKGV LLCAAGSMAW VCYAVAQKLL SAQFGPQQIL LLIYAASAAV
```

-continued

```
201 FLPFAEPAHI GSLDGTLAWV CFAYCCLNTL IGYGSFGEAL KHWEASKVSA

251 VTTLLPVFTV IXXLLGHYVM PETFAAP...
```

Computer analysis of this amino acid sequence gave the following results:

Homology with Hypothetical HI0878 Protein of *H. influenzae* (Accession Number U32769)

ORF104 and HI0878 show 40% aa identity in 277aa overlap:

```
orf104    4 QRPLLGFRLALLAAMTWGTLPXSVRQVLKFVDAPTLVWXXXXXXXXXXXXXXXXXXXXXP-    62
            Q+PLLGF  AL+ AM WG+LP +++QVL  ++A T+VW                      P
HI0878    3 QQPLLGFTFALITAMAWGSLPIALKQVLSVMNAQTIVWYRFIIAAVSLLALLAYKKQLPE    62 orf104   63 --KRRDFSWCSFALLLLGVAGISANFVLIAQGLHYISPTTTQVLWQISPFTMIVVGVLVF   120
              K R ++W    ++L+GV G+++NF+L +   L+YI P+   Q+   +S F M++ GVL+F
HI0878   63 LMKVRQYAW----IMLIGVIGLTSNFLLFSSSLNYIEPSVAQIFIHLSSFGMLICGVLIF   118 orf104  121 KDRMTAAOKIXXXXXXXXXXXMYFNDKFGELSGLGAYXKGVLLCAAGSMAWVCNAVAQKLL   180
            K+++    QKI           ++FND+F  +GL  Y  GV+L   G++ WV   +AQKL+
HI0878  119 KEKLGLHQKIGLFLLLIGLGLFFNDRFDAFAGLNQYSTGVILGVGGALIWVAYGMAQKLM   178 orf104  181 SAQFGPQQILLLIYAASAAVFLPFAEPAHIGSMDGTLAWVCIAYCCLNTLIGYGSFGEAL   240
            +F  QQILL++Y  A  F+P A+ + +   +   LA +C  YCCLNTLIGYGS+ EAL
HI0878  179 LRKFNSQQILLMMYLGCAIAFMPMADFSQVQELT-PLALICFIYCCLNTLIGYGSYAEAL   237 orf104  241 KHWEASKVSAVTTLLPVFTVINTLLGHYVMPETFAAP                         277
            W+ SKVS V TL+P+FT++ + + HY  P  FAAP
HI0878  238 NRWDVSKVSVVITLVPLFTILFSHIAHYFSPADFAAP                         274
```

Homology with a Predicted ORF from *N. meningitidis* (Strain A)

ORF104 shows 95.3% identity over a 277aa overlap with an ORF (ORF104a) from strain A of *N. meningitidis*:

```
                    10         20         30         40         50         60
orf104.pep  MENQRPLLGFRLALLAAMTWGTLPXSVRQVLKFVDAPTLVWVRFTVAAAVLFVLLALGGR
            |||||||||| ||||||||||||||| :||||||||||||||||||||||||||||||||
orf104a     MENQRPLLGFALALLAAMTWGTLPIAVRQVLKFVDAPTLVWVRFTVAAAVLFVLLALGGR
                    10         20         30         40         50         60
                    70         80         90        100        110        120
orf104.pep  LPKRRDFSWCSFRLLLLGVAGISANFVLIAQGLHYISPTTTQVLWQISPFTMIVVGVLVF
            ||| |||||||||||||||||||||||||||||||||||||||||||||||||||||||
orf104a     LPKWRDFSWCSFRLLLLGVAGISANFVLIAQGLHYISPTTTQVLWQISPFTMIVVGVLVF
                    70         80         90        100        110        120
                   130        140        150        160        170        180
orf104.pep  KDRMTAAQKIGLVLLLAGLLMYFNDKFGELSGLGAYXKGVLLCAAGSMAWVCNAVAQKLL
            |||||||||||||||||||||:|||||||||||||| |||||||||||||| |||||||
orf104a     KDRMTAAQKIGLVLLLAGLLMFFNDKFGELSGLGAYAKGVLLCAAGSMAWVCYAVAQKLL
                   130        140        150        160        170        180
                   190        200        210        220        230        240
orf104.pep  SAQFGPQQILLLIYAASAAVFLPFAEPAHIGSMDGTLAWVCIAYCCLNTLIGYGSFGEAL
            ||||||||||||||||||||||||||:||||| :|||||||:||||||||||||||||||
orf104a     SAQFGPQQILLLIYAASAAVFLPFAELAHIGSLDGTLAWVCFAYCCLNTLIGYGSFGEAL
                   190        200        210        220        230        240
                   250        260        270
orf104.pep  KHWEASKVSAVTTLLPVFTVINTLLGHYVMPETFAAP
            |||||||||||||||||||| :|||||||||:|||||
orf104a     KHWEASKVSAVTTLLPVFTVIFSLLGHYVMPDTFAAPDMNGLGYAGALVVVGGAVTAAVG
                   250        260        270        280        290        300
```

The complete length ORF104a nucleotide sequence <SEQ ID 403> is:

```
  1 ATGGAAAACC AAAGGCCGCT CCTAGGCTTC GCGTTGGCAC TTTTGGCGGC

51 GATGACGTGG GGAACGCTGC CGATTGCCGT GCGGCAGGTA TTGAAGTTTG

101 TCGATGCGCC GACGCTGGTG TGGGTGCGTT TTACCGTGGC GGCGGCGGTA
```

-continued

```
151 TTGTTTGTTT TGCTGGCATT GGGCGGGCGG CTGCCGAAGT GGCGGGATTT

201 TTCTTGGTGC TCATTCAGGC TGCTGCTGCT CGGCGTGGCG GGCATTTCGG

251 CAAACTTTGT GCTGATTGCC CAAGGGCTGC ATTATATTTC GCCGACCACG

301 ACGCAGGTTT TGTGGCAGAT TTCGCCGTTT ACGATGATTG TTGTCGGTGT

351 GTTGGTGTTT AAAGACCGGA TGACTGCCGC TCAGAAAATC GGCTTGGTTT

401 TGCTGCTTGC CGGTTTGCTT ATGTTTTTTA ACGATAAATT CGGCGAGTTG

451 TCGGGTTTGG GCGCGTATGC GAAGGGCGTG TTGCTGTGTG CGGCAGGCAG

501 TATGGCATGG GTGTGTTATG CCGTGGCGCA AAAGCTGCTG TCGGCGCAAT

551 TCGGGCCGCA ACAGATTCTG CTGTTGATTT ATGCGGCAAG TGCCGCCGTG

601 TTCCTGCCGT TTGCCGAACT GGCACACATC GGAAGTTTGG ACGGTACGTT

651 GGCGTGGGTT TGTTTTGCGT ATTGCTGCTT GAATACGTTA ATCGGTTACG

701 GCTCGTTCGG CGAGGCGTTG AAACATTGGG AGGCTTCCAA AGTCAGCGCG

751 GTAACAACCT TGCTCCCCGT GTTTACCGTA ATATTTTCTT TGCTCGGGCA

801 TTATGTGATG CCTGATACTT TTGCCGCGCC GGATATGAAC GGTTTGGGTT

851 ATGCCGGCGC ACTGGTCGTG GTCGGGGGTG CGGTTACGGC GGCGGTGGGG

901 GACAGGCTGT TCAAACGCCG CTAG
```

This encodes a protein having amino acid sequence <SEQ ID 404>:

```
  1 MENQRPLLGF ALALLAAMTW GTLPIAVRQV LKFVDAPTLV WVRFTVAAAV

51 LFVLLALGGR LPKWRDFSWC SFRLLLLGVA GISANFVLIA QGLHYISPTT

101 TQVLWQISPF TMIVVGVLVF KDRMTAAQKI GLVLLLAGLL MFFNDKFGEL

151 SGLGAYAKGV LLCAAGSMAW VCYAVAQKLL SAQFGPQQIL LLIYAASAAV

201 FLPFAELAHI GSLDGTLAWV CFAYCCLNTL IGYGSFGEAL KHWEASKVSA

251 VTTLLPVFTV IFSLLGHYVM PDTFAAPDMN GLGYAGALVV VGGAVTAAVG

301 DRLFKRR*
```

ORF104a and ORF104-1 show 98.2% identity in 277 aa overlap:

```
                  10        20        30        40        50        60
orf104a.pep  MENQRPLLGFALALLAAMTWGTLPIAVRQVLKFVDAPTLVWVRFTVAAAVLFVLLALGGR
             ||||||||||||||||||||||||||||||||||||||||||||||||||||||||||||
orf104-1     MENQRPLLGFALALLAAMTWGTLPIAVRQVLKFVDAPTLVWVRFTVAAAVLFVLLALGGR
                  10        20        30        40        50        60

70        80        90       100       110       120
orf104a.pep  LPKWRDFSWCSFRLLLLGVAGISANFVLIAQGLHYISPTTTQVLWQISPFTMIVVGVLVF
             |||  |||||||||||||||||||||||||||||||||||||||||||||||||||||||
orf104-1     LPKRRDFSWCSFRLLLLGVAGISANFVLIAQGLHYISPTTTQVLWQISPFTMIVVGVLVF
                  70        80        90       100       110       120

130       140       150       160       170       180
orf104a.pep  KDRMTAAQKIGLVLLLAGLLMFFNDKFGELSGLGAYAKGVLLCAAGSMAWVCYAVAQKLL
             ||||||||||||||||||||||||||||||||||||||||||||||||||||||||||||
orf104-1     KDRMTAAQKIGLVLLLAGLLMFFNDKFGELSGLGAYAKGVLLCAAGSMAWVCYAVAQKLL
                 130       140       150       160       170       180

190       200       210       220       230       240
orf104a.pep  SAQFGPQQILLLIYAASAAVFLPFAELAHIGSLDGTLAWVCFAYCCLNTLIGYGSFGEAL
             ||||||||||||||||||||||||||||| ||||||||||||||||||||||||||||||
orf104-1     SAQFGPQQILLLIYAASAAVFLPFAEPAHIGSLDGTLAWVCFAYCCLNTLIGYGSFGEAL
                 190       200       210       220       230       240
```

```
                          250       260       270       280       290       300
orf104a.pep  KHWEASKVSAVTTLLPVFTVIFSLLGHYVMPDTFAAPDMNGLGYAGALVVVGGAVTAAVG
             ||||||||||||||||||||||| |||||||||:|||||
orf104-1     KHWEASKVSAVTTLLPVFTVIXXLLGHYVMPETFAAP
                          250       260       270
```

Homology with a Predicted ORF from *N. gonorrhoeae*

ORF104 shows 93.9% identity over a 277aa overlap with a predicted ORF (ORF104.ng) from *N. gonorrhoeae*:

```
orf104.pep   MENQRPLLGFRLALLAAMTWGTLPXSVRQVLKFVDAPTLVWVRFTVAAAVLFVLLALGGR   60
             ||||||||||:||||||||||||||| :||||||||||||||||||||||||||||||||
orf104ng     MENQRPLLGFALALLAAMTWGTLPIAVRQVLKFVDAPTLVWVRFTVAAAVLFVLLALGGR   60
orf104.pep   LPKRRDFSWCSFRLLLLGVAGISANFVLIAQGLHYISPTTTQVLWQISPFTMIVVGVLVF  120
             |||||||||| |||||||||:|||||||||||||||||||||||||||||||||||||||
orf104ng     LPKRRDFSWHSFRLLLLGVTGISANFVLIAQGLHYISPTTTQVLWQISPFTMIVVGVLVF  120
orf104.pep   KDRMTAAQKIGLVLLLAGLLMYFNDKFGELSGLGAYXKGVLLCAAGSMAWVCNAVAQKLL  180
             ||||||||||||||||:||||:||||||||||||||| ||||||||||||||||||||||
orf104ng     KDRMTAAQKIGLVLLLVGLLMFFNDKFGELSGLGAYAKGVLLCAAGSMAWVCNAVAQKLL  180
orf104.pep   SAQFGPQQILLLIYAASAAVFLPFAEPAHIGSMDGTLAWVCIAYCCLNTLIGYGSFGEAL  240
             ||||||||||||||||||||||| ::|||||||: ||||||||: |||||||||||||||
orf104ng     SAQFGPQQILLLIYAASAAVFLLXAEPAHIGSLDGTLAWVCFVYCCLNTLIGYGSFGEAL  240
orf104.pep   KHWEASKVSAVTTLLPVFTVINTLLGHYVMPETFAAP                         300
             ||||||||||||||||||||||: ||||||||:|||||
orf104ng     KHWEASKVSAVTTLLPVFTVIFSLLGHYVMPDTFAAPDMNGLGYVGALVVVGGAVTAAVG  300
```

The complete length ORF104ng nucleotide sequence <SEQ ID 405> is predicted to encode a protein having amino acid sequence <SEQ ID 406>:

```
  1  MENQRPLLGF ALALLAAMTW GTLPIAVRQV LKFVDAPTLV WVRFTVAAAV
 51  LFVLLALGGR LPKRRDFSWH SFRLLLLGVT GISANFVLIA QGLHYISPTT
101  TQVLWQISPF TMIVVGVLVF KDRMTAAQKI GLVLLLVGLL MFFNDKFGEL
151  SGLGAYAKGV LLCAAGSMAW VCYAVAQKLL SAQFGPQQIL LLIYAASAAV
201  FLLXAEPAHI GSLDGTLAWV CFVYCCLNTL IGYGSFGEAL KHWEASKVSA
251  VTTLLPVFTV IFSLLGHYVM PDTFAAPDMN GLGYVGALVV VGGAVTAAVG
301  DRPFKRR*
```

Further work revealed the complete gonococcal nucleotide sequence <SEQ ID 407>:

```
  1  ATGGAAAACC AAAGGCCGCT CCTAGGCTTC GCGTTGGCAC TTTTGGCGGC
 51  GATGACGTGG GGGACGCTGC CGATTGCCGT GCGGCAGGTA TTGAAGTTTG
101  TCGATGCGCC GACGCTGGTG TGGGTGCGTT TTACCGTGGC GGCGGCGGTA
151  TTGTTTGTTT TGCTGGCATT GGGCGGGCGG CTGCCGAAGC GGCGGGATTT
201  TTCTTGGCAT TCATTCAGGC TGCTGCTGCT CGGCGTGACG GGCATTTCGG
251  CAAACTTTGT GCTGATTGCC CAAGGGCTGC ATTATATTTC GCCGACCACG
301  ACGCAGGTTT TGTGGCAGAT TTCGCCGTTT ACGATGATTG TTGTCGGCGT
351  GTTGGTGTTT AAAGACCGGA tgaCTGCCGC GCAGAAAATC GGTTTGGTTT
401  TGCTGCttgT CGGTttgCTT ATGTTTTta ACGACAAATT CGGCGAGTTG
451  TCGGGTTTGG GCGCGTATGC GAAGGGCGTG TTGCTGTGTG CGGCAGGCAG
501  TATGGCCTGG GTGTGTTATG CCGTGGCGCA AAAGCTGCTG TCGGCGCAAT
551  TCGGGCCGCA ACAGATTCTG CTGTTGATTT ATGCGGcaag tgccgccGTG
```

-continued
```
601 TTCCtgccgT TGgccgaaCC GGCACACATC GGAAGTTTgg aCGGTACGtt

651 GGCGTGGGTT TGTTTTGTGT ATTGCTGCTT GAATACGTTA ATCGGTTACG

701 GCTCGTTCGG CGAGGCGTTG AAACATTGGG AGGCTTCCAA AGTCAGCGCG

751 GTAACAACCT TGCTCCCCGT GTTTACCGTA ATATTTTCTT TGCTCGGGCA

801 TTATGTGATG CCTGATACTT TTGCCGCGCC GGATATGAAC GGTTTGGGTT

851 ATGTCGGCGC ACTGGTCGTG GTCGGGGGTG CGGTTACGGC GGCGGTGGGG

901 GACAGGCCGT TCAAACGCCG CTAG
```

This corresponds to the amino acid sequence <SEQ ID 408; ORF104ng-1>:

```
  1 MENQRPLLGF ALALLAAMTW GTLPIAVRQV LKFVDAPTLV WVRFTVAAAV

51 LFVLLALGGR LPKRRDFSWH SFRLLLLGVT GISANFVLIA QGLHYISPTT

101 TQVLWQISPF TMIVVGVLVF KDRMTAAQKI GLVLLLVGLL MFFNDKFGEL

151 SGLGAYAKGV LLCAAGSMAW VCYAVAQKLL SAQFGPQQIL LLIYAASAAV

201 FLPFAEPAHI GSLDGTLAWV CFVYCCLNTL IGYGSFGEAL KHWEASKVSA

251 VTTLLPVFTV IFSLLGHYVM PDTFAAPDMN GLGYVGALVV VGGAVTAAVG

301 DRPFKRR*
```

ORF104ng-1 and ORF104-1 show 97.5% identity in 277 aa overlap:

```
                    10         20         30         40         50         60
     orf104-1.pep MENQRPLLGFALALLAAMTWGTLPIAVRQVLKFVDAPTLVWVRFTVAAAVLFVLLALGGR
                  ||||||||||||||||||||||||||||||||||||||||||||||||||||||||||||
     orf104ng-1   MENQRPLLGFALALLAAMTWGTLPIAVRQVLKFVDAPTLVWVRFTVAAAVLFVLLALGGR
                    10         20         30         40         50         60

70         80         90        100        110        120
     orf104-1.pep LPKRRDFSWCSFRLLLLGVAGISANFVLIAQGLHYISPTTTQVLWQISPFTMIVVGVLVF
                  ||||||||||  ||||||||| :|||||||||||||||||||||||||||||||||||||
     orf104ng-1   LPKRRDFSWHSFRLLLLGVTGISANFVLIAQGLHYISPTTTQVLWQISPFTMIVVGVLVF
                    70         80         90        100        110        120

130        140        150        160        170        180
     orF104-1.pep KDRMTAAQKIGLVLLLAGLLMFFNDKFGELSGLGAYAKGVLLCAAGSMAWVCYAVAQKLL
                  |||||||||||||||| :||||||||||||||||||||||||||||||||||||||||||
     orF104ng-1   KDRMTAAQKIGLVLLLTGLLMFFNDKFGELSGLGAYAKGVLLCAAGSMAWVCYAVAQKLL
                   130        140        150        160        170        180

190        200        210        220        230        240
     orf104-1.pep SAWFGPQQILLLIYAASAAVFLPFAEPAHIGSLDGTLAWVCFAYCCLNTLIGYGSFGEAL
                  |||||||||||||||||||||||||||||||||||||||||| :||||||||||||||||
     orF104ng-1   SAWFGPQQILLLIYAASAAVFLPFAEPAHIGSLDGTLAWVCFVYCCLNTLIGYGSFGEAL
                   190        200        210        220        230        240

250        260        270
     orf104-1.pep KHWEASKVSAVTTLLPVFTVIXXLLGHYVMPETFAAP
                  |||||||||||||||||||||   |||||||: ||||
     orf104ng-1   KHWEASKVSAVTTLLPVFTVIFSLLGHYVMPDTFAAPDMNGLGYVGALVVVGGAVTAAVG
                   250        260        270        280        290        300
```

In addition, ORF104ng-1 shows significant homology with a hypothetical *H. influenzae* protein:

```
gi|1573895 (U32769) hypothetical [Haemophilus influenzae] Length = 306
Score = 237 bits (598), Expect = 8e-62
Identities = 114/280 (40%), Positives = 168/280 (59%), Gaps = 8/280 (2%)

Query:  30 QRPXXXXXXXXXXXMTWGTLPIAVRQVLKFVDAPTLVWXXXXXXXXXXXXXXXXXXXXP-  88
           Q+P           M WG+LPIA++QVL  ++A T+VW                    P
Sbjct:   3 QQPLLGFTFALITAMAWGSLPIALKQVLSVMNAQTIVWYRFIIAAVSLLALLAYKKQLPE  62
```

```
Query:  89 --KRRDFSWHSFRLLLLGVTGISANFVLIAQGLHYISPTTTQVLWQISPFTMIVVGVLVF 146
            K R ++W    ++L+GV G+++NF+L +  L+YI P+   Q+   +S F M++ GVL+F
Sbjct:  63 LMKVRQYAW----IMLIGVIGLTSNFLLFSSSLNYIEPSVAQIFIHLSSFGMLICGVLIF 118

Query: 147 KDRMTAAQKIXXXXXXXXXXXMFFNDKFGELSGLGAYAKGVLLCAAGSMAWVCYAVAQKLL 206
            K+++   QKI           +FFND+F  +GL  Y+GV+L  G++ WV Y +AQKL+
Sbjct: 119 KEKLGLHQKIGLFLLLIGLGLFFNDRFDAFAGLNQYSTGVILGVGGALIWVAYGMAQKLM 178

Query: 207 SAQFGPQQILLLIYAASAAVFLPFAEPAHIGSLDGTLAWVCFVYCCLNTLIGYGSFGEAL 266
            +F  QQILL++Y  A  F+P A+ + +  L    LA +CF+YCCLNTLIGYGS+ EAL
Sbjct: 179 LRKFNSQQILLMMYLGCAIAFMPMADFSQVQELT-PLALICFIYCCLNTLIGYGSYAEAL 237

Query: 267 KHWEASKVSAVTTLLPVFTVIFSLLGHYVMPDTFAAPDMN 306
            +W+ SKVS V TL+P+FT++FS + HY  P  FAAP++N
Sbjct: 238 NRWDVSKVSVVITLVPLFTILFSHIANYFSPADFAAPELN 277
```

Based on this analysis, including the presence of a putative leader sequence and several putative transmembrane domains in the gonococcal protein, it is predicted that the proteins from *N. meningitidis* and *N. gonorrhoeae*, and their epitopes, could be useful antigens for vaccines or diagnostics, or for raising antibodies.

Example 48

The following partial DNA sequence was identified in *N. meningitidis* <SEQ ID 409>:

```
  1 ATGGTAGCTC GTCGGGCTCA TAACCCGAAG GTCGTAGGTT CGAATCCTGT

51 .CCCGCAACC TAATTTCAAA CCCCTCGGTT CAATGCCGAG GG.GTTTTGT

101 T.TTGCCTGT TTCCTGTTTC CTGTTTCCTG CCGCCTCCGT TTTTTGCCGG

151 ATTTTCCTTC CGGCCGCAAT ATCGGAACGG CAGACCGCCG TCTGTTTGCG

201 GTTGCAAATT CAGGCAGTTT GGCTACAATC TTCCGCATTG TCTTCAAGAA

251 AGCCAACCAT GCCGACCGTC CGTTTTACCG AATCCGTCAG CAAACAAGAC

301 CTTGATGCTC TGTTCGAGTG GGCAAAAGCA AGTTACGGTG CAGAAAGTTG

351 CTGGAAAACG CTGTATCTGA ACGGTCysCC TTTGGGCAAC CTGTCGCCGG

401 AATGGGTGGA ACGCGTsmmA AAAGACTGGG AGGCAGGCTG CyCGGAGTCT

451 TCAGACGGCA TTTTTCTGAA TgCGGACGGc TGgCctGATA TGGgCGGAcg 501 cTTACAGCAC CTCGCCCTCG GTTGGCACTG TGCGGGGCTG TTGGACGgsT

551 GGCGCAACGA GTGTTTCGAC CTGACCGACG GCGGCGGCAA CCCCTTGTTC

601 ACGCTCGaAc GCGCCGyTTT mCGTCCTkTC GGACTGCTCA GCCGCGCCGT

651 CCATCTCAAC GGTCTGACCG AATCGGACGG CCGATGGCAT TTCTGGATAG

701 GCAGGCGCAG TCCGCACAAA GCAGTCGATC CCAACAAACT CGACAATACT 751 rCCGCCGGCG GTGTTTCCGG CGGCGAAATG CCGTCTGAAG CCGTGTGTCG

801 CGAAAGCAGC GAAGAAGCCG GTTTGGATAA AACGCTGcTT CCGCTCATCC

851 GCCCGGTATC GCAGCTGCAC AGCCTGCGCT CCGTCAGCCG GGGTGTACAC

901 AATGAAATCC TGTATGTATT CGATGCCGTC CTGCCG...
```

This corresponds to the amino acid sequence <SEQ ID 410; ORF105>:

```
  1 MVARRAHNPK VVGSNPXPAT XFQTPRFNAE XVLXLPVSCF LFPAASVFCR

51 IFLPAAISER QTAVCLRLQI QAVWLQSSAL SSRKPTMPTV RFTESVSKQD

101 LDALFEWAKA SYGAESCWKT LYLNGXPLGN LSPEWVERVX KDWEAGCXES

151 SDGIFLNADG WPDMGGRLQH LALGWHCAGL LDGWRNECFD LTDGGGNPLF

201 TLERAXXRPX GLLSRAVHLN GLTESDGRWH FWIGRRSPHK AVDPNKLDNT

251 XAGGVSGGEM PSEAVCRESS EEAGLDKTLL PLIRPVSQLH SLRSVSRGVH

301 NEILYVFDAV LP...
```

Further work revealed the complete nucleotide sequence <SEQ ID 411>:

```
  1 ATGCCGACCG TCCGTTTTAC CGAATCCGTC AGCAAACAAG ACCTTGATGC

51 TCTGTTCGAG TGGGCAAAAG CAAGTTACGG TGCAGAAAGT TGCTGGAAAA

101 CGCTGTATCT GAACGGTCTG CCTTTGGGCA ACCTGTCGCC GGAATGGGTG

151 GAACGCGTCA AAAAGACTG GGAGGCAGGC TGCTCGGAGT CTTCAGACGG

201 CATTTTTCTG AATGCGGACG GCTGGCCTGA TATGGGCGGA CGCTTACAGC

251 ACCTCGCCCT CGGTTGGCAC TGTGCGGGGC TGTTGGACGG CTGGCGCAAC

301 GAGTGTTTCG ACCTGACCGA CGGCGGCGGC AACCCCTTGT TCACGCTCGA

351 ACGCGCCGCT TTCCGTCCTT TCGGACTGCT CAGCCGCGCC GTCCATCTCA

101 ACGGTCTGAC CGAATCGGAC GGCCGATGGC ATTTCTGGAT AGGCAGGCGC

451 AGTCCGCACA AAGCAGTCGA TCCCAACAAA CTCGACAATA CTGCCGCCGG

501 CGGTGTTTCC GGCGGCGAAA TGCCGTCTGA AGCCGTGTGT CGCGAAAGCA

551 GCGAAGAAGC CGGTTTGGAT AAAACGCTGC TTCCGCTCAT CCGCCCGGTA

601 TCGCAGCTGC ACAGCCTGCG CTCCGTCAGC CGGGGTGTAC ACAATGAAAT

651 CCTGTATGTA TTCGATGCCG TCCTGCCCGA AACCTTCCTG CCTGAAAATC

701 AGGATGGCGA AGTGGCGGGT TTTGAGAAAA TGGACATCGG CGGTCTGTTG

751 GATGCCATGT TGTCGGGAAA CATGATGCAC GACGCGCAAC TGGTTACGCT

801 GGACGCGTTT TGCCGTTACG GTCTGATTGA TGCCGCCCAT CCGCTGTCCG

851 AGTGGCTGGA CGGCATACGT TTATAG
```

This corresponds to the amino acid sequence <SEQ ID 412; ORF105-1>:

```
  1   MPTVRFTESV SKQDLDALFE WAKASYGAES CWKTLYLNGL PLGNL-
        SPEWV

51   ERVKKDWEAG CSESSDGIFL NADGWPDMGG RLQHLALGWH
        CAGLLDGWRN

101   ECFDLTDGGG NPLFTLERAA FRPFGLLSRA VHLNGLTESD GRWHF-
        WIGRR

151   SPHKAVDPNK LDNTAAGGVS GGEMPSEAVC RESSEEAGLD KTLLP-
        LIRPV

201   SQLHSLRSVS RGVHNEILYV FDAVLPETFL PENQDGEVAG FEKM-
        DIGGLL

251   DAMLSGNMMH DAQLVTLDAF CRYGLIDAAH PLSEWLDGIR L*
```

Computer analysis of this amino acid sequence gave the following results:

Homology with a Predicted ORF from *N. meningitidis* (Strain A)

ORF105 shows 89.4% identity over a 226aa overlap with an ORF (ORF105a) from strain A of *N. meningitidis*.

```
                60        70        80        90       100       110
   orf105.pep ISERQTAVCLRLQIQAVWLQSSALSSRKPTMPTVRFTESVSKQDLDALFEWAKASYGAES
                                        |||||||||||:||||||||||||||||
       or105a                           MPTVRFTESVSKHDLDALFEWAKASYGAES
                                              10        20        30
               120       130       140       150       160       170
   orf105.pep CWKTLYLNGXPLGNLSPEWVERVXKDWEAGCXESSDGIFLNADGWPDMGGRLQHLALGWH
              |||||||||| |||||||||:||| ||||||| |||||||||||||||| ||||| |:
      orf105a CWKTLYLNGLPLGNLSPEWAERVKKDWEAGCSESSDGIFLNADGWPDMGRRLQHLARIWK
                40        50        60        70        80        90
               180       190       200       210       220       230
   orf105.pep CAGLLDGWRNECFDLTDGGGNPLFTLERAXXRPXGLLSRAVHLNGLTESDGRWHFWIGRR
              ||||| |||:||||||||||:||||:||||   || |||||||||||:||||||||||||
      orf105a CAGLLHGWRDECFDLTDGGSNPLFALERAAFRPXGLLSRAVHLNGLVESDGRWHFWIGRR
                100       110       120       130       140       150
               240       250       260       270       280       290
   orF105.pep SPHKAVDPNKLDNTXAGGVSGGEMPSEAVCRESSEEAGLDKTLLPLIRPVSQLHSLRSVS
              ||||||||:|||| |||||:||:|||:|||||||||||||||||||||||||||| ||
      orf105a SPHKAVDPDKLDNTAAGGVSSGELPSETVCRESSEEAGLDKTLLPLIRPVSQLHSLRPVS
                160       170       180       190       200       210
               300       310
   orf105.pep RGVHNEILYVFDAVLP
              ||||||||||||||||
      orf105a RGVHNEILYVFDAVLPETFLPENQDGEVAGFEKMDIGGLLAAMLSGNMMHDAQLVTLDAF
                220       230       240       250       260       270
```

The complete length ORF105a nucleotide sequence <SEQ ID 413> is:

```
  1 ATGCCGACCG TCCGTTTTAC CGAATCCGTC AGCAAACACG ACCTTGATGC

51 CCTATTCGAG TGGGCAAAGG CAAGTTACGG TGCGGAAAGT TGCTGGAAAA

101 CGCTGTATCT GAACGGTCTG CCTTTGGGCA ATCTGTCGCC GGAATGGGCG

151 GAGCGCGTCA AAAAGACTG GGAGGCAGGC TGCTCGGAGT CTTCAGACGG

201 CATTTTCCTG AATGCGGACG GCTGGCCAGA TATGGGCAGA CGCTTGCAGC

251 ACCTCGCCCG AATATGGAAA GAAGCGGGAC TGCTTCACGG CTGGCGCGAC

301 GAGTGTTTCG ACCTGACCGA CGGCGGCAGC AATCCCTTGT TCGCGCTCGA

351 ACGCGCCGCT TTCCGTCCGT TCGGACTGCT CAGCCGCGCC GTCCATCTCA

401 ACGGTTTGGT CGAATCGGAC GGCCGATGGC ATTTCTGGAT AGGCAGGCGC

451 AGTCCGCACA AAGCAGTCGA TCCCGACAAA CTCGACAATA CTGCCGCCGG

501 CGGTGTTTCC AGCGGTGAAT TGCCGTCTGA AACCGTGTGT CGCGAAAGCA

551 GCGAAGAAGC CGGTTTGGAT AAAACGCTGC TTCCGCTCAT CCGCCCGGTA

601 TCGCAGCTGC ACAGCCTGCG CCCCGTCAGC CGGGGTGTGC ACAATGAAAT

651 CCTGTATGTA TTCGATGCCG TCCTGCCCGA AACCTTCCTG CCTGAAAATC

701 AGGATGGCGA AGTGGCGGGT TTTGAGAAAA TGGACATCGG CGGTCTGTTG

751 GCTGCCATGT TGTCGGGAAA CATGATGCAC GACGCGCAAC TGGTTACGCT

801 GGACGCGTTT TGCCGTTACG GTCTGATTGA TGCCGCCCAT CCGCTGTCCG

851 AGTGGCTGGA CGGCATACGT TTATAG
```

This encodes a protein having amino acid sequence <SEQ ID 414>:

```
  1 MPTVRFTESV SKHDLDALFE WAKASYGAES CWKTLYLNGL PLGNLSPEWA
 51 ERVKKDWEAG CSESSDGIFL NADGWPDMGR RLQHLARIWK EAGLLHGWRD
101 ECFDLTDGGS NPLFALERAA FRPFGLLSRA VHLNGLVESD GRWHFWIGRR
151 SPHKAVDPDK LDNTAAGGVS SGELPSETVC RESSEEAGLD KTLLPLIRPV
201 SQLHSLRPVS RGVHNEILYV FDAVLPETFL PENQDGEVAG FEKMDIGGLL
251 AAMLSGNMMH DAQLVTLDAF CRYGLIDAAH PLSEWLDGIR L*
```

ORF105a and ORF105-1 show 93.8% identity in 291 aa overlap:

```
                   10         20         30         40         50         60
orF105a.pep MPTVRFTESVSKHDLDALFEWAKASYGAESCWKTLYLNGLPLGNLSPEWAERVKKDWEAG
            ||||||||||:|||||||||||||||||||||||||||||||||||||||:|||||||||
orF105-1    MPTVRFTESVSKQDLDALFEWAKASYGAESCWKTLYLNGLPLGNLSPEWVERVKKDWEAG
                   10         20         30         40         50         60

70         80         90        100        110        120
orf105a.pep CSESSDGIFLNADGWPDMGRRLQHLARIWKEAGLLHGWRDECFDLTOGGSNPLFALERAA
            |||||||||||||||||||||| ||||||  |:   ||||   |||||||:||||:||||
orf105-1    CSESSDGIFLNADGWPDMGGRLQHLALGWHCAGLLDGWRNECFDLTOGGGNPLFTLERAA
                   70         80         90        100        110        120

130        140        150        160        170        180
orf105a.pep FRPFGLLSRAVHLNGLVESDGRWHFWIGRRSPHKAVDPDKLDNTAAGGVSSGELPSETVC
            ||||||||||||||||:|||||||||||||||||||||:|||||||||||:|:|||:||
orf105-1    FRPFGLLSRAVHLNGLTESDGRWHFWIGRRSPHKAVDPNKLDNTAAGGVSGGEMPSEAVC
                  130        140        150        160        170        180

190        200        210        220        230        240
orf105a.pep RESSEEAGLDKTLLPLIRPVSQLHSLRPVSRGVHNEILYVFDAVLPETFLPENQDGEVAG
            ||||||||||||||||||||||||||| ||||||||||||||||||||||||||||||||
orf105-1    RESSEEAGLDKTLLPLIRPVSQLHSLRSVSRGVHNEILYVFDAVLPETFLPENQDGEVAG
                  190        200        210        220        230        240

250        260        270        280        290
orf105a.pep FEKMDIGGLLAAMLSGNMMHDAQLVTLDAFCRYGLIDAAHPLSEWLDGIRLX
            ||||||||||| |||||||||||||||||||||||||||||||||||||||
orf105-1    FEKMDIGGLLDAMLSGNMMHDAQLVTLDAFCRYGLIDAAHPLSEWLDGIRLX
                  250        260        270        280        290
```

Homology with a Predicted ORF from *N. gonorrhoeae*

ORF105 shows 87.5% identity over a 312aa overlap with a predicted ORF (ORF105.ng) from *N. gonorrhoeae*:

```
orf105.pep MVARRAHNPKVVGSNPXPATXFQTPRFNAEXVLXLPVSCFLFPAASVFCRIFLPAAISER  60
           |||||||||||||||||  :||||||||| ||     |||||||||||||||||||||||
orf105ng   MVARRAHNPKVVGSNPAPATKYQTPRFNAEGVLF-----FLPAASVFCRIFLPAAISER   55 orf105.pep QTAVCLRLQIQAVWLOSSALSSRKPTMPTVRFTESVSKODLDALFEWAKASYGAESCWKT 120
           |:|||||||||||||||||||:|| ||||||||||||||||||||| |||||||||||||
orF105ng   QAAVCLRLQIQAVWLOSSALCFSRKPAMPTVRFTESVSKODLDALFERAKASYGAESCWKT 115 orf105.pep LYLNGXPLGNLSPEWVERVXKDWEAGCXESSDGIFLNADGWPDMGGRLQHLALGWHCAGL 180
           ||||  ||||||||||:||: |||||| |||| ||||||||||||||||||| |:  |||
orf105ng   LYLNRLPLGNLSPEWAERIKKDWEAGCSESSNGIFLNADGWPDMGGRLQHLARTWNKAGL 175 orf105.pep LDGWRNECFDLTDGGGNPLFTLERAXXRPXGLLSRAVHLNGLTESDGRWHFWIGRRSPHK 240
           | ||||||||||||||||||||||||  || |||:||:||||||||||||||||||||||
orf105ng   LHGWRNECFDLTDGGGNPLFTLERAAFRPFGLLIRAVHLNGLVESNGRWHFWIGRRSPHK 235 orf105.pep AVDPNKLDNTXAGGVSGGEMPSEAVCRESSEEAGLDKTLLPLIRPVSQLHSLRSVSRGVH 300
           ||||  ||||    ||||||||||||||||||||||||| ||||||||:|||||||||||
orf105ng   AVDPGKLDNIAGGGVSGGEMPSEAVCRESSEEAGLDKTLFPLIRPVSRLHSLRSVSRGVH 295 orf105.pep NEILYVFDAVLP                                                 312
           ||||||||||||
orf105ng   NEILYVFDAVLPETFLPENQDGEVAGFEKMDIGGLLDAMLSKNMMHDAQLVTLDAFYRYG 355
```

A complete length ORF105ng nucleotide sequence <SEQ ID 415> was predicted to encode a protein having amino acid sequence <SEQ ID 416>:

```
  1 MVARRAHNPK VVGSNPAPAT KYQTPRFNAE GVLFFLFPAA SVFCRIFLPA

51 AISERQAAVC LRLQIQAVWL QSSALCSRKP AMPTVRFTES VSKQDLDALF

101 ERAKASYGAE SCWKTLYLNR LPLGNLSPEW AERIKKDWEA GCSESSNGIF

151 LNADGWPDMG GRLQHLARTW NKAGLLHGWR NECFDLTDGG GNPLFTLERA

201 AFRPFGLLIR AVHLNGLVES NGRWHFWIGR RSPHKAVDPG KLDNIAGGGV

251 SGGEMPSEAV CRESSEEAGL DKTLFPLIRP VSRLHSLRPV SRGVHNEILY

301 VFDAVLPETF LPENQDGEVA GFEKMDIGGL LDAMLSKNMM HDAQLVTLDA

351 FYRYGLIDAA HPLSEWLDGI RL*
```

Further work revealed the complete nucleotide sequence <SEQ ID 417>:

```
  1 ATGCCGACCG TCCGTTTTAC CGAATCCGTC AGCAAACAAG ACCTTGATGC

51 CCTGTTCGAG CGGGCAAAAG CAAGTTACGG TGCCGAAAGT TGCTGGAAAA

101 CGCTGTATCT GAACCGTCTT CCTTTGGGCA ATCTGTCGCC GGAATGGGCT

151 GAGCGCATCA AAAAGACTG GGAGGCAGGC TGCTCCGAGT CTTCAGACGG

201 CATTTTTCTG AATGCGGACG GCTGGCCGGA TATGGGCGGA CGCTTGCAGC

251 ACCTCGCCCG CACATGGAAC AAGGCGGGGC TGCTTCACGG ATGGCGCAAC

301 GAGTGTTTCG ACCTGACCGA CGGCGGCGGC AACCCCTTGT TCACGCTCGA

351 ACGCGCCGCT TTCCGTCCGT TCGGACTACT CAGCCGCGCC GTCCATCTCA

401 ACGGTTTGGT CGAATCGAAC GGCAGATGGC ATTTTTGGAT AGGCAGGCGC

451 AGTCCGCACA AAGCAGTCGa tcCCGGCAAG CTCGACAATA TTGCCGGCGG

501 CGGTGTTTCC GGCGGCGAAA TGCCGTCTGA AGCCGTGTGC CGCGAAAGCA

551 GCGAAGAAGC CGGTTTGGAT AAAACGCTGT TTCCGCTCAT CCGCCCAGTA

601 TCGCGGCTGC ACAGCCTTCG CCCCGTCAGC CGAGGTGTGC ACAATGAAAT

651 CCTGTATGTG TTCGATGCCG TCCTGCCCGA AACCTTCCTG CCTGAAAATC

701 AGGATGGCGA GGTAGCGGGT TTTGAAAAGA TGGACATTGG CGGCCTATTG

751 GATGCCATGT TGTCGAAAAA CATGATGCAC GACGCGCAAC TGGTTACGCT

801 GGACGCGTTT TACCGTTACG GTCTGATTGA TGCCGCCCAT CCGCTGTCCG

851 AGTGGCTGGA CGGCATACGT TTATAG
```

This corresponds to the amino acid sequence <SEQ ID 418; ORF105ng-1>:

```
  1 MPTVRFTESV SKQDLDALFE RAKASYGAES CWKTLYLNRL PLGNLSPEWA

51 ERIKKDWEAG CSESSDGIFL NADGWPDMGG RLQHLARTWN KAGLLHGWRN

101 ECFDLTDGGG NPLFTLERAA FRPFGLLSRA VHLNGLVESN GRWHFWIGRR

151 SPHKAVDPGK LDNIAGGGVS GGEMPSEAVC RESSEEAGLD KTLFPLIRPV

201 SRLHSLRPVS RGVHNEILYV FDAVLPETFL PENQDGEVAG FEKMDIGGLL

251 DAMLSKNMMH DAQLVTLDAF YRYGLIDAAH PLSEWLDGIR L*
```

ORG105ng-1 and ORF105-1 show 93.5% identity in 291 aa overlap:

```
                  10         20         30         40         50         60
orf105-1.pep  MPTVRFTESVSKQDLDALFEWAKASYGAESCWKTLYLNGLPLGNLSPEWVERVKKDWEAG
              ||||||||||||||||||||||| ||||||||||||||||:||:||||||||
orf105ng-1    MPTVRFTESVSKQDLDALFERAKASYGAESCWKTLYLNRLPLGNLSPEWAERIKKDWEAG
                  10         20         30         40         50         60

70         80         90        100        110        120
orf105-1.pep  CSESSDGIFLNADGWPDMGGRLQHLALGWHCAGLLDGWRNECFDLTDGGGNPLFTLERAA
              |||||||||||||||||||||||||  |:|||| ||||||||||||||||||||||||
orF105ng-1    CSESSDGIFLNADGWPDMGGRLQHLARTWNCAGLLHGWRNECFDLTDGGGNPLFTLERAA
                  70         80         90        100        110        120

130        140        150        160        170        180
orf105-1.pep  FRPFGLLSRAVHLNGLTESDGRWHFWIGRRSPHKAVDPNKLDNTAAGGVSGGEMPSEAVC
              ||||||||||||||||||:||:||||||||||||||||:||| |:|||||||||||||||
orF105ng-1    FRPFGLLSRAVHLNGLVESNGRWHFWIGRRSPHKAVDPGKLDNIAGGGVSGGEMPSEAVC
                 130        140        150        160        170        180

190        200        210        110        120        240
orf105-1.pep  RESSEEAGLDKTLLPLIRPVSQLHSLRSVSRGVHNEILYVFDAVLPETFLPENQDGEVAG
              ||||||||||||:||||||||:|||||:|||||||||||||||||||||||||||||||
orf105ng-1    RESSEEAGLDKTLFPLIRPVSRLHSLRPVSRGVHNEILYVFDAVLPETFLPENQDGEVAG
                 190        200        210        110        120        240

250        260        270        280        290
orF105-1.pep  FEKMDIGGLLDAMLSGNMMHDAQLVTLDAFCRYGLIDAAHPLSEWLDGIRLX
              |||||||||||||||| |||||||||||||| ||||||||||||||||||||
orF105ng-1    FEKMDIGGLLDAMLSKNMMHDAQLVTLDAFYRYGLIDAAHPLSEWLDGIRLX
                 250        260        270        280        290
```

Furthermore, ORF105ng-1 shows homology with a yeast enzyme:

```
sp|P41888|TNR3_SCHPO THIAMIN PYROPHOSPHOKINASE (TPK) (THIAMIN KINASE)
>gi|1076928|pir||S52350 thiamin pyrophosphokinase (EC 2.7.6.2) - fission
yeast (Schizosaccharomyces pombe) >gi|666111 (X84417) thiamin
pyrophosphokinase [Schizosaccharomyces pombe] >gi|2330852|gnl|PID|e334056
(Z98533) thiamin pyrophosphokinase [Schizosaccharomyces pombe]
Length = 569  Score = 105 bits (259), Expect = 4e-22
Identities = 64/192 (33%), Positives = 94/192 (48%), Gaps = 3/192 (1%)

Query:  268 NKAGLLHGWRNECFDLTDGGGNPLFTLERAAFRPFGLLSRAVHLNGLVESNGRW--HFWI  441
              N  G+   WRNE  + +        P+  +ER  F  FG LS  VH  +  +       W+
Sbjct:   96 NTFGIADQWRNELYTVYGKSKKPVLAVERGGFWLFGFLSTGVHCTMYIPATKEHPLRIWV  155

Query:  442 GRRSPHKAVDPGKLDNIAGGGVSGGEMPSEAVCRESSEEAGLDKTLFPLIRPVSRLHSLR  621
              RRSP K   P  LDN   GG++ G+     + +E SEEA LD +  LI P   +  ++
Sbjct:  156 PRRSPTKQTWPNYLDNSVAGGIAHGDSVIGTMIKEFSEEANLDVSSMNLI-PCGTVSYIK  214

Query:  622 PVSRG-VHNEILYVFDAVLPETFLPENQDGEVAGFEKMDIGGLLDAMLSKNMMHDAQLVT  798
                    R  +  E+ YVFD  +  +P   DGEVAGF + +L  + K+     + LV
Sbjct:  215 MEKRHWIQPELQYVFDLPVDDLVIPRINDGEVAGFSLLPLNQVLHELELKSFKPNCALVL  274

Query:  799 LDAFYRYGLIDAAHP                                              843
              LD    R+G+I   HP
Sbjct:  275 LDFLIRHGIITPQHP                                              289
```

Based on this analysis, including the presence of a putative transmembrane domain in the gonococcal protein, it is predicted that the proteins from N. meningitidis and N. gonorrhoeae, and their epitopes, could be useful antigens for vaccines or diagnostics, or for raising antibodies.

Example 49

The following DNA sequence, believed to be complete, was identified in N. meningitidis <SEQ ID 419>:

```
  1 ATGAATAGAC CAAGCAACC CTTCTTCCGT CCCGAAGTCG CCGTTGCCCG

51 CCAAACCAGC CTGACGGGTA AAGTGATTCT GACACGACCG TTGTCATTTT
```

```
101 CCCTATGGAC GACATTTGCA TCGATATCTG CGTTATTGAT TATCCTGTTT

151 TTGATATTTG GTAACTATAC GCGAAAGACA ACAGTGGAGG GACAAATTTT

201 ACCTGCATCG GGCGTAATCA GGGTGTATGC ACCGgATACG rGkACAATTA

251 CAGCGAAATT CGTGGAAGAT GGmsAAAAGG TTAAGGCTGG CGACAAGCTA

301 TTTGCGCTTT CGACCTCACG TTTCGGCGCA GGAGGTAGCG TGCAGCAGCA

351 GTTGAAAACG GAGGCAGTTT TGAAGAAAAC GTTGGCAGAA CAGGAACTGG

401 GTCGTCTGAA GCTGATACAC GGGAATGAAA CGCGCAgCcT TAAAGCAACT

451 GTCGAACGTT TGGAAAACCA GGAACTCCAT ATTTCGCAAC AGATAGACGG

501 TCAGAAAAGG CGCATTAGAC TTGCGGAAGA AATGTTGCAG AAATATCGTT

551 TCCTATCCGC .CAATGA
```

This corresponds to the amino acid sequence <SEQ ID 420; ORF107>:

```
  1 MNRPKQPFFR PEVAVARQTS LTGKVILTRP LSFSLWTTFA SISALLIILF

51 LIFGNYTRKT TVEGQILPAS GVIRVYAPDT XTITAKFVED GXKVKAGDKL

101 FALSTSRFGA GGSVQQQLKT EAVLKKTLAE QELGRLKLIH GNETRSLKAT

151 VERLENQELH ISQQIDGQKR RIRLAEEMLQ KYRFLSXQ*
```

Computer analysis of this amino acid sequence gave the following results:

Homology with a Predicted ORF from *N. meningitidis* (Strain A)

ORF107 shows 97.8% identity over a 186aa overlap with an ORF (ORF107a) from strain A of *N. meningitidis*:

```
                       10         20         30         40         50         60
    orf107.pep MNRPKQPFFRPEVAVARQTSLTGKVILTRPLSFSLWTTFASISALLIILFLIFGNYTRKT
               ||||||||||||||||||||||||||||||||||||||||||||||||||||||||||||
       orf107a MNRPKQPFFRPEVAVARQTSLTGKVILTRPLSFSLWTTFASISALLIILFLIFGNYTRKT
                       10         20         30         40         50         60

70         80         90        100        110        120
    orf107.pep TVEGQILPASGVIRVYAPDTXTITAKFVEDGXKVKAGDKLFALSTSRFGAGGSVQQQLKT
               ||||||||||||||||||||| |||||| ||| |||||||||||||||||| ||||||||
       orf107a TVEGQILPASGVIRVYAPDTGTITAKFXEDGEKVKAGDKLFALSTSRFGAGDSVQQQLKT
                       70         80         90        100        110        120

130        140        150        160        170        180
    orf107.pep EAVLKKTLAEQELGRLKLIHGNETRSLKATVERLENQELHISQQIDGQKRRIRLAEEMLQ
               ||||||||||||||||||||||||||||||||||||||||||||||||||||||||||||
       orf107a EAVLKKTLAEQELGRLKLIHGNETRSLKATVERLENQELHISQQIDGQKRRIRLAEEMLQ
                      130        140        150        160        170        180

189
    orf107.pep KYRFLSXQX
               ||||||
       orf107a KYRFLSANDAVPKQEMMNVKAELLEQKAKLDAYRREEVGLLQEIRTQNLTLXSLPQAAX
                      190        200        210        220        230
```

The complete length ORF107a nucleotide sequence <SEQ ID 421> is:

```
  1 ATGAATAGAC CCAAGCAACC NTTCTTCCGT CCCGAAGTCG CCGTTGCCCG

51 CCAAACCAGC CTGACGGGTA AAGTGATTCT GACACGACCG TTGTCATTTT

101 CCCTATGGAC GACATTTGCA TCGATATCTG CGTTATTGAT TATCCTGTTT

151 TTGATATTTG GTAACTATAC GCGAAAGACA ACAGTGGAGG GACAAATTTT
```

```
201 ACCTGCATCG GGCGTAATCA GGGTGTATGC ACCGGATACG GGGACAATTA

251 CNGCGAAATT CNTGGAAGAT GGAGAAAAGG TTAAGGCTGG CGACAAGCTA

301 TTTGCGCTTT CGACCTCACG TTTCGGCGCA GGAGATAGCG TGCAGCAGCA

351 GTTGAAAACG GAGGCAGTTT TGAAGAAAAC GTTGGCAGAA CAGGAACTGG

401 GTCGTCTGAA GCTGATACAC GGGAATGAAA CGCGCAGCCT TAAAGCAACT

451 GTCGAACGTT TGGAAAACCA GGAACTCCAT ATTTCGCAAC AGATAGACGG

501 TCAGAAAAGG CGCATTAGAC TTGCGGAAGA AATGTTGCAG AAATATCGTT

551 TCCTATCCGC CAATGATGCA GTGCCAAAAC AAGAAATGAT GAATGTCAAG

601 GCAGAGCTTT TAGAGCAGAA AGCCAAACTT GATGCCTACC GCCGAGAAGA

651 AGTCGGGCTG CTTCAGGAAA TCCGCACGCA GAATCTGACA TTGGNNAGCC

701 TCCCCCAAGC GGCATGA
```

This encodes a protein having amino acid sequence <SEQ ID 422>:

```
  1 MNRPKQPFFR PEVAVARQTS LTGKVILTRP LSFSLWTTFA SISALLIILF

51 LIFGNYTRKT TVEGQILPAS GVIRVYAPDT GTITAKFXED GEKVKAGDKL

101 FALSTSRFGA GDSVQQQLKT EAVLKKTLAE QELGRLKLIH GNETRSLKAT

151 VERLENQELH ISQQIDGQKR RIRLAEEMLQ KYRFLSANDA VPKQEMMNVK

201 AELLEQKAKL DAYRREEVGL LQEIRTQNLT LXSLPQAA*
```

Homology with a Predicted ORF from *N. gonorrhoeae*

ORF107 shows 95.7% identity over a 188aa overlap with a predicted ORF (ORF107.ng) from *N. gonorrhoeae*:

```
orf107.pep MNRPKQPFFRPEVAVARQTSLTGKVILTRPLSFSLWTTFASISALLIILFLIFGNYTRKT  60
           ||||||||||||:|||||||||||||||||||||||||||||||||||||||||||||||
 orf107ng  MNRPKQPFFRPEVAIARQTSLTGKVILTRPLSFSLWTTFASISALLIILFLIFGNYTRKT  60 orf107.pep TVEGQILPASGVIRVYAPDTXTITAKFVEDGXKVKAGDKLFALSTSRFGAGGSVQQQLKT 120
           |:||||||||||||||||||| |||||||||| |||||||||||||||||||||||||||
 orf107ng  TMEGQILPASGVIRVYAPDTGTITAKFVEDGEKVKAGDKLFALSTSRFGAGGSVQQQLKT 120 orf107.pep EAVLKKTLAEQELGRLKLIHGNETRSLKATVERLENQELHISQQIDGQKRRIRLAEEMLQ 180
           ||||||||||||||||||| |||||||||||||||||||:||||||||||||||||||:
 orf107ng  EAVLKKTLAEQELGRLKLIHENETRSLKATVERLENQKLHISQQIDGQKRRIRLAEEMLR 180 orf107.pep KYRFLSXQ 188
           |||||| |
 orf107ng  KYRFLSAQ 188
```

The complete length ORF107ng nucleotide sequence <SEQ ID 423> is predicted to encode a protein having amino acid sequence <SEQ ID 424>:

```
  1 MNRPKQPFFR PEVAIARQTS LTGKVILTRP LSFSLWTTFA SISALLIILF

51 LIFGNYTRKT TMEGQILPAS GVIRVYAPDT GTITAKFVED GEKVKAGDKL

101 FALSTSRFGA GGSVQQQLKT EAVLKKTLAE QELGRLKLIH ENETRSLKAT

151 VERLENQKLH ISQQIDGQKR RIRLAEEMLR KYRFLSAQ*
```

Based on the presence of a putative ransmembrane domain in the gonococcal protein, it is predicted that the proteins from *N. meningitidis* and *N. gonorrhoeae*, and their epitopes, could be useful antigens for vaccines or diagnostics, or for raising antibodies.

Example 50

The following DNA sequence, believed to be complete, was identified in *N. meningitidis* <SEQ ID 425>:

```
  1 ATGCTGAATA CTTTTTTTGC CGTATTGGGC GGCTGCCTGC TGCT.TTGCC
 51 GTGCGGCAAA TCCGTAAATA CGGCGGTACA GCCGCAAAAC GCGGTACAAA
101 GCGCGCCGAA ACCGGTTTTC AAAGTCATAT ATATCGACAA TACGGCGATT
151 GCCGGTTTGG ATTTGGGACA AAGCAGCGAA GGCAAAACCA ACGACGGCAA
201 AAAACAAATC AGTTATCCGA TTAAAGGCTT GCCGGAACAA AATGTTATCC
251 GACTGATCGG CAAGCATCCC GGCGACTTGG AAGCCGTCAG CGGCAAATGT
301 ATGGAAACCG ATGATAAGGA CAGTCCGGCA GGTTGGGCAG AAAACGGCGT
351 GTGCCATACC TTGTTTGCCA AACTGGTGGG CAATATCGCC GAAGACGGCG
401 GCAAACTGAC GGATTACCTA GTTTCGCATG CCGCCCTGCA ACCCTATCAG
451 GCAGGCAAAA GCGGCTATGC CGCCGTGCAG AACGGACGCT ATGTGCTGGA
501 AATCGACAGC GAAGGGGCGT TTTATTTCCG CCGCCGCCAT TATTGA
```

This corresponds to the amino acid sequence <SEQ ID 426; ORF108>:

```
  1 MLNTFFAVLG GCLLXLPCGK SVNTAVQPQN AVQSAPKPVF KVIYIDNTAI
 51 AGLDLGQSSE GKTNDGKKQI SYPIKGLPEQ NVIRLIGKHP GDLEAVSGKC
101 METDDKDSPA GWAENGVCHT LFAKLVGNIA EDGGKLTDYL VSHAALQPYQ
151 AGKSGYAAVQ NGRYVLEIDS EGAFYFRRRH Y*
```

Further work revealed the following DNA sequence <SEQ ID 427>:

```
  1 ATGCTGAAAA CATCTTTTGC CGTATTGGGC GGCTGCCTGC TGCTTGCCGC
 51 CTGCGGCAAA TCCGAAAATA CGGCGGAACA GCCGCAAAAC GCGGTACAAA
101 GCGCGCCGAA ACCGGTTTTC AAAGTCAAAT ATATCGACAA TACGGCGATT
151 GCCGGTTTGG ATTTGGGACA AAGCAGCGAA GGCAAAACCA ACGACGGCAA
201 AAAACAAATC AGTTATCCGA TTAAAGGCTT GCCGGAACAA AATGTTATCC
251 GACTGATCGG CAAGCATCCC GGCGACTTGG AAGCCGTCAG CGGCAAATGT
301 ATGGAAACCG ATGATAAGGA CAGTCCGGCA GGTTGGGCAG AAAACGGCGT
351 GTGCCATACC TTGTTTGCCA AACTGGTGGG CAATATCGCC GAAGACGGCG
401 GCAAACTGAC GGATTACCTA GTTTCGCATG CCGCCCTGCA ACCCTATCAG
451 GCAGGCAAAA GCGGCTATGC CGCCGTGCAG AACGGACGCT ATGTGCTGGA
501 AATCGACAGC GAAGGGGCGT TTTATTTCCG CCGCCGCCAT TATTGA
```

This corresponds to the amino acid sequence <SEQ ID 428; ORF108-1>:

```
  1 MLKTSFAVLG GCLLLAACGK SENTAEQPQN AVQSAPKPVF KVKYIDNTAI
 51 AGLDLGQSSE GKTNDGKKQI SYPIKGLPEQ NVIRLIGKHP GDLEAVSGKC
101 METDDKDSPA GWAENGVCHT LFAKLVGNIA EDGGKLTDYL VSHAALQPYQ
151 AGKSGYAAVQ NGRYVLEIDS EGAFYFRRRH Y*
```

Computer analysis of this amino acid sequence gave the following results:

Homology with a Predicted ORF from *N. gonorrhoeae*

ORF108 shows 88.4% identity over a 18 laa overlap with a predicted ORF (ORF108.ng) from *N. gonorrhoeae*:

```
orf108.pep  MLNTFFAVLGGCLLXLPCGKSVNTAVQPQNAVQSAPKPVFKVIYIDNTAIAGLDLGQSSE  60
            ||: |||||||||    ||||  |||  |||||:||||||||||| |||||||| |||||
orf108ng    MLKIPFAVLGGCLLLAACGKSENTAEQPQNAAQSAPKPVFKVKYIDNTAIAGLALGQSSE  60
orf108.pep  GKTNDGKKQISYPIKGLEPQNVIRLIGKHPGDLEAVSGKCMETDDKDSPAGWAENGVCHT  120
            |||||||||||||||||||||::|| ||||:||||| ||||||||| ||:|||||||||
orf108ng    GKTNDGKKQISYPIKGLEPQNAVRLTGKHPNDLEAVVGKCMETDGKDAPSGWAENGVCHT  120
orf108.pep  LFAKLVGNIAEDGGKLTDYLVSHAALQPYQAGKSGYAAVQNGRYVLEIDSEGAFYFRRRHY  181
            |||||||||||||||||||||:||:|||||||||||||||||||||||||||||||||||
orf108ng    LFAKLVGNIAEDGGKLTDYLiSHSALQPYQAGKSGYAAVQNGRYVLEIDSEGAFYFRRRHY  181
```

ORF108-1 shows 92.3% identity with ORF108ng over the same 181 aa overlap:

```
orf108-1.pep  MLKTSFAVLGGCLLLAACGKSENTAEQPQNAVQSAPKPVFKVKYIDNTAIAGLDLGQSSE  60
              |||  |||||||||||||||||||||||||||:||||||||||||||||||||  |||||
orf108ng-1    MLKIPFAVLGGCLLLAACGKSENTAEQPQNAAQSAPKPVFKVKYIDNTAIAGLALGQSSE  60
orf108-1.pep  GKTNDGKKQISYPIKGLPEQNVIRLIGKHPGDLEAVSGKCMETDDKDSPAGWAENGVCHT  120
              |||||||||||||||||::|| ||||:||||| ||||||| ||:|:||||||||
orf108ng-1    GKTNDGKKQISYPIKGLPEQNAVRLTGKHPNDLEAVVGKCMETDGKDAPAGWAENGVCHT  120
orf108-1.pep  LFAKLVGNIAEDGGKLTDYLVSHAALQPYQAGKSGYAAVQNGRYVLEIDSEGAFYFRRRHY  181
              |||||||||||||||||||||:||:|||||||||||||||||||||||||||||||||||
orf108ng-1    LFAKLVGNIAEDGGKLTDYLISHSALQPYQAGKSGYAAVQNGRYVLEIDSEGAFYFRRRHY  181
```

The complete length ORF108ng nucleotide sequence <SEQ ID 429> is:

```
  1 ATGCTGAAAa tacctTTTGC CGTGTtgggc ggCtgcctGC TGCTTGCCGC

51 CTGCGGCAAA TCCGAAAATa cggcggaACA GCCGCAAAAT gcggCACAAA

101 GCGCGCCGAA ACCGGTTTTC AAAGTCAAAT ACATCGACAA TACGGCGATT

151 GCCGGTTTGG CTTTGGGACA AGTAGCGAA GGCAAAACCA acgacgGCAA

201 AAAACAAATC AGTTATccgA TTAAAGGCTT GCCGGAACAA Aacgccgtcc 251 gGCTGACCGG AAAGCATCCC AACGACTTGG AagccgtcgT CGGCAAATGT

301 ATGGAAACCG ACGGAAAGGA CGCGCCTTCG GGCTGGGCGG AAAACGGCGT

351 GTGCCATACC TTGTTTGCCA AACTGGTGGG CAATATCGCC GAAGACGGCG

401 GCAAACTGAC TGATTACCTG ATTTCGCATT CCGCCCTGCA ACCCTATCAG

451 GCAGGCAAAA GCGGCTATGC CGCCGTGCAG AACGGACGCT ATGTGCTGGA

501 AATCGACAGC GagggGGCGT TTTATttccg ccgccgccat tattgA
```

This encodes a protein having amino acid sequence <SEQ ID 430>:

```
  1 MLKIPFAVLG GCLLLAACGK SENTAEQPQN AAQSAPKPVF KVKYIDNTAI

51 AGLALGQSSE GKTNDGKKQI SYPIKGLPEQ NAVRLTGKHP NDLEAVVGKC

101 METDGKDAPS GWAENGVCHT LFAKLVGNIA EDGGKLTDYL ISHSALQPYQ

151 AGKSGYAAVQ NGRYVLEIDS EGAFYFRRRH Y*
```

Based on this analysis, including the presence of a predicted prokaryotic membrane lipoprotein lipid attachment site (underlined) and a putative ATP/GTP-binding site motif A (P-loop, double-underlined) in the gonococcal protein, it is predicted that the proteins from *N. meningitidis* and *N. gonorrhoeae*, and their epitopes, could be useful antigens for vaccines or diagnostics, or for raising antibodies.

Example 51

The following DNA sequence was identified in *N. meningitidis* <SEQ ID 431>:

```
  1 ATGGAAGATT TATATATAAT ACTCGCTTTG GGTTTGGTTG CGATGATTGC

51 CGgATTTATC GATgcgatTg cGggCGGGGG TGGTTTGATT ACGCTGCCCG

101 CACTCTTGTT GGCAGGTATT CCTCCCGTGT CGGCAATTGC CACCAACAAG

151 CTGCAAgCAG CCGCTGCTAC GTTTTCAGCT ACGGTTTCTT TTGCACGCAA

201 AGGTTTGATT GATTGGAAGA AAGGTCTCCC GATTGCCGCA GCATCGTTTG

251 TAGGCGGCGT GGcCGGTGCA TTATCGGTCA GCTTGGTTTC CAAAGATATT

301 CTgCTgGCGG TCGTGCCGGT TTTGTTGATA TTTGTCGCAC TGTATTTTGT

351 GTTTTCGCCC AAGCTCGACG GCAGTAAGGA AGGCAAAGCC AGAATGTCTT

401 TTTTTCTGTT cGGGCTGACG GTCGC.ACCG CTTTTGGGTT TTTACGACGG

451 TGTGTTCGGA CCGGGTGTCG GCTCGTTTTT TCTGATTGCC TTTATTGTTT

501 TGCTCGGCTG CAAgCTGTTG AACGCGATGT CTTACACCAA ATTGGCGAAC

551 GTTGCCTGCA ATCTTGGTTC GCTATCGGTA TTCCTGCTGC ACGGTTCGAT

601 TATTTTCCCG ATTGCGGCAA CGaTGGCGGT CGGTGCGTTT GTCGGtGCGA

651 ATTTAgGTGC GAGATTTGCC GTaCgctTCG GTTCGAAGCT GATTAA
```

This corresponds to the amino acid sequence <SEQ ID 432; ORF109>:

```
  1 MEDLYIILAL GLVAMIAGFI DAIAGGGGLI TLPALLLAGI PPVSAIATNK

51 LQAAAATFSA TVSFARKGLI DWKKGLPIAA ASFVGGVAGA LSVSLVSKDI

101 LLAVVPVLLI FVALYFVFSP KLDGSKEGKA RMSFFLFGLT VXTAFGFLRR

151 CVRTGCRLVF SDCLYCFARL QAVERDVLHQ IGERCLQSWF AIGIPAARFD

201 YFPDCGNDGG RCVCRCEFRC EICRTLRFEA D*
```

Further work revealed the following DNA sequence <SEQ ID 433>:

```
  1 ATGGAAGATT TATATATAAT ACTCGCTTTG GGTTTGGTTG CGATGATTGC

51 CGGATTTATC GATGCGATTG CGGGCGGGGG TGGTTTGATT ACGCTGCCCG

101 CACTCTTGTT GGCAGGTATT CCTCCCGTGT CGGCAATTGC CACCAACAAG

151 CTGCAAGCAG CCGCTGCTAC GTTTTCAGCT ACGGTTTCTT TTGCACGCAA

201 AGGTTTGATT GATTGGAAGA AAGGTCTCCC GATTGCCGCA GCATCGTTTG

251 TAGGCGGCGT GGCCGGTGCA TTATCGGTCA GCTTGGTTTC CAAAGATATT

301 CTGCTGGCGG TCGTGCCGGT TTTGTTGATA TTTGTCGCAC TGTATTTTGT

351 GTTTTCGCCC AAGCTCGACG GCAGTAAGGA AGGCAAAGCC AGAATGTCTT

401 TTTTTCTGTT CGGGCTGACG GTCGCACCGC TTTTGGGTTT TTACGACGGT

451 GTGTTCGGAC CGGGTGTCGG CTCGTTTTTT CTGATTGCCT TTATTGTTTT

501 GCTCGGCTGC AAGCTGTTGA ACGCGATGTC TTACACCAAA TTGGCGAACG
```

-continued
```
551 TTGCCTGCAA TCTTGGTTCG CTATCGGTAT TCCTGCTGCA CGGTTCGATT

601 ATTTTCCCGA TTGCGGCAAC GATGGCGGTC GGTGCGTTTG TCGGTGCGAA

651 TTTAGGTGCG AGATTTGCCG TCCGCTTCGG TTCGAAGCTG ATTAAGCCGC

701 TGCTGATTGT CATCAGCATT TCGATGGCTG TGAAATTGTT GATAGACGAG

751 AGAAATCCGC TGTATCAGAT GATTGTTTCG ATGTTTTAA
```

This corresponds to the amino acid sequence <SEQ ID 434; ORF109-1>:

```
  1 MEDLYIILAL GLVAMIAGFI DAIAGGGGLI TLPALLLAGI PPVSAIATNK

51 LQAAAATFSA TVSFARKGLI DWKKGLPIAA ASFVGGVAGA LSVSLVSKDI

101 LLAVVPVLLI FVALYFVFSP KLDGSKEGKA RMSFFLFGLT VAPLLGFYDG

151 VFGPGVGSFF LIAFIVLLGC KLLNAMSYTK LANVACNLGS LSVFLLHGSI

201 IFPIAATMAV GAFVGANLGA RFAVRFGSKL IKPLLIVISI SMAVKLLIDE

251 RNPLYQMIVS MF*
```

Computer analysis of this amino acid sequence gave the following results:
Homology with a Predicted ORF from *N. meningitidis* (Strain A)

ORF109 shows 95.9% identity over a 147aa overlap with an ORF (ORF109a) from strain A of *N. meningitidis*.

```
                     10         20         30         40         50         60
    orf109.pep MEDLYIILALGLVAMIAGFIDAIAGGGGLITLPALLLAGIPPVSAIATNKLQAAAATFSA
               ||||||||||||||||||||||||||||||||||||||||||||||||||||||||||||
    orf109a    MEDLYIILALGLVAMIAGFIDAIAGGGGLITLPALLLAGIPPVSAIATNKLQAAAATFSA
                     10         20         30         40         50         60
                     70         80         90        100        110        120
    orf109.pep TVSFARKGLIDWKKGLPIAAASFVGGVAGALSVSLVSKDILLAVVPVLLIFVALYFVFSP
               ||||||||||||||||||||||||:|||:|||||||||||||||||||||||||||||||
    orf109a    TVSFARKGLIDWKKGLPIAAASFAGGVVGALSVSLVSKDILLAVVPVLLIFVALYFVFSP
                     70         80         90        100        110        120
                    130        140        150        160        170        180
    orf109.pep KLDGSKEGKARMSFFLFGLTVXTAFGFLRRCVRTGCRLVFSDCLYCFARLQAVERDVLHQ
               |||||||||||||||||||||    :||
    orf109a    KLDGSKEGKARMSFFLFGLTVAPLLGFYDGVFGPGVGSFFLIAFIVLLGCKLLNAMSYTK
                    130        140        150        160        170        180
```

The complete length ORF109a nucleotide sequence <SEQ ID 435> is:

```
  1 ATGGAAGATT TATACATAAT ACTCGCTTTG GGTTTGGTTG CGATGATTGC

51 CGGATTTATC GATGCGATTG CGGGTGGGGG TGGTTTGATT ACGCTGCCTG

101 CACTCTTGTT GGCAGGTATT CCTCCCGTGT CGGCAATTGC CACCAACAAG

151 CTGCAAGCAG CCGCTGCTAC GTTTTCGGCT ACGGTTTCTT TTGCACGCAA

201 AGGTTTGATT GATTGGAAGA AAGGTCTCCC GATTGCGGCA GCATCGTTTG

251 CAGGCGGCGT GGTCGGTGCA TTATCGGTCA GCTTGGTTTC CAAAGATATT

301 CTGCTGGCGG TCGTGCCGGT TTTGTTGATA TTTGTCGCGC TGTATTTTGT

351 GTTTTCGCCC AAGCTCGACG GCAGTAAGGA AGGCAAAGCC AGAATGTCTT

401 TTTTTCTGTT CGGTCTGACG GTTGCACCAC TTTTGGGTTT TTACGACGGT

451 GTGTTCGGAC CGGGTGTCGG CTCGTTTTTT CTGATTGCCT TTATTGTTTT
```

```
501 GCTCGGCTGC AAGCTGTTGA ACGCGATGTC TTACACCAAA TTGGCGAACG

551 TTGCCTGCAA TCTTGGTTCG CTATCGGTAT TCCTGCTGCA CGGTTCGATT

601 ATTTTCCCGA TTGCGGCAAC GATGGCGGTC GGTGCGTTTG TCGGTGCGAA

651 TTTAGGTGCG AGATTTGCCG TCCGCTTCGG TTCGAAGCTG ATTAAGCCGC

701 TGCTGATTGT CATCAGCATT TCGATGGCTG TGAAATTGTT GATAGACGAG

751 AGAAATCCGC TGTATCAGAT GATTGTTTCG ATGTTTTAA
```

This encodes a protein having amino acid sequence <SEQ ID 436>:

```
  1 MEDLYIILAL GLVAMIAGFI DAIAGGGGLI TLPALLLAGI PPVSAIATNK

51 LQAAAATFSA TVSFARKGLI DWKKGLPIAA ASFAGGVVGA LSVSLVSKDI

101 LLAVVPVLLI FVALYFVFSP KLDGSKEGKA RMSFFLFGLT VAPLLGFYDG

151 VFGPGVGSFF LIAFIVLLGC KLLNAMSYTK LANVACNLGS LSVFLLHGSI

201 IFPIAATMAV GAFVGANLGA RFAVRFGSKL IKPLLIVISI SMAVKLLIDE

251 RNPLYQMIVS MF*
```

ORF109a and ORF109-1 show 99.2% identity in 262 aa overlap:

```
                   10         20         30         40         50         60
orf109a.pep  MEDLYIILALGLVAMIAGFIDAIAGGGGLITLPALLLAGIPPVSAIATNKLQAAAATFSA
             ||||||||||||||||||||||||||||||||||||||||||||||||||||||||||||
  orf109-1   MEDLYIILALGLVAMIAGFIDAIAGGGGLITLPALLLAGIPPVSAIATNKLQAAAATFSA
                   10         20         30         40         50         60

70         80         90        100        110        120
orf109a.pep  TVSFARKGLIDWKKGLPIAAASFAGGVVGALSVSLVSKDILLAVVPVLLIFVALYFVFSP
             |||||||||||||||||||||:|||:||||||||||||||||||||||||||||||||||
  orf109-1   TVSFARKGLIDWKKGLPIAAASFVGGVVGALSVSLVSKDILLAVVPVLLIFVALYFVFSP
                   70         80         90        100        110        120

130        140        150        160        170        180
orf109a.pep  KLDGSKEGKARMSFFLFGLTVAPLLGFYDGVFGPGVGSFFLIAFIVLLGCKLLNAMSYTK
             ||||||||||||||||||||||||||||||||||||||||||||||||||||||||||||
  orf109-1   KLDGSKEGKARMSFFLFGLTVAPLLGFYDGVFGPGVGSFFLIAFIVLLGCKLLNAMSYTK
                  130        140        150        160        170        180

190        200        210        220        230        240
orf109a.pep  LANVACNLGSLSVFLLHGSIIFPIAATMAVGAFVGANLGARFAVRFGSKLIKPLLIVISI
             ||||||||||||||||||||||||||||||||||||||||||||||||||||||||||||
  orf109-1   LANVACNLGSLSVFLLHGSIIFPIAATMAVGAFVGANLGARFAVRFGSKLIKPLLIVISI
                  190        200        210        220        230        240

250        260
orf109a.pep  SMAVKLLIDERNPLYQMIVSMFX
             |||||||||||||||||||||||
  orf109-1   SMAVKLLIDERNPLYQMIVSMFX
                  250        260
```

Homology with a Predicted ORF from *N. gonorrhoeae*

ORF109 shows 98.3% identity over a 231aa overlap with a predicted ORF (ORF109.ng) from *N. gonorrhoeae*:

```
orf109.pep  MEDLYIILALGLVAMIAGFIDAIAGGGGLITLPALLLAGIPPVSAIATNKLQAAAATFSA   60
            ||||||||||||||||||||||||||||||||||||||||||||||||||||||||||||
 orf109ng   MEDLYIILALGLVAMIAGFIDAIAGGGGLITLPALLLAGIPPVSAIATNKLQAAAATFSA   60 orf109.pep  TVSFARKGLIDWKKGLPIAAASFVGGVAGALSVSLVSKDILLAVVPVLLIFVALYFVFSP  120
            |||||||||||||||||||||:|||:||||||||||||||||||||||||||||||||||
 orf109ng   TVSFARKGLIDWKKGLPIAAASFAGGVVGALSVSLVSKDILLAVVPVLLIFVALYFVFSP  120 orf109.pep  KLDGSKEGKARMSFFLFGLTVXTAFGFLRRCVRTGCRLVFSDCLYCFARLQAVERDVLHQ  180
            ||||||||||||||||||||| ||||||||||||||||||||||||||||||||||||||
 orf109ng   KLDGSKEGKARMSFFLFGLTVATAFGFLRRCVRTGCRLVFSDCLYCFARLQAVERDVLHQ  180
```

```
orf109.pep  IGERCLQSWFAIGIPAARFDYFPDCGNDGGRCVCRCEFRCEICRTLRFEAD  231
            ||||||||||||||||||||||||||||||||||||||||||| ||||||
orf109ng    IGERCLQSWFAIGIPAARFDYFPDCGNDGGRCVCRCEFRCEICRPLRFEAD  231
```

An ORF109ng nucleotide sequence <SEQ ID 437> was predicted to encode a protein having amino acid sequence <SEQ ID 438>:

```
  1 MEDLYIILAL GLVAMIAGFI DAIAGGGGLI TLPALLLAGI PPVSAIATNK

51 LQAAAATFSA TVSFARKGLI DWKKGLPIAA ASFAGGVVGA LSVSLVSKDI

101 LLAVVPVLLI FVALYFVFSP KLDGSKEGKA RMSFFLFGLT VATAFGFLRR

151 CVRTGCRLVF SDCLYCFARL QAVERDVLHQ IGERCLQSWF AIGIPAARFD

201 YFPDCGNDGG RCVCRCEFRC EICRPLRFEA D*
```

Further work revealed the following gonococcal DNA sequence <SEQ ID 439>:

```
  1 ATGGAAGATT TATACATAAT ACTCGCTTTG GGTTTGGTTG CGATGATCGC

51 CGGATTTATC GATGCGATTG CGGGCGGGGG TGGTTTGATT ACGCTGCCTG

101 CACTCTTGTT GGCAGGTATT CCTCCCGTGT CGGCAATTGC CACCAACAAG

151 CTGCAAGCAG CCGCTGCTAC GTTTTCGGCT ACGGTTTCTT TTGCACGCAA

201 AGGTTTGATT GATTGGAAGA AAGGTCTCCC GATTGCCGCA GCATCGTTTG

251 CAGGCGGCGT GGTCGGTGCA TTATCGGTCA GCTTGGTTTC CAAAGATATT

301 TTGCTGGCGG TCGTGCCGGT TTTGTTGATA TTTGTCGCGC TGTATTTTGT

351 GTTTTCGCCC AAGCTCGACG GCAGTAAGGA AGGCAAAGCC AGAATGTCTT

401 TTTTTCTATT CGGGCTGACG GTTGCACCGC TTTTGGGTTT TTACGACGGT

451 GTGTTCGGAC CGGGTGTCGG CTCGTTTTTT CTGATTGCCT TTATTGTTTT

501 GCTCGGCTGC AAGCTGTTGA ACGCGATGTC TTACACCAAA TTGGCGAACG

551 TTGCTTGCAA TCTTGGTTCG CTATCGGTAT TCCTGCTGCA CGGTTCGATT

601 ATTTTCCCGA TTGTGGCAAC GATGGCGGTC GGTGCGTTTG TCGGTGCGAA

651 TTTAGGTGCG AGATTTGCCG TCCGCTTCGG TTCGAAGCTG ATTAAGCCGC

701 TGCTGATTGT CATCAGCATT TCGATGGCTG TGAAATTGTT GATAGACGAG

751 AGAAATCCGC TGTATCAGAT GATTGTTTCG ATGTTTTAA
```

This corresponds to the amino acid sequence <SEQ ID 440; ORF109ng-1>:

```
  1 MEDLYIILAL GLVAMIAGFI DAIAGGGGLI TLPALLLAGI PPVSAIATNK

51 LQAAAATFSA TVSFARKGLI DWKKGLPIAA ASFAGGVVGA LSVSLVSKDI

101 LLAVVPVLLI FVALYFVFSP KLDGSKEGKA RMSFFLFGLT VAPLLGFYDG

151 VFGPGVGSFF LIAFIVLLGC KLLNAMSYTK LANVACNLGS LSVFLLHGSI

201 IFPIVATMAV GAFVGANLGA RFAVRFGSKL IKPLLIVISI SMAVKLLIDE

251 RNPLYQMIVS MF*
```

ORF109ng-1 and ORF109-1 show 98.9% identity in 262 aa overlap:

```
                  10         20         30         40         50         60
orf109ng-1.pep MEDLYIILALGLVAMIAGFIDAIAGGGGLITLPALLLAGIPPVSAIATNKLQAAAATFSA
               ||||||||||||||||||||||||||||||||||||||||||||||||||||||||||||
    orf109-1   MEDLYIILALGLVAMIAGFIDAIAGGGGLITLPALLLAGIPPVSAIATNKLQAAAATFSA
                  10         20         30         40         50         60

70         80         90        100        110        120
orf109ng-1.pep TVSFARKGLIDWKKGLPIAAASFAGGVVGALSVSLVSKDILLAVVPVLLIFVALYFVFSP
               ||||||||||||||||||||||:|||:|||||||||||||||||||||||||||||||||
    orf109-1   TVSFARKGLIDWKKGLPIAAASFVGGVAGALSVSLVSKDILLAVVPVLLIFVALYFVFSP
                  70         80         90        100        110        120

130        140        150        160        170        180
orf109ng-1.pep KLDGSKEGKARMSFFLFGLTVAPLLGFYDGVFGPGVGSFFLIAFIVLLGCKLLNAMSYTK
               ||||||||||||||||||||||||||||||||||||||||||||||||||||||||||||
    orf109-1   KLDGSKEGKARMSFFLFGLTVAPLLGFYDGVFGPGVGSFFLIAFIVLLGCKLLNAMSYTK
                 130        140        150        160        170        180

190        200        210        220        230        240
orf109ng-1.pep LANVACNLGSLSVFLLHGSIIFPIVATMAVGAFVGANLGARFAVRFGSKLIKPLLIVISI
               |||||||||||||||||||||||:|||||||||||||||||||||||||||||||||||||
    orf109-1   LANVACNLGSLSVFLLHGSIIFPIAATMAVGAFVGANLGARFAVRFGSKLIKPLLIVISI
                 190        200        210        220        230        240

250        260
orf109ng-1.pep SMAVKLLIDERNPLYQMIVSMFX
               |||||||||||||||||||||||
    orf109-1   SMAVKLLIDERNPLYQMIVSMFX
                 250        260
```

In addition, ORF109ng-1 shows homology to a hypothetical *Pseudomonas* protein:

```
sp|P29942|YCB9_PSEDE HYPOTHETICAL 27.4 KD PROTEIN IN COBO 3'REGION (ORF9)
>gi|94984|pir||I38164 hypothetical protein 9 - Pseudomonas sp >gi|551929
(M62866) ORF9 [Pseudomonas denitrificans] Length = 261
Score = 175 bits (439), Expect = 3e-43
Identities = 83/214 (38%), Positives = 131/214 (60%), Gaps = 1/214 (0%)

Query:   41 PPVSAIATNKLQXXXXXXXXXXXXXXRKGLIDWKKGLPIXXXXXXXXXXXXXXXXXXXKDI 100
            PP+  + TNKLQ              R+G ++ K+ LP+                   D+
Sbjct:   43 PPLQTLGTNKLQGLFGSGSATLSYARRGHVNLKEQLPMALMSAAGAVLGALLATIVPGDV 102

Query:  101 LLAVVPVLLIFVALYFVFSPKLDGSKEGKARMSFFLFGLTVAPLLGFYDGVFGPGVGSFF 160
            L A++P LLI +ALYF   P + G   +  +R++ F+F LT+ PL+GFYDGVFGPG GSFF
Sbjct:  103 LKAILPFLLIAIALYFGLKPNM-GDVDQHSRVTPFVFTLTLVPLIGFYDGVFGPGTGSFF 161

Query:  161 LIAFIVLLGCKLLNAMSYTKLANVACNLGSLSVFLLHGSIIFPIVATMAVGAFVGANLGA 220
            ++ F+ L G +L A ++TK N    N+G+  VFL G++++ +   M +G F+GA +G+
Sbjct:  162 MLGFVTLAGFGVLKATAHTKFLNFGSNVGAFGVFLFFGAVLWKVGLLMGLGQFLGAQVGS 221

Query:  221 RFAVRFGSKLIKPLLIVISISMAVKLLIDERNPL 254
            R+A+  G+K+IKPLL+++SI++A++LL D  +PL
Sbjct:  222 RYAMAKGAKIIKPLLVIVSIALAIRLLADPTHPL 255
```

Based on this analysis, including the presence of a putative leader sequence (double-underlined) and several putative transmembrane domains (single-underlined) in the gonococcal protein, it is predicted that the proteins from *N. meningitidis* and *N. gonorrhoeae*, and their epitopes, could be useful antigens for vaccines or diagnostics, or for raising antibodies.

Example 52

The following partial DNA sequence was identified in *N. meningitidis* <SEQ ID 441>:

```
  1 ..CTGCTAGGGT ATTGCATCGG TTATCGGTAC GGCTGTTGCA GCAAAACCAG

51   CCGCAGACGG ATTATTTGGT CAAATTCGGA TCGTTTTGGG CGAG.ATTTT
```

-continued
```
101   TGGTTTTCTG  GGACTGTATG  ACGTCTATGC  TTCGGCATGG  TTTGTCGTTA

151   TCATGATGTT  TTTGGTGGTT  TCTACCAGTT  TGTGCCTGAT  TCGCAATGTG

201   CCGCCGTTCT  GGCGCGAAAT  GAAGTCTTTT  CGGGAAAAGG  TTAAAGAAAA

251   ATCTCTGGCG  GCGATGCGCC  ATTCTTCGCT  GTTGGATGTA  AAAATTGCGC

301   CCGAGGTTGC  CAAACGTTAT  CTGGAAGTAC  AAGGTTTTCA  GGGGAAAACC

351   ATTAACCGTG  AAGACGGGTC  GGTTCTGATT  GCCGCCAAAA  AAGGCACAAT

401   GAACAAATGG  GGCTATATCT  TTGCCCATGT  TGCTTTGATT  GTCATTTGCC

451   TGGGCGGGTT  GATAGACAGT  AACCTGCTGT  TGAAACTGGG  TATGCTGACC

501   GGTCGGATTG  TTCCGGACAA  TCAGGCGGTT  TATGCCAAGG  ATTTC.AAGC

551   CCGAAAGTAT  .TTTGGGTGC  gTCCAATCTC  TCATTTAGGG  GCAACGTCAA

601   TATTTCCG.A  GGGGCAGAgT  GCGGATGTGG  TTTTCCTGA
```

This corresponds to the amino acid sequence <SEQ ID 442; ORF110>:

```
  1   ..LLGIASVIGT  LLQQNQPQTD  YLVKFGSFWA  XIFGFLGLYD  VYASAWFVVI

51   MMFLVVSTSL   CLIRNVPPFW  REMKSFREKV  KEKSLAAMRH  SSLLDVKIAP

101   EVAKRYLEVQ   GFQGKTINRE  DGSVLIAAKK  GTMNKWGYIF  AHVALIVICL

151   GGLIDSNLLL   KLGMLTGRIF  RTIRRFMPRI  XKPESXFGCV  QSLI*GQRQY

201   FXRGRVRMWF   S*
```

Computer analysis of this amino acid sequence gave the following results:

Homology with ORF88a from *N. meningitidis* (Strain A)

ORF110 shows 91.5% identity over a 188aa overlap with ORF88a from strain A of *N. meningitidis*:

```
                    10         10         30         40         50         60
orf88a.pep  MSKSRRSPPLLSRPWFAFFSSMRFAVALLSLLGIASVIGTVLQQNQPQTDYLVKFGSFWA
                                          ||||||||||:|||||||||||||||||
orf110                                    LLGIASVIGTLLQQNQPQTDYLVKFGSFWA
                                                   10         20         30

70         80         90        140        150        120
orf88a.pep  QIFGFLGLYDVYASAWFVVIMMFLVVSTSLCLIRNVPPFWREMKSFREKVKEKSLAAMRH
            |||||||||||||||||||||||||||||||||||||||||||||||||||||||||||
orf110      XIFGFLGLYDVYASAWFVVIMMFLVVSTSLCLIRNVPPFWREMKSFREKVKEKSLAAMRH
                    40         50         60         70         80         90

130        140        150        160        170        180
orf88a.pep  SSLLDVKIAPEVAKRYLEVQGFQGKTINREDGSVLIAAKKGTMNKWGYIFAHVALIVICL
            ||||||||||||||||||||||||||||||||||||||||||||||||||||||||||||
orf110      SSLLDVKIAPEVAKRYLEVQGFQGKTINREDGSVLIAAKKGTMNKWGYIFAHVALIVICL
                   100        110        120        130        140        150

190        200        210        220        230        240
orf88a.pep  GGLIDSNLLLKLGMLTGRIVPDNQAVYAKDFKPESILGASNLSFRGNVNISEGQSADVVF
            ||||||||||||||||||||    :  :   ||||  :|
orf110      GGLIDSNLLLKLGMLTGRIFRTIRRFMPRIXKPESXFGCVQSLIXGQRQYFXRGRVRMWF
                   160        170        180        190        200        210

250        260        270        280        290        300
orf88a.pep  LNADNGILVQDLPFEVKLKKFHIDFYNTGMPRDFASDIEVTDKATGEKLERTIRVNHPLT orf110      SX
```

However, ORF88 and ORF110 do not align, because they represent two different fragments of the same protein.

Homology with a Predicted ORF from *N. gonorrhoeae*

ORF110 shows 88.6% identity over a 21laa overlap with a predicted ORF (ORF110.ng) from *N. gonorrhoeae*:

```
  orf110.pep                       LLGIASVIGTLLQQNQPQTDYLVKFGSFWA  30
                                   ||||||||||:||||||||||||||| ||:
  orf110ng  MSKSRISPTLLSRPWFAFFSSMRFAVALLSLLGIASVIGTVLQQNQPQTDYLVKFGPFWT  60
  orf110.pep XIFGFLGLYDVYASAWFVVIMMFLVVSTSLCLIRNVPPFWREMKSFREKVKEKSLAAMRH  90
             || |||||||||||||||||||||||||||||||||||||||||||||||||||||||||
  orf110ng  RIFDFLGLYDVYASAWFVVIMMFLVVSTSLCLIRNVPPFWREMKSFREKVKEKSLAAMRH 120
  orf110.pep SSLLDVKIAPEVAKRYLEVQGFQGKTINREDGSVLIAAKKGTMNKWGYIFAHVALIVICL 150
             |||||||||||||||||||:||||||::||||||||||||||||||||| ||||||||||
  orf110ng  SSLLDVKIAPEVAKRYLEVRGFQGKTVSREDGSVLIAAKKGTMNKWGYIXAHVALIVICL 180
  orf110.pep GGLIDSNLLLKLGMLTGRIFRTIRRFMPRIXKPESXFGCVQSLIXGQRQYFXRGRVRMWF 210
             | ||: |||||||||:| |||: || |||| |||  :| ||||| |||||| ||:|||||
  orf110ng  GRLINXNLLLKLGMLAGSIFRNNRRVMPRISKPESIWGGVQSLIKGQRQYFQRGKVRMWF 240
  orf110.pep S                                                            211
             |
  orf110ng  S                                                            241
```

The complete length ORF110ng nucleotide sequence <SEQ ID 443> is predicted to encode a protein having amino acid sequence <SEQ ID 444>:

```
  1 MSKSRISPTL LSRPWFAFFS SMRFAVALLS LLGIASVIGT VLQQNQPQTD
 51 YLVKFGPFWT RIFDFLGLYD VYASAWFVVI MMFLVVSTSL CLIRNVPPFW
101 REMKSFREKV KEKSLAAMRH SSLLDVKIAP EVAKRYLEVR GFQGKTVSRE
151 DGSVLIAAKK GTMNKWGYIX AHVALIVICL GRLINXNLLL KLGMLAGSIF
201 RNNRRVMPRI SKPESIWGGV QSLIKGQRQY FQRGKVRMWF S*
```

Based on the putative transmembrane domains in the gonococcal protein, it is predicted that the proteins from *N. meningitidis* and *N. gonorrhoeae*, and their epitopes, could be useful antigens for vaccines or diagnostics, or for raising antibodies.

Example 53

The following DNA sequence was identified in *N. meningitidis* <SEQ ID 445>:

```
  1 ATGCCGTCTG AAACACGCCT GCCGAACTTT ATCCGCGTCT TGATATTTGC
 51 CCTGGGTTTC ATCTTCCTGA ACGCCTGTTC GGAACAAACC GCGCAAACCG
101 TTACCCTGCA AGGCGAAACG ATGGGCACGA CCTATACCGT CAAATACCTT
151 TCAAATAATC GGGACAAACT CCCCTCACCT GCCGAAATAC AAAAACGCAT
201 CGATGACGCG CTTAAAGAAG TCAACCGGCA GATGTCCACC TATCAGCCCG
251 ACTCCGAAAT CAGCCGGTTC AACCAACACA CAGCCGGCAA GCCCCTCCGC
301 ATTTCAAGCG ACTTCGCACA CGTTACTGCC GAAGCCGTCC GCCTGAACCG
351 CCTGACACAC GGCGCGCTGG ACGTAACCGT CGGCCCCTTG GTCAACCTTT
401 GGGGATTCGG CCCCGACAAA TCCGTTACCC GTGAACCGTC GCCGGAACAA
451 ATCAAACAGG CGGCATCTTA TACGGGCATA GACAAAATCA TTTTGAAACA
501 AGGCAAAGAT TACGCTTCCT TGAGCAAAAC CCACCCCAAG GCCTATTTGG
551 ATTTATCTTC GATTGCCAAA GGCTTCGGCG TTGATAAAGT TGCGGGCGAA
601 CTGGAAAAAT ACGGCATTCA AAATTATCTG GTCGAAATCG GCGGCGAGTT
651 GCACGGCAAA GGCAAAAACG CGCGCGGCGA ACCGTGGCGC ATCGGTATCG
701 AGCAGCCCAA TATCGTCCAA GGCGGCAATA CGCAGATTAT CGTCCCGCTG
```

```
 751 AACAACCGTT CGCTTGCCAC TTCCGGCGAT TACCGTATTT TCCACGTCGA

801 TAAAAACGGC AAACGCCTCT CCCATATCAT CAACCCGAAC AACAAACGAC

851 CCATCAGCCA CAACCTCGCC TCCATCAGCG TGGTCGCAGA CAGTGCGATG

901 ACGGCGGACG GCTTGTCCAC AGGATTATTC GTATTGGGCG AAACCGAAGC

951 CTTAAAGCTG GCAGAGCGCG AAAAACTCGC TGTTTTCCTG ATTGTCAGGG

1001 ATAAAGGCGG CTACCGCACC GCCATGTCTT CCGAATTTGA AAAACTGCTC

1051 CGCTAA
```

This corresponds to the amino acid sequence <SEQ ID 446; ORF111>:

```
  1 MPSETRLPNF IRVLIFALGF IFLNACSEQT AQTVTLQGET MGTTYTVKYL

51 SNNRDKLPSP AEIQKRIDDA LKEVNRQMST YQPDSEISRF NQHTAGKPLR

101 ISSDFAHVTA EAVRLNRLTH GALDVTVGPL VNLWGFGPDK SVTREPSPEQ

151 IKQAASYTGI DKIILKQGKD YASLSKTHPK AYLDLSSIAK GFGVDKVAGE

201 LEKYGIQNYL VEIGGELHGK GKNARGEPWR IGIEQPNIVQ GGNTQIIVPL

251 NNRSLATSGD YRIFHVDKNG KRLSHIINPN NKRPISHNLA SISVVADSAM

301 TADGLSTGLF VLGETEALKL AEREKLAVFL IVRDKGGYRT AMSSEFEKLL

351 R*
```

Computer analysis of this amino acid sequence gave the following results:

Homology with a Predicted ORF from *N. meningitidis* (Strain A)

ORF111 shows 96.9% identity over a 351 aa overlap with an ORF (ORF111a) from strain A of *N. meningitidis*:

```
                        10         20         30         40         50         60
    orf111a.pep MPSETRLPNFIRTLIFALSFIFLNACSEQTAQTVTLQGETMGTTYTVKYLSNNRDXLPSP
                ||||||||||:|||||:|||||||||||||||||||||||||||||||||||||  ||||
    orf111      MPSETRLPNFIRVLIFALGFIFLNACSEQTAQTVTLQGETMGTTYTVKYLSNNRDKLPSP
                        10         20         30         40         50         60

70         80         90        100        110        120
    orf111a.pep AEIQXRIDDALKEVNRQMSTYQPDSEISRFNQHTAGKPLRISSDFAHVTAEAVHLNRLTH
                ||||  ||||||||||||||||||||||||||||||||||||||||||||||:|||||
    orf111      AEIQKRIDDALKEVNRQMSTYQPDSEISRFNQHTAGKPLRISSDFAHVTAEAVRLNRLTH
                        70         80         90        100        110        120

130        140        150        160        170        180
    orf111a.pep GALDVTVGPLVNLWGFGPDKSVTREPSPEQIKQAASYTGIDKIILKQGKDYASLSKTHPK
                ||||||||||||||||||||||||||||||||||||||||||||||||||||||||||||
    orf111      GALDVTVGPLVNLWGFGPDKSVTREPSPEQIKQAASYTGIDKIILKQGKDYASLSKTHPK
                       130        140        150        160        170        180

190        200        210        220        230        240
    orf111a.pep AYLDLSSIAKGFGVDXVAGELEKYGIQNYLVEIGGELHGKXKNARGEPWRIGIEQPNIVQ
                |||||||||||||||  ||||||||||||||||||||||| |||||||||||||||||||
    orf111      AYLDLSSIAKGFGVDKVAGELEKYGIQNYLVEIGGELHGKGKNARGEPWRIGIEQPNIVQ
                       190        200        210        220        230        240

250        260        270        280        290        300
    orf111a.pep GGNTQIIVPLNNRSXATSGDYRIFHVDKSGKRLSHIINPNNKRPISHNLASISVXADSAM
                ||||||||||||||  |||||||||||||:|||||||||||||||||||||||| ||||
    orf111      GGNTQIIVPLNNRSLATSGDYRIFHVDKNGKRLSHIINPNNKRPISHNLASISVVADSAM
                       250        260        270        280        290        300

310        320        330        340        350
    orf111a.pep TADGXSTGLFVLGETEALKLAEREKLAVFLIVRDKGGYRTAMSSEFEKLLRX
                ||||  ||||||||||||||||||||||||||||||||||||||||||||||
    orf111      TADGLSTGLFVLGETEALKLAEREKLAVFLIVRDKGGYRTAMSSEFEKLLRX
                       310        320        330        340        350
```

The complete length ORF111a nucleotide sequence <SEQ ID 447> is:

```
   1 ATGCCGTCTG AAACACGCCT GCCGAACTTT ATCCGCACCT TGATATTTGC
  51 CCTGAGTTTT ATCTTCCTGA ACGCCTGTTC GGAACAAACC GCGCAAACCG
 101 TTACCCTGCA AGGTGAAACG ATGGGCACGA CCTATACCGT CAAATACCTT
 151 TCAAATAATC GGGACNAACT CCCNTCACCT GCCGAAATAC AAAANCGCAT
 201 CGATGACGCG CTTAAAGAAG TCAACCGGCA GATGTCCACC TATCAGCCCG
 251 ACTCCGAAAT CAGCCGGTTC AACCAACACA CAGCCGGCAA GCCCCTCCGC
 301 ATTTCAAGCG ACTTCGCACA CGTTACTGCC GAAGCCGTCC ACCTGAACCG
 351 CCTGACACAC GGCGCGCTGG ACGTAACCGT CGGCCCCTTG GTCAACCTTT
 401 GGGGATTCGG CCCCGACAAA TCCGTTACCC GTGAACCGTC GCCGGAACAA
 451 ATCAAACAAG CAGCATCTTA TACGGGCATA GACAAAATCA TTTTGAAACA
 501 AGGCAAAGAT TACGCTTCCT TGAGCAAAAC CCACCCCAAG GCCTATTTGG
 551 ATTTATCTTC GATTGCCAAA GGCTTCGGCG TTGATNANGT TGCGGGCGAA
 601 CTGGAAAAAT ACGGCATTCA AAATTATCTG GTCGAAATCG GCGGNGAGTT
 651 GCACGGCAAA GNCAAAAACG CGCGCGGCGA ACCTTGGCGC ATCGGCATCG
 701 AACAGCCCAA CATCGTCCAA GGCGGCAATA CGCAGATTAT CGTCCCGCTG
 751 AACAACCGTT CGNTTGCCAC TTCCGGCGAT TACCGTATTT TCCACGTCGA
 801 TAAAAGCGGC AAACGCCTCT CCCATATCAT TAATCCGAAC AACAAACGAC
 851 CCATCAGCCA CAACCTCGCC TCCATCAGCG TGNTCGCAGA CAGTGCGATG
 901 ACGGCGGACG GCTTNTCCAC AGGATTATTC GTATTGGGCG AAACCGAAGC
 951 CTTAAAGCTG GCAGAGCGCG AAAAACTCGC TGTTTTCCTG ATTGTCAGGG
1001 ATAAAGGCGG CTACCGCACC GCCATGTCTT CCGAATTTGA AAAACTGCTC
1051 CGCTAA
```

This encodes a protein having amino acid sequence <SEQ ID 448>:

```
  1 MPSETRLPNF IRTLIFALSF IFLNACSEQT AQTVTLQGET MGTTYTVKYL
 51 SNNRDXLPSP AEIQXRIDDA LKEVNRQMST YQPDSEISRF NQHTAGKPLR
101 ISSDFAHVTA EAVHLNRLTH GALDVTVGPL VNLWGFGPDK SVTREPSPEQ
151 IKQAASYTGI DKIILKQGKD YASLSKTHPK AYLDLSSIAK GFGVDXVAGE
201 LEKYGIQNYL VEIGGELHGK XKNARGEPWR IGIEQPNIVQ GGNTQIIVPL
251 NNRSXATSGD YRIFHVDKSG KRLSHIINPN NKRPISHNLA SISVXADSAM
301 TADGXSTGLF VLGETEALKL AEREKLAVFL IVRDKGGYRT AMSSEFEKLL
351 R*
```

Homology with a Predicted ORF from *N. gonorrhoeae*

ORF111 shows 96.6% identity over a 351aa overlap with a predicted ORF (ORF111.ng) from *N. gonorrhoeae*.

```
                    10         20         30         40         50         60
   orf111ng MPSETRLPNLIRALIFALGFIFLNACSEQTAQTVTLQGETMGTTYTVKYLSNNRDKLPSP
            ||||||||:||:|||||||||||||||||||||||||||||||||||||||||||||||
     orf111 MPSETRLPNFIRVLIFALGFIFLNACSEQTAQTVTLQGETMGTTYTVKYLSNNRDKLPSP
                    10         20         30         40         50         60
```

```
                70        80        90       100       110       120
orf111ng   AKIQKRIDDALKEVNRQMSTYQTDSEISRFNQHTAGKPLRISSDFAHVTAEAVRLNRLTH
           |:||||||||||||||||||||||| |||||||||||||||||||||||||||||||||
orf111     AEIQKRIDDALKEVNRQMSTYQPDSEISRFNQHTAGKPLRISSDFAHVTAEAVRLNRLTH
                70        80        90       100       110       120

130       140       150       160       170       180
orf111ng   GALDVTVGPLVNLWGFGPDKSVTREPSPEQIKQAASYTGIDKIILQQGKDYASLSKTHPK
           ||||||||||||||||||||||||||||||||||||||||||:|||||||||||||||||
orf111     GALDVTVGPLVNLWGFGPDKSVTREPSPEQIKQAASYTGIDKIILKQGKDYASLSKTHPK
               130       140       150       160       170       180

190       200       210       220       230       240
orf111ng   AYLDLSSIAKGFGVDKVAGELEKYGIQNYLVEIGGELHGKGKNAHGEPWRIGIEQPNIIQ
           ||||||||||||||||||||||||||||||||||||||||||||:|||||||||||||:|
orf111     AYLDLSSIAKGFGVDKVAGELEKYGIQNYLVEIGGELHGKGKNARGEPWRIGIEQPNIVQ
               190       200       210       220       230       240

250       260       270       280       290       300
orf111ng   GGNTQIIVPLNNRSLATSGDYRIFHVDKNGKRLSHIINPNNKRPISHNLASISVVSDSAM
           |||||||||||||||||||||||||||||||||||||||||||||||||||||||:|||
orf111     GGNTQIIVPLNNRSLATSGDYRIFHVDKNGKRLSHIINPNNKRPISHNLASISVVADSAM
               250       260       270       280       290       300

310       320       330       340       350
orf111ng   TADGLSTGLFVLGETEALRLAEQEKLAVFLIVRDKDGYRTAMSSEFAKLLRX
           ||||||||||||||||||:|||:|||||||||||| |||||||||:||||||
orf111     TADGLSTGLFVLGETEALKLAEREKLAVFLIVRDKGGYRTAMSSEFEKLLRX
               310       320       330       340       350
```

The complete length ORF111ng nucleotide sequence <SEQ ID 449> is:

```
   1  ATGCCGTCTG AAACACGCCT GCCGAACCTT ATCCGCGCCT TGATATTTGC

51  CCTGGGTTTC ATCTTCCTGA ACGCCTGTTC GGaacaaacC GCGCAaaccg

101  TTACCCTGCA AGGCGAAAcg aTGGGTACGA CCTATACCGT CAAATACCTT

151  TCAAATAATC GGGACAAACT CCCCTCCCCT GCCAAAATAC AAAAGCGCAT

201  TGATGATGCG CTTAAAGAAG TCAACCGGCA GATGTCCACC TACCAGACCG

251  ATTCCGAAAT CAGCCGGTTC AACCAACACA CAGCCGGCAA GCCCCTCCGC

301  ATTTCAAGCG ATTTCGCACA CGTTACCGCC GAAGCCGTCC GCCTGAACCG

351  CCTGACTCAC GGCGCACTGG ACGTAACCGT CGGCCCTTTG GTCAACCTTT

401  GGGGGTTCGG CCCCGACAAA TCCGTTACCC GTGAACCGTC GCCGGAACAA

451  ATCAAACAGG CGGCATCTTA TACGGGCATA GACAAAATCA TTTTGCAACA

501  AGGCAAAGAT TACGCTTCCT TGAGCAAAAC CCACCCCAAA GCCTATTTGG

551  ATTTATCTTC GATTGCCAAA GGCTTCGGCG TTGATAAAGT TGCGGGCGAA

601  CTGGAAAAAT ACGGCATTCA AAATTATCTG GTCGAAAtcg gcggcGAGTT

651  GCACGGCAAA GGCAAAAATG CGCACGGCGA ACCGTGGCGC ATCGGTATAG

701  AGCAACCCAA TATCATCCAA GgcgGCAata CGCAGATTAt cgtcccgctg 751  aaCaaccgtt cgctTGCCAC TTCCGGCGAT TAccgtaTTT tccacgtcgA 801  TAAAAAcggc aaacgcctttcccacaTCAT CAATCCCaAC aacAAACgac 851  ccATCAGcca caacctcgcc tccatcagcg tggtctcAGA CAGTGCAATG 901  ACGGCGGACG GTTtatCCAC AGGATTATTT GTTTTAGGCG AAACCGAAGC

951  CTTAAGGCTG GCAGAACAAG AAAAACTCGC TGTTTTCCTA ATTGTCCGGG

1001  ATAAGGACGG CTACCGCACC GCCATGTCTT CCGAATTTGC CAAGCTGCTC

1051  CGCTAA
```

This encodes a protein having amino acid sequence <SEQ ID 450>:

```
  1 MPSETRLPNL IRALIFALGF IFLNACSEQT AQTVTLQGET MGTTYTVKYL

51 SNNRDKLPSP AKIQKRIDDA LKEVNRQMST YQTDSEISRF NQHTAGKPLR

101 ISSDFAHVTA EAVRLNRLTH GALDVTVGPL VNLWGFGPDK SVTREPSPEQ

151 IKQAASYTGI DKIILQQGKD YASLSKTHPK AYLDLSSIAK GFGVDKVAGE

201 LEKYGIQNYL VEIGGELHGK GKNAHGEPWR IGIEQPNIIQ GGNTQIIVPL

251 NNRSLATSGD YRIFHVDKNG KRLSHIINPN NKRPISHNLA SISVVSDSAM

301 TADGLSTGLF VLGETEALRL AEQEKLAVFL IVRDKDGYRT AMSSEFAKLL

351 R*
```

This protein shows homology with a hypothetical lipoprotein precursor from *H. influenzae*:

```
sp|P44550|YOJL_HAEIN HYPOTHETICAL LIPOPROTEIN
HI0172 PRECURSOR >gi|1074292|pir|4
hypothetical protein HI0172 - Haemophilus influenzae (strain Rd KW20)
>gi|1573128 (U32702) hypothetical [Haemophilus influenzae]
Length = 346
Score = 353 bits (896), Expect = 9e-97
Identities = 181/344 (52%), Positives = 247/344 (71%),
Gaps = 4/344 (1%)

Query:     7 LPNLIRALIFALGFIFLNACSEQTAQTVTLQGETMGTTYTVKYLSNNRDKLPSPAKIQKR    66
             + LI +I   + L AC ++T + ++L G+TMGTTY VKYL +      S K +
Sbjct:     1 MKKLISGIIAVAMALSLAACQKET-KVISLSGKTMGTTYHVKYLDDGSITATSE-KTHEE   58

Query:    67 IDDALKEVNRQMSTYQTDSEISRFNQHT-AGKPLRISSDFAHVTAEAVRLNRLTHGALDV   125
             I+  LK+VN +MSTY+ DSE+SRFNQ+T    P+ IS+DFA V AEA+RLN++T GALDV
Sbjct:    59 IEAILKDVNAKMSTYKKDSELSRFNQNTQVNTPIEISADFAKVLAEAIRLNKVTEGALDV   118

Query:   126 TVGPLVNLWGFGPDKSVTREPSPEQIKQAASYTGIDKIILQQGKDYASLSKTHPKAYLDL   185
             TVGP+VNLWGFGP+K  ++P+PEQ+ +  ++ GIDKI L   K+ A+LSK  P+ Y+DL
Sbjct:   119 TVGPVVNLWGFGPEKRPEKQPTPEQLAERQAWVGIDKITLDTNKEKATLSKALPQVYVDL   178

Query:   186 SSIAKGFGVDKVAGELEKYGIQNYLVEIGGELHGKGKNAHGEPWRIGIEQPNIIQGGNTQ   245
             SSIAKGFGVD+VA +LE+   QNY+VEIGGE+  KGKN  G+PW+I IE+P        +
Sbjct:   179 SSIAKGFGVDQVAEKLEQLNAQNYMVEIGGEIRAKGKNIEGKPWQIAIEKPTTTGERAVE   238

Query:   246 IIVPLNNRSLATSGDYRIFHVDKNGKRLSHIINPNNKRPISHNLASISVVSDSAMTADGL   305
              ++ LNN  +A+SGDYRI+  ++NGKR +H I+P     PI H+LASI+V++ ++MTADGL
Sbjct:   239 AVIGLNNMGMASSGDYRIY-FEENGKRFAHEIDPKTGYPIQHHLASITVLAPTSMTADGL   297

Query:   306 STGLFVLGETEALRLAEQEKLAVFLIVRDKDGYRTAMSSEFAKL                  349
             STGLFVLGE +AL +AE+ LAV+LI+R +G+ T SS F KL
Sbjct:   298 STGLFVLGEDKALEVAEKNNLAVYLIIRTDNGFVTKSSSAFKKL                 341
```

Based on this analysis, it is predicted that the proteins from *N. meningitidis* and *N. gonorrhoeae*, and their epitopes, could be useful antigens for vaccines or diagnostics, or for raising antibodies.

Example 54

The following partial DNA sequence was identified in *N. meningitidis* <SEQ ID 451>:

```
  1 ..CCGTGCCGCC GACAGGGCGA CGACGTGTAT GCGGCGCACG CGTCCCGTCA

51 AAAATTGTGG CTGCGCTTCA TCGGCGGCCG GTCGCATCAA AATATACGGG

101 GCGGCGCGGC TGCGGACGGG TGGCGCAAAG GCGTGCAAAT CGGCGGCGAG

151 GTGTTTGTAC GGCAAAATGA AGGCAGCCkA yTGGCAATCG GCGTGATGGG
```

-continued
```
201  CGGCAGGGCC GGCCAGCACG CwTCAGTCAA CGGCAAAGGC GGTGCGGCAG 251  gCAGTGATTT GTATGGTTAT GgCGGGGgTG TTTATGCTgC GTGGCATCAG 301  TTGCGCGATA AACAAACGGG TgCGTATTTG GACGGCTGGT TGCAATACCA 351  ACGTTTCAAA CACCGCATCA ATGATGAAAA CCGTGCGGAA CgCTACAAAA

401  CCAAAGGTTG GACGGCTTCT GTCGAAGGCG GCTACAACGC GCTTGTGGCG

451  GAAGGCATTG TCGGAAAAGG CAATAATGTG CGGTTTTACC TACAACCGCA

501  GgCGCAGTTT ACCTACTTGG GCGTAAACGG CGGCTTTACC GACAGCGAGG

551  GGACGGCGGT CGGACTGCTC GGCAGCGGTC AGTGGCAAAG CCGCGCCGGC

601  AtTCGGGCAA AAACCCGTTT TGCTTTGCGT AACGGTGTCA ATCTTCAGCC

651  TTTTGCCGCT TTTAATGTtt TGCACAGGTC AAAATCTTTC GGCGTGGAAA

701  TGGACGGCGA AAAACAGACG CTGGCAGGCA GGACGGCACT CGAAGGGCGG

751  TTCGGTATTG AAGCCGGTTG GAAAGGCCAT ATGTCCGCA..
```

This corresponds to the amino acid sequence <SEQ ID 452; ORF35>:

```
  1..PCRRQGDDVY AAHASRQKLW LRFIGGRSHQ NIRGGAAADG WRKGVQIGGE

51  VFVRQNEGSX LAIGVMGGRA GQHASVNGKG GAAGSDLYGY GGGVYAAWHQ

101  LRDKQTGAYL DGWLQYQRFK HRINDENRAE RYKTKGWTAS VEGGYNALVA

151  EGIVGKGNNV RFYLQPQAQF TYLGVNGGFT DSEGTAVGLL GSGQWQSRAG

201  IRAKTRFALR NGVNLQPFAA FNVLHRSKSF GVEMDGEKQT LAGRTALEGR

251  FGIEAGWKGH MSA..
```

Computer analysis of this amino acid sequence gave the following results:

Homology with Putative Secreted VirG-Homologue of *N. meningitidis* (Accession Number A32247)

ORF and virg-h protein show 51% aa identity in 261aa overlap:

```
Orf35    5 QGDDVYAAHASRQKLWLRFIGGRSHQNIRGGAA-ADGWRKGVQIGGEVFVRQNEGSXLAI   63
           +  D++       R+ LWLR I G S+Q ++G  A  +G+RKGVQ+GGEVF  QNE + L+I
virg-h 396 KNSDIFDRTLPRKGLWLRVIDGHSNQWVQGKTAPVEGYRKGVQLGGEVFTWQNESNQLSI  455

Orf35   64 GVMGGRAGQHASVNGKG--GAAGSDLYGYGGGVYAAWHQLRDKQTGAYLDGWLQYQRFKH  121
           G+MGG+A Q ++ +         ++ G+G GVYA WHQL+DKQTGAY D W+QYQRF+H
virg-h 456 GLMGGQAEQRSTFHNPDTDNLTTGNVKGFGAGVYATWHQLQDKQTGAYADSWMQYQRFRH  515

Orf35  122 RINDENRAERYKTKGWTASVEGGYNALVAEGIVGKGNNVRFYLQPQAQFTYLGVNGGFTD  181
           RIN E+   ER+ +KG TAS+E GYNAL+AE    KGN++R YLQPQAQ TYLGVNG F+D
virg-h 516 RINTEDGTERFTSKGITASIEAGYNALLAEHFTKKGNSLRVYLQPQAQLTYLGVNGKFSD  575

Orf35  182 SEGTAVGLLGSGQWQSRAGIRAKTRFALRNGVNLQPFAAFNVLHRSKSFGVEMDGEKQTL  241
           SE    V LLGS Q Q+R G++AK +F+L   +  ++PFAA N L+ +K FGVEMDGE++ +
virg-h 576 SENAHVNLLGSRQLQTRVGVQAKAQFSLYKNIAIEPFAAVNALYHNKPFGVEMDGERRVI  635

Orf35  242 AGRTALEGRFGIEAGWKGHMS                                         262
           +TA+E + G+    K H++
virg-h 636 NNKTAIESQLGVAVKIKSHLT                                         656
```

Homology with a Predicted ORF from *N. meningitidis* (Strain A)

ORF35 shows 96.9% identity over a 259aa overlap with an ORF (ORF35a) from strain A of *N. meningitidis*.

```
                              10        20        30
orf35.pep                     PCRRQGDDVYAAHASRQKLWLRFIGGRSHQNIRG
                              :||||||  |||||||||||||||||||
orf35a    QRLAIPEAEAVLYAQQAYAANTLFGLRAADRGDDVYAADPSRQKLWLRFIGGRSHQNIRG
          310       320       330       340       350       360

40        50        60        70        80        90
orf35.pep  GAAADGWRKGVQIGGEVFVRQNEGSXLAIGVMGGRAGQHASVNGKGGAAGSDLYGYGGGV
           |||||  ||||||||||||||||||| |||||||||||||||||||||||| : |||||
orf35a     GAAADGRRKGVQIGGEVFVRQNEGSRLAIGVMGGRAGQHASVNGKGGAAGSYLHGYGGGV
           370       380       390       400       410       420

100       110       120       130       140       150
orf35.pep  YAAWHQLRDKQTGAYLDGWLQYQRFKHRINDENRAERYKTKGWTASVEGGYNALVAEGIV
           |||||||||||||||||||||||||||||||||||||||||||||||||||||||||:|
orf35a     YAAWHQLRDKQTGAYLDGWLQYQRFKHRINDENRAERYKTKGWTASVEGGYNALVAEGVV
           430       440       450       460       470       480

160       170       180       190       200       210
orf35.pep  GKGNNVRFYLQPQAQFTYLGVNGGFTDSEGTAVGLLGSGQWQSRAGIRAKTRFALRNGVN
           ||||||||||||||||||||||||||||||||||||||||||||||||||||||||||||
orf35a     GKGNNVRFYLQPQAQFTYLGVNGGFTDSEGTAVGLLGSGQWQSRAGIRAKTRFALRNGVN
           490       500       510       520       530       540

220       230       240       250       260
orf35.pep  LQPFAAFNVLHRSKSFGVEMDGEKQTLAGRTALEGRFGIEAGWKGHMSA
           |||||||||||||||||||||||||||||||||||||||||||||||||
orf35a     LQPFAAFNVLHRSKSFGVEMDGEKQTLAGRTALEGRFGIEAGWKGHMSARIGYGKRTDGD
           550       560       570       580       590       600 orf35a     KEAALSLKWLFX
           610       620
```

The complete length ORF35a nucleotide sequence <SEQ ID 453> is:

```
  1   ATGTTCAGAG CTCAGCTTGG TTCAAATACT CGTTCTACCA AAATCGGCGA

51   CGATGCCGAT TTTTCATTTT CAGACAAGCC GAAACCCGGC ACTTCCCATT

101   ATTTTTCCAG CGGTAAAACC GATCAAAATT CATCCGAATA TGGGTATGAC

151   GAAATCAATA TCCAAGGTAA AAACTACAAT AGCGGCATAC TCGCCGTCGA

201   TAATATGCCC GTTGTTAAGA AATATATTAC AGATACTTAC GGGGATAATT

251   TAAAGGATGC GGTTAAGAAG CAATTACAGG ATTTATACAA AACAAGACCC

301   GAAGCTTGGG AAGAAAATAA AAAACGGACT GAGGAGGCGT ATATAGAACA

351   GCTTGGACCA AAATTTAGTA TACTCAAACA GAAAAACCCC GATTTAATTA

401   ATAAATTGGT AGAAGATTCC GTACTCACTC CTCATAGTAA TACATCACAG

451   ACTAGTCTCA ACAACATCTT CAATAAAAAA TTACACGTCA AAATCGAAAA

501   CAAATCCCAC GTCGCCGGAC AGGTGTTGGA ACTGACCAAG ATGACGCTGA

551   AAGATTCCCT TGGGAACCG CGCCGCCATT CCGACATCCA TATGCTGGAA

601   ACTTCCGATA ATGCCCGCAT CCGCCTGAAC ACGAAAGATG AAAAACTGAC

651   CGTCCATAAA GCGTATCAGG GCGGTGCGGA TTTCCTGTTC GGCTACGACG

701   TGCGGGAGTC GGACAAACCC GCCCTGACCT TTGAAGAAAA AGTCAGCGGA

751   CAATCCGGCG TGGTTTTGGA ACGCCGGCCG GAAAATCTGA AAACGCTCGA

801   CGGGCGCAAA CTGATTGCGG CGGAAAAGGC AGACTCTAAT TCGTTTGCGT

851   TTAAACAAAA TTACCGGCAG GGACTGTACG AATTATTGCT CAAGCAATGC
```

```
 901 GAAGGCGGAT TTTGCTTGGG CGTGCAGCGT TTGGCTATCC CCGAGGCGGA

951 AGCGGTTTTA TATGCCCAAC AGGCTTATGC GGCAAATACT TTGTTCGGGC

1001 TGCGTGCCGC CGACAGGGGC GACGACGTGT ATGCCGCCGA TCCGTCCCGT

1051 CAAAAATTGT GGCTGCGCTT CATCGGCGGC CGGTCGCATC AAAATATACG

1101 GGGCGGCGCG GCTGCGGACG GCGGCGCAA AGGCGTGCAA ATCGGCGGCG

1151 AGGTGTTTGT ACGGCAAAAT GAAGGCAGCC GGCTGGCAAT CGGCGTGATG

1201 GGCGGCAGGG CTGGCCAGCA CGCATCAGTC AACGGCAAAG GCGGTGCGGC

1251 AGGCAGTTAT TTGCATGGTT ATGGCGGGGG TGTTTATGCT GCGTGGCATC

1301 AGTTGCGCGA TAAACAAACG GGTGCGTATT TGGACGGCTG GTTGCAATAC

1351 CAACGTTTCA AACACCGCAT CAATGATGAA AACCGTGCGG AACGCTACAA

1401 AACCAAAGGT TGGACGGCTT CTGTCGAAGG CGGCTACAAC GCGCTTGTGG

1451 CGGAAGGCGT TGTCGGAAAA GGCAATAATG TGCGGTTTTA CCTGCAACCG

1501 CAGGCGCAGT TTACCTACTT GGGCGTAAAC GGCGGCTTTA CCGACAGCGA

1551 GGGGACGGCG GTCGGACTGC TCGGCAGCGG TCAGTGGCAA AGCCGCGCCG

1601 GCATTCGGGC AAAAACCCGT TTTGCTTTGC GTAACGGTGT CAATCTTCAG

1651 CCTTTTGCCG CTTTTAATGT TTTGCACAGG TCAAATCTT TCGGCGTGGA

1701 AATGGACGGC GAAAAACAGA CGCTGGCAGG CAGGACGGCG CTCGAAGGGC

1751 GGTTCGGCAT TGAAGCCGGT TGGAAAGGCC ATATGTCCGC ACGCATCGGA

1801 TACGGCAAAA GGACGGACGG CGACAAAGAA GCCGCATTGT CGCTCAAATG

1851 GCTGTTTTGA
```

This encodes a protein having amino acid sequence <SEQ ID 454>:

```
  1 MFRAQLGSNT RSTKIGDDAD FSFSDKPKPG TSHYFSSGKT DQNSSEYGYD

51 EINIQGKNYN SGILAVDNMP VVKKYITDTY GDNLKDAVKK QLQDLYKTRP

101 EAWEENKKRT EEAYIEQLGP KFSILKQKNP DLINKLVEDS VLTPHSNTSQ

151 TSLNNIFNKK LHVKIENKSH VAGQVLELTK MTLKDSLWEP RRHSDIHMLE

201 TSDNARIRLN TKDEKLTVHK AYQGGADFLF GYDVRESDKP ALTFEEKVSG

251 QSGVVLERRP ENLKTLDGRK LIAAEKADSN SFAFKQNYRQ GLYELLLKQC

301 EGGFCLGVQR LAIPEAEAVL YAQQAYAANT LFGLRAADRG DDVYAADPSR

351 QKLWLRFIGG RSHQNIRGGA AADGRRKGVQ IGGEVFVRQN EGSRLAIGVM

401 GGRAGQHASV NGKGGAAGSY LHGYGGGVYA AWHQLRDKQT GAYLDGWLQY

451 QRFKHRINDE NRAERYKTKG WTASVEGGYN ALVAEGVVGK GNNVRFYLQP

501 QAQFTYLGVN GGFTDSEGTA VGLLGSGQWQ SRAGIRAKTR FALRNGVNLQ

551 PFAAFNVLHR SKSFGVEMDG EKQTLAGRTA LEGRFGIEAG WKGHMSARIG

601 YGKRTDGDKE AALSLKWLF*
```

Homology with a Predicted ORF from *N. gonorrhoeae*

ORF35 shows 51.7% identity over a 261aa overlap with a predicted ORF (ORF35ngh) from *N. gonorrhoeae*.

```
    orf35.pep           PCRRQGDDVYAAHASRQKLWLRFIGGRSHQNIRG  34
                        :::|::    |:  ||||  |  |:|:|  ::|
    orf35ngh FTKVQERDDIAIYAQQAQAANTLFALRLNDKNSDIFDRTLPRKGLWLRVIDGHSNQWVQG 370
```

-continued

```
orf35.pep  GAA-ADGWRKGVQIGGEVFVRQNEGSXLAIGVMGGRAGQHASVNGKG--GAAGSDLYGYG  91
           :|  ::|:|||||:|||||:  |||::  |:||:|||:|  |:::    :    : :::  |:|
orf35ngh   KTAPVEGYRKGVQLGGEVFTWQNESNQLSIGLMGGQAEQRSTFRNPDTDNLTTGNVKGFG  430
orf35.pep  GGVYAAWHQLRDKQTGAYLDGWLQYQRFKHRINDENRAERYKTKGWTASVEGGYNALVAE  151
           :||||:||||:||||||||:|:|:||||||||| |  :||: :|| |||:|:||||||:||
orf35ngh   AGVYATWHQLQDKQTGAYVDSWMQYQRFRHRINTEYATERFTSKGITASIEAGYNALLAE  490
orf35ngh   GIVGKGNNVRFYLQPQAQFTYLGVNGGFTDSEGTAVGLLGSGQWQSRAGIRAKTRFALRN  211
           ::  |||::| |||||||||:|||||||  |:|||::  |:||||  |  |||:::||::||: |
orf35ngh   HFTKKGNSLRVYLQPQAQLTYLGVNGKFSDSENAQVNLLGSRQLQSRVGVQAKAQFAFTN  550
orf35.pep  GVNLQPFAAFNVLHRSKSFGVEMDGEKQTLAGRTALEGRFGIEAGWKGHMSA          263
           ||::|||:| |  :::::| ||||:||::::  ::|::| ::|:|  |   |:|::
orf35ngh   GVTFQPFVAVNSIYQQKPFGVEIDGDRRVINNKTVIETQLGVAAKIKSHLTLQASFNRQT  610
```

A partial ORF35ngh nucleotide sequence <SEQ ID 455> is predicted to encode a protein having partial amino acid sequence <SEQ ID 456>:

```
  1..KKLRDRNSEY WKEETYHIKS NGRTYPNIPA LFPKHPFDPF ENINNSKKIS

51   FYDKEYTEDY LVGFARGFGV EKRNGEEEKP LRQYFKDCVN TENSNNDNCK

101   ISSFGNYGPI LIKSDIFALA SQIKNSHINS EILSVGNYIE WLRPTLNKLT

151   GWQEHLYAGL DPFHYIEVTD NSHVIGQTID LGALELTNSL WKPRWNSNID

201   YLITKNAEIR FNTKNESLLV KEDYAGGARF RFAYDLKDKV PEIPVLTFEK

251   NITGTSDIIF EGKALDNLKH LDGHQIVKVN DTADKDAFRL SSKYRKGIYT

301   LSLQQRPEGF FTKVQERDDI AIYAQQAQAA NTLFALRLND KNSDIFDRTL

351   PRKGLWLRVI DGHSNQWVQG KTAPVEGYRK GVQLGGEVFT WQNESNQLSI

401   GLMGGQAEQR STFRNPDTDN LTTGNVKGFG AGVYATWHQL QDKQTGAYVD

451   SWMQYQRFRH RINTEYATER FTSKGITASI EAGYNALLAE HFTKKGNSLR

501   VYLQPQAQLT YLGVNGKFSD SENAQVNLLG SRQLQSRVGV QAKAQFAFTN

551   GVTFQPFVAV NSIYQQKPFG VEIDGDRRVI NNKTVIETQL GVAAKIKSHL

601   TLQASFNRQT SKHHHAKQGA LNLQWTF*
```

Based on this prediction, these proteins from *N. meningitidis* and *N. gonorrhoeae*, and their epitopes, could be useful antigens for vaccines or diagnostics, or for raising antibodies.

Example 55

The following partial DNA sequence was identified in *N. meningitidis* <SEQ ID 457>:

```
  1..GCGGAATATG TTCAGTTCTC TATAGATTTG TTCAGTGTGG GTAAATCGGG

51   GGGCGGTATA CCTAAGGCTA AGCCTGTGTT TGATGCGAAA CCGAGATGGG

101   AGGTTGATAG GAAGCTTAAT AAATTGACAA CTCGTGAGCA GGTGGAGAAA

151   AATGTTCAGG AAACGAGAAG AAGGAGTCAG AGTAGTCAGT TTAAAGCCCA

201   TGCGCAACGA GAATGGGAAA ATAAAACAGG GTTAGATTTT AATCATTTTA

251   TAGGTGGTGA TATCAATAAA AAAGGCACAG TAACAGGAGG GCATAGTCTA

301   ACCCGTGGTG ATGTACGGGT GATACAACAA ACCTCGGCAC CTGATAAACA

351   TGGGGT.TTA TCAAGCGACA GTGGAAATTN A
```

This corresponds to the amino acid sequence <SEQ ID 458; ORF46>:

```
  1..AEYVQFSIDL FSVGKSGGGI PKAKPVFDAK PRWEVDRKLN KLTTREQVEK

51  NVQETRRRSQ SSQFKAHAQR EWENKTGLDF NHFIGGDINK KGTVTGGHSL

101  TRGDVRVIQQ TSAPDKHGXL SSDSGNX
```

Further work revealed further partial nucleotide sequence <SEQ ID 459>:

```
  1 ..GCAGTGTGCC TnCCGATGCA TGCACACGCC TCAnATTTGG CAAACGATTC

51    TTTTATCCGG CAGGTTCTCG ACCGTCAGCA TTTCGAACCC GACGGGAAAT

101    ACCACCTATT CGGCAGCAGG GGGGAACTTG CCGAGCGCCA GTCTCATATC

151    GGATTGGGAA AAATACAAAG CCATCAGTTG GGCAACCTGA TGATTCAACA

201    GGCGGCCATT AAAGGAAATA TCGGCTACAT TGTCCGCTTT TCCGATCACG

251    GGCACGAAGT CCATTCCCCs TTCGACAACC ATGCCTCACA TTCCGATTCT

301    GATGAAGCCG GTAGTCCCGT TGACGGATTT AGCCTTTACC GCATCCATTG

351    GGACGGATAC GAACACCATC CCGCCGACGG CTATGACGGG CCACAGGGCG

401    GCGGCTATCC CGCTCCCAAA GGCGCGAGGG ATATATACAG TTACGACATA

451    AAAGGCGTTG CCCAAAATAT CCGCCTCAAC CTGACCGACA ACCGCAGCAC

501    CGGACAACGG CTTGCCGACC GTTTCCACAA TGCCGGTAGT ATGCTGACGC

551    AAGGAGTAGG CGACGGATTC AAACGCGCCA CCCGATACAG CCCCGAGCTG

601    GACAGATCGG GCAATGCCGC CGAAGCCTTC AACGGCACTG CAGATATCGT

651    TAAAAACATC ATCGGCGCTG CAGGAGAAAT TGT
```

This corresponds to the amino acid sequence <SEQ ID 460; ORF46-1>:

```
  1 ..AVCLPMHAHA SXLANDSFIR QVLDRQHFEP DGKYHLFGSR GELAERQSHI

51    GLGKIQSHQL GNLMIQQAAI KGNIGYIVRF SDHGHEVHSP FDNHASHSDS

101    DEAGSPVDGF SLYRIHWDGY EHHPADGYDG PQGGGYPAPK GARDIYSYDI

151    KGVAQNIRLN LTDNRSTGQR LADRFHNAGS MLTQGVGDGF KRATRYSPEL

201    DRSGNAAEAF NGTADIVKNI IGAAGEI
```

Computer analysis of this amino acid sequence gave the following results:

Homology with a Predicted ORF from *N. gonorrhoeae*

ORF46 shows 98.2% identity over a 111 aa overlap with a predicted ORF (ORF46ng) from *N. gonorrhoeae*:

```
orf46.pep            AEYVQFSIDLFSVGKSGGGIPKAKPVFDAKPRWEVDRKLNKLTTR   45
                                       ||||||||||||||||||||||||||||
orf46ng    PKTGVPFDGKGFPNFEKHVKYDTKLDIQELSGGGIPKAKPVFDAKPRWEVDRKLNKLTTR  217 orf46.pep  EQVEKNVQETRRRSQSSQFKAHAQREWENKTGLDFNHFIGGDINKKGTVTGGHSLTRGDV  105
           |||||||||||||||||||||||||||||||||||||||||||||||:||||||||||||
orf46ng    EQVEKNVQETRRRSQSSQFKAHAQREWENKTGLDFNHFIGGDINKKGAVTGGHSLTRGDV  277 orf46.pep  RVIQQTSAPDKHGXLSSDSGN  126
           ||||||||||||||| ||||||
orf46ng    RVIQQTSAPDKHGVLSSDSGN  298
```

A partial ORF46ng nucleotide sequence <SEQ ID 461> is predicted to encode a protein having partial amino acid sequence <SEQ ID 462>:

```
  1 ..RRLKHCCHAR LGSAFHRKQD GAHQRFGRYG ATQRLCRSSH PRLGSPKPQC

51   RTRHRSRQQY LYGSHPHQRD WSCPGKIQLG RHHGTSCRAV ADXRDRICER

101   EIRRQRQXCR CRLGKIPSLS IPKYPLKLEQ RYGKENITSS TVPPSNGKNV

151   KLADQRHPKT GVPFDGKGFP NFEKHVKYDT KLDIQELSGG GIPKAKPVFD

201   AKPRWEVDRK LNKLTTREQV EKNVQETRRR SQSSQFKAHA QREWENKTGL

251   DFNHFIGGDI NKKGAVTGGH SLTRGDVRVI QQTSAPDKHG VLSSDSGN*
```

Further work revealed the complete gonococcal DNA[15] sequence <SEQ ID 463>:

```
   1 TTGGGCATTT CCCGCAAAAT ATCCCTTATT CTGTCCATAC TGGCAGTGTG

51 CCTGCCGATG CATGCACACG CCTCAGATTT GGcaAACGAT CCCTTTATCC

101 GgCaggttcT CGaccGTCAG CATTTCGaac ccgacggGAa ATACCaCCTA

151 TTcggCaGCA GGGGGGAGCT TgccnagcGC aacggccATa tcggattggG 201 aaacaTAcaa Agccatcagt tGggccacct gatgattcaa caggcggccg 251 ttgaaggaaA TAtcgGctac attgtccgct tttccgatca cgggcacaaa 301 ttccattcgc ccttcGAcaa ccaTGCCTCA CATTCCGATT CTGACGAAGC

351 CGGTAGTCCC GTTGACGGAT TCAGCCTTTA CCGCATCCAT TGGGACGGAT

401 ACGAACACCA TCCCGCCGAC GGCTATGACG GGCCACAGGG CGGCGGCTAT

451 CCCGCTCCCA AAGGCGCGAG GGATATATAC AGCTACGACA TAAAAGGCGT

501 TGCCCAAAAT ATCCGCCTCA ACCTGACCGA CAACCGCAGC ACCGGACAAC

551 GGCTTGCCGA CCGTTTCCAC AATGCCGGCG CTATGCTGAC GCAAGGAGTA

601 GGCGACGGAT TCAAACGCGC CACCCGATAC AGCCCCGAGC TGGACAGATC

651 GGGCAATGCc gccGAAGCCT TCAACGGCAC TGCAGATATC GTCAAAAACA

701 TCATCGGCGC GGCAGGAGAA ATTGTCGGCG CAGGCGATGC CGTGCagGGT

751 ATAAGCGAAG GCTCAAACAT TGCTGTCATG CACGGCTTGG GTCTGCTTTC

801 CACCGAAAAC AAGATGGCGC GCATCAACGA TTTGGCAGAT ATGGCGCAAC

851 TCAAAGACTA TGCCGCAGCA GCCATCCGCG ATTGGGCAGT CCAAAACCCC

901 AATGCCGCAC AAGGCATAGA AGCCGTCAGC AATATCTTTA TGGCAGCCAT

951 CCCCATCAAA GGGATTGGAG CTGTCCGGGG AAAATACGGC TTGGGCGGCA

1001 TCACGGCACA TCCTGTCAAG CGGTCGCAGA TGGGCGCGAT CGCATTGCCG

1051 AAAGGGAAAT CCGCCGTCAG CGACAATTTT GCCGATGCGG CATACGCCAA

1101 ATACCCGTCC CCTTACCATT CCCGAAATAT CCGTTCAAAC TTGGAGCAGC

1151 GTTACGGCAA AGAAAACATC ACCTCCTCAA CCGTGCCGCC GTCAAACGGC

1201 AAAAATGTCA AACTGGCAGA CCAACGCCAC CCGAAGACAG GCGTACCGTT

1251 TGACGGTAAA GGGTTTCCGA ATTTTGAGAA GCACGTGAAA TATGATACGA

1301 AGCTCGATAT TCAAGAATTA TCGGGGGGCG GTATACCTAA GGCTAAGCCT

1351 GTGTTTGATG CGAAACCGAG ATGGGAGGTT GATAGGAAGC TTAATAAATT

1401 GACAACTCGT GAGCAGGTGG AGAAAAATGT TCAGGAAACG AGAAGAAGGA

1451 GTCAGAGTAG TCAGTTTAAA GCCCATGCGC AACGAGAATG GGAAAATAAA
```

```
1501  ACAGGGTTAG ATTTTAATCA TTTTATAGGT GGTGATATCA ATAAGAAAGG

1551  CACAGTAACA GGAGGGCATA GTCTAACCCG TGGTGATGTA CGGGTGATAC

1601  AACAAACCTC GGCACCTGAT AAACATGGGG TTTATCAAGC GACAGTGGAA

1651  ATTAAAAAGC CTGATGGAAG TTGGGAGGTG AAAACGAAAA AAGGTGGGAA

1701  AGTGATGACC AAGCACACCA TGTTCCCAAA AGATTGGGAT GAGGCTAGAA

1751  TTAGGGCTGA AGTTACTTCG GCTTGGGAAA GTAGAATAAT GCTTAAGGAT

1801  AATAAATGGC AGGGTACAAG TAAATCGGGT ATTAAAATAG AAGGATTTAC

1851  CGAACCTAAT AGAACAGCAT ATCCCATTTA TGAATAG
```

This corresponds to the amino acid sequence <SEQ ID 464; ORF46ng-1>:

```
  1  LGISRKISLI LSILAVCLPM HAHASDLAND PFIRQVLDRQ HFEPDGKYHL

51  FGSRGELAXR NGHIGLGNIQ SHQLGHLMIQ QAAVEGNIGY IVRFSDHGHK

101  FHSPFDNHAS HSDSDEAGSP VDGFSLYRIH WDGYEHHPAD GYDGPQGGGY

151  PAPKGARDIY SYDIKGVAQN IRLNLTDNRS TGQRLADRFH NAGAMLTQGV

201  GDGFKRATRY SPELDRSGNA AEAFNGTADI VKNIIGAAGE IVGAGDAVQG

251  ISEGSNIAVM HGLGLLSTEN KMARINDLAD MAQLKDYAAA AIRDWAVQNP

301  NAAQGIEAVS NIFMAAIPIK GIGAVRGKYG LGGITAHPVK RSQMGAIALP

351  KGKSAVSDNF ADAAYAKYPS PYHSRNIRSN LEQRYGKENI TSSTVPPSNG

401  KNVKLADQRH PKTGVPFDGK GFPNFEKHVK YDTKLDIQEL SGGGIPKAKP

451  VFDAKPRWEV DRKLNKLTTR EQVEKNVQET RRRSQSSQFK AHAQREWENK

501  TGLDFNHFIG GDINKKGTVT GGHSLTRGDV RVIQQTSAPD KHGVYQATVE

551  IKKPDGSWEV KTKKGGKVMT KHTMFPKDWD EARIRAEVTS AWESRIMLKD

601  NKWQGTSKSG IKIEGFTEPN RTAYPIYE*
```

ORF46ng-1 and ORF46-1 show 94.7% identity in 227 aa overlap:

```
                     10         20         30         40
orf46-1.pep          AVCLPMHAHASXLANDSFIRQVLDRQHFEPDGKYHLFGSRGELAER
                     ||||||||||||    ||||||||||||||||||||||||||||| |
orf46ng-1   LGISRKISLILSILAVCLPMHAHASDLANDPFIRQVLDRQHFEPDGKYHLFGSRGELAXR
                  10         20         30         40         50         60

50         60         70         80         90        100
orf46-1.pep  QSHIGLGKIQSHQLGNLMIQQAAIKGNIGYIVRFSDHGHEVHSPFDNHASHSDSDEAGSP
             ::|||||:||||||:|||||||::||||||||||||||||: ||||||||||||||||||
orf46ng-1    NGHIGLGNIQSHQLGHLMIQQAAVEGNIGYIVRFSDHGHKFHSPFDNHASHSDSDEAGSP
                     70         80         90        100        110        120

110        120        130        140        150        160
orf46-1.pep  VDGFSLYRIHWDGYEHHPADGYDGPQGGGYPAPKGARDIYSYDIKGVAQNIRLNLTDNRS
             ||||||||||||||||||||||||||||||||||||||||||||||||||||||||||||
orf46ng-1    VDGFSLYRIHWDGYEHHPADGYDGPQGGGYPAPKGARDIYSYDIKGVAQNIRLNLTDNRS
                    130        140        150        160        170        180

170        180        190        200        210        220
orf46-1.pep  TGQRLADRFHNAGSMLTQGVGDGFKRATRYSPELDRSGNAAEAFNGTADIVKNIIGAAGE
             ||||||||||||:|||||||||||||||||||||||||||||||||||||||||||||||
orf46ng-1    TGQRLADRFHNAGAMLTQGVGDGFKRATRYSPELDRSGNAAEAFNGTADIVKNIIGAAGE
                    190        200        210        220        230        240 orf46-1.pep  I
             |
orf46ng-1    IVGAGDAVQGISEGSNIAVMHGLGLLSTENKMARINDLADMAQLKDYAAAAIRDWAVQNP
                    250        260        270        280        290        300
```

Homology with a Predicted ORF from *N. meningitidis* (Strain A)

ORF46ng-1 shows 87.4% identity over a 486aa overlap with an ORF (ORF46a) from strain A of *N. meningitidis*:

```
                   10         20         30         40         50         60
     orf46a.pep  LGISRKISLILSILAVCLPMHAHASDLANDSFIRQVLDRQHFEPDGKYHLFGSRGELAER
                 |||||||||||||||||||||||||||||| ||||||||||||||||||||||||||| |
     orf46ng-1  LGISRKISLILSILAVCLPMHAHASDLANDPFIRQVLDRQHFEPDGKYHLFGSRGELAXR
                   10         20         30         40         50         60

70         80         90        100        110        120
     orf46a.pep  SGHIGLGNIQSHQLGNLFIQQAAIKGNIGYIVRFSDHGHEVHSPFDNHASHSDSDEAGSP
                 :||||||||||||:|:||||::||||||||||||||||: ||||||||||||||||||||
     orf46ng-1  NGHIGLGNIQSHQLGHLMIQQAAVEGNIGYIVRFSDHGHKFHSPFDNHASHSDSDEAGSP
                   70         80         90        100        110        120

130        140        150        160        170        180
     orf46a.pep  VDGFSLYRIHWDGYEHHPADGYDGPQGGGYPAPKGARDIYSYDIKGVAQNIRLNLTDNRS
                 ||||||||||||||||||||||||||||||||||||||||||||||||||||||||||||
     orf46ng-1  VDGFSLYRIHWDGYEHHPADGYDGPQGGGYPAPKGARDIYSYDIKGVAQNIRLNLTDNRS
                  130        140        150        160        170        180

190        200        210        220        230        240
     orf46a.pep  TGQRLVDRFHNTGSMLTQGVGDGFKRATRYSPELDRSGNAAEAFNGTADIVKNIIGAAGE
                 |||||:|||||:|:||||||||||||||||||||||||||||||||||||||||||||||
     orf46ng-1  TGQRLADRFHNAGAMLTQGVGDGFKRATRYSPELDRSGNAAEAFNGTADIVKNIIGAAGE
                  190        200        210        220        230        240

250        260        270        280        290        300
     orf46a.pep  IVGAGDAVQGISEGSNIAVMHGLGLLSTENKMARINDLADMAQLKDYAAAAIRDWAVQNP
                 ||||||||||||||||||||||||||||||||||||||||||||||||||||||||||||
     orf46ng-1  IVGAGDAVQGISEGSNIAVMHGLGLLSTENKMARINDLADMAQLKDYAAAAIRDWAVQNP
                  250        260        270        280        290        300

310        320        330        340        350        360
     orf46a.pep  NAAQGIEAVSNIFTAVIPVKGIGAVRGKYGLGGITAHPVKRSQMGEIALPKGKSAVSDNF
                 |||||||||||||:||:|||||||||||||||||||||||||||||||||||||||||||
     orf46ng-1  NAAQGIEAVSNIFMAAIPIKGIGAVRGKYGLGGITAHPVKRSQMGEIALPKGKSAVSDNF
                  310        320        330        340        350        360

370        380        390        400        410        420
     orf46a.pep  ADAAYAKYPSPYHSRNIRSNLEQRYGKENITSSTVPPSNGKNVKLANKRHPKTKVPFDGK
                 |||||||||||||||||||||||||||||||||||||||||||||::|||||  ||||||
     orf46ng-1  ADAAYAKYPSPYHSRNIRSNLEQRYGKENITSSTVPPSNGKNVKLADQRHPKTGVPFDGK
                  370        380        390        400        410        420

430        440        450        460        470
     orf46a.pep  GFPNFEKDVKYDTRINTAVPQVN----PIDEPVFN--PKGSVGSAHSWSITARIQYAKLP
                 ||||||:||||||:::   : :::   |  :|||:  |:    |   : ::|:| |   |
     orf46ng-1  GFPNFEKHVKYDTKLD--IQELSGGGIPKAKPVFDAKPRWEVDRKLN-KLTTREQVEKNV
                    430        440        450        460        470

480        490        500        510        520        530
     orf46a.pep  RQGRIRYIPPKNYSPSAPLPKGPNNGYLDKFGNEWTKGPSRTKGQEFEWDVQLSKTGREQ
                 ::      | |
     orf46ng-1  QETRRRSQSSQFKAHAQREWENKTGLDFNHFIGGDINKKGTVTGGHSLTRGDVRVIQQTS
                  480        490        500        510        520        530
```

45

The complete length ORF46a DNA sequence <SEQ ID 465> is:

```
  1  TTGGGCATTT CCCGCAAAAT ATCCCTTATT CTGTCCATAC TGGCAGTGTG

51  CCTGCCGATG CATGCACACG CCTCAGATTT GGCAAACGAT TCTTTTATCC

101  GGCAGGTTCT CGACCGTCAG CATTTCGAAC CCGACGGGAA ATACCACCTA

151  TTCGGCAGCA GGGGGGAACT TGCCGAGCGC AGCGGTCATA TCGGATTGGG

201  AAACATACAA AGCCATCAGT TGGGCAACCT GTTCATCCAG CAGGCGGCCA

251  TTAAAGGAAA TATCGGCTAC ATTGTCCGCT TTTCCGATCA CGGGCACGAA

301  GTCCATTCCC CCTTCGACAA CCATGCCTCA CATTCCGATT CTGATGAAGC

351  CGGTAGTCCC GTTGACGGAT TCAGCCTTTA CCGCATCCAT GGGACGGAT

401  ACGAACACCA TCCCGCCGAC GGCTATGACG GCCACAGGG CGGCGGCTAT

451  CCCGCTCCCA AAGGCGCGAG GGATATATAC AGCTACGACA TAAAGGCGT

501  TGCCCAAAAT ATCCGCCTCA ACCTGACCGA CAACCGCAGC ACCGGACAAC
```

-continued

```
 551 GGCTTGTCGA CCGTTTCCAC AATACCGGTA GTATGCTGAC GCAAGGAGTA
 601 GGCGACGGAT TCAAACGCGC CACCCGATAC AGCCCCGAGC TGGACAGATC
 651 GGGCAATGCC GCCGAAGCTT TCAACGGCAC TGCAGATATC GTCAAAAACA
 701 TCATCGGCGC GGCAGGAGAA ATTGTCGGCG CAGGCGATGC CGTGCAGGGT
 751 ATAAGCGAAG GCTCAAACAT TGCTGTTATG CACGGCTTGG GTCTGCTTTC
 801 CACCGAAAAC AAGATGGCGC GCATCAACGA TTTGGCAGAT ATGGCGCAAC
 851 TCAAAGACTA TGCCGCAGCA GCCATCCGCG ATTGGGCAGT CCAAAACCCC
 901 AATGCCGCAC AAGGCATAGA AGCCGTCAGC AATATCTTTA CGGCAGTCAT
 951 CCCCGTCAAA GGGATTGGAG CTGTTCGGGG AAAATACGGC TTGGGCGGCA
1001 TCACGGCACA TCCTGTCAAG CGGTCGCAGA TGGGCGAGAT CGCATTGCCG
1051 AAAGGGAAAT CCGCCGTCAG CGACAATTTT GCCGATGCGG CATACGCCAA
1101 ATACCCGTCC CCTTACCATT CCCGAAATAT CCGTTCAAAC TTGGAGCAGC
1151 GTTACGGCAA AGAAAACATC ACCTCCTCAA CCGTGCCGCC GTCAAACGGA
1201 AAGAATGTGA AACTGGCAAA CAAACGCCAC CCGAAGACCA AAGTGCCGTT
1251 TGACGGTAAA GGGTTTCCGA ATTTTGAAAA AGACGTAAAA TACGATACGA
1301 GAATTAATAC CGCTGTACCA CAAGTGAATC CTATAGATGA ACCCGTCTTT
1351 AATCCTAAAG GTTCTGTCGG ATCGGCTCAT TCTTGGTCTA TAACTGCCAG
1401 AATTCAATAC GCAAAATTAC CAAGGCAAGG TAGAATCAGA TATATCCCAC
1451 CTAAAAATTA CTCTCCTTCA GCACCGCTAC CAAAAGGACC TAATAATGGA
1501 TATTTGGATA AATTTGGTAA TGAATGGACT AAAGGTCCAT CAAGAACTAA
1551 AGGTCAAGAA TTTGAATGGG ATGTTCAATT GTCTAAAACA GGAAGAGAGC
1601 AACTTGGATG GGCTAGTAGG GATGGTAAGC ATTTAAATAT ATCAATTGAT
1651 GGAAAGATTA CACACAAATG A
```

This corresponds to the amino acid sequence <SEQ ID 
NO 466>:

```
  1 LGISRKISLI LSILAVCLPM HAHASDLAND SFIRQVLDRQ HFEPDGKYHL
 51 FGSRGELAER SGHIGLGNIQ SHQLGNLFIQ QAAIKGNIGY IVRFSDHGHE
101 VHSPFDNHAS HSDSDEAGSP VDGFSLYRIH WDGYEHHPAD GYDGPQGGGY
151 PAPKGARDIY SYDIKGVAQN IRLNLTDNRS TGQRLVDRFH NTGSMLTQGV
201 GDGFKRATRY SPELDRSGNA AEAFNGTADI VKNIIGAAGE IVGAGDAVQG
251 ISEGSNIAVM HGLGLLSTEN KMARINDLAD MAQLKDYAAA AIRDWAVQNP
301 NAAQGIEAVS NIFTAVIPVK GIGAVRGKYG LGGITAHPVK RSQMGEIALP
351 KGKSAVSDNF ADAAYAKYPS PYHSRNIRSN LEQRYGKENI TSSTVPPSNG
401 KNVKLANKRH PKTKVPFDGK GFPNFEKDVK YDTRINTAVP QVNPIDEPVF
451 NPKGSVGSAH SWSITARIQY AKLPRQGRIR YIPPKNYSPS APLPKGPNNG
501 YLDKFGNEWT KGPSRTKGQE FEWDVQLSKT GREQLGWASR DGKHLNISID
551 GKITHK*
```

Based on this analysis, including the presence of a RGD sequence in the gonococcal protein, typical of adhesins, it is predicted that the proteins from *N. meningitidis* and *N. gonorrhoeae*, and their epitopes, could be useful antigens for vaccines or diagnostics, or for raising antibodies.

Example 56

The following partial DNA sequence was identified in *N. meningitidis* <SEQ ID 467>:

```
  1  ATGAATATTC ACACCCTGCT CTCCAAACAA TGGACGCTGC CGCCATTCCT
 51  GCCGAAACGG CTGCTGCTGT CCCTGCTGAT ACTGCTTGCC CCCAATGCGG
101  TGTTTTGGGT TTTGGCACTG CTGACCGCCA CCGCCCGCCC GATTGTCAAT
151  TTGGACTATC TTCCCGCCGC GCTGCTGATC GCCCTGCCTT GGCGTTTCGT
201  CAAAATTGCC GGCGTATTGG CGTTTTGGCT GGCGGTTTTG TTTGACGGGC
251  TGATGATGGT GATCCAACTC TTCCCTTTTA TGGATCTCAT CGGCGCCATC
301  AACCTCGTCC CCTTCATCCT GACCGCCCCC GCCCCTTATC AGATAATGAC
351  CGGGCTG...
```

This corresponds to the amino acid sequence <SEQ ID 468; ORF48>:

```
  1  MNIHTLLSKQ WTLPPFLPKR LLLSLLILLA PNAVFWVLAL LTATARPIVN
 51  LDYLPAALLI ALPWRFVKIA GVLAFWLAVL FDGLMMVIQL FPFMDLIGAI
101  NLVPFILTAP APYQIMTGL...
```

Further work revealed the complete nucleotide sequence <SEQ ID 469>:

```
  1  ATGAATATTC ACACCCTGCT CTCCAAACAA TGGACGCTGC CGCCATTCCT
 51  GCCGAAACGG CTGCTGCTGT CCCTGCTGAT ACTGCTTGCC CCCAATGCGG
101  TGTTTTGGGT TTTGGCACTG CTGACCGCCA CCGCCCGCCC GATTGTCAAT
151  TTGGACTATC TTCCCGCCGC GCTGCTGATC GCCCTGCCTT GGCGTTTCGT
201  CAAAATTGCC GGCGTATTGG CGTTTTGGCT GGCGGTTTTG TTTGACGGGC
251  TGATGATGGT GATCCAACTC TTCCCTTTTA TGGATCTCAT CGGCGCCATC
301  AACCTCGTCC CCTTCATCCT GACCGCCCCC GCCCCTTATC AGATAATGAC
351  CGGGCTGTTG CTGCTGTATA TGCTGGCGAT GCCGTTTGTG TTGCAGAAAG
401  CCGCCGCCAA AACCGACTTC CGGCACATTG CCGTCTGCGC CGCCGTTGTG
451  GCGGCAGCCG GCTATTTCAC CGGCCATTTG AGTTACTACG ACCGGGGTCG
501  GATGGCCAAT ATCTTCGGCG CAAACAACTT CTACTACGCC AAAAGTCAGG
551  CGATGCTCTA CACCGTCAGC CAGAATGCCG ACTTTATTAC CGCCGGCCTG
601  GTCGATCCCG TCTTCCTCCC CTTGGGCAAT CAACAGCGTG CCGCCACGCA
651  TCTGAACGAG CCGAAATCTC AAAAAATCCT CTTTATCGTC GCCGAATCTT
701  GGGGGCTGCC GGCCAATCCC GAACTTCAAA ACGCCACTTT TGCCAAACTG
751  CTGGCGCAAA AAGACCGTTT TTCGGTTTGG GAAAGCGGCA GTTTTCCCTT
801  CATCGGCGCG ACGGTCGAAG GCGAAATGCG CGAACTGTGT GCCTACGGCG
```

```
 851 GTTTGCGCGG GTTCGCACTG CGCCGCGCGC CCGACGAAAA ATTTGCCCGC

901 TGCCTCCCCA ACCGTTTGAA ACAAGAAGGT TACGCCACCT TTGCGATGCA

951 CGGCGCGGGC AGTTCGCTTT ACGACCGCTT CAGCTGGTAT CCGAGGGCGG

1001 GCTTTCAAGA AATCAAAACC GCCGAAAACC TGATCGGTAA AAAAACCTGC

1051 GCCATTTTCG GCGGCGTGTG CGACAGCGAG CTGTTCGGCG AAGTGTCGGC

1101 ATTTTTCAAA AAACACGACA AGGGACTGTT TTACTGGATG ACGCTGACCA

1151 GCCACGCCGA CTATCCCGAA TCCGACATTT TCAACCACAG GCTCAAATGC

1201 ACCGAATATG GCCTGCCCGC CGAAACCGAC CTCTGCCGCA ATTTCAGCCT

1251 GCACACCCAA TTCTTCGACC AACTGGCGGA TTTGATCCAA CGCCCCGAAA

1301 TGAAAGGCAC GGAAGTCATC ATCGTCGGCG ACCATCCGCC GCCCGTCGGC

1351 AACCTCAATG AAACCTTCCG CTACCTCAAA CAGGGGCACG TCGCCTGGCT

1401 GAACTTCAAA ATCAAATAA
```

This corresponds to the amino acid sequence <SEQ ID 470; ORF48-1>:

```
  1 MNIHTLLSKQ WTLPPFLPKR LLLSLLILLA PNAVFWVLAL LTATARPIVN

51 LDYLPAALLI ALPWRFVKIA GVLAFWLAVL FDGLMMVIQL FPFMDLIGAI

101 NLVPFILTAP APYQIMTGLL LLYMLAMPFV LQKAAAKTDF RHIAVCAAVV

151 AAAGYFTGHL SYYDRGRMAN IFGANNFYYA KSQAMLYTVS QNADFITAGL

201 VDPVFLPLGN QQRAATHLNE PKSQKILFIV AESWGLPANP ELQNATFAKL

251 LAQKDRFSVW ESGSFPFIGA TVEGEMRELC AYGGLRGFAL RRAPDEKFAR

301 CLPNRLKQEG YATFAMHGAG SSLYDRFSWY PRAGFQEIKT AENLIGKKTC

351 AIFGGVCDSE LFGEVSAFFK KHDKGLFYWM TLTSHADYPE SDIFNHRLKC

401 TEYGLPAETD LCRNFSLHTQ FFDQLADLIQ RPEMKGTEVI IVGDHPPPVG

451 NLNETFRYLK QGHVAWLNFK IK*
```

Computer analysis of this amino acid sequence gave the following results:

Homology with a Predicted ORF from *N. meningitidis* (Strain A)

ORF48 shows 94.1% identity over a 119aa overlap with an ORF (ORF48a) from strain A of *N. meningitidis*:

```
                    10         20         30         40         50         60
    orf48.pep   MNIHTLLSKQWTLPPFLPKRLLLSLLILLAPNAVFWVLALLTATARPIVNLDYLPAALLI
                |||||||||||||||||||||||||||||| |||||||||||||||||||| ||||||||
    orf48a      MNIHTLLSKQWTLPPFLPKRLLLSLLILLXPNAVFWVLALLTATARPIVNLXYLPAALLI
                    10         20         30         40         50         60

70         80         90        100        110    119
    orf48.pep   ALPWRFVKIAGVLAFWLAVLFDGLMMVIQLFPFMDLIGAINLVPFILTAPAPYQIMTGL
                ||||| |||| |||| ||||||||||||||||||||||||||| ||| ||| |||||| 
    orf48a      ALPWRXVKIXGVLAXWLAVLFDGLMMVIQLFPFMDLIGAINLVPFIXTAPALYQIMTGLL
                    70         80         90        100        110        120 orf48a      LLYMLAMPFVLQKAAAKTDFRHIAACAAVVVAAGYFTGHLSXYDRGRMANIFGANNFYYA
                    130        140        150        160        170        180
```

The complete length ORF48a nucleotide sequence <SEQ ID 471> is:

```
   1 ATGAATATTC ACACCCTGCT CTCCAAACAA TGGACGCTGC CGCCATTCCT
  51 GCCGAAACGG CTGCTGCTGT CCCTGCTGAT ACTGCTNNCC CCCAATGCGG
 101 TGTTTTGGGT TTTGGCACTG CTGACCGCCA CCGCCCGCCC GATTGTCAAT
 151 TTGGANTACC TTCCCGCCGC GCTGCTGATC GCCCTGCCTT GGCGTNTCGT
 201 CAAAATTGNC GGCGTATTGG CGTNTTGGCT GGCGGTTTTG TTTGACGGGC
 251 TGATGATGGT GATCCAACTC TTCCCTTTTA TGGATCTCAT CGGCGCCATC
 301 AACCTCGTCC CCTTCATCNT GACCGCCCCC GCCCTTTATC AGATAATGAC
 351 CGGGCTGTTA CTGCTGTATA TGCTGGCGAT GCCGTTTGTG TTGCAGAAAG
 401 CCGCCGCCAA AACCGACTTC CGACACATTG CCGCCTGTGC CGCCGTTGTG
 451 GTGGCAGCCG GCTATTTTAC CGGCCATTTG AGTTANTACG ACCGGGGGCG
 501 GATGGCCAAT ATCTTCGGCG CAAACAACTT CTATTACGCC AAAAGTCAGG
 551 CGATGCTCTA CACCGTCAGC CAGAATGCCG ACTTTATTAC CGCCGGCCTG
 601 GTCGATCCCG TCTTCCTCCC CTTGGGCAAT CAACAGCGTG CCGCCACGCA
 651 TCTGAACGAG CCGAAATCTC AAAAAATCCT CTTTATCGTC GCCGAATCTT
 701 GGGGGCTGCC GGCCAATCCC GAACTTCAAA ACGCCACTTT TGCCAAACTG
 751 CTGGCGCAAA AAGANCGTTT TTCGGTTTGG GAAAGCGGCA GTTTTCCCTT
 801 CATCGGCGCG ACGATCGAAG GCGAAATGCG CGAACTGTGT GCCTACGGCG
 851 GTTTGCGCGG GTTCGCACTG CGCCGCGCGC CGACGAAAA ATTTGCCCGC
 901 TGCCTCCCCA ACCGTTTGAA ACAAGAAGGT TACGCCACCT TTGCGATGCA
 951 CGGCGCGGGC AGTTCGCTTT ACGACCGCTT CAGCTGGTAT CCGAGGGCGG
1001 GCTTTCAAGA AATCAAAACC GCCGAAAACC TGATCGGTAA AAAAACCTGC
1051 GCCATTTTCG GCGGCGTGTG CGACAGCGAG CTGTTCGGCG AAGTGTCGGC
1101 ANTTTTCAAA AAACACGACA AGGGACTGTT TTACTGGATG ACGCTGACCA
1151 GCCACGCCGA CTATCCCGAA TCNGACATTT TCAACCACAG GCTCAAATGC
1201 ACCGAATATG GCCTGCCCGC CGAAACCGAC NTCTGCCGCA ATTTCAGCCT
1251 GCACACCCAA TTCTTCGACC AACTGGCGGA TTTGATCCAA CGCCCCGAAA
1301 TGAAAGGCAC GGAAGTCATC ATCGTCGGCG ACCATCCGCC GCCCGTCGGC
1351 AACCTCAATG AAACCTTCCG CTACCTCAAA CAGGGGCACG TCGNCTGGCT
1401 GAACTTCAAA ATCAAATAA
```

This encodes a protein having amino acid sequence <SEQ ID 472>:

```
  1 MNIHTLLSKQ WTLPPFLPKR LLLSLLILLX PNAVFWVLAL LTATARPIVN
 51 LXYLPAALLI ALPWRXVKIX GVLAXWLAVL FDGLMMVIQL FPFMDLIGAI
101 NLVPFIXTAP ALYQIMTGLL LLYMLAMPFV LQKAAAKTDF RHIAACAAVV
151 VAAGYFTGHL SXYDRGRMAN IFGANNFYYA KSQAMLYTVS QNADFITAGL
201 VDPVFLPLGN QQRAATHLNE PKSQKILFIV AESWGLPANP ELQNATFAKL
251 LAQKXRFSVW ESGSFPFIGA TIEGEMRELC AYGGLRGFAL RRAPDEKFAR
301 CLPNRLKQEG YATFAMHGAG SSLYDRFSWY PRAGFQEIKT AENLIGKKTC
```

```
-continued
351 AIFGGVCDSE LFGEVSAXFK KHDKGLFYWM TLTSHADYPE SDIFNHRLKC

401 TEYGLPAETD XCRNFSLHTQ FFDQLADLIQ RPEMKGTEVI IVGDHPPPVG

451 NLNETFRYLK QGHVXWLNFK IK*
```

ORF48a and ORF48-1 show 96.8% identity in 472 aa overlap:

```
                   10         20         30         40         50         60
orf48a.pep MNIGTLLSKQWTLPPFLPKRLLLSLLILLXPNAVFWVLALLTATARPIVNLXYLPAALLI
           ||||||||||||||||||||||||||||| ||||||||||||||||||||||| ||||||
  orf48-1  MNIGTLLSKQWTLPPFLPKRLLLSLLILLAPNAVFWVLALLTATARPIVNLDYLPAALLI
                   10         20         30         40         50         60

70         80         90        100        110        120
orf48a.pep ALPWRXVKIXGVLAXWLAVLFDGLMMVIQLFPFMDLIGAINLVPFIXTAPALYQIMTGLL
           ||||| ||| ||||  ||||||||||||||||||||||||||||||| |||| |||||||
  orf48-1  ALPWRFVKIAGVLAFWLAVLFDGLMMVIQLFPFMDLIGAINLVPFILTAPAPYQIMTGLL
                   70         80         90        100        110        120

130        140        150        160        170        180
orf48a.pep LLYMLAMPFVLQKAAAKTDFRHIAACAAVVVAAGYFTGHLSXYDRGRMANIFGANNFYYA
           |||||||||||||||||||||||||:|||||:||||||||||| ||||||||||||||||
  orf48-1  LLYMLAMPFVLQKAAAKTDFRHIAVCAAVVAAAGYFTGHLSYYDRGRMANIFGANNFYYA
                  130        140        150        160        170        180

190        200        210        220        230        240
orf48a.pep KSQAMLYTVSQNADFITAGLVDPVFLPLGNQQRAATHLNEPKSQKILFIVAESWGLPANP
           ||||||||||||||||||||||||||||||||||||||||||||||||||||||||||||
  orf48-1  KSQAMLYTVSQNADFITAGLVDPVFLPLGNQQRAATHLNEPKSQKILFIVAESWGLPANP
                  190        200        210        220        230        240

250        260        270        280        290        300
orf48a.pep ELQNATFAKLLAQKXRFSVWESGSFPFIGATIEGEMRELCAYGGLRGFALRRAPDEKFAR
           |||||||||||||| ||||||||||||||||:|||||||||||||||||||||||||||
  orf48-1  ELQNATFAKLLAQKDRFSVWESGSFPFIGATVEGEMRELCAYGGLRGFALRRAPDEKFAR
                  250        260        270        280        290        300

310        320        330        340        350        360
orf48a.pep CLPNRLKQEGYATFAMHGAGSSLYDRFSWYPRAGFQEIKTAENLIGKKTCAIFGGVCDSE
           ||||||||||||||||||||||||||||||||||||||||||||||||||||||||||||
  orf48-1  CLPNRLKQEGYATFAMHGAGSSLYDRFSWYPRAGFQEIKTAENLIGKKTCAIFGGVCDSE
                  310        320        330        340        350        360

370        380        390        400        410        420
orf48a.pep LFGEVSAXFKKHDKGLFYWMTLTSHADYPESDIFNHRLKCTEYGLPAETDXCRNFSLHTQ
           ||||||| |||||||||||||||||||||||||||||||||||||||||| |||||||||
  orf48-1  LFGEVSAFFKKHDKGLFYWMTLTSHADYPESDIFNHRLKCTEYGLPAETDLCRNFSLHTQ
                  370        380        390        400        410        420

430        440        450        460        470
orf48a.pep FFDQLADLIQRPEMKGTEVIIVGDHPPPVGNLNETFRYLKQGHVXWLNFKIKX
           ||||||||||||||||||||||||||||||||||||||||||| ||||||||
  orf48-1  FFDQLADLIQRPEMKGTEVIIVGDHPPPVGNLNETFRYLKQGHVAWLNFKIKX
                  430        440        450        460        470
```

Homology with a Predicted ORF from *N. gonorrhoeae*

ORF48 shows 97.5% identity over a 119aa overlap with a predicted ORF (ORF48ng) from *N. gonorrhoeae*.

```
orf48.pep  MNIHTLLSKQWTLPPFLPKRLLLSLLILLAPNAVFWVLALLTATARPIVNLDYLPAALLI  60
           ||||:|||:|||||||||||||||||||||||||||||||||||||||||||||||||||
orf48ng    MNIHALLSEQWTLPPFLPKRLLLSLLILLAPNAVFWVLALLTATARPIVNLDYLPAALLI  60
orf48.pep  ALPWRFVKIAGVLAFWLAVLFDGLMMVIQLFPFMDLIGAINLVPFILTAPAPYQIMTGL   119
           |||||||||||||||| |||||||||||||||||||||||||||||||||||||||||
orf48ng    ALPWRFVKIAGVLAFWPAVLFDGLMMVIQLFPFMDLIGAINLVPFILTAPAPYQIMTGLL 120
```

The ORF48ng nucleotide sequence <SEQ ID 473> was predicted to encode a protein having amino acid sequence <SEQ ID 474>:

```
  1 MNIHALLSEQ WTLPPFLPKR LLLSLLILLA PNAVFWVLAL LTATARPIVN

51 LDYLPAALLI ALPWRFVKIA GVLAFWPAVL FDGLMMVIQL FPFMDLIGAI

101 NLVPFILTAP APYQIMTGLL LLYMLAMPFV LQKAAVKTDF RHIAVCAAVV
```

```
151  AAARYFTGPF ELLRTGGRWQ YVQHRRLLLS GSRASFRRRQ KADVLRRLGN

201  PYASMGNGG..
```

Further work identified the complete gonococcal DNA sequence <SEQ ID 475>:

```
   1  ATGAATATTC ACGCCCTGCT CTCCGAACAA TGGACGCTGC CGCCATTCCT

51  GCCGAAACGG CTGCTGCTGT CCCTGCTGAT ACTGCTGGCC CCCAATGCGG

101  TGTTTTGGGT TTTGGCACTG CTGACCGCCA CCGCCCGCCC GATTGTCAAT

151  TTGGACTACC TTCCCGCCGC GCTGCTGATC GCCCTGCCTT GGCGTTTCGT

201  CAAAATTGCC GGCGTATTGG CGTTTTGGCC GGCGGTTTTG TTTGACGGGC

251  TGATGATGGT GATCCAACTC TTCCCTTTTA TGGACCTCAT CGGCGCCATC

301  AACCTCGTCC CCTTCATCCT GACCGCCCCC GCCCCTTATC AGATAATGAC

351  CGGGCTGTTG CTGCTGTATA TGCTGGCGAT GCCGTTTGTG TTGCAAAAAG

401  CCGCCGTCAA AACCGACTTC CGACACATTG CCGTCTGTGC CGCCGTTGTG

451  GCGGCAGCCG GCTATTTCAC CGGCCATTTG AGTTACTACG ACCGGGGGCG

501  GATGGCCAAT ATCTTCGGCG CAAACAACTT CTATTACGCc aAAAGTCAGG

551  CGATGCTCTA CACCGTCAGC CAGAATGCCG ACTTTATTAC CGCCGgcctG

601  GTCGACCCCG TCTTCCTCCC CTTGGGCAAT CAGCAGCGTG CCGCCACGCG

651  GCTGAGTGAG CCGAAATCTC AAAAAATCCT CTTTATCGTC GCCGAATCTT

701  GGGGGCTGCC GGGCAATCCC GAGCTTCAAA ACGCCACTTT TGCCAAACTG

751  CTGGCGCAAA AGACCGTTTT TTCGGTTTGG GAAAGCGGCA GTTTTCCCTT

801  CATCGGCGCG ACGGTCGAAG GCGAAATGCG CGAATTGTGC GCCTACGGCG

851  GTTTGCGCGG GTTCGCACTG CGCCGCGCGC CCGACGAAAA ATTTGCCCGC

901  TGCCTCCCCA ACCGTTTGAA ACAAGAAGGT TACGCCACCT TTGCGATGCA

951  CGGCGCGGGT AGTTCGCTTT ACGACCGCTT CAGCTGGTAT CCGAGGGCGG

1001  GCTTTCAAAA AATCAAAACC GCCGAAAACC TGATCGGTAA AAAAACCTGC

1051  GCCATTTTCG GCGGCGTGTG CGACAGCGAG CTGTTCGGCG AAGTGTCGGC

1101  ATTTTTCAAA AAACACGACA AGGGACTGTT TTACTGGATG ACGCTGACCA

1151  GCCACGCCGA CTATCCCGAA TCCGACATTT TCAACCACAG GCTCAAATGC

1201  ACCGAATACG GCCTGCCCGC CGAAACCGAC CTCTGCCGCA ATTTCAGCCT

1251  GCACACCCAA TtcttcgACC AACTGGCGGA TTTGATCCGA CGCCCCGAAA

1301  TGAAAGGCAC GGAAGTCATC ATCGTCGGCG ACCATCCGCC GCCCGTCGGC

1351  AACCTCAATG AAACCTTCCG CTACCTCAAA CAGGGACACG TCGCCTGGCT

1401  GCACTTCAAA ATCAAATAA
```

This encodes a protein having amino acid sequence <SEQ ID 476; ORF48ng-1>:

```
   1  MNIHALLSEQ WTLPPFLPKR LLLSLLILLA PNAVFWVLAL LTATARPIVN

51  LDYLPAALLI ALPWRFVKIA GVLAFWPAVL FDGLMMVIQL FPFMDLIGAI

101  NLVPFILTAP APYQIMTGLL LLYMLAMPFV LQKAAVKTDF RHIAVCAAVV

151  AAAGYFTGHL SYYDRGRMAN IFGANNFYYA KSQAMLYTVS QNADFITAGL
```

```
201 VDPVFLPLGN QQRAATRLSE PKSQKILFIV AESWGLPGNP ELQNATFAKL

251 LAQKDRFSVW ESGSFPFIGA TVEGEMRELC AYGGLRGFAL RRAPDEKFAR

301 CLPNRLKQEG YATFAMHGAG SSLYDRFSWY PRAGFQKIKT AENLIGKKTC

351 AIFGGVCDSE LFGEVSAFFK KHDKGLFYWM TLTSHADYPE SDIFNHRLKC

401 TEYGLPAETD LCRNFSLHTQ FFDQLADLIR RPEMKGTEVI IVGDHPPPVG

451 NLNETFRYLK QGHVAWLHFK IK*
```

ORG48ng-1 and ORF48-1 show 97.9% identity in 472 aa overlap:

```
                    10         20         30         40         50         60
   orf48-1.pep   MNIHTLLSKQWTLPPFLPKRLLLSLLILLAPNAVFWVLALLTATARPIVNLDYLPAALLI
                 ||||:|||:||||||||||||||||||||||||||||||||||||||||||||||||||
   orf48ng-1     MNIHALLSEQWTLPPFLPKRLLLSLLILLAPNAVFWVLALLTATARPIVNLDYLPAALLI
                    10         20         30         40         50         60

70         80         90        100        110        120
   orf48-1.pep   ALPWRFVKIAGVLAFWLAVLFDGLMMVIQLFPFMDLIGAINLVPFILTAPAPYQIMTGLL
                 ||||||||||||||||| |||||||||||||||||||||||||||||||||||||||||
   orf48ng-1     ALPWRFVKIAGVLAFWPAVLFDGLMMVIQLFPFMDLIGAINLVPFILTAPAPYQIMTGLL
                    70         80         90        100        110        120

130        140        150        160        170        180
   orf48-1.pep   LLYMLAMPFVLQKAAAKTDFRHIAVCAAVVAAAGYFTGHLSYYDRGRMANIFGANNFYYA
                 ||||||||||||||||:|||||||||||||||||||||||||||||||||||||||||
   orf48ng-1     LLYMLAMPFVLQKAAVKTDFRHIAVCAAVVAAAGYFTGHLSYYDRGRMANIFGANNFYYA
                   130        140        150        160        170        180

190        200        210        220        230        240
   orf48-1.pep   KSQAMLYTVSQNADFITAGLVDPVFLPLGNQQRAATHLNEPKSQKILFIVAESWGLPANP
                 |||||||||||||||||||||||||||||||||||:|:|||||||||||||||||:||
   orf48ng-1     KSQAMLYTVSQNADFITAGLVDPVFLPLGNQQRAATRLSEPKSQKILFIVAESWGLPGNP
                   190        200        210        220        230        240

250        260        270        280        290        300
   orf48-1.pep   ELQNATFAKLLAQKDRFSVWESGSFPFIGATVEGEMRELCAYGGLRGFALRRAPDEKFAR
                 ||||||||||||||||||||||||||||||||||||||||||||||||||||||||||
   orf48ng-1     ELQNATFAKLLAQKDRFSVWESGSFPFIGATVEGEMRELCAYGGLRGFALRRAPDEKFAR
                   250        260        270        280        290        300

310        320        330        340        350        360
   orf48-1.pep   CLPNRLKQEGYATFAMHGAGSSLYDRFSWYPRAGFQEIKTAENLIGKKTCAIFGGVCDSE
                 |||||||||||||||||||||||||||||||||||:||||||||||||||||||||||
   orf48ng-1     CLPNRLKQEGYATFAMHGAGSSLYDRFSWYPRAGFQKIKTAENLIGKKTCAIFGGVCDSE
                   310        320        330        340        350        360

370        380        390        400        410        420
   orf48-1.pep   LFGEVSAFFKKHDKGLFYWMTLTSHADYPESDIFNHRLKCTEYGLPAETDLCRNFSLHTQ
                 ||||||||||||||||||||||||||||||||||||||||||||||||||||||||||
   orf48ng-1     LFGEVSAFFKKHDKGLFYWMTLTSHADYPESDIFNHRLKCTEYGLPAETDLCRNFSLHTQ
                   370        380        390        400        410        420

430        440        450        460        470
   orf48-1.pep   FFDQLADLIQRPEMKGTEVIIVGDHPPPVGNLNETFRYLKQGHVAWLNFKIKX
                 ||||||||:|||||||||||||||||||||||||||||||||||||:|||||
   orf48ng-1     FFDQLADLIRRPEMKGTEVIIVGDHPPPVGNLNETFRYLKQGHVAWLHFKIKX
                   430        440        450        460        470
```

Based on this analysis, including the presence of a putative leader sequence (double-underlined) and two putative transmembrane domains (single-underlined) in the gonococcal protein, it is predicted that the proteins from *N. meningitidis* and *N. gonorrhoeae*, and their epitopes, could be useful antigens for vaccines or diagnostics, or for raising antibodies.

Example 57

The following partial DNA sequence was identified in *N. meningitidis* <SEQ ID 477>:

```
 1 ..GTGAGCGGAC GTTACCGCGC TTTGGATCGC GTTTCCAAAA TCATCATCGT

51   TACTTTGAGT ATCGCCACGC TTGCCGCCGC CGGCATCGCT ATGTCGCGCG
```

-continued

```
101  GTATGCAGAT GCAGTCCGAT TTTATCGAGC CGACACCGTG GACGCTTGCC

151  GGTTTGGGCT TCCTGATCGC GCTGATGGGC TGGATGCCCG CGCCGATTGA

201  AATTTCCGCC ATCAATTCTT TGTGGGTAAC CGAAAAACAA CGCATCAATC

251  CTTCCGAATA CCGCGACGGG ATTTTTGAAT TCAACGTCGG TTATATCGCC

301  AGTGCGGTTT TGGCTTTGGT TTTCCTTGCA CTGGGCGC.G TAGCGCCGAA

351  CGGCAACGGC GA.ACAGTGC AGATGGCGGG CGGCAAATAT AACGGGCAAT

401  TGATCAATAT GTACGCC..
```

This corresponds to the amino acid sequence <SEQ ID 478; ORF53>:

```
  1..VSGRYRALDR VSKIIIVTLS IATLAAAGIA MSRGMQMQSD FIEPTPWTLA

51  GLGFLIALMG WMPAPIEISA INSLWVTEKQ RINPSEYRDG IFEFNVGYIA

101  SAVLALVFLA LGXVAPNGNG XTVQMAGGKY NGQLINMYA..
```

Further work revealed the complete nucleotide sequence <SEQ ID 479>:

```
   1 ATGTCCGAAC AACATATTTC GACTTGGAAA AGTAAAATCA ACGCATTGGG

51 TCCGGGGATC ATGATGGCTT CGGCGGCGGT CGGCGGTTCG CACCTGATTG

101 CCTCGACGCA GGCGGGCGCG CTTTACGGCT GGCAGATCGC GCTCATCATC

151 ATCCTGACCA ACCTCTTCAA ATACCCGTTT TTCCGCTTCA GCGCGCATTA

201 CACGCTGGAC ACGGGCAAGA GCCTGATTGA AGGTTATGCC GAGAAAAGCC

251 GCGTTTATTT GTGGGTATTC CTGATTTTGT GCATCCTCTC CGCCACGATT

301 AACGCGGGCG CGGTCGCCAT TGTAACCGCC GCCATCGTCA AAATGGCGAT

351 TCCCTCGCTG ATGTTTGATG CCGGCACGGT TGCCGCCTTG ATTATGGCAT

401 CCTGCCTGAT TATTTTGGTG AGCGGACGTT ACCGCGCTTT GGATCGCGTT

451 TCCAAAATCA TCATCGTTAC TTTGAGTATC GCCACGCTTG CCGCCGCCGG

501 CATCGCTATG TCGCGCGGTA TGCAGATGCA GTCCGATTTT ATCGAGCCGA

551 CACCGTGGAC GCTTGCCGGT TTGGGCTTCC TGATCGCGCT GATGGGCTGG

601 ATGCCCGCGC CGATTGAAAT TTCCGCCATC AATTCTTTGT GGGTAACCGA

651 AAAACAACGC ATCAATCCTT CCGAATACCG CGACGGGATT TTTGATTTCA

701 ACGTCGGTTA TATCGCCAGT GCGGTTTTGG CTTTGGTTTT CCTTGCACTG

751 GGCGCGTTTG TGCAATACGG CAACGGCGAA GCAGTGCAGA TGGCGGGCGG

801 CAAATATATC GGGCAATTGA TCAATATGTA CGCCGTTACC ATCGGCGGCT

851 GGTCGCGCCC GCTGGTGGCG TTTATCGCGT TTGCCTGTAT GTACGGCACG

901 ACGATTACCG TCGTGGACGG CTATGCCCGT GCCATTGCCG AACCCGTGCG

951 CCTGCTGCGC GGAAAAGACA AAACGGGCAA CGCCGAATTC TTTGCCTGGA

1001 ATATTTGGGT GGCGGGCAGC GGTTTGGCGG TGATTTTCTG GTTTGACGGC

1051 GTAATGGCGA ATCTGCTCAA ATTTGCGATG ATTGCCGCTT TTGTGTCCGC

1101 CCCTGTGTTT GCCTGGCTGA ATTACCGTTT GGTTAAAGGT GATGAAAAAC

1151 ACAAACTCAC ATCAGGTATG AATGCCCTTG CATTGGCAGG CTTGATTTAT
```

```
1201 CTGACCGGTT TACCGTTTT GTTCTTATTG AATTTGGCGG GAATGTTCAA

1251 ATGA
```

This corresponds to the amino acid sequence <SEQ ID 480; ORF53-1>:

```
  1 MSEQHISTWK SKINALGPGI MMASAAVGGS HLIASTQAGA LYGWQIALII

51 ILTNLFKYPF FRFSAHYTLD TGKSLIEGYA EKSRVYLWVF LILCILSATI

101 NAGAVAIVTA AIVKMAIPSL MFDAGTVAAL IMASCLIILV SGRYRALDRV

151 SKIIIVTLSI ATLAAAGIAM SRGMQMQSDF IEPTPWTLAG LGFLIALMGW

201 MPAPIEISAI NSLWVTEKQR INPSEYRDGI FDFNVGYIAS AVLALVFLAL

251 GAFVQYGNGE AVQMAGGKYI GQLINMYAVT IGGWSRPLVA FIAFACMYGT

301 TITVVDGYAR AIAEPVRLLR GKDKTGNAEF FAWNIWVAGS GLAVIFWFDG

351 VMANLLKFAM IAAFVSAPVF AWLNYRLVKG DEKHKLTSGM NALALAGLIY

401 LTGFTVLFLL NLAGMFK*
```

Computer analysis of this amino acid sequence gave the following results:

Homology with a Predicted ORF from *N. meningitidis* (Strain A)

ORF53 shows 93.5% identity over a 139aa overlap with an ORF (ORF53a) from strain A of *N. meningitidis*:

```
                                          10        20        30
orf53.pep                            VSGRYRALDRVSKIIIVTLSIATLAAAGIA
                                     ||||||||||||||||||||||||||||||
orf53a    AAIVKMAIPSLMFDAGTVAALIMASCLIILVSGRYRALDRVSKIIIVTLSIATLAAAGIA
           110       120       130       140       150       160
                   40        50        60        70        80        90
orf53.pep  MSRGMQMQSDFIEPTPWTLAGLGFLIALMGWMPAPIEISAINSLWVTEKQRINPSEYRDG
           ||||||||||||||||||||||||||||||||||||||||||||||||||||||||||||
orf53a     MSRGMQMQSDFIEPTPWTLAGLGFLIALMGWMPAPIEISAINSLWVTEKQRINPSEYRDG
           170       180       190       200       210       220
                    100       110       120       130      139
orf53.pep  IFEFNVGYIASAVLALVFLALGXVAPNGNGXTVQMAGGKYNGQLINMYA
           ||:|||||||||||||||||||  :|||  :|||||||||  ||||||||
orf53a     IFDFNVGYIASAVLALVFLALGAFVQYGNGEAVQMAGGKYIGQLINMYAVTIGGWSRPLV
           230       240       250       260       270       280
orf53a     AFIAFACMYGTTITVVDGYARAIAEPVRLLRGKDKTGNAEFFAWNIWVAGSGLAVIFWFD
           290       300       310       320       330       340
```

The complete length ORF53a nucleotide sequence <SEQ ID 481> is:

```
  1 ATGTCCGAAC AACATATTTC GACTTGGAAA AGTAAAATCA ACGCATTGGG

51 ACCGGGGATT ATGATGGCTT CGGCGGCGGT CGGCGGTTCG CACCTGATTG

101 CCTCGACGCA GGCGGGCGCG CTTTACGGCT GGCAGATCGC GCTCATCATC

151 ATCCTGACCA ACCTCTTCAA ATACCCGTTT TTCCGCTTCA GCGCGCATTA

201 CACGCTGGAC ACGGGCAAGA GCCTGATTGA AGGTTATGCC GAGAAAAGCC

251 GCGTTTATTT GTGGGTATTC CTGATTTTGT GCATCCTCTC CGCCACGATT

301 AACGCGGGCG CGGTCGCCAT TGTAACCGCC GCCATCGTCA AAATGGCGAT

351 TCCCTCGCTG ATGTTTGATG CCGGCACGGT TGCCGCCTTG ATTATGGCAT

401 CCTGCCTGAT TATTTTGGTG AGCGGACGTT ACCGCGCTTT GGATCGCGTT
```

```
 451 TCCAAAATCA TCATCGTTAC TTTGAGTATC GCCACGCTTG CCGCCGCCGG

501 CATCGCTATG TCGCGCGGTA TGCAGATGCA GTCCGATTTT ATCGAGCCGA

551 CACCGTGGAC GCTTGCCGGT TTGGGCTTCC TGATCGCGCT GATGGGCTGG

601 ATGCCCGCGC CGATTGAAAT TTCCGCCATC AATTCTTTGT GGGTAACCGA

651 AAAACAACGC ATCAATCCTT CCGAATACCG CGACGGGATT TTTGATTTCA

701 ACGTCGGTTA TATCGCCAGT GCGGTTTTGG CTTTGGTTTT CCTTGCACTG

751 GGCGCGTTTG TGCAATACGG CAACGGCGAA GCAGTGCAGA TGGCGGGCGG

801 CAAATATATC GGGCAATTGA TCAATATGTA CGCCGTTACC ATCGGCGGCT

851 GGTCGCGCCC GCTGGTGGCG TTTATCGCGT TTGCCTGTAT GTACGGCACG

901 ACGATTACCG TTGTGGACGG CTATGCCCGT GCCATTGCCG AACCCGTGCG

951 CCTGCTGCGC GGAAAAGACA AAACGGGCAA CGCCGAATTC TTTGCCTGGA

1001 ATATTTGGGT GGCGGGCAGC GGTTTGGCGG TGATTTTCTG GTTTGACGGC

1051 GTAATGGCGA ATCTGCTCAA ATTTGCGATG ATTGCCGCTT TTGTGTCCGC

1101 CCCTGTGTTT GCCTGGCTGA ATTACCGTTT GGTCAAAGGT GATGAAAAAC

1151 ACAAACTCAC ATCAGGTATG AATGCCCTTG CATTGGCAGG CTTGATTTAT

1201 CTGACCGGTT TTACCGTTTT GTTCTTATTG AATTTGGCGG GAATGTTCAA

1251 ATGA
```

This encodes a protein having amino acid sequence <SEQ ID 482>:

```
  1 MSEQHISTWK SKINALGPGI MMASAAVGGS HLIASTQAGA LYGWQIALII

51 ILTNLFKYPF FRFSAHYTLD TGKSLIEGYA EKSRVYLWVF LILCILSATI

101 NAGAVAIVTA AIVKMAIPSL MFDAGTVAAL IMASCLIILV SGRYRALDRV

151 SKIIIVTLSI ATLAAAGIAM SRGMQMQSDF IEPTPWTLAG LGFLIALMGW

201 MPAPIEISAI NSLWVTEKQR INPSEYRDGI FDFNVGYIAS AVLALVFLAL

251 GAFVQYGNGE AVQMAGGKYI GQLINMYAVT IGGWSRPLVA FIAFACMYGT

301 TITVVDGYAR AIAEPVRLLR GKDKTGNAEF FAWNIWVAGS GLAVIFWFDG

351 VMANLLKFAM IAAFVSAPVF AWLNYRLVKG DEKHKLTSGM NALALAGLIY

401 LTGFTVLFLL NLAGMFK*
```

ORF 53a shows 100.0% identity in 417 aa overlap with ORF53-1:

```
                    10         20         30         40         50         60
    orf53a.pep MSEQHISTWKSKINALGPGIMMASAAVGGSHLIASTQAGALYGWQIALIIILTNLFKYPF
               ||||||||||||||||||||||||||||||||||||||||||||||||||||||||||||
      orf53-1 MSEQHISTWKSKINALGPGIMMASAAVGGSHLIASTQAGALYGWQIALIIILTNLFKYPF
                    10         20         30         40         50         60

70         80         90        100        110        120
    orf53a.pep FRFSAHYTLDTGKSLIEGYAEKSRVYLWVFLILCILSATINAGAVAIVTAAIVKMAIPSL
               ||||||||||||||||||||||||||||||||||||||||||||||||||||||||||||
      orf53-1 FRFSAHYTLDTGKSLIEGYAEKSRVYLWVFLILCILSATINAGAVAIVTAAIVKMAIPSL
                    70         80         90        100        110        120

130        140        150        160        170        180
    orf53a.pep MFDAGTVAALIMASCLIILVSGRYRALDRVSKIIIVTLSIATLAAAGIAMSRGMQMQSDF
               ||||||||||||||||||||||||||||||||||||||||||||||||||||||||||||
      orf53-1 MFDAGTVAALIMASCLIILVSGRYRALDRVSKIIIVTLSIATLAAAGIAMSRGMQMQSDF
                   130        140        150        160        170        180
```

```
                     190        200        210        220        230        240
orf53a.pep  IEPTPWTLAGLGFLIALMGWMPAPIEISAINSLWVTEKQRINPSEYRDGIFDFNVGYIAS
            ||||||||||||||||||||||||||||||||||||||||||||||||||||||||||||
   orf53-1  IEPTPWTLAGLGFLIALMGWMPAPIEISAINSLWVTEKQRINPSEYRDGIFDFNVGYIAS
                     190        200        210        220        230        240

250        260        270        280        290        300
orf53a.pep  AVLALVFLALGAFVQYGNGEAVQMAGGKYIGQLINMYAVTIGGWSRPLVAFIAFACMYGT
            ||||||||||||||||||||||||||||||||||||||||||||||||||||||||||||
   orf53-1  AVLALVFLALGAFVQYGNGEAVQMAGGKYIGQLINMYAVTIGGWSRPLVAFIAFACMYGT
                     250        260        270        280        290        300

310        320        330        340        350        360
orf53a.pep  TITVVDGYARAIAEPVRLLRGKDKTGNAEFFAWNIWVAGSGLAVIFWFDGVMANLLKFAM
            ||||||||||||||||||||||||||||||||||||||||||||||||||||||||||||
   orf53-1  TITVVDGYARAIAEPVRLLRGKDKTGNAEFFAWNIWVAGSGLAVIFWFDGVMANLLKFAM
                     310        320        330        340        350        360

370        380        390        400        410
orf53a.pep  IAAFVSAPVFAWLNYRLVKGDEKHKLTSGMNALALAGLIYLTGFTVLFLLNLAGMFKX
            |||||||||||||||||||||||||||||||||||||||||||||||||||||||||
   orf53-1  IAAFVSAPVFAWLNYRLVKGDEKHKLTSGMNALALAGLIYLTGFTVLFLLNLAGMFKX
                     370        380        390        400        410
```

Homology with a Predicted ORF from *N. gonorrhoeae*

ORF53 shows 92.1% identity over a 139aa overlap with a predicted ORF (ORF53ng) from *N. gonorrhoeae*:

```
orf53.pep                              VSGRYRALDRVSKIIIVTLSIATLAAAGIA   30
                                       ||||||||||||||||||||||||||||||
orf53ng    AAIVKMAIPSLMFDAGTVAALIMASCLIILVSGRYRALDRVSKIIIVTLSIATLAAAGIA   91 orf53.pep  MSRGMQMQSDFIEPTPWTLAGLGFLIALMGWMPAPIEISAINSLWVTEKQRINPSEYRDG   90
           |||||||| |||||||||||||||||||||||||||||||||||||||||||||||||||
orf53ng    MSRGMQMQPDFIEPTPWTLAGLGFLIALMGWMPAPIEISAINSLWVTEKQRINPSEYRDG  151 orf53.pep  IFEFNVGYIASAVLALVFLALGXVAPNGNGXTVQMAGGKYNGQLINMYA            139
           ||:||||||||||||||||||| :  ||| :|||:|||| |||||||||
orf53ng    IFDFNVGYIASAVLALVFLALGAFVQYGNGEAVQMGGGKYIGQLINMYAVTIGGGSRPLV  211
```

An ORF53ng nucleotide sequence <SEQ ID 483> was predicted to encode a protein having amino acid sequence <SEQ ID 484>:

```
  1 MPKKSCVYLW VFLILCIASA TINAGAVAIV TAAIVKMAIP SLMFDAGTVA

51 ALIMASCLII LVSGRYRALD RVSKIIIVTL SIATLAAAGI AMSRGMQMQP

101 DFIEPTPWTL AGLGFLIALM GWMPAPIEIS AINSLWVTEK QRINPSEYRD

151 GIFDFNVGYI ASAVLALVFL ALGAFVQYGN GEAVQMGGGK YIGQLINMYA

201 VTIGGGSRPL VAFIAFACMY GAASTVVDGY ARAIAEPVRL LRGKDKTARP

251 IVLLEKLGGR HRFGRDFLV*
```

Further analysis revealed further partial DNA gonococcal sequence <SEQ ID 485>:

```
  1 ..aagaAAAGCT GCGTTTATTT GTGGGTTTTT TTGATTTTGT GTATCGCCTC

51 CGCCACGATT AACGCGGGCG CGGTCGCCAT TGTAACCGCC GCCATCGTCA

101 AAATGGCGAT TCCCTCGCTG ATGTTTGATG CCGGCACGGT TGCCGCCTTG

151 ATTATGGCAT CCTGCCTGAT TATTTTGGTG AGCGGACGTT ACCGCGCTTT

201 GGATCGTGTT TCCAAAATCA TCATTGTTAC TTTGAGCATC GCCACGCTTG

251 CCGCCGCCGG CATCGCTATG TCGCGCGGTA TGCAGATGCA GCCCGATTTT

301 ATCGAGCCGA CACCGTGGAC GCTTGCCGGT TTGGGCTTCC TGATCGCGCT

351 GATGGGCTGG ATGCCCGCGC CGATCGAAAT TTCCGCCATC AATTCTTTGT

401 GGGTAACCGA AAAACAACGC ATCAATCCTT CTGAATACCG CGACGGGATT
```

-continued

```
 451   TTCGATTTCA ACGTCGGTTA TATCGCcagT GCGGTTTTGG CTTTGGTTTT
 501   CCTTGCACTG GGCGCGTTTG TGCAATACGG CAACGGCGAA GCAGTGCAGA
 551   TGGCGGGCGG CAAATATATC GGGCAATTGA TTAATATGTA TGCCGTAACC
 601   ATCGGCGGCT GGTCTCGTCC GCTGGTGGCG TTTATCGCGT TTGCCTGTAT
 651   GTACGGCACG ACGATTACCG TTGTGGACGG TTATGCGCGT GCCATTGCCG
 701   AACCCGTGCG CCTGCTGCGC GGCAGGGATA AAACCGGCAA CGCCGAGTTG
 751   TTtgccTGGA ATATTTGGGT GGCGGGCAGC GGTTTGGCGG TGATTTTCTG
 801   GTTTGACggc gcaaTGGCgG AACtgcTCAA ATTTGCGATG ATtgccgcCT
 851   TTGTGTCCGC CCCTGTGTTC GCCTGGCTCA ACTACCGCCT CGTCAAAGGG
 901   GACAAACGCC ACAGGCTTAC CGCCGGTATG AACGCCCTTG CCATTGTCGG
 951   CCTGCTCTAC CTGGCCGGGT TTGCCGTTTT GTTCCTGTTG AACCTTACCG
1001   GACTTTTGGC ATAG
```

This corresponds to the amino acid sequence <SEQ ID 486; ORF53ng-1>:

```
  1..KKSCVYLWVF LILCIASATI NAGAVAIVTA AIVKMAIPSL MFDAGTVAAL

51   IMASCLIILV SGRYRALDRV SKIIVTLSI ATLAAAGIAM SRGMQMQPDF

101   IEPTPWTLAG LGFLIALMGW MPAPIEISAI NSLWVTEKQR INPSEYRDGI

151   FDFNVGYIAS AVLALVFLAL GAFVQYGNGE AVQMAGGKYI GQLINMYAVT

201   IGGWSRPLVA FIAFACMYGT TITVVDGYAR AIAEPVRLLR GRDKTGNAEL

251   FAWNIWVAGS GLAVIFWFDG AMAELLKFAM IAAFVSAPVF AWLNYRLVKG

301   DKRHRLTAGM NALAIVGLLY LAGFAVLFLL NLTGLLA*
```

ORF53ng-1 and ORF53-1 show 94.0% identity in 336 aa overlap:

```
                    60         70         80         90        100        110
    orf53-1.pep  ILTNLFKYPFFRFSAHYTLDTGKSLIEGYAEKSRVYLWVFLILCILSATINAGAVAIVTA
                                                 :|| |||||||||||| ||||||||||||
    orf53ng-1                                   KKSCVYLWVFLILCIASATINAGAVAIVTA
                                                          10         20         30

120        130        140        150        160        170
    orf53-1.pep  AIVKMAIPSLMFDAGTVAALIMASCLIILVSGRYRALDRVSKIIVTLSIATLAAAGIAM
                 ||||||||||||||||||||||||||||||||||||||||||||||||||||||||||
    orf53ng-1    AIVKMAIPSLMFDAGTVAALIMASCLIILVSGRYRALDRVSKIIVTLSIATLAAAGIAM
                          30         40         50         60         70         80

180        190        200        210        220        230
    orf53-1.pep  SRGMQMQSDFIEPTPWTLAGLGFLIALMGWMPAPIEISAINSLWVTEKQRINPSEYRDGI
                 ||||||| ||||||||||||||||||||||||||||||:|:||||||||||||||||:||
    orf53ng-1    SRGMQMQPDFIEPTPWTLAGLGFLIALMGWMPAPIEISAINSLWVTEKQRINPSEYRDGI
                          100        110        120        130        140        150

240        250        260        270        280        290
    orf53-1.pep  FDFNVGYIASAVLALVFLALGAFVQYGNGEAVQMAGGKYIGQLINMYAVTIGGWSRPLVA
                 ||||||||||||||||||||||||||||||||||||||||||||||||||||||||||
    orf53ng-1    FDFNVGYIASAVLALVFLALGAFVQYGNGEAVQMAGGKYIGQLINMYAVTIGGWSRPLVA
                          160        170        180        190        200        210

300        310        320        330        340        350
    orf53-1.pep  FIAFACMYGTTITVVDGYARAIAEPVRLLRGKDKTGNAEFFAWNIWVAGSGLAVIFWFDG
                 ||||||||||||||||||||||||||||||:||||||:||||||||||||||||||||
    orf48ng-1    FIAFACMYGTTITVVDGYARAIAEPVRLLRGRDKTGNAELFAWNIWVAGSGLAVIFWFDG
                          220        230        240        250        260        270

360        370        380        390        400        410
    orf53-1.pep  VMANLIKFAMIAAFVSAPVFAWLNYRLVKGDEKHKLTSGMNALALAGLIYLTGFTVLFLL
                 :||:||||||||||||||||||||||||||::|:|:||||||::||||:|:||:||||
    orf53ng-1    AMAELIKFAMIAAFVSAPVFAWLNYRLVKGDKRHRLTAGMNALAIVGLLYLAGFAVLFLL
                          280        290        300        310        320        330
```

```
orf53-1.pep  NLAGMFKX
             ||:|::
orf53ng-1    NLTGLLAX
```

Based on this analysis, including the presence of a putative leader sequence (double-underlined) and several putative transmembrane domains (single-underlined) in the gonococcal protein, it is predicted that the proteins from *N. meningitidis* and *N. gonorrhoeae*, and their epitopes, could be useful antigens for vaccines or diagnostics, or for raising antibodies.

Example 58

The following partial DNA sequence was identified in *N. meningitidis* <SEQ ID 487>:

```
  1..TTGCGGGAAA CGGCATATGT TTTGGATAGT TTTGATCGTT ATTTTGTTGT

51   TGCGCTTGCC GGCTTGTTTT TTGTCCGCGC ACAATCCGAA CGCGAGTGGA

101   TGCGCGAGGT TTCTGCGTGG CAGGAAAAGA AGGGGAAAA ACAGGCGGAG

151   CTGCCTGAAA TCAAAGACGG TATGCCCGAT TTTCCCGAAC TTGCCCTGAT

201   GCTTTTCCAC GCCGTCAAAA CGGCAGTGTA TTGGCTGTTT GTCGGTGTCG

251   TCCGTTTCTG CCGAAACTAT CTGGCGCACG AATCCGAACC GGACAGGCCC

301   GTTCCGCCT..
```

This corresponds to the amino acid sequence <SEQ ID 488; ORF58>:

```
  1..LRETAYVLDS FDRYFVVALA GLFFVRAQSE REWMREVSAW QEKKGEKQAE

51   LPEIKDGMPD FPELALMLFH AVKTAVYWLF VGVVRFCRNY LAHESEPDRP

101   VPP..
```

Further work revealed the complete nucleotide sequence <SEQ ID 489>:

```
  1   ATGTTTTGGA TAGTTTTGAT CGTTATTTTG TTGCTTGCGC TTGCCGGCTT

51   GTTTTTTGTC CGCGCACAAT CCGAACGCGA GTGGATGCGC GAGGTTTCTG

101   CGTGGCAGGA AAAGAAAGGG GAAAACAGG CGGAGCTGCC TGAAATCAAA

151   GACGGTATGC CCGATTTTCC CGAACTTGCC CTGATGCTTT TCCATGCCGT

201   CAAAACGGCA GTGTATTGGC TGTTTGTCGG TGTCGTCCGT TTCTGCCGAA

251   ACTATCTGGC GCACGAATCC GAACCGGACA GGCCCGTTCC GCCTGCTTCT

301   GCAAACCGTG CGGATGTTCC GACCGCATCC GACGGATATT CAGACAGTGG

351   AAACGGGACG GAAGAAGCGG AAACGGAAGA AGCAGAAGCT GCGGAGGAAG

401   AGGCTGCCGA TACGGAAGAC ATTGCAACTG CCGTAATCGA CAACCGCCGC

451   ATCCCATTCG ACCGGAGTAT TGCTGAAGGG TTGATGCCGT CTGAAAGCGA

501   AATTTCGCCC GTCCGTCCGG TTTTTAAAGA AATCACTTTG GAAGAAGCAA

551   CGCGTGCTTT AAACAGCGCG GCTTTAAGGG AAACGAAAAA ACGCTATATC

601   GATGCATTTG AGAAAAACGA AACAGCGGTC CCCAAAGTCC GCGTGTCCGA

651   TACCCCGATG GAAGGGCTGC AGATTATCGG TTTGGACGAC CCTGTGCTTC
```

-continued

```
 701 AACGCACGTA TTCCCATATG TTCGATGCGG ACAAAGAAGC GTTTTCCGAG
 751 TCTGCGGATT ACGGATTTGA GCCGTATTTT GAGAAGCAGC ATCCGTCTGC
 801 CTTTTCTGCA GTCAAAGCCG AAAATGCACG GAATGCGCCG TTCCACCGTC
 851 ATGCAGGGCA GGGGAAAGGG CAGGCGGAGG CAAAATCCCC GGATGTTTCC
 901 CAAGGGCAGT CCGTTTCAGA CGGCACGGCC GTCCGCGATG CCCGCCGCCG
 951 CGTTTCCGTC AATTTGAAAG AACCGAACAA GGCAACGGTT TCTGCGGAGG
1001 CGCGAATTTC TCGCCTGATT CCGGAAAGTC AGACGGTTGT CGGGAAACGG
1051 GATGTCGAAA TGCCGTCTGA AACCGAAAAT GTTTTCACGG AAACCGTTTC
1101 GTCTGTGGGA TACGGCGGTC CGGTTTATGA TGAAACTGCC GATATCCATA
1151 TTGAAGAACC TGCCGCGCCC GATGCTTGGG TGGTCGAACC ACCCGAAGTG
1201 CCGAAAGTTC CCATGACCGC AATCGATATT CAGCCGCCGC CTCCCGTATC
1251 GGAAATCTAC AACCGTACCT ATGAACCGCC GTCAGGATTC GAGCAGGTGC
1301 AACGCAGCCG CATTGCCGAG ACCGACCATC TTGCCGATGA TGTTTTGAAT
1351 GGAGGTTGGC AGGAGGAAAC CGCCGCTATT GCGGATGACG GCAGTGAAGG
1401 TGCGGCAGAG CGGTCAAGCG GGCAATATCT GTCGGAAACC GAAGCGTTCG
1451 GGCATGACAG TCAGGCGGTT TGTCCGTTTG AAAATGTGCC GTCTGAACGC
1501 CCGTCCTGCC GGGTATCGGA TACGGAAGCG GATGAAGGGG CGTTCCCATC
1551 TGAAGAAACC GGTGCGGTAT CCGAACACCT GCCGACAACC GACCTGCTTC
1601 TGCCTCCGCT GTTCAATCCC GAGGCGACGC AAACCGAAGA AGAACTGTTG
1651 GAAAACAGCA TCACCATCGA AGAAAAATTG GCGGAGTTCA AAGTCAAGGT
1701 CAAGGTTGTC GATTCTTATT CCGGCCCCGT AATTACGCGT TATGAAATCG
1751 AACCCGATGT CGGCGTGCGC GGCAATTCCG TTCTGAATCT GGAAAAAGAT
1801 TTGGCGCGTT CGCTCGGCGT GGCTTCCATC CGCGTTGTCG AAACCATCCC
1851 CGGCAAAACC TGCATGGGTT TGGAACTTCC GAACCCGAAA CGCCAAATGA
1901 TACGCCTGAG CGAAATCTTC AATTCGCCCG AGTTTGCCGA ATCCAAATCC
1951 AAGCTGACGC TCGCGCTCGG TCAGGACATC ACCGGACAGC CCGTCGTAAC
2001 CGACTTGGGA AAAGCACCGC ATTTGTTGGT TGCCGGCACG ACCGGTTCGG
2051 GCAAATCGGT GGGTGTCAAC GCGATGATTC TGTCTATGCT TTTCAAAGCC
2101 GCGCCGGAAG ACGTGCGTAT GATTATGATC GATCCGAAAA TGCTGGAATT
2151 GAGCATTTAC GAAGGCATCC CGCACCTGCT CGCCCCTGTC GTTACCGATA
2201 TGAAGCTGGC GGCAAACGCG CTGAACTGGT GTGTTAACGA AATGGAAAAA
2251 CGCTACCGCC TGATGAGCTT TATGGGCGTG CGTAATCTTG CGGGCTTCAA
2301 TCAAAAAATC GCCGAAGCCG CAGCAAGGGG AGAAAAAATC GGCAATCCGT
2351 TCAGCCTCAC GCCCGACGAT CCCGAACCTT GGAAAAACT GCCGTTTATC
2401 GTGGTCGTGG TCGATGAGTT TGCCGACCTG ATGATGACGG CAGGCAAGAA
2451 AATCGAAGAA CTGATTGCCC GCCTCGCCCA AAAGCCCGC GCGGCAGGCA
2501 TCCATTTGAT TCTTGCCACA CAACGCCCCA GCGTCGATGT CATCACGGGT
2551 CTGATTAAGG CGAACATCCC GACGCGTATC GCGTTCCAAG TGTCCAGCAA
2601 AATCGACAGC CGCACGATTC TCGACCAAAT GGGCGCGGAA AACCTGCTCG
2651 GTCAGGGCGA TATGCTGTTC CTGCTGCCGG GTACTGCCTA TCCGCAGCGC
```

```
2701 GTTCACGGCG CGTTTGCCTC GGATGAAGAG GTGCACCGCG TGGTCGAATA
2751 TTTGAAACAG TTTGGCGAAC CGGACTATGT TGACGATATT TTGAGCGGCG
2801 GCGGCAGCGA AGAGCTGCCC GGCATCGGGC GCAGCGGCGA CGACGAAACC
2851 GATCCGATGT ACGACGAGGC CGTATCCGTT GTCCTGAAAA CGCGCAAAGC
2901 CAGCATTTCG GGCGTACAGC GCGCCTTGCG TATCGGCTAC AACCGCGCCG
2951 CGCGTCTGAT TGACCAGATG GAGGCGGAAG GCATTGTGTC CGCACCGGAA
3001 CACAACGGCA ACCGTACGAT TCTCGTCCCC TTGGACAATG CTTGA
```

This corresponds to the amino acid sequence <SEQ ID 490; ORF58-1>:

```
   1 MFWIVLIVIL LLALAGLFFVRAQSEREWMR EVSAWQEKKG EKQAELPEIK
  51 DGMPDFPELA LMLFHAVKTAVYWLFVGVVR FCRNYLAHES EPDRPVPPAS
 101 ANRADVPTAS DGYSDSGNGT EEAETEEAEA AEEEAADTED IATAVIDNRR
 151 IPFDRSIAEG LMPSESEISP VRPVFKEITL EEATRALNSA ALRETKKRYI
 201 DAFEKNETAV PKVRVSDTPM EGLQIIGLDD PVLQRTYSHM FDADKEAFSE
 251 SADYGFEPYF EKQHPSAFSA VKAENARNAP FHRHAGQGKG QAEAKSPDVS
 301 QGQSVSDGTA VRDARRRVSV NLKEPNKATV SAEARISRLI PESQTVVGKR
 351 DVEMPSETEN VFTETVSSVG YGGPVYDETA DIHIEEPAAP DAWVVEPPEV
 401 PKVPMTAIDI QPPPPVSEIY NRTYEPPSGF EQVQRSRIAE TDHLADDVLN
 451 GGWQEETAAI ADDGSEGAAE RSSGQYLSET EAFGHDSQAV CPFENVPSER
 501 PSCRVSDTEA DEGAFPSEET GAVSEHLPTT DLLLPPLFNP EATQTEEELL
 551 ENSITIEEKL AEFKVKVKVV DSYSGPVITR YEIEPDVGVR GNSVLNLEKD
 601 LARSLGVASI RVVETIPGKT CMGLELPNPK RQMIRLSEIF NSPEFAESKS
 651 KLTLALGQDI TGQPVVTDLG KAPHLLVAGT TGSGKSVGVN AMILSMLFKA
 701 APEDVRMIMI DPKMLELSIY EGIPHLLAPV VTDMKLAANA LNWCVNEMEK
 751 RYRLMSFMGV RNLAGFNQKI AEAAARGEKI GNPFSLTPDD PEPLEKLPFI
 801 VVVVDEFADL MMTAGKKIEE LIARLAQKAR AAGIHLILAT QRPSVDVITG
 851 LIKANIPTRI AFQVSSKIDS RTILDQMGAE NLLGQGDMLF LLPGTAYPQR
 901 VHGAFASDEE VHRVVEYLKQ FGEPDYVDDI LSGGGSEELP GIGRSGDDET
 951 DPMYDEAVSV VLKTRKASIS GVQRALRIGY NRAARLIDQM EAEGIVSAPE
1001 HNGNRTILVP LDNA*
```

Computer analysis of this amino acid sequence predicts the indicated transmembrane region, and also gave the following results:

Homology with a Predicted ORF from *N. meningitidis* (Strain A)

ORF58 shows 96.6% identity over a 89aa overlap with an ORF (ORF58a) from strain A of *N. meningitidis*:

```
                  10        20        30        40        50        60
    orf58.pep  LRETAYVLDSFDRYFVVALAGLFFVRAQSEREWMREVSAWQEKKGEKQAELPEIKDGMPD
                      :::|||||||||||||||||||||||||||||||||||||||||||||
    orf58a         MFWIVLIVILLLALAGLFFVRAQSEREWMREVSAWQEKKGEKQAELPEIKDGMPD
                           10        20        30        40        50
```

```
                       70        80        90       100
orf58.pep  FPELALMLFHAVKTAVYWLFVGVVRFCRNYLAHESEPDRPVPP
           ||||||||||||||||||||||||||||||||||||||||||
orf58a     FPELALMLFHAVKTAVYWLFVGVVRFCRNYLAHESEPDRPVPPASANRADVPTASDGYSD
                    60        70        80        90       100       110
```

The complete length ORF58a nucleotide sequence <SEQ ID 491> is:

```
   1 ATGTTTTGGA TAGTTTTGAT CGTTATTTTG TTGCTTGCGC TTGCCGGCTT
  51 GTTTTTTGTC CGCGCACAAT CCGAACGCGA GTGGATGCGC GAGGTTTCTG
 101 CGTGGCAGGA AAAGAAAGGG GAAAAACAGG CGGAGCTGCC TGAAATCAAA
 151 GACGGTATGC CCGATTTTCC CGAACTTGCC CTGATGCTTT TCCATGCCGT
 201 CAAAACGGCA GTGTATTGGC TGTTTGTCGG TGTCGTCCGT TTCTGCCGAA
 251 ACTATCTGGC GCACGAATCC GAACCGGACA GGCCCGTTCC GCCTGCTTCT
 301 GCAAATCGTG CGGATGTTCC GACCGCATCC GACGGATATT CAGACAGTGG
 351 AAACGGGACG GAAGAAGCGG AAACGGAAGA AGCAGAAGCT GCGGAGGAAG
 401 AGGCTGCCGA TACGAAGAC ATTGCAACTG CCGTAATCGA CAACCGCCGC
 451 ATCCCATTCG ACCGGAGTAT TGCTGAAGGG TTGATGCCGT CTGAAAGCGA
 501 AATTTCGCCC GTCCGTCCGG TTTTTAAGGA AATCACTTTG AAGAAGCAA
 551 CGCGTGCTTT AAACAGCGCG GCTTTAAGGG AAACGAAAAA ACGCTATATC
 601 GATGCATTTG AGAAAAACGA AACAGCGGTC CCCAAAGTCC GCGTGTCCGA
 651 TACCCCGATG GAAGGGCTGC AGATTATCGG TTTGGACGAC CCTGTGCTTC
 701 AACGCACGTA TTCCCGTATG TTCGATGCGG ACAAAGAAGC GTTTTCCGAG
 751 TCTGCGGATT ACGGATTTGA GCCGTATTTT GAGAAGCAGC ATCCGTCTGC
 801 CTTTTCTGCA GTCAAAGCCG AAAATGCACG GAATGCGCCG TTCCGCCGTC
 851 ATGCAGGGCA GGGNAAAGGG CAGGCGGAGG CNAAATCCCC GGATGTTTCC
 901 CAAGGGCAGT CCGTTTCAGA CGGCACAGCC GTCCGCGATG CCNGCCGCCG
 951 CGTTTCCGTC AATTTGAAAG AACCGAACAA GGCAACGGTT TCTGCGGAGG
1001 CGCGGATTTC GCGCCTGATT CCGGAAAGTC GGACGGTTGT CGGGAAACGG
1051 GATGTCGAAA TGCCGTCTGA AACCGAAAAT GTTTTCACGG AAANTGTTTC
1101 GTCTGTGGGA TACGGCGNTC CGGTTTATGA TGAAACTGCC GATATCCATA
1151 TTGAAGAACC TGCCGCGCCC GATGCTTGGG TGGTCGAACC ACCCGAAGTG
1201 CCGAAAGTTC CCATGCCCGC AATNGATATT CCGCCGCCGC CTCCCGTATC
1251 GGAAATCTAC AACCGTACCT ATGAACCGCC GGCAGGATTC GAGCAGGTGC
1301 AACGCAGCCG CATTGCCGAA ACCGATCATC TTGCCGATGA TGTTTTGAAT
1351 GGAGGTTGGC AGGAGGAAAC CGCCGCTATT GCGAATGACG GCAGTGAGGG
1401 TGTGGCAGAG CGGTCAAGCG GGCAATATTT GTCGGAAACC GAAGCGTTCG
1451 GGCATGACAG TCAGGCGGTT TGTCCGTTTG AAAATGTGCC GTCTGAACGC
1501 CCGTCCCGCC GGGCATNGGA TACGGAAGCG GATGAAGGGG CGTTCCAATC
1551 TGAAGAAACC GGTGCGGTAT CCGAACACCT GCCGACAACC GACCTGCTTC
1601 TGCCGCCGCT GTTCAATCCC GGGGCGACGC AAACCGAAGA AGANCTGTTG
1651 GANAACAGCA TCACCATCGA AGAAAAATNG GCGGAGTTCA AAGTCAAGGT
1701 CAAGGTTGTC GATTCTTATT CCGGCCCCGT GATTACGCGT TATGAAATCG
```

-continued

```
1751 AACCCGATGT CGGCGTGCGC GGCAATTCCG TTCTAAATCT GGAAAAAGAN
1801 TTGGCGCGTT CGCTCGGCGT GGCTTCCATC CGCGTTGTCG AAACCATCCT
1851 CGGCAAAACC TGTATGGGTT TGGAACTTCC GAACCCGAAA CGCCAAATGA
1901 TACGCCTGAG CGAAATCTTC AATTCGCCCG AGTTTGCCGA ATCCAAATCC
1951 AAGCTGACGC TCGCGCTCGG TCAGGACATC ACCGGACAGC CCGTCGTAAC
2001 CGACTTGGGC AAAGCACCGC ATTTGTTGGT TGCCGGCACG ACCGGTTCGG
2051 GCAAATCGGT GGGTGTCAAC GCGATGATTC TGTCTATGCT TTTCAAAGCC
2101 GCGCCGGAAG ACGTGCGTAT GATTATGATC GATCCGAAAA TGCTGGAATT
2151 GAGCATTTAC GAAGGCATCC CGCACCTGCT CGCCCCTGTC GTTACCGATA
2201 TGAAGCTGGC GGCAAACGCG CTGAACTGGT GTGTTAACGA AATGGAAAAA
2251 CGCTACCGCC TGATGAGCTT TATGGGCGTG CGCAATCTTG CGGGTNTCAA
2301 TCAAAAAATC GCCGAAGCCG CAGCAAGGGG GGAGAAAATC GGCAACCCGT
2351 TCAGCCTCAC GCCCGACAAT CCCGAACCTT TGGANAAATT GCCGTTTATC
2401 GTGGTCGTGG TTGATGAGTT TGCCGACCTG ATGATGACGG CAGGCAAGAA
2451 AATCGAAGAA CTGATTGCCC GCCTCGCCCA AAAGCCCGC GCGGCAGGCA
2501 TCCATCTTAT CCTTGCCACA CAACGCCCCA GTGTCGATGT CATCACGGGT
2551 CTGATTAAGG CGAACATCCC GACGCGTATC GCGTTCCAAG TGTCCAGCAA
2601 AATCGACAGC CGCACGATTC TTGACCAAAT GGGTGCGGAA AACCTGCTCG
2651 GGCAGGGCGA TATGCTGTTC CTGCCGCCGG GTACGGCCTA TCCGCAGCGC
2701 GTTCACGGCG CGTTTGCCTC GGATGAAGAG GTGCACCGCG TGGTCGAATA
2751 TCTGAAACAG TTTGGCGAAC CGGACTATGT TGACGATATN TTGAGCGGCG
2801 GTATGTCCGA CGATTTGCTG GGAATCAGCC GGAGCGGCGA CGGCGAAACC
2851 GATCCGATGT ACGACGAGGC CGTGTCNGTT GTTTTGAAAA CGCGCAAAGC
2901 CAGCATTTCT GGCGTGCAGC GCGCATTGCG TATCGGCTAT AATCGCGCCG
2951 CGCGTCTGAT TGACCAGATG GAGGCGGAAG GCATTGTGTC CGCACCGGAA
3001 CACAACGGCA ACCGTACGAT TCTCGTCCCC TTNGACAATG CTTGA
```

This encodes a protein having amino acid sequence <SEQ ID 492>:

```
  1 MFWIVLIVIL LLALAGLFFV RAQSEREWMR EVSAWQEKKG EKQAELPEIK
 51 DGMPDFPELA LMLFHAVKTA VYWLFVGVVR FCRNYLAHES EPDRPVPPAS
101 ANRADVPTAS DGYSDSGNGT EEAETEEAEA AEEEAADTED IATAVIDNRR
151 IPFDRSIAEG LMPSESEISP VRPVFKEITL EEATRALNSA ALRETKKRYI
201 DAFEKNETAV PKVRVSDTPM EGLQIIGLDD PVLQRTYSRM FDADKEAFSE
251 SADYGFEPYF EKQHPSAFSA VKAENARNAP FRRHAGQGKG QAEAKSPDVS
301 QGQSVSDGTA VRDAXRRVSV NLKEPNKATV SAEARISRLI PESRTVVGKR
351 DVEMPSETEN VFTEXVSSVG YGXPVYDETA DIHIEEPAAP wDAWVVEPPEV
401 PKVPMPAXDI PPPPPVSEIY NRTYEPPAGF EQVQRSRIAE TDHLADDVLN
451 GGWQEETAAI ANDGSEGVAE RSSGQYLSET EAFGHDSQAV CPFENVPSER
501 PSRRAXDTEA DEGAFQSEET GAVSEHLPTT DLLLPPLFNP GATQTEEXLL
```

-continued
```
551 XNSITIEEKX AEFKVKVKVV DSYSGPVITR YEIEPDVGVR GNSVLNLEKX

601 LARSLGVASI RVVETILGKT CMGLELPNPK RQMIRLSEIF NSPEFAESKS

651 KLTLALGQDI TGQPVVTDLG KAPHLLVAGT TGSGKSVGVN AMILSMLFKA

701 APEDVRMIMI DPKMLELSIY EGIPHLLAPV VTDMKLAANA LNWCVNEMEK

751 RYRLMSFMGV RNLAGXNQKI AEAAARGEKI GNPFSLTPDN PEPLXKLPFI

801 VVVVDEFADL MMTAGKKIEE LIARLAQKAR AAGIHLILAT QRPSVDVITG

851 LIKANIPTRI AFQVSSKIDS RTILDQMGAE NLLGQGDMLF LPPGTAYPQR

901 VHGAFASDEE VHRVVEYLKQ FGEPDYVDDX LSGGMSDDLL GISRSGDGET

951 DPMYDEAVSV VLKTRKASIS GVQRALRIGY NRAARLIDQM EAEGIVSAPE

1001 HNGNRTILVP XDNA*
```

ORF58a and ORF58-1 show 96.6% identity in 1014 aa overlap:

```
                  10         20         30         40         50         60
orf58a.pep MFWIVLIVILLLALAGLFFVRAQSEREWMREVSAWQEKKGEKQAELPEIKDGMPDFPELA
           ||||||||||||||||||||||||||||||||||||||||||||||||||||||||||||
orf58-1    MFWIVLIVILLLALAGLFFVRAQSEREWMREVSAWQEKKGEKQAELPEIKDGMPDFPELA
                  10         20         30         40         50         60

70         80         90        100        110        120
orf58a.pep LMLFHAVKTAVYWLFVGVVRFCRNYLAHESEPDRPVPPASNRADVPTASDGYSDSGNGT
           ||||||||||||||||||||||||||||||||||||||||||||||||||||||||||||
orf58-1    LMLFHAVKTAVYWLFVGVVRFCRNYLAHESEPDRPVPPASNRADVPTASDGYSDSGNGT
                  70         80         90        100        110        120

130        140        150        160        170        180
orf58a.pep EEAETEEAEAAEEEAADTEDIATAVIDNRRIPFDRSIAEGLMPSESEISPVRPVFKEITL
           ||||||||||||||||||||||||||||||||||||||||||||||||||||||||||||
orf58-1    EEAETEEAEAAEEEAADTEDIATAVIDNRRIPFDRSIAEGLMPSESEISPVRPVFKEITL
                 130        140        150        160        170        180

190        200        210        220        230        240
orf58a.pep EEATRALNSAALRETKKRYIDAFEKNETAVPKVRVSDTPMEGLQIIGLDDPVLQRTYSRM
           |||||||||||||||||||||||||||||||||||||||||||||||||||||||||:|
orf58-1    EEATRALNSAALRETKKRYIDAFEKNETAVPKVRVSDTPMEGLQIIGLDDPVLQRTYSHM
                 190        200        210        220        230        240

250        260        270        280        290        300
orf58a.pep FDADKEAFSESADYGFEPYFEKQHPSAFSAVKAENARNAPFRRHAGQGKGQAEAKSPDVS
           |||||||||||||||||||||||||||||||||||||||||:||||||||||||||||||
orf58-1    FDADKEAFSESADYGFEPYFEKQHPSAFSAVKAENARNAPFHRHAGQGKGQAEAKSPDVS
                 250        260        270        280        290        300

310        320        330        340        350        360
orf58a.pep QGQSVSDGTAVRDAXRRVSVNLKEPNKATVSAEARISRLIPESRTVVGKRDVEMPSETEN
           ||||||||||||||| ||||||||||||||||||||||||:|||||||||||||||||||
orf58-1    QGQSVSDGTAVRDARRRVSVNLKEPNKATVSAEARISRLIPESQTVVGKRDVEMPSETEN
                 310        320        330        340        350        360

370        380        390        400        410        420
orf58a.pep VFTEXVSSVGYGXPVYDETADIHIEEPAAPDAWVVEPPEVPKVPMPAXDIPPPPPVSEIY
           ||||:||||||||  |||||||||||||||||||||||||||||| :|||||||||||||
orf58-1    VFTETVSSVGYGGPVYDETADIHIEEPAAPDAWVVEPPEVPKVPMTAIDIPPPPPVSEIY
                 370        380        390        400        410        420

430        440        450        460        470        480
orf58a.pep NRTYEPPAGFEQVQRSRIAETDHLADDVLNGGWQEETAAIANDGSEGVAERSSGQYLSET
           ||||||:||||||||||||||||||||||||||||||||||:|||||:||||||||||||
orf58-1    NRTYEPPSGFEQVQRSRIAETDHLADDVLNGGWQEETAAIADDGSEGAAERSSGQYLSET
                 430        440        450        460        470        480

490        500        510        520        530        540
orf58a.pep EAFGHDSQAVCPFENVPSERPSRRAXDTEADEGAFQSEETGAVSEHLPTTDLLLPPLFNP
           |||||||||||||||||||||||| |:|||||||||:||||||||||||||||||||||
orf58-1    EAFGHDSQAVCPFENVPSERPSCRVSDTEADEGAFPSEETGAVSEHLPTTDLLLPPLFNP
                 490        500        510        520        530        540

550        560        570        280        590        600
orf58a.pep GATQTEEXLLXNSITIEEKXAEFKVKVKVVDSYGPVITRYEIEPDVGVRGNSVLNLEKX
           |||||||| || |||||||| |||||||||||||||||||||||||||||||||||||||
orf58-1    GATQTEEELLENSITIEEKLAEFKVKVKVVDSYGPVITRYEIEPDVGVRGNSVLNLEKX
                 550        560        570        280        590        600
```

-continued

```
                      610        620        630        640        650        660
orf58a.pep  LARSLGVASIRVVETILGKTCMGLELPNPKRQMIRLSEIFNSPEFAESKSKLTLALGQDI
            ||||||||||||||||| ||||||||||||||||||||||||||||||||||||||||||
orf58-1     LARSLGVASIRVVETIPGKTCMGLELPNPKRQMIRLSEIFNSPEFAESKSKLTLALGQDI
                      610        620        630        640        650        660

670        680        690        700        710        720
orf58a.pep  TGQPVVTDLGKAPHLLVAGTTGSGKSVGVNAMILSMLFKAAPEDVRMIMIDPKMLELSIY
            ||||||||||||||||||||||||||||||||||||||||||||||||||||||||||||
orf58-1     TGQPVVTDLGKAPHLLVAGTTGSGKSVGVNAMILSMLFKAAPEDVRMIMIDPKMLELSIY
                      670        680        690        700        710        720

730        740        750        760        770        780
orf58a.pep  EGIPHLLAPVVTDMKLAANALNWCVNEMEKRYRLMSFMGVRNLAGXNQKIAEAAARGEKI
            |||||||||||||||||||||||||||||||||||||||||||||| |||||||||||||
orf58-1     EGIPHLLAPVVTDMKLAANALNWCVNEMEKRYRLMSFMGVRNLAGFNQKIAEAAARGEKI
                      730        740        750        760        770        780

790        800        810        820        830        840
orf58a.pep  GNPFSLTPDNPEPLXKLPFIVVVVDEFADLMMTAGKKIEELIARLAQKARAAGIHLILAT
            |||||||||:||| ||||||||||||||||||||||||||||||||||||||||||||||
orf58-1     GNPFSLTPDDPEPLEKLPFIVVVVDEFADLMMTAGKKIEELIARLAQKARAAGIHLILAT
                      790        800        810        820        830        840

850        860        870        880        890        900
orf58a.pep  QRPSVDVITGLIKANIPTRIAFQVSSKIDSRTILDQMGAENLLGQGDMLFLPPGTAYPQR
            ||||||||||||||||||||||||||||||||||||||||||||||||||||||||||||
orf58-1     QRPSVDVITGLIKANIPTRIAFQVSSKIDSRTILDQMGAENLLGQGDMLFLLPGTAYPQR
                      850        860        870        880        890        900

910        920        930        940        950        960
orf58a.pep  VHGAFASDEEVHRVVEYLKQFGEPDYVDDXLSGGMSDDLLGISRSGDGETDPMYDEAVSV
            ||||||||||||||||||||||||||||| |||  |::| ||:|||||:|||||||||||
orf58-1     VHGAFASDEEVHRVVEYLKQFGEPDYVDDILSGGGSEELPGIGRSGDDETDPMYDEAVSV
                      910        920        930        940        950        960

970        980        990       1000       1010
orf58a.pep  VLKTRKASISGVQRALRIGYNRAARLIDQMEAEGIVSAPEHNGNRTILVPXDNAX
            ||||||||||||||||||||||||||||||||||||||||||||||||||| |||
orf58-1     VLKTRKASISGVQRALRIGYNRAARLIDQMEAEGIVSAPEHNGNRTILVPLDNAX
                      970        980        990       1000       1010
```

Homology with a Predicted ORF from *N. gonorrhoeae*

ORF58 shows complete identity over a 9aa overlap with a predicted ORF (ORF58ng) from *N. gonorrhoeae*.

```
orf58.pep   ALMLFHAVKTAVYWLFVGVVRFCRNYLAHESEPDRPVPP                      103
                                           |||||||||
orf58ng                                    SEPDRPVPPASANRADVPTASDGYSDSGNG  30
```

The ORF58ng nucleotide sequence <SEQ ID 493> is predicted to encode a protein having partial amino acid sequence <SEQ ID 494>:

```
  1..SEPDRPVPPA SANRADVPTA SDGYSDSGNG TEEAETEAAE AAEEEAADTE

51   DIATAVIDNR RIPFDRSIAE GLMQSESKTS PVRPVFKEIT LEEATRALSS

101   AALRETKKRY IDAFEKNGTA VPKVRVSDTP MEGLQIIGLD DPVLQRTYSR

151   MFDADKEAFS ESADYGFEPY FEKQHPSAFS AVKAENARNA PFRRHAGQEK

201   GQAEAKSPDV SQGQSVSDGT AVRDARRRVS VNLKEPNKAT VSAEARISRL

251   IPESRTVVGK RDVEMPSETE NVFTETVSSV GYGGPVYDEA ADIHIEEPAA

301   PDAWVVEPPE VPEVAVPEID ILPPPPVSEI YNRTYEPPAG FEQAQRSRIA

351   ETDHLAADVL NGGWQEETAA IADDGSEGAA ERSSGQYLSE TEAFGHDSQA

401   VCPFEDVPSE RPSCRVSDTE ADEGAFQSEE TGAVSEHLPT TDLLLPPLFN

451   PEATQTEEEL LENSITIEEK LAEFKVKVKV VDSYSGPVIT RYEIEPDVGV

501   RGNSVLNLEK DLARSLGVAS IRVVETIPGK TCMGLELPNP KRQMIRLSEI

551   FNSPEFAESK SKLTLALGQD ITGQPVVTDL GKAPHLLVAGTTGSGKSVGV

601   NAMILSMLFK AAPEDVRMIM IDPKMLELSI YEGITHLLAP VVTDMKLAAN
```

```
651  ALNWCVNEME KRYRLMSFMG VRNLAGFNQK IAEAAARGEK IGNPFSLTPD

701  DPEPLEKLPF IVVVVDEFAD LMMTAGKKIE ELIARLAQKA RAAGIHLILA

751  TQRPSVDVIT GLIKANIPTR IAFQVSSKID SRTILDQMGA ENLLGQGDML

801  FLPPGTAYPQ RVHGAFASDE EVHRVVEYLK QFGEPDYVDD ILSGGGSEEL

851  PGIGRSGDGE TDPMYDEAVS VVLKTRKASI SGVQRALRIG YNRAARLIDQ

901  MEAEGIVSAP EHNGNRTILV PLDNA*
```

This partial gonococcal sequence contains a predicted transmembrane region and a predicted ATP/GTP-binding site motif A (P-loop; double underlined). Furthermore, it has a domain homologous to the FTSK cell division protein of *E. coli*. Alignment of ORF58ng and FtsK (accession number p46889) show a 65% amino acid identity in 459 overlap:

```
ORF58ng:    467 IEEKLAEFKVKVKVVDSYSGPVITRYEIEPDVGVRGNSVLNLEKDLARSLGVASIRVVET    526
                +E +LA+F++K VV+   GPVITR+E+    GV+  + NL +DLARSL  ++RVVE
FtsK:       868 VEARLADFRIKADVVNYSPGPVITRFELNLAPGVKAARISNLSRDLARSLSTVAVRVVEV    927

ORF58ng:    527 IPGKTCMGLELPNPKRQMIRLSEIFNSPEFAESKSKLTLALGQDITGQPVVTDLGKAPHL    586
                IPGK  +GLELPN KRQ + L E+ ++ +F ++ S LT+ LG+DI G+PVV DL K PHL
FtsK:       928 IPGKPYVGLELPNKKRQTVYLREVLDNAKFRDNPSPLTVVLGKDIAGEPVVADLAKMPHL    987

ORF58ng:    587 LVAGTTGSGKSVGVNAMILSMLFKAAPEDVRMIMIDPKMLELSIYEGITHLLAPVVTDMK    646
                LVAGTTGSGKSVGVNAMILSML+KA  PEDVR IMIDPKMLELS+YEGI HLL  VVTDMK
FtsK:       988 LVAGTTGSGKSVGVNAMILSMLYKAQPEDVRFIMIDPKMLELSVYEGIPHLLTEVVTDMK   1047

ORF58ng:    647 LAANALNWCVNEMEKRYRLMSFMGVRNLAGFNQKIAEAAARGEKIGNPFSLTPDDPEP--    704
                 AANAL WCVNEME+RY+LMS +GVRNLAG+N+KIAEA    I +P+   D +
FtsK:      1048 DAANALRWCVNEMERRYKLMSALGVRNLAGYNEKIAEADRMMRPIPDPYWKPGDSMDAQH   1107

ORF58ng:    705 --LEKLPFIVVVVDEFADLMMTAGKKIEELIARLAQKARAAGIHLILATQRPSVDVITGL    762
                  L+K P+IVV+VDEFADLMMT GKK+EELIARLAQKARAAGIHL+LATQRPSVDVITGL
FtsK:      1108 PVLKKEPYIVVLVDEFADLMMTVGKKVEELIARLAQKARAAGIHLVLATQRPSVDVITGL   1167

ORF58ng:    763 IKANIPTRIAFQVSSKIDSRTILDQMGAENLLGQGDMLFLPPGTAYPQRVHGAFASDEEV    822
                IKANIPTRIAF VSSKIDSRTILDQ GAE+LLG GDML+   P + P RVHGAF D+EV
FtsK:      1168 IKANIPTRIAFTVSSKIDSRTILDQAGAESLLGMGDMLYSGPNSTLPVRVHGAFVRDQEV   1227

ORF58ng:    823 HRVVEYLKQFGEPDYVDDILSGGGSEELPGIGRSGDGETDPMYDEAVSVVLKTRKASISG    882
                H VV+    K  G P YVD I S    SE   G G   E DP++D+AV V + RKASISG
FtsK:      1228 HAVVQDWKARGRPQYVDGITSDSESEGGAG-GFDGAEELDPLFDQAVQFVTEKRKASISG   1286

ORF58ng:    883 VQRALRIGYNRAARLIDQMEAEGIVSAPEHNGNRTILVP                        921
                VQR  RIGYNRAAR+I+QMEA+GIVS    HNGNR +L P
FtsK:      1287 VQRQFRIGYNRAARIIEQMEAQGIVSEQGHNGNREVLAP                       1325
```

Further work on ORF58ng revealed the complete gonococcal DNA sequence to be <SEQ ID 495>:

```
  1  ATGTTTTGGA TAGTTTTGAT CGTTATgtg TTGCTTGCGC TTGCCGGCCT

51  GTTTTTTGTC CGCGCACAAT CCGAACGCGA GTGGATGCGC GAGGTTTCTG

101  CGTGGCAGGA AAAGAAGGG GAAAAACAGG CGGAGCTGCC TGAAATCAAA

151  GACGGTATGC CCGATTTTCC CGAGTTTTCC CTGATGCTTT TCCATGCCGT

201  CAAAACGGCA GTGTATTGGC TGTTTGTCGG TGTCGTCCGT TTCTGCCGAA

251  ACTATCTGGC GCACGAATCC GAACCGGACA GGCCCGTTCC GCCTGCTTCT

301  GCAAACCGTG CGGATGTTCC GACCGCATCC GACGGGTATT CAGACAGTGG

351  AAACGGGACG GAAGAAGCGG AAACGGAAGC AGCAGAAGCT GCGGAGGAAG

401  AGGCTGCCgA TACgGAAGAC ATTGCAACTG CCGTAATCGA CAACCGCCGC

451  ATCCcatTCG ACCGGAGTAT TGCTGAAGGG TTGATGCAGT CTGAAAGCAA
```

-continued

```
 501 AACTTCGCCC GTCCGTCCGG TTTTTAAGGA AATCACTTTG GAAGAAGCAA

551 CGCGTGCTTT AAGCAGCGCG GCTTTAAGGG AAACGAAAAA ACGCTATATC

601 GATGCATTTG AGAAAAACGG AACAGCCGTC CCCAAAGTAC GCGTGTCCGA

651 TACCCCGATG AAGGGCTGC AGATTATCGG TTTGGACGAC CCTGTGCTTC

701 AACGCACGTA TTCCCGTATG TTTGATGCGG ACAAAGAAGC GTTTTCCGAG

751 TCTGCGGATT ACGGATTTGA GCCGTATTTT GAGAAGCAGC ATCCGTCTGC

801 CTTTTCTGCA GTCAAAGCCG AAAATGCACG GAATGCGCCG TTCCGCCGTC

851 ATGCAGGGCA GGAGAAAGGG CAGGCGGAGG CAAAATCCCC GGATGTTTCC

901 CAAGGGCAGT CCGTTTCAGA CGGCACAGCC GTCCGCGATG CCCGCCGCCG

951 CGTTTCCGTC AATTTGAAAG AACCGAACAA GGCAACGGTT TCTGCGGAGG

1001 CGCGGATTTC GCGCCTGATT CCGGAAAGTC GGACGGTTGT CGGGAAACGG

1051 GATGTCGAAA TGCCGTCTGA AACCGAAAAT GTTTTCACGG AAACCGTTTC

1101 GTCTGTGGGA TACGGCGGTC CGGTTTATGA TGAAGCTGCC GATATCCATA

1151 TTGAAGAGCC TGCCGCGCCC GATGCTTGGG TGGTCGAACC ACCCGAAGTG

1201 CCGGAGGTAG CCGTACCCGA AATCGATATT CTGCCGCCGC CTCCCGTATC

1251 GGAAATCTAC AACCGTACCT ATGAGCCGCC GGCAGGATTC GAGCAGGCGC

1301 AACGCAGCCG CATTGCCGAA ACCGACCATC TTGCCGCTGA TGTTTTGAAT

1351 GGAGGTTGGC AGGAGGAAAC CGCCGCTATT GCAGATGACG GCAGTGAGGG

1401 TGCGGCAGAG CGGTCAAGCG GCAATATCT GTCGGAAACC GAAGCGTTCG

1451 GGCATGACAG TCAGGCGGTT TGTCCGTTTG AAGATGTGCC GTCTGAACGC

1501 CCGTCCTGCC GGGTATCGGA TACGGAAGCG GATGAAGGGG CGTTCCAATC

1551 GGAAGAGACC GGTGCGGTAT CCGAACACCT GCCGACAACC GACCTGCTTC

1601 TGCCTCCGCT GTTCAATCCC GAGGCGACGC AAACCGAAGA AGAACTGTTG

1651 GAAAACAGCA TCACCATCGA AGAAAAATTG GCGGAGTTCA AAGTCAAGGT

1701 CAAGGTTGTC GATTCTTATT CCGGCCCCGT GATTACGCGT TATGAAATCG

1751 AACCCGATGT CGGCGTGCGC GGCAATTCCG TTCTGAATTT GGAAAAAGAC

1801 TTGGCGCGTT CGCTCGGCGT GGCTTCCATC CGCGTTGTCG AAACCATCCC

1851 CGGCAAAACC TGCATGGGTT TGGAACTTCC GAACCCGAAA CGCCAAATGA

1901 TACGCCTGAG CGAAATTTTC AATTCGCCCG AGTTTGCCGA ATCCAAATCC

1951 AAGCTGACGC TCGCGCTCGG TCAGGACATT ACCGGACAGC CGTCGTAAC

2001 CGACTTGGGC AAAGCACCGC ATTTGCTGGT TGCCGGCACG ACCGGTTCGG

2051 GCAAATCGGT GGGTGTCAAC GCGATGATTC TGTCTATGCT TTTCAAAGCC

2101 GCGCCGGAAG ACGTGCGTAT GATTATGATC GATCCGAAAA TGCTGGAATT

2151 GAGCATTTAC GAAGGCATCA CGCACCTGCT CGCCCCTGTC GTTACCGATA

2201 TGAAGCTGGC GGCAAACGCG CTGAACTGGT GTGTTAACGA AATGGAAAAA

2251 CGCTACCGCC TGATGAGCTT TATGGGCGTG CGCAATCTTG CGGGCTTCAA

2301 CCAAAAAATC GCCGAAGCCG CAGCAAGGGG AGAAAAAATC GGCAATCCGT

2351 TCAGCCTCAC GCCCGACGAT CCGAACCTT TGGAAAAACT GCCGTTTATC

2401 GTGGTCGTGG TCGATGAGTT TGCCGATTTG ATGATGACGG CAGGCAAGAA

2451 AATCGAAGAA CTGATTGCGC GCCTCGCCCA AAAGCCCGC GCGGCAGGCA

2501 TCCACCTTAT CCTTGCCACA CAACGCCCCA GCGTCGATGT CATCACGGGT
```

```
2551  CTGATTAAGG CGAACATCCC GACGCGTATC GCGTTCCAAG TGTCCAGCAA
2601  AATCGACAGC CGCACGATTC TCGACCAAAT GGGCGCGGAA AACCTGCTCG
2651  GTCAGGGCGA TATGCTGTTC CTGCCGCCGG GTACTGCCTA TCCGCAGCGC
2701  GTTCACGGCG CGTTTGCCTC GGATGAAGAG GTGCACCGCG TGGTCGAATA
2751  TCTGAAGCAG TTTGGCGAGC CGGACTATGT TGACGATATT TTGAGCGGCG
2801  GCGGCAGCGA AGAGCTGCCC GGCATCGGGC GCAGCGGCGA CGGCGAAACC
2851  GATCCGATGT ACGACGAGGC CGTATCCGTT GTCCTGAAAA CGCGCAAAGC
2901  CAGCATTTCG GGCGTACAGC GCGCCTTGCG CATCGGCTAC AACCGCGCCG
2951  CGCGTCTGAT TGACCAAATG GAAGCGGAAG GCATTGTGTC CGCACCGGAA
3001  CACAACGGCA ACCGTACGAT TCTCGTCCCC TTGGACAATG CTTGA
```

This corresponds to the amino acid sequence <SEQ ID 496; ORF58ng-1>:

```
   1  MFWIVLIVIV LLALAGLFFV RAQSEREWMR EVSAWQEKKG EKQAELPEIK
  51  DGMPDFPEFS LMLFHAVKTA VYWLFVGVVR FCRNYLAHES EPDRPVPPAS
 101  ANRADVPTAS DGYSDSGNGT EEAETEAAEA AEEEAADTED IATAVIDNRR
 151  IPFDRSIAEG LMQSESKTSP VRPVFKEITL EEATRALSSA ALRETKKRYI
 201  DAFEKNGTAV PKVRVSDTPM EGLQIIGLDD PVLQRTYSRM FDADKEAFSE
 251  SADYGFEPYF EKQHPSAFSA VKAENARNAP FRRHAGQEKG QAEAKSPDVS
 301  QGQSVSDGTA VRDARRRVSV NLKEPNKATV SAEARISRLI PESRTVVGKR
 351  DVEMPSETEN VFTETVSSVG YGGPVYDEAA DIHIEEPAAP DAWVVEPPEV
 401  PEVAVPEIDI LPPPPVSEIY NRTYEPPAGF EQAQRSRIAE TDHLAADVLN
 451  GGWQEETAAI ADDGSEGAAE RSSGQYLSET EAFGHDSQAV CPFEDVPSER
 501  PSCRVSDTEA DEGAFQSEET GAVSEHLPTT DLLLPPLFNP EATQTEEELL
 551  ENSITIEEKL AEFKVKVKVV DSYSGPVITR YEIEPDVGVR GNSVLNLEKD
 601  LARSLGVASI RVVETIPGKT CMGLELPNPK RQMIRLSEIF NSPEFAESKS
 651  KLTLALGQDI TGQPVVTDLG KAPHLLVAGT TGSGKSVGVN AMILSMLFKA
 701  APEDVRMIMI DPKMLELSIY EGITHLLAPV VTDMKLAANA LNWCVNEMEK
 751  RYRLMSFMGV RNLAGFNQKI AEAAARGEKI GNPFSLTPDD PEPLEKLPFI
 801  VVVVDEFADL MMTAGKKIEE LIARLAQKAR AAGIHLILAT QRPSVDVITG
 851  LIKANIPTRI AFQVSSKIDS RTILDQMGAE NLLGQGDMLF LPPGTAYPQR
 901  VHGAFASDEE VHRVVEYLKQ FGEPDYVDDI LSGGGSEELP GIGRSGDGET
 951  DPMYDEAVSV VLKTRKASIS GVQRALRIGY NRAARLIDQM EAEGIVSAPE
1001  HNGNRTILVP LDNA*
```

ORF58ng-1 and ORF58-1 show 97.2% identity in 1014 aa overlap:

```
                      10         20         30         40         50         60
orf58-1.pep  MFWIVLIVILLLALAGLFFVRAQSEREWMREVSAWQEKKGEKQAELPEIKDGMPDFPELA
             ||||||||||:||||||||||||||||||||||||||||||||||||||||||||||::
orf58ng-1    MFWIVLIVIVLLALAGLFFVRAQSEREWMREVSAWQEKKGEKQAELPEIKDGMPDFPEFS
                      10         20         30         40         50         60
```

```
                      70         80         90        100        110        120
orf58-1.pep   LMLFHAVKTAVYWLFVGVVRFCRNYLAHESEPDRPVPPASANRADVPTASDGYSDSGNGT
              ||||||||||||||||||||||||||||||||||||||||||||||||||||||||||||
orf58ng-1     LMLFHAVKTAVYWLFVGVVRFCRNYLAHESEPDRPVPPASANRADVPTASDGYSDSGNGT
                      70         80         90        100        110        120

130        140        150        160        170        180
orf58-1.pep   EEAETEEAEAAEEEAADTEDIATAVIDNRRIPFDRSIAEGLMPSESEISPVRPVFKEITL
              ||||||:|||||||||||||||||||||||||||||||||:||||:|:||||||||||||
orf58ng-1     EEAETEAAEAAEEEAADTEDIATAVIDNRRIPFDRSIAEGLMQSESKTSPVRPVFKEITL
                     130        140        150        160        170        180

190        200        210        220        230        240
orf58-1.pep   EEATRALNSAALRETKKRYIDAFEKNETAVPKVRVSDTPMEGLQIIGLDDPVLQRTYSHM
              ||||||:||||||||||||||||||||:||||||||||||||||||||||||||||||:|
orf58ng-1     EEATRALSSAALRETKKRYIDAFEKNGTAVPKVRVSDTPMEGLQIIGLDDPVLQRTYSRM
                     190        200        210        220        230        240

250        260        270        280        290        300
orf58-1.pep   FDADKEAFSESADYGFEPYFEKQHPSAFSAVKAENARNAPFHRHAGQGKGQAEAKSPDVS
              |||||||||||||||||||||||||||||||||||||||||:|||||:||||||||||||
orf58ng-1     FDADKEAFSESADYGFEPYFEKQHPSAFSAVKAENARNAPFRRHAGQEKGQAEAKSPDVS
                     250        260        270        280        290        300

310        320        330        340        350        360
orf58-1.pep   QGQSVSDGTAVRDARRRVSVNLKEPNKATVSAEARISRLIPESQTVVGKRDVEMPSETEN
              ||||||||||||||||||||||||||||||||||||||||||||:|||||||||||||||
orf58ng-1     QGQSVSDGTAVRDARRRVSVNLKEPNKATVSAEARISRLIPESRTVVGKRDVEMPSETEN
                     310        320        330        340        350        360

370        380        390        400        410        420
orf58-1.pep   VFTETVSSVGYGGPVYDETADIHIEEPAAPDAWVVEPPEVPKVPMTAIDIQPPPPVSEIY
              ||||||||||||||||||:|||||||||||||||||||||:|:|||||:||||||||||
orf58ng-1     VFTETVSSVGYGGPVYDEAADIHIEEPAAPDAWVVEPPEVAVPEIDILPPPPVSEIY
                     370        380        390        400        410        420

430        440        450        460        470        480
orf58-1.pep   NRTYEPPSGFEQVQRSRIAETDHLADDVLNGGWQEETAAIADDGSEGAAERSSGQYLSET
              ||||||:||||:||||||||||||||||||||||||||||||||||||||||||||||||
orf58ng-1     NRTYEPPAGFEQAQRSRIAETDHLAADVLNGGWQEETAAIADDGSEGAAERSSGQYLSET
                     430        440        450        460        470        480

490        500        510        520        530        540
orf58-1.pep   EAFGHDSQAVCPFENVPSERPSCRVSDTEADEGAFPSEETGAVSEHLPTTDLLLPPLFNP
              |||||||||||||:|||||||||||||||||||||:||||||||||||||||||||||||
orf58ng-1     EAFGHDSQAVCPFEDVPSERPSCRVSDTEADEGAFQSEETGAVSEHLPTTDLLLPPLFNP
                     490        500        510        520        530        540

550        560        570        580        590        600
orf58-1.pep   EATQTEEELLENSITIEEKLAEFKVKVKVVDSYSGPVITRYEIEPDVGVRGNSVLNLEKD
              ||||||||||||||||||||||||||||||||||||||||||||||||||||||||||||
orf58ng-1     EATQTEEELLENSITIEEKLAEFKVKVKVVDSYSGPVITRYEIEPDVGVRGNSVLNLEKD
                     550        560        570        580        590        600

610        620        630        640        650        660
orf58-1.pep   LARSLGVASIRVVETIPGKTCMGLELPNPKRQMIRLSEIFNSPEFAESKSKLTLALGQDI
              ||||||||||||||||||||||||||||||||||||||||||||||||||||||||||||
orf58ng-1     LARSLGVASIRVVETIPGKTCMGLELPNPKRQMIRLSEIFNSPEFAESKSKLTLALGQDI
                     610        620        630        640        650        660

670        680        690        700        710        720
orf58-1.pep   TGQPVVTDLGKAPHLLVAGTTGSGKSVGVNAMILSMLFKAAPEDVRMIMIDPKMLELSIY
              ||||||||||||||||||||||||||||||||||||||||||||||||||||||||||||
orf58ng-1     TGQPVVTDLGKAPHLLVAGTTGSGKSVGVNAMILSMLFKAAPEDVRMIMIDPKMLELSIY
                     670        680        690        700        710        720

730        740        750        760        770        780
orf58-1.pep   EGIPHLLAPVVTDMKLAANALNWCVNEMEKRYRLMSFMGVRNLAGFNQKIAEAAARGEKI
              ||||||||||||||||||||||||||||||||||||||||||||||||||||||||||||
orf58ng-1     EGIPHLLAPVVTDMKLAANALNWCVNEMEKRYRLMSFMGVRNLAGFNQKIAEAAARGEKI
                     730        740        750        760        770        780

790        800        810        820        830        840
orF58-1.pep   GNPFSLTPDDPEPLEKLPFIVVVVDEFADLMMTAGKKIEELIARLAQKARAAGIHLILAT
              ||||||||||||||||||||||||||||||||||||||||||||||||||||||||||||
orf58ng-1     GNPFSLTPDDPEPLEKLPFIVVVVDEFADLMMTAGKKIEELIARLAQKARAAGIHLILAT
                     790        800        810        820        830        840

850        860        870        880        890        900
orF58-1.pep   QRPSVDVITGLIKANIPTRIAFQVSSKIDSRTILDQMGAENLLGQGDMLFLLPGTAYPQR
              ||||||||||||||||||||||||||||||||||||||||||||||||||||:|||||||
orf58ng-1     QRPSVDVITGLIKANIPTRIAFQVSSKIDSRTILDQMGAENLLGQGDMLFLPPGTAYPQR
                     850        860        870        880        890        900

910        920        930        940        950        960
orF58-1.pep   VHGAFASDEEVHRVVEYLKQFGEPDYVDDILSGGGSEELPGIGRSGDDETDPMYDEAVSV
              ||||||||||||||||||||||||||||||||||||||||||||||||||||||||||||
orf58ng-1     VHGAFASDEEVHRVVEYLKQFGEPDYVDDILSGGGSEELPGIGRSGDDETDPMYDEAVSV
                     910        920        930        940        950        960
```

```
                      970       980       990      1000      1010
orf58-1.pep    VLKTRKASISGVQRALRIGYNRAARLIDQMEAEGIVSAPEHNGNRTILVPLDNAX
               ||||||||||||||||||||||||||||||||||||||||||||||||||||||
orf58ng-1      VLKTRKASISGVQRALRIGYNRAARLIDQMEAEGIVSAPEHNGNRTILVPLDNAX
                      970       980       990      1000      1010
```

Furthermore, ORF58ng-1 shows significant homology to the *E. coli* protein FtsK:

```
sp|P46889|FTSK_ECOLI CELL DIVISION PROTEIN FTSK >gi|1651412|gnl|PID|d1015290 (Dl
division protein FtsK [Escherichia coli] >gi|1651418|gnl|PID|d1015296 (D90727) Cell
division protein FtsK [Escherichia coli] >gi|1787117 (AE000191) cell division
protein FtsK [Escherichia coli] Length = 1329
Score = 576 bits (1469), Expect = e-163
Identities = 301/459 (65%), Positives = 353/459 (76%), Gaps = 5/459 (1%)

Query:   556  IEEKLAEFKVKVKVVDSYSGPVITRYEIEPDVGVAGNSVLNLEKDLARSLGVASIRVVET     615
              +E +LA+F++K  VV+     GPVITR+E+      GV+   + NL +DLARSL    ++RVVE
Sbjct:   868  VEARLADFRIKADVVNYSPGPVITRFELNLAPGVKAARISNLSRDLARSLSTVAVRVVEV     927

Query:   616  IPGKTCMGLELPNPKRQMIRLSEIFNSPEFAESKSKLTLALGQDITGQPVVTDLGKAPHL     675
              IPGK  +GLELPN KRQ + L E+ ++ +F ++ S LT+ LG+DI G+PVV DL K PHL
Sbjct:   928  IPGKPYVGLELPNKKRQTVYLREVLDNAKFRDNPSPLTVVLGKDIAGEPVVADLAKMPHL     987

Query:   676  LVAGTTGSGKSVGVNAMILSMLFKAAPEDVRMIMIDPKMLELSIYEGITHLLAPVVTDMK     735
              LVAGTTGSGKSVGVNAMILSML+KA  PEDVR IMIDPKMLELS+YEGI HLL   VVTDMK
Sbjct:   988  LVAGTTGSGKSVGVNAMILSMLYKAQPEDVRFIMIDPKMLELSVYEGIPHLLTEVVTDMK    1047

Query:   736  LAANALNWCVNEMEKRYRLMSFMGVRNLAGFNQKIAEAAARGEKIGNPFSLTPDDPEP--     793
              AANAL WCVNEME+RY+LMS +GVRNLAG+N+KIAEA      I +P+    D  +
Sbjct:  1048  DAANALRWCVNEMERRYKLMSALGVRNLAGYNEKIAEADRMMRPIPDPYWKPGDSMDAQH    1107

Query:   794  --LEKLPFIVVVVDEFADLMMTAGKKIEELIARLAQKARAAGIHLILATQRPSVDVITGL     851
                L+K P+IVV+VDEFADLMMT GKK+EELIARLAQKARAAGIHL+LATQRPSVDVITGL
Sbjct:  1108  PVLKKEPYIVVLVDEFADLMMTVGKKVEELIARLAQKARAAGIHLVLATQRPSVDVITGL    1167

Query:   852  IKANIPTRIAFQVSSKIDSRTILDQMGAENLLGQGDMLFLPPGTAYPQRVHGAFASDEEV     911
              IKANIPTRIAF VSSKIDSRTILDQ GAE+LLG GDML+   P +  P RVHGAF  D+EV
Sbjct:  1168  IKANIPTRIAFTVSSKIDSRTILDQAGAESLLGMGDMLYSGPNSTLPVRVHGAFVRDQEV    1227

Query:   912  HRVVEYLKQFGEPDYVDDILSGGGSEELPGIGRSGDGETDPMYDEAVSVVLKTRKASISG     971
               H VV+   K  G P YVD I S     SE     G G   E DP++D+AV  V + RKASISG
Sbjct:  1228  HAVVQDWKARGRPQYVDGITSDSESEGGAG-GFDGAEELDPLFDQAVQFVTEKRKASISG    1286

Query:   972  VQRALRIGYNRAARLIDQMEAEGIVSAPEHNGNRTILVP                         1010
              VQR  RIGYNRAAR+I+QMEA+GIVS   HNGNR +L P
Sbjct:  1287  VQRQFRIGYNRAARIIEQMEAQGIVSEQGHNGNREVLAP                         1325
```

Based on this analysis, it is predicted that the proteins from *N. meningitidis* and *N. gonorrhoeae*, and their epitopes, could be useful antigens for vaccines or diagnostics, or for raising antibodies.

Example 59

The following partial DNA sequence was identified in *N. meningitidis* <SEQ ID 497>:

```
    1  ATGATTTATC AAAGAAACCT CATCAAAGAA CTCTCTTTTA CCGCCGTCGG
   51  CATTTTCGTC GTCCTCTTGG CGGTATTGGT CTCCACGCAG GCAATCAACC
  101  TGCTCGGCCG TGCCGCCGAC GGGC..GTGA TCGCCATCGA TGCCGTGTTG
  151  GCATTGGTCG GCTTCTGGGT C.......... .......... ..........
                                  //
  901  .........A TTGCCATCGG TTTGTTTTTA ATTTACCAAA ACGGGCTGAC
  951  CCTGCTTTTT GAAGCCGTGG AAGACGGCAA AATCCATTTT TGGCTCGGAC
 1001  TGCTGCCTAT GCACATTATC ATGTTTGTCC TTGCACTCAT CCTGTTGCGC
 1051  GTCCGCAGTA TGCCCAGCCA GCCCTTCTGG CAGGCGGTTG GCAAAAGTCT
 1101  GACATTGAAA GGCGGAAAAT GA
```

This corresponds to the amino acid sequence <SEQ ID 498; ORF101>:

```
  1 MIYQRNLIKE LSFTAVGIFV VLLAVLVSTQ AINLLGRAAD GXVIAIDAVL
 51 ALVGFWV... .......... .......... .......... ..........
                              //
301 ...IAIGLFL IYQNGLTLLF EAVEDGKIHF WLGLLPMHII MFVLALILLR
351 VRSMPSQPFW QAVGKSLTLK GGK*
```

Further work revealed the complete nucleotide sequence <SEQ ID 499>:

```
   1 ATGATTTATC AAAGAAACCT CATCAAAGAA CTCTCTTTTA CCGCCGTCGG
  51 CATTTTCGTC GTCCTCTTGG CGGTATTGGT CTCCACGCAG GCAATCAACC
 101 TGCTCGGCCG TGCCGCCGAC GGGCGTGTCG CCATCGATGC CGTGTTGGCA
 151 TTGGTCGGCT TCTGGGTCAT CGGTATGACG CCGCTTTTGC TGGTGTTGAC
 201 CGCATTTATC AGTACGTTGA CCGTGTTGAC CCGCTACTGG CGCGACAGCG
 251 AAATGTCGGT CTGGCTATCC TGCGGATTGG CATTGAAACA ATGGATACGC
 301 CCGGTGATGC AGTTTGCCGT GCCGTTTGCC GTTTTGGTTG CCGTCATGCA
 351 GCTTTGGGTG ATACCGTGGG CAGAGCTACG CAGCCGCGAA TACGCTGAAA
 401 TCCTGAAGCA GAAGCAGGAA TTGTCTTTGG TGGAGGCAGG CGAGTTCAAC
 451 AGTTTGGGCA AGCGCAACGG CAGGGTTTAT TTTGTCGAAA CCTTCGATAC
 501 CGAATCCGGC ATCATGAAAA ACCTGTTCCT GCGCGAACAG GACAAAAACG
 551 GCGGCGACAA CATCATCTTC GCCAAAGAAG GTAACTTCTC GCTGAACGAC
 601 AACAAACGCA CGCTCGAATT GCGCCACGGC TACCGTTACA GCGGCACGCC
 651 CGGACGCGCC GACTACAATC AGGTTTCCTT CCAAAAACTC AACCTGATTA
 701 TCAGCACCAC GCCCAAACTC ATCGACCCCG TTTCCCACCG CCGTACCATT
 751 CCGACCGCCC AACTGATTGG CAGCAGCAAC CCGCAACATC AGGCGGAATT
 801 GATGTGGCGC ATCTCGCTGA CCGTCAGCGT CCTCCTACTC TGCCTGCTTG
 851 CCGTGCCGCT TTCCTATTTC AACCCGCGCA GCGGACATAC CTACAATATC
 901 TTGATTGCCA TCGGTTTGTT TTTAATTTAC CAAAACGGGC TGACCCTGCT
 951 TTTTGAAGCC GTGGAAGACG GCAAAATCCA TTTTTGGCTC GGACTGCTGC
1001 CTATGCACAT TATCATGTTT GCCGTTGCAC TCATCCTGTT GCGCGTCCGC
1051 AGTATGCCCA GCCAGCCCTT CTGGCAGGCG GTTGGCAAAA GTCTGACATT
1101 GAAAGGCGGA AAATGA
```

This corresponds to the amino acid sequence <SEQ ID 500; ORF101-1>:

```
  1 MIYQRNLIKE LSFTAVGIFV VLLAVLVSTQ AINLLGRAAD GRVAIDAVLA
 51 LVGFWVIGMT PLLLVLTAFI STLTVLTRYW RDSEMSVWLS CGLALKQWIR
101 PVMQFAVPFA VLVAVMQLWV IPWAELRSRE YAEILKQKQE LSLVEAGEFN
151 SLGKRNGRVY FVETFDTESG IMKNLFLREQ DKNGGDNIIF AKEGNFSLND
201 NKRTLELRHG YRYSGTPGRA DYNQVSFQKL NLIISTTPKL IDPVSHRRTI
251 PTAQLIGSSN PQHQAELMWR ISLTVSVLLL CLLAVPLSYF NPRSGHTYNI
```

```
301 LIAIGLFLIY QNGLTLLFEA VEDGKIHFWL GLLPMHIIMF AVALILLRVR

351 SMPSQPFWQA VGKSLTLKGG K*
```

Computer analysis of this amino acid sequence gave the following results:

Homology with a Predicted ORF from *N. meningitidis* (Strain A)

ORF101 shows 91.2% identity over a 57aa overlap and 95.7% identity over a 69aa overlap with an ORF (ORF101a) from strain A of *N. meningitidis*:

```
                    10         20         30         40         50
   orf101.pep  MIYQRNLIKELSFTAVGIFVVLLAVLVSTQAINLLGRAADGXVIAIDAVLALVGFWVX
               |||||||||||||||||||||||||||||||||||   |||  ||||||||||||||
   orf101a     MIYQRNLIKELSFTAVGIFVVLLAVLVSTQAINLLGXAADXRX-AIDAVLALVGFWVXXM
                    10         20         30         40         50
                                         //
                                                  90        100        110
   orf101.pep  ..........................IAIGLFLIYQNGLTLLFEAVEDGKIHFWLGL
                                         ||||||||||||||||||||||||||||||
   orf101a     LTVSVLLLCLLAVPLSYFNPRSGHTYNILXAIGLFLIYQNGLTLLFEAVEDGKIHFWLGL
                      280       290        300       310       320       330
                   120        130       140        150
   orf101.pep  LPMHIIMFVLALILLRVRSMPSQPFWQAVGKSLTLKGGKX
               ||||||||| ||||||||||||||||||||||||||||||
   orf101a     LPMHIIMFVIAIVLLRVRSMPSQPFWQAVGKSLTLKGGKX
                   340        350       360        370
```

The complete length ORF101a nucleotide sequence <SEQ ID 501> is:

```
   1 ATGATTTATC AAAGAAACCT CATCAAAGAA CTCTCTTTTA CCGCCGTCGG

51 CATTTTCGTC GTCCTCTTGG CGGTATTGGT CTCCACGCAG GCAATCAACC

101 TGCTCGGCCN TGCCGCCGAC NGGCGTNTCG CCATCGATGC CGTGTTGGCA

151 TTGGTCGGCT TCTGGGTCNN NNGNATGACG CCGCTTTTGC TNGTGTTGAC

201 CGCATTTATC AGTACGTTGA CCGTGTTGAC CCGCTACTGG CGNGACAGCG

251 AAATGTCGGT CTGGNTATCC TGCGGATTGG CATTGAAACA ATGGATACGC

301 CCGGTGATGC AGTTTGCCGT GCCGTTTGCC GTTTTGGTTG CCGTCATGCA

351 GCTTTGGGTG ATACCGTGGG CAGAGCTACG CAGCCGCGAA TACGCTGAAA

401 TCCTGAAGCA GAAGCAGGAA TTGTCTTTGG TGGAGGCAGG CGGGTTCAAC

451 AGTTTGGGCA AGCGCAACGG CAGGGTTTAT TTTGTCGAAA CCTTCGATAC

501 CGAATCCGGC ATCATGAAAA ACCTGTTCCT GCGCGAACAG GACAAAAACG

551 GCGGCGACAA CATCATCTTC NCCAAAGAAA GTAACTTCTC GCTGAACGAC

601 AACAAACGCA CGCTCGAATT GCGCCACGGC TACCGTTACA GCGGCACGCC

651 CGGACGCGCC GACTACAATC AGGTTTCCTT CCNAAAACTC AACCTGATTA

701 TCAGCACCAC GCCCAAACTC ATCGACCCCG TTTCCCACCG CCGTACNATN

751 CCNACNGCCC AACTGATTGG CAGCAGCAAC CCGCAACATC ANGCGGAATT

801 GATGTGGCGC ATCTCGCTGA CCGTCAGCGT CCTCCTACTC TGCCTGCTTG

851 CCGTGCCGCT TTCCTATTTC AACCCGCGCA GCGGACATAC CTACAATATC

901 TTGANTGCCA TCGGTTTGTT TTTAATTTAC CAAAACGGGC TGACCCTGCT

951 TTTTGAAGCC GTGGAAGACG GCAAAATCCA TTTTTGGCTC GGACTGCTGC

1001 CTATGCACAT CATCATGTTC GTCATCGCAA TCGTACTTCT GCGCGTCCGC
```

```
1051  AGCATGCCCA GCCAGCCCTT CTGGCAGGCG GTTGGCAAAA GTCTGACATT

1101  GAAAGGCGGA AAATGA
```

This encodes a protein having amino acid sequence <SEQ ID 502>:

```
  1  MIYQRNLIKE LSFTAVGIFV VLLAVLVSTQ AINLLGXAAD XRXAIDAVLA

51  LVGFWVXXMT PLLLVLTAFI STLTVLTRYW RDSEMSVWXS CGLALKQWIR

101  PVMQFAVPFA VLVAVMQLWV IPWAELRSRE YAEILKQKQE LSLVEAGGFN

151  SLGKRNGRVY FVETFDTESG IMKNLFLREQ DKNGGDNIIF XKESNFSLND

201  NKRTLELRHG YRYSGTPGRA DYNQVSFXKL NLIISTTPKL IDPVSHRRTX

251  PTAQLIGSSN PQHXAELMWR ISLTVSVLLL CLLAVPLSYF NPRSGHTYNI

301  LXAIGLFLIY QNGLTLLFEA VEDGKIHFWL GLLPMHIIMF VIAIVLLRVR

351  SMPSQPFWQA VGKSLTLKGG K*
```

ORF101a and ORF101-1 show 95.4% identity in 371 aa overlap:

```
orf101a.pep  MIYQRNLIKELSFTAVGIFVVLLAVLVSTQAINLLGXAADXRXAIDAVLALVGFWVXXMT   60
             |||||||||||||||||||||||||||||||||||| ||| |||||||||||||||| ||
 orf101-1    MIYQRNLIKELSFTAVGIFVVLLAVLVSTQAINLLGRAADVRXAIDAVLALVGFWVIGMT   60
orf101a.pep  PLLLVLTAFISTLTVLTRYWRDSEMSVWXSCGLALKQWIRPVMQFAVPFAVLVAVMQLWV  120
             ||||||||||||||||||||||||||||| ||||||||||||||||||||||||||||||
 orf101-1    PLLLVLTAFISTLTVLTRYWRDSEMSVWLSCGLALKQWIRPVMQFAVPFAVLVAVMQLWV  120
orf101a.pep  IPWAELRSREYAEILKQKQELSLVEAGGFNSLGKRNGRVYFVETFDTESGIMKNLFLREQ  180
             ||||||||||||||||||||||||||||| ||||||||||||||||||||||||||||||
 orf101-1    IPWAELRSREYAEILKQKQELSLVEAGEFNSLGKRNGRVYFVETFDTESGIMKNLFLREQ  180
orf101a.pep  DKNGGDNIIFXKESNFSLNDNKRTLELRHGYRYSGTPGRADYNQVSFXKLNLIISTTPKL  240
             ||||||||||  ||:||||||||||||||||||||||||||||||| |||||||||||||
 orF101-1    DKNGGDNIIFAKEGNFSLNDNKRTLELRHGYRYSGTPGRADYNQVSFQKLNLIISTTPKL  240
orf101a.pep  IDPVSHRRTXPTAQLIGSSNPQHXAELMWRISLTVSVLLLCLLAVPLSYFNPRSGHTYNI  300
             |||||||||  |||||||||||| ||||||||||||||||||||||||||||||||||||
 orf101-1    IDPVSHRRTIPTAQLIGSSNPQHQAELMWRISLTVSVLLLCLLAVPLSYFNPRSGHTYNI  300
orf101a.pep  LXAIGLFLIYQNGLTLLFEAVEDGKIHFWLGLLPMHIIMFVIAIVLLRVRSMPSQPFWQA  360
             | ||||||||||||||||||||||||||||||||||||||::|::||||||||||||||
 orF101-1    LIAIGLFLIYQNGLTLLFEAVEDGKIHFWLGLLPMHIIMFAVALILLRVRSMPSQPFWQA  360
orf101a.pep  VGKSLTLKGGK                                                  371
             |||||||||||
 orf101-1    VGKSLTLKGGK                                                  371
```

Homology with a Predicted ORF from *N. gonorrhoeae*

ORF101 shows 96.5% identity in 57aa overlap at the N-terminal domain and 95.1% identity in 61 aa overlap at the C-terminal domain, respectively, with a predicted ORF (ORF101ng) from *N. gonorrhoeae*:

```
orf101.pep  MIYQRNLIKELSFTAVGIFVVLLAVLVSTQAINLLGRAADGXVIAIDAVLALVGFWV     57
            ||||||||||||||||||||||||||||||||||||||||| |||||||||||||||
orf101ng    MIYQRNLIKELSFTAVGIFVVLLAVLVSTQAINLLGRAADGRV-AIDAVLALVGFWVIGM  59
                                           //
orf101.pep                      IAIGLFLIYQNGLTLLFEAVEDGKIHFWLG            333
                                |||||||||||||||||||||||||||||
orf101ng    SLTVSVLLLCLLAVPLSYFNPRSGHTYNILIAIGLFLIYQNGLTLLFEAVEDGKIHFWLG  331
orf101.pep  LLPMHIIMFVLALILLRVRSMPSQPFWQAVGKSLTLKGGK                      373
            ||||||||||:|::|||||||||||||||||
orf101ng    LLPMHIIMFVIAIVLLRVRSMPSQPFWQAVG                               362
```

The ORF101ng nucleotide sequence <SEQ ID 503> is predicted to encode a protein having partial amino acid sequence <SEQ ID 504>:

```
  1 MIYQRNLIKE LSFTAVGIFV VLLAVLVSTQ AINLLGRAAD GRVAIDAVLA
 51 LVGFWVIGMT PLLLVLTAFI STLTVLTRYW RDSEMSVWLS CGLALKQWIR
101 PVMQFAVPFA ILIAVMQLWV IPWAELRSRE YAEILKQKQE LSLVEAGEFN
151 NLGKRNGRVY FVETFDTESG IMKNLFLREQ DKNGGDNIIF AKEGNFSLKD
201 NKRTLELRHG YRYSGTPGRA DYNQVSFQKL NLIISTTPKL IDPVSHRRTI
251 STAQLIGSSN PQHQAELMWR ISLTVSVLLL CLLAVPLSYF NPRSGHTYNI
301 LIAIGLFLIY QNGLTLLFEA VEDGKIHFWL GLLPMHIIMF VIAIVLLRVR
351 SMPSQPFWQA VG...
```

Further work revealed the complete nucleotide sequence <SEQ ID 505>:

```
   1 ATGATTTATC AAAGAAACCT CATCAAAGAA CTCTCTTTTA CCGCCGTCGG
  51 CATTTTCGTC GTCCTCTTGG CGGTGTTGGT GTCCACGCAG GCGATCAACC
 101 TGCTTGGCCG CGCAGCTGAC GGGCGTGTCG CCATCGATGC CGTGTTGGCC
 151 TTAGTCGGCT TCTGGGTCAT CGGTATGACC CCGCTTTTGC TGGTGTTGAC
 201 CGCATTCATC AGCACGCTGA CCGTATTGAC CCGCTACTGG CGCGACAGCG
 251 AAATGTCGGT CTGGCTATCC TGCGGATTGG CGTTGAAACA GTGGATACGC
 301 CCCGTCATGC AGTTTGCCGT GCCGTTTGCC ATCCTGATTG CCGTCATGCA
 351 GCTTTGGGTG ATACCGTGGG CAGAGCTGCG CAGCCGCGAA TATGCCGAAA
 401 TTTTGAAGCA GAAGCAGGAA TTGTCTTTGG TGGAAGCCGG CGAGTTCAAT
 451 AACTTGGGCA AGCGCAACGG CAgggtttaT TtcgtcgaaA CCTTTGACAC
 501 CGaatccgGC ATCATGAAAA ACCTGTtcct GcGCGAACAG GACAAAAACG
 551 gcggcgacaA CATCATCTTC GCcaaaGAag gtaactTctc gctgaaggaC
 601 AACAAAcgca cgctcgaATT GCGCCACGGC TACCGTTACA GCGGcacgcC
 651 CGGacGCGCc gactaCAATC AGGTTtcctt cCAAAAacTc aacctgATta
 701 TCAGCACCAC GCCCAAacTT ATCGaccCCG TTTCCCACCG CCGCACCATT
 751 tcgacCGCCC AAcTGATTGG CAGCAGCAAT CCGCAACATC AGGCAGAATT
 801 GATGTGGCGC ATCTCGCTGA CCGTCAGCGT CCTCCTGCTC TGCCTACTCG
 851 CCGTGCCGCT TTCCTATTTC AACCCGCGCA GCGGACATAC CTACAATATC
 901 TTGATTGCCA TCGGTTTGTT TTTAATTTAC CAAAACGGGC TGACCCTGCT
 951 TTTTGAAGCC GTGGAAGACG GCAAAATCCA TTTTTGGCTC GGACTGCTGC
1001 CTATGCACAT CATCATGTTC GTCATCGCAA TCGTACTTCT GCGCGTCCGC
1051 AGTATGCCCA GCCAGCCCTT CTGGCAGGCG GTTGGCAAAA GTCTGACATT
1101 GAAAGgcgGA AAATGA
```

This corresponds to the amino acid sequence <SEQ ID 506; ORF101ng-1>:

```
  1 MIYQRNLIKE LSFTAVGIFV VLLAVLVSTQ AINLLGRAAD GRVAIDAVLA
 51 LVGFWVIGMT PLLLVLTAFI STLTVLTRYW RDSEMSVWLS CGLALKQWIR
```

```
101 PVMQFAVPFA ILIAVMQLWV IPWAELRSRE YAEILKQKQE LSLVEAGEFN

151 NLGKRNGRVY FVETFDTESG IMKNLFLREQ DKNGGDNIIF AKEGNFSLKD

201 NKRTLELRHG YRYSGTPGRA DYNQVSFQKL NLIISTTPKL IDPVSHRRTI

251 STAQLIGSSN PQHQAELMWR ISLTVSVLLL CLLAVPLSYF NPRSGHTYNI

301 LIAIGLFLIY QNGLTLLFEA VEDGKIHFWL GLLPMHIIMF VIAIVLLRVR

351 SMPSQPFWQA VGKSLTLKGG K*
```

ORF101ng-1 and ORF101-1 show 97.6% identity in 371 aa overlap:

```
                         10         20         30         40         50         60
         orf101-1.pep    MIYQRNLIKELSFTAVGIFVVLLAVLVSTQAINLLGRAADGRVAIDAVLALVGFWVIGMT
                         |||||||||||||||||||||||||||||||||||||||||||||||||||||||||||
         orf101ng-1      MIYQRNLIKELSFTAVGIFVVLLAVLVSTQAINLLGRAADGRVAIDAVLALVGFWVIGMT
                         10         20         30         40         50         60
                         70         80         90        100        110        120
         orf101-1.pep    PLLLVLTAFISTLTVLTRYWRDSEMSVWLSCGLALKQWIRPVMQFAVPFAVLVAVMQLWV
                         |||||||||||||||||||||||||||||||||||||||||||||||||:|:|||||||
         orf101ng-1      PLLLVLTAFISTLTVLTRYWRDSEMSVWLSCGLALKQWIRPVMQFAVPFAILIAVMQLWV
                         70         80         90        100        110        120
                        130        140        150        160        170        180
         orf101-1.pep    IPWAELRSREYAEILKQKQELSLVEAGEFNSLGKRNGRVYFVETFDTESGIMKNLFLREQ
                         |||||||||||||||||||||||||||||||:||||||||||||||||||||||||||||
         orf101ng-1      IPWAELRSREYAEILKQKQELSLVEAGEFNNLGKRNGRVYFVETFDTESGIMKNLFLREQ
                        130        140        150        160        170        180
                        190        200        210        220        230        240
         orf101-1.pep    DKNGGDNIIFAKEGNFSLNDNKRTLELRHGYRYSGTPGRADYNQVSFQKLNLIISTTPKL
                         |||||||||||||||||||:||||||||||||||||||||||||||||||||||||||||
         orf101ng-1      DKNGGDNIIFAKEGNFSLKDNKRTLELRHGYRYSGTPGRADYNQVSFQKLNLIISTTPKL
                        190        200        210        220        230        240
                        250        260        270        280        290        300
         orf101-1.pep    IDPVSHRRTIPTAQLIGSSNPQHQAELMWRISLTVSVLLLCLLAVPLSYFNPRSGHTYNI
                         ||||||||||||||||||||||||||||||||||||||||||||||||||||||||||||
         orf101ng-1      IDPVSHRRTIPTAQLIGSSNPQHQAELMWRISLTVSVLLLCLLAVPLSYFNPRSGHTYNI
                        250        260        270        280        290        300
                        310        320        330        340        350        360
         orf101-1.pep    LIAIGLFLIYQNGLTLLFEAVEDGKIHFWLGLLPMHIIMFAVALILLRVRSMPSQPFWQA
                         |||||||||||||||||||||||||||||||||||||||:::|::||||||||||||||
         orf101ng-1      LIAIGLFLIYQNGLTLLFEAVEDGKIHFWLGLLPMHIIMFVIAIVLLRVRSMPSQPFWQA
                        310        320        330        340        350        360
                        370
         orf101-1.pep    VGKSLTLKGGKX
                         ||||||||||||
         orf101ng-1      VGKSLTLKGGKX
                        370
```

Based on this analysis, including the presence of a putative leader sequence (double-underlined) and several putative transmembrane domains (single-underlined) in the gonococcal protein, it is predicted that the proteins from *N. meningitidis* and *N. gonorrhoeae*, and their epitopes, could be useful antigens for vaccines or diagnostics, or for raising antibodies.

Example 60

The following partial DNA sequence was identified in *N. meningitidis* <SEQ ID 507>:

```
  1 ..GGTGGTGGTT TTATCAATGC TTCCTGTGCC ACTTTGACGA CAGCCAAACC

51   GCAATATCAA GCAGGAGACC TTAGCGCTTT TAAGATAAGG CAAGGCAATG

101   TTGTAATCGC CGGACACGGT TTGGATGCAC GTGATACCGA TTACACACGT

151   ATTCTCAGTT ATCATTCCAA AATCGATGCA CCCGTATGGG GACAAGATGT

201   TCGTGTCGTC GCGGGACAAA ACGATGTGGC CGCAACAGGT GATGCACATT
```

```
-continued
251  CGCCTATTCT  CAATAATGCT  GCTGCCAATA  CGTCAAACAA  TACAGCCAAC

301  AACGGCACAC  ATATCCCTTT  ATTTGCGATT  GATACAGGCA  AATTAGGAGG

351  TAT.GTATGC  CAACAAAATC  ACCTTGATCA  GTACGGTCGA  GCAAGCAGGC

401  ATTCGTAA
```

This corresponds to the amino acid sequence <SEQ ID 508; ORF113>:

```
  1 ..GGGFINASCA  TLTTAKPQYQ  AGDLSAFKIR  QGNVVIAGHG  LDARDTDYTR

51   ILSYHSKIDA  PVWGQDVRVV  AGQNDVAATG  DAHSPILNNA  AANTSNNTAN

101   NGTHIPLFAI  DTGKLGGXVC  QQNHLDQYGR  ASRHS*
```

Computer analysis of this amino acid sequence gave the following results:

Homology with pspA Putative Secreted Protein of *N. meningitidis* (Accession AF030941)

ORF and pspA show 44% aa identity in 179aa overlap:

```
orf113  GGGFINASCATLTTAKPQYQAGDLSAFKIRQGNVVIAGHGLDARDTDYTRILSYHSKIDA   60
        GGG INA+  TLT+  P    G+L+ F +  G VVI G GLD  D DYTRILS  ++I+A
pspa    GGGLINAASVTLTSGVPVLNNGNLTGFDVSSGKVVIGGKGLDTSDADYTRILSRAAEINA  256 orf113  PVWGQDVRVVAGQNDVAATGDAHSPILXXXXXXXXXXXXXXXGTHIPLFAIDTGKLGGMYA  120
        VWG+DV+VV+G+N +   G                       + P  AIDT  LGGMYA
pspa    GVWGKDVKVVSGKNKLDFDG---------SLAKTASAPSSSDSVTPTVAIDTATLGGMYA  307 orf113  NKITLISTVEQAGIRNQGQWFASAGNVAVNAEGKLVNTGMIAATGENHAVSLHARNVHN   179
        +KITLIST    A IRN+G+ FA+ G V ++A+GKL N+G I A      +++ A+ V N
pspa    DKITLISTDNGAVIRNKGRIFAATGGVTLSADGKLSNSGSIDAA----EITISAQTVDN   362
```

Homology with a Predicted ORF from *N. gonorrhoeae*

ORF113 shows 86.5% identity in 52aa overlap at the N-terminal part and 94.1% identity in 17aa overlap at the C-terminal part with a predicted ORF (ORF113ng) from *N. gonorrhoeae*:

```
orf113                          GGGFINASCATLTTAKPQYQAGDLSAFKIR   30
                                ||||||||  ||||::||||||:|:||||
orf113ng SHPSQLNGYIEVGGRRAEVVIANPAGIAVNGGGFINASRATLTTGQPQYQAGDFSGFKIR  224
orf113   QGNVVIAGHGLDARDTDYTRILSYHSKIDAPVWGQDVRVVAGQNDVAATGDAHSPILNNA   90
         |||:||||||||||||||:||||
orf113ng QGNAVIAGHGLDARDTDFTRILVCQQNHLDQYGRTSRHS                      263
orf113                 IDTGKLGGXVCQQNHLDQYGRASRHS                    135
                        ||||||||||||:||||
orf113ng DFSGFKIRQGNAVIAGHGLDARDTDFTRILVCQQNHLDQYGRTSRHS              263
```

The complete length ORF113ng nucleotide sequence <SEQ ID 509> is predicted to encode a protein having amino acid sequence <SEQ ID 510>:

```
  1 MNKTLYRVIF  NRKRGAVVAV  AETTKREGKS  CADSGSGSVY  VKSVSFIPTH

51 SKAFCFSALG  FSLCLALGTV  NIAFADGIIT  DKAAPKTQQA  TILQTGNGIP

101 QVNIQTPTSA  GVSVNQYAQF  DVGNRGAILN  NSRSNTQTQL  GGWIQGNPWL

151 TRGEARVVVN  QINSSHPSQL  NGYIEVGGRR  AEVVIANPAG  IAVNGGGFIN

201 ASRATLTTGQ  PQYQAGDFSG  FKIRQGNAVI  AGHGLDARDT  DFTRILVCQQ

251 NHLDQYGRTS  RHS*
```

Based on this analysis, it is predicted that these proteins from *N. meningitidis* and *N. gonorrhoeae*, and their epitopes, could be useful antigens for vaccines or diagnostics, or for raising antibodies.

Example 61

The following partial DNA sequence was identified in *N. meningitidis* <SEQ ID 511>:

```
  1..TCAACGGGAC ATAGCGAACA AAATTACACT TTGCCGCGAG AAATCACACG

51   CAACATTTCA CTGGGTTCAT TTGCCTATGA ATCGCATCGC AAAGCATTAA

101   GCCATCATGC GCCCAGCCAA GGCACTGAGT TGCCGCAAAG CAACGGTATT

151   TCGCTACCCT ATACGTCCAA TTCTTTTACC CCATTACCCA GCAGCAGCTT

201   ATACATTATC AATCCTGTCA ATAAAGGCTA TCTTGTTGAA ACCGATCCAC

251   GCTTTGCCAA CTACCGTCAA TGGTTGGGTA GTGACTATAT GCtGGACAGC

301   CTCAAACTAG ACCCAAACAA TTTACATAAA CGTTTGGGTG ATGGTTATTA

351   CGAGCAACGT TTAATCAATG AACAAATCGC AGAGCTGACA GGGCATCGTC

401   GTTTAGAcGG TTATCAAAAC GACGAAGAAC AATTTAAAGC CTTAATGGAT

451   AATGGCGCGA CTGCGGCACG TTcGATGAAT CTCAGCGTTG GCATTGCATT

501   AAGTGCCGAG CAAGTAGCGC AACTGACCAG CGATATTGTT TGGTTGGTAC

551   AAAAAGAAGT TAAGCTTCCT GATGGCGGCA CACAAACCGT ATTGGTGCCA

601   CAGGTTTATG TACGCGTTAA AAATGGCGAC ATAGACGGTA AAGGTGCATT

651   GTTGTCAGGC AGCAATACAC AAATCAATGT TTCAGGCAGC CTGAAAAACT

701   CAGGCACGAT TGCAGGgCGC AATGCGCTTA TTATCAATAC CGATACGCTA

751   GACAATATCG GTGGGCGTAT TCATGCGCAA AAATCAGCGG TTACGGCCAC

801   ACAAGACATC AATAATATTG GCGGCATGCT TTCTGCCGAA CAGACATTAT

851   TGCTCAACGC AGGCAACAAC ATCAACAGCC AAAGCACCAC CGCCAGCAGT

901   CAAAATACAC AAGGCAGCAG CACCTACCTA GACCGAATGG CAGGTATTTA

951   TATCACAGGC AAAGAAAAAG GTGTTT..
```

This corresponds to the amino acid sequence <SEQ ID 512; ORF115>:

```
  1..STGHSEQNYT LPREITRNIS LGSFAYESHR KALSHHAPSQ GTELPQSNGI

51   SLPYTSNSFT PLPSSSLYII NPVNKGYLVE TDPRFANYRQ WLGSDYMLDS

101   LKLDPNNLHK RLGDGYYEQR LINEQIAELT GHRRLDGYQN DEEQFKALMD

151   NGATAARSMN LSVGIALSAE QVAQLTSDIV WLVQKEVKLP DGGTQTVLVP

201   QVYVRVKNGD IDGKGALLSG SNTQINVSGS LKNSGTIAGR NALIINTDTL

251   DNIGGRIHAQ KSAVTATQDI NNIGGMLSAE QTLLLNAGNN INSQSTTASS

301   QNTQGSSTYL DRMAGIYITG KEKGV..
```

Computer analysis of this amino acid sequence gave the following results:
Homology with the pspA Putative Secreted Protein of *N. meningitidis* (Accession Number AF030941)

ORF115 and pspA protein show 50% aa identity in 325aa overlap:

```
Orf115:     1 STGHSEQNYTLPREITRNISLGSFAYESHRKALSHHAPSQGTELPQSNGISLPYTSNSFT    60
              STG+S    Y   E++ +I +G  AY+ +    +   P    +    NGI   +T
pspA:     778 STGYSRSPYEPAPEVS-SIRMGISAYKGYAPQQASDIPGTVVPVVAENGIHPTFT-----   831

Orf115:    61 PLPSSSLYIINPVNKGYLVETDPRFANYRQWLGSDYMLDSLKLDPNNLHKRLGDGYYEQR   120
              LP+SSL+  I P NKGYL+ETDP F +YR+WLGS YML +L+ DPN++HKRLGDGYYEQ+
pspA:     832 -LPNSSLFAIAPNNKGYLIETDPAFTDYRKWLGSGYMLAALQQDPNHIHKRLGDGYYEQK   890

Orf115:   121 LINEQIAELTGHRRLDGYQNDEEQFKALMDNGATAARSMNLSVGIALSAEQVAQLTSDIV   180
              L+NEQIA+LTG+RRLDGY NDEEQFKALMDNG T A+ + L+ GIALSAEQVA+LTSDIV
pspA:     891 LVNEQIAKLTGYRRLDGYTNDEEQFKALMDNGITIAKELQLTPGIALSAEQVARLTSDIV   950

Orf115:   181 WLVQKEVKLPDGGTQTVLVPQVYVRVKNGDIDGKGALLSGSNTQINVSGSLKN-SGTIAG   239
              WL   + V LPDG TQTVL P+VYVR  +  D++G+GALLSGS    I  SG+++N  G IAG
pspA:     951 WLENETVTLPDGTTQTVLKPKVYVRARPKDMNGQGALLSGSVVDIG-SGAIENRGGLIAG  1009

Orf115:   240 RNALIINTDTLDNIGGRIHAQKSAVTATQDINNIGGMLSAEQTLLLNAGXXXXXXXXXXX   299
              R  ALI+N   + N+   G +   +      A   DI N   G    + AE    LLL   A
pspA:    1010 REALILNAQNIKNLQGDLQGKNIFAAAGSDITNTGS-IGAENALLLKASNNIESRSETRS  1068

Orf115:   300 XXXXXXXXXYLDRMAGIYITGKEKG   324
                       +  R+AGIY+TG++  G
pspA:    1069 NQNEQGSVRNIGRVAGIYLTGRQNG  1093
```

Homology with a Predicted ORF from *N. gonorrhoeae*

ORF115 shows 91.9% identity over a 334aa overlap with a predicted ORF (ORF115ng) from *N. gonorrhoeae*:

```
orf115.pep                                STGHSEQNYTLPREITRNISLGSFAYESHRK   31
                                          ||| |||||||||:||||:||||||||||| |
orf115ng    NEQTFGEKKVFSENGKLHNYWRARRKGHDETGHREQNYTLPEEITRDISLGSFAYESHSK   71 orf115.pep  ALSHHAPSQGTELPQSN----------GISLPYTSNSFTPLPSSSLYIINPVNKGYLVET   81
            |||:|||||||||||||           |||||||| ||||| |||||||||:||||||
orf115ng    ALSRHAPSQGTELPQSNRDNIRTAKSNGISLPYTPNSFTPLPGSSLYIINPANKGYLVET  131 orf115.pep  DPRFANYRQWLGSDYMLDSLKLDPNNLHKRLGDGYYEQRLINEQIAELTGHRRLDGYQND  141
            ||||||||||||||||| ||||||||||||||||||||||||||||||||||||||||
orf115ng    DPRFANYRQWLGSDYMLGSLKLDPNNLHKRLGDGYYEQRLINEQIAELTGHRRLDGYQND  191 orf115.pep  EEQFKALMDNGATAARSMNLSVGIALSAEQVAQLTSDIVWLVQKEVKLPDGGTQTVLVPQ  201
            ||||||||||||||||||||||||||||||:|||||||||||||||||||||||||:||
orf115ng    EEQFKALMDNGATAARSMNLSVGIALSAEQAAQLTSDIVWLVQKEVKLPDGGTQTVLMPQ  251 orf115.pep  VYVRVKNGDIDGKGALLSGSNTQINVSGSLKNSGTIAGRNALIINTDTLDNIGGRIHAQK  261
            ||||||||:|||||||||||||||||||||||||||||||||||||||||||||||||
orf115ng    VYVRVKNGGIDGKGALLSGSNTQINVSGSLKNSGTIAGRNALIINTDTLDNIGGRIHAQK  311 orf115.pep  SAVTATQDINNIGGMLSAEQTLLLNAGNNINSQSTTASSQNTQGSSTYLDRMAGIYITGK  321
            |||||||||||||||:|||||||||||||:||:  ||||:|||||||||||||||||||
orf115ng    SAVTATQDINNIGGILSAEQTLLLNAGNNINNQSTAKSSQNAQGSSTYLDRMAGIYITGK  371 orf115.pep  EKGV                                                          325
            ||||
orf115ng    EKGVLAAQAGKDINIIAGQISNQSDQGQTRLQAGRDINLDTVQTGKYQEIHFDADNHTIR  431
```

An ORF115ng nucleotide sequence <SEQ ID 513> was predicted to encode a protein having amino acid sequence <SEQ ID 514>:

```
  1 MLVQTEKDGL HNEQTFGEKK VFSENGKLHN YWRARRKGHD ETGHREQNYT

51 LPEEITRDIS LGSFAYESHS KALSRHAPSQ GTELPQSNRD NIRTAKSNGI

101 SLPYTPNSFT PLPGSSLYII NPANKGYLVE TDPRFANYRQ WLGSDYMLGS

151 LKLDPNNLHK RLGDGYYEQR LINEQIAELT GHRRLDGYQN DEEQFKALMD

201 NGATAARSMN LSVGIALSAE QAAQLTSDIV WLVQKEVKLP DGGTQTVLMP

251 QVYVRVKNGG IDGKGALLSG SNTQINVSGS LKNSGTIAGR NALIINTDTL

301 DNIGGRIHAQ KSAVTATQDI NNIGGILSAE QTLLLNAGNN INNQSTAKSS

351 QNAQGSSTYL DRMAGIYITG KEKGVLAAQA GKDINIIAGQ ISNQSDQGQT

401 RLQAGRDINL DTVQTGKYQE IHFDADNHTI RGSTNEVGSS IQTKGDVTLL
```

```
451 SGNNLNAKAA EVGSAKGTLA VYAKNDITIS SGIHAGQVDD ASKHTGRSGG

501 GNKLVITDKA QSHHETAQSS TFEGKQVVLQ AGNDANILGS NVISDNGTRI

551 QAGNHVRIGT TQTQSQSETY HQTQKSGLMS AGIGFTIGSK TNTQENQSQS

601 NEHTGSTVGS LKGDTTIVAS KHYEQTGSNV SSPEGNNLIS TQSMDIGAAQ

651 NQLNSKTTQT YEQKGLTVAF SSPVTDLAQQ AIAVAHKAAK QFDKAKTTAL

701 MPWRLPMQVG RLFKQAKAPK K*
```

Further work revealed the following partial gonococcal
DNA sequence <SEQ ID 515>:

```
   1 TTGCTTGTGC AAACAGAAAA AGACGGTTTG CATAACGAGC AAACCTTTGG

51 CGAGAAGAAA GTCTTCAGCG AAAATGGTAA GTTGCACAAC TACTGGCGTG

101 CGCGTCGTAA AGGACATGAT GAAACAGGGC ATCGTGAACA AAATTATACT

151 TTGCCGGAGG AAATCACACG CGACATTTCA CTGGGTTCAT TTGCCTATGA

201 ATCGCATAGC AAAGCATTAA GCCGTCATGC GCCCAGCCAA GGCACTGAGT

251 TGCCACAAAG TAACCGGGAT AATATCCGTA CTGCGAAAAG CAACGGTATT

301 TCGCTACCCT ATACGCCCAA TTCTTTTACC CCATTACCCG GCAGCAGCTT

351 ATACATTATC AATCCTGCCA ATAAAGGCTA TCTTGTTGAA ACCGATCCAC

401 GCTTTGCCAA CTACCGTCAA TGGTTGGGTA GTGACTATAT GCTGGGCAGC

451 CTCAAACTAG ACCCAAACAA TTTACATAAA CGTTTGGGTG ATGGTTATTA

501 CGAGCAACGT TTAATCAATG AACAAATCGC AGAGCTGACA GGGCATCGTC

551 GTTTAGACGG TTATCAAAAC GACGAAGAAC AATTTAAAGC CTTAATGGAT

601 AATGGCGCGA CTGCGGCACG TTCGATGAAT CTCAGCGTTG GCATTGCATT

651 AAGTGCCGAG CAAGCAGCGC AACTGACCAG CGATATTGTT TGGTTGGTAC

701 AAAAAGAAGT TAAACTTCCT GATGGCGGCA CACAAACCGT ATTGATGCCA

751 CAGGTTTATG TACGCGTTAA AAATGGCGGC ATAGACGGTA AAGGTGCATT

801 GTTGTCAGGC AGCAATACAC AAATCAATGT TTCAGGCAGC CTGAAAAACT

851 CAGGCACGAT TGCAGGGCGC AATGCGCTTA TTATCAATAC CGATACGCTA

901 GACAATATCG GTGGGCGTAT TCATGCGCAA AAATCAGCGG TTACGGCCAC

951 ACAAGACATC AATAATATTG GCGGCATTCT TTCTGCCGAA CAGACATTAT

1001 TGCTCAATGC GGGTAACAAC ATCAACAACC AAAGCACGGC CAAGAGCAGT

1051 CAAAATGCAC AAGGTAGCAG CACCTACCTA GACCGAATGG CAGGTATTTA

1101 TATCACAGGC AAAGAAAAAG GTGTTTTAGC AGCGCAGGCA GGCAAAGACA

1151 TCAACATCAT TGCCGGTCAA ATCAGCAATC AATCAGATCA AGGGCAAACC

1201 CGGCTGCAGG CAGGACGCGA CATTAACCTG GATCGGTAC AAACCGGCAA

1251 ATATCAAGAA ATCCATTTTG ATGCCGATAA CCATACCATC CGAGGTTCAA

1301 CGAACGAAGT CGGCAGCAGC ATTCAAACAA AAGGCGATGT TACCCtatTG

1351 TCAGGGAATA ATCTCAATGC CAAAGCTGCC GAAGTCGGCA GCGCAAAAGG

1401 CACACTTGCC GTGTATGCTA AAAATGACAT TACTATCAGC TCAGGCATCC

1451 ATGCCGGCCA AGTTGATGAT GCGTCCAAAC ATACAGGCAG AAGCGGCGGC

1501 GGTAATAAAT TAGTCATTAC CGATAAAGCC CAAAGTCATC ACGAAACTGC
```

```
1551 TCAAAGCAGC ACCTTTGAAG GCAAGCAAGT TGTATTGCAG GCAGGAAACG

1601 ATGCCAACAT CCTTGGCAGT AATGTTATTT CCGATAATGG CACCCGGATT

1651 CAAGCAGGCA ATCATGTTCG CATTGGTACA ACCCAAACTC AAAGCCAAAG

1701 CGAAACCTAT CATCAAACCC AAAAATCAGG ATTGATGAGT GCAGGTATCG

1751 GCTTCACTAT TGGCAGCAAG ACAAACACAC AAGAAAACCA ATCCCAAAGC

1801 AACGAACATA CAGGCAGTAC CGTAGGCAGC CTGAAAGGCG ATACCACCAT

1851 TGTTGCAAGC AAACACTACG AACAAACCGG CAGCAACGTT TCCAGCCCTG

1901 AGGGCAACAA CCTTATCAGC ACGCAAAGTA TGGATATTGG CGCAGCACAA

1951 AACCAATTAA ACAGCAAAAC CACCCAAACC TACGAACAAA AAGGCTTAAC

2001 GGTGGCATTC AGTTCGCCCG TTACCGATTT GGCACAACAA GCGATTGCCG

2051 TAGCACACAA AGCAGCAAAC AAGTCGGACA AAGCAAAAAC GACCGCGTTA

2101 ATGCCATGGC GGCTGCCAAT GCAGGTTGGC AGGCCTATCA AACAGGCAAA

2151 GGCGCACAAA ACTTAG
```

This corresponds to the amino acid sequence <SEQ ID 516; ORF115ng-1>:

```
  1 LLVQTEKDGL HNEQTFGEKK VFSENGKLHN YWRARRKGHD ETGHREQNYT

51 LPEEITRDIS LGSFAYESHS KALSRHAPSQ GTELPQSNRD NIRTAKSNGI

101 SLPYTPNSFT PLPGSSLYII NPANKGYLVE TDPRFANYRQ WLGSDYMLGS

151 LKLDPNNLHK RLGDGYYEQR LINEQIAELT GHRRLDGYQN DEEQFKALMD

201 NGATAARSMN LSVGIALSAE QAAQLTSDIV WLVQKEVKLP DGGTQTVLMP

251 QVYVRVKNGG IDGKGALLSG SNTQINVSGS LKNSGTIAGR NALIINTDTL

301 DNIGGRIHAQ KSAVTATQDI NNIGGILSAE QTLLLNAGNN INNQSTAKSS

351 QNAQGSSTYL DRMAGIYITG KEKGVLAAQA GKDINIIAGQ ISNQSDQGQT

401 RLQAGRDINL DTVQTGKYQE IHFDADNHTI RGSTNEVGSS IQTKGDVTLL

451 SGNNLNAKAA EVGSAKGTLA VYAKNDITIS SGIHAGQVDD ASKHTGRSGG

501 GNKLVITDKA QSHHETAQSS TFEGKQVVLQ AGNDANILGS NVISDNGTRI

551 QAGNHVRIGT TQTQSQSETY HQTQKSGLMS AGIGFTIGSK TNTQENQSQS

601 NEHTGSTVGS LKGDTTIVAS KHYEQTGSNV SSPEGNNLIS TQSMDIGAAQ

651 NQLNSKTTQT YEQKGLTVAF SSPVTDLAQQ AIAVAHKAAN KSDKAKTTAL

701 MPWRLPMQVG RPIKQAKAHK T*
```

This gonococcal protein (ORF115ng-1) shows 91.9% identity with ORF 115 over 334aa:

```
                  20         30         40         50         60         70
orf115ng-1.p NEQTFGEKKVFSENGKLHNYWRARRKGHDETGHREQNYTLPEEITRDISLGSFAYESHSK
                 |||  ||||||||:||||:|||||||||||| |
      orF115                     STGHSEQNYTLPREITRNISLGSFAYESHRK
                                         10         20         30

80         90        100        110        120        130
orf115ng-1.p ALSRHAPSQGTELPQSNRDNIRTAKSNGISLPYTPNSFTPLPGSSLYIINPANKGYLVET
             |||:||||||||||||||          ||||  |||||||||||:||||||||:||||||
      orf115 ALSHHAPSQGTELPQSN----------GISLSYTPNSFTPLPSSLYIINPVNKGYLVET
                       40         50         60         70         80
```

```
                       140        150        160        170        180        190
   orf115ng-1.p DPRFANYRQWLGSDYMLGSLKLDPNNLHKRLGDGYYEQRLINEQIAELTGHRRLDGYQND
                |||||||||||||||| ||||||||||||||||||||||||||||||||||||||||||||
         orf115 DPRFANYRQWLGSDYMLDSLKLDPNNLHKRLGDGYYEQRLINEQIAELTGHRRLDGYQND
                       90        100        110        120        130        140

200        210        220        230        240        250
   orf115ng-1.p EEQFKALMDNGATAARSMNLSVGIALSAEQAAQLTSDIVWLVQKEVKLPDGGTQTVLMPQ
                ||||||||||||||||||||||||||||||||:|||||||||||||||||||||||:||
         orF115 EEQFKALMDNGATAARSMNLSVGIALSAEQVAQLTSDIVWLVQKEVKLPDGGTQTVLVPQ
                       150       160        170        180        190        200

260        270        280        290        30         310
   orf115ng-1.p VYVRVKNGGIDGKGALLSGSNTQINVSGSLKNSGTIAGRNALIINTDTLDNIGGRIHAQK
                ||||||||| ||||||||||||||||||||||||||||||||||||||||||||||||||
         orf115 VYVRVKNGDIDGKGALLSGSNTQINVSGSLKNSGTIAGRNALIINTDTLDNIGGRIHAQK
                       210       220        230        240        250        260

320        330        340        350        360        370
   orf115ng-1.p SAVTATQDINNIGGILSAEQTLLLNAGNNINNQSTAKSSQNAQGSSTYLDRMAGIYITGK
                ||||||||||||||||||||||||||||||:|||:|||||||||:|||||||||||||||
         orF115 SAVTATQDINNIGGMLSAEQTLLLNAGNNINSQSTTASSQNTQGSSTYLDRMAGIYITGK
                       270       280        290        300        310        320

380        390        400        410        420        430
   orf115ng-1.p EKGVLAAQAGKDINIIAGQISNQSDQGQTRLQAGRDINLDTVQTGKYQEIHFDADNHTIR
                ||||
         orf115 EKGV
```

In addition, it shows homology with a secreted *N. meningitidis* protein in the database:

```
gi|2623258 (AF030941) putative secreted protein
[Neisseria meningitidis] Length = 2273
Score = 604 bits (1541), Expect = e-172
Identities = 325/678 (47%), Positives = 449/678 (65%), Gaps = 22/678 (3%)

Query:    1 LLVQTEKDGLHNEQTFGEKKVFSENGKLHNYWRARRKGHDETGHREQNYTLPEEITRDIS   60
            L+V T +  L N++T G K + ++ G LH Y R   +KG D TG+     Y  E++  I
Sbjct:  739 LIVGTPESALDNDETLGTKTI-TDKGDLHRYHRHHKKGRDSTGYSRSPYEPAPEVS-SIR  796

Query:   61 LGSFAYESHSKALSRHAPSQGTELPQSNRDNIRTAKSNGISLPYTPNSFTPLPGSSLYII  120
            +G  AY+ +        AP Q +++P +   +    NGI   +T    LP SSL+ I
Sbjct:  797 MGISAYKGY-------APQQASDIPGTV---VPVVAENGIHPTFT------LPNSSLFAI  840

Query:  121 NPANKGYLVETDPRFANYRQWLGSDYMLGSLKLDPNNLHKRLGDGYYEQRLINEQIAELT  180
              P NKGYL+ETDP F +YR+WLGS YML +L+ DPN++HKRLGDGYYEQ+L+NEQIA+LT
Sbjct:  841 APNNKGYLIETDPAFTDYRKWLGSGYMLAALQQDPNHIHKRLGDGYYEQKLVNEQIAKLT  900

Query:  181 GHRRLDGYQNDEEQFKALMDNGATAARSMNLSVGIALSAEQAAQLTSDIVWLVQKEVKLP  240
            G+RRLDGY NDEEQFKALMDNG T A+ + L+ GIALSAEQ A+LTSDIVWL  + V LP
Sbjct:  901 GYRRLDGYTNDEEQFKALMDNGITIAKELQLTPGIALSAEQVARLTSDIVWLENETVTLP  960

Query:  241 DGGTQTVLMPQVYVRVKNGGIDGKGALLSGSNTQINVSGSLKN-SGTIAGRNALIINTDT  299
            DG TQTVL P+VYVR +   ++G+GALLSGS   I  SG+++N G IAGR ALI+N
Sbjct:  961 DGTTQTVLKPKVYVRARPKDMNGQGALLSGSVVDIG-SGAIENRGGLIAGREALILNAQN 1019

Query:  300 LDNIGGRIHAQKSAVTATQDINNIGGILSAEQTLLLNAGNNINNQSTAKSSQNAQGSSTY  359
             + N+ G + +       A DI G I  AE  LLL A NNI ++S  +S+QN QGS
Sbjct: 1020 IKNLQGDLQGKNIFAAAGSDITNTGSI-GAENALLLKASNNIESRSETRSNQNEQGSVRN 1078

Query:  360 LDRMAGIYITGKEKGVLAAQAGKDINIIAGQISNQSDQGQTRLQAGRDINLDTVQTGKYQ  419
            + R+AGIY+TG++ G +    AG +I + A +++NQS+ GQT L AG DI  DT   + Q
Sbjct: 1079 IGRVAGIYLTGRQNGSVLLDAGNNIVLTASELTNQSEDGQTVLNAGGDIRSDTTGISRNQ 1138

Query:  420 EIHFDADNHTIRGSTNEVGSSIQTKGDVTLLSGNNLNAKAAEVGSAKGTLAVYAKNDITI  479
                FD+DN+ IR   NEVGS+I+T+G+++L +   ++  +AAEVGS +G L + A  DI +
Sbjct: 1139 NTIFDSDNYVIRKEQNEVGSTIRTRGNLSLNAKGDIRIRAAEVGSEQGRLKLAAGRDIKV 1198

Query:  480 SSGIHAGQVDDASKHTGRSGGGNKLVITDKAQSHHETAQSSTFEGKQVVLQAGNDANILG  539
            +G   + +DA K+TGRSGGG K +T  ++   A ST  +GK+++L +G D   + G
Sbjct: 1199 EAGKAHTETEDALKYTGRSGGGIKQKMTRHLKNQNGQAVSGTLDGKEIILVSGRDITVTG 1258

Query:  540 SNVISDNGTRIQAGNHVRIGTTQTQSQSETYHQTQKSGLM-SAGIGFTIGSKTNTQENQS  598
            SN+I+DN T + A N+ +   +T+S+S   + +KSGLM S GIGFT GSK +TQ N+S
Sbjct: 1259 SNIIADNHTILSAKNNIVLKAAETRSRSAEMNKKEKSGLMGSSGGIGFTAGSKKDTQTNRS 1318

Query:  599 QSNEHTGSTVGSLKGDTTIVASKHYEQTGSNVSSPEGNNLISTQSMDIGAAQNQLNSKTT  658
            ++  HT S VGSL G+T I A KHY QTGS +SSP+G+  IS+   + I AAQN+ + ++
Sbjct: 1319 ETVSHTESVVGSLNGNTLISAGKHYTQTGSTISSPQGDVGISSGKISIDAAQNRYSQESK 1378
```

```
Query:  659 QTYEQKGLTVAFSSPVTD                                              676
            Q YEQKG+TVA S PV +
Sbjct: 1379 QVYEQKGVTVAISVPVVN                                             1396
```

Based on this analysis, it is predicted that the proteins from *N. meningitidis* and *N. gonorrhoeae*, and their epitopes, could be useful antigens for vaccines or diagnostics, or for raising antibodies.

Example 62

The following partial DNA sequence was identified in *N. meningitidis* <SEQ ID 517>:

```
  1..TCAGGGAATA ACCTCAATGC CAAAGCTGCC GAAGTCAGCA GCGCAAACGG

51  TACACTCGCT GTGTCTGCCA ATAATGACAT CAACATCAGC GCAGGCATCA

101  ACACGACCCA TGTTGATGAT GCGTCCAAAC ACACAGGCAG AAGCGGTGGT

151  GGCAATAAAT TAGTCATTAC CGATAAAGCC CAAAGTCATC ACGAAACCGC

201  CCAAAGCAGC ACCTTTGAAG GCAAGCAAGT TGTATTGCAG GCAGGAAACG

251  ATGCCAACAT CCTTGGCAGC AATGTTATTT CCGATAATGG CACCCAGATT

301  CAAGCAGGCA ATCATGTTCG CATTGGTACA ACCCAAACTC AAAGCCAAAG

351  CGAAACCTAT CATCAAACCC AGAAATCAGG ATTGATGAGT GCAGGTATCG

401  GCTTCACTAT TGGCAGCAAG ACAAACACAC AAGAAAACCA ATCCCAAAGC

451  AACGAACATA CAGGCAGTAC CGTAGGCAGC TTGAAAGGCG ATACCACCAT

501  TGTTGCAGGC AAACACTACG AACAAATCGG CAGTACCGTT TCCAGCCCGG

551  AAGGCAACAA TACCATCTAT GCCCAAAGCA TAGACATTCA AGCGGCACAC

601  AACAAATTAA ACAGTAATAC CACCCAAACC TATGAACAAA AAGG.CTAAC

651  GGTGGCATTC AGTTCGCCCG TTACCGATTT GGCACAACAA ...
```

This corresponds to the amino acid sequence <SEQ ID 518; ORF117>:

```
  1..SGNNLNAKAA EVSSANGTLA VSANNDINIS AGINTTHVDD ASKHTGRSGG

51  GNKLVITDKA QSHHETAQSS TFEGKQVVLQ AGNDANILGS NVISDNGTQI

101  QAGNHVRIGT TQTQSQSETY HQTQKSGLMS AGIGFTIGSK TNTQENQSQS

151 NEHTGSTVGS LKGDTTIVAG KHYEQIGSTV SSPEGNNTIY AQSIDIQAAH

201 NKLNSNTTQT YEQKXLTVAF SSPVTDLAQQ ...
```

Computer analysis of this amino acid sequence gave the following results:
Homology with the pspA Putative Secreted Protein of *N. meningitidis* (Accession Number AF030941)

ORF117 and pspA protein show 45% aa identity in 224aa overlap:

```
Orf117:    4 NLNAKAAEVSSANGTLAVSANNDINISAGINTTHVDDASKHTGRSGGGNKLVITDKAQSH      63
             ++  +AAEV S  G L ++A  DI + AG   T  +DA K+TGRSGGG K  +T     ++
pspA:   1173 DIRIRAAEVGSEQGRLKLAAGRDIKVEAGKAHTETEDALKYTGRSGGGIKQKMTRHLKNQ    1232
```

```
Orf117:     64 HETAQSSTFEGKQVVLQAGNDANILGSNVISDNGTQIQAGNHVRIGTTQTQSQSETYHQT   123
               +  A S T +GK+++L +G D  +  GSN+I+DN T +  A N++ +    +T+S+S    ++
pspA:     1233 NGQAVSGTLDGKEIILVSGRDITVTGSNIIADNHTILSAKNNIVLKAAETRSRSAEMNKK  1292

Orf117:    124 QKSGLM-SAGIGFTIGSKTNTQENQSQSNEHTGSTVGSLKGDTTIVAGKHYEQIGSTVSS   182
               +KSGLM S  GIGFT GSK +TQ N+S++    HT S VGSL  G+T  I AGKHY Q GST+SS
pspA:     1293 EKSGLMGSGGIGFTAGSKKDTQTNRSETVSHTESVVGSLNGNTLISAGKHYTQTGSTISS  1352

Orf117:    183 PEGNNTIYAQSIDIQAAHNKLNSNTTQTYEQKXLTVAFSSPVTD                  226
               P+G+   I +  I  I AA N+  +  + Q YEQK +TVA S PV +
pspA:     1353 PQGDVGISSGKISIDAAQNRYSQESKQVYEQKGVTVAISVPVVN                 1396
```

Homology with a Predicted ORF from *N. gonorrhoeae*

ORF117 shows 90% identity over a 230aa overlap with a predicted ORF (ORF117ng) from *N. gonorrhoeae*:

```
orf117.pep                                     SGNNLNAKAAEVSSANGTLAVSANNDINIS   30
                                               ||||||||||||:||:|||||  :|||:||
orf117ng   IHFDADNHTIRGSTVEVGSSIQTKGDVTLLSGNNLNAKAAEVGSAKGTLAVYAKNDITIS  480 orf117.pep AGINTTHVDDASKHTGRSGGGNKLVITDKAQSHHETAQSSTFEGKQVVLQAGNDANILGS   90
           :||::: |||||||||||||||||||||||||||||||||||||||||||||||||||||
orf117ng   SGIHAGQVDDASKHTGRSGGGNKLVITDKAQSHHETAQSSTFEGKQVVLQAGNDANILGS  540 orf117.pep NVISDNGTQIQAGNHVRIGTTQTQSQSETYHQTQKSGLMSAGIGFTIGSKTNTQENQSQS  150
           ||||||||:|||||||||||||||||||||||||||||||||||||||||||||||||||
orf117ng   NVISDNGTRIQAGNHVRIGTTQTQSQSETYHQTQKSGLMSAGIGFTIGSKTNTQENQSQS  600 orf117.pep NEHTGSTVGSLKGDTTIVAGKHYEQIGSTVSSPEGNNTIYAQSIDIQAAHNKLNSNTTQT  210
           |||||||||||||||||||:||||  ||:||||||||| | :||:||  ||:|:|||:|||
orf117ng   NEHTGSTVGSLKGDTTIVASKHYEQTGSNVSSPEGNNLISTQSMDIGAAQNQLNSKTTQT  660 orf117.pep YEQKXLTVAFSSPVTDLAQQ                                         230
           ||||  ||||||||||||||
orf117ng   YEQKGLTVAFSSPVTDLAQQAIAVAHKAAKQFDKAKTTALMPWRLPMQVGRLFKQAKAPK  720
```

An ORF117ng nucleotide sequence <SEQ ID 519> was predicted to encode a protein having amino acid sequence <SEQ ID 520>:

```
  1..LLVQTEKDGL HNEQTFGEKK VFSENGKLHN YWRARRKGHD ETGHREQNYT

51   LPEEITRDIS LGSFAYESHS KALSRHAPSQ GTELPQSNRD NIRTAKSNGI

101   SLPYTPNSFT PLPGSSLYII NPANKGYLVE TDPRFANYRQ WLGSDYMLGS

151   LKLDPNNLHK RLGDGYYEQR LINEQIAELT GHRRLDGYQN DEEQFKALMD

201   NGATAARSMN LSVGIALSAE QAAQLTSDIV WLVQKEVKLP DGGTQTVLMP

251   QVYVRVKNGG IDGKGALLSG SNTQINVSGS LKNSGTIAGR NALIINTDTL

301   DNIGGRIHAQ KSAVTATQDI NNIGGILSAE QTLLLNAGNN INNQSTAKSS

351   QNAQGSSTYL DRMAGIYITG KEKGVLAAQA GKDINIIAGQ ISNQSDQGQT

401   RLQAGRDINL DTVQTGKYQE IHFDADNHTI RGSTNEVGSS IQTKGDVTLL

451   SGNNLNAKAA EVGSAKGTLA VYAKNDITIS SGIHAGQVDD ASKHTGRSGG

501   GNKLVITDKA QSHHETAQSS TFEGKQVVLQ AGNDANILGS NVISDNGTRI

551   QAGNHVRIGT TQTQSQSETY HQTQKSGLMS AGIGFTIGSK TNTQENQSQS

601   NEHTGSTVGS LKGDTTIVAS KHYEQTGSNV SSPEGNNLIS TQSMDIGAAQ

651   NQLNSKTTQT YEQKGLTVAF SSPVTDLAQQ AIAVAHKAAE QFDKAKTTAL

701   MPWRLPMQVG RLFKQAKAPK K*
```

Further work revealed the following gonococcal partial DNA sequence <SEQ ID 521>:

```
   1 TTGCTTGTGC AAACAGAAAA AGACGGTTTG CATAACGAGC AAACCTTTGG
  51 CGAGAAGAAA GTCTTCAGCG AAAATGGTAA GTTGCACAAC TACTGGCGTG
 101 CGCGTCGTAA AGGACATGAT GAAACAGGGC ATCGTGAACA AAATTATACT
 151 TTGCCGGAGG AAATCACACG CGACATTTCA CTGGGTTCAT TTGCCTATGA
 201 ATCGCATAGC AAAGCATTAA GCCGTCATGC GCCCAGCCAA GGCACTGAGT
 251 TGCCACAAAG TAACCGGGAT AATATCCGTA CTGCGAAAAG CAACGGTATT
 301 TCGCTACCCT ATACGCCCAA TTCTTTTACC CCATTACCCG GCAGCAGCTT
 351 ATACATTATC AATCCTGCCA ATAAAGGCTA TCTTGTTGAA ACCGATCCAC
 401 GCTTTGCCAA CTACCGTCAA TGGTTGGGTA GTGACTATAT GCTGGGCAGC
 451 CTCAAACTAG ACCCAAACAA TTTACATAAA CGTTTGGGTG ATGGTTATTA
 501 CGAGCAACGT TTAATCAATG AACAAATCGC AGAGCTGACA GGGCATCGTC
 551 GTTTAGACGG TTATCAAAAC GACGAAGAAC AATTTAAAGC CTTAATGGAT
 601 AATGGCGCGA CTGCGGCACG TTCGATGAAT CTCAGCGTTG GCATTGCATT
 651 AAGTGCCGAG CAAGCAGCGC AACTGACCAG CGATATTGTT TGGTTGGTAC
 701 AAAAAGAAGT TAAACTTCCT GATGGCGGCA CACAAACCGT ATTGATGCCA
 751 CAGGTTTATG TACGCGTTAA AAATGGCGGC ATAGACGGTA AAGGTGCATT
 801 GTTGTCAGGC AGCAATACAC AAATCAATGT TTCAGGCAGC CTGAAAAACT
 851 CAGGCACGAT TGCAGGGCGC AATGCGCTTA TTATCAATAC CGATACGCTA
 901 GACAATATCG GTGGGCGTAT TCATGCGCAA AAATCAGCGG TTACGGCCAC
 951 ACAAGACATC AATAATATTG GCGGCATTCT TTCTGCCGAA CAGACATTAT
1001 TGCTCAATGC GGGTAACAAC ATCAACAACC AAAGCACGGC CAAGAGCAGT
1051 CAAAATGCAC AAGGTAGCAG CACCTACCTA GACCGAATGG CAGGTATTTA
1101 TATCACAGGC AAAGAAAAAG GTGTTTTAGC AGCGCAGGCA GGCAAAGACA
1151 TCAACATCAT TGCCGGTCAA ATCAGCAATC AATCAGATCA AGGGCAAACC
1201 CGGCTGCAGG CAGGACGCGA CATTAACCTG GATACGGTAC AAACCGGCAA
1251 ATATCAAGAA ATCCATTTTG ATGCCGATAA CCATACCATC CGAGGTTCAA
1301 CGAACGAAGT CGGCAGCAGC ATTCAAACAA AAGGCGATGT TACCCtatTG
1351 TCAGGGAATA ATCTCAATGC CAAAGCTGCC GAAGTCGGCA GCGCAAAAGG
1401 CACACTTGCC GTGTATGCTA AAAATGACAT TACTATCAGC TCAGGCATCC
1451 ATGCCGGCCA AGTTGATGAT GCGTCCAAAC ATACAGGCAG AAGCGGCGGC
1501 GGTAATAAAT TAGTCATTAC CGATAAAGCC CAAAGTCATC ACGAAACTGC
1551 TCAAAGCAGC ACCTTTGAAG GCAAGCAAGT TGTATTGCAG GCAGGAAACG
1601 ATGCCAACAT CCTTGGCAGT AATGTTATTT CCGATAATGG CACCCGGATT
1651 CAAGCAGGCA ATCATGTTCG CATTGGTACA ACCCAAACTC AAAGCCAAAG
1701 CGAAACCTAT CATCAAACCC AAAAATCAGG ATTGATGAGT GCAGGTATCG
1751 GCTTCACTAT TGGCAGCAAG ACAAACACAC AAGAAAACCA ATCCCAAAGC
1801 AACGAACATA CAGGCAGTAC CGTAGGCAGC CTGAAAGGCG ATACCACCAT
1851 TGTTGCAAGC AAACACTACG AACAAACCGG CAGCAACGTT TCCAGCCCTG
1901 AGGGCAACAA CCTTATCAGC ACGCAAAGTA TGGATATTGG CGCAGCACAA
```

```
-continued
1951 AACCAATTAA ACAGCAAAAC CACCCAAACC TACGAACAAA AAGGCTTAAC

2001 GGTGGCATTC AGTTCGCCCG TTACCGATTT GGCACAACAA GCGATTGCCG

2051 TAGCACACAA AGCAGCAAAC AAGTCGGACA AGCAAAAAC GACCGCGTTA

2101 ATGCCATGGC GGCTGCCAAT GCAGGTTGGC AGGCCTATCA AACAGGCAAA

2151 GGCGCACAAA ACTTAG
```

This corresponds to the amino acid sequence <SEQ ID 522; ORF117ng-1>:

```
  1 LLVQTEKDGL HNEQTFGEKK VFSENGKLHN YWRARRKGHD ETGHREQNYT

51 LPEEITRDIS LGSFAYESHS KALSRHAPSQ GTELPQSNRD NIRTAKSNGI

101 SLPYTPNSFT PLPGSSLYII NPANKGYLVE TDPRFANYRQ WLGSDYMLGS

151 LKLDPNNLHK RLGDGYYEQR LINEQIAELT GHRRLDGYQN DEEQFKALMD

201 NGATAARSMN LSVGIALSAE QAAQLTSDIV WLVQKEVKLP DGGTQTVLMP

251 QVYVRVKNGG IDGKGALLSG SNTQINVSGS LKNSGTIAGR NALIINTDTL

301 DNTGGRIHAQ KSAVTATQDI NNIGGILSAE QTLLLNAGNN INNQSTAKSS

351 QNAQGSSTYL DRMAGIYITG KEKGVLAAQA GKDINIIAGQ ISNQSDQGQT

401 RLQAGRDINL DTVQTGKYQE IHFDADNHTI RGSTNEVGSS IQTKGDVTLL

451 SGNNLNAKAA EVGSAKGTLA VYAKNDITIS SGIHAGQVDD ASKHTGRSGG

501 GNKLVITDKA QSHHETAQSS TFEGKQVVLQ AGNDANILGS NVISDNGTRI

551 QAGNHVRIGT TQTQSQSETY HQTQKSGLMS AGIGFTIGSK TNTQENQSQS

601 NEHTGSTVGS LKGDTTIVAS KHYEQTGSNV SSPEGNNLIS TQSMDIGAAQ

651 NQLNSKTTQT YEQKGLTVAF SSPVTDLAQQ AIAVAHKAAN KSDKAKTTAL

701 MPWRLPMQVG RPIKQAKAHK T*
```

ORF117ng-1 shows the same 90% identity over a 230aa overlap with ORF117. In addition, it shows homology with a secreted *N. meningitidis* protein in the database:

```
gi|2623258 (AF030941) putative secreted protein [Neisseria meningitidis]
Length = 2273
Score = 604 bits (1541), Expect = e-172
Identities = 325/678 (47%), Positives = 449/678 (65%), Gaps = 22/678 (3%)

Query:    1 LLVQTEKDGLHNEQTFGEKKVFSENGKLHNYWRARRKGHDETGHREQNYTLPEEITRDIS    60
            L+V T +   L N++T G K + ++ G LH Y R  +KG D  TG+       E++  I
Sbjct:  739 LIVGTPESALDNDETLGTKTI-TDKGDLHRYHRHHKKGRDSTGYSRSPYEPAPEVS-SIR  796

Query:   61 LGSFAYESHSKALSRHAPSQGTELPQSNRDNIRTAKSNGISLPYTPNSFTPLPGSSLYII  120
            +G  AY+ +      AP Q +++P +    +   NGI   +T       LP SSL+ I
Sbjct:  797 MGISAYKGY-------APQQASDIPGTV---VPVVAENGIHPTFT------LPNSSLFAI  840

Query:  121 NPANKGYLVETDPRFANYRQWLGSDYMLGSLKLDPNNLHKRLGDGYYEQRLINEQIAELT  180
             P NKGYL+ETDP F +YR+WLGS YML +L+  DPN++HKRLGDGYYEQ+L+NEQIA+LT
Sbjct:  841 APNNKGYLIETDPAFTDYRKWLGSGYMLAALQQDPNHIHKRLGDGYYEQKLVNEQIAKLT  900

Query:  181 GHARLDGYQNDEEQFKALMDNGATAARSMNLSVGIALSAEQAAQLTSDIVWLVQKEVKLP  240
            G+RRLDGY NDEEQFKALMDNG T A+ + L+ GIALSAEQ A+LTSDIVWL + V LP
Sbjct:  901 GYRRLDGYTNDEEQFKALMDNGITIAKELQLTPGIALSAEQVARLTSDIVWLENETVTLP  960

Query:  241 DGGTQTVLMPQVYVRVKNGGIDGKGALLSGSNTQINVSGSLKN-SGTIAGRNALIINTDT  299
            DG TQTVL P+VYVR +   ++G+GALLSGS    I  SG+++  G IAGR ALI+N
Sbjct:  961 DGTTQTVLKPKVYVRARPKDMNGQGALLSGSVVDIG-SGAIENRGGLIAGREALILNAQN 1019

Query:  300 LDNIGGRIHAQKSAVTATQDINNIGGILSAEQTLLLNAGNNINNQSTAKSSONAQGSSTY  359
             + N+ G + +    A DI N G I  AE  LLL A NNI ++S +S+QN QGS
Sbjct: 1020 IKNLQGDLQGKNIFAAAGSDITNTGSI-GAENALLLKASNNIESRSETRSNQNEQGSVRN 1078
```

```
Query:   360 LDRMAGIYITGKEKGVLAAQAGKDINIIAGQISNQSDQGQTRLQAGRDINLDTVQTGKYQ   419
             + R+AGIY+TG++ G +   AG +I + A +++NQS+ GQT L AG DI  DT    + Q
Sbjct:  1079 IGRVAGIYLTGRQNGSVLLDAGNNIVLTASELTNQSEDGQTVLNAGGDIRSDTTGISRNQ  1138

Query:   420 EIHFDADNHTIRGSTNEVGSSIQTKGDVTLLSGNNLNAKAAEVGSAKGTLAVYAKNDITI   479
               FD+DN+ IR   NEVGS+I+T+G+++L +   ++   +AAEVGS +G L + A  DI +
Sbjct:  1139 NTIFDSDNYVIRKEQNEVGSTIRTRGNLSLNAKGDIRIRAAEVGSEQGRLKLAAGRDIKV  1198

Query:   480 SSGIHAGQVDDASKHTGRSGGGNKLVITDKAQSHHETAQSSTFEGKQVVLQAGNDANILG   539
              +G    + +DA K+TGRSGGG K  +T   ++ +   A S T +GK+++L +G D  + G
Sbjct:  1199 EAGKAHTETEDALKYTGRSGGGIKQKMTRHLKNQNGQAVSGTLDGKEIILVSGRDITVTG  1258

Query:   540 SNVISDNGTRIQAGNHVRIGTTQTQSQSETYHQTKSGLM-SAGIGFTIGSKTNTQENQS   598
              SN+I+DN T + A N++ +    +T+S+S    ++ +KSGLM S GIGFT GSK +TQ N+S
Sbjct:  1259 SNIIADNHTILSAKNNIVLKAAETRSRSAEMNKKEKSGLMGSGGIGFTAGSKKDTQTNRS  1318

Query:   599 QSNEHTGSTVGSLKGDTTIVASKHYEQTGSNVSSPEGNNLISTQSMDIGAAQNQLNSKTT  658
              ++   HT S VGSL G+T I A KHY QTGS +SSP+G+   IS+ +  I AAQN+ + ++
Sbjct:  1319 ETVSHTESVVGSLNGNTLISAGKHYTQTGSTISSPQGDVGISSGKISIDAAQNRYSQESK  1378

Query:   659 QTYEQKGLTVAFSSPVTD                                            676
              Q YEQKG+TVA S PV +
Sbjct:  1379 QVYEQKGVTVAISVPVVN                                           1396
```

Based on this analysis, it is predicted that the proteins from *N. meningitidis* and *N. gonorrhoeae*, and their epitopes, could be useful antigens for vaccines or diagnostics, or for raising antibodies.

Example 63

The following partial DNA sequence was identified in *N. meningitidis* <SEQ ID 523>:

```
  1 ATGATTTACA TCGTACTGTT TCTAGCTGTC GTCCTCGCCG TTGTCGCCTA

51 CAACATGTAT CAGGAAAACC AATACCGCAA AAAAGTGCGC GACCAGTTCG

101 GACACTCCGA CAAAGATGCC CTGCTCAACA GCAwAACCAG CCATGTCCGC

151 GACGGCAAAC CGTCCGGCGG GTCAGTCATG ATGCCGAAAC CCCAACCGGC

201 GGTCAAAAAA ACGGCAAAAC CCCAAGACCC CGyCATGCGC AACCTGCAAG

251 AACAGGATGC CGTCTACATC GCCAAGCAGA AACAGGCAAA AGCCTCCCCG

301 TTCAAAACCG AAATCGAAAC CGCCTTGGAA GAAAGCGGCA TTATCGGCAA

351 CTCCGCCCAC ACCGTTTCCG AACCCCAAAC CGGACATTCC GCAACGAAAC

401 CTGCCGACGC GTCGGCAAAA CCTGCACCCG TTCCGCAAAC ACCTGCAAAA

451 CCGCTGATTA CGCTCAAAGA ACTGTCAAAA GTCGAATTAT CCTGGTTTGA

501 CGTGCGCATC GACTTCATCT CCTAT...
```

This corresponds to the amino acid sequence <SEQ ID 524; ORF119>:

```
  1 MIYIVLFLAV VLAVVAYNMY QENQYRKKVR DQFGHSDKDA LLNSXTSHVR

51 DGKPSGGSVM MPKPQPAVKK TAKPQDPXMR NLQEQDAVYI AKQKQAKASP

101 FKTEIETALE ESGIIGNSAH TVSEPQTGHS ATKPADASAK PAPVPQTPAK

151 PLITLKELSK VELSWFDVRI DFISY...
```

Further work revealed the complete nucleotide sequence <SEQ ID 525>:

```
   1 ATGATTTACA TCGTACTGTT TCTAGCTGTC GTCCTCGCCG TTGTCGCCTA
  51 CAACATGTAT CAGGAAAACC AATACCGCAA AAAAGTGCGC GACCAGTTCG
 101 GACACTCCGA CAAAGATGCC CTGCTCAACA GCAAAACCAG CCATGTCCGC
 151 GACGGCAAAC CGTCCGGCGG GTCAGTCATG ATGCCGAAAC CCCAACCGGC
 201 GGTCAAAAAA ACGGCAAAAC CCCAAGACCC CGCCATGCGC AACCTGCAAG
 251 AACAGGATGC CGTCTACATC GCCAAGCAGA AACAGGCAAA AGCCTCCCCG
 301 TTCAAAACCG AAATCGAAAC CGCCTTGGAA GAAAGCGGCA TTATCGGCAA
 351 CTCCGCCCAC ACCGTTTCCG AACCCCAAAC CGGACATTCC GCACCGAAAC
 401 CTGCCGACGC GCCGGCAAAA CCTGCACCCG TTCCGCAAAC ACCTGCAAAA
 451 CCGCTGATTA CGCTCAAAGA ACTGTCAAAA GTCGAATTAC CTGGTTTGA
 501 CGTGCGCTTC GACTTCATCT CCTATATCGC GCTGACCGAA GCCAAAGAAC
 551 TGCACGCACT GCCGCGCCTT TCCAACCGCT GCCGCTACCA GATTGTCGGC
 601 TGCACCATGG ACGACCATTT CCAGATTGCC GAACCCATCC CGGGCATCCG
 651 CTATCAGGCA TTTATCGTGG GTATTCAGGC AGTCAGCCGC AACGGACTTG
 701 CCTCGCAGGA AGAACTCTCC GCATTCAACC GCCAGGTGGA CGCATTCGCA
 751 CAAAGCATGG GCGGTCAGAC GCTGCACACC GACCTTGCCG CCTTTATCGA
 801 AGTGGCTTCC GCACTGGACG CATTCTGCGC GCGCGTCGAC CAGACCATCG
 851 CCATCCATTT GGTTTCCCCG ACCAGCATCA GCGGCGTAGA ACTGCGTTCC
 901 GCCGTAACGG GCGTGGGTTT CGTTTTGGAA GACGACGGCG CGTTCCACTA
 951 TACCGACACG TCGGGCTCGA CCATGTTCTC CATCTGCTCG CTCAACAACG
1001 AGCCGTTTAC CAACGCCCTT TTGGACAACC AGTCCTACAA AGGCTTCAGT
1051 ATGCTGCTCG ACATCCCGCA CTCTCCGGCA GGCGAAAAAA CCTTCGACGA
1101 TTTGTTTATG GATTTGGCGG TACGCCTGTC CGGCCAGTTG AACCTGAATC
1151 TGGTCAACGA CAAAATGGAA GAAGTTTCGA CCCAATGGCT CAAAGACGTG
1201 CGCACTTATG TATTGGCGCG TCAGTCCGAG ATGCTCAAAG TCGGTATCGA
1251 ACCGGGCGGC AAAACCGCAT TGCGCCTGTT CTCCTAA
```

This corresponds to the amino acid sequence <SEQ ID 526; ORF119-1>:

```
   1 MIYIVLFLAV VLAVVAYNMY QENQYRKKVR DQFGHSDKDA LLNSKTSHVR
  51 DGKPSGGSVM MPKPQPAVKK TAKPQDPAMR NLQEQDAVYI AKQKQAKASP
 101 FKTEIETALE ESGIIGNSAH TVSEPQTGHS APKPADAPAK PAPVPQTPAK
 151 PLITLKELSK VELPWFDVRF DFISYIALTE AKELHALPRL SNRCRYQIVG
 201 CTMDDHFQIA EPIPGIRYQA FIVGIQAVSR NGLASQEELS AFNRQVDAFA
 251 QSMGGQTLHT DLAAFIEVAS ALDAFCARVD QTIAIHLVSP TSISGVELRS
 301 AVTGVGFVLE DDGAFHYTDT SGSTMFSICS LNNEPFTNAL LDNQSYKGFS
 351 MLLDIPHSPA GEKTFDDLFM DLAVRLSGQL NLNVNDKME EVSTQWLKDV
 401 RTYVLARQSE MLKVGIEPGG KTALRLFS*
```

Computer analysis of this amino acid sequence gave the following results:

Homology with a Predicted ORF from *N. meningitidis* (Strain A)

ORF119 shows 93.7% identity over a 175aa overlap with an ORF (ORF119a) from strain A of *N. meningitidis*:

```
                  10        20        30        40        50        60
orf119.pep  MIYIVLFLAVVLAVVAYNMYQENQYRKKVRDQFGHSDKDALLNSXTSHVRDGKPSGGSVM
            |||||||||:||||||||||||||||||||||||||||||||| |||||||||||||| ||
orf119a     MIYIVLFLAAVLAVVAYNMYQENQYRKKVRDQFGHSDKDALLNSKTSHVRDGKPSGGPVM
                  10        20        30        40        50        60

70        80        90       100       110       120
orf119.pep  MPKPQPAVKKTAKPQDPXMRNLQEQDAVYIAKQKQAKASPFKTEIETALEESGIIGNSAH
            |||||||||||||| ||| |||||||||||||||||||||||||||||||||||||||||
orf119a     MPKPQPAVKKTAKSQDPAMRNLQEQDAVYIAKQKQAKASPFKTEIETALEESGIIGNSAH
                  70        80        90       100       110       120

130       140       150       160       170
orf119.pep  TVSEPQTGHSATKPADASAKPAPVPQTPAKPLITLKELSKVELSWFDVRIDFISY
            || ||||||||| |||| |||:||||||||||||||||||||| |||||:||||
orf119a     TVPEPQTGHSAPKPADAPAKPVPVPQTPAKPLITLKELSKVELPWFDVRFDFISYIALTE
                 130       140       150       160       170       180 orf119a     AKELHALPRLSNRCRYQIVGCTMDDHFQIAEPIPGIRYQAFIVGIQAVSRNGLASQEELS
                 190       200       210       220       230       240
```

The complete length ORF119a nucleotide sequence <SEQ ID 527> is:

```
   1 ATGATTTACA TCGTACTGTT CCTCGCCGCC GTCCTCGCCG TTGTCGCCTA
  51 CAATATGTAT CAGGAAAACC AATACCGCAA AAAAGTGCGC GACCAGTTCG
 101 GGCACTCCGA CAAAGATGCC CTGCTCAACA GCAAAACCAG CCATGTCCGC
 151 GACGGCAAAC CGTCCGGCGG GCCAGTCATG ATGCCGAAAC CCCAACCGGC
 201 GGTCAAAAAA ACGGCAAAAT CCCAAGACCC CGCCATGCGC AACCTGCAAG
 251 AGCAGGATGC CGTCTACATC GCCAAGCAGA AACAGGCAAA AGCCTCCCCG
 301 TTCAAAACCG AAATCGAAAC CGCCTTGGAA GAAAGCGGCA TTATCGGCAA
 351 CTCCGCCCAC ACCGTTCCCG AACCCAAAC CGGACATTCC GCACCAAAAC
 401 CTGCCGACGC GCCGGCAAAA CCTGTTCCCG TTCCGCAAAC GCCGGCAAAA
 451 CCGCTGATTA CGCTCAAAGA GCTGTCGAAG GTCGAGCTGC CCTGGTTTGA
 501 CGTGCGCTTC GACTTCATCT CTTATATCGC GCTGACCGAA GCCAAAGAAC
 551 TGCACGCACT GCCGCGCCTT TCCAACCGCT GCCGCTACCA GATTGTCGGC
 601 TGCACCATGG ACGACCATTT CCAGATTGCC GAACCCATCC CGGGCATCCG
 651 CTATCAGGCA TTTATCGTGG GTATTCAGGC AGTCAGCCGC AACGGACTTG
 701 CCTCGCAGGA AGAACTCTCC GCATTCAACC GCCAGGTGGA TGCATTCGCA
 751 CACAGCATGG GCGGTCAGAC GCTGCACACC GACCTTGCCG CCTTTATCGA
 801 AGTGGCTTCC GCACTGGACG CATTCTGCGC GCGCGTCGAC CAGACTATCG
 851 CCATCCATTT GGTTTCCCCG ACCAGCATCA GCGGCGTAGA ACTGCGTTCC
 901 GCCGTAACGG GCGTGGGTTT CGTTTTGGAA GACGACGGCG CGTTCCACTA
 951 TACCGACACG TCGGGCTCGA CCATGTTCTC CATCTGCTCG CTCAACAACG
1001 AGCCGTTTAC CAATGCCCTT TTGGACAACC AGTCCTATAA AGGCTTCAGT
1051 ATGCTGCTCG ACATCCCGCA CTCTCCGGCA GGCGAAAAAA CCTTCGACGA
1101 TTTGTTTATG GATTTGGCGG TACGCCTGTC CGGCCAGTTG AACCTGAATC
1151 TGGTCAACGA CAAAATGGAA GAAGTTTCGA CCCAATGGCT CAAAGACGTG
```

```
-continued
1201 CGCACTTATG TATTGGCTCG TCAGTCCGAG ATGCTCAAAG TCGGTATCGA

1251 ACCGGCGGC AAAACCGCAT TGCGCCTGTT CTCCTAA
```

This encodes a protein having amino acid sequence <SEQ ID 528>:

```
  1 MIYIVLFLAA VLAVVAYNMY QENQYRKKVR DQFGHSDKDA LLNSKTSHVR

51 DGKPSGGPVM MPKPQPAVKK TAKSQDPAMR NLQEQDAVYI AKQKQAKASP

101 FKTEIETALE ESGIIGNSAH TVPEPQTGHS APKPADAPAK PVPVPQTPAK

151 PLITLKELSK VELPWFDVRF DFISYIALTE AKELHALPRL SNRCRYQIVG

201 CTMDDHFQIA EPIPGIRYQA FIVGIQAVSR NGLASQEELS AFNRQVDAFA

251 HSMGGQTLHT DLAAFIEVAS ALDAFCARVD QTIAIHLVSP TSISGVELRS

301 AVTGVGFVLE DDGAFHYTDT SGSTMFSICS LNNEPFTNAL LDNQSYKGFS

351 MLLDIPHSPA GEKTFDDLFM DLAVRLSGQL NLNLVNDKME EVSTQWLKDV

401 RTYVLARQSE MLKVGIEPGG KTALRLFS*
```

ORF119a and ORF119-1 show 98.6% identity in 428 aa overlap:

```
                   10          20         30         40          50        60
orf119a.pep MIYIVLFLAAVLAVVAYNMYQENQYRKKVRDQFGHSDKDALLNSKTSHVRDGKPSGGPVM
            ||||||||| :|||||||||||||||||||||||||||||||||||||||||||||| ||
  orf119-1 MIYIVLFLAVVLAVVAYNMYQENQYRKKVRDQFGHSDKDALLNSKTSHVRDGKPSGGSVM
                   10          20         30         40          50        60

70          80         90        100         110       120
orf119a.pep MPKPQPAVKKTAKSQDPAMRNLQEQDAVYIAKQKQAKASPFKTEIETALEESGIIGNSAH
            ||||||||||||| ||||||||||||||||||||||||||||||||||||||||||||||
  orf119-1 MPKPQPAVKKTAKPQDPAMRNLQEQDAVYIAKQKQAKASPFKTEIETALEESGIIGNSAH
                   70          80         90        100         110       120

130         140        150         160         170       180
orf119a.pep TVPEPQTGHSAPKPADAPAKPVPVPQTPAKPLITLKELSKVELPWFDVRFDFISYIALTE
            || |||||||||||||||||:|||||||||||||||||||||||||||||||||||||||
  orf119-1 TVSEPQTGHSAPKPADAPAKPAPVPQTPAKPLITLKELSKVELPWFDVRFDFISYIALTE
                  130         140        150         160         170       180

190         200        210         220         230       240
orf119a.pep AKELHALPRLSNRCRYQIVGCTMDDHFQIAEPIPGIRYQAFIVGIQAVSRNGLASQEELS
            ||||||||||||||||||||||||||||||||||||||||||||||||||||||||||||
  orf119-1 AKELHALPRLSNRCRYQIVGCTMDDHFQIAEPIPGIRYQAFIVGIQAVSRNGLASQEELS
                  190         200        210         220         230       240

250         260        270         280         290       300
orf119a.pep AFNRQVDAFAHSMGGQTLHTDLAAFIEVASALDAFCARVDQTIAIHLVSPTSISGVELRS
            |||||||||| :||||||||||||||||||||||||||||||||||||||||||||||||
  orf119-1 AFNRQVDAFAQSMGGQTLHTDLAAFIEVASALDAFCARVDQTIAIHLVSPTSISGVELRS
                  250         260        270         280         290       300

310         320        330         340         350       360
orf119a.pep AVTGVGFVLEDDGAFHYTDTSGSGTMFSICSLNNEPFTNALLDNQSYKGFSMLLDIPHSPA
            ||||||||||||||||||||||||||||||||||||||||||||||||||||||||||||
  orf119-1 AVTGVGFVLEDDGAFHYTDTSGSGTMFSICSLNNEPFTNALLDNQSYKGFSMLLDIPHSPA
                  310         320        330         340         350       360

370         380        390         400         410       420
orf119a.pep GEKTFDDLFMDLAVRLSGQLNLNLVNDKMEEVSTQWLKDVRTYVLARQSEMLKVGIEPGG
            ||||||||||||||||||||||||||||||||||||||||||||||||||||||||||||
  orf119-1 GEKTFDDLFMDLAVRLSGQLNLNLVNDKMEEVSTQWLKDVRTYVLARQSEMLKVGIEPGG
                  370         380        390         400         410       420

429
orf119a.pep KTALRLFSX
            |||||||||
  orf119-1 KTALRLFSX
```

Homology with a Predicted ORF from *N. gonorrhoeae*

ORF119 shows 93.1% identity over a 175aa overlap with a predicted ORF (ORF119ng) from *N. gonorrhoeae*:

```
orf119.pep  MIYIVLFLAVVLAVVAYNMYQENQYRKKVRDQFGHSDKDALLNSXTSHVRDGKPSGGSVM  60
            ||||||||:|||||||||||||||||||||||||||||||||| ||||||||||||| ||
orf119ng    MIYIVLFLAAVLAVVAYNMYQENQYRKKVRDQFGHSDKDALLNSKTSHVRDGKPSGGPVM  60 orf119.pep  MPKPQPAVKKTAKPQDPXMRNLQEQDAVYIAKQKQAKASPFKTEIETALEESGIIGNSAH 120
            |||||||||| ||||| ||||||||||||||||||||||||||||||||||| ||||||
orf119ng    MPKPQPAVKKPAKPQDSAMRNLQEQDAVYIAKQKQAKASPFKTEIETALEEIGIIGNSAH 120 orf119.pep  TVSEPQTGHSATKPADASAKPAPVPQTPAKPLITLKELSKVELSWFDVRIDFISY      175
            |||||||||| ||||| |||:|||||||||||||||||||||| |||| :||||
orf119ng    TVSEPQTGHSAPKPADAPAKPVPVPQTPAKPLITLKELSKVELPWFDVRFDFISYIALTE 180
```

The complete length ORF119ng nucleotide sequence <SEQ ID 529> is:

```
   1 ATGATTTACA TCGTACTGTT CCTCGCCGCC GTCCTCGCCG TTGTCGCCTA
  51 CAATATGTAT CAGGAAAACC AATACCGCAA AAAAGTGCGC GACCAGTTCG
 101 GACACTCCGA CAAAGATGCC CTGCTCAACA GCAAAACCAG CCATGTCCGC
 151 GACGGCAAAC CGTCCGGCGG GCCAGTCATG ATGCCGAAAC CCCAACCGGC
 201 GGTCAAAAAA CCGGCCAAAC CCCAAGACTC CGCCATGCGC AACCTGCAAG
 251 AACAGGATGC CGTCTACATC GCCAAGCAGA AACAGGCAAA AGCCTCCCCG
 301 TTCAAAACCG AAATCGAAAC CGCCTTGGAA GAAATCGGCA TTATCGGCAA
 351 CTCCGCCCAC ACCGTTTCCG AACCCCAAAC CGGACATTCC GCACCGAAAC
 401 CTGCCGACGC GCCGGCAAAA CCCGTTCCCG TTCCGCAAAC GCCGGCAAAA
 451 CCGCTGATTA CGCTCAAAGA GCTGTCGAAG GTCGAGCTGC CTGGTTTGA
 501 CGTGCGCTtc gACTTCATCT CCTATATCGC GCTGACCGAA GCCAAAGAAC
 551 TGCACGCACT GCCGCGCCTT tccAACCGCT GCCGCTACCA GATTGTCGGC
 601 TGCACCATGG ACGACCATTT CCAGATTGCC GAACCCATCC CGGGCATCCG
 651 CTATCAGGCA TTTATCGTGG GTATCCAGGC AGTCAGCCGC AACGGACTTG
 701 CCTCGCAGGA AGAACTCTCC GCATTCAACC GCCAGGCGGA CGCATTCGCA
 751 CAAAGCATGG GCGGTCAGAC GCTGCACACC GACCTTGCCG CCTTTATCGA
 801 AGTGGCTTCC GCACTGGACG CATTCTGCGC GCGCGTCGAC CAGACCATCG
 851 CCATCCATTT GGTTTCGCCG ACCAGCATCA GCGGCGTAGA ACTGCGTTCC
 901 GCCGTAACGG GCGTGGGTTT CGTTTTGGAA GACGACGGCG CGTTCCACTA
 951 TACCGACACG TCGGGCTCGA CCATGTTCTC CATCTGCTCG CTCAACAACG
1001 AGCCGTTTAC CAATGCCCTT TTGGACAACC AGTCCTACAA AGGCTTCAGT
1051 ATGCTGCTCG ACATCCCGCA CTCTCCGGCA GGCGAAAAAA CCTTCGACGA
1101 TTTGTTTATG GATTTGGCGG TACGCCTGTC CGGTCAGTTG AACCTGAATC
1151 TGGTCAACGA CAAAATGGAA GAAGTTTCGA CCCAATGGCT CAAAGACGTA
1201 CGCACTTATG TATTGGCGCG TCAGTCCGAG ATGCTCAAAG TCGGTATCGA
1251 ACCGGGCGGC AAAACCGCCC TGCGCCTGTT TTCATAA
```

This encodes a protein having amino acid sequence <SEQ ID 530>:

```
  1 MIYIVLFLAA VLAVVAYNMY QENQYRKKVR DQFGHSDKDA LLNSKTSHVR
 51 DGKPSGGPVM MPKPQPAVKK PAKPQDSAMR NLQEQDAVYI AKQKQAKASP
```

```
101 FKTEIETALE EIGIIGNSAH TVSEPQTGHS APKPADAPAK PVPVPQTPAK

151 PLITLKELSK VELPWFDVRF DFISYIALTE AKELHALPRL SNRCRYQIVG

201 CTMDDHFQIA EPIPGIRYQA FIVGIQAVSR NGLASQEELS AFNRQADAFA

251 QSMGGQTLHT DLAAFIEVAS ALDAFCARVD QTIAIHLVSP TSISGVELRS

301 AVTGVGFVLE DDGAFHYTDT SGSTMFSICS LNNEPFTNAL LDNQSYKGFS

351 MLLDIPHSPA GEKTFDDLFM DLAVRLSGQL NLNLVNDKME EVSTQWLKDV

401 RTYVLARQSE MLKVGIEPGG KTALRLFS*
```

ORF119ng and ORF119-1 show 98.4% identity over 428 aa overlap:

```
                  10        20        30        40        50        60
     orf119ng MIYIVLFLAAVLAVVAYNMYQENQYRKKVRDQFGHSDKDALLNSKTSHVRDKGPSGGPVM
              ||||||||:||||||||||||||||||||||||||||||||||||||||||||||| ||
     orf119-1 MIYIVLFLAVVLAVVAYNMYQENQYRKKVRDQFGHSDKDALLNSKTSHVRDKGPSGGSVM
                  10        20        30        40        50        60

70        80        90       100       110       120
     orf119ng MPKPQPAVKKPAKPQDSAMRNLQEQDAVYIAKQKQAKASPFKTEIETALEEIGIIGNSAH
              |||||||||| |||| ||||||||||||||||||||||||||||||||||   |||||||
     orf119-1 MPKPQPAVKKTAKPQDPAMRNLQEQDAVYIAKQKQAKASPFKTEIETALEESGIIGNSAH
                  70        80        90       100       110       120

130       140       150       160       170       180
     orf119ng TVSEPQTGHSAPKPADAPAKPVPVPQTPAKPLITLKELSKVELPWFDVRFDFISYIALTE
              |||||||||||||||||||||:||||||||||||||||||||||||||||||||||||||
     orf119-1 TVSEPQTGHSAPKPADAPAKPAPVPQTPAKPLITLKELSKVELPWFDVRFDFISYIALTE
                 130       140       150       160       170       180

190       200       210       220       230       240
     orf119ng AKELHALPRLSNRCRYQIVGCTMDDHFQIAEPIPGIRYQAFIVGIQAVSRNGLASQEELS
              ||||||||||||||||||||||||||||||||||||||||||||||||||||||||||||
     orf119-1 AKELHALPRLSNRCRYQIVGCTMDDHFQIAEPIPGIRYQAFIVGIQAVSRNGLASQEELS
                 190       200       210       220       230       240

250       260       270       280       290       300
     orf119ng AFNRQADAFAQSMGGQTLHTDLAAFIEVASALDAFCARVDQTIAIHLVSPTSISGVELRS
              |||| :||||||||||||||||||||||||||||||||||||||||||||||||||||||
     orf119-1 AFNRQVDAFAQSMGGQTLHTDLAAFIEVASALDAFCARVDQTIAIHLVSPTSISGVELRS
                 250       260       270       280       290       300

310       320       330       340       350       360
     orf119ng AVTGVGFVLEDDGAFHYTDTSGSTMFSICSLNNEPFTNALLDNQSYKGFSMLLDIPHSPA
              ||||||||||||||||||||||||||||||||||||||||||||||||||||||||||||
     orf119-1 AVTGVGFVLEDDGAFHYTDTSGSTMFSICSLNNEPFTNALLDNQSYKGFSMLLDIPHSPA
                 310       320       330       340       350       360

370       380       390       400       410       420
     orf119ng GEKTFDDLFMDLAVRLSGQLNLNLVNDKMEEVSTQWLKDVRTYVLARQSEMLKVGIEPGG
              ||||||||||||||||||||||||||||||||||||||||||||||||||||||||||||
     orf119-1 GEKTFDDLFMDLAVRLSGQLNLNLVNDKMEEVSTQWLKDVRTYVLARQSEMLKVGIEPGG
                 370       380       390       400       410       420

429
     orf119ng KTALRLFSX
              |||||||||
     orf119-1 KTALRLFSX
```

Based on this analysis, including the presence of a putative leader sequence in the gonococcal protein, it is predicted that the proteins from *N. meningitidis* and *N. gonorrhoeae*, and their epitopes, could be useful antigens for vaccines or diagnostics, or for raising antibodies.

Example 64

The following partial DNA sequence was identified in *N. meningitidis* <SEQ ID 531>

```
 1 ..GCGCGGCACG GCACGGAAGA TTTCTTCATG AACAACAGCG ACAC.ATCAG

51   GCAGATAGTC GAAAGCACCA CCGGTACGAT GAAGCTGCTG ATTTCCTCCA
```

-continued

```
101  TCGCCCTGAT TTCATTGGTA GTCGGCGGCA TCGGCGTGAT GAACATCATG

151  CTGGTGTCCG TTACCGAGCG CACCAAAGAA ATCGGCATAC GGATGGCAAT

201  CGGCGCGCGG CGCGGCAATA TTTyGCAGCA GTTTTTGATT GAGGCGGTGT

251  TAATCTGCGT CATCGGCGGT TTGGTCGGCG TGGGTTTGTC CGCCGCCGTC

301  AGCCTCGTGT TCAATCATTT TGTAACCGAC TTCCCGATGG ACATTTCCGC

351  CATGTCCGTC ATCGGCGCGG TCGCCTGTTC GACCGGAATC GGCATCGCGT

401  TCGGCTTTAT GCCTGCCAAT AAAGCAGCCA AACTCAATCC GATAGACGCA

451  TTGGCACAGG ATTGA
```

This corresponds to the amino acid sequence <SEQ ID 532; ORF134>:

```
  1..ARHGTEDFFM NNSDXIRQIV ESTTGTMKLL ISSIALISLV VGGIGVMNIM

51  LVSVTERTKE IGIRMAIGAR RGNIXQQFLI EAVLICVIGG LVGVGLSAAV

101  SLVFNHFVTD FPMDISAMSV IGAVACSTGI GIAFGFMPAN KAAKLNPIDA

151  LAQD*
```

Further work revealed the complete nucleotide sequence <SEQ ID 533>:

```
   1  ATGTCGGTGC AAGCAGTATT GGCGCACAAA ATGCGTTCGC TTCTGACGAT

51  GCTCGGCATC ATCATCGGTA TCGCGTCGGT GGTTTCCGTC GTCGCATTGG

101  GCAATGGTTC GCAGAAAAAA ATCCTTGAAG ACATCAGTTC GATAGGGACG

151  AACACCATCA GCATCTTCCC GGGGCGCGGC TTCGGCGACA GGCGCAGCGG

201  CAGGATTAAA ACCCTGACCA TAGACGACGC AAAAATCATC GCCAAACAAA

251  GCTACGTTGC TTCCGCCACG CCCATGACTT CGAGCGGCGG CACGCTGACT

301  TACCGCAACA CCGACCTGAC CGCCTCGCTT TACGGCGTGG GCGAACAATA

351  TTTCGACGTG CGCGGACTGA AGCTGGAAAC GGGGCGGCTG TTTGACGAAA

401  ACGATGTGAA AGAAGACGCG CAGGTCGTCG TCATCGACCA AAATGTCAAA

451  GACAAACTCT TGCGGACTC GGATCCGTTG GGTAAAACCA TTTTGTTCAG

501  GAAACGCCCC TTGACCGTCA TCGGCGTGAT GAAAAAAGAC GAAAACGCTT

551  TCGGCAATTC CGACGTGCTG ATGCTTTGGT CGCCCTATAC GACGGTGATG

601  CACCAAATCA CAGGCGAGAG CCACACCAAC TCCATCACCG TCAAAATCAA

651  AGACAATGCC AATACCCAGG TTGCCGAAAA AGGGCTGACC GATCTGCTCA

701  AAGCGCGGCA CGGCACGGAA GATTTCTTCA TGAACAACAG CGACAGCATC

751  AGGCAGATAG TCGAAAGCAC CACCGGTACG ATGAAGCTGC TGATTTCCTC

801  CATCGCCCTG ATTTCATTGG TAGTCGGCGG CATCGGCGTG ATGAACATCA

851  TGCTGGTGTC CGTTACCGAG CGCACCAAAG AAATCGGCAT ACGGATGGCA

901  ATCGGCGCGC GGCGCGGCAA TATTTTGCAG CAGTTTTTGA TTGAGGCGGT

951  GTTAATCTGC GTCATCGGCG GTTTGGTCGG CGTGGGTTTG TCCGCCGCCG

1001  TCAGCCTCGT GTTCAATCAT TTTGTAACCG ACTTCCCGAT GGACATTTCC

1051  GCCATGTCCG TCATCGGCGC GGTCGCCTGT CGACCGGAA TCGGCATCGC
```

-continued

```
1101 GTTCGGCTTT ATGCCTGCCA ATAAAGCAGC CAAACTCAAT CCGATAGACG

1151 CATTGGCACA GGATTGA
```

This corresponds to the amino acid sequence <SEQ ID 534; ORF134-1>:

```
  1 MSVQAVLAHK MRSLLTMLGI IIGIASVVSV VALGNGSQKK ILEDISSIGT

51 NTISIFPGRG FGDRRSGRIK TLTIDDAKII AKQSYVASAT PMTSSGGTLT

101 YRNTDLTASL YGVGEQYFDV RGLKLETGRL FDENDVKEDA QVVVIDQNVK

151 DKLFADSDPL GKTILFRKRP LTVIGVMKKD ENAFGNSDVL MLWSPYTTVM

201 HQITGESHTN SITVKIKDNA NTQVAEKGLT DLLKARHGTE DFFMNNSDSI

251 RQIVESTTGT MKLLISSIAL ISLVVGGIGV MNIMLVSVTE RTKEIGIRMA

301 IGARRGNILQ QFLIEAVLIC VIGGLVGVGL SAAVSLVFNH FVTDFPMDIS

351 AMSVIGAVAC STGIGIAFGF MPANKAAKLN PIDALAQD*
```

Computer analysis of this amino acid sequence gave the following results:

Homology with the Hypothetical Protein o648 of *E. coli* (Accession Number AE000189)

ORF134 and o648 protein show 45% aa identity in 153aa overlap:

```
Orf134:    2 RHGTEDFFMNNSDXIRQIVESTTGTMKXXXXXXXXXXXXVVGGIGVMNIMLVSVTERTKEI    61
             RHG +DFF  N D + + VE TT T++          VVGGIGVMNIMLVSVTERT+EI
o648:    496 RHGKKDFFTWNMDGVLKTVEKTTRTLQLFLTLVAVISLVVGGIGVMNIMLVSVTERTREI   555

Orf134:   62 GIRMAIGARRGNIXQQFLIEAXXXXXXXXXXXXXXXXXXXXXXFNHFVTDFPMDISAMSVI   121
             GIRMA+GAR  ++ QQFLIEA                     F+   + S ++++
o648:    556 GIRMAVGARASDVLQQFLIEAVLVCLVGGALGITLSLLIAFTLQLFLPGWEIGFSPLALL   615

Orf134:  122 GAVACSTGIGIAFGFMPANKAAKLNPIDALAQD                              154
             A  CST  GI FG++PA  AA+L+P+DALA++
o648:    616 LAFLCSTVTGILFGWLPARNAARLDPVDALARE                              648
```

Homology with a Predicted ORF from *N. meningitidis* (Strain A)

ORF134 shows 98.7% identity over a 154aa overlap with an ORF (ORF134a) from strain A of *N. meningitidis*:

```
                                               10        20         30
  orf134.pep                          ARHGTEDFFMNNSDXIRQIVESTTGTMKLL
                                      ||||||||||||||  ||||||||||||||
  orf134a    GESHTNSITVKIKDNANTQVAEKGLTDLLKARHGTEDFFMNNSDSIRQIVESTTGTMKLL
               210       220       230       240       250       260

40        50        60        70        80        90
  orf134.pep ISSIALISLVVGGIGVMNIMLVSVTERTKEIGIRMAIGARRGNIXQQFLIEAVLICVIGG
             |||||||||||||||||||||||||||||||||||||||||||| |||||||||||||||
  orf134a    ISSIALISLVVGGIGVMNIMLVSVTERTKEIGIRMAIGARRGNILQQFLIEAVLICVIGG
               270       280       290       300       310       320

100       110       120       130       140       150
  orf134.pep LVGVGLSAAVSLVFNHFVTDFPMDISAMSVIGAVACSTGIGIAFGFMPANKAAKLMPIDA
             ||||||||||||||||||||||||||||||||||||||||||||||||||||||||||||
  orf134a    LVGVGLSAAVSLVFNHFVTDFPMDISAMSVIGAVACSTGIGIAFGFMPANKAAKLMPIDA
               330       340       350       360       370       380 orf134.pep LAQDX
             |||||
  orf134a    LAQDX
```

The complete length ORF134a nucleotide sequence <SEQ ID 535> is:

```
   1 ATGTCGGTGC AAGCAGTATT GGCGCACAAA ATGCGTTCGC TTCTGACGAT
  51 GCTCGGCATC ATCATCGGTA TCGCTTCGGT TGTCTCCGTC GTCGCATTGG
 101 GCAACGGTTC GCAGAAAAAA ATCCTTGAAG ACATCAGTTC GATAGGGACG
 151 AACACCATCA GCATCTTCCC AGGGCGCGGC TTCGGCGACA GGCGCAGCGG
 201 CAGGATTAAA ACCCTGACCA TAGACGACGC AAAAATCATC GCCAAACAAA
 251 GCTACGTTGC TTCCGCCACG CCCATGACTT CGAGCGGCGG CACGCTGACT
 301 TACCGCAATA CCGACCTGAC CGCTTCTTTG TACGGTGTGG GCGAACAATA
 351 TTTCGACGTG CGCGGGCTGA AGCTGGAAAC GGGGCGGCTG TTTGACGAAA
 401 ACGATGTGAA AGAAGACGCG CAGGTCGTCG TCATCGACCA AAATGTCAAA
 451 GACAAACTCT TTGCGGACTC GGATCCGTTG GGTAAAACCA TTTTGTTCAG
 501 GAAACGCCCC TTGACCGTCA TCGGCGTGAT GAAAAAAGAC GAAAACGCTT
 551 TCGGCAATTC CGACGTGCTG ATGCTTTGGT CGCCCTATAC GACGGTGATG
 601 CACCAAATCA CAGGCGAGAG CCACACCAAC TCCATCACCG TCAAAATCAA
 651 AGACAATGCC AATACCCAGG TTGCCGAAAA AGGGCTGACC GATCTGCTCA
 701 AAGCGCGGCA CGGCACGGAA GATTTCTTCA TGAACAACAG CGACAGCATC
 751 AGGCAGATAG TCGAAAGCAC CACCGGTACG ATGAAGCTGC TGATTTCCTC
 801 CATCGCCCTG ATTTCATTGG TAGTCGGCGG CATCGGCGTG ATGAACATCA
 851 TGCTGGTGTC CGTTACCGAG CGCACCAAAG AAATCGGCAT ACGGATGGCA
 901 ATCGGCGCGC GGCGCGGCAA TATTTTGCAG CAGTTTTTGA TTGAGGCGGT
 951 GTTAATCTGC GTCATCGGCG GTTTGGTCGG CGTGGGTTTG TCCGCCGCCG
1001 TCAGCCTCGT GTTCAATCAT TTTGTAACCG ACTTCCCGAT GGACATTTCC
1051 GCCATGTCCG TCATCGGCGC GGTCGCCTGT TCGACCGGAA TCGGCATCGC
1101 GTTCGGCTTT ATGCCTGCCA ATAAAGCAGC CAAACTCAAT CCGATAGATG
1151 CATTGGCGCA GGATTGA
```

This encodes a protein having amino acid sequence <SEQ ID 536>:

```
  1 MSVQAVLAHK MRSLLTMLGI IIGIASVVSV VALGNGSQKK ILEDISSIGT
 51 NTISIFPGRG FGDRRSGRIK TLTIDDAKII AKQSYVASAT PMTSSGGTLT
101 YRNTDLTASL YGVGEQYFDV RGLKLETGRL FDENDVKEDA QVVVIDQNVK
151 DKLFADSDPL GKTILFRKRP LTVIGVMKKD ENAFGNSDVL MLWSPYTTVM
201 HQITGESHTN SITVKIKDNA NTQVAEKGLT DLLKARHGTE DFFMNNSDSI
251 RQIVESTTGT MKLLISSIAL ISLVVGGIGV MNIMLVSVTE RTKEIGIRMA
301 IGARRGNILQ QFLIEAVLIC VGGLVGVGL SAAVSLVFNH FVTDFPMDIS
351 AMSVIGAVAC STGIGIAFGF MPANKAAKLN PIDALAQD*
```

ORF134a and ORF134-1 show 100.0% identity in 388 aa overlap:

```
orf134a.pep  MSVQAVLAHKMRSLLTMLGIIIGIASVVSVVALGNGSQKKILEDISSIGTNTISIFPGRG
             ||||||||||||||||||||||||||||||||||||||||||||||||||||||||||||
orf134-1     MSVQAVLAHKMRSLLTMLGIIIGIASVVSVVALGNGSQKKILEDISSIGTNTISIFPGRG
```

```
orf134a.pep  FGDRRSGRIKTLTIDDAKIIAKQSYVASATPMTSSGGTLTYRNTDLTASLYGVGEQYFDV
             ||||||||||||||||||||||||||||||||||||||||||||||||||||||||||||
orf134-1     FGDRRSGRIKTLTIDDAKIIAKQSYVASATPMTSSGGTLTYRNTDLTASLYGVGEQYFDV orf134a.pep  RGLKLETGRLFDENDVKEDAQVVVIDQNVKDKLFADSDPLGKTILFRKRPLTVIGVMKKD
             ||||||||||||||||||||||||||||||||||||||||||||||||||||||||||||
orf134-1     RGLKLETGRLFDENDVKEDAQVVVIDQNVKDKLFADSDPLGKTILFRKRPLTVIGVMKKD orf134a.pep  ENAFGNSDVLMLWSPYTTVMHQITGESHTNSITVKIKDNANTQVAEKGLTDLLKARHGTE
             ||||||||||||||||||||||||||||||||||||||||||||||||||||||||||||
orf134-1     ENAFGNSDVLMLWSPYTTVMHQITGESHTNSITVKIKDNANTQVAEKGLTDLLKARHGTE orf134a.pep  DFFMNNSDSIRQIVESTTGTMKLLISSIALISLVVGGIGVMNIMLVSVTERTKEIGIRMA
             ||||||||||||||||||||||||||||||||||||||||||||||||||||||||||||
orf134-1     DFFMNNSDSIRQIVESTTGTMKLLISSIALISLVVGGIGVMNIMLVSVTERTKEIGIRMA orf134a.pep  IGARRGNILQQFLIEAVLICVIGGLVGVGLSAAVSLVFNHFVTDFPMDISAMSVIGAVAC
             ||||||||||||||||||||||||||||||||||||||||||||||||||||||||||||
orf134-1     IGARRGNILQQFLIEAVLICVIGGLVGVGLSAAVSLVFNHFVTDFPMDISAMSVIGAVAC orf134a.pep  STGIGIAFGFMPANKAAKLNPIDALAQDX
             |||||||||||||||||||||||||||||
orf134-1     STGIGIAFGFMPANKAAKLNPIDALAQDX
```

Homology with a Predicted ORF from *N. gonorrhoeae*

ORF134 shows 96.8% identity over a 154aa overlap with a predicted ORF (ORF134.ng) from *N. gonorrhoeae*:

```
orf134.pep                                     ARHGTEDFFMNNSDXIRQIVESTTGTMKLL   30
                                               ||||||||||||| |||:||||||||||||
orf134ng    GESHTNSITVKIKDNANTRVAEKGLAELLKARHGTEDFFMNNSDSIRQMVESTTGTMKLL  264
orf134.pep  ISSIALISLVVGGIGVMNIMLVSVTERTKEIGIRMAIGARRGNIXQQFLIEAVLICVIGG   90
            |||||||||||||||||||||||||||||||||||||||||||| |||||||||||:|||
orf134ng    ISSIALISLVVGGIGVMNIMLVSVTERTKEIGIRMAIGARRGNILQQFLIEAVLICIIGG  324
orf134.pep  LVGVGLSAAVSLVFNHFVTDFPMDISAMSVIGAVACSTGIGIAFGFMPANKAAKLNPIDA  150
            |||||||||||||||||||||||||||| ||||||||||||||||||||||||||||||| 
orf134ng    LVGVGLSAAVSLVFNHFVTDFPMDISAASVIGAVACSTGIGIAFGFMPANKAAKLNPIDA  384
orf134.pep  LAQD                                                          154
            ||||
orf134ng    LAQD                                                          388
```

The complete length ORF134ng nucleotide sequence <SEQ ID 537> is:

```
  1  ATGTCGGTGC AAGCAGTATT GGCGCACAAA ATGCGTTCGC TTCTGACCAT
 51  GCTCGGCATC ATCATCGGTA TCGCTTCGGT TGTCTCCGTC GTCGCGCTGG
101  GCAACGGTTC GCAGAAAAAA ATCCTCGAAG ACATCAGTTC GATGGGGACG
151  AACACCATCA GCATCTTCCC CGGGCGCGGC TTCGGCGACA GGCGCAGCGG
201  CAAAATCAAA ACCCTGACCA TAGACGACGC AAAAATCATC GCCAAACAAA
251  GCTACGTTGC CTCCGCCACG CCCATGACTT CGAGCGGCGG CACGCTGACC
301  TACCGCAATA CCGACCTGAC CGCTTCTTTG TACGGTGTGG GCGAACAATA
351  TTTCGACGTG CGCGGGCTGA AGCTGGAAAC GGGGCGGCTG TTTGATGAGA
401  ACGATGTGAA AGAAGACGCG CAAGTCGTCG TCATCGACCA AAATGTCAAA
451  GACAAACTCT TTGCGGACTC GGATCCGTTG GGTAAAACCA TTTTGTTCAG
501  GAAACGCCCC TTGACCGTCA TCGGCGTGAT GAAAAAGAC  GAAAACGCTT
551  TCGGCAATTC CGACGTGCTG ATGCTTTGGT CGCCCTATAC GACGGTGATG
601  CACCAAATCA CAGGCGAGAG CCACACCAAC TCCATCACCG TCAAAATCAA
651  AGACAATGCC AATACCCGGG TTGCCGAAAA AGGGCTGGCC GAGCTGCTCA
701  AAGCACGGCA CGGCACGGAA GACTTCTTTA TGAACAACAG CGACAGCATC
751  AGGCAGATGG TCGAAAGCAC CACCGGTACG ATGAAGCTGC TGATTTCCTC
801  CATCGCCCTG ATTTCATTGG TAGTCGGCGG CATCGGTGTG ATGAACATTA
851  TGCTGGTGTC CGTTACCGAG CGCACCAAAG AAATCGGCAT ACGGATGGCA
```

-continued

```
 901 ATCGGCGCGC GGCGCGGCAA TATTTTGCAG CAGTTTTTGA TTGAGGCGGT
 951 GTTAATCTGC ATCATCGGAG GCTTGGTCGG CGTAGGTTTG TCCGCCGCCG
1001 TCAGCCTCGT GTTCAATCAT TTTGTAACCG ATTTCCCGAT GGACATTTCG
1051 GCGGCATCCG TTATCGGGGC GGTCGCCTGT TCGACCGGAA TCGGCATCGC
1101 GTTCGGCTTT ATGCCTGCCA ATAAGGCAGC CAAACTCAAT CCGATAGATG
1151 CATTGGCGCA GGATTGA
```

This encodes a protein having amino acid sequence <SEQ ID 538>:

```
  1 MSVQAVLAHK MRSLLTMLGI IIGIASVVSV VALGNGSQKK ILEDISSMGT
 51 NTISIFPGRG FGDRRSGKIK TLTIDDAKII AKQSYVASAT PMTSSGGTLT
101 YRNTDLTASL YGVGEQYFDV RGLKLETGRL FDENDVKEDA QVVVIDQNVK
151 DKLFADSDPL GKTILFRKRP LTVIGVMKKD ENAFGNSDVL MLWSPYTTVM
201 HQITGESHTN SITVKIKDNA NTRVAEKGLA ELLKARHGTE DFFMNNSDSI
251 RQMVESTTGT MKLLISSIAL ISLVVGGIGV MNIMLVSVTE RTKEIGIRMA
301 IGARRGNILQ QFLIEAVLIC IIGGLVGVGL SAAVSLVFNH FVTDFPMDIS
351 AASVIGAVAC STGIGIAFGF MPANKAAKLN PIDALAQD*
```

ORF134ng and ORF134-1 show 97.9% identity in 388 aa overlap:

```
orf134ng  MSVQAVLAHKMPSLLTMLGIIIGIASVVSVVALGNGSQKKILEDISSMGTNTISIFPGRG
          |||||||||||||||||||||||||||||||||||||||||||||||:||||||||||||
orf134-1  MSVQAVLAHKMPSLLTMLGIIIGIASVVSVVALGNGSQKKILEDISSIGTNTISIFPGRG orf134ng  FGDRRSGKIKTLTIDDAKIIAKQSYVASATPMTSSGGTLTYRNTDLTASLYGVGEQYFDV
          ||||||||:|||||||||||||||||||||||||||||||||||||||||||||||||||
orf134-1  FGDRRSGRIKTLTIDDAKIIAKQSYVASATPMTSSGGTLTYRNTDLTASLYGVGEQYFDV orf134ng  RGLKLETGRLFDENDVKEDAQVVVIDQNVKDKLFADSDPLGKTILFRKRPLTVIGVMKKD
          ||||||||||||||||||||||||||||||||||||||||||||||||||||||||||||
orf134-1  RGLKLETGRLFDENDVKEDAQVVVIDQNVKDKLFADSDPLGKTILFRKRPLTVIGVMKKD orf134ng  ENAFGNSDVLMLWSPYTTVMHQITGESHTNSITVKIKDNANTRVAEKGLAELLKARHGTE
          |||||||||||||||||||||||||||||||||||||||||||:||||||::||||||||
orf134-1  ENAFGNSDVLMLWSPYTTVMHQITGESHTNSITVKIKDNANTQVAEKGLTDLLKARHGTE orf134ng  DFFMNNSDSIRQMVESTTGTMKLLISSIALISLVVGGIGVMNIMLVSVTERTKEIGIRMA
          |||||||||||:||||||||||||||||||||||||||||||||||||||||||||||||
orf134-1  DFFMNNSDSIRQIVESTTGTMKLLISSIALISLVVGGIGVMNIMLVSVTERTKEIGIRMA orf134ng  IGARRGNILQQFLIEAVLICIIGGLVGVGLSAAVSLVFNHFVTDFPMDISAASVIGAVAC
          ||||||||||||||||||||:|||||||||||||||||||||||||||||| ||||||||
orf134-1  IGARRGNILQQFLIEAVLICVIGGLVGVGLSAAVSLVFNHFVTDFPMDISAMSVIGAVAC orf134ng  STGIGIAFGFMPANKAAKLNPIDALAQDX
          |||||||||||||||||||||||||||||
orf134-1  STGIGIAFGFMPANKAAKLNPIDALAQDX
```

ORF134ng also shows homology to an *E. coli* ABC transporter:

```
sp|P75831|YBJZ_ECOLI HYPOTHETICAL ABC TRANSPORTER ATP-BINDING
PROTEIN YBJZ >gi5 (AE000189) 0648; similar to YBBA_HAEIN SW:
P45247 [Escherichia coli] Length = 648
Score = 297 bits (753), Expect = 6e-80
Identities = 162/389 (41%), Positives = 230/389 (58%), Gaps = 1/389 (0%)

Query:   1 MSVQAVLAHKMRSLLTMLXXXXXXXXXXXXXXXLGNGSQKKILEDISSMGTNTISIFPGRG  60
           M+ +A+ A+KMR+LLTML               +G+ +++ +L DI S+GTNTI ++PG+
Sbjct: 260 MAWRALAANKMRTLLTMLGIIIGIASVVSIVVVGDAAKQMVLADIRSIGTNTIDVYPGKD  319
```

```
Query:  61 FGDRRSGKIKTLTIDDAKIIAKQSYVASATPMTSSGGTLTYRNTDLTASLYGVGEQYFDV 120
           FGD      + L  DD    I KQ +VASATP S     L Y N D+ AS  GV   YF+V
Sbjct: 320 FGDDDPQYQQALKYDDLIAIQKQPWVASATPAVSQNLRLRYNNVDVAASANGVSGDYFNV 379

Query: 121 RGLKLETGRLFDENDVKEDAQVVVIDQNVKDKLFAD-SDPLGKTILFRKRPLTVIGVMKK 179
              G+     G F++  +   AQVVV+D N + +LF   +D +G+ IL    P  VIGV ++
Sbjct: 380 YGMTFSEGNTFNQEQLNGRAQVVVLDSNTRRQLFPHKADVVGEVILVGNMPARVIGVAEE 439

Query: 180 DENAFGNSDVLMLWSPYTTVMHQITGESHTNSITVKIKDNANTRVAEKGLAELLKARHGT 239
              ++ FG+S VL +W PY+T+  ++ G+S  NSITV++K+   +  AE+ L   LL  REG
Sbjct: 440 KQSMFGSSKVLRVWLPYSTMSGRVMGQSWLNSITVRVKEGFDSAEAEQQLTRLLSLRHGK 499

Query: 240 EDFFMNNSDSIRQMVESTTGTMKXXXXXXXXXXXXVVGGIGVMNIMLVSVTERTKEIGIRM 299
              +DFF  N D + + VE TT T++           VVGGIGVMNIMLVSVTERT+EIGIRM
Sbjct: 500 KDFFTWNMDGVLKTVEKTTRTLQLFLTLVAVISLVVGGIGVMNIMLVSVTERTREIGIRM 559

Query: 300 AIGARRGNILQQFLIEXXXXXXXXXXXXXXXXXXXXXXXFNHFVTDFPMDISAASVIGAVA 359
           A+GAR  ++LQQFLIE                       F+  + +  S   +++ A
Sbjct: 560 AVGARASDVLQQFLIEAVLVCLVGGALGITLSLLIAFTLQLFLPGWEIGFSPLALLLAFL 619

Query: 360 CSTGIGIAFGFMPANKAAKLNPIDALAQD 388
           CST  GI FG++PA  AA+L+P+DALA++
Sbjct: 620 CSTVTGILFGWLPARNAARLDPVDALARE 648
```

Based on this analysis, including the presence of the leader peptide and transmembrane regions in the gonococcal protein, it is predicted that these proteins from *N. meningitidis* and *N. gonorrhoeae*, and their epitopes, could be useful antigens for vaccines or diagnostics, or for raising antibodies.

Example 65

The following partial DNA sequence was identified in *N. meningitidis* <SEQ ID 539>:

```
  1 ..GGGACGGGAG CGATGCTGCT GCTGTTTTAC GCGGTAACGA T.CTGCCTTT
 51   GGCCACTGGC GTTACCCTGA GTTACACCTC GTCGATTTTT TTGGCGGTAT
101   TTTCCTTCCT GATTTTGAAA GAACGGATTT CCGTTTACAC GCAGGCGGTG
151   CTGCTCCTTG GTTTTGCCGG CGTGGTATTG CTGCTTAATC CCTCGTTCCG
201   CAGCGGTCAG GAAACGGCGG CACTCGCCGG GCTGGCGGGC GGCGCGATGT
251   CCGGCTGGGC GTATTTGAAA GTGCGCGAAC TGTCTTTGGC GGGCGAACCC
301   GGCTGGCGCG TCGTGTTTTA CCTTTCCGTG ACAGGTGTGG CGATGTCGTC
351   GGTTTGGGCG ACGCTGACCG GCTGGCACAC CCTGTCCTTT CCATCGGCAG
401   TTTATCTGTC GTGCATCGGC GTGTCCGCGC TGATTGCCCA ACTGTCGATG
451   ACGCGCGCCT ACAAAGTCGG CGACAAATTC ACGGTTGCCT CGCTTTCCTA
501   TATGACCGTC GTTTTTTCCG CTCTGTCTGC CGCATTTTTT CTGGGCGAAG
551   AGCTTTTCTG GCAGGAAATA CTCGGTATGT GCATCATCAT CCTCAGCGGT
601   ATTTTGA
```

This corresponds to the amino acid sequence <SEQ ID 540; ORF135>:

```
  1 ..*GTGAM*LLLFY AVTILPLATG VTLSYTSSIF LAVFSFLILK ERISVYTQAV
 51   LLLGFAGVVL LLNPSFRSGQ ETAALAGLAG GAMSGWAYLK VRELSLAGEP
101   GWRVVFYLSV TGVAMSSVWA TLTGWHTLSF PSAVYLSCIG VSALIAQLSM
```

```
151 TRAYKVGDKF TVASLSYMTV VFSALSAAFF LGEELFWQEI LGMCIIISAV

201 F*
```

Further work revealed the complete nucleotide sequence <SEQ ID 541>:

```
  1 ATGGATACCG CAAAAAAGA CATTTTAGGA TCGGGCTGGA TGCTGGTGGC

51 GGCGGCCTGC TTTACCATTA TGAACGTATT GATTAAAGAG GCATCGGCAA

101 AATTTGCCCT CGGCAGCGGC GAATTGGTCT TTTGGCGCAT GCTGTTTTCA

151 ACCGTTGCGC TCGGGGCTGC CGCCGTATTG CGTCGGGACA mCTTCCGCAC

201 GCCCCATTGG AAAAACCACT TAAACCGCAG TATGGTCGGG ACGGGGCGA

251 TGCTGCTGCT GTTTTACGCG GTAACGCATC TGCCTTTGGC CACTGGCGTT

301 ACCCTGAGTT ACACCTCGTC GATTTTTTTG GCGGTATTTT CCTTCCTGAT

351 TTTGAAAGAA CGGATTTCCG TTTACACGCA GGCGGTGCTG CTCCTTGGTT

401 TTGCCGGCGT GGTATTGCTG CTTAATCCCT CGTTCCGCAG CGGTCAGGAA

451 ACGGCGGCAC TCGCCGGGCT GGCGGGCGGC GCGATGTCCG GCTGGGCGTA

501 TTTGAAAGTG CGCGAACTGT CTTTGGCGGG CGAACCCGGC TGGCGCGTCG

551 TGTTTTACCT TTCCGTGACA GGTGTGGCGA TGTCGTCGGT TTGGGCGACG

601 CTGACCGGCT GGCACACCCT GTCCTTTCCA TCGGCAGTTT ATCTGTCGTG

651 CATCGGCGTG TCCGCGCTGA TTGCCCAACT GTCGATGACG CGCGCCTACA

701 AAGTCGGCGA CAAATTCACG GTTGCCTCGC TTTCCTATAT GACCGTCGTT

751 TTTTCCGCTC TGTCTGCCGC ATTTTTTCTG GGCGAAGAGC TTTTCTGGCA

801 GGAAATACTC GGTATGTGCA TCATCATCCT CAGCGGTATT TTGAGCAGCA

851 TCCGCCCCAC TGCCTTCAAA CAGCGGCTGC AATCCCTGTT CCGCCAAAGA

901 TAA
```

This corresponds to the amino acid sequence <SEQ ID 542; ORF135-1>:

```
  1 MDTAKKDILG SGWMLVAAAC FTIMNVLIKE ASAKFALGSG ELVFWRMLFS

51 TVALGAAAVL RRDXFRTPHW KNHLNRSMVG TGAMLLLFYA VTHLPLATGV

101 TLSYTSSIFL AVFSFLILKE RISVYTQAVL LLGFAGVVLL LNPSFRSGQE

151 TAALAGLAGG AMSGWAYLKV RELSLAGEPG WRVVFYLSVT GVAMSSVWAT

201 LTGWHTLSFP SAVYLSCIGV SALIAQLSMT RAYKVGDKFT VASLSYMTVV

251 FSALSAAFFL GEELFWQEIL GMCIIILSGI LSSIRPTAFK QRLQSLFRQR

301 *
```

Computer analysis of this amino acid sequence gave the following results:

Homology with a Predicted ORF from *N. meningitidis* (Strain A)

ORF135 shows 99.0% identity over a 197aa overlap with an ORF (ORF135a) from strain A of *N. meningitidis*:

```
                                       10        20        30
orf135.pep                     GTGAMLLLFYAVTILPLATGVTLSYTSSIF
                               ||||||||||||| ||||||||||||||||
orf135a     STVALGAAAVLRRDTFRTPHWKNHLNRSMVGTGAMLLLFYAVTHLPLATGVTLSYTSSIF
         50        60        70        80        90       100
                40        50        60        70        80        90
orf119.pep  LAVFSFLILKERISVYTQAVLLLGFAGVVLLLNPSFRSGQETAALAGLAGGAMSGWAYLK
            ||||||||||||||||||||||||||||||||||||||||||||||||||||||||||||
orf119a     LAVFSFLILKERISVYTQAVLLLGFAGVVLLLNPSFRSGQETAALAGLAGGAMSGWAYLK
          110       120       130       140       150       160
                   100       110       120       130       140       150
orf135.pep  VRELSLAGEPGWRVVFYLSVTGVAMSSVWATLTGWHTLSFPSAVYLSCIGVSALIAQLSM
            ||||||||||||||||||||||||||||||||||||||||||||||||||||||||||||
orf135a     VRELSLAGEPGWRVVFYLSVTGVAMSSVWATLTGWHTLSFPSAVYLSCIGVSALIAQLSM
          170       180       190       200       210       220
                  160       170       180       190       200
orf135.pep  TRAYKVGDKFTVASLSYMTVVFSALSAAFFLGEELFWQEILGMCIIISAVFX
            |||||||||||||||||||||||||||||||| :|||||||||||||
orf135a     TRAYKVGDKFTVASLSYMTVVFSALSAAFFLAEELFWQEILGMCIIILSGILSSIRPTAF
          230       240       250       260       270       280 orf135a     KQRLQSLFRQRX
          290       300
```

The complete length ORF135a nucleotide sequence <SEQ ID 543> is:

```
  1 ATGGATACCG CAAAAAAGA CATTTTAGGA TCGGGCTGGA TGCTGGTGGC
 51 GGCGGCCTGC TTTACCATTA TGAACGTATT GATTAAAGAG GCATCGGCAA
101 AATTTGCCCT CGGCAGCGGC GAATTGGTCT TTTGGCGCAT GCTGTTTTCA
151 ACCGTTGCGC TCGGGGCTGC CGCCGTATTG CGTCGGGACA CCTTCCGCAC
201 GCCCCATTGG AAAAACCACT TAAACCCAG TATGGTCGGG ACGGGGCGA
251 TGCTGCTGCT GTTTTACGCG GTAACGCATC TGCCTTTGGC CACCGGCGTT
301 ACCCTGAGTT ACACCTCGTC GATTTTTTTG GCGGTATTTT CCTTCCTGAT
351 TTTGAAAGAA CGGATTTCCG TTTACACGCA GGCGGTGCTG CTCCTTGGTT
401 TTGCCGGCGT GGTATTGCTG CTTAATCCCT CGTTCCGCAG CGGTCAGGAA
451 ACGGCGGCAC TCGCCGGGCT GGCGGGCGGC GCGATGTCCG GCTGGGCGTA
501 TTTGAAAGTG CGCGAACTGT CTTTGGCGGG CGAACCCGGC TGGCGCGTCG
551 TGTTTTACCT TTCCGTGACA GGTGTGGCGA TGTCATCGGT TTGGGCGACG
601 CTGACCGGCT GGCACACCCT GTCCTTTCCA TCGGCAGTTT ATCTGTCGTG
651 CATCGGCGTG TCCGCGCTGA TTGCCCAACT GTCGATGACG CGCGCCTACA
701 AAGTCGGCGA CAAATTCACG GTTGCCTCGC TTTCCTATAT GACCGTCGTT
751 TTTTCCGCTC TGTCTGCCGC ATTTTTTCTG GCCGAAGAGC TTTTCTGGCA
801 GGAAATACTC GGTATGTGCA TCATCATCCT CAGCGGTATT TTGAGCAGCA
851 TCCGCCCCAC TGCCTTCAAA CAGCGGCTGC AATCCCTGTT CCGCCAAAGA
901 TAA
```

This encodes a protein having amino acid sequence <SEQ ID 544>:

```
  1 MDTAKKDILG SGWMLVAAAC FTIMNVLIKE ASAKFALGSG ELVFWRMLFS
 51 TVALGAAAVL RRDTFRTPHW KNHLNRSMVG TGAMLLLFYA VTHLPLATGV
101 TLSYTSSIFL AVFSFLILKE RISVYTQAVL LLGFAGVVLL NPSFRSGQE
151 TAALAGLAGG AMSGWAYLKV RELSLAGEPG WRVVFYLSVT GVAMSSVWAT
201 LTGWHTLSFP SAVYLSCIGV SALIAQLSMT RAYKVGDKFT VASLSYMTVV
```

```
251 FSALSAAFFL AEELFWQEIL GMCIIILSGI LSSIRPTAFK QRLQSLFRQR

301 *
```

ORF135a and ORF135-1 show 99.3% identity in 300 aa overlap:

```
orf135a.pep  MDTAKKDILGSGWMLVAAACFTIMNVLIKEASAKFALGSGELVFWRMLFSTVALGAAAVL
             ||||||||||||||||||||||||||||||||||||||||||||||||||||||||||||
orf135-1     MDTAKKDILGSGWMLVAAACFTIMNVLIKEASAKFALGSGELVFWRMLFSTVALGAAAVL orf135a.pep  RRDTFRTPHWKNHLNRSMVGTGAMLLLFYAVTHLPLATGVTLSYTSSIFLAVFSFLILKE
             ||||||||||||||||||||||||||||||||||||||||||||||||||||||||||||
orf135-1     RRDTFRTPHWKNHLNRSMVGTGAMLLLFYAVTHLPLATGVTLSYTSSIFLAVFSFLILKE orf135a.pep  RISVYTQAVLLLGFAGVVLLLNPSFRSGQETAALAGLAGGAMSGWAYLKVRELSLAGEPG
             ||||||||||||||||||||||||||||||||||||||||||||||||||||||||||||
orf135-1     RISVYTQAVLLLGFAGVVLLLNPSFRSGQETAALAGLAGGAMSGWAYLKVRELSLAGEPG orf135a.pep  WRVVFYLSVTGVAMSSVWATLTGWHTLSFPSAVYLSCIGVSALIAQLSMTRAYKVGDKFT
             ||||||||||||||||||||||||||||||||||||||||||||||||||||||||||||
orf135-1     WRVVFYLSVTGVAMSSVWATLTGWHTLSFPSAVYLSCIGVSALIAQLSMTRAYKVGDKFT orf135a.pep  VASLSYMTVVFSALSAAFFLAEELFWQEILGMCIIILSGILSSIRPTAFKQRLQSLFRQR
             |||||||||||||||||||||||:||||||||||||||||||||||||||||||||||||
orf135-1     VASLSYMTVVFSALSAAFFLGEELFWQEILGMCIIILSGILSSIRPTAFKQRLQSLFRQR
```

Homology with a Predicted ORF from *N. gonorrhoeae*

ORF135 shows 97% identity over a 201aa overlap with a predicted ORF (ORF135ng) from *N. gonorrhoeae*:

```
orf135.pep                         GTGAMLLLFYAVTXLPLATGVTLSYTSSIF   30
                                   ||||||||||||| |||:||||||||||||
orf135ng     STVTLGAAAVLRRDTFRTPHWKNHLNRSMVGTGAMLLLFYAVTHLPLTTGVTLSYTSSIF  335 orf135.pep   LAVFSFLILKERISVYTQAVLLLGFAGVVLLLNPSFRSGQETAALAGLAGGAMSGWAYLK   90
             ||||||||||||||||||||||||||||||||||||||||:|||||||||||||||||||
orf135ng     LAVFSFLILKERISVYTQAVLLLGFAGVVLLLNPSFRSGQEPAALAGLAGGAMSGWAYLK  395 orf135.pep   VRELSLAGEPGWRVVFYLSVTGVAMSSVWATLTGWHTLSFPSAVYLSCIGVSALIAQLSM  150
             |||||||||||||||||||:||||||||||||||||||||||||||:|||||||||||||
orf135ng     VRELSLAGEPGWRVVFYLSATGVAMSSVWATLTGWHTLSFPSAVYLSGIGVSALIAQLSM  455 orf135.pep   TRAYKVGDKFTVASLSYMTVVFSALSAAFFLGEELFWQEILGMCIIISAVF           201
             ||||||||||||||||||||||||||||||||||||||||||||||||:|
orf135ng     TRAYKVGDKFTVASLSYMTVVFSALSAAFFLGEELFWQEILGMCIIISAAF          506
```

An ORF135ng nucleotide sequence <SEQ ID 545> was predicted to encode a protein having amino acid sequence <SEQ ID 546>:

```
  1 MPSEKAFRRH LRTASFQGLH LHHFHQKVGK CGIIGFGIHI FPTLLPAAQG

51 ILDIQLGLFR IDFAALAVYR RTQVDFIHTV IDGIASDQAF SEVVQILRRL

101 NLGHFTDTHL IAQARRFIAD FGNIRPMRRG EAKTFCRCFR FDGIDGIHGD

151 FRQCGHINRL APGKDCRNGK RDKVFFHTRH YNQVCLEKTN CSARKIKFRH

201 QKQAKTHSTS LAARFTIRPS LSQRPFMDTA KKDILGSGWM LVAAACFTVM

251 NVLIKEASAK FALGSGELVF WRMLFSTVTL GAAAVLRRDT FRTPHWKNHL

301 NRSMVGTGAM LLLFYAVTHL PLTTGVTLSY TSSIFLAVFS FLILKERISV

351 YTQAVLLLGF AGVVLLLNPS FRSGQEPAAL AGLAGGAMSG WAYLKVRELS

401 LAGEPGWRVV FYLSATGVAM SSVWATLTGW HTLSFPSAVY LSGIGVSALI

451 AQLSMTRAYK VGDKFTVASL SYMTVVFSAL SAAFFLGEEL FWQEILGMCI

501 IISAAF*
```

Further work revealed the following gonococcal sequence
<SEQ ID 547>:

```
  1 ATGGATACCG CAAAAAAGA CATTTTAGGA TCGGGCTGGA TGCTGGTGGC

51 GGCGGCCTGC TTCACCGTTA TGAACGTATT GATTAAAGAG GCATCGGCAA

101 AATTTGCCCT CGGCAGCGGC GAATTGGTCT TTTGGCGCAT GCTGTTTTCA

151 ACCGTTACGC TCGGTGCTGC CGCCGTATTG CGGCGCGACA CCTTCCGCAC

201 GCCCCATTGG AAAAACCACT TAAACCGCAG TATGGTCGGG ACGGGGCGA

251 TGCTGCTGCT GTTTTACGCG GTAACGCATC TGCCTTTGAC AACCGGCGTT

301 ACCCTGAGTT ACACCTCGTC GATTTTTttg GCGGTATTTT CCTTCCTCAT

351 TTTGAAAGAA CGGATTTCCG TTTACACGCA GGCGGTGCTG CTCCTTGGTT

401 TTGCCGGCGT GGTATTGCTG CTTAATCCCT CGTTCCGCAG CGGTCAGGAA

451 CCGGCGGCAC TCGCCGGGCT GGCGGGCGGC GCGATGTCCG GCTGGGCGTA

501 TTTGAAAGTG CGCGAACTGT CTTTGGCGGG CGAACCCGGC TGGCGCGTCG

551 TGTTTTACCT TTCCGCAACC GGCGTGGCGA TGTCGTCggt ttgggcgacg

601 Ctgaccggct ggCACAcccT GTCCTTTcca tcggcagttt ATCtgtCGGG

651 CATCGGCGTG tccgcgCtgA TTGCCCAaCT GtcgatgAcg cGCGcctaca 701 aaGTCGGCGA CAAATTCACG GTTGCCTCGC tttcctaTAt gaccgtcGTC 751 TTTTCCGCCC TGTCTGCCGC ATTTTTTCTg ggcgaagagc tttTCtggCA 801 GGAAATACTC GGTATGTGCA TCATTAtccT CAGCGGCATT TTGAGCAGCA

851 TCCGCCCCAT TGCCTTCAAA CAGCGGCTGC AAGCCCTCTT CCGCCAAAGA

901 TAA
```

This corresponds to the amino acid sequence <SEQ ID 548; ORF135ng-1>:

```
  1 MDTAKKDILG SGWMLVAAAC FTVMNVLIKE ASAKFALGSG ELVFWRMLFS

51 TVTLGAAAVL RRDTFRTPHW KNHLNRSMVG TGAMLLLFYA VTHLPLTTGV

101 TLSYTSSIFL AVFSFLILKE RISVYTQAVL LLGFAGVVLL LNPSFRSGQE

151 PAALAGLAGG AMSGWAYLKV RELSLAGEPG WRVVFYLSAT GVAMSSVWAT

201 LTGWHTLSFP SAVYLSGIGV SALIAQLSMT RAYKVGDKFT VASLSYMTVV

251 FSALSAAFFL GEELFWQEIL GMCIIILSGI LSSIRPIAFK QRLQALFRQR

301 *
```

ORF135ng-1 and ORF135-1 show 97.0% identity in 300 aa overlap:

```
orf135ng-1.pep  MDTAKKDILGSGWMLVAAACFTVMNVLIKEASAKFALGSGELVFWRMLFSTVTLGAAAVL
                ||||||||||||||||||||:|||||||||||||||||||||||||||||:|||||||
orf135-1        MDTAKKDILGSGWMLVAAACFTIMNVLIKEASAKFALGSGELVFWRMLFSTVALGAAAVL orf135ng-1.pep  RRDTFRTPHWKNHLNRSMVGTGAMLLLFYAVTHLPLTTGVTLSYTSSIFLAVFSELILKE
                |||:||||||||||||||||||||||||||||||||:||| ||||||||||||||||||
orf135-1        RRDXFRTPHWKNHLNRSMVGTGAMLLLFYAVTHLPLATFVTLSYTSSIFLAVFSELILKE orf135ng-1.pep  RISVYTQAVLLLGFAGVVLLLNPSFRSGQEPAALAGLAGGAMSGWAYLKVRELSLAGEPG
                ||||||||||||||||||||||||||||| ||||||||||||||||||||||||||||||
orf135-1        RISVYTQAVLLLGFAGVVLLLNPSFRSGQETAALAGLAGGAMSGWAYLKVRELSLAGEPG orf135ng-1.pep  WRVVFYLSATGVAMSSVWATLTGWHTLSFPSAVYLSGIGVSALIAQLSMTRAYKVGDKET
                ||||||||:||||||||||||||||||||||||||| |||||||||||||||||||||||
orf135-1        WRVVFYLSVTGVAMSSVWATLTGWHTLSFPSAVYLSCIGVSALIAQLSMTRAYKVGDKET
```

```
orf135ng-1.pep  VASLSYMTVVFSALSAAFFLGEELFWQEILGMCIIILSGILSSIRPIAFKQRLQALFRQR
                ||||||||||||||||||||||||||||||||||||||||||||| ||||||:|||||
orf135-1        VASLSYMTVVFSALSAAFFLGEELFWQEILGMCIIILSGILSSIRPTAFKQRLQSLFRQR
```

Based on this analysis, including the presence of several putative transmembrane domains in the gonococcal protein, it is predicted that the proteins from *N. meningitidis* and *N. gonorrhoeae*, and their epitopes, could be useful antigens for vaccines or diagnostics, or for raising antibodies.

Example 66

The following DNA sequence was identified in *N. meningitidis* <SEQ ID 549>:

```
  1 ATGAAGCGGC GTATAGCCGT CTTCGTCCTG TTCCCGCAGA TAATCCGAGT

51 TTTGGGACAA CTGTTGCCGA AAATCGTCAA TACAGTTCCG GCACATCGGA

101 TGCTCTTCCA GATTTTCGGG ATGTTCTTTT TCTTCATACA CCAGCAATAT

151 CTGCCCGGGA TCGCCGAAAT CGATTCCCCA TGCGGCATCG TGTTCGGTGC

201 GCTCCTCTTC CGTCATCTGC CCGCGCATTG CCTGTATGGT AAAGCCGCCG

251 TAGGGGATGC CgTTGCACAC GAACATCCAG TCGCTGATGT CGTCAACCGG

301 AACGCAAACG cTTTCGCCTT GTTCGACATT GGTCAGTTCG CCsGGTTCAT

351 TGTTCAGCAC ACCGTAAATA TAAAGACCGT CAAAATAAAT ATCGTCGATC

401 CACATATGTT CGCAAATTTC GCCGTCTTCG CCGTCTTGGA AAAAGGGAC

451 TTTGACCATG GCAAAATCCA AGGCGGAAAT AATGCGGCGG CGTTCCCAAA

501 AAAGcTCGCG CCAAAAATAT TTGAATGTTT TACGGGCGCG TTCGTCGGCA

551 CGGTTTACCG GTTCGTCTGC CTGTTCTACA TAATAAATGA CGGAATCGCC

601 CATCATaTCT GCTCCTCAAC GTGTACGGTA TCTGTTTGCA CCTTACTGCG

651 GCTTTCTgcC kTCGGCATCC GATTCGGATT TGAAAAGTTC mmrwyATTCG

701 GAATAG
```

This corresponds to the amino acid sequence <SEQ ID 550; ORF136>:

```
  1 MKRRIAVFVL FPQIIRVLGQ LLPKIVNTVP AHRMLFQIFG MFFFFIHQQY

51 LPGIAEIDSP CGIVFGALLF RHLPAHCLYG KAAVGDAVAE EHPVADVVNR

101 NANAFALFDI GQFAXFIVQH TVNIKTVKIN IVDPHMFANF AVFAVLEKRD

151 FDHGKIQGGN NAAAFPKKLA PKIFECFTGA FVGTVYRFVC LFYIINDGIA

201 HHSAPQRVRY LFAPYCGFLP SASDSDLKSS XXSE*
```

Further work revealed the complete nucleotide sequence <SEQ ID 551>:

```
  1 ATGATGAAGC GGCGTATAGC CGTCTTCGTC CTGTTCCCGC AGATAATCCG

51 AGTTTTGGGA CAACTGTTGC CGAAAATCGT CAATACAGTT CCGGCACATC

101 GGATGCTCTT CCAGATTTTC GGGATGTTCT TTTCTTCAT ACACCAGCAA

151 TATCTGCCCG GGATCGCCGA AATCGATTCC CCATGCGGCA TCGTGTTCGG
```

-continued
```
201 TGCGCTCCTC TTCCGTCATC TGCCCGCGCA TTGCCTGTAT GGTAAAGCCG

251 CCGTAGGGGA TGCCGTTGCA CACGAACATC CAGTCGCTGA TGTCGTCAAC

301 CGGAACGCAA ACGCTTTCGC CTTGTTCGAC ATTGGTCAGT TCGCCGGGTT

351 CATTGTTCAG CACACCGTAA ATATAAAGAC CGTCAAAATA AATATCGTCG

401 ATCCACATAT GTTCGCAAAT TTCGCCGTCT TCGCCGTCTT GGAAAAAAGG

451 GACTTTGACC ATGGCAAAAT CCAAGGCGGA AATAATGCGG CGGCGTTCCC

501 AAAAAGCTC GCGCCAAAAA TATTTGAATG TTTTACGGGC GCGTTCGTCG

551 GCACGGTTTA CCGGTTCGTC TGCCTGTTCT ACATAATAAA TGACGGAATC

601 GCCCATCATT CTGCTCCTCA ACGTGTACGG TATCTGTTTG CACCTTACTG

651 CGGCTTTCTG CCTTCGGCAT CCGATTCGGA TTTGAAAAGT TCCAAATATT

701 CGGAATAG
```

This corresponds to the amino acid sequence <SEQ ID 552; ORF136-1>:

```
  1 MMKRRIAVFV LFPQIIRVLG QLLPKIVNTV PAHRMLFQIF
    GMFFFFIHQQ

51 YLPGIAEIDS PCGIVFGALL FRHLPAHCLY GKAAVGDAVA
    HEHPVADVVN

101 RNANAFALFD IGQFAGFIVQ HTVNIKTVKI NIVDPHMFAN
    FAVFAVLEKR

151 DFDHGKIQGG NNAAAFPKKL APKIFECFTG
    AFVG TVYRFV CLFYIINDGI

201 AHHSAPQRVR YLFAPYCGFL PSASDSDLKS
    SKYSE*
```

Computer analysis of this amino acid sequence gave the following results:

Homology with a Predicted ORF from *N. meningitidis* (Strain A)

ORF136 shows 71.7% identity over a 237aa overlap with an ORF (ORF136a) from strain A of *N. meningitidis*:

```
                    10         20         30         40         50         59
  orf136.pep   MKRRIAVFVLFPQIIRVLGQLLPKIVNTVPAHRMLFQIFGMFFFFIHQQYLPGIAEIDS
               ||||||||||:  | ||:||||||||||||||||||||  ||||||||||||||||||
  orf136a      MMKRRIAVFVLLMQKIRILGQLLPKIVNTVPAHRMLFQXFGMFFFFIHQQYLPGIAEIDS
                     10         20         30         40         50         60

60         70         80         90        100        110       119
  orf136.pep   PCGIVFGALLFRHLPAHCLYGKAAVGDAVAHEHPVADVVNRNANAFALFDIGQFAXFIVQ
               ||||||:|||| :|||||||||||||:|||||||||||||||||||||||||||  ||||
  orf136a      PCGIVFGTLLFRHXSTHCLYGKAAVGNAVAHEHPVADVVNRNANAFALFDIGQFAGFIVQ
                     70         80         90        100        110        120

120        130        140        150        160        170       179
  orf136.pep   HTVNIKTVKINIVDPHMFANFAVFAVLEKRDFDHGKIQGGNNAAAFPKKLAPKIFECFTG
               |::|||||||||||||||||||  |||||||||||   :| :            |:  | :: :
  orf136a      HAINVKTVKINIVDPHMFANFAXFAVLEKRALTMAKSKXXXMRRRSQKSSRQKYLNVLRA
                     130        140        150        160        170        180

180        190        200        210        220        230
  orf136.pep   AFVGTVYRFVCLFYIINDGIAHH---SAPQRVRYLFAPYCGFLPSASDSDLKSSXXSEX
                  : ||: |   :  :::   ||||||||||||||||||||||||||||||  |||
  orf136a      R---SPARFTGLSACSTXXMTESPIISAPQRVRYLFAPYCGFLPSASDSDLKSSKYSEX
                       190        200        210        220        230
```

The complete length ORF136a nucleotide sequence <SEQ ID 553> is:

```
  1 ATGATGAAGC GGCGTATAGC CGTCTTCGTC CTGCTCATGC AGAAAATCCG
 51 GATTTTGGGA CAACTGTTGC CGAAAATCGT CAATACAGTT CCGGCACATC
101 GGATGCTCTT CCAGATNTTC GGGATGTTCT TTTTCTTCAT ACACCAGCAA
151 TACCTGCCCG GGATCGCCGA ATCGATTCC CCATGCGGCA TCGTGTTCGG
201 TACGCTCCTC TTCCGTCATC NGTCCACGCA TTGCCTGTAT GGTAAAGCCG
251 CCGTAGGGAA TGCCGTTGCA CACGAACATC CAGTCGCTGA TGTCGTCAAC
301 CGGAACGCAA ACGCTTTCGC CTTGTTCGAC ATTGGTCAGT TCGCCGGGTT
351 CATTGTTCAG CACGCCATAA ATGTAAAGAC CGTCAAAATA AATATCGTCG
401 ATCCACATAT GTTCGCAAAT TTCGCCNTCT TCGCCGTCTT GGAAAAAAGG
451 GCTTTGACCA TGGCAAAATC TAAGGNGNNA NNGATGCGGC GGCGTTCCCA
501 AAAAAGCTCG CGCCAAAAAT ATTTGAATGT TTTGCGGGCG CGTTCGCCGG
551 CACGGTTTAC CGGTTTGTCT GCCTGTTCTA CATAATAAAT GACGGAATCG
601 CCCATCATAT CTGCTCCTCA ACGTGTACGG TATCTGTTTG CACCTTACTG
651 CGGCTTTCTG CCTTCGGCAT CCGATTCGGA TTTGAAAAGT TCCAAATATT
701 CGGAATAG
```

This encodes a protein having amino acid sequence <SEQ ID 554>:

```
  1 MMKRRIAVFV LLMQKIRILG QLLPKIVNTV PAHRMLFQXF GMFFFFIHQQ
 51 YLPGIAEIDS PCGIVFGTLL FRHXSTHCLY GKAAVGNAVA HEHPVADVVN
101 RNANAFALFD IGQFAGFIVQ HAINVKTVKI NIVDPHMFAN FAXFAVLEKR
151 ALTMAKSKXX XMRRRSQKSS RQKYLNVLRA RSPARFTGLS ACST**MTES
201 PIISAPQRVR YLFAPYCGFL PSASDSDLKS SKYSE*
```

ORF136a and ORF136-1 show 73.1% identity in 238 aa overlap:

```
                  10         20         30         40         50         60
orf136a.pep   MMKRRIAVFVLLMQKIRILGQLLPKIVNTVPAHRMLFQXFGMFFFFIHQQYLPGIAEIDS
              ||||||||||: | ||:|||||||||||||||||||| ||||||||||||||||||||
orf136-1      MMKRRIAVFVLFPQIIRVLGQLLPKIVNTVPAHRMLFQIFGMFFFFIHQQYLPGIAEIDS
                  10         20         30         40         50         60

70         80         90        100        110        120
orf136a.pep   PCGIVFGTLLFRHXSTHCLYGKAAVGNAVAHEHPVADVVNRNANAFALFDIGQFAGFIVQ
              |||||| :||||  :||||||||||||:||||||||||||||||||||||||||||||
orf136-1      PCGIVFGALLFRHLPAHCLYGKAAVGDAVAHEHPVADVVNRNANAFALFDIGQFAGFIVQ
                  70         80         90        100        110        120

130        140        150        160        170        180
orf136a.pep   HAINVKTVKINIVDPHMFANFAXFAVLEKRALTMAKSKXXXMRRRSQKSSRQKYLNVLRA
              |::|:|||||||||||||||| |||||||  : |:      |:   |  | :: : :
orf136-1      HTVNIKTVKINIVDPHMFANFAVFAVLEKRDFDHGKIQGGNNAAAFPKKLAPKIFECFTG
                 130        140        150        160        170        180

190        200        210        220        230
orf136a.pep   R---SPARFTGLSACSTXXMTESPIISAPQRVRYLFAPYCGFLPSASDSDLKSSKYSEX
              :  ||: |          : :::  ||||||||||||||||||||||||||||||||||
orf136-1      AFVGTVYRFVCLFYIINDGIAHH---SAPQRVRYLFAPYCGFLPSASDSDLKSSKYSEX
                 190        200        210        220        230
```

Homology with a Predicted ORF from *N. gonorrhoeae*

ORF136 shows 92.3% identity over a 234aa overlap with a predicted ORF (ORF136ng) from *N. gonorrhoeae*:

```
orf136a.pep  MKRRIAVFVLFPQIIRVLGQLLPKIVNTVPAHRMLFQIFGMFFFFIHQQYLPGIAEIDS   59
             ||||||||||:|||:||||||||||||||||||||||||||||||:||||||||||
orf136ng     MMKRRIAVFVLLMQKIRILGQLLPKIVNTVPAHRMLFQIFGMFFFFIHRQYLPGIAEIDS  60 orf136.pep   PCGIVFGALLFRHLPAHCLYGKAAVGDAVAHEHPVADVVNRNANAFALFDIGQFAXFIVQ 119
             | ||||:||||||| ||||||||||||||||||||||:||||||||||||| | ||||
orf136ng     PGGIVFGTLLFRHLSAHCLYGKAAVGDAVAHEHPVADVANRNANAFALFDIGQSAGFIVQ 120 orf136a.pep  HTVNIKTVKINIVDPHMFANFAVFAVLEKRDFDHGKIQGGNNAAAFPKKLAPKIFECFTG 179
             |||||||||||||||||||||||||||||||||||||||||||||||||||:|||||||
orf136ng     HTVNIKTVKINIVDPHMFANFAVFAVLEKRDFDHGKIQGGNNAAAFPKKLAPKVFECFTG 180 orf136a.pep  AFVGTVYRFVCLFYIINDGIAHHSAPQRVRYLFAPYCGFLPSASDSDLKSSXXSE      234
             ||:||||||||||||||||||||:|||||||||||||  ||||||||||||   ||
orf136ng     AFAGTVYRFVCLFYIINDGIAHHTAPQRVRYLFAPYRGFLPPASDSDLKSSKYSE      235
```

The complete length ORF136ng nucleotide sequence <SEQ ID 555> is:

```
  1 ATGATGAAGC GGCGTATAGC CGTCTTCGTC CTGCTCATGC AGAAAATCCG
 51 GATTTTGGGA CAACTGTTGC CGAAAATCGT CAATACAGTT CCGGCACATC
101 GGATGCTCTT CCAAATTTTC GGGATGTTCT TTTTCTTCAT ACACCGGCAA
151 TACCTGCCCG GGATCGCCGA AATCGATTCC CCAGGCGGTA TCGTGTTCGG
201 TACGCTCCTC TTCCGTCATC TGTCCGCGCA TTGCCTGTAC GGTAAAGCCG
251 CCGTAGGGGA TGCCGTTGCA CACGAACATC CAGTCGCTGA TGTCGCCAAC
301 CGGAACGCAA ACGCTTTCGC CTTGTTCGAC ATTGGTCAGT CCGCCGGGTT
351 CATTGTTCAG CACACCGTAA ATATAAAGAC CGTCAAAATA AATATCGTCG
401 ATCCACATAT GTTCGCAAAT TTCGCCGTCT TCGCCGTCTT GGAAAAAAGG
451 GACTTTGACC ATGGCAAAAT CCAAGGCGGA ATAATGCGG CGGCGTTCCC
501 AAAAAAGCTC GCGCCAAAAG TATTTGAATG TTTTACGGGC GCGTTCGCCG
551 GCACGGTTTA CCGGTTCGTC TGCCTGTTCT ACATAATAAA TGACGGAATC
601 GCCCATCATA CTGCTCCTCA ACGTGTACGG TATCTGTTTG CACCTTACCG
651 CGGTTTTCTA CCTCCGGCAT CCGATTCGGA TTTGAAAAGT TCCAAATATT
701 CGGAATAG
```

This encodes a protein having amino acid sequence <SEQ ID 556>:

```
  1 MMKRRIAVFV LLMQKIRILG QLLPKIVNTV PAHRMLFQIF GMFFFFIHRQ
 51 YLPGIAEIDS PGGIVFGTLL FRHLSAHCLY GKAAVGDAVA HEHPVADVAN
101 RNANAFALFD IGQSAGFIVQ HTVNIKTVKI NIVDPHMFAN FAVFAVLEKR
151 DFDHGKIQGG NNAAAFPKKL APKVFECFTG AFAGTVYRFVP CLFYIINDGI
201 AHHTAPQRVR YLFAPYRGFL PPASDSDLKS SKYSE*
```

ORF136ng and ORF136-1 show 93.6% identity in 235 aa overlap:

```
orf136ng  MMKRRIAVFVLLMQKIRILGQLLPKIVNTVPAHRMLFQIFGMFFFFIHRQYLPGIAEIDS
          ||||||||||:|||:|||||||||||||||||||||||||||||||:||||||||||||
orf136-1  MMKRRIAVFVLFPQIIRVLGQLLPKIVNTVPAHRMLFQIFGMFFFFIHQQYLPGIAEIDS
```

```
           -continued
orf136ng   PGGIVFGTLLFRHLSAHCLYGKAAVGDAVAHEHPVADVANRNANAFALFDIGQSAGFIVQ
           ||||||:||||||||||||||||||||||||||||||:||||||||||||| ||||||
orf136-1   PCGIVFGALLFRHLPAHCLYGKAAVGDAVAHEHPVADVVNRNANAFALFDIGQFAGFIVQ orf136ng   HTVNIKTVKINIVDPHMFANFAVFAVLEKRDFDHGKIQGGNNAAAFPKKLAPKVFECFTG
           ||||||||||||||||||||||||||||||||||||||||||||||||||||:||||||
orf136-1   HTVNIKTVKINIVDPHMFANFAVFAVLEKRDFDHGKIQGGNNAAAFPKKLAPKIFECFTG orf136ng   AFAGTVYRFVCLFYIINDGIAHHTAPQRVRYLFAPYRGFLPPASDSDLKSSKYSEX
           ||:||||||||||||||||||:|||||||||||||| |||| ||||||||||||
orf136-1   AFVGTVYRFVCLFYIINDGIAHHSAPQRVRYLFAPYCGFLPSASDSDLKSSKYSEX
```

Based on the presence of the putative transmembrane domains in the gonococcal protein, it is predicted that the proteins from *N. meningitidis* and *N. gonorrhoeae*, and their epitopes, could be useful antigens for vaccines or diagnostics, or for raising antibodies.

Example 67

The following partial DNA sequence was identified in *N. meningitidis* <SEQ ID 557>:

```
  1 ATGGAAAATA TGGTAACGTT TTCAAAAATC AGACCGCTTT TGGCAATCGC

51 CGCCGCCGCG TTGCTTGCCG CC.TGCGGAC GGCGGGAAAT AATGCTGTCC

101 GCAAGCCGGT GCAAACCGCC AAACCCGCCG CAGTGGTCGG TTTGGCACTC

151 GGTGGCGGCG CATCTAAAGG ATTTGCCCAT GTAGGTATTA TTAAGGTTTT

201 GAAAGAAAAC GGTATTCCTG TGAAGGTGGT TACCGGCACC TCCGCAGGTT

251 CGATTGTCGG CAACCTTTTT GCATCGGGTA TGTCGCCCGA CCGCCTCGAA

301 TTGGAAGCCG AAATTTTAGG CAAAACCGAT TTGGTCGATT TAACCTTGTC

351 CACCAATGGG TTTATCAAAG GCGCAAAGCT GCAAAATTAC ATCAACCGAA

401 AACTCCGCGG CATGCAGATT CAGCAGTTTC CCATCAAATT TGCCGCC..
```

This corresponds to the amino acid sequence <SEQ ID 558; ORF137>:

```
  1 MENMVTFSKI RPLLAIAAAA LLAAXRTAGN NAVRKPVQTA KPAAVVGLAL

51 GGGASKGFAH VGIIKVLKEN GIPVKVVTGT SAGSIVGNLF ASGMSPDRLE

101 LEAEILGKTD LVDLTLSTNG FIKGAKLQNY INRKLRGMQI QQFPIKFAA..
```

Further work revealed the complete nucleotide sequence <SEQ ID 559>:

```
  1 ATGGAAAATA TGGTAACGTT TTCAAAAATC AGACCGCTTT TGGCAATCGC

51 CGCCGCCGCG TTGCTTGCCG CCTGCGGCAC GGCGGGAAAT AATGCTGTCC

101 GCAAGCCGGT GCAAACCGCC AAACCCGCCG CAGTGGTCGG TTTGGCACTC

151 GGTGGCGGCG CATCTAAAGG ATTTGCCCAT GTAGGTATTA TTAAGGTTTT

201 GAAAGAAAAC GGTATTCCTG TGAAGGTGGT TACCGGCACA TCGGCAGGTT

251 CGATTGTCGG CAGCCTTTTT GCATCGGGTA TGTCGCCCGA CCGCCTCGAA

301 TTGGAAGCCG AAATTTTAGG CAAAACCGAT TTGGTCGATT TAACCTTGTC

351 CACCAGTGGT TTTATCAAAG GCGAAAAGCT GCAAAATTAC ATCAACCGAA

401 AAGTCGGCGG CAGGCAGATT CAGCAGTTTC CCATCAAATT TGCCGCCGTT
```

-continued

```
451 GCTACTGATT TTGAAACCGG CAAGGCCGTC GCTTTCAATC AGGGGAATGC

501 CGGGCAGGCT GTGCGCGCTT CCGCCGCCAT TCCCAATGTG TTCCAACCCG

551 TTATCATCGG CAGGCATACA TATGTTGACG GCGGTCTGTC GCAGCCCGTG

601 CCCGTCAGTG CCGCCCGGCG GCAGGGGGCG AATTTCGTGA TTGCCGTCGA

651 TATTTCCGCC CGTCCGGGCA AAAACATCAG CCAAGGTTTC TTCTCTTATC

701 TCGATCAGAC GCTGAACGTA ATGAGCGTTT CTGCGTTGCA AAATGAGTTG

751 GGGCAGGCGG ATGTGGTTAT CAAACCGCAG GTTTTGGATT TGGGTGCAGT

801 CGGCGGATTC GATCAGAAAA AACGCGCCAT CCGGTTGGGT GAGGAGGCAG

851 CACGTGCCGC ATTGCCTGAA ATCAAACGCA AACTGGCGGC ATACCGTTAT

901 TGA
```

This corresponds to the amino acid sequence <SEQ ID 560; ORF137-1>:

```
  1 MENMVTFSKI RPLLAIAAAA LLAACGTAGN NAVRKPVQTA KPAAVVGLAL

51 GGGASKGFAH VGIIKVLKEN GIPVKVVTGT SAGSIVGSLF ASGMSPDRLE

101 LEAEILGKTD LVDLTLSTSG FIKGEKLQNY INRKVGGRQI QQFPIKFAAV

151 ATDFETGKAV AFNQGNAGQA VRASAAIPNV FQPVIIGRHT YVDGGLSQPV

201 PVSAARRQGA NFVIAVDISA RPGKNISQGF FSYLDQTLNV MSVSALQNEL

251 GQADVVIKPQ VLDLGAVGGF DQKKRAIRLG EEAARAALPE IKRKLAAYRY

301 *
```

Computer analysis of this amino acid sequence gave the following results:

Homology with a Predicted ORF from *N. meningitidis* (Strain A)

ORF137 shows 93.3% identity over a 149aa overlap with an ORF (ORF137a) from strain A of *N. meningitidis*.

```
                    10         20         30         40         50         60
   orf137.pep MENMVTFSKIRPLLAIAAAALLAAXRTAGNNAVRKPVQTAKPAAVVGLALGGGASKGFAH
              ||||||||||||||||||||||||| ||||||:||||||||||||||||||||||||||||
       orf137a MENMVTFSKIRPLLAIAAAALLAACGTAGNNAARKPVQTAKPAAVVGLALGGGASKGFAH
                    10         20         30         40         50         60

70         80         90        100        110        120
   orf137.pep VGIIKVLKENGIPVKVVTGTSAGSIVGNLFASGMSPDRLELEAEILGKTDLVDLTLSTNG
              |||||||||||||||||||||||||||||:||||||||||||||||||||||||||||:|
       orf137a VGIIKVLKENGIPVKVVTGTSAGSIVGSLFASGMSPDRLELEAEILGKTDLVDLTLSTSG
                    70         80         90        100        110        120

130        140       149
   orf137.pep FIKGAKLQNYINRKLRGMQIQQFPIKFAA
              ||||  |||||||||:  |  :|||||||||
       orf137a FIKGEKLQNYINRKVGGRRIQQFPIKFAAVATDFETGKAVAFNQGNAGQAVRASAAIPNV
                   130        140        150        160        170        180
```

The complete length ORF137a nucleotide sequence <SEQ ID 561> is:

```
  1 ATGGAAAATA TGGTAACGTT TTCAAAAATC AGACCGCTTT TGGCAATCGC

51 CGCCGCCGCG TTGCTTGCCG CCTGCGGCAC GGCGGGAAAT AATGCTGCCC

101 GCAAGCCGGT GCAAACCGCC AAACCCGCCG CAGTGGTCGG TTTGGCACTC

151 GGTGGCGGCG CATCTAAAGG ATTTGCCCAT GTAGGTATTA TTAAGGTTTT
```

-continued

```
201 GAAAGAAAAC GGTATTCCTG TGAAGGTGGT TACCGGCACA TCGGCAGGTT

251 CGATAGTCGG CAGCCTTTTT GCATCGGGTA TGTCGCCCGA CCGCCTCGAA

301 TTGGAAGCCG AAATTTTAGG TAAAACCGAT TTGGTCGATT TAACCTTGTC

351 CACCAGTGGT TTTATCAAAG GCGAAAAGCT GCAAAATTAC ATCAACCGAA

401 AAGTCGGCGG CAGGCGGATT CAGCAGTTTC CCATCAAATT TGCCGCCGTT

451 GCTACTGATT TTGAAACCGG CAAGGCCGTC GCTTTCAATC AAGGGAATGC

501 CGGGCAGGCT GTGCGCGCTT CCGCCGCCAT TCCCAATGTG TTCCAACCCG

551 TTATCATCGG CAGGCATACA TATGTTGACG GCGGTCTGTC GCAGCCCGTG

601 CCCGTCAGTG CCGCCCGGCG GCANGNNNNG NATNTCGTGA TTGCCGTCGA

651 TATTTCCGCC CGTCCGAGCA AAACATCAG CCAAGGCTTC TTCTCTTATC

701 TCGATCAGAC GCTGAACGTA ATGAGCGTTT CCGCGTTGCA AAATGAGTTG

751 GGGCAGGCGG ATGTGGTTAT CAAACCGCAG GTTTTGGATT TGGGTGCAGT

801 CGGCGGATTC GATCAGAAAA AACGCGCCAT CCGGTTGGGT GAGGAGGCAG

851 CACGTGCCGC ATTGCCTGAA ATCAAACGCA AACTGGCGGC ATACCGTTAT

901 TGA
```

This encodes a protein having amino acid sequence <SEQ ID 562>:

```
  1 MENMVTFSKI RPLLAIAAAA LLAACGTAGN NAARKPVQTA KPAAVVGLAL

51 GGGASKGFAH VGIIKVLKEN GIPVKVVTGT SAGSIVGSLF ASGMSPDRLE

101 LEAEILGKTD LVDLTLSTSG FIKGEKLQNY INRKVGGRRI QQFPIKFAAV

151 ATDFETGKAV AFNQGNAGQA VRASAAIPNV FQPVIIGRHT YVDGGLSQPV

201 PVSAARRXXX XXVIAVDISA RPSKNISQGF FSYLDQTLNV MSVSALQNEL

251 GQADVVIKPQ VLDLGAVGGF DQKKRAIRLG EEAARAALPE IKRKLAAYRY

301 *
```

ORF137a and ORF137-1 show 97.3% identity in 300 aa overlap:

```
orf137a.pep  MENMVTFSKIRPLLAIAAAALLAACGTAGNNAARKPVQTAKPAAVVGLALGGGASKGFAH
             ||||||||||||||||||||||||||||||:||||||||||||||||||||||||||||
orf137-1     MENMVTFSKIRPLLAIAAAALLAACGTAGNNAVRKPVQTAKPAAVVGLALGGGASKGFAH orf137a.pep  VGIIKVLKENGIPVKVVTGTSAGSIVGSLFASGMSPDRLELEAEILGKTDLVDLTLSTSG
             ||||||||||||||||||||||||||||||||||||||||||||||||||||||||||||
orf137-1     VGIIKVLKENGIPVKVVTGTSAGSIVGSLFASGMSPDRLELEAEILGKTDLVDLTLSTSG orf137a.pep  FIKGEKLQNYINRKVGGRRIQQFPIKFAAVATDFETGKAVAFNQGNAGQAVRASAAIPNV
             |||||||||||||||||:||||||||||||||||||||||||||||||||||||||||||
orf137-1     FIKGEKLQNYINRKVGGRQIQQFPIKFAAVATDFETGKAVAFNQGNAGQAVRASAAIPNV orf137a.pep  FQPVIIGRHTYVDGGLSQPVPVSAARRXXXXXVIAVDISARPSKNISQGFFSYLDQTLNV
             |||||||||||||||||||||||||||     ||||||||||:|||||||||||||||
orf137-1     FQPVIIGRHTYVDGGLSQPVPVSAARRQGANFVIAVDISARPGKNISQGFFSYLDQTLNV orf137a.pep  MSVSALQNELGQADVVIKPQVLDLGAVGGFDQKKRAIRLGEEAARAALPEIKRKLAAYRY
             ||||||||||||||||||||||||||||||||||||||||||||||||||||||||||||
orf137-1     MSVSALQNELGQADVVIKPQVLDLGAVGGFDQKKRAIRLGEEAARAALPEIKRKLAAYRY
```

Homology with a Predicted ORF from *N. gonorrhoeae*

ORF137 shows 89.9% identity over a 149aa overlap with a predicted ORF (ORF137ng) from *N. gonorrhoeae*:

```
orf137.pep    MENMVTFSKIRPLLAIAAAALLAAXRTAGNNAVRKPVQTAKPAAVVGLALGGGASKGFAH    60
              |||||||||||:||||||||||    ||||||:|||||||||||||||:|||||||||||
orf137ng      MENMVTFSKIRSFLAIAAAALLAACGTAGNNAARKPVQTAKPAAVVALALGGGASKGFAH    60
orf137.pep    VGIIKVLKENGIPVKVVTGTSAGSIVGNLFASGMSPDRLELEAEILGKTDLVDLTLSTNG   120
              :||:||||||||||||||||||||||||:|:|||||||||||||||||||||||||||:
orf137ng      IGIVKVLKENGIPVKVVTGTSAGSIVGSLLASGMSPDRLELEAEILGKTDLVDLTLSTSG   120
orf137.pep    FIKGAKLQNYINRKLRGMQIQQFPIKFAA                                 149
              ||||:|||||||||:|  |  :|||||||
orf137ng      FIKGEKLQNYINRKVGGRRIQQFPIKFAAVATDFETGKAVAFNQGNAGQAVRASAAIPNV  180
```

The complete length ORF137ng nucleotide sequence <SEQ ID 563> is:

```
  1 ATGGAAAATA TGGTAACGTT TTCAAAAATC AGATCATTTT TGGCAATCGC
 51 CGCCGCCGCG TTGCTTGCCG CCTGCGGTAC GGCGGGAAAC AATGCCGCCC
101 GCAAGCCGGT GCAAACCGCC AAACCCGCCG CAGTGGTCGC TTTGGCACTC
151 GGTGGCGGCG CATCTAAAGG ATTTGCCCAT ATAGGAATTG TTAAGGTTTT
201 GAAAGAAAAC GGTATTCCTG TGAAGGTGGT TACCGGCACA TCGGCAGGTT
251 CGATAGTCGG CAGCCTTTTG GCATCGGGTA TGTCGCCCGA CCGCCTCGAA
301 TTGGAAGCCG AGATTTTAGG TAAAACCGAT TTAGTCGATT TAACCTTGTC
351 CACCAGTGGT TTTATCAAAG GCGAAAAGCT GCAAAATTAC ATCAACCGAA
401 AAGTCGGCGG CAGGCAGATT CAGCAGTTTC CCATCAAATT TGCCGCCGTT
451 GCCACTGATT TTGAAACCGG CAAGGCCGTC GCTTTCAATC AAGGGAATGC
501 CGGGCAGGCG GTTCGTGCTT CCGCCGCCAT TCCCAATGTG TTCCAGCCAG
551 TCATCATCGG CAGGCACAAA TATGTTGACG GCGGTCTGTC GCAGCCCGTG
601 CCCGTCAGTG CCGCTCGGCG GCAGGGGCGA AATTTCGTGA TTGCCGTCGA
651 TATTTCCGCA CGTCCGAGCA AAAATGTCGG TCAAGGTTTC TTCTCTTATC
701 TCGATCAGAC GCTGAACGTG ATGAGCGTTT CCGTGTTGCA AAACGAGTTG
751 gggcAGGCGG ATGTGGTTAT CAAACCGCag gtTTTGGATT TGGGTGCAGT
801 CGGCGGATTC GATCAGAAAA AGCGCGCCAT CCGGTTGGGC GAGGAGGCAG
851 CACGTGCCGC ATTGCCTGAA ATCAAACGCA AACTGGCGGC ATACCGTTAT
901 TGA
```

This encodes a protein having amino acid sequence <SEQ ID 564>:

```
  1 MENMVTFSKI RSFLAIAAAA LLAACGTAGN NAARKPVQTA KPAAVVALAL

51 GGGASKGFAH IGIVKVLKEN GIPVKVVTGT SAGSIVGSLL ASGMSPDRLE

101 LEAEILGKTD LVDLTLSTSG FIKGEKLQNY INRKVGGRQI QQFPIKFAAV

151 ATDFETGKAV AFNQGNAGQA VRASAAIPNV FQPVIIGRHK YVDGGLSQPV

201 PVSAARRQGA NFVIAVDISA RPSKNVGQGF FSYLDQTLNV MSVSVLQNEL

251 GQADVVIKPQ VLDLGAVGGF DQKKRAIRLG EEAARAALPE IKRKLAAYRY

301 *
```

ORF137ng and ORF137-1 show 96.0% identity in 300 aa overlap:

```
orf137ng  MENMVTFSKIRSFLAIAAAALLAACGTAGNNAARKPVQTAKPAAVVALALGGGASKGFAH
          |||||||||||:||||||||||||||||||:|||||||||||||||:|||||||||||
orf137-1  MENMVTFSKIRPLLAIAAAALLAACGTAGNNAVRKPVQTAKPAAVVGLALGGGASKGFAH orf137ng  IGIVKVLKENGIPVKVVTGTSAGSIVGSLLASGMSPDRLELEAEILGKTDLVDLTLSTSG
          :||:||||||||||||||||||||||||||:|||||||||||||||||||||||||||
orf137-1  VGIIKVLKENGIPVKVVTGTSAGSIVGSLFASGMSPDRLELEAEILGKTDLVDLTLSTSG orf137ng  FIKGEKLQNYINRKVGGRQIQQFPIKFAAVATDFETGKAVAFNQGNAGQAVRASAAIPNV
          ||||||||||||||||||||||||||||||||||||||||||||||||||||||||||
orf137-1  FIKGEKLQNYINRKVGGRQIQQFPIKFAAVATDFETGKAVAFNQGNAGQAVRASAAIPNV orf137ng  FQPVIIGRHKYVDGGLSQPVPVSAARRQGNAFVIAVDISARPSKNVGQGFFSYLDQTLNV
          ||||||||| ||||||||||||||||||||:||||||||||||:||::|||||||||||
orf137-1  FQPVIIGRHTYVDGGLSQPVPVSAARRQGANFVIAVDISARPGKNISQGFFSYLDQTLNV orf137ng  MSVSVLQNELGQADVVIKPQVLDLGAVGGFDQKKRAIRLGEEAARAALPEIKRKLAAYRY
          ||||:|||||||||||||||||||||||||||||||||||||||||||||||||||||
orf137-1  MSVSALQNELGQADVVIKPQVLDLGAVGGFDQKKRAIRLGEEAARAALPEIKRKLAAYRY
```

Based on the presence of a predicted prokaryotic membrane lipoprotein lipid attachment site (underlined) in the gonococcal protein, it is predicted that the proteins from *N. meningitidis* and *N. gonorrhoeae*, and their epitopes, could be useful antigens for vaccines or diagnostics, or for raising antibodies.

Example 68

The following partial DNA sequence was identified in *N. meningitidis* <SEQ ID 565>:

```
  1 ATGTTTCGTT TACAATTCAG GCTGTTTCCC CCTTTGCGAA CCGCCATGCA

51 CATCCTGTTG ACCGCCCTGC TCAAATGCCT CTCCCTGcTG CCGCTTTCCT

101 GTCTGCACAC GCTGGGAAAC CGGCTCGGAC ATCTGGCGTT TTACCTTTTA

151 AAGGAAGACC GCGCGCGCAT CGTCGCCmAT ATGCGGCAGG CGGGTTTGAA

201 CCCCGACCCC AAAACGGTCA AAGCCGTTTT TGCGGAAACG GCAAAAGGCG

251 GTTTGGAACT TGCCCCCGCG TTTTTCAGAA AACCGGAAGA CATAGAAACA

301 ATGTTCAAAG CGGTACACGG CTGGGAACAT GTGCAGCAGG CTTTGGACAA

351 ACACGAAGGG CTGCTATTC..
```

This corresponds to the amino acid sequence <SEQ ID 566; ORF138>:

```
  1 MFRLQFRLFP PLRTAMHILL TALLKCLSLL PLSCLHTLGN RLGHLAFYLL

51 KEDRARIVAX MRQAGLNPDP KTVKAVFAET AKGGLELAPA FFRKPEDIET

101 MFKAVHGWEH VQQALDKHEG LLF
```

Further work revealed the complete nucleotide sequence <SEQ ID 567>:

```
  1 ATGTTTCGTT TACAATTCAG GCTGTTTCCC CCTTTGCGAA CCGCCATGCA

51 CATCCTGTTG ACCGCCCTGC TCAAATGCCT CTCCCTGCTG CCGCTTTCCT

101 GTCTGCACAC GCTGGGAAAC CGGCTCGGAC ATCTGGCGTT TTACCTTTTA

151 AAGGAAGACC GCGCGCGCAT CGTCGCCAAT ATGCGGCAGG CGGGTTTGAA

201 CCCCGACCCC AAAACGGTCA AAGCCGTTTT TGCGGAAACG GCAAAAGGCG
```

```
251 GTTTGGAACT TGCCCCCGCG TTTTTCAGAA AACCGGAAGA CATAGAAACA

301 ATGTTCAAAG CGGTACACGG CTGGGAACAT GTGCAGCAGG CTTTGGACAA

351 ACACGAAGGG CTGCTATTCA TCACGCCGCA CATCGGCAGC TACGATTTGG

401 GCGGACGCTA CATCAGCCAG CAGCTTCCGT TCCCGCTGAC CGCCATGTAC

451 AAACCGCCGA AAATCAAAGC GATAGACAAA ATCATGCAGG CGGGCAGGGT

501 TCGCGGCAAA GGAAAAACCG CGCCTACCAG CATACAAGGG GTCAAACAAA

551 TCATCAAAGC CCTGCGTTCG GGCGAAGCAA CCATCGTCCT GCCCGACCAC

601 GTCCCCTCCC CTCAAGAAGG CGGGGAAGGC GTATGGGTGG ATTTCTTCGG

651 CAAACCTGCC TATACCATGA CGCTGGCGGC AAAATTGGCA CACGTCAAAG

701 GCGTGAAAAC CCTGTTTTTC TGCTGCGAAC GCCTGCCTGG CGGACAAGGT

751 TTCGATTTGC ACATCCGCCC CGTCCAAGGG GAATTGAACG GCGACAAAGC

801 CCATGATGCC GCCGTGTTCA ACCGCAATGC CGAATATTGG ATACGCCGTT

851 TTCCGACGCA GTATCTGTTT ATGTACAACC GCTACAAAAT GCCGTAA
```

This corresponds to the amino acid sequence <SEQ ID 568; ORF138-1>:

```
  1 MFRLQFRLFP PLRTAMHILL TALLKCLSLL PLSCLHTLGN RLGHLAFYLL

51 KEDRARIVAN MRQAGLNPDP KTVKAVFAET AKGGLELAPA FFRKPEDIET

101 MFKAVHGWEH VQQALDKHEG LLFITPHIGS YDLGGRYISQ QLPFPLTAMY

151 KPPKIKAIDK IMQAGRVRGK GKTAPTSIQG VKQIIKALRS GEATIVLPDH

201 VPSPQEGGEG VWVDFFGKPA YTMTLAAKLA HVKGVKTLFF CCERLPGGQG

251 FDLHIRPVQG ELNGDKAHDA AVFNRNAEYW IRRFPTQYLF MYNRYKMP*
```

Computer analysis of this amino acid sequence gave the following results:

Homology with a Predicted ORF from *N. meningitidis* (Strain A)

ORF138 shows 99.2% identity over a 123aa overlap with an ORF (ORF138a) from strain A of *N. meningitidis*.

```
                     10         20         30         40         50         60
   orf138.pep MFRLQFRLFPPLRTAMHILLTALLKCLSLLPLSCLHTLGNRLGHLAFYLLKEDRARIVAX
              ||||||||||||||||||||||||||||||||||||||||||||||||||||||||||
   orf138a    MFRLQFRLFPPLRTAMHILLTALLKCLSLLPLSCLHTLGNRLGHLAFYLLKEDRARIVAN
                     10         20         30         40         50         60

70         80         90        100        110        120
   orf138.pep MRQAGLNPDPKTVKAVFAETAKGGLELAPAFFRKPEDIETMFKAVHGWEHVQQALDKHEG
              ||||||||||||||||||||||||||||||||||||||||||||||||||||||||||
   orf138a    MRQAGLNPDPKTVKAVFAETAKGGLELAPAFFRKPEDIETMFKAVHGWEHVQQALDKHEG
                     70         80         90        100        110        120 orf138.pep LLF
              |||
   orf138a    LLFITPHIGSYDLGGRYISQQLPFPLTAMYKPPKIKAIDKIMQAGRVRGKGKTAPTSIQG
                    130        140        150        160        170        180
```

The complete length ORF138a nucleotide sequence <SEQ ID 569> is:

```
  1 ATGTTTCGTT TACAATTCAG GCTGTTTCCC CCTTTGCGAA CCGCCATGCA

51 CATCCTGTTG ACCGCCCTGC TCAAATGCCT CTCCCTGCTG CCGCTTTCCT
```

```
-continued
101 GTCTGCACAC GCTGGGAAAC CGGCTCGGAC ATCTGGCGTT TTACCTTTTA

151 AAGGAAGACC GCGCGCGCAT CGTCGCCAAT ATGCGTCAGG CAGGCATGAA

201 TCCCGACCCC AAAACGGTCA AGCCGTTTT TGCGGAAACG GCAAAAGGCG

251 GTTTGGAACT TGCCCCCGCG TTTTTCAGAA AACCGGAAGA CATAGAAACA

301 ATGTTCAAAG CGGTACACGG CTGGGAACAT GTGCAGCAGG CTTTGGACAA

351 ACACGAAGGG CTGCTATTCA TCACGCCGCA CATCGGCAGC TACGATTTGG

401 GCGGACGCTA CATCAGCCAG CAGCTTCCGT TCCCGCTGAC CGCCATGTAC

451 AAACCGCCGA AAATCAAAGC GATAGACAAA ATCATGCAGG CGGGCAGGGT

501 TCGCGGCAAA GGAAAAACCG CGCCTACCAG CATACAAGGG GTCAAACAAA

551 TCATCAAAGC CCTGCGTTCG GGCGAAGCAA CCATCGTCCT GCCCGACCAC

601 GTCCCCTCCC CTCAAGAAGG CGGGGAAGGC GTATGGGTGG ATTTCTTCGG

651 CAAACCTGCC TATACCATGA CGCTGGCGGC AAAATTGGCA CACGTCAAAG

701 GCGTGAAAAC CCTGTTTTTC TGCTGCGAAC GCCTGCCTGG CGGACAAGGT

751 TTCGATTTGC ACATCCGCCC CGTCCAAGGG GAATTGAACG GCGACAAAGC

801 CCATGATGCC GCCGTGTTCA ACCGCAATGC CGAATATTGG ATACGCCGTT

851 TTCCGACGCA GTATCTGTTT ATGTACAACC GCTACAAAAT GCCGTAA
```

This encodes a protein having amino acid sequence <SEQ ID 570>:

```
  1 MFRLQFRLFP PLRTAMHILL TALLKCLSLL PLSCLHTLGN RLGHLAFYLL

51 KEDRARIVAN MRQAGLNPDP KTVKAVFAET AKGGLELAPA FFRKPEDIET

101 MFKAVHGWEH VQQALDKHEG LLFITPHIGS YDLGGRYISQ QLPFPLTAMY

151 KPPKIKAIDK IMQAGRVRGK GKTAPTSIQG VKQIIKALRS GEATIVLPDH

201 VPSPQEGGEG VWVDFFGKPA YTMTLAAKLA HVKGVKTLFF CCERLPGGQG

251 FDLHIRPVQG ELNGDKAHDA AVFNRNAEYW IRRFPTQYLF MYNRYKMP*
```

ORF138a and ORF138-1 show 99.7% identity over a 298aa overlap:

```
orf138a.pep  MFRLQFRLFPPLRTAMHILLTALLKCLSLLPLSCLHTLGNRLGHLAFYLLKEDRARIVAN
             ||||||||||||||||||||||||||||:|||||||||||||||||||||||||||||||
orf138-1     MFRLQFRLFPPLRTAMHILLTALLKCLSLLPLSCLHTLGNRLGHLAFYLLKEDRARIVAN orf138a.pep  MRQAGMNPDPKTVKAVFAETAKGGLELAPAFFRKPEDIETMFKAVHGWEHVQQALDKHEG
             |||||:||||||||||||||||||||||||||||||||||||||||||||||||||||||
orf138-1     MRQAGLNPDPKTVKAVFAETAKGGLELAPAFFRKPEDIETMFKAVHGWEHVQQALDKHEG orf138a.pep  LLFITPHIGSYDLGGRYISQQLPFPLTAMYKPPKIKAIDKIMQAGRVRGKGKTAPTSIQG
             ||||||||||||||||||||||||||||||||||||||||||||||||||||||||||||
orf138-1     LLFITPHIGSYDLGGRYISQQLPFPLTAMYKPPKIKAIDKIMQAGRVRGKGKTAPTSIQG orf138a.pep  VKQIIKALRSGEATIVLPDHVPSPQEGGEGVWVDFFGKPAYTMTLAAKLAHVKGVKTLFF
             ||||||||||||||||||||||||||||||||||||||||||||||||||||||||||||
orf138-1     VKQIIKALRSGEATIVLPDHVPSPQEGGEGVWVDFFGKPAYTMTLAAKLAHVKGVKTLFF orf138a.pep  CCERLPGGQGFDLHIRPVQGELNGDKAHDAAVFNRNAEYWIRRFPTQYLFMYNRYKMP
             ||||||||||||||||||||||||||||||||||||||||||||||||||||||||||
orf138-1     CCERLPGGQGFDLHIRPVQGELNGDKAHDAAVFNRNAEYWIRRFPTQYLFMYNRYKMP
```

Homology with a Predicted ORF from *N. gonorrhoeae*

ORF138 shows 94.3% identity over a 123aa overlap with a predicted ORF (ORF138ng) from *N. gonorrhoeae*:

```
orf138.pep  MFRLQFRLFPPLRTAMHILLTALLKCLSLLPLSCLHTLGNRLGHLAFYLLKEDRARIVAX   60
            |||||||||||||||||||||||||||||||| |||||||||||||||||||||||||||
orf138ng    MFRLQFRLFPPLRTAMHILLTALLKCLSLLSLSCLHTLGNRLGHLAFYLLKEDRARIVAN   60 orf138.pep  MRQAGLNPDPKTVKAVFAETAKGGLELAPAFFRKPEDIETMFKAVHGWEHVQQALDKHEG  120
            ||||||||||:|||||||||||||| ||||||||||:||||||||||||||||||||| ||
orf138ng    MRQAGLNPDTQTVKAVFAETAKCGLELAPAFFKKPEDIETMFKAVHGWEHVQQALDKGEG  120 orf138.pep  LLF                                                           123
            |||
orf138ng    LLFITPHIGSYDLGGRYISQQLPFHLTAMYKPPKIKAIDKIMQAGRVRGKGKTAPTGIQG  180
```

The complete length ORF138ng nucleotide sequence <SEQ ID 571> is:

```
  1 ATGTTTCGTT TACAATTCAG GCTGTTTCCC CCTTTGCGAA CCGCCATGCA
 51 CATCCTGTTG ACCGCCCTGC TCAAATGCCT CTCCCTGCTG TCGCTTTCCT
101 GTCTGCACAC GCTGGGAAAC CGGCTCGGAC ATCTGGCGTT TTACCTTTTA
151 AAGGAAGACC GCGCGCGCAT CGTCGCCAAT ATGCGGCAGG CGGGTTTGAA
201 CCCCGACACG CAGACGGTCA AGCCGTTTT TGCGGAAACG GCAAAATGCG
251 GTTTGGAACT TGCCCCCGCG TTTTTCAAAA AACCGGAAGA CATCGAAACA
301 ATGTTCAAAG CGGTACACGG CTGGGAACAC GTGCAGCAGG CTTTGGACAA
351 GGGCGAAGGG CTGCTGTTCA TCACGCCGCA CATCGGCAGC TACGATTTGG
401 GCGGACGCTA CATCAGCCAG CAGCTTCCGT TCCACCTGAC CGCCATGTAC
451 AAGCCGCCGA AAATCAAAGC GATAGACAAA ATCATGCAGG CGGGCAGGGT
501 GCGCGGCAAA GGCAAAACcg cgcccaccgg catACAAGGG GTCAAACAAA
551 tcatcaAGGC CCTGCGCGCG GGCGAGGCAA CCAtcATCCT GCCCGACCAC
601 GTCCCTTCTC CGCAGGAagg cggCGGCGTG TGGGCGGATT TTTTCGGCAA
651 ACCTGCATAC acCATGACAC TGGCGGCAAA ATTGGCACAC GTCAAAGGCG
701 TGAAAACCCT GTTTTTCTGC TGCGAACGCC TGCCCGACGG ACAAGGCTTC
751 GTGTTGCACA TCCGCCCCGT CCAAGGGGAA TTGAACGGCA ACAAAGCCCA
801 CGATGCCGCC GTGTTCAACC GCAATACCGA ATATTGGATA CGCCGTTTTC
851 CGACGCAGTA TCTGTTTATG TACAACCGCT ATAAAACGCC GTAA
```

This encodes a protein having amino acid sequence <SEQ ID 572>:

```
  1 MFRLQFRLFP PLRTAMHILL TALLKCLSLL SLSCLHTLGN RLGHLAFYLL
 51 KEDRARIVAN MRQAGLNPDT QTVKAVFAET AKCGLELAPA FFKKPEDIET
101 MFKAVHGWEH VQQALDKGEG LLFITPHIGS YDLGGRYISQ QLPFHLTAMY
151 KPPKIKAIDK IMQAGRVRGK GKTAPTGIQG VKQIIKALRA GEATIILPDH
201 VPSPQEGGGV WADFFGKPAY TMTLAAKLAH VKGVKTLFFC CERLPDGQGF
251 VLHIRPVQGE LNGNKAHDAA VFNRNTEYWI RRFPTQYLFM YNRYKTP*
```

ORF138ng and ORF138-1 show 94.3% identity over 299aa overlap:

```
orf138-1.pep  MFRLQFRLFPPLRTAMHILLTALLKCLSLLPLSCLHTLGNRLGHLAFYLLKEDRARIVAN
              |||||||||||||||||||||||||||||||| |||||||||||||||||||||||||||
orf138ng      MFRLQFRLFPPLRTAMHILLTALLKCLSLLSLSCLHTLGNRLGHLAFYLLKEDRARIVAN
```

-continued

```
orf138-1.pep  MRQAGLNPDPKTVKAVFAETAKGGLELAPAFFRKPEDIETMFKAVHGWEHVQQALDKHEG
              |||||||||| :|||||||||||| ||||||||||:||||||||||||||||||||| ||
orf138ng      MRQAGLNPDTQTVKAVFAETAKCGLELAPAFFKKPEDIETMFKAVHGWEHVQQALDKGEG orf138-1.pep  LLFITPHIGSYDLGGRYISQQLPFPLTAMYKPPKIKAIDKIMQAGRVRGKGKTAPTSIQG
              ||||||||||||||||||||||||||| ||||||||||||||||||||||||||||:|||
orf138ng      LLFITPHIGSYDLGGRYISQQLPFHLTAMYKPPKIKAIDKIMQAGRVRGKGKTAPTGIQG orf138-1.pep  VKQIIKALRSGEATIVLPDHVPSPQEGGEGVWVDFFGKPAYTMTLAAKLAHVKGVKTLFF
              ||||||||| :||||| :|||||||||||  |||: ||||||||||||||||||||||||
orf138ng      VKQIIKALRAGEATIILPDHVPSPQEGG-GVWADFFGKPAYTMTLAAKLAHVKGVKTLFF orf138-1.pep  CCERLPGGQGFDLHIRPVQGELNGDKAHDAAVFNRNAEYWIRRFPTQYLFMYNRYKMP
              |||||| |||| |||||||||||||||:||||||||||:|||||||||||||||||| |
orf138ng      CCERLPDGQGFVLHIRPVQGELNGNKAHDAAVFNRNTEYWIRRFPTQYLFMYNRYKTP
```

In addition, ORF138ng is homologous to htrB protein from *Pseudomonas fluorescens*:

```
gnl|PID|e334283 (Y14568) htrB [Pseudomonas fluorescens] Length = 253
Score = 80.8 bits (196), Expect = 9e-15
Identities = 49/151 (32%), Positives = 79/151 (51%), Gaps = 6/151 (3%)

Query: 101 MFKAVHGWEHVQQALDKGEGLLFITPHIGSYD-LGGRYISQQLPFHLTAMYKPPKIKAID   159
             + + V G E +++AL  G+G++ IT H+G+++ L    Y SQ  P      Y+PPK+KA+D
Sbjct:  94 LVREVEGLEVLKEALASGKGVVGITSHLGNWEVLNHFYCSQCKPI---IFYRPPKLKAVD   150

Query: 160 KIMQAGRVRGKGKTAPTGIQGVKQIIKALRAGEATIILPDHVPSPQEGGGVWADFFGKPA   219
            ++++  RV+    K A +  +G+  +IK +R G     I  D  P P E  G++  FF   A
Sbjct: 151 ELLRKQRVQLGNKVAASTKEGILSVIKEVRKGGQVGIPAD--PEPAESAGIFVPFFATQA   208

Query: 220 YTMTLAAKLAHVKGVKTLFFCCERLPDGQGF                              250
               T    +       +F  RLPDG G+
Sbjct: 209 LTSKFVPNMLAGGKAVGVFLHALRLPDGSGY                              239
```

Based on this analysis, including the presence of a putative transmembrane domain in the gonococcal protein, it was predicted that the proteins from *N. meningitidis* and *N. gonorrhoeae*, and their epitopes, could be useful antigens for vaccines or diagnostics, or for raising antibodies.

Figures 14, 14A, 14B:
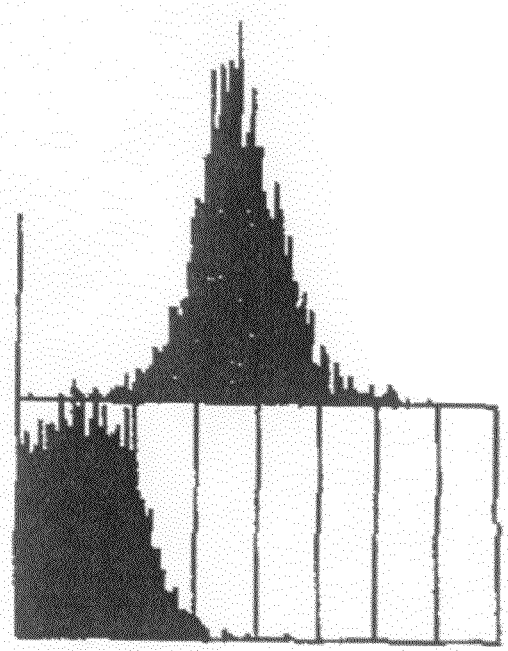

ORF138-1 (57 kDa) was cloned in the pGex vectors and expressed in *E. coli*, as described above. The products of protein expression and purification were analyzed by SDS-PAGE. FIG. 14A shows the results of affinity purification of the GST-fusion protein. Purified GST-fusion protein was used to immunise mice, whose sera were used for ELISA (positive result) and FACS analysis (FIG. 14B). These experiments confirm that ORF138-1 is a surface-exposed protein, and that it is a useful immunogen.

Example 69

The following partial DNA sequence was identified in *N. meningitidis* <SEQ ID 573>:

```
  1..GCGTGGTCGG CCGGCGAATC GTGGCGTGTG TTAATGGAAA GTGAAACGTG

51  GCATGCGGTG TGGAATACTT TGCGCTTCTC GGCGGCGGCG GTGTATGCGG

101  CAGCGGTTTT GGGTGTGGTG TATGCGGCGC CGGCGCGGCG GTCGGCGTGG

151  ATGCGCGGGC TGATGTTTTA GCCGTTTATG GTGTCGCCGG TTTGTGTTTC

201  GGCGGGCGTG CTGCTGCTTT ATCCGCAGTG GACGGCTTCG TTGCCGTTGC

251  TGCTGGCGAT GTATGCGCTG CTGGCGTATC CGTTTGTGGC AAAAGATGTT

301  TTATCAGCCT GGGATGCACT GCCGCCGGAT TACGGCAGGG CGGCGGCGGG

351  TTTGGGTGCA AACGGCTTTC AGACGGCATG CCGCATCACG TTCCCCCTCT
```

```
-continued
401  TGAAACCGGC GTTGCGGCGC GGTCTGACTT TGGCGGCGGC AACCTGCGTG

451  GGCGAATTTG CGGCGACATT GTTTCTGTCG CGTCCGGAAT GGCAGACGCT

501  GACGACTTTG ATTTATGCCT ATTTGGGACG CGCGGGTGAG GATAATTACG

551  CGCGGGCGAT GGTGCTG..
```

This corresponds to the amino acid sequence <SEQ ID 574; ORF139>:

```
  1..AWSAGESWRV LMESETWHAV WNTLRFSAAA VYAAAVLGVV YAAPARRSAW

51  MRGLMFXPFM VSPVCVSAGV LLLYPQWTAS LPLLLAMYAL LAYPFVAKDV

101  LSAWDALPPD YGRAAAGLGA NGFQTACRIT FPLLKPALRR GLTLAAATCV

151  GEFAATLFLS RPEWQTLTTL IYAYLGRAGE DNYARAMVL..
```

Further work revealed the complete nucleotide sequence <SEQ ID 575>:

```
   1  ATGGATGGAC GGCGTTGGGT GGTATGGGGT GCTTTTGCCC TGCTGCCTTC

51  GGCTTTTTTG GCGGTAATGG TCGTTGCGCC TTTGTGGGCG GTGGCGGCGT

101  ATGACGGTTT GGCGTGGCGC GCGGTGCTGT CGGATGCCTA TATGCTCAAA

151  CGTTTGGCGT GGACGGTATT TCAGGCAGCG GCAACCTGTG TGCTGGTGCT

201  GCCTTTGGGC GTGCCTGTCG CGTGGGTGCT GGCGCGGCTG GCGTTTCCGG

251  GGCGGGCTTT GGTGCTGCGC CTGCTGATGC TGCCTTTTGT GATGCCCACG

301  TTGGTGGCGG GCGTGGGCGT GCTGGCCCTG TTCGGGGCGG ACGGGCTGTT

351  GTGGCGCGGC AGGCAGGATA CGCCGTATCT GTTGTTGTAC GGCAATGTGT

401  TTTTCAACCT TCCTGTGTTG GTCAGGGCGG CGTATCAGGG GTTTGTGCAA

451  GTGCCTGCGG CACGGCTTCA GACGGCACGG ACGTTGGGCG CGGGGGCGTG

501  GCGGCGGTTT TGGGACATTG AAATGCCCGT TTTGCGCCCG TGGCTTGCCG

551  GCGGCGTGTG CCTTGTCTTT CTGTATTGTT TTTCCGGGTT CGGGCTGGCG

601  CTGCTGCTGG GCGGCAGCCG TTATGCCACG GTCGAAGTGG AAATTTACCA

651  GTTGGTCATG TTCGAACTCG ATATGGCGGT TGCTTCGGTG CTGGTGTGGC

701  TGGTGTTGGG GGTAACGGCG GCGGCAGGGT TGCTGTATGC GTGGTTCGGC

751  AGGCGCGCGG TTTCGGATAA GGCGGTTTCC CCTGTGATGC CGTCGCCGCC

801  GCAGTCGGTC GGGGAATATG TGCTGCTGGC GTTTGCGGCG CGGTGTTGT

851  CTGTGTGCTG CCTGTTTCCT TTGTTGGCAA TTGTTGTGAA AGCGTGGTCG

901  GCCGGCGAAT CGTGGCGTGT GTTAATGGAA AGTGAAACGT GGCAGGCGGT

951  GTGGAATACT TTGCGCTTCT CGGCGGCGGC GGTGTATGCG GCGGCGGTTT

1001  TGGGTGTGGT GTATGCGGCG GCGGCGCGGC GGTCGGCGTG GATGCGCGGG

1051  CTGATGTTTT TGCCGTTTAT GGTGTCGCCG GTTTGTGTTT CGGCGGGCGT

1101  GCTGCTGCTT TATCCGCAGT GGACGGCTTC GTTGCCGTTG CTGCTGGCGA

1151  TGTATGCGCT GCTGGCGTAT CCGTTTGTGG CAAAAGATGT TTTATCAGCC

1201  TGGGATGCAC TGCCGCCGGA TTACGGCAGG GCGGCGGCGG GTTTGGGTGC

1251  AAACGGCTTT CAGACGGCAT GCCGCATCAC GTTCCCCCTC TTGAAACCGG

1301  CGTTGCGGCG CGGTCTGACT TTGGCGGCGG CAACCTGCGT GGGCGAATTT
```

```
-continued
1351 GCGGCGACAT TGTTTCTGTC GCGTCCGGAA TGGCAGACGC TGACGACTTT

1401 GATTTATGCC TATTTGGGAC GCGCGGGTGA GGATAATTAC GCGCGGGCGA

1451 TGGTGCTGAC ATTGCTGTTG GCGGCGTTCG CGCTGGGTAT TTTCCTGCTG

1501 TTGGACGGCG GCGAAGGCGG AAAACAGACG GAAACGTTAT AA
```

This corresponds to the amino acid sequence <SEQ ID 576; ORF139-1>:

```
  1 MDGRRWVVWG AFALLPSAFL AVMVVAPLWA VAAYDGLAWR AVLSDAYMLK

51 RLAWTVFQAA ATCVLVLPLG VPVAWVLARL AFPGRALVLR LLMLPFVMPT

101 LVAGVGVLAL FGADGLLWRG RQDTPYLLLY GNVFFNLPVL VRAAYQGFVQ

151 VPAARLQTAR TLGAGAWRRF WDIEMPVLRP WLAGGVCLVFLYCFSGFGLA

201 LLLGGSRYAT VEVEIYQLVM FELDMAVASV LVWLVLGVTA AAGLLYAWFG

251 RRAVSDKAVS PVMPSPPQSV GEYVLLAFAA AVLSVCCLFP LLAIVVKAWS

301 AGESWRVLME SETWQAVWNT LRFSAAAVYA AAVLGVVYAA AARRSAWMRG

351 LMFLPFMVSP VCVSAGVLLL YPQWTASLPL LLAMYALLAY PFVAKDVLSA

401 WDALPPDYGR AAAGLGANGF QTACRITFPL LKPALRRGLT LAAATCVGEF

451 AATLFLSRPE WQTLTTLIYA YLGRAGEDNY ARAMVLTLLL AAFALGIFLL

501 LDGGEGGKQT ETL*
```

Computer analysis of this amino acid sequence gave the following results:

Homology with a Predicted ORF from *N. meningitidis* (Strain A)

ORF139 shows 94.7% identity over a 189aa overlap with an ORF (ORF139a) from strain A of *N. meningitidis*:

```
                                            10         20         30
orf139.pep                           AWSAGESWRVLMESETWHAVWNTLRFSAAA
                                     ||||||||||||||||| ||||| |||||
orf139a    QSVGEYVLLAFAAAVXSVCCLFXLLAIVVKAWSAGESWRVLMESETWQAVWNTXRFSAAA
           270        280        290        300        310        320
                   40         50         60         70         80         90
orf139.pep VYAAAVLGVVYAAPARRSAWMRGLMFXPFMVSPVCVSAGVLLLYPQWTASLPLLLAMYAL
           |||||||||||||  ||||||||||||| |||||||||||||| ||||||||||||||||
orf139a    VYAAAVLGVVYAAAARRSAWMRGLMFLPFMVSPVCVSAGVLLLXPQWTASLPLLLAMYAL
           330        340        350        360        370        380
                   100        110        120        130        140        150
orf139.pep LAYPFVAKDVLSAWDALPPDYGRAAAGLGANGFQTACRITFPLLKPALRRGLTLAAATCV
           ||||||||||||| ||||||||||||||||||||||||||||||||||||||||||||||
orf139a    LAYPFVAKDVLSAXDALPPDYGRAAAGLGANGFQTACRITFPLLKPALRRGLTLAAATCV
           390        400        410        420        430        440
                   100        110        120        189
orf139.pep GEFAATLFLSRPEWQTLTTLIYAYLGRAGEDNYARAMVL
           |||||||| || ||||||||||||| |||| ||||||||
orf139a    GEFAATLFXSRXEWQTLTTLIYAYXGRAGXDNYARAMVLTLLLAAFALGXFLLLDGGEGG
           450        460        470        480        490        500
```

The complete length ORF139a nucleotide sequence <SEQ ID 577> is:

```
  1 ATGGATGGAC GGCGTTGGGC GGTATGGGGT GCTTTTGCCC TGCTGCCTTC

51 GGCTTTTTTG GCGGCAATGG TCGTTGCGCC TTTGTGGGCG GTGGCGGCGT

101 ATGACGGTTT GGCGTGGCGC GCGGTGCTGT CGGATGCCTA TATGCTCAAA
```

```
151 CGTTTGGCGT GGACGGTATT TCAGGCAGCG GCAACCTGTG TGCTGGTGCT

201 GCCTTTGGGC GTGCCTGTCG CGTGGGTGCT GGCGCGGCTG GCGTTTCCGG

251 GGCGGGCTTT GGTGCTGCGC CTGCTGATGC TGCCTTTTGT GATGCCCACG

301 TTGGTGGCGG GCGTGGGCGT GCTGGCTCTG TTCGGGCGG ACGGCCTGTN

351 GTGGCGCGGC TGGCAGGATA CGCCGTATCT GTTGTTGTAC GGCAATGTGT

401 TTTTTNACCT TCCTGTGTTG GTCAGGGCGG CATATCAGGG GTTTGTGCAA

451 GTGCCTGCGG CACGGCTTCA GACGGCACNG ACATTGGGCG CGGGGGCGTG

501 GCGGCGGTTT TGGGACATTG AAATGCCCGT TTTGCGCCCG TGGCTTGCCG

551 GCGGCGTGTG CCTTGTCTTC CTGTATTGTT TTTCGGGGTT CGGGCTGGCA

601 TTGCTGCTGG GCGGCAGCCG TTATGCCACG GTCGAAGTGG AAATTTACCA

651 GTTGGTCATG TTCGAACTCG ATATGGCGGT TGCTTCGGTG CTNGTGTGGC

701 TGGTGTNGGG GGTAACNGCG GCGGCAGGGT TGCTGTATGC GTGGTTCGGC

751 AGGCGCGCGG TTTCGGATAA GGCNGTTTCC CCTGTGATGC CGTCGCCGCC

801 GCAGTCGGTC GGGGAATATG TGCTNCTGGC GTTTGCGGCG GCGGTGTNGT

851 CTGTGTGCTG CCTGTTTCNT TTGTTGGCAA TTGTTGTGAA AGCGTGGTCG

901 GCCGGCGAAT CGTGGCGTGT GTTAATGGAA AGTGAAACGT GGCAGGCGGT

951 GTGGAATACT NTGCGCTTCT CGGCGGCGGC GGTGTATGCG GCGGCGGTTT

1001 TGGGTGTGGT GTATGCGGCG GCGGCGCGGC GGTCGGCGTG GATGCGCGGG

1051 CTGATGTTTT TGCCGTTTAT GGTGTCGCCG GTTTGTGTTT CGGCGGGCGT

1101 GCTGCTGCTT NATCCGCAGT GGACGGCTTC GTTGCCGCTG CTGCTGGCGA

1151 TGTATGCGCT GCTGGCGTAT CCGTTTGTGG CAAAAGATGT TTTATCAGCC

1201 TGNGATGCAC TGCCGCCGGA TTACGGCAGG GCGGCGGCGG GTTTGGGTGC

1251 AAACGGCTTT CAGACGGCAT GCCGCATCAC GTTCCCCCTC TTGAAACCGG

1301 CGTTGCGGCG CGGTCTGACT TTGGCGGCGG CAACCTGCGT GGGCGAATTT

1351 GCGGCAACCT TGTTCNTGTC GCGTCNCGAG TGGCAGACGC TGACGACTTT

1401 GATTTATGCC TATNTGGGAC GCGCGGGTGA NGATAATTAC GCGCGGGCGA

1451 TGGTGCTGAC ATTGCTGTTG GCGGCGTTCG CGCTGGGTAT NTTCCTGCTG

1501 TTGGACGGCG GCGAAGGCGG AAAACGGACG GAAACGTTAT AA
```

This encodes a protein having amino acid sequence <SEQ ID 578>:

```
  1 MDGRRWAVWG AFALLPSAFL AAMVVAPLWA VAAYDGLAWR AVLSDAYMLK

51 RLAWTVFQAA ATCVLVLPLG VPVAWVLARL AFPGRALVLR LLMLPFVMPT

101 LVAGVGVLAL FGADGLXWRG WQDTPYLLLY GNVFFXLPVL VRAAYQGFVQ

151 VPAARLQTAX TLGAGAWRRF WDIEMPVLRP WLAGGVCLVF LYCFSGFGLA

201 LLLGGSRYAT VEVEIYQLVM FELDMAVSV LVWLVXGVTA AAGLLYAWFG

251 RRAVSDKAVS PVMPSPPQSV GEYVLLAFAA AVXSVCCLFX LLAIVVKAWS

301 AGESWRVLME SETWQAVWNT XRFSAAAVYA AAVLGVVYAA ARRSAWMRG

351 LMFLPFMVSP VCVSAGVLLL XPQWTASLPL LLAMYALLAY PFVAKDVLSA

401 XDALPPDYGR AAAGLGANGF QTACRITFPL LKPALRRGLT LAAATCVGEF
```

```
451 AATLFXSRXE WQTLTTLIYA YXGRAGXDNY ARAMVLTLLL AAFALGXFLL

501 LDGGEGGKRT ETL*
```

ORF139a and ORF139-1 show 96.5% homology over a 514aa overlap:

```
orf139a.pep  MDGRRWAVWGAFALLPSAFLAAMVVAPLWAVAAYDGLAWRAVLSDAYMLKRLAWTVFQAA
             ||||||:||||||||||||||:||||||||||||||||||||||||||||||||||||||
orf139-1     MDGRRWVVWGAFALLPSAFLAVMVVAPLWAVAAYDGLAWRAVLSDAYMLKRLAWTVFQAA orf139a.pep  ATCVLVLPLGVPVAWVLARLAFPGRALVLRLLMLPFVMPTLVAGVGVLALFGADGLXWRG
             ||||||||||||||||||||||||||||||||||||||||||||||||||||||||||||
orf139-1     ATCVLVLPLGVPVAWVLARLAFPGRALVLRLLMLPFVMPTLVAGVGVLALFGADGLLWRG orf139a.pep  WQDTPYLLLYGNVFFXLPVLVRAAYQGFVQVPAARLQTAXTLGAGAWRRFWDIEMPVLRP
             |||||||||||||| ||||||||||||||||||||||||| ||||||||||||||||||
orf139-1     RQDTPYLLLYGNVFFNLPVLVRAAYQGFVQVPAARLQTARTLGAGAWRRFWDIEMPVLRP orf139a.pep  WLAGGVCLVFLYCFSGFGLALLLGGSRYATVEVEIYQLVMFELDMAVASVLVWLVXGVTA
             ||||||||||||||||||||||||||||||||||||||||||||||||||||||| ||||
orf139-1     WLAGGVCLVFLYCFSGFGLALLLGGSRYATVEVEIYQLVMFELDMAVASVLVWLVLGVTA orf139a.pep  AAGLLYAWFGRRAVSDKAAVSVMPSPPQSVGEYVLLAFAAAVXSVCCLFXLLAIVVKAWS
             |||||||||||||||||||||||||||||||||||||||||| ||||| |||||||||||
orf139-1     AAGLLYAWFGRRAVSDKAAVSVMPSPPQSVGEYVLLAFAAAVLSVCCLFPLLAIVVKAWS orf139a.pep  AGESWRVLMESETWQAVWNTXRFSAAAVYAAAVLGVVYAAAARRSAWMRGLMFLPFMVSP
             ||||||||||||||||||||| ||||||||||||||||||||||||||||||||||||||
orf139-1     AGESWRVLMESETWQAVWNTLRFSAAAVYAAAVLGVVYAAAARRSAWMRGLMFLPFMVSP orf139a.pep  VCVSAGVLLLXPQWTASLPLLLAMYALLAYPFVAKDVLSAXDALPPDYGRAAAGLGANGF
             |||||||||| |||||||||||||||||||||||||||| ||||||||||||||||||||
orf139-1     VCVSAGVLLLYPQWTASLPLLLAMYALLAYPFVAKDVLSAWDALPPDYGRAAAGLGANGF orf139a.pep  QTACRITFPLLKPALRRGLTLAAATCVGEFAATLFXSRXEWQTLTTLIYAYXGRAGXDNY
             ||||||||||||||||||||||||||||||||||| || |||||||||||| |||| |||
orf139-1     QTACRITFPLLKPALRRGLTLAAATCVGEFAATLFLSRPEWQTLTTLIYAYLGRAGEDNY orf139a.pep  ARAMVLTLLLAAFALGXFLLLDGGEGGKRTETLX
             |||||||||||||||| |||||||||||:|||||
orf139-1     ARAMVLTLLLAAFALGIFLLLDGGEGGKQTETLX
```

Homology with a Predicted ORF from *N. gonorrhoeae*

ORF139 shows 95.2% identity over a 189aa overlap with a predicted ORF (ORF139ng) from *N. gonorrhoeae*:

```
orf139.pep               AWSAGESWRVLMESETWHAVWNTLRFSAAA  30
                         ||||||| ||||||||||:|||||||||||
orf139ng     QSVGEYVLLAFSVAVLSVCCLFPLSAIVVKAWSAGESRRVLMESETWQAVWNTLRFSAAA 327 orf139.pep   VYAAAVLGVVYAAPARRSAWMRGLMFXPFMVSPVCVSAGVLLLYPQWTASLPLLLAMYAL  90
             |:||||||||||  |||:||||||||  |||||||||||||||||||||||||||||||
orf139ng     VFAAAVLGVVYAAAARRLVWMRGLVFLPFMVSPVCVSAGVLLLYPGWTASLPLLLAMYAL 387 orf139.pep   LAYPFVAKDVLSAWDALPPDYGRAAAGLGANGFQTACRITFPLLKPALRRGLTLAAATCV 150
             ||||||||||||||||||||||||||||||||||||||||||||||||||||||||||||
orf139ng     LAYPFVAKDVLSAWDALPPDYGRAAAGLGANGFQTACRITFPLLKPALRRGLTLAAATCV 387 orf139.pep   GEFAATLFLSRPEWQTLTTLIYAYLGRAGEDNYARAMVL                      189
             |||||||||||||||||||||||||||||||||||||||
orf139ng     GEFAATLFLSRPEWQTLTTLIYAYLGRAGEDNYARAMVLTLLLSAFAVCIFLLLDNGEGG 387
```

The complete length ORF139ng nucleotide sequence <SEQ ID 579> is predicted to encode a protein having amino acid sequence <SEQ ID 580>:

```
  1 MDGRCWAVRG AFSLLPSAFL AVMVVAPLWA VAAYDGLAWR AVLSDAYMLK

51 RLAWTVFQAA ATCVLVLPLG VPVAWVLARL AFPGRALVLR LLMLPFVMPT

101 LVAGVGVLAL FGADGLLWRG RQDTPYLLLY GNVFFNLPVL VRAAYQGFAQ

151 VPAARLQTAR TLGAGAWRPF WDIEMPVLRP WLAGGVCLVF LYCFSGFGLA

201 LLLGGSRYAT VEVEIYQLVM FELDMAGASA LVWLVLGVTA AAGLLYAWFG

251 RRAVSDKAVS PVMPSPPQSV GEYVLLAFSV AVLSVCCLFP LSAIVVKAWS

301 AGESRRVLME SETWQAVWNT LRFSAAAVFA AAVLGVVYAA AARRLVWMRG
```

```
351 LVFLPFMVSP VCVSAGVLLL YPGWTASLPL LLAMYALLAY PFVAKDVLSA

401 WDALPPDYGR AAAGLGANGF QTACRITFPL LKPALRRGLT LAAATCVGEF

451 AATLFLSRPE WQTLTTLIYA YLGRAGEDNY ARAMVLTLLL SAFAVCIFLL

501 LDNGEGGKRT ETL*
```

Further work revealed a variant gonococcal DNA sequence <SEQ ID 581>:

```
   1 ATGGATGGAC GGTGTTGGGC GGTACGGGGT GCTTTTTCCC TGCTGCCTTC

51 GGCTTTTTTG GCGGTAATGG TCGTTGCGCC TTTGTGGGCG GTGGCGGCGT

101 ATGACGGTTT GGCGTGGCGC GCGGTGCTGT CGGATGCCTA TATGCTCAAA

151 CGTTTGGCGT GGACGGTGTT TCAGGCGGCG GCAACCTGTG TGCTGGTGCT

201 GCCTTTGGGC GTGCCTGTCG CGTGGGTGCT GGCGCGGCTG GCGTTCCCGG

251 GGCGGGCTTT GGTGCTGCGC CTGCTGATGC TGCCGTTTGT GATGCCCACG

301 CTGGTGGCGG GCGTGGGCGT GCTGGCTCTG TTCGGGCGG ACGGGCTGTT

351 GTGGCGCGGC CGGCAGGATA CGCCGTATCT GTTGTTGTAC GGCAATGTGT

401 TTTTCAACCT GCCCGTGTTG GTCAGGGCGG CGTATCAGGG GTTTGCTCAA

451 GTGCCTGCGG CACGGCTTCA GACGGCACGG ACGTTGGGCG CGGGGGCGTG

501 GCGGCGGTTT TGGGACATTG AAATGCCCGT TTTGCGCCCG TGGCTTGCCG

551 GCGGCGTGTG CCTTGTCTTC CTGTATTGTT TTCGGGGTT CGGGCTGGCA

601 TTGCTGTTGG GCGGCAGCCG TTATGCCACG GTCGAAGTGG AAATTTACCA

651 GTTGGTTATG TTCGAACTCG ATATGGCGGG GGCTTCGGCG CTGGTGTGGC

701 TGGTGTTGGG GGTAACGGCG GCGGCAGGGT TGCTGTATGC GTGGTTCGGC

751 AGGCGCGCGG TTTCGGATAA GGCGGTTTCC CCCGTGATGC CGTCGCCGCC

801 GCAATCGGTG GGGGAATATG TATTGCTGGC ATTTTCGGTG GCGGTGTTGT

851 CCGTGTGCTG CCTGTTTCCT TTGTCGGCAA TTGTTGTGAA AGCGTGGTCG

901 GCCGGCGAAT CGCGGCGTGT GTTAATGGAA AGTGAAACGT GGCAGGCAGT

951 GTGGAATACt tGCGCTTTT CGGCGGCGGC GGTGTTTGCG GCGGCGGTTT

1001 TGGGTGTGGT GTATGCGGCG GCGGCGCGGC GGCTGGTGTG GATGCGCGGA

1051 CTGGTGTTTT TACCGTTTAT GGTGTCGCCG GTTTGTGTTT CGGCGGGCGT

1101 GCTGCTGCTT TATCCGGGGT GGACGGCTTC GTTACCGCTG CTGCTGGCGA

1151 TGTATGCGCT GCTGGCGTAT CCGTTTGTGG CAAAAGATGT TTTATCGGCC

1201 TGGGATGCAC TGCCGCCGGA TTACGGCAGG GCGGCGGCAG GTTTGGGCGC

1251 AAACGGCTTT CAGACGGCAT GCCGTATCAC GTTCCCCCTC TTGAAACCGG

1301 CGTTGCGGCG CGGTCTGACT TTGGCGGCGG CGACGTGTGT GGGCGAATTT

1351 GCGGCAACCT TGTTCCTGTC GCGTCCGGAA TGGCAGACGT TGACGACTTT

1401 GATTTATGCC TATTTGGGGC GTGCGGGTGA GGACAATTAT GCGCGGGCAA

1451 TGGTGTTGAC ATTGCTGTTG TCGGCATTTG CGGTGTGCAT TTTCCTGCTG

1501 TTGGACAACG GCGAAGGCGg aaaACGGACG GAAACGTTAT AA
```

This corresponds to the amino acid sequence <SEQ ID 582; ORF139ng-1>:

```
  1  MDGRCWAVRG AFSLLPSAFL AVMVVAPLWA VAAYDGLAWR AVLSDAYMLK

51  RLAWTVFQAA ATCVLVLPLG VPVAWVLARL AFPGRALVLR LLMLPFVMPT

101  LVAGVGVLAL FGADGLLWRG RQDTPYLLLY GNVFFNLPVL VRAAYQGFAQ

151  VPAARLQTAR TLGAGAWRRF WDIEMPVLRP WLAGGVCLVF LYCFSGFGLA

201  LLLGGSRYAT VEVEIYQLVM FELDMAGASA LVWLVLGVTA AAGLLYAWFG

251  RRAVSDKAVS PVMPSPPQSV GEYVLLAFSV AVLSVCCLFP LSAIVVKAWS

301  AGESRRVLME SETWQAVWNT LRFSAAAVFA AAVLGVVYAA AARRLVWMRG

351  LVFLPFMVSP VCVSAGVLLL YPGWTASLPL LLAMYALLAY PFVAKDVLSA

401  WDALPPDYGR AAAGLGANGF QTACRITFPL LKPALRRGLT LAAATCVGEF

451  AATLFLSRPE WQTLTTLIYA YLGRAGEDNY ARAMVLTLLL SAFAVCIFLL

501  LDNGEGGKRT ETL*
```

ORF139ng-1 and ORF139-1 show 95.9% identity over 513aa overlap:

```
orf139ng   MDGRCWAVRGAFSLLPSAFLAVMVVAPLWAVAAYDGLAWRAVLSDAYMLKRLAWTVFQAA
           ||||  :|  |||:||||||||||||||||||||||||||||||||||||||||||||||
orf139-1   MDGRRWVVWGAFALLPSAFLAVMVVAPLWAVAAYDGLAWRAVLSDAYMLKRLAWTVFQAA orf139ng   ATCVLVLPLGVPVAWVLARLAFPGRALVLRLLMLPFVMPTLVAGVGVLALFGADGLLWRG
           ||||||||||||||||||||||||||||||||||||||||||||||||||||||||||||
orf139-1   ATCVLVLPLGVPVAWVLARLAFPGRALVLRLLMLPFVMPTLVAGVGVLALFGADGLLWRG orf139ng   RQDTPYLLLYGNVFFNLPVLVRAAYQGFAQVPAARLQTARTLGAGAWRRFWDIEMPVLRP
           |||||||||||||||||||||||||||||:||||||||||||||||||||||||||||||
orf139-1   RQDTPYLLLYGNVFFNLPVLVRAAYQGFVQVPAARLQTARTLGAGAWRRFWDIEMPVLRP orf139ng   WLAGGVCLVFLYCFSGFGLALLLGGSRYATVEVEIYQLVMFELDMAGASALVWLVLGVTA
           |||||||||||||||||||||||||||||||||||||||||||||||  ||::|||||||
orf139-1   WLAGGVCLVFLYCFSGFGLALLLGGSRYATVEVEIYQLVMFELDMAVASVLVWLVLGVTA orf139ng   AAGLLYAWFGRRAVSDKAAVSVMPSPPQSVGEYVLLAFSVAVLSVCCLFPLSAIVVKAWS
           |||||||||||||||||||||||||||||||||||||||::|||||||||| ||||||||
orf139-1   AAGLLYAWFGRRAVSDKAAVSVMPSPPQSVGEYVLLAFAAAVLSVCCLFPLLAIVVKAWS orf139ng   AGESRRVLMESETWQAVWNTLRFSAAAVFAAAVLGVVYAAAARRLVWMRGLVFLPFMVSP
           ||||  ||||||||||||||||||||||:||||||||||||||:  :|||||  ||||||
orf139-1   AGESWRVLMESETWQAVWNTLRFSAAAVYAAAVLGVVYAAAARRSAWMRGLMFLPFMVSP orf139ng   VCVSAGVLLLYPGWTASLPLLLAMYALLAYPFVAKDVLSAWDALPPDYGRAAAGLGANGF
           ||||||||||||||||||||||||||||||||||||||||||||||||||||||||||||
orf139-1   VCVSAGVLLLYPQWTASLPLLLAMYALLAYPFVAKDVLSAWDALPPDYGRAAAGLGANGF orf139ng   QTACRITFPLLKPALRRGLTLAAATCVGEFAATLFLSRPEWQTLTTLIYAYLGRAGEDNY
           ||||||||||||||||||||||||||||||||||||||||||||||||||||||||||||
orf139-1   QTACRITFPLLKPALRRGLTLAAATCVGEFAATLFLSRPEWQTLTTLIYAYLGRAGEDNY orf139ng   ARAMVLTLLLSAFAVCIFLLLDNGEGGKRTETL
           ||||||||||:|||: |||||:|||||:||||
orf139-1   ARAMVLTLLLAAFALGIFLLLDGGEGGKQTETL
```

Based on the presence of a predicted binding-protein-dependent transport systems inner membrane component signature (underlined) in the gonococcal protein, it is predicted that the proteins from *N. meningitidis* and *N. gonorrhoeae*, and their epitopes, could be useful antigens for vaccines or diagnostics, or for raising antibodies.

Example 70

The following partial DNA sequence was identified in *N. meningitidis* <SEQ ID 583>:

```
  1 ATGGACGGCT GGACACAGAC GCTGTCCGCG CAAACCCTGT TGGGCATTTC
 51 GGCGGCGGCA ATCATCCTCA TTCTGATTTT AATCGTCAGA TTCCGCATCC
101 ACGCGCTGCT GACACTGGTC ATCGTCAGCC TGCTGACGGC TTTGGCAACC
151 GGTTTGCCCA CAGGCAGCAT TGTCAAAGAC ATACTGGTCA AAAACTTCGG
201 CGGCACGCTC GGCGGCGTGG CGCTTCTGGT CGGCCTGGGC GCGATGCTCG
251 AACGTTTGGT C...
```

This corresponds to the amino acid sequence <SEQ ID 584; ORF140>:

```
  1 MDGWTQTLSA QTLLGISAAA IILILILIVR FRIHALLTLV IVSLLTALAT
 51 GLPTGSIVKD ILVKNFGGTL GGVALLVGLG AMLERLV..
```

Further work revealed the complete nucleotide sequence <SEQ ID 585>:

```
   1 ATGGACGGCT GGACACAGAC GCTGTCCGCG CAAACCCTGT TGGGCATTTC
  51 GGCGGCGGCA ATCATCCTCA TTCTGATTTT AATCGTCAAA TTCCGCATCC
 101 ACGCGCTGCT GACACTGGTC ATCGTCAGCC TGCTGACGGC TTTGGCAACC
 151 GGTTTGCCCA CAGGCAGCAT TGTCAACGAC ATACTGGTCA AAAACTTCGG
 201 CGGCACGCTC GGCGGCGTGG CGCTTCTGGT CGGCCTGGGC GCGATGCTCG
 251 GACGTTTGGT CGAAACATCC GGCGGCGCAC AGTCGCTGGC GGACGCGCTG
 301 ATCCGGATGT TCGGCGAAAA ACGCGCACCG TTCGCGCTGG GCGTTGCCTC
 351 GCTGATTTTC GGCTTCCCGA TTTTCTTCGA TGCCGGACTA ATCGTCATGC
 401 TGCCCATCGT GTTCGCCACC GCACGGCGCA TGAAACAGGA CGTACTGCCC
 451 TTCGCGCTTG CCTCCATCGG CGCATTTTCC GTCATGCACG TCTTCCTGCC
 501 GCCCCATCCG GGCCCGATTG CCGCTTCCGA ATTTTACGGC GCGAACATCG
 551 GCCAAGTTTT GATTTTGGGT CTGCCGACCG CCTTCATCAC ATGGTATTTC
 601 AGCGGCTATA TGCTCGGCAA AGTGTTGGGG CGCACCATCC ATGTTCCCGT
 651 TCCCGAACTG CTCAGCGGCG GCACGCAAGA CAACGACCTG CCGAAAGAAC
 701 CTGCCAAAGC AGGAACGGTC GTCGCCATCA TGCTGATTCC CATGCTGCTG
 751 ATTTTCCTGA ATACCGGCGT ATCGGCCCTC ATCAGCGAAA AACTCGTAAG
 801 TGCGGACGAA ACCTGGGTTC AGACGGCAAA AATAATCGGT TCGACACCGA
 851 TCGCCCTTCT GATTTCCGTA TTGGTCGCAC TGTTTGTCTT GGGACGCAAA
 901 CGCGGCGAAA GCGGCAGCGC GTTGGAAAAA ACCGTGGACG GCGCACTCGC
 951 CCCCGTCTGT TCCGTGATTC TGATTACCGG CGCGGGCGGT ATGTTCGGCG
1001 GCGTTTTGCG CGCTTCCGGC ATCGGCAAGG CACTCGCCGA CAGCATGGCG
1051 GATTTGGGCA TTCCCGTCCT TTTGGGCTGT TTCCTTGTCG CCTTGGCACT
1101 GCGTATCGCG CAAGGTTCGG CAACCGTCGC CCTGACCACC GCCGCCGCGC
1151 TGATGGCTCC TGCCGTTGCC GCCGCCGGCT TTACCGACTG GCAGCTCGCC
```

```
                             -continued
1201 TGTATCGTAT TGGCAACGGC GGCAGGTTCG GTCGGTTGCA GCCACTTCAA

1251 CGACTCCGGC TTCTGGCTGG TCGGCCGTCT CTTGGACATG GACGTACCGA

1301 CCACGCTGAA AACCTGGACG GTCAACCAAA CCCTCATCGC ACTCATCGGC

1351 TTTGCCTTGT CCGCACTGCT GTTCGCCATC GTCTGA
```

This corresponds to the amino acid sequence <SEQ ID 586; ORF140-1>:

```
  1  MDGWTQTLSA QTLLGISAAA IILILILIVK FRIHALLTLV IVSLLTALAT

51  GLPTGSIVND ILVKNFGGTL GGVALLVGLG AMLGRLVETS GGAQSLADAL

101  IRMFGEKRAP FALGVASLIF GFPIFFDAGL IVMLPIVFAT ARRMKQDVLP

151  FALASIGAFS VMHVFLPPHP GPIAASEFYG ANIGQVLILG LPTAFITWYF

201  SGYMLGKVLG RTIHVPVPEL LSGGTQDNDL PKEPAKAGTV VAIMLIPMLL

251  IFLNTGVSAL ISEKLVSADE TWVQTAKIIG STPIALLISV LVALFVLGRK

301  RGESGSALEK TVDGALAPVC SVILITGAGG MFGGVLRASG IGKALADSMA

351  DLGIPVLLGC FLVALALRIA QGSATVALTT AAALMAPAVA AAGFTDWQLA

401  CIVLATAAGS VGCSHFNDSG FWLVGRLLDM DVPTTLKTWT VNQTLIALIG

451  FALSALLFAI V*
```

Computer analysis of this amino acid sequence gave the following results:

Homology with a Predicted ORF from *N. meningitidis* (Strain A)

ORF140 shows 95.4% identity over a 87aa overlap with an ORF (ORF140a) from strain A of *N. meningitidis*.

```
                    10        20        30        40        50        60
orf140.pep  MDGWTQTLSAQTLLGISAAAIILILILIVRFRIHALLTLVIVSLLTALATGLPTGSIVKD
            ||||||||||||||||||||||||||||| :||||||||||||||||||||||||||| :|
orf140a     MDGWTQTLSAQTLLGISAAAIILILILIVKFRIHALLTLVIVSLLTALATGLPTGSIVND
                    10        20        30        40        50        60

70        80
orf140.pep  ILVKNFGGTLGGVALLVGLGAMLERLV
            :||||||||||||||||||||||| |||
orf140a     VLVKNFGGTLGGVALLVGLGAMLGRLVETSGGAQSLADALIRMFGEKRAPFALGVASLIF
                    70        80        90       100       110       120
```

The complete length ORF140a nucleotide sequence <SEQ ID 587> is:

```
  1  ATGGACGGCT GGACACAGAC GCTGTCCGCG CAAACCCTGT TGGGCATTTC

51  GGCGGCGGCA ATCATCCTCA TTCTGATTTT AATCGTCAAA TTCCGCATCC

101  ACGCGCTGCT GACACTGGTC ATCGTCAGCC TGCTGACGGC TTTGGCAACC

151  GGTTTGCCCA CAGGCAGCAT TGTCAACGAC GTACTGGTCA AAAACTTCGG

201  CGGCACGCTC GGCGGCGTGG CGCTTCTGGT CGGCCTGGGC GCGATGCTCG

251  GACGTTTGGT CGAAACATCC GGCGGCGCAC AGTCGCTGGC GGACGCGCTG

301  ATCCGGATGT TCGGCGAAAA ACGCGCACCG TTCGCGCTGG GCGTTGCCTC

351  GCTGATTTTC GGCTTCCCGA TTTTCTTCGA TGCCGGACTA ATCGTCATGC

401  TGCCCATCGT GTTCGCCACC GCACGGCGCA TGAAACAGGA CGTACTGCCC

451  TTCGCGCTTG CCTCCATCGG CGCATTTTCC GTCATGCACG TCTTCCTGCC
```

```
 501 GCCCCATCCG GGCCCGATTG CCGCTTCCGA ATTTTACGGC GCGAACATCG

551 GCCAAGTTTT GATTTTGGGT CTGCCGACCG CCTTCATCAC ATGGTATTTC

601 AGCGGCTATA TGCTCGGCAA AGTGTTGGGG CGCACCATCC ATGTTCCCGT

651 TCCCGAACTG CTCAGCGGCG GCACGCAAGA CAACGACCTG CCGAAAGAAC

701 CTGCCAAAGC AGGAACGGTC GTCGCCATCA TGCTGATTCC CATGCTGCTG

751 ATTTTCCTGA ATACCGGCGT ATCGGCCCTC ATCAGCGAAA AACTCGTAAG

801 TGCGGACGAA ACCTGGGTTC AGACGGCAAA ATAATCGGT TCGACACCGA

851 TCGCCCTTCT GATTTCCGTA TTGGTCGCAC TGTTTGTCTT GGGACGCAAA

901 CGCGGCGAAA GCGGCAGCGC GTTGGAAAAA ACCGTGGACG GCGCACTCGC

951 CCCCGTCTGT TCCGTGATTC TGATTACCGG CGCGGGCGGT ATGTTCGGCG

1001 GCGTTTTGCG CGCTTCCGGC ATCGGCAAGG CACTCGCCGA CAGCATGGCG

1051 GATTTGGGCA TTCCCGTCCT TTTGGGCTGT TTCCTTGTCG CCTTGGCACT

1101 GCGTATCGCG CAAGGTTCGG CAACCGTCGC CCTGACCACC GCCGCCGCGC

1151 TGATGGCTCC TGCCGTTGCC GCCGCCGGCT TTACCGACTG GCAGCTCGCC

1201 TGTATCGTAT TGGCAACGGC GGCAGGTTCG GTCGGTTGCA GCCACTTCAA

1251 CGACTCCGGC TTCTGGCTGG TCGCCGCCT CTTGGACATG GACGTACCGA

1301 CCACGCTGAA AACCTGGACG GTCAACCAAA CCCTCATCGC ACTCATCGGC

1351 TTTGCCTTGT CCGCACTGCT GTTCGCCATC GTCTGA
```

This encodes a protein having amino acid sequence <SEQ ID 588>:

```
  1 MDGWTQTLSA QTLLGISAAA IILILILIVK FRIHALLTLV IVSLLTALAT

51 GLPTGSIVND VLVKNFGGTL GGVALLVGLG AMLGRLVETS GGAQSLADAL

101 IRMFGEKRAP FALGVASLIF GFPIFFDAGL IVMLPIVFAT ARRMKQDVLP

151 FALASIGAFS VMHVFLPPHP GPIAASEFYG ANIGQVLILG LPTAFITWYF

201 SGYMLGKVLG RTIHVPVPEL SGGTQDNDL PKEPAKAGTV VAIMLIPMLL

251 IFLNTGVSAL ISEKLVSADE TWVQTAKIIG STPIALLISV LVALFVLGRK

301 RGESGSALEK TVDGALAPVC SVILITGAGG MFGGVLRASG IGKALADSMA

351 DLGIPVLLGC FLVALALRIA QGSATVALTT AAALMAPAVA AAGFTDWQLA

401 CIVLATAAGS VGCSHFNDSG FWLVGRLLDM DVPTTLKTWT VNQTLIALIG

451 FALSALLFAI V*
```

ORF140a and ORF140-1 show 99.8% identity over a 461aa overlap:

```
orf140-1.pep MDGWTQTLSAQTLLGISAAAIILILILIVKFRIHALLTLVIVSLLTALATGLPTGSIVND  60
             |||||||||||||||||||||||||||||||||||||||||||||||||||||||||||
orf140a      MDGRTQTLSAQTLLGISAAAIILILILIVKFRIHALLTLVIVSLLTALATGLPTGSIVND  60 orf140-1.pep ILVKNFGGTLGGVALLVGLGAMLGRLVETSGGAQSLADALIRMFGEKRAPFALGVASLIF 120
             :|||||||||||||||||||||||||||||||||||||||||||||||||||||||||
orf140a      VLVKNFGGTLGGVALLVGLGAMLGRLVETSGGAQSLADALIRMFGEKRAPFALGVASLIF 120 orf140-1.pep GFPIFFDAGLIVMLPIVFATARRMKQDVLPFALASIGAFSVMHVFLPPHPGPIAASEFYG 180
             ||||||||||||||||||||||||||||||||||||||||||||||||||||||||||||
orf140a      GFPIFFDAGLIVMLPIVFATARRMKQDVLPFALASIGAFSVMHVFLPPHPGPIAASEFYG 810 orf140-1.pep ANIGQVLILGLPTAFITWYFSGYMLGKVLGRTIHVPVPELLSGGTQDNDLPKEPAKAGTV 240
             ||||||||||||||||||||||||||||||||||||||||||||||||||||||||||||
orf140a      ANIGQVLILGLPTAFITWYFSGYMLGKVLGRTIHVPVPELLSGGTQDNDLPKEPAKAGTV 240
```

```
orf140-1.pep  VAIMLIPMLLIFLNTGVSALISEKLVSADETWVQTAKIIGSTPIALLISVLVALFVLGRK  300
              ||||||||||||||||||||||||||||||||||||||||||||||||||||||||||||
orf140a       VAIMLIPMLLIFLNTGVSALISEKLVSADETWVQTAKIIGSTPIALLISVLVALFVLGRK  300 orf140-1.pep  RGESGSALEKTVDGALAPVCSVILITGAGGMFGGVLRASGIGKALADSMADLGIPVLLGC  360
              ||||||||||||||||||||||||||||||||||||||||||||||||||||||||||||
orf140a       RGESGSALEKTVDGALAPVCSVILITGAGGMFGGVLRASGIGKALADSMADLGIPVLLGC  360 orf140-1.pep  FLVALALRIAQGSATVALTTAAALMAPAVAAAGFTDWQLACIVLATAAGSVGCSHFNDSG  420
              ||||||||||||||||||||||||||||||||||||||||||||||||||||||||||||
orf140a       FLVALALRIAQGSATVALTTAAALMAPAVAAAGFTDWQLACIVLATAAGSVGCSHFNDSG  420 orf140-1.pep  FWLVGRLLDMDVPTTLKTWTVNQTLIALIGFALSALLFAIV                    461
              ||||||||||||||||||||||||||||||||||||||||
orf140a       FWLVGRLLDMDVPTTLKTWTVNQTLIALIGFALSALLFAIV                    461
```

Homology with a Predicted ORF from *N. gonorrhoeae*

ORF140 shows 92% identity over a 87aa overlap with a predicted ORF (ORF140ng) from *N. gonorrhoeae*:

```
orf140.pep   MDGWTQTLSAQTLLGISAAAIILILILIVRFRIHALLTLVIVSLLTALATGLPTGSIVKD  60
             |||  |||||||||||||||||||||||:|||:||||||||:||||||||||||||||:|
orf140ng     MDGRTQTLSAQTLLGISAAAIILILILIVKFRIRALLTLVIASLLTALATGLPTGSIVND  60 orf140.pep   ILVKNFGGTLGGVALLVGLGAMLERLV                                   87
             :||||||||||||||||||||||| |||
orf140ng     VLVKNFGGTLGGVALLVGLGAMLGRLVETSGGAQSLADALIRMFGEKRAPFAPGVASLIF 120
```

The complete length ORF140ng nucleotide sequence <SEQ ID 589> was predicted to encode a protein having amino acid sequence <SEQ ID 590>:

```
  1  MDGRTQTLSA QTLLGISAAA IILILILIVK FRIRALLTLV IASLLTALAT

51  GLPTGSIVND VLVKNFGGTL GGVALLVGLG AMLGRLVETS GGAQSLADAL

101  IRMFGEKRAP FAPGVASLIF GFPIFFDAGL IVMLPIVFAT ARRMKQDVLP

151  FALASVGAFS VMHVFLPPHP GPIAASEFYG ANIGQVLILG LPTAFITWYF

201  SGYMLGKVLG RAIHVPVPEL LSGGTQDSDP PKEPAKAGTV VAVMLIPMLL

251  IFLNTGVSAL ISEKLVSADE TWVQTAKMIG STPVALLISV LAALLVLGRK

301  RGESGSTLEK TVDGALAPAC SVILITGAGG MFGGVLRASG IGKALADSMA

351  DLGIPVLLGC FLVALALRIA QGSATVALTT AAALMAPAVA AAGFTDWQLA

401  CIVLATAAGS VGCSHFNDSG FWLVGRLSDM DVPTTLKTWT VNQTLIAFIG

451  FALSALLFAI V*
```

Further work revealed a variant gonococcal DNA sequence <SEQ ID 591>:

```
  1  ATGGACGGCC GGACACAGAC GCTGTCCGCG CAAACCTTGT TGGGCATTTC

51  GGCGGCGGCA ATCATCCTCA TTCTGATTTT AATCGTCAAA TTCCGCATCC

101  GCGCGCTGCT GACACTGGTC ATCGCCAGCC TGCTGACGGC TTTGGCAACC

151  GGTTTGCCCA CAGGCAGCAT CGTCAACGAC GTACTGGTCA AAAACTTCGG

201  CGGCACGCTC GGCGGCGTGG CGCTTCTGGT CGGTCTGGGC GCAATGCTCG

251  GACGTTTGGT AGAAACATCC GGCGGCGCAC AGTCGCTGGC GGACGCGCTG

301  ATCCGGATGT TCGGCGAAAA ACGCGCACCG TTCGCTCCGG GCGTTGCCTC

351  GCTGATTTTC GGCTTCCCGA TTTTCTTCGA TGCCGGACTA ATCGTCATGC

401  TGCCCATCGT ATTCGCCACC GCACGGCGCA TGAAACAGGA CGTACTGCCC

451  TTCGCGCTTG CCTCCGTCGG CGCATTTTCC GTCATGCACG TCTTCCTGCC
```

-continued

```
 501 GCCCCATCCG GGCCCGATTG CCGCTTCCGA ATTTTACGGC GCGAACATCG
 551 GCCAGGTTTT GATTTTGGGT CTGCCGACCG CCTTCATCAC ATGGTATTTC
 601 AGCGGCTATA TGCTCGGCAA AGTGTTGGGG CGCGCCATCC ATGTTCCCGT
 651 TCCCGAACTG CTCAGCGGCG GCACGCAAGA CAGCGACCCG CCGAAAGAAC
 701 CTGCCAAAGC AGGAACGGTC GTCGCCGTCA TGCTGATTCC CATGCTGCTG
 751 ATTTTCCTGA ATACCGGCGT ATCAGCCCTC ATCAGCGAAA AACTCGTAAG
 801 TGCGGACGAA ACTTGGGTTC AGACGGCAAA AATGATCGGT TCGACACCTG
 851 TCGCCCTTCT GATTTCCGTA TTGGCCGCAC TGTTGGTCTT GGGACGCAAA
 901 CGCGGCGAAA GCGGCAGCAC GTTGGAAAAA ACCGTGGACG GCGCACTCGC
 951 CCCCGCCTGT TCCGTGATTC TGATTACCGG CGCGGGCGGT ATGTTCGGCG
1001 GCGTTTTGCG CGCTTCCGGC ATCGGCAAGG CACTCGCCGA CAGCATGGCG
1051 GATTTGGGCA TTCCCGTCCT TTTGGGCTGC TTCCTTGTCG CCTTGGCACT
1101 GCGTATCGCG CAAGGTTCGG CAACCGTCGC CCTGACCACA GCCGCCGCGC
1151 TGATGGCTCC TGCCGTTGCC GCCGCCGGCT TTACCGACTG GCAGCTCGCC
1201 TGTATCGTAT TGGCAACGGC GGCAGGTTCG GTCGGTTGCA GCCACTTCAA
1251 CGACTCCGGC TTCTGGCTGG TCGGCCGCCT CTTGGATATG GACGTACCGA
1301 CCACGCTGAA AACCTGGACG GTCAACCAAA CCCTCATCGC ATTCATCGGC
1351 TTTGCCTTGT CCGCACTGCT GTTTGCCATC GTCTGA
```

This corresponds to the amino acid sequence <SEQ ID 592; ORF140ng-1>:

```
  1 MDGRTQTLSA QTLLGISAAA IILILILIVK FRIRALLTLV IASLLTALAT
 51 GLPTGSIVND VLVKNFGGTL GGVALLVGLG AMLGRLVETS GGAQSLADAL
101 IRMFGEKRAP FAPGVASLIF GFPIFFDAGL IVMLPIVFAT ARRMKQDVLP
151 FALASVGAFS VMHVFLPPHP GPIAASEFYG ANIGQVLILG LPTAFITWYF
201 SGYMLGKVLG RAIHVPVPEL LSGGTQDSDP PKEPAKAGTV VAVMLIPMLL
251 IFLNTGVSAL ISEKLVSADE TWVQTAKMIG STPVALLISV LAALLVLGRK
301 RGESGSTLEK TVDGALAPAC SVILITGAGG MFGGVLRASG IGKALADSMA
351 DLGIPVLLGC FLVALALRIA QGSATVALTT AAALMAPAVA AAGFTDWQLA
401 CIVLATAAGS VGCSHFNDSG FWLVGRLLDM DVPTTLKTWT VNQTLIAFIG
451 FALSALLFAI V*
```

ORF140ng-1 and ORF140-1 show 96.3% identity over 461aa overlap:

```
orf140ng-1.pep  MDGRTQTLSAQTLLGISAAAIILILILIVKFRIRALLTLVIASLLTALATGLPTGSIVND
                |||.||||||||||||||||||||||||||:||||||:||||||||||||||||||||||
orf140-1        MDGWTQTLSAQTLLGISAAAIILILILIVKFRIHALLTLVIVSLLTALATGLPTGSIVND orf140ng-1.pep  VLVKNFGGTLGGVALLVGLGAMLGRLVETSGGAQSLADALIRMFGEKRAPFAPGVASLIF
                :|||||||||||||||||||||||||||||||||||||||||||||||||||.|||||||
orf140-1        ILVKNFGGTLGGVALLVGLGAMLGRLVETSGGAQSLADALIRMFGEKRAPFALGVASLIF orf140ng-1.pep  GFPIFFDAGLIVMLPIVFATARRMKQDVLPFALASVGAFSVMHVFLPPHPGPIAASEFYG
                |||||||||||||||||||||||||||||||||||:|||||||||||||||||||||||
orf140-1        GFPIFFDAGLIVMLPIVFATARRMKQDVLPFALASIGAFSVMHVFLPPHPGPIAASEFYG orf140ng-1.pep  ANIGQVLILGLPTAFITWYFSGYMLGKVLGRAIHVPVPELLSGGTQDSDPPKEPAKAGTV
                |||||||||||||||||||||||||||||||:||||||||||||||||:||||||||||
orf140-1        ANIGQVLILGLPTAFITWYFSGYMLGKVLGRTIHVPVPELLSGGTQDNDLPKEPAKAGTV
```

```
orf140ng-1.pep  VAVMLIPMLLIFLNTGVSALISEKLVSADETWVQTAKMIGSTPVALLISVLAALLVLGRK
                ||:||||||||||||||||||||||||||||||||:|||||:||||||||:||:|||||
orf140-1        VAIMLIPMLLIFLNTGVSALISEKLVSADETWVQTAKIIGSTPIALLISVLVALFVLGRK orf140ng-1.pep  RGESGSTLEKTVDGALAPACSVILITGAGGMFGGVLRASGIGKALADSMADLGIPVLLGC
                |||||:|||||||||||:||||||||||||||||||||||||||||||||||||||||||
orf140-1        RGESGSALEKTVDGALAPVCSVILITGAGGMFGGVLRASGIGKALADSMADLGIPVLLGC orf140ng-1.pep  FLVALALRIAQGSATVALTTAAALMAPAVAAAGFTDWQLACIVLATAAGSVGCSHFNDSG
                ||||||||||||||||||||||||||||||||||||||||||||||||||||||||||||
orf140-1        FLVALALRIAQGSATVALTTAAALMAPAVAAAGFTDWQLACIVLATAAGSVGCSHFNDSG orf140ng-1.pep  FWLVGRLLDMDVPTTLKTWTVNQTLIAFIGFALSALLFAIV
                ||||||||||||||||||||||||||||:|||||||||||
orf140-1        FWLVGRLLDMDVPTTLKTWTVNQTLIALIGFALSALLFAIV
```

Furthermore, ORF140ng-1 is homologous to an *E. coli* protein:

```
gi|882633 (U29579) ORF_o454 [Escherichia coli] >gi|1789097 (AE000358) o454;
This 454 aa ORF is 34% identical (9 gaps) to 444 residues of an approx. 456 aa
protein GNTP_BACLI SW: P46832 [Escherichia coli] Length = 454
Score = 210 bits (529), Expect = 1e-53
Identities = 130/384 (33%), Positives = 194/384 (49%), Gaps = 19/384 (4%)

Query:   88  ETSGGAQSLADALIRMFGEKRAPFAPGVASLIFGFPIFFDAGLIVMLPIVFATARRMKQD   147
             E SGGA+SLA+    R  G+KR  A  +A+    G P+FFD G I++ PI++  A+  K
Sbjct:   80  EHSGGAESLANYFSRKLGDKRTIAALTLAAFFLGIPVFFDVGFIILAPIIYGFAKVAKIS  139

Query:  148  VLPFALASVGAFSVMHVFLPPHPGPIAASEFYGANIGQVLILGLPTAFITWYFSGYMLGK  207
              L F L   G    +HV +PPHPGP+AA+     A+IG + I+G+  + I    GY  K
Sbjct:  140  PLKFGLPVAGIMLTVHVAVPPHPGPVAAAGLLHADIGWLTIIGIAIS-IPVGVVGYFAAK  198

Query:  208  VLGRAIHVPVPELL----------SGGTQDSDPPKEPAKAGTVVAVMLIPMLLIFLNTGV  257
              ++ +  +       E+L             G T+ SD    P  A  V ++++IP+ +I      T
Sbjct:  199  IINKRQYAMSVEVLEQMQLAPASEEGATKLSDKINPPGVA-LVTSLIVIPIAIIMAGT--  255

Query:  258  SALISEKLVSADETWVQTAKMIGSTPXXXXXXXXXXXXXXXXGRKRGESGSTLEKTVDGALA  317
               +S  L+     + T  ++IGS                    +RG S        + AL
Sbjct:  256  ---VSATLMPPSHPLLGTLQLIGSPMVALMIALVLAFWLLALRRGWSLQHTSDIMGSALP  312

Query:  318  PACSVILITGAGGMFGGVLRASGIGKALADSMADLGIPVLLGCFLVALALRIAQGSXXXX  377
              A  VIL+TGAGG+FG VL  SG+GKALA+  +  +P+L    F+++LALR +QGS
Sbjct:  313  TAAVVILVTGAGGVFGKVLVESGVGKALANMLQMIDLPLLPAAFIISLALRASQGS--AT  370

Query:  378  XXXXXXXXXXXXXXXGFTDWQLACIVLATAAGSVGCSHFNDSGFWLVGRLLDMDVPTTLK  437
                            G  Q  + LA   G +G SH NDSGFW+V + L +V     LK
Sbjct:  371  VAILTTGGLLSEAVMGLNPIQCVLVTLAACFGGLGASHINDSGFWIVTKYLGLSVADGLK  430

Query:  438  TWTVNQTLIAFIGFALSALLFAIV                                     461
             TWTV T++ F GF  ++   ++A++
Sbjct:  431  TWTVLTTILGFTGFLITWCVWAVI                                     454
```

Based on this analysis, including the identification of the presence of a putative leader sequence (double-underlined) and several putative transmembrane domains (single-underlined) in the gonococcal protein, it is predicted that the proteins from *N. meningitidis* and *N. gonorrhoeae*, and their epitopes, could be useful antigens for vaccines or diagnostics, or for raising antibodies.

Example 71

The following partial DNA sequence was identified in *N. meningitidis* <SEQ ID 593>:

```
  1 ..GATTTCGGCA TATCGCCCGT GTATCTTTGG GTTGCCGCCG CGTTCAAACA

51   TTTGCTGTCG CCGTGGGCTG CCGACTCATA CGATGTCGCA CGCTTTGCAG

101   GCGTATTTTT TGCCGTTATC GGACTGACTT CCTGCGGCTT TGCCGGTTTC

151   AACTTTTTGG GCAGACACCA CGGGCGCAC. GTCGTCCTGA TTCTCATCGG
```

```
                               -continued
201    CTGTATCGGG CTGATTCCAG TTGCCCATTT CCTCAACCCC GCTGCCGCCG

251    CCTTTGCCGC CGCCGGACTG GTGCTGCACG GTTATTCTTT GGCTCGCCGG

301    CGCGTGATTG CCGCCTCTTT TCTGCTCGGT ACGGGCTGGA CGCTGATGTC

351    GTTGGCAGCA GCTTATCCGG CAGCATTTGC CCTGATGCTG CCCTTGCCCG

401    TACTGATGTT TTTCCGTCCG ..
```

This corresponds to the amino acid sequence <SEQ ID 594; ORF141>:

```
  1    ..DFGISPVYLW VAAAFKHLLS PWAADSYDVA RFAGVFFAVI GLTSCGFAGF

51    NFLGRHHGRX VVLILIGCIG LIPVAHFLNP AAAAFAAAGL VLHGYSLARR

101    RVIAASFLLG TGWTLMSLAA AYPAAFALML PLPVLMFFRP ..
```

Further work revealed the complete nucleotide sequence <SEQ ID 595>:

```
   1   ATGCTGACCT ATACCCCGCC CGATGCCCGC CCGCCCGCCA AAACCCACGA

51   AAAGCCGTGG CTGCTGCTGT TGATGGCGTT TGCCTGGTTG TGGCCCGGCG

101   TGTTTTCCCA CGATTTGTGG AATCCTGACG AACCTGCCGT CTATACCGCC

151   GTCGAAGCAC TGGCAGGCAG CCCCACCCCC TTGGTTGCCC ATCTGTTCGG

201   TCAAACCGAT TTCGGCATAC CGCCCGTGTA TCTTTGGGTT GCCGCCGCGT

251   TCAAACATTT GCTGTCGCCG TGGGCTGCCG ACTCATACGA TGCCGCACGC

301   TTTGCAGGCG TATTTTTTGC CGTTATCGGA CTGACTTCCT GCGGCTTTGC

351   CGGTTTCAAC TTTTTGGGCA GACACCACGG GCGCAgCGTC GTCCTGATTC

401   TCATCGGCTG TATCGGGCTG ATTCCAGTTG CCCATTTCCT CAACCCCGCT

451   GCCGCCGCCT TTGCCGCCGC CGGACTGGTG CTGCACGGTT ATTCTTTGGC

501   TCGCCGGCGC GTGATTGCCG CCTCTTTTCT GCTCGGTACG GGCTGGACGC

551   TGATGTCGTT GGCAGCAGCT TATCCGGCAG CATTTGCCCT GATGCTGCCC

601   TTGCCCGTAC TGATGTTTTT CCGTCCGTGG CAAAGCAGGC GTTTGATGTT

651   GACGGCAGTC GCCTCACTTG CCTTTGCCCT GCCGCTTATG ACCGTTTACC

701   CGCTGCTCTT GGCAAAAACG CAGCCCGCGC TGTTCGCGCA ATGGCTCGAC

751   TATCACGTTT TCGGTACGTT CGGCGGCGTG CGGCACGTTC AGACGGCATT

801   CAGTTTGTTT TACTATCTGA AAAACCTGCT TTGGTTTGCA TTGCCCGCGC

851   TGCCGCTGGC GGTTTGGACG GTTTGCCGCA CGCGCCTGTT TTCGACCGAC

901   TGGGGGATTT TGGGCGTCGT CTGGATGCTT GCCGTTTTGG TGCTGCTTGC

951   CGTCAATCCG CAGCGTTTTC AGGATAACCT CGTCTGGCTG CTTCCGCCGC

1001   TTGCCCTGTT CGGCGCGGCG CAACTGGACA GCCTGAGGCG CGGCGCGGCG

1051   GCGTTTGTCA ACTGGTTCGG CATTATGGCG TTCGGACTGT TGCCGTGTT

1101   CCTGTGGACG GGCTTTTTCG CCATGAATTA CGGCTGGCCC GCCAAGCTTG

1151   CCGAACGCGC CGCCTATTTC AGCCCGTATT ATGTTCCTGA TATCGATCCC

1201   ATTCCGATGG CGGTTGCCGT ACTGTTCACA CCCTTGTGGC TGTGGGCGAT

1251   TACCCGGAAA AACATACGCG GCAGGCAGGC GGTTACCAAC TGGGCGGCAG

1301   GCGTTACCCT GACCTGGGCT TTGCTGATGA CGCTGTTCCT GCCGTGGCTG
```

-continued

```
1351 GACGCGGCGA AAAGCCACGC GCCGGTCGTC CGGAGTATGG AGGCATCGCT

1401 TTCCCCGGAA TTGAAACGGG AGCTTTCAGA CGGCATCGAG TGTATCGGCA

1451 TAGGCGGCGG CGACCTGCAC ACGCGGATTG TTTGGACGCA GTACGGCACA

1501 TTGCCGCACC GCGTCGGCGA TGTACAATGC CGCTACCGCA TCGTCCTCCT

1551 GCCCCAAAAT GCGGATGCGC CGCAAGGCTG GCAGACGGTT TGGCAGGGTG

1601 CGCGTCCGCG CAACAAAGAC AGTAAGTTCG CACTGATACG GAAAATCGGG

1651 GAAAATATAT AA
```

This corresponds to the amino acid sequence <SEQ ID 596; ORF141-1>:

```
  1 MLTYTPPDAR PPAKTHEKPW LLLLMAFAWL WPGVFSHDLW NPDEPAVYTA

51 VEALAGSPTP LVAHLFGQTD FGIPPVYLWV AAAFKHLLSP WAADSYDAAR

101 FAGVFFAVIG LTSCGFAGFN FLGRHHGRSV VLILIGCIGL IPVAHFLNPA

151 AAAFAAAGLV LHGYSLARRR VIAASFLLGT GWTLMSLAAA YPAAFALMLP

201 LPVLMFFRPW QSRRLMLTAV ASLAFALPLM TVYPLLLAKT QPALFAQWLD

251 YHVFGTFGGV RHVQTAFSLF YYLKNLLWFA LPALPLAVWT VCRTRLFSTD

301 WGILGVVWML AVLVLLAVNP QRFQDNLVWL LPPLALFGAA QLDSLRRGAA

351 AFVNWFGIMA FGLFAVFLWT GFFAMNYGWP AKLAERAAYF SPYYVPDIDP

401 IPMAVAVLFT PLWLWAITRK NIRGRQAVTN WAAGVTLTWA LLMTLFLPWL

451 DAAKSRAPVV RSMEASLSPE LKRELSDGIE CIGIGGGDLH TRIVWTQYGT

501 LPHRVGDVQC RYRIVLLPQN ADAPQGWQTV WQGARPRNKD SKFALIRKIG

551 ENI*
```

Computer analysis of this amino acid sequence gave the following results:

Homology with a Predicted ORF from *N. meningitidis* (Strain A)

ORF141 shows 95.0% identity over a 140aa overlap with an ORF (ORF141a) from strain A of *N. meningitidis*.

```
                               10        20        30
orf141.pep                DFGISPVYLWVAAAFKHLLSPWAADSYDVA
                          ||||  |||||||||||||||||||  ||:|
orf141a     WNPDEPAVYTAVEALAGSPTPLVAHLFGQIDFGIPPVYLWVAAAFKHLLSPWAADPYDAA
               40        50        60        70        80        90

40        50        60        70        80        90
orf141.pep   RFAGVFFAVIGLTSCGFAGFNFLGRHHGRXVVLILIGCIGLIPVAHFLNPAAAAFAAAGL
             ||||||||:||||||||||||||||||||| ||||||||||||::|||||||||||||||
orf141a      RFAGVFFAVVGLTSCGFAGFNFLGRHHGRSVVLILIGCIGLIPTVHFLNPAAAAFAAAGL
                  100       110       120       130       140       150

100       110       120       130       140
orf141.pep   VLHGYSLARRRVIAASFLLGTGWTLMSLAAAYPAAFALMLPLPVLMFFRP
             ||||||||||||||||||||||||||||||||||||||||||||||||||
orf141a      VLHGYSLARRRVIAASFLLGTGWTLMSLAAAYPAAFALMLPLPVLMFFRPWQSRRLMLTA
                  160       170       180       190       200       210 orf141a      VASLAFALPLMTVYPLLLAKTQPALFAQWLDDHVFGTFGGVRHIQTAFSLFYYLKNLLWF
                  220       230       240       250       260       270
```

The complete length ORF141a nucleotide sequence <SEQ ID 597> is:

```
   1 ATGCTGACCT ATACCCCGCC CGATGCCCGC CCGCCCGCCA AAACCCACGA
  51 AAAGCCGTGG CTGTTGCTGT TGATGGCGTT TGCCTGGTTG TGGCCCGGCG
 101 TGTTTTCCCA CGATTTGTGG AATCCTGACG AACCTGCCGT CTATACCGCC
 151 GTCGAAGCAC TGGCAGGCAG CCCCACCCCT TTGGTTGCCC ATCTGTTCGG
 201 TCAAATCGAT TTCGGCATAC CGCCCGTGTA TCTTTGGGTT GCCGCCGCGT
 251 TCAAACATTT GCTGTCGCCG TGGGCTGCCG ACCCGTATGA TGCCGCACGC
 301 TTTGCCGGCG TGTTTTTCGC CGTTGTCGGA CTGACTTCCT GCGGCTTTGC
 351 CGGTTTCAAC TTTTTGGGCA GACACCACGG GCGCAGCGTC GTCCTGATTC
 401 TCATCGGCTG TATCGGGCTG ATTCCGACCG TACACTTTCT CAACCCCGCT
 451 GCCGCCGCCT TTGCCGCCGC CGGACTGGTG CTGCACGGTT ATTCTTTGGC
 501 TCGCCGGCGC GTGATTGCCG CCTCTTTTCT GCTCGGTACG GGTTGGACGC
 551 TGATGTCGTT GGCAGCAGCT TATCCGGCGG CATTTGCCCT GATGCTGCCC
 601 CTGCCCGTGC TGATGTTTTT CCGTCCGTGG CAAAGCAGGC GTTTGATGTT
 651 GACGGCAGTC GCCTCGCTTG CCTTTGCCCT GCCGCTTATG ACCGTTTACC
 701 CGCTGCTCTT GGCAAAAACG CAGCCCGCGC TGTTCGCGCA ATGGCTCGAC
 751 GATCACGTTT TCGGTACGTT CGGCGGCGTG CGGCACATTC AGACGGCATT
 801 CAGTTTGTTT TACTATCTGA AAAACCTGCT TTGGTTTGCA TTGCCTGCGC
 851 TGCCGCTGGC GGTTTGGACG GTTTGCCGCA CGCGCCTGTT TTCGACCGAC
 901 TGGGGGATTT TGGGCGTCGT CTGGATGCTT GCCGTTTTGG TGCTGCTTGC
 951 CGTCAATCCG CAGCGTTTTC AGGATAACCT CGTCTGGCTG CTTCCGCCGC
1001 TTGCCCTGTT CGGCGCGGCG CAACTGGACA GCCTGAGACG CGGCGCGGCG
1051 GCGTTTGTCA ACTGGTTCGG CATTATGGCG TTCGGACTGT TTGCCGTGTT
1101 CCTGTGGACG GGCTTTTTCG CCATGAATTA CGGCTGGCCC GCCAAGCTTG
1151 CCGAACGCGC CGCCTATTTC AGCCCGTATT ATGTTCCTGA TATCGATCCC
1201 ATTCCGATGG CGGTTGCCGT ACTGTTCACA CCCTTGTGGC TGTGGGCGAT
1251 TACCCGCAAA AACATACGCG GCAGGCAGGC GGTTACCAAC TGGGCGGCAG
1301 GCGTTACCCT GACCTGGGCT TGCTGATGA CGCTGTTCCT GCCGTGGCTG
1351 GACGCGGCGA AAAGCCACGC GCCCGTCGTC CGGAGTATGG AGGCATCGCT
1401 TTCCCCGGAA TTAAAACGGG AGCTTTCAGA CGGCATCGAG TGTATCGACA
1451 TAGGCGGCGG CGACCTACAC ACGCGGATTG TTTGGACGCA GTACGGCACA
1501 TTGCCGCACC GCGTCGGCGA TGTACAATGC CGCTACCGCA TCGTCCGCTT
1551 GCCCCAAAAC GCGGATGCGC CGCAAGGCTG GCAGACGGTC TGGCAGGGTG
1601 CGCGCCCGCG CAACAAAGAC AGTAAGTTCG CACTGATACG GAAAACCGGG
1651 GAAATATAT TAAAAACAAC AGATTGA
```

This encodes a protein having amino acid sequence <SEQ ID 598>:

```
  1 MLTYTPPDAR PPAKTHEKPW LLLLMAFAWL WPGVFSHDLW NPDEPAVYTA
 51 VEALAGSPTP LVAHLFGQID FGIPPVYLWV AAAFKHLLSP WAADPYDAAR
```

-continued

```
101 FAGVFFAWG LTSCGFAGFN FLGRHHGRSV VLILIGCIGL IPTVHFLNPA

151 AAAFAAAGLV LHGYSLARRR VIAASFLLGT GWTLMSLAAA YPAAFALMLP

201 LPVLMFFRPW QSRRLMLTAV ASLAFALPLM TVYPLLLAKT QPALFAQWLD

251 DHVFGTFGGV RHIQTAFSLF YYLKNLLWFA LPALPLAVWT VCRTRLFSTD

301 WGILGVVWML AVLVLLAVNP QRFQDNLVWL LPPLALFGAA QLDSLRRGAA

351 AFVNWFGIMA FGLFAVFLWT GFFAMNYGWP AKLAERAAYF SPYYVPDIDP

401 IPMAVAVLFT PLWLWAITRK NIRGRQAVTN WAAGVTLTWA LLMTLFLPWL

451 DAAKSHAPVV RSMEASLSPE LKRELSDGIE CIDIGGGDLH TRIVWTQYGT

501 LPHRVGDVQC RYRIVRLPQN ADAPQGWQTV WQGARPRNKD SKFALIRKTG

551 ENILKTTD*
```

ORF141a and ORF141-1 show 98.2% identity in 553 aa overlap:

```
orf141a.pep  MLTYTPPDARPPAKTHEKPWLLLLMAFAWLWPGVFSHDLWNPDEPAVYTAVEALAGSPTP
             ||||||||||||||||||||||||||||||||||||||||||||||||||||||||||||
orf141-1     MLTYTPPDARPPAKTHEKPWLLLLMAFAWLWPGVFSHDLWNPDEPAVYTAVEALAGSPTP orf141a.pep  LVAHLFGQIDFGIPPVYLWVAAAFKHLLSPWAADPYDAARFAGVFFAVVGLTSCGFAGFN
             |||||||| |||||||||||||||||||||||||| ||||||||||||| :|||||||||
orf141-1     LVAHLFGQTDFGIPPVYLWVAAAFKHLLSPWAADSYDAARFAGVFFAVIGLTSCGFAGFN orf141a.pep  FLGRHHGRSVVLILIGCIGLIPTVHFLNPAAAAFAAAGLVLHGYSLARRRVIAASFLLGT
             |||||||||||||||||||||::|||||||||||||||||||||||||||||||||||||
orf141-1     FLGRHHGRSVVLILIGCIGLIPVAHFLNPAAAAFAAAGLVLHGYSLARRRVIAASFLLGT orf141a.pep  GWTLMSLAAAYPAAFALMLPLPVLMFFRPWQSRRLMLTAVASLAFALPLMTVYPLLLAKT
             ||||||||||||||||||||||||||||||||||||||||||||||||||||||||||||
orf141-1     GWTLMSLAAAYPAAFALMLPLPVLMFFRPWQSRRLMLTAVASLAFALPLMTVYPLLLAKT orf141a.pep  QPALFAQWLDDHVFGTFGGVRHIQTAFSLFYYLKNLLWFALPALPLAVWTVCRTRLFSTD
             |||||||||| :||||||||||:|||||||||||||||||||||||||||||||||||||
orf141-1     QPALFAQWLDYHVFGTFGGVRHVQTAFSLFYYLKNLLWFALPALPLAVWTVCRTRLFSTD orf141a.pep  WGILGVVWMLAVLVLLAVNPQRFQDNLVWLLPPLALFGAAQLDSLRRGAAAFVNWFGIMA
             ||||||||||||||||||||||||||||||||||||||||||||||||||||||||||||
orf141-1     WGILGVVWMLAVLVLLAVNPQRFQDNLVWLLPPLALFGAAQLDSLRRGAAAFVNWFGIMA orf141a.pep  FGLFAVFLWTGFFAMNYGWPAKLAERAAYFSPYYVPDIDPIPMAVAVLFTPLWLWAITRK
             ||||||||||||||||||||||||||||||||||||||||||||||||||||||||||||
orf141-1     FGLFAVFLWTGFFAMNYGWPAKLAERAAYFSPYYVPDIDPIPMAVAVLFTPLWLWAITRK orf141a.pep  NIRGRQAVTNWAAGVTLTWALLMTLFLPWLDAAKSHAPVVRSMEASLSPELKRELSDGIE
             ||||||||||||||||||||||||||||||||||||||||||||||||||||||||||||
orf141-1     NIRGRQAVTNWAAGVTLTWALLMTLFLPWLDAAKSHAPVVRSMEASLSPELKRELSDGIE orf141a.pep  CIDIGGGDLHTRIVWTQYGTLPHRVGDVQCRYRIVRLPQNADAPQGWQTVWQGARPRNKD
             || |||||||||||||||||||||||||||||||| ||||||||||||||||||||||||
orf141-1     CIGIGGGDLHTRIVWTQYGTLPHRVGDVQCRYRIVLLPQNADAPQGWQTVWQGARPRNKD orf141a.pep  SKFALIRKTGENI
             |||||||| ||||
orf141-1     SKFALIRKIGENI
```

Homology with a Predicted ORF from *N. gonorrhoeae*

ORF141 shows 95% identity over a 140aa overlap with a predicted ORF (ORF141ng) from *N. gonorrhoeae*:

```
orf141.pep                DFGISPVYLWVAAAFKHLLSPWAADSYDVA   30
                          |||| ||||||||||||||||||||||  :|
orf141ng    WNPAEPAVYTAVEALAGSPTPLVAHLFGQTDFGIPPVYLWVAAAFKHLLSPWAAHPYDAA 126 orf141.pep  RFAGVFFAVIGLTSCGFAGFNFLGRHHGRXVVLILIGCIGLIPVAHFFNPAAAAFAAAGL   90
            |||||||||||||||||||||||||||||| ||||||||||||||:||||||||||||||
orf141ng    RFAGVFFAVIGLTSCGFAGFNFLGRHHGRSVVLIHIGCIGLIPVAHFFNPAAAAFAAAGL 186 orf141.pep  VLHGYSLARRRVIAASFLLGTWTLMSLAAAYPAAFALMLPLPVLMFFRP            140
            ||||||||||||||||||||||||||||||||||||||||||||||||
orf141ng    VLHGYSLARRRVIAASFLLGTWTLMSLAAAYPAAFALMLPLPVLMFFRPWQSRRLMLTA  246
```

An ORF141ng nucleotide sequence <SEQ ID 599> was predicted to encode a protein having amino acid sequence <SEQ ID 600>:

```
  1 MPSEAVSARP LCEYLLHLAI RPFLLTLMLT YTPPDARPPA KTHEKPWLLL
 51 LMAFAWLWFG VFSHDLWNPA EPAVYTAVEA LAGSPTPLVA HLFGQTDFGI
101 PPVYLWVAAA FKHLLSPWAA HPYDAARFAG VFFAVIGLTS CGFAGFNFLG
151 RHHGRSVVLI HIGCIGLIPV AHFFNPAAAA FAAAGLVLHG YSLARRRVIA
201 ASFLLGTGWT LMSLAAAYPA AFALMLPLPV LMFFRPWQSR RLMLTAVASL
251 AFALPLMTVY PLLLAKTQPA LFAQWLNYHV FGTFGGVRHI QRAFSLFHYL
301 KNLLWFAPPG LPLAVWTVCR TRLFSTDWGI LGIVWMLAVL VLLAFNPQRF
351 QDNLVWLLPP LALFGAAQLD SLRRGAAAFV NWFGIMAFGL FAVFLWTGFF
401 AMNYGWPAKL AERAAYFSPY YVPDIDPIPM AVAVLFTPLW LWAITRKNIR
451 GRQAVTNWAA GVTLTWALLM TLFLPWLDAA KSHAPVVRSM EASFSPELKR
501 ELSDGIECIG IGGGDLHTRI VWTQYGTLPH RVGDVRCRYR IVRLPQNADA
551 PQGWQTVWQG ARPRNKDSKF ALIRKIGENI LKTTD*
```

Further work revealed the following gonococcal DNA sequence <SEQ ID 601>:

```
   1 ATGCTGACCT ATACCCCGCC CGATGCCCGC CCGCCCGCCA AAACCCACGA
  51 AAAACCGTGG CTGCTGCTGT TGATGGCGTT TGCCTGGCTG TGGCCCGGCG
 101 TGTTTTCCCA CGATTTGTGG AATCCTGCCG AACCTGCCGT CTATACCGCC
 151 GTCGAAGCAC TGGCAGGCAG CCCCACCCCC TTGGTTGCCC ATCTGTTCGG
 201 TCAAACCGAT TTCGGCATAC CGCCCGTGTA TCTTTGGGTT GCCGCCGCAT
 251 TCAAACATTT GCTGTCGCCG TGGGCAGCCG ACCCGTATGA TGCCGCACGC
 301 TTTGCAGGCG TATTTTTTGC CGTTATCGGA CTGACTTCTT GCGGCTTTGC
 351 CGGTTTCAAC TTTTTGGGCA GACACCACGG GCGCAGCGTT GTTTTAATCC
 401 ATATCGGCTG TATCGGGCTG ATTCCGGTTG CCCATTTCCT CAATCCcgcc
 451 gccgccgcct tGCCGCCGCC CGGACTGGTG CTGCacggct actcgctgGC
 501 ACGCCGGCGC GTGATtgccg cctctTtccT GCTCGGTACG GGTTGGACGT
 551 TGATGTCGCT GGCGGCAGCT TATCCGGCGG CGTTTGCGCT GATGCTGCCC
 601 CTGCCCGTGC TGATGTTTTT CCGTCCGTGG CAAAGCAGGC GTTTGATGTT
 651 GACGGCAGTC GCCTCGCTTG CCTTTGCCCT GCCGCTTATG ACCGTTTACC
 701 CGCTGCTCtt gGCAAAAACG CAGCCCGCGC TGTTTGCGCA ATGGCTCAAC
 751 TATCACGTTT TCGGTACGTt cggcgGCGTG CGGCAcaTTC AGAggGCatT
 801 CagtttgtttT cactatctgA AAaatctgct ttggttcgca ccgcccgggC
 851 TGCCGCTGGC GGTTTGGACG GTTTGCCGCA CACGCCTGTT TTCGACCGAC
 901 TGGGGGATTT TGGGCATTGT CTGGATGCTT GCCGTTTTGG TGCTGCTCGC
 951 CTTTAATCCG CAGCGTTTTC AAGACAACCT CGTCTGGCTG CTGCCGCCGC
1001 TTGCCCTGTT CGGCGCGGCG CAACTGGACA GCCTGAGGCG CGGCGCGGCG
1051 GCTTTTGTCA ACTGGTTCGG CATTATGGCG TTCGGGCTGT TTGCCGTGTT
1101 CCTGTGGACG GGCTTTTTCG CCATGAATTA CGGCTGGCCC GCCAAGCTTG
1151 CCGAACGCGC CGCCTACTTC AGCCCGTATT ACGTTCCCGA CATCGATCCC
```

-continued

```
1201  ATTCCGATGG CGGTTGCCGT ACTGTTCACA CCCTTGTGGC TGTGGGCGAT

1251  TACCCGGAAA ACATACGCG GCAGGCAGGC GGTTACCAAC TGGGCGGCAG

1301  GCGTTACCCT GACCTGGGCT TTGCTGATGA CGCTGTTCCT GCCGTGGCTG

1351  GACGCGGCGA AAGCCACGC GCCCGTCGTC CGGAGTATGG AGGCATCGTT

1401  TTCCCCGGAA TTAAAACGGG AGCTTTCAGA CGGCATCGAG TGTATCGGCA

1451  TAGGCGGCGG CGACCTGCAC ACGCGGATTG TTTGGACGCA GTACGGCACA

1501  TTGCCGCACC GCGTCGGCGA TGTCCGTTGC CGCTACCGTA TCGTCCGCCT

1551  GCCCCAAAAC GCGGATGCGC CGCAAGGCTG GCAGACGGTC TGGCAGGGTG

1601  CGCGCCCGCG CAACAAAGAC AGTAAGTTTG CACTGATACG GAAAATCGGG

1651  GAAATATAT TAAAAACAAC AGATTGA
```

This corresponds to the amino acid sequence <SEQ ID 602; ORF141ng-1>:

```
  1  MLTYTPPDAR PPAKTHEKPW LLLLMAFAWL WPGVFSHDLW NPAEPAVYTA

51  VEALAGSPTP LVAHLFGQTD FGIPPVYLWV AAAFKHLLSP WAADPYDAAR

101  FAGVFFAVIG LTSCGFAGFN FLGRHHGRSV VLIHIGCIGL IPVAHFLNPA

151  AAAFAAAGLV LHGYSLARRR VIAASFLLGT GWTLMSLAAA YPAAFALMLP

201  LPVLMFFRPW QSRRLMLTAV ASLAFALPLM TVYPLLLAKT QPALFAQWLN

251  YHVFGTFGGV RHIQRAFSLF HYLKNLLWFA PPGLPLAVWT VCRTRLFSTD

301  WGILGIVWML AVLVLLAFNP QRFQDNLVWL LPPLALFGAA QLDSLRRGAA

351  AFVNWFGIMA FGLFAVFLWT GFFAMNYGWP AKLAERAAYF SPYYVPDIDP

401  IPMAVAVLFT PLWLWAITRK NIRGRQAVTN WAAGVTLTWA LLMTLFLPWL

451  DAAKSHAPVV RSMEASFSPE LKRELSDGIE CIGIGGGDLH TRIVWTQYGT

501  LPHRVGDVRC RYRIVRLPQN ADAPQGWQTV WQGARPRNKD SKFALIRKIG

551  ENILKTTD*
```

ORF141ng-1 and ORF141-1 show 97.5% identity in 553 aa overlap:

```
orf141ng-1.pep  MLTYTPPDARPPAKTHEKPWLLLLMAFAWLWPGVFSHDLWNPAEPAVYTAVEALAGSPTP
                ||||||||||||||||||||||||||||||||||||||||||||||:|||||||||||||
orf141-1        MLTYTPPDARPPAKTHEKPWLLLLMAFAWLWPGVFSHDLWNPDEPAVYTAVEALAGSPTP orf141ng-1.pep  LVAHLFGQTDFGIPPVYLWVAAAFKHLLSPWAADPYDAARFAGVFFAVIGLTSCGFAGFN
                ||||||||||||||||||||||||||||||||||:|||||||||||||||||||||||||
orf141-1        LVAHLFGQTDFGIPPVYLWVAAAFKHLLSPWAADSYDAARFAGVFFAVIGLTSCGFAGFN orf141ng-1.pep  FLGRHHGRSVVLIHIGCIGLIPVAHFLNPAAAAFAAAGLVLHGYSLARRRVIAASFLLGT
                |||||||||||||:||||||||||||||||||||||||||||||||||||||||||||||
orf141-1        FLGRHHGRSVVLILIGCIGLIPVAHFLNPAAAAFAAAGLVLHGYSLARRRVIAASFLLGT orf141ng-1.pep  GWTLMSLAAAYPAAFALMLPLPVLMFFRPWQSRRLMLTAVASLAFALPLMTVYPLLLAKT
                ||||||||||||||||||||||||||||||||||||||||||||||||||||||||||||
orf141-1        GWTLMSLAAAYPAAFALMLPLPVLMFFRPWQSRRLMLTAVASLAFALPLMTVYPLLLAKT orf141ng-1.pep  QPALFAQWLNYHVFGTFGGVRHIQRAFSLFHYLKNLLWFAPPGLPLAVWTVCRTRLFSTD
                ||||||||||:|||||||||||:||||||:||||||||||:|:||||||||||||||||
orf141-1        QPALFAQWLDYHVFGTFGGVRHVQTAFSLFYYLKNLLWFALPALPLAVWTVCRTRLFSTD orf141ng-1.pep  WGILGIVWMLAVLVLLAFNPQRFQDNLVWLLPPLALFGAAQLDSLRRGAAAFVNWFGIMA
                |||||:||||||||||||:|||||||||||||||||||||||||||||||||||||||||
orf141-1        WGILGVVWMLAVLVLLAVNPQRFQDNLVWLLPPLALFGAAQLDSLRRGAAAFVNWFGIMA orf141ng-1.pep  FGLFAVFLWTGFFAMNYGWPAKLAERAAYFSPYYVPDIDPIPMAVAVLFTPLWLWAITRK
                ||||||||||||||||||||||||||||||||||||||||||||||||||||||||||||
orf141-1        FGLFAVFLWTGFFAMNYGWPAKLAERAAYFSPYYVPDIDPIPMAVAVLFTPLWLWAITRK orf141ng-1.pep  NIRGRQAVTNWAAGVTLTWALLMTLFLPWLDAAKSHAPVVRSMEASFSPELKRELSDGIE
                ||||||||||||||||||||||||||||||||||||||||||||||:|||||||||||||
orf141-1        NIRGRQAVTNWAAGVTLTWALLMTLFLPWLDAAKSHAPVVRSMEASLSPELKRELSDGIE
```

```
orf141ng-1.pep  CIGIGGGDLHTRIVWTQYGTLPHRVGDVRCRYRIVRLPQNADAPQGWQTVWQGARPRNKD
                ||||||||||||||||||||||||||||| |||||| |||||||||||||||||||||||
orf141-1        CIGIGGGDLHTRIVWTQYGTLPHRVGDVQCRYRIVLLPQNADAPQGWQTVWQGARPRNKD orf141ng-1.pep  SKFALIRKIGENILKTTDX
                |||||||||||||
orf141-1        SKFALIRKIGENIX
```

Based on the presence of several putative transmembrane domains in the gonococcal protein, it is predicted that the proteins from *N. meningitidis* and *N. gonorrhoeae*, and their epitopes, could be useful antigens for vaccines or diagnostics, or for raising antibodies.

Example 72

The following partial DNA sequence was identified in *N. meningitidis* <SEQ ID 603>:

```
  1 ..CAATCCGCCA AATGGTTATC GGGCCAAACT CTAGTCGGCA CAGCAATTGG
 51   GATACGCGGG CAGATAAAGC TTGGCGGCAA CCTGCATTAC GATATATTTA
101   CCGGCCGCGC ATTGAAAAAG CCCGAATTTT TCCAATCAAG GAAATGGGCA
151   AGCGGTTTTC AGGTAGGCTA TACGTTTTAA
```

This corresponds to the amino acid sequence <SEQ ID 604; ORF142>:

```
 1 ..QSAKWLSGQT LVGTAIGIRG QIKLGGNLHY DIFTGRALKK PEFFQSRKWA
51   SGFQVGYTF*
```

Further work revealed the complete nucleotide sequence <SEQ ID 605>:

```
  1 ATGGATAATT CGGGTAGTGA GGCGACAGGA AAATACCAAG GAAATATCAC
 51 TTTCTCTGCC GACAATCCTT TGGGACTGAG TGATATGTTC TATGTAAATT
101 ATGGACGTTC GATTGGCGGT ACGCCCGATG AGGAAAGTTT TGACGGCCAT
151 CGCAAAGAAG GCGGATCAAA CAATTACGCC GTACATTATT CAGCCCCTTT
201 CGGTAAATGG ACATGGGCAT TCAATCACAA TGGCTACCGT TACCATCAGG
251 CAGTTTCCGG ATTATCGGAA GTCTATGACT ATAATGGAAA AAGTTACAAT
301 ACTGATTTCG GCTTCAACCG CCTGTTGTAT CGTGATGCCA AACGCAAAAC
351 CTATCTCGGT GTAAAACTGT GGATGAGGGA AACAAAAAGT TACATTGATG
401 ATGCCGAACT GACTGTACAA CGGCGTAAAA CTGCGGGTTG GTTGGCAGAA
451 CTTTCCCACA AGAATATAT CGGTCGCAGT ACGGCAGATT TTAAGTTGAA
501 ATATAAACGC GGCACCGGCA TGAAAGATGC TCTGCGCGCG CCTGAAGAAG
551 CCTTTGGCGA AGGCACGTCA CGTATGAAAA TTTGGACGGC ATCGGCTGAT
601 GTAAATACTC CTTTTCAAAT CGGTAAACAG CTATTTGCCT ATGACACATC
651 CGTTCATGCA CAATGGAACA AAACCCCGCT AACATCGCAA GACAAACTGG
701 CTATCGGCGG ACACCACACC GTACGTGGCT TCGACGGTGA AATGAGTTTG
751 TCTGCCGAGC GGGGATGGTA TTGGCGCAAC GATTTGAGCT GGCAATTTAA
801 ACCAGGCCAT CAGCTTTATC TTGGGGCTGA TGTAGGACAT GTTTCAGGAC
```

```
 851 AATCCGCCAA ATGGTTATCG GGCCAAACTC TAGTCGGCAC AGCAATTGGG

901 ATACGCGGGC AGATAAAGCT TGGCGGCAAC CTGCATTACG ATATATTTAC

951 CGGCCGCGCA TTGAAAAAGC CCGAATTTTT CCAATCAAGG AAATGGGCAA

1001 GCGGTTTTCA GGTAGGCTAT ACGTTTTAA
```

This corresponds to the amino acid sequence <SEQ ID 606; ORF142-1>:

```
  1 MDNSGSEATG KYQGNITFSA DNPLGLSDMF YVNYGRSIGG TPDEESFDGH

51 RKEGGSNNYA VHYSAPFGKW TWAFNHNGYR YHQAVSGLSE VYDYNGKSYN

101 TDFGFNRLLY RDAKRKTYLG VKLWMRETKS YIDDAELTVQ RRKTAGWLAE

151 LSHKEYIGRS TADFKLKYKR GTGMKDALRA PEEAFGEGTS RMKIWTASAD

201 VNTPFQIGKQ LFAYDTSVHA QWNKTPLTSQ DKLAIGGHHT VRGFDGEMSL

251 SAERGWYWRN DLSWQFKPGH QLYLGADVGH VSGQSAKWLS GQTLVGTAIG

301 IRGQIKLGGN LHYDIFTGRA LKKPEFFQSR KWASGFQVGY TF*
```

Computer analysis of this amino acid sequence gave the following results:

Homology with a Predicted ORF from *N. gonorrhoeae*

ORF142 shows 88.1% identity over a 59aa overlap with a predicted ORF (ORF142ng) from *N. gonorrhoeae*:

```
orf142.pep                                QSAKWLSGQTLVGTAIGIRGQIKLGGNLHY  30
                                          |||||||||||:|||||||||||||||||
orf142ng   RGWYWRNDLSWQFKPGHQLYLGADVGHVSGQSAKWLSGQTLAGTAIGIRGQIKLGGNLHY 313
orf142.pep DIFTGRALKKPEFFQSRKWASGFQVGYTF                                 59
           ||||||||||||:||::||::||||||:|
orf142ng   DIFTGRALKKPEYFQTKKWVTGFQVGYSF                                342
```

The complete length ORF142ng nucleotide sequence <SEQ ID 607> is:

```
  1 ATGGATAATT CGGGTAGTGA GGCGACAGGA AAATACCAAG GAAATATCAC

51 TTTCTCTGCC GACAATCCTT TGGACTGAG TGATATGTTC TATGTAAATT

101 ATGGACGTTC AATTGGCGGT ACGCCCGATG AGGAAAATTT TGACGGCCAT

151 CGCAAAGAAG GCGGATCAAA CAATTACGCC GTACATTATT CAGCCCCTTT

201 CGGTAAATGG ACATGGGCAT TCAATCACAA TGGCTACCGT TACCATCAGG

251 CGGTTTCCGG ATTATCGGAA GTCTATGACT ATAATGGAAA AAGTTACAAC

301 ACTGATTTCG GCTTCAACCG CCTGTTGTAT CGTGATGCCA AACGCAAAAC

351 CTATCTCAGT GTAAAACTGT GGACGAGGGA ACAAAAAGT TACATTGATG

401 ATGCCGAACT GACTGTACAA CGGCGTAAAA CCACAGGTTG GTTGGCAGAA

451 CTTTCCCACA AAGGATATAT CGGTCGCAGT ACGGCAGATT TTAAGTTGAA

501 ATATAAACAC GGCACCGGCA TGAAAGATGC TCTGCGCGCG CCTGAAGAAG

551 CCTTTGGCGA AGGCACGTCA CGTATGAAAA TTTGGACGGC ATCGGCTGAT

601 GTAAATACTC CTTTTCAAAT CGGTAAACAG CTATTTGCCT ATGACACATC

651 CGTTCATGCA CAATGGAACA AAACCCCGCT AACATCGCAA GACAAACTGG

701 CTATCGGCGG ACACCACACC GTACGTGGCT TCGACGGTGA AATGAGTTTG
```

-continued

```
 751 CCTGCCGAGC GGGGATGGTA TTGGCGCAAC GATTTGAGCT GGCAATTTAA

801 ACCAGGCCAT CAGCTTTATC TTGGGGCTGA TGTAGGACAT GTTTCAGGAC

851 AATCCGCCAA ATGGTTATCG GGCCAAACTC TAGCCGGCAC AGCAATTGGG

901 ATACGCGGGC AGATAAAGCT TGGCGGCAAC CTGCATTACG ATATATTTAC

951 CGGCCGTGCA TTGAAAAAGC CCGAATATTT TCAGACGAAG AAATGGGTAA

1001 CGGGGTTTCA GGTGGGTTAT TCGTTTTGA
```

This encodes a protein having amino acid sequence <SEQ ID 608>:

```
  1 MDNSGSEATG KYQGNITFSA DNPFGLSDMF YVNYGRSIGG TPDEENFDGH

51 RKEGGSNNYA VHYSAPFGKW TWAFNHNGYR YHQAVSGLSE VYDYNGKSYN

101 TDFGFNRLLY RDAKRKTYLS VKLWTRETKS YIDDAELTVQ RRKTTGWLAE

151 LSHKGYIGRS TADFKLKYKH GTGMKDALRA PEEAFGEGTS RMKIWTASAD

201 VNTPFQIGKQ LFAYDTSVHA QWNKTPLTSQ DKLAIGGHHT VRGFDGEMSL

251 PAERGWYWRN DLSWQFKPGH QLYLGADVGH VSGQSAKWLS GQTLAGTAIG

301 IRGQIKLGGN LHYDIFTGRA LKKPEYFQTK KWVTGFQVGY SF*
```

The underlined sequence (aromatic-Xaa-aromatic amino acid motif) is usually found at the C-terminal end of outer membrane proteins.

ORF142ng and ORF142-1 show 95.6% identity over 342aa overlap:

```
orf142-1.pep  MDNSGSEATGKYQGNITFSADNPLGLSDMFYVNYGRSIGGTPDEESFDGHRKEGGSNNYA
              |||||||||||||||||||||||||:|||||||||||||||||||:||||||||||||||
orf142ng-1    MDNSGSEATGKYQGNITFSADNPFGLSDMFYVNYGRSIGGTPDEENFDGHRKEGGSNNYA orf142-1.pep  VHYSAPFGKWTWAFNHNGYRYHQAVSGLSEVYDYNGKSYNTDFGFNRLLYRDAKRKTYLG
              |||||||||||||||||||||||||||||||||||||||||||||||||||||||||||:
orf142ng-1    VHYSAPFGKWTWAFNHNGYRYHQAVSGLSEVYDYNGKSYNTDFGFNRLLYRDAKRKTYLS orf142-1.pep  VKLWMRETKSYIDDAELTVQRRKTAGWLAELSHKEYIGRSTADFKLKYKRGTGMKDALRA
              ||||  |||||||||||||||||||:|||||||| ||||||||||||||||:||||||||
orf142ng-1    VKLWTRETKSYIDDAELTVQRRKTTGWLAELSHKGYIGRSTADFKLKYKHGTGMKDALRA orf142-1.pep  PEEAFGEGTSRMKIWTASADVNTPFQIGKQLFAYDTSVHAQWNKTPLTSQDKLAIGGHHT
              ||||||||||||||||||||||||||||||||||||||||||||||||||||||||||||
orf142ng-1    PEEAFGEGTSRMKIWTASADVNTPFQIGKQLFAYDTSVHAQWNKTPLTSQDKLAIGGHHT orf142-1.pep  VRGFDGEMSLSAERGWYWRNDLSWQFKPGHQLYLGADVGHVSGQSAKWLSGQTLVGTAIG
              ||||||||||| |||||||||||||||||||||||||||||||||||||||||:|||||
orf142ng-1    VRGFDGEMSLPAERGWYWRNDLSWQFKPGHQLYLGADVGHVSGQSAKWLSGQTLAGTAIG orf142-1.pep  IRGQIKLGGNLHYDIFTGRALKKPEFFQSRKWASGFQVGYTF
              ||||||||||||||||||||||||||:||::||::||||||:|
orf142ng-1    IRGQIKLGGNLHYDIFTGRALKKPEYFQTKKWVTGFQVGYSF
```

In addition, ORF142ng is homologous to the HecB protein of *E. chrysanthemi*:

```
gi|1772622 (L39897) HecB [Erwinia chrysanthemi] Length = 558
Score = 119 bits (295), Expect = 3e-26
Identities = 88/346 (25%), Positives = 151/346 (43%), Gaps = 22/346 (6%)

Query:    2 DNSGSEATGKYQGNITFSADNPFGLSDMFYVNYGRSIGGTPDEENFDGHRKEGGSNNYAV   61
            DNSG ++TG+ Q N + + DN FGL+D ++++ G S   +    + D      + G
Sbjct:  230 DNSGQKSTGEEQLNGSLALDNVFGLADQWFISAGHS---SRFATSHDAESLQAG------  280

Query:   62 HYSAPFGKWTWAFNHNGYRYHQAVSGLSEVYDYNGKSYNTDFGFNRLLYRDAKRKTYLSV  121
             +S  P+G W   +N++   RY            +   G S      F   +R+++RD    KT ++
Sbjct:  281 -FSMPYGYWNLGYNYSQSRYRNTFINRDFPWHSTGDSDTHRFSLSRVVFRDGTMKTAIAG  339
```

```
-continued
Query:  122 KLWTRETKSYIDDAELTVQRRKTTGWLAELSHKGYIGRSTADFKLKYKHGTMKDALRAP  181
            R   +Y++ + L       RK +     ++H  +   A F   Y G        +
Sbjct:  340 TFSQRTGNNYLNGSLLPSSSRKLSSVSLGVNHSQKLWGGLATFNPTYNRGVRWLGSETDT 399

Query:  182 EEAFGEGTSRMKIWTASADVNTPFQIGKQLFAYDTSVHAQWNKTPLTSQDKLAIGGHHTV  241
            +++   E +    WT SA    P        Y  S++ Q++    L    ++L +GG  ++
Sbjct:  400 DKSADEPRAEFNKWTLSASYYHPV---TDSITYLGSLYGQYSARALYGSEQLTLGGESSI  456

Query:  242 RGFDGEMSLPAERGWYWRNDLSWQFKP----GHQLYLGA-DVGHVSGQSAKWLSGQTLAG  296
            RGF    E     RG YWRN+L+WQ        G+ ++ A D GH+         +  +L G
Sbjct:  457 RGF-REQYTSGNRGAYWRNELNWQAWQLPVLGNVTFMAAVDGGHLYNHKQDNSTAASLWG  515

Query:  297 TAIGIRGQIKLGGNLHYDIFTGRALKKPEYFQTKKWVTGFQVGYSF                342
            A+G+    +      L   + G  +  P  + Q      V G++VG SF
Sbjct:  516 GAVGMTVASRW---LSQQVTVGWPISYPAWLQPDTMVVGYRVGLSF                558
```

On the basis of this analysis, it is predicted that the proteins from *N. meningitidis* and *N. gonorrhoeae*, and their epitopes, could be useful antigens for vaccines or diagnostics, or for raising antibodies.

Example 73

The following partial DNA sequence was identified in *N. meningitidis* <SEQ ID 609>:

```
  1 ATGCGGACGA AATGGTCAGC AGTGAGAAGC TGCTTACTTG GgCGGACACC

51 GCCGACATCG ATACCGCTTT GAACCTGTTG TACCGTTTGC AAAAACTCGA

101 ATTCCTCTAT GGCGATGAAA ACGGTCATTC AGACGGCATC AATTTGwCGG

151 ACGAGCAATT GCCGTTGCTG ATGGAACAAT TGTCCGGCAG CGGTAAGGCG

201 TTATTGGTCG ATCGGAACGG TCTGTATCTT GCCAACGCCA ATTTCCATCA

251 TGAGGCGGCG GAAGAGTTGG GGTTGTTGGC GGCAGAAGTC GCACAGATGG

301 AAAAGAAATA CCGGCTGCTG ATTAAGAACA AC..
```

This corresponds to the amino acid sequence <SEQ ID 610; ORF143>:

```
  1 MRTKWSAVRS CTWADTADID TALNLLYRLQ KLEFLYGDEN GHSDGINLXD

51 EQLPLLMEQL SGSGKALLVD RNGLYLANAN FHHEAAEELG LLAAEVAQME

101 KKYRLLIKNN ..
```

Further work revealed the complete nucleotide sequence <SEQ ID 611>:

```
  1 ATGGAATCAA CACTTTCACT ACAAGCAAAT TTATATCCCC GCCTGACTCC

51 TGCCGGTGCA TTTTATGCCG TATCCAGCGA TGCCCCCAGT GCCGGTAAAA

101 CTTTGTTGCA CAGCCTGTTG AAAGCAGATG CGGACGAAAT GGTCAGCAGT

151 GAGAAGCTGC TTACTTGGGC GGACACCGCC GACATCGATA CCGCTTTGAA

201 CCTGTTGTAC CGTTTGCAAA AACTCGAATT CCTCTATGGC GATGAAAACG

251 GTCATTCAGA CGGCATCAAT TGTCGGACG AGCAATTGCC GTTGCTGATG

301 GAACAATTGT CCGGCAGCGG TAAGGCGTTA TTGGTCGATC GGAACGGTCT

351 GTATCTTGCC AACGCCAATT TCCATCATGA GGCGGCGGAA GAGTTGGGGT

401 TGTTGGCGGC AGAAGTCGCA CAGATGGAAA AGAAATACCG GCTGCTGATT
```

```
451 AAGAACAACC TGTATATCAA CAATAACGCT TGGGGCGTTT GCGATCCTTC

501 CGGTCAGAGC GAATTGACAT TTTTCCCATT GTATATCGGT TCAACCAAAT

551 TTATTTTGGT TATCGGCGGC ATTCCCGATT TGGGCAAAGA GGCATTTGTT

601 ACTTTGGTAA GGATTTTATA CCGCCGTTAC AGCAACCGCG TGTAA
```

This corresponds to the amino acid sequence <SEQ ID 612; ORF143-1>:

```
  1 MESTLSLQAN LYPRLTPAGA FYAVSSDAPS AGKTLLHSLL KADADEMVSS

51 EKLLTWADTA DIDTALNLLY RLQKLEFLYG DENGHSDGIN LSDEQLPLLM

101 EQLSGSGKAL LVDRNGLYLA NANFHHEAAE ELGLLAAEVA QMEKKYRLLI

151 KNNLYINNNA WGVCDPSGQS ELTFFPLYIG STKFILVIGG IPDLGKEAFV

201 TLVRILYRRY SNRV*
```

Computer analysis of this amino acid sequence gave the following results:

Homology with a Predicted ORF from *N. meningitidis* (Strain A)

ORF143 shows 92.4% identity over a 105aa overlap with an ORF (ORF143a) from strain A of *N. meningitidis*:

```
                              10         20         30
orf143.pep               MRTKWSAVRSCTWADTADIDTALNLLYRLQKLEFL
                         |: :  ||| |||||||||||||||||||||
orf143a      GAFYAVSSDXPSAGKTLLHSLLKADADEMVSSEKLLTWAXTADIDTALNLLYRLQKLEFL
             20        30        40        50        60        70

40         50         60         70         80         90
orf143.pep   YGDENGHSDGINLXDEQLPLLMEQLSGSGKALLVDRNGLYLANANFHHEAAEELGLLAAE
             |||||||||||| ||||||||||||||||||||||||||||||||||||||||||||||
orf143a      YGDENGHSDGINLSDEQLPLLMEQLSGSGKALLVDRNGLYLANANFHHEAAEELGLLAAE
             80        90        100       110       120       130

100        110
orf143.pep   VAQMEKKYRLLIKNN
             ||||||||| ||||
orf143a      VAQMEKKYRLXIKNNLYINNNAWGVCDPSGQSELTFFPLYIGSTKFILVIGGIPDLGKEA
             140       150       160       170       180       190
```

The complete length ORF143a nucleotide sequence <SEQ ID 613> is:

```
  1 ATGGAATCAA CANTTTCACT ACAAGCAAAT TTATATCNCC GCCTGACTCC

51 TGCCGGTGCA TTTTATGCCG TATCCAGCGA TGNCCCCAGT GCCGGTAAAA

101 CTTTGTTGCA CAGCCTGTTG AAAGCGGATG CGGACGAAAT GGTNAGCAGT

151 GAGAAGCTGC TTACCTGGGC GGANACCGCC GACATCGATA CCGCTTTGAA

201 CCTGTTGTAC CGTTTGCAAA AACTCGAATT CCTCTATGGC GATGAAAACG

251 GTCATTCAGA CGGCATCAAT TTGTCGGACG AGCAATTGCC GTTGCTGATG

301 GAACAATTGT CCGGCAGCGG TAAGGCGTTA TTGGTCGATC GGAACGGTCT

351 GTATCTTGCC AACGCCAATT TCCATCATGA GGCGGCGGAA GAGTTGGGGT

401 TGTTGGCGGC AGAAGTCGCA CAGATGGAAA AGAAATACCG GCTGCNNATT

451 AAGAACAACC TGTATATCAA CAATAACGCT TGGGGCGTTT GCGATCCTTC

501 CGGTCAGAGC GAATTGACAT TTTTCCCATT GTATATCGGT TCAACCAAAT

551 TTATTTTGGT TATCGGCGGC ATTCCCGATT TGGGCAAAGA GGCATTTGTT
```

-continued
```
601 ACTTTGGTAA GGATNTTATA CCNCCNGTTA CAGCAACCGC GTGTAAAACT

651 TGGGAGAGAG GANGGGTTAT GCAGCAATTA TTGA
```

This encodes a protein having amino acid sequence <SEQ ID 614>:

```
  1 MESTXSLQAN LYXRLTPAGA FYAVSSDXPS AGKTLLHSLL KADADEMVSS

51 EKLLTWAXTA DIDTALNLLY RLQKLEFLYG DENGHSDGIN LSDEQLPLLM

101 EQLSGSGKAL LVDRNGLYLA NANFHHEAAE ELGLLAAEVA QMEKKYRLXI

151 KNNLYINNNA WGVCDPSGQS ELTFFPLYIG STKFILVIGG IPDLGKEAFV

201 TLVRXLYXXL QQPRVKLGRE XGLCSNY*
```

ORF143a and ORF143-1 show 97.1% identity in 207 aa overlap:

```
orf143a.pep  MESTXSLQANLYXRLTPAGAFYAVSSDXPSAGKTLLHSLLKADADEMVSSEKLLTWAXTA
             ||||  ||||||| ||||||||||||| |||||||||||||||||||||||||||| ||
orf143-1     MESTLSLQANLYPRLTPAGAFYAVSSDAPSAGKTLLHSLLKADADEMVSSEKLLTWADTA orf143a.pep  DIDTALNLLYRLQKLEFLYGDENGHSDGINLSDEQLPLLMEQLSGSGKALLVDRNGLYLA
             ||||||||||||||||||||||||||||||||||||||||||||||||||||||||||||
orf143-1     DIDTALNLLYRLQKLEFLYGDENGHSDGINLSDEQLPLLMEQLSGSGKALLVDRNGLYLA orf143a.pep  NANFHHEAAEELGLLAAEVAQMEKKYRLXIKNNLYINNNAWGVCDPSGQSELTFFPLYIG
             ||||||||||||||||||||||||||||| ||||||||||||||||||||||||||||||
orf143-1     NANFHHEAAEELGLLAAEVAQMEKKYRLLIKNNLYINNNAWGVCDPSGQSELTFFPLYIG orf143a.pep  STKFILVIGGIPDLGKEAFVTLVRXLY
             ||||||||||||||||||||||| ||
orf143-1     STKFILVIGGIPDLGKEAFVTLVRILY
```

Homology with a Predicted ORF from *N. gonorrhoeae*

ORF143 shows 95.5% identity over a 110aa overlap with a predicted ORF (ORF143ng) from *N. gonorrhoeae*:

```
orf143.pep  MRTKWSAVRSCTWADTADIDTALNLLYRLQKLEFLYGDENGHSDGINLXDEQLPLLMEQL   60
            ||||||||||| : |||||||||||||||||||||||||||||||||| |||||||||||
orf143ng    MRTKWSAVRSCSRADTADIDTALNLLYRLQKLEFLYGDENGHSDGINLSDEQLPLLMEQL   60
orf143.pep  SGSGKALLVDRNGLYLANANFHHEAAEELGLLAAEVAQMEKKYRLLIKNN            110
            ||||||||||||||||||||||||| |||||||||||||||||||| :||
orf143ng    SGSGKALLVDRNGLYLANANFHHESAEELGLLAAEVAQMEKKYRLLIRNNLYINNNAWGV 120
```

An ORF143ng nucleotide sequence <SEQ ID 615> was predicted to encode a protein having amino acid sequence <SEQ ID 616>:

```
  1 MRTKWSAVRS CSRADTADID TALNLLYRLQ KLEFLYGDEN GHSDGINLSD

51 EQLPLLMEQL SGSGKALLVD RNGLYLANAN FHHESAEELG LLAAEVAQME

101 KKYRLLIRNN LYINNNAWGV CDPSGQSELT FFPLYIGSTK FILVIAGIPD

151 LSKGGICYFG KDFIPPLQQP RVKLGTGGIM RQLLISILED LNNTSTDIIA

201 SAVISTDGLP MATMLPSHLN SDRVGAISAT LLALGSRSVQ ELACGELEQV

251 MIKGKSGYIL LSQAGKDAVL VLVAKETGRL GLILLDAKRA ARHIAEAI*
```

Further work revealed the following gonococcal DNA sequence <SEQ ID 617>:

```
  1 ATGGAATCAA CACTTTCACT ACAAGCGAAT TTATATCCCT GCCTGACTCC

51 TGCCGGTGCA TTTTATGCCG TATCCAGCGA TGCCCCCAGT GCCGGTAAAA

101 CTTTGTTGCG CAGCCTGTTG AAAGCGGATG CGGACGAAGT GGTCAGCAGT

151 GAGAAGCTGC TCGCGGCGGA CACCGCCGAC ATCGATACCG CTTTGAACCT

201 GTTGTACCGT TTGCAAAAAC TCGAATTCCT CTATGGCGAT GAAAACGGTC

251 ATTCAGACGG CATCAATTTG TCGGACGAGC AATTGCCGTT GCTGATGGAA

301 CAATTGTCCG GCAGCGGTAA GGCATTATTG GTCGATCGGA ACGGTCTGTA

351 TCTTGCCAAC GCCAATTTCC ATCATGAGTC GGCGGAAGAG TTGGGGTTGT

401 TGGCGGCAGA AGTCGCACAG ATGGAAAAGA AATACCGGCT GCTGATTAGG

451 AACAACCTGT ATATCAACAA TAACGCTTGG GGCGTTTGCG ATCCTTCCGG

501 TCAGAGCGAA TTGACATTTT TCCCATTGTA TATCGGTTCA ACCAAATTTA

551 TTTTGGTTAT CGCCGGCATT CCCGATTTGA GCAAAGAGGC ATTTGTTACT

601 TTGGTAAGGA TTTTATACCG CCGTTACAGC AACCGCGTGT AA
```

This corresponds to the amino acid sequence <SEQ ID 618; ORF143ng-1>:

```
  1 MESTLSLQAN LYPCLTPAGA FYAVSSDAPS AGKTLLRSLL KADADEVVSS

51 EKLLAADTAD IDTALNLLYR LQKLEFLYGD ENGHSDGINL SDEQLPLLME

101 QLSGSGKALL VDRNGLYLAN ANFHHESAEE LGLLAAEVAQ MEKKYRLLIR

151 NNLYINNNAW GVCDPSGQSE LTFFPLYIGS TKFILVIAGI PDLSKEAFVT

201 LVRILYRRYS NRV*
```

ORF143ng-1 and ORF143-1 show 95.8% identity in 214 aa overlap:

```
orf143ng-1.pep MESTLSLQANLYPCLTPAGAFYAVSSDAPSAGKTLLRSLLKADADEVVSSEKLLA-ADTA  59
               |||||||||||||| ||||||||||||||||||||:|||||||||:|||||||: ||||
orf143-1       MESTLSLQANLYPRLTPAGAFYAVSSDAPSAGKTLLHSLLKADADEMVSSEKLLTWADTA  60 orf143ng-1.pep DIDTALNLLYRLQKLEFLYGDENGHSDGINLSDEQLPLLMEQLSGSGKALLVDRNGLYLA 119
               ||||||||||||||||||||||||||||||||||||||||||||||||||||||||||||
orf143-1       DIDTALNLLYRLQKLEFLYGDENGHSDGINLSDEQLPLLMEQLSGSGKALLVDRNGLYLA 120 orf143ng-1.pep NANFHHESAEELGLLAAEVAQMEKKYRLLIRNNLYINNNAWGVCDPSGQSELTFFPLYIG 179
               |||||||:||||||||||||||||||||||:|||||||||||||||||||||||||||||
orf143-1       NANFHHEAAEELGLLAAEVAQMEKKYRLLIKNNLYINNNAWGVCDPSGQSELTFFPLYIG 180 orf143ng-1.pep STKFILVIAGIPDLSKEAFVTLVRILYRRYSNRV                           213
               |||||||||:||||| :||||||||||||||||||
orf143-1       STKFILVIGGIPDLGKEAFVTLVRILYRRYSNRV                           214
```

Based on the presence of the putative transmembrane domains in the gonococcal protein, it is predicted that the proteins from N. meningitidis and N. gonorrhoeae, and their epitopes, could be useful antigens for vaccines or diagnostics, or for raising antibodies.

Example 74

The following partial DNA sequence was identified in *N. meningitidis* <SEQ ID 619>:

```
  1 ATGACCTTTT TACAACGTTT GCAAGGTTTG GCAGACAATA AAATCTGTGC

51 GTTTGCATGG TTCGTCGTCC GCCGCTTTGA TGAAGAACGC GTACCGCAGr

101 CGGCGGCAAG CATGACGTTT ACGACGCTGC TGGCACTCGT CCCCGTGCTG

151 ACCGTGATGG TGGCGGTCGC TTCGATTTTC CCCGTGTTCG ACCGCTGGTC

201 GGATTCGTTC GTCTCCTTCG TCAACCAAAC CATTGTGCCG CA.GGCGCGG

251 ACATGGTGTT CGACTATATC AATGCGTTCC GCGAGCAGGC GAACCGGCTG

301 ACGGCAATCG GCAGCGTGAT GCTGGTCGTT ACCTCGCTGA TGCTGATTCG

351 GACGATAGAC AATACGTTCA ACCGCATCTG GaCGGGTCAA wTyCCAGCGT

401 CCGTGGATG..
```

This corresponds to the amino acid sequence <SEQ ID 620; ORF144>:

```
  1 MTFLQRLQGL ADNKICAFAW FVVRRFDEER VPQXAASMTF TTLLALVPVL

51 TVMVAVASIF PVFDRWSDSF VSFVNQTIVP XGADMVFDYI NAFREQANRL

101 TAIGSVMLVV TSLMLIRTID NTFNRIWRVX XQRPWM...
                                                    30
```

Further work revealed the complete nucleotide sequence <SEQ ID 621>:

```
  1 ATGACCTTTT TACAACGTTT GCAAGGTTTG GCAGACAATA AAATCTGTGC

51 GTTTGCATGG TTCGTCGTCC GCCGCTTTGA TGAAGAACGC GTACCGCAGG

101 CGGCGGCAAG CATGACGTTT ACGACGCTGC TGGCACTCGT CCCCGTGCTG

151 ACCGTGATGG TGGCGGTCGC TTCGATTTTC CCCGTGTTCG ACCGCTGGTC

201 GGATTCGTTC GTCTCCTTCG TCAACCAAAC CATTGTGCCG CAGGGCGCGG

251 ACATGGTGTT CGACTATATC AATGCGTTCC GCGAGCAGGC GAACCGGCTG

301 ACGGCAATCG GCAGCGTGAT GCTGGTCGTT ACCTCGCTGA TGCTGATTCG

351 GACGATAGAC AATACGTTCA ACCGCATCTG GCGGGTCAAT TCCCAGCGTC

401 CGTGGATGAT GCAGTTTCTC GTCTATTGGG CTTTACTGAC GTTCGGGCCG

451 CTGTCTTTGG GCGTGGGCAT TTCCTTTATG GTCGGCTCGG TACAGGATGC

501 CGCGCTTGCC TCAGGTGCGC CGCAGTGGTC GGGCGCGTTG CGAACGGCGG

551 CGACGCTGAC CTTCATGACG CTTTTGCTGT GGGGGCTGTA CCGCTTCGTG

601 CCAAACCGCT TCGTTCCCGC GCGGCAGGCG TTTGTCGGGG CTTTGGCAAC

651 AGCGTTTTGT CTGGAAACCG CGCGCTCCCT CTTCACTTGG TATATGGGCA

701 ATTTCGACGG CTACCGCTCG ATTTACGGCG CGTTTGCCGC CGTGCCGTTT

751 TTTCTGTTGT GGCTGAACCT GTTGTGGACG CTGGTCTTGG GCGGCGCGGT

801 GCTGACTTCT TCACTCTCCT ACTGGCAGGG AGAAGCGTTC CGCAGGGGCT

851 TCGACTCGCG CGGACGGTTT GACGACGTGT TGAAAATCCT GCTGCTTCTG

901 GATGCGGCGC AAAAAGAAGG CAAAGCCTTG CCTGTTCAGG AGTTCAGACG

951 GCATATCAAT ATGGGCTACG ACGAGTTGGG CGAGCTTTTG GAAAAGCTGG
```

```
1001  CGCGGCACGG CTACATCTAT TCCGGCAGAC AGGGTTGGGT GTTGAAAACG

1051  GGGGCGGATT CGATTGAGTT GAACGAACTC TTCAAGCTCT TCGTTTACCG

1101  TCCGTTGCCT GTGGAAAGGG ATCATGTGAA CCAAGCTGTC GATGCGGTAA

1151  TGACACCGTG TTTGCAGACT TTGAACATGA CGCTGGCAGA GTTTGACGCT

1201  CAGGCGAAAA AACGGCAGTA G
```

This corresponds to the amino acid sequence <SEQ ID 622; ORF144-1>:

```
  1  MTFLQRLQGL ADNKICAFAW FVVRRFDEER VPQAAASMTF TTLLALVPVL

51  TVMVAVASIF PVFDRWSDSF VSFVNQTIVP QGADMVFDYI NAFREQANRL

101  TAIGSVMLVV TSLMLIRTID NTFNRIWRVN SQRPWMMQFL VYWALLTFGP

151  LSLGVGISFM VGSVQDAALA SGAPQWSGAL RTAATLTFMT LLLWGLYRFV

201  PNRFVPARQA FVGALATAFC LETARSLFTW YMGNFDGYRS IYGAFAAVPF

251  FLLWLNLLWT LVLGGAVLTS SLSYWQGEAF RRGFDSRGRF DDVLKILLLL

301  DAAQKEGKAL PVQEFRRHIN MGYDELGELL EKLARHGYIY SGRQGWVLKT

351  GADSIELNEL FKLFVYRPLP VERDHVNQAV DAVMTPCLQT LNMTLAEFDA

401  QAKKRQ*
```

Computer analysis of this amino acid sequence gave the following results:

Homology with a Predicted ORF from *N. meningitidis* (Strain A)

ORF144 shows 96.3% identity over a 136aa overlap with an ORF (ORF144a) from strain A of *N. meningitidis*:

```
                    10         20         30         40         50         60
orf144.pep  MTFLQRLQGLADNKICAFAWFVVRRFDEERVPQXAASMTFTTLLALVPVLTVMVAVASIF
            ||||||||||||||||||||||||||||||||| ||||||||||||||||||||||||||
orf144a     MTFLQRLQGLADNKICAFAWFVVRRFDEERVPQAAASMTFTTLLALVPVLTVMVAVASIF
                    10         20         30         40         50         60

70         80         90        100        110        120
orf144.pep  PVFDRWSDSFVSFVNQTIVPXGADMVFDYINAFREQANRLTAIGSVMLVVTSLMIRTID
            |||||||||||||||||||| |||||||||||||||||||||||||||||||| |||||
orf144a     PVFDRWSDSFVSFVNQTIVPQGADMVFDYINAFREQANRLTAIGSVMLVVTSXMLIRTID
                    70         80         90        100        110        120

130
orf144.pep  NTFNRIWRVXXQRPWM
            ||||||||| ||||||||||||||||||||||||||||||||||||||||||||||||||
orf144a     NTFNRIWRVNSQRPWMMQFLVYWALLTFGPLSLGVGISFXVGSVQDAALASGAPQWSGAL
                   130        140        150        160        170        180
```

The complete length ORF144a nucleotide sequence <SEQ ID 623> is:

```
  1  ATGACCTTTT TACAACGTTT GCAAGGTTTG GCAGACAATA AAATCTGTGC

51  GTTTGCATGG TTCGTCGTCC GCCGCTTTGA TGAAGAACGC GTACCGCAGG

101  CGGCGGCAAG CATGACGTTT ACGACACTGC TGGCACTCGT CCCCGTGCTG

151  ACCGTGATGG TGGCGGTCGC TTCGATTTTC CCCGTGTTCG ACCGNTGGTC

201  GGATTCGTTC GTCTCCTTCG TCAACCAAAC CATTGTGCCG CAGGGCGCGG

251  ACATGGTNTT CGACTATATC AATGCGTTCC GCGAGCAGGC GAACCGGCTG

301  ACGGCAATCG GCAGCGTGAT GCTGGTCGTT ACCTCGCNGA TGCTGATTCG
```

```
 351 GACGATAGAC AATACGTTCA ACCGCATCTG GCGGGTCAAT TCCCAGCGTC

401 CGTGGATGAT GCAGTTTCTC GTCTATTGGG CTTTACTGAC GTTCGGGCCG

451 CTGTCTTTGG GCGTGGGCAT TTCCTTTATN GTCGGCTCGG TACAGGATGC

501 CGCGCTTGCC TCAGGTGCGC CGCAGTGGTC GGGCGCGTTG CGAACGGCGG

551 CGACGCTGAN CTTCATGACG CTTTTGCTGT GGGGGCTGTA CCGCTNCGTG

601 CCAAACCGCT TCGTTCCCGC GCGGCANGCG TTTGTCGGGG CTTTGGCAAC

651 AGCGTTCTGT CTGGAAACCG CGCGTTCCCT CTTTACTTGG TATATGGGCA

701 ATTTCGACGG CTACCGCTCG ATTTACGGNG CGTTTGCCGC CGTGCCGTTT

751 TTTCTGTTGT GGCTGAACCT GTTGTGGACG CTGGTCTTGG GCGGCGCGGT

801 GCTGACTTCT TCACTCTCCT ACTGGCAGGG AGAAGCGTTC CGCAGGGNCT

851 TCGACTCGCG CGGACGGTTT GACGACGTGT TGAAAATCCT GCTGCTTCTG

901 GATGCGGCGC AAAAAGAAGG CNAAGCCTTG CCTGTTCAGG AGTTCAGACG

951 GCATATCAAT ATGGGCTACG ACGAGTTGGG CGAGCTTTTG GAAAAGCTGG

1001 CGCGGCACGG CTACATCTAT TCCGGCAGAC AGGGTTGGGT GTTGAAAACG

1051 GGGGCGGATT CGATTGAGTT GAACGAACTC TTCAAGCTCT TCGTTTACCG

1101 TCCGTTGCCT GTGGAAAGGG ATCATGTGAA CCAAGCTGTC GATGCGGTAA

1151 TGATGCCGTG TTTGCAGACT TTGAACATGA CGCTGGCAGA GTTTGACGCT

1201 CAGGCGAAAA AACAGCAGCA ATCTTGA
```

This encodes a protein having amino acid sequence <SEQ ID 624>:

```
  1 MTFLQRLQGL ADNKICAFAW FVVRRFDEER VPQAAASMTF TTLLALVPVL

51 TVMVAVASIF PVFDRWSDSF VSFVNQTIVP QGADMVFDYI NAFREQANRL

101 TAIGSVMLVV TSXMLIRTID NTFNRIWRVN SQRPWMMQFL VYWALLTFGP

151 LSLGVGISFX VGSVQDAALA SGAPQWSGAL RTAATLXFMT LLLWGLYRXV

201 PNRFVPARXA FVGALATAFC LETARSLFTW YMGNFDGYRS IYGAFAAVPF

251 FLLWLNLLWT LVLGGAVLTS SLSYWQGEAF RRXFDSRGRF DDVLKILLLL

301 DAAQKEGXAL PVQEFRRHIN MGYDELGELL EKLARHGYIY SGRQGWVLKT

351 GADSIELNEL FKLFVYRPLP VERDHVNQAV DAVMMPCLQT LNMTLAEFDA

401 QAKKQQS*
```

ORF144a and ORF144-1 show 97.8% identity in 406 aa overlap:

```
orf144a.pep  MTFLQRLQGLADNKICAFAWFVVRRFDEERVPQAAASMTFTTLLALVPVLTVMVAVASIF
             ||||||||||||||||||||||||||||||||||||||||||||||||||||||||||||
orf144-1     MTFLQRLQGLADNKICAFAWFVVRRFDEERVPQAAASMTFTTLLALVPVLTVMVAVASIF orf144a.pep  PVFDRWSDSFVSFVNQTIVPQGADMVFDYINAFREQANRLTAIGSVMLVVTSXMLIRTID
             ||||||||||||||||||||||||||||||||||||||||||||||||||||| ||||||
orf144-1     PVFDRWSDSFVSFVNQTIVPQGADMVFDYINAFREQANRLTAIGSVMLVVTSLMLIRTID orf144a.pep  NTFNRIWRVNSQRPWMMQFLVYWALLTFGPLSLGVGISFXVGSVQDAALASGAPQWSGAL
             ||||||||||||||||||||||||||||||||||||||| ||||||||||||||||||||
orf144-1     NTFNRIWRVNSQRPWMMQFLVYWALLTFGPLSLGVGISFMVGSVQDAALASGAPQWSGAL orf144a.pep  RTAATLXFMTLLLWGLYRXVPNRFVPARXAFVGALATAFCLETARSLFTWYMGNFDGYRS
             ||||||| ||||||||||| ||||||||| ||||||||||||||||||||||||||||||
orf144-1     RTAATLTFMTLLLWGLYRFVPNRFVPARQAFVGALATAFCLETARSLFTWYMGNFDGYRS orf144a.pep  IYGAFAAVPFFLLWLNLLWTLVLGGAVLTSSLSYWQGEAFRRXFDSRGRFDDVLKILLLL
             ||||||||||||||||||||||||||||||||||||||||| ||||||||||||||||||
orf144-1     IYGAFAAVPFFLLWLNLLWTLVLGGAVLTSSLSYWQGEAFRRGFDSRGRFDDVLKILLLL
```

-continued
```
orf144a.pep  DAAQKEGXALPVQEFRRHINMGYDELGELLEKLARHGYIYSGRQGWVLKTGADSIELNEL
             ||||||| |||||||||||||||||||||||||||||||||||||||||||||||||||
orf144-1     DAAQKEGKALPVQEFRRHINMGYDELGELLEKLARHGYIYSGRQGWVLKTGADSIELNEL orf144a.pep  FKLFVYRPLPVERDHVNQAVDAVMMPCLQTLNMTLAEFDAQAKKQQQS  408
             |||||||||||||||||||||||| |||||||||||||||||||||:|
orf144-1     FKLFVYRPLPVERDHVNQAVDAVMTPCLQTLNMTLAEFDAQAKKRQ    406
```

Homology with a Predicted ORF from *N. gonorrhoeae*

ORF144 shows 91.2% identity over a 136aa overlap with a predicted ORF (ORF144ng) from *N. gonorrhoeae*:

```
orf144.pep  MTFLQRLQGLADNKICAFAWFVVRRFDEERVPQXAASMTFTTLLALVPVLTVMVAVASIF  60
            ||||| || |||||||||||||| |||:|||:|||||| |||||||||||||||||||||
orf144ng    MTFLQCWQGSADNKICAFAWFVIRRFSEERVPQAAASMTFTTLLALVPVLTVMVAVASIF  60
orf144.pep  PVFDRWSDSFVSFVNQTIVPXGADMVFDYINAFREQANRLTAIGSVMLVVTSLMLIRTID  120
            ||||||||||||||||||||| ||||||||||:|||:||||||||||||||||||||||
orf144ng    PVFDRWSDSFVSFVNQTIVPQGADMVFDYIDAFRDQANRLTAIGSVMLVVTSLMLIRTID  120
orf144.pep  NTFNRIWRVXXQRPWM                                             136
            |:||||||||  :|||||
orf144ng    NAFNRIWRVNTQRPWMMQFLVYWALLTFGPLSLGVGISFMVGSVQDSVLSSGAQQWADAL 180
```

The complete length ORF144ng nucleotide sequence <SEQ ID 625> is predicted to encode a protein having amino acid sequence <SEQ ID 626>:

```
  1  MTFLQCWQGS ADNKICAFAW FVIRRFSEER VPQAAASMTF TTLLALVPVL

51  TVMVAVASIF PVFDRWSDSF VSFVNQTIVP QGADMVFDYI DAFRDQANRL

101  TAIGSVMLVV TSLMLIRTID NAFNRIWRVN TQRPWMMQFL VYWALLTFGP

151  LSLGVGISFM VGSVQDSVLS SGAQQWADAL KTAARLAFMT LLLWGLYRFV

201  PNRFVPARQA FVGALITAFC LETARFLFTW YMGNFDGYRS IYGAFAAVPF

251  FLLWLNLLWT LVLGGAVLTS SLSYWQGEAF RRGFDSRGRF DDVLKILLLL

301  DAAQKEGRTL SVQEFRRHIN MGYDELGELL EKLARYGYIY SGRQGWVLKT

351  GADSIELSEL FKLFVYRPLP VERDHVNQAV DAVMTPCLQT LNMTLAEFDA

401  QAKKQQQS*
```

Further work revealed the following gonococcal DNA sequence <SEQ ID 627>:

```
  1  ATGACCTTTT TACAACGTTG GCAAGGTTTG GCGGACAATA AAATCTGTGC

51  ATTTGCATGG TTCGTCATCC GCCGTTTCAG TGAAGAGCGC GTACCGCAGG

101  CAGCGGCGAG CATGACGTTT ACGACACTGC TGGCACTCGT CCCCGTACTG

151  ACCGTAATGG TCGCGGTCGC TTCGATTTTC CCCGTGTTCG ACCGCTGGTC

201  GGATTCGTTC GTCTCCTTCG TCAACCAAAC CATTGTGCCG CAGGGCGCGG

251  ATATGGTGTT CGACTATATC GACGCATTCC GCGATCAGGC AAACCGGCTG

301  ACCGCCATCG GCAGCGTGAT GCTGGTCGTA ACCTCGCTGA TGCTGATTCG

351  GACGATAGAC AATGCGTTCA ACCGCATCTG GCGGGTTAAC ACGCAACGCC

401  CCTGGATGAT GCAGTTCCTC GTTTATTGGG CGTTGCTGAC TTTCGGGCCT

451  TTGTCTTTGG GTGTGGGCAT TTCCTTTATG GTCGGGTCGG TTCAAGACTC

501  CGTACTCTCC TCCGGAGCGC AACAATGGGC GGACGCGTTG AAGACGGCGG

551  CAAGGCTGGC TTTCATGACG CTTTTGCTGT GGGGGCTGTA CCGCTTCGTG

601  CCCAACCGCT TCGTGCCCGC CCGGCAGGCG TTTGTCGGAG CTTTGATTAC
```

```
 651 GGCATTCTGC CTGGAGACGG CACGTTTCCT GTTCACCTGG TATATGGGCA

701 ATTTCGACGG CTACCGCTCG ATTTACGGCG CATTTGCCGC CGTGCCGTTT

751 TTCCTGCTGT GGTTAAACCT GCTGTGGACG CTGGTCTTGG GCGGGGCGGT

801 GCTGACTTCG TCGCTGTCTT ATTGGCAGGG CGAGGCCTTC CGCAGGGGAT

851 TCGACTCGCG CGGACGGTTT GACGACGTGT TGAAAATCCT GCTGCTTCTG

901 GATGCGGCGC AAAAAGAAGG CCGAACCCTG TCCGTTCAGG AGTTCAGACG

951 GCATATCAAT ATGGGTTACG ATGAATTGGG CGAGCTTTTG GAAAAGCTGG

1001 CGCGGTACGG CTATATCTAT TCCGGCAGAC AGGGCTGGGT TTTGAAAACG

1051 GGGGCGGATT CGATTGAGTT GAGCGAACTC TTCAAGCTCT TCGTGTACCG

1101 CCCGTTGCct gtggaAAGGG ATCATGTGAA CCAAGCTGtc gaTGCGGTAA

1151 TGAcgccgtG TTTGCAGACT TTGAACATGA CGCTGGCGGA GTTTGACGCT

1201 CAGgcgAAAA AACAGCAGCA GTCTTGA
```

This encodes a variant of ORF144ng, having the amino acid sequence <SEQ ID 628; ORF144ng-1>:

```
  1 MTFLQRWQGL ADNKICAFAW FVIRRFSEER VPQAAASMTF TTLLALVPVL

51 TVMVAVASIF PVFDRWSDSF VSFVNQTIVP QGADMVFDYI DAFRDQANRL

101 TAIGSVMLVV TSLMLIRTID NAFNRIWRVN TQRPWMMQFL VYWALLTFGP

151 LSLGVGISFM VGSVQDSVLS SGAQQWADAL KTAARLAFMT LLLWGLYRFV

201 PNRFVPARQA FVGALITAFC LETARFLFTW YMGNFDGYRS IYGAFAAVPF

251 FLLWLNLLWT LVLGGAVLTS SLSYWQGEAF RRGFDSRGRF DDVLKILLLL

301 DAAQKEGRTL SVQEFRRHIN MGYDELGELL EKLARYGYIY SGRQGWVLKT

351 GADSIELSEL FKLFVYRPLP VERDHVNQAV DAVMTPCLQT LNMTLAEFDA

401 QAKKQQQS*
```

40

ORF144ng-1 and ORF144-1 show 94.1% identity in 406 aa overlap:

```
orf144ng-1.pep  MTFLQRWQGLADNKICAFAWFVIRRFSEERVPQAAASMTFTTLLALVPVLTVMVAVASIF
                ||||| ||||||||||||||||:|||:||||||||||||||||||||||||||||||||
orf144-1        MTFLQRLQGLADNKICAFAWFVVRRFDEERVPQAAASMTFTTLLALVPVLTVMVAVASIF orf144ng-1.pep  PVFDRWSDSFVSFVNQTIVPQGADMVFDYIDAFRDQANRLTAIGSVMLVVTSLMLIRTID
                ||||||||||||||||||||||||||||||:|||:|||||||||||||||||||||||
orf144-1        PVFDRWSDSFVSFVNQTIVPQGADMVFDYINAFREQANRLTAIGSVMLVVTSLMLIRTID orf144ng-1.pep  NAFNRIWRVNTQRPWMMQFLVYWALLTFGPLSLGVGISFMVGSVQDSVLSSGAQQWADAL
                |:||||||||:||||||||||||||||||||||||||||||||||| :||| ||  ||
orf144-1        NTFNRIWRVNSQRPWMMQFLVYWALLTFGPLSLGVGISFMVGSVQDAALASGAPQWSGAL orf144ng-1.pep  KTAARLAFMTLLLWGLYRFVPNRFVPARQAFVGALITAFCLETARFLFTWYMGNFDGYRS
                :||| |:|||||||||||||||||||||||||||||:||||||||:|||||||||||||
orf144-1        RTAATLTFMTLLLWGLYRFVPNRFVPARQAFVGALATAFCLETARSLFTWYMGNFDGYRS orf144ng-1.pep  IYGAFAAVPFFLLWLNLLWTLVLGGAVLTSSLSYWQGEAFRRGFDSRGRFDDVLKILLLL
                ||||||||||||||||||||||||||||||||||||||||||||||||||||||||||||
orf144-1        IYGAFAAVPFFLLWLNLLWTLVLGGAVLTSSLSYWQGEAFRRGFDSRGRFDDVLKILLLL orf144ng-1.pep  DAAQKEGRTLSVQEFRRHINMGYDELGELLEKLARYGYIYSGRQGWVLKTGADSIELSEL
                ||||||||: | |||||||||||||||||||||||:||||||||||||||||||||:||
orf144-1        DAAQKEGKALPVQEFRRHINMGYDELGELLEKLARHGYIYSGRQGWVLKTGADSIELNEL orf144ng-1.pep  FKLFVYRPLPVERDHVNQAVDAVMTPCLQTLNMTLAEFDAQAKKQQQS
                ||||||||||||||||||||||||||||||||||||||||||||::|
orf144-1        FKLFVYRPLPVERDHVNQAVDAVMTPCLQTLNMTLAEFDAQAKKRQ
```

On this basis of this analysis, including the identification of several putative transmembrane domains in the gonococcal protein, it is predicted that the proteins from *N. meningitidis* and *N. gonorrhoeae*, and their epitopes, could be useful antigens for vaccines or diagnostics, or for raising antibodies.

Example 75

The following partial DNA sequence was identified in *N. meningitidis* <SEQ ID 629>:

```
  1 ..AGACACGCCC GCCGCATCCG CATCGACACC GCCATCAACC CCGAACTGGA
 51   AGCCCTCGCC GAACACCTCC ACTACCAATG GCAGGGCTTC CTCTGGCTCA
101   GCACCGATAT GCGTCAGGAA ATTTCCGCCC TCGTCATCCT GCTGCAACGC
151   ACCCGCCGCA AATGGCTGGA TGCCCACGAA CGCCAACACC TGCGCCAAAG
201   CCTGCTTGAA ACACGGGAAC ACGGCTGA
```

This corresponds to the amino acid sequence <SEQ ID 630; ORF146>:

```
  1 ..RHARRIRIDT AINPELEALA EHLHYQWQGF LWLSTDMRQE ISALVILLQR
 51   TRRKWLDAHE RQHLRQSLLE TREHG*
```

Further work revealed the complete nucleotide sequence <SEQ ID 631>:

```
   1 ATGAACACCT CGCAACGCAA CCGCCTCGTC AGCCGCTGGC TCAACTCCTA
  51 CGAACGCTAC CGCTACCGCC GCCTCATCCA CGCCGTCCGG CTCGGCGGGG
 101 CCGTCCTGTT CGCCACCGCC TCCGCCCGGC TGCTCCACCT CCAACACGGC
 151 GAGTGGATAG GGATGACCGT CTTCGTCGTC CTCGGCATGC TCCAGTTTCA
 201 AGGGGCGATT TACTCCAAGG CGGTGGAACG TATGCTCGGC ACGGTCATCG
 251 GGCTGGGCGC GGGTTTGGGC GTTTTATGGC TGAACCAGCA TTATTTCCAC
 301 GGCAACCTCC TCTTCTACCT CACCGTCGGC ACGGCAAGCG CACTGGCCGG
 351 CTGGGCGGCG GTCGGCAAAA ACGGCTACGT CCCTATGCTG GCAGGGCTGA
 401 CGATGTGTAT GCTCATCGGC GACAACGGCA GCGAATGGCT CGACAGCGGA
 451 CTCATGCGCG CCATGAACGT CCTCATCGGC GCGGCCATCG CCATCGCCGC
 501 CGCCAAACTG CTGCCGCTGA AATCCACACT GATGTGGCGT TTCATGCTTG
 551 CCGACAACCT GGCCGACTGC AGCAAAATGA TTGCCGAAAT CAGCAACGGC
 601 AGGCGCATGA CCCGCGAACG CCTCGAGGAG AACATGGCGA AAATGCGCCA
 651 AATCAACGCA CGCATGGTCA AAAGCCGCAG CCATCTCGCC GCCACATCGG
 701 GCGAAAGCCG CATCAGCCCC GCCATGATGG AAGCCATGCA GCACGCCCAC
 751 CGTAAAATCG TCAACACCAC CGAGCTGCTC CTGACCACCG CCGCCAAGCT
 801 GCAATCTCCC AAACTCAACG GCAGCGAAAT CCGGCTGCTT GACCGCCACT
 851 TCACACTGCT CCAAACCGAC CTGCAACAAA CCGTCGCCCT TATCAACGGC
 901 AGACACGCCC GCCGCATCCG CATCGACACC GCCATCAACC CCGAACTGGA
 951 AGCCCTCGCC GAACACCTCC ACTACCAATG GCAGGGCTTC CTCTGGCTCA
1001 GCACCAATAT GCGTCAGGAA ATTTCCGCCC TCGTCATCCT GCTGCAACGC
```

```
1051  ACCCGCCGCA AATGGCTGGA TGCCCACGAA CGCCAACACC TGCGCCAAAG

1101  CCTGCTTGAA ACACGGGAAC ACGGCTGA
```

This corresponds to the amino acid sequence <SEQ ID 632; ORF146-1>:

```
  1  MNTSQRNRLV SRWLNSYERY RYRRLIHAVR LGGAVLFATA SARLLHLQHG

51  EWIGMTVFVV LGMLQFQGAI YSKAVERMLG TVIGLGAGLG VLWLNQHYFH

101  GNLLFYLTVG TASALAGWAA VGKNGYVPML AGLTMCMLIG DNGSEWLDSG

151  LMRAMNVLIG AAIAIAAAKL LPLKSTLMWR FMLADNLADC SKMIAEISNG

201  RRMTRERLEE NMAKMRQINA RMVKSRSHLA ATSGESRISP AMMEAMQHAH

251  RKIVNTTELL LTTAAKLQSP KLNGSEIRLL DRHFTLLQTD LQQTVALING

301  RHARRIRIDT AINPELEALA EHLHYQWQGF LWLSTNMRQE ISALVILLQR

351  TRRKWLDAHE RQHLRQSLLE TREHG*
```

Computer analysis of this amino acid sequence gave the following results:

Homology with a Predicted ORF from *N. meningitidis* (Strain A)

ORF146 shows 98.6% identity over a 74aa overlap with an ORF (ORF146a) from strain A of *N. meningitidis*:

```
                                       10         20         30
  orf146.pep                    RHARRIRIDTAINPELEALAEHLHYQWQGF
                                |||||||||||||||||||||||||||||
  orf146a    KLNGSEIRLLDRHFTLLQTDLQQTVALINGRHARRIRIDTAINPELEALAEHLHYQWQGF
                  280        290        300        310        320        330
                     40         50         60         70
  orf146.pep LWLSTDMRQEISALVILLQRTRRKWLDAHERQHLRQSLLETREHGX
             ||||||:|||||||||||||||||||||||||||||||||||||:
  orf146a    LWLSTNMRQEISALVILLQRTRRKWLDAHERQHLRQSLLETREHSX
                  340        350        360        370
```

The complete length ORF146a nucleotide sequence <SEQ ID 633> is:

```
  1  ATGAACACCT CGCAACGCAA CCGCCTCGTC AGCCGCTGGC TCAACTCCTA

51  CGAACGCTAC CGCTACCGCC GCCTCATCCA CGCCGTCCGG CTCGGCGGGG

101  CCGTCCTGTT CGCCACCGCC TCCGCCCGGC TGCTCCACCT CCAACACGGC

151  GAGTGGATAG GGATGACCGT CTTCGTCGTC CTCGGCATGC TCCAGTTTCA

201  AGGGGCGATT TACTCCAAGG CGGTGGAACG TATGCTCGGC ACGGTCATCG

251  GGCTGGGCGC GGGTTTGGGC GTTTTATGGC TGAACCAGCA TTATTTCCAC

301  GGCAACCTCC TCTTCTACCT CACCGTCGGC ACGGCAAGCG CACTGGCCGG

351  CTGGGCGGCG GTCGGCAAAA ACGGCTACGT CCCTATGCTG GCGGGGCTGA

401  CGATGTGCAT GCTCATCGGC GACAACGGCA GCGAATGGTT CGACAGCGGC

451  CTGATGCGCG CGATGAACGT CCTCATCGGC GCGGCCATCG CCATCGCCGC

501  CGCCAAACTG CTGCCGCTGA AATCCACACT GATGTGGCGT TTCATGCTTG

551  CCGACAACCT GACCGACTGC AGCAAAATGA TTGCCGAAAT CAGCAACGGC

601  AGGCGCATGA CCCGCGAACG CCTCGAAGAG AACATGGCGA AAATGCGCCA
```

```
-continued
 651 AATCAACGCA CGCATGGTCA AAAGCCGCAG CCACCTCGCC GCCACATCGG

701 GCGAAAGCCG CATCAGCCCC GCCATGATGG AAGCCATGCA GCACGCCCAC

751 CGTAAAATTG TCAACACCAC CGAGCTGCTC CTGACCACCG CCGCCAAGCT

801 GCAATCTCCC AAACTCAACG GCAGCGAAAT CCGGCTGCTT GACCGCCACT

851 TCACACTGCT CCAAACCGAC CTGCAACAAA CCGTCGCCCT TATCAACGGC

901 AGACACGCCC GCCGCATCCG CATCGACACC GCCATCAACC CCGAACTGGA

951 AGCCCTCGCC GAACACCTCC ACTACCAATG GCAGGGCTTC CTCTGGCTCA

1001 GCACCAATAT GCGTCAGGAA ATTTCCGCCC TCGTCATCCT GCTGCAACGC

1051 ACCCGCCGCA AATGGCTGGA TGCCCACGAA CGCCAACACC TGCGCCAAAG

1101 CCTGCTTGAA ACACGGGAAC ACAGTTGA
```

This encodes a protein having amino acid sequence <SEQ ID 634>:

```
  1 MNTSQRNRLV SRWLNSYERY RYRRLIHAVR LGGAVLFATA SARLLHLQHG

51 EWIGMTVFVV LGMLQFQGAI YSKAVERMLG TVIGLGAGLG VLWLNQHYFH

101 GNLLFYLTVG TASALAGWAA VGKNGYVPML AGLTMCMLIG DNGSEWFDSG

151 LMRAMNVLIG AAIAIAAAKL LPLKSTLMWR FMLADNLTDC SKMIAEISNG

201 RRMTRERLEE NMAKMRQINA RMVKSRSHLA ATSGESRISP AMMEAMQHAH

251 RKIVNTTELL LTTAAKLQSP KLNGSEIRLL DRHFTLLQTD LQQTVALING

301 RHARRIRIDT AINPELEALA EHLHYQWQGF LWLSTNMRQE ISALVILLQR

351 TRRKWLDAHE RQHLRQSLLE TREHS*
```

ORF146a and ORF146-1 show 99.5% identity in 374 aa overlap:

```
orf146a.pep  MNTSQRNRLVSRWLNSYERYRYRRLIHAVRLGGAVLFATASARLLHLQHGEWIGMTVFVV
             ||||||||||||||||||||||||||||||||||||||||||||||||||||||||||||
orf146-1     MNTSQRNRLVSRWLNSYERYRYRRLIHAVRLGGAVLFATASARLLHLQHGEWIGMTVFVV
orf146a.pep  LGMLQFQGAIYSKAVERMLGTVIGLGAGLGVLWLNQHYFHGNLLFYLTVGTASALAGWAA
             ||||||||||||||||||||||||||||||||||||||||||||||||||||||||||||
orf146-1     LGMLQFQGAIYSKAVERMLGTVIGLGAGLGVLWLNQHYFHGNLLFYLTVGTASALAGWAA
orf146a.pep  VGKNGYVPMLAGLTMCMLIGDNGSEWFDSGLMRAMNVLIGAAIAIAAAKLLPLKSTLMWR
             |||||||||||||||||||||||||||||:||||||||||||||||||||||||||||||
orf146-1     VGKNGYVPMLAGLTMCMLIGDNGSEWLDSGLMRAMNVLIGAAIAIAAAKLLPLKSTLMWR
orf146a.pep  FMLADNLTDCSKMIAEISNGRRMTRERLEENMAKMRQINARMVKSRSHLAATSGESRISP
             ||||||:|||||||||||||||||||||||||||||||||||||||||||||||||||||
orf146-1     FMLADNLADCSKMIAEISNGRRMTRERLEENMAKMRQINARMVKSRSHLAATSGESRISP
orf146a.pep  AMMEAMQHAHRKIVNTTELLLTTAAKLQSPKLNGSEIRLLDRHFTLLQTDLQQTVALING
             ||||||||||||||||||||||||||||||||||||||||||||||||||||||||||||
orf146-1     AMMEAMQHAHRKIVNTTELLLTTAAKLQSPKLNGSEIRLLDRHFTLLQTDLQQTVALING
orf146a.pep  RHARRIRIDTAINPELEALAEHLHYQWQGFLWLSTNMRQEISALVILLQRTRRKWLDAHE
             ||||||||||||||||||||||||||||||||||||||||||||||||||||||||||||
orf146-1     RHARRIRIDTAINPELEALAEHLHYQWQGFLWLSTNMRQEISALVILLQRTRRKWLDAHE
orf146a.pep  RQHLRQSLLETREHSX
             |||||||||||||||:
orf146-1     RQHLRQSLLETREHGX
```

Homology with a Predicted ORF from *N. gonorrhoeae*

ORF146 shows 97.3% identity over a 75aa overlap with a predicted ORF (ORF146ng) from *N. gonorrhoeae*:

```
orf146.pep                         RHARRIRIDTAINPELEALAEHLHYQWQGF  30
                                   ||||||||||||||||||||||||||||||
orf146ng     KLNGSEIRLLDRHFTLLQTDLQQTAALINGRHARRIRIDTAINPELEALAEHLHYQWQGF 364
```

```
orf146.pep  LWLSTDMRQEISALVILLQRTRRKWLDAHERQHLRQSLLETREHG       75
            |||||:|||||||||| ||||||||||||||||||||||||||||
orf146ng    LWLSTNMRQEISALVIPLQRTRRKWLDAHERQHLRQSLLETREHG       409
```

An ORF146ng nucleotide sequence <SEQ ID 635> was predicted to encode a protein having amino acid sequence <SEQ ID 636>:

```
  1 MSGVRFPSPA PIPSTDPPSG SLCFFTFPLQ TASDMNSSQR KRLSGRWLNS

51 YERYRHRRLI HAVRLGGTVL FATALARLLH LQHGEWIGMT VFVVLGMLQF

101 QGAIYSNAVE RMLGTVIGLG AGLGVLWLNQ HYFHGNLLFY LTIGTASALA

151 GWAAVGKNGY VPMLAGLTMC MLIGDNGSEW LDSGLMRAMN VLIGAAIAIA

201 AAKLLPLKST LMWRFMLADN LADCSKMIAE ISNGRRMTRE RLEQNMVKMR

251 QINARMVKSR SHLAATSGES RISPSMMEAM QHAHRKIVNT TELLLTTAAK

301 LQSPKLNGSE IRLLDRHFTL LQTDLQQTAA LINGRHARRI RIDTAINPEL

351 EALAEHLHYQ WQGFLWLSTN MRQEISALVI PLQRTRRKWL DAHERQHLRQ

401 SLLETREHG*
```

Further work revealed the following gonococcal DNA sequence <SEQ ID 637>:

```
   1 ATGAACTCCT CGCAACGCAA ACGCCTTTCC GgccGCTGGC TCAACTCCTA

51 CGAACGCTac cGCCaccGCC GCCTCATACA TGCCGTGCGG CTCGGCggaa 101 ccgtCCTGTT CGCCACCGCA CTCGCCCGgc tACTCCACCT CCAacacggc 151 gAATGGATAG GGAtgaCCGT CTTCGTCGTC CTCGGCATGC TCCAGTTCCA 201 AGGCgcgatt tActccaacg cggtgGAacg taTGctcggt acggtcatcg 251 ggctgGGCGC GGGTTTGGGc gTTTTATGGC TGAACCAGCA TTAtttccac 301 ggcaacCTcc tcttctacct gaccatcggc acggcaagcg cactggccgg 351 ctGGGCGGCG GTCGGCAAAA acggctacgt ccctatgctg GCGGGGctgA 401 CGATGTGCAT gctcatcggc gACAACGGCA GCGAATGGCT CGACAGCGGC

451 CTGATGCGCG CGATGAACGT CCTCATCGGC GCCGCCATCG CCATTGCCGC

501 CGCCAAACTG CTGCCGCTGA AATCCACACT GATGTGGCGT TTCATGCTTG

551 CCGACAACCT GGCCGACTGC AGCAAAATGA TTGCCGAAAT CAGCAACGGC

601 AGGCGTATGA CGCGCGAACG TTTGGAGCAG AATATGGTCA AAATGCGCCA

651 AATCAACGCA CGCATGGTCA AAAGCCGCAG CCACCTCGCC GCCACATCGG

701 GCGAAAGCCG CATCAGCCCC TCCATGATGG AAGCCATGCA GCACGCCCAC

751 CGCAAAATCG TCAACACCAC CGAGCTGCTC CTGACCACCG CCGCCAAGCT

801 GCAATCTCCC AAACTCAACG GCAGCGAAAT CCGGCTGCTC GACCGCCACT

851 TCACACTGCT CCAAACCGAC CTGCAACAAA CCGCCGCCCT CATCAACGGC

901 AGACACGCCC GCCGCATCCG CATCGACACC GCCATCAACC CCGAACTGGA

951 AGCCCTCGCC GAACACCTCC ACTACCAATG GCAGGGCTTC CTCTGGCTCA

1001 GCACCAATAT GCGTCAGGAA ATTTCCGCCC TCGTCATCCT GCTGCAACGC

1051 ACCCGCCGCA AATGGCTGGA TGCCCACGAA CGCCAACACC TGCGCCAAAG

1101 CCTGCTTGAA ACACGGGAAC ACGGCTGA
```

This corresponds to the amino acid sequence <SEQ ID 638; ORF146ng-1>:

```
  1 MNSSQRKRLS GRWLNSYERY RHRRLIHAVR LGGTVLFATA LARLLHLQHG

51 EWIGMTVFVV LGMLQFQGAI YSNAVERMLG TVIGLGAGLG VLWLNQHYFH

101 GNLLFYLTIG TASALAGWAA VGKNGYVPML AGLTMCMLIG DNGSEWLDSG

151 LMRAMNVLIG AAIAIAAAKL LPLKSTLMWR FMLADNLADC SKMIAEISNG

201 RRMTRERLEQ NMVKMRQINA RMVKSRSHLA ATSGESRISP SMMEAMQHAH

251 RKIVNTTELL LTTAAKLQSP KLNGSEIRLL DRHFTLLQTD LQQTAALING

301 RHARRIRIDT AINPELEALA EHLHYQWQGF LWLSTNMRQE ISALVILLQR

351 TRRKWLDAHE RQHLRQSLLE TREHG*
```

ORF146ng-1 and ORF146-1 show 96.5% identity in 375 aa overlap

```
orf146-1.pep  MNTSQRNRLVSRWLNSYERYRYRRLIHAVRLGGAVLFATASARLLHLQHGEWIGMTVFVV
              ||:|||:|| :|||||||||:|||||||||:||||| |||||||||||||||||||||
orf146ng-1    MNSSQRKRLSGRWLNSYERYRHRRLIHAVRLGGTVLFATALARLLHLQHGEWIGMTVFVV orf146-1.pep  LGMLQFQGAIYSKAVERMLGTVIGLGAGLGVLWLNQHYFHGNLLFYLTVGTASALAGWAA
              ||||||||||||:|||||||||||||||||||||||||||||||||||:|||||||||||
orf146ng-1    LGMLQFQGAIYSNAVERMLGTVIGLGAGLGVLWLNQHYFHGNLLFYLTIGTASALAGWAA orf146-1.pep  VGKNGYVPMLAGLTMCMLIGDNGSEWLDSGLMRAMNVLIGAAIAIAAAKLLPLKSTLMWR
              ||||||||||||||||||||||||||||||||||||||||||||||||||||||||||||
orf146ng-1    VGKNGYVPMLAGLTMCMLIGDNGSEWLDSGLMRAMNVLIGAAIAIAAAKLLPLKSTLMWR orf146-1.pep  FMLADNLADCSKMIAEISNGRRMTRERLEENMAKMRQINARMVKSRSHLAATSGESRISP
              |||||||||||||||||||||||||||||:||:|||||||||||||||||||||||||||
orf146ng-1    FMLADNLADCSKMIAEISNGRRMTRERLEQNMVKMRQINARMVKSRSHLAATSGESRISP orf146-1.pep  AMMEAMQHAHRKIVNTTELLLTTAAKLQSPKLNGSEIRLLDRHFTLLQTDLQQTVALING
              :|||||||||||||||||||||||||||||||:||:|||||||||||||||||||:||||
orf146ng-1    SMMEAMQHAHRKIVNTTELLLTTAAKLQSPKLNGSEIRLLDRHFTLLQTDLQQTAALING orf146-1.pep  RHARRIRIDTAINPELEALAEHLHYQWQGFLWLSTNMRQEISALVILLQRTRRKWLDAHE
              ||||||||||||||||||||||||||||||||||||||||||||||||||||||||||||
orf146ng-1    RHARRIRIDTAINPELEALAEHLHYQWQGFLWLSTNMRQEISALVILLQRTRRKWLDAHE orf146-1.pep  RQHLRQSLLETREHGX
              ||||||||||||||||
orf146ng-1    RQHLRQSLLETREHGX
```

Furthermore, ORF146ng-1 shows homology with a hypothetical *E. coli* protein:

```
sp|P33011|YEEA_ECOLI HYPOTHETICAL 40.0 KD PROTEIN IN COBU-SBMC INTERGENIC
REGION >gi|1736674|gnl|PID|d1016553 (D90838) ORF_ID: o348#20; similar to
[SwissProt Accession Number P33011] [Escherichia coli]
>gi|1736682|gnl|PID|d1016560 (D90839) ORF_ID: o348#20; similar to
[SwissProt Accession Number P33011] [Escherichia coli] >gi|1788318
(AE000292) f352; 100% identical to fragment YEEA_ECOLI SW: P33011 but has
203 additional C-terminal residues [Escherichia coli] Length = 352
Score = 109 bits (271), Expect = 2e-23
Identities = 89/347 (25%),   Positives = 150/347 (42%), Gaps = 21/347 (6%)

Query:  20 YRHRRLIHAVRLGGTVLFATALARLLHLQHGEWIGMTVFVVLGMLQFQGAIYSNAVERML    79
           YRH R++H  R+     L   + RL  +     W +T+ V++G + F G +    A ER+
Sbjct:  15 YRHYRIVHGTRVALAFLLTFLIIRLFTIPESTWPLVTMVVIMGPISFWGNVVPRAFERIG    74

Query:  80 GTVIGLGAGLGVLWLNQHYFHGNLLFYLTIGTASALAGWAAVGKNGYVPMLAGLTMCMLI   139
           GTV+G  GL  L L         L +    A  L GW A+GK Y +L G+T+ +++
Sbjct:  75 GTVLGSILGLIALQLE---LISLPLMLVWCAAAMFLCGWLALGKKPYQGLLIGVTLAIVV   131

Query: 140 GDNGSEWLDSGLMRAMNVLIGXXXXXXXXXXKLLPLKSTLMWRFMLADNLADCSKMIAEISN   199
           G    E +D+ L R+ +V++G         + P ++ + WR  LA +L +  +++  +
Sbjct: 132 GSPTGE-IDTALWRSGDVILGSLLAMLFTGIWPQRAFIHWRIQLAKSLTEYNRVYQSAFS   190

Query: 200 GRRMTRERLEQNMVKMRQINARMVKSRSHLAATSGESRISPSMMEAMQHAHRKIVNXXXX   259
            + R  RLE ++  K+       VK R  +A   S  E+RI  S+  E +Q   +R +V
Sbjct: 191 PNLLERPRLESHLQKLL---TDAVKMRGLIAPASKETRIPKSIYEGIQTINRNLVCMLEL   247
```

```
Query:  260 XXXXXXXXQSPK---LNGSEIRLLDRHFXXXXXXXXXXXAALINGRHARRIRIDTAINPEL   316
                    +       LN ++R D              AL G            +N +
Sbjct:  248 QINAYWATRPSHFVLLNAQKLR--DTQHMMQQILLSLVHALYEGNPQPVFANTEKLNDAV   305

Query:  317 EALAEHL--HYQWQ-------GFLWLSTNMRQEISALVILLQRTRRK              354
            E L + L  H+ +        G++WL+    ++ L  L+ R RK
Sbjct:  306 EELRQLLNNHHDLKVVETPIYGYVWLNMETAHQLELLSNLICRALRK              352
```

On the basis of this analysis, including the identification of several transmembrane domains in the gonococcal protein, it is predicted that the proteins from *N. meningitidis* and *N. gonorrhoeae*, and their epitopes, could be useful antigens for vaccines or diagnostics, or for raising antibodies.

Example 76

The following partial DNA sequence was identified in *N. meningitidis* <SEQ ID 639>

```
  1  ..GCCGAAGACA CGCGCGTTAC CGCACAGCTT TTGAGCGCGT ACGGCATTCA
 51    GGGCAAACTC GTCAGTGTGC GCGAACACAA CGAACGGCAG ATGGCGGACA
101    AGATTGTCGG CTATCTTTCA GACGGCATGG TTGTGGCACA GGTTTCCGAT
151    GCGGGTACGC CGGCCGTGTG CGACCCGGGC GCGAAACTCG CCCGCCGCGT
201    GCGTGAGGCC GGGTTTAAAG TCGTTCCCGT CGTGGGCGCA AC.GCGGTGA
251    TGGCGGCTTT GAGCGTGGCC GGTGTGGAAG GATCCGATTT TTATTTCAAC
301    GGTTTTGTAC CGCCGAAATC GGGAGAACGC AGGAAACTGT TTGCCAAATG
351    GGTGCGGGCG GCGTTTCCTA TCGTCATGTT TGAAACGCCG CACCGCATCG
401    GTGCAGCGCT TGCCGATATG GCGGAACTGT TCCCCGAACG CCGATTAATG
451    CTGGCGCGCG AAATTACGAA AACGTTTGAA ACGTTCTTAA GCGGCACGGT
501    TGGGGAAATT CAGACGGCAT TGTCTGCCGA CGGCGACCAA TCGCGCGGCG
551    AGATGGTGTT GGTGCTTTAT CCGGCGCAGG ATGAAAAACA CGAAGGCTTG
601    TCCGAGTCCG CGCAAAACAT CATGAAAATC CTCACAGCCG AGCTGCCGAC
651    CAAACAGGCG GCGGAGCTTG CTGCCAAAAT CACGGGCGAG GGAAAGAAAG
701    CTTTGTACGA T..
```

This corresponds to the amino acid sequence <SEQ ID 640; ORF147>:

```
  1  ..AEDTRVTAQL LSAYGIQGKL VSVREHNERQ MADKIVGYLS DGMVVAQVSD
 51    AGTPAVCDPG AKLARRVREA GFKVVPVVGA XAVMAALSVA GVEGSDFYFN
101    GFVPPKSGER RKLFAKWVRA AFPIVMFETP HRIGAALADM AELFPERRLM
151    LAREITKTFE TFLSGTVGEI QTALSADGDQ SRGEMVLVLY PAQDEKHEGL
201    SESAQNIMKI LTAELPTKQA AELAAKITGE GKKALYD..
```

Further work revealed the complete nucleotide sequence <SEQ ID 641>:

```
  1  ATGTTTCAGA AACATTTGCA GAAAGCCTCC GACAGCGTCG TCGGAGGGAC
 51  ATTATACGTG GTTGCCACGC CCATCGGCAA TTTGGCGGAC ATTACCCTGC
```

```
101 GCGCTTTGGC GGTATTGCAA AAGGCGGACA TCATCTGTGC CGAAGACACG

151 CGCGTTACCG CACAGCTTTT GAGCGCGTAC GGCATTCAGG GCAAACTCGT

201 CAGTGTGCGC GAACACAACG AACGGCAGAT GGCGGACAAG ATTGTCGGCT

251 ATCTTTCAGA CGGCATGGTT GTGGCACAGG TTTCCGATGC GGGTACGCCG

301 GCCGTGTGCG ACCCGGGCGC GAAACTCGCC CGCCGCGTGC GTGAGGCCGG

351 GTTTAAAGTC GTTCCCGTCG TGGGCGCAAG CGCGGTGATG GCGGCTTTGA

401 GCGTGGCCGG TGTGGAAGGA TCCGATTTTT ATTTCAACGG TTTTGTACCG

451 CCGAAATCGG GAGAACGCAG GAAACTGTTT GCCAAATGGG TGCGGGCGGC

501 GTTTCCTATC GTCATGTTTG AAACGCCGCA CCGCATCGGT GCGACGCTTG

551 CCGATATGGC GGAACTGTTC CCCGAACGCC GATTAATGCT GGCGCGCGAA

601 ATTACGAAAA CGTTTGAAAC GTTCTTAAGC GGCACGGTTG GGGAAATTCA

651 GACGGCATTG TCTGCCGACG GCAACCAATC GCGCGGCGAG ATGGTGTTGG

701 TGCTTTATCC GGCGCAGGAT GAAAAACACG AAGGCTTGTC CGAGTCCGCG

751 CAAAACATCA TGAAAATCCT CACAGCCGAG CTGCCGACCA AACAGGCGGC

801 GGAGCTTGCT GCCAAAATCA CGGGCGAGGG AAAGAAAGCT TTGTACGATC

851 TGGCTCTGTC TTGGAAAAAC AAATAG
```

This corresponds to the amino acid sequence <SEQ ID 642; ORF147-1>:

```
  1 MFQKHLQKAS DSVVGGTLYV VATPIGNLAD ITLRALAVLQ KADIICAEDT

51 RVTAQLLSAY GIQGKLVSVR EHNERQMADK IVGYLSDGMV VAQVSDAGTP

101 AVCDPGAKLA RRVREAGFKV VPVVGASAVM AALSVAGVEG SDFYFNGFVP

151 PKSGERRKLF AKWVRAAFPI VMFETPHRIG ATLADMAELF PERRLMLARE

201 ITKTFETFLS GTVGEIQTAL SADGNQSRGE MVLVLYPAQD EKHEGLSESA

251 QNIMKILTAE LPTKQAAELA AKITGEGKKA LYDLALSWKN K*
```

Computer analysis of this amino acid sequence gave the following results:

Homology with Hypothetical Protein ORF286 of *E. coli* (Accession Number U18997)

ORF147 and *E. coli* ORF286 protein show 36% aa identity in 237aa overlap:

```
Orf147:    1 AEDTRVTAQLLSAYGIQGKLVSVREHNERQMADKIVGYLSDGMVVAQVSDAGTPAVCDPG   60
             AEDTR T  LL +GI  +L ++ +HNE+Q A+ ++   L +G  +A VSDAGTP + DPG
Orf286:   43 AEDTRHTGLLLQHFGINARLFALHDHNEQQKAETLLAKLQEGQNIALVSDAGTPLINDPG  102

Orf147:   61 AKLARRVREXXXXXXXXXXXXXXXXXXXXXXXXXXXEGSDFYFNGFVPPKSGERRKLFAKWVRA  120
             L   R   RE                              F + GF+P KS  RR
Orf286:  103 YHLVRTCREAGIRVVPLPGPCAAITALSAAGLPSDRFCYEGFLPAKSKGRRDALKAIEAE  162

Orf147:  121 AFPIVMFETPHRIGAALADMAELFPERR-LMLAREITKTFETFLSGTVGEIQTALSADGD  179
                ++ +E+ HR+  +L D+  +  E R  ++LARE+TKT+ET     VGE+   + D +
Orf286:  163 PRTLIFYESTHRLLDSLEDIVAVLGESRYVVLARELTKTWETIHGAPVGELLAWVKEDEN  222

Orf147:  180 QSRGEMVLVLYPAQDEKHEGLSESAQNIMKILTAELPTKQAAELAAKITGEGKKALY    236
             +  +GEMVL++     +  E  L   A     + +L AELP K+AA LAA+I G  K ALY
Orf286:  223 RRKGEMVLIV-EGHKAQEEDLPADALRTLALLQAELPLKKAAALAAEIHGVKKNALY    278
```

Homology with a Predicted ORF from *N. meningitidis* (Strain A)

ORF147 shows 96.6% identity over a 237aa overlap with ORF75a from strain A of *N. meningitidis*:

```
                                            10        20        30
    orf147.pep                      AEDTRVTAQLLSAYGIQGKLVSVREHNERQ
                                    ||||||||||||||||||||||||||||||
    orf75a      TLYVVATPIGNLADITLRALAVLQKADIICAEDTRVTAQLLSAYGIQGKLVSVREHNERQ
                    20        30        40        50        60        70
                        40        50        60        70        80        90
    orf147.pep  MADKIVGYLSDGMVVAQVSDAGTPAVCDPGAKLARRVREAGFKVVPVVGAXAVMAALSVA
                ||||||||||||||||||||||||||||||||||||||||:|||||||| ||||||||||
    orf75a      MADKIVGYLSDGMVVAQVSDAGTPAVCDPGAKLARRVREVGFKVVPVVGASAVMAALSVA
                    80        90       100       110       120       130
                       100       110       120       130       140       150
    orf147.pep  GVEGSDFYFNGFVPPKSGERRKLFAKWVRAAFPIVMFETPHRIGAALADMAELFPERRLM
                || |||||||||||||||||||||||||||||:|||:|||||||||:|||||||||||||
    orf75a      GVAGSDFYFNGFVPPKSGERRKLFAKWVRVAFPVVMFETPHRIGATLADMAELFPERRLM
                   140       150       160       170       180       190
                       160       170       180       190       200       210
    orf147.pep  LAREITKTFETFLSGTVGEIQTALSADGDQSRGEMVLVLYPAQDEKHEGLSESAQNIMKI
                || |||||||||||||||||||||||:|||:|||||||||||||||||||||||||||||
    orf75a      LAREITKTFETFLSGTVGEIQTALAADGNQSRGEMVLVLYPAQDEKHEGLSESAQNIMKI
                   200       210       220       230       240       250
                       220       230
    orf147.pep  LTAELPTKQAAELAAKITGEGKKALYD
                |||||||||||||||||||||||||||
    orf75a      LTAELPTKQAAELAAKITGEGKKALYDLALSWKNKX
                   260       270       280       290
```

ORF147a is identical to ORF75a, which includes aa 56-292 of ORF75.

Homology with a Predicted ORF from *N. gonorrhoeae*

ORF147 shows 94.1% identity over a 237aa overlap with a predicted ORF (ORF147ng) from *N. gonorrhoeae*:

```
    orf147.pep                      AEDTRVTAQLLSAYGIQGKLVSVREHNERQ   30
                                    |||||||||||||||||:||||||||||||
    orf147ng    TLYVVATPIGNLADITLRALAVLQKADIICAEDTRVTAQLLSAYGIQGRLVSVREHNERQ   85
    orf147.pep  MADKIVGYLSDGMVVAQVSDAGTPAVCDPGAKLARRVREAGFKVVPVVGAXAVMAALSVA   90
                ||||::|:||||:|||||||||||||||||||||||||||||||||||||:|||||||||
    orf147ng    MADKVIGFLSDGLVVAQVSDAGTPAVCDPGAKLARRVREAGFKVVPVVGASAVMAALSVA  145
    orf147.pep  GVEGSDFYFNGFVPPKSGERRKLFAKWVRAAFPIVMFETPHRIGAALADMAELFPERRLM  150
                || |||||||||||||||||||||||||||||:|||||||||||||:|||||||||||||
    orf147ng    GVAESDFYFNGFVPPKSGERRKLFAKWVRAAFPVVMFETPHRIGATLADMAELFPERRLM  205
    orf147.pep  LAREITKTFETFLSGTVGEIQTALSADGDQSRGEMVLVLYPAQDEKHEGLSESAQNIMKI  210
                ||||||||||||||||||||||||:|||:|||||||||||||||||||||||||||:|||
    orf147ng    LAREITKTFETFLSGTVGEIQTALAADGNQSRGEMVLVLYPAQDEKHEGLSESAQNAMKI  265
    orf147.pep  LTAELPTKQAAELAAKITGEGKKALYD                                   237
                |:|||||||||||||||||||||||||
    orf147ng    LAAELPTKQAAELAAKITGEGKKALYDLALSWKNK                           300
```

An ORF147ng nucleotide sequence <SEQ ID 643> was predicted to encode a protein having amino acid sequence <SEQ ID 644>:

```
  1 MSVFQTAFFM FQKHLQKASD SVVGGTLYVV ATPIGNLADI TLRALAVLQK

51 ADIICAEDTR VTAQLLSAYG IQGRLVSVRE HNERQMADKV IGFLSDGLVV

101 AQVSDAGTPA VCDPGAKLAR RVREAGFKVV PVVGASAVMA ALSVAGVAES

151 DFYFNGFVPP KSGERRKLFA KWVRAAFPVV MFETPHRIGA TLADMAELFP

201 ERRLMLAREI TKTFETFLSG TVGEIQTALA ADGNQSRGEM VLVLYPAQDE

251 KHEGLSESAQ NAMKILAAEL PTKQAAELAA KITGEGKKAL YDLALSWKNK

301 *
```

Further work revealed the following gonococcal DNA sequence <SEQ ID 645>:

```
  1 ATGTTTCAGA AACACTTGCA GAAAGCCTCC GACAGCGTCG TCGGAGGGAC
 51 ATTATACGTG GTTGCCACGC CCATCGGCAA TTTGGCAGAC ATTACCCTGC
101 GCGCTTTGGC GGTATTGCAA AAGGCGGACA TCATTTGTGC CGAAGACACG
151 CGCGTTACTG CGCAGCTTTT GAGCGCGTAC GGCATTCAGG GCAGGTTGGT
201 CAGTGTGCGC GAACACAACG AGCGGCAGAT GGCGGACAAG GTAATCGGTT
251 TCCTTTCAGA CGGCCTGGTT GTGGCGCAGG TTTCCGATGC GGGTACGCCG
301 GCCGTGTGCG ACCCGGGCGC GAAACTCGCC CGCCGCGTGC GCGAAGCAGG
351 GTTCAAAGTC GTTCCCGTCG TGGGCGCAAG CGCGGTAATG GCGGCGTTGA
401 GTGTGGCCGG TGTGGCGGAA TCCGATTTTT ATTTCAACGG TTTTGTACCG
451 CCGAAATCGG GCGAACGTAG GAAATTGTTT GCCAAATGGG TGCGGGCGGC
501 ATTTCCTGTC GTCATGTTTG AAACGCCGCA CCGAATCGGG GCAACGCTTG
551 CCGATATGGC GGAATTGTTC CCCGAACGCC GTCTGATGCT GGCGCGCGAA
601 ATCACGAAAA CGTTTGAAAC GTTCTTAAGC GGCACGGTTG GGGAAATTCA
651 GACGGCATTG GCGGCGGACG GCAACCAATC GCGCGGCGAG ATGGTGTTGG
701 TGCTTTATCC GGCGCAGGAT GAAAAACACG AAGGCTTGTC CGAGTCTGCG
751 CAAAATGCGA TGAAAATCCT TGCGGCCGAG CTGCCGACCA AGCAGGCGGC
801 GGAGCTTGCC GCCAAGATTA CAGGTGAGGG CAAAAAGGCT TTGTACGATT
851 TGGCACTGTC GTGGAAAAAC AAATGA
```

This corresponds to the amino acid sequence <SEQ ID 646; ORF147ng-1>:

```
  1 MFQKHLQKAS DSVVGGTLYV VATPIGNLAD ITLRALAVLQ KADIICAEDT
 51 RVTAQLLSAY GIQGRLVSVR EHNERQMADK VIGFLSDGLV VAQVSDAGTP
101 AVCDPGAKLA RRVREAGFKV VPVVGASAVM AALSVAGVAE SDFYFNGFVP
151 PKSGERRKLF AKWVRAAFPV VMFETPHRIG ATLADMAELF PERRLMLARE
201 ITKTFETFLS GTVGEIQTAL AADGNQSRGE MVLVLYPAQD EKHEGLSESA
251 QNAMKILAAE LPTKQAAELA AKITGEGKKA LYDLALSWKN K*
```

ORF147ng shows homology to a hypothetical *E. coli* protein:

```
sp|P45528|YRAL_ECOLI HYPOTHETICAL 31.3 KD
PROTEIN IN AGAI-MTR INTERGENIC REGION (F286)
>gi|606086 (U18997) ORF_f286 [Escherichia coli]
>gi|1789535 (AE000395) hypothetical 31.3 kD protein in agai-mtr inter-
genic region
[Escherichia coli] Length = 286
Score = 218 bits (550), Expect = 3e-56
Identities = 128/284 (45%), Positives = 171/284 (60%),
Gaps = 4/284 (1%)

Query:   4 KHLQKASDSVVGGTLYVVATPIGNLADITLRALAVLQKADIICAEDTRVTAQLLSAYGIQ 63
           K Q A +S  G LY+V TPIGNLADIT RAL VLQ  D+I AEDTR T LL  +GI
Sbjct:   2 KQHQSADNSQ--GQLYIVPTPIGNLADITQRALEVLQAVDLIAAEDTRHTGLLLQHFGIN 59

Query:  64 GRLVSVREHNERQMADKVIGFLSDGLVVAQVSDAGTPAVCDPGAKLARRVREAGFKVVPV 123
           RL ++ +HNE+Q A+ ++  L +G +A VSDAGTP + DPG L R  REAG +VVP+
Sbjct:  60 ARLFALHDHNEQQKAETLLAKLQEGQNIALVSDAGTPLINDPGYHLVRTCREAGIRVVPL 119
```

-continued

```
Query: 124 VGASAVMAALSVAGVAESDFYFNGFVPPKSGERRKLFAKWVRAAFPVVMFETPHRIGATL 183
            G  A +  ALS  AG+     F +  GF+P KS  RR          ++ +E+ HR+   +L
Sbjct: 120 PGPCAAITALSAAGLPSDRFCYEGFLPAKSKGRRDALKAIEAEPRTLIFYESTHRLLDSL 179

Query: 184 ADMAELFPERR-LMLAREITKTFETFLSGTVGEIQTALAADGNQSRGEMVLVLYPAQDEK 242
            D+    +  E R  ++LARE+TKT+ET       VGE+   +  D N+ +GEMVL++          +
Sbjct: 180 EDIVAVLGESRYVVLARELTKTWETIHGAPVGELLAWVKEDENRRKGEMVLIV-EGHKAQ 238

Query: 243 HEGLSESAQNAMKILAAELPTKQAAELAAKITGEGKKALYDLAL                  286
              E L   A    + +L AELP K+AA LAA+I  G   K ALY   AL
Sbjct: 239 EEDLPADALRTLALLQAELPLKKAAALAAEIHGVKKNALYKYAL                  282
```

Based on the computer analysis and the presence of a putative transmembrane domain in the gonococcal protein, it is predicted that these proteins from *N. meningitidis* and *N. gonorrhoeae*, and their epitopes, could be useful antigens for vaccines or diagnostics, or for raising antibodies.

Example 77

The following partial DNA sequence was identified in *N. meningitidis* <SEQ ID 647>

```
   1 ATGAAAACAA CCGACAAACG GACAACCGAA ACACACCGCA AAGCCCCGAA
  51 AACCGGTCGC ATCCGCTTCT C.GCTGCTTA CTTAGCCATA TGCCTGTCGT
 101 TCGGCATTCT TCCCCAAGCC TGGGCGGGAC ACACTTATTT CGGCATCAAC
 151 TACCAATACT ATCGCGACTT TGCCGAAAAT AAAGGCAAGT TTGCAGTCGG
 201 GGCGAAAGAT ATTGAGGTTT ACAACAAAAA AGGGGAGTTG GTCGGCAAAT
 251 CAATGACAAA AGCCCCGATG ATTGATTTTT CTGTGGTGTC GCGTAACGGC
 301 GTGGCGGcAT TGGTGGGCGt ATCAATATAT TGTGAGCGTG GCACATAACG
 351 GCGGCTATAA CAACGTTGAT TTTGGTGCGG AAGGAAk.AA tATCCC.GAT
 401 CAACAwCGww TTACTTATAA AATTGTGAAA CGGAATAATT ATAAAGCAGG
 451 GACTAAAGGC CATCCTTATG GCGGCGATTA TCATATGCCG CGTTTGCATA
 501 AATwTGTCAC AGATGCAGAA CCTGTTGAAA TGACCAGTTA TATGGATGGG
 551 CGGAAATATA TCGATCAAAA TAATTACCCT GACCGTGTTC GTATTGGGGC
 601 AGGCAGGCAA TATTGGCGAT CTGATGAAGA TGAGCCCAAT AACCGCGAAA
 651 GTTCATATCA TATTGCAAGT .......... .......... ..........
 701 .......... .....GGCTC ACCAATGTTT ATCTATGATG CCCAAAAGCA
 751 AAAGTGGTTA ATTAATGGGG TATTGCAAAC GGGCAACCCC TATATAGGAA
 801 AAAGCAATGG CTTCCAGCTG GTTCGTAAAG ATTGGTTCTA TGATGAAATC
 851 TTTGCTGGAG ATACCCATTC AGTATTCTAC GAACCACGTC AAAATGGGAA
 901 ATACTCTTTT AACGACGATA ATAATGCAC AGGAAAAATC AATGCCAAAC
 951 AATGAACACAA TTCTCTGCCT AATAGATTAA AAACACGAAC CGTTCAATTG
1001 TTTAATGTTT CTTTATCCGA GACAGCAAGA GAACCTGTTT ATCATGCTGC
1051 AGGTGGTGTC AACAGTTATC GACCCAGACT GAATAATGGA GAAAATATTT
1101 CCTTTATTGA CGAAGGAAAA GGCGAATTGA TACTTACCAG CAACATCAAT
1151 CAAGGTGCTG GAGGATTATA TTTCCAAGGA GATTTTACGG TCTCGCCTGA
1201 AAATAACGAA ACTTGGCAAG GCGCGGGCGT TCATATCAGT GAAGACAGTA
1251 CCGTTACTTG GAAAGTAAAC GGCGTGGCAA ACGACCGCCT GTCCAAAATC
1301 GGCAAAGGCA CGCTG..... .......... .......... ..........
                                 //
2101 .......... .......... .......... .......... ...GATAAAG
2151 TGACTGCTTC ATTGACTAAG ACCGACATCA GCGGCAATGT CGATCTTGCC
2201 GATCACGCTC ATTTAAATCT CACAGGGCTT GCCACACTCA ACGGCAATCT
2251 TAGTGCAAAT GGCGATACAC GTTATACAGT CAGCCACAAC GCCACCCAAA
2301 ACGGCAACCk TAgCCtCGtG G.sAATGcCC AAGCAACATT TAATCAAGCC
2351 ACATTAAACG GCAACACATC GGCTTCgGGC AATGCTTCAT TTAATCTAAG
2401 CGACCACGCC GTACAAAACG GCAGTCTGAC GCTTTCCGGC AACGCTAAGG
2451 CAAACGTAAG CCATTCCGCA CTCAACGGTA ATGTCTCCCT AGCCGATAAG
2501 GCAGTATTCC ATTTTCAAAG CAGCCGCTTT ACCGGACAAA TCAGCGGCGG
2551 CAagGATACG GCATTACACT TAAAAGACAG CGAATGGACG CTGCCGTCAg
2601 GarCGGAATT AGGCAATTTA AACCTTGACA ACGCCACCAT TACaCTCAAT
2651 TCCGCCTATC GCCACGATGC GGCAGGGGCG CAAACCGGCA GTGCGACAGA
2701 TGCGCCGCGC CGCCGTTCGC GCCGTTCGCG CCGTTCCCTA TTAtmCGTTA
2751 CACCGCCAAC TTCGGTAGAA TCCCGTTTCA ACACGCTGAC GGTAAACGGC
2801 AAATTGAACG GRCAGGGAAC ATTCCGCTTT ATGTCGGAAC TCTTCGGCTA
2851 CCGCAGCGAC AAATTGAAGC TGGCGGAAAG TTCCGAAGGC ACTTACACCT
2901 TGGCGGTCAA CAATACCGGC AACGAACCTG CAAGCCTCGA ACAATTGACG
2951 GTAGTGGAAG GAAAAGACAA CAAACCGCTG TCCGAAAACC TTAATTTCAC
3001 CCTGCAAAAC GAACACGTCG ATGCAGGCGC GTGG...... ..........
                                 //
3551 .......... .......... ....TTAGAC CGCGTATTTG CCGAAGACCG
3601 CCGCAACGCC GTTTGGACAA GCGGCATCCG GGACACCAAA CACTACCGTT
3651 CGCAAGATTT CCGCGCCTAC CGCCAACAAA CCGACCTGCG CCAAATCGGT
3701 ATGCAGAAAA ACCTCGGCAG CGGGCGCGTC GGCATCCTGT TTTCGCACAA
3751 CCGGACCGAA AACACCTTCG ACGACGGCAT CGGCAACTCG GCACGGCTTG
3801 CCCACGGCGC CGTTTTCGGG CAATACGGCA TCGACAGGTT CTACATCGGC
3851 ATCAGnCGCG GGCGCGGGTT TTAGCAGCGG CAGCCTTTcA GACGGCATCG
3901 GAGsmAAAwT CCGCCGCCGC GTGCtGCATT ACGGCATTCA GGCACGAtAC
3951 CGCGCCGgtt tCggCGgATt CGGCATCGAA CCGCACATCG GCGCAACGCg
4001 ctATTTCGTC CAAAAAGCGG ATTACCGCTA CGAAAACGTC AATATCGCCA
4051 CCCCCGGCCT TGCATTCAAC CGcTACCGCG CGGGCATTAa GGCAGATTAT
4101 TCATTCAAAC CGGCGCAACA CATTTCCATC ACGCCTTATT TGAGCCTGTC
4151 CTATACCGAT GCCGCTTCGG GCAAAGTCCG AACACGCGTC AATACCGCCG
4201 TATTGGCTCA GGATTTCGGC AAAACCCGCA GTGCGGAATG GGgCGTAAAC
4251 GCCGAAATCA AAGGTTTCAC GCTGTCCCTC CACGCTGCCG CCGCCAAAGG
4301 CCCGCAACTG GAAGCGCAAC ACAGCGCGGG CATCAAATTA GGCTACCGCT
4351 GGTAA...
```

This corresponds to the amino acid sequence <SEQ ID 648; ORF1>:

```
   1 MKTTDKRTTE THRKAPKTGR IRFXAAYLAI CLSFGILPQA WAGHTYFGIN
  51 YQYYRDFAEN KGKFAVGAKD IEVYNKKGEL VGKSMTKAPM IDFSVVSRNG
 101 VAALVGVQYI VSVAHNGGYN NVDFGAEGXN IXDQXRXTYK IVKRNNYKAG
 151 TKGHPYGGDY HMPRLHKXVT DAEPVEMTSY MDGRKYIDQN NYPDRVRIGA
 201 GRQYWRSDED EPNNRESSYH IAS....... ........GS PMFIYDAQKQ
 251 KWLINGVLQT GNPYIGKSNG FQLVRKDWFY DEIFAGDTHS VFYEPRQNGK
 301 YSFNDDNNGT GKINAKHEHN SLPNRLKTRT VQLFNVSLSE TAREPVYHAA
 351 GGVNSYRPRL NNGENISFID EGKGELILTS NINQGAGGLY FQGDFTVSPE
 401 NNETWQGAGV HISEDSTVTW KVNGVANDRL SKIGKGTL.. ..........
                                //
 701 .......... ....DKVTAS LTKTDISGNV DLADHAHLNL TGLATLNGNL
 751 SANGDTRYTV SHNATQNGNX SLVXNAQATF NQATLNGNTS ASGNASFNLS
 801 DHAVQNGSLT LSGNAKANVS HSALNGNVSL ADKAVFHFES SRFTGQISGG
 851 KDTALHLKDS EWTLPSGXEL GNLNLDNATI TLNSAYRHDA AGAQTGSATD
 901 APRRRSRRSR RSLLXVTPPT SVESRFNTLT VNGKLNGQGT FRFMSELFGY
 951 RSDKLKLAES SEGTYTLAVN NTGNEPASLE QLTVVEGKDN KPLSENLNFT
1001 LQNEXVDAGA W......... .......... .......... ..........
                                //
1151 .......... .......... .......... .......... .LDRVFAEDR
1201 RNAVWTSGIR DTKHYRSQDF RAYRQQTDLR QIGMQKNLGS GRVGILFSHN
1251 RTENTFDDGI GNSARLAHGA VFGQYGIDRF YIGISAGAGF SSGSLSDGIG
1301 XKXRRRVLHY GIQARYRAGF GGFGIEPHIG ATRYFVQKAD YRYENVNIAT
1351 PGLAFNRYRA GIKADYSFKP AQHISITPYL SLSYTDAASG KVRTRVNTAV
1401 LAQDFGKTRS AEWGVNAEIK GFTLSLHAAA AKGPQLEAQH SAGIKLGYRW
1451 *
```

Further sequencing analysis revealed the complete nucleotide sequence <SEQ ID 649>:

```
   1 ATGAAAACAA CCGACAAACG GACAACCGAA ACACACCGCA AAGCCCCGAA
  51 AACCGGCCGC ATCCGCTTCT CGCCTGCTTA CTTAGCCATA TGCCTGTCGT
 101 TCGGCATTCT TCCCCAAGCC TGGGCGGGAC ACACTTATTT CGGCATCAAC
 151 TACCAATACT ATCGCGACTT TGCCGAAAAT AAAGGCAAGT TTGCAGTCGG
 201 GGCGAAAGAT ATTGAGGTTT ACAACAAAAA AGGGGAGTTG GTCGGCAAAT
 251 CAATGACAAA AGCCCCGATG ATTGATTTTT CTGTGGTGTC GCGTAACGGC
 301 GTGGCGGCAT TGGTGGGCGA TCAATATATT GTGAGCGTGG CACATAACGG
 351 CGGCTATAAC AACGTTGATT TTGGTGCGGA AGGAAGAAAT CCCGATCAAC
 401 ATCGTTTTAC TTATAAAATT GTGAAACGGA ATAATTATAA AGCAGGGACT
 451 AAAGGCCATC CTTATGGCGG CGATTATCAT ATGCCGCGTT TGCATAAATT
 501 TGTCACAGAT GCAGAACCTG TTGAAATGAC CAGTTATATG GATGGGCGGA
 551 AATATATCGA TCAAAATAAT TACCCTGACC GTGTTCGTAT TGGGGCAGGC
 601 AGGCAATATT GGCGATCTGA TGAAGATGAG CCCAATAACC GCGAAAGTTC
 651 ATATCATATT GCAAGTGCGT ATTCTTGGCT CGTTGGTGGC AATACCTTTG
 701 CACAAAATGG ATCAGGTGGT GGCACAGTCA ACTTAGGTAG TGAAAAAATT
 751 AAACATAGCC CATATGGTTT TTTACCAACA GGAGGCTCAT TTGGCGACAG
 801 TGGCTCACCA ATGTTTATCT ATGATGCCCA AAAGCAAAAG TGGTTAATTA
 851 ATGGGGTATT GCAAACGGGC AACCCCTATA TAGGAAAAAG CAATGGCTTC
 901 CAGCTGGTTC GTAAAGATTG GTTCTATGAT GAAATCTTTG CTGGAGATAC
 951 CCATTCAGTA TTCTACGAAC CACGTCAAAA TGGGAAATAC TCTTTTAACG
1001 ACGATAATAA TGGCACAGGA AAAATCAATG CCAAACATGA ACACAATTCT
1051 CTGCCTAATA GATTAAAAAC ACGAACCGTT CAATTGTTTA ATGTTTCTTT
1101 ATCCGAGACA GCAAGAGAAC CTGTTTATCA TGCTGCAGGT GGTGTCAACA
1151 GTTATCGACC CAGACTGAAT AATGGAGAAA ATATTTCCTT TATTGACGAA
```

```
-continued
1201 GGAAAAGGCG AATTGATACT TACCAGCAAC ATCAATCAAG GTGCTGGAGG

1251 ATTATATTTC CAAGGAGATT TTACGGTCTC GCCTGAAAAT AACGAAACTT

1301 GGCAAGGCGC GGGCGTTCAT ATCAGTGAAG ACAGTACCGT TACTTGGAAA

1351 GTAAACGGCG TGGCAAACGA CCGCCTGTCC AAAATCGGCA AAGGCACGCT

1401 GCACGTTCAA GCCAAAGGGG AAAACCAAGG CTCGATCAGC GTGGGCGACG

1451 GTACAGTCAT TTTGGATCAG CAGGCAGACG ATAAAGGCAA AAAACAAGCC

1501 TTTAGTGAAA TCGGCTTGGT CAGCGGCAGG GGTACGGTGC AACTGAATGC

1551 CGATAATCAG TTCAACCCCG ACAAACTCTA TTTCGGCTTT CGCGGCGGAC

1601 GTTTGGATTT AAACGGGCAT TCGCTTTCGT TCCACCGTAT TCAAATACC

1651 GATGAAGGGG CGATGATTGT CAACCACAAT CAAGACAAAG AATCCACCGT

1701 TACCATTACA GGCAATAAAG ATATTGCTAC AACCGGCAAT AACAACAGCT

1751 TGGATAGCAA AAAGAAATT GCCTACAACG GTTGGTTTGG CGAGAAAGAT

1801 ACGACCAAAA CGAACGGGCG GCTCAACCTT GTTTACCAGC CCGCCGCAGA

1851 AGACCGCACC CTGCTGCTTT CCGGCGGAAC AAATTTAAAC GGCAACATCA

1901 CGCAAACAAA CGGCAAACTG TTTTTCAGCG GCAGACCAAC ACCGCACGCC

1951 TACAATCATT TAAACGACCA TTGGTCGCAA AAAGAGGGCA TTCCTCGCGG

2001 GGAAATCGTG TGGGACAACG ACTGGATCAA CCGCACATTT AAAGCGGAAA

2051 ACTTCCAAAT TAAAGGCGGA CAGGCGGTGG TTTCCCGCAA TGTTGCCAAA

2101 GTGAAAGGCG ATTGGCATTT GAGCAATCAC GCCCAAGCAG TTTTTGGTGT

2151 CGCACCGCAT CAAAGCCACA CAATCTGTAC ACGTTCGGAC TGGACGGGTC

2201 TGACAAATTG TGTCGAAAAA ACCATTACCG ACGATAAAGT GATTGCTTCA

2251 TTGACTAAGA CCGACATCAG CGGCAATGTC GATCTTGCCG ATCACGCTCA

2301 TTTAAATCTC ACAGGGCTTG CCACACTCAA CGGCAATCTT AGTGCAAATG

2351 GCGATACACG TTATACAGTC AGCCACAACG CCACCCAAAA CGGCAACCTT

2401 AGCCTCGTGG GCAATGCCCA AGCAACATTT AATCAAGCCA CATTAAACGG

2451 CAACACATCG GCTTCGGGCA ATGCTTCATT TAATCTAAGC GACCACGCCG

2501 TACAAAACGG CAGTCTGACG CTTTCCGGCA ACGCTAAGGC AAACGTAAGC

2551 CATTCCGCAC TCAACGGTAA TGTCTCCCTA GCCGATAAGG CAGTATTCCA

2601 TTTTGAAAGC AGCCGCTTTA CCGGACAAAT CAGCGGCGGC AAGGATACGG

2651 CATTACACTT AAAAGACAGC GAATGGACGC TGCCGTCAGG CACGGAATTA

2701 GGCAATTTAA ACCTTGACAA CGCCACCATT ACACTCAATT CCGCCTATCG

2751 CCACGATGCG GCAGGGGCGC AAACCGGCAG TGCGACAGAT GCGCCGCGCC

2801 GCCGTTCGCG CCGTTCGCGC CGTTCCCTAT TATCCGTTAC ACCGCCAACT

2851 TCGGTAGAAT CCCGTTTCAA CACGCTGACG GTAAACGGCA AATTGAACGG

2901 TCAGGGAACA TTCCGCTTTA TGTCGGAACT CTTCGGCTAC CGCAGCGACA

2951 AATTGAAGCT GGCGGAAAGT TCCGAAGGCA CTTACACCTT GGCGGTCAAC

3001 AATACCGGCA ACGAACCTGC AAGCCTCGAA CAATTGACGG TAGTGGAAGG

3051 AAAAGACAAC AAACCGCTGT CCGAAAACCT TAATTTCACC CTGCAAAACG

3101 AACACGTCGA TGCCGGCGCG TGGCGTTACC AACTCATCCG CAAAGACGGC

3151 GAGTTCCGCC TGCATAATCC GGTCAAAGAA CAAGAGCTTT CCGACAAACT

3201 CGGCAAGGCA GAAGCCAAAA AACAGGCGGA AAAAGACAAC GCGCAAAGCC
```

```
-continued
3251 TTGACGCGCT GATTGCGGCC GGGCGCGATG CCGTCGAAAA GACAGAAAGC
3301 GTTGCCGAAC CGGCCCGGCA GGCAGGCGGG GAAAATGTCG GCATTATGCA
3351 GGCGGAGGAA GAGAAAAAAC GGGTGCAGGC GGATAAAGAC ACCGCCTTGG
3401 CGAAACAGCG CGAAGCGGAA ACCCGGCCGG CTACCACCGC CTTCCCCCGC
3451 GCCCGCCGCG CCCGCCGGGA TTTGCCGCAA CTGCAACCCC AACCGCAGCC
3501 CCAACCGCAG CGCGACCTGA TCAGCCGTTA TGCCAATAGC GGTTTGAGTG
3551 AATTTTCCGC CACGCTCAAC AGCGTTTTCG CCGTACAGGA CGAATTAGAC
3601 CGCGTATTTG CCGAAGACCG CCGCAACGCC GTTTGGACAA GCGGCATCCG
3651 GGACACCAAA CACTACCGTT CGCAAGATTT CCGCGCCTAC CGCCAACAAA
3701 CCGACCTGCG CCAAATCGGT ATGCAGAAAA ACCTCGGCAG CGGGCGCGTC
3751 GGCATCCTGT TTTCGCACAA CCGGACCGAA AACACCTTCG ACGACGGCAT
3801 CGGCAACTCG GCACGGCTTG CCCACGGCGC CGTTTTCGGG CAATACGGCA
3851 TCGACAGGTT CTACATCGGC ATCAGCGCGG GCGCGGGTTT TAGCAGCGGC
3901 AGCCTTTCAG ACGGCATCGG AGGCAAAATC CGCCGCCGCG TGCTGCATTA
3951 CGGCATTCAG GCACGATACC GCGCCGGTTT CGGCGGATTC GGCATCGAAC
4001 CGCACATCGG CGCAACGCGC TATTTCGTCC AAAAAGCGGA TTACCGCTAC
4051 GAAAACGTCA ATATCGCCAC CCCCGGCCTT GCATTCAACC GCTACCGCGC
4101 GGGCATTAAG GCAGATTATT CATTCAAACC GGCGCAACAC ATTTCCATCA
4151 CGCCTTATTT GAGCCTGTCC TATACCGATG CCGCTTCGGG CAAAGTCCGA
4201 ACACGCGTCA ATACCGCCGT ATTGGCTCAG GATTTCGGCA AAACCCGCAG
4251 TGCGGAATGG GGCGTAAACG CCGAAATCAA AGGTTTCACG CTGTCCCTCC
4301 ACGCTGCCGC CGCCAAAGGC CCGCAACTGG AAGCGCAACA CAGCGCGGGC
4351 ATCAAATTAG GCTACCGCTG GTAA
```

This corresponds to the amino acid sequence <SEQ ID 650; ORF1-1>:

```
  1 MKTTDKRTTE THRKAPKTGR IRFSPAYLAI CLSFGILPQA WAGHTYFGIN
 51 YQYYRDFAEN KGKFAVGAKD IEVYNKKGEL VGKSMTKAPM IDFSVVSRNG
101 VAALVGDQYI VSVAHNGGYN NVDFGAEGRN PDQHRFTYKI VKRNNYKAGT
151 KGHPYGGDYH MPRLHKFVTD AEPVEMTSYM DGRKYIDQNN YPDRVRIGAG
201 RQYWRSDEDE PNNRESSYHI ASAYSWLVGG NTFAQNGSGG GTVNLGSEKI
251 KHSPYGFLPT GGSFGDSGSP MFIYDAQKQK WLINGVLQTG NPYIGKSNGF
301 QLVRKDWFYD EIFAGDTHSV FYEPRQNGKY SFNDDNNGTG KINAKHEHNS
351 LPNRLKTRTV QLFNVSLSET AREPVYHAAG GVNSYRPRLN NGENISFIDE
401 GKGELILTSN INQGAGGLYF QGDFTVSPEN NETWQGAGVH ISEDSTVTWK
451 VNGVANDRLS KIGKGTLHVQ AKGENQGSIS VGDGTVILDQ QADDKGKKQA
501 FSEIGLVSGR GTVQLNADNQ FNPDKLYFGF RGGRLDLNGH SLSFHRIQNT
551 DEGAMIVNHN QDKESTVTIT GNKDIATTGN NNSLDSKKEI AYNGWFGEKD
601 TTKTNGRLNL VYQPAAEDRT LLSGGTNLN GNITQTNGKL FFSGRPTPHA
651 YNHLNDHWSQ KEGIPRGEIV WDNDWINRTF KAENFQIKGG QAWSRNVAK
```

```
 701 VKGDWHLSNH AQAVFGVAPH QSHTICTRSD WTGLTNCVEK TITDDKVIAS

751 LTKTDISGNV DLADHAHLNL TGLATLNGNL SANGDTRYTV SHNATQNGNL

801 SLVGNAQATF NQATLNGNTS ASGNASFNLS DHAVQNGSLT LSGNAKANVS

851 HSALNGNVSL ADKAVFHFES SRFTGQISGG KDTALHLKDS EWTLPSGTEL

901 GNLNLDNATI TLNSAYRHDA AGAQTGSATD APRRRSRRSR RSLLSVTPPT

951 SVESRFNTLT VNGKLNGQGT FRFMSELFGY RSDKLKLAES SEGTYTLAVN

1001 NTGNEPASLE QLTVVEGKDN KPLSENLNFT LQNEHVDAGA WRYQLIRKDG

1051 EFRLHNPVKE QELSDKLGKA EAKKQAEKDN AQSLDALIAA GRDAVEKTES

1101 VAEPARQAGG ENVGIMQAEE EKKRVQADKD TALAKQREAE TRPATTAFPR

1151 ARRARRDLPQ LQPQPQPQPQ RDLISRYANS GLSEFSATLN SVFAVQDELD

1201 RVFAEDRRNA VWTSGIRDTK HYRSQDFRAY RQQTDLRQIG MQKNLGSGRV

1251 GILFSHNRTE NTFDDGIGNS ARLAHGAVFG QYGIDRFYIG ISAGAGFSSG

1301 SLSDGIGGKI RRRVLHYGIQ ARYRAGFGGF GIEPHIGATR YFVQKADYRY

1351 ENVNIATPGL AFNRYRAGIK ADYSFKPAQH ISITPYLSLS YTDAASGKVR

1401 TRVNTAVLAQ DFGKTRSAEW GVNAEIKGFT LSLHAAAAKG PQLEAQHSAG

1451 IKLGYRW*
```

Computer analysis of these sequences gave the following results:

Homology with a Predicted ORF from N. meningitidis (Strain A)

ORF1 shows 57.8% identity over a 1456aa overlap with an ORF (ORF1a) from strain A of N. meningitidis:

```
                   10         20         30         40         50         60
    orf1.pep  MKTTDKRTTETHRKAPKTGRIRFXAAYLAICLSFGILPQAWAGHTYFGINYQYYRDFAEN
              ||||||||||||||||||||||   |||||||||||||||||||||||||||||||||||
    orf1a     MKTTDKRTTETHRKAPKTGRIRFSPAYLAICLSFGILPQAWAGHTYFGINYQYYRDFAEN
                   10         20         30         40         50         60
                   70         80         90        100        110        120
    orf1.pep  KGKFAVGAKDIEVYNKKGELVGKSMTKAPMIDFSVVSRNGVAALVGVQYIVSVAHNGGYN
              ||||||||||||||||||||||||||||||||||||||||||||| |:||||||||||||
    orf1a     KGKFAVGAKDIEVYNKKGELVGKSMTKAPMIDFSVVSRNGVAALVGDQYIVSVAHNGGYN
                   70         80         90        100        110        120
                  130        140        150        160        170        180
    orf1.pep  NVDFGAEGXNIXGQXRXTYKIVKRNNYKAGTKGHPYGGDYHMPRLHKXVTDAEPVEMTSY
              |||||||||||  || |:|||||||||  ::||||||||||||||:|||||||||||||:
    orf1a     NVDFGAEGXN-PDQHRFSYQIVKRNNYKPDNS-HPYNGDYHMPRLHKFVTDAEPVEMTSD
                  130        140        150        160        170        180
                  190        200        210
    orf1.pep  MDGRKYIDQNNYPDRVTIGAGRQYWRSDEDEP--------------------NN-----
              | |   | |:::||:||||:|:::|||  |:|:                    ||
    orf1a     MRGNTYSDKEKYPERVRIGSGHHYWRYDDDKHGDLSYSGAWLIGGNTHMQGWGNNGVXSL
                180        190        200        210        220        230
                  190        200        210
    orf1.pep  ----RESSYH----IA-----SGSPMFIYDAQKQKWLINGVLQTGNPYIGKSNGFQLVRK
                  |:::  :      ||     ||||||||| :::|||||||||:|||:|||||||:||
    orf1a     SGDVRHANDYGPMPIAGAAGDSGSPMFIYDKTNNKWLLNGVLQTGYPYSGRENGFQLIRK
                240        250        260        270        280        290
                  270        280        290        300        310        320
    orf1.pep  DWFYDEIFAGDTHSVFYEPRQNGKYSFNDDNNGTGKINAKHEHNSLPNRLKTRTVQLFNV
              ||||| :| ||||:| :|||:|| ::||:|::||||| ||   :| | | :||::||:|:
    orf1a     DWFYDDIYRGDTHTVXFEPRSNGHFSFTSNNNGTGTVTETNEKVSNP-KLKVQTVRLFDE
                300        310        320        330        340        350
                  330        340        350        360        370        380
    orf1.pep  SLSETAREPVYHAAGGVNSYRPRLNNGENISFIDEGKGELILTSNINQGAGGLYFQGDFT
              ||:|| :|||| ||||:|||||||||||||||||||| |:|:|||::||||||||||||:||||
    orf1a     SLSETAREPVYHAAGGVNSYRPRLNNGENISFIDEGKGELILTSNINQGAGGLYFQGDFT
                360        370        380        390        400        410
                  390        400        410        420        430
    orf1.pep  VSPENNETWQGAGVHISEDSTVTWKVNGVANDRLSKIGKGTL------------------
              |||||||||||||||||||||||||||||||||||||||||
    orf1a     VSPENNETWQGAGVHISEDSTVTWKVNGVANDRLSKIGKGTLHVQAKGENQGSISVGDGT
                420        430        440        450        460        470
```

```
                                    -continued
orfl.pep  ------------------------------------------------------------ orfla     VILDQQADDKGKKQAFSEIGLXSGRGTVQLNADNQFNPDKLYFGFRGGRLDLNGHSLSFH
              480       490       500       510       520       530 orfl.pep  ------------------------------------------------------------ orfla     RIQNTDEGAMIXXHNATTTSTVTITGNESITQPSGKNINRLNYSKEIAYNGWFGEKDTTK
              540       550       560       570       580       590 orfl.pep  ------------------------------------------------------------ orfla     TNGRLNLVYQPAAEDRTXLLSGGTNLNGNITQTNGKLFFSGRPTPHAYNHLGSGWSKMEG
              600       610       620       630       640       650 orfl.pep  ------------------------------------------------------------ orfla     IPQGEIVWDNDWIXRTFKAENFHIQGGQAVISRNVAKVEGDXHLSNHAQAVFGVAPHQSH
              660       670       680       690       700       710

420       450       460       470       480
orfl.pep  ----------------XXXXXDKVTASLTKTDISGNVDLADHAHLNLTGLATLNGNLSAN
                          :  ||  :  ||| ||||||| ||| :|  |:| ||||||
orfla     TICTRSDWTGLTNCVEXXITDDKVIASLTKTDXSGXVXLXXXXXXXLXGXAXLXGNLSAN
              720       730       740       750       760       770

490       500       510       520       530       540
orfl.pep  GDTRYTVSHNATQNGNXSLVXNAQATFNQATLNGNTSASGNASFNLSDHAVQNGSLTLSG
          ||||||||||||||||  |||  ||||||||||| |:|||||||||:: :||||||||
orfla     GDTRYTVSHNATQNGNLSLVGNAQATFNQATLNGNXSXSGNASFNLSNNAAQNGSLTLSD
              780       790       800       810       820       830

550       560       570       580       590       600
orfl.pep  NAKANVSHSALNGNVSLADKAVFHFESSRFTGQISGGKDTALHLKDSEWTLPSGXELGNL
          |||||||||||||||||||||||||||:|||||:| :| |||||||||||||||:||||
orfla     NAKANVSHSALNGNVSLADKAVFHFENSRFTGQLSGSKXTALHLKDSEWTLPSGTELGNL
              840       850       860       870       880       890

610       620       630       640       650       660
orfl.pep  NLDNATITLNSAYRHDAAGAQTGSATDAPRRRSRRSRRSLLXVTPPTSVESRFNTLTVNG
          ||||||||||||||||||||||| ::| :||||||||||   |||||||||||||||||
orfla     NLDNATITLNSAYRHDAAGAQTGXVSDTPRRRSRRSRRS---LLSVTPPTSVESRFNTLTVNG
              900       910       920       930       940       950

670       680       690       700       710       720
orfl.pep  KLNGQGTFRFMSELFGYRSDKLKLAESSEGTYTLAVNNTGNEPASLEQLTVVEGKDNKPL
          ||| ||||||||||||||||||||||||||||||||||||||| |::||||||||||||
orfla     KLNXQGTFRFMSELFGYRSDKLKLAESSEGTYTLAVNNTGNEPVSLDQLTVVEGKDNKPL
              960       970       980       990       1000      1010

730       740       750
orfl.pep  SENLNFTLQNEHVDAGAW-------------------------------------------
          ||||||||||||||||||
orfla     SENLNFTLQNEHVDAGAWRYQLIRKDGEFRLHNPVKEQELSDKLGKAEAKKQAEKDNAQS
              1020      1030      1040      1050      1060      1070 orfl.pep  ------------------------------------------------------------ orfla     LDALIAAGRDAAEKTESVAEPARXAGGENVGIMQAEEEKKRVQADKDSALAKQREAETRP
              1080      1090      1100      1110      1120      1130 orfl.pep  ---------------------------------------------------------LDR
                                                                   |||
orfla     XTTAFPRARXARRDLPQPQPQPQPQPQPQRDLXSRYANSGLSEFSATLNSVFAVQDELDR
              1140      1150      1160      1170      1180      1190

770       780       790       800       810       820
orfl.pep  VFAEDRRNAVWTSGIRDTKHYRSQDFRAYRQQTDLRQIGMQKNLGSGRVGILFSHNRTEN
          |||||||||||| || |:|||||||||||||||||||||||||||||||||||||||||
orfla     VFAEDRRNAVWTSXIRXTKHYRSQDFRAYRQQTDLRQIGMQKNLGSGRVGILFSHNRTEN
              1200      1210      1220      1230      1240      1250

830       840       850       860       870       880
orfl.pep  TFDDGIGNSARLAHGAVFGQYGIDRFYIGISAGAGFSSGSLSDIGXKXRRRVLHYGIQA
          :||||||||||||||||||||||||:|||| ||:|||||:||||||||:|||||||||
orfla     XFDDGIGNSARLAHGAVFGQYGIGRFDIGISTGAGFSSGXLSDIGGKIRRRVLHYGIQA
              1260      1270      1280      1290      1300      1310

890       900       910       920       930       940
orfl.pep  RYRAGFGGFGIEPHIGATRYFVQKADYRYENVNIATPGLAFNRYRAGIKADYSFKPAQHI
          |||||||||||||| |||||||||||||||||||||||||||||||||||||||||||||
orfla     RYRAGFGGFGIEPYIGATRYFVQKADYRYENVNIATPGLAFNRYRAGIKADYSFKPAQHI
              1320      1330      1340      1350      1360      1370

890       900       910       920       930       940
orfl.pep  SITPYLSLSYTDAASGKVRTRVNTAVLAQDFGKTRSAEWGVNAEIKGFTLSLHAAAAKGP
          ||||||| ||||||||||||||||||||||||||||||||||||||||||| |||||||
orfla     SITPYLSXSYTDAASGKVRTRVNTAVLAQDFGKTRSAEWGVNAEIKGFTLSXHAAAAKGP
              1380      1390      1400      1410      1420      1430

1010      1020
orfl.pep  QLEAQHSAGIKLGYRWX
          |||||||||||||||||
orfla     QLEAQHSAGIKLGYRWX
              1440      1450
```

The complete length ORF1a nucleotide sequence <SEQ ID 651> is:

```
   1 ATGAAAACAA CCGACAAACG GACAACCGAA ACACACCGCA AAGCCCCGAA
  51 AACCGGCCGC ATCCGCTTCT CGCCTGCTTA CTTAGCCATA TGCCTGTCGT
 101 TCGGCATTCT TCCCCAAGCT TGGGCGGGAC ACACTTATTT CGGCATCAAC
 151 TACCAATACT ATCGCGACTT TGCCGAAAAT AAAGGCAAGT TTGCAGTCGG
 201 GGCGAAAGAT ATTGAGGTNT ACAACAAAAA AGGGGAGTTG GTCGGCAAAT
 251 CAATGACAAA AGCCCCGATG ATTGATTTTT CTGTGGTGTC GCGTAACGGC
 301 GTGGCGGCAT TGGTGGGCGA TCAATATATT GTGAGCGTGG CACATAACGG
 351 CGGCTATAAC AACGTTGATT TTGGTGCGGA AGGAAGNAAT CCCGATCAGC
 401 ACCGTTTTTC TTACCAAATT GTGAAAAGAA ATAATTATAA GCCTGACAAT
 451 TCACACCCTT ACAACGGCGA TTANCATATG CCGCGTTTGC ATAAATTTGT
 501 CACAGATGCA GAACCTGTCG AAATGACGAG TGACATGAGG GGGAATACCT
 551 ATTCCGATAA AGAAAAATAT CCCGAGCGTG TCCGCATCGG CTCAGGACAC
 601 CACTATTGGC GTTATGATGA TGACAAACAC GGCGATTTAT CCTACTCCGG
 651 CGCATGGTTA ATTGGCGGCA ATACACATAT GCAGGGTTGG GGAAATAATG
 701 GCGTANTTAG TTTGAGCGGC GATGTGCGCC ATGCCAACGA CTATGGCCCT
 751 ATGCCGATTG CAGGTGCGGC AGGCGACAGC GGTTCGCCAA TGTTTATTTA
 801 TGACAAAACA AACAATAAAT GGCTGCTCAA CGGAGTTTTA CAAACCGGCT
 851 ACCCTTATTC CGGCAGGGAA AACGGTTTCC AGCTGATACG CAAAGATTGG
 901 TTCTACGATG ACATTTACAG AGGCGATACA CATACCGTCT NTTTTGAACC
 951 GCGCAGTAAC GGACATTTTT CCTTTACATC CAACAACAAC GGTACGGGTA
1001 CGGTAACAGA AACCAACGAA AAGGTNTCCA ATCCAAAGCT TAAAGTACAG
1051 ACAGTCCGAC TGTTTGACGA ATCTTTGAAT GAAACTGATA AAGAACCAGT
1101 TTACGCGGCA GGGGGTGTTA ATCAGTACCG TCCAAGGTTA AACAACGGTG
1151 AAAACCTTTC TTTTATCGAT TACGGCAACG GCAAACTCAT CTTATCAAAC
1201 AACATCAACC AAGGCGCGGG CGGTTTGTAT TTTGAAGGTG ATTTTACGGT
1251 CTCGCCTGAA AACAACGAAA CGTGGCAAGG CGCGGGCGTT CATATCAGTG
1301 AAGACAGTAC CGTTACTTGG AAAGTAAACG GCGTGGCAAA CGACCGCCTG
1351 TCCAAAATCG GCAAAGGCAC GCTGCACGTT CAAGCCAAAG GGGAAAACCA
1401 AGGCTCGATC AGCGTGGGCG ACGGTACAGT CATTTTGGAT CAGCAGGCAG
1451 ACGATAAAGG CAAAAAACAA GCCTTTAGTG AAATCGGCTT GNTCAGCGGC
1501 AGGGGTACGG TGCAACTGAA TGCCGATAAT CAGTTCAACC CCGACAAACT
1551 CTATTTCGGC TTTCGCGGCG GACGTTTGGA TTTAAACGGG CATTCGCTTT
1601 CGTTCCACCG TATTCAAAAT ACCGATGAAG GGGCGATGAT TGNCNATCAT
1651 AATGCCACAA CAACATCCAC CGTTACCATT ACAGGGAATG AAAGTATTAC
1701 ACAACCGAGT GGTAAGAATA TCAATAGACT TAATTACAGC AAAGAAATTG
1751 CCTACAACGG TTGGTTTGGC GAGAAAGATA CGACCAAAAC GAACGGGCGG
1801 CTCAACCTTG TTTACCAGCC CGCCGCAGAA GACCGCACCC NGCTGCTTTC
1851 CGGCGGAACA AATTTAAACG GCAACATCAC GCAAACAAAC GGCAAACTGT
1901 TTTTCAGCGG CAGACCGACA CCGCACGCCT ACAATCATTT AGGAAGCGGG
```

```
1951 TGGTCAAAAA TGGAAGGTAT CCCACAAGGA GAAATCGTGT GGGACAACGA
2001 CTGGATCNAC CGCACGTTTA AAGCGGAAAA TTTCCATATT CAGGGCGGGC
2051 AGGCGGTGAT TTCCCGCAAT GTTGCCAAAG TGGAAGGCGA TTGNCATTTG
2101 AGCAATCACG CCCAAGCAGT TTTTGGTGTC GCACCGCATC AAAGCCATAC
2151 AATCTGTACA CGTTCGGACT GGACNGGTCT GACAAATTGT GTCGAANAAA
2201 NCATTACCGA CGATAAAGTG ATTGCTTCAT TGACTAAGAC NGACNTNAGC
2251 GGCANTGTNA GNCTNNCCNA TNACGNTNNT TNAAANCTCN CNGGGCNTGC
2301 NNCACTNAAN GGCAATCTTA GTGCAAATGG CGATACACGT TATACAGTCA
2351 GCCACAACGC CACCCAAAAC GGCAACCTTA GCCTCGTGGG CAATGCCCAA
2401 GCAACATTTA ATCAAGCCAC ATTAAACGGC AACNCATCGG NTTCGGGCAA
2451 TGCTTCATTT AATCTAAGCA CAACGCCGC ACAAAACGGC AGTCTGACGC
2501 TTTCCGACAA CGCTAAGGCA AACGTAAGCC ATTCCGCACT CAACGGCAAT
2551 GTCTCCCTAG CCGATAAGGC AGTATTCCAT TTTGAAAACA GCCGCTTTAC
2601 CGGACAACTC AGCGGCAGCA AGGANACAGC ATTACACTTA AAAGACAGCG
2651 AATGGACGCT GCCGTCAGGC ACGGAATTAG GCAATTTAAA CCTTGACAAC
2701 GCCACCATTA CACTCAATTC CGCCTATCGC CACGATGCTG CAGGCGCGCA
2751 AACCGGCAGN GTGTCAGACA CGCCGCGCCG CCGTTCGCGC CGTTCCCTAT
2801 TATCCGTTAC ACCGCCAACT TCGGTAGAAT CCCGTTTCAA CACGCTGACG
2851 GTAAACGGCA AATTGAACNG TCAAGGAACA TTCCGCTTTA TGTCGGAACT
2901 CTTCGGCTAC CGAAGCGACA AATTGAAGCT GGCGGAAAGT TCCGAAGGNA
2951 CTTACACCTT GGCGGTCAAC AATACCGGCA ACGAACCCGT AAGCCTCGAT
3001 CAATTGACGG TAGTGGAAGG GAAAGACAAC AAACCGCTGT CCGAAAACCT
3051 TAATTTCACC CTGCAAAACG AACACGTCGA TGCCGGCGCG TGGCGTTACC
3101 AACTCATCCG CAAAGACGGC GAGTTCCGCC TGCATAATCC GGTCAAAGAA
3151 CAAGAGCTTT CCGACAAACT CGGCAAGGCA GAAGCCAAAA AACAGGCGGA
3201 AAAAGACAAC GCGCAAAGCC TTGACGCGCT GATTGCGGCC GGGCGCGATG
3251 CCGCCGAAAA GACAGAAAGC GTTGCCGAAC CGGCCCGGCN GGCAGGCGGG
3301 GAAAATGTCG GCATTATGCA GGCGGAGGAA GAGAAAAAAC GGGTGCAGGC
3351 GGATAAAGAC AGCGCNTTGG CGAAACAGCG CGAAGCGGAA ACCCGGCCGG
3401 NTACCACCGC CTTCCCCCGC GCCCGCNGCG CCCGCCGGGA TTTGCCGCAA
3451 CCGCAGCCCC AACCGCAACC TCAACCCCAA CCGCAGCGCG ACCTGATNAG
3501 CCGTTATGCC AATAGCGGTT TGAGTGAATT TTCCGCCACG CTCAACAGCG
3551 TTTTCGCCGT ACAGGACGAA TTGGACCGCG TGTTTGCCGA AGACCGCCGC
3601 AACGCNGTTT GGACAAGCNG CATCCGGNAC ACCAAACACT ACCGTTCGCA
3651 AGATTTCCGC GCCTACCGCC AACAAACCGA CCTGCGCCAA ATCGGTATGC
3701 AGAAAAACCT CGGCAGCGGG CGCGTCGGCA TCCTGTTTTC GCACAACCGG
3751 ACCGAAAACA NCTTCGACGA CGGCATCGGC AACTCGGCAC GGCTTGCCCA
3801 CGGCGCCGTT TTCGGGCAAT ACGGCATCGG CAGGTTCGAC ATCGGCATCA
3851 GCACGGGCGC GGGTTTTAGC AGCGGCANTC TNTCAGACGG CATCGGAGGC
3901 AAAATCCGCC GCCGCGTGCT GCATTACGGC ATTCAGGCAC GATACCGCGC
3951 CGGTTTCGGC GGATTCGGCA TCGAACCGTA CATCGGCGCA ACGCGCTATT
```

-continued

```
4001 TCGTCCAAAA AGCGGATTAC CGCTACGAAA ACGTCAATAT CGCCACCCCC
4051 GGTCTTGCGT TCAACCGNTA CCGNGCGGGC ATTAAGGCAG ATTATTCATT
4101 CAAACCGGCG CAACACATNT CCATCACNCC TTATTTNAGC CTGTCCTATA
4151 CCGATGCCGC TTCGGGCAAA GTCCGAACAC GCGTCAATAC CGCNGTATTG
4201 GCTCAGGATT TCGGCAAAAC CCGCAGTGCG GAATGGGGCG TAAACGCCGA
4251 AATCAAAGGT TTCACGCTGT CCNTCCACGC TGCCGCCGCC AAAGGNCCGC
4301 AACTGGAAGC GCAACACAGC GCGGGCATCA AATTAGGCTA CCGCTGGTAA
```

This encodes a protein having amino acid sequence <SEQ ID 652>:

```
   1 MKTTDKRTTE THRKAPKTGR IRFSPAYLAI CLSFGILPQA WAGHTYFGIN
  51 YQYYRDFAEN KGKFAVGAKD IEVYNKKGEL VGKSMTKAPM IDFSVVSRNG
 101 VAALVGDQYI VSVAHNGGYN NVDFGAEGXN PDQHRFSYQI VKRNNYKPDN
 151 SHPYNGDXHM PRLHKFVTDA EPVEMTSDMR GNTYSDKEKY PERVRIGSGH
 201 HYWRYDDDKH GDLSYSGAWL IGGNTHMQGW GNNGVXSLSG DVRHANDYGP
 251 MPIAGAAGDS GSPMFIYDKT NNKWLLNGVL QTGYPYSGRE NGFQLIRKDW
 301 FYDDIYRGDT HTVXFEPRSN GHFSFTSNNN GTGTVTETNE KVSNPKLKVQ
 351 TVRLFDESLN ETDKEPVYAA GGVNQYRPRL NNGENLSFID YGNGKLILSN
 401 NINQGAGGLY FEGDFTVSPE NNETWQGAGV HISEDSTVTW KVNGVANDRL
 451 SKIGKGTLHV QAKGENQGSI SVGDGTVILD QQADDKGKKQ AFSEIGLXSG
 501 RGTVQLNADN QFNPDKLYFG FRGGRLDLNG HSLSFHRIQN TDEGAMIXXH
 551 NATTTSTVTI TGNESITQPS GKNINRLNYS KEIAYNGWFG EKDTTKTNGR
 601 LNLVYQPAAE DRTXLLSGGT NLNGNITQTN GKLFFSGRPT PHAYNHLGSG
 651 WSKMEGIPQG EIVWDNDWIX RTFKAENFHI QGGQAVISRN VAKVEGDXHL
 701 SNHAQAVFGV APHQSHTICT RSDWTGLTNC VEXXITDDKV IASLTKTDXS
 751 GXVXLXXXXX XXLXGXAXLX GNLSANGDTR YTVSHNATQN GNLSLVGNAQ
 801 ATFNQATLNG NXSXSGNASF NLSNNAAQNG SLTLSDNAKA NVSHSALNGN
 851 VSLADKAVFH FENSRFTGQL SGSKXTALHL KDSEWTLPSG TELGNLNLDN
 901 ATITLNSAYR HDAAGAQTGX VSDTPRRRSR RSLLSVTPPT SVESRFNTLT
 951 VNGKLNXQGT FRFMSELFGY RSDKLKLAES SEGTYTLAVN NTGNEPVSLD
1001 QLTVVEGKDN KPLSENLNFT LQNEHVDAGA WRYQLIRKDG EFRLHNPVKE
1051 QELSDKLGKA EAKKQAEKDN AQSLDALIAA GRDAAEKTES VAEPARXAGG
1101 ENVGIMQAEE EKKRVQADKD SALAKQREAE TRPXTTAFPR ARXARRDLPQ
1151 PQPQPQPQPQ PQRDLXSRYA NSGLSEFSAT LNSVFAVQDE LDRVFAEDRR
1201 NAVWTSXIRX TKHYRSQDFR AYRQQTDLRQ IGMQKNLGSG RVGILFSHNR
1251 TENXFDDGIG NSARLAHGAV FGQYGIGRFD IGISTGAGFS SGXLSDGIGG
1301 KIRRRVLHYG IQARYRAGFG GFGIEPYIGA TRYFVQKADY RYENVNIATP
1351 GLAFNRYRAG IKADYSFKPA QHXSITPYXS LSYTDAASGK VRTRVNTAVL
1401 AQDFGKTRSA EWGVNAEIKG FTLSXHAAAA KGPQLEAQHS AGIKLGYRW*
```

A transmembrane region is underlined.
ORF1-1 shows 86.3% identity over a 1462aa overlap with ORF1a:

```
                  10         20         30         40         50         60
orf1a.pep MKTTDKRTTETHRKAPKTGRIRFSPAYLAICLSFGILPQAWAGHTYFGINYQYYRDFAEN
          ||||||||||||||||||||||||||||||||||||||||||||||||||||||||||||
orf1-1    MKTTDKRTTETHRKAPKTGRIRFSPAYLAICLSFGILPQAWAGHTYFGINYQYYRDFAEN
                  10         20         30         40         50         60

70         80         90        100        110        120
orf1a.pep KGKFAVGAKDIEVYNKKGELVGKSMTKAPMIDFSVVSRNGVAALVGDQYIVSVAHNGGYN
          ||||||||||||||||||||||||||||||||||||||||||||||||||||||||||||
orf1-1    KGKFAVGAKDIEVYNKKGELVGKSMTKAPMIDFSVVSRNGVAALVGDQYIVSVAHNGGYN
                  70         80         90        100        110        120

130        140        150        160        170       179
orf1a.pep NVDFGAEGXNPDQHRFSYQIVKRNNYKPDNS-HPYNGDXHMPRLHKFVTDAEPVEMTSDM
          |||||||| :||||||| || :|||||||||   | ||| ||||||||||||||||||:|
orf1-1    NVDFGAEGRNPDQHRFTYKIVKRNNYKAGTKGHPYGGDYHMPRLHKFVTDAEPVEMTSYM
                 130        140        150        160        170        180

180        190        200        210        220        230
orf1a.pep RGNTYSDKEKYPERVRIGSGHHYWRYDDDKHGDL--SYSGA----WLIGGNTHMQGWGNN
          |  |   |::||||||| :|:|| ||:|: ::   ||   ||    |:  :::
orf1-1    DGRKYIDQNNYPDRVRIGAGRQYWRSDEDEPNNRESSYHIASAYSWLVGGNTFAQNGSGG
                 190        200        210        220        230        240

240        250        260        270        280        290
orf1a.pep GVXSLSGD-VRHANDYGPMPIAGAAGDSGSPMFIYDKTNNKWLLNGVLQTGYPYSGRENG
          |: :|:::: :|: || |:|:  ||||||||||||:  |:|||:|||||||:| |: ||
orf1-1    GTVNLGSEKIKHS-PYGFLPTGGSFGDSGSPMFIYDAQKQKWLINGVLQTGNPYIGKSNG
                 250        260        270        280        290

300        310        320        330        340        350
orf1a.pep FQLIRKDWFYDDIYRGDTHTVXFEPRSNGHFSPTSNNNGTGTVTETNEKVSNP-KLKVQT
          |||:|||||||:| || ||:|| |||::||:| || ::||| :|  :|: : | :||:|
orf1-1    FQLVRKDWFYDEIFAGDTHSVFYEPRQNGKYSFNDDNNGTGKINAKHEHNSLPNRLKTRT
          300        310        320        330        340        350

360        370        380        390        400        410
orf1a.pep VRLFDESLNETDKEPVY-AAGGVNQYRPRLNNGENLSFIDYGNGKLILSNNINQGAGGLY
          |:|| :||: ||| || |||| |:|||||||||| ||||: ||| |||:||||||||||
orf1-1    VQLFNVSLSETAREPVYHAAGGVNSYRPRLNNGENISFIDEGKGELILTSNINQGAGGLY
          360        370        380        390        400        410

420        430        440        450        460        470
orf1a.pep FEGDFRVSPENNETWQGAGVHISEDSTVTWKVNGVANDRLSKIGKGTLHVQAKGENQGSI
          | ||||||||||||||||||||||||||||||||||||||||||||||||||||||||||
orf1-1    FQGDFRVSPENNETWQGAGVHISEDSTVTWKVNGVANDRLSKIGKGTLHVQAKGENQGSI
          420        430        440        450        460        470

480        490        500        510        520        530
orf1a.pep SVGDGTVILDQQADDKGKKQAFSEIGLXSGRGTVQLNADNQFNPDKLYFGFRGGRLDLNG
          |||||||||||||||||||||||||||:||||||||||||||||||||||||||||||||
orf1-1    SVGDGTVILDQQADDKGKKQAFSEIGLVSGRGTVQLNADNQFNPDKLYFGFRGGRLDLNG
          480        490        500        510        520        530

540        550        560        570        580        590
orf1a.pep HSLSFHRIQNTDEGAMIXXHNATTTSTVTITGNESITQPSGKNINRLNYSKEIAYNGWFG
          |||||||||||||||||  ||: ||:|||||||: ||| |:|:  |: |||||||||||
orf1-1    HSLSFHRIQNTDEGAMIVNHNQDKESTVTITGNKDIAT-TGNN-NSLDSKKEIAYNGWFG
          540        550        560        570        580        590

600        610        620        630        640        650
orf1a.pep EKDTTKTNGRLNLVYQPAAEDRTXLLSGGTNLNGNITQTNGKLFFSGRPTPHAYNHLGSG
          |||||||||||||||||||||||| |||||||||||||||||||||||||||||||:: 
orf1-1    EKDTTKTNGRLNLVYQPAAEDRTLLLSGGTNLNGNITQTNGKLFFSGRPTPHAYNHLNDH
          600        610        620        630        640        650

660        670        680        690        700        710
orf1a.pep WSKMEGIPQGEIVWDNDWIXRTFKAENFHIQGGQAVISRNVAKVEGDXHLSNHAQAVPGV
          ||::|||| ||||||||||| ||||||| |:||||| ||||||| ||| ||||||||||
orf1-1    WSQKEGIPRGEIVWDNDWINRTFKAENFQIKGGQAVVSRNVAKVKGDWHLSNHAQAVPGV
          660        670        680        690        700        710

720        730        740        750        760        770
orf1a.pep APHQSHTICTRSDWTGLTNCVEXXITDDKVIASLTKTDXSGXVXLXXXXXXXXLXGXAXL X
          ||||||||||||||||||||||::|||||||||||||| ||:|           :|: |
orf1-1    APHQSHTICTRSDWTGLTNCVEKTITDDKVIASLTKTDISGNVDLADHAHLNLTGLATLN
          720        730        740        750        760        770

780        790        800        810        820        830
orf1a.pep GNLSANGDTRYTVSHNATQNGNLSLVGNAQATFNQATLNGNXSXSGNASFNLSNNAAQNG
          |||||||||||||||||||||||||||||||||||||||||:|:|||||||| :|| ||
orf1-1    GNLSANGDTRYTVSHNATQNGNLSLVGNAQATFNQATLNGNTSASGNASFNLSDHAVQNG
          840        850        860        870        880        890

840        850        860        870        880        890
orf1a.pep SLTLSDNAKANVSHSALNGNVSLADKAVFHFENSRFTGQLSGSKXTALHLKDSEWTLPSG
          |||||:||||||||||||||||||||||||| ||||||| |:|| ||||||||||||||
orf1-1    SLTLSGNAKANVSHSALNGNVSLADKAVFHFESSRFTGQISGGKDTALHLKDSEWTLPSG
          840        850        860        870        880        890
```

```
            900       910       920       930       940
orfla.pep  TELGNLNLDNATITLNSAYRHDAAGAQTGXVSDTPRRRSRRS---LLSVTPPTSVESRFN
           ||||||||||||||||||||||||||||:::|:|||||||||   ||||||||||||||||
orfl-1     TELGNLNLDNATITLNSAYRHDAAGAQTGSATDAPRRRSRRSRRSLLSVTPPTSVESRFN
            900       910       920       930       940       950

950       960       970       980       990      1000
orfla.pep  TLTVNGKLNXQGTFRFMSELFGYRSDKLKLAESSEGTYTLAVNNTGNEPVSLDQLTVVEG
           ||||||||||| ||||||||||||||||||||||||||||||||||||| ::|||||||
orfl-1     TLTVNGKLNGQGTFRFMSELFGYRSDKLKLAESSEGTYTLAVNNTGNEPASLEQLTVVEG
            960       970       980       990      1000      1010

1010      1020      1030      1040      1050      1060
orfla.pep  KDNKPLSENLNFTLQNEHVDAGAWRYQLIRKDGEFRLHNPVKEQELSDKLGKAEAKKQAE
           ||||||||||||||||||||||||||||||||||||||||||||||||||||||||||||
orfl-1     KDNKPLSENLNFTLQNEHVDAGAWRYQLIRKDGEFRLHNPVKEQELSDKLGKAEAKKQAE
           1020      1030      1040      1050      1060      1070

1070      1080      1090      1100      1110      1120
orfla.pep  KDNAQSLDALIAAGRDAAEKTESVAEPARXAGGENVGIMQAEEEKKRVQADKDSALAKQR
           |||||||||||||||||:||||||||||| ||||||||||||||||||||||| |||||
orfl-1     KDNAQSLDALIAAGRDAVEKTESVAEPARQAGGENVGIMQAEEEKKRVQADKDTALAKQR
           1080      1090      1100      1110      1120      1130

1130      1140      1150      1160      1170      1180
orfla.pep  EAETRPXTTAFPPRARXARRDLPQPQPQPQPQPQPQRDLXSRYANSGLSEFSATLNSVFAV
           ||||||  |||||||| |||||| ||||||||  |||| |||||||||||||||||||||
orfl-1     EAETRPATTAFPPRARRARRDLPQLQPQPQPQP--QRDLISRYANSGLSEFSATLNSVFAV
           1140      1150      1160      1170      1180      1190

1190      1200      1210      1220      1230      1240
orfla.pep  QDELDRVFAEDRRNAVWTSXIRXTKHYRSQDFRAYRQQTDLRQIGMQKNLGSGRVGILFS
           |||||||||||||||||||| ||||||||||||||||||||||||||||||||||||||
orfl-1     QDELDRVFAEDRRNAVWTSGIRDTKHYRSQDFRAYRQQTDLRQIGMQKNLGSGRVGILFS
           1200      1210      1220      1230      1240      1250

1250      1260      1270      1280      1290      1300
orfla.pep  HNRTENXFDDGIGNSARLAHGAVFGQYGIGRFDIGISTGAGFSSGXLSDGIGGKIRRRVL
           ||||||| ||||||||||||||||||||| ||:||||:|||||| ||||||||||||||
orfl-1     HNRTENTFDDGIGNSARLAHGAVFGQYGIDRFYIGISAGAGFSSGSLSDGIGGKIRRRVL
           1260      1270      1280      1290      1300      1310

1310      1320      1330      1340      1350      1360
orfla.pep  HYGIQARYRAGFGGFGIEPYIGATRYFVQKADYRYENVNIATPGLAFNRYRAGIKADYSF
           |||||||||||||||||:||||||||||||||||||||||||||||||||||||||||||
orfl-1     HYGIQARYRAGFGGFGIEPHIGATRYFVQKADYRYENVNIATPGLAFNRYRAGIKADYSF
           1320      1330      1340      1350      1360      1370

1370      1380      1390      1400      1410      1420
orfla.pep  KPAQHXSITPYXSLSYTDAASGKVRTRVNTAVLAQDFGKTRSAEWGVNAEIKGFTLSXHA
           |||||| ||||| |||||||||||||||||||||||||||||||||||||||||||| ||
orfl-1     KPAQHISITPYLSLSYTDAASGKVRTRVNTAVLAQDFGKTRSAEWGVNAEIKGFTLSLHA
           1380      1390      1400      1410      1420      1430

1430      1440      1450
orfla.pep  AAAKGPQLEAQHSAGIKLGYRWX
           ||||||||||||||||||||||
orfl-1     AAAKGPQLEAQHSAGIKLGYRWX
           1440      1450
```

Homology with Adhesion and Penetration Protein Hap Precursor of *H. influenzae* (Accession Number P45387)

Amino acids 23-423 of ORF1 show 59% aa identity with hap protein in 450aa overlap:

```
orf1   23 FXAAYLAICLSFGILPQAWAGHTYFGINYQYYRDFAENKGKFAVGAKDIEVYNKKGELVG   82
             F   +L  C+S GI  QAWAGHTYFGI+YQYYRDFAENKGKF VGAK+IEVYNK+G+LVG
hap     6 FRLNFLTACVSLGIASQAWAGHTYFGIDYQYYRDFAENKGKFTVGAKNIEVYNKEGQLVG   65 orf1   83 KSMTKAPMIDFSVVSRNGVAALVGVQYIVSVAHNGGYNNVDFGAEGXNIXDQXRXTYKIV  142
             SMTKAPMIDFSVVSRNGVAALVG QYIVSVAHNGGYN+VDFGAEG N  DQ R TY+IV
hap    66 TSMTKAPMIDFSVVSRNGVAALVGDQYIVSVAHNGGYNDVDFGAEGRN-PDQHRFTYQIV  124 orf1  143 KRNNYKAGTKGHPYGGDYHMPRLHKXVTDAEPVEMTSYMDGRKYIDQNNYPDRVRIGAGR  202
             KRNNY+A  + HPY GDYHMPRLHK VT+AEPV MT+ MDG+ Y D+ NYP+RVRIG+GR
hap   125 KRNNYQAWERKHPYDGDYHMPRLHKFVTEAEPVGMTTNMDGKVYADRENYPERVRIGSGR  184 orf1  203 QYWRSDEDEPNNRESSYHIA----------------------------------------  222
             QYWR+D+DE  N  SSY+++
hap   185 QYWRTDKDEETNVHSSYYVSGAYRYLTAGNTHTQSGNGNGTVNLSGNVVSPNHYGPLPTG  244 orf1  223 -----SGSPMFIYDAQKQKWLINGVLQTGNPYIGKSNGFQLVRKDWFYDEIFAGDTHSVF  277
             SGSPMFIYDA+K++WLIN VLQTG+P+  G+ NGFQL+R++WFY+E+  A DT SVF
hap   245 GSKGDSGSPMFIYDAKKKQWLINAVLQTGHPFFGRGNGFQLIREEWFYNEVLAVDTPSVF  304 orf1  278 --YEPRQNGKYSFNDDNNGTGKIN-AKHEHNSLPNRLKTRTVQLFNVSLSETAREPVYHA  334
              Y P  NG YSF +N+GTGK+    +     + + TV+LFN SL++TA+E V  A
hap   305 QRYIPPINGHYSFVSNNDGTGKLTLTRPSKDGSKAKSEVGTVKLFNPSLNQTAKEHV-KA  363
```

-continued

```
orf1  335 AGGVNSYRPRLNNGENISFIDEKGELILTSNINQGAGGLYFQGDFTV-SPENNETWQGA  393
          A G N Y+PR+  G+NI   D+GKG L + +NINQGAGGLYF+G+F V   +NN TWQGA
hap   364 AAGYNIYQPRMEYGKNIYLGDQGKGTLTIENNINQGAGGLYFEGNFVVKGKQNNITWQGA  423 orf1  394 GVHISEDSTVTWKVNGVANDRLSKIGKGTL                               423
          GV I +D+TV WKV+   NDRLSKIG GTL
hap   424 GVSIGQDATVEWKVHNPENDRLSKIGIGTL                               453
```

Amino acids 715-1011 of ORF1 show 50% aa identity with hap protein in 258aa overlap:

```
Orf1   41 DTRYTVSHNATQ-NGNXSLVXNAQATFNQ-ATLNGNTSASGNASFNLSDHAVQNGSLTLS   98
          DT+    S   TQ NG+ +L  NA    +  A LNGN +   ++ F LS++A Q G++ LS
hap   733 DTKVINSIPITQINGSINLTNNATVNIHGLAKLNGNVTLIDHSQFTLSNNATQTGNIKLS  792 orf1   99 GNAKANVSHSALNGNVSLADKAVFHFESSRFTGQISGGKDTALHLKDSEWTLPSGXELGN  158
          +A A V+++ LNGNV L D A F  ++S F  QI G KDT + L+++ WT+PS   L N
hap   793 NHANATVNNATLNGNVHLTDSAQFSLKNSHFWHQIQGDKDTTVTLENATWTMPSDTTLQN  852 orf1  159 LNLDNATITLNSAYRHDAAGAQTGSATDAPXXXXXXXXXXXLLXVTPPTSVESRFNTLTVN  218
          L L+N+T+TLNSAY         + S+ +AP           L   T PTS E RFNTLTVN
hap   853 LTLNNSTVTLNSAY--------SASSNNAPRHRRS-----LETETTPTSAEHRFNTLTVN  899 orf1  219 GKLNGQGTFRFMSELFGYRSDKLKLAESSEGTYTLAVNNTGNEPASLEQLTVVEGKDNKP  278
          GKL+GQGTF+F S LFGY+SDKLKL+  +EG YTL+V NTG EP +LEQLT++E  DNKP
hap   900 GKLSGQGTFQFTSSLFGYKSDKLKLSNDAEGDYTLSVRNTGKEPVTLEQLTLIESLDNKP  959 orf1  279 LSENLNFTLQNEHVDAGA                                           296
          LS+ L FTL+N+HVDAGA
hap   960 LSDKLKFTLENDHVDAGA                                           977
```

Amino acids 1192-1450 of ORF1 show 41% aa identity with hap protein in 259aa overlap:

```
Orf1     1 LDRVFAEDRRNAVWTSGIRDTKHYRSQDFRAYRQQTDLRQIGMQKNLGSGRVGILFSHNR   60
           LDR+F +  ++AVWT+  +D + Y S  FRAY+Q+T+LRQIG +QK L +GR+G +FSH+R
hap   1135 LDRLFVDQAQSAVWTNIAQDKRRYDSDAFRAYQQKTNLRQIGVQKALANGRIGAVFSHSR 1194 orf1    61 TENTFDDGIGNSARLAHGAVFGQYGIDRFYXXXXXXXXXXXXXXXXXXIGXKXRRRVLHYG  120
           ++NTFD+ + N A L   ++F QY          G          K  R+ ++YG
hap   1195 SDNTFDEQVKNHATLTMMSGFAQYQWGDLQFGVNVGTGISASKMAEEQSRKIHRKAINYG 1254 orf1   121 IQARYRAGFGGFGIEPHIGATRYFVQKADYRYENVNIATPGLAFNRYRAGIKADYSFKPA  180
           + A Y+   G   GI+P+ G  RYF+++ +Y+ E V + TP LAFNRY AGI+ DY+F P
hap   1255 VNASYQFRLGQLGIQPYFGVNRYFIERENYQSEEVRVKTPSLAFNRYNAGIRVDYTFTPT 1314 orf1   181 QHISITPYLSLSYTDAASGKVRTRVNTAVLAQDFGKTRSAEWGVNAEIKGFTLSLHAAAA  240
           +IS+ PY  ++Y D ++   V+T VN  VL Q FG+     E G+ AEI  F +S    + +
hap   1315 DNISVKPYFFVNYVDVSNANVQTTVNLTVLQQPFGRYWQKEVGLKAEILHFQISAFISKS 1374 orf1   241 KGPQLEAQHSAGIKLGYRW                                           259
           +G  QL  Q +  G+KLGYRW
hap   1375 QGSQLGKQQNVGVKLGYRW                                          1393
```

Homology with a Predicted ORF from *N. gonorrhoeae*

The blocks of ORF1 show 83.5%, 88.3%, and 97.7% identities in 467, 298, and 259 aa overlap, respectively with a predicted ORF (ORF1ng) from *N. gonorrhoeae*:

```
orf1.pep  MKTTDKRTTETHRKAPKTGRIRFXAAYLAICLSFGILPQAWAGHTYFGINYQYYRDFAEN   60
          ||||||||||||||||||||||| |||||||||||||||| |||||||||||||||||||
orf1ng    MKTTDKRTTETHRKAPKTGRIRFSPAYLAICLSFGILPQARAGHTYFGINYQYYRDFAEN   60 orf1.pep  KGKFAVGAKDIEVYNKKGELVGKSMTKAPMIDFSVVSRNGVAALVGVQYIVSVAHNGGYN  120
          |||||||||||||||||||||||||||||||||||||||||||:| |||||||||||||
orf1ng    KGKFAVGAKDIEVYNKKGELVGKSMTKAPMIDFSVVSRNGVAALAGDQYIVSVAHNGGYN  120 orf1.pep  NVDFGAEGXNIXDQXRXTYKIVKRNNYKAGTKGHPYGGDYHMPRLHKXVTDAEPVEMTSY  180
          |||||||| |  |  |:|:|||||||||||| ||||||||||||||| ||||||||||||
orf1ng    NVDFGAEGSN-PDQHRFSYKIVKRNNYKAGTNGHPYGGDYHMPRLHKFVTDAEPVEMTSY  179 orf1.pep  MDGRKYIDQNNYPDRVRIGAGRQYWRSDEDEPNNRESSYHIAS----------------  223
          ||| |||| |:|||||||||||||||||||||||||||||||
orf1ng    MDGWKYADLNKYPDRVRIGAGRQYWRSDEDEPNNRESSYHIASAYSWLVGGNTFAQNGSG  239
```

```
        -continued
orf1.pep  --------------------------GSPMFIYDAQKQKWLINGVLQTGNPYIGKSNG  255
                                    ||||||||||||||||||||||||||||||
orf1ng    GGTVNLGSEKIHSPYGFLPTGGSFGDSGSPMFIYDAQKQKWLINGVLQTGNPYIGKSNG  289 orf1.pep  FQLVRKDWFYDEIFAGDTHSVFYEPRQNGKYSFNDDNNGTGKINAKHEHNSLPNRLKTRT  315
          ||||||||||||||||||||||||:|||||:|||||||:||:||:|:||||:|||||||
orf1ng    FQLVRKDWFYDEIFAGDTHSVFYEPHQNGKYFFNDNNNGAGKIDAKHKHYSLPYRLKTRT  359 orf1.pep  VQLFNVSLSETAREPVYHAAGGVNSYRPRLNNGENISFIDEGKGELILTSNINQGAGGLY  375
          ||||||||||||||||||||||||||||||||||||||:|||||||||||||||||||||
orf1ng    VQLFNVSLSETAREPVYHAAGGVNSYRPRLNNGENISFIDKGKGELILTSNINQGAGGLY orf1.pep  FQGDFTVSPENNETWQGAGVHISEDSTVTWKVNGVANDRLSKIGKGT              422
          |:|:||||:|||||||||||||||:|:|||||||||||||||||||
orf1ng    FEGNFTVSPKNNETWQGAGVHISDGSTVTWKVNGVANDRLSKIGKGTLLVQAKGENQGSV  479
                                       // orf1.pep              DKVTASLTKTDISGNVDLADHAHLNLTGLA                   744
                      |||  |||:|||:  |||:|||||||||||
orf1ng    FGVAPHQSHTICTRSDWTGLTSCTEKTITDDKVIASLSKTDVRGNVSLADHAHLNLTGLA  774 orf1.pep  TLNGNLSANGDTR-YTVSHNATQNGNXSLVXNAQATFNQATLNGNTSASGNASFNLSDHA  803
          :|||| :::::|:   :  ||||||||:||:||||||||||||||||:|||||||:::|
orf1ng    TFNGNL-VQAETRTIRLRANATQNGNLSLVGNAQATFNQATLNGNTSASDNASFNLSNNA  833 orf1.pep  VQNGSLTLSGNAKANVSHSALNGNVSLADKAVFHFESSRFTGQISGGKDTALHLKDSEWT  863
          |||||||||:||||||||||||||||||||||||||:||||||:|||||||||||||||
orf1ng    VQNGSLTLSDNAKANVSHSALNGNVSLADKAVFHFENSRFTGKISGGKDTALHLKDSEWT  893 orf1.pep  LPSGXELGNLNLDNATITLNSAYRHDAAGAQTGSATDAPRRRSRRSRRSLLXVTPPTSVE  923
          ||||:|||||||||||||||||||||||||||||:||||||||||   |||:|||||:|
orf1ng    LPSGTELGNLNLDNATITLNSAYRHDAAGAQTGSAADAPRRRSRRS---LLSVTPPTSAE  950 orf1.pep  SRFNTLTVNGKLNGQGTFRFMSELFGYRSDKLKLAESSEGTYTLAVNNTGNEPASLEQLT  983
          ||||||||||||||||||||||||||||||:|||||||||||||||||||:|||||||
orf1ng    SRFNTLTVNGKLNGQGTFRFMSELFGYRSGKLKLAESSEGTYTLAVNNTGNEPVSLEQLT  1010 orf1.pep  VVEGKDNKPLSENLNFTLQNEHVDAGAW                                 1011
          ||||||||:|||||||||||||||||||
orf1ng    VVEGKDNTPLSENLNFTLQNEHVDAGAWRYQLIRKDGEFRLHNPVKEQELSDKLGKAGET  1070
                                     // orf1.pep              LDRVFAEDRRNAVWTSGIRDTKHYRSQDFR                   1211
                      ||||||||||||||||||||||||||||||
orf1ng    PQRDLISRYANSGLSEFSATLNSVFAVQDELDRVFAEDRRNAVWTSGIRDTKHYRSQDFR  1239 orf1.pep  AYRQQTDLRQIGMQKNLGSGRVGILFSHNRTENTFDDGIGNSARLAHGAVFGQYGIDRFY  1271
          ||||||||||||||||||||||||||||||| || |||||||||||||||||||| |||
orf1ng    AYRQQTDLRQIGMQKNLGSGRVGILFSHNRTGNTFDDGIGNSARLAHGAVFGQYGIGRFY  1299 orf1.pep  IGISAGAGFSSGSLSDGIGXKXRRRVLHYGIQARYRAGFGGFGIEPHIGATRYFVQKADY  1331
          ||||||||||||||||||| | ||||||||||||||||||||||||||||||||||||
orf1ng    IGISAGAGFSSGSLSDGIRGKIRRRVLHYGIQARYRAGFGGFGIEPHIGATRYFVQKADY  1359 orf1.pep  RYENVNIATPGLAFNRYRAGIKADYSFKPAQHISITPYLSLSYTDAASGKVRTRVNTAVL  1391
          ||||||||||||||||||||||||||||||||||||||||||||||||||||||||||
orf1ng    RYENVNIATPGLAFNRYRAGIKADYSFKPAQHISITPYLSLSYTDAASGKVRTRVNTAVL  1419 orf1.pep  AQDFGKTRSAEWGVNAEIKGFTLSLHAAAAKGPQLEAQHSAGIKLGYRW            1440
          |||||||||||||||||||||||||||||||||||||||||||||||
orf1ng    AQDFGKTRSAEWGVNAEIKGFTLSLHAAAAKGPQLEAQHSAGIKLGYRW            1468
```

The complete length ORF1ng nucleotide sequence was identified <SEQ ID 653>:

```
  1 ATGAAAACAA CCGACAAACG GACAACCGAA ACACACCGCA AAGCCCCTAA

51 AACCGGCCGC ATCCGCTTCT CGCCCGCTTA CTTAGCCATA TGCCTGTCGT

101 TCGGCATTCT GCCCCAAGCC CGGGCGGGAC ACACTTATTT CGGCATCAAC

151 TACCAATACT ATCGCGACTT TGCCGAAAAT AAAGGCAAGT TTGCAGTCGG

201 GGCGAAAGAT ATTGAGGTTT ACAACAAAAA AGGGGAGTTG GTCGGCAAAT

251 CGATGACGAA AGCCCCGATG ATTGATTTTT CTGTGGTATC GCGTAACGGC

301 GTGGCGGCAT TGGCGGGCGA TCAATATATT GTGAGCGTGG CACATAACGG

351 CGGCTATAAC AATGTTGATT TGGTGCGGA GGGAAGCAAT CCCGATCAGC

401 ACCGCTTTTC TTACCAAATT GTGAAAAGAA ATAATTATAA AGCAGGGACT

451 AACGGCCATC CTTATGGCGG CGATTATCAT ATGCCGCGTT TGCACAAATT

501 TGTCACAGAT GCAGAACCTG TTGAGATGAC CAGTTATATG GATGGGTGGA

551 AATACGCTGA TTTAAATAAA TACCCTGATC GTGTTCGAAT CGGAGCAGGC

601 AGACAATATT GGCGGTCTGA TGAAGACGAA CCCAATAACC GCGAAAGTTC
```

-continued

```
 651 ATATCATATT GCAAGCGCAT ATTCTTGGCT CGTCGGTGGC AATACCTTTG
 701 CACAAAATGG ATCAGGTGGT GGCACAGTCA ACTTAGGTAG CGAAAAAATT
 751 AAACATAGCC CATATGGTTT TTTACCAACA GGAGGCTCAT TTGGCGACAG
 801 TGGCTCACCA ATGTTTATCT ATGATGCCCA AAAGCAAAAG TGGTTAATTA
 851 ATGGGGTATT GCAAACAGGC AACCCCTATA TAGGAAAAAG CAATGGCTTC
 901 CAGCTAGTTC GTAAAGATTG GTTCTATGAT GAAATCTTTG CTGGAGATAC
 951 CCATTCAGTA TTCTACGAAC CACATCAAAA TGGGAAATAC TTTTTTAACG
1001 ACAATAATAA TGGCGCAGGA AAAATCGATG CCAAACATAA ACACTATTCT
1051 CTACCTTATA GATTAAAAAC ACGAACCGTT CAATTGTTTA ATGTTTCTTT
1101 ATCCGAGACA GCAAGAGAAC CTGTTTATCA TGCTGCAGGT GGGGTCAACA
1151 GTTATCGACC CAGACTGAAT AATGGAGAAA ATATTTCCTT TATTGACAAA
1201 GGAAAAGGTG AATTGATACT TACCAGCAAC ATCAACCAAG GCGCGGGCGG
1251 TTTGTATTTT GAGGGTAATT TTACGGTCTC GCCTAAAAAC AACGAAACGT
1301 GGCAAGGCGC GGGCGTTCAT ATCAGTGATG GCAGTACCGT TACTTGGAAA
1351 GTAAACGGCG TGGCAAACGA CCGCCTGTCC AAAATCGGCA AAGGCACGCT
1401 GCTGGTTCAA GCCAAAGGGG AAAACCAAGG CTCGGTCAGC GTGGGCGACG
1451 GTAAAGTCAT CTTAGATCAG CAGGCGGACG ATCAAGGCAA AAAACAAGCC
1501 TTTAGTGAAA TCGGCTTGGT CAGCGGCAGG GGGACGGTGC AACTGAATGC
1551 CGATAATCAG TTCAACCCCG ACAAACTCTA TTTCGGCTTT CGCGGCGGAC
1601 GTTTGGATTT GAACGGGCAT TCGCTTTCGT TCCACCGCAT TCAAAATACC
1651 GATGAAGGGG CGATGATTGT CAACCACAAT CAAGACAAAG AATCCACCGT
1701 TACCATTACA GGCAATAAAG ATATTACTAC AACCGGCAAT AACAACAACT
1751 TGGATAGCAA AAAAGAAATT GCCTACAACG GTTGGTTTGG CGAGAAAGAT
1801 GCAACCAAAA CGAACGGGCG GCTCAATCTG AATTACCAAC CGGAAGAAGC
1851 GGATCGCACT TTACTGCTTT CCGGCGGAAC AAATTTAAAC GGCAATATCA
1901 CGCAAACAAA CGGCAAACTG TTTTTCAGCG GCAGACCGAC ACCGCACGCC
1951 TACAATCATT TAGGAAGCGG GTGGTCAAAA ATGGAAGGTA TCCCACAAGG
2001 AGAAATCGTG TGGGACAACG ATTGGATCGA CCGCACATTT AAAGCGGAAA
2051 ACTTCCATAT TCAGGGCGGA CAAGCGGTGG TTTCCCGCAA TGTTGCCAAA
2101 GTGGAAGGCG ATTGGCATTT AAGCAATCAC GCCCAAGCAG TTTTCGGTGT
2151 CGCACCGCAT CAAAGCCACA CAATCTGTAC ACGTTCGGAC TGGACGGGTC
2201 TGACAAGTTG TACCGAAAAA ACCATTACCG ACGATAAAGT GATTGCTTCA
2251 TTGAGCAAGA CCGACATCAG AGGCAATGTC AGCCTTGCCG ATCACGCTCA
2301 TTTAAATCTC ACAGGACTTG CCACACTCAA CGGCAATCTT AGTGCAGGCG
2351 GAGACACGCA CTATACGGTT ACGCGCAACG CCACCCAAAA CGGCAACCTC
2401 AGCCTCGTGG GCAATGCCCA AGCAACATTT AATCAAGCCA CATTAAACGG
2451 CAACACATCG GCTTCGGACA ATGCTTCATT TAATCTAAGC AACAACGCCG
2501 TACAAAACGG CAGTCTGACG CTTTCCGACA ACGCTAAGGC AAACGTAAGC
2551 CATTCCGCAC TCAACGGCAA TGTCTCCCTA GCCGATAAGG CAGTATTCCA
2601 TTTTGAAAAC AGCCGCTTTA CCGGAAAAAT CAGCGGCGGC AAGGATACGG
2651 CATTACACTT AAAAGACAGC GAATGGACGC TGCCGTCGGG CACGGAATTA
```

-continued

```
2701 GGCAATTTAA ACCTTGACAA CGCCACCATT ACACTCAATT CCGCCTATCG
2751 ACACGATGCG GCAGGCGCGC AAACCGGCAG TGCGGCAGAT GCGCCGCGCC
2801 GCCGTTCGCG CCGTTCCCTA TTATCCGTTA CGCCGCCAAC TTCGGCAGAA
2851 TCCCGTTTCA ACACGCTGAC GGTAAACGGC AAATTGAACG GTCAGGGAAC
2901 ATTCCGCTTT ATGTCGGAAC TCTTCGGCTA CCGCAGCGGC AAATTGAAGC
2951 TGGCGGAAAG TTCCGAAGGC ACTTACACCT TGGCTGTCAA CAATACCGGC
3001 AACGAACCCG TAAGTCTCGA GCAATTGACG GTAGTGGAAG GAAAAGACAA
3051 CACACCGCTG TCCGAAAATC TTAATTTCAC CCTGCaaaAc gaacacgtcg
3101 atgccggcgc atggCGTTAT CAGCTTATCC gcaaagacgG CGAGTTCCgc
3151 CTGCATAATC CGGTCAAAGA ACAAGAGCTT TCCGACAAAC TCGGCAAGgc
3201 gggagaaACA GAggccgccT TGACGGCAAA ACAGGCacaA CTTGCCGCCA
3251 AAcaacaggc ggaaaAAGAC AACgcgcaaa gccttgAcgc gctgattgcg
3301 gCcgggcgca atgccaccga AAAGGCAgaa agtgttgccg aaccgGCCCG
3351 GCAGGCAGGC GGGGAAAAtg ccgGCATTAT GCAGGCGGAG GAAGAGAAAA
3401 AACGGGTGCA GGCGGATAAA GACACCGCCT TGGCGAAACA GCGCGAAGCG
3451 GAAACCCGGC CGGCTACCAC CGCCTTCCCC CGCGCCCGCC GCGCCCGCCG
3501 GGATTTGCCG CAACCGCAGC CCCAACCGCA ACCCCAACCG CAGCGCGACC
3551 TGATCAGCCG TTATGCCAAT AGCGGTTTGA GTGAATTTTC CGCCACGCTC
3601 AACAGCGTTT TCGCCGTACA GGACGAATTG GACCGCGTGT TGCCGAAGA
3651 CCGCCGCAAC GCCGTTTGGA CAAGCGGCAT CCGGGACACC AAACACTACC
3701 GTTCGCAAGA TTTCCGCGCC TACCGCCAAC AAACCGACCT GCGCCAAATC
3751 GGTATGCAGA AAAACCTCGG CAGCGGGCGC GTCGGCATCC TGTTTTCGCA
3801 CAACCGGACC GGAAACACCT TCGACGACGG CATCGGCAAC TCGGCACGGC
3851 TTGCCCACGG TGCCGTTTTC GGGCAATACG GCATCGGCAG GTTCGACATC
3901 GGCATCAGCG CGGGCGCGGG TTTTAGTAGC GGCAGCCTTT CAGACGGCAT
3951 CAGAGGCAAA ATCCGCCGCC GCGTGCTGCA TTACGGCATT CAGGCAAGAT
4001 ACCGCGCAGG TTTCGGCGGA TTCGGCATCG AACCGCACAT CGGCGCAACG
4051 CGCTATTTCG TCCAAAAAGC GGATTACCGA TACGAAAACG TCAATATCGC
4101 CACCCCGGGC CTTGCATTCA ACCGCTACCG CGCGGGCATT AAGGCAGATT
4151 ATTCATTCAA ACCGGCGCAA CACATTTCCA TCACGCCTTA TTTGAGCCTG
4201 TCCTATACCG ATGCCGCTTC CGGCAAAGTC CGAACGCGCG TCAATACCGC
4251 CGTATTGGCG CAGGATTTCG GCAAAACCCG CAGTGCGGAA TGGGGCGTAA
4301 ACGCCGAAAT CAAAGGTTTC ACGCTGTCCC TCCACGCTGC CGCCGCCAAG
4351 GGGCCGCAAT TGGAAGCGCA GCACAGCGCG GGCATCAAAT TAGGCTACCG
4401 CTGGTAA
```

This is predicted to encode a protein having amino acid sequence <SEQ ID 654>:

```
  1 MKTTDKRTTE THRKAPKTGR IRFSPAYLAI CLSFGILPQA RAGHTYFGIN
 51 YQYYRDFAEN KGKFAVGAKD IEVYNKKGEL VGKSMTKAPM IDFSVVSRNG
```

-continued

```
 101  VAALAGDQYI  VSVAHNGGYN  NVDFGAEGSN  PDQHRFSYQI  VKRNNYKAGT
 151  NGHPYGGDYH  MPRLHKFVTD  AEPVEMTSYM  DGWKYADLNK  YPDRVRIGAG
 201  RQYWRSDEDE  PNNRESSYHI  ASAYSWLVGG  NTFAQNGSGG  GTVNLGSEKI
 251  KHSPYGFLPT  GGSFGDSGSP  MFIYDAQKQK  WLINGVLQTG  NPYIGKSNGF
 301  QLVRKDWFYD  EIFAGDTHSV  FYEPHQNGKY  FFNDNNNGAG  KIDAKHKHYS
 351  LPYRLKTRTV  QLFNVSLSET  AREPVYHAAG  GVNSYRPRLN  NGENISFIDK
 401  GKGELILTSN  INQGAGGLYF  EGNFTVSPKN  NETWQGAVH   ISDGSTVTWK
 451  VNGVANDRLS  KIGKGTLLVQ  AKGENQGSVS  VGDGKVILDQ  QADDQGKKQA
 501  FSEIGLVSGR  GTVQLNADNQ  FNPDKLYFGF  RGGRLDLNGH  SLSFHRIQNT
 551  DEGAMIVNHN  QDKESTVTIT  GNKDITTTGN  NNNLDSKKEI  AYNGWFGEKD
 601  ATKTNGGLNL  NYPPEEADRT  LLLSGGTNLN  GNITQTNGKL  FFSGRPTPHA
 651  YNHLGSGWSK  MEGIPQGEIV  WDNDWIDRTF  KAENFHIQGG  QAVVSRNVAK
 701  VEGDWHLSNH  AQAVFGVAPH  QSHTICTRSD  WTGLTSCTEK  TITDDKVIAS
 751  LSKTDVRGNV  SLADHAHLNL  TGLATFNGNL  VQAETRTIRL  RANATQNGNL
 801  SLVGNAQATF  NQATLNGNTS  ASDNASFNLS  NNAVQNGSLT  LSDNAKANVS
 851  HSALNGNVSL  ADKAVFHFEN  SRFTGKISGG  KDTALHLKDS  EWTLPSGTEL
 901  GNLNLDNATI  TLNSAYRHDA  AGAQTGSAAD  APRRRSRRSL  LSVTPPTSAE
 951  SRFNTLTVNG  KLNGQGTFRF  MSELFGYRSG  KLKLAESSEG  TYTLAVNNTG
1001  NEPVSLEQLT  VVEGKDNTPL  SENLNFTLQN  EHVDAGAWRY  QLIRKDGEFR
1051  LHNPVKEQEL  SDKLGKAGET  EAALTAKQAQ  LAAKQQAEKD  NAQSLDALIA
1101  AGRNATEKAE  SVAEPARQAG  GENAGIMQAE  EEKKRVQADK  DTALAKQREA
1151  ETRPATTAFP  RARRARRDLP  QPQPQPQPQP  QRDLISRYAN  SGLSEFSATL
1201  NSVFAVQDEL  DRVFAEDRRN  AVWTSGIRDT  KHYRSQDFRA  YRQQTDLRQI
1251  GMQKNLGSGR  VGILFSHNRT  GNTFDDGIGN  SARLAHGAVF  GQYGIGRFDI
1301  GISAGAGFSS  GSLSDGIRGK  IRRRVLHYGI  QARYRAGFGG  FGIEPHIGAT
1351  RYFVQKADYR  YENVNIATPG  LAFNRYRAGI  KADYSFKPAQ  HISITPYLSL
1401  SYTDAASGKV  RTRVNTAVLA  QDFGKTRSAE  WGVNAEIKGF  TLSLHAAAAK
1451  GPQLEAQHSA  GIKLGYRW*
```

Underlined and double-underlined sequences represent the active site of a serine protease (trypsin family) and an ATP/GTP-binding site motif A (P-loop).

ORF1-1 and ORF1 ng show 93.7% identity in 1471 aa overlap:

```
                    10         20         30         40         50         60
   orf1-1.pep  MKTTDKRTTETHRKAPKTGRIRFSPAYLAICLSFGILPQAWAGHTYFGINYQYYRDFAEN
               ||||||||||||||||||||||||||||||||||||||||| |||||||||||||||||||
   orflng-1    MKTTDKRTTETHRKAPKTGRIRFSPAYLAICLSFGILPQARAGHTYFGINYQYYRDFAEN
                    10         20         30         40         50         60

70         80         90        100        110        120
   orf1-1.pep  KGKFAVGAKDIEVYNKKGELVGKSMTKAPMIDFSVVSRNGVAALVGDQYIVSVAHNGGYN
               ||||||||||||||||||||||||||||||||||||||||||||:|||||||||||||||
   orflng-1    KGKFAVGAKDIEVYNKKGELVGKSMTKAPMIDFSVVSRNGVAALAGDQYIVSVAHNGGYN
                    70         80         90        100        110        120

130        140        150        160        170        180
   orf1-1.pep  NVDFGAEGRNPDQHRFTYKIVKRNNYKAGTKGHPYGGDYHMPRLHKFVTDAEPVEMTSYM
               |||||||||:||||||:|:|||||||||||:||||||:||||||||||||||||||||||
   orflng-1    NVDFGAEGSNPDQHRFSYQIVKRNNYKAGTNGHPYGNDYHMPRLHKFVTDAEPVEMTSYM
                   130        140        150        160        170        180
```

```
                    190         200         210         220         230         240
orf1-1.pep  DGRKYIDQNNYPDRVRIGAGRQYWRSDEDEPNNRESSYHIASAYSWLVGGNTFAQNGSGG
            ||  | |  ||||||||||||||||||||||||||||||||||||||||||||||||
orf1ng-1    DGWKYADLNKYPDRVRIGAGRQYWRSDEDEPNNRESSYHIASAYSWLVGGNTFAQNGSGG
                    190         200         210         220         230         240

250         260         270         280         290         300
orf1-1.pep  GTVNLGSEKIKHSPYGFLPTGGSFGDSGSPMFIYDAQKQKWLINGVLQTGNPYIGKSNGF
            ||||||||||||||||||||||||||||||||||||||||||||||||||||||||||||
orf1ng-1    GTVNLGSEKIKHSPYGFLPTGGSFGDSGSPMFIYDAQKQKWLINGVLQTGNPYIGKSNGF
                    250         260         270         280         290         300

310         320         330         340         350         360
orf1-1.pep  QLVRKDWFYDEIFAGDTHSVFYEPRQNGKYSFNDDNNGTGKINAKHEHNSLPNRLKTRTV
            |||||||||||||||||||||||||||:|||||:||||:||:||:|:|:|||:||||||
orf1ng-1    QLVRKDWFYDEIFAGDTHSVFYEPHQNGKYFFNDNNNGAGKIDAKHKHYSLPYRLKTRTV
                    310         320         330         340         350         360

370         380         390         400         410         420
orf1-1.pep  QLFNVSLSETAREPVYHAAGGVNSYRPRLNNGENISFIDEGKGELILTSNINQGAGGLYF
            ||||||||||||||||||||||||||||||||||||||:|||||||||||||||||||||
orf1ng-1    QLFNVSLSETAREPVYHAAGGVNSYRPRLNNGENISFIDKGKGELILTSNINQGAGGLYF
                    370         380         390         400         410         420

430         440         450         460         470         480
orf1-1.pep  QGDFTVSPENNETWQGAGVHISEDSTVTWKVNGVANDRLSKIGKGTLHVQAKGENQGSIS
            :|||||||:|||||||||||||||:|||||||||||||||||||||:|||||||||||:|
orf1ng-1    EGNFTVSPKNNETWQGAGVHISDGSTVTWKVNGVANDRLSKIGKGTLLVQAKGENQGSVS
                    430         440         450         460         470         480

490         500         510         520         530         540
orf1-1.pep  VGDGTVILDQQADDKGKKQAFSEIGLVSGRGTVQLNADNQFNPDKLYFGFRGGRLDLNGH
            ||||::||||||||:|||||||||||||||||||||||||||||||||||||||||||||
orf1ng-1    VGDGKVILDQQADDQGKKQAFSEIGLVSGRGTVQLNADNQFNPDKLYFGFRGGRLDLNGH
                    490         500         510         520         530         540

550         560         570         580         590         600
orf1-1.pep  SLSFHRIQNTDEGAMIVNHNQDKESTVTITGNKDIATTGNNNSLDSKKEIAYNGWFGEKD
            ||||||||||||||||||||||||||||||||||||:|||||:|||||||||||||||||
orf1ng-1    SLSFHRIQNTDEGAMIVNHNQDKESTVTITGNKDITTTGNNNNLDSKKEIAYNGWFGEKD
                    550         560         570         580         590         600

610         620         630         640         650         660
orf1-1.pep  TTKTNGRLNLVYQPAAEDRTLLLSGGTNLNGNITQTNGKLFFSGRPTPHAYNHLNDHWSQ
            :|||||||||||:|||||||||||||||||||||||||||||||||||||||::|||::
orf1ng-1    ATKTNGRLNLNYQPEEADRTLLLSGGTNLNGNITQTNGKLFFSGRPTPHAYNHLGSGWSK
                    610         620         630         640         650         660

670         680         690         700         710         720
orf1-1.pep  KEGIPRGEIVWDNDWINRTFKAENFQIKGGQAVVSRNVAKVKGDWHLSNHAQAVFGVAPH
            :|||:|:|||||||||:|||||||||:||||||||||||||:||||||||||||||||||
orf1ng-1    MEGIPQGEIVWDNDWIDRTFKAENFHIQGGQAVVSRNVAKVEGDWHLSNHAQAVFGVAPH
                    670         680         690         700         710         720

730         740         750         760         770         780
orf1-1.pep  QSHTICTRSDWTGLTNCVEKTITDDKVIASLTKTDISGNVDLADHAHLNLTGLATLNGNL
            ||||||||||||||||:|:|||||||||||||||:||:|:|||||||||||||||||||
orf1ng-1    QSHTICTRSDWTGLTSCTEKTITDDKVIASLSKTDIRGNVSLADHAHLNLTGLATLNGNL
                    730         740         750         760         770         780

790         800         810         820         830         840
orf1-1.pep  SANGDTRYTVSHNATQNGNLSLVGNAQATFNQATLNGNTSASGNASFNLSDHAVQNGSLT
            || ||||:|||:||||||||||||||||||||||||||||||||:||||||:||||||||
orf1ng-1    SAGGDTHYTVTRNATQNGNLSLVGNAQATFNQATLNGNTSASDNASFNLSNNAVQNGSLT
                    790         800         810         820         830         840

850         860         870         880         890         900
orf1-1.pep  LSGNAKANVSHSALNGNVSLADKAVFHFESSRFTGQISGGKDTALHLKDSEWTLPSGTEL
            ||:||||||||||||||||||||||||||||:|||:||||||||||||||||||||||||
orf1ng-1    LSDNAKANVSHSALNGNVSLADKAVFHFENSRFTGKISGGKDTALHLKDSEWTLPSGTEL
                    850         860         870         880         890         900

910         920         930         940         950         960
orf1-1.pep  GNLNLDNATITLNSAYRHDAAGAQTGSATDAPRRRSRRSRRSLLSVTPPTSVESRFNTLT
            ||||||||||||||||||||||||||||:|||||||||   ||||||||||:|||||||
orf1ng-1    GNLNLDNATITLNSAYRHDAAGAQTGSAADAPRRRSR---RSLLSVTPPTSAESRFNTLT
                    910         920         930         940         950

970         980         990        1000        1010        1020
orf1-1.pep  VNGKLNGQGTFRFMSELFGYRSDKLKLAESSEGTYTLAVNNTGNEPASLEQLTVVEGKDN
            ||||||||||||||||||||||:||||||||||||||||||||||||:||||||||||||
orf1ng-1    VNGKLNGQGTFRFMSELFGYRSGKLKLAESSEGTYTLAVNNTGNEPVSLEQLTVVEGKDN
              960         970         980         990        1000        1010

1030        1040        1050        1060        1070
orf1-1.pep  KPLSENLNFTLQNEHVDAGAWRYQLIRKDGEFRLHNPVKEQELSDKLGKA----------
            :|||||||||||||||||||||||||||||||||||||||||||||||||
orf1ng-1    TPLSENLNFTLQNEHVDAGAWRYQLIRKDGEFRLHNPVKEQELSDKLGKAGETEAALTAK
                   1020        1030        1040        1050        1060        1070
```

```
                   1080      1090      1100      1110      1120
orf1-1.pep     ----EAKKQAEKDNAQSLDALIAAGRDAVEKTESVAEPARQAGGENVGIMQAEEEKKRVQ
                   ||||||||||||||||||||:|||:|:||||||||||||||:||||||||||||||
orf1ng-1       QAQLAAKQQAEKDNAQSLDALIAAGRNATEKAESVAEPARQAGGENAGIMQAEEEKKRVQ
               1080      1090      1100      1110      1120      1130

1130      1140      1150      1160      1170      1170
orf1-1.pep     ADKDTALAKQREAETRPATTAFPRARRARRDLPQLQPQPQPQPQRDLISRYANSGLSEFS
               ||||||||||||||||||||||||||||||||||||||||||||||||||||||||||||
orf1ng-1       ADKDTALAKQREAETRPATTAFPRARRARRDLPQLQPQPQPQPQRDLISRYANSGLSEFS
               1140      1150      1160      1170      1180      1190

1190      1200      1210      1220      1230      1240
orf1-1.pep     ATLNSVFAVQDELDRVFAEDRRNAVWTSGIRDTKHYRSQDFRAYRQQTDLRQIGMQKNLG
               ||||||||||||||||||||||||||||||||||||||||||||||||||||||||||||
orf1ng-1       ATLNSVFAVQDELDRVFAEDRRNAVWTSGIRDTKHYRSQDFRAYRQQTDLRQIGMQKNLG
               1200      1210      1220      1230      1240      1250

1250      1260      1270      1280      1290      1300
orf1-1.pep     SGRVGILFSHNRTENTFDDGIGNSARLAHGAVFGQYGIDRFYIGISAGAGFSSGSLSDGI
               |||||||||||||:|||||||||||||||||||||:||:|||||||||||||||||||||
orf1ng-1       SGRVGILFSHNRTGNTFDDGIGNSARLAHGAVFGQYGIGRFDIGISAGAGFSSGSLSDGI
               1260      1270      1280      1290      1300      1310

1310      1320      1330      1340      1350      1360
orf1-1.pep     GGKIRRRVLHYGIQARYRAGFGGFGIEPHIGATRYFVQKADYRYENVNIATPGLAFNRYR
               :|||||||||||||||||||||||||||||||||||||||||||||||||||||||||||
orf1ng-1       RGKIRRRVLHYGIQARYRAGFGGFGIEPHIGATRYFVQKADYRYENVNIATPGLAFNRYR
               1320      1330      1340      1350      1360      1370

1370      1380      1390      1400      1410      1420
orf1-1.pep     AGIKADYSFKPAQHISITPYLSLSYTDAASGKVRTRVNTAVLAQDFGKTRSAEWGVNAEI
               ||||||||||||||||||||||||||||||||||||||||||||||||||||||||||||
orf1ng-1       AGIKADYSFKPAQHISITPYLSLSYTDAASGKVRTRVNTAVLAQDFGKTRSAEWGVNAEI
               1380      1390      1400      1410      1420      1430

1430      1440      1450
orf1-1.pep     KGFTLSLHAAAAKGPQLEAQHSAGIKLGYRWX
               ||||||||||||||||||||||||||||||||
orf1ng-1       KGFTLSLHAAAAKGPQLEAQHSAGIKLGYRWX
               1440      1450      1460
```

In addition, ORF1ng shows 55.7% identity with hap protein (P45387) over a 1455aa overlap:

```
SCORES Init1: 1104 Initn: 4632 Opt: 2680
Smith-Waterman score: 5165; 55.7% identity in 1455 aa overlap 10        20        30        40        50        60
orf1ng-1.pep   MKTTDKRTTETHRKAPKTGRIRFSPAYLAICLSFGILPQARAGHTYFGINYQYYRDFAEN
                                    ::|  |:|:|:  |  ||||||||||:||||||||||
p45387                             MKKTVFRLNFLTACISLGIVSQAWAGHTYFGIDYQYYRDFAEN
                                            10        20        30        40

70        80        90       100       110       120
orf1ng-1.pep   KGKFAVGAKDIEVYNKKGELVGKSMTKAPMIDFSVVSRNGVAALAGDQYIVSVAHNGGYN
               ||||:|||:|::|||||:|:|||||||||||||||||||||||: :|||||||||:|:|
p45387         KGKFTVGAQNIKVYNKQGQLVGTSMTKAPMIDFSVVSRNGVAALVENQYIVSVAHNVGYT
                       50        60        70        80        90       100

130       140       150       160       170       180
orf1ng-1.pep   NVDFGAEGSNPDQHRFSYQIVKRNNYKAGTNGHPYGGDYHMPRLHKFVTDAEPVEMTSYM
               :||||||| |||||||| ||:||||||| |  ||| ||||:|||||||:  |::||| |
p45387         DVDFGAEGNNPDQHRFTYKIVKRNNYKKD-NLHPYEDDYHNPRLHKFVTEAAPIDMTSNM
                      110       120       130       140       150       160

190       200       210       220       230       240
orf1ng-1.pep   DGWKYADLNKYPDRVRIGAGRQYWRSDEDEPNNRESSYHIASAYSWLVGGNTFAQNGSGG
               :  | |   :||:|||| |||:||| |:|:|      |: |||||| |||| | ||| |
p45387         NGSTYSDRTKYPERVRIGSGRQFWRNDQDKGD------QVAGAYHYLTAGNTHNQRGAGN
                      170       180       190        200       210

250       260       270       280       290       300
orf1ng-1.pep   GTVNLGSEKIKHSPYGFLPTGGSFGDSGSPMFIYDAQKQKWLINGVLQTGNPYIGKSNGF
                |::|| | :  ||| |  || ||||||||||||||:||||||||:| |||| | |||
p45387         GYSYLGGDVRKAGEYGPLPIAGSKGDSGSPMFIYDAEKQKWLINGILREGNPFEGKENGF
                      220       230       240       250       260       270

310       320       330       340       350       360
orf1ng-1.pep   QLVRKDWFYDEIFAGDTHSVFYEPHQNGKYFFNDNNNGAGKIDAKHKHYSLPYRLKTRTV
               |||||  : ||||  |  ||| |  ::|||  |:  | |  |::  ::|:|::   :
p45387         QLVRKSYF-DEIFERDLHTSLYTRAGNGVYTISGNDNGQGSITQKS---GIPSEIK---I
                      280       290       300       310       320
```

```
              370       380       390       400       410   419
orflng-1.pep  QLFNVSLSETAREPVYHAA-GGVNSYRPRLNNGENISFIDKGKGELILTSNINQGAGGLY
              |::||    ::  ::    |  | ||||||||  :|:  :|   ::|||||||||
p45387        TLANMSLPLKEKDKVHNPRYDGPNIYSPRLNNGETLYFMDQKQGSLIFASDINQGAGGLY
              330       340       350       360       370       380

420       430       440       450       460       470   479
orflng-1.pep  FEGNFTVSPKNNETWQGAGVHISDGSTVTWKVNGVANDRLSKIGKGTLLVQAKGENQGSV
              ||||||||| :| |||||:|| : ||||||||||| :|||||||||||:|||||| |:
p45387        FEGNFTVSPNSNQTWQGAGIHVSENSTVTWKVNGVEHDRLSKIGKGTLHVQAKGENKGSI
              390       400       410       420       430       440

480       490       500       510       520       530   539
orflng-1.pep  SVGDGKVILDQQADDQGKKQAFSEIGLVSGRGTVQLNADNQFNPDKLYFGFRGGRLDLNG
              |||||||||:|||||:||:|||||||||||||||||:|::| | |:|||||||||||||
p45387        SVGDGKVILEQQADDQGNKQAFSEIGLVSGRGTVQLNDDKQFDTDKFYFGFRGGRLDLNG
              450       460       470       480       490       500

540       550       560       570       580       590
orflng-1.pep  HSLSFHRIQNTDEGAMIVNHNQDKESTVTITGNKDITT-TGNN-NNLDSKKEIAYNGWFG
              |||:|:|||||||||||||||: :: |||||||::|:  |||| :||| |||||||||||
p45387        HSLTFKRIQNTDEGAMIVNHNTTQAANVTITGNESIVLPNGNNINKLDYRKEIAYNGWFG
              510       520       530       540       550       560

600       610       620       630       640       650
orflng-1.pep  EKDATKTNGRLNLNYQPEEADRTLLLSGGTNLNGNITQTNGKLFFSGRPTPHAYNHLGSG
              | || |:|||||||:|  ::|||||||||||| |||||:|||||||||||||||||:
p45387        ETDKNKHNGRLNLIYKPTTEDRTLLLSGGTNLKGDITQTKGKLFFSGRPTPHAYNHLNKR
              570       580       590       600       610       620

660       670       680       690       700       710
orflng-1.pep  WSKMEGIPQGEIVWDNDWIDRTFKAENFHIQGGQAVVSRNVAKVEGDWHLSNHAQAVFGV
              || ||||||||||||:|||:|||||||| |||:|||||||:  : |||:| : :|||||
p45387        WSEMEGIPQGEIVWDHDWINRTFKAENFQIKGGSAVVSRNVSSIEGNWTVSNNANATFGV
              630       640       650       660       670       680

720       730       740       750       760       770
orflng-1.pep  APHQSHTICTRSDWTGLTSCTEKTITDDKVIASLSKTDIRGNVSLADHAHLNLTGLATLN
              :|:::||||||||||||:| |:|||:|:|| |||:|:|| ||:|||| ||||| || ||
p45387        VPNQQNTICTRSDWTGLTTCQKVDLTDTKVINSIPKTQINGSLNLTDNATANVKGLAKLN
              690       700       710       720       730       740

780       790       800       810       820       830
orflng-1.pep  GNLSAGGDTHYTVTRNATQNGNLSLVGNAQATFNQATLNGNTSASDNASFNLSNNAVQNG
              ||:::                                    :::::|||||:| |
p45387        GNVTL-------------------------------------TNHSQFTLSNNATQIG
              750                                         760       770

840       850       860       870       880       890
orflng-1.pep  SLTLSDNAKANVSHSALNGNVSLADKAVFHFENSRFTGKISGGKDTALHLKDSEWTLPSG
              :::  ||||:| |: :|||||:|:|:|:| ::|:  :|:|  ||||:|:|:|| |||:|
p45387        NIRLSDNSTATVDNANLNGNVHLTDSAQFSLKNSHFSHQIQGDKGTTVTLENATWTMPSD
                        780       790       800       810       820       830

900       910       920       930       940       950
orflng-1.pep  TELGNLNLDNATITLNSAYRHDAAGAQTGSAADAPRRRSLLSVTPPTSAESRFNTLT
              | | ||:|:|:|||||||       ::|: ::||||||   |:  ||||| ||||||
p45387        TTLQNLTLNNSTITLNSAY--------SASSNNTPRRRS---LETETTPTSAEHRFNTLT
                        840           850       860       870

960       970       980       990      1000      1010
orflng-1.pep  VNGKLNGQGTFRFMSELFGYRSGKLKLAESSEGTYTLAVNNTGNEPVSLEQLTVVEGKDN
              |||||:|||||:| |||||| |||||| |::||||||:|||||| |:||||| ||||||
p45387        VNGKLSGQGTFQFTSSLFGYKSDKLKLSNDAEGDYILSVRNTGKEPETLEQLTLVESKDN
              880       890       900       910       920       930

1020      1030      1040      1050      1060      1070
orflng-1.pep  TPLSENLNFTLQNEHVDAGAWRYQLIRKDGEFRLHNPVKEQELSDKLGKAGETEAALTAK
              ||||:|| ||||||:|||||| ||:::|||||||||:|||||::|: |:   |  |||||
p45387        QPLSDKLKFTLENDHVDAGALRYKLVKNDGERFLHNPIKEQELHNDLVRAEQAERTLEAK
              940       950       960       970       980       990

1080      1090      1100      1110      1120      1130
orflng-1.pep  QAQLAAKQQAEKDNAQSLDALIAAGRNAT-EKAESVAEPARQAGGENAGIMQAEEEKKRV
              |: : |: ::| :|   |: : |  ||:  :| ::  :  ||:|    |  ::|||:|
p45387        QVEPTAKTQTGEPKVRSRRAARAAFPDTLPDQSLLNALEAKQAE-LTAETQKSKAKTKKV
              1000      1010      1020      1030      1040      1050

1140      1150      1160      1170      1180      1190
orflng-1.pep  QADK---DTALAKQREAETRPATTAFPRARRARRD-LPQPQPQPQPQRDLISRYANSG
              :|:|    : | | ::::|       | :|:  |::|||::|::|||   :|||||:: |
p45387        RSKRAVFSDPLLDQSLFALEAALEVIDAPQQSEKDRLAQEEAEKQ-RKQKDLISRYSNSA
              1060      1070      1080      1090      1100      1110

1200      1210      1220      1230      1240      1250
orflng-1.pep  LSEFSATLNSVFAVQDELDRVFAEDRRNAVWTSGIRDTKHYRSQDFRAYRQQ-TDLRQIG
              |||:||||||:|:|||||||:|:||:::| ||| |:|:::|:|||||| |:| |:||||||
p45387        LSELSATVNSMLSVQDELDRLFVDQAQSSAVWTNIAQDKRRYDSDAFRAYQQQKTNLRQIG
              1120      1130      1140      1150      1160      1170

1260      1270      1280      1290      1300      1310
orflng-1.pep  MQKNLGSGRVGILFSHNRTGNTFDDGIGNSARLAHGAVFGQYGIGRFDIGISAGAGFSSG
              :||:|| |||| :||| |: :|||| :::| | |  ||  | |:  ||  ||:|:||||::
p45387        VQKALANGRIGAVFSHSRSDNTFDEQVKNHATLTMMSGFAQYQWGDLQFGVNVGTGISAS
              1180      1190      1200      1210      1220      1230
```

```
                  1320       1330       1340       1350       1360       1370
orflng-1.pep  SLSDGIRGKIRRRVLHYGIQARYRAGFGGFGIEPHIGATRYFVQKADYRYENVNIATPGL
              ::: ||| ||::::||::|    :     ::|:::||||::  :|: |:|   :  ||:|
p45387        KMAEEQSRKIHRKAINYGVNASYQFRLGQLGIQPYFGVNRYFIERENYQSEEVRVKTPSL
              1240       1250       1260       1270       1280       1290

1380       1390       1400       1410       1420       1430
orflng-1.pep  AFNRYRAGIKADYSFKPAQHISITPYLSLSYTDAASGKVRTRVNTAVLAQDFGKTRSAEW
              ||||||| |  :|: |:    :: || | ::::::|::  :|| :|||: :|  :  :
p45387        AFNRYNAGIRVDYTFTPTDNISVKPYFFVNYVDVSNANVQTTVNLTVLQQPFGRYWQKEV
              1300       1310       1320       1330       1340       1350

1440       1450       1460  1469
orflng-1.pep  GVNAEIKGFTLSLHAAAAKGPQLEAQHSAGIKLGYRWX
              |  ||| |  ::|  :   | ::::  ||:|||||||
p45387        GLKAEILHFQISAFISKSQGSQLGKQQNVGVKLGYRW
              1360       1370       1380       1390
```

Based on this analysis, it is predicted that these proteins from *N. meningitidis* and *N. gonorrhoeae*, and their epitopes, could be useful antigens for vaccines or diagnostics, or for raising antibodies.

Example 78

The following partial DNA sequence was identified in *N. meningitidis* <SEQ ID 655>:

```
  1..AAGGTGTGGC AATTTGTCGA AGA.CCGCTG CGTGCCGTCG TGCCTGCCGA

51  CAGTTTTGAA CCGACCGCGC AAAAATTGAA CCTGTTTAAG GCGGGTGCGG

101  CAACCATTTT GTTTTATGAA GATCAAAATG TCGTCAAAGG TTTGCAGGAG

151  CAGTTCCCTG CTTATGCCGC TAACTTCCCC GTTTGGGCGg ATCAGGCAAA

201  CGCGATGGTG CAGTATGCCG TTTGGACGAC ACTTGCCGCG GTCGGCGTAG

251  GTGCAAACCT GCAACATTAC AATCCCTTGC CCGATGCGGC GATTGCCAAA

301  GCGTGGAATA TCCCCGAAAA CTGGTTGTTG CGCGCACAAA TGGTTATCGG

351  CGGTATTGAA GGGGCGGCAG GTGAAAAGAC CTTTGAACCC GTTGCAGAAC

401  GTTTGAAAGT GTTCGGCGCA TAA
```

This corresponds to the amino acid sequence <SEQ ID 656; ORF6>:

```
  1..KVWQFVEXPL RAVVPADSFE PTAQKLNLFK AGAATILFYE DQNVVKGLQE

51  QFPAYAANFP VWADQANAMV QYAVWTTLAA VGVGANLQHY NPLPDAAIAK

101  AWNIPENWLL RAQMVIGGIE GAAGEKTFEP VAERLKVFGA *
```

Further sequence analysis revealed a further partial DNA sequence <SEQ ID 657>:

```
  1..CTGCGTGCCG TCGTGCCTGC CGACAGTTTT GAACCGACCG CGCAAAAATT

51  GAACCTGTTT AAGGCGGGTG CGGCAACCAT TTTGTTTTAT GAAGATCAAA

101  ATGTCGTCAA AGGTTTGCAG GAGCAGTTCC CTGCTTATGC CGCTAACTTC

151  CCCGTTTGGG CGGATCAGGC AAACGCGATG GTGCAGTATG CCGTTTGGAC

201  GACACTTGCC GCGGTCGGCG TAGGTGCAAA CCTGCAACAT TACAATCCCT

251  TGCCCGATGC GGCGATTGCC AAAGCGTGGA ATATCCCCGA AAACTGGTTG
```

```
301  TTGCGCGCAC AAATGGTTAT CGGCGGTATT GAAGGGGCGG CAGGTGAAAA

351  GACCTTTGAA CCCGTTGCAG AACGTTTGAA AGTGTTCGGC GCATAA
```

This corresponds to the amino acid sequence <SEQ ID 658; ORF6-1>:

```
  1..LRAVVPADSF EPTAQKLNLF KAGAATILFY EDQNVVKGLQ EQFPAYAANF

51  PVWADQANAM VQYAVWTTLA AVGVGANLQH YNPLPDAAIA KAWNIPENWL

101  LRAQMVIGGI EGAAGEKTFE PVAERLKVFG A*
```

Computer analysis of this amino acid sequence gave the following results:

Homology with a Predicted ORF from *N. meningitidis* (Strain A)

ORF6 shows 98.6% identity over a 140aa overlap with an ORF (ORF6a) from strain A of *N. meningitidis*.

```
                                                  10         20         30
   orf6.pep                                KVWQFVEXPLRAVVPADSFEPTAQKLNLFK
                                           |||||||||||||||||||||||||||||
   orf6a     QIVEHAVLKTPSSFNSQSARVVVLFGEEHDKVWQFVEDALRAVVPADSFEPTAQKLNLFK
                  40        50        60        70        80        90
                         40        50        60        70        80        90
   orf6.pep  AGAATILFYEDQNVVKGLQEQFPAYAANFPVWADQANAMVQYAVWTTLAAVGVGANLQHY
             ||||||||||||||||||||||||||||||||||||||||||||||||||||||||||||
   orf6a     AGAATILFYEDQNVVKGLQEQFPAYAANFPVWADQANAMVQYAVWTTLAAVGVGANLQHY
                        100       110       120       130       140       150
                        100       110       120       130       140
   orf6.pep  NPLPDAAIAKAWNIPENWLLRAQMVIGGIEGAAGEKTFEFPVAERLKVFGAX
             ||||||||||||||||||||||||||||||||||||||||||||||||||||
   orf6a     NPLPDAAIAKAWNIPENWLLRAQMVIGGIEGAAGEKTFEFPVAERLKVFGAX
                        160       170       180       190       200
```

The complete length ORF6a nucleotide sequence <SEQ ID 659> is:

```
  1 ATGACCCGTC AATCTCTGCA ACAGGCTGCC GAAAGCCGCC GTTCCATTTA

51 TTCGTTAAAT AAAAATCTGC CCGTCGGCAA AGATGAAATC GTCCAAATCG

101 TCGAACACGC CGTTTTGCAC ACACCTTCTT CGTTCAATTC CCAATCTGCC

151 CGTGTGGTCG TGCTGTTTGG CGAAGAGCAT GATAAGGTGT GGCAATTTGT

201 CGAAGACGCG CTGCGTGCCG TCGTGCCTGC CGACAGTTTT GAACCGACCG

251 CGCAAAAATT GAACCTGTTT AAGGCGGGTG CGGCAACTAT TTTGTTTTAT

301 GAAGATCAAA ATGTCGTCAA AGGTTTGCAG GAGCAGTTCC CTGCTTATGC

351 CGCCAACTTT CCCGTTTGGG CGGACCAGGC GAACGCGATG GTGCAGTATG

401 CCGTTTGGAC GACACTTGCC GCGGTCGGCG TAGGTGCAAA CCTGCAACAT

451 TACAATCCCT TGCCCGATGC GGCGATTGCC AAAGCGTGGA ATATCCCCGA

501 AAACTGGTTG TTGCGCGCAC AAATGGTTAT CGGCGGTATT GAAGGGGCGG

551 CAGGTGAAAA GACCTTTGAA CCAGTTGCAG AACGTTTGAA AGTGTTCGGC

601 GCATAA
```

This is predicted to encode a protein having amino acid sequence <SEQ ID 660>:

```
  1 MTRQSLQQAA ESRRSIYSLN KNLPVGKDEI VQIVEHAVLH TPSSFNSQSA

51 RVVVLFGEEH DKVWQFVEDA LRAVVPADSF EPTAQKLNLF KAGAATILFY

101 EDQNVVKGLQ EQFPAYAANF PVWADQANAM VQYAVWTTLA AVGVGANLQH

151 YNPLPDAAIA KAWNIPENWL LRAQMVIGGI EGAAGEKTFE PVAERLKVFG

201 A*
```

ORF6a and ORF6-1 show 100.0% identity in 131 aa overlap:

```
                    50         60         70         80         90        100
    orf6a.pep TPSSFNSQSARVVVLFGEEHDKVWQFVEDALRAVVPADSFEPTAQKLNLFKAGAATILFY
                                        ||||||||||||||||||||||||||||||
    orf6-1                              LRAVVPADSFEPTAQKLNLFKAGAATILFY
                                                  10        20        30
                   110        120        130        140        150        160
    orf6a.pep EDQNVVKGLQEQFPAYAANFPVWADQANAMVQYAVWTTLAAVGVGANLQHYNPLPDAAIA
              ||||||||||||||||||||||||||||||||||||||||||||||||||||||||||||
    orf6-1    EDQNVVKGLQEQFPAYAANFPVWADQANAMVQYAVWTTLAAVGVGANLQHYNPLPDAAIA
                       40        50        60        70        80        90
                   170        180        190        200
    orf6a.pep KAWNIPENWLLRAQMVIGGIEGAAGEKTFEPVAERLKVFGAX
              |||||||||||||||||||||||||||||||||||||||||
    orf6-1    KAWNIPENWLLRAQMVIGGIEGAAGEKTFEPVAERLKVFGAX
                     100       110       120       130
```

Homology with a Predicted ORF from *N. gonorrhoeae*

ORF6 shows 95.7% identity over a 140aa overlap with a predicted ORF (ORF6ng) from *N. gonorrhoeae*:

```
    orf6.pep                                      KVWQFVEXPLRAVVPADSFEPTAQKLNLFK  30
                                                  ||||||| ||||||||||||||||||:|||
    orf6ng   SNVSLDMSNPTVLRMGLPLYIASLRRGAIYKVWQFVEDALRAVVPADSFEPTAQKLKLFK  64
    orf6.pep AGAATILFYEDQNVVKGLQEQFPAYAANFPVWADQANAMVQYAVWTTLAAVGVGANLQHY  90
             ||||||||||||||||||||||||||||||||||||||||||||||||||||:||||||
    orf6ng   AGAATILFYEDQNVVKGLQEQFPAYAANFPVWADQANAMVQYAVWTTLAAVGAGANLQHY 124
    orf6.pep NPLPDAAIAKAWNIPENWLLRAQMVIGGIEGAAGEKTFEPVAERLKVFGA           140
             |||||:||||||||||||||||||||||||||||||:|||||||||||||
    orf6ng   NPLPDVAIAKAWNIPENWLLRAQMVIGGIEGAAGEKVFEPVAERLKVFGA           174
```

The complete length ORF6ng nucleotide sequence <SEQ ID 661> was identified as:

```
  1 ATGGCCGTTG CGTCAAATGT CAGCTTGGAT ATGTCCAATC CTACGGTGTT

51 ACGCATGGGA TTACCCTTAT ATATTGCGTC CCTAAGAAGG GGCGCAATAT

101 ATAAGGTGTG GCAATTTGTC GAAGACGCGC TGCGTGCCGT CGTGCCTGCC

151 GACAGTTTTG AACCGACCGC GCAAAAATTG AAGCTGTTTA AGGCGGGCGC

201 GGCAACCATT TTGTTTTATG AAGATCAAAA TGTCGTCAAA GGTTTGCAGG

251 AGCAGTTCCC TGCTTATGCC GCCAACTTTC CCGTTTGGGC GGACCAGGCG

301 AACGCTATGG TACAGTATGC CGTCTGGACG ACACTTGCCG CGGTCGGTGC

351 AGGTGCAAAT CTGCAACATT ACAACCCCTT GCCCGATGTG GCGATTGCTA

401 AAGCGTGGAA TATTCCCGAA AACTGGCTGT TGCGCGCGCA AATGGTTATC

451 GGTGGTATTG AAGGGGcggc aggtgaaaaa gtctttgaac CCGTTGCgga 501 acgtttgAAA GTGTTCGGCG CATAA
```

This encodes a protein having amino acid sequence <SEQ ID 662>:

```
  1 MAVASNVSLD MSNPTVLRMG LPLYIASLRR GAIYKVWQFV EDALRAVVPA

51 DSFEPTAQKL KLFKAGAATI LFYEDQNVVK GLQEQFPAYA ANFPVWADQA

101 NAMVQYAVWT TLAAVGAGAN LQHYNPLPDV AIAKAWNIPE NWLLRAQMVI

151 GGIEGAAGEK VFEPVAERLK VFGA*
```

ORF6ng and ORF6-1 show 96.9% identity in 131 aa overlap:

```
                                    10        20        30
   orf6-1.pep                LRAVVPADSFEPTAQKLNLFKAGAATILFY
                             |||||||||||||||:|||||||||||||
   orf6ng     PTVLRMGLPLYIASLRRGAIYKVWQFVEDALRAVVPADSFEPTAQKLKLFKAGAATILFY
                  20        30        40        50        60        70

40        50        60        70        80        90
   orf6-1.pep EDQNVVKGLQEQFPAYAANFPVWADQANAMVQYAVWTTLAAVGVGANLQHYNPLPDAAIA
              ||||||||||||||||||||||||||||||||||||||||||:||||||||||||:|||
   orf6ng     EDQNVVKGLQEQFPAYAANFPVWADQANAMVQYAVWTTLAAVGAGANLQHYNPLPDVAIA
                  80        90       100       110       120       130

100       110       120       130
   orf6-1.pep KAWNIPENWLLRAQMVIGGIEGAAGEKTFEPVAERLKVFGAX
              |||||||||||||||||||||||||||:|||||||||||||
   orf6ng     KAWNIPENWLLRAQMVIGGIEGAAGEKVFEPVAERLKVFGAX
                  140       150       160       170
```

It is predicted that the proteins from *N. meningitidis* and *N. gonorrhoeae*, and their epitopes, could be useful antigens for vaccines or diagnostics, or for raising antibodies.

Example 79

The following partial DNA sequence was identified in *N. meningitidis* <SEQ ID 663>

```
  1..GGCTACAACT ACCTGTTCGC GCGCGGCAGC CGCATCGCCA ACTACCAAAT

51   CAACGGCATC CCCGTTGCCG ACGCGCTGGC CGATACGGGt CAATGCCAAC

101   ACCGCCGCCT ATGAGCGCGT AGAAGTCGTG CGCGGCGTGG CGGGGCTGCT

151   GGACGGCACG GGCGAGCCTT CCGCCACCGT CAATCTGGTG CGCAAACGCC

201   TGACCCGCAA GCCATTGTTT GAAGTCCGCG CCGAAGCgGG CAACCGcAAA

251   CATTTCGGGC TGGACGCGGA CGTATCGGGC AGCCTGAACA CCGAAG.crC

301rCTGCGCgGC CGCCTGGTTT CCAcCTTCGG ACGCGGCGAC TCGTGGCGGC

351GGCGCGAACG CAGCCGskAT GCCGAACTCT ACGGCATTTT GGAATACGAC

401ATCGCACCGC AAACCCGCGT CCACGCArGC ATGGACTACC AGCAGGCGAA

451AGAAACCGCC GACGCGCCGC TCAGcTACGC CGTGTACGAC AGCCAAGGTT

501ATGCCACCGC CTTCGGCCCG AAAGACAACC CCGCCACAAA TTGGGCGAAC

551AGCCACCACC GTGCGCTCAA CCTGTTCGCC GGCATCGAAC ACCGCTTCAA

601CCAAGACTGG AAACTCAAAG CCGAATACGA CTAC..
```

This corresponds to the amino acid sequence <SEQ ID 664; ORF23>:

```
  1 ..GYNYLFARGS RIANYQINGI PVADALADTG NANTAAYERV EVVRGVAGLL

51   DGTGEPSATV NLVRKRLTRK PLFEVRAEAG NRKHFGLDAD VSGSLNTEXX
```

```
101  LRGRLVSTFG RGDSWRRRER SRXAELYGIL EYDIAPQTRV HAXMDYQQAK

151  ETADAPLSYA VYDSQGYATA FGPKDNPATN WANSHHRALN LFAGIEHRFN

201  QDWKLKAEYD Y..
```

Further work revealed the complete nucleotide sequence <SEQ ID 665>:

```
   1  ATGACACGCT TCAAATATTC CCTGCTGTTT GCCGCCCTGT TGCCCGTGTA

51  CGCGCAGGCC GATGTTTCTG TTTCAGACGA CCCCAAACCG CAGGAAAGCA

101  CTGAATTGCC GACCATCACC GTTACCGCCG ACCGCACCGC GAGTTCCAAC

151  GACGGCTACA CTGTTTCCGG CACGCACACC CCGCTCGGGC TGCCCATGAC

201  CCTGCGCGAA ATCCCGCAGA GCGTCAGCGT CATCACATCG CAACAAATGC

251  GCGACCAAAA CATCAAAACG CTCGACCGCG CCCTGTTGCA GGCGACCGGC

301  ACCAGCCGCC AGATTTACGG CTCCGACCGC GCGGGCTACA ACTACCTGTT

351  CGCGCGCGGC AGCCGCATCG CCAACTACCA AATCAACGGC ATCCCCGTTG

401  CCGACGCGCT GGCCGATACG GGCAATGCCA ACACCGCCGC CTATGAGCGC

451  GTAGAAGTCG TGCGCGGCGT GGCGGGGCTG CTGGACGGCA CGGGCGAGCC

501  TTCCGCCACC GTCAATCTGG TGCGCAAACG CCTGACCCGC AAGCCATTGT

551  TTGAAGTCCG CGCCGAAGCG GGCAACCGCA AACATTTCGG GCTGGACGCG

601  GACGTATCGG GCAGCCTGAA CACCGAAGGC ACGCTGCGCG GCCGCCTGGT

651  TTCCACCTTC GGACGCGGCG ACTCGTGGCG GCGGCGCGAA CGCAGCCGCG

701  ATGCCGAACT CTACGGCATT TTGGAATACG ACATCGCACC GCAAACCCGC

751  GTCCACGCAG GCATGGACTA CCAGCAGGCG AAAGAAACCG CCGACGCGCC

801  GCTCAGCTAC GCCGTGTACG ACAGCCAAGG TTATGCCACC GCCTTCGGCC

851  CGAAAGACAA CCCCGCCACA AATTGGGCGA ACAGCCGCCA CCGTGCGCTC

901  AACCTGTTCG CCGGCATCGA ACACCGCTTC AACCAAGACT GGAAACTCAA

951  AGCCGAATAC GACTACACCC GCAGCCGCTT CCGCCAGCCC TACGGCGTAG

1001  CAGGCGTGCT TTCCATCGAC CACAACACCG CCGCCACCGA CCTGATTCCC

1051  GGTTATTGGC ACGCCGACCC GCGCACCCAC AGCGCCAGCG TGTCATTGAT

1101  CGGCAAATAC CGCCTGTTCG GCCGCGAACA CGATTTAATC GCGGGTATCA

1151  ACGGTTACAA ATACGCCAGC AACAAATACG GCGAACGCAG CATCATCCCC

1201  AACGCCATTC CCAACGCCTA CGAATTTTCC CGCACGGGTG CCTACCCGCA

1251  GCCTGCATCG TTTGCCCAAA CCATCCCGCA ATACGGCACC AGGCGGCAAA

1301  TCGGCGGCTA TCTCGCCACC CGTTTCCGCG CCGCCGACAA CCTTTCGCTG

1351  ATTTTGGGCG GACGATACAC CCGTTACCGC ACCGGCAGCT ACGACAGCCG

1401  CACACAAGGC ATGACCTATG TGTCCGCCAA CCGTTTCACC CCCTACACAG

1451  GCATCGTGTT CGACCTGACC GGCAACCTGT CTCTTTACGG CTCGTACAGC

1501  AGCCTGTTCG TCCCGCAATC GCAAAAAGAC GAACACGGCA GCTACCTGAA

1551  ACCCGTAACC GGCAACAATC TGGAAGCCGG CATCAAAGGC GAATGGCTTG

1601  AAGGCCGTCT GAACGCATCC GCCGCCGTGT ACCGCGCCCG TAAAAACAAC

1651  CTCGCCACCG CAGCAGGACG CGACCCGAGC GGCAACACCT ACTACCGCGC

1701  CGCCAACCAA GCCAAAACCC ACGGCTGGGA AATCGAAGTC GGCGGCCGCA
```

-continued

```
1751 TCACGCCCGA ATGGCAGATA CAGGCAGGTT ACAGCCAAAG CAAAACCCGC
1801 GACCAAGACG GCAGCCGCCT GAACCCCGAC AGCGTACCCG AACGCAGCTT
1851 CAAACTCTTC ACTGCCTACC ACTTTGCCCC CGAAGCCCCC AGCGGCTGGA
1901 CCATCGGCGC AGGCGTGCGC TGGCAGAGCG AAACCACAC CGACCCTGCC
1951 ACGCTCCGCA TCCCCAACCC CGCCGCCAAA GCCCGCGCCG CCGACAACAG
2001 CCGCCAAAAA GCCTACGCCG TCGCCGACAT CATGGCGCGT TACCGCTTCA
2051 ATCCGCGCGC CGAACTGTCG CTGAACGTGG ACAATCTGTT CAACAAACAC
2101 TACCGCACCC AGCCCGACCG CCACAGCTAC GGCGCACTGC GGACAGTGAA
2151 CGCGGCGTTT ACCTATCGGT TTAAATAA
```

This corresponds to the amino acid sequence <SEQ ID 666; ORF23-1>:

```
  1 MTRFKYSLLF AALLPVYAQA DVSVSDDPKP QESTELPTIT VTADRTASSN
 51 DGYTVSGTHT PLGLPMTLRE IPQSVSVITS QQMRDQNIKT LDRALLQATG
101 TSRQIYGSDR AGYNYLFARG SRIANYQING IPVADALADT GNANTAAYER
151 VEVVRGVAGL LDGTGEPSAT VNLVRKRLTR KPLFEVRAEA GNRKHFGLDA
201 DVSGSLNTEG TLRGRLVSTF GRGDSWRRRE RSRDAELYGI LEYDIAPQTR
251 VHAGMDYQQA KETADAPLSY AVYDSQGYAT AFGPKDNPAT NWANSRHRAL
301 NLFAGIEHRF NQDWKLKAEY DYTRSRFRQP YGVAGVLSID HNTAATDLIP
351 GYWHADPRTH SASVSLIGKY RLFGREHDLI AGINGYKYAS NKYGERSIIP
401 NAIPNAYEFS RTGAYPQPAS FAQTIPQYGT RRQIGGYLAT RFRAADNLSL
451 ILGGRYTRYR TGSYDSRTQG MTYVSANRFT PYTGIVFDLT GNLSLYGSYS
501 SLFVPQSQKD EHGSYLKPVT GNNLEAGIKG EWLEGRLNAS AAVYRARKNN
551 LATAAGRDPS GNTYYRAANQ AKTHGWEIEV GGRITPEWQI QAGYSQSKTR
601 DQDGSRLNPD SVPERSFKLF TAYHFAPEAP SGWTIGAGVR WQSETHTDPA
651 TLRIPNPAAK ARAADNSRQK AYAVADIMAR YRFNPRAELS LNVDNLFNKH
701 YRTQPDRHSY GALRTVNAAF TYRFK*
```

Computer analysis of this amino acid sequence gave the following results:

Homology with the Ferric-Pseudobactin Receptor PupB of *Pseudomonas putida* (Accession Number P38047)

ORF23 and PupB protein show 32% aa identity in 205aa overlap:

```
Orf23    6 FARGSRIANYQINGIPVADALADTGNANTAAYERVEVVRGVAGLLDGTGEPSATVNLVRK  65
             ++RG  I NY+++G+P +  L D  + + A ++RVE+VRG  GL+ G G PSAT+NL+RK
PupB   215 WSRGFAIQNYEVDGVPTSTRL-DNYSQSMAMFDRVEIVRGATGLISGMGNPSATINLIRK 273

Orf23   66 RLTRKPLFEVRAEAGNRKHFGLDADVSGSLNTEXXLRGRLVSTFXXXXXXXXXXXXXXAE 125
              R T +     + EAGN    +G   DVSG L       +RGR V+ +
PupB   274 RPTAEAQASITGEAGNWDRYGTGFDVSGPLTETGNIRGRFVADYKTEKAWIDRYNQQSQL 333

Orf23  126 LYGILEYDIAPQTRVHAXMDYQQAKETADAPLSYAVYD--SQGYATAFGPKDNPATNWAN 183
             +YGI E+D++  T  +   Y  +  D+PL +    S G T     N A +W+
PupB   334 MYGITEFDLSEDTLLTVGFSY--LRSDIDSPLRSGLPTRFSTGERTNLKRSLNAAPDWSY 391

Orf23  184 SHHRALNLFAGIEHRFNQDWKLKAE                                    208
             + H   + F  IE +   W K E
PupB   392 NDHEQTSFFTSIEQQLGNGWSGKIE                                    416
```

Homology with a Predicted ORF from *N. meningitidis* (Strain A)

ORF23 shows 95.7% identity over a 211aa overlap with an ORF (ORF23a) from strain A of *N. meningitidis*:

```
                                          10        20        30
    orf23.pep                      GYNYLFARGSRIANYQINGIPVADALADTG
                                   ||||||||||||||||||||||||||||||
    orf623a   QMRDQNIKALDRALLQATGTSRQIYGSDRAGYNYLFARGSRIANYQINGIPVADALADTG
                      90        100       110       120       130       140
                  40        50        60        70        80        90
    orf23.pep NANTAAYERVEVVRGVAGLLDGTGEPSATVNLVRKRLTRKPLFEVRAEAGNRKHFGLDAD
              |||||||||||||||||||||||||||||||||| ||||||||||||||||||||||| |
    orf23a    NANTAAYERVEVVRGVAGLLDGTGEPSATVNLVRKRPTRKPLFEVRAEAGNRKHFGLGAD
                      150       160       170       180       190       200
                  100       110       120       130       140       150
    orf23.pep VSGSLNTEXXLRGRLVSTFGRGDSWRRRERSRXAELYGILEYDIAPQTRVHAXMDYQQAK
              ||||||:|  :|||||||||||||||||:||||| |||||||||||||||||||:||||||
    orf23a    VSGSLNAEGTLRGRLVSTFGRGDSWRQRERSRDAELYGILEYDIAPQTRVHAGMDYQQAK
                      210       220       230       240       250       260
                  160       170       180       190       200       210
    orf23.pep ETADAPLSYAVYDSQGYATAFGPKDNPATNWANSHHRALNLFAGIEHRFNQDWKLKAEYD
              ||||||||||||||||||||||||||||||||||| ||||||||||||||||||||||||
    orf23a    ETADAPLSYAVYDSQGYATAFGPKDNPATNWANSRHRALNLFAGIEHRFNQDWKLKAEYD
                      270       280       290       300       310       320 orf23.pep Y
              |
    orf23a    YTRSRFRQPYGVAGVLSIDHNTAATDLIPGYWHADPRTHSASVSLIGKYRLFGREHDLIA
                      330       340       350       360       370       380
```

The complete length ORF23a nucleotide sequence <SEQ ID 667> is:

```
    1 ATGACACGCT TCAAATATTC CCTGCTGTTT GCCGCCCTGT TGCCCGTGTA

51 CGCGCAGGCC GATGTTTCTG TTTCAGACGA CCCAAAACCG CAGGAAAGCA

101 CTGAATTGCC GACCATCACC GTTACCGCCG ACCGCACCGC GAGTTCCAAC

151 GACGGCTACA CTGTTTCCGG CACGCACACC CCGCTCGGGC TGCCCATGAC

201 CCTGCGCGAA ATCCCGCAGA GCGTCAGCGT CATCACATCG CAACAAATGC

251 GCGACCAAAA CATCAAAGCG CTCGACCGCG CCCTGTTGCA GGCGACCGGC

301 ACCAGCCGCC AGATTTACGG CTCCGACCGC GCGGGCTACA ACTACCTGTT

351 CGCGCGCGGC AGCCGCATCG CCAACTACCA AATCAACGGC ATCCCCGTTG

401 CCGACGCGCT GGCCGATACG GGCAATGCCA ACACCGCCGC CTATGAGCGC

451 GTAGAAGTCG TGCGCGGCGT GGCGGGGCTG CTGGACGGCA CGGGCGAGCC

501 TTCCGCCACC GTCAATCTGG TGCGCAAACG CCCGACCCGC AAGCCATTGT

551 TTGAAGTCCG CGCCGAAGCG GGCAACCGCA AACATTTCGG GCTGGGCGCG

601 GACGTATCGG GCAGCCTGAA TGCCGAAGGC ACGCTGCGCG GCCGCCTGGT

651 TTCCACCTTC GGACGCGGCG ACTCGTGGCG GCAGCGCGAA CGCAGCCGCG

701 ATGCCGAACT CTACGGCATT TTGGAATACG ACATCGCACC GCAAACCCGC

751 GTCCACGCAG GCATGGACTA CCAGCAGGCG AAAGAAACCG CCGACGCGCC

801 GCTCAGCTAC GCCGTGTACG ACAGCCAAGG TTATGCCACC GCCTTCGGCC

851 CGAAAGACAA CCCCGCCACA AATTGGGCGA ACAGCCGCCA CCGTGCGCTC

901 AACCTGTTCG CCGGCATCGA ACACCGCTTC AACCAAGACT GGAAACTCAA

951 AGCCGAATAC GACTACACCC GCAGCCGCTT CCGCCAGCCC TACGGCGTAG

1001 CAGGCGTGCT TTCCATCGAC CACAACACCG CCGCCACCGA CCTGATTCCC

1051 GGTTATTGGC ACGCCGACCC GCGCACCCAC AGCGCCAGCG TGTCATTAAT
```

-continued

```
1101 CGGCAAATAC CGCCTGTTCG GCCGCGAACA CGATTTAATC GCGGGTATCA
1151 ACGGTTACAA ATACGCCAGC AACAAATACG GCGAACGCAG CATCATCCCC
1201 AACGCCATTC CCAACGCCTA CGAATTTTCC CGCACGGGTG CCTACCCGCA
1251 GCCTGCATCG TTTGCCCAAA CCATCCCGCA ATACGGCACC AGGCGGCAAA
1301 TCGGCGGCTA TCTCGCCACC CGTTTCCGCG CCGCCGACAA CCTTTCGCTG
1351 ATACTCGGCG GCAGATACAG CCGTTACCGC ACCGGCAGCT ACGACAGCCG
1401 CACACAAGGC ATGACCTATG TGTCCGCCAA CCGTTTCACC CCCTACACAG
1451 GCATCGTGTT CGACCTGACC GGCAACCTGT CGCTTTACGG CTCGTACAGC
1501 AGCCTGTTCG TCCCGCAATC GCAAAAGAC GAACACGGCA GCTACCTGAA
1551 ACCCGTAACC GGCAACAATC TGGAAGCCGG CATCAAAGGC GAATGGCTTG
1601 AAGGCCGTCT GAACGCATCC GCCGCCGTGT ACCGCGCCCG TAAAAACAAC
1651 CTCGCCACCG CAGCAGGACG CGACCCGAGC GGCAACACCT ACTACCGCGC
1701 CGCCAACCAA GCCAAAACCC ACGGCTGGGA AATCGAAGTC GGCGGCCGCA
1751 TCACGCCCGA ATGGCAGATA CAGGCAGGTT ACAGCCAAGG CAAAACCCGC
1801 GACCAAGACG GCAGCCGCCT GAACCCCGAC AGCGTACCCG AACGCAGCTT
1851 CAAACTCTTC ACTGCCTACC ACTTTGCCCC CGAAGCCCCC AGCGGCTGGA
1901 CCATCGGCGC AGGCGTGCGC TGGCAGAGCG AAACCCACAC CGACCCTGCC
1951 ACGCTCCGCA TCCCCAACCC CGCCGCCAAA GCCCGCGCCG CCGACAACAG
2001 CCGCCAAAAA GCCTACGCCG TCGCCGACAT CATGGCGCGT ACCGCTTCA
2051 ATCCGCGCGC CGAACTGTCG CTGAACGTGG ACAATCTGTT CAACAAACAC
2101 TACCGCACCC AGCCCGACCG CCACAGCTAC GGCGCACTGC GGACAGTGAA
2151 CGCGGCGTTT ACCTATCGGT TTAAATAA
```

This encodes a protein having amino acid sequence <SEQ ID 668>:

```
  1 MTRFKYSLLF AALLPVYAQA DVSVSDDPKP QESTELPTIT VTADRTASSN
 51 DGYTVSGTHT PLGLPMTLRE IPQSVSVITS QQMRDQNIKA LDRALLQATG
101 TSRQIYGSDR AGYNYLFARG SRIANYQING IPVADALADT GNANTAAYER
151 VEVVRGVAGL LDGTGEPSAT VNLVRKRPTR KPLFEVRAEA GNRKHFGLGA
201 DVSGSLNAEG TLRGRLVSTF GRGDSWRQRE RSRDAELYGI LEYDIAPQTR
251 VHAGMDYQQA KETADAPLSY AVYDSQGYAT AFGPKDNPAT NWANSRHRAL
301 NLFAGIEHRF NQDWKLKAEY DYTRSRFRQP YGVAGVLSID HNTAATDLIP
351 GYWHADPRTH SASVSLIGKY RLFGREHDLI AGINGYKYAS NKYGERSIIP
401 NAIPNAYEFS RTGAYPQPAS FAQTIPQYGT RRQIGGYLAT RFRAADNLSL
451 ILGGRYSRYR TGSYDSRTQG MTYVSANRFT PYTGIVFDLT GNLSLYGSYS
501 SLFVPQSQKD EHGSYLKPVT GNNLEAGIKG EWLEGRLNAS AAVYRARKNN
551 LATAAGRDPS GNTYYRAANQ AKTHGWEIEV GGRITPEWQI QAGYSQSKTR
601 DQDGSRLNPD SVPERSFKLF TAYHFAPEAP SGWTIGAGVR WQSETHTDPA
651 TLRIPNPAAK ARAADNSRQK AYAVADIMAR YRFNPRAELS LNVDNLFNKH
701 YRTQPDRHSY GALRTVNAAF TYRFK*
```

ORF23a and ORF23-1 show 99.2% identity in 725 aa overlap:

```
                   10         20         30         40         50         60
orf23a.pep   MTRFKYSLLFAALLPVYAQADVSVSDDPKPQESTELPTITVTADRTASSNDGYTVSGTHT
             ||||||||||||||||||||||||||||||||||||||||||||||||||||||||||||
orf23-1      MTRFKYSLLFAALLPVYAQADVSVSDDPKPQESTELPTITVTADRTASSNDGYTVSGTHT
                   10         20         30         40         50         60

70         80         90        100        110        120
orf23a.pep   PLGLPMTLREIPQSVSVITSQQMRDQNIKALDRALLQATGTSRQIYGSDRAGYNYLFARG
             |||||||||||||||||||||||||||||| :|||||||||||||||||||||||||||
orf23-1      PLGLPMTLREIPQSVSVITSQQMRDQNIKTLDRALLQATGTSRQIYGSDRAGYNYLFARG
                   70         80         90        100        110        120

130        140        150        160        170        180
orf23a.pep   SRIANYQINGIPVADALADTGNANTAAYERVEVVRGVAGLLDGTGEPSATVNLVRKRPTR
             ||||||||||||||||||||||||||||||||||||||||||||||||||||||||| ||
orf23-1      SRIANYQINGIPVADALADTGNANTAAYERVEVVRGVAGLLDGTGEPSATVNLVRKRLTR
                  130        140        150        160        170        180

190        200        210        220        230        240
orf23a.pep   KPLFEVRAEAGNRKHFGLGADVSGSLNAEGTLRGRLVSTFGRGDSWRQRERSRDAELYGI
             |||||||||||||||||||| ||||||| :|||||||||||||||||  |||||||||||
orf23-1      KPLFEVRAEAGNRKHFGLDADVSGSLNTEGTLRGRLVSTFGRGDSWRRRERSRDAELYGI
                  190        200        210        220        230        240

250        260        270        280        290        300
orf23a.pep   LEYDIAPQTRVHAGMDYQQAKETADAPLSYAVYDSQGYATAFGPKDNPATNWANSRHRAL
             ||||||||||||||||||||||||||||||||||||||||||||||||||||||||||||
orf23-1      LEYDIAPQTRVHAGMDYQQAKETADAPLSYAVYDSQGYATAFGPKDNPATNWANSRHRAL
                  250        260        270        280        290        300

310        320        330        340        350        360
orf23a.pep   NLFAGIEHRFNQDWKLKAEYDYTRSRFRQPYGVAGVLSIDHNTAATDLIPGYWHADPRTH
             ||||||||||||||||||||||||||||||||||||||||||||||||||||||||||||
orf23-1      NLFAGIEHRFNQDWKLKAEYDYTRSRFRQPYGVAGVLSIDHNTAATDLIPGYWHADPRTH
                  310        320        330        340        350        360

370        380        390        400        410        420
orf23a.pep   SASVSLIGKYRLFGREHDLIAGINGYKYASNKYGERSIIPNAIPNAYEFSRTGAYPQPAS
             ||||||||||||||||||||||||||||||||||||||||||||||||||||||||||||
orf23-1      SASVSLIGKYRLFGREHDLIAGINGYKYASNKYGERSIIPNAIPNAYEFSRTGAYPQPAS
                  370        380        390        400        410        420

430        440        450        460        470        480
orf23a.pep   FAQTIPQYGTRRQIGGYLATRFRAADNLSLILGGRYSRYRTGSYDSRTQGMTYVSANRFT
             ||||||||||||||||||||||||||||||||||||| :||||||||||||||||||||
orf23-1      FAQTIPQYGTRRQIGGYLATRFRAADNLSLILGGRYTRYRTGSYDSRTQGMTYVSANRFT
                  430        440        450        460        470        480

490        500        510        520        530        540
orf23a.pep   PYTGIVFDLTGNLSLYGSYSSLFVPQSQKDEHGSYLKPVTGNNLEAGIKGEWLEGRLNAS
             ||||||||||||||||||||||||||||||||||||||||||||||||||||||||||||
orf23-1      PYTGIVFDLTGNLSLYGSYSSLFVPQSQKDEHGSYLKPVTGNNLEAGIKGEWLEGRLNAS
                  490        500        510        520        530        540

550        560        570        580        590        600
orf23a.pep   AAVYRARKNNLATAAGRDPSGNTYYRAANQAKTHGWEIEVGGRITPEWQIQAGYSQSKTR
             ||||||||||||||||||||||||||||||||||||||||||||||||||||||||||||
orf23-1      AAVYRARKNNLATAAGRDPSGNTYYRAANQAKTHGWEIEVGGRITPEWQIQAGYSQSKTR
                  550        560        570        580        590        600

610        620        630        640        650        660
orf23a.pep   DQDGSRLNPDSVPERSFKLETAYHFAPEAPSGWTIGAGVRWQSETHTDPATLRIPNPAAK
             ||||||||||||||||||||||||||||||||||||||||||||||||||||||||||||
orf23-1      DQDGSRLNPDSVPERSFKLETAYHFAPEAPSGWTIGAGVRWQSETHTDPATLRIPNPAAK
                  610        620        630        640        650        660

670        680        690        700        710        720
orf23a.pep   ARAADNSRQKAYAVADIMARYRFNPRAELSLNVDNLFNKHYRTQPDRHSYGALRTVNAAF
             ||||||||||||||||||||||||||||||||||||||||||||||||||||||||||||
orf23-1      ARAADNSRQKAYAVADIMARYRFNPRAELSLNVDNLFNKHYRTQPDRHSYGALRTVNAAF
                  670        680        690        700        710        720 orf23a.pep   TYRFKX
             ||||||
orf23-1      TYRFKX
```

Homology with a Predicted ORF from *N. gonorrhoeae*
ORF23 shows 93.4% identity over a 211aa overlap with a predicted ORF (ORF23.ng) from *N. gonorrhoeae*:

```
orf23.pep              GYNYLFARGSRIANYQINGIPVADALADTGNANTAAYERVEVVRGVAGLLD  51
                       ||||||||||||||||||||||||||||||||||||||||||||||||| |
orf23ng      SAVDACRIPGYNYLFARGSRIANYQINGIPVADALADTGNANTAAYERVEVVRGVAGLPD  60
```

```
orf23.pep  GTGEPSATVNLVRKRLTRKPLFEVRAEAGNRKHFGLDADVSGSLNTEXXLRGRLVSTFGR  111
           ||||||||||||||| :||||||||||||||||||||| ||||||||:| :||||||||||
orf23ng    GTGEPSATVNLVRKHPTRKPLFEVRAEAGNRKHFGLGADVSGSLNAEGTLRGRLVSTFGR  120 orf23.pep  GDSWRRRERSRXAELYGILEYDIAPQTRVHAXMDYQQAKETADAPLSYAVYDSQGYATAF  171
           |||||: ||||  |||||||||||||||||| ||||||||||||||||||||||||||
orf23ng    GDSWRQLERSRDAELYGILEYDIAPQTRVHAGMDYQQAKETADAPLSYAVYDSQGYATAF  180 orf23.pep  GPKDNPATNWANSHHRALNLFAGIEHRFNQDWKLKAEYDY                      211
           |||||||||||:||::|||||||||||||||||||||||
orf23ng    GPKDNPATNWSNSRNRALNLFAGIEHRFNQDWKLKAEYDYTRSRFRQPYGVAGVLSIDHS  240
```

The ORF23ng nucleotide sequence <SEQ ID 669> is predicted to encode a protein comprising amino acid sequence <SEQ ID 670>:

```
  1  SAVDACRIPG YNYLFARGSR IANYQINGIP VADALADTGN ANTAAYERVE

51  VVRGVAGLPD GTGEPSATVN LVRKHPTRKP LFEVRAEAGN RKHFGLGADV

101  SGSLNAEGTL RGRLVSTFGR GDSWRQLERS RDAELYGILE YDIAPQTRVH

151  AGMDYQQAKE TADAPLSYAV YDSQGYATAF GPKDNPATNW SNSRNRALNL

201  FAGIEHRFNQ DWKLKAEYDY TRSRFRQPYG VAGVLSIDHS TAATDLIPGY

251  WHADPRTHSA SMSLTGKYRL FGREHDLIAG INGYKYASNK YGERSIIPNA

301  IPNAYEFSRT GAYPQPSSFA QTIPQYDTRR QIGGYLATRF RAADNLSLIL

351  GGRYSRYRAG SYNSRTQGMT YVSANRFTPY TGIVFDLTGN LSLYGSYSSL

401  FVPQLQKDEH GSYLKPVTGN NLEADIKGEW LEGRLNASAA VYRARKNNLA

451  TAAGRDQSGN TYYRAANQAK THGWEIEVGG RITPEWQIQA GYSQSKPRDQ

501  DGSRLNPDSV PERSFKLFTA YHLAPEAPSG RTIGAGVRRQ GETHTDPAAL

551  RIPNPAAKAR AVANSRQKAY AVADIMARYR FNPRTELSLN VDNLFNKHYR

601  TQPDRHSYGA LRTVNAAFTY RFK*
```

Further work revealed the complete nucleotide sequence <SEQ ID 671>:

```
  1  ATGACACGCT TCAAATACTC CCTGCTTTTT GCCGCCCTGC TACCCGTGTA

51  CGCGCAGGCC GATGTTTCTG TTTCAGACGA CCCCAAACCG CAGGAAAGCA

101  CCGAATTGCC GACCATCACC GTTACCGCCG ACCGCACCGC GAGTTCCAAC

151  GACGGCTACA CCGTTTCCGG CACGCACACC CCGTTCGGGC TGCCCATGAC

201  CCTGCGCGAA ATCCCGCAGA GCGTCAGCGT CATCACATCG CAACAAATGC

251  GCGACCAAAA CATCAAAACG CTCGACCGCG CCCTGTTGCA GGCGACCGGC

301  ACCAGCCGCC AGATTTACGG CTCCGACCGC GCGGGCTACA ACTACCTGTT

351  CGCGCGCGGC AGCCGCATCG CCAACTACCA AATCAACGGC ATCCCCGTTG

401  CCGACGCGCT GGCCGATACG GGCAATGCCA ACACCGCCGC CTATGAGCGC

451  GTAGAAGTCG TGCGCGGCGT GGCGGGGCTG CCGGACGGCA CGGGCGAGCC

501  TTCTGCCACC GTCAATCTGG TACGCAAACA CCCGACCCGC AAGCCATTGT

551  TTGAAGTCCG CGCCGAAGCC GGCAACCGCA AACATTTCGG GCTGGGCGCG

601  GACGTATCGG GCAGCCTGAA CGCCGAAGGC ACGCTGCGCG GCCGCCTGGT

651  TTCCACCTTC GGACGCGGCG ACTCGTGGCG GCAGCTCGAA CGCAGCCGCG

701  ATGCCGAACT CTACGGCATT TTGGAATACG ACATCGCACC GCAAACCCGC

751  GTCCACGCAG GCATGGACTA CCAGCAGGCG AAAGAAACCG CAGACGCGCC
```

-continued
```
 801 GCTCAGCTAC GCCGTGTACG ACAGCCAAGG TTATGCCACC GCCTTCGGCC

851 CAAAAGACAA CCCCGCCACA AATTGGTCGA ACAGCCGCAA CCGTGCGCTC

901 AACCTGTTCG CCGGCATAGA ACACCGCTTC AACCAAGACT GGAAACTCAA

951 AGCCGAATAC GACTACACCC GTAGCCGCTT CCGCCAGCCC TACGGTGTGG

1001 CAGGCGTACT TTCCATCGAC CACAGCACTG CCGCCACCGA CCTGATTCCC

1051 GGTTATTGGC ACGCcgatcc GCGCACCCAC AGCGCCAGCA TGTCATTGAC

1101 CGGCAAATAC CgcctGTTCG GCCGCGAGCA CGATTTAATC GCGGGTATCA

1151 ACGGCTACAA ATACGCCAGC AACAAATACG GCGAACGCAG CATCATTCCC

1201 AACGCCATTC CCAACGCCTA CGAATTTTCC CGCACGGGCG CCTATCCGCA

1251 GCCATCATCG TTTGCCCAAA CCATCCCGCA ATACGACACC AGGCGGCAAA

1301 TCGGCGGCTA TCTCGCCACC CGTTTCCGCG CCGCCGACAA CCTTTCGCTG

1351 ATACTCGGCG GCAGATACAG CCGCTACCGC GCAGGCAGCT ACAACAGCCG

1401 CACACAAGGC ATGACCTATG TGTCCGCCAA CCGTTTCACC CCCTACACAG

1451 GCATCGTGTT CGATCTGACC GGCAACCTGT CGCTTTACGG CTCGTACAGC

1501 AGCCTGTTCG TCCCGCAATT GCAAAAAGAC GAACACGGCA GCTACCTGAA

1551 ACCCGTAACC GGCAACAATC TGGAAGCCGA CATCAAAGGC GAATGGCTTG

1601 AAGGGCGTCT GAACGCATCC GCCGCCGTGT ACCGCGCCCG TAAAAACAAC

1651 CTCGCCACCG CAGCAGGACG CGACCAGAGC GGCAACACCT ACTATCGCGC

1701 CGCCAACCAA GCCAAAACCC ACGGCTGGGA AATCGAAGTC GGCGGCCGCA

1751 TCACGCCCGA ATGGCAGATA CAGGCAGGCT ACAGCCAAAG CAAACCCCGC

1801 GACCAAGACG GCAGCCGCCT GAACCCCGAC AGCGTAcCCG AACGCAGCTT

1851 CAAACTCTTC ACCGCCTACC ACTTAGCCCC CGAAGCCCCC AGCGGCCGGA

1901 CCATcggTGC GGGTGTGCGC CGGCAGGGCG AAACCCACAC CGACCCAGCC

1951 GCGCTCCGCA TCCCCAACCC CGCCGCCAAA GCCCGCGCCG TCGCCAACAG

2001 CCGCCAGAAA GCCTACGCCG TCGCCGACAT CATGGCGCGT ACCGCTTCA

2051 ATCCGCGCAC CGAACTGTCG CTGAACGTGG ACAACCTGTT CAACAAACAC

2101 TACCGCACCC AGCCCGACCG CCACAGCTAC GGCGCACTGC GGACAGTGAA

2151 CGCGGCGTTT ACCTATCGGT TTAAATAA
```

This corresponds to the amino acid sequence <SEQ ID 672; ORF23ng-1>:

```
  1 MTRFKYSLLF AALLPVYAQA DVSVSDDPKP QESTELPTIT VTADRTASSN

51 DGYTVSGTHT PFGLPMTLRE IPQSVSVITS QQMRDQNIKT LDRALLQATG

101 TSRQIYGSDR AGYNYLFARG SRIANYQING IPVADALADT GNANTAAYER

151 VEVVRGVAGL PDGTGEPSAT VNLVRKHPTR KPLFEVRAEA GNRKHFGLGA

201 DVSGSLNAEG TLRGRLVSTF GRGDSWRQLE RSRDAELYGI LEYDIAPQTR

251 VHAGMDYQQA KETADAPLSY AVYDSQGYAT AFGPKDNPAT NWSNSRNRAL

301 NLFAGIEHRF NQDWKLKAEY DYTRSRFRQP YGVAGVLSID HSTAATDLIP

351 GYWHADPRTH SASMSLTGKY RLFGREHDLI AGINGYKYAS NKYGERSIIP

401 NAIPNAYEFS RTGAYPQPSS FAQTIPQYDT RRQIGGYLAT RFRAADNLSL

451 ILGGRYSRYR AGSYNSRTQG MTYVSANRFT PYTGIVFDLT GNLSLYGSYS
```

```
501 SLFVPQLQKD EHGSYLKPVT GNNLEADIKG EWLEGRLNAS AAVYRARKNN

551 LATAAGRDQS GNTYYRAANQ AKTHGWEIEV GGRITPEWQI QAGYSQSKPR

601 DQDGSRLNPD SVPERSFKLF TAYHLAPEAP SGRTIGAGVR RQGETHTDPA

651 ALRIPNPAAK ARAVANSRQK AYAVADIMAR YRFNPRTELS LNVDNLFNKH

701 YRTQPDRHSY GALRTVNAAF TYRFK*
```

ORF23ng-1 and ORF23-1 show 95.9% identity in 725 aa overlap:

```
                  10         20         30         40         50         60
orf23-1.pep   MTRFKYSLLFAALLPVYAQADVSVSDDPKPQESTELPTITVTADRTASSNDGYTVSGTHT
              |||||||||||||||||||||||||||||||||||||||||||||||||||||||||||
orf23ng-1     MTRFKYSLLFAALLPVYAQADVSVSDDPKPQESTELPTITVTADRTASSNDGYTVSGTHT
                  10         20         30         40         50         60

70         80         90        100        110        120
orf23-1.pep   PLGLPMTLREIPQSVSVITSQQMRDQNIKTLDRALLQATGTSRQIYGSDRAGYNYLFARG
              |:|||||||||||||||||||||||||||||||||||||||||||||||||||||||||
orf23ng-1     PFGLPMTLREIPQSVSVITSQQMRDQNIKTLDRALLQATGTSRQIYGSDRAGYNYLFARG
                  70         80         90        100        110        120

130        140        150        160        170        180
orf23-1.pep   SRIANYQINGIPVADALADTGNANTAAYERVEVVRGVAGLLDGTGEPSATVNLVRKRLTR
              ||||||||||||||||||||||||||||||||||||||| |||||||||||||||:  ||
orf23ng-1     SRIANYQINGIPVADALADTGNANTAAYERVEVVRGVAGLPDGTGEPSATVNLVRKHPTR
                 130        140        150        160        170        180

190        200        210        220        230        240
orf23-1.pep   KPLFEVRAEAGNRKHFGLDADVSGSLNTEGTLRGRLVSTFGRGDSWRRRERSRDAELYGI
              |||||||||||||||||||:|||||||:|||||||||||||||||| :|||||||||||
orf23ng-1     KPLFEVRAEAGNRKHFGLGADVSGSLNAEGTLRGRLVSTFGRGDSWRQLERSRDAELYGI
                 190        200        210        220        230        240

250        260        270        280        290        300
orf23-1.pep   LEYDIAPQTRVHAGMDYQQAKETADAPLSYAVYDSQGYATAFGPKDNPATNWANSRHRAL
              ||||||||||||||||||||||||||||||||||||||||||||||||||||||||||||
orf23ng-1     LEYDIAPQTRVHAGMDYQQAKETADAPLSYAVYDSQGYATAFGPKDNPATNWANSRHRAL
                 250        260        270        280        290        300

310        320        330        340        350        360
orf23-1.pep   NLFAGIEHRFNQDWKLKAEYDYTRSRFRQPYGVAGVLSIDHNTAATDLIPGYWHADPRTH
              |||||||||||||||||||||||||||||||||||||||||||:||||||||||||||||
orf23ng-1     NLFAGIEHRFNQDWKLKAEYDYTRSRFRQPYGVAGVLSIDHSTAATDLIPGYWHADPRTH
                 310        320        330        340        350        360

370        380        390        400        410        420
orf23-1.pep   SASVSLIGKYRLFGREHDLIAGINGYKYASNKYGERSIIPNAIPNAYEFSRTGAYPQPAS
              ||||:||||||||||||||||||||||||||||||||||||||||||||||||||||| :
orf23ng-1     SASMSLTGKYRLFGREHDLIAGINGYKYASNKYGERSIIPNAIPNAYEFSRTGAYPQPSS
                 370        380        390        400        410        420

430        440        450        460        470        480
orf23-1.pep   FAQTIPQYGTRRQIGGYLATRFRAADNLSLILGGRYTRYRTGSYDSRTQGMTYVSANRFT
              ||||||||:|||||||||||||||||||||||||||:||:||:|:||||||||||||||
orf23ng-1     FAQTIPQYDTRRQIGGYLATRFRAADNLSLILGGRYSRYRAGSYNSRTQGMTYVSANRFT
                 430        440        450        460        470        480

490        500        510        520        530        540
orf23-1.pep   PYTGIVFDLTGNLSLYGSYSSLFVPQSQKDEHGSYLKPVTGNNLEAGIKGEWLEGRLNAS
              ||||||||||||||||||||||||||:|||||||||||||||||||:||||||||||||
orf23ng-1     PYTGIVFDLTGNLSLYGSYSSLFVPQLQKDEHGSYLKPVTGNNLEADIKGEWLEGRLNAS
                 490        500        510        520        530        540

550        560        570        580        590        600
orf23-1.pep   AAVYRARKNNLATAAGRDPSGNTYYRAANQAKTHGWEIEVGGRITPEWQIQAGYSQSKTR
              ||||||||||||||||||:|||||||||||||||||||||||||||||||||||||||:|
orf23ng-1     AAVYRARKNNLATAAGRDQSGNTYYRAANQAKTHGWEIEVGGRITPEWQIQAGYSQSKPR
                 550        560        570        580        590        600

610        620        630        640        650        660
orf23-1.pep   DQDGSRLNPDSVPERSFKLETAYHFAPEAPSGWTIGAGVRWQSETHTDPATLRIPNPAAK
              ||||||||||||||||||||||||:|||||||:|||||||:|||||||||:|||||||||
orf23ng-1     DQDGSRLNPDSVPERSFKLETAYHLAPEAPSGRTIGAGVRRQGETHTDPAALRIPNPAAK
                 610        620        630        640        650        660

670        680        690        700        710        720
orf23-1.pep   ARAADNSRQKAYAVADIMARYRFNPRAELSLNVDNLFNKHYRTQPDRHSYGALRTVNAAF
              ||:|||||||||||||||||||||||:||||||||||||||||||||||||||||||||
orf23ng-1     ARAVANSRQKAYAVADIMARYRFNPRTELSLNVDNLFNKHYRTQPDRHSYGALRTVNAAF
                 670        680        690        700        710        720
```

```
orf23-1.pep    TYRFKX
               ||||||
orf23ng-1      TYRFKX
```

In addition, ORF1ing-1 shows significant homology with an OMP from *E. coli*:

```
sp|P16869|FHUE_ECOLI OUTER-MEMBRANE RECEPTOR FOR FE(III)-COPROGEN, FE(III)-
FERRIOXAMINE B AND FE(III)-RHODOTRULIC ACID PRECURSOR
>gi|1651542|gnl|PID|d1015403
(D90745) Outer membrane protein FhuE precursor [Escherichia coli]
>gi|1651545|gnl|PID|d1015405 (D90746) Outer membrane protein FhuE precursor
[Escherichia coli] >gi|1787344 (AE000210) outer-membrane receptor for
Fe(III)-coprogen, Fe(III)-ferrioxamine B and Fe(III)-rhodotrulic acid pre-
cursor
[Escherichia coli] Length = 729
Score = 332 bits (843), Expect = 3e-90
Identities = 228/717 (31%), Positives = 350/717 (48%), Gaps = 60/717 (8%)

Query:  38 TITVTADRTASSN--DGYTVSGTHTPFGLPMTLREIPQSVSVITSQQMRDQNIKTLDRAL   95
           T+ V     TA +  + Y+V+ T     + MT R+IPQSV++++ Q+M DQ ++TL   +
Sbjct:  43 TVIVEGSATAPDDGENDYSVTSTSAGTKMQMTQRDIPQSVTIVSQQRMEDQQLQTLGEVM  102

Query:  96 LQATGTSRQIYGSDRAGYNYLFARGSRIANYQINGIP--------VADALADTGNANTAA  147
              G S+     SDRA Y    ++RG +I NY ++GIP        + DAL+D    A
Sbjct: 103 ENTLGISKSQADSDRALY---YSRGFQIDNYMVDGIPTYFESRWNLGDALSDM-----AL  154

Query: 148 YERVEVVRGVAGLPDGTGEPSATVNLVRKHPTRKPLF-EVRAEAGNRKHFGLGADVSGSL  206
           +ERVEVVRG  GL GTG PSA +N+VRKH T +     +V AE G+        AD+   L
Sbjct: 155 FERVEVVRGATGLMTGTGNPSAAINMVRKHATSREFKGDVSAEYGSWNKERYVADLQSPL  214

Query: 207 NAEGTLRGRLVSTFGRGDSWRQLERSRDAELYGILEYDIAPQTRVHAGMDYQQAKETADA  266
           +G +R R+V +    DSW   S        GI++ D+   T + AG +YQ+       +
Sbjct: 215 TEDGKIRARIVGGYQNNDSWLDRYNSEKTFFSGIVDADLGDLTTLSAGYEYQRIDVNSPT  274

Query: 267 PLSYAVYDSQGYATAFGPKDNPATNWSNSRNRALNLFAGIEHRFNQDWKLKAEYDYTRSR  326
              +++ G + ++     + A +W+ +       +F ++ +F     w+        ++
Sbjct: 275 WGGLPRWNTDGSSNSYDRARSTAPDWAYNDKEINKVFMTLKQQFADTWQATLNATHSEVE  334

Query: 327 F--RQPYGVAGVLSIDHSTAA--TDLIPGY-------WHADPRTHSA-SMSLTGKYRLFG  374
               F  + Y A V   D      ++ PG+       W++  R   A  + G Y LFG
Sbjct: 335 FDSKMMYVDAYVNKADGMLVGPYSNYGPGFDVGGTGWNSGKRKVDALDLFADGSYELFG  394

Query: 375 REHDLIAGINGYKYASNKYGER--SIIPNAIPNAYEFSRTGAYPQPSSFAQTIPQYDTRR  432
           R+H+L+  G    Y  +N+Y     +I P+ I + Y F+   G +PQ       Q++  Q DT
Sbjct: 395 RQHNLMFG-GSYSKQNNRYFSSWANIFPDEIGSFYNFN--GNFPQTDWSPQSLAQDDTTH  451

Query: 433 QIGGYLATRFRAADNLSLILGGRYSRYRAGSYNSRTQGMTY-VSANRFTPYTGIVFDXXX  491
            Y ATR    AD L LILG RY+ +R +         +TY +  N  TPY G+VFD
Sbjct: 452 MKSLYAATRVTLADPLHLILGARYTNWRVDT-------LTYSMEKNHTTPYAGLVFDIND  504

Query: 492 XXXXXXXXXXXFVPQLQKDEHGSYLKPVTGNNLEADIKGEWLEGRLNASAAVYRARKNNL  551
                        F PQ  +D  G YL P+TGNN E  +K +W+  RL  + A++R  ++N+
Sbjct: 505 NWSTYASYTSIFQPQNDRDSSGKYLAPITGNNYELGLKSDWMNSRLTTTLAIFRIEQDNV  564

Query: 552 ATAAGR---DQSGNTYYRAANQAKTHGWEIEVGGRITPEWQIQAGYSQSKPRDQDGSRLN  608
             A + G         +G T Y+A +     + G E+ G IT  WQ+  G ++    D +G+ +N
Sbjct: 565 AQSTGTPIPGSNGETAYKAVDGTVSKGVEFELNGAITDNWQLTFGATRYIAEDNEGNAVN  624

Query: 609 PDSVPERSFKLFTAYHLAPEAPSGRTIGAGVRRQGETHTDPAALRIPNPAAKARAVANSR  668
           P ++P  + K+FT+Y L P  P      T+G GV  Q    +TD         P     RA
Sbjct: 625 P-NLPRTTVKMFTSYRL-PVMPE-LTVGGGVNWQNRVYTDTV-----TPYGTFRA----E  672

Query: 669 QKAYAVADIMARYRFNPRTELSLNVDNLFNKHYRTQPDRH-SYGALRTVNAAFTYRF     724
           Q +YA+ D+  RY+       L NV+NLF+K Y T +       YG R +    TY+F
Sbjct: 673 QGSYALVDLFTRYQVTKNFSLQGNVNNLFDKTYDTNVEGSIVYGTPRNFSITGTYQF     729
```

Based on this analysis, it was predicted that these proteins from *N. meningitidis* and *N. gonorrhoeae*, and their epitopes, could be useful antigens for vaccines or diagnostics, or for raising antibodies.

ORF23-1 (77.5 kDa) was cloned in pET and pGex vectors and expressed in *E. coli*, as described above. The products of protein expression and purification were analyzed by SDS-PAGE. FIG. 15A shows the results of affinity purification of the His-fusion protein, and FIG. 15B shows the results of expression of the GST-fusion in *E. coli*. Purified His-fusion protein was used to immunise mice, whose sera were used for Western blot (FIG. 15C) and for ELISA (positive result). These experiments confirm that ORF23-1 is a surface-exposed protein, and that it is a useful immunogen.

Example 80

The following partial DNA sequence was identified in *N. meningitidis* <SEQ ID 673>:

```
  1 ATGCGCACGG CAGTGGTTTT GCTGTTGATC ATGCCGATGG CGGCTTCGTC
 51 GGCAATGATG CCGGAAATGG TGTGCGCGGG CGTGTCGCCG GGAACGGCAA
101 TCATATCCAA GCCGACCGAA CAAACGGCGG TCATGGCTTC GAGTTTGTCC
151 AGCGTCAgcA CGCCTGCTTC GGCGgcGgCa ATCATACCTT CGTCTTCGGA
201 AACGGGGATA AACGcGCCAC TCAAACCCCC GACCGCGCTG GAAGCCATCA
251 TGCCGCCTTT TTTCACGGCA TCGTTCAGCA ATGCCAAAGC TGCTGTTGTG
301 CCGTGCGTAC CGCAGACGCT CAAGCCCATT TnTTCAAGAA TGCGTGCCAC
351 TnAGTCGCCG ACGGGG..
```

This corresponds to the amino acid sequence <SEQ ID 674; ORF24>:

```
  1 MRTAVVLLLI MPMAASSAMM PEMVCAGVSP GTAIISKPTE QTAVMASSLS
 51 SVSTPASAAA IIPSSSETGI NAPLKPPTAL EAIMPPFFTA SFSNAKAAVV
101 PCVPQTLKPI XSRMRATXSP TG..
```

Further work revealed the complete nucleotide sequence <SEQ ID 675>:

```
  1 ATGCGCACGG CAGTGGTTTT GCTGTTGATC ATGCCGATGG CGGCTTCGTC
 51 GGCAATGATG CCGGAAATGG TGTGCGCGGG CGTGTCGCCG GGAACGGCAA
101 TCATATCCAA GCCGACCGAA CAAACGGCGG TCATGGCTTC GAGTTTGTCC
151 AGCGTCAGCA CGCCTGCTTC GGCGGCGGCA ATCATACCTT CGTCTTCGGA
201 AACGGGGATA AACGCGCCAC TCAAACCCCC GACCGCGCTG GAAGCCATCA
251 TGCCGCCTTT TTTCACGGCA TCGTTCAGCA ATGCCAAAGC TGCTGTTGTG
301 CCGTGCGTAC CGCAGACGCT CAAGCCCATT TCTTCAAGAA TGCGTGCCAC
351 TGAGTCGCCG ACGGCGGGG TCGGCGCCAG CGACAAGTCG AGAATACCAA
401 ACGGGATATT CAGCATTTTT GAGGCTTCGC GGCCGATGAG TTCGCCCACG
451 CGGGTAATTT TGAAAGCAGT TTTCTTCACT ACTTCCGCAA CTTCGGTCAA
501 TGTCGTTGCA TCTGAATTTT CCAACGCGGC TTTTACGACA CCTGGGCCGG
551 ATACGCCGAC ATTGATAACG GCATCCGCTT CGCCCGAACC ATGAAACGCG
601 CCCGCCATAA ACGGGTTGTC TTCCACCGCG TTGCAGAACA CGACAATTTT
651 AGCGCAGCCG AAACCTTCGG GCGTGATTTC CGCCGTGCGT TTGACGGTTT
701 CGCCCGCCAG CTTGACCGCA TCCATATTGA TACCGGCACG CGTACTGCCG
751 ATATTGATGG AGCTGCACAC AATATCGGTA GTCTTCATCG CTTCGGGAAT
801 GGAGCGGATT AACACCTCAT CCGAAGGCGA CATCCCTTTT TGCACCAACG
851 CGGAAAAACC GCCGATAAAA GACACACCGA TGGCTTTGGC AGCTTTATCC
901 AAAGTTTGCG CCACGCTGAC GTAA
```

This corresponds to the amino acid sequence <SEQ ID 676; ORF24-1>:

```
  1 MRTAVVLLLI MPMAASSAMM PEMVCAGVSP GTAIISKPTE QTAVMASSLS

51 SVSTPASAAA IIPSSSETGI NAPLKPPTAL EAIMPPFFTA SFSNAKAAVV

101 PCVPQTLKPI SSRMRATESP TAGVGASDKS RIPNGIFSIF EASRPMSSPT

151 RVILKAVFFT TSATSVNVVA SEFSNAAFTT PGPDTPTLIT ASASPEP*NA

201 PAINGLSSTA LQNTTILAQP KPSGVISAVR LTVSPASLTA SILIPARVLP

251 ILMELHTISV VFIASGMERI NTSSEGDIPF CTNAEKPPIK DTPMALAALS

301 KVCATLT*
```

Computer analysis of this amino acid sequence gave the following results:

Homology with a Predicted ORF from *N. meningitidis* (Strain A)

ORF24 shows 96.4% identity over a 307 aa overlap with an ORF (ORF24a) from strain A of *N. meningitidis*.

```
                       10        20        30        40        50        60
orf24a.pep    MRTAVVLLLIMPMAASSAMMPEMVCAGVSPGTAIISXPTEQTAVIASSLSNVSTPASAAA
              ||||||||||||||||||||||||||||||||| ||||||:||||:|||||||||||
orf24         MRTAVVLLLIMPMAASSAMMPEMVCAGVSPGTAIISKPTEQTAVMASSLSSVSTPASAAA
                       10        20        30        40        50        60
                       70        80        90       100       110       120
orf24a.pep    IIPSSSXTGINAPLKPPTALEAIMPPFFTASFSNAKAAVVPCVPQTLKPISSRMRATESP
              |||||| |||||||||||||||||||||||||||||||||||||||||||||||||||||
orf24         IIPSSSETGINAPLKPPTALEAIMPPFFTASFSNAKAAVVPCVPQTLKPISSRMRATESP
                       70        80        90       100       110       120
                      130       140       150       160       170       180
orf24a.pep    TAGVGASDKSRIPNGIFSIFEASRPMSSPTRVILKAVFFTTSATSVNVVASEFSNAAFTT
              ||||||||||||||||||||||||||||||||||||||||||||||||||||||||||||
orf24         TAGVGASDKSRIPNGIFSIFEASRPMSSPTRVILKAVFFTTSATSVNVVASEFSNAAFTT
                      130       140       150       160       170       180
                      190       200       210       220       230       240
orf24a.pep    PGPDTPTLITASASPEPXNAPAIXGLSSXALQNTTILAQPKPSSVISXVRLMVSPASLTA
              ||||||||||||||||| |||||:||||:||||||||||||||||| ||||||||||||
orf24         PGPDTPTLITASASPEPXNAPAIXGLSSXALQNTTILAQPKPSSVISXVRLMVSPASLTA
                      190       200       210       220       230       240
                      250       260       270       280       290       300
orf24a.pep    SILIPARVLPILMELHTISVVFIASGMERXNTSSEGDIPFCTSAEKPPIKDTPMALAALS
              |||||||||||||||||||||||||||||| ||||||||||:||||||||||||||||
orf24         SILIPARVLPILMELHTISVVFIASGMERINTSSEGDIPFCTNAEKPPIKDTPMALAALS
                      250       260       270       280       290       300
orf24a.pep    KVCATLTX
              ||||||||
orf24         KVCATLTX
```

The complete length ORF24a nucleotide sequence <SEQ ID 677> is:

```
  1 ATGCGCACGG CAGTGGTTTT GCTGTTGATC ATGCCGATGG CGGCTTCGTC

51 GGCAATGATG CCGGAAATGG TGTGCGCGGG TGTGTCGCCG GGAACGGCAA

101 TCATATCCAA NCCGACCGAA CAAACGGCGG TCATCGCTTC GAGTTTATCC

151 AACGTCAGCA CGCCTGCTTC GGCGGCGGCA ATCATACCTT CGTCTTCGGA

201 NACGGGGATA AACGCGCCAC TCAAACCGCC AACCGCGCTC GAAGCCATCA

251 TGCCGCCCTT TTTCACGGCA TCGTTCAGCA ATGCCAAAGC TGCTGTTGTG

301 CCGTGCGTAC CGCAGACGCT CAAACCCATT TCTTCAAGAA TGCGCGCCAC

351 CGAGTCGCCG ACGGCAGGGG TCGGTGCCAG CGACAAGTCG AGAATACCAA
```

```
401 ACGGGATATT CAGCATTTTT GAGGCTTCGC GGCCGATGAG TTCGCCCACG

451 CGGGTAATTT TGAAGGCGGT TTTCTTCACA ACTTCGGCAA CTTCGGTCAA

501 TGTCGTTGCA TCCGAATTTT CCAACGCGGC TTTTACGACA CCCGGGCCGG

551 ATACGCCGAC ATTAATCACA GCATCCGCTT CGCCTGAGCC GTGAAACGCG

601 CCCGCCATAN ACGGGTTGTC TTCCNCCGCG TTGCAGAACA CGACGATTTT

651 GGCGCAGCCG AAACCTTCTA GTGTGATTTC ANCCGTGCGT TTGATGGTTT

701 CGCCCGCCAG TCTGACCGCG TCCATATTGA TACCGGCGCG CGTACTGCCG

751 ATATTGATGG AGCTGCACAC GATATCAGTA GTCTTCATCG CTTCGGGAAT

801 GGAACGGATN AACACCTCGT CAGAAGGCGA CATACCTTTT TGCACCAGCG

851 CGGAAAAGCC GCCAATAAAA GACACGCCGA TGGCTTTGGC AGCCTTATCC

901 AAAGTTTGCG CCACGCTGAC GTAA
```

This encodes a protein having amino acid sequence <SEQ ID 678>:

```
  1 MRTAVVLLLI MPMAASSAMM PEMVCAGVSP GTAIISXPTE QTAVIASSLS

51 NVSTPASAAA IIPSSSXTGI NAPLKPPTAL EAIMPPFFTA SFSNAKAAVV

101 PCVPQTLKPI SSRMRATESP TAGVGASDKS RIPNGIFSIF EASRPMSSPT

151 RVILKAVFFT TSATSVNVVA SEFSNAAFTT PGPDTPTLIT ASASPEP*NA

201 PAIXGLSSXA LQNTTILAQP KPSSVISXVR LMVSPASLTA SILIPARVLP

251 ILMELHTISV VFIASGMERX NTSSEGDIPF CTSAEKPPIK DTPMALAALS

301 KVCATLT*
```

It should be noted that this protein includes a stop codon at position 198.

ORF24a and ORF24-1 show 96.4% identity in 307 aa overlap:

```
                  10        20        30        40        50        60
orf24a.pep  MRTAVVLLLIMPMAASSAMMPEMVCAGVSPGTAIISXPTEQTAVIASSLSNVSTPASAAA
            |||||||||||||||||||||||||||||||||||:||||||:|||||||||
orf24-1     MRTAVVLLLIMPMAASSAMMPEMVCAGVSPGTAIISKPTEQTAVMASSLSVSTPASAAA
                  10        20        30        40        50        60

70        80        90       100       110       120
orf24a.pep  IIPSSSXTGINAPLKPPTALEAIMPPFFTASFSNAKAAVVPCVPQTLKPISSRMRATESP
            |||||  |||||||||||||||||||||||||||||||||||||||||||||||||||||
orf24-1     IIPSSSETGINAPLKPPTALEAIMPPFFTASFSNAKAAVVPCVPQTLKPISSRMRATESP
                  70        80        90       100       110       120

130       140       150       160       170       180
orf24a.pep  TAGVGASDKSRIPNGIFSIFEASRPMSSPTRVILKAVFFTTSATSVNVVASEFSNAAFTT
            ||||||||||||||||||||||||||||||||||||||||||||||||||||||||||||
orf24-1     TAGVGASDKSRIPNGIFSIFEASRPMSSPTRVILKAVFFTTSATSVNVVASEFSNAAFTT
                 130       140       150       160       170       180

190       200       210       220       230       240
orf24a.pep  PGPDTPTLITASASPEPXNAPAIXGLSSXALQNTTILAQPKPSSVISXVRLMVSPASLTA
            |||||||||||||||||||||||:|||||||||||||||:||||||||||
orf24-1     PGPDTPTLITASASPEPXNAPAINGLSSTALQNTTILAQPKPSGVISAVRLTVSPASLTA
                 190       200       210       220       230       240

250       260       270       280       290       300
orf24a.pep  SILIPARVLPILMELHTISVVFIASGMERXNTSSEGDIPFCTSAEKPPIKDTPMALAALS
            |||||||||||||||||||||||||||||||||||||||||:||||||||||||||||
orf24-1     SILIPARVLPILMELHTISVVFIASGMERINTSSEGDIPFCTNAEKPPIKDTPMALAALS
                 250       260       270       280       290       300 orf24a.pep  KVCATLTX
            ||||||||
orf24-1     KVCATLTX
```

Homology with a Predicted ORF from *N. gonorrhoeae*
ORF24 shows 96.7% identity over a 121 aa overlap with a predicted ORF (ORF24ng) from *N. gonorrhoeae*:

```
orf24.pep  MRTAVVLLLIMPMAASSAMMPEMVCAGVSPGTAIISKPTEQTAVMASSLSSVSTPASAAA  60
           ||||||||||||||||||||||||||||||:||||||||||||||||||||:|||||||
orf24ng    MRTAVVLLLIMPMAASSAMMPEMVCAGVSPGTAIMSKPTEQTAVMASSLSSVNTPASAAA  60
orf24.pep  IIPSSSETGINAPLKPPTALEAIMPPFFTASFSNAKAAVVPCVPQTLKPIXSRMRATXSP  120
           ||||||||||||||||||||||||||||||||||||||||||||||||| |||||| ||
orf24ng    IIPSSSETGINAPLKPPTALEAIMPPFFTASFSNAKAAVVPCVPQTLKPISSRMRATESP  120
orf24.pep  TG                                                           122
           |:
orf24ng    TAGVGASDKSRMPNGIFSIFEASRPMSSPTRVILKAVFFTTSATSVRLTASEFSSAALTT  180
```

The complete length ORF24ng nucleotide sequence <SEQ ID 679> is:

```
  1 ATGCGCACGG CGGTGGTTTT GCTGTTGATC ATGCCGATGG CGGCTTCGTC

51 GGCGATGATG CCGGAAATGG TGTGCGCGGG CGTGTCGCCG GGAACGGCAA

101 TCATGTCCAA ACCAACGGAG CAGACGGCGG TCATGGCTTC GAGTTTGTCC

151 AGCGTCAACA CGCCTGCCTC GGCGGCGGCA ATCATACCTT CGTCTTCGGA

201 AACGGGGATA AACGCGCCGC TCAAACCGCC GACCGCGCTG AAGCCATCA

251 TGCCGCCCTT TTTCACGGCA TCGTTCAGCA ATGCCAAAGC TGCTGTTGTG

301 CCGTGCGTAC CGCAGACGCT CAAGCCCATT TCTTCAAGAA TGCGCGCCAC

351 CGAGTCGCCG ACGGCGGGGG TCGGTGCCAG CGACAAATCG AGAATGCCGA

401 ACGGGATATT CAGCATTTTT GAGGCTTCGC GACCGATGAG TTCGCCCACG

451 CGGGTGATTT TGAAAGCGGT TTTCTTCACG ACTTCGGCGA CCTCGGTCAG

501 GCTGACCGCG TCCGAATTTT CCAGCGCGGC TTTGACCACG CCTGGACCGG

551 ATACGCCGAC ATTAATCACA GCATCCGCTT CGCCCGAGCC GTGGAACGCA

601 CCCGCCATAA ACGGATTGTC TTCCACCGCG TTGCAGAACA CGACGATTTT

651 GGCGCAGCCG AAACCTTCGG GTGTGATTTC AGCCGTGCGT TTGATGGTTT

701 CGCCTGCCAG CTTGACCGCA TCCATATTGA TACCGGCACG CGTGCTGCCG

751 ATATTGATGG AGCTGCACAC GATATCGGTA GTTTTCATCG CTTCGGGAAC

801 GGAACGGATC AACACCTCAT CCGAAGGCGA CATACCTTTT TGCACCAGCG

851 CGGAAAAGCC GCCGATAAAG GACACGCCGA TGGCTTTGGC TGCCTTGTCC

901 AAAGTCTGCG CCACGCTGAC ATAA
```

This encodes a protein having amino acid sequence <SEQ ID 680>:

```
  1 MRTAVVLLLI MPMAASSAMM PEMVCAGVSP GTAIMSKPTE QTAVMASSLS

51 SVNTPASAAA IIPSSSETGI NAPLKPPTAL EAIMPPFFTA SFSNAKAAVV

101 PCVPQTLKPI SSRMRATESP TAGVGASDKS RMPNGIFSIF EASRPMSSPT

151 RVILKAVFFT TSATSVRLTA SEFSSAALTT PGPDTPTLIT ASASPEPWNA

201 PAINGLSSTA LQNTTILAQP KPSGVISAVR LMVSPASLTA SILIPARVLP

251 ILMELHTISV VFIASGTERI NTSSEGDIPF CTSAEKPPIK DTPMALAALS

301 KVCATLT*
```

ORF24ng and ORF24-1 show 96.1% identity in 307 aa overlap:

```
                        10         20         30         40         50         60
    orf24-1.pep  MRTAVVLLLIMPMAASSAMMPEMVCAGVSPGTAIISXPTEQTAVIASSLSNVSTPASAAA
                 ||||||||||||||||||||||||||||||||:|||||||||||||||||||:|||||||
    orf24ng      MRTAVVLLLIMPMAASSAMMPEMVCAGVSPGTAIMSXPTEQTAVIASSLSNVNTPASAAA
                        10         20         30         40         50         60

70         80         90        100        110        120
    orf24-1.pep  IIPSSSETGINAPLKPPTALEAIMPPFFTASFSNAKAAVVPCVPQTLKPISSRMRATESP
                 ||||||||||||||||||||||||||||||||||||||||||||||||||||||||||||
    orf24ng      IIPSSSETGINAPLKPPTALEAIMPPFFTASFSNAKAAVVPCVPQTLKPISSRMRATESP
                        70         80         90        100        110        120

130        140        150        160        170        180
    orf24-1.pep  TAGVGASDKSRIPNGIFSIFEASRPMSSPTRVILKAVFFTTSATSVNVVASEFSNAAFTT
                 ||||||||||:|||||||||||||||||||||||||||||||||||::|||||:|:|||
    orf24ng      TAGVGASDKSRMPNGIFSIFEASRPMSSPTRVILKAVFFTTSATSVRLTASEFSSAALTT
                       130        140        150        160        170        180

190        200        210        220        230        240
    orf24-1.pep  PGPDTPTLITASASPEPXNAPAINGLSSTALQNTTILAQPKPSGVISAVRLTVSPASLTA
                 ||||||||||||||||||:|||||||||||||||||||||||||||||||||:|||||||
    orf24ng      PGPDTPTLITASASPEPWNAPAINGLSSTALQNTTILAQPKPSGVISAVRLMVSPASLTA
                       190        200        210        220        230        240

250        260        270        280        290        300
    orf24-1.pep  SILIPARVLPILMELHTISVVFIASGMERINTSSEGDIPFCTNAEKPPIKDTPMALAALS
                 ||||||||||||||||||||||||||||:|||||||||||||:|||||||||||||||||
    orf24ng      SILIPARVLPILMELHTISVVFIASGTERINTSSEGDIPFCTSAEKPPIKDTPMALAALS
                       250        260        270        280        290        300 orf24-1.pep  KVCATLTX
                 ||||||||
    orf24ng      KVCATLTX
```

Based on this analysis, including the presence of a putative leader sequence (first 18 aa—double-underlined) and putative transmembrane domains (single-underlined) in the gonococcal protein, it is predicted that the proteins from *N. meningitidis* and *N. gonorrhoeae*, and their epitopes, could be useful antigens for vaccines or diagnostics, or for raising antibodies.

Example 81

The following partial DNA sequence was identified in *N. meningitidis* <SEQ ID 681>:

```
  1..ACCGACGTGC AAAAAGAGTT GGTCGGCGAA CAACGCAAGT GGGCGCAGGA

51   AAAAATCAGC AACTGCCGAC AAGCCGCCGC GCAGGCAGAC CGGCAGGAAT

101   ACGCCGAATA CCTCAAGCTG CAATGCGACA CGCGGATGAC GCGCGAACGG

151   ATACAGTATC TTCGCGGCTA TTCCATCGAT TAG
```

This corresponds to the amino acid sequence <SEQ ID 682; ORF25>:

```
  1..TDVQKELVGE QRKWAQEKIS NCRQAAAQAD RQEYAEYLKL QCDTRMTRER

51   IQYLRGYSID *
```

Further work revealed the complete nucleotide sequence <SEQ ID 683>:

```
  1 ATGTATCGGA AACTCATTGC GCTGCCGTTT GCCCTGCTGC TTGCCGCTTG

51 CGGCAGGGAA GAACCGCCCA AGGCATTGGA ATGCGCCAAC CCCGCCGTGT

101 TGCAAGGCAT ACGCGGCAAT ATTCAGGAAA CGCTCACGCA GGAAGCGCGT
```

-continued

```
 151 TCTTTCGCGC GCGAAGACGG CAGGCAGTTT GTCGATGCCG ACAAAATTAT
 201 CGCCGCCGCC TACGGTTTGG CGTTTTCTTT GGAACACGCT TCGGAAACGC
 251 AGGAAGGCGG GCGCACGTTC TGTATCGCCG ATTTGAACAT TACCGTGCCG
 301 TCTGAAACGC TTGCCGATGC CAAGGCAAAC AGCCCCCTGT TGTACGGGGA
 351 AACTGCTTTG TCGGATATTG TGCGGCAGAA GACGGGCGGC AATGTCGAGT
 401 TTAAAGACGG CGTATTGACG GCAGCCGTCC GCTTCCTGCC CGTCAAAGAC
 451 GGTCAGACGG CATTTGTCGA CAACACGGTC GGTATGGCGG CGCAAACGCT
 501 GTCTGCCGCG CTGCTGCCTT ACGGCGTGAA GAGCATCGTG ATGATAGACG
 551 GCAAGGCGGT GAAAAAGAA GACGCGGTCA GGATTTTGAG CGGAAAAGCC
 601 CGTGAAGAAG AACCGTCCAA ACCCACGCCC GAAGACATTT TGGAACACAA
 651 TGCCGCCGGC GGCGATGCGG GCGTACCCCA AGCCGCAGAA GGCGCGCCCG
 701 AACCGGAAAT CCTGCATCCT GACGACGGCG AGCGTGCCGA TACCGTTACC
 751 GTATCACGGG GCGAAGTGGA AGAGGCGCGC GTACAAAACC AGCGTGCGGA
 801 ATCCGAAATT ACCAAACTTT GGGGAGGACT CGATACCGAC GTGCAAAAAG
 851 AGTTGGTCGG CGAACAACGC AAGTGGGCGC AGGAAAAAAT CAGCAACTGC
 901 CGACAAGCCG CCGCGCAGGC AGACCGGCAG GAATACGCCG AATACCTCAA
 951 GCTGCAATGC GACACGCGGA TGACGCGCGA ACGGATACAG TATCTTCGCG
1001 GCTATTCCAT CGATTAG
```

This corresponds to the amino acid sequence <SEQ ID 684; ORF25-1>:

```
  1 MYRKLIALPF ALLLAACGRE EPPKALECAN PAVLQGIRGN IQETLTQEAR
 51 SFAREDGRQF VDADKIIAAA YGLAFSLEHA SETQEGGRTF CIADLNITVP
101 SETLADAKAN SPLLYGETAL SDIVRQKTGG NVEFKDGVLT AAVRFLPVKD
151 GQTAFVDNTV GMAAQTLSAA LLPYGVKSIV MIDGKAVKKE DAVRILSGKA
201 REEEPSKPTP EDILEHNAAG GDAGVPQAAE GAPEPEILHP DDGERADTVT
251 VSRGEVEEAR VQNQRAESEI TKLWGGLDTD VQKELVGEQR KWAQEKISNC
301 RQAAAQADRQ EYAEYLKLQC DTRMTRERIQ YLRGYSID*
```

Computer analysis of this amino acid sequence gave the following results:

Homology with a Predicted ORF from *N. meningitidis* (Strain A)

ORF25 shows 98.3% identity over a 60aa overlap with an ORF (ORF25a) from strain A of *N. meningitidis*:

```
                                  10        20        30
orf25.pep                   TDVQKELVGEQRKWAQEKISNCRQAAAQAD
                            |||||||||| |||||||||||||||||||
orf25a      VTVSRGEVEEARVQNQRAESEITKLWGGLDTDVQKELVGEXRKWAQEKISNCRQAAAQAD
              250       260       270       280       290       300

40        50        60
orf25.pep   RQEYAEYLKLQCDTRMTRERIQYLRGYSIDX
            |||||||||||||||||||||||||||||||
orf25a      RQEYAEYLKLQCDTRMTRERIQYLRGYSIDX
              310       320       330
```

The complete length ORF25a nucleotide sequence <SEQ ID 685> is:

```
   1 ATGTATCGGA AACTCATTGC GCTGCCGTTT GCCCTGCTGC TTGCCGCTTG
  51 CGGCAGGGAA GAACCGCCCA AGGCATTGGA ATGCGCCAAC CCCGCCGTGT
 101 TGCAANGCAT ACGCNGCAAT ATTCAGGAAA CGCTCACGCA GGAAGCGCGT
 151 TCTTTCGCGC GCGAAGACNG CANGCAGTTT GTCGATGCCG ACNAAATTAT
 201 CGCCGCCGCC TANGNTNNGN NGNTNTCTTT GGAACACGCT TCGGAAACGC
 251 AGGAAGGCGG GCGCACGTTC TGTNTCGCCG ATTTGAACAT TACCGTGCCG
 301 TCTGAAACGC TTGCCGATGC CAAGGCAAAC AGCCCCCTGC TGTACGGGGA
 351 AACCGCTTTG TCGGATATTG TGCGGCAGAA GACGGGCGGC AATGTCGAGT
 401 TTAAAGACGG CGTATTGACG GCAGCCGTCC GCTTCCTACC CGTCAAAGAC
 451 GGTCAGANGG CATTTGTCGA CAACACGGTC GGTATGGCGG CGCAAACGCT
 501 GTCTGCCGCG TTGCTGCCTT ACGGCGTGAA GAGCATCGTG ATGATAGACG
 551 GCAAGGCGGT AAAAAAAGAA GACGCGGTCA GGATTNTGAG CNGANAAGCC
 601 CGTGAANAAG AACCGTCCAA ANCCNNGCCC GAAGACATTT TGGAACATAA
 651 TGCCGCCGGA GGGGATGCAG ACGTACCCCA AGCCGGAGAA GACGCGCCCG
 701 AACCGGAAAT CCTGCATCCT GACGACGGCG AGCGTGCCGA TACCGTTACC
 751 GTATCACGGG GCGAAGTGGA AGAGGCGCGN GTACAAAACC AGCGTGCGGA
 801 ATCCGAAATT ACCAAACTTT GGGGAGGACT CGATACCGAC GTGCAAAAAG
 851 AGTTGGTCGG CGAANAACGC AAGTGGGCGC AGGAAAAAAT CAGCAACTGC
 901 CGACAAGCCG CCGCGCAGGC AGACCGGCAG GAATACGCCG AATACCTCAA
 951 GCTGCAATGC GACACGCGGA TGACGCGCGA ACGGATACAG TATCTTCGCG
1001 GCTATTCCAT CGATTAG
```

This encodes a protein having amino acid sequence <SEQ ID 686>:

```
  1 MYRKLIALPF ALLLAACGRE EPPKALECAN PAVLQXIRXN IQETLTQEAR
 51 SFAREDXXQF VDADXIIAAA XXXXXSLEHA SETQEGGRTF CXADLNITVP
101 SETLADAKAN SPLLYGETAL SDIVRQKTGG NVEFKDGVLT AAVRFLPVKD
151 GQXAFVDNTV GMAAQTLSAA LLPYGVKSIV MIDGKAVKKE DAVRIXSXXA
201 REXEPSKXXP EDILEHNAAG GDADVPQAGE DAPEPEILHP DDGERADTVT
251 VSRGEVEEAR VQNQRAESEI TKLWGGLDTD VQKELVGEXR KWAQEKISNC
301 RQAAAQADRQ EYAEYLKLQC DTRMTRERIQ YLRGYSID*
```

ORF25a and ORF25-1 show 93.5% identity in 338 aa overlap:

```
                   10         20         30         40         50         60
   orf25a.pep  MYRKLIALPFALLLAACGREEPPKALECANPAVLQXIRXNIQETLTQEARSFAREDXXQF
               ||||||||||||||||||||||||||||||||||||| || |||||||||||||||  ||
   orf25-1     MYRKLIALPFALLLAACGREEPPKALECANPAVLQGIRGNIQETLTQEARSFAREDGRQF
                   10         20         30         40         50         60

70         80         90        100        110        120
   orf25a.pep  VDADXIIAAAXXXXXSLEHASETQEGGRTFCXADLNITVPSETLADAKANSPLLYGETAL
               |||| |||||     |||||||||||||||| ||||||||||||||||||||||||||||
   orf25-1     VDADKIIAAAYGLAFSLEHASETQEGGRTFCIADLNITVPSETLADAKANSPLLYGETAL
                   70         80         90        100        110        120
```

```
                  130       140       150       160       170       180
orf25a.pep   SDIVRQKTGGNVEFKDGVLTAAVRFLPVKDGQXAFVDNTVGMAAQTLSAALLPYGVKSIV
             ||||||||||||||||||||||||||||||:||||||||||||||||||||||||||||
orf25-1      SDIVRQKTGGNVEFKDGVLTAAVRFLPVKDGQTAFVDNTVGMAAQTLSAALLPYGVKSIV
                  130       140       150       160       170       180

190       200       210       220       230       240
orf25a.pep   MIDGKAVKKEDAVRIXSXXAREXEPSKXXPEDILEHNAAGGDADVPQAGEDAPEPEILHP
             ||||||||||||||  |||  ||||  :|||||||||||||| :||||| |||||||||
orf25-1      MIDGKAVKKEDAVRILSGKAREEEPSKPTPEDILEHNAAGGDAGVPQAAEGAPEPEILHP
                  190       200       210       220       230       240

250       260       270       280       290       300
orf25a.pep   DDGERADTVTVSRGEVEEARVQNQRAESEITKLWGGLDTDVQKELVGEXRKWAQEKISNC
             |||||||||||||||||||||||||||||||||||||||||||||||| ||||||||||
orf25-1      DDGERADTVTVSRGEVEEARVQNQRAESEITKLWGGLDTDVQKELVGEQRKWAQEKISNC
                  250       260       270       280       290       300

310       320       330    339
orf25a.pep   RQAAAQADRQEYAEYLKLQCDTRMTRERIQYLRGYSIDX
             |||||||||||||||||||||||||||||||||||||||
orf25-1      RQAAAQADRQEYAEYLKLQCDTRMTRERIQYLRGYSIDX
                  310       320       330
```

Homology with a Predicted ORF from *N. gonorrhoeae*

ORF25 shows 100% identity over a 60aa overlap with a predicted ORF (ORF25ng) from *N. gonorrhoeae*:

```
orf25.pep                         TDVQKELVGEQRKWAQEKISNCRQAAAQAD  30
                                  ||||||||||||||||||||||||||||||
orf25ng    VTVSRGEVEEARVQNQRAESEITKLWGGLDTDVQKELVGEQRKWAQEKISNCRQAAAQAD 308 orf25.pep  RQEYAEYLKLQCDTRMTRERIQYLRGYSID                              60
           ||||||||||||||||||||||||||||||
orf24ng    RQEYAEYLKLQCDTRMTRERIQYLRGYSID                             338
```

The complete length ORF25ng nucleotide sequence <SEQ ID 687> is:

```
  1  ATGTATCGGA AACTCATTGC GCTGCCGTTT GCCCTGCTGC TTGCAGCGTG
 51  CGGCAGGGAA GAACCGCCCA AGGCGTTGGA ATGCGCCAAC CCCGCCGTGT
101  TGCAGGACAT ACGCGGCAGT ATTCAGGAAA CGCTCACGCA GGAAGCGCGT
151  TCTTTCGCGC GCGAAGACGG CAGGCAGTTT GTCGATGCCG ACAAAATTAT
201  CGCCGCCGCC TACGGTTTGG CGTTTTCTTT GGAACACGCT TCGGAAACGC
251  AGGAAGGCGG GCGCACGTTC TGTATCGCCG ATTTGAACAT TACCGTGCCG
301  TCTGAAACGC TTGCCGATGC CGAGGCAAAC AGCCCCCTGC TGTATGGGGA
351  AACGTCTTTG GCAGACATCG TGCAGCAGAA GACGGGCGGC AATGTCGAGT
401  TTAAAGACGG CGTATTGACG GCAGCCGTCC GCTTCCTGCC CGCCAAAGAC
451  GCTCGGACGG CATTTATCGA CAACACGGTC GGTATGGCGA CGCAAACGCT
501  GTCTGCCGCG TTGCTGCCTT ACGGCGTGAA GAGCATCGTG ATGATAGACG
551  GCAAGGCGGT GACAAAAGAA GACGCGGTCA GGGTTTTGAG CGGCAAAGCC
601  CGTGAAGAAG AACCGTCCAA ACCCACCCCC GAAGACATTT TGGAACACAA
651  TGCCGCCGGC GGCGATGCGG GCGTACCCCA AGCCGCAGAA GGCGCACCCG
701  AACCCGAAAT CCTGCATCCC GACGACGTCG AGCGTGCCGA TACCGTTACC
751  GTATCACGGG GCGAAGTGGA AGAGGCGCGC GTACAAAACC AACGTGCGGA
801  ATCCGAAATT ACCAAACTTT GGGGAGGACT CGATACCGAC GTGCAAAAAG
851  AGTTGGTCGG CGAACAGCGC AAGTGGGCGC AGGAAAAAAT CAGcaactgc
901  cgACAAGCCG CCGCGCAGGC AGACCGGCAG GAATACGCCG AATACCTCAA
```

```
 951 GCTCCAATGC GACACGCGGA TGACGCGCGA ACggaTACAG TATCTTCGCG

1001 GCTATTCCAT CGATTAG
```

This encodes a protein having amino acid sequence <SEQ ID 688>:

```
  1 MYRKLIALPF ALLLAACGRE EPPKALECAN PAVLQDIRGS IQETLTQEAR

51 SFAREDGRQF VDADKIIAAA YGLAFSLEHA SETQEGGRTF CIADLNITVP

101 SETLADAEAN SPLLYGETSL ADIVQQKTGG NVEFKDGVLT AAVRFLPAKD

151 ARTAFIDNTV GMATQTLSAA LLPYGVKSIV MIDGKAVTKE DAVRVLSGKA

201 REEEPSKPTP EDILEHNAAG GDAGVPQAAE GAPEPEILHP DDVERADTVT

251 VSRGEVEEAR VQNQRAESEI TKLWGGLDTD VQKELVGEQR KWAQEKISNC

301 RQAAAQADRQ EYAEYLKLQC DTRMTRERIQ YLRGYSID*
```

ORF25ng and ORF25-1 show 95.9% identity in 338 aa overlap:

```
                    10         20         30         40         50         60
orf25-1.pep MYRKLIALPFALLLAACGREEPPKALECANPAVLQGIRGNIQETLTQEARSFAREDGRQF
            ||||||||||||||||||||||||||||||||||| :||| |||||||||||||||||||
orf25ng     MYRKLIALPFALLLAACGREEPPKALECANPAVLQDIRGSIQETLTQEARSFAREDGRQF
                    10         20         30         40         50         60

70         80         90        100        110        120
orf25-1.pep VDADKIIAAAYGLAFSLEHASETQEGGRTFCIADLNITVPSETLADAKANSPLLYGETAL
            ||||||||||||||||||||||||||||||||||||||||||||||: |||||||||| :|
orf25ng     VDADKIIAAAYGLAFSLEHASETQEGGRTFCIADLNITVPSETLADAEANSPLLYGETSL
                    70         80         90        100        110        120

130        140        150        160        170        180
orf25-1.pep SKIVRQKTGGNVEFKDGVLTAAVRFLPVKDGQTAFVDNTVGMAAQTLSAALLPYGVKSIV
            :|||:|||||||||||||||||||||||||:||:|||:||||||||:|||||||||||||
orf25ng     ADIVQQKTGGNVEFKDGVLTAAVRFLPAKDARTAFIDNTVGMATQTLSAALLPYGVKSIV
                   130        140        150        160        170        180

190        200        210        220        230        240
orf25-1.pep MIDGKAVKKEDAVRILSGKAREEEPSKPTPEDILEHNAAGGDAGVPQAAEGAPEPEILHP
            |||||||: ||||:|||||||||||||||||||||||||||||||||||||||||||||
orf25ng     MIDGKAVTKEDAVRVLSGKAREEEPSKPTPEDILEHNAAGGDAGVPQAAEGAPEPEILHP
                   190        200        210        220        230        240

250        260        270        280        290        300
orf25-1.pep DDGERADTVTVSRGEVEEARVQNQRAESEITKLWGGLDTDVQKELVGEQRKWAQEKISNC
            || |||||||||||||||||||||||||||||||||||||||||||||||||||||||||
orf25ng     DDVERADTVTVSRGEVEEARVQNQRAESEITKLWGGLDTDVQKELVGEQRKWAQEKISNC
                   250        260        270        280        290        300

310        320        330   339
orf25-1.pep RQAAAQADRQEYAEYLKLQCDTRMTRERIQYLRGYSIDX
            |||||||||||||||||||||||||||||||||||||||
orf25ng     RQAAAQADRQEYAEYLKLQCDTRMTRERIQYLRGYSIDX
                   310        320        330
```

Based on this analysis, including the presence of a predicted prokaryotic membrane lipoprotein lipid attachment site (underlined) in the gonococcal protein, it was predicted that the proteins from *N. meningitidis* and *N. gonorrhoeae*, and their epitopes, could be useful antigens for vaccines or diagnostics, or for raising antibodies.

Figure 16A:
Figure 16B:
Figure 16C:
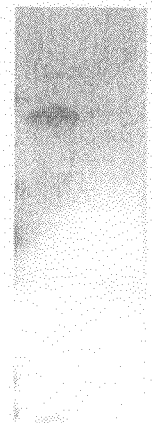
Figure 16D:
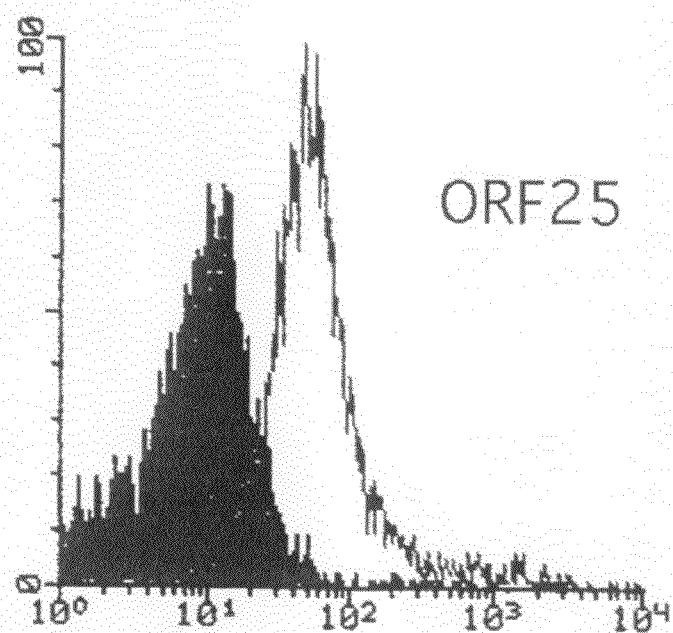
Figure 16E:
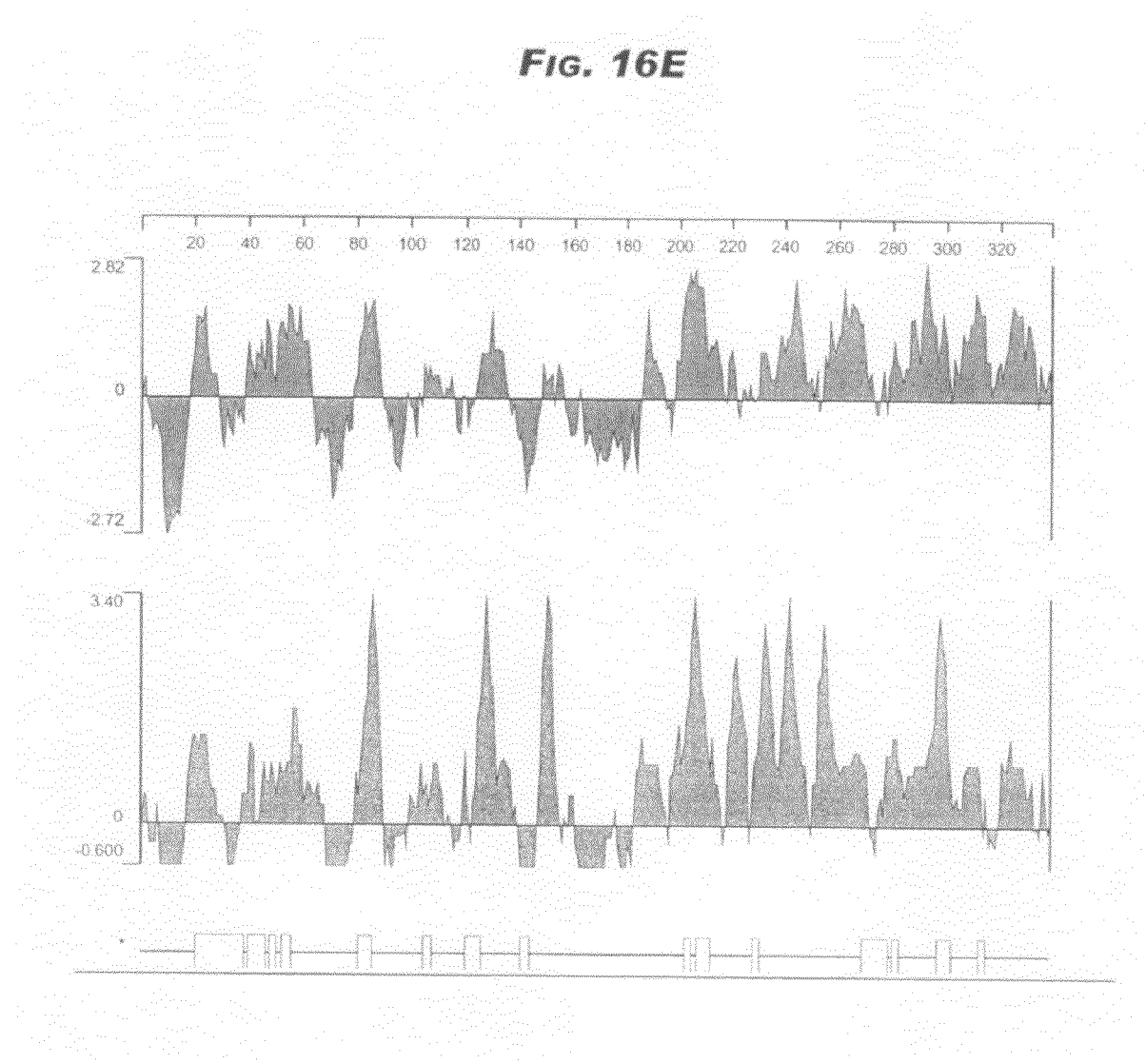

ORF25-1 (37 kDa) was cloned in pET and pGex vectors and expressed in *E. coli*, as described above. The products of protein expression and purification were analyzed by SDS-PAGE. FIG. 16A shows the results of affinity purification of the GST-fusion protein, and FIG. 16B shows the results of expression of the His-fusion in *E. coli*. Purified His-fusion protein was used to immunise mice, whose sera were used for Western blot (FIG. 16C), ELISA (positive result), and FACS analysis (FIG. 16D). These experiments confirm that ORF25-1 is a surface-exposed protein, and that it is a useful immunogen. FIG. 16E shows plots of hydrophilicity, antigenic index, and AMPHI regions for ORF25-1.

Example 82

The following partial DNA sequence was identified in *N. meningitidis* <SEQ ID 689>

```
   1 ATGCAGCTGA TCGACTATTC ACATTCATTT TTCTCGGTTG TGCCACCCTT
  51 TTTGGCACTG GCACTTGCCG TCATTACCCG CCGCGTACTG CTGTCTTTAG
 101 GCATCGGTAT TCTGGwysGC GTTGCCTTTT TGGTCGGCGG CAACCCCGTC
 151 GACGGTCTGA CACACCTGAA AGACATGGTC GTCGGCTTGG CTTGGTCAGA
 201 CGsyGATTGG TCGCTGGGCA AACCAAAAAT CTTGGTTTTC CkGATACTTT
 251 TGGGTATTTT TACTTCCCTG CTGACCTACT CCGGCAGCAA T.........
                                //
 851 .......... .......... ..........         ........AC TTCGCTGGTA
 901 TTCGGCGGCA CTTGCGGCGT CTTTGCCGTC GTTCTCTGCA CGCTCGGCAC
 951 GATTAAAACC GCCGACTATC CCAAAGCCGT TTGGCAGGGT GCGAAATCTA
1001 TGTTCGGCGC AATCGCCATT TTAATCCTCG CTTGGCTCAT CAGTACGGTT
1051 GTCGGCGAAA TGCACACCGG CGATTACCTC TCCACACTGG TTGCGGGCAA
1101 CATCCATCCC GGCTTCCTGC CCGTCATCCT CTTCCTGCTC GCCAGCGTGA
1151 TGGCGTTTGC CACAGGCACA AGCTGGGGGA CGTTCGGCAT TATGCTGCCG
1201 ATTGCCGCCG CCATGGCGGT CAAAGTCGAA CCCGCGCTGA TTATCCCGTG
1251 TATGTCCGCA GTAATGGCGG GGGCGGTATG CGGCGACCAC TGCTCGCCCA
1301 TTTCCGACAC GACCATCCTG TCGTCCACCG GCGCGCGCTG CAACCACATC
1351 GACCACGTTA CCTCGCAACT GCCTTACGCC TTAACCGTTG CCGCCGCCGC
1401 CGCATCGGGC TACCTCGCAT GGGTCTGAC AAAATCCGCG CTGTTGGGCT
1451 TTGGCACGAC AGGCATTGTA TTGGCGGTGC TGATTTTTCT GTTGAAAGAT
1501 AAAAAA..
```

This corresponds to the amino acid sequence <SEQ ID 690; ORF26>:

```
  1 MQLIDYSHSF FSVVPPFLAL ALAVITRRVL LSLGIGILXX VAFLVGGNPV
 51 DGLTHLKDMV VGLAWSDXDW SLGKPKILVF XILLGIFTSL LTYSGSN...
                         //
251 .......... .......... ..........  .......... ......TSLV
301 FGGTCGVFAV VLCTLGTIKT ADYPKAVWQG AKSMFGAIAI LILAWLISTV
351 VGEMHTGDYL STLVAGNIHP GFLPVILFLL ASVMAFATGT SWGTFGIMLP
401 IAAAMAVKVE PALIIPCMSA VMAGAVCGDH CSPISDTTIL SSTGARCNHI
451 DHVTSQLPYA LTVAAAASG YLALGLTKSA LLGFGTTGIV LAVLIFLLKD
501 KK..
```

Further work revealed the complete nucleotide sequence <SEQ ID 691>:

```
   1 ATGCAGCTGA TCGACTATTC ACATTCATTT TTCTCGGTTG TGCCACCCTT

51 TTTGGCACTG GCACTTGCCG TCATTACCCG CCGCGTACTG CTGTCTTTAG

101 GCATCGGTAT TCTGGTCGGC GTTGCCTTTT TGGTCGGCGG CAACCCCGTC

151 GACGGTCTGA CACACCTGAA AGACATGGTC GTCGGCTTGG CTTGGTCAGA

201 CGGCGATTGG TCGCTGGGCA AACCAAAAAT CTTGGTTTTC CTGATACTTT

251 TGGGTATTTT TACTTCCCTG CTGACCTACT CCGGCAGCAA TCAGGCGTTT

301 GCCGACTGGG CAAAACGGCA CATTAAAAAC CGGCGCGGCG CGAAAATGCT

351 GACCGCCTGC CTCGTGTTCG TAACCTTTAT CGACGACTAT TTCCACAGTC

401 TCGCCGTCGG TGCGATTGCC CGCCCCGTTA CCGACAAGTT TAAAGTTTCC

451 CGCACCAAAC TCGCCTACAT CCTCGACTCC ACTGCCGCTC CTATGTGCGT

501 GCTGATGCCC GTTTCAAGCT GGGGCGCGTC GATTATCGCC ACGCTTGCCG

551 GACTGCTCGT TACCTACAAA ATCACCGAAT ACACGCCGAT GGGGACGTTT

601 GTCGCCATGA GCCTGATGAA CTATTACGCA CTGTTTGCCC TGATTATGGT

651 GTTCGTCGTC GCATGGTTTT CCTTCGACAT CGGCTCGATG GCACGTTTCG

701 AACAAGCCGC GTTGAACGAA GCCCACGATG AAACTGCCGT TCAGACGCT

751 ACCAAAGGTC GTGTTTACGC ACTGATTATT CCCGTTTTGG CCTTAATCGC

801 CTCAACGGTT TCCGCCATGA TCTACACCGG CGCGCAGGCA AGCGAAACCT
```

-continued

```
 851  TCAGCATTTT GGGGGCATTT GAAAACACGG ACGTAAACAC TTCGCTGGTA
 901  TTCGGCGGCA CTTGCGGCGT CCTTGCCGTC GTTCTCTGCA CGCTCGGCAC
 951  GATTAAAACC GCCGACTATC CCAAAGCCGT TTGGCAGGGT GCGAAATCTA
1001  TGTTCGGCGC AATCGCCATT TTAATCCTCG CTTGGCTCAT CAGTACGGTT
1051  GTCGGCGAAA TGCACACCGG CGATTACCTC TCCACACTGG TTGCGGGCAA
1101  CATCCATCCC GGCTTCCTGC CCGTCATCCT CTTCCTGCTC GCCAGCGTGA
1151  TGGCGTTTGC CACAGGCACA AGCTGGGGGA CGTTCGGCAT TATGCTGCCG
1201  ATTGCCGCCG CCATGGCGGT CAAAGTCGAA CCCGCGCTGA TTATCCCGTG
1251  TATGTCCGCA GTAATGGCGG GGGCGGTATG CGGCGACCAC TGCTCGCCCA
1301  TTTCCGACAC GACCATCCTG TCGTCCACCG GCGCGCGCTG CAACCACATC
1351  GACCACGTTA CCTCGCAACT GCCTTACGCC TTAACCGTTG CCGCCGCCGC
1401  CGCATCGGGC TACCTCGCAT GGGTCTGAC AAAATCCGCG CTGTTGGGCT
1451  TTGGCACGAC AGGCATTGTA TTGGCGGTGC TGATTTTTCT GTTGAAAGAT
1501  AAAAAACGCG CCAACGCCTG A
```

This corresponds to the amino acid sequence <SEQ ID 692; ORF26-1>:

```
  1 MQLIDYSHSF FSVVPPFLAL ALAVITRRVL LSLGIGILVG VAFLVGGNPV
 51 DGLTHLKDMV VGLAWSDGDW SLGKPKILVF LILLGIFTSL LTYSGSNQAF
101 ADWAKRHIKN RRGAKMLTAC LVFVTFIDDY FHSLAVGAIA RPVTDKFKVS
151 RTKLAYILDS TAAPMCVLMP VSSWGASIIA TLAGLLVTYK ITEYTPMGTF
201 VAMSLMNYYA LFALIMVFVV AWFSFDIGSM ARFEQAALNE AHDETAVSDA
251 TKGRVYALII PVLALIASTV SAMIYTGAQA SETFSILGAF ENTDVNTSLV
301 FGGTCGVLAV VLCTLGTIKT ADYPKAVWQG AKSMFGAIAI LILAWLISTV
351 VGEMHTGDYL STLVAGNIHP GFLPVILFLL ASVMAFATGT SWGTFGIMLP
401 IAAAMAVKVE PALIIPCMSA VMAGAVCGDH CSPISDTTIL SSTGARCNHI
451 DHVTSQLPYA LTVAAAAASG YLALGLTKSA LLGFGTTGIV LAVLIFLLKD
501 KKRANA*
```

Computer analysis of this amino acid sequence gave the following results:

Homology with the Hypothetical Transmembrane Protein HI1586 of *H. influenzae* (Accession Number P44263)

ORF26 and HI1586 show 53% and 49% amino acid identity in 97 and 221 aa overlap at the N-terminus and C-terminus, respectively:

```
Orf26    1  MQLIDYSHSFFSVVPPFLALALAVITRRVXXXXXXXXXXXXVAFLVGGNPVDGLTHLKDMV  60
            M+LID+S S +S+VP  LA+ LA+ TRRV            L        +L     V
HI1586  14  MELIDFSSSVWSIVPALLAIILAIATRRVLVSLSAGIIIGSLMLSDWQIGSAFNYLVKNV  73

Orf26   61  VGLAWSDXDWSLGKPKILVFXILLGIFTSLLTYSGSN                          97
            V L ++D + +    I++F +LLG+ T+LLT SGSN
HI1586  74  VSLVYADGEIN-SNMNIVLFLLLLGVTALLTVSGSN                          109

//

Orf26   86  IFTSLLTYSGS--NTSLVFGGTCGVFAVVLCTL--GTIKTADYPKAVWQGAKSMFGXXXX 141
            +F+ L T+  +   TSLV GG C +   L +    +Y ++    G KSM G
HI1586 299  VFSVLGTFENTVVGTSLVVGGFCSIIISTLLIILDRQVSVPEYVRSWIVGIKSMSGAIAI 358
```

-continued

```
Orf26   142 XXXXXXXSTVVGEMHTGDYLSTLVAGNIHPGFLPVILFLLASVMAFATGTSWGTFGIMLP 201
              + +VG+M TG YLS+LV+GNI   FLPVILF+L + MAF+TGTSWGTFGIMLP
HI1586  359 LFFAWTINKIVGDMQTGKYLSSLVSGNIPMQFLPVILFVLGAAMAFSTGTSWGTFGIMLP 418

Orf26   202 IAAAMAVKVEPALIIPCMSAVMAGAVCGDHCSPISDTTILSSTGARCNHIDHVTSQXXXX 261
            IAAAMA    P L++PC+SAVMAGAVCGDHCSP+SDTTILSSTGA+CNHIDHVT+Q
HI1586  419 IAAAMAANAAPELLLPCLSAVMAGAVCGDHCSPVSDTTILSSTGAKCNHIDHVTTQLPYA 478

Orf26   262 XXXXXXXXXXXXXXXXXKSALLGFGTTGIVLAVLIFLLKDK                    302
                             S L GF T + L V+IF +K +
HI1586  479 ATVATATSIGYIVVGFTYSGLAGFAATAVSLIVIIFAVKKR                    519
```

Homology with a Predicted ORF from *N. meningitidis* (Strain A)

ORF26 shows 58.2% identity over a 502aa overlap with an ORF (ORF26a) from strain A of *N. meningitidis*.

```
                  10         20         30         40         50         60
orf26.pep    MQLIDYSHSFFSVVPPFLALALAVITRRVLLSLGIGILXXVAFLVGGNPVDGLTHLKDMV
             ||||||||||||||||||||||||||||||||||||||   ||||||||||||||||||
orf26a       MQLIDYSHSFFSVVPPFLALALAVITRRVLLSLGIGILVGVAFLVGGNPVDGLTHLKDMV
                  10         20         30         40         50         60

70         80         90         99
orf26.pep    VGLAWSDXDWSLGKPKILVFXILLGIFTSLLTYSGSNXX---------------------
             ||||||| ||||||||| || ||||||||||||||||||
orf26a       VGLAWSDGDWSLGKPKXLVFLILLGIFTSLLTYSGSNQAFADWAKRHIKNRRGAKMLTAC
                  70         80         90        100        110        120 orf26.pep    ------------------------------------------------------------
orf26a       LVFVTFIDDYFHSLAVGAXARPVTDKFKVSRAKLAYILDSTAAPMCVLMPVSSWGASIIA
                 130        140        150        160        170        180 orf26.pep    ------------------------------------------------------------
orf26a       TLAGLLVTYKITEYTPMGTFVAMSLMNYYALFALIMVFVVAWFSFDIGSMARFEQAALNE
                 190        200        210        220        230        240

100        110
orf26.pep    ---------------------------------------------------------TSLV
orf26a       AHDETAVSDGSWGRVYALIIPVLALIASTVSAMIYTGAQASETFSILGAFENTDVNTSLV
                 250        260        270        280        290        300

120        130        140        150        160        170
orf26.pep    FGGTCGVFAVVLCTLGTIKTADYPKAVWQGAKSMFGAIAILILAWLISTVVGEMHTGDYL
             ||||||| :|||||||||||||||||||||||||||||||||||||||||||||||||
orf26a       FGGTCGVLAVVLCTLGTIKTADYPKAVWQGAKSMFGAIAILILAWLISTVVGEMHTGDYL
                 310        320        330        340        350        360

180        190        200        210        220        230
orf26.pep    STLVAGNIHPGFLPVILFLLASVMAFATGTSWGTFGIMLPIAAAMAVKVEPALIIPCMSA
             ||||||||||||| || ||||||||||||||||||||||||||||||| : :||||||
orf26a       STLVAGNIHPGFLXVILFLLASVMAFATGTSWGTFGIMLPIAAAMAVKVDPSLIIPCMSA
                 370        380        390        400        410        420

240        250        260        270        280        290
orf26.pep    VMAGAVCGDHCSPISDTTILSSTGARCNHIDHVTSQLPYALTVAAAAASGYLALGLTKSA
             ||||||||||||||||||||||||||||||||||||||||||||||||||||||||||
orf26a       VMAGAVCGDHCSPISDTTILSSTGARCNHIDHVTSQLPYALTVAAAAASGYLALGLTKSA
                 430        440        450        460        470        480

300        310
orf26.pep    LLGFGTTGIVLAVLIFLLKDKK
             ||||:|||||||||||||||||
orf26a       LLGFXTGIVLAVLIFLLKDKKRANAX
                 490        500
```

The complete length ORF26a nucleotide sequence <SEQ ID 693> is:

```
  1 ATGCAGCTGA TCGACTATTC ACATTCATTT TTCTCGGTTG TGCCACCCTT

51 TTTGGCACTG GCACTTGCCG TCATTACCCG CCGCGTACTG CTGTCTTTAG

101 GCATCGGTAT TCTGGTCGGC GTTGCCTTTT TGGTCGGCGG CAACCCCGTC

151 GACGGTCTGA CACACCTGAA AGACATGGTC GTCGGCTGG  CTTGGTCAGA

201 CGGCGATTGG TCGCTGGGCA AACCAAAANT CTTGGTTTTC CTGATACTTT
```

-continued

```
 251 TGGGTATTTT TACTTCCCTG CTGACCTACT CCGGCAGCAA TCAGGCGTTT

301 GCCGACTGGG CAAAACGGCA CATTAAAAAC CGGCGCGGCG CGAAAATGCT

351 GACCGCCTGC CTCGTGTTCG TAACCTTTAT CGACGACTAT TTCCACAGTC

401 TCGCCGTCGG TGCGNTTGCC CGCCCCGTTA CCGACAAGTT TAAAGTTTCC

451 CGCGCCAAAC TCGCCTACAT CCTCGACTCC ACTGCCGCGC CTATGTGCGT

501 GCTGATGCCC GTTTCAAGCT GGGGCGCGTC GATTATCGCC ACGCTTGCCG

551 GACTGCTCGT TACCTACAAA ATCACCGAAT ACACGCCGAT GGGGACGTTT

601 GTCGCCATGA GCCTGATGAA CTATTACGCA CTGTTTGCCC TGATTATGGT

651 GTTCGTCGTC GCATGGTTCT CCTTCGACAT CGGCTCGATG GCACGTTTCG

701 AACAAGCCGC GTTGAACGAA GCCCACGATG AAACTGCCGT TCAGACGGC

751 AGCTGGGGCA GGGTTTACGC ATTGATTATT CCCGTTTTGG CCTTAATCGC

801 CTCAACGGTT TCCGCCATGA TCTACACCGG TGCACAGGCA AGCGAAACCT

851 TCAGCATTTT GGGTGCATTT GAAAATACGG ACGTGAACAC TTCGCTGGTA

901 TTCGGCGGCA CTTGCGGCGT GCTTGCCGTC GTCCTCTGCA CGCTCGGCAC

951 GATTAAAATC GCCGATTATC CCAAAGCCGT TTGGCAGGGT GCGAAATCCA

1001 TGTTCGGCGC AATCGCCATT TTAATCCTTG CCTGGCTCAT CAGTACGGTT

1051 GTCGGCGAAA TGCACACAGG CGACTACCTC TCCACGCTGG TTGCGGGCAA

1101 CATCCATCCC GGCTTCCTGN CCGTCATCCT TTTCCTGCTC GCCAGCGTGA

1151 TGGCGTTTGC CACAGGCACA AGCTGGGGGA CGTTCGGCAT CATGCTGCCG

1201 ATTGCCGCCG CCATGGCGGT CAAAGTCGAT CCCTCACTGA TTATCCCGTG

1251 TATGTCCGCC GTGATGGCGG GGGCGGTATG CGGCGACCAC TGCTCGCCCA

1301 TTTCCGACAC GACCATCCTG TCGTCCACCG GCGCGCGCTG CAACCACATC

1351 GACCACGTTA CNTCGCAACT GCCTTACGCC TTAACCGTTG CCGCCGCCGC

1401 CGCATCGGGN TACCTCGCAT GGGTCTGAC AAAATCCGCG CTGTTGGGTT

1451 TTGGCANGAC AGGCATTGTA TTGGCGGTGC TGATTTTTCT GTTGAAAGAT

1501 AAAAAACGCG CCAACGCCTG A
```

This encodes a protein having amino acid sequence <SEQ ID 694>:

```
  1 MQLIDYSHSF FSVVPPFLAL ALAVITRRVL LSLGIGILVG VAFLVGGNPV

51 DGLTHLKDMV VGLAWSDGDW SLGKPKXLVF LILLGIFTSL LTYSGSNQAF

101 ADWAKRHIKN RRGAKMLTAC LVFVTFIDDY FHSLAVGAXA RPVTDKFKVS

151 RAKLAYILDS TAAPMCVLMP VSSWGASIIA TLAGLLVTYK ITEYTPMGTF

201 VAMSLMNYYA LFALIMVFVV AWFSFDIGSM ARFEQAALNE AHDETAVSDG

251 SWGRVYALII PVLALIASTV SAMIYTGAQA SETFSILGAF ENTDVNTSLV

301 FGGTCGVLAV VLCTLGTIKI ADYPKAVWQG AKSMFGAIAI LILAWLISTV

351 VGEMHTGDYL STLVAGNIHP GFLXVILFLL ASVMAFATGT SWGTFGIMLP

401 IAAAMAVKVD PSLIIPCMSA VMAGAVCGDH CSPISDTTIL SSTGARCNHI

451 DHVTSQLPYA LTVAAAAASG YLALGLTKSA LLGFGXTGIV LAVLIFLLKD

501 KKRANA*
```

ORF26a and ORF26-1 show 97.8% identity in 506 aa overlap:

```
              10        20        30        40        50        60
orf26a.pep   MQLIDYSHSFFSVVPPFLALALAVITRRVLLSLGIGILVGVAFLVGGNPVDGLTHLKDMV
             ||||||||||||||||||||||||||||||||||||||||||||||||||||||||||||
orf26-1      MQLIDYSHSFFSVVPPFLALALAVITRRVLLSLGIGILVGVAFLVGGNPVDGLTHLKDMV
              10        20        30        40        50        60

70        80        90       100       110       120
orf26a.pep   VGLAWSDGDWSLGKPKXLVFLILLGIFTSLLTYSGSNQAFADWAKRHIKNRRGAKMLTAC
             ||||||||||||||||| ||||||||||||||||||||||||||||||||||||||||||
orf26-1      VGLAWSDGDWSLGKPKILVFLILLGIFTSLLTYSGSNQAFADWAKRHIKNRRGAKMLTAC
              70        80        90       100       110       120

130       140       150       160       170       180
orf26a.pep   LVFVTFIDDYFHSLAVGAXARPVTDKFKVSRAKLAYILDSTAAPMCVLMPVSSWGASIIA
             |||||||||||||||||| ||||||||||||||:||||||||||||||||||||||||||
orf26-1      LVFVTFIDDYFHSLAVGAIARPVTDKFKVSRTKLAYILDSTAAPMCVLMPVSSWGASIIA
             130       140       150       160       170       180

190       200       210       220       230       240
orf26a.pep   TLAGLLVTYKITEYTPMGTFVAMSLMNYYALFALIMVFVVAWFSFDIGSMARFEQAALNE
             ||||||||||||||||||||||||||||||||||||||||||||||||||||||||||||
orf26-1      TLAGLLVTYKITEYTPMGTFVAMSLMNYYALFALIMVFVVAWFSFDIGSMARFEQAALNE
             190       200       210       220       230       240

250       260       270       280       290       300
orf26a.pep   AHDETAVSDGSWGRVYALIIPVLALIASTVSAMIYTGAQASETFSILGAFENTDVNTSLV
             ||||||||||::||||||||||||||||||||||||||||||||||||||||||||||||
orf26-1      AHDETAVSDATKGRVYALIIPVLALIASTVSAMIYTGAQASETFSILGAFENTDVNTSLV
             250       260       270       280       290       300

310       320       330       340       350       360
orf26a.pep   FGGTCGVLAVVLCTLGTIKIADYPKAVWQGAKSMFGAIAILILAWLISTVVGEMHTGDYL
             ||||||||||||||||||| ||||||||||||||||||||||||||||||||||||||||
orf26-1      FGGTCGVLAVVLCTLGTIKTADYPKAVWQGAKSMFGAIAILILAWLISTVVGEMHTGDYL
             310       320       330       340       350       360

370       380       390       400       410       420
orf26a.pep   STLVAGNIHPGFLXVILFLLASVMAFATGTSWGTFGIMLPIAAAMAVKVDPSLIIPCMSA
             |||||||||||||| |||||||||||||||||||||||||||||||||:|:|||||||||
orf26-1      STLVAGNIHPGFLPVILFLLASVMAFATGTSWGTFGIMLPIAAAMAVKVEPALIIPCMSA
             370       380       390       400       410       420

430       440       450       460       470       480
orf26a.pep   VMAGAVCGDHCSPISDTTILSSTGARCNHIDHVTSQLPYALTVAAAAASGYLALGLTKSA
             ||||||||||||||||||||||||||||||||||||||||||||||||||||||||||||
orf26-1      VMAGAVCGDHCSPISDTTILSSTGARCNHIDHVTSQLPYALTVAAAAASGYLALGLTKSA
             430       440       450       460       470       480

490       500
orf26a.pep   LLGFGXTGIVLAVLIFLLKDKKRANAX
             |||||:|||||||||||||||||||||
orf26-1      LLGFGTTGIVLAVLIFLLKDKKRANAX
             490       500
```

40

Homology with a Predicted ORF from *N. gonorrhoeae*
ORF26 shows 94.8% and 99% identity in 97 and 206 aa overlap at the N-terminus and C-terminus, respectively, with a predicted ORF (ORF26ng) from *N. gonorrhoeae*:

```
orf26.pep    MQLIDYSHSFFSVVPPFLALALAVITRRVLLSLGIGILXXVAFLVGGNPVDGLTHLKDMV   60
             ||||||||||||||||||||||||||||||||||||||  ||||||||||||||||||||
orf26ng      MQLIDYSHSFFSVVPPFLALALAVITRRVLLSLGIGILVGVAFLVGGNPVDGLTHLKDMV   60 orf26.pep    VGLAWSKXDWSLGKPKILVFXILLGIFTSLLTYSGSN                          97
             |||||| :|||||||||||| |||||||||||||||
orf26ng      VGLAWADGDWSLGKPKILVFLILLGIFTSLLTYSGSNQAFADWAKRHIKNRCGAKMLTAC  120

// orf26.pep                                      TSLVFGGTCGVFAVVLCTLGTIKTADYPKA  326
                                                ||||||||||||:||||| :||||||||||
orf26ng      ASTVSAMIYTGAQASETFSILGAFENTDVNTSLVFGGTCGVLAVVLCTFGTIKTADYPKA  326 orf26.pep    VWQGAKSMFGAIAILILAWLISTVVGEMHTGDYLSTLVAGNIHPGFLPVILFLLASVMAF  386
             ||||||||||||||||||||||||||||||||||||||||||||||||||||||||||||
orf26ng      VWQGAKSMFGAIAILILAWLISTVVGEMHTGDYLSTLVAGNIHPGFLPVILFLLASVMAF  386 orf26.pep    ATGTSWGTFGIMLPIAAAMAVKVEPALIIPCMSAVMAGAVCGDHCSPISDTTILSSTGAR  446
             ||||||||||||||||||||||||||||||||||||||||||||||||||||||||||||
orf26ng      ATGTSWGTFGIMLPIAAAMAVKVEPALIIPCMSAVMAGAVCGDHCSPISDTTILSSTGAR  446 orf26.pep    CNHIDHVTSQLPYALTVAAAAASGYLALGLTKSALLGFGTTGIVLAVLIFLLKDKK      502
             ||||||||||||||||||||||||||||||||||||||||||||||||||||||||
orf26ng      CNHIDHVTSQLPYALTVAAAAASGYLALGLTKSALLGFGTTGIVLAVLIFLLKDKKRADV 506
```

The complete length ORF26ng nucleotide sequence <SEQ ID 695> is:

```
   1 ATGCAGCTGA TTGACTATTC ACATTCATTT TTCTCGGTTG TGCCACCCTT
  51 TTTGGCACTG GCACTTGCCG TCATTACCCG CCGCGTACTG CTGTCTTTAG
 101 GCATCGGTAT TTTGGTCGGC GTTGCCTTTT TGGTCGGCGG CAACCCCGTC
 151 GACGGTCTGA CACACCTGAA AGACATGGTC GTCGGCTTGG CTTGGGCAGA
 201 CGGCGATTGG TCGCTGGGCA AACCAAAAAT CTTGGTTTTC CTGATACTTT
 251 TGGGCATTTT CACTTCACTG CTGACCTACT CCGGCAGCAA TCAGGCGTTT
 301 GCCGACTGGG CAAAACGGCA CATTAAAAAC CGGTGCGGCG CGAAAATGCT
 351 GACCGCCTGC CTCGTGTTCG TAACCTTTAT CGACGACTAT TTCCACAGCC
 401 TCGCCGTCGG TGCGATTGCC CGCCCCGTTA CCGACAAGTT TAAAGTTTCC
 451 CGCGCCAAAC TCGCCTACAT CCTCGACTCC ACTGCCTCGC CCATGTGCGT
 501 GCTGATGCCC GTTTCAAGCT GGGGCGCGTC GATTATCGCC ACGCTTGCCG
 551 GATTGCTCGT TACCTACAAA ATTACCGAAT ACACGCCGAT GGGGACGTTT
 601 GTCGCCATGA GCCTGATGAA CTATTACGCG CTGTTTGCCC TGATTATGGT
 651 ATTCGTCGTC GCATGGTTCT CCTTCGACAT CGGCTCGAtg gCGCGTTTCG
 701 AACAGGCTGC GTTGAACGAA gcccaggacg aaaccgccgc tTCAGACgCT
 751 ACCAAAGGTC GTGTTTACGC ATTGATTATT CCCGTTTTGG CCTTAATCGC
 801 CTCAACGGTT TCCGCCATGA TCTACACCGG CGCGCAGGCA AGCGAAACCT
 851 TCAGCATTTT GGGGGCATTT GAAAATACCG ACGTAAACAC TTCGCTGGTA
 901 TTCGGCGGCA CTTGCGGCGT GCTTGCCGTC GTCCTCTGCA CGTTCGGCAC
 951 GATTAAAACC GCCGATTATC CCAAAGCCGT GTGGCAGGGT GCGAAATCCA
1001 TGTTCGGCGC AATCGCCATT TTAATCCTCG CCTGGCTCAT CAGTACGGTT
1051 GTCGGCGAAA TGCACACGGG CGACTACCTC TCCACGCTGG TTGCGGGCAA
1101 CATCCATCCC GGCTTCCTGC CCGTCATCCT CTTCCTGCTC GCCAGCGTGA
1151 TGGCGTTTGC CACAGGCACA AGCTGGGGGA CGTTCGGCAT TATGCTGCCG
1201 ATTGCCGCCG CCATGGCGGT CAAAGTCGAA CCCGCGCTGA TTAtcccGTG
1251 TATGTCCGCA GTAATGGCGG GGGCGGTATG CGGCGACCAC TGTTCGCCCA
1301 TCTCCGACAC GACCATCCTG TCGTCCACCG GCGCGCGCTG CAACCACATC
1351 GACCACGTTA CCTCGCAACT GCCTTATGCC CTGACGGTTG CCGCCGCCGC
1401 CGCATCGGGC TACCTCGCAT GGGTCTGAC AAAATCCGCG CTGTTGGGCT
1451 TTGGCACGAC CGGTATTGTA TTGGCGGTGC TGATTTTTCT GTTGAAAGAT
1501 AAAAAACGCG CCGACGTTTG A
```

This encodes a protein having amino acid sequence <SEQ ID 696>:

```
  1 MQLIDYSHSF FSVVPPFLAL ALAVITRRVL LSLGIGILVG VAFLVGGNPV
 51 DGLTHLKDMV VGLAWADGDW SLGKPKILVF LILLGIFTSL LTYSGSNQAF
101 ADWAKRHIKN RCGAKMLTAC LVFVTFIDDY FHSLAVGAIA RPVTDKFKVS
151 RAKLAYILDS TASPMCVLMP VSSWGASIIA TLAGLLVTYK ITEYTPMGTF
201 VAMSLMNYYA LFALIMVFVV AWFSFDIGSM ARFEQAALNE AQDETAASDA
```

-continued

```
251 TKGRVYALII PVLALIASTV SAMIYTGAQA SETFSILGAF ENTDVNTSLV

301 FGGTCGVLAV VLCTFGTIKT ADYPKAVWQG AKSMFGAIAI LILAWLISTV

351 VGEMHTGDYL STLVAGNIHP GFLPVILFLL ASVMAFAGTFGIMLP

401 IAAAMAVKVE PALIIPCMSA VMAGAVCGDH CSPISDTTIL SSTGARCNHI

451 DHVTSQLPYA LTVAAAAASG YLALGLTKSA LLGFGTTGIV LAVLIFLLKD

501 KKRADV*
```

ORF26ng and ORF26-1 show 98.4% identity in 505 aa overlap:

```
                  10         20         30         40         50         60
orf26-1.pep  MQLIDYSHSFFSVVPPFLALALAVITRRVLLSLGIGILVGVAFLVGGNPVDGLTHLKDMV
             ||||||||||||||||||||||||||||||||||||||||||||||||||||||||||||
orf26ng      MQLIDYSHSFFSVVPPFLALALAVITRRVLLSLGIGILVGVAFLVGGNPVDGLTHLKDMV
                  10         20         30         40         50         60
                  70         80         90        100        110        120
orf26-1.pep  VGLAWSDGDWSLGKPKILVFLILLGIFTSLLTYSGSNQAFADWAKRHIKNRRGAKMLTAC
             ||||| :|||||||||||||||||||||||||||||||||||||||||||| |||||||
orf26ng      VGLAWADGDWSLGKPKILVFLILLGIFTSLLTYSGSNQAFADWAKRHIKNRCGAKMLTAC
                  70         80         90        100        110        120
                 130        140        150        160        170        180
orf26-1.pep  LVFVTFIDDYFHSLAVGAIARPVTDKFKVSRTKLAYILDSTAAPMCVLMPVSSWGASIIA
             |||||||||||||||||||||||||||||||:||||||||||:|||||||||||||||||
orf26ng      LVFVTFIDDYFHSLAVGAIARPVTDKFKVSRAKLAYILDSTASPMCVLMPVSSWGASIIA
                 130        140        150        160        170        180
                 190        200        210        220        230        240
orf26-1.pep  TLAGLLVTYKITEYTPMGTFVAMSLMNYYALFALIMVFVVAWFSFDIGSMARFEQAALNE
             ||||||||||||||||||||||||||||||||||||||||||||||||||||||||||||
orf26ng      TLAGLLVTYKITEYTPMGTFVAMSLMNYYALFALIMVFVVAWFSFDIGSMARFEQAALNE
                 190        200        210        220        230        240
                 250        260        270        280        290        300
orf26-1.pep  AHDETAVSDATKGRVYALIIPVLALIASTVSAMIYTGAQASETFSILGAFENTDVNTSLV
             |:||||  |||||||||||||||||||||||||||||||||||||||||||||||||||
orf26ng      AQDETAASDATKGRVYALIIPVLALIASTVSAMIYTGAQASETFSILGAFENTDVNTSLV
                 250        260        270        280        290        300
                 310        320        330        340        350        360
orf26-1.pep  FGGTCGVLAVVLCTLGTIKTADYPKAVWQGAKSMFGAIAILILAWLISTVVGEMHTGDYL
             |||||||||||||:||||||||||||||||||||||||||||||||||||||||||||||
orf26ng      FGGTCGVLAVVLCTFGTIKTADYPKAVWQGAKSMFGAIAILILAWLISTVVGEMHTGDYL
                 310        320        330        340        350        360
                 370        380        390        400        410        420
orf26-1.pep  STLVAGNIHPGFLPVILFLLASVMAFATGTSWGTFGIMLPIAAAMAVKVEPALIIPCMSA
             ||||||||||||||||||||||||||||||||||||||||||||||||||||||||||||
orf26ng      STLVAGNIHPGFLPVILFLLASVMAFATGTSWGTFGIMLPIAAAMAVKVEPALIIPCMSA
                 370        380        390        400        410        420
                 430        440        450        460        470        480
orf26-1.pep  VMAGAVCGDHCSPISDTTILSSTGARCNHIDHVTSQLPYALTVAAAASGYLALGLTKSA
             ||||||||||||||||||||||||||||||||||||||||||||||||||||||||||||
orf26ng      VMAGAVCGDHCSPISDTTILSSTGARCNHIDHVTSQLPYALTVAAAASGYLALGLTKSA
                 430        440        450        460        470        480
                 490        500
orf26-1.pep  LLGFGTTGIVLAVLIFLLKDKKRANAX
             ||||||||||||||||||||||||:::
orf26ng      LLGFGTTGIVLAVLIFLLKDKKRADVX
                 490        500
```

In addition, ORF26ng shows significant homology to a hypothetical *H. influenzae* protein:

```
sp|P44263|YF86_HAEIN HYPOTHETICAL PROTEIN HI1586 >gi|1074850|pir||C64037
hypothetical
portein HI1586-Haemophilus influenzae (strain Rd KW20) >gi|1574427 (U32832) H.
influenzae predicted coding region HI1586 [Haemophilus influenzae] Length = 519
Score = 538 bits (1370), Expect = e-152
Identities = 280/507 (55%), Positives = 346/507 (68%), Gaps = 7/507 (1%)

Query:   1 MQLIDYSHSFFSVVPPFLALALAVITRRXXXXXXXXXXXXXXAFLVGGNPVDGLTHLKDMV  60
           M+LID+S S +S+VP LA+ LA TRR         L       +L     V
Sbjct:  14 MELIDFSSSVWSIVPALLAIILAIATRRVLVSLSAGIIIGSLMLSDWQIGSAFNYLVKNV   73

Query:  61 VGLAWADGDWSLGKPKILVFLILLGIFTSLLTYSGSNQAFADWAKRHIKNRCGAKMLTAC  60
           V L  +ADG+ +     I++FL+LLG+ T+LLT SGSN+AFA+WA+  IK R GAK+L A
Sbjct:  74 VSLVYADGEIN-SNMNIVLFLLLLGVLTALLTVSGSNRAFAEWAQSRIKGRRGAKLLAAS 132
```

-continued

```
Query: 121 LVFVTFIDDYFHSLAVGAIARPVTDKFKVSRAKLAYILDSTASPMCVLMPVSSWGASIIA 180
            LVFVTFIDDYFHSLAVGAIARPVTD+FKVSRAKLAYILDSTA+PMCV+MPVSSWGA II
Sbjct: 133 LVFVTFIDDYFHSLAVGAIARPVTDRFKVSRAKLAYILDSTAAPMCVMMPVSSWGAYIIT 192

Query: 181 TLAGLLVTYKITEYTPMGTFVAMSLMNYYALFALIMVFVVAWFSFDIGSMARFEQAALNE 240
            + GLL TY ITEYTP+G FVAMS MN+YA+F++IMVF VA+FSFDI SM R E+ AL
Sbjct: 193 LIGGLLATYSITEYTPIGAFVAMSSMNFYAIFSIIMVFFVAYFSFDIASMVRHEKLALKN 252

Query: 241 AQDETAASDATKGRVYALIIPVLALIASTVSAMIYTGAQA----SETFSILGAFENTDVN 290
            +D+      TKG+V LI+P+L LI +TVS MIYTGA+A    + FS+LG FENT V
Sbjct: 253 TEDQLEEETGTKGQVRNLILPILVLIIATVSMMIYTGAEALAADGKVFSVLGTFENTVVG 312

Query: 297 TSLVFGGTCGVL--AVVLCTFGTIKTADYPKAVWQGAKSMFGXXXXXXXXXXXXSTVVGEM 354
            TSLV GG C ++   +++      +  +Y ++    G KSM G              + +VG+M
Sbjct: 313 TSLVVGGFCSIIISTLLIILDRQVSVPEYVRSWIVGIKSMSGAIAILFFAWTINKIVGDM 372

Query: 355 HTGDYLSTLVAGNIHPGFLPVILFLLASVMAFATGTSWGTFGIMLPIAAAMAVKVEPALI 414
                TG YLS+LV+GNI    FLPVILF+L +   MAF+TGTSWGTFGIMLPIAAAMA    P L+
Sbjct: 373 QTGKYLSSLVSGNIPMQFLPVILFVLGAAMAFSTGTSWGTFGIMLPIAAAMAANAAPELL 432

Query: 415 IPCMSAVMAGAVCGDHCSPISDTTILSSTGARCNHIDHVTSQXXXXXXXXXXXXXXXXXX 474
            +PC+SAVMAGAVCGDHCSP+SDTTILSSTGA+CNHIDHVT+Q
Sbjct: 433 LPCLSAVMAGAVCGDHCSPVSDTTILSSTGAKCNHIDHVTTQLPYAATVATATSIGYIVV 492

Query: 475 XXXKSALLGFGTTGIVLAVLIFLLKDK                                  501
               S  L GF  T + L V+IF +K +
Sbjct: 493 GFTYSGLAGFAATAVSLIVIIFAVKKR                                  519
```

Based on this analysis, it is predicted that these proteins from *N. meningitidis* and *N. gonorrhoeae*, and their epitopes, could be useful antigens for vaccines or diagnostics, or for raising antibodies.

Example 83

The following partial DNA sequence was identified in *N. meningitidis* <SEQ ID 697>:

```
  1 ..AAGCAATGGT ATGCCGACGN .AGTATCAAG ACGGAAATGG TTATGGTCAA

51   CGATGAGCCT GCCAAAATTC TGACTTGGGA TGAAAGCGGC CGATTACTCT

101   CGGAACTGTC TATCCGCCAC CATCAACGCA ACGGGGTGGT TTTGGAGTGG

151   TATGAAGATG GTTCTAAAAA GAGCGAAGT. GTTTATCAGG ATGACAAGTT

201   GGTCAGGAAA ACCCAGTGGG ATAAGGATGG TTATTTAATC GAACCCTGA
```

This corresponds to the amino acid sequence <SEQ ID 698; ORF27>:

```
 1 ..KQWYADXSIK TEMVMVNDEP AKILTWDESG RLLSELSIRH HQRNGVVLEW

51   YEDGSKKSEX VYQDDKLVRK TQWDKDGYLI EP*
```

Further work revealed the complete nucleotide sequence <SEQ ID 699>:

```
  1 ATGAAAAAAT TATCTCGGAT TGTATTTTCA ACTGTCCTGT TGGGTTTTTC

51 GGCCGCTTTG CCGGCGCAGA CCTATTCTGT TTATTTTAAT CAGAACGGAA

101 AGCTGACGGC GACGATGTCT TCTGCCGCTT ATATCAGGCA ATATAGTGTG

151 GTGGCGGGTA TTGCGCACGC GCAGGATTTT TATTATCCGT CGATGAAGAA

201 ATATTCTGAA CCTTATATCG TTGCTTCAAC GCAAATCAAA TCTTTTGTGC

251 CTACCCTGCA AAACGGTATG TTGATTTTGT GGCATTTTAA TGGTCAGAAA

301 AAAATGGCGG GGGGCTTCAG CAAGGGTAAG CCGGACGGGG AGTGGGTCAA

351 CTGGTATCCG AACGGTAAAA AATCTGCCGT TATGCCTTAT AAAAATGGCT
```

```
401 TGAGTGAGGG TACGGGATAC CGCTATTACC GTAACGGCGG CAAGGAAAGC

451 GAAATCCAGT TTAAGCAAAA TAAGGCAAAC GGCGTATGGA AGCAATGGTA

501 TGCCGACGGC AGTATCAAGA CGGAAATGGT TATGGTCAAC GATGAGCCTG

551 CCAAAATTCT GACTTGGGAT GAAAGCGGCC GATTACTCTC GGAACTGTCT

601 ATCCGCCACC ATCAACGCAA CGGGGTGGTT TTGGAGTGGT ATGAAGATGG

651 TTCTAAAAAG AGCGAAGCTG TTTATCAGGA TGACAAGTTG GTCAGGAAAA

701 CCCAGTGGGA TAAGGATGGT TATTTAATCG AACCCTGA
```

This corresponds to the amino acid sequence <SEQ ID 700; ORF27-1>:

```
  1 MKKLSRIVFS TVLLGFSAAL PAQTYSVYFN QNGKLTATMS SAAYIRQYSV

51 VAGIAHAQDF YYPSMKKYSE PYIVASTQIK SFVPTLQNGM LILWHFNGQK

101 KMAGGFSKGK PDGEWVNWYP NGKKSAVMPY KNGLSEGTGY RYYRNGGKES

151 EIQFKQNKAN GVWEQWYADG SIKTEMVMVN DEPAKILTWD ESGRLLSELS

201 IRHHQRNGVV LEWYEDGSKK SEAVYQDDKL VRKTQWDKDG YLIEP*
```

Computer analysis of this amino acid sequence gave the following results:

Homology with a Predicted ORF from *N. meningitidis* (Strain A)

ORF27 shows 91.5% identity over a 82aa overlap with an ORF (ORF27a) from strain A of *N. meningitidis*:

```
                               10        20        30
orf27.pep                      KQWYADXSIKTEMVMVNDEPAKILTWDESG
                               |||||| :||||||||||||||||||||||
orf27a    LSEGTGXRYYRNGGKESEIQFKQNKANGVWKQWYADGNIKTEMVMVNDEPAKILTWDESG
              140       150       160       170       180       190

40        50        60        70        80
orf27.pep RLLSELSIRHHQRNGVVLEWYEDGSKKSEXVYQDDKLVRKTQWDKDGYLIEPX
          |||||||:||||||||||||||||||| ||||||||||||||||||||||||
orf27a    RLLSELSIHHHXRNGVVLEWYEDGSKKXEAVYQDDKLVRKTQWDKDGYLIEPX
              200       210       220       230       240
```

The complete length ORF27a nucleotide sequence <SEQ ID 701> is:

```
  1 ATGAAAAAAT TATCTCGGAT TGTATTTTCA ACTGTCCTGT TGGGTTTTTC

51 GGCCGCTTTG CCGGCGCAGA NCTATTCTGT TTATTTTAAT CAGAACGGGA

101 AACTGACGGC GACGNTGTCT TCTGCCGCNT ATATCAGGCA ATATAGTGTG

151 GCGGAGGGTA TTGCGCACGC GCAGGANTTT TANTATCCGT CGATGAAGAA

201 ATATTCCGAA CCTTATATCG TTGCTTCAAC GCAAATCAAA TCTTTTGTGC

251 CTACCCTGCA AAACGGTATG TTGATTTTGT GGCATTTTAA NGGTCAGAAA

301 AAAATGGCNG GGGGCTTCAG CAAGGGTAAG CCGGACGGGG AGTGGGTCAA

351 CTGGTATCCG AACGGTAAAA AATCTGCCGT TATGCCTTAT AAAAATGGTT

401 TGAGTGAAGG TACGGGGTNN CGCTATTACC GTAACGGCGG CAAGGAAAGC

451 GAAATCCAGT TTAAACAGAA TAAGGCAAAC GGCGTATGGA AGCAATGGTA

501 TGCCGACGGC AATATCAAAA CGGAAATGGT TATGGTCAAT GATGAGCCTG

551 CCAAAATTCT GACATGGGAT GAAAGCGGTC GATTACTCTC GGAACTGTCT
```

```
601 ATCCATCATC ATNAACGTAA TGGAGTAGTC TTAGAGTGGT ATGAAGATGG

651 TTCTAAAAAG ANTGAAGCTG TTTATCAGGA TGATAAGTTG GTCAGGAAAA

701 CCCAGTGGGA TAANGATGGT TATTTAATCG AACCCTGA
```

This encodes a protein having amino acid sequence <SEQ ID 702>:

```
  1 MKKLSRIVFS TVLLGFSAAL PAQXYSVYFN QNGKLTATXS SAAYIRQYSV

51 AEGIAHAQXF XYPSMKKYSE PYIVASTQIK SFVPTLQNGM LILWHFXGQK

101 KMAGGFSKGK PDGEWVNWYP NGKKSAVMPY KNGLSEGTGX RYYRNGGKES

151 EIQFKQNKAN GVWKQWYADG NIKTEMVMVN DEPAKILTWD ESGRLLSELS

201 IHHHXRNGVV LEWYEDGSKK XEAVYQDDKL VRKTQWDXDG YLIEP*
```

ORF27a and ORF27-1 show 94.7% identity in 245 aa overlap:

```
                   10        20        30        40        50        60
    orf27a.pep MKKLSRIVFSTVLLGFSAALPAQXYSVYFNQNGKLTATXSSAAYIRQYSVAEGIAHAQXF
               ||||||||||||||||||||||| :|||||||||||| ||||||||||||: |||||| |
    orf27-1    MKKLSRIVFSTVLLGFSAALPAQTYSVYFNQNGKLTATMSSAAYIRQYSVVAGIAHAQDF
                   10        20        30        40        50        60
                   70        80        90       100       110       120
    orf27a.pep XYPSMKKYSEPYIVASTQIKSFVPTLQNGMLILWHFXGQKKMAGGFSKGKPDGEWVNWYP
                |||||||||||||||||||||||||||||||||||| |||||||||||||||||||||||
    orf27-1    YYPSMKKYSEPYIVASTQIKSFVPTLQNGMLILWHFNGQKKMAGGFSKGKPDGEWVNWYP
                   70        80        90       100       110       120
                  130       140       150       160       170       180
    orf27a.pep NGKKSAVMPYKNGLSEGTGXRYYRNGGKESEIQFKQNKANGVWKQWYADGNIKTEMVMVN
               ||||||||||||||||||| ||||||||||||||||||||||||||||||:|||||||||
    orf27-1    NGKKSAVMPYKNGLSEGTGYRYYRNGGKESEIQFKQNKANGVWKQWYADGSIKTEMVMVN
                  130       140       150       160       170       180
                  190       200       210       220       230       240
    orf27a.pep DEPAKILTWDESGRLLSELSIHHHXRNGVVLEWYEDGSKKXEAVYQDDKLVRKTQWDXDG
               |||||||||||||||||||||:|| |||||||||||||||| |||||||||||||||| ||
    org27-1    DEPAKILTWDESGRLLSELSIRHHQRNGVVLEWYEDGSKKSEAVYQDDKLVRKTQWDKDG
                  190       200       210       220       230       240
    orf27a.pep YLIEPX
               ||||||
    orf27-1    YLIEPX
```

Homology with a Predicted ORF from *N. gonorrhoeae*

ORF27 shows 96.3% identity over 82 aa overlap with a predicted ORF (ORF27ng) from *N. gonorrhoeae*:

```
    orf27.pep                         KQWYADXSIKTEMVMVNDEPAKILTWDESG  30
                                      ||||| ||||||||||||||||||||||||
    orf27ng   LSEGTGYRYYRNGGKESEIQFKQNKANGVWKQWYADGSIKTEMVMVNDEPAKILTWDESG 193
    orf27.pep RLLSELSIRHHQRNGVVLEWYEDGSKKSEXVYQDDKLVRKTQWDKDGYLIEP         82
              ||||||||||:|||||||||||||||||| ||||||||||||||||||||||
    orf27ng   RLLSELSIRHHKRNGVVLEWYEDGSKKSEAVYQDDKLVRKTQWDKDGYLIEP        245
```

The complete length ORF27ng nucleotide sequence <SEQ ID 703> is:

```
  1 ATGAAGAAAT TATCTCGGAT TGTATTTTCA ATCGTACTGT TGGGTTTTTC

51 GGCCGCTTTG CCGGCGCAGA CCTATTCTGT TTATTTTAAT CAGAACGGGA

101 AACTGACGGC GACGATGTCT TCTGCCGCTT ATATCAGGCA ATATAGTGTG

151 GCGGCGGGTA TCGCACACGC GCAGGATTTT TATTATCCGT CGATGAAGAA

201 ATATTCCGAA CCTTATATCG TTGCTTCAAC GCAAATCAAA TCTTTTGTGC
```

```
251 CTACCCTGCA AAACGGTATG TTGATTTTGT GGCATTTTAA TGGTCAGAAA

301 AAAATGGCGG GGGGCTTCAG CAAGGGTAAG CCGGACGGGG AATGGGTCAA

351 CTGGTATCCG AACGGTAAAA AATCTGCGGT TATGCCTTAT AAAAATGGCT

401 TGAGTGAGGG TACGGGATAC CGTTATTACC GTAACGGCGG CAAGGAAAGC

451 GAAATCCAGT TTAAGCAAAA TAAGGCGAAC GGCGTATGGA AGCAATGGTA

501 TGCCGATGGA AGTATCAAGA CGGAAATGGT TATGGTCAAC GATGAGCCTG

551 CCAAAATTCT GACTTGGGAT GAAAGCGGCC GATTACTTTC GGAACTGTCT

601 ATCCGCCACC ATAAACGCAA CGGGGTGGTT TTGGAGTGGT ATGAAGATGG

651 TTCTAAAAAG AGCGAGGCTG TTTATCAGGA TGACAAGTTG GTCAGGAAAA

701 CCCAATGGGA TAAGGATGGT TATTTAATCG AACCCTGA
```

This encodes a protein having amino acid sequence <SEQ ID 704>:

```
  1 MKKLSRIVFS IVLLGFSAAL PAQTYSVYFN QNGKLTATMS SAAYIRQYSV

51 AAGIAHAQDF YYPSMKKYSE PYIVASTQIK SFVPTLQNGM LILWHFNGQK

101 KMAGGFSKGK PDGEWVNWYP NGKKSAVMPY KNGLSEGTGY RYYRNGGKES

151 EIQFKQNKAN GVWKQWYADG SIKTEMVMVN DEPAKILTWD ESGRLLSELS

201 IRHHKRNGVV LEWYEDGSKK SEAVYQDDKL VRKTQWDKDG YLIEP*
```

ORF27ng and ORF27-1 show 98.8% identity in 245 aa overlap:

```
                    10         20         30         40         50         60
orf27-1.pep  MKKLSRIVFSTVLLGFSAALPAQTYSVYFNQNGKLTATMSSAAYIRQYSVVAGIAHAQDF
             ||||||||||| |||||||||||||||||||||||||||||||||||||:|||||||||
orf27ng      MKKLSRIVFSIVLLGFSAALPAQTYSVYFNQNGKLTATMSSAAYIRQYSVAAGIAHAQDF
                    10         20         30         40         50         60

70         80         90        100        110        120
orf27-1.pep  YYPSMKKYSEPYIVASTQIKSFVPTLQNGMLILWHFNGQKKMAGGFSKGKPDGEWVNWYP
             ||||||||||||||||||||||||||||||||||||||||||||||||||||||||||||
orf27ng      YYPSMKKYSEPYIVASTQIKSFVPTLQNGMLILWHFNGQKKMAGGFSKGKPDGEWVNWYP
                    70         80         90        100        110        120

130        140        150        160        170        180
orf27-1.pep  NGKKSAVMPYKNGLSEGTGYRYYRNGGKESEIQFKQNKANGVWKQWYADGSIKTEMVMVN
             ||||||||||||||||||||||||||||||||||||||||||||||||||||||||||||
orf27ng      NGKKSAVMPYKNGLSEGTGYRYYRNGGKESEIQFKQNKANGVWKQWYADGSIKTEMVMVN
                   130        140        150        160        170        180

190        200        210        220        230        240
orf27-1.pep  DEPAKILTWDESGRLLSELSIRHHQRNGVVLEWYEDGSKKSEAVYQDDKLVRKTQWDKDG
             |||||||||||||||||||||||||:||||||||||||||||||||||||||||||||||
orf27ng      DEPAKILTWDESGRLLSELSIRHHKRNGVVLEWYEDGSKKSEAVYQDDKLVRKTQWDKDG
                   190        200        210        220        230        240 orf27-1.pep  YLIEPX
             ||||||
orf27ng      YLIEPX
```

Based on this analysis, including the putative leader sequence in the gonococcal protein, it was predicted that the proteins from N. meningitidis and N. gonorrhoeae, and their epitopes, could be useful antigens for vaccines or diagnostics, or for raising antibodies.

ORF27-1 (24.5 kDa) was cloned in pET and pGex vectors and expressed in E. coli, as described above. The products of protein expression and purification were analyzed by SDS-PAGE. FIG. 17A shows the results of affinity purification of the GST-fusion protein, and FIG. 17B shows the results of expression of the His-fusion in E. coli. Purified GST-fusion protein was used to immunise mice, whose sera were used for ELISA, which gave a positive result, confirming that ORF27-1 is a surface-exposed protein and a useful immunogen.

Example 84

The following partial DNA sequence was identified in *N. meningitidis* <SEQ ID 705>:

```
  1 ATGAAATTTA CCAAGCACCC CGTCTGGGCA ATGGCGTTCC GCCCATTTTA
 51 TTCGCTGGCG GCTCTGTACG GCGCATTGTC CGTATTGCTG TGGGGTTTCG
101 GCTACACGGG AACGCACkAG CTGTCCGGTT TCTATTGGCA CGCGCATGAg
151 ATGATTTGGG GTTATGCCGG ACTGGTCGTC ATCGCCTTCC TGCTGACCGC
201 CGTCGCCACT TGGACGGGGC AGCCGCCCAC GCGGGGCGGC GTaTCTGGTC
251 GGCTTGACTA TCTTTTGGCT GGCTGCGCGG ATTGCCGCCT TTATCCCGGG
301 TTGGGGTGCG TCGGCAAGCG GCATACTCGG TACGCTGTTT TTCTGGTACG
351 GCGCGGTGTG CATGGCTTTG CCCGTTATCC GTTCGCAGAA TCAACGCAAC
401 TATGTTgCCG TGTTCGCGCT GTTCGTCTTG GGCGGCACGC ATGCGGCGTT
451 CCACGTCCAG CTGCACAACG GCAACCTAGG CGGACTCTTG AGCGGATTGC
501 AGTCGGGCTT GGTGATG
```

This corresponds to the amino acid sequence <SEQ ID 706; ORF47>:

```
  1 MKFTKHPVWA MAFRPFYSLA ALYGALSVLL WGFGYTGTHX LSGFYWHAHE
 51 MIWGYAGLVV IAFLLTAVAT WTGQPPTRGG VLVGLTIFWL AARIAAFIPG
101 WGASASGILG TLFFWYGAVC MALPVIRSQN QRNYVAVFAL FVLGGTHAAF
151 HVQLHNGNLG GLLSGLQSGL VM
```

Further work revealed the complete nucleotide sequence <SEQ ID 707>:

```
  1 ATGAAATTTA CCAAGCACCC CGTCTGGGCA ATGGCGTTCC GCCCATTTTA
 51 TTCGCTGGCG GCTCTGTACG GCGCATTGTC CGTATTGCTG TGGGGTTTCG
101 GCTACACGGG AACGCACGAG CTGTCCGGTT TCTATTGGCA CGCGCATGAG
151 ATGATTTGGG GTTATGCCGG ACTGGTCGTC ATCGCCTTCC TGCTGACCGC
201 CGTCGCCACT TGGACGGGGC AGCCGCCCAC GCGGGGCGGC GTTCTGGTCG
251 GCTTGACTAT CTTTTGGCTG GCTGCGCGGA TTGCCGCCTT TATCCCGGGT
301 TGGGGTGCGT CGGCAAGCGG CATACTCGGT ACGCTGTTTT TCTGGTACGG
351 CGCGGTGTGC ATGGCTTTGC CCGTTATCCG TTCGCAGAAT CAACGCAACT
401 ATGTTGCCGT GTTCGCGCTG TTCGTCTTGG GCGGCACGCA TGCGGCGTTC
451 CACGTCCAGC TGCACAACGG CAACCTAGGC GGACTCTTGA GCGGATTGCA
501 GTCGGGCTTG GTGATGGTGT CGGGTTTTAT CGGTCTGATT GGTACGCGGA
551 TTATTTCGTT TTTTACGTCC AAACGCTTGA ATGTGCCGCA GATTCCCAGT
601 CCGAAATGGG TGGCGCAGGC TTCGCTGTGG CTGCCCATGC TGACTGCCAT
651 GCTGATGGCG CACGGTGTGT TGGCTTGGCT GTCTGCCGTT TTTGCCTTTG
701 CGGCAGGTGT GATTTTTACC GTGCAGGTGT ACCGCTGGTG GTATAAACCC
751 GTGTTGAAAG AGCCGATGCT GTGGATTCTG TTTGCCGGCT ATCTGTTTAC
801 CGGATTGGGG CTGATTGCGG TCGGCGCGTC TTATTTCAAA CCCGCTTTCC
851 TCAATCTGGG TGTGCATCTG ATCGGGGTCG GCGGTATCGG CGTGCTGACT
```

-continued

```
 901 TTGGGCATGA TGGCGCGTAC CGCGCTTGGT CATACGGGCA ATCCGATTTA

951 TCCGCCGCCC AAAGCCGTTC CCGTTGCGTT TTGGCTGATG ATGGCGGCAA

1001 CCGCCGTCCG TATGGTTGCC GTATTTTCTT CCGGCACTGC CTACACGCAC

1051 AGCATCCGCA CCTCTTCGGT TTTGTTTGCA CTCGCGCTTT TGGTGTATGC

1101 GTGGAAGTAT ATTCCTTGGC TGATTCGTCC GCGTTCGGAC GGCAGGCCCG

1151 GTTGA
```

This corresponds to the amino acid sequence <SEQ ID 708; ORF47-1>:

```
  1 MKFTKHPVWA MAFRPFYSLA ALYGALSVLL WGFGYTGTHE LSGFYWHAHE

51 MIWGYAGLVV IAFLLTAVAT WTGQPPTRGG VLVGLTIFWL AARIAAFIPG

101 WGASASGILG TLFFWYGAVC MALPVIRSQN QRNYVAVFAL FVLGGTHAAF

151 HVQLHNGNLG GLLSGLQSGL VMVSGFIGLI GTRIISFFTS KRLNVPQIPS

201 PKWVAQASLW LPMLTAMLMA HGVLAWLSAV FAFAAGVIFT VQVYRWWYKP

251 VLKEPMLWILFAGYLFTGLG LIAVGASYFK PAFLNLGVHL IGVGGIGVLT

301 LGMMARTALG HTGNPIYPPP KAVPVAFWLM MAATAVRMVA VFSSGTAYTH

351 SIRTSSVLFA LALLVYAWKY IPWLIRPRSD GRPG*
```

Computer analysis of this amino acid sequence predicts a leader peptide and also gave the following results:

Homology with a Predicted ORF from *N. meningitidis* (Strain A)

ORF47 shows 99.4% identity over a 172aa overlap with an ORF (ORF47a) from strain A of *N. meningitidis*.

```
                     10        20        30        40        50        60
   orf47.pep  MKFTKHPVWAMAFRPFYSLAALYGALSVLLWGFGYTGTHXLSGFYWHAHEMIWGYAGLVV
              ||||||||||||||||||||||||||||||||||||||| ||||||||||||||||||||
   orf47a     MKFTKHPVWAMAFRPFYSLAALYGALSVLLWGFGYTGTHELSGFYWHAHEMIWGYAGLVV
                     10        20        30        40        50        60
                     70        80        90       100       110       120
   orf47.pep  IAFLLTAVATWTGQPPTRGGVLVGLTIFWLAARIAAFIPGWGASASGILGTLFFWYGAVC
              |||||:||||||||||||||||||||||||||||||||||||||||||||||||||||||
   orf47a     IAFLLTAVATWTGQPPTRGGVLVGLTIFWLAARIAAFIPGWGASASGILGTLFFWYGAVC
                     70        80        90       100       110       120
                    130       140       150       160       170
   orf47.pep  MALPVIRSQNQRNYVAVFALFVLGGTHAAFHVQLHNGNLGGLLSGLQSGLVM
              ||||||||||||||||||||||||||||||||||||||||||||||||||||
   orf47a     MALPVIRSQNQRNYVAVFALFVLGGTHAAFHVQLHNGNLGGLLSGLQSGLVMVSGFIGLI
                    130       140       150       160       170       180
   orf47a     GTRIISFFTSKRLNVPQIPSPKWVAQASLWLPMLTAMLMAHGVMPWLSAAFAFAAGVIFT
                    190       200       210       220       230       240
```

The complete length ORF47a nucleotide sequence <SEQ ID 709> is:

```
  1 ATGAAATTTA CCAAGCACCC CGTTTGGGCA ATGGCGTTCC GCCCGTTTTA

51 TTCACTGGCG GCTCTGTACG GCGCATTGTC CGTATTGCTG TGGGGTTTCG

101 GCTACACGGG AACGCACGAG CTGTCCGGTT TCTATTGGCA CGCGCATGAG

151 ATGATTTGGG GTTATGCCGG ACTGGTCGTC ATCGCCTTCC TGCTGACCGC

201 CGTCGCCACT TGGACGGGGC AGCCGCCCAC GCGGGGCGGC GTTCTGGTCG

251 GCTTGACTAT CTTTTGGCTG GCTGCGCGGA TTGCCGCCTT TATCCCGGGT
```

-continued

```
 301  TGGGGTGCGT CGGCAAGCGG CATACTCGGT ACGCTGTTTT TCTGGTACGG
 351  CGCGGTGTGC ATGGCTTTGC CCGTTATCCG TTCGCAGAAT CAACGCAATT
 401  ATGTTGCCGT GTTCGCGCTG TTCGTCTTGG GCGGTACGCA CGCGGCGTTC
 451  CACGTCCAGC TGCACAACGG CAACCTAGGC GGACTCTTGA GCGGATTGCA
 501  GTCGGGCTTG GTGATGGTGT CGGGTTTTAT CGGTCTGATT GGTACGCGGA
 551  TTATTTCGTT TTTTACGTCC AAACGGTTGA ATGTGCCGCA GATTCCCAGT
 601  CCGAAATGGG TGGCGCAGGC TTCGCTGTGG CTGCCCATGC TGACCGCCAT
 651  GCTGATGGCG CACGGCGTGA TGCCTTGGCT GTCGGCGGCT TTCGCGTTTG
 701  CGGCAGGTGT GATTTTTACC GTGCAGGTGT ACCGCTGGTG GTATAAGCCT
 751  GTGTTGAAAG AGCCGATGCT GTGGATTCTG TTTGCCGGCT ATCTGTTTAC
 801  CGGATTGGGG CTGATTGCGG TCGGCGCGTC TTATTTCAAA CCCGCTTTCC
 851  TCAATCTGGG TGTGCATCTG ATCGGGGTCG GCGGTATCGG CGTGCTGACT
 901  TTGGGCATGA TGGCGCGTAC CGCGCTCGGT CATACGGGCA ATCCGATTTA
 951  TCCGCCGCCC AAAGCCGTTC CCGTTGCGTT TTGGCTGATG ATGGCGGCAA
1001  CCGCCGTCCG TATGGTTGCC GTATTTTCTT CCGGCACTGC CTACACGCAC
1051  AGCATACGCA CCTCTTCGGT TTTGTTTGCA CTCGCGCTTT TGGTGTATGC
1101  GTGGAAGTAT ATTCCTTGGC TGATTCGTCC GCGTTCGGAC GGCAGGCCCG
1151  GTTGA
```

This encodes a protein having amino acid sequence <SEQ ID 710>:

```
  1 MKFTKHPVWA MAFRPFYSLA ALYGALSVLL WGFGYTGTHE LSGFYWHAHE
 51 MIWGYAGLVV IAFLLTAVAT WTGQPPTRGG VLVGLTIFWL AARIAAFIPG
101 WGASASGILG TLFFWYGAVC MALPVIRSQN QRNYVAVFAL FVLGGTHAAF
151 HVQLHNGNLG GLLSGLQSGL VMVSGFIGLI GTRIISFFTS KRLNVPQIPS
201 PKWVAQASLWLPMLTAMLMA HGVMPWLSAA FAFAAGVIFT VQVYRWWYKP
251 VLKEPMLWILFAGYLFTGLG LIAVGASYFK PAFLNLGVHL IGVGGIGVLT
301 LGMMARTALG HTGNPIYPPP KAVPVAFWLM MAATAVRMVA VFSSGTAYTH
351 SIRTSSVLFA LALLVYAWKY IPWLIRPRSD GRPG*
```

ORF47a and ORF47-1 show 99.2% identity in 384 aa overlap:

```
                  10        20        30        40        50        60
orf47a.pep  MKFTKHPVWAMAFRPFYSLAALYGALSVLLWGFGYTGTHELSGFYWHAHEMIWGYAGLVV
            ||||||||||||||||||||||||||||||||||||||||||||||||||||||||||||
orf47-1     MKFTKHPVWAMAFRPFYSLAALYGALSVLLWGFGYTGTHELSGFYWHAHEMIWGYAGLVV
                  10        20        30        40        50        60

70        80        90       100       110       120
orf47a.pep  IAFLLTAVATWTGQPPTRGGVLVGLTIFWLAARIAAFIPGWGASASGILGTLFFWYGAVC
            ||||||||||||||||||||||||||||||||||||||||||||||||||||||||||||
orf47-1     IAFLLTAVATWTGQPPTRGGVLVGLTIFWLAARIAAFIPGWGASASGILGTLFFWYGAVC
                  70        80        90       100       110       120

130       140       150       160       170       180
orf47a.pep  MALPVIRSQNQRNYVAVFALFVLGGTHAAFHVQLHNGNLGGLLSGLQSGLVMVSGFIGLI
            ||||||||||||||||||||||||||||||||||||||||||||||||||||||||||||
orf47-1     MALPVIRSQNQRNYVAVFALFVLGGTHAAFHVQLHNGNLGGLLSGLQSGLVMVSGFIGLI
                 130       140       150       160       170       180
```

-continued

```
                     190         200         210         220         230         240
orf47a.pep   GTRIISFFTSKRLNVPQIPSPKWVAQASLWLPMLTAMLMAHGVMPWLSAAFAFAAGVIFT
             ||||||||||||||||||||||||||||||||||||||:||||:|||||||||||
orf47-1      GTRIISFFTSKRLNVPQIPSPKWVAQASLWLPMLTAMLMAHGVLAWLSAVFAFAAGVIFT
                     190         200         210         220         230         240

250         260         270         280         290         300
orf47a.pep   VQVYRWWYKPVLKEPMLWILFAGYLFTGLGLIAVGASYFKPAFLNLGVHLIGVGGIGVLT
             ||||||||||||||||||||||||||||||||||||||||||||||||||||||||||||
orf47-1      VQVYRWWYKPVLKEPMLWILFAGYLFTGLGLIAVGASYFKPAFLNLGVHLIGVGGIGVLT
                     250         260         270         280         290         300

310         320         330         340         350         360
orf47a.pep   LGMMARTALGHTGNPIYPPPKAVPVAFWLMMAATAVRMVAVFSSGTAYTHSIRTSSVLFA
             ||||||||||||||||||||||||||||||||||||||||||||||||||||||||||||
orf47-1      LGMMARTALGHTGNPIYPPPKAVPVAFWLMMAATAVRMVAVFSSGTAYTHSIRTSSVLFA
                     310         320         330         340         350         360

370         380
orf47a.pep   LALLVYAWKYIPWLIRPRSDGRPGX
             |||||||||||||||||||||||||
orf47-1      LALLVYAWKYIPWLIRPRSDGRPGX
                     370         380
```

Homology with a Predicted ORF from *N. gonorrhoeae*

ORF47 shows 97.1% identity over 172 aa overlap with a predicted ORF (ORF47ng) from *N. gonorrhoeae*:

```
ORF47     MKFTKHPVWAMAFRPFYSLAALYGALSVLLWGFGYTGTHELSGFYWHAHEMIWGYAGLVV   60
          ||||||||||||||||||||||||||||||||||||||||||||||||||||||||||||
ORF47ng   MKFTKHPVWAMAFRPFYSLAALYGALSVLLWGFGYTGTHELSGFYWHAHEMIWGYAGLVV   60
ORF47     IAFLLTAVATWTGQPPTRGGVLVGLTIFWLAARIAAFIPGWGASASGILGTLFFWYGAVC  120
          |||||||||||||||||||||||||||||:||||||||||||||||:|||||||||||||
ORF47ng   IAFLLTAVATWTGQPPTRGGVLVGLTAFWLAARIAAFIPGWGAAASGILGTLFFWYGAVC  120
ORF47     MALPVIRSQNQRNYVAVFALFVLGGTHAAFHVQLHNGNLGGLLSGLQSGLVM         120
          |||||||||:|||||||||:||||||||||||||||||||||||||||||||
ORF47ng   MALPVIRSQNRRNYVAVFAIFVLGGTHAAFHVQLHNGNLGGLLSGLQSGLVMVWGFIGLI  120
```

The ORF47ng nucleotide sequence <SEQ ID 711> is predicted to encode a protein comprising amino acid sequence <SEQ ID 712>:

```
  1  MKFTKHPVWA MAFRPFYSLA ALYGALSVLL WGFGYTGTHE LSGFYWHAHE

51  MIWGYAGLVV IAFLLTAVAT WTGQPPTRGG VLVGLTAFWL AARIAAFIPG

101  WGAAASGILG TLFFWYGAVC MALPVIRSQN RRNYVAVFAI FVLGGTHAAF

151  HVQLHNGNLG GLLSGLQSGL VMVWGFIGLI GMKIISFFTS KRLKLPQIPS

201  PKWVAHASLW LPMLNAILMA HRVMPWLSAA FPFAAGVIFT VQVYAGGITP

251  IEETSCGSVA GICYRLGNSS G
```

The predicted leader peptide and transmembrane domains are identical (except for an Ile/Ala substitution at residue 87 and an Leu/Ile substitution at position 140) to sequences in the meningococcal protein (see also *Pseudomonas stutzeri* orf396, accession number e246540):

| TM segments in ORF47ng | | | |
|---|---|---|---|
| INTEGRAL | Likelihood = −5.63 | Transmembrane | 52-68 |
| INTEGRAL | Likelihood = −3.88 | Transmembrane | 169-185 |

-continued

| TM segments in ORF47ng | | | |
|---|---|---|---|
| INTEGRAL | Likelihood = −3.08 | Transmembrane | 82-98 |
| INTEGRAL | Likelihood = −1.91 | Transmembrane | 134-150 |
| INTEGRAL | Likelihood = −1.44 | Transmembrane | 107-123 |
| INTEGRAL | Likelihood = −1.38 | Transmembrane | 227-243 |

Further work revealed the complete gonococcal DNA sequence <SEQ ID 713>:

```
  1  ATGAAATTTA CCAAACATCC CGTCTGGGCA ATGGCGTTCC GCCCGTTTTA

51  TTCACTGGCG GCACTGTACG GCGCATTGTC CGTATTGCTG TGGGGTTTCG

101  GCTACACGGG AACGCACGAG CTGTCCGGTT TCTATTGGCA CGCGCATGAG

151  ATGATTTGGG GTTATGCCGG TCTCGTCGTC ATCGCCTTCC TGCTGACCGC
```

-continued

```
 201 CGTCGCCACT TGGACGGGAC AGCCGCCCAC GAGGGGCGGC GTTCTGGTCG
 251 GCTTGACCGC CTTTTGGCTG GCTGCGCGGA TTGCCGCCTT TATCCCGGGT
 301 TGGGGTGCGG CGGCAAGCGG CATACTCGGT ACGCTGTTTT TCTGGTACGG
 351 CGCGGTGTGC ATGGCTTTGC CCGTTATCCG TtcgCAAAAC CGGCGCAACT
 401 ATGtcgCCGT ATTCGCAATA TTTGTGCTGG GCGGTACGCA TGCGgcgTTC
 451 CACGtccAgc tGCACAACGG CAACCTAGGC GGACTCTTGA GCGGATTGCA
 501 GTCGGGCCTG GTTATGGTGT CGGGCTTTAT CGGCCTGATT GGGATGAGGA
 551 TTATTTCGTT TTTTACGTCC AAACGGTTGA ACGTGCCGCA GATTCCCAGT
 601 CCGAAATGGG TGGCGCAGGC TTCGCTGTGG CTACCCATGC TGACCGCCAT
 651 ACTGATGGCG CACGGCGTGA TGCCTTGGCT GTCGGCGGCT TTCGCGTTTG
 701 CGGCGGGCGT GATTTTTACC GTACAGGTGT ACCGCTGGTG GTATAAACCC
 751 GTATTGAAAG AACCGATGCT GTGGATTCTG TTTGCCGGCT ATCTGTTTAC
 801 CGGATTGGGG CTGATTGCGG TCGGCGCGTC TTATTTCAAA CCTGCCTTCC
 851 TCAATCTGGG CGTACATCTG ATCGGGGTCG GCGGTATCGG CGTGCTGACT
 901 TTGGGCATGA TGGCGCGTAC CGCGCTCGGT CATACGGGCA ATTCGATTTA
 951 TCCGCCGCCC AAAGCCGTTC CCGTTGCGTT TTGGCTGATG ATGGCGGCAA
1001 CCGCCGTCCG TATGGTTGCC GTATTTTCTT CCGGCACTGC CTACACGCAC
1051 AGCATCCGCA CGTCTTCGGT TTTGTTTGCA CTCGCGCTGC TGGTGTATGC
1101 GTGGAAATAC ATTCCGTGGC TGATCCGTCC GCGTTCGGAC GGCAGGCCCG
1151 GTTGA
```

This encodes a protein having amino acid sequence <SEQ ID 714; ORF47ng-1>:

```
  1 MKFTKHPVWA MAFRPFYSLA ALYGALSVLL WGFGYTGTHE LSGFYWHAHE
 51 MIWGYAGLVV IAFLLTAVAT WTGQPPTRGG VLVGLTAFWL AARIAAFIPG
101 WGAAASGILG TLFFWYGAVC MALPVIRSQN RRNYVAVFAI FVLGGTHAAF
151 HVQLHNGNLG GLLSGLQSGL VMVSGFIGLI GMRIISFFTS KRLNVPQIPS
201 PKWVAQASLW LPMLTAILMA HGVMPWLSAA FAFAAGVIFT VQVYRWWYKP
251 VLKEPMLWIL FAGYLFTGLG LIAVGASYFK PAFLNLGVHL IGVGGIGVLT
301 LGMMARTALG HTGNSIYPPP KAVPVAFWLM MAATAVRMVA VFSSGTAYTH
351 SIRTSSVLFA LALLVYAWKY IPWLIRPRSD GRPG*
```

ORF47ng-1 and ORF47-1 show 97.4% identity in 384 aa overlap:

```
                   10         20         30         40         50         60
orf47-1.pep  MKFTKHPVWAMAFRPFYSLAALYGALSVLLWGFGYTGTHELSGFYWHAHEMIWGYAGLVV
             ||||||||||||||||||||||||||||||||||||||||||||||||||||||||||||
orf47ng-1    MKFTKHPVWAMAFRPFYSLAALYGALSVLLWGFGYTGTHELSGFYWHAHEMIWGYAGLVV
                   10         20         30         40         50         60

70         80         90        100        110        120
orf47-1.pep  IAFLLTAVATWTGQPPTRGGVLVGLTIFWLAARIAAFIPGWGASASGILGTLFFWYGAVC
             ||||||||||||||||||||||||||| |||||||||||||||:||||||||||||||||
orf47ng-1    IAFLLTAVATWTGQPPTRGGVLVGLTAFWLAARIAAFIPGWGAAASGILGTLFFWYGAVC
                   70         80         90        100        110        120
```

-continued

```
              130        140        150        160        170        180
orf47-1.pep   MALPVIRSQNQRNYVAVFALFVLGGTHAAFHVQLHNGNLGGLLSGLQSGLVMVSGFIGLI
              ||||||||||||:||||||||:|||||||||||||||||||||||||||||||||||||
orf47ng-1     MALPVIRSQNRRNYVAVFAIFVLGGTHAAFHVQLHNGNLGGLLSGLQSGLVMVSGFIGLI
              130        140        150        160        170        180

190        200        210        220        230        240
orf47-1.pep   GTRIISFFTSKRLNVPQIPSPKWVAQASLWLPMLTAMLMAHGVLAWLSAVFAFAAGVIFT
              |:||||||||||||||||||||||||||||||||||:|||||||:||||:||||||||||
orf47ng-1     GMRIISFFTSKRLNVPQIPSPKWVAQASLWLPMLTAILMAHGVMPWLSAAFAFAAGVIFT
              190        200        210        220        230        240

250        260        270        280        290        300
orf47-1.pep   VQVYRWWYKPVLKEPMLWILFAGYLFTGLGLIAVGASYFKPAFLNLGVHLIGVGGIGVLT
              ||||||||||||||||||||||||||||||||||||||||||||||||||||||||||||
orf47ng-1     VQVYRWWYKPVLKEPMLWILFAGYLFTGLGLIAVGASYFKPAFLNLGVHLIGVGGIGVLT
              250        260        270        280        290        300

310        320        330        340        350        360
orf47-1.pep   LGMMARTALGHTGNPIYPPPKAVPVAFWLMMAATAVRMVAVFSSGTAYTHSIRTSSVLFA
              ||||||||||||||||:||||||||||||||||||||||||||||||||||||||||||
orf47ng-1     LGMMARTALGHTGNSIYPPPKAVPVAFWLMMAATAVRMVAVFSSGTAYTHSIRTSSVLFA
              310        320        330        340        350        360

370        380
orf47-1.pep   LALLVYAWKYIPWLIRPRSDGRPGX
              |||||||||||||||||||||||||
orf47ng-1     LALLVYAWKYIPWLIRPRSDGRPGX
              370        380
```

Furthermore, ORF47ng-1 shows significant homology to an ORF from *Pseudomonas stutzeri*:

```
gnl|PID|e246540 (z73914) ORF396 protein (Pseudomonas stutzeri) Length = 396
Score = 155 bits (389), Expect = 5e-37
Identities = 121/391 (30%), Positives = 169/391 (42%), Gaps = 21/391 (5%)

Query:     7  PVWAMAFRPFYSLAALYGALSVLLWGFYTGTHELSGFY-------WHAHEMIWGYAGLV   59
              P+W +AFRPF+    +LY L++ LW   +TG      GF         WH HEM++G+A  +
Sbjct:    14  PIWRLAFRPFFLAGSLYALLAIPLWVAAWTGLWP--GFQPTGGWLAWHRHEMLFGFAMAI   71

Query:    60  VIAFLLTAVATWTGQPPTRGGVLVGLTAFWLAARIAAFIPGWGAAASGILGTLFFWYGAV  119
              V   FLLTAV TWTGQ     G  LVGL A WLAAR+  ++ G  AA     L   LF
Sbjct:    72  VAGFLLTAVQTWTGQTAPSGNRLVGLAAVWLAARL-GWLFGLPAAWLAPLDLLFLVALVW  130

Query:   120  CMALPVIRSQNRRNYVAVFAIFVLGGTHAAFXXXXXXXXXXXXXXXXXXXXXXMVSGFIGL  179
              MA  +   + +RNY V  +  ++ G                           +V+   + L
Sbjct:   131  MMAQMLWAVRQKRNYPIVVVLSLMLGADVLILTGLLQGNDALQRQGVLAGLWLVAALMAL  190

Query:   180  IGMRIISFFTSKRLNVPQIPSP-KWVAQASLWLPMLTAILMAHGV----MPWLSAAFAFA  234
              IG R+I FFT + L      P    W+  A L     +   A+L  A GV     P L   F A
Sbjct:   191  IGGRVIPFFTQRGLGKVDAVKPWVWLDVALLVGTGVIALLHAFGVAMRPQPLLGLLFV-A  249

Query:   235  AGVIFTVQVYRWWYKPVLKEPMLWILFAGYLFTGLGLIAVGASYF-KPAFXXXXXXXXXX  293
                GV   +++ RW+  K + K  +LW L    L+ +  +     +F    A
Sbjct:   250  IGVGHLLRLMRWYDKGIWKVGLLWSLHVAMLWLVVAAFGLALWHFGLLAQSSPSLHALSV  309

Query:   294  XXXXXXXXXMMARTALGHTGNSIYPPPKAVPVAFWLXXXXXXXXXXXXXFSSGTAYTHSIR  353
                       M+AR  LGHTG  +   P   +  AF L                  FS   +
Sbjct:   310  GSMSGLILAMIARVTLGHTGRPLQLPAGIIG-AFVL---FNLGTAARVFLSVAWPVGGLW  365

Query:   354  TSSVLFALALLVYAWKYIPWLIRPRSDGRPG   384
              ++V  + LA  +Y W+Y P L+   R DG PG
Sbjct:   366  LAAVCWTLAFALYVWRYAPMLVAARVDGHPG   396
```

Based on this analysis, it is predicted that the proteins from *N. meningitidis* and *N. gonorrhoeae*, and their epitopes, could be useful antigens for vaccines or diagnostics, or for raising antibodies.

Example 85

The following partial DNA sequence was identified in *N. meningitidis* <SEQ ID 715>:

```
  1..ATGCCGTCTG AAGGTTCAGA CGGCmTCGGT GyCGGGGAAy CAGAAGyGGT
 51  AGCGCATGCC CAATGAGACT TCGTGGGTTT TGAAGCGGGT GTTTTCCAAG
101  CGTCCCCAGT TGTGGTAACG GTATCCGGTG TCyAArGTCA GCTTGGGyGT
151  GATGTCGAAa CCGACACCGG CGATGACACC AAGACCyAmG CTGCTGATrC
201  TGTkGCTTTC GTGATAGGsA GGTTTGyTGG kmksAsyTTG TAyrATwkkG
251  CCTssCwsTG kAGmGCCkTk CkyTGGTkkA swGrwArTAG TCGTGGTTTy
301  TkTTyyCACC GAATGAACyT GATGTTTAAC GTGTCCGTAG GCGACGCGCG
351  CGCCGATATA GGGTTTGAAT TTATCGTTGA GTTTGAAATC GTAAATGGCG
```

```
401  GACAAGCCGA GAGAAGAAAC GGCGTGGAAG CTGCCGTTTC CCTGATGTTT

451  TGTTTGGGTT TCTTTGTAGT TGTTGTTTAT CTCTTCAGTA ACTTTTTTAG

501  TAGAAGAATT ACTTTCTTTC CATTTTCTGT AACTGGCATA ATCTGCCGCT

551  ATTCTCCAGC CGCCGAAATC ..
```

This corresponds to the amino acid sequence <SEQ ID 716; ORF67>:

```
  1..MPSEGSDGXG XGEXEXVAHA QXDFVGFEAG VFQASPVVVT VSGVXXQLGX

51  DVETDTGDDT KTXAADXVAF VIGRFXGXXL YXXAXXXXAX XWXXXXSRGF

101  XXHRMNLMFN VSVGDARADI GFEFIVEFEI VNGGQAERRN GVEAAVSLMF

151  CLGFFVVVVY LFSNFFSRRI TFFPFSVTGI ICRYSPAAEI ..
```

Computer analysis of this amino acid sequence gave the following results:

Homology with a Predicted ORF from *N. gonorrhoeae*

ORF67 shows 51.8% identity over 199 aa overlap with a predicted ORF (ORF67ng) from *N. gonorrhoeae*:

```
orf67.pep                                       MPSEGSDGXGXGEXEXVAHAQXDFVGFEAG  30
                                                |||||||||| || | ||||| ||||||||
orf67ng    TNFEIAVLSGMTVRVFYCARPAPVNGGRLKMPSEGSDGIGIGESEAVAHAQRGFVGFEAG 146
                   90        100       110       120       130       140 orf67.pep  VFQASPVVVTSGVXXQLGXDVETDTGDDTKTXAADXVAFVIGRFXGXXLYXXAXXXXAX    90
           ||||||||:|:||   |  |||  :  :   ::: ||   |||:||  |          :
orf67ng    VFQASPVVVAVAGVQGQAGRDVYAHARHRAEAQAAAAVAFLIGVFLRMSVRINRNCCVSI 206 orf67.pep  XWXXXXSRGFXXHRMNLMFNVSVGDARADIGFEFIVEFEIVNGGQAERRNGVEAAVSLMF 150
           :     |  | :: :  :|||||||:||||||:|||||||||||||||||||| || ||
orf67ng    TRVGGKSTCYFFSRIDAVSDVSVGDARTDIGFEFVVEFEIVNGGQAERRNGVECAVFLMF 266 orf67.pep  CLGFFVV--------VVYLFSNFFSRRITFF-PFSVTGIICRYSPAAEI             190
           |  | |          :: |: |: : |  : || ||||| :||||:
orf67ng    RLLVFYVKLVAAKSFIILSFQLFYVHGIFIVVPFPVTGIIRGDAPAAEVVADRHPGVDGM 326
```

The ORF67ng nucleotide sequence <SEQ ID 717> is predicted to encode a protein comprising amino acid sequence <SEQ ID 718>:

```
  1  MPSETVGSIV NVGVDESVGF SPPFPSIQHF YRFHRIHRIR LFRPPGPMQL

51  NRHSHGSGNL GRGVWATVLS DKFPCGQVRI PACAGMTNFE IAVLSGMTVR

101  VFYCARPAPV NGGRLKMPSE GSDGIGIGES EAVAHAQRGF VGFEAGVFQA

151  SPVVVAVAGV QGQAGRDVYA HARHRAEAQA AAAVAFLIGV FLRMSVRINR

201  NCCVSITRVG GKSTCYFFSR IDAVSDVSVG DARTDIGFEF VVEFEIVNGG

251  QAERRNGVEC AVFLMFRLLV FYVKLVAAKS FIILSFQLFY VHGIFIVVPF

301  PVTGIIRGDA PAAEVVADRH PGVDGMRTDV SEIIAYRAYF VFAWSGWFRI

351  IVGNAFGGVG *
```

Based on the presence of a several putative transmembrane domains in the gonococcal protein, it is predicted that the proteins from *N. meningitidis* and *N. gonorrhoeae*, and their epitopes, could be useful antigens for vaccines or diagnostics, or for raising antibodies.

Example 86

The following partial DNA sequence was identified in *N. meningitidis* <SEQ ID 719>

```
  1 ATGTTTGCTT TTTTAGAAGC CTTTTTTGTC GAATACGGTT ATGCGGCTGT
 51 TTTTTTTGTA TTGGTCATCT GCGGTTTCGG CGTGCCGATT CCCGAGGATT
101 TGACCTTGGT AACAGGCGGC GTGATTTCGG GTATGGGTTA TACCAATCCG
151 CATATTATGT TTGCAGTCGG TATGCTCGGC GTATTGGTCG GGGACGGCAT
201 CATGTTCGCC GCCGGACGAA TTTGGGGGCA GArArTCCTA rGGTTCArAC
251 CTATTGCGsG CATCATGACG CCGrAACGTT ATGAGCAGGT TCAGGAAAAA
301 TTCGACAAAT ACGGTAACTG GGTCTTATTT GTCGCCCGTT TCCTGCCCGG
351 TTTGAGAACG GCCGTATTTG TTACAGCCGG TATCAGCCGC AAGGTTTCAT
401 ACTTGCGTTT TATCATTATG GATGGACTGG CCGCA...
```

This corresponds to the amino acid sequence <SEQ ID 720; ORF78>:

```
  1 MFAFLEAFFV EYGYAAVFFV LVICGFGVPI PEDLTLVTGG VISGMGYTNP
 51 HIMFAVGMLG VLVGDGIMFA AGRIWGQXXL XFXPIAXIMT PXRYEQVQEK
101 FDKYGNWVLF VARFLPGLRT AVFVTAGISR KVSYLRFIIM DGLAA...
```

Further work revealed the complete nucleotide sequence <SEQ ID 721>:

```
  1 ATGTTTGCTT TTTTAGAAGC CTTTTTTGTC GAATACGGTT ATGCGGCTGT
 51 TTTTTTTGTA TTGGTCATCT GCGGTTTCGG CGTGCCGATT CCCGAGGATT
101 TGACCTTGGT AACAGGCGGC GTGATTTCGG GTATGGGTTA TACCAATCCG
151 CATATTATGT TTGCAGTCGG TATGCTCGGC GTATTGGTCG GGGACGGCAT
201 CATGTTCGCC GCCGGACGAA TTTGGGGGCA GAAAATCCTA AGGTTCAAAC
251 CTATTGCGCG CATCATGACG CCGAAACGTT ATGAGCAGGT TCAGGAAAAA
301 TTCGACAAAT ACGGTAACTG GGTCTTATTT GTCGCCCGTT TCCTGCCCGG
351 TTTGAGAACG GCCGTATTTG TTACAGCCGG TATCAGCCGC AAGGTTTCAT
401 ACTTGCGTTT TATCATTATG GATGGACTGG CCGCACTGAT TTCCGTCCCT
451 ATTTGGATTT ATCTGGGCGA ATACGGTGCG CACAACATCG ATTGGCTGAT
501 GGCGAAAATG CACAGCCTGC AATCGGGTAT TTTTGTTATC TTGGGTATAG
551 GTGCGACCGT TGTCGCTTGG ATTTGGTGGA AAAAACGCCA ACGTATCCAG
601 TTTTACCGCA GCAAATTGAA AGAAAAGCGG GCGCAACGCA AAGCCGCCAA
651 GGCAGCCAAA AAAGCCGCGC AAAGCAAACA ATAA
```

This corresponds to the amino acid sequence <SEQ ID 722; ORF78-1>:

```
  1 MFAFLEAFFV EYGYAAVFFV LVICGFGVPI PEDLTLVTGG VISGMGYTNP
 51 HIMFAVGMLG VLVGDGIMFA AGRIWGQKIL RFKPIARIMT PKRYEQVQEK
101 FDKYGNWVLF VARFLPGLRT AVFVTAGISR KVSYLRFIIM DGLAALISVP
```

```
151 IWIYLGEYGA HNIDWLMAKM HSLQSGIFVI LGIGATVVAW IWWKKRQRIQ
201 FYRSKLKEKR AQRKAAKAAK KAAQSKQ*
```

Computer analysis of this amino acid sequence predicts several transmembrane domains, and also gave the following results:

Homology with the dedA Homologue of *H. influenzae* (Accession Number P45280)

ORF78 and the dedA homologue show 58% aa identity in 144aa overlap:

```
Orf78:    4 FLEAFFVEYGYAAVFFVLVICGFGVPIPEDLTLVTGGVISGM--GYTNPHIMFAVGMLGV   61
            FL  FF EYGY AV FVL+ICGFGVPIPED+TLV+GGVI+G+    N H+M  V M+GV
DedA:    20 FLIGFFTEYGYWAVLFVLIICGFGVPIPEDITLVSGGVIAGLYPENVNSHLMLLVSMIGV   79

Orf78:   62 LVGDGIMFAAGRIWGQXXLXFXPIAXIMTPXRYEQVQEKFDKYGNWVLFVARFLPGLRTA  121
            L GD  M+  GRI+G    L F PI  I+T R   V+EKF +YGN VLFVARFLPGLR
DedA:    80 LAGDSCMYWLGRIYGTKILRFRPIRRIVTLQRLRMVREKFSQYGNRVLFVARFLPGLRAP  139

Orf78:  122 VFVTAGISRKVSYLRFIIMDGLAA                                      145
            +++ +GI+R+VSY+RF+++D AA
DedA:   140 IYMVSGITRRVSYVRFVLIDFCAA                                      163
```

Homology with a Predicted ORF from *N. meningitidis* (Strain A)

ORF78 shows 93.8% identity over a 145aa overlap with an ORF (ORF78a) from strain A of *N. meningitidis*.

```
                    10         20         30         40         50         60
   orf78.pep  MFAFLEAFFVEYGYAAVFFVLVICGFGVPIPEDLTLVTGGVISGMGYTNPHIMFAVGMLG
              ||| |||||||||||||||||||||||||||||||||||||||||||||||||||||||
   orf78a     MFALLEAFFVEYGYAAVFFVLVICGFGVPIPEDLTLVTGGVISGMGYTNPHIMFAVGMLG
                    10         20         30         40         50         60
                    70         80         90        100        110        120
   orf78.pep  VLVGDGIMFAAGRIWGQXXLXFXPIAXIMTPXRYEQVQEKFDKYGNWVLFVARFLPGLRT
              |||||||||||||||||   |||||  |||  || |||||||||||||||||||||||
   orf78a     VLVGDGIMFAAGRIWGQKILKFKPIARIMTPKRYAQVQEKFDKYGNWVLFVARFLPGLRT
                    70         80         90        100        110        120
                   130        140
   orf78.pep  AVFVTAGISRKVSYLRFIIMDGLAA
              |||||||||||||||||:|||||||
   orf78ng    AVFVTAGISRKVSYLRFLIMDGLAALISVPVWIYLGEYGAHNIDWLMAKMHSLQSGIFIA.
                   130        140        150        160        170        180
```

The complete length ORF78a nucleotide sequence <SEQ ID 723> is:

```
  1 ATGTTTGCCC TTTTGGAAGC CTTTTTTGTC GAATACGGCT ATGCGGCCGT

51 GTTTTTCGTT TTGGTCATCT GCGGTTTCGG CGTGCCGATT CCCGAGGATT

101 TGACCTTGGT AACAGGCGGC GTGATTTCGG GTATGGGTTA TACCAATCCG

151 CATATTATGT TTGCAGTCGG TATGCTCGGC GTATTGGTCG GGGACGGCAT

201 CATGTTCGCC GCCGGACGCA TCTGGGGGCA GAAAATCCTC AAGTTCAAAC

251 CGATTGCGCG CATCATGACG CCGAAACGTT ACGCACAGGT TCAGGAAAAA

301 TTCGACAAAT ACGGCAACTG GGTGTTATTT GTCGCTCGTT TCCTGCCCGG

351 TTTGCGGACT GCCGTTTTCG TTACCGCCGG CATCAGCCGC AAAGTATCGT

401 ATCTGCGCTT TCTGATTATG GACGGGCTTG CCGCGCTGAT TTCCGTGCCC

451 GTTTGGATTT ACTGGGCGA GTACGGCGCG CACAACATCG ATTGGCTGAT

501 GGCGAAAATG CACAGCCTGC AATCCGGCAT CTTCATCGCA TTGGGCGTGC
```

```
-continued
551 TGGCGGCGGC GCTGGCGTGG TTCTGGTGGC GCAAACGCCG ACATTATCAG

601 CTTTACCGCG CACAATTGAG CGAAAAACGC GCCAAACGCA AGGCGGAAAA

651 GGCAGCGAAA AAGCGGCAC AGAAGCAGCA GTAA
```

This encodes a protein having amino acid sequence <SEQ ID 724>:

```
  1 MFALLEAFFV EYGYAAVFFV LVICGFGVPI PEDLTLVTGG VISGMGYTNP

51 HIMFAVGMLG VLVGDGIMFA AGRIWGQKIL KFKPIARIMT PKRYAQVQEK

101 FDKYGNWVLF VARFLPGLRT AVFVTAGISR KVSYLRFLIM DGLAALISVP

151 VWIYLGEYGA HNIDWLMAKM HSLQSGIFIA LGVLAAALAW FWWRKRRHYQ

201 LYRAQLSEKR AKRKAEKAAK KAAQKQQ*
```

ORF78a and ORF78-1 show 89.0% identity in 227 aa overlap:

```
                       10        20        30        40        50        60
    orf78a.pep  MFALLEAFFVEYGYAAVFFVLVICGFGVPIPEDLTLVTGGVISGMGYTNPHIMFAVGMLG
                ||||:|||||||||||||||||||||||||||||||||||||||||||||||||||||||
    orf78-1     MFAFLEAFFVEYGYAAVFFVLVICGFGVPIPEDLTLVTGGVISGMGYTNPHIMFAVGMLG
                       10        20        30        40        50        60

70        80        90       100       110       120
    orf78a.pep  VLVGDGIMFAAGRIWGQKILKFKPIARIMTPKRYAQVQEKFDKYGNWVLFVARFLPGLRT
                |||||||||||||||||||||:||||||||||||||:|||||||||||||||||||||||
    orf78-1     VLVGDGIMFAAGRIWGQKILRFKPIARIMTPKRYEQVQEKFDKYGNWVLFVARFLPGLRT
                       70        80        90       100       110       120

130       140       150       160       170       180
    orf78a.pep  AVFVTAGISRKVSYLRFLIMDGLAALISVPVWIYLGEYGAHNIDWLMAKMHSLQSGIFIA
                ||||||||||||||||||:|||||||||||:|||||||||||||||||||||||||||:
    orf78-1     AVFVTAGISRKVSYLRFIIMDGLAALISVPIWIYLGEYGAHNIDWLMAKMHSLQSGIFVI
                      130       140       150       160       170       180

190       200       210       220
    orf78a.pep  LGVLAAALAWFWWRKRRHYQLYRAQLSEKRAKRKAEKAAKKAAQKQQX
                ||: |:::||:||:||:: |:||::|:||||:||||||||||:||
    orf78-1     LGIGATVVAWIWWKKRQRIQFYRSKLEKRAQRKAAKAAKKAAQSKQX
                      190       200       210       220
```

Homology with a Predicted ORF from *N. gonorrhoeae*

ORF78 shows 97.4% identity over 38 aa overlap with a predicted ORF (ORF78ng) from *N. gonorrhoeae*:

```
    orf78.pep  XXLXFXPIAXIMTPXRYEQVQEKFDKYGNWVLFVARFLPGLRTAVFVTAGISRKVSYLRF  137
                                  ||||||||||||||||||||||||||||||||
    orf78ng                       YPVLFVARFLPGLRTAVFVTAGISRKVSYLRF   32
    orf78.pep  IIMDGLAA                                                     145
               :|||||||
    orf78ng    LIMDGLAALISVPVWIYLGEYGAHNIDWLMAKMHSLQSGIFIALGVLAAALAWFWWRKRR  92
```

The ORF78ng nucleotide sequence <SEQ ID 725> is predicted to encode a protein comprising amino acid sequence <SEQ ID 726>:

```
  1 ..YPVLFVARFL PGLRTAVFVT AGISRKVSYL RFLIMDGLAA LISVPVWIYL

51    GEYGAHNIDW LMAKMHSLQS GIFIALGVLA AALAWFWWRK RRHYQLYRAQ

101    LSEKRAKRKA EKAAKKAAQKN QQ*
```

Further work revealed the complete gonococcal nucleotide sequence <SEQ ID 727>:

```
  1 atgtttgccc tttTggaagc CTTTTTTGTC GAAtacggCt atgcGGCCGT

51 GTTTTTCGTT TTGGTCATCT GCGGTTTCGG CGTGCCGATT CCCGAAGATT

101 TGACCTTGGT AACGGGCGGC GTGATTTCGG GTATGGGTTA TACCAATCCG

151 CATATTATGT TTGCGGTCGG TATGCTCGGC GTGTTGGCGG GCGACGGCGT

201 GATGTTTGCC GCCGGACGCA TCTGGGGGCA GAAAATCCTC AAGTTCAAAC

251 CGATTGCGCG CATCATGACG CCGAAACGTT ACGCGCAGGT TCAGGAAAAA

301 TTCGACAAAT ACGGCAACTG GGTTCTGTTT GTCGCCCGTT TCCTGCCGGG

351 TTTGCGGACT GCCGTTTTCG TTACCGCCGG CATCAGCCGC AAAGTATCGT

401 ATCTGCGCTT TCTGATTATG GACGGGCTGG CCGCGCTGAT TTCCGTGCCC

451 GTTTGGATTT ACTTGGGCGA GTACGGCGCG CACAACATCG ATTGGCTGAT

501 GGCGAAAATG CACAGCCTGC AATCGGGCAT CTTCATCGCA TTGGGCGTGC

551 TGGCGGCGGC GCTGGCGTGG TTCTGGTGGC GCAAACGCCG ACATTATCAG

601 CTTTACCGCG CACAATTGAG CGAAAAACGC GCCAAACGCA AGGCGGAAAA

651 GGCAGCGAAA AAAGCGGCAC AGAAGCAGCA GTAa
```

This corresponds to the amino acid sequence <SEQ ID 728; ORF78ng-1>:

```
  1 MFALLEAFFV EYGYAAVFFV LVICGFGVPI PEDLTLVTGG VISGMGYTNP

51 HIMFAVGMLG VLAGDGVMFA AGRIWGQKIL KFKPIARIMT PKRYAQVQEK

101 FDKYGNWVLF VARFLPGLRT AVFVTAGISR KVSYLRFLIM DGLAALISVP

151 VWIYLGEYGA HNIDWLMAKM HSLQSGIFIA LGVLAAALAW FWWRKRRHYQ

201 LYRAQLSEKR AKRKAEKAAK KAAQKQQ*
```

ORF78ng-1 and ORF78-1 show 88.1% identity in 227 aa overlap:

```
                    10         20         30         40         50         60
      orf78-1.pep   MFAFLEAFFVEYGYAAVFFVLVICGFGVPIPEDLTLVTGGVISGMGYTNPHIMFAVGMLG
                    |||:||||||||||||||||||||||||||||||||||||||||||||||||||||||||
      orf78ng-1     MFALLEAFFVEYGYAAVFFVLVICGFGVPIPEDLTLVTGGVISGMGYTNPHIMFAVGMLG
                    10         20         30         40         50         60
                    70         80         90        100        110        120
      orf78-1.pep   VLVGDGIMFAAGRIWGQKILRFKPIARIMTPKRYEQVQEKFDKYGNWVLFVARFLPGLRT
                    ||:|||:||||||||||||||:|||||||||||||:||||||||||||||||||||||||
      orf78ng-1     VLAGDGVMFAAGRIWGQKILKFKPIARIMTPKRYAQVQEKFDKYGNWVLFVARFLPGLRT
                    70         80         90        100        110        120
                   130        140        150        160        170        180
      orf78-1.pep   AVFVTAGISRKVSYLRFIIMDGLAALISVPIWIYLGEYGAHNIDWLMAKMHSLQSGIFVI
                    |||||||||||||||||:|||||||||||||:||||||||||||||||||||||||||:
      orf78ng-1     AVFVTAGISRKVSYLRFLIMDGLAALISVPVWIYLGEYGAHNIDWLMAKMHSLQSGIFIA
                   130        140        150        160        170        180
                   190        200        210        220
      orf78-1.pep   LGIGATVVAWIWWKKRQRIQFYRSKLKEKRAQRKAAKAAKKAAQSKQX
                    ||: |:::||:||::  |:||::|:|||||||:|||||||||::||
      orf78ng-1     LGVLAAALAWFWWRKRRHYQLYRAWLSEKRAKRKAEKAAKKAAQKQQX
                   190        200        210        220
```

Furthermore, orf78ng-1 shows homology to the dedA protein from *H. influenzae*:

```
sp|P45280|YG29_HAEIN HYPOTHETICAL PROTEIN HI1629 >gi|1073983|pir||D64133
dedA protein (dedA) homolog - Haemophilus influenzae (strain Rd KW20)
>gi|1574476| (U32836) dedA protein (dedA) [Haemophilus
```

-continued

```
influenzae] Length = 212
Score = 223 bits (563), Expect = 7e-58
Identities = 108/182 (59%), Positives = 140/182 (76%), Gaps = 2/182 (1%)

Query:    5 LEAFFVEYGYAAVFFVLVICGFGVPIPEDLTLVTGGVISGM--GYTNPHIMFAVGMLGVL   62
            L  FF EYGY AV FVL+ICGFGVPIPED+TLV+GGVI+G+     N H+M  V M+GVL
Sbjct:   21 LIGFFTEYGYWAVLFVLIICGFGVPIPEDITLVSGGVIAGLYPENVNSHLMLLVSMIGVL   80

Query:   63 AGDGVMFAAGRIWGQKILKFKPIARIMTPKRYAQVQEKFDKYGNWVLFVARFLPGLRTAV  122
            AGD  M+  GRI+G KIL+F+PI RI+T +R   V+EKF +YGN VLFVARFLPGLR  +
Sbjct:   81 AGDSCMYWLGRIYGTKILRFRPIRRIVTLQRLRMVREKFSQYGNRVLFVARFLPGLRAPI  140

Query:  123 FVTAGISRKVSYLRFLIMDGLAALISVPVWIYLGEYGAHNIDWLMAKMHSLQSGIFIALG  182
            ++  +GI+R+VSY+RF+++D  AA+ISVP+WIYLGE GA N+DWL  ++   Q   I+I +G
Sbjct:  141 YMVSGITRRVSYVRFVLIDFCAAIISVPIWIYLGELGAKNLDWLHTQIQKGQIVIYIFIG  200

Query:  183 VL                                                           184
            L
Sbjct:  201 YL                                                           202
```

Based on this analysis, including the presence of putative transmembrane domains, it is predicted that these proteins from *N. meningitidis* and *N. gonorrhoeae*, and their epitopes, could be useful antigens for vaccines or diagnostics, or for raising antibodies.

Example 87

The following partial DNA sequence was identified in *N. meningitidis* <SEQ ID 729>:

```
  1 ATGAAAAAAT TATTGGCGGC CGTGATGATG GCAGGTTTGG CAGGCGCGGT
 51 TTCCGCCGCC GGAGTCCACG TTGAGGACGG CTGGGCGCGC ACCACCGTCG
101 AAGGTATGAA AATAGGCGGC GCGTTCATGA AAATCCACAA CGACGAAGCC
151 AAACAAGACT TTTTGCTCGG CGGAAGCAGC CCCGTTGCCG ACCGCGTCGA
201 AGTGCATACC CACATCAACG ACAACGGCGT GATGCGGATG CGCGAAGTCG
251 AAGGCGGCGT GCCTTTGGAA GCGAAATCCG TTACCGAACT CAAACCCGGC
301 AGCTATCATG TGATGTTTAT GGGTTTGAAA AAACAATTAA AAGAGGGCGA
351 TAAAATTCCC GTTACCCTGA AATTTAAAAA CGCCAAAGCG CAAACCGTCC
401 AACTGGAAGT CAAAATCGCG CCGATGCCGG CAATGAACCA C...
```

This corresponds to the amino acid sequence <SEQ ID 730; ORF79>:

```
  1 MKKLLAAVMM AGLAGAVSAA GVHVEDGWAR TTVEGMKIGG AFMKIHNDEA
 51 KQDFLLGGSS PVADRVEVHT HINDNGVMRM REVEGGVPLE AKSVTELKPG
101 SYHVMFMGLK KQLKEGDKIP VTLKFKNAKA QTVQLEVKIA PMPAMNH..
```

Further work revealed the complete nucleotide sequence <SEQ ID 731>:

```
  1 ATGAAAAAAT TATTGGCGGC CGTGATGATG GCAGGTTTGG CAGGCGCGGT
 51 TTCCGCCGCC GGAGTCCACG TTGAGGACGG CTGGGCGCGC ACCACCGTCG
101 AAGGTATGAA AATAGGCGGC GCGTTCATGA AAATCCACAA CGACGAAGCC
151 AAACAAGACT TTTTGCTCGG CGGAAGCAGC CCCGTTGCCG ACCGCGTCGA
201 AGTGCATACC CACATCAACG ACAACGGCGT GATGCGGATG CGCGAAGTCG
```

-continued

```
251 AAGGCGGCGT GCCTTTGGAA GCGAAATCCG TTACCGAACT CAAACCCGGC

301 AGCTATCATG TGATGTTTAT GGGTTTGAAA AAACAATTAA AAGAGGGCGA

351 TAAAATTCCC GTTACCCTGA AATTTAAAAA CGCCAAAGCG CAAACCGTCC

401 AACTGGAAGT CAAAATCGCG CCGATGCCGG CAATGAACCA CGGTCATCAC

451 CACGGCGAAG CGCATCAGCA CTAA
```

This corresponds to the amino acid sequence <SEQ ID 732; ORF79-1>:

```
  1 MKKLLAAVMM AGLAGAVSAA GVHVEDGWAR TTVEGMKIGG AFMKIHNDEA

51 KQDFLLGGSS PVADRVEVHT HINDNGVMRM REVEGGVPLE AKSVTELKPG

101 SYHVMFMGLK KQLKEGDKIP VTLKFKNAKA QTVQLEVKIA PMPAMNHGHH

151 HGEAHQH*
```

Computer analysis of this amino acid sequence revealed a putative leader peptide and also gave the following results:

Homology with a Predicted ORF from *N. meningitidis* (Strain A)

ORF79 shows 94.6% identity over a 147aa overlap with an ORF (ORF79a) from strain A of *N. meningitidis*.

```
                    10         20         30         40         50         60
    orf79.pep  MKKLLAAVMMAGLAGAVSAAGVHVEDGWARTTVEGMKIGGAFMKIHNDEAKQDFLLGGSS
               || |||||||||||||||||:||||||||||||||:|||||||||||||||||||||||
    orf79a     MKXLLAAVMMAGLAGAVSAAGIHVEDGWARTTVEGMKMGGAFMKIHNDEAKQDFLLGGSS
                    10         20         30         40         50         60
                    70         80         90        100        110        120
    orf79.pep  PVADRVEVHTHINDNGVMRMREVEGGVPLEAKSVTELKPGSYHVMFMGLKKQLKEGDKIP
               |||||||||||||||||||||||||||||||||||||||||||||| ||||| |||||
    orf79a     PVADRVEVHTHINDNGVMRMREVEGGVPLEAKSVTELKPGSYHVMFMGXKKQLKXGDKIP
                    70         80         90        100        110        120
                   130        140
    orf79.pep  VTLKFKNAKAQTVQLEVKIAPMPAMNH
               |||||||||||||||||||| ||| :|
    orf79a     VTLKFKNAKAQTVQLEVKTAPMSAMDHGHHHGEAHQHX
                   130        140        150
```

The complete length ORF79a nucleotide sequence <SEQ ID 733> is:

```
  1 ATGAAANAAC TATTGGCAGC CGTGATGATG GCAGGTTTGG CAGGCGCGGT

51 TTCCGCCGCC GGAATCCACG TTGAGGACGG CTGGGCGCGC ACCACCGTCG

101 AAGGTATGAA AATGGGCGGC GCGTTCATGA AATCCACAA CGACGAAGCC

151 AAACAAGACT TTTTGCTCGG CGGAAGCAGC CCTGTTGCCG ACCGCGTCGA

201 AGTGCATACC CATATCAATG ATAACGGTGT GATGCGGATG CGCGAAGTCG

251 AAGGCGGCGT GCCTTTGGAG GCGAAATCCG TTACCGAACT CAAACCCGGC

301 AGCTATCATG TCATGTTTAT GGGTNTGAAA AAACAATTAA AAGANGGCGA

351 CAAGATTCCC GTTACCCTGA AATTTAAAAA CGCCAAAGCA CAAACCGTCC

401 AACTGGAAGT CAAAACCGCG CCGATGTCGG CAATGGACCA CGGTCATCAC

451 CACGGCGAAG CGCATCAGCA CTAA
```

This encodes a protein having amino acid sequence <SEQ ID 734>:

```
  1 MKXLLAAVMM AGLAGAVSAA GIHVEDGWAR TTVEGMKMGG AFMKIHNDEA

51 KQDFLLGGSS PVADRVEVHT HINDNGVMRM REVEGGVPLE AKSVTELKPG

101 SYHVMFMGXK KQLKXGDKIP VTLKFKNAKA QTVQLEVKTA PMSAMDHGHH

151 HGEAHQH*
```

ORF79a and ORF79-1 show 94.9% identity in 157 aa overlap:

```
                     10         20         30         40         50         60
    orf79a.pep   MKXLLAAVMMAGLAGAVSAAGIHVEDGWARTTVEGMKMGGAFMKIHNDEAKQDFLLGGSS
                 || ||||||||||||||||||:|||||||||||||||:||||||||||||||||||||||
    orf79-1      MKKLLAAVMMAGLAGAVSAAGVHVEDGWARTTVEGMKIGGAFMKIHNDEAKQDFLLGGSS
                     10         20         30         40         50         60
                     70         80         90        100        110        120
    orf79a.pep   PVADRVEVHTHINDNGVMRMREVEGGVPLEAKSVTELKPGSYHVMFMGXKKQLKXGDKIP
                 |||||||||||||||||||||||||||||||||||||||||||||||| ||||| ||||
    orf79-1      PVADRVEVHTHINDNGVMRMREVEGGVPLEAKSVTELKPGSYHVMFMGLKKQLKEGDKIP
                     70         80         90        100        110        120
                    130        140        150
    orf79a.pep   VTLKFKNAKAQTVQLEVKTAPMSAMDHGHHHGEAHQHX
                 |||||||||||||||||||| |||:|||||||||||||
    orf79-1      VTLKFKNAKAQTVQLEVKIAPMPAMNHGHHHGEAHQHX
                    130        140        150
```

Homology with a Predicted ORF from *N. gonorrhoeae*

ORF79 shows 96.1% identity over 76 aa overlap with a predicted ORF (ORF79ng) from *N. gonorrhoeae*:

```
    orf79.pep   FMKIHNDEAKQDFLLGGSSPVADRVEVHTHINDNGVMRMREVEGGVPLEAKSVTELKPGS  101
                                                |||||||||||:||||||||||||||||||
    orf79ng                                 INDNGVMRMREVKGGVPLEAKSVTELKPGS   30
    orf79.pep   YHVMFMGLKKQLKEGDKIPVTLKFKNAKAQTVQLEVKIAPMPAMNH              147
                |||||||||||||||||||||||||||||||||||||| || ||||
    orf79ng     YHVMFMGLKKQLKEGDKIPVTLKFKNAKAQTVQLEVKTAPMSAMNHGHHHGEAHQH     86
```

An ORF79ng nucleotide sequence <SEQ ID 735> was predicted to encode a protein comprising amino acid sequence <SEQ ID 736>:

```
 1 ..INDNGVMRMR EVKGGVPLEA KSVTELKPGS YHVMFMGLKK QLKEGDKIPV

51    TLKFKNAKAQ TVQLEVKTAP MSAMNHGHHH GEAHQH*
```

Further work revealed the complete gonococcal DNA sequence <SEQ ID 737>:

```
  1 ATGAAAAAAT TATTGGCAGC CGTGATGATG GCAGGTTTGG CAGGCGCGGT

51 TTccgccgCc GGagTccAtG TCGAggACGG CTGGGCGCGc accaCTGtcg 101 aaggtATgaa aatggGCGGC GCgttCATga aaATCCACAA CGACGaaGcc 151 atacaaGACt ttgtgcTCgg CGGaagcatg cccgttgccg accgcGTCGA 201 AGTGCAtaca cacATCAACG ACAACGGCGT GATGCGTATG CGCGAAGTCA

251 AAGGCGGCGT GCCTTTGGAG GCGAAATCCG TTACCGAACT CAAACCCGGC

301 AGCTATCACG TGATGTTTAT GGGTTTGAAA AAACAACTGA AAGAGGGCGA

351 CAAGATTCCC GTTACCCTGA AATTTAAAAA CGCCAAAGCG CAAACCGTCC
```

```
401 AACTGGAAGT CAAAACCGCG CCGATGTCGG CAATGAACCA CGGTCATCAC

451 CACGGCGAAG CGCATCAGCA CTAA
```

This corresponds to the amino acid sequence <SEQ ID 738; ORF79ng-1>:

```
  1 MKKLLAAVMM AGLAGAVSAA GVHVEDGWAR TTVEGMKMGG AFMKIHNDEA

51 IQDFVLGGSM PVADRVEVHT HINDNGVMRM REVKGGVPLE AKSVTELKPG

101 SYHVMFMGLK KQLKEGDKIP VTLKFKNAKA QTVQLEVKTA PMSAMNHGHH

151 HGEAHQH*
```

ORF79ng-1 and ORF79-1 show 95.5% identity in 157 aa overlap:

```
                       10         20         30         40         50         60
      orf79-1.pep  MKKLLAAVMMAGLAGAVSAAGVHVEDGWARTTVEGMKIGGAFMKIHNDEAKQDFLLGGSS
                   |||||||||||||||||||||||||||||||||||:||||||||||| |||:||||
      orf79ng-1    MKKLLAAVMMAGLAGAVSAAGVHVEDGWARTTVEGMKMGGAFMKIHNDEAIQDFVLGGSM
                       10         20         30         40         50         60
                       70         80         90        100        110        120
      orf79-1.pep  PVADRVEVHTHINDNGVMRMREVEGGVPLEAKSVTELKPGSYHVMFMGLKKQLKEGDKIP
                   |||||||||||||||||||||||:||||||||||||||||||||||||||||||||||||
      orf79ng-1    PVADRVEVHTHINDNGVMRMREVKGGVPLEAKSVTELKPGSYHVMFMGLKKQLKEGDKIP
                       70         80         90        100        110        120
                      130        140        150
      orf79-1.pep  VTLKFKNAKAQTVQLEVKIAPMPAMNHGHHHGEAHQHX
                   |||||||||||||||||||| ||| ||||||||||||
      orf79ng-1    VTLKFKNAKAQTVQLEVKTAPMSAMNHGHHHGEAHQHX
                      130        140        150
```

Furthermore, ORF79ng-1 shows significant homology to a protein from *Aquifex aeolicus*:

```
gi|2983695 (AE000731) putative protein [Aquifex aeolicus] Length = 151
Score = 63.6 bits (152), Expect = 6e-10
Identities = 38/114 (33%), Positives = 58/114 (50%), Gaps = 1/114 (0%)

Query:  24 VEDGWARTTVEGMKMGGAFMKIHNDEAIQDFVLGGSMPVADRVEVHTHINDNGVMRMREV    83
           V+  W       G     M I N+    D+++G    +A RVE+H  + +N V +M
Sbjct:  27 VKHPWVMEPPPGPNTTMMGMIIVNEGDEPDYLIGAKTDIAQRVELHKTVIENDVAKMVPQ    86

Query:  84 KGGVPLEAKSVTELKPGSYHVMFMGLKKQLKEGDKIPVTLKFKNAKAQTVQLEV       137
           + + +   K    E K   YHVM +GLKK++KEGDK+ V L F+ +   TV+  V
Sbjct:  87 ER-IEIPPKGKVEFKHHGYHVMIIGLKKRIKEGDKVKVELIFEKSGKITVEAPV       139
```

Based on this analysis, it is predicted that the proteins from *N. meningitidis* and *N. gonorrhoeae*, and their epitopes, could be useful antigens for vaccines or diagnostics, or for raising antibodies.

ORF79-1 (15.6 kDa) was cloned in the pET vector and expressed in *E. coli*, as described above. The products of protein expression and purification were analyzed by SDS-PAGE. FIG. 18A shows the results of affinity purification of the His-fusion protein. Purified His-fusion protein was used to immunise mice, whose sera were used for ELISA (positive result) and FACS analysis (FIG. 18B) These experiments confirm that ORF79-1 is a surface-exposed protein, and that it is a useful immunogen.

Example 88

The following DNA sequence, believed to be complete, was identified in *N. meningitidis* <SEQ ID 739>:

```
  1 ATGACGGTAA CTGCGGCCGA AGGCGGCAAA GCTGCCAAGG CGTTAAAAAA

51 ATATCTGATT ACGGGCATTT TGGTCTGGCT GCCGATTGCG GTAACGGTTT

101 GGGTGGTTTC CTATATCGTT TCCGCGTCCG ATCAGCTCGT CAACCTGCTG

151 CCGAAGCAAT GGCGGCCGCA ATATGTTTTG GGGTTTAATA TCCCGGGGCT

201 GGGCGTTATC GTTGCCATTG CCGTATTGTT TGTAACCGGA TTGTTTGCCG
```

-continued

```
251 CCAACGTATT GGGTCGGCAG ATCCTCGCCG CGTGGGACAG CCTGTTGGGG

301 CGGATTCCGG TTGTGAAAtC CATCTATTCG AGTGTGAAAA AAGTATCCGA

351 ATacgTGCTG TCCGACAGCA GCCGTTCGTT TAAAACGCCG GTACTCGTGC

401 CGTTTCCCCA GCCCGGTATT TGGACGATyG CTTTCGTGTC AGGGCAGGTG

451 TCGAATGCGG TTAAGGCCGC ATTGCCGAAs GACGGCGATT ATCTTTCCGT

501 GTATGTTCCG ACCACGCCGA ATCCGACCGG CGGTTACTAT ATTATGGTAA

551 AGAAAAGCGA TGTGCGCGAA CTCGATATGA GCGTGGACGA AsCATTGAAA

601 TATGTGATTT CGCTGGGTAT GGTCATCCCT GACGACCTGC CCGTCAAAAC

651 ATTGGCAsGA CCTATGCCGT CTGAAAAGGC GGATTTGCCC GAACAACAAT

701 AA
```

This corresponds to the amino acid sequence <SEQ ID 740; ORF98>:

```
  1 MTVTAAEGGK AAKALKKYLI TGILVWLPIA VTVWVVSYIV SASDQLVNLL

51 PKQWRPQYVL GFNIPGLGVI VAIAVLFVTG LFAANVLGRQ ILAAWDSLLG

101 RIPVVKSIYS SVKKVSEYVL SDSSRSFKTP VLVPFPQPGI WTIAFVSGQV

151 SNAVKAALPX DGDYLSVYVP TTPNPTGGYY IMVKKSDVRE LDMSVDEXLK

201 YVISLGMVIP DDLPVKTLAX PMPSEKADLP EQQ*
```

Further work revealed the complete nucleotide sequence <SEQ ID 741>:

```
  1 ATGACGGAAC nTGCGGCCGA AGGCGGCAAA GCTGCCAArG CGTTAAAAAA

51 ATATCTGATT ACGGGCATTT TGGTCTGGCT GCCGATTGCG GTAACGGTTT

101 GGGTGGTTTC CTATATCGTT TCCGCGTCCG ATCAGCTCGT CAACCTGCTG

151 CCGAAGCAAT GGCGGCCGCA ATATGTTTTG GGGTTTAATA TCCCGGGGCT

201 GGGCGTTATC GTTGCCATTG CCGTATTGTT TGTAACCGGA TTGTTTGCCG

251 CCAACGTATT GGGTCGGCAG ATCCTCGCCG CGTGGGACAG CCTGTTGGGG

301 CGGATTCCGG TTGTGAAATC CATCTATTCG AGTGTGAAAA AAGTATCCGA

351 ATCGCTGCTG TCCGACAGCA GCCGTTCGTT TAAAACGCCG GTACTCGTGC

401 CGTTTCCCCA GCCCGGTATT TGGACGATTG CTTTCGTGTC AGGGCAGGTG

451 TCGAATGCGG TTAAGGCCGC ATTGCCGAAG GACGGCGATT ATCTTTCCGT

501 GTATGTTCCG ACCACGCCGA ATCCGACCGG CGGTTACTAT ATTATGGTAA

551 AGAAAAGCGA TGTGCGCGAA CTCGATATGA GCGTGGACGA AGCATTGAAA

601 TATGTGATTT CGCTGGGTAT GGTCATCCCT GACGACCTGC CCGTCAAAAC

651 ATTGGCAGGA CCTATGCCGT CTGAAAAGGC GGATTTGCCC GAACAACAAT

701 AA
```

This corresponds to the amino acid sequence <SEQ ID 742; ORF98-1>:

```
 1 MTEXAAEGGK AAKALKKYLI TGILVWLPIA VTVWVVSYIV SASDQLVNLL

51 PKQWRPQYVL GFNIPGLGVI VAIAVLFVTG LFAANVLGRQ ILAAWDSLLG
```

-continued

```
101 RIPVVKSIYS SVKKVSESLL SDSSRSFKTP VLVPFPQPGI WTIAFVSGQV

151 SNAVKAALPK DGDYLSVYVP TTPNPTGGYY IMVKKSDVRE LDMSVDEALK

201 YVISLGMVIP DDLPVKTLAG PMPSEKADLP EQQ*
```

Computer analysis of this amino acid sequence gave the following results:

Homology with a Predicted ORF from *N. meningitidis* (Strain A)

ORF98 shows 96.1% identity over a 233aa overlap with an ORF (ORF98a) from strain A of *N. meningitidis*.

```
                    10        20        30        40        50        60
orf98.pep  MTVTAAEGGKAAKALKKYLITGILVWLPIAVTVWVVSYIVSASDQLVNLLPKQWRPQYVL
           ||  ||||||||||||||||||||||||||||||||||||||||||||||||||||||||
orf98a     MTEPAAEGGKAAKALKKYLITGILVWLPIAVTVWVVSYIVSASDQLVNLLPKQWRPQYVL
                    10        20        30        40        50        60
                    70        80        90       100       110       120
orf98.pep  GFNIPGLGVIVAIAVLFVTGLFAANVLGRQILAAWDSLLGRIPVVKSIYSSVKKVSEYVL
           |||||||||||||||||||||||||||||||||||||||||||||||||||||||| :|
orf98a     GFNIPGLGVIVAIAVLFVTGLFAANVLGRQILAAWDSLLGRIPVVKSIYSSVKKVSXSLL
                    70        80        90       100       110       120
                   130       140       150       160       170       180
orf98.pep  SDSSRSFKTPVLVPFPQPGIWTIAFVSGQVSNAVKAALPXDGDYLSVYVPTTPNPTGGYY
           ||||||||||||||||| ||||||||||||||||||||| ||||||||||||||||||||
orf98a     SDSSRSFKTPVLVPFPQSGIWTIAFVSGQVSNAVKAALPKDGDYLSVYVPTTPNPTGGYY
                   130       140       150       160       170       180
                   190       200       210       220
orf98.pep  IMVKKSDVRELDMSVDEXLKYVISLGMVIPDDLPVKTLAXPMPSEKADLPEQQX
           ||||||||||||||||||| |||||||||||||||||| |||||||||||||||
orf98a     IMVKKSDVRELDMSVDEALKYVISLGMVIPDDLPVKTLAGPMPSEKADLPEQQX
                   190       200       210       220
```

The complete length ORF98a nucleotide sequence <SEQ ID 743> is:

```
  1 ATGACGGAAC CTGCGGCCGA AGGCGGCAAA GCTGCCAAGG CGTTAAAAAA

51 ATATCTGATT ACGGGCATTT TGGTCTGGCT GCCGATTGCG GTAACGGTTT

101 GGGTGGTTTC CTATATCGTT CCGCGTCCG ATCAGCTCGT CAACCTGCTG

151 CCGAAGCAAT GGCGGCCGCA ATATGTTTTG GGGTTTAATA TCCCGGGGCT

201 GGGCGTTATC GTTGCCATTG CCGTATTGTT TGTAACCGGA TTATTTGCCG

251 CAAACGTATT GGGCCGGCAG ATTCTTGCCG CGTGGGACAG CTTGTTGGGG

301 CGGATTCCGG TTGTGAAGTC CATCTATTCG AGTGTGAAAA AAGTATCCGA

351 NTCGTTGCTG TCCGACAGCA GCCGTTCGTT TAAAACACCA GTACTCGTGC

401 CGTTTCCCCA ATCGGGTATT TGGACAATCG CATTCGTGTC CGGTCAGGTG

451 TCGAATGCGG TTAAGGCCGC ATTGCCGAAG GACGGCGATT ATCTTTCCGT

501 GTATGTTCCG ACCACGCCGA ATCCGACCGG CGGTTACTAT ATTATGGTAA

551 AGAAAAGCGA TGTGCGCGAA CTCGATATGA GCGTGGACGA AGCGTTGAAA

601 TATGTGATTT CGCTGGGTAT GGTCATCCCT GACGACCTGC CCGTCAAAAC

651 ATTGGCAGGA CCTATGCCGT CTGAAAAGGC GGATTTGCCC GAACAACAAT

701 AA
```

This encodes a protein having amino acid sequence <SEQ ID 744>:

```
  1 MTEPAAEGGK AAKALKKYLI TGILVWLPIA VTVWVVSYIV SASDQLVNLL

51 PKQWRPQYVL GFNIPGLGVI VAIAVLFVTG LFAANVLGRQ ILAAWDSLLG

101 RIPVVKSIYS SVKKVSXSLL SDSSRSFKTP VLVPFPQSGI WTIAFVSGQV

151 SNAVKAALPK DGDYLSVYVP TTPNPTGGYY IMVKKSDVRE LDMSVDEALK

201 YVISLGMVIP DDLPVKTLAG PMPSEKADLP EQQ*
```

ORF98a and ORF98-1 show 98.7% identity in 233 aa overlap:

```
                    10         20         30         40         50         60
    orf98a.pep  MTEPAAEGGKAAKALKKYLITGILVWLPIAVTVWVVSYIVSASDQLVNLLPKQWRPQYVL
                ||| |||||||||||||||||||||||||||||||||||||||||||||||||||||||
    orf98-1     MTEXAAEGGKAAKALKKYLITGILVWLPIAVTVWVVSYIVSASDQLVNLLPKQWRPQYVL
                    10         20         30         40         50         60
                    70         80         90        100        110        120
    orf98a.pep  GFNIPGLGVIVAIAVLFVTGLFAANVLGRQILAAWDSLLGRIPVVKSIYSSVKKVSXSLL
                |||||||||||||||||||||||||||||||||||||||||||||||||||||||| |||
    orf98-1     GFNIPGLGVIVAIAVLFVTGLFAANVLGRQILAAWDSLLGRIPVVKSIYSSVKKVSESLL
                    70         80         90        100        110        120
                   130        140        150        160        170        180
    orf98a.pep  SDSSRSFKTPVLVPFPQSGIWTIAFVSGQVSNAVKAALPKDGDYLSVYVPTTPNPTGGYY
                ||||||||||||||||| ||||||||||||||||||||||||||||||||||||||||||
    orf98-1     SDSSRSFKTPVLVPFPQPGIWTIAFVSGQVSNAVKAALPKDGDYLSVYVPTTPNPTGGYY
                   130        140        150        160        170        180
                   190        200        210        220        230
    orf98a.pep  IMVKKSDVRELDMSVDEALKYVISLGMVIPDDLPVKTLAGPMPSEKADLPEQQX
                ||||||||||||||||||||||||||||||||||||||||||||||||||||||
    orf98-1     IMVKKSDVRELDMSVDEALKYVISLGMVIPDDLPVKTLAGPMPSEKADLPEQQX
                   190        200        210        220        230
```

Homology with a Predicted ORF from *N. gonorrhoeae*

ORF98 shows 95.3% identity over a 233 aa overlap with a predicted ORF (ORF98ng) from *N. gonorrhoeae*:

```
                    10         20         30         40         50         60
    orf98.pep   MTVTAAEGGKAAKALKKYLITGILVWLPIAVTVWVVSYIVSASDQLVNLLPKQWRPQYVL   60
                ||  ||||||||||||||||||||||||||||||||||||||||||||||||||||||||
    orf98ng     MTEPAAEGGKAAKALKKYLITGILVWLPIAVTVWVVSYIVSASDQLVNLLPKQWRPQYVL   60
    orf98.pep   GFNIPGLGVIVAIAVLFVTGLFAANVLGRQILAAWDSLLGRIPVVKSIYSSVKKVSEYVL  120
                |||||||||||||||||||||||||||||||||||||||| ||||||||||||||| :|
    orf98ng     GFNIPGLGVIVAIAVLFVTGLFAANVLGRQILAAWDSLLXRIPVVKSIYSSVKKVSESLL  120
    orf98.pep   SDSSRSFKTPVLVPFPQPGIWTIAFVSGQVSNAVKAALPXDGDYLSVYVPTTPNPTGGYY  180
                |||||||||||||||||| |||||||||||||||||||| ||||||||||||||||||||
    orf98ng     SDSSRSFKTPVLVPFPQSGIWTIAFVSGQVSNAVKAALPQDGDYLSVYVPTTPNPTGGYY  180
    orf98.pep   IMVKKSDVRELDMSVDEXLKYVISLGMVIPDDLPVKTLAXPMPSEKADLPEQQ         233
                |||||||||||||||||| |||||||||||||||||||| ||| ||| :||||
    orf98.pep   IMVKKSDVRELDMSVDEALKYVISLGMVIPDDLPVKTLAGPMPPEKAELPEQQ         233
```

The complete length ORF98ng nucleotide sequence <SEQ ID 745> is predicted to encode a protein having amino acid sequence <SEQ ID 746>:

```
  1 MTEPAAEGGK AAKALKKYLI TGILVWLPIA VTVWVVSYIV SASDQLVNLL

51 PKQWRPQYVL GFNIPGLGVI VAIAVLFVTG LFAANVLGRQ ILAAWDSLLX

101 RIPVVKSIYS SVKKVSESLL SDSSRSFKTP VLVPFPQSGI WTIAFVSGQV

151 SNAVKAALPQ DGDYLSVYVP TTPNPTGGYY IMVKKSDVRE LDMSVDEALK

201 YVISLGMVIP DDLPVKTLAG PMPPEKAELP EQQ*
```

Further work revealed the complete nucleotide sequence <SEQ ID 747>:

```
  1 ATGACGGAAC CTGCGGCCGA AGGCGGCAAA GCTGCCAAGG CGTTAAAAAA

51 ATATCTGATT ACAGGCATTT TGGTCTGGCT GCCGATTGCG GTAACGGTTT

101 GGGTGGTTTC CTATATCGTT TCCGCGTCCG ACCAGCTTGT CAACCTGCTG

151 CCGAAGCAAT GGCGGCCGCA ATATGTTTTG GGGTTTAATA TCCCCGGGCT

201 CGGCGTTATT GTTGCCATTG CCGTATTGTT TGTAACCGGA TTATTTGCCG

251 CAAACGTGTT GGGCCGGCAG ATTCTTGCCG CGTGGGACAG CCTGTTgggg 301 cggaTTCCGG TTGTCAAATC CATCTATTCG AGTGTGAAAA AAGTATCCGA

351 ATCGCTGCTG TCCGACAGCA GCCGTTCGTT TAAAACGCCG GTACTCGTGC

401 CGTTTCCCCA ATCGGGTATT TGGACAATCG CATTCGTGTC CGGTCAGGTG

451 TCGAATGCGG TTAAGGCCGC ATTGCCGCAG GATGGCGATT ATCTTTCCGT

501 GTATGTCCCG ACCACGCCCA ACCCGACCGG CGGTTACTAT ATTATGGTAA

551 AGAAAAGCGA TGTGCGCGAA CTCGATATGA GCGTGGACGA AGCGTTGAAA

601 TATGTGATTT CGCTGGGTAT GGTCATCCCT GACGACCTGC CCGTCAAAAC

651 ATTGGCAGGA CCTATGCCGC CTGAAAAGGC GGAGTTGCCC GAACAACAAT

701 AA
```

This corresponds to the amino acid sequence <SEQ ID 748; ORF98ng-1>:

```
  1 MTEPAAEGGK AAKALKKYLI TGILVWLPIA VTVWVVSYIV SASDQLVNLL

51 PKQWRPQYVL GFNIPGLGVI VAIAVLFVTG LFAANVLGRQ ILAAWDSLLG

101 RIPVVKSIYS SVKKVSESLL SDSSRSFKTP VLVPFPQSGI WTIAFVSGQV

151 SNAVKAALPQ DGDYLSVYVP TTPNPTGGYY IMVKKSDVRE LDMSVDEALK

201 YVISLGMVIP DDLPVKTLAG PMPPEKAELP EQQ*
```

ORF98ng-1 and ORF98-1 show 97.9% identity in 233 aa overlap:

```
                       10         20         30         40         50         60
    orf98-1.pep  MTEXAAEGGKAAKALKKYLITGILVWLPIAVTVWVVSYIVSASDQLVNLLPKQWRPQYVL
                 ||| ||||||||||||||||||||||||||||||||||||||||||||||||||||||||
    orf98ng-1    MTEPAAEGGKAAKALKKYLITGILVWLPIAVTVWVVSYIVSASDQLVNLLPKQWRPQYVL
                       10         20         30         40         50         60

70         80         90        100        110        120
    orf98-1.pep  GFNIPGLGVIVAIAVLFVTGLFAANVLGRQILAAWDSLLGRIPVVKSIYSSVKKVSESLL
                 ||||||||||||||||||||||||||||||||||||||||||||||||||||||||||||
    orf98ng-1    GFNIPGLGVIVAIAVLFVTGLFAANVLGRQILAAWDSLLGRIPVVKSIYSSVKKVSESLL
                       70         80         90        100        110        120

130        140        150        160        170        180
    orf98-1.pep  SDSSRSFKTPVLVPFPQPGIWTIAFVSGQVSNAVKAALPKDGDYLSVYVPTTPNPTGGYY
                 ||||||||||||||||| |||||||||||||||||||||:||||||||||||||||||||
    orf98ng-1    SDSSRSFKTPVLVPFPQSGIWTIAFVSGQVSNAVKAALPQDGDYLSVYVPTTPNPTGGYY
                      130        140        150        160        170        180

190        200        210        220        230
    orf98-1.pep  IMVKKSDVRELDMSVDEALKYVISLGMVIPDDLPVKTLAGPMPSEKADLPEQQX
                 |||||||||||||||||||||||||||||||||||||||||||:|||:|||||
    orf98ng-1    IMVKKSDVRELDMSVDEALKYVISLGMVIPDDLPVKTLAGPMPPEKAELPEQQX
                      190        200        210        220        230
```

Based on this analysis, including the fact that the putative transmembrane domains in the gonococcal protein are identical to the sequences in the meningococcal protein, it is predicted that the proteins from N. meningitidis and N. gonorrhoeae, and their epitopes, could be useful antigens for vaccines or diagnostics, or for raising antibodies.

Example 89

The following partial DNA sequence was identified in *N. meningitidis* <SEQ ID 749>:

```
   1 ATgAAAACGG TAGTCTGGAT TGTCGTCCTG TTTGCCGCCG CCGTCGGACT
  51 GGCGCTGGCT TCGGGCATTT ACACCGGCGA CGTGTATATC GTACTCGGAC
 101 AGACCATGCT CAGAATCAAC CTGCACGCCT TTGTGTTAGG TTCGCTGATT
 151 GCCGTCGTGG TGTGGTATTT CTTGTTTAAA TTCATTATCG GsGgTACTCA
 201 ATATCCCCGA AAAGATGCAG CGTTTCGGTT CGGCnCGTAA AGGCCkCAAG
 251 ssCGsGCTTG CCTTGAACAA GGCGGGTTTG GCGTATTTTG AAGGGCGTTT
 301 TGAAAAGGCG GAACTAGAAG CCTCACGCGT GTTGGTCAAC AAAGtAGGCC
 351 GaGAGACAAC CGGACTTTGG CATTGATGCT GrGCGCGCAC GCCGCCGGAC
 401 AGATGGAAAA CATCGAssTG CGCGACCGTT ATCTTGCGGA AATCGCCAAA
 451 CTGCCGGAAA AACAGCAGCT TTCCCGTTAT CTTTTGTTGG CGGAATCGGC
 501 GTTGAACCGG CGCGATTACG AAGCGGCGGA AGCCAATCTT CATGCGGCGG
 551 CGAAGATGAA TGCCAACCTT ACGCGCCTCG TGCGTCTGCA .ATTCGTTAC
 601 GCTTTCGACA GGGGCGACGC GTTGCAGGTT CTGGCAAAAA CCGAAAAACT
 651 TTCCAAGGCG GGCGCGTTGG GCAAATCGGA AATGGAACGG TATCAAAATT
 701 GGGCATATCC GTCGCCAGCT GGCGGATGCT GCCGATGCCG CCGCTTTGAA
 751 AACCTGCCTG AAGCGGATTC CCGACAGCCT CAAAAACGGG GAATTGAGCG
 801 TATCGGTTGC GGAAAAGTAC GAACGTTTGG GACTGTATGC CGATGCGGTC
 851 AAATGGGTCA AACAGCATTA TCCGCAsAAC CGCCGCCCCG AGCTTTTGGA
 901 AGCCTTTGTC GAAAGCGTGC GCTTTTTGGG CGAGCGCGAA CAGCAGAAAG
 951 CCATCGATTT TGCCGATGCT TGGCTGAAAG AACAGCCCGA TAACGCGCTT
1001 CTGCTGATGT ATCTCGGTCG GCTCGCCTTC GGCCGCAAAC TTTGGGGCAA
1051 GGCAAAAGGC TACCTTGAAG CGAGCATTGC ATTAAAGCCG AGTATTTCCG
1101 CGCGTTTGGT TCTAACAAAG GTTTTCGACG AAATCGGAGA ACCGCAGAAG
1151 GCGGAGGCGC AC...
```

This corresponds to the amino acid sequence <SEQ ID 750; ORF100>:

```
  1 MKTVVWIVVL FAAAVGLALA SGIYTGDVYI VLGQTMLRIN LHAFVLGSLI

51 AVVVWYFLFK FIIGVLNIPE KMQRFGSARK GXKXXLALNK AGLAYFEGRF

101 EKAELEASRV LVNKVGRDNR TLALMLXAHA AGQMENIXXR DRYLAEIAKL

151 PEKQQLSRYL LLAESALNRR DYEAAEANLH AAAKMNANLT RLVRLXIRYA

201 FDRGDALQVL AKTEKLSKAG ALGKSEMERY QNWAYRRQLA DAADAAALKT

251 CLKRIPDSLK NGELSVSVAE KYERLGLYAD AVKWVKQHYP XNRRPELLEA

301 FVESVRFLGE REQQKAIDFA DAWLKEQPDN ALLLMYLGRL AFGRKLWGKA

351 KGYLEASIAL KPSISARLVL TKVFDEIGEP QKAEAH...
```

Further work revealed the complete nucleotide sequence <SEQ ID 751>:

```
   1 ATGAAAACGG TAGTCTGGAT TGTCGTCCTG TTTGCCGCCG CCGTCGGACT
  51 GGCGCTGGCT TCGGGCATTT ACACCGGCGA CGTGTATATC GTACTCGGAC
 101 AGACCATGCT CAGAATCAAC CTGCACGCCT TTGTGTTAGG TTCGCTGATT
 151 GCCGTCGTGG TGTGGTATTT CTTGTTTAAA TTCATTATCG GCGTACTCAA
 201 TATCCCCGAA AAGATGCAGC GTTTCGGTTC GGCGCGTAAA GGCCGCAAGG
 251 CCGCGCTTGC CTTGAACAAG GCGGGTTTGG CGTATTTTGA AGGGCGTTTT
 301 GAAAAGGCGG AACTAGAAGC CTCACGCGTG TTGGTCAACA AGGAGGCCGG
 351 AGACAACCGG ACTTTGGCAT TGATGCTGGG CGCGCACGCC GCCGGACAGA
 401 TGGAAAACAT CGAGCTGCGC GACCGTTATC TTGCGGAAAT CGCCAAACTG
 451 CCGGAAAAAC AGCAGCTTTC CCGTTATCTT TGTTGGCGG AATCGGCGTT
 501 GAACCGGCGC GATTACGAAG CGGCGGAAGC CAATCTTCAT GCGGCGGCGA
 551 AGATGAATGC CAACCTTACG CGCCTCGTGC GTCTGCAACT TCGTTACGCT
 601 TTCGACAGGG GCGACGCGTT GCAGGTTCTG GCAAAAACCG AAAAACTTTC
 651 CAAGGCGGGC GCGTTGGGCA AATCGGAAAT GGAACGGTAT CAAAATTGGG
 701 CATACCGCCG CCAGCTGGCG GATGCTGCCG ATGCCGCCGC TTTGAAAACC
 751 TGCCTGAAGC GGATTCCCGA CAGCCTCAAA ACGGGGAAT TGAGCGTATC
 801 GGTTGCGGAA AAGTACGAAC GTTTGGGACT GTATGCCGAT GCGGTCAAAT
 851 GGGTCAAACA GCATTATCCG CACAACCGCC GCCCCGAGCT TTTGGAAGCC
 901 TTTGTCGAAA GCGTGCGCTT TTTGGGCGAG CGCGAACAGC AGAAAGCCAT
 951 CGATTTTGCC GATGCTTGGC TGAAAGAACA GCCCGATAAC GCGCTTCTGC
1001 TGATGTATCT CGGTCGGCTC GCCTACGGCC GCAAACTTTG GGGCAAGGCA
1051 AAAGGCTACC TTGAAGCGAG CATTGCATTA AAGCCGAGTA TTTCCGCGCG
1101 TTTGGTTCTA GCAAAGGTTT TCGACGAAAT CGGAGAACCG CAGAAGGCGG
1151 AGGCGCAGCG CAACTTGGTT TTGGAAGCCG TCTCCGATGA CGAACGTCAC
1201 GCAGCGTTAG AGCAGCATAG CTGA
```

This corresponds to the amino acid sequence <SEQ ID 752; ORF100-1>:

```
   1 MKTVVWIVVL FAAAVGLALA SGIYTGDVYI VLGQTMLRIN LHAFVLGSLI
  51 AVVVWYFLFK FIIGVLNIPE KMQRFGSARK GRKAALALNK AGLAYFEGRF
 101 EKAELEASRV LVNKEAGDNR TLALMLGAHA AGQMENIELR DRYLAEIAKL
 151 PEKQQLSRYL LAESALNRR DYEAAEANLH AAAKMNANLT RLVRLQLRYA
 201 FDRGDALQVL AKTEKLSKAG ALGKSEMERY QNWAYRRQLA DADAAALKT
 251 CLKRIPDSLK NGELSVSVAE KYERLGLYAD AVKWVKQHYP HNRRPELLEA
 301 FVESVRFLGE REQQKAIDFA DAWLKEQPDN ALLLMYLGRL AYGRKLWGKA
 351 KGYLEASIAL KPSISARLVL AKVFDEIGEP QKAEAQRNLV LEAVSDDERH
 401 AALEQHS*
```

Computer analysis of this amino acid sequence gave the following results:

Homology with a Predicted ORF from *N. meningitidis* (Strain A)

ORF100 shows 93.5% identity over a 386aa overlap with an ORF (ORF100a) from strain A of *N. meningitidis*.

```
                     10         20         30         40         50         60
    orf100.pep  MKTVVWIVVLFAAAVGLALASGIYTGDVYIVLGQTMLRINLHAFVLGSLIAVVVWYFLFK
                ||||||||||||| ||||||||| |||||||||||||||||||||||||||||||||||
    orf100a     MKTVVWIVVLFAAAXGLALASGIXTGDVYIVLGQTMLRINLHAFVLGSLIAVVVWYFLFK
                     10         20         30         40         50         60

70         80         90        100        110        120
    orf100.pep  FIIGVLNIPEKMQRFGSARKGXKXXLALNKAGLAYFEGRFEKAELEASRVLVNKVGRDNR
                ||||||| ||||||||||||| |  |||||||||||||||||||||||||| : |||
    orf100a     FIIGVLNXPEKMQRFGSARKGRKAALALNKAGLAYFEGRFEKAELEASRVLGNKEAGDNR
                     70         80         90        100        110        120

130        140        150        160        170        180
    orf100.pep  TLALMLXAHAAGQMENIXXRDRYLAEIAKLPEKQQLSRYLLLAESALNRRDYEAAEANLH
                |||||| |||||||||| |||||||||||||||||||||||||||||||||||||||||
    orf100a     TLALMLGAHAAGQMENIELRDRYLAEIAKLPEKQQLSRYLLLAESALNRRDYEAAEANLH
                    130        140        150        160        170        180

190        200        210        220        230        240
    orf100.pep  AAAKMNANLTRLVRLXIRYAFDRGDALQVLAKTEKLSKAGALGKSEMERYQNWAYRRQLA
                |||||||||||||||:||||||||||||||||||| |||| |||||||||||||||||
    orf100a     AAAKMNANLTRLVRLQLRYAFDRGDALQVLAKTEKXSKAGAXGKSEMERYQNWAYRRQLX
                    190        200        210        220        230        240

250        260        270        280        290        300
    orf100.pep  DAADAAALKTCLKRIPDSLKNGELSVSVAEKYERLGLYADAVKWVKQHYPXNRRPELLEA
                ||||||||||||||||||||||||||||||||||||||||||||||||||| ||||||
    orf100a     DAADAAALKTCLKRIPDSLKNGELSVSVAEKYERLGLYADAVKWVKQHYPHNRRPELLEA
                    250        260        270        280        290        300

310        320        330        340        350        360
    orf100.pep  FVESVRFLGEREQQKAIDFADAWLKEQPDNALLLMYLGRLAFGRKLWGKAKGYLEASIAL
                |||||||||:|||||||||||||||||||||||| ||||:||||||||||||||||||
    orf100a     FVESVRFLGERDQQKAIDFADAWLKEQPDNALLLXYLGRLAYGRKLWGKAKGYLEASIAL
                    310        320        330        340        350        360

370        380
    orf100.pep  KPSISARLVLTKVFDEIGEPQKAEAH
                |||||||||| :||||| ||||||| :
    orf100a     KPSISARLVLAKVFDETGEPQKAEAQRNLVLASVAEENRPSAETHX
                    370        380        390        400
```

The complete length ORF100a nucleotide sequence <SEQ ID 753>

```
  1  ATGAAAACGG TAGTCTGGAT TGTCGTCCTG TTTGCCGCCG CNNTCGGGCT
 51  GGCATTGGCG TCGGGCATTN ACACCGGCGA CGTGTATATC GTACTCGGAC
101  AGACCATGCT CAGAATCAAC CTGCACGCCT TTGTGTTAGG TTCGCTGATT
151  GCCGTCGTGG TGTGGTATTT CCTGTTCAAA TTCATCATCG GCGTACTCAA
201  TANCCCCGAA AAGATGCAGC GTTTCGGTTC GGCGCGTAAA GGCCGCAAGG
251  CCGCGCTTGC TTTGAACAAG GCGGGTTTGG CGTATTTTGA AGGGCGTTTT
301  GAAAAGGCGG AACTTGAAGC CTCGCGCGTA TTGGGAAACA AAGAGGCGGG
351  GGATAACCGG ACTTTGGCAT TGATGTTGGG CGCACATGCC GCCGGGCAGA
401  TGGAAAACAT CGAGCTGCGC GACCGTTATC TTGCGGAAAT CGCCAAACTG
451  CCGGAAAAGC AGCAGCTTTC CCGTTATCTT TTGTTGGCGG AATCGGCGTT
501  GAACCGGCGC GATTACGAAG CGGCGGAAGC CAATCTTCAT GCGGCGGCGA
551  AGATGAATGC AACCTTACG CGCCTCGTGC GTCTGCAACT TCGTTACGCT
601  TTCGACAGGG GCGACGCGTT GCAGGTTCTG GCAAAAACCG AAAAANTTTC
651  CAAGGCGGGC GCGTNGGGCA AATCGGAAAT GGAACGGTAT CAAAATTGGG
701  CATACCGCCG CCAGCTGNCG GATGCTGCCG ATGCCGCCGC TTTGAAAACC
751  TGCCTGAAGC GGATTCCCGA CAGCCTCAAA AACGGGGAAT TGAGCGTATC
```

-continued

```
 801 GGTTGCGGAA AAGTACGAAC GTTTGGGACT GTATGCCGAT GCGGTCAAAT
 851 GGGTCAAACA GCATTATCCG CACAACCGCC GACCCGAACT TTTGGAAGCN
 901 TTTGTCGAAA GCGTGCGCTT TTTGGGCGAA CGCGATCAGC AGAAAGCCAT
 951 CGATTTTGCC GATGCTTGGC TGAAAGAACA GCCCGATAAT GCGCTTCTGC
1001 TGANGTATCT CGGTCGGCTC GCCTACGGCC GCAAACTTTG GGGCAAGGCA
1051 AAAGGCTACC TTGAAGCGAG CATTGCATTA AAGCCGAGTA TTTCCGCGCG
1101 TTTGGTTCTG GCAAAGGTTT TTGACGAAAC CGGAGAACCG CAGAAGGCGG
1151 AGGCGCAGCG CAACTTGGTT TTGGCAAGCG TTGCCGAGGA AAACCGNCCT
1201 TCCGCCGAAA CCCATTGA
```

This encodes a protein having amino acid sequence <SEQ ID 754>:

```
  1 MKTVVWIVVL FAAAXGLALA SGIXTGDVYI VLGQTMLRIN LHAFVLGSLI
 51 AVVVWYFLFK FIIGVLNXPE KMQRFGSARK GRKAALALNK AGLAYFEGRF
101 EKAELEASRV LGNKEAGDNR TLALMLGAHA AGQMENIELR DRYLAEIAKL
151 PEKQQLSRYL LLAESALNRR DYEAAEANLH AAAKMNANLT RLVRLQLRYA
201 FDRGDALQVL AKTEKXSKAG AXGKSEMERY QNWAYRRQLX DAADAAALKT
251 CLKRIPDSLK NGELSVSVAE KYERLGLYAD AVKWVKQHYP HNRRPELLEA
301 FVESVRFLGE RDQQKAIDFA DAWLKEQPDN ALLLXYLGRL AYGRKLWGKA
351 KGYLEASIAL KPSISARLVL AKVFDETGEP QKAEAQRNLV LASVAEENRP
401 SAETH*
```

ORF100a and ORF100-1 show 95.1% identity in 406 aa overlap:

```
                       10        20        30        40        50        60
    orf100a.pep  MKTVVWIVVLFAAAXGLALASGIXTGDVYIVLGQTMLRINLHAFVLGSLIAVVVWYFLFK
                 |||||||||||||||||||| ||||||| |||||||||||||||||||||||||||||||
       orf100-1  MKTVVWIVVLFAAAVGLALASGIYTGDVYIVLGQTMLRINLHAFVLGSLIAVVVWYFLFK
                       10        20        30        40        50        60

70        80        90       100       110       120
    orf100a.pep  FIIGVLNXPEKMQRFGSARKGRKAALALNKAGLAYFEGRFEKAELEASRVLGNKEAGDNR
                 ||||||| ||||||||||||||||||||||||||||||||||||||||||||| ||||||
       orf100-1  FIIGVLNIPEKMQRFGSARKGRKAALALNKAGLAYFEGRFEKAELEASRVLVNKEAGDNR
                       70        80        90       100       110       120

130       140       150       160       170       180
    orf100a.pep  TLALMLGAHAAGQMENIELRDRYLAEIAKLPEKQQLSRYLLLAESALNRRDYEAAEANLH
                 ||||||||||||||||||||||||||||||||||||||||||||||||||||||||||||
       orf100-1  TLALMLGAHAAGQMENIELRDRYLAEIAKLPEKQQLSRYLLLAESALNRRDYEAAEANLH
                      130       140       150       160       170       180

190       200       210       220       230       240
    orf100a.pep  AAAKMNANLTRLVRLQLRYAFDRGDALQVLAKTEKXSKAGAXGKSEMERYQNWAYRRQLX
                 |||||||||||||||||||||||||||||||||||| ||||| |||||||||||||||| 
       orf100-1  AAAKMNANLTRLVRLQLRYAFDRGDALQVLAKTEKLSKAGALGKSEMERYQNWAYRRQLA
                      190       200       210       220       230       240

250       260       270       280       290       300
    orf100a.pep  DAADAAALKTCLKRIPDSLKNGELSVSVAEKYERLGLYADAVKWVKQHYPHNRRPELLEA
                 ||||||||||||||||||||||||||||||||||||||||||||||||||||||||||||
       orf100-1  DAADAAALKTCLKRIPDSLKNGELSVSVAEKYERLGLYADAVKWVKQHYPHNRRPELLEA
                      250       260       270       280       290       300

310       320       330       340       350       360
    orf100a.pep  FVESVRFLGERDQQKAIDFADAWLKEQPDNALLLXYLGRLAYGRKLWGKAKGYLEASIAL
                 |||||||||||:||||||||||||||||||||||  |||||||||||||||||||||||
       orf100-1  FVESVRFLGEREQQKAIDFADAWLKEQPDNALLLMYLGRLAYGRKLWGKAKGYLEASIAL
                      310       320       330       340       350       360
```

```
                      370        380        390        400
orf100a.pep   KPSISARLVLAKVFDETGEPQKAEAQRNLVLASVAEENRPSA-ETHX
              ||||||||||||||||| ||||||||||||||| :|::::| :| | |
orf100-1      KPSISARLVLAKVFDEIGEPQKAEAQRNLVLEAVSDDERHAALEQHSX
                      370        380        390        400
```

Homology with a Predicted ORF from *N. gonorrhoeae*

ORF100 shows 93.3% identity over a 386 aa overlap with a predicted ORF (ORF100ng) from *N. gonorrhoeae*:

```
orf100.pep    MKTVVWIVVLFAAAVGLALASGIYTGDVYIVLGQTMLRINLHAFVLGSLIAVVVWYFLFK    60
              ||||||||||||||||||||||||||||||||||||||||||||||||||||||||||||
orf100ng      MKTVVWIVVLFAAAVGLALASGIYTGDVYIVLGQTMLRINLHAFVLGSLIAVVVWYFLFK    60
orf100.pep    FIIGVLNIPEKMQRFGSARKGXKXXLALNKAGLAYFEGRFEKAELEASRVLVNKVGRDNR   120
              |||||||||:|:| |||||| |  |||||||||||||||||||||||||||| : |||
orf100ng      FIIGVLNIPENMRRSGSARKGRKAALALNKAGLAYFEGRFEKAELEASRVLGNKEAGDNR   120
orf100.pep    TLALMLXAHAAGQMENIXXRDRYLAEIAKLPEKQQLSRYLLLAESALNRRDYEAAEANLH   180
              ||||||  ||||||||| ||||||||||||||||||||||||||||||||||||||||||
orf100ng      TLALMLGAHAAGQMENIELRDRYLAEIAKLPEKQQLSRYLLLAESALNRRDYEAAEANLH   180
orf100.pep    AAAKMNANLTRLVRLXIRYAFDRGDALQVLAKTEKLSKAGALGKSEMERYQNWAYRRQLA   240
              ||||||||||||||| :|||||||||||||||||||||||||||||||||||||||:|
orf100ng      AAAKMNANLTRLVRLQLRYAFDRGDALQVLAKTEKLSKAGALGKSEMERYQNWAYRRQMA   240
orf100.pep    DAADAAALKTCLKRIPDSLKNGELSVSVAEKYERLGLYADAVKWVKQHYPXNRRPELLEA   300
              |||||||||||||||||||||||||||||||||||||||||||||||||| ||||||||
orf100ng      DAADAAALKTCLKRIPDSLKNGELSVSVAEKYERLGLYADAVKWVKQHYPHNRRPELLEA   300
orf100.pep    FVESVRFLGEREQQKAIDFADAWLKEQPDNALLLMYLGRLAFGRKLWGKAKGYLEASIAL   360
              |||||||||||||||||||||:|||||||||||||||||||:||||||||||||||||||
orf100ng      FVESVRFLGEREQQKAIDFADSWLKEQPDNALLLMYLGRLAYGRKLWGKAKGYLEASIAL   360
orf100.pep    KPSISARLVLTKVFDEIGEPQKAEAH                                    386
              ||||  ||||||:||||  ::  |||||:
orf100ng      KPSIPARLVLAKVFDETAQSQKAEAQRNLVLASVAGENRPSAETR                 405
```

The complete length ORF100ng nucleotide sequence <SEQ ID 755> is:

```
  1  ATGAAAACGG TAGTCTGGAT TGTTGTCCTG TTTGCCGCCG CCGTCGGACT
 51  GGCGCTGGCT TCGGGCATTT ACACCGGCGA CGTGTATATC GTACTCGGAC
101  AGACCATGCT CAGAATCAAC CTGCACGCCT TTGTGTTAGG TTCGCTGATT
151  GCCGTCGTGG TGTGGTATTT CCTGTTTAAA TTCATCATCG GCGTACTCAA
201  TATCCCCGAA AATATGCGGC GTTCCGGTTC GGCGCGGAAA GGCCGCAAGG
251  CCGCGCTTGC CTTGAATAAG GCGGGTTTGG CGTATTTCGA AGGGCGTTTT
301  GAAAAGGCGG AACTCGAAGC CTCTCGAGTG TTGGGCAACA AGAGGCCGG
351  AGACAACCGG ACTTTGGCAT TGATGCTGGG CGCGCACGCG GCAGGACAGA
401  TGGAAAATAT CGAGCTGCGC GACCGTTATC TTGCGGAAAT CGCCAAACTG
451  CCGGAAAAAC AGCAGCTTTC CCGCTATCTT CTGCTGGCGG AATCGGCGTT
501  AAACCGGCGC GATTACGAAG CGGCGGAAGC CAATCTTCAT GCGGCGGCGA
551  AGATGAATGC CAACCTTACG CGCCTCGTGC GTCTGCAACT TCGTTACGCC
601  TTCGATCGGG GCGATGCGTT GCAGGTTCTG GCAAAAaccG AAAAACTTTC
651  CAAGGCGGGC GCGTTGGGCA AATCGGAAAT GGAACGGTAT CAAAATTGGG
701  CATACCGCCG CCAGATGGCG GATGCTGCCG ATGCCGCCGC TTTGAAAACC
751  TGCCTGAAGC GGATTCCCGA CAGCCTCAAA ACGGGGAAT TGagcGTATC
801  GGTTGCGGAA AAGTACGAAC GTTTGGGACT GTATGCCGAT GCGGTCAAAT
851  GGGTCAAACA GCATTATCCG CACAACCGCC GCCCCGAGCT TTTGGAAGCC
901  TTTGTCGAAA GCGTGCGCTT TTTGGGCGAG CGCGAACAGC AGAAAGCCAT
951  CGATTTTGCC GATTCTTGGC TGAAAGAACA GCCCGATAAC GCGCTTCTGC
```

```
1001 TGATGTATCT CGGCCGGCTC GCCTACGGCC GCAAACTTTG GGGTAAGGCA

1051 AAAGGCTACC TTGAAGCGAG TATTGCACTG AAGCCGAGTA TTCCGGCGCG

1101 TTTGGTGTTG GCAAAGGTTT TTGACGAAAC CGCACAGTCG CAAAAAGCCG

1151 AAGCACAGCG CAACTTGGTT TTGGCAAGCG TTGCCGGGGA AAACCGCCCT

1201 TCCGCCGAAA CCCGTTGA
```

This encodes a protein having amino acid sequence <SEQ ID 756>:

```
  1 MKTVVWIVVL FAAAVGLALA SGIYTGDVYI VLGQTMLRIN LHAFVLGSLI

51 AVVVWYFLFK FIIGVLNIPE NMRRSGSARK GRKAALALNK AGLAYFEGRT

101 EKAELEASRV LGNKEAGDNR TLALMLGAHA AGQMENIELR DRYLAEIAKL

151 PEKQQLSRYL LLAESALNRR DYEAAEANLH AAAKMNANLT RLVRLQLRYA

201 FDRGDALQVL AKTEKLSKAG ALGKSEMERY QNWAYRRQMA DAADAAALKT

251 CLKRIPDSLK NGELSVSVAE KYERLGLYAD AVKWVKQHYP HNRRPELLEA

301 FVESVRFLGE REQQKAIDFA DSWLKEQPDN ALLLMYLGRL AYGRKLWGKA

351 KGYLEASIAL KPSIPARLVL AKVFDETAQS QKAEAQRNLV LASVAGENRP

401 SAETR*
```

ORF100ng and ORF100-1 show 95.3% identity in 402 aa overlap:

```
                      10         20         30         40         50         60
    orf100-1.pep  MKTVVWIVVLFAAAVGLALASGIYTGDVYIVLGQTMLRINLHAFVLGSLIAVVVWYFLFK
                  ||||||||||||||||||||||||||||||||||||||||||||||||||||||||||||
      orf100ng    MKTVVWIVVLFAAAVGLALASGIYTGDVYIVLGQTMLRINLHAFVLGSLIAVVVWYFLFK
                      10         20         30         40         50         60

70         80         90        100        110        120
    orf100-1.pep  FIIGVLNIPEKMQRFGSARKGRKAALALNKAGLAYFEGRFEKAELEASRVLVNKEAGDNR
                  ||||||||||: :| |||||||||||||||||||||||||||||||||||| ||||||||
      orf100ng    FIIGVLNIPENMRRSGSARKGRKAALALNKAGLAYFEGRFEKAELEASRVLGNKEAGDNR
                      70         80         90        100        110        120

130        140        150        160        170        180
    orf100-1.pep  TLALMLGAHAAGQMENIELRDRYLAEIAKLPEKQQLSRYLLLAESALNRRDYEAAEANLH
                  ||||||||||||||||||||||||||||||||||||||||||||||||||||||||||||
      orf100ng    TLALMLGAHAAGQMENIELRDRYLAEIAKLPEKQQLSRYLLLAESALNRRDYEAAEANLH
                     130        140        150        160        170        180

190        200        210        220        230        240
    orf100-1.pep  AAAKMNANLTRLVRLQLRYAFDRGDALQVLAKTEKLSKAGALGKSEMERYQNWAYRRQLA
                  |||||||||||||||||||||||||||||||||||||||||||||||||||||||||:|
      orf100ng    AAAKMNANLTRLVRLQLRYAFDRGDALQVLAKTEKLSKAGALGKSEMERYQNWAYRRQMA
                     190        200        210        220        230        240

250        260        270        280        290        300
    orf100-1.pep  DAADAAALKTCLKRIPDSLKNGELSVSVAEKYERLGLYADAVKWVKQHYPHNRRPELLEA
                  ||||||||||||||||||||||||||||||||||||||||||||||||||||||||||||
      orf100ng    DAADAAALKTCLKRIPDSLKNGELSVSVAEKYERLGLYADAVKWVKQHYPHNRRPELLEA
                     250        260        270        280        290        300

310        320        330        340        350        360
    orf100-1.pep  FVESVRFLGEREQQKAIDFADAWLKEQPDNALLLMYLGRLAYGRKLWGKAKGYLEASIAL
                  |||||||||||||||||||||:||||||||||||||||||||||||||||||||||||||
      orf100ng    FVESVRFLGEREQQKAIDFADSWLKEQPDNALLLMYLGRLAYGRKLWGKAKGYLEASIAL
                     310        320        330        340        350        360

370        380        390        400
    orf100-1.pep  KPSISARLVLAKVFDEIGEPQKAEAQRNLVLEAVSDDERHAALEQHSX
                  |||| ||||||||||| :: |||||||||||| :|: ::| :|
      orf100n     KPSIPARLVLAKVFDETAQSQKAEAQRNLVLASVAGENRPSAETRX
                     370        380        390        400
```

Based on this analysis, including the presence of a putative leader sequence, a putative transmembrane domain, and a RGD motif, it is predicted that the proteins from *N. meningitidis* and *N. gonorrhoeae*, and their epitopes, could be useful antigens for vaccines or diagnostics, or for raising antibodies.

Example 90

The following DNA sequence, believed to be complete, was identified in *N. meningitidis* <SEQ ID 757>

```
  1 ATGATGTTTT CTTGGTTCAA GCTGTTTCAC TTGTTTTTTG TCATTTCGTG
 51 GTTTGCAGGG CTGTTTTACC TGCCGAGGAT TTTCGTCAAT ATGGCGATGA
101 TTGATGTGCC GCGCGGCAAT CCCGAGTATG TGCGTCTGTC GGGCATGGCG
151 GTGCGGCTGT ACCGTTTTAT GTCGCCGTTG GGCTTCGGCG CGGTCGTGTT
201 CGGCGCGGCG ATACCGTTTG CCGCCGGCTG GTGGGGCAGC GGCTGGGTAC
251 ACGTCAAACT GTGTTTGGGC TTGATGCTCT TGGCTTACCA GTTGTATTGC
301 GGCGTGCTGC TGCGCCGTTT TCAGGATTAC AGCAATGCTT TTTCACACCG
351 CTGGTACCGC GTGTTCAACG AAATCCCCGT GCTGCTGATG GTTGCCGCGC
401 TGTATsTGGT CGTGTTCAAA CCGTTTTGA
```

This corresponds to the amino acid sequence <SEQ ID 758; ORF102>:

```
  1 MMFSWFKLFH LFFVISWFAG LFYLPRIFVN MAMIDVPRGN PEYVRLSGMA
 51 VRLYRFMSPL GFGAVVFGAA IPFAAGWWGS GWVHVKLCLG LMLLAYQLYC
101 GVLLRRFQDY SNAFSHRWYR VFNEIPVLLM VAALYXVVFK PF*
```

Further work revealed the complete nucleotide sequence <SEQ ID 759>:

```
  1 ATGATGTTTT CTTGGTTCAA GCTGTTTCAC TTGTTTTTTG TCATTTCGTG
 51 GTTTGCAGGG CTGTTTTACC TGCCGAGGAT TTTCGTCAAT ATGGCGATGA
101 TTGATGTGCC GCGCGGCAAT CCCGAGTATG TGCGTCTGTC GGGCATGGCG
151 GTGCGGCTGT ACCGTTTTAT GTCGCCGTTG GGCTTCGGCG CGGTCGTGTT
201 CGGCGCGGCG ATACCGTTTG CCGCCGGCTG GTGGGGCAGC GGCTGGGTAC
251 ACGTCAAACT GTGTTTGGGC TTGATGCTCT TGGCTTACCA GTTGTATTGC
301 GGCGTGCTGC TGCGCCGTTT TCAGGATTAC AGCAATGCTT TTTCACACCG
351 CTGGTACCGC GTGTTCAACG AAATCCCCGT GCTGCTGATG GTTGCCGCGC
401 TGTATCTGGT CGTGTTCAAA CCGTTTTGA
```

This corresponds to the amino acid sequence <SEQ ID 760; ORF102-1>:

```
  1 MMFSWFKLFH LFFVISWFAG LFYLPRIFVN MAMIDVPRGN PEYVRLSGMA
 51 VRLYRFMSPL GFGAVVFGAA IPFAAGWWGS GWVHVKLCLG LMLLAYQLYC
101 GVLLRRFQDY SNAFSHRWYR VFNEIPVLLM VAALYLVVFK PF*
```

Computer analysis of this amino acid sequence gave the following results:
Homology with HP1484 Hypothetical Integral Membrane Protein of *H. pylori* (Accession Number AE000647)

ORF102 and HP1484 show 33% aa identity in 143aa overlap:

```
orf102    3 FSWFKLFHLFFVISWFAGLFYLPRIFVNMAMIDVPRGNPEYVRLSGMAVRLYRFMSPLGF   62
            F W KFH+ VISW A LFYLPR+FV  A     +     V++     +LY F++
HP1484    8 FLWVKAFHVIAVISWMAALFYLPRLFVYHAENAHKKEFVGVVQIQEK--KLYSFIASPAM  65 orf102   63 GAVVFGAAIPFAAG---WWGSGWVHVKLCGLMLLAYQLYCGVLLRRFQDYSNAFSHRWY  119
            G  +   +         +  GW+H KL L ++LLAY  YC  +R  +     + R+Y
HP1484   66 GFTLITGILMLLIEPTLFKSGWLHAKLALVVLLLAYHFYCKKCMRELEKDPTRRNARFY  125 orf102  120 RVFNEIPXXXXXXXXXXXXXFKPF                                    142
            RVFNE P             KPF
HP1484  126 RVFNEAPTILMILIVILVVVKPF                                     148
```

15

Homology with a Predicted ORF from *N. meningitidis* (Strain A)

ORF102 shows 99.3% identity over a 142aa overlap with an ORF (ORF102a) from strain A of *N. meningitidis*:

```
                    10        20        30        40        50        60
orf102.pep  MMFSWFKLFHLFFVISWFAGLFYLPRIFVNMAMIDVPRGNPEYVRLSGMAVRLYRFMSPL
            ||||||||||||||||||||||||||||||||||||||||||||||||||||||||||||
orf102a     MMFSWFKLFHLFFVISWFAGLFYLPRIFVNMAMIDVPRGNPEYVRLSGMAVRLYRFMSPL
                    10        20        30        40        50        60

70        80        90       100       110       120
orf102.pep  GFGAVVFGAAIPFAAGWWGSGWVHVKLCGLMLLAYQLYCGVLLRRFQDYSNAFSHRWYR
            ||||||||||||||||||||||||||||||||||||||||||||||||||||||||||||
orf102a     GFGAVVFGAAIPFAAGWWGSGWVHVKLCGLMLLAYQLYCGVLLRRFQDYSNAFSHRWYR
                    70        80        90       100       110       120

130       140
orf102.pep  VFNEIPVLLMVAALYXVVFKPFX
            ||||||||||||||| |||||||
orf102a     VFNEIPVLLMVAALYLVVFKPFX
                   130       140
```

The complete length ORF102a nucleotide sequence <SEQ ID 761> is:

```
  1 ATGATGTTTT CTTGGTTCAA GCTGTTTCAC TTGTTTTTTG TCATTTCGTG

51 GTTTGCAGGG CTGTTTTACC TGCCGAGGAT TTTCGTCAAT ATGGCGATGA

101 TTGATGTGCC GCGCGGCAAT CCCGAGTATG TGCGTCTGTC GGGCATGGCG

151 GTGCGGCTGT ACCGTTTTAT GTCGCCGTTG GGCTTCGGCG CGGTCGTGTT

201 CGGCGCGGCG ATACCGTTTG CCGCCGGCTG GTGGGGCAGC GGCTGGGTAC

251 ACGTCAAACT GTGTTTGGGC TTGATGCTCT TGGCTTACCA GTTGTATTGC

301 GGCGTGCTGC TGCGCCGTTT TCAGGATTAC AGCAATGCTT TTTCACACCG

351 CTGGTACCGC GTGTTCAACG AAATCCCCGT GCTGCTGATG GTTGCCGCGC

401 TGTATCTGGT CGTGTTCAAA CCGTTTTGA
```

This encodes a protein having amino acid sequence <SEQ ID 762>:

```
  1 MMFSWFKLFH LFFVISWFAG LFYLPRIFVN MAMIDVPRGN PEYVRLSGMA

51 VRLYRFMSPL GFGAVVFGAA IPFAAGWWGS GWVHVKLCLG LMLLAYQLYC

101 GVLLRRFQDY SNAFSHRWYR VFNEIPVLLM VAALYLVVFK PF*
```

ORF102a and ORF102-1 show complete identity in 142 aa overlap:

```
                     10         20         30         40         50         60
    orf102a.pep  MMFSWFKLFHLFFVISWFAGLFYLPRIFVNMAMIDVPRGNPEYVRLSGMAVRLYRFMSPL
                 ||||||||||||||||||||||||||||||||||||||||||||||||||||||||||||
    orf102-1     MMFSWFKLFHLFFVISWFAGLFYLPRIFVNMAMIDVPRGNPEYVRLSGMAVRLYRFMSPL
                     10         20         30         40         50         60

70         80         90        100        110        120
    orf102a.pep  GFGAVVFGAAIPFAAGWWGSGWVHVKLCLGLMLLAYQLYCGVLLRRFQDYSNAFSHRWYR
                 ||||||||||||||||||||||||||||||||||||||||||||||||||||||||||||
    orf102-1     GFGAVVFGAAIPFAAGWWGSGWVHVKLCLGLMLLAYQLYCGVLLRRFQDYSNAFSHRWYR
                     70         80         90        100        110        120

130        140
    orf102a.pep  VFNEIPVLLMVAALYLVVFKPFX
                 |||||||||||||||||||||||
    orf102-1     VFNEIPVLLMVAALYLVVFKPFX
                    130        140
```

Homology with a Predicted ORF from *N. gonorrhoeae*

ORF102 shows 97.9% identity over a 142 aa overlap with a predicted ORF (ORF102ng) from *N. gonorrhoeae*:

```
    orf102.pep   MMFSWFKLFHLFFVISWFAGLFYLPRIFVNMAMIDVPRGNPEYVRLSGMAVRLYRFMSPL   60
                 ||||||||||||||||||||||||||||||||||||||:|||||||||||||||||||||
    orf102ng     MMFSWFKLFHLFFVISWFAGLFYLPRIFVNMAMIDAPRGNPEYVRLSGMAVRLYRFMSPL   60 orf102.pep   GFGAVVFGAAIPFAAGWWGSGWVHVKLCLGLMLLAYQLYCGVLLRRFQDYSNAFSHRWYR  120
                 |||||||||||||||||||| |||||||||||||||||||||||||||||||||||||||
    orf102ng     GFGAVVFGAAIPFAAGRWGSGWVHVKLCLGLMLLAYQLYCGVLLRRFQDYSNAFSHRWYR  120 orf102.pep   VFNEIPVLLMVAALYXVVFKPF  142
                 ||||||||||||||| ||||||
    orf102ng     VFNEIPVLLMVAALYLVVFKPF  142
```

The complete length ORF102ng nucleotide sequence <SEQ ID 763> is:

```
  1 ATGATGTTTT CTTGGTTCAA GCTGTTTCAC TTGTTTTTTG TCATTTCGTG

51 GTTTGCAGGG CTGTTTTACC TGCCGAGGAT TTTCGTCAAT ATGGCGATGA

101 TTGATGCGCC GCGCGGCAAT CCCGAGTATG TGCGCCTGTC GGGGATGGCG

151 GTGCGGTTGT ACCGTTTTAT GTCGCCTTTG GGTTTCGGCG CGGTCGTGTT

201 CGGCGCGGCG ATACCGTTTG CCGCcggccg GTGGGGCagc ggctggGTTC

251 ACGTCAAACT GTGTTTGGGC TTGATGCTCT TGGCTTATCA GTTGTATTGC

301 GGCGTGCTGC TGCGCCGTTT TCAGGATTAC AGCAATGCTT TTTCACACCG

351 CTGGTACCGC GTGTTCAAcg aAATCCCCGT GCTGCTGATG GTTGCCGCGC

401 TGTATCTGGT CGTGTTCAAA CCGTTTTGA
```

This encodes a protein having amino acid sequence <SEQ ID 764>:

```
  1 MMFSWFKLFH LFFVISWFAG LFYLPRIFVN MAMIDAPRGN PEYVRLSGMA

51 VRLYRFMSPL GFGAVVFGAA IPFAAGRWGS GWVHVKLCLG LMLLAYQLYC

101 GVLLRRFQDY SNAFSHRWYR VFNIPVLLM VAALYLVVFKPF*
```

ORF102ng and ORF102-1 show 98.6% identity in 142 aa overlap:

```
                    10        20        30        40        50        60
orf102-1.pep  MMFSWFKLFHLFFVISWFAGLFYLPRIFVNMAMIDVPRGNPEYVRLSGMAVRLYRFMSPL
              ||||||||||||||||||||||||||||||||||:|||||||||||||||||||||||||
orf102ng      MMFSWFKLFHLFFVISWFAGLFYLPRIFVNMAMIDAPRGNPEYVRLSGMAVRLYRFMSPL
                    10        20        30        40        50        60

70        80        90       100       110       120
orf102-1.pep  GFGAVVFGAAIPFAAGWWGSGWVHVKLCLGLMLLAYQLYCGVLLRRFQDYSNAFSHRWYR
              |||||||||||||||||||| |||||||||||||||||||||||||||||||||||||||
orf102ng      GFGAVVFGAAIPFAAGRWGSGWVHVKLCLGLMLLAYQLYCGVLLRRFQDYSNAFSHRWYR
                    70        80        90       100       110       120

130       140
orf102-1.pep  VFNEIPVLLMVAALYLVVFKPFX
              |||||||||||||||||||||||
orf102ng      VFNEIPVLLMVAALYLVVFKPFX
                   130       140
```

In addition, ORF102ng shows significant homology to a membrane protein from *H. pylori*:

```
gi|2314656 (AE000647) conserved hypothetical integral membrane protein
[Helicobacter pylori] Length = 148
Score = 79.2 bits (192), Expect = 1e-14
Identities = 50/147 (34%), Positives = 68/147 (46%), Gaps = 13/147 (8%)

Query:   3 FSWFKLFHLFFVISWFAGLFYLPRIFVNMAMIDAPRGNPEYVRLSGMAVRLYRFMSPLGF   62
           F W K FH+  VISW A LFYLPR+FV  A    +     V++     +LY F++
Sbjct:   8 FLWVKAFHVIAVISWMAALFYLPRLFVYHAENAHKKEFVGVVQIQEK--KLYSFIASPAM  65

Query:  63 GAVVFGAAIP-------FAAGRWGSGWVHVKLCLGLMLLAYQLYCGVLLRRFQDYSNAFS 115
           G  +    +        F +G    GW+H KL L ++LLAY  YC   +R  +      +
Sbjct:  66 GFTLITGILMLLIEPTLFKSG----GWLHAKLALVVLLLAYHFYCKKCMRELEKDPTRRN 121

Query: 116 HRWYRVFNEIPXXXXXXXXXXXXFKPF                                  142
           R+YRVFNE P             KPF
Sbjct: 122 ARFYRVFNEAPTILMLIVILVVVKPF                                   148
```

Based on this analysis, it is predicted that these proteins from *N. meningitidis* and *N. gonorrhoeae*, and their epitopes, could be useful antigens for vaccines or diagnostics, or for raising antibodies.

Example 91

The following partial DNA sequence was identified in *N. meningitidis* <SEQ ID 765>:

```
    1  ATGGCAAAAA TGATGAAATG GGCGGCTGTT GCGGCGGTCG CGGCGGCAGC
   51  GGTTTGGGGC GGATGGTCTT AACTGAAGCC CGAGCCGCAC GTGCTTGATA
  101  TTACGGAAAC GGTCAGGCGC GGC // .....
 //..  ATTTCGTTTA CGATTTTGTC CGAACCGGAT ACGCCGATTA AGGCGAAGCT
   51  CGACAGCGTC GACCCCGGGC TGACCACGAT GTCGTCGGGC GGTTACAACA
  101  GCAGTACGGA TACGGCTTCC AATGCGGTCT ACTATTATGC CCGTTCGTTT
  151  GTGCCGAATC CGGACGGCAA ACTCGCCACG GGATGACGA CGCAGAATAC
  201  GGTTGAAATC GACGGCGTGA AAAATGTGCT GATTATTCCG TCGCTGACCG
  251  TGAAAAATCG CGGCGGCAAG GCGTTTGTGC GCGTGTTGGG TGCGGACGGC
  301  AAGGCGGCGG AACGCGAAAT CCGGACCGGT ATGAGAGACA GTATGAATAC
  351  CGAAGTAAAA AGCGGGTTGA AGAGGGGGA CAAAGTGGTC ATCTCCGAAA
  401  TAACCGCCGC CGAGCAACAG GAAAGCGGCG AACGCGCCCT AGGCGGCCCG
  451  CCGCGCCGAT AA
```

This corresponds to the amino acid sequence <SEQ ID 766; ORF85>:

```
  1 MAKMMKWAAV AAVAAAAVWG GWS.LKPEPH VLDITETVRR G.........

51 .......... .......... .......... .......... ..........
```

```
101..........  ..........  ..........  ..........  ..........
151..........  ..........  ..........  ..........  ..........
201..........  ..........  ..........  ..........I SFTILSEPDT
251PIKAKLDSVD PGLTTMSSGG YNSSTDTASN AVYYYARSFV PNPDGKLATG
301MTTQNTVEID GVKNVLIIPS LTVKNRGGKA FVRVLGADGK AAEREIRTGM
351RDSMNTEVKS GLKEGDKVVI SEITAAEQQE SGERALGGPP RR*
```

Further work revealed the further partial nucleotide sequence <SEQ ID 767>:

```
   1 ..GTATCGGTCG GCGCGCAGGC ATCGGGGCAG ATTAAGATAC TTTATGTCAA
  51   ACTCGGGCAA CAGGTTAAAA AGGGCGATTT GATTGCGGAA ATCAATTCGA
 101   CCTCGCAGAC CAATACGCTC AATACGGAAA AATCCAAGTT GGAAACGTAT
 151   CAGGCGAAGC TGGTGTCGGC ACAGATTGCA TTGGGCAGCG CGGAGAAGAA
 201   ATATAAGCGT CAGGCGGCGT TATGGAAGGA AAACGCGACT TCCAAAGAGG
 251   ATTTGGAAAG CGCGCAGGAT GCGTTTGCCG CCGCCAAAGC CAATGTTGCC
 301   GAGCTGAAGG CTTTAATCAG ACAGAGCAAA ATTTCCATCA ATACCGCCGA
 351   GTCGGAATTG GGCTACACGC GCATTACCGC AACGATGGAC GGCACGGTGG
 401   TGGCGATTCT CGTGGAAGAG GGGCAGACTG TGAACGCGGC GCAGTCTACG
 451   CCGACGATTG TCCAATTGGC GAATCTGGAT ATGATGTTGA ACAAAATGCA
 501   GATTGCCGAG GGCGATATTA CCAAGGTGAA GGCGGGGCAG GATATTTCGT
 551   TTACGATTTT GTCCGAACCG GATACGCCGA TTAAGGCGAA GCTCGACAGC
 601   GTCGACCCCG GGCTGACCAC GATGTCGTCG GGCGGTTACA ACAGCAGTAC
 651   GGATACGGCT TCCAATGCGG TCTACTATTA TGCCCGTTCG TTTGTGCCGA
 701   ATCCGGACGG CAAACTCGCC ACGGGGATGA CGACGCAGAA TACGGTTGAA
 751   ATCGACGGCG TGAAAAATGT GCTGATTATT CCGTCGCTGA CCGTGAAAAA
 801   TCGCGGCGGC AAGGCGTTTG TGCGCGTGTT GGGTGCGGAC GGCAAGGCGG
 851   CGGAACGCGA AATCCGGACC GGTATGAGAG ACAGTATGAA TACCGAAGTA
 901   AAAAGCGGGT TGAAAGAGGG GGACAAAGTG GTCATCTCCG AAATAACCGC
 951   CGCCGAGCAA CAGGAAAGCG GCGAACGCGC CCTAGGCGGC CCGCCGCGCC
1001   GATAA
```

This corresponds to the amino acid sequence <SEQ ID 768; ORF85-1>:

```
   1 ..VSVGAQASGQ IKILYVKLGQ QVKKGDLIAE INSTSQTNTL NTEKSKLETY
  51   QAKLVSAQIA LGSAEKKYKR QAALWKENAT SKEDLESAQD AFAAAKANVA
 101   ELKALIRQSK ISINTAESEL GYTRITATMD GTVVAILVEE GQTVNAAQST
 151   PTIVQLANLD MMLNKMQIAE GDITKVKAGQ DISFTILSEP DTPIKAKLDS
 201   VDPGLTTMSS GGYNSSTDTA SNAVYYYARS FVPNPDGKLA TGMTTQNTVE
 251   IDGVKNVLII PSLTVKNRGG KAFVRVLGAD GKAAEREIRT GMRDSMNTEV
 301   KSGLKEGDKV VISEITAAEQ QESGERALGG PPRR*
```

Computer analysis of this amino acid sequence gave the following results:

Homology with a Predicted ORF from *N. meningitidis* (Strain A)

ORF85 shows 87.8% identity over a 41aa overlap and 99.3% identity over a 153aa overlap with an ORF (ORF85a) from strain A of *N. meningitidis*:

```
                  10        20        30        40
orf85.pep  MAKMMKWAAVAAVAAAAVWGGWS-LKPEPHVLDITETVRRG
           |||||||||||||||||||||| ||||::  ||||||||||
orf85a     MAKMMKWAAVAAVAAAAVWGGWSYLKPEPQAAYITETVRRGDISRTVSATGEISPSNLVS
                  10        20        30        40        50        60
                                //
                                         80        90       100
orf85.pep  ..........................ISFTILSEPDTPIKAKLDSVDPGLTTMSSG
                                     ||||||||||||||||||||||||||||||
orf85a     TIVQLANLDMMLNKMQIAEGDITKVKAGQDISFTILSEPDTPIKAKLDSVDPGLTTMSSG
               210       220       230       240       250       260
                110       120       130       140       150       160
orf85.pep  GYNSSTDTASNAVYYYARSFVPNPDGKLATGMTTQNTVEIDGVKNVLIIPSLTVKNRGGK
           |||||||||||||||||||||||||||||||||||||||||||||||||||||||||||:
orf85a     GYNSSTDTASNAVYYYARSFVPNPDGKLATGMTTQNTVEIDGVKNVLIIPSLTVKNRGGR
               270       280       290       300       310       320
                170       180       190       200       210       220
orf85.pep  AFVRVLGADGKAAEREIRTGMRDSMNTEVKSGLKEGDKVVISEITAAEQQESGERALGGP
           ||||||||||||||||||||||||||||||||||||||||||||||||||||||||||||
orf85a     AFVRVLGADGKAAEREIRTGMRDSMNTEVKSGLKEGDKVVISEITAAEQQESGERALGGP
               330       340       350       360       370       380
                230
orf85.pep  PRRX
           ||||
orf85a     PRRX
               390
```

The complete length ORF85a nucleotide sequence <SEQ ID 769> is:

```
  1  ATGGCAAAAA TGATGAAATG GGCGGCTGTT GCGGCGGTCG CGGCGGCAGC
 51  GGTTTGGGGC GGATGGTCTT ATCTGAAGCC CGAGCCGCAG GCTGCTTATA
101  TTACGGAAAC GGTCAGGCGC GGCGACATCA GCCGGACGGT TTCTGCAACA
151  GGGGAGATTT CGCCGTCCAA CCTGGTATCG GTCGGCGCGC AGGCATCGGG
201  GCAGATTAAG AAACTTTATG TCAAACTCGG GCAACAGGTT AAAAAGGGCG
251  ATTTGATTGC GGAAATCAAT TCGACCTCGC AGACCAATAC GCTCAATACG
301  GAAAAATCCA AATTGGAAAC GTATCAGGCG AAGCTGGTGT CGGCACAGAT
351  TGCATTGGGC AGCGCGGAGA AGAAATATAA GCGTCAGGCG GCGTTGTGGA
401  AGGATGATGC GACCGCTAAA GAAGATTTGG AAAGCGCACA GGATGCGCTT
451  GCCGCCGCCA AAGCCAATGT TGCCGAGCTG AAGGCTCTAA TCAGACAGAG
501  CAAAATTTCC ATCAATACCG CCGAGTCGGA ATTGGGCTAC ACGCGCATTA
551  CCGCAACGAT GGACGGCACG GTGGTGGCGA TTCTCGTGGA AGAGGGGCAG
601  ACTGTGAACG CGGCGCAGTC TACGCCGACG ATTGTCCAAT TGGCGAATCT
651  GGATATGATG TTGAACAAAA TGCAGATTGC CGAGGGCGAT ATTACCAAGG
701  TGAAGGCGGG GCAGGATATT TCGTTTACGA TTTTGTCCGA ACCGGATACG
751  CCGATTAAGG CGAAGCTCGA CAGCGTCGAC CCCGGGCTGA CCACGATGTC
801  GTCGGGCGGC TACAACAGCA GTACGGATAC GGCTTCCAAT GCGGTCTACT
851  ATTATGCCCG TTCGTTTGTG CCGAATCCGG ACGGCAAACT CGCCACGGGG
901  ATGACGACGC AGAATACGGT TGAAATCGAC GGTGTGAAAA ATGTGCTGAT
```

```
 951 TATTCCGTCG CTGACCGTGA AAAATCGCGG CGGCAGGGCG TTTGTGCGCG

1001 TGTTGGGTGC AGACGGCAAG GCGGCGGAAC GCGAAATCCG GACCGGTATG

1051 AGAGACAGTA TGAATACCGA AGTAAAAAGC GGGTTGAAAG AGGGGGACAA

1101 AGTGGTCATC TCCGAAATAA CCGCCGCCGA GCAGCAGGAA AGCGGCGAAC

1151 GCGCCCTAGG CGGCCCGCCG CGCCGATAA
```

This encodes a protein having amino acid sequence <SEQ ID 770>:

```
  1 MAKMMKWAAV AAVAAAAVWG GWSYLKPEPQ AAYITETVRR GDISRTVSAT

51 GEISPSNLVS VGAQASGQIK KLYVKLGQQV KKGDLIAEIN STSQTNTLNT

101 EKSKLETYQA KLVSAQIALG SAEKKYKRQA ALWKDDATAK EDLESAQDAL

151 AAAKANVAEL KALIRQSKIS INTAESELGY TRITATMDGT VVAILVEEGQ

201 TVNAAQSTPT IVQLANLDMM LNKMQIAEGD ITKVKAGQDI SFTILSEPDT

251 PIKAKLDSVD PGLTTMSSGG YNSSTDTASN AVYYYARSFV PNPDGKLATG

301 MTTQNTVEID GVKNVLIIPS LTVKNRGGRA FVRVLGADGK AAEREIRTGM

351 RDSMNTEVKS GLKEGDKVVI SEITAAEQQE SGERALGGPP RR*
```

ORF85a and ORF85-1 show 98.2% identity in 334 aa overlap:

```
                     30        40        50        60        70        80
   orf85a.pep  PQAAYITETVRRGDISRTVSATGEISPSNLVSVGAQASGQIKKLYVKLGQQVKKGDLIAE
                                        |||||||||||||||||||||||||||||
   orf85-1                              VSVGAQASGQIKILYVKLGQQVKKGDLIAE
                                                10        20        30

90       100       110       120       130       140
   orf85a.pep  INSTSQTNTLNTEKSKLETYQAKLVSAQIALGSAEKKYKRQAALWKDDATAKEDLESAQD
               ||||||||||||||||||||||||||||||||||||||||||||::||:||||||||||
   orf85-1     INSTSQTNTLNTEKSKLETYQAKLVSAQIALGSAEKKYKRQAALWKENATSKEDLESAQD
                       40        50        60        70        80        90

150       160       170       180       190       200
   orf85a.pep  ALAAAKANVAELKALIRQSKISINTAESELGYTRITATMDGTVVAILVEEGQTVNAAQST
               |:||||||||||||||||||||||||||||||||||||||||||||||||||||||||
   orf85-1     AFAAAKANVAELKALIRQSKISINTAESELGYTRITATMDGTVVAILVEEGQTVNAAQST
                      100       110       120       130       140       150

210       220       230       240       250       260
   orf85a.pep  PTIVQLANLDMMLNKMQIAEGDITKVKAGQDISFTILSEPDTPIKAKLDSVDPGLTTMSS
               ||||||||||||||||||||||||||||||||||||||||||||||||||||||||||||
   orf85-1     PTIVQLANLDMMLNKMQIAEGDITKVKAGQDISFTILSEPDTPIKAKLDSVDPGLTTMSS
                      160       170       180       190       200       210

270       280       290       300       310       320
   orf85a.pep  GGYNSSTDTASNAVYYYARSFVPNPDGKLATGMTTQNTVEIDGVKNVLIIPSLTVKNRGG
               ||||||||||||||||||||||||||||||||||||||||||||||||||||||||||||
   orf85-1     GGYNSSTDTASNAVYYYARSFVPNPDGKLATGMTTQNTVEIDGVKNVLIIPSLTVKNRGG
                      220       230       240       250       260       270

330       340       350       360       370       380
   orf85a.pep  RAFVRVLGADGKAAEREIRTGMRDSMNTEVKSGLKEGDKVVISEITAAEQQESGERALGG
               :|||||||||||||||||||||||||||||||||||||||||||||||||||||||||||
   orf85-1     KAFVRVLGADGKAAEREIRTGMRDSMNTEVKSGLKEGDKVVISEITAAEQQESGERALGG
                      280       290       300       310       320       330

390
   orf85a.pep  PPRRX
               |||||
   orf85-1     PPRRX
```

Figure 19D:
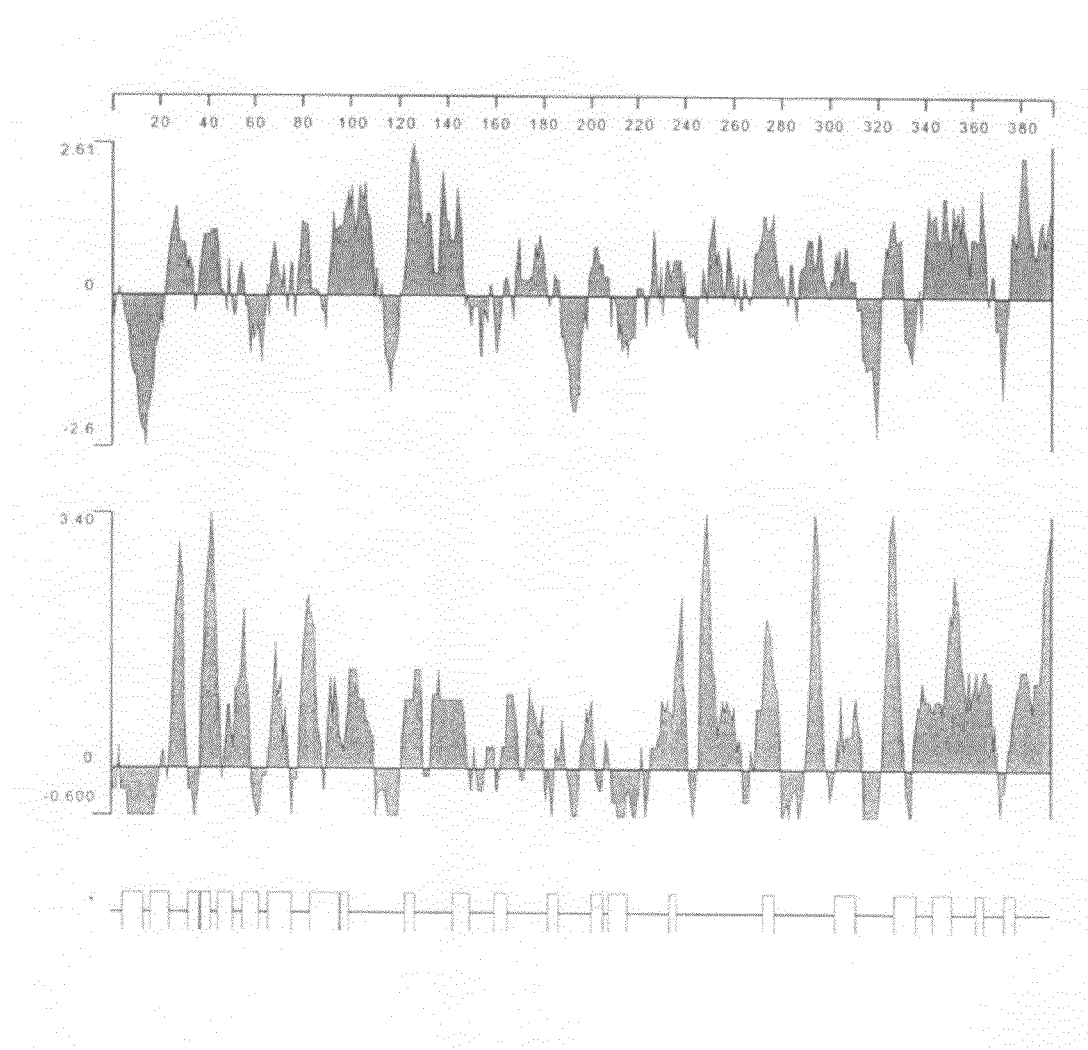

FIG. 19D shows plots of hydrophilicity, antigenic index, and AMPHI regions for ORF85a.

Homology with a predicted ORF from *N. gonorrhoeae*

ORF85 shows a high degree of identity with a predicted ORF (ORF85ng) from *N. gonorrhoeae*:

```
ORF85      1 MAKMMKWAAVAAVAAAAVWGGWS.LKPEPHVLDITETVRRG.........  40
             ||||||||||||||||||||||| ||||::  |||:||||
ORF85ng    1 MAKMMKWAAVAAVAAAAVWGGWSYLKPEPQAAYITEAVRRGDISRTVSAT  50
                       •         •         •         •         •
ORF85        .................................ISFTILSEPDT 250
                                              |||||||||||||
ORF85ng  201 TVNAAQSTPTIVQLANLDMMLNKMQIAEGDITKVKAGQDISFTILSEPDT 250
                       •         •         •         •         •
ORF85    251 PIKAKLDSVDPGLTTMSSGGYNSSTDTASNAVYYYARSFVPNPDGKLATG 300
             ||||||||||||||||||||||||||||||||||||||||||||||||||
ORF85ng  251 PIKAKLDSVDPGLTTMSSGGYNSSTDTASNAVYYYARSFVPNPDGKLATG 300
                       •         •         •         •         •
ORF85    301 MTTQNTVEIDGVKNVLIIPSLTVKNRGGKAFVRVLGADGKAAEREIRTGM 350
             |||||||||||||||||:||||||||||||||||||||||||:|||||||
ORF85ng  301 MTTQNTVEIDGVKNVLLIPSLTVKNRGGKAFVRVLGADGKAVEREIRTGM 350
                       •         •         •         •         •
ORF85    152 RDSMNTEVKSGLKEGDKVVISEITAAEQQESGERALGGPPRR 393
             :||||||||||||||||||||||||||||||||||||||||
ORF85ng  351 KDSMNTEVKSGLKEGDKVVISEITAAEQQESGERALGGPPRR 393
```

The complete length ORF85ng nucleotide sequence <SEQ ID 771> is:

```
   1 ATGGCAAAAA TGATGAAATG GCGGCTGTT  GCGGCGGTCG CGGCGGCaac

51 GGTTTGGGGC GGATGGTCTT ATCTGAAGCC CGAACCGCAG GCTGCTTATA

101 TTACGGAaac ggTCAGGCGC GGCGATATCA GCCGGACGGT TTCCGCGACG

151 GgcgAGATTT CGCCGTCCAA CCTGGTATCG GTCGGCGCGC AGGCTTCGGG

201 GCAGATTAAA AAGCTTTATG TCAAACTCGG CAACAGGTC  AAAAAGGGCG

251 ATTTGATTGC GGAAATCAAT TCGACCACGC AGACCAACAC GATCGATATG

301 GAAAAATCCA AATTGGAAAC GTATCAGGCG AAGCTGGTGT CGGCACAGAT

351 TGCATTGGGC AGCGCGGAGA AGAAATATAA GCGTCAGGCG GCGTTGTGGA

401 AGGATGATGC GACCTCTAAA GAAGATTTGG AAAGCGCGCA GGATGCGCTT

451 GCCGCCGCCA AAGCCAATGT TGCCGAGTTG AAGGCTTTAA TCAGACAGAG

501 CAAAATTTCC ATCAATACCG CCGAGTCGGA TTTGGGCTAC ACGCGCATTA

551 CCGCGACGAT GGACGGCACG GTGGTGGCGA TTCCCGTGGA AGAGGGGCAG

601 ACTGTGAACG CGGCGCAGTC TACGCCGACG ATTGTCCAAT TGGCGAATCT

651 GGATATGATG TTGAACAAAA TGCAGATTGC CGAGGGCGAT ATTACCAAGG

701 TGAAGGCGGG GCAGGATATT TCGTTTACGA TTTTGTCCGA ACCGGATACG

751 CCGATTAAGG CGAAGCTCGA CAGCGTCGAC CCCGGGCTGA CCACGATGTC

801 GTCGGGCGGC TACAACAGCA GTACGGATAC GGCTTCCAAT GCGGTCTATT

851 ATTATGCCCG TTCGTTTGTG CCGAATCCGG ACGGCAAACT CGCCACGGGG

901 ATGACGACGC AGAATACGGT TGAAATCGAC GGTGTGAAAA ATGTGTTGCT

951 TATTCCGTCG CTGACCGTGA AAAATCGCGG CGGCAAGGCG TTCGTACGCG

1001 TGTTGGGTGC GGACGGCAAG GCAGTGGAAC GCGAAATCCG GACCGGTATG

1051 AAAGACAGTA TGAATACCGA AGTGAAAAGC GGGTTGAAAG AGGGGGACAA

1101 AGTGGTCATC TCCGAAATAA CCGCCGCCGA GCAGCAGGAA AGCGGCGAAC

1151 GCGCCCTAGG CGGCCCGCCG CGCCGATAA
```

This encodes a protein having amino acid sequence <SEQ ID 772>:

```
  1 MAKMMKWAAV AAVAAAAVWG GWSYLKPEPQ AAYITEAVRR GDISRTVSAT
 51 GEISPSNLVS VGAQASGQIK KLYVKLGQQV KKGDLIAEIN STTQTNTIDM
101 EKSKLETYQA KLVSAQIALG SAEKKYKRQA ALWKDDATSK EDLESAQDAL
151 AAAKANVAEL KALIRQSKIS INTAESDLGY TRITATMDGT VVAIPVEEGQ
201 TVNAAQSTPT IVQLANLDMM LNKMQIAEGD ITKVKAGQDI SFTILSEPDT
251 PIKAKLDSVD PGLTTMSSGG YNSSTDTASN AVYYYARSFV PNPDGKLATG
301 MTTQNTVEID GVKNVLLIPS LTVKNRGGKA FVRVLGADGK AVEREIRTGM
351 KDSMNTEVKS GLKEGDKVVI SEITAAEQQE SGERALGGPP RR*
```

ORF85ng and ORF85-1 show 96.1% identity in 334 aa overlap:

```
                30         40         50         60         70         80
  orf85ng   PQAAYITETVRRGDISRTVSATGEISPSNLVSVGAQASGQIKKLYVKLGQQVKKGDLIAE
                                       ||||||||||||| ||||||||||||||||||
  orf85-1                              VSVGAQASGQIKILYVKLGQQVKKGDLIAE
                                       10         20         30

90        100        110        120        130        140
  orf85ng   INSTTQTNTIDMEKSKLETYQAKLVSAQIALGSAEKKYKRQAALWKDDATSKEDLESAQD
             ||||:||||::| |||||||||||||||||||||||||||||||||::||||||||||
  orf85-1   INSTSQTNTLNTEKSKLETYQAKLVSAQIALGSAEKKYKRQAALWKENATSKEDLESAQD
                40         50         60         70         80         90

150        160        170        180        190        200
  orf85ng   ALAAAKANVAELKALIRQSKISINTAESDLGYTRITATMDGTVVAIPVEEGQTVNAAQST
            |:||||||||||||||||||||||||||:|||||||||||||| ||||||||||||||
  orf85-1   AFAAAKANVAELKALIRQSKISINTAESELGYTRITATMDGTVVAILVEEGQTVNAAQST
                100        110        120        130        140        150

210        220        230        240        250        260
  orf85ng   PTIVQLANLDMMLNKMQIAEGDITKVKAGQDISFTILSEPDTPIKAKLDSVDPGLTTMSS
            ||||||||||||||||||||||||||||||||||||||||||||||||||||||||||
  orf85-1   PTIVQLANLDMMLNKMQIAEGDITKVKAGQDISFTILSEPDTPIKAKLDSVDPGLTTMSS
                160        170        180        190        200        210

270        280        290        300        310        320
  orf85ng   GGYNSSTDTASNAVYYYARSFVPNPDGKLATGMTTQNTVEIDGVKNVLLIPSLTVKNRGG
            |||||||||||||||||||||||||||||||||||||||||||||||:||||||||||
  orf85-1   GGYNSSTDTASNAVYYYARSFVPNPDGKLATGMTTQNTVEIDGVKNVLIIPSLTVKNRGG
                220        230        240        250        260        270

330        340        350        360        370        380
  orf85ng   KAFVRVLGADGKAVEREIRTGMKDSMNTEVKSGLKEGDKVVISEITAAEQQESGERALGG
            |||||||||||||:|||||||||:||||||||||||||||||||||||||||||||||
  orf85-1   KAFVRVLGADGKAAEREIRTGMRDSMNTEVKSGLKEGDKVVISEITAAEQQESGERALGG
                280        290        300        310        320        330

390
  orf85ng   PPRRX
            |||||
  orf85-1   PPRRX
```

In addition, ORF85ng shows significant homology to an *E. coli* membrane fusion protein:

```
gi|1787104 (AE000189) o380; 27% identical (27 gaps) to 332 residues from
membrane fusion protein precursor, MTRC_NEIGO SW: P43505 (412 aa)
[Escherichia coli] Length = 380
Score = 193 bits (485), Expect = 2e-48
Identities = 120/345 (34%), Positives = 182/345 (51%), Gaps = 13/345 (3%)

Query:  29 PQAAYITETVRRGDISRTVSATGEISPSNLVSVGAQASGQIKKLYVKLGQQVKKGDLIAE  88
              P   Y T  VR GD+ ++V ATG++      V VGAQ SGQ+K L V +G +VKK  L+
Sbjct:  41 PVPTYQTLIVRPGDLQQSVLATGKLDALRKVDVGAQVSGQLKTLSVAIGDKVKKDQLLGV 100

Query:  89 INSTTQTNTIDMEKSKLETYQAKLVSAQIALGSAEKKYKRQAALWKDDATSKEXXXXXXX 148
              I+     N I   ++ L    +A+   A+   L A   Y RQ  L+    A  S++
Sbjct: 101 IDPEQAENQIKEVEATLMELRAQRQQAEAELKLARVTYSROQRLAQTKAVSQQDLDTAAT 160
```

-continued

```
Query: 149 XXXXXXXXXXXXXXXXXIRQSKISINTAESDLGYTRITATMDGTVVAIPVEEGQTVNAAQST 208
                           I++++ S++TA+++L YTRI A M G V  I   +GQTV AAQ
Sbjct: 161 EMAVKQAQIGTIDAQIKRNQASLDTAKTNLDYTRIVAPMAGEVTQITTLQGQTVIAAQQA 220

Query: 209 PTIVQLANLDMMLNKMQIAEGDITKVKAGQDISFTILSEPDTPIKAKLDSVDPGLTTMSS 268
           P I+ LA++  ML K Q++E D+  +K GQ    FT+L +P T  + ++   V P
Sbjct: 221 PNILTLADMSAMLVKAQVSEADVIHLKPGQKAWFTVLGDPLTRYEGQIKDVLP------- 273

Query: 269 GGYNSSTDTASNAVYYYARSFVPNPDGKLATGMTTQNTVEIDGVKNVLLIPSLTVKNRGG 328
             + +  ++A++YYAR  VPNP+G L    MT Q  +++  VKNVL IP   + +  G
Sbjct: 274 -----TPEKVNDAIFYYARFEVPNPNGLLRLDMTAQVHIQLTDVKNVLTIPLSALGDPVG 328

Query: 329 KAFVRV-LGADGKAVEREIRTGMKDSMNTEVKSGLKEGDKVVISE                 372
            +V L  +G+  ERE+  G ++  + E+   GL+ GD+VVI E
Sbjct: 329 DNRYKVKLLRNGETREREVTIGARNDTDVEIVKGLEAGDEVVIGE                 373
```

Based on this analysis, it was predicted that the proteins from *N. meningitidis* and *N. gonorrhoeae*, and their epitopes, could be useful antigens for vaccines or diagnostics, or for raising antibodies.

ORF85-1 (40.4 kDa) was cloned in the pGex vectors and expressed in *E. coli*, as described above. The products of protein expression and purification were analyzed by SDS-PAGE. FIG. 19A shows the results of affinity purification of the GST-fusion protein. Purified GST-fusion protein was used to immunise mice, whose sera were used for Western blot (FIG. 19B), FACS analysis (FIG. 19C), and ELISA (positive result). These experiments confirm that ORF85-1 is a surface-exposed protein, and that it is a useful immunogen.

Example 92

The following partial DNA sequence was identified in *N. meningitidis* <SEQ ID 773>:

```
  1..ATTCCCGCCA CGATGACATT TGAACGCAGC GGCAATGCTT ACAAAATCGT
 51   TTCGACGATT AAAGTGCCGC TATACAATAT CCGTTTCGAG TCCGGCGGTA
101   CGGTTGTCGG CAATACCCTG CACCCTACCT ACTATAGAGA CATACGCAGG
151   GGCAAACTGT ATGCGGAAgc CAAATTCGCC GACgGcAGCG TAACTTACGG
201   CAAAGCGGGC GAGAGCAAAA CCGAGCAAAG CCCCAAGGCT ATGGATTTGT
251   TCACGCTTGC CTGGCAGTTG GCGGCAAATG ACGCGAAACT CCCCCCGGGG
301   CTGAAAATCA CCAACGGCAA AAAACTTTAT TCCGTCGGCG GTTTGAATAA
351   GGCGGGTACA GGAAAATACA GCATAGGCGG CGTGGAAACC GAAGTCGTCA
401   AATATCGGGT GCGGCGCGGC GACGATGCGG TAATGTATTT cTTCGCACCG
451   TCCCTGAACA ATATTCCGGC ACAAATCGGC TATACCGACG ACGGCAAAAC
501   CTATACGCTG AAACTCAAAT CGGTGCAGAT CAACGGCCAG GCAGCCAAAC
551   CGTAA
```

This corresponds to the amino acid sequence <SEQ ID 774; ORF120>:

```
  1..IPATMTFERS GNAYKIVSTI KVPLYNIRFE SGGTVVGNTL HPTYYRDIRR
 51   GKLYAEAKFA DGSVTYGKAG ESKTEQSPKA MDLFTLAWQL AANDAKLPPG
101   LKITNGKKLY SVGGLNKAGT GKYSIGGVET EVVKYRVRRG DDAVMYFFAP
151   SLNNIPAQIG YTDDGKTYTL KLKSVQINGQ AAKP*
```

Further work revealed the complete nucleotide sequence <SEQ ID 775>:

```
  1 ATGATGAAGA CTTTTAAAAA TATATTTTCC GCCGCCATTT TGTCCGCCGC

51 CCTGCCGTGC GCGTATGCGG CAGGGCTGCC CCAATCCGCC GTGCTGCACT

101 ATTCCGGCAG CTACGGCATT CCCGCCACGA TGACATTTGA ACGCAGCGGC

151 AATGCTTACA AAATCGTTTC GACGATTAAA GTGCCGCTAT ACAATATCCG

201 TTTCGAGTCC GGCGGTACGG TTGTCGGCAA TACCCTGCAC CCTACCTACT

251 ATAGAGACAT ACGCAGGGGC AAACTGTATG CGGAAGCCAA ATTCGCCGAC

301 GGCAGCGTAA CTTACGGCAA AGCGGGCGAG AGCAAAACCG AGCAAAGCCC

351 CAAGGCTATG GATTTGTTCA CGCTTGCCTG GCAGTTGGCG GCAAATGACG

401 CGAAACTCCC CCCGGGGCTG AAAATCACCA ACGGCAAAAA ACTTTATTCC

451 GTCGGCGGTT TGAATAAGGC GGGTACAGGA AAATACAGCA TAGGCGGCGT

501 GGAAACCGAA GTCGTCAAAT ATCGGGTGCG GCGCGGCGAC GATGCGGTAA

551 TGTATTTCTT CGCACCGTCC CTGAACAATA TTCCGGCACA AATCGGCTAT

601 ACCGACGACG GCAAAACCTA TACGCTGAAA CTCAAATCGG TGCAGATCAA

651 CGGCCAGGCA GCCAAACCGT AA
```

This corresponds to the amino acid sequence <SEQ ID 776; ORF120-1>:

```
  1 MMKTFKNIFS AAILSAALPC AYAAGLPQSA VLHYSGSYGI PATMTFERSG

51 NAYKIVSTIK VPLYNIRFES GGTVVGNTLH PTYYRDIRRG KLYAEAKFAD

101 GSVTYGKAGE SKTEQSPKAM DLFTLAWQLA ANDAKLPPGL KITNGKKLYS

151 VGGLNKAGTG KYSIGGVETE VVKYRVRRGD DAVMYFFAPS LNNIPAQIGY

201 TDDGKTYTLK LKSVQINGQA AKP*
```

Computer analysis of this amino acid sequence gave the following results:
Homology with a Predicted ORF from *N. meningitidis* (Strain A)

ORF120 shows 92.4% identity over a 184aa overlap with an ORF (ORF120a) from strain A of *N. meningitidis*.

```
                                     10         20         30
    orf120.pep                 IPATMTFERSGNAYKIVSTIKVPLYNIRFE
                               ||||  :    || |||||||||||||||
    orf120a     SAAILSAALPCAYAAGLPXSAVLHYSGSYGIPATXXXXXXXNAXKIVSTIKVPLYNIRFE
                10        20        30        40        50        60

40        50        60        70        80        90
    orf120.pep  SGGTVVGNTLHPTYYRDIRRGKLYAEAKFADGSVTYGKAGESKTEQSPKAMDLFTLAWQL
                ||||||||||||||||||||||||||||||||||||||        :  |||||||||||
    orf120a     SGGTVVGNTLHPTYYRDIRRGKLYAEAKFADGSVTYGKAXXXXXXXQSPKAMDLFTLAWQL
                70        80        90       100       110       120

100       110       120       130       140       150
    orf120.pep  AANDAKLPPGLKITNGKKLYSVGGLNKAGTGKYSIGGVETEVVKYRVRRGDDAVMYFFAP
                ||||||||||||||||||||||||||||||||||||||||||||||||||||||||||||
    orf120a     AANDAKLPPGLKITNGKKLYSVGGLNKAGTGKYSIGGVETEVVKYRVRRGDDAVMYFFAP
                130       140       150       160       170       180

160       170       180
    orf120.pep  SLNNIPAQIGYTDDGKTYTLKLKSVQINGQAAKPX
                |||||||||||||||||||||||||||||||||||
    orf120a     SLNNIPAQIGYTDDGKTYTLKLKSVQINGQAAKPX
                190       200       210       220
```

The complete length ORF120a nucleotide sequence <SEQ ID 777> is:

```
  1 ATGATGAAGA CTTTTAAAAA TATATTTTCC GCCGCCATTT TGTCCGCCGC

51 CCTGCCGTGC GCGTATGCGG CAGGGCTGCC CNAATCCGCC GTGCTGCACT

101 ATTCCGGCAG CTACGGCATT CCCGCCACNA NNANNTNNGN ACNNNGNGNC

151 AATGCTTNCA AAATCGTTTC GACGATTAAA GTGCCGCTAT ACAATATCCG

201 TTTCGAGTCC GGCGGTACGG TTGTCGGCAA TACCCTGCAC CCTACCTACT

251 ATAGAGACAT ACGCAGGGGC AAACTGTATG CGGAAGCCAA ATTCGCCGAC

301 GGCAGCGTAA CCTACGGCAA AGCGGNNNNN ANCNNNNNNG NGCAAAGCCC

351 CAAGGCTATG GATTTGTTCA CGCTTGCNTG GCAGTTGGCG GCAAATGACG

401 CGAAACTCCC CCCGGGGCTG AAAATCACCA ACGGCAAAAA ACTTTATTCC

451 GTCGGCGGTT TGAATAAGGC GGGTACAGGA AAATACAGCA TAGGCGGCGT

501 GGAAACCGAA GTCGTCAAAT ATCGGGTGCG GCGCGGCGAC GATGCGGTAA

551 TGTATTTCTT CGCACCGTCC CTGAACAATA TTCCGGCACA AATCGGCTAT

601 ACCGACGACG GCAAAACCTA TACGCTGAAA CTCAAATCGG TGCAGATCAA

651 CGGCCAGGCA GCCAAACCGT AA
```

This encodes a protein having amino acid sequence <SEQ ID 778>:

```
  1 MMKTFKNIFS AAILSAALPC AYAAGLPXSA VLHYSGSYGI PATXXXXXXX

51 NAXKIVSTIK VPLYNIRFES GGTVVGNTLH PTYYRDIRRG KLYAEAKFAD

101 GSVTYGKAXX XXXXQSPKAM DLFTLAWQLA ANDAKLPPGL KITNGKKLYS

151 VGGLNKAGTG KYSIGGVETE VVKYRVRRGD DAVMYFFAPS LNNIPAQIGY

201 TDDGKTYTLK LKSVQINGQA AKP*
```

ORF120a and ORF120-1 show 93.3% identity in 223 aa overlap:

```
                    10         20         30         40         50         60
   orf120a.pep  MMKTFKNIFSAAILSAALPCAYAAGLPXSAVLHYSGSYGIPATXXXXXXXNAXKIVSTIK
                ||||||||||||||||||||||||||| |||||||||||||||        || |||||||
   orf120-1     MMKTFKNIFSAAILSAALPCAYAAGLPQSAVLHYSGSYGIPATMTFERSGNAYKIVSTIK
                    10         20         30         40         50         60

70         80         90        100        110        120
   orf120a.pep  VPLYNIRFESGGTVVGNTLHPTYYRDIRRGKLYAEAKFADGSVTYGKAXXXXXXQSPKAM
                ||||||||||||||||||||||||||||||||||||||||||||||||||     ||||||
   orf120-1     VPLYNIRFESGGTVVGNTLHPTYYRDIRRGKLYAEAKFADGSVTYGKAGESKTEQSPKAM
                    70         80         90        100        110        120

130        140        150        160        170        180
   orf120a.pep  DLFTLAWQLAANDAKLPPGLKITNGKKLYSVGGLNKAGTGKYSIGGVETEVVKYRVRRGD
                ||||||||||||||||||||||||||||||||||||||||||||||||||||||||||||
   orf120-1     DLFTLAWQLAANDAKLPPGLKITNGKKLYSVGGLNKAGTGKYSIGGVETEVVKYRVRRGD
                   130        140        150        160        170        180

190        200        210        220
   orf120a.pep  DAVMYFFAPSLNNIPAQIGYTDDGKTYTLKLKSVQINGQAAKPX
                ||||||||||||||||||||||||||||||||||||||||||||
   orf120-1     DAVMYFFAPSLNNIPAQIGYTDDGKTYTLKLKSVQINGQAAKPX
                   190        200        210        220
```

Homology with a Predicted ORF from *N. gonorrhoeae*
ORF120 shows 97.8% identity over 184 aa overlap with a predicted ORF (ORF120ng) from *N. gonorrhoeae*:

```
orf120.pep                                      IPATMTFERSGNAYKIVSTIKVPLYNIRFE  30
                                                ||||||||||||||||||||||||||||||
orf120ng   SAAILSAALPCAYAARLPQSAVLHYSGSYGIPATMTFERSGNAYKIVSTIKVPLYNIRFE  69
orf120.pep SGGTVVGNTLHPTYYRDIRRGKLYAEAKFADGSVTYGKAGESKTEQSPKAMDLFTLAWQL  90
           ||||||||||||:||:||||||||||||||||||||||||||||||||||||||||||||
orf120ng   SGGTVVGNTLHPAYYKDIRRGKLYAEAKFADGSVTYGKAGESKTEQSPKAMDLFTLAWQL  129
orf120.pep AANDAKLPPGLKITNGKKLYSVGGLNKAGTGKYSIGGVETEVVKYRVRRGDDAVMYFFAP  150
           |||||||||||||||||||||||||||||||||||||||||||||||||||:|  |||||
orf120ng   AANDAKLPPGLKITNGKKLYSVGGLNKAGTGKYSIGGVETEVVKYRVRRGDDTVTYFFAP  189
orf120.pep SLNNIPAQIGYTDDGKTYTLKLKSVQINGQAAKP                           184
           ||||||||||||||||||||||||||||||||||
orf120ng   SLNNIPAQIGYTDDGKTYTLKLKSVQINGQAAKP                           223
```

The complete length ORF120ng nucleotide sequence <SEQ ID 779> is:

```
  1 ATGATGAAGA CTTTTAAAAA TATATTTTCC GCCGCCATTT TGTCCGCCGC
 51 CCTGCCGTGC GCGTATGCGG CAAGGCTACC CCAATCCGCC GTGCTGCACT
101 ATTCCGGCAG CTACGGCATT CCCGCCACGA TGACATTTGA ACGCAGCGGC
151 AATGCTTACA AAATCGTTTC GACGATTAAA GTGCCGCTAT ACAATATCCG
201 TTTCGAATCC GGCGGTACGG TTGTCGGCAA TACCCTGCAC CCTGCCTACT
251 ATAAAGACAT ACGCAGGGGC AAACTGTATG CGGAAGCCAA ATTCGCCGAC
301 GGCAGCGTAA CCTACGGCAA AGCGGGCGAG AGCAAAACCG AGCAAAGCCC
351 CAAGGCTATG GATTTGTTCA CGCTTGCCTG GCAGTTGGCG GCAAATGACG
401 CGAAACTCCC CCCGGGTCTG AAAATCACCA ACGGCAAAAA ACTTTATTCC
451 GTCGGCGGCC TGAATAAGGC GGGTACGGGA AAATACAGCA TaggCGGCGT
501 GGAAACCGAA GTCGTCAAAT ATCGGGTGCG GCGCGGCGAC GATACGGTAA
551 CGTATTTCTT CGCACCGTCC CTGAACAATA TTCCGGCACA AATCGGCTAT
601 ACCGACGACG GCAAAACCTA TACGCTGAAG CTCAAATCGG TGCAGATCAA
651 CGGACAGGCC GCCAAACCGT AA
```

This encodes a protein having amino acid sequence <SEQ ID 780>:

```
  1 MMKTFKNIFS AAILSAALPC AYAARLPQSA VLHYSGSYGI PATMTFERSG
 51 NAYKIVSTIK VPLYNIRFES GGTVVGNTLH PAYYKDIRRG KLYAEAKFAD
101 GSVTYGKAGE SKTEQSPKAM DLFTLAWQLA ANDAKLPPGL KITNGKKLYS
151 VGGLNKAGTG KYSIGGVETE VVKYRVRRGD DTVTYFFAPS LNNIPAQIGY
201 TDDGKTYTLK LKSVQINGQA AKP*
```

In comparison with ORF120-1, ORF120ng shows 97.8% identity in 223 aa overlap:

```
                     10         20         30         40         50         60
orf120-1.pep MMKTFKNIFSAAILSAALPCAYAAGLPQSAVLHYSGSYGIPATMTFERSGNAYKIVSTIK
             |||||||||||||||||||||||||  |||||||||||||||||||||||||||||||||
orf120ng     MMKTFKNIFSAAILSAALPCAYAARLPQSAVLHYSGSYGIPATMTFERSGNAYKIVSTIK
                     10         20         30         40         50         60
```

```
              70         80         90        100        110        120
orf120-1.pep  VPLYNIRFESGGTVVGNTLHPTYYRDIRRGKLYAEAKFADGSVTYGKAGESKTEQSPKAM
              ||||||||||||||||||||||:||:||||||||||||||||||||||||||||||||||
orf120ng      VPLYNIRFESGGTVVGNTLHPAYYKDIRRGKLYAEAKFADGSVTYGKAGESKTEQSPKAM
              70         80         90        100        110        120

130        140        150        160        170        180
orf120-1.pep  DLFTLAWQLAANDAKLPPGLKITNGKKLYSVGGLNKAGTGKYSIGGVETEVVKYRVRRGD
              ||||||||||||||||||||||||||||||||||||||||||||||||||||||||||||
orf120ng      DLFTLAWQLAANDAKLPPGLKITNGKKLYSVGGLNKAGTGKYSIGGVETEVVKYRVRRGD
             130        140        150        160        170        180

190        200        210        220
orf120-1.pep  DAVMYFFAPSLNNIPAQIGYTDDGKTYTLKLKSVQINGQAAKPX
              |:||||||||||||||||||||||||||||||||||||||||||
orf120ng      DTVTYFFAPSLNNIPAQIGYTDDGKTYTLKLKSVQINGQAAKPX
             190        200        210        220
```

This analysis, including the presence of a putative leader sequence in the gonococcal protein suggests that the proteins from *N. meningitidis* and *N. gonorrhoeae*, and their epitopes, could be useful antigens for vaccines or diagnostics, or for raising antibodies.

Example 93

The following partial DNA sequence was identified in *N. meningitidis* <SEQ ID 781>:

```
  1 ATGTATCGGA GGAAAGGGCG GGGCATCAAG CCGTGGATGG GTGCCGGTGC

51 .GCGTTTGCC GCCTTGGTCT GGCTGGTTTT CGCGCTCGGC GATACTTTGA

101 CTCCGTTTGC GGTTGCGGCG GTGCTGGCGT ATGTATTGGA CCCTTTGGTC

151 GAATGGTTGC AGAAAAAGGG TTTGAACCGT GCATCCGCTT CGATGTCTGT

201 GATGGTGTTT TCCTTGATTT TGTTGTTGGC ATTATTGTTG ATTATCGTCC

251 CTATGCTGGT CGGGCAGTTC AACAATTTGG CATCGCGCCT GCCCCAATTA

301 ATCGGTTTTA TGCAGAACAC GCTGCTGCCG TGGTTGAAAA ATACAATCGG

351 CGGATATGTG GAAATCGATC AGGCATCTAT TATTGCGTGG CTTCAGGCGC

401 ATACGGGAGA GTTGAGCAAC GCGCTTAAGG CGTGGTTTCC CGTTTTGATG

451 AGGCAGGGCG GCAATATT..
```

This corresponds to the amino acid sequence <SEQ ID 782; ORF121>:

```
  1 MYRRKGRGIK PWMGAGXAFA ALVWLVFALG DTLTPFAVAA VLAYVLDPLV

51 EWLQKKGLNR ASASMSVMVF SLILLLALLL IIVPMLVGQF NNLASRLPQL

101 IGFMQNTLLP WLKNTIGGYV EIDQASIIAW LQAHTGELSN ALKAWFPVLM

151 RQGGNI..
```

Further work revealed the complete nucleotide sequence <SEQ ID 783>:

```
  1 ATGTATCGGA GGAAAGGGCG GGGCATCAAG CCGTGGATGG GTGCCGGTGC

51 GGCGTTTGCC GCCTTGGTCT GGCTGGTTTT CGCGCTCGGC GATACTTTGA

101 CTCCGTTTGC GGTTGCGGCG GTGCTGGCGT ATGTATTGGA CCCTTTGGTC

151 GAATGGTTGC AGAAAAAGGG TTTGAACCGT GCATCCGCTT CGATGTCTGT

201 GATGGTGTTT TCCTTGATTT TGTTGTTGGC ATTATTGTTG ATTATCGTCC
```

-continued

```
 251 CTATGCTGGT CGGGCAGTTC AACAATTTGG CATCGCGCCT GCCCCAATTA
 301 ATCGGTTTTA TGCAGAACAC GCTGCTGCCG TGGTTGAAAA ATACAATCGG
 351 CGGATATGTG GAAATCGATC AGGCATCTAT TATTGCGTGG CTTCAGGCGC
 401 ATACGGGAGA GTTGAGCAAC GCGCTTAAGG CGTGGTTTCC CGTTTTGATG
 451 AGGCAGGGCG GCAATATTGT CAGCAGTATC GGCAACCTGC TGCTGCTTCC
 501 CTTGCTGCTT TACTATTTCC TGCTGGATTG GCAGCGGTGG TCGTGCGGCA
 551 TTGCCAAACT GGTTCCGAgG CGTTTTGCCG GTGCTTATAC GCGCATTACA
 601 GGCAATTTGA ACGAGGTATT GGGCGAATTT TTGCGCGGGC AGCTTCTGGT
 651 AATGCTGATT ATGGGCTTGG TTTACGGTTT GGGATTGGTG CTGGTCGGGC
 701 TGGATTCGGG GTTTGCCATC GGTATGCTTG CCGGTATTTT GGTGTTTGTC
 751 CCTTATCTCG GGGCGTTTAC GGGATTGCTG CTTGCCACCG TCGCCGCCTT
 801 GCTCCAGTTC GGTTCGTGGA ACGGCATCCT ATCGGTTTGG GCGGTTTTTG
 851 CCGTAGGACA GTTTCTCGAA AGTTTTTTCA TTACGCCGAA AATCGTGGGA
 901 GACCGTATCG GGCTGTCGCC GTTTTGGGTT ATCTTTTCGC TGATGGCGTT
 951 CGGGCAGCTG ATGGGCTTTG TCGGAATGTT GGCGGGATTG CCTTTGGCCG
1001 CCGTAACCTT GGTCTTGCTT CGCGAGGGCG TGCAGAAATA TTTTGCCGGC
1051 AGTTTTTACC GGGGCAGGTA G
```

This corresponds to the amino acid sequence <SEQ ID 784; ORF121-1>:

```
  1 MYRRKGRGIK PWMGAGAAFA ALVWLVFALG DTLTPFAVAA VLAYVLDPLV
 51 EWLQKKGLNR ASASMSVMVF SLILLLALLL IIVPMLVGQF NNLASRLPQL
101 IGFMQNTLLP WLKNTIGGYV EIDQASIIAW LQAHTGELSN ALKAWFPVLM
151 RQGGNIVSSI GNLLLLPLLL YYFLLDWQRW SCGIAKLVPR RFAGAYTRIT
201 GNLNEVLGEF LRGQLLVMLI MGLVYGLGLV LVGLDSGFAI GMLAGILVFV
251 PYLGAFTGLL LATVAALLQF GSWNGILSVW AVFAVGQFLE SFFITPKIVG
301 DRIGLSPFWV IFSLMAFGQL MGFVGMLAGL PLAAVTLVLL REGVQKYFAG
351 SFYRGR*
```

Computer analysis of this amino acid sequence gave the following results:

Homology with a Predicted ORF from *N. meningitidis* (Strain A)

ORF121 shows 98.7% identity over a 156aa overlap with an ORF (ORF121a) from strain A of *N. meningitidis*.

```
                  10         20         30         40         50         60
    orf121.pep MYRRKGRGIKPWMGAGXAFAALVWLVFALGDTLTPFAVAAVLAYVLDPLVEWLQKKGLNR
               |||||||||||||| || |||||||||||||||||||||||||||||||||||||||||
    orf121a    MYRRKGRGIKPWMDAGAAFAALVWLVFALGDTLTPFAVAAVLAYVLDPLVEWLQKKGLNR
                  10         20         30         40         50         60

70         80         90        100        110        120
    orf121.pep ASASMSVMVFSLILLLALLLIIVPMLVGQFNNLASRLPQLIGFMQNTLLPWLKNTIGGYV
               ||||||||||||||||||||||||||||||||||||||||||||||||||||||||||||
    orf121a    ASASMSVMVFSLILLLALLLIIVPMLVGQFNNLASRLPQLIGFMQNTLLPWLKNTIGGYV
                  70         80         90        100        110        120
```

```
                        130       140       150
orf121.pep  EIDQASIIAWLQAHTGELSNALKAWFPVLMRQGGNI
            |||||||||||||||||||||||||||||||||||
orf121a     EIDQASIIAWLQAHTGELSNALKAWFPVLMRQGGNIVSSIGNLLLLPLLLYYFLLDWQRW
                        130       140       150       160       170       180
orf121a     SCGIAKLVPRRFAGAYTRITGNLNEVLGEFLRGQLLVMLIMGLVYGLVLVGLDSGFAI
                        190       200       210       220       230       240
```

The complete length ORF121a nucleotide sequence <SEQ ID 785> is:

```
   1  ATGTATCGGA GGAAAGGGCG GGGCATCAAG CCGTGGATGG ATGCCGGTGC
  51  GGCGTTTGCC GCCTTGGTCT GGCTGGTTTT CGCGCTCGGC GATACTTTGA
 101  CTCCGTTTGC GGTTGCGGCG GTGCTGGCGT ATGTATTGGA CCCTTTGGTC
 151  GAATGGTTGC AGAAAAAGGG TTTGAACCGT GCATCCGCTT CGATGTCTGT
 201  GATGGTGTTT TCCTTGATTT TGTTGTTGGC ATTATTGTTG ATTATTGTCC
 251  CTATGCTGGT CGGGCAGTTC AACAATTTGG CATCGCGCCT GCCCCAATTA
 301  ATCGGTTTTA TGCAGAACAC GCTGCTGCCG TGGTTGAAAA ATACAATCGG
 351  CGGATATGTG GAAATCGATC AGGCATCTAT TATTGCGTGG CTTCAGGCGC
 401  ATACGGGCGA GTTGAGCAAC GCGCTTAAGG CGTGGTTTCC CGTTTTGATG
 451  AGGCAGGGCG GCAATATTGT CAGCAGTATC GGCAACCTGC TGCTGCTTCC
 501  CTTGCTGCTT TACTATTTCC TGCTGGATTG GCAGCGGTGG TCGTGCGGCA
 551  TTGCCAAACT GGTTCCGAGG CGTTTTGCCG GTGCTTATAC GCGCATTACA
 601  GGCAATTTGA ACGAGGTATT GGGCGAATTT TGCGCGGGC AGCTTCTGGT
 651  GATGCTGATT ATGGGTTTGG TTTACGGCTT GGGGTTGGTG CTGGTCGGGC
 701  TGGATTCGGG GTTTGCAATC GGTATGGTTG CCGGTATTTT GGTTTTTGTT
 751  CCCTATTTGG GCGCGTTTAC AGGACTGCTG CTGGCAACCG TCGCCGCCTT
 801  GCTCCAGTTC GGTTCGTGGA ACGGCATCTT GGCTGTTTGG GCGGTTTTTG
 851  CCGTAGGACA GTTTCTCGAA AGTTTTTTCA TTACGCCGAA AATCGTGGGA
 901  GACCGTATCG GCCTGTCGCC GTTTTGGGTT ATCTTTTCGC TGATGGCGTT
 951  CGGGCAGCTG ATGGGCTTTG TCGGAATGTT GGCCGGATTG CCTTTGGCCG
1001  CCGTAACCTT GGTCTTGCTT CGCGAGGGCG TGCAGAAATA TTTTGCCGGC
1051  AGTTTTTACC GGGGCAGGTA G
```

This encodes a protein having amino acid sequence <SEQ ID 786>:

```
  1  MYRRKGRGIK PWMDAGAAFA ALVWLVFALG DTLTPFAVAA VLAYVLDPLV
 51  EWLQKKGLNR ASASMSVMVF SLILLLALLL IIVPMLVGQF NNLASRLPQL
101  IGFMQNTLLP WLKNTIGGYV EIDQASIIAW LQAHTGELSN ALKAWFPVLM
151  RQGGNIVSSI GNLLLLPLLL YYFLLDWQRW SCGIAKLVPR RFAGAYTRIT
201  GNLNEVLGEF LRGQLLVMLI MGLVYGLGLV LVGLDSGFAI GMVAGILVFV
251  PYLGAFTGLL LATVAALLQF GSWNGILAVW AVFAVGQFLE SFFITPKIVG
301  DRIGLSPFWV IFSLMAFGQL MGFVGMLAGL PLAAVTLVLL REGVQKYFAG
351  SFYRGR*
```

ORF121a and ORF121-1 show 99.2% identity in 356 aa overlap:

```
                       10        20        30        40        50        60
orf121a.pep  MYRRKGRGIKPWMDAGAAFAALVWLVFALGDTLTPFAVAAVLAYVLDPLVEWLQKKGLNR
             ||||||||||||| |||||||||||||||||||||||||||||||||||||||||||||
orf121-1     MYRRKGRGIKPWMGAGAAFAALVWLVFALGDTLTPFAVAAVLAYVLDPLVEWLQKKGLNR
                       10        20        30        40        50        60

70        80        90       100       110       120
orf121a.pep  ASASMSVMVFSLILLLALLLIIVPMLVGQFNNLASRLPQLIGFMQNTLLPWLKNTIGGYV
             ||||||||||||||||||||||||||||||||||||||||||||||||||||||||||||
orf121-1     ASASMSVMVFSLILLLALLLIIVPMLVGQFNNLASRLPQLIGFMQNTLLPWLKNTIGGYV
                       70        80        90       100       110       120

130       140       150       160       170       180
orf121a.pep  EIDQASIIAWLQAHTGELSNALKAWFPVLMRQGGNIVSSIGNLLLLPLLLYYFLLDWQRW
             ||||||||||||||||||||||||||||||||||||||||||||||||||||||||||||
orf121-1     EIDQASIIAWLQAHTGELSNALKAWFPVLMRQGGNIVSSIGNLLLLPLLLYYFLLDWQRW
                      130       140       150       160       170       180

190       200       210       220       230       240
orf121a.pep  SCGIAKLVPRRFAGAYTRITGNLNEVLGEFLRGQLLVMLIMGLVYGLGLVLVGLDSGFAI
             ||||||||||||||||||||||||||||||||||||||||||||||||||||||||||||
orf121-1     SCGIAKLVPRRFAGAYTRITGNLNEVLGEFLRGQLLVMLIMGLVYGLGLVLVGLDSGFAI
                      190       200       210       220       230       240

250       260       270       280       290       300
orf121a.pep  GMVAGILVFVPYLGAFTGLLLATVAALLQFGSWNGILAVWAVFAVGQPLESFFITPKIVG
             ||:|||||||||||||||||||||||||||||||||||:|||||||||||||||||||||
orf121-1     GMLAGILVFVPYLGAFTGLLLATVAALLQFGSWNGILSVWAVFAVGQPLESFFITPKIVG
                      250       260       270       280       290       300

310       320       330       340       350
orf121a.pep  DRIGLSPFWVIFSLMAFGQLMGFVGMLAGLPLAAVTLVLLREGVQKYFAGSFYRGRX
             ||||||||||||||||||||||||||||||||||||||||||||||||||||||||
orf121-1     DRIGLSPFWVIFSLMAFGQLMGFVGMLAGLPLAAVTLVLLREGVQKYFAGSFYRGRX
                      310       320       330       340       350
```

Homology with a Predicted ORF from *N. gonorrhoeae*

ORF121 shows 97.4% identity over a 156 aa overlap with a predicted ORF (ORF121ng) from *N. gonorrhoeae*:

```
orf121.pep  MYRRKGRGIKPWMGAGXAFAALVWLVFALGDTLTPFAVAAVLAYVLDPLVEWLQKKGLNR  60
            |||||||||||||||| ||||||||||:||||||||||||||||||||||||||||||||
orf121ng    MYRRKGRGIKPWMGAGAAFAALVWLVYALGDTLTPFAVAAVLAYVLDPLVEWLQKKGLNR  60
orf121.pep  ASASMSVMVFSLILLLALLLIIVPMLVGQFNNLASRLPQLIGFMQNTLLPWLKNTIGGYV  120
            ||||||||||||||||||||||||||||||||||||||||||||||||||||||||||||
orf121ng    ASASMSVMVFSLILLLALLLIIVPMLVGQFNNLASRLPQLIGFMQNTLLPWLKNTIGGYV  120
orf121.pep  EIDQASIIAWLQAHTGELSNALKAWFPVLMRQGGNI                         156
            ||||||||||:|||||||||||||||||||:||||
orf121ng    EIDQASIIAWFQAHTGELSNALKAWFPVLMKQGGNIVSTIGNLLLPPLLLYYFLLDWHRW  180
```

An ORF121ng nucleotide sequence <SEQ ID 787> was predicted to encode a protein having amino acid sequence <SEQ ID 788>:

```
  1 MYRRKGRGIK PWMGAGAAFA ALVWLVYALG DTLTPFAVAA VLAYVLDPLV

51 EWLQKKGLNR ASASMSVMVF SLILLLALLL IIVPMLVGQF NNLASRLPQL

101 IGFMQNTLLP WLKNTIGGYV EIDQASIIAW FQAHTGELSN ALKAWFPVLM

151 KQGGNIVSTI GNLLLPPLLL YYFLLDWHRW SCGIPKLVPR RFAGAYTRIT

201 GNLNKVWGKF LRGQLLGETE RGAVVCRVGR ECWEGGGARS RPSDDGWPRW

251 GGG*
```

Further work revealed the following gonoccocal DNA sequence <SEQ ID 789>:

```
   1 ATGTATCGGA GAAAAGGACG GGGCATCAAG CCGTGGATGG GTGCCGGCGC

51 GGCGTTTGCC GCCTTGGTCT GGCTGGTTTA CGCGCTCGGC GATACTTTGA

101 CTCCGTTTGC GGTTGCGGCG GTGCTGGCGT ATGTGTTGGA CCCTTTGGTC

151 GAATGGTTGC AGAAAAAGGG TTTGAACCGT GCATCCGCTT CGATGTCTGT

201 GATGGTGTTT TCCTTGATTT TGTTGTTGGC ATTATTGTTG ATTATTGTCC

251 CTATGCTGGT CGGGCAGTTC AATAATTTGG CATCTCGCCT GCCCCAATTA

301 ATCGGTTTTA TGCAGAACAC GCTGCTGCCG TGGTTGAAAA ATACAATCGG

351 CGGATATGTG GAAATCGATC AGGCATCTAT TATTGCGTGG TTTCAGGCGC

401 ATACGGGCGA GTTGAGCAAC GCGCTTAAGG CGTGGTTTCC CGTTTTGATG

451 AAACAGGGCG GCAATATTGT CAGCAGTATC GGCAACCTGC TGCTGCCGCC

501 CTTGCTGCTT TACTATTTCC TGCTGGATTG GCAGCGGTGG TCGTGCGGCA

551 TCGCCAAACT GGTTCCGAGG CGTTTTGCCG GTGCTTATAC GCGCATTACG

601 GGTAATTTGA ACGAGGTATT GGGCGAATTT TTGCGCGGTC AGCTTCTGGT

651 GATGCTGATT ATGGGCTTGG TTTACGGTTT GGGATTGATG CTAGTCGGAC

701 TGGATTCGGG ATTTGCCATC GGTATGGTTG CCGGTATTTT GGTGTTTGTC

751 CCCTATTTGG GTGCGTTTAC GGGATTGCTG CTTGCCACTG TTGCAGCCTT

801 GCTCCAGTTC GGTTCGTGGA ACGGAATCTT GGCTGTTTGG GCGGTTTTTG

851 CCGTCGGTCA GTTTCTCGAA AGTTTTTTCA TTACGCCGAA AATTGTAGGA

901 GACCGTATCG GCCTGTCGCC GTTTTGGGTT ATCTTTTCGC TGATGGCGTT

951 CGGAGAGCTG ATGGGCTTTG TCGGAATGTT GGCCGGATTG CCTTTGGCCG

1001 CCGTAACCTT GGTCTTGCTT CGCGAGGGCG CGCAGAAATA TTTTGCCGGC

1051 AGTTTTTACC GGGGCAGGTA G
```

This corresponds to the amino acid sequence <SEQ ID 790; ORF121ng-1>:

```
  1 MYRRKGRGIK PWMGAGAAFA ALVWLVYALG DTLTPFAVAA VLAYVLDPLV

51 EWLQKKGLNR ASASMSVMVF SLILLLALLL IIVPMLVGQF NNLASRLPQL

101 IGFMQNTLLP WLKNTIGGYV EIDQASIIAW FQAHTGELSN ALKAWFPVLM

151 KQGGNIVSSI GNLLLPPLLL YYFLLDWQRW SCGIAKLVPR RFAGAYTRIT

201 GNLNEVLGEF LRGQLLVMLI MGLVYGLGLM LVGLDSGFAI GMVAGILVFV

251 PYLGAFTGLL LATVAALLQF GSWNGILAVW AVFAVGQFLE SFFITPKIVG

301 DRIGLSPFWV IFSLMAFGEL MGFVGMLAGL PLAAVTLVLL REGAQKYFAG

351 SFYRGR*
```

ORF121ng-1 and ORF121-1 show 97.5% identity in 356 aa overlap:

```
                    10        20        30        40        50        60
     orf121-1.pep MYRRKGRGIKPWMGAGAAFAALVWLVFALGDTLTPFAVAAVLAYVLDPLVEWLQKKGLNR
                  |||||||||||||||||||||||||:||||||||||||||||||||||||||||||||||
     orf121ng-1   MYRRKGRGIKPWMGAGAAFAALVWLVYALGDTLTPFAVAAVLAYVLDPLVEWLQKKGLNR
                    10        20        30        40        50        60

70        80        90       100       110       120
     orf121-1.pep ASASMSVMVFSLILLLALLLIIVPMLVGQFNNLASRLPQLIGFMQNTLLPWLKNTIGGYV
                  ||||||||||||||||||||||||||||||||||||||||||||||||||||||||||||
     orf121ng-1   ASASMSVMVFSLILLLALLLIIVPMLVGQFNNLASRLPQLIGFMQNTLLPWLKNTIGGYV
                    70        80        90       100       110       120

130       140       150       160       170       180
     orf121-1.pep EIDQASIIAWLQAHTGELSNALKAWFPVLMRQGGNIVSSIGNLLLLPLLLYYFLLDWQRW
                  ||||||||||:|||||||||||||||||||:|||||||||||||:||||||||||||||
     orf121ng-1   EIDQASIIAWFQAHTGELSNALKAWFPVLMKQGGNIVSSIGNLLLPPLLLYYFLLDWQRW
                   130       140       150       160       170       180

190       200       210       220       230       240
     orf121-1.pep SCGIAKLVPRRFAGAYTRITGNLNEVLGEFLRGQLLVMLIMGLVYGLGLVLVGLDSGFAI
                  ||||||||||||||||||||||||||||||||||||||||||||||||:|||||||||||
     orf121ng-1   SCGIAKLVPRRFAGAYTRITGNLNEVLGEFLRGQLLVMLIMGLVYGLGLMLVGLDSGFAI
                   190       200       210       220       230       240

250       260       270       280       290       300
     orf121-1.pep GMLAGILVFVPYLGAFTGLLLATVAALLQFGSWNGILSVWAVFAVGQFLESFFITPKIVG
                  ||:|||||||||||||||||||||||||||||||||||:|||||||||||||||||||||
     orf121ng-1   GMVAGILVFVPYLGAFTGLLLATVAALLQFGSWNGILAVWAVFAVGQFLESFFITPKIVG
                   250       260       270       280       290       300

310       320       330       340       350
     orf121-1.pep DRIGLSPFWVIFSLMAFGQLMGFVGMLAGLPLAAVTLVLLREGVQKYFAGSFYRGRX
                  |||||||||||||||||||:|||||||||||||||||||||||||:|||||||||||
     orf121ng-1   DRIGLSPFWVIFSLMAFGELMGFVGMLAGLPLAAVTLVLLREGAQKYFAGSFYRGRX
                   310       320       330       340       350
```

In addition, ORF121ng-1 shows homology to a permease from *H. influenzae*:

```
sp|P43969|PERM_HAEIN PUTATIVE PERMEASE PERM HOMOLOG Length = 349
Score = 69.9 bits (168), Expect = 2e-11
Identities = 67/317 (21%), Positives = 120/317 (37%), Gaps = 7/317 (2%)

Query:  26 VYALGDTLTPFAVAAVLAYVLDPLVEWL-QKKGLNRASASMSVMVFSXXXXXXXXXXXXVP   84
           +Y  GD + P +A VL+Y+L+  + +L Q     R  A++ +              VP
Sbjct:  32 IYFFGDLIAPLLIALVLSYLLEIPINFLNQYLKCPRMLATILIFGSFIGLAAVFFLVLVP   91

Query:  85 MLVGQFNNLASRLPQLIGFMQNTLLPWLKNTIGGYVE-IDQASIIAWFQAHTGELSNALK  143
           ML  Q  +L S LP +      N   WL N     Y E ID + + F +   ++    +
Sbjct:  92 MLWNQTISLLSDLPAMF----NKSNEWLLNLPKNYPELIDYSMVDSIFNSVREKILGFGE  147

Query: 144 AWFPVLMKQGGNIVSSIGNXXXXXXXXXXXXXDWQRWSCGIAKLVPRRFAGAYTRITGNL  203
              + +   N+VS              D       G+++ +P+   A+ R  +
Sbjct: 148 SAVKLSLASIMNLVSLGIYAFLVPLMMFFMLKDKSELLQGVSRFLPKNRNLAFXRWK-EM  206

Query: 204 NEVLGEFLRGQXXXXXXXXXXXXXXXXXXXXXXDSGFAIGMVAGILVFVPYXXXXXXXXXXX  263
           + +  ++ G+                      +     +  G+ V  VPY
Sbjct: 207 QQQISNYINGKLLEILIVTLITYIIFLIFGLNYPLLLAFAVGLSVLVPYIGAVIVTIPVA  266

Query: 264 XXXXXQFGSWNGILAVWAVFAVGQFLESFFITPKIVGDRIGLSPFWVIFSLMAFGELMGF  323
                QFG        +  FAV Q L+   + P +  + +  L P  +I S++  FG L GF
Sbjct: 267 LVALFQFGISPTFWYIIIAFAVSQLLDGNLLVPYLFSEAVNLHPLIIIISVLIFGGLWGF  326

Query: 324 VGMLAGLPLAAVTLVLL                                             340
            G+    +PLA +    ++
Sbjct: 327 WGVFFAIPLATLVKAVI                                             343
```

Based on this analysis, including the presence of a putative leader sequence and transmembrane domains in the two proteins, it is predicted that the proteins from *N. meningitidis* and *N. gonorrhoeae*, and their epitopes, could be useful antigens for vaccines or diagnostics, or for raising antibodies.

Example 94

The following partial DNA sequence was identified in *N. meningitidis* <SEQ ID 791>:

```
  1..ACTGCTTTTT CGGCGGCGCT GCGCTTGAGT CCATCATGAC TCGTCATATT
 51  TTTGTCCTTT GGGAAACCGT ATCAACAAAC AGCCGCCATC TTAACATTTT
101  TTTGCACGTC CTGCCCGCCG CGTTCAAATG CGTACCAGCA ATACCGCCGC
151  CTGCGCCTCT ATGCCTTCCA TCCGCCCGAG ATAGCCGAGT TTTTCGTTGG
201  TTTTGCCTTT GATGTTGACG CACGAAATGT CTATGCCCAA ATCGGCGGCG
251  ATGTTGGCAC GCATTTGCGG AATGTGCGGC GCGAGTGTGG GTTTCTGTGC
301  AATCACGGTC GTATCGACAT TGACCGCCTG CCAACCCTGC GCCTGAACGC
351  TTTGATACGC CGCACGCAAA AGGACGCGGC TGTCCGCATC TTTGAACTCT
401  GCGGCGGTGT CGGGGAAATG GCTGCCGATA TCGCCCAAAC CTGCCGCACC
451  GAGCAGCGCG TCGGTAACGG CGTGCAGCAG CGCATCGGCA TCGGAGTGTC
501  CGAGCAGCCC TTTTTCAAAT GGGATTTCAA CTCCGCCAAG TATCAG..
```

This corresponds to the amino acid sequence <SEQ ID 792; ORF122>:

```
  1 ..TAFSAALRLS PSXLVIFLSF GKPYQQTAAI LTFFCTSCPP RSNAYQQYRR
 51   LRLYAFHPPE IAEFFVGFAF DVDARNVYAQ IGGDVGTHLR NVRRECGFLC
101   NHGRIDIDRL PTLRLNALIR RTQKDAAVRI FELCGGVGEM AADIAQTCRT
151   EQRVGNGVQQ RIGIGVSEQP FFKWDFNSAK YQ..
```

Further work revealed the complete nucleotide sequence <SEQ ID 793>:

```
  1 ATATCGTACT GGGCAAGCAG TTCGCCGGAT TTTTTGGAAG TAGATACCGC
 51 GCCTTTGATT TTTTTGCCGC TCTTACCCAA GGCTTCGATG AAAAAGTTGA
101 TGGTCGAGCC GGTACCGATG CCGATATATT CATTTTCGGG TACGAATTCG
151 ACTGCTTTTT CGGCGGCGAT GCGCTTGAGT TCGTCTTGTG TCGTCATATT
201 TTTGTCCTTT GGGAAACCGT ATCAACAAAC AGCCGCCATC TTAACATTTT
251 TTTGCACGTC CTGCCCGCCG CGTTCAAATG CGTACCAGCA ATACCGCCGC
301 CTGCGCCTCT ATGCCTTCCA TCCGCCCGAG ATAGCCGAGT TTTTCGTTGG
351 TTTTGCCTTT GATGTTGACG CACGAAATGT CTATGCCCAA ATCGGCGGCG
401 ATGTTGGCAC GCATTTGCGG AATGTGCGGC GCGAGTTTGG GTTTCTGTGC
451 AATCACGGTC GTATCGACAT TGACCGCCTG CCAACCCTGC GCCTGAACGC
501 TTTGATACGC CGCACGCAAA AGGACGCGGC TGTCCGCATC TTTGAACTCT
551 GCGGCGGTGT CGGGGAAATG GCTGCCGATA TCGCCCAAAC CTGCCGCACC
601 GAGCAGCGCG TCGGTAACGG CGTGCAGCAG CGCATCGGCA TCGGAGTGTC
651 CGAGCAGCCC TTTTTCAAAT GGGATTTCAA CTCCGCCAAG TATCAGCTTT
701 CTGCCTTCGG TCAGTTGGTG GACATCGTAG CCCTGTCCGA TACGGATGTT
751 CGTCATCGTT TGTGTTCCTG A
```

This corresponds to the amino acid sequence <SEQ ID 794; ORF122-1>:

```
  1 ISYWASSSPD FLEVDTAPLI FLPLLPKASM KKLMVEPVPM PIYSFSGTNS

51 TAFSAAMRLS SSCVVIFLSF GKPYQQTAAI LTFFCTSCPP RSNAYQQYRR

101 LRLYAFHPPE IAEFFVGFAF DVDARNVYAQ IGGDVGTHLR NVRREFGFLC

151 NHGRIDIDRL PTLRLNALIR RTQKDAAVRI FELCGGVGEM AADIAQTCRT

201 EQRVGNGVQQ RIGIGVSEQP FFKWDFNSAK YQLSAFGQLV DIVALSDTDV

251 RHALCS*
```

Computer analysis of this amino acid sequence gave the following results:

Homology with a Predicted ORF from *N. meningitidis* (Strain A)

ORF122 shows 94.0% identity over a 182aa overlap with an ORF (ORF122a) from strain A of *N. meningitidis*:

```
                                     10         20         30
    orf122.pep                        TAFSAALRLSPSXLVIFLSFGKPYQQTAAI
                                      ||||| :||| | :||||||||||||||
    orf122a    FLPLLPKASMKKLMVEPVPMPMYSFSGTNSTAFSAAMRLSSSCVVIFLSFGKPYQQTAAI
                    30        40        50        60        70        80

40        50        60        70        80        90
    orf122.pep LTFFCTSCPPRSNAYQQYRRLRLYAFHPPEIAEFFVGFAFDVDARNVYAQIGGDVGTHLR
               |||| |||||||| |||||||||||||||| |::|||||| |||||||||||||||||||
    orf122a    LTFFXTSCPPRSNPYQQYRRLRLYAFHAPEITEFFVGFAFXVDARNVYAQIGGDVGTHLR
                    90       100       110       120       130       140

100       110       120       130       140       150
    orf122.pep NVRRECGFLCNHGRIDIDRLPTLRLNALIRRTQKDAAVRIFELCGGVGEMAADIAQTCRT
               |:||| ||||||||||||||||||||||||||||||||||||||||||||||||||||||
    orf122a    NMRREFGFLCNHGRIDIDRLPTLRLNALIRRTQKDAAVRIFELCGGVGEMAADIAQTCRT
                   150       160       170       180       190       200

160       170       180
    orf122.pep EQRVGNGVQQRIGIGVSEQPFFKWDFNSAKYQ
               ||||||||||||||||||||||||||||||||
    orf122a    EQRVGNGVQQRIGIGVSEQPFFKWDFNSAKYQLSAFGQLVDIVALSDTDVRHRLCSX
                   210       220       230       240       250
```

The complete length ORF122a nucleotide sequence <SEQ ID 795> is:

```
  1 ATATCATATT GGGCAAGCAG TTCACTGGAT TTTTTGGAAG TAGATACCGC

51 GCCTTTGATT TTTTTGCCGC TCTTACCCAA GGCTTCGATG AAAAAGTTGA

101 TGGTCGAACC GGTACCGATG CCGATGTATT CGTTTTCGGG TACGAATTCG

151 ACTGCNTTTT CGGCGGCGAT GCGCTTGAGT TCGTCTTGTG TCGTCATATT

201 TTTGTCCTTT GGGAAACCGT ATCAACAAAC AGCCGCCATC TTAACATTTT

251 TTNNNACGTC CTGCCCGCCG CGTTCAAATC CTTACCAGCA ATACCGCCGC

301 CTGCGACTCT ATGCCTTCCA TGCGCCCGAG ATAACCGAGT TTTTCGTTGG

351 TTTTGCCTTT GANGTTGACG CACGAAATGT CTATGCCCAA ATCGGCGGCG

401 ATGTTGGCAC GCATTTGCGG AATATGCGGC GCGAGTTTGG GTTTCTGTGC

451 AATCACGGTC GTATCGACAT TGACCGCCTG CCAACCCTGC GCCTGAACGC

501 TTTGATACGC CGCACGCAAA AGGACGCGGC TGTCCGCATC TTTGAACTCT

551 GCGGCGGTGT CGGGGAAATG GCTGCCGATA TCGCCCAAAC CTGCCGCACC

601 GAGCAGCGCG TCGGTAACGG CGTGCAGCAG CGCATCGGCA TCGGAGTGTC
```

```
 651 CGAGCAGCCC TTTTTCAAAT GGGATTTCAA CTCCGCCAAG TATCAGCTTT

701 CTGCCTTCGG TCAGTTGGTG GACATCGTAG CCCTGTCCGA TACGGATGTT

751 CGTCATCGTT TGTGTTCCTG A
```

This encodes a protein having amino acid sequence <SEQ ID 796>:

```
  1 ISYWASSSLD FLEVDTAPLI FLPLLPKASM KKLMVEPVPM PMYSFSGTNS

51 TAFSAAMRLS SSCVVIFLSF GKPYQQTAAI LTFFXTSCPP RSNPYQQYRR

101 LRLYAFHAPE ITEFFVGFAF XVDARNVYAQ IGGDVGTHLR NMRREFGFLC

151 NHGRIDIDRL PTLRLNALIR RTQKDAAVRI FELCGGVGEM AADIAQTCRT

201 EQRVGNGVQQ RIGIGVSEQP FFKWDFNSAK YQLSAFGQLV DIVALSDTDV

251 RHRLCS*
```

ORF122a and ORF122-1 show 96.9% identity in 256 aa overlap:

```
                    10         20         30         40         50         60
orf122a.pep ISYWASSSLDFLEVDTAPLIFLPLLPKASMKKLMVEPVPMPMYSFSGTNSTAFSAAMRLS
            ||||||||| |||||||||||||||||||||||||||||||:||||||||||||||||||
orf122-1    ISYWASSSPDFLEVDTAPLIFLPLLPKASMKKLMVEPVPMPIYSFSGTNSTAFSAAMRLS
                    10         20         30         40         50         60

70         80         90        100        110        120
orf122a.pep SSCVVIFLSFGKPYQQTAAILTFFXTSCPPRSNPYQQYRRLRLYAFHAPEITEFFVGFAF
            ||||||||||||||||||||||||| ||||||||:|||||||||||||||:|:|||||||
orf122-1    SSCVVIFLSFGKPYQQTAAILTFFCTSCPPRSNAYQQYRRLRLYAFHPPEIAEFFVGFAF
                    70         80         90        100        110        120

130        140        150        160        170        180
orf122a.pep XVDARNVYAQIGGDVGTHLRNMRREFGFLCNHGRIDIDRLPTLRLNALIRRTQKDAAVRI
             |||||||||||||||||||:||||||||||||||||||||||||||||||||||||||
orf122-1    DVDARNVYAQIGGDVGTHLRNVRREFGFLCNHGRIDIDRLPTLRLNALIRRTQKDAAVRI
                   130        140        150        160        170        180

190        200        210        220        230        240
orf122a.pep FELCGGVGEMAADIAQTCRTEQRVGNGVQQRIGIGVSEQPFFKWDFNSAKYQLSAFGQLV
            ||||||||||||||||||||||||||||||||||||||||||||||||||||||||||||
orf122-1    FELCGGVGEMAADIAQTCRTEQRVGNGVQQRIGIGVSEQPFFKWDFNSAKYQLSAFGQLV
                   190        200        210        220        230        240

250
orf122a.pep DIVALSDTDVRHRLCSX
            |||||||||||||||||
orf122-1    DIVALSDTDVRHRLCSX
                   250
```

Homology with a Predicted ORF from *N. gonorrhoeae*

ORF122 shows 89.6% identity over a 182 aa overlap with a predicted ORF (ORF122ng) from *N. gonorrhoeae*:

```
orf122.pep                        TAFSAALRLSPSXLVIFLSFGKPYQQTAAI  30
                                  ||||||:||| | :||||||||||||||||
orf121ng    FLPLLPKASMKKLMVEPVPMPMYSFSGTNSTAFSAAMRLSSSCVVIFLSFGKPYQQTAAI  80 orf122.pep  LTFFCTSCPPRSNAYQQYRRLRLYAFHPPEIAEFFVGFAFDVDARNVYAQIGGDVGTHLR  90
            |||||| ||||| |||||||||||||||||||||||||||||:||||: :||||||||||
orf122ng    LTFFCTSWPPRSNPYQQYRRLRLYAFHPPEIAEFFVGFAFDIDARNIDTQIGGDVGTHLR 140 orf122.pep  NVRRECGFLCNHGRIDIDRLPTLRLNALIRRTQKDAAVRIFELCGGVGEMAADIAQTCRT 150
            ||| |:|||||||||||||:||||||||||||||||||||||||||||:||||:||||||
orf122ng    NVRCEFGFLCNHGRIDIDHLPTLRLNALIRRTQKDAAVRIFELCGGVGKMAADVAQTCRT 200 orf122.pep  EQRVGNGVQQRIGIGVSEQPFFKWDFNSAKYQ                             182
            |||||||||||:|| : ||||||||||||||
orf121ng    EQRVGNGVQQRVGIRMPEQPFFKWDFNSAKYQLSAFGQLVDIVALSDTDIRHRLCS     256
```

The complete length ORF122ng nucleotide sequence <SEQ ID 797> is:

```
  1 ATGTCGTACC GGGCAAGCAG TTCGCCGGAT TTTTTGGAGG TTGAAACCGC
 51 GCCTTTGATT TTTTTACCGC TTTTGCCCAA GGCTTCGATG AAGAAATTGa
101 tgGTCGAACC GgtaCCGATG CCGATGTATT CGTTTTCGGG TACGAATTCG
151 ACTGCTTTTT CGGCGGCGAT GCGCttgAgt TCgtcttgcg TcgTCATATT
201 TTTAtcettt gGGAAaccct atcaAcaAAc agccgccatC TTAACATTTT
251 TTTGCACGtc ctggccgccg cgttcaAATc cgtaccaGca ataccgccgc
301 ctgcgcctCT AtgcCTTCCA TCCGCCCGAG ATAGCCGAGT TTTTCGTTGG
351 TTTTGCCTTT GATatTGACG CACGAAATAT CGatacCCAa atcggcgGCG
401 ATGTTGGCAC GCATTTGCGG AATGTGCGGT GCGAGTTTGG GTTTCTGTGC
451 AATCACGGTC GTATCGACAT TGACCACCTG CCAACCCTGC GCCTGAACGC
501 TTTGATACGC CGCACGCAAA AGGACGCGGC TGTCCGCATC TTTGAACTCT
551 GCGGCGGTGT CGGGAAAATG GCTGCCGATG TCGCCCAAAC CTGCCGCACC
601 GAGCAGCgcg tcggtaaCGG CGTGCAGCAG cgcgTcgGCA TCCGAATGCC
651 CGAGCAGCCC TTTTTCAAAT GGGATTTCAA CTCCGCCAAG TATCAGCTTT
701 CTGCCTTCGG TCAATTGGTG GACATCGTAG CCCTGTCCGA TACGGATATT
751 CGTCATCGTT TGTGTTCCTG A
```

This encodes a protein having amino acid sequence <SEQ ID 798>:

```
  1 MSYRASSSPD FLEVETAPLI FLPLLPKASM KKLMVEPVPM PMYSFSGTNS
 51 TAFSAAMRLS SSCVVIFLSF GKPYQQTAAI LTFFCTSWPP RSNPYQQYRR
101 LRLYAFHPPE IAEFFVGFAF DIDARNIDTQ IGGDVGTHLR NVRCEFGFLC
151 NHGRIDIDHL PTLRLNALIR RTQKDAAVRI FELCGGVGKM AADVAQTCRT
201 EQRVGNGVQQ RVGIRMPEQP FFKWDFNSAK YQLSAFGQLV DIVALSDTDI
251 RHRLCS*
```

ORF122ng and ORF122-1 show 92.6% identity in 256 aa overlap:

```
                      10         20         30         40         50         60
    orf122-1.pep ISYWASSSPDFLEVDTAPLIFLPLLPKASMKKLMVEPVPMPIYSFSGTNSTAFSAAMRLS
                 :|| |||||||||||:||||||||||||||||||||||||||:|||||||||||||||||
    orf122ng     MSYWASSSPDFLEVETAPLIFLPLLPKASMKKLMVEPVPMPMYSFSGTNSTAFSAAMRLS
                      10         20         30         40         50         60

70         80         90        100        110        120
    orf122-1.pep SSCVVIFLSFGKPYQQTAAILTFFCTSCPPRSNAYQQYRRLRLYAFHPPEIAEFFVGFAF
                 ||||||||||||||||||||||||||||||||||||||||||||||||||||||||||||
    orf122ng     SSCVVIFLSFGKPYQQTAAILTFFCTSCPPRSNAYQQYRRLRLYAFHPPEIAEFFVGFAF
                      70         80         90        100        110        120

130        140        150        160        170        180
    orf122-1.pep DVDARNVYAQIGGDVGTHLRNVRREFGFLCNHGRIDIDRLPTLRLNALIRRTQKDAAVRI
                 |:|||| :|||||||||||||||:|||||||||||||:||||||||||||||||||||||
    orf122ng     DIDARNIYTQIGGDVGTHLRNVRCEFGFLCNHGRIDIDHLPTLRLNALIRRTQKDAAVRI
                     130        140        150        160        170        180

190        200        210        220        230        240
    orf122-1.pep FELCGGVGEMAADIAQTCRTEQRVGNGVQQRIGIGVSEQPFFKWDFNSAKYQLSAFGQLV
                 ||||||||:|||| ||||||||||||||||||:|| : ||||||||||||||||||||||
    orf122ng     FELCGGVGKMAADVAQTCRTEQRVGNGVQQRVGIRMSEQPFFKWDFNSAKYQLSAFGQLV
                     190        200        210        220        230        240

250
    orf122-1.pep DIVALSDTDVRHRLCSX
                 |||||||||:|||||||
    orf122ng     DIVALSDTDIRHRLCSX
                     250
```

Based on this analysis, it is predicted that the proteins from *N. meningitidis* and *N. gonorrhoeae*, and their epitopes, could be useful antigens for vaccines or diagnostics, or for raising antibodies.

Example 95

The following partial DNA sequence was identified in *N. meningitidis* <SEQ ID 799>:

```
  1 ..GCCGGCGCGA GTGCGAACAA CATTTCCGCG CGTTTTGCGG AAACACCCGT
 51   CGCTGTCAGC GTTACCCTGA TCGGCACGGT ACTTGCCGTC ATGCTGCCCG
101   TTACCGAATA TGAAAACTTC CTGCTGCTTA TCGGCTCGGT ATTTGCGCCG
151   ATGGGGCGGA TTTTGATTGC CGACTTTTTC GTCTTGAAAC GGCGTGA
```

This corresponds to the amino acid sequence <SEQ ID 800; ORF125>:

```
  1 ..AGASANNISA RFAETPVAVS VTLIGTVLAV MLPVTEYENF LLLIGSVFAP
 51   MGGFDCRLFR LETA*
```

Further work revealed the complete nucleotide sequence <SEQ ID 801>:

```
   1 ATGTCGGGCA ATGCCTCCTC TCCTTCATCT TCCTCCGCCA TCGGGCTGAT
  51 TTGGTTCGGC GCGGCGGTAT CGATTGCCGA AATCAGCACG GGTACGCTGC
 101 TTGCGCCTTT GGGCTGGCAG CGCGGTCTGG CGGCTCTACT TTTGGGTCAT
 151 GCCGTCGGCG GCGCGCTGTT TTTTGCGGCG GCGTATATCG GCGCACTGAC
 201 CGGACGCAGC TCGATGGAAA GCGTGCGCCT GTCGTTCGGC AAACGCGGTT
 251 CAGTGCTGTT TTCCGTGGCG AATATGCTGC AACTGGCCGG CTGGACGGCG
 301 GTGATGATTT ACGCCGGCGC AACGGTCAGC TCCGCTTTGG GCAAAGTGTT
 351 GTGGGACGGC GAATCTTTTG TCTGGTGGGC ATTGGCAAAC GGCGCGCTGA
 401 TTGTGCTGTG GCTGGTTTTC GGCGCACGCA AAACAGGCGG GCTGAAAACC
 451 GTTTCGATGC TGCTGATGCT GTTGGCGGTT CTGTGGCTGA GTGCCGAAGT
 501 CTTTTCCACG GCAGGCAGCA CCGCCGCACA GGTTTCAGAC GGCATGAGTT
 551 TCGGAACGGC AGTCGAGCTG TCCGCCGTGA TGCCGCTTTC CTGGCTGCCG
 601 CTTGCCGCCG ACTACACGCG CCACGCGCGC CGCCCGTTTG CGGCAACCCT
 651 GACGGCAACG CTCGCCTACA CGCTGACCGG CTGCTGGATG TATGCCTTGG
 701 GTTTGGCAGC GGCGTTGTTC ACCGGAGAAA CCGACGTGGC AAAAATCCTG
 751 CTGGGCGCAG GTTTGGGTGC GGCAGGCATT TTGGCGGTCG TCCTCTCCAC
 801 CGTTACCACA ACGTTTCTCG ATGCCTATTC CGCCGGCGCG AGTGCGAACA
 851 ACATTTCCGC GCGTTTTGCG GAAACACCCG TCGCTGTCGG CGTTACCCTG
 901 ATCGGCACGG TACTTGCCGT CATGCTGCCC GTTACCGAAT ATGAAAACTT
 951 CCTGCTGCTT ATCGGCTCGG TATTTGCGCC GATGGCGCG GTTTTGATTG
1001 CCGACTTTTT CGTCTTGAAA CGGCGTGAGG AGATTGAAGG CTTTGACTTT
1051 GCCGGACTGG TTCTGTGGCT TGCGGGCTTC ATCCTCTACC GCTTCCTGCT
1101 CTCGTCCGGC TGGGAAAGCA GCATCGGTCT GACCGCCCCC GTAATGTCTG
```

-continued

```
1151  CCGTTGCCAT TGCCACCGTA TCGGTACGCC TTTTCTTTAA AAAAACCCAA

1201  TCTTTACAAA GGAACCCGTC ATGA
```

This corresponds to the amino acid sequence <SEQ ID 802; ORF125-1>:

```
  1  MSGNASSPSS SSAIGLIWFG AAVSIAEIST GTLLAPLGWQ RGLAALLLGH

51  AVGGALFFAA AYIGALTGRS SMESVRLSFG KRGSVLFSVA NMLQLAGWTA

101  VMIYAGATVS SALGKVLWDG ESFVWWALAN GALIVLWLVF GARKTGGLKT

151  VSMLLMLLAV LWLSAEVFST AGSTAAQVSD GMSFGTAVEL SAVMPLSWLP

201  LAADYTRHAR RPFAATLTAT LAYTLTGCWM YALGLAAALF TGETDVAKIL

251  LGAGLGAAGI LAVVLSTVTT TFLDAYSAGA SANNISARFA ETPVAVGVTL

301  IGTVLAVMLP VTEYENFLLL IGSVFAPMAA VLIADFFVLK RREEIEGFDF

351  AGLVLWLAGF ILYRFLLSSG WESSIGLTAP VMSAVAIATV SVRLFFKKTQ

401  SLQRNPS*
```

Computer analysis of this amino acid sequence gave the following results:

Homology with a Predicted ORF from *N. meningitidis* (Strain A)

ORF125 shows 76.5% identity over a 51aa overlap with an ORF (ORF125a) from strain A of *N. meningitidis*:

```
                                            10         20         30
    orf125.pep                      AGASANNISARFAETPVAVSVTLIGTVLAV
                                    ||:||||||:::| |:||:|:::||:|||
    orf125a    KILLGAGLGAAGILAVVLSTVTTTFLDAYSAGVSANNISAKLSEIPIAVAVAVVGTLLAV
               250        260       270       280       290       300

40         50         60
    orf125.pep  MLPVTEYENFLLLIGSVFAPMGGFDCRLFRLETAX
                :|||||||||||||||||||||:
    orf125a     LLPVTEYENFLLLIGSVFAPMAAVLIADFFVLKRREEIEG
                310        320       330       340
```

The ORF125a partial nucleotide sequence <SEQ ID 803> is:

```
  1  ATGTCGGGCA ATGCCTCCTC TCNTTCATCT TCCGCCGCCA TCGGGCTGAT

51  TTGGTTCGGC GCGGCGGTAT CGATTGCCGA AATCAGCACG GGTACACTGC

101  TTGCGCCTTT GGGCTGGCAG CGCGGTCTGG CNGCTCTGCT TTTGGGTCAT

151  GCCGTCGGCG GCGCGCTGTT TTTTGCGGCG GCGTATATCG GCGCACTGAC

201  CGGACNCANC TCGATGGAAA GCGTGCGCCT GTCGTTCGGC AAACGCGGTT

251  CAGTGCTGTT TTCCGTGGCG AATATGCTGC AACTGGCCGG CTGGACGGCG

301  GTGATGATTT ACGCCGGCGC AACGGTCAGC TCCGCTTTGG GCAAAGTGTT

351  GTGGGACGGC GAATCTTTTG TCTGGTGGGC ATTGGCAAAC GGCGCGCTGA

401  TTGTGCTGTG GCTGGTTTTC GGCGCACGCA AAACAGGCGG GCTGAAAACC

451  GTTTCGATGC TGCTGATGCT GTTGGCGGTT CTGTGGCTGA GTGCCGAANT

501  NTTTTCCACG GCAGGCAGCA CCGCCGCANN GGTNNCAGAC GGCATGAGTT

551  TCGGAACGGC AGTCGAGCTG TCCGCCGTNA TGCCGCTTTC TTGGCTGCCG
```

-continued

```
 601 CTGGCCGCCG ACTACACGCG CCACGCGCGC CGCCCGTTTG CGGCAACCCT

651 GACGGCAACG CTCGCCTACA CGCTGACCGG CTGCTGGATG TATGCCTTGG

701 GTTTGGCAGC GGCGTTGTTC ACCGGAGAAA CCGACGTGGC AAAAATCCTG

751 CTGGGCGCAG GTTTGGGTGC GGCAGGCATT TTGGCGGTCG TCCTGTCGAC

801 CGTTACCACC ACTTTTCTCG ATGCNTACTC CGCCGGCGTA AGTGCCAACA

851 ATATTTCCGC CAAACTTTCG GAAATACCNA TCGCCGTTGC CGTCGCCGTT

901 GTCGGCACAC TGCTTGCCGT CCTCCTGCCC GTTACCGAAT ATGAAAACTT

951 CCTGCTGCTT ATCGGCTCGG TATTTGCGCC GATGGCGGCG GTTTTGATTG

1001 CCGACTTTTT CGTCTTGAAA CGGCGTGAGG AGATTGAAGG C..
```

This encodes a protein having the partial amino acid sequence <SEQ ID 804>:

```
  1 MSGNASSXSS SAAIGLIWFG AAVSIAEIST GTLLAPLGWQ RGLAALLLGH

51 AVGGALFFAA AYIGALTGXX SMESVRLSFG KRGSVLFSVA NMLQLAGWTA

101 VMIYAGATVS SALGKVLWDG ESFVWWALAN GALIVLWLVF GARKTGGLKT

151 VSMLLMLLAV LWLSAEXFST AGSTAAXVXD GMSFGTAVEL SAVMPLSWLP

201 LAADYTRHAR RPFAATLTAT LAYTLTGCWM YALGLAAALF TGETDVAKIL

251 LGAGLGAAGI LAVVLSTVTT TFLDAYSAGV SANNISAKLS EIPIAVAVAV

301 VGTLLAVLLP VTEYENFLLL IGSVFAPMAA VLIADFFVLK RREEIEG..
```

ORF125a and ORF125-1 show 94.5% identity in 347 aa overlap:

```
                    10        20        30        40        50        60
       orf125a.pep  MSGNASSXSSSSAAIGLIWFGAAVSIAEISTGTLLAPLGWQRGLAALLLGHAVGGALFFAA
                    ||||||| |||:||||||||||||||||||||||||||||||||||||||||||||||||
       orf125-1     MSGNASSPSSSSAAIGLIWFGAAVSIAEISTGTLLAPLGWQRGLAALLLGHAVGGALFFAA
                    10        20        30        40        50        60

70        80        90       100       110       120
       orf125a.pep  AYIGALTGXXSMESVRLSFGKRGSVLFSVANMLQLAGWTAVMIYAGATVSSALGKVLWDG
                    ||||||||  ||||||||||||||||||||||||||||||||||||||||||||||||||
       orf125-1     AYIGALTGRSSMESVRLSFGKRGSVLFSVANMLQLAGWTAVMIYAGATVSSALGKVLWDG
                    70        80        90       100       110       120

130       140       150       160       170       180
       orf125a.pep  ESFVWWALANGALIVLWLVFGARKTGGLKTVSMLLMLLAVLWLSAEXFSTAGSTAAXVXD
                    |||||||||||||||||||||||||||||||||||||||||||||| ||||||||| | |
       orf125-1     ESFVWWALANGALIVLWLVFGARKTGGLKTVSMLLMLLAVLWLSAEVFSTAGSTAAQVSD
                   130       140       150       160       170       180

190       200       210       220       230       240
       orf125a.pep  GMSFGTAVELSAVMPLSWLPLAADYTRHARRPFAATLTATLAYTLTGCWMYALGLAAALF
                    ||||||||||||||||||||||||||||||||||||||||||||||||||||||||||||
       orf125-1     GMSFGTAVELSAVMPLSWLPLAADYTRHARRPFAATLTATLAYTLTGCWMYALGLAAALF
                   190       200       210       220       230       240

250       260       270       280       290       300
       orf125a.pep  TGETDVAKILLGAGLGAAGILAVVLSTVTTTFLDAYSAGVSANNISAKLSEIPIAVAVAV
                    ||||||||||||||||||||||||||||||||||||||||:|||||||:::| |::|::
       orf125-1     TGETDVAKILLGAGLGAAGILAVVLSTVTTTFLDAYSAGASANNISARFAETPVAVGVTL
                   250       260       270       280       290       300

310       320       330       340
       orf125a.pep  VGTLLAVLLPVTEYENFLLLIGSVFAPMAAVLIADFFVLKRREEIEG
                    :||:||||:|||||||||||||||||||||||||||||||:|||||||
       orf125-1     IGTVLAVMLPVTEYENFLLLIGSVFAPMAAVLIADFFVLKRREEIEGFDFAGLVLWLAGF
                   310       320       330       340       350       360
```

Homology with a Predicted ORF from *N. gonorrhoeae*
ORF125 shows 86.2% identity over a 65aa overlap with a predicted ORF (ORF125ng) from *N. gonorrhoeae*:

```
orf125.pep                                 AGASANNISARFAETPVAVSVTLIGTVLAV    30
                                           ||||||||||||| ||||:|||| |||||
orf125ng   KILLGAGLGITGILAVVLSTVTTTFLDTYSAGASANNISARFAEIPVAVGVTLIRTVLAV   308 orf125.pep MLPVTEYENFLLLIGSVFAPM-GGFDCRLFRLETA   64
           ||||||||:||||| |||:|| |||||||| |:||
orf125ng   MLPVTEYKNFLLLIRSVFGPMAGGFDCRLFCLKTA   343
```

An ORF125ng nucleotide sequence <SEQ ID 805> was predicted to encode a protein having amino acid sequence <SEQ ID 806>:

```
  1 MSGNASSPSS SAAIGLVWFG AAVSIAEIST GTLLAPLGWQ RGLAALLLGH

51 AVGGALFFAA AYIGALTGRS SMESVRLSFG KCGSVLFSVA NMLQLAGWTA

101 VMIYVGATVS SALGKVLWDG ESFVWWALAN GALIVLWLVF GARRTGGLKT

151 VSMLLMLLAV LWLSVEVFAS SGTNAAPAVS DGMTFGTAVE LSAVMPLSWL

201 PLAADYTRQA RRPFAATLTA TLAYTLTGCW MYALGLAAAL FTGETDVAKI

251 LLGAGLGITG ILAVVLSTVT TTFLDTYSAG ASANNISARF AEIPVAVGVT

301 LIRTVLAVML PVTEYKNFLL LIRSVFGPMA GGFDCRLFCL KTA*
```

Further work revealed the following gonococcal DNA sequence <SEQ ID 807>:

```
   1 ATGTCGGGCA ATGCCTCCTC TCCTTCATCT TCCGCCGCCA TCGGGCTGGT

51 TTGGTTCGGC GCGGCGGTAT CGATTGCCGA AATCAGCACG GGTACGCTGC

101 TCGCCCCCTT GGGCTGGCAG CGCGGTCTGG CGGCCCTGCT TTTGGGTCAT

151 GCCGTCGGCG GCGCGCTGTT TTTTGCGGCG GCGTATATCG GCGCACTGAC

201 CGGACGCAGC TCGATGGAAA GTGTGCGCCT GTCGTTCGGC AAATGCGGTT

251 CAGTGCTGTT TTCCGTGGCG AATATGCTGC AACTGGCCGG CTGGACGGCG

301 GTGATGATTT ACGTCGGCGC AACGGTCAGC TCCGCTTTGG GCAAAGTGTT

351 GTGGGACGGC GAATCCTTTG TCTGGTGGGC ATTGGCAAAC GGCGCACTGA

401 TCGTGCTGTG GCTGGTTTTC GGCGCACGCA GAACGGGCGG GCTGAAAACC

451 GTTTCGATGC TGCTGATGCT GCTTGCCGTG TTGTGGTTGA GCGTCGAAGT

501 GTTCGCTTCG TCCGGCACAA ACGCCGCGCC CGCCGTTTCA GACGGCATGA

551 CCTTCGGAAC GGCAGTCGAA CTGTCCGCCG TCATGCCGCT TTCCTGGCTG

601 CCGCTGGCCG CCGACTACAC GCGCCAAGCA CGCCGCCCGT TGCGGCAAC

651 CCTGACGGCA ACGCTCGCCT ATACGCTGAC GGGCTGCTGG ATGTATGCCT

701 TGGGTTTGGC GGCGGCTCTG TTTACCGGAG AAACCGACGT GGCGAAAATC

751 CTGTTGGGCG CGGGCTTGGG CATAACGGGC ATTCTGGCAG TCGTCCTCTC

801 CACCGTTACC ACAACGTTTC TCGATACCTA TTCCGCCGGC GCGAGTGCGA

851 ACAACATTTC CGCGCGTTTT GCGGAAATAC CCGTCGCTGT CGGCGTTACC

901 CTGATCGGCA CGGTGCTTGC CGTCATGCTG CCCGTTACCG AATATAAAAA

951 CTTCCTGCTG CTTATCGGCT CGGTATTTGC GCCGATGGCG GCGGTTTTGA

1001 TTGCCGACTT TTTCGTCTTA AAACGGCGTG AGGAGATTGA AGGCTTTGAC
```

-continued
```
1051 TTTGCCGGAC TGGTTCTGTG GCTGGCAGGC TTCATCCTCT ACCGCTTCCT

1101 GCTCTCGTCC GGTTGGGAAA GCAGCATCGG TCTGACCGCC CCCGTAATGT

1151 CTGCCGTTGC CATTGCCACC GTATCGGTAC GCCTTTTCTT TAAAAAAACC

1201 CAATCTTTAC AAAGGAACCC GTCATGA
```

This corresponds to the amino acid sequence <SEQ ID 808; ORF125ng-1>:

```
  1 MSGNASSPSS SAAIGLVWFG AAVSIAEIST GTLLAPLGWQ RGLAALLLGH

51 AVGGALFFAA AYIGALTGRS SMESVRLSFG KCGSVLFSVA NMLQLAGWTA

101 VMIYVGATVS SALGKVLWDG ESFVWWALAN GALIVLWLVF GARRTGGLKT

151 VSMLLMLLAV LWLSVEVFAS SGTNAAPAVS DGMTFGTAVE LSAVMPLSWL

201 PLAADYTRQA RRPFAATLTA TLAYTLTGCW MYALGLAAAL FTGETDVAKI

251 LLGAGLGITG ILAVVLSTVT TTFLDTYSAG ASANNISARF AEIPVAVGVT

301 LIGTVLAVML PVTEYKNFLL LIGSVFAPMA AVLIADFFVL KRREEIEGFD

351 FAGLVLWLAG FILYRFLLSS GWESSIGLTA PVMSAVAIAT VSVRLFFKKT

401 QSLQRNPS*
```

ORF125ng-1 and ORF125-1 show 95.1% identity in 408 aa overlap:

```
                    10         20         30         40         50         60
orf125-1.pep   MSGNASSPSSSSAIGLIWFGAAVSIAEISTGTLLAPLGWQRGLAALLLGHAVGGALFFAA
               ||||||||||:||||:||||||||||||||||||||||||||||||||||||||||||||
orf125ng-1     MSGNASSPSSSAAIGLVWFGAAVSIAEISTGTLLAPLGWQRGLAALLLGHAVGGALFFAA
                    10         20         30         40         50         60

70         80         90        100        110        120
orf125-1.pep   AYIGALTGRSSMESVRLSFGKRGSVLFSVANMLQLAGWTAVMIYAGATVSSALGKVLWDG
               ||||||||||||||||||||| |||||||||||||||||||||||:||||||||||||||
orf125ng-1     AYIGALTGRSSMESVRLSFGKCGSVLFSVANMLQLAGWTAVMIYVGATVSSALGKVLWDG
                    70         80         90        100        110        120

130        140        150        160        170        179
orf125-1.pep   ESFVWWALANGALIVLWLVFGARKTGGLKTVSMLLMLLAVLWLSAEVFSTAGSTAAQ-VS
               ||||||||||||||||||||||:|||||||||||||||||||||:|||:::|::||  ||
orf125ng-1     ESFVWWALANGALIVLWLVFGARRTGGLKTVSMLLMLLAVLWLSVEVFASSGTNAAPAVS
                   130        140        150        160        170        180

180        190        200        210        220        230        239
orf125-1.pep   DGMSFGTAVELSAVMPLSWLPLAADYTRHARRPFAATLTATLAYTLTGCWMYALGLAAAL
               |||:|||||||||||||||||||||||:||||||||||||||||||||||||||||||||
orf125ng-1     DGMTFGTAVELSAVMPLSWLPLAADYTRQARRPFAATLTATLAYTLTGCWMYALGLAAAL
                   190        200        210        220        230        240

240        250        260        270        280        290        299
orf125-1.pep   FTGETDVAKILLGAGLGAAGILAVVLSTVTTTFLDAYSAGASANNISARFAETPVAVGVT
               ||||||||||||||||:||||||||||||||||||:||||||||||||||||||||||||
orf125ng-1     FTGETDVAKILLGAGLGITGILAVVLSTVTTTFLDTYSAGASANNISARFAETPVAVGVT
                   250        260        270        280        290        300

300        310        320        330        340        350        359
orf125-1.pep   LIGTVLAVMLPVTEYENFLLLIGSVFAPMAAVLIADFFVLKRREEIEGFDFAGLVLWLAG
               ||||||||||||||:|||||||||||||||||||||||||||||||||||||||||||||
orf125ng-1     LIGTVLAVMLPVTEY5NFLLLIGSVFAPMAAVLIADFFVLKRREEIEGFDFAGLVLWLAG
                   310        320        330        340        350        360

360        370        380        390        400
orf125-1.pep   FILYRFLLSSGWESSIGLTAPVMSAVAIATVSVRLFFKKTQSLQRNPSX
               |||||||||||||||||||||||||||||||||||||||||||||||||
orf125ng-1     FILYRFLLSSGWESSIGLTAPVMSAVAIATVSVRLFFKKTQSLQRNPSX
                   370        380        390        400
```

Based on this analysis, including the presence of putative leader sequence and transmembrane domains in the gonococcal protein, it is predicted that the proteins from *N. meningitidis* and *N. gonorrhoeae*, and their epitopes, could be useful antigens for vaccines or diagnostics, or for raising antibodies.

Example 96

The following partial DNA sequence was identified in *N. meningitidis* <SEQ ID 809>:

```
  1 ATGACCCGTA TCGCCATCCT CGGCGGCGGC CTCTCGGGAA GGCTGACCGC
 51 GTTGCAGCTT GCAGAACAAG GTTATCAGAT TGCACTTTTC GATAAAAGCT
101 GCCGCCGGGG CGAACACGCC GCCGCCTATG TAGCCGCCGC CATGCTCGCG
151 CCTGCAGCGG A.ACGGTCGA AGCCACGCCC GAAGTGGTCA GGCTGGGCAG
201 GCAGAGCATC CCGCTTTGGC GCGGCATCCG ATGCCGTCTG AACACGCACA
251 CGATGATGCA GGAAAACGGC AGCCTGATTG TATGGCACGG GCAGGACAAG
301 CCATTATCCA GCGAGTTCGT CCGCCATCTC AAACGCGGCG GCGT.ACGGA
351 TGACGAAATC GTCCGTTGGC GCGCCGACGA CATCGCCGAA CGCGAACCGC
401 AACTCGGCGG ACGTTTTTAA GACGGCATCT ACCTGCCGAC CGAAGC.CAG
451 CTCGACGGGC GGCAATTATA GTCTGCACTT GCCGACGCTT TGGACGAACT
501 GAACGTCCCC TGCCATTGGG AACACGAATG CGTCCCCGAA GCCTGCAAG..
```

This corresponds to the amino acid sequence <SEQ ID 810; ORF126>:

```
  1 MTRIAILGGG LSGRLTALQL AEQGYQIALF DKSCRRGEHA AAYVAAAMLA
 51 PAAXTVEATP EVVRLGRQSI PLWRGIRCRL NTHTMMQENG SLIVWHGQDK
101 PLSSEFVRHL KRGGXTDDEI VRWRADDIAE REPQLGGRFX DGIYLPTEXQ
151 LDGRQLXSAL ADALDELNVP CHWEHECVPE ACK...
```

Further work revealed the complete nucleotide sequence <SEQ ID 811>:

```
  1 ATGACCCGTA TCGCCATCCT CGGCGGCGGC CTCTCGGGAA GGCTGACCGC
 51 GTTGCAGCTT GCAGAACAAG GTTATCAGAT TGCACTTTTC GATAAAGGCT
101 GCCGCCGGGG CGAACACGCC GCCGCCTATG TTGCCGCCGC CATGCTCGCG
151 CCTGCGGCGG AAGCGGTCGA AGCCACGCCC GAAGTGGTCA GGCTGGGCAG
201 GCAGAGCATC CCGCTTTGGC GCGGCATCCG ATGCCGTCTG AACACGCACA
251 CGATGATGCA GGAAAACGGC AGCCTGATTG TGTGGCACGG GCAGGACAAG
301 CCATTATCCA GCGAGTTCGT CCGCCATCTC AAACGCGGCG GCGTAGCGGA
351 TGACGAAATC GTCCGTTGGC GCGCCGACGA CATCGCCGAA CGCGAACCGC
401 AACTCGGCGG ACGTTTTTCA GACGGCATCT ACCTGCCGAC CGAAGGCCAG
451 CTCGACGGGC GGCAAATATT GTCTGCACTT GCCGACGCTT TGGACGAACT
501 GAACGTCCCC TGCCATTGGG AACACGAATG CGTCCCCGAA GGCCTGCAAG
551 CCCAATACGA CTGGCTGATC GACTGCCGCG GCTACGGCGC AAAAACCGCG
601 TGGAACCAAT CCCCCGAGCA CACCAGCACC CTGCGCGGCA TACGCGGCGA
651 AGTGGCGCGG GTTTACACAC CCGAAATCAC GCTCAACCGC CCCGTGCGTC
701 TGCTCCATCC GCGTTATCCG CTCTACATCG CCCCGAAAGA AAACCACGTC
751 TTCGTCATCG GCGCGACCCA AATCGAAAGC GAAAGCCAAG CCCCCGCCAG
801 CGTGCGTTCA GGGTTGGAAC TCTTGTCCGC ACTCTATGCC ATCCACCCCG
851 CCTTCGGCGA AGCCGACATC CTCGAAATCG CCACCGGCCT GCGCCCCACG
```

-continued

```
 901 CTCAACCACC ACAACCCCGA AATCCGTTAC AACCGCGCCC GACGCCTGAT

951 TGAAATCAAC GGCCTTTTCC GCCACGGTTT CATGATCTCC CCCGCCGTAA

1001 CCGCCGCCGC CGCCAGATTG GCAGTGGCAC TGTTTGACGG AAAAGACGCG

1051 CCCGAACGCG ATAAAGAAAG CGGTTTGGCG TATATCCGAA GACAAGATTA

1101 A
```

This corresponds to the amino acid sequence <SEQ ID 812; ORF126-1>:

```
  1 MTRIAILGGG LSGRLTALQL AEQGYQIALF DKGCRRGEHA AAYVAAAMLA

51 PAAEAVEATP EVVRLGRQSI PLWRGIRCRL NTHTMMQENG SLIVWHGQDK

101 PLSSEFVRHL KRGGVADDEI VRWRADDIAE REPQLGGRFS DGIYLPTEGQ

151 LDGRQILSAL ADALDELNVP CHWEHECVPE GLQAQYDWLI DCRGYGAKTA

201 WNQSPEHTST LRGIRGEVAR VYTPEITLNR PVRLLHPRYP LYIAPKENHV

251 FVIGATQIES ESQAPASVRS GLELLSALYA IHPAFGEADI LEIATGLRPT

301 LNHHNPEIRY NRARRLIEIN GLFRHGFMIS PAVTAAAARL AVALFDGKDA

351 PERDKESGLA YIRRQD*
```

Computer analysis of this amino acid sequence gave the following results:

Homology with a Predicted ORF from *N. meningitidis* (Strain A)

ORF126 shows 90.0% identity over a 180aa overlap with an ORF (ORF126a) from strain A of *N. meningitidis*:

```
                    10        20        30        40        50        60
orf126.pep  MTRIAILGGGLSGRLTALQLAEQGYQIALFDKSCRRGEHAAAYVAAAMLAPAAXTVEATP
            ||||||||||||||||||||||||||||||||:||||||||||||||||||| :|||||
orf126a     MTRIAILGGGLSGRLTALQLAEQGYQIALFDKGCRRGEHAAAYVAAAMLAPAAEAVEATP
                    10        20        30        40        50        60

70        80        90       100       110       120
orf126.pep  EVVRLGRQSIPLWRGIRCRLNTHTMMQENGSLIVWHGQDKPLSSEFVRHLKRGGXTDDEI
            ||||||| |||||||||||| :|: :||||||||||||||||| :||||||||| ||:|
orf126a     EVVRLGRQXIPLWRGIRCHLKTPAMMXENGSLIVWHGQDKPLSNEFVRHLKRGGVADDXI
                    70        80        90       100       110       120

130       140       150       160       170       180
orf126.pep  VRWRADDIAEREPQLGGRFXDGIYLPTEXQLDGRQLXSALADALDELNVPCHWEHECVPE
            ||||||||||||||||||| ||||||| ||||||| :|||||||||||||||||||:||
orf126a     VRWRADDIAEREPQLGGRFSDGIYLPTEGQLDGRQILSALADALDELNVPCHWEHECAPE
                   130       140       150       160       170       180
```

The complete length ORF126a nucleotide sequence <SEQ ID 813> is:

```
   1 ATGACCCGTA TCGCCATCCT CGGCGGCGGC CTCTCNGGAA GGCTGACCGC
  51 ACTGCAGCTT GCAGAACAAG GTTATCAGAT TGCACTTTTC GATAAAGGCT
 101 GCCGCCGGGG CGAACACGCC GCCGCCTATG TTGCCGCCGC CATGCTCGCG
 151 CCTGCGGCGG AAGCGGTCGA AGCCACGCCT GAAGTGGTCA GGCTGGGCAG
 201 GCAGANCATC CCGCTTTGGC GCGGCATCCG ATGCCATCTG AAAACGCCTG
 251 CCATGATGCA NGAAACGGC AGCCTGATTG TGTGGCACGG GCAGGACAAA
 301 CCTTTATCCA ACGAGTTCGT CCGCCATCTC AAACGCGGCG GCGTAGCGGA
 351 TGACNAAATC GTCCGTTGGC GCGCCGACGA CATCGCCGAA CGCGAACCGC
 401 AACTCGGCGG ACGTTTTTCA GACGGCATCT ACCTGCCGAC CGAAGGCCAG
 451 CTCGACGGGC GGCAAATATT GTCTGCACTT GCCGACGCTT GGACGAACT
 501 GAACGTCCCC TGCCATTGGG AACACGAATG TGCCCCCGAA GACTTGCAAG
 551 CCCAATACGA CTGGCTGATC GACTGCCGCG GCTACGGCGC AAAAACCGCG
 601 TGGAACCAAT CCCCCGANNA NACCAGCACC CTGCGCGGCA TACGCGGCGA
 651 AGTGGCGCGG GTTTACACAC CCGAAATCAC GCTCAACCGC CCCGTGCGCC
 701 TGCTACACCC GCGCTATCCG CTNTACATCG CCCCGAAAGA AAACCNCGTC
 751 TTCGTCATCG GCGCGACCCA AATCGAAAGC GAAAGCCAAG CACCTGCCAG
 801 CGTGCGTTCC GGGCTGGAAC TCTTATCCGC ACTCTATGCC GTCCACCCCG
 851 CCTTCGGCGA AGCCGACATC CTCGAAATCG CCACCGGCCT GCGCCCCACG
 901 CTCAATCACC ACAACCCCGA AATCCGTTAC AACCGCGCCC GACGCCTGAT
 951 TGAAATCAAC GGCCTTTTCC GCCACGGTTT CATGATCTCC CCCGCCGTAA
1001 CCGCCGCCGC CGTCAGATTG GCAGTGGCAC TGTTTGACGG AAAAGANGCG
1051 CCCGAACGCG ATGAAGAAAG CGGTTTGGCG TATATCCGAA GACAAGATTA
1101 A
```

This encodes a protein having amino acid sequence <SEQ ID 814>:

```
  1 MTRIAILGGG LSGRLTALQL AEQGYQIALF DKGCRRGEHA AAYVAAAMLA
 51 PAAEAVEATP EVVRLGRQXI PLWRGIRCHL KTPAMMXENG SLIVWHGQDK
101 PLSNEFVRHL KRGGVADDXI VRWRADDIAE REPQLGGRFS DGIYLPTEGQ
151 LDGRQILSAL ADALDELNVP CHWEHECAPE DLQAQYDWLI DCRGYGAKTA
201 WNQSPXXTST LRGIRGEVAR VYTPEITLNR PVRLLHPRYP LYIAPKENXV
251 FVIGATQIES ESQAPASVRS GLELLSALYA VHPAFGEADI LEIATGLRPT
301 LNHHNPEIRY NRARRLIEIN GLFRHGFMIS PAVTAAAVRL AVALFDGKXA
351 PERDEESGLA YIRRQD*
```

ORF126a and ORF126-1 show 95.4% identity in 366 aa overlap:

```
                  10        20        30        40        50        60
orf126a.pep  MTRIAILGGGLSGRLTALQLAEQGYQIALFDKGCRRGEHAAAYVAAAMLAPAAEAVEATP
             ||||||||||||||||||||||||||||||||||||||||||||||||||||||||||||
orf126-1     MTRIAILGGGLSGRLTALQLAEQGYQIALFDKGCRRGEHAAAYVAAAMLAPAAEAVEATP
                  10        20        30        40        50        60

70        80        90       100       110       120
orf126a.pep  EVVRLGRQXIPLWRGIRCHLKTPAMMXENGSLIVWHGQDKPLSNEFVRHLKRGGVAFFXI
             ||||||||| ||||||||||:|:| :|| ||||||||||||||:|||||||||||||| |
orf126-1     EVVRLGRQSIPLWRGIRCRLNTHTMMQENGSLIVWHGQDKPLSSEFVRHLKRGGVADDEI
                  70        80        90       100       110       120

130       140       150       160       170       180
orf126a.pep  VRWRADDIAEREPQLGGRFSDGIYLPTEGQLDGRQILSALADALDELNVPCHWEHECAPE
             |||||||||||||||||||||||||||||||||||||||||||||||||||||||||:||
orf126-1     VRWRADDIAEREPQLGGRFSDGIYLPTEGQLDGRQILSALADALDELNVPCHWEHECVPE
                 130       140       150       160       170       180

190       200       210       220       230       240
orf126a.pep  DLQAQYDWLIDCRGYGAKTAWNQSPXXTSTLRGIRGEVARVYTPEITLNRPVRLLHPRYP
              ||||||||||||||||||||||||||  ||||||||||||||||||||||||||||||||
orf126-1     GLQAQYDWLIDCRGYGAKTAWNQSPEHTSTLRGIRGEVARVYTPEITLNRPVRLLHPRYP
                 190       200       210       220       230       240

250       260       270       280       290       300
orf126a.pep  LYIAPKENXVFVIGATQIESESQAPASVRSGLELLSALYAVHPAFGEADILEIATGLRPT
             ||||||||| ||||||||||||||||||||||||||||||:|||||||||||||||||||
orf126-1     LYIAPKENHVFVIGATQIESESQAPASVRSGLELLSALYAIHPAFGEADILEIATGLRPT
                 250       260       270       280       290       300

310       320       330       340       350       360
orf126a.pep  LNHHNPEIRYNRARRLIEINGLFRHGFMISPAVTAAAVRLAVALFDGKXAPERDEESGLA
             |||||||||||||||||||||||||||||||||||||||:||||||||| ||||:|||||
orf126-1     LNHHNPEIRYNRARRLIEINGLFRHGFMISPAVTAAAARLAVALFDGKDAPERDKESGLA
                 310       320       330       340       350       360 orf126a.pep  YIRRQDX
             |||||||
orf126-1     YIRRQDX
```

Homology with a Predicted ORF from *N. gonorrhoeae*
ORF126 shows 90% identity over a 180 aa overlap with a predicted ORF (ORF126ng) from *N. gonorrhoeae*:

```
orf126.pep   MTRIAILGGGLSGRLTALQLAEQGYQIALFDKSCRRGEHAAAYVAAAMLAPAAXTVEATP   60
             ||||:|||||||||||||||||||||:|||| |:|||||||||||||||||||  :||||
orf126ng     MTRIAVLGGGLSGRLTALQLAEQGYQIELFDKGTRQGEHAAAYVAAAMLAPAAEAVEATP   60 orf126.pep   EVVRLGRQSIPLWRGIRCRLNTHTMMQENGSLIVWHGQDKPLSSEFVRHLKRGGXTDDEI  120
             ||:|||||||||||||||||||| |||||||||||||||||||||||||||||| :||||
orf126ng     EVIRLGRQSIPLWRGIRCRLNTLTMMQENGSLIVWHGQDKPLSSEFVRHLKRGGVADDEI  120 orf126.pep   VRWRADDIAEREPQLGGRFXDGIYLPTEXQLDGRQLXSALADALDELNVPCHWEHECVPE  180
             |||||:|||||||||||||| |||||||| |||||| :||||||||||||||||||:|:
orf126ng     VRWRADEIAEREPQLGGRFSDGIYLPTEGQLDGRQILSALADALDELNVPCHWEHECAPQ  180
```

An ORF126ng nucleotide sequence <SEQ ID 815> was predicted to encode a protein having amino acid sequence <SEQ ID 816>:

```
  1 MTRIAVLGGG LSGRLTALQL AEQGYQIELF DKGTRQGEHA AAYVAAAMLA

51 PAAEAVEATP EVIRLGRQSI PLWRGIRCRL NTLTMMQENG SLIVWHGQDK

101 PLSSEFVRHL KRGGVADDEI VRWRADEIAE REPQLGGRFS DGIYLPTEGQ

151 LDGRQILSAL ADALDELNVP CHWEHECAPQ DLQAQYDWVI DCRGYGAKTA

201 WNQSPEHTST LRGIRGEVRG FTRPKSRSTA PCACCTRAIR STSPRKKTTS

251 SSSARPKSKA KAKPPPAYVP GWNSYPRSMP STPPSAKPTS SKWRPGLRPT

301 LNHHNPEIRY SRERRLIEIN GLFRHGFMIS PAVTAAAVRL AVALFDGKDA

351 PERDEESGLA YIGRQD*
```

Further work revealed the following gonococcal DNA sequence <SEQ ID 817>:

```
   1 ATGACCCGTA TCGCCGTCCT CGGAGGCGGC CTTTCCGGAA GGCTGACCGC

51 ATTGCAGCTT GCAGAACAAG GTTATCAGAT TGAACTTTTC GACAAGGGCA

101 CCCGCCAAGG CGAACACGCC GCCGCCTATG TTGCCGCCGC GATGCTCGCG

151 CCTGCGGCGG AAGCGGTCGA GGCAACGCCC GAAGTCATCA GGCTGGGCAG

201 GCAGAGCATT CCGCTTTGGC GCGGCATCCG ATGCCGTCTG AACACGCTCA

251 CGATGATGCA GGAAAACGGC AGCCTGATTG TGTGGCACGG GCAGGACAAG

301 CCATTATCCA GCGAGTTCGT CCGCCATCTC AAACGCGGCG GCGTAGCGGA

351 TGACGAAATC GTCCGTTGGC GCGCCGATGA AATCGCCGAA CGCGAACCGC

401 AACTCGGCGG ACGTTTTTCA GACGGCATCT ACCTGCCGAC CGAAGGCCAG

451 CTCGACGGGC GGCAAATATT GTCTGCACTT GCCGACGCTT TGGACGAACT

501 GAACGTCCCT TGCCATTGGG AACACGAATG CGCCCCCCAA GACCTGCAAG

551 CCCAATACGA CTGGGTAATC GACTGCCGGG GCTACGGCGC GAAAACCGCG

601 TGGAACCAAT CCCCCGAGCA CACCAGCACC TTGCGCGGCA TACGCGGCGA

651 AGTGGCGCGG GTTTACACGC CCGAAATCAC GCTCAACCGC CCCGTGCGCC

701 TGCTGCACCC GCGCTATCCG CTCTACATCG CCCCGAAAGA AAACCACGTC

751 TTCGTCATCG GCGCGACCCA AATCGAAAGC GAAAGCCAAG CCCCCGCCAG

801 CGTACGTTCC GGGCTGGAAC TCTTATCCGC GCTCTATGCC GTCCACCCCG

851 CCTTCGGCGA AGCCGACATC CTCGAAATCG CCGCCGGCCT GCGCCCCACG

901 CTCAACCACC ACAACCCCGA AATCCGCTAC AGCCGCGAAC GCCGCCTCAT

951 CGAAATCAAC GGCCTTTTCC GGCACGGCTT TATGATTTCC CCCGCCGTAA

1001 CCGCCGCCGC CGTCAGATTG GCAGTGGCAC TGTTTGACGG AAAAGACGCG

1051 CCCGAACGTG ATGAAGAAAG CGGTTTGGCG TATATCGGAA GACAAGATTA

1101 A
```

This corresponds to the amino acid sequence <SEQ ID 818; ORF126ng-1>:

```
   1 MTRIAVLGGG LSGRLTALQL AEQGYQIELF DKGTRQGEHA AAYVAAAMLA

51 PAAEAVEATP EVIRLGRQSI PLWRGIRCRL NTLTMMQENG SLIVWHGQDK

101 PLSSEFVRHL KRGGVADDEI VRWRADEIAE REPQLGGRFS DGIYLPTEGQ

151 LDGRQILSAL ADALDELNVP CHWEHECAPQ DLQAQYDWVI DCRGYGAKTA

201 WNQSPEHTST LRGIRGEVAR VYTPEITLNR PVRLLHPRYP LYIAPKENHV

251 FVIGATQIES ESQAPASVRS GLELLSALYA VHPAFGEADI LEIAAGLRPT

301 LNHHNPEIRY SRERRLIEIN GLFRHGFMIS PAVTAAAVRL AVALFDGKDA

351 PERDEESGLA YIGRQD*
```

ORF126ng-1 and ORF126-1 show 95.1% identity in 366 aa overlap:

```
                   10         20         30         40         50         60
orf126-1.pep  MTRIAILGGGLSGRLTALQLAEQGYQIALFDKGCRRGEHAAAYVAAAMLAPAAEAVEATP
              |||||:||||||||||||||||||||||| |||||:||||||||||||||||||||||||
orf126ng-1    MTRIAVLGGGLSGRLTALQLAEQGYQIELFDKGTRQGEHAAAYVAAAMLAPAAEAVEATP
                   10         20         30         40         50         60
```

```
                       70         80         90        100        110        120
orf126-1.pep  EVVRLGRQSIPLWRGIRCRLNTHTMMQENGSLIVWHGQDKPLSSEFVRHLKRGGVADDEI
              ||:|||||||||||||||||||| |||||||||||||||||||||||||||||||||||
orf126ng-1    EVIRLGRQSIPLWRGIRCRLNTLTMMQENGSLIVWHGQDKPLSSEFVRHLKRGGVADDEI
                       70         80         90        100        110        120

130        140        150        160        170        180
orf126-1.pep  VRWRADDIAEREPQLGGRFSDGIYLPTEGQLDGRQILSALADALDELNVPCHWEHECVPE
              ||||||:|||||||||||||||||||||||||||||||||||||||||||||||||:|:
orf126ng-1    VRWRADEIAEREPQLGGRFSDGIYLPTEGQLDGRQILSALADALDELNVPCHWEHECAPQ
                      130        140        150        160        170        180

190        200        210        220        230        240
orf126-1.pep  GLQAQYDWLIDCRGYGAKTAWNQSPEHTSTLRGIRGEVARVYTPEITLNRPVRLLHPRYP
              |||||||:||||||||||||||||||||||||||||||||||||||||||||||||||||
orf126ng-1    DLQAQYDWVIDCRGYGAKTAWNQSPEHTSTLRGIRGEVARVYTPEITLNRPVRLLHPRYP
                      190        200        210        220        230        240

250        260        270        280        290        300
orf126-1.pep  LYIAPKENHVFVIGATQIESESQAPASVRSGLELLSALYAIHPAFGEADILEIATGLRPT
              |||||||||||||||||||||||||||||||||||||||||:|||||||||||:|||||
orf126ng-1    LYIAPKENHVFVIGATQIESESQAPASVRSGLELLSALYAVHPAFGEADILEIAAGLRPT
                      250        260        270        280        290        300

310        320        330        340        350        360
orf126-1.pep  LNHHNPEIRYNRARRLIEINGLFRHGFMISPAVTAAAARLAVALFDGKDAPERDKESGLA
              ||||||||||:|||||||||||||||||||||||||||:||||||||||||||:|||||
orf126ng-1    LNHHNPEIRYSRERRLIEINGLFRHGFMISPAVTAAAVRLAVALFDGKDAPERDEESGLA
                      310        320        330        340        350        360 orf126-1.pep  YIRRQDX
              || ||||
orf126ng-1    YIGRQDX
```

Furthermore, ORF126ng-1 shows homology to a putative *Rhizobium* oxidase flavoprotein:

```
gi|2627327 (AF004408) putative amino acid oxidase flavoprotein
[Rhizobium etli]
Length = 327
Score = 169 bits (423), Expect = 3e-41
Identities = 112/329 (34%), Positives = 163/329 (49%), Gaps = 25/329 (7%)

Query:   3 RIAVLGGGLSGRLTALQLAEQGYQIELFDKGTRQGEHXXXXXXXXXXXXXXXXXXXXXXX   62
           RI V G G++G   A QL   G+++ L ++    G
Sbjct:   2 RILVNGAGVAGLTVAWQLYRHGFRVTLAERAGTVGA-GASGFAGGMLAPWCERESAEEPV   60

Query:  63 IRLGRQSIPLWRGIRCRLNTLTMMQENGSLIVWHGQDKPLSSEFVRHLKRGGVADDEIVR  122
              + LGR +   W             +   G+L+V  G+D     F R    G   DE+
Sbjct:  61 LTLGRLAADWWEAA-----LPGHVRRGTLVVAGGRDTGELDRFSRRTS-GWEWLDEVA-  113

Query: 123 WRADEIAEREPQLGGRFSDGIYLPTEGQLDGRQILSALADALDELNVPCHWEHECAPQDL  182
                   IA  EP L GRF   ++   E   LD RQ L+ALA  L++  +              +
Sbjct: 114 -----IAALEPDLAGRFRRALFFRQEAHLDPRQALAALAAGLEDARMRLTLG---VVGES  165

Query: 183 QAQYDWVIDCRGYGAKTAWNQSPEHTSTLRGIRGEVARVYTPEITLNRPVRLLHPRYPLY  242
             +D V+DC G                    LRG+RGE+  V T E++L+RPVRLLHPR+P+Y
Sbjct: 166 DVDHDRVVDCTGAA-------QIGRLPGLRGVRGEMLCVETTEVSLSRPVRLLHPRHPIY  218

Query: 243 IAPKENHVFVIGATQIESESQAPASVRSGLELLSALYAVHPAFGEADILEIAAGLRPTLN  302
           I P++ + F++GAT IES+   P + RS +ELL+A YA+HPAFGEA + E   AG+RP
Sbjct: 219 IVPRDKNRFMVGATMIESDDGGPITARSLMELLNAAYAMHPAFGEARVTETGAGVRPAYP  278

Query: 303 HHNPEIRYSRERRLIEINGLFRHGFMISP                                331
            + P   R ++E R +  +NGL+RHGF+++P
Sbjct: 279 DNLP--RVTQEGRTLHVNGLYRHGFLLAP                                305
```

This analysis suggests that the proteins from *N. meningitidis* and *N. gonorrhoeae*, and their epitopes, could be useful antigens for vaccines or diagnostics, or for raising antibodies.

Example 97

The following DNA sequence, believed to be complete, was identified in *N. meningitidis* <SEQ ID 819>:

```
  1 ATGACTGATA ATCGGGGGTT TACGCTGGTT GAATTAATAT CAGTGGTCTT

51 GATATTGTCT GTACTTGCTT TAATTGTTTA TCCGAGCTAT CGCAATTATG
```

-continued

```
101 TTGAGAAAGC AAAGATAAAT GCAGTGCGGG CAGCCTTGTT AGAAAATGCA

151 CATTTTATGG AAAAGTTTTA TCTGCAGAAT GGGAGGTTTA AACAAACATC

201 TACCAAGTGG CCAAGTTTGC CGATTAAAGA GGCAGAAGGC TTTTGTATCC

251 GTTTGAATGG AATCGtCGCG CGGG..GCTT TAGACAGTAA ATTCATGTTG

301 AAGGCGGTAG CCATAGATAA AGATAAAAAT CCTTTTATTA TTAAGATGAA

351 TGAAAATCTA GTAACCTTTA aTTTGCAAGA AGTCCGCCAG TTCGTGTAGT

401 GACGGGCTGG ATTATTTTAA AGGAAATGAT AAGGACTGCA AGTTACTTAA

451 GTAG
```

This corresponds to the amino acid sequence <SEQ ID 820; ORF127>:

```
  1 MTDNRGFTLV ELISVVLILS VLALIVYPSY RNYVEKAKIN AVRAALLENA

51 HFMEKFYLQN GRFKQTSTKW PSLPIKEAEG FCIRLNGIVA RXALDSKFML

101 KAVAIDKDKN PFIIKMNENL VTFICKKSAS SCSDGLDYFK GNDKDCKLLK

151 *
```

Further work revealed the following DNA sequence <SEQ ID 821>:

```
  1 ATGACTGATA ATCGGGGGTT TACGCTGGTT GAATTAATAT CAGTGGTCTT

51 GATATTGTCT GTACTTGCTT TAATTGTTTA TCCGAGCTAT CGCAATTATG

101 TTGAGAAAGC AAAGATAAAT GCAGTGCGGG CAGCCTTGTT AGAAAATGCA

151 CATTTTATGG AAAAGTTTTA TCTGCAGAAT GGGAGGTTTA AACAAACATC

201 TACCAAGTGG CCAAGTTTGC CGATTAAAGA GGCAGAAGGC TTTTGTATCC

251 GTTTGAATGG AATCGCGCGC GGGGCTTTAG ACAGTAAATT CATGTTGAAG

301 GCGGTAGCCA TAGATAAAGA TAAAAATCCT TTTATTATTA AGATGAATGA

351 AAATCTAGTA ACCTTTATTT GCAAGAAGTC CGCCAGTTCG TGTAGTGACG

401 GGCTGGATTA TTTTAAAGGA AATGATAAGG ACTGCAAGTT ACTTAAGTAG
```

This corresponds to the amino acid sequence <SEQ ID 822; ORF127-1>:

```
  1 MTDNRGFTLV ELISVVLILS VLALIVYPSY RNYVEKAKIN AVRAALLENA

51 HFMEKFYLQN GRFKQTSTKW PSLPIKEAEG FCIRLNGIAR GALDSKFMLK

101 AVAIDKDKNP FIIKMNENLV TFICKKSASS CSDGLDYFKG NDKDCKLLK*
```

Computer analysis of this amino acid sequence gave the following results:
Homology with a Predicted ORF from *N. meningitidis* (Strain A)
ORF127 shows 98.0% identity over a 150aa overlap with an ORF (ORF127a) from strain A of *N. meningitidis*.

```
                 10         20         30         40         50         60
orf127.pep  MTDNRGFTLVELISVVLILSVLALIVYPSYRNYVEKAKINAVRAALLENAHFMEKFYLQN
            ||||||||||||||||||||||||||||||||||||:|||||||||||||||||||||||
orf127A     MTDNRGFTLVELISVVLILSVLALIBYPSYRNYVEKAKINTVRAALLENAHFMEKFYLQN
                 10         20         30         40         50         60

70         80         90        100        110        120
orf127.pep  GRFKQTSTKWPSLPIKEAEGFCIRLNGIVARXALDSKFMLKAVAIDKDKNPFIIKMNENL
            ||||||||||||||||||||||||||||| || |||||||||||||||||||||||||||
orf127A     GRFKQTSTKWPSLPIKEAEGFCIRLNGI-ARGALDSKFMLKAVAIDKDKNPFIIKMNENL
                 70         80         90        100        110

130        140        150
orf127.pep  VTFICKKSASSCSDGLDYFKGNDKDCKLLKX
            ||||||||||||||||||||||||||||||
orf127A     VTFICKKSASSCSDGLDYFKGNDKDCKLLKX
               120        130        140        150
```

The complete length ORF127a nucleotide sequence <SEQ ID 823> is:

```
  1 ATGACTGATA ATCGGGGGTT TACGCTGGTT GAATTAATAT CAGTGGTCTT

51 GATATTGTCT GTACTTGCTT TAATTGTTTA TCCGAGCTAT CGCAATTATG

101 TTGAGAAAGC AAAGATAAAT ACAGTGCGGG CAGCCTTGTT AGAAAATGCA

151 CATTTTATGG AAAAGTTTTA TCTGCAGAAT GGGAGATTTA AACAAACATC

201 TACCAAATGG CCAAGTTTGC CGATTAAAGA GGCAGAAGGC TTTTGTATCC

251 GTTTGAATGG AATCGCGCGC GGGGCCTTAG ACAGTAAATT CATGTTGAAG

301 GCGGTAGCCA TAGATAAAGA TAAAAATCCT TTTATTATTA AGATGAATGA

351 AAATCTAGTA ACCTTTATTT GCAAGAAGTC CGCCAGTTCG TGTAGTGACG

401 GGCTGGATTA TTTTAAAGGA AATGATAAGG ACTGCAAGTT ACTTAAGTAG
```

This encodes a protein having amino acid sequence <SEQ ID 824>:

```
  1 MTDNRGFTLV ELISVVLILS VLALIVYPSY RNYVEKAKIN TVRAALLENA

51 HFMEKFYLQN GRFKQTSTKW PSLPIKEAEG FCIRLNGIAR GALDSKFMLK

101 AVAIDKDKNP FIIKMNENLV TFICKKSASS CSDGLDYFKG NDKDCKLLK*
```

ORF127a and ORF127-1 show 99.3% identity in 149 aa overlap:

```
                 10         20         30         40         50         60
orf127a.pep MTDNRGFTLVELISVVLILSVLALIVYPSYRNYVEKAKINTVRAALLENAHFMEKFYLQN
            ||||||||||||||||||||||||||||||||||||:|||||||||||||||||||||||
orf127-1    MTDNRGFTLVELISVVLILSVLALIVYPSYRNYVEKAKINAVRAALLENAHFMEKFYLQN
                 10         20         30         40         50         60

70         80         90        100        110        120
orf127a.pep GRFKQTSTKWPSLPIKEAEGFCIRLNGIARGALDSKFMLKAVAIDKDKNPFIIKMNENLV
            ||||||||||||||||||||||||||||||||||||||||||||||||||||||||||||
orf127-1    GRFKQTSTKWPSLPIKEAEGFCIRLNGIARGALDSKFMLKAVAIDKDKNPFIIKMNENLV
                 70         80         90        100        110        120

130        140        150
orf127a.pep TFICKKSASSCSDGLDYFKGNDKDCKLLKX
            ||||||||||||||||||||||||||||||
orf127-1    TFICKKSASSCSDGLDYFKGNDKDCKLLKX
               130        140        150
```

Homology with a Predicted ORF from *N. gonorrhoeae*

ORF127 shows 97.3% identity over a 150 aa overlap with a predicted ORF (ORF127ng) from *N. gonorrhoeae*:

```
orf127.pep  MTDNRGFTLVELISVVLILSVLALIVYPSYRNYVEKAKINAVRAALLENAHFMEKFYLQN   60
            ||||||||||||||||||||||||||||||||||||:|||||||||||||
orf127ng    MTDNRGFTLVELISVVLILSVLALIVYPSYRNYVEKAKINAVRAAFLENAHFMEKFYLQN   60 orf127.pep  GRFKQTSTKWPSLPIKEAEGFCIRLNGIVARXALDSKFMLKAVAIDKDKNPFIIKMNENL  120
            |||||||||||||||||||||||||||| || ||||||||||||||||||||||||||
orf127ng    GRFKQTSTKWPSLPIKEAEGFCIRLNGI-ARGALDSKFMLKAVAIDKDKNPFIIKMNENL  119 orf127.pep  VTFICKKSASSCSDGLDYFKGNDKDCKLLK                               150
            |||||||||||||| ||||||||||||||
orf127ng    VTFICKKSASSCSDRLDYFKGNDKDCKLLK                               149
```

The complete length ORF127ng nucleotide sequence <SEQ ID 825> is:

```
  1 ATGACTGATA ATCGGGGGTT TACACTGGTT GAATTAATAT CAGTGGTCTT
 51 GATATTGTCT GTACTTGCTT TAATTGTTTA TCCGAGCTAT CGCAATTATG
101 TTGAGAAAGC AAAGATAAAT GCAGTGCGGG CAGCCTTGTT AGAAAATGCA
151 CATTTTATGG AAAAGTTTTA TCTGCAGAAT GGGAGATTTA AACAAACATC
201 TACCAAATGG CCAAGTTTGC CGATTAAAGA GGCAGAAGGC TTTTGTATCC
251 GTTTGAATGG AATCGCGCGC GGGGCTTTAG ACAGTAAATT CATGTTGAAG
301 GCGGTAGCCA TAGATAAAGA TAAAAATCCT TTTATTATTA AGATGAATGA
351 AAATCTAGTA ACCTTTATTT GCAAGAAGTC CGCCAGTTCG TGTAGTGACG
401 GGCTGGATTA TTTTAAAGGA AATGATAAGG ACTGCAAGTT ACTTAAGTAG
```

This encodes a protein having amino acid sequence <SEQ ID 826>:

```
  1 MTDNRGFTLV ELISVVLILS VLALIVYPSY RNYVEKAKIN AVRAAFLENA
 51 HFMEKFYLQN GRFKQTSTKW PSLPIKEAEG FCIRLNGIAR GALDSKFMLK
101 AVAIDKDKNP FIIKMNENLV TFICKKSASS CSDRLDYFKG NDKDCKLLK*
```

ORF127ng and ORF127-1 show 100.0% identity in 149 aa overlap:

```
                   10         20         30         40         50         60
orf127-1.pep  MTDNRGFTLVELISVVLILSVLALIVYPSYRNYVEKAKINAVRAALLENAHFMEKFYLQN
              ||||||||||||||||||||||||||||||||||||||||||||||||||||||||||||
orf127ng-1    MTDNRGFTLVELISVVLILSVLALIVYPSYRNYVEKAKINAVRAALLENAHFMEKFYLQN
                   10         20         30         40         50         60

70         80         90        100        110        120
orf127-1.pep  GRFKQTSTKWPSLPIKEAEGFCIRLNGIARGALDSKFMLKAVAIDKDKNPFIIKMNENLV
              ||||||||||||||||||||||||||||||||||||||||||||||||||||||||||||
orf127ng-1    GRFKQTSTKWPSLPIKEAEGFCIRLNGIARGALDSKFMLKAVAIDKDKNPFIIKMNENLV
                   70         80         90        100        110        120

130        140        150
orf127-1.pep  TFICKKSASSCSDGLDYFKGNDKDCKLLKX
              |||||||||||||||||||||||||||||
orf127ng-1    TFICKKSASSCSDGLDYFKGNDKDCKLLKX
                  130        140        150
```

This analysis, including the fact that the predicted transmembrane domain is shared by the meningococcal and gonococcal proteins, suggests that the proteins from N. meningitidis and N. gonorrhoeae, and their epitopes, could be useful antigens for vaccines or diagnostics, or for raising antibodies.

Example 98

The following partial DNA sequence was identified in N. meningitidis <SEQ ID 827>

```
  1 ..GTGTCGCTGG CTTCGGTGAT TGCCTCTCAA ATCTTCCTTT ACGAAGATTT
 51   CAACCAAATG CGGAAAACCC GTGGAGCTAT CTGCGGTTTT CTTGTCCAAT
```

-continued

```
101  ATTTATCTGG GGTTTCAGCA GGGGTATTTC GATTTGAGTG CCGACGAGAA
151  CCCCGTACTG CATATCTGGT CTTTGGCAGT AGAGGAACAG TATTACCTCC
201  TGTATCCCCT TTTGCTGATA TTTTGCTGCA AAAAAACCAA ATCGCTACGG
251  GTGCTGCGTA ACATCAGCAT CATCCTGTTT TTGATTTTGA CTGCCTCATC
301  GTTTTTGCCA AGCGGGTTTT ATACCGACAT CCTCAACCAA CCCAATACTT
351  ATTACCTTTC GACACTGAGG TTTCCCGAGC TGTTGGCAGG TTCGCTGCTG
401  GCGGTTTACG GGCAAACGCA AAACGGCAGA CGGCAAACAG CAAATGGAAA
451  ACGGCAGTTG CTTTCATCAC TCTGCTTCGG CGCATTGCTT GCCTGCCTGT
501  TCGTGATTGA CAAACACAAT CCGTTTATCC CGGGAATGAC CCTGCTCCTT
551  CCCTGCCTGC TGACGGCACT GCTTATCCGG AGTATGCAAT ACGGGACACT
601  TCCGACCCGC ATCCTGTCGG CAAGCCCCAT CGTATTTGTC GGCAAAATCT
651  CTTATTCCCT ATACCTGTAC CATTGGATTT TTATTGCTTT CGCTCCGCTC
701  ATTAGAGGCG GGAAACAGCT CGGACTGCCT GCCG..
```

This corresponds to the amino acid sequence <SEQ ID 828; ORF128>:

```
  1..VSLASVIASQ IFLYEDFNQM RKTVELSAVF LSNIYLGFQQ GYFDLSADEN
 51  PVLHIWSLAV EEQYYLLYPL LLIFCCKKTK SLRVLRNISI ILFLILTASS
101  FLPSGFYTDI LNQPNTYYLS TLRFPELLAG SLLAVYGQTQ NGRRQTANGK
151  RQLLSSLCFG ALLACLFVID KHNPFIPGMT LLLPCLLTAL LIRSMQYGTL
201  PTRILSASPI VFVGKISYSL YLYHWIFIAF APLIRGGKQL GLPA..
```

Further work revealed the complete nucleotide sequence <SEQ ID 829>:

```
  1  ATGCAAGCTG TCCGATACAG ACCGGAAATT GACGGATTGC GGGCCGTCGC
 51  CGTGCTATCC GTCATGATTT TCCACCTGAA TAACCGCTGG CTGCCCGGAG
101  GATTCCTGGG GGTGGACATT TTCTTTGTCA TCTCAGGATT CCTCATTACC
151  GGCATCATTC TTTCTGAAAT ACAGAACGGT TCTTTTTCTT TCCGGGATTT
201  TTATACCCGC AGGATTAAGC GGATTTATCC TGCCTTTATT GCGGCCGTGT
251  CGCTGGCTTC GGTGATTGCC TCTCAAATCT TCCTTTACGA AGATTTCAAC
301  CAAATGCGGA AAACCGTGGA GCTTTCTGCG GTTTTCTTGT CCAATATTTA
351  TCTGGGGTTT CAGCAGGGGT ATTTCGATTT GAGTGCCGAC GAGAACCCCG
401  TACTGCATAT CTGGTCTTTG GCAGTAGAGG AACAGTATTA CCTCCTGTAT
451  CCCCTTTTGC TGATATTTTG CTGCAAAAAA CCAAATCGC TACGGGTGCT
501  GCGTAACATC AGCATCATCC TGTTTTTGAT TTTGACTGCC TCATCGTTTT
551  TGCCAAGCGG GTTTTATACC GACATCCTCA ACCAACCCAA TACTTATTAC
601  CTTTCGACAC TGAGGTTTCC CGAGCTGTTG CAGGTTCGC TGCTGGCGGT
651  TTACGGGCAA ACGCAAAACG GCAGACGGCA AACAGCAAAT GGAAAACGGC
701  AGTTGCTTTC ATCACTCTGC TTCGGCGCAT TGCTTGCCTG CCTGTTCGTG
751  ATTGACAAAC ACAATCCGTT TATCCCGGGA ATGACCCTGC TCCTTCCCTG
801  CCTGCTGACG GCACTGCTTA TCCGGAGTAT GCAATACGGG ACACTTCCGA
```

```
 851 CCCGCATCCT GTCGGCAAGC CCCATCGTAT TTGTCGGCAA AATCTCTTAT

901 TCCCTATACC TGTACCATTG GATTTTTATT GCTTTCGCCC ATTACATTAC

951 AGGCGACAAA CAGCTCGGAC TGCCTGCCGT ATCGGCGGTT GCCGCGTTGA

1001 CGGCCGGATT TTCCCTGTTG AGTTATTATT TGATTGAACA GCCGCTTAGA

1051 AAACGGAAGA TGACCTTCAA AAAGGCATTT TTCTGCCTCT ATCTCGCCCC

1101 GTCCCTGATA CTTGTCGGTT ACAACCTGTA CGCAAGGGGG ATATTGAAAC

1151 AGGAACACCT CCGCCCGTTG CCCGGCGCGC CCCTTGCTGC GGAAAATCAT

1201 TTTCCGGAAA CCGTCCTGAC CCTCGGCGAC TCGCACGCCG GACACCTGAG

1251 GGGGTTTCTG GATTATGTCG GCAGCCGGGA AGGGTGGAAA GCCAAAATCC

1301 TGTCCCTCGA TTCGGAGTGT TTGGTTTGGG TAGATGAGAA GCTGGCAGAC

1351 AACCCGTTAT GTCGAAAATA CCGGGATGAA GTTGAAAAAG CCGAAGCCGT

1401 TTTCATTGCC CAATTCTATG ATTTGAGGAT GGGCGGCCAG CCTGTGCCGA

1451 GATTTGAAGC GCAATCCTTC CTAATACCCG GGTTCCCAGC CCGATTCAGG

1501 GAAACCGTCA AAAGGATAGC CGCCGTCAAA CCCGTCTATG TTTTTGCAAA

1551 CAACACATCA ATCAGCCGTT CGCCCCTGAG GGAGGAAAAA TTGAAAAGAT

1601 TTGCCGCAAA CCAATATCTC CGCCCCATTC AGGCTATGGG CGACATCGGC

1651 AAGAGCAATC AGGCGGTCTT TGATTTGATT AAAGATATTC CAATGTGCA

1701 TTGGGTGGAC GCACAAAAAT ACCTGCCCAA AAACACGGTC GAAATATACG

1751 GCCGCTATCT TTACGGCGAC CAAGACCACC TGACCTATTT CGGTTCTTAT

1801 TATATGGGGC GGGAATTCCA CAAACACGAA CGCCTGCTTA AATCTTCCCA

1851 CGGCGGCGCA TTGCAGTAG
```

This corresponds to the amino acid sequence <SEQ ID 830; ORF128-1>:

```
  1 MQAVRYRPEI DGLRAVAVLS VMIFHLNNRW LPGGFLGVDI FFVISGFLIT

51 GIILSEIQNG SFSFRDFYTR RIKRIYPAFI AAVSLASVIA SQIFLYEDFN

101 QMRKTVELSA VFLSNIYLGF QQGYFDLSAD ENPVLHIWSL AVEEQYYLLY

151 PLLLIFCCKK TKSLRVLRNI SIILFLILTA SSFLPSGFYT DILNQPNTYY

201 LSTLRFPELL AGSLLAVYGQ TQNGRRQTAN GKRQLLSSLC FGALLACLFV

251 IDKHNPFIPG MTLLLPCLLT ALLIRSMQYG TLPTRILSAS PIVFVGKISY

301 SLYLYHWIFI AFAHYITGDK QLGLPAVSAV AALTAGFSLL SYYLIEQPLR

351 KRKMTFKKAF FCLYLAPSLI LVGYNLYARG ILKQEHLRPL PGAPLAAENH

401 FPETVLTLGD SHAGHLRGFL DYVGSREGWK AKILSLDSEC LVWVDEKLAD

451 NPLCRKYRDE VEKAEAVFIA QFYDLRMGGQ PVPRFEAQSF LIPGFPARFR

501 ETVKRIAAVK PVYVFANNTS ISRSPLREEK LKRFAANQYL RPIQAMGDIG

551 KSNQAVFDLI KDIPNVHWVD AQKYLPKNTV EIYGRYLYGD QDHLTYFGSY

601 YMGREFHKHE RLLKSSHGGA LQ*
```

Computer analysis of this amino acid sequence gave the following results:

Homology with Hypothetical Integral Membrane Protein HI0392 of *H. influenzae* (Accession Number U32723)

ORF128 and HI0392 show 52% aa identity in 180aa overlap:

```
Orf128:    1 VSLASVIASQIFLYEDFNQMRKTVELSAVFLSNIYLGFQQGYFDLSADENPVLHIWSLAV   60
             ++L S IAS IF+Y DFN++RKT+EL+  FLSN YLG QGYFDLSA+ENPVLHIWSLAV
HI0392:   46 MALVSFIASAIFIYNDFNKLRKTIELAIAFLSNFYLGLTQGYFDLSANENPVLHIWSLAV  105

Orf128:   61 EEQXXXXXXXXXIFCCKKTKSLRVLRNISIILFLILTASSFLPSGFYTDILNQPNTYYLS  120
             E Q         I   KK + ++VL  I++ILF IL A+SF+ + FY ++L+QPN YYLS
HI0392:  106 EGQYYLIFPLILILAYKKFREVKVLFIITLILFFILLATSFVSANFYKEVLHQPNIYYLS  165

Orf128:  121 TLRFPELLAGSLLAVYGQTQNGRRQTANGKRQLLSSLCFGALLACLFVIDKHNPFIPGMT  180
             LRFPELL GSLLA+Y    N + Q +    +L+ L    L +CLF+++ +  FIPG+T
HI0392:  166 NLRFPELLVGSLLAIYHNLSN-KVQLSKQVNNILAILSTLLLFSCLFLMNNNIAFIPGIT  224
```

Homology with a Predicted ORF from *N. meningitidis* (Strain A)

ORF128 shows 98.0% identity over a 244aa overlap with an ORF (ORF128a) from strain A of *N. meningitidis*.

```
                                                  10         20         30
orf128.pep                                 VSLASVIASQIFLYEDFNQMRKTVELSAVF
                                           ||||||||||||||||||||||||||||||
orf128a    ILSEIQNGSFSFRDFYTRRIKRIYPAFIAAVSLASVIASQIFLYEDFNQMRKTVELSAVF
                 60        70        80        90       100       100
                   40         50         60         70         80         90
orf128.pep LSNIYLGFQQGYFDLSADENPVLHIWSLAVEEQYYLLYPLLLIFCCKKTKSLRVLRNISI
           ||||||||||||||||||||||||||||||||||||||||||||||||||||||||||||
orf128a    LSNIYLGFQQGYFDLSADENPVLHIWSLAVEEQYYLLYPLLLIFCCKKTKSLRVLRNISI
                 120       130       140       150       160       170
                  100        110        120        130        140        150
orf128.pep ILFLILTASSFLPSGFYTDILNQPNTYYLSTLRFPELLAGSLLAVYGQTQNGRRQTANGK
           ||||||||:|||||||||||||||||||||||||||||||||||||||||||||||||||
orf128a    ILFLILTATSFLPSGFYTDILNQPNTYYLSTLRFPELLAGSLLAVYGQTQNGRRQTANGK
                 180       190       200       210       220       230
                  160        170        180        190        200        210
orf128.pep RQLLSSLCFGALLACLFVIDKHNPFIPGMTLLLPCLLTALLIRSMQYGTLPTRILSASPI
           ||||||||||||||||||||||||||||||||||||||||||||||||||||||||||||
orf128a    RQLLSSLCFGALLACLFVIDKHNPFIPGMTLLLPCLLTALLIRSMQYGTLPTRILSASPI
                 240       250       260       270       280       290
                  220        230        240
orf128.pep VFVGKISYSLYLYHWIFIAFAPLIRGGKQLGLPA
           |||||||||||||||||||||||  |||||||
orf128a    VFVGKISYSLYLYHWIFIAFAHYITGDKQLGLPAVSAVAALTAGFSLLSYYLIEQPLRKR
                 300       310       320       330       340       350
orf128a    KMTFKKAFFCLYLAPSLILVGYNLYARGILKQEHLRPLPGAPLAAENHFPETVLTLGDSH
                 360       370       380       390       400       410
```

The complete length ORF128a nucleotide sequence <SEQ ID 831> is:

```
  1  ATGCAAGCTG TCCGATACAG ACCGGAAATT GACGGATTGC GGGCCGTCGC
 51  CGTGCTATCC GTCATGATTT TCCACCTGAA TAACCGCTGG CTGCCCGGAG
101  GATTCCTGGG GGTGGACATT TTCTTTGTCA TCTCAGGATT CCTCATTACC
151  GGCATCATTC TTTCTGAAAT ACAGAACGGT TCTTTTTCTT TCCGGGATTT
201  TTATACCCGC AGGATTAAGC GGATTTATCC TGCTTTTATT GCGGCCGTGT
251  CGCTGGCTTC GGTGATTGCC TCTCAAATCT TCCTTTACGA AGATTTCAAC
301  CAAATGCGGA AAACCGTGGA GCTTTCTGCG GTTTTCTTGT CCAATATTTA
351  TCTGGGGTTT CAGCAGGGGT ATTTCGATTT GAGTGCCGAC GAGAACCCCG
401  TACTGCATAT CTGGTCTTTG GCAGTAGAGG AACAGTATTA CCTCCTGTAT
451  CCTCTTTTGC TGATATTTTG CTGCAAAAAA ACAAAATCGC TACGGGTGCT
501  GCGTAACATC AGCATCATCC TATTTCTGAT TTTGACTGCC ACATCGTTTT
551  TGCCAAGCGG GTTTTATACC GATATTCTCA ACCAACCCAA TACTTATTAC
```

```
 601 CTTTCGACAC TGAGGTTTCC CGAGCTGTTG GCAGGTTCGC TGCTGGCGGT

651 TTACGGGCAA ACGCAAAACG GCAGACGGCA AACAGCAAAT GGAAAACGGC

701 AGTTGCTTTC ATCACTCTGC TTCGGCGCAT TGCTTGCCTG CCTGTTCGTG

751 ATTGACAAAC ACAATCCGTT TATCCCGGGA ATGACCCTGC TCCTTCCCTG

801 CCTGCTGACG GCACTGCTTA TCCGGAGTAT GCAATACGGG ACACTTCCGA

851 CCCGCATCCT GTCGGCAAGC CCCATCGTAT TTGTCGGCAA AATCTCTTAT

901 TCCCTATACC TGTACCATTG GATTTTTATT GCTTTCGCCC ATTACATTAC

951 AGGCGACAAA CAGCTCGGAC TGCCTGCCGT ATCGGCGGTT GCCGCGTTGA

1001 CGGCCGGATT TTCCCTGTTG AGTATTATT  TGATTGAACA GCCGCTTAGA

1051 AAACGGAAGA TGACCTTCAA AAAGGCATTT TTCTGCCTCT ATCTCGCCCC

1101 GTCCCTGATA CTTGTCGGTT ACAACCTGTA CGCAAGGGGG ATATTGAAAC

1151 AGGAACACCT CCGCCCGTTG CCCGGCGCGC CCCTTGCTGC GGAAAATCAT

1201 TTTCCGGAAA CCGTCCTGAC CCTCGGCGAC TCGCACGCCG GACACCTGCG

1251 GGGGTTTCTG GATTATGTCG GCAGCCGGGA AGGGTGGAAA GCCAAAATCC

1301 TGTCCCTCGA TTCGGAGTGT TTGGTTTGGG TAGATGAGAA GCTGGCAGAC

1351 AACCCGTTAT GTCGAAAATA CCGGGATGAA GTTGAAAAAG CCGAAGCCGT

1401 TTTCATTGCC CAATTCTATG ATTTGAGGAT GGGCGGCCAG CCCGTGCCGA

1451 GATTTGAAGC GCAATCCTTC CTAATACCCG GGTTCCCAGC CCGATTCAGG

1501 GAAACCGTCA AAAGGATAGC CGCCGTCAAA CCCGTCTATG TTTTTGCAAA

1551 CAACACATCA ATCAGCCGTT CGCCCCTGAG GGAGGAAAAA TTGAAAAGAT

1601 TTGCCGCAAA CCAATATCTC CGCCCCATTC AGGCTATGGG CGACATCGGC

1651 AAGAGCAATC AGGCGGTCTT TGATTTGATT AAAGATATTC CCAATGTGCA

1701 TTGGGTGGAC GCACAAAAAT ACCTGCCCAA AAACACGGTC GAAATATACG

1751 GCCGCTATCT TTACGGCGAC CAAGACCACC TGACCTATTT CGGTTCTTAT

1801 TATATGGGGC GGGAATTTCA CAAACACGAA CGCCTGCTTA AATCTTCTCG

1851 CGACGGCGCA TTGCAGTAG
```

This encodes a protein having amino acid sequence <SEQ ID 832>:

```
  1 MQAVRYRPEI DGLRAVAVLS VMIFHLNNRW LPGGFLGVDI FFVISGFLIT

51 GIILSEIQNG SFSFRDFYTR RIKRIYPAFI AAVSLASVIA SQIFLYEDFN

101 QMRKTVELSA VFLSNIYLGF QQGYFDLSAD ENPVLHIWSL AVEEQYYLLY

151 PLLLIFCCKK TKSLRVLRNI SIILFLILTA TSFLPSGFYT DILNQPNTYY

201 LSTLRFPELL AGSLLAVYGQ TQNGRRQTAN GKRQLLSSLC FGALLACLFV

251 IDKHNPFIPG MTLLLPCLLT ALLIRSMQYG TLPTRILSAS PIVFVGKISY

301 SLYLYHWIFI AFAHYITGDK QLGLPAVSAV AALTAGFSLL SYYLIEQPLR

351 KRKMTFKKAF FCLYLAPSLI LVGYNLYARG ILKQEHLRPL PGAPLAAENH

401 FPETVLTLGD SHAGHLRGFL DYVGSREGWK AKILSLDSEC LVWVDEKLAD

451 NPLCRKYRDE VEKAEAVFIA QFYDLRMGGQ PVPRFEAQSF LIPGFPARFR

501 ETVKRIAAVK PVYVFANNTS ISRSPLREEK LKRFAANQYL RPIQAMGDIG
```

```
551 KSNQAVFDLI KDIPNVHWVD AQKYLPKNTV EIYGRYLYGD QDHLTYFGSY

601 YMGREFHKHE RLLKSSRDGA LQ*
```

ORF128a and ORF128-1 show 99.5% identity in 622 aa overlap:

```
orf128a.pep  MQAVRYRPEIDGLRAVAVLSVMIFHLNNRWLPGGFLGVDIFFVISGFLITGIILSEIQNG
             ||||||||||||||||||||||||||||||||||||||||||||||||||||||||||||
orf128-1     MQAVRYRPEIDGLRAVAVLSVMIFHLNNRWLPGGFLGVDIFFVISGFLITGIILSEIQNG orf128a.pep  SFSFRDFYTRRIKRIYPAFIAAVSLASVIASQIFLYEDFNQMRKTVELSAVFLSNIYLGF
             ||||||||||||||||||||||||||||||||||||||||||||||||||||||||||||
orf128-1     SFSFRDFYTRRIKRIYPAFIAAVSLASVIASQIFLYEDFNQMRKTVELSAVFLSNIYLGF orf128a.pep  QQGYFDLSADENPVLHIWSLAVEEQYYLLYPLLLIFCCKKTKSLRVLRNISIILFLILTA
             ||||||||||||||||||||||||||||||||||||||||||||||||||||||||||||
orf128-1     QQGYFDLSADENPVLHIWSLAVEEQYYLLYPLLLIFCCKKTKSLRVLRNISIILFLILTA orf128a.pep  TSFLPSGFYTDILNQPNTYYLSTLRFPELLAGSLLAVYGQTQNGRRQTANGKRQLLSSLC
             :|||||||||||||||||||||||||||||||||||||||||||||||||||||||||||
orf128-1     SSFLPSGFYTDILNQPNTYYLSTLRFPELLAGSLLAVYGQTQNGRRQTANGKRQLLSSLC orf128a.pep  FGALLACLFVIDKHNPFIPGMTLLLPCLLTALLIRSMQYGTLPTRILSASPIVFVGKISY
             ||||||||||||||||||||||||||||||||||||||||||||||||||||||||||||
orf128-1     FGALLACLFVIDKHNPFIPGMTLLLPCLLTALLIRSMQYGTLPTRILSASPIVFVGKISY orf128a.pep  SLYLYHWIFIAFAHYITGDKQLGLPAVSAVAALTAGFSLLSYYLIEQPLRKRKMTFKKAF
             ||||||||||||||||||||||||||||||||||||||||||||||||||||||||||||
orf128-1     SLYLYHWIFIAFAHYITGDKQLGLPAVSAVAALTAGFSLLSYYLIEQPLRKRKMTFKKAF orf128a.pep  FCLYLAPSLILVGYNLYARGILKQEHLRPLPGAPLAAENHFPETVLTLGDSHAGHLRGFL
             ||||||||||||||||||||||||||||||||||||||||||||||||||||||||||||
orf128-1     FCLYLAPSLILVGYNLYARGILKQEHLRPLPGAPLAAENHFPETVLTLGDSHAGHLRGFL orf128a.pep  DYVGSREGWKAKILSLDSECLVWVDEKLADNPLCRKYRDEVEKAEAVFIAQFYDLRMGGQ
             ||||||||||||||||||||||||||||||||||||||||||||||||||||||||||||
orf128-1     DYVGSREGWKAKILSLDSECLVWVDEKLADNPLCRKYRDEVEKAEAVFIAQFYDLRMGGQ orf128a.pep  PVPRFEAQSFLIPGFPARFRETVKRIAAVKPVYVFANNTSISRSPLREEKLKRFAANQYL
             ||||||||||||||||||||||||||||||||||||||||||||||||||||||||||||
orf128-1     PVPRFEAQSFLIPGFPARFRETVKRIAAVKPVYVFANNTSISRSPLREEKLKRFAANQYL orf128a.pep  RPIQAMGDIGKSNQAVFDLIKDIPNVHWVDAQKYLPKNTVEIYGRYLYGDQDHLTYFGSY
             ||||||||||||||||||||||||||||||||||||||||||||||||||||||||||||
orf128-1     RPIQAMGDIGKSNQAVFDLIKDIPNVHWVDAQKYLPKNTVEIYGRYLYGDQDHLTYFGSY orf128a.pep  YMGREFHKHERLLKSSRDGALQX
             |||||||||||||:|||||
orf128-1     YMGREFHKHERLLKSSRDGALQX
```

45

Homology with a Predicted ORF from *N. gonorrhoeae*

ORF128 shows 93.4% identity over 244 aa overlap with a predicted ORF (ORF128ng) from *N. gonorrhoeae*:

```
orf128.pep                         VSLASVIASQIFLYEDFNQMRKTVELSAVF   30
                                   |||||||||||||||||||||||||:|||:||
orf128ng   ILSEIQNGSFSFRDFYTRRIKRIYPAFIAAVSLASVIASQIFLYEDFNQMRKTIELSTVF  112 orf128.pep  LSNIYLGFQQGYFDLSADENPVLHIWSLAVEEQYYLLYPLLLIFCCKKTKSLRVLRNISI   90
            ||||||||:||||||||||||||||||||||||||||||||||||:|||||||||||||
orf128ng    LSNIYLGFRLGYFDLSADENPVLHIWSLAVEEQYYLLYPLLLIFCYKKTKSLRVLRNISI  172 orf128.pep  ILFLILTASSFLPSGFYTDILNQPNTYYLSTLRFPELLAGSLLAVYGQTQNGRRQTANGK  150
            ||||||||||||||:|||||||||||||||||||||||:||||||||||||||||||:|||
orf128ng    ILFLILTASSFLPAGFYTDILNQPNTYYLSTLRFPELLVGSLLAVYGQTQNGRRQTENGK  232 orf128.pep  RQLLSSLCFGALLACLFVIDKHNPFIPGMTLLLPCLLTALLIRSMQYGTLPTRILSASPI  210
            |||||| |||||||:|||||||:|||||:|||||||:||||||||||||||||||||||
orf128ng    RQLLSLLCFGALLVCLFVIDKHDPFIPGITLLLPCLLTALLIRSMQYGTLPTRILSASPI  292 orf128.pep  VFVGKISYSLYLYHWIFIAFAPLIRGGKQLGLPA                            244
            ||||||||||||||||||||||  |  ||||||
orf128ng    VFVGKISYSLYLYHWIFIAFAHYITGDKQLGLPAVSAVAALTAGFSLLSYYLIEQPLRKR  352
```

The complete length ORF128ng nucleotide sequence
<SEQ ID 833> is:

```
   1 ATGCAAGCTG TCCGATACAG GCCTGAAATT GACGGATTGC GGGCCGTCGC
  51 CGTGCTATCC GTCATTATTT TCCACCTGAA TAACCGCTGG CTGCCCGGAG
 101 GATTCCTGGG GGTGGACATT TTCTTTGTCA TCTCGGGATT CCTCATTACC
 151 AACATCATTC TTTCTGAAAT ACAGAACGGT TCTTTTTCTT TCCGGGATTT
 201 TTATACCCGC AGGATTAAGC GGATTTATCC TGCTTTTATT GCGGCCGTGT
 251 CCCTGGCTTC GGTGATTGCT TCTCAAATCT TCCTTTACGA AGATTTCAAC
 301 CAAATGAGGA AAACCATAGA GCTTTCTACG GTTTTTTTGT CCAATATTTA
 351 TTTGGGGTTC CGATTGGGGT ATTTCGATTT GAGTGCCGAC GAGAACCCCG
 401 TACTGCATAT CTGGTCTTTG GCGGTAGAGG AACAGTATTA CCTCCTGTAT
 451 CCTCTTTTGC TGATATTCTG TTACAAAAAA ACCAAATCAC TACGGGTGCT
 501 GCGTAATATC AGCATCATCC TGTTTCTGAT TTGACCGCA TCATCGTTTT
 551 TGCCGGCCGG GTTTTATACC GACATCCTCA ACCAACCcaa TACTTATTAC
 601 CTTTCGACAC TGAGGTTTCC CGAGCTGTTG GTGGGTTCGC TGTTGGCGGT
 651 TTACGGGCAA ACGCAAAACG GCAGACGGCA AACAGAAAAT GGAAAACGGC
 701 AGTTGCTTTC ATTACTCTGT TTCGGCGCat tgCTTGTCTG CCTGTTCGTG
 751 ATCGACAAAC ACGATCCGTT TATCCCGGGA ATAACCCTGC TCCTTCCCTG
 801 CCTGCTGACG GCGCTGCTTA TCCGGAGTAT GCAATACGGG ACACTTCCGA
 851 CCCGCATCCT GTCGGCAAGC CCCATCGTAT TTGTCGGCAA AATCTCTTAT
 901 TCCCTATACC TGTACCATTG GATTTTTATT GCCTTCGCCC ATTACATTAC
 951 AGGCGACAAA CAGCTCGGAC TGCCTGCCGT ATCGGCGGTT GCCGCGTTGA
1001 CGGCCGGATT TTCCCTGTTG AGCTATTATT TGATTGAACA GCCGCTTAGA
1051 AAACGGAAGA TGACCTTCAA AAAGGCATTT TTCTGCCTTT ATCTCGCCCC
1101 GTCCCTGATG CTTGTCGGTT ACAACCTGTA TTCAAGAGGG ATATTGAAAC
1151 AGGAACACCT CCGCCCGCTG CCCGGCACGC CCGTTGCTGC GGAAAATAAT
1201 TTTCCGGAAA CCGTCTTGAC CCTCGGCGAC TCGCACGCCG GACACCTGCG
1251 GGGGTTTCTG GATTATGTCG GCGGCAGGGA AGGGTGGAAA GCTAAAATCC
1301 TGTCCCTCGA TTCGGAGTGT TTGGTTTGGG TGGATGAGAA GCTGGCAGAC
1351 AACCCGTTGT GCCGAAAATA CCGGGATGAA GTTGAAAAAG CCGAAGCTGT
1401 TTTCATTGCC CAATTCTATG ATTTGAGGAT GGGCGGCCAG CCCGTGCCGA
1451 GATTTGAAGC GCAATCCTTC CTGATACCCG GGTTCAAAGC CCGATTCAGG
1501 GAAACCGTCA AGAGGATAGC CGCCGTCAAA CCTGTATATG TTTTTGCAAA
1551 CAATACATCA ATCAGCCGTT CTCCCTTGAG GGAGGAAAAA TTGAAAAGAT
1601 TTGCTATAAA CCAATACCTC CGGCCTATTC GGGCTATGGG CGACATCGGC
1651 AAGAGCAATC AGGCGGTCTT TGATTTGGTT AAAGATATTC CAATGTGCA
1701 TTGGGTGGAC GCACAAAAAT ACCTGCCCAA AAACACGGTC GAAATACACG
1751 GACGCTATCT TTACGGCGAC CAAGACCACC TGACCTATTT CGGTTCTTAT
1801 TATATGGGGC GGGAATTTCA CAAACACGAA CGCCTGCTCA AGCATTCCCG
1851 AGGCGGCGCA TTGCAGTAG
```

This encodes a protein having amino acid sequence <SEQ ID 834>:

```
  1 MQAVRYRPEI DGLRAVAVLS VIIFHLNNRW LPGGFLGVDI FFVISGFLIT

51 NIILSEIQNG SFSFRDFYTR RIKRIYPAFI AAVSLASVIA SQIFLYEDFN

101 QMRKTIELST VFLSNIYLGF RLGYFDLSAD ENPVLHIWSL AVEEQYYLLY

151 PLLLIFCYKK TKSLRVLRNI SIILFLILTA SSFLPAGFYT DILNQPNTYY

201 LSTLRFPELL VGSLLAVYGQ TQNGRRQTEN GKRQLLSLLC FGALLVCLFV

251 IDKHDPFIPG ITLLLPCLLT ALLIRSMQYG TLPTRILSAS PIVFVGKISY

301 SLYLYHWIFI AFAHYITGDK QLGLPAVSAV AALTAGFSLL SYYLIEQPLR

351 KRKMTFKKAF FCLYLAPSLM LVGYNLYSRG ILKQEHLRPL PGTPVAAENN

401 FPETVLTLGD SHAGHLRGFL DYVGGREGWK AKILSLDSEC LVWVDEKLAD

451 NPLCRKYRDE VEKAEAVFIA QFYDLRMGGQ PVPRFEAQSF LIPGFKARFR

501 ETVKRIAAVK PVYVFANNTS ISRSPLREEK LKRFAINQYL RPIRAMGDIG

551 KSNQAVFDLV KDIPNVHWVD AQKYLPKNTV EIHGRYLYGD QDHLTYFGSY

601 YMGREFHKHE RLLKHSRGGA LQ*
```

ORF128ng and ORF128-1 show 95.7% identity in 622 aa overlap:

```
orf128-1.pep MQAVRYRPEIDGLRAVAVLSVMIFHLNNRWLPGGFLGVDIFFVISGFLITGIILSEIQNG
             |||||||||||||||||||||:|||||||||||||||||||||||||||| |||||||||
orf128ng     MQAVRYRPEIDGLRAVAVLSVIIFHLNNRWLQGGFLGVDIFFVISGFLITNIILSEIQNG orf128-1.pep SFSFRDFYTRRIKRIYPAFIAAVSLASVIASQIFLYEDFNQMRKTVELSAVFLSNIYLGF
             ||||||||||||||||||||||||||||||||||||||||||||||:|||:||||||||
orf128ng     SFSFRDFYTRRIKRIYPAFIAAVSLASVIASQIFLYEDFNQMRKTIELSTVFLSNIYLGF orf128-1.pep QQGYFDLSADENPVLHIWSLAVEEQYYLLYPLLLIFCCKKTKSLRVLRNISIILFLILTA
             : ||||||||||||||||||||||||||||||||| ||||||||||||||||||||||
orf128ng     RLGYFDLSADENPVLHIWSLAVEEQYYLLYPLLLIFCYKKTKSLRVLRNISIILFLILTA orf128-1.pep SSFLPSGFYTDILNQPNTYYLSTLRFPELLAGSLLAVYGQTQNGRRQTANGKRQLLSSLC
             |||||:||||||||||||||||||||||||:|||||||||||||||||:|||||||| ||
orf128ng     SSFLPAGFYTDILNQPNTYYLSTLRFPELLVGSLLAVYGQTQNGRRQTENGKRQLLSLLC orf128-1.pep FGALLACLFVIDKHNPFIPGMTLLLPCLLTALLIRSMQYGTLPTRILSASPIVFVGKISY
             |||||:||||||||:||||| :|||||||||||||||||||||||||||||||||||||
orf128ng     FGALLVCLFVIDKHDPFIPGITLLLPCLLTALLIRSMQYGTLPTRILSASPIVFVGKISY orf128-1.pep SLYLYHWIFIAFAHYITGDKQLGLPAVSAVAALTAGFSLLSYYLIEQPLRKRKMTFKKAF
             ||||||||||||||||||||||||||||||||||||||||||||||||||||||||||||
orf128ng     SLYLYHWIFIAFAHYITGDKQLGLPAVSAVAALTAGFSLLSYYLIEQPLRKRKMTFKKAF orf128-1.pep FCLYLAPSLILVGYNLYARGILKQEHLRPLPGAPLAAENHFPETVLTLGDSHAGHLRGFL
             |||||||||:|||||||:||||||||||||||: :||| |||||||||||||||||||
orf128ng     FCLYLAPSLMLVGYNLYSRGILKQEHLRPLPGTPVAAENNFPETVLTLGDSHAGHLRGFL orf128-1.pep DYVGSREGWKAKILSLDSECLVWVDEKLADNPLCRKYRDEVEKAEAVFIAQFYDLRMGGQ
             ||||:|||||||||||||||||||||||||||||||||||||||||||||||||||||||
orf128ng     DYVGGREGWKAKILSLDSECLVWVDEKLADNPLCRKYRDEVEKAEAVFIAQFYDLRMGGQ orf128-1.pep PVPRFEAQSFLIPGFPARFRETVKRIAAVKPVYVFANNTSISRSPLREEKLKRFAANQYL
             ||||||||||||||| ||||||||||||||||||||||||||||||||||||||| ||||
orf128ng     PVPRFEAQSFLIPGFKARFRETVKRIAAVKPVYVFANNTSISRSPLREEKLKRFAINQYL orf128-1.pep RPIQAMGDIGKSNQAVFDLIKDIPNVHWVDAQKYLPKNTVEIYGRYLYGDQDHLTYFGSY
             |||:|||||||||||||||:||||||||||||||||||||||:||||||||||||||||
orf128ng     RPIRAMGDIGKSNQAVFDLVKDIPNVHWVDAQKYLPKNTVEIHGRYLYGDQDHLTYFGSY orf128-1.pep YMGREFHKHERLLKSSHGGALQX
             ||||||||||||||| :||||||
orf128ng     YMGREFHKHERLLKHSRGGALQX
                      610        620
```

In addition, ORF218ng shows homology to a hypothetical *H. influenzae* protein:

```
sp|P43993|Y392_HAEIN HYPOTHETICAL PROTEIN HI0392 >gi|1074385|pir||B64007
hypothetical protein HI0392 - Haemophilus influenzae (strain Rd KW20)
>gi|1573364 (U32723) H. influenzae predicted coding region HI0392 [Haemophi-
lus
influenzae] Length = 245
```

```
                              -continued
Score = 239 bits (604), Expect = 3e-62
Identities = 124/225 (55%), Positives = 152/225 (67%), Gaps = 1/225 (0%)

Query:   38 VDIFFVISGFLITNIILSEIQNGSFSRDFYTRRIKRIYPXXXXXXXXXXXXXXXXFLYE    97
            +DIFFVISGFLIT II++EIQ  SFS + FYTRRIKRIYP                F+Y
Sbjct:    1 MDIFFVISGFLITGIIITEIQQNSFSLKQFYTRRIKRIYPAFITVMALVSFIASAIFIYN   60

Query:   98 DFNQMRKTIELSTVFLSNIYLGFRLGYFDLSADENPVLHIWSLAVEEQXXXXXXXXXXIFC  157
            DFN++RKTIEL+ FLSN YLG  GYFDLSA+ENPVLHIWSLAVE Q          I
Sbjct:   61 DFNKLRKTIELAIAFLSNFYLGLTQGYFDLSANENPVLHIWSLAVEGQYYLIFPLILILA  120

Query:  158 YKKTKSLRVLRNISIILFLILTASSFLPAGFYTDILNQPNTYYLSTLRFPELLVGSLLAV  217
            YKK + ++VL  I++ILF IL A+SF+ A FY ++L+QPN YYLS LRFPELLVGSLLA+
Sbjct:  121 YKKFREVKVLFIITLILFFILLATSFVSANFYKEVLHQPNIYYLSNLRFPELLVGSLLAI  180

Query:  218 YGQTQNGRRQTENGKRQLLSLLCFGALLVCLFVIDKHDPFIPGIT                 262
            Y    N + Q      +L++L   L  CLF+++ +  FIPGIT
Sbjct:  181 YHNLSN-KVQLSKQVNNILAILSTLLLFSCLFLMNNNIAFIPGIT                 224
```

This analysis, including the identification of several putative transmembrane domains, suggests that these proteins from *N. meningitidis* and *N. gonorrhoeae*, and their epitopes, could be useful antigens for vaccines or diagnostics, or for raising antibodies.

Example 99

The following partial DNA sequence was identified in *N. meningitidis* <SEQ ID 835>:

```
  1..ATTATTTACG AATACCGCTG GATGTTTCTT TACGGCGCAC TGACGACCTT

51   GGGGCTGACG GTCGTGGCAA C.GCGGGCGG TTCGGTATTG GGTCTGTTGT

101   TGGCGTTGGC GCGCCTGATT CACTTGGAAA AAGCCGGTGC GCCGATGCGC

151   GTGCTGGCGT GGGCGTTGCG TAAAGTTTCG CTGCTGTATG TTACGCTGTT

201   CCGGGGTACG CCGCTGTTTG TGCAGATTGT GATTTGGGCG TATGTGTGGT

251   TTCCGTTTTT CGTC..
```

This corresponds to the amino acid sequence <SEQ ID 836; ORF129>:

```
  1..IIYEYRWMFL YGALTTLGLT VVAXAGGSVL GLLLALARLI HLEKAGAPMR

51   VLAWALRKVS LLYVTLFRGT PLFVQIVIWA YVWFPFFV..
```

Further work revealed the complete nucleotide sequence <SEQ ID 837>:

```
  1 ATGGATTTTC GTTTTGACAT TATTTACGAA TACCGCTGGA TGTTTCTTTA

51 CGGCGCACTG ACGACCTTGG GGCTGACGGT CGTGGCAACG GCGGGCGGTT

101 CGGTATTGGG TCTGTTGTTG GCGTTGGCGC GCCTGATTCA CTTGGAAAAA

151 GCCGGTGCGC CGATGCGCGT GCTGGCGTGG GCGTTGCGTA AAGTTTCGCT

201 GCTGTATGTT ACGCTGTTCC GGGGTACGCC GCTGTTTGTG CAGATTGTGA

251 TTTGGGCGTA TGTGTGGTTT CCGTTTTTCG TCCATCCTTC AGACGGCATT

301 TTGGTCAGCG GCGAGGCGGC AATCGCGCTG CGTCGCGGAT ACGGGCCGCT

351 GATTGCCGGT TCTTTGGCAC TGATCGCCAA CTCGGGGGCG TATATCTGTG

401 AGATTTTCCG CGCGGGCATC CAGTCTATAG ACAAAGGACA GATGGAGGCG
```

-continued
```
451 GCGCGTTCTT TGGGGCTGAC CTATCCGCAG GCGATGCGCT ATGTGATTCT

501 GCCGCAGGCA TTGCGCCGCA TGCTGCCGCC TTTGGCGAGC GAGTTCATCA

551 CGCTCTTGAA AGACAGCTCG CTGCTGTCGG TCATTGCTGT GGCGGAGTTG

601 GCGTATGTTC AGAATACGAT TACGGGCCGG TATTCGGTTT ATGAAGAACC

651 GCTTTACACC GTCGCCCTGA TTTATCTGTT GATGACGACT TTCTTAGGCT

701 GGATATTCCT GCGTTTGGAA AAACGTTACA ATCCGCAACA CCGCTGA
```

This corresponds to the amino acid sequence <SEQ ID 838; ORF129-1>:

```
  1 MDFRFDIIYE YRWMFLYGAL TTLGLTVVAT AGGSVLGLLL ALARLIHLEK

51 AGAPMRVLAW ALRKVSLLYV TLFRGTPLFV QIVIWAYVWF PFFVHPSDGI

101 LVSGEAAIAL RRGYGPLIAG SLALIANSGA YICEIFRAGI QSIDKGQMEA

151 ARSLGLTYPQ AMRYVILPQA LRRMLPPLAS EFITLLKDSS LLSVIAVAEL

201 AYVQNTITGR YSVYEEPLYT VALIYLLMTT FLGWIFLRLE KRYNPQHR*
```

Computer analysis of this amino acid sequence gave the following results:

Homology with a Predicted ORF from *N. meningitidis* (Strain A)

ORF129 shows 98.9% identity over a 88aa overlap with an ORF (ORF129a) from strain A of *N. meningitidis*:

```
                    10        20        30        40        50
  orf129.pep        IIYEYRWMFLYGALTTLGLTVVAXAGGSVLGLLLALARLIHLEKAGAPMRVLAW
                    ||||||||||||||||||||||:|||||||||||||||||||||||||||||
  orf129a  MDFRFDIIYEYRWMFLYGALTTLGLTVVATAGGSVLGLLLALARLIHLEKAGAPMRVLAW
                 10        20        30        40        50        60

60        70        80
  orf129.pep        ALRKVSLLYVTLFRGTPLFVQIVIWAYVWFPFFV
                    |||||||||||||||||||||||||||||||||
  orf129a           ALRKVSLLYVTLFRGTPLFVQIVIWAYVWFPFFVHPSDGILVSGEAAIALRRGYGPLIAG
                 70        80        90       100       110       120 orf129a           SLALIANSGAYICEIFRAGIQSIDKGQMEAARSLGLTYPQAMRYVILPQALRRMLPPLAS
                       130       140       150       160       170       180
```

The complete length ORF129a nucleotide sequence <SEQ ID 839> is:

```
  1 ATGGATTTTC GTTTTGACAT TATTTACGAA TACCGCTGGA TGTTTCTTTA

51 CGGCGCACTG ACGACCTTGG GGCTGACGGT CGTGGCGACG GCGGGCGGTT

101 CGGTATTGGG TCTGTTGTTG GCGTTGGCGC GCCTGATTCA CTTGGAAAAA

151 GCCGGTGCGC CGATGCGCGT GCTGGCGTGG GCGTTGCGTA AGGTTTCGCT

201 GCTGTATGTT ACGCTGTTCC GGGGTACGCC GCTGTTTGTG CAGATTGTGA

251 TTTGGGCGTA TGTGTGGTTT CCGTTTTTCG TCCATCCTTC AGACGGCATT

301 TTGGTTAGCG GCGAGGCGGC AATCGCGCTG CGTCGCGGAT ACGGGCCGCT

351 GATTGCCGGT TCTTTGGCAC TGATCGCCAA CTCGGGGGCG TATATCTGTG

401 AGATTTTCCG CGCGGGCATC CAGTCTATAG ACAAAGGACA GATGGAGGCG

451 GCGCGTTCTT TGGGGCTGAC CTATCCGCAG GCGATGCGCT ATGTGATTCT

501 GCCGCAGGCA TTGCGCCGTA TGCTGCCGCC TTTGGCGAGC GAGTTCATCA
```

```
551 CGCTCTTGAA AGACAGCTCG CTGCTGTCGG TCATTGCTGT GGCGGAGTTG

601 GCGTATGTTC AGAATACGAT TACGGGCCGG TATTCGGTTT ATGAAGAACC

651 GCTTTACACC GTCGCCCTGA TTTATCTGTT GATGACGACT TTCTTAGGCT

701 GGATATTCCT GCGTTTGGAA AAACGTTACA ATCCGCAACA CCGCTGA
```

This encodes a protein having amino acid sequence <SEQ ID 840>:

```
  1 MDFRFDIIYE YRWMFLYGAL TTLGLTVVAT AGGSVLGLLL ALARLIHLEK

51 AGAPMRVLAW ALRKVSLLYV TLFRGTPLFV QIVIWAYVWF PFFVHPSDGI

101 LVSGEAAIAL RRGYGPLIAG SLALIANSGA YICEIFRAGI QSIDKGQMEA

151 ARSLGLTYPQ AMRYVILPQA LRRMLPPLAS EFITLLKDSS LLSVIAVAEL

201 AYVQNTITGR YSVYEEPLYT VALIYLLMTT FLGWIFLRLE KRYNPQHR*
```

ORF129a and ORF129-1 show 100.0% identity in 248 aa overlap:

```
orf122a.pep  MDFRFDIIYEYRWMFLYGALTTLGLTVVATAGGSVLGLLLALARLIHLEKAGAPMRVLAW
             ||||||||||||||||||||||||||||||||||||||||||||||||||||||||||||
orf129-1     MDFRFDIIYEYRWMFLYGALTTLGLTVVATAGGSVLGLLLALARLIHLEKAGAPMRVLAW orf122a.pep  ALRKVSLLYVTLFRGTPLFVQIVIWAYVWFPFFVHPSDGILVSGEAAIALRRGYGPLIAG
             ||||||||||||||||||||||||||||||||||||||||||||||||||||||||||||
orf129-1     ALRKVSLLYVTLFRGTPLFVQIVIWAYVWFPFFVHPSDGILVSGEAAIALRRGYGPLIAG orf122a.pep  SLALIANSGAYICEIFRAGIQSIDKGQMEAARSLGLTYPQAMRYVILPQALRRMLPPLAS
             ||||||||||||||||||||||||||||||||||||||||||||||||||||||||||||
orf129-1     SLALIANSGAYICEIFRAGIQSIDKGQMEAARSLGLTYPQAMRYVILPQALRRMLPPLAS orf122a.pep  EFITLLKDSSLLSVIAVAELAYVQNTITGRYSVYEEPLYTVALIYLLMTTFLGWIFLRLE
             ||||||||||||||||||||||||||||||||||||||||||||||||||||||||||||
orf129-1     EFITLLKDSSLLSVIAVAELAYVQNTITGRYSVYEEPLYTVALIYLLMTTFLGWIFLRLE orf129a.pep  KRYNPQHRX
             |||||||||
orf129-1     KRYNPQHRX
```

Homology with a Predicted ORF from *N. gonorrhoeae*

ORF129 shows 98.9% identity over a 88 aa overlap with a predicted ORF (ORF129ng) from *N. gonorrhoeae*:

```
orf129.pep        IIYEYRWMFLYGALTTLGLTVVAXAGGSVLGLLLALARLIHLEKAGAPMRVLAW   54
                  |||||||||||||||||||||||:||||||||||||||||||||||||||||||
orf129ng   MDFRFDIIYEYRWMFLYGALTTLGLTVVATAGGSVLGLLLALARLIHLEKAGAPMRVLAW   60 orf129.pep  ALRKVSLLYVTLFRGTPLFVQIVIWAYVWFPFFV                            88
            |||||||||||||||||||||||||||||||||
orf129ng    ALRKVSLLYVTLFRGTPLFVQIVIWAYVWFPFFVILHTAFLGNAMRQSRRVPDKGRWIAG  120
```

An ORF129ng nucleotide sequence <SEQ ID 841> was predicted to encode a protein having amino acid sequence <SEQ ID 842>:

```
  1 MDFRFDIIYE YRWMFLYGAL TTLGLTVVAT AGGSVLGLLL ALARLIHLEK

51 AGAPMRVLAW ALRKVSLLYV TLFRGTPLFV QIVIWAYVWF PFFVILHTAF

101 LGNAMRQSRR VPDKGRWIAG SLELNCQPRG RKTRGEFPPG ESNLGTEPRN

151 PLSMGQRRFP GCENWYPPQN FIKK*
```

Further work revealed the following gonococcal sequence <SEQ ID 843>:

```
  1 ATGGATTTTc gtTTTGACAT TATTTAcgaA TACCGCTGGA TGTTTCTTTA

51 CGGCGCACTG Acgaccttgg ggctgacggt cgtggcgacg gCGGGCGGTT

101 CGGtattggG TCTGTTGTTG GCGTTGGCGC GCCTGATTCA CTTGGAAAAA

151 GCCGGTGCGC CGATGCGCGT GCTGGCGTGG GCGTTGCGTA AGGTTTCGCT

201 GCTGTACGTT ACCCTGTTCC GGGGTACGCC GCTGTTTGTG CAGATTGTGA

251 TTTGGGCGTA TGTGTGGTTT CCGTTTTTCG TCCATCCTTC AGACGGCATT

301 TTGGTCAGCG GCGAGGCGGC AATCGCGCTG CGTCGCGGAT ACGGGCCGCT

351 GATTGCCGGT TCTTTGGCAC TGATCGCCAA CTCGGGGGCG TATATCTGTG

401 AGATTTTCCG CGCGGGCATC CAGTCTATAG ACAAAGGACA GATGGAGGCG

451 GCGTGTTCTT TGGGACTGAC CTATCCGCAG GCGATGCGCT ATGTGATTCT

501 GCCGCAGGCA TTGCGCCGTA TGCTGCCGCC TTTGGCGAGC GAGTTCATCA

551 CGCTCTTGAA AGACAGCTCG CTGCTGTCGG TCATTGCTGT GGCGGAGTTG

601 GCGTATGTTC AGAATACGAT TACGGGCCGG TATTCGGTTT ATGAAGAACC

651 GCTTTACACC GCCGCCCTGA TTTATCTGTT GATGACGACT TTCTTAGGCT

701 GGATATTCCT GCGTTTGGAA AAACGTTACA ATCCGCAACA CCGCTGA
```

This corresponds to the amino acid sequence <SEQ ID 844; ORF129ng-1>:

```
  1 MDFRFDIIYE YRWMFLYGAL TTLGLTVVAT AGGSVLGLLL ALARLIHLEK

51 AGAPMRVLAW ALRKVSLLYV TLFRGTPLFV QIVIWAYVWF PFFVHPSDGI

101 LVSGEAAIAL RRGYGPLIAG SLALIANSGA YICEIFRAGI QSIDKGQMEA

151 ARSLGLTYPQ AMRYVILPQA LRRMLPPLAS EFITLLKDSS LLSVIAVAEL

201 AYVQNTITGR YSVYEEPLYT VALIYLLMTT FLGWIFLRLE KRYNPQHR*
                                                      40
```

ORF129ng-1 and ORF129-1 show 99.2% identity in 248 aa overlap:

```
orf129-1.pep  MDFRFDIIYEYRWMFLYGALTTLGLTVVATAGGSVLGLLLALARLIHLEKAGAPMRVLAW
              ||||||||||||||||||||||||||||||||||||||||||||||||||||||||||||
orf129ng-1    MDFRFDIIYEYRWMFLYGALTTLGLTVVATAGGSVLGLLLALARLIHLEKAGAPMRVLAW orf129-1.pep  ALRKVSLLYVTLFRGTPLFVQIVIWAYVWPPFFVHPSDGILVSGEAAIALRRGYGPLIAG
              ||||||||||||||||||||||||||||||||||||||||||||||||||||||||||||
orf129ng-1    ALRKVSLLYVTLFRGTPLFVQIVIWAYVWPPFFVHPSDGILVSGEAAIALRRGYGPLIAG orf129-1.pep  SLALIANSGAYICEIFRAGIQSIDKGQMEAARSLGLTYPQAMRYVILPQALRRMLPPLAS
              |||||||||||||||||||||||||||||||| |||||||||||||||||||||||||||
orf129ng-1    SLALIANSGAYICEIFRAGIQSIDKGQMEAACSLGLTYPQAMRYVILPQALRRMLPPLAS orf129-1.pep  EFITLLKDSSLLSVIAVAELAYVQNTITGRYSVYEEPLYTVALIYLLMTTFLGWIFLRLE
              |||||||||||||||||||||||||||||||||||||||| :||||||||||||||||||
orf129ng-1    EFITLLKDSSLLSVIAVAELAYVQNTITGRYSVYEEPLYTAALIYLLMTTFLGWIFLRLE orf129-1.pep  KRYNPQHRX
              |||||||||
orf129ng-1    KRYNPQHRX
```

In addition, ORF129ng-1 is homologous to an ABC transporter from *A. fulgidus*:

```
2650409(AE001090) glutamine ABC transporter, permease protein (glnP)
[Archaeoglobus fulgidus]Length = 224
Score = 132 bits (329), Expect = 2e-30
Identities = 86/178 (48%), Positives = 103/178 (57%), Gaps = 18/178 (10%)
```

```
Query:   65 VSLLYVTLFRGTPLFVQIVIWAYVWFPFFVHPSDGILVSGEAAIALRRGYGPLIAGSLAL 124
            +S  YV + RGTPL VQI+I      +F  P+ GI +  E A            G +AL
Sbjct:   58 ISTAYVEVIRGTPLLVQILI------VYFGLPAIGINLQPEPA-----------GIIAL  99

Query:  125 IANSGAYICEIFRAGIQSIDKGQMEAACSLGLTYPQAMRYVILPQALRRMLPPLASEFIT 184
               SGAYI EI RAGI+SI  GQMEAA SLG+TY QAMRYVI PQA R +LP L +EFI
Sbjct:  100 SICSGAYIAEIVRAGIESIPIGQMEAARSLGMTYLQAMRYVIFPQAFRNILPALGNEFIA 159

Query:  185 LLKDSSLLSVIAVAELAYVQNTITGRYSVYEEPLYTAALIYLLMTTFLGWIFLRLEKR   242
            LLKDSSLLSVI++ EL  V  I           P   AL YL+MT  L  +    +K+
Sbjct:  160 LLKDSSLLSVISIVELTRVGRQIVNTTFNAWTPFLGVALFYLMMTIPLSRLVAYSQKK   217
```

This analysis, including the identification of transmembrane domains in the two proteins, suggests that the proteins from *N. meningitidis* and *N. gonorrhoeae*, and their epitopes, could be useful antigens for vaccines or diagnostics, or for raising antibodies.

Example 100

The following partial DNA sequence was identified in *N. meningitidis* <SEQ ID 845>:

```
  1..CTGAAAGAAT GCCGTCTGAA AGACCCTGTT TTTATTCCAA ATATCGTTTA

51  TAAGAACATC GCCATTACTT TCCTGCTCTT GCACGCCGCC GCCGAACTTT

101  GGCTGCCCGC GCAAACCGCC GGTTTTACCG CGCTCGCCGT CGGCTTCATC

151  CTGCTCGCCA AGCTGCGTGA gCTTCACCAT CACGAACTCT TACGTAAACA 201  cTACGTCCGC ACTTATTACy TGCTCCAACT CTTTGCCGCC GCAGgcTAgT

251  TTGTGGACAG GCGCGGCGwA ATTACAAAAC CTGCCCGCyT CCGCGCCCCT

301  GCACCTGATT ACCCTCGGCG GCATGATGGG CGGCGTGATG ATGGTGTGGc

351  TGACCGCCGG ACTGTGGCAC AGCGGCTTTA CCAAACTCGA CTACCCCAAA

401  CTCTGCCGCA TTGCCGTCCC CATCCTTTTC GCCGCCGCCG TCTCGCGCGC

451  TTTCTTGrTG AACGTGAACC CGrTATTTTT CATTACCGTT CCTGCGATTC

501  TGACCGCCGC CGTATTCGTA CTGTATCTTT TCrCGTTTAT ACCGATATTT

551  CGGGCGAATG CGTTTACAGA CGATCCGGAr TAr
```

This corresponds to the amino acid sequence <SEQ ID 846; ORF130>:

```
  1..LKECRLKDPV FIPNIVYKNI AITFLLLHAA AELWLPAQTA GFTALAVGFI

51  LLAKLRELHH HELLRKHYVR TYYLLQLFAA AGSLWTGAAX LQNLPASAPL

101  HLITLGGMMG GVMMVWLTAG LWHSGFTKLD YPKLCRIAVP ILFAAAVSRA

151  FLXNVNPXFF ITVPAILTAA VFVLYLFXFI PIFRANAFTD DPE*
```

Further work revealed the complete nucleotide sequence <SEQ ID 847>:

```
  1  ATGCGGCCGT TTTTCGTCGG CGCGGCGGTG CTTGCCATAC TCGGTGCGCT

51  GGTGTTTTTC ATCAACCCCG GTGCCATCGT CCTGCACCGC CAAATTTTCT

101  TGGAACTTAT GCTGCCGGCG GCATACGGCG GTTTTTTGAC TGCGGCTTTG

151  TTGGACTGGA CGGGTTTTTC GGGTAACCTG AAACCTGTCG CGACTTTGAT
```

-continued

```
 201 GGCGGCATTA TTGCTCGCCG CATCCGCTAT ACTGCCCTTT TCGCCGCAAA

251 CTGCCTCGTT TTTCGTCGCC GCCTATTGGC TGGTGTTGCT GCTGTTCTGC

301 GCCCGGCTGA TTTGGCTAGA CCGAAACACC GACAACTTCG CCCTGCTAAT

351 GTTACTTGCC GCGTTCACTG TTTTTCAGAC GGCATATGCC GTCAGCGGCG

401 ATTTGAACCT GTTGCGCGCG CAAGTGCATC TAAATATGGC GGCGGTGATG

451 TTCGTATCCG TGCGCGTCAG TATTCTTTTG GGCGCGGAAG CCCTGAAAGA

501 ATGCCGTCTG AAAGACCCTG TTTTTATTCC AAATATCGTT TATAAAAACA

551 TCGCCATTAC TTTCCTGCTC TTGCACGCCG CCGCCGAACT TTGGCTGCCC

601 GCGCAAACCG CCGGTTTTAC CGCGCTCGCC GTCGGCTTCA TCCTGCTCGC

651 CAAGCTGCGT GAGCTTCACC ATCACGAACT CTTACGTAAA CACTACGTCC

701 GCACTTATTA CCTGCTCCAA CTCTTTGCCG CCGCAGGCTA TTTGTGGACA

751 GGCGCGGCGA AATTACAAAA CCTGCCCGCC TCCGCGCCCC TGCACCTGAT

801 TACCCTCGGC GGCATGATGG GCGGCGTGAT GATGGTGTGG CTGACCGCCG

851 GACTGTGGCA CAGCGGCTTT ACCAAACTCG ACTACCCCAA ACTCTGCCGC

901 ATTGCCGTCC CCATCCTTTT CGCCGCCGCC GTCTCGCGCG CTTTCTTGAT

951 GAACGTGAAC CCGATATTTT TCATTACCGT TCCTGCGATT CTGACCGCCG

1001 CCGTATTCGT ACTGTATCTT TTCACGTTTA TACCGATATT TCGGGCGAAT

1051 GCGTTTACAG ACGATCCGGA ATAA
```

This corresponds to the amino acid sequence <SEQ ID 848; ORF130-1>:

```
  1 MRPFFVGAAV LAILGALVFF INPGAIVLHR QIFLELMLPA AYGGFLTAAL

51 LDWTGFSGNL KPVATLMAAL LLAASAILPF SPQTASFFVA AYWLVLLLFC

101 ARLIWLDRNT DNFALLMLLA AFTVFQTAYA VSGDLNLLRA QVHLNMAAVM

151 FVSVRVSILL GAEALKECRL KDPVFIPNIV YKNIAITFLL LHAAAELWLP

201 AQTAGFTALA VGFILLAKLR ELHHHELLRK HYVRTYYLLQ LFAAAGYLWT

251 GAAKLQNLPA SAPLHLITLG GMMGGVMMVW LTAGLWHSGF TKLDYPKLCR

301 IAVPILFAAA VSRAFLMNVN PIFFITVPAI LTAAVFVLYL FTFIPIFRAN

351 AFTDDPE*
```

Computer analysis of this amino acid sequence gave the following results:

Homology with a Predicted ORF from *N. meningitidis* (Strain A)

ORF130 shows 94.3% identity over a 193aa overlap with an ORF (ORF130a) from strain A of *N. meningitidis*:

```
                                         10        20        30
    orf130.pep                    LKECRLKDPVFIPNIVYKNIAITFLLLHAA
                                  ||||||||||||:||||||||:||||||||
    orf130a    LNLLRAQVHLNMAAVMFVSVRVSILLGAEALKECRLKDPVFIPNVVYKNIAITFLLLHAA
                  140       150       160       170       180       190

40        50        60        70        80        90
    orf130.pep  AELWLPAQTAGFTALAVGFILLAKLRELHHHELLRKHYVRTYYLLQLFAAAGSLWTGAAX
                ||||||||||||:|||||||||||||||||||||||||||||||||||||||||||||||
    orf130a     AELWLPAQTAGFTSLAVGFILLAKLRELHHHELLRKHYVRTYYLLQLFAAAGYLWTGAAX
                     200       210       220       230       240       250
```

```
                   100        110        120        130        140        150
orf130.pep   LQNLPASAPLHLITLGGMMGGVMMVWLTAGLWHSGFTKLDYPKLCRIAVPILFAAAVSRA
             ||||||||||||||||||||||:|||||||||||||||||||||||||||||||||||||
orf130a      LQNLPASAPLHLITLGGMMGSVMMVWLTAGLWHSGFTKLDYPKLCRIAVPILFAAAVSRA
                   260        270        280        290        300        310
                   160        170        180        190
orf130.pep   FLXNVNPXFFITVPAILTAAVFVLYLFXFIPIFRANAFTDDPEX
             | ||| |||||||||||||||||||||::|:||||||||||||
orf130a      VLMNVNPIFFITVPAILTAAVFVLYLLTFVPIFRANAFTDDPEX
                   320        330        340        350
```

The complete length ORF130a nucleotide sequence <SEQ ID 849> is:

```
   1 ATGCGGCCGT TTTTCGTCGG CGCGGCGGTG CTTGCCATAC TCGGTGCGCT
  51 GGTGTTTTTC ATCAACCCCG GTGCCATCGT CCTGCACCGC CAAATTTTCT
 101 TGGAACTTAT GCTGCCGGCG GCATACGGCG GTTTTTTGAC TGCGGCTTTG
 151 TTGGACTGGA CGGGTTTTTC GGGTAACCTG AAACCTGTCG GACTTTGAT
 201 GGCGGCATTA TTGCTCGCCG CATCCGCTAT ACTGCCCTTT TCGCCGCAAA
 251 CTGCCTCGTT TTTCGTCGCC GCCTATTGGC TGGTGTTGCT GCTGTTCTGC
 301 GCCCGGCTGA TTTGGCTAGA CCGAAACACC GACAACTTCG CCCTGCTAAT
 351 GTTACTTGCC GCGTTCACTG TTTTTCAGAC GGCATATGCC GTCAGCGGCG
 401 ATTTGAACCT GTTGCGCGCG CAAGTGCATC TAAATATGGC GGCGGTGATG
 451 TTCGTATCCG TGCGCGTCAG TATTCTTTTG GGCGCGGAAG CCCTGAAAGA
 501 ATGCCGTCTG AAAGACCCAG TATTCATCCC CAATGTCGTC TATAAAAACA
 551 TCGCCATTAC CTTCCTGCTC CTGCACGCCG CCGCCGAACT TTGGCTGCCT
 601 GCGCAAACCG CCGGTTTTAC CTCGCTCGCC GTCGGCTTTA TCCTGCTTGC
 651 CAAGCTGCGT GAGCTTCACC ATCACGAACT CCTGCGCAAA CACTACGTCC
 701 GCACTTATTA CCTGCTCCAA CTCTTTGCCG CCGCAGGCTA TTTGTGGACA
 751 GGCGCGGCGA AATTACAAAA CCTGCCCGCC TCCGCGCCCC TGCACCTGAT
 801 TACCCTCGGT GGCATGATGG GCAGCGTGAT GATGGTGTGG CTGACTGCCG
 851 GACTGTGGCA CAGCGGCTTT ACCAAGCTCG ACTACCCGAA ACTCTGCCGC
 901 ATCGCCGTCC CCATCCTNTT CGCCGCCGCC GTTTCGCGCG CTGTTTTAAT
 951 GAACGTAAAC CCGATATTCT TCATCACCGT CCCCGCAATT CTGACCGCCG
1001 CCGTGTTCGT GCTTTACCTG CTGACATTCG TACCGATCTT TCGGGCGAAC
1051 GCGTTTACAG ACGATCCGGA ATAA
```

This encodes a protein having amino acid sequence <SEQ ID 850>:

```
  1 MRPFFVGAAV LAILGALVFF INPGAIVLHR QIFLELMLPA AYGGFLTAAL
 51 LDWTGFSGNL KPVATLMAAL LLAASAILPF SPQTASFFVA AYWLVLLLFC
101 ARLIWLDRNT DNFALLMLLA AFTVFQTAYA VSGDLNLLRA QVHLNMAAVM
151 FVSVRVSILL GAEALKECRL KDPVFIPNVV YKNIAITFLL LHAAAELWLP
201 AQTAGFTSLA VGFILLAKLR ELHHHELLRK HYVRTYYLLQ LFAAAGYLWT
251 GAAKLQNLPA SAPLHLITLG GMMGSVMMVW LTAGLWHSGF TKLDYPKLCR
301 IAVPILFAAA VSRAVLMNVN PIFFITVPAI LTAAVFVLYL LTFVPIFRAN
351 AFTDDPE*
```

ORF130a and ORF130-1 show 98.3% identity in 357 aa overlap:

```
orf130a.pep  MRPFFVGAAVLAILGALVFFINPGAIVLHRQIFLELMLPAAYGGFLTAALLDWTGFSGNL
             ||||||||||||||||||||||||||||||||||||||||||||||||||||||||||||
orf130-1     MRPFFVGAAVLAILGALVFFINPGAIVLHRQIFLELMLPAAYGGFLTAALLDWTGFSGNL orf130a.pep  KPVATLMAALLLAASAILPFSPQTASFFVAAYWLVLLLFCARLIWLDRNTDNFALLMLLA
             ||||||||||||||||||||||||||||||||||||||||||||||||||||||||||||
orf130-1     KPVATLMAALLLAASAILPFSPQTASFFVAAYWLVLLLFCARLIWLDRNTDNFALLMLLA orf130a.pep  AFTVFQTAYAVSGDLNLLRAQVHLNMAAVMFVSVRVSILLGAEALKECRLKDPVFIPNVV
             |||||||||||||||||||||||||||||||||||||||||||||||||||||||||:|
orf130-1     AFTVFQTAYAVSGDLNLLRAQVHLNMAAVMFVSVRVSILLGAEALKECRLKDPVFIPNIV orf130a.pep  YKNIAITFLLLHAAAELWLPAQTAGFTSLAVGFILLAKLRELHHHELLRKHYVRTYYLLQ
             |||||||||||||||||||||||||||:|||||||||||||||||||||||||||||||
orf130-1     YKNIAITFLLLHAAAELWLPAQTAGFTALAVGFILLAKLRELHHHELLRKHYVRTYYLLQ orf130a.pep  LFAAAGYLWTGAAKLQNLPASAPLHLITLGGMMGSVMMVWLTAGLWHSGFTKLDYPKLCR
             ||||||||||||||||||||||||||||||||||:|||||||||||||||||||||||||
orf130-1     LFAAAGYLWTGAAKLQNLPASAPLHLITLGGMMGGVMMVWLTAGLWHSGFTKLDYPKLCR orf130a.pep  IAVPILFAAAVSRAVLMNVNPIFFITVPAILTAAVFVLYLLTFVPIFRANAFTDDPE
             ||||||||||||||| ||||||||||||||||||||||||||:||:|||||||||||
orf130-1     IAVPILFAAAVSRAFLMNVNPIFFITVPAILTAAVFVLYLFTFIPIFRANAFTDDPE
```

20

Homology with a Predicted ORF from *N. gonorrhoeae*

ORF130 shows 91.7% identity over a 193 aa overlap with a predicted ORF (ORF130ng) from *N. gonorrhoeae*:

```
orf130.pep                          LKECRLKDPVFIPNIVYKNIAITFLLLHAA    30
                                    ||||||||||||||::|||||| ||||||
orf130ng    LNLLRAQVHLNMAAVMFVSVRVSVLLGTETLKECRLKDPVFIPNVIYKNIAIT-LLLHAA   201 orf130.pep  AELWLPAQTAGFTALAVGFILLAKLRELHHHELLRKHYVRTYYLLQLFAAAGSLWTGAAX    90
            |||||||||||||||||||||||||||||||||||||||||||||||||||||| ||||
orf130ng    AELWLPAQTAGFTALAVGFILLAKLRELHHHELLRKHYVRTYYLLQLFAAAGYLWTGAAK   261 orf130.pep  LQNLPASAPLHLITLGGMMGGVMMVWLTAGLWHSGFTKLDYPKLCRIAVPILFAAAVSRA   150
            ||||||||||||||||||||:|||||||||||||||||||||||||||||  |||:||||
orf130ng    LQNLPASAPLHLITLGGMTGGVMMVWLTAGLWHSGFTKLDYPKLCRIAVSILFASAVSRA   321 orf130.pep  FLXNVNPXFFITVPAILTAAVFVLYLFXFIPIFRANAFTDDPE   193
            | |||| |||||| ||||||::|||::|:|||||||||||||
orf130ng    VLMNVNPIFFITVPEILTAAVFMLYLLTFVPIFRANAFTDDPE   364
```

An ORF130ng nucleotide sequence <SEQ ID 851> was predicted to encode a protein having amino acid sequence <SEQ ID 852>:

```
  1 MNKFFTHPMR PFFVGAAVLA ILGALVFFHQ PRRYHPAPPN FLGTYAAGCI

51 RRFFDYRFVG PDGFFRQPET CRYFDGGVVA CCGCFIAVFT ATCRIFRRRL

101 LAGVAAVLRL ADLARRQHRT LRSVDVTAAF TVFQTAYAVS GDLNLLRAQV

151 HLNMAAVMFV SVRVSVLLGT ETLKECRLKD PVFIPNVIYK NIAITLLLHA

201 AAELWLPAQT AGFTALAVGF ILLAKLRELH HHELLRKHYV RTYYLLQLFA

251 AAGYLWTGAA KLQNLPASAP LHLITLGGMT GGVMMVWLTA GLWHSGFTKL

301 DYPKLCRIAV SILFASAVSR AVLMNVNPIF FITVPEILTA AVFMLYLLTF

351 VPIFRANAFT DDPE*
```

55

Further work revealed the following gonococcal DNA sequence <SEQ ID 853>:

```
  1 ATGCGCCCGT TTTTCGTCGG TGCGGCAGTA CTTGCCATAC TCGGTGCGTT

51 GGTGTTTTTT ATCAACCCCG GCGCTATCAT CCTGCACCGC CAAATTTTCT

101 TGGAACTTAT GCTGCCGGCT GCATACGGCG GTTTTTTGAC TACCGCTTTG

151 TTGGACCGGA CGGGTTTTTC AGGCAACCTG AAACCTGCCG CTACTTTGAT

201 GGCGGTGTTG TTGCTTGTTG CGGCTGTTTT ATTGCCGTTT TTACCGCAAC
```

-continued

```
 251 TTGCCGCATT TTTCGTCGCC GCCTATTGGC TGGTGTTGCT GCTGTTCTGC

301 GCCTGGCTGA TTTGGCTCGA CCGCAACACC GACAACTTCG CTCTGTTGAT

351 GTTACTTGCC GCATTTACCG TTTTTCAGAC GGCCTATGCC GTCAGCGGCG

401 ATTTGAACTT ACTGCGCGCG CAAGTGCATT TGAATATGGC GGCGGTCATG

451 TTCGTATCCG TCCGCGTCAG CGTCCTTTTG GGCACGGAAA CCCTGAAAGA

501 ATGCCGTCTG AAAGACCCCG TATTCATCCC CAACGTTATC TATAAAAACA

551 TCGCCATCAC CCTGCTGCTG CACGCCGCCG CCGAACTTTG GCTGCCCGCG

601 CAAACCGCCG GTTTTACTGC GCTTGCCGTC GGCTTCATCC TGCTCGCCAA

651 GCTGCGCGAA CTGCACCATC ACGAACTCTT ACGCAAACAC TACGTCCGCA

701 CTTATTACCT GCTCCAGCTC TTTGCCGCCG CAGGTTATCT GTGGACAGGC

751 GCGGCGAAAC TGCAAAACCT GCCCGCCTCC GCGCCCCTGC ACCTGATTAC

801 CCTCGGCGGC ATGACGGGTG GCGTGATGAT GGTGTGGCTG ACTGCCGGAC

851 TGTGGCACAG CGGCTTTACC AAACTCGACT ACCCGAAACT CTGCCGCATC

901 GCCGTCTCCA TCCTTTTCGC CTCCGCCGTT TCGCGCGCTG TTTTAATGAA

951 CGTGAATCCG ATATTCTTCA TCACCGTTCC CGAGATTCTG ACCGCCGCCG

1001 TGTTCATGCT TTACCTGCTG ACGTTCGTAC CGATTTTTCG AGCGAACGCG

1051 TTTACAGACG ATCCGGAATA A
```

This corresponds to the amino acid sequence <SEQ ID
854; ORF130ng-1>:

```
  1 MRPFFVGAAV LAILGALVFF INPGAIILHR QIFLELMLPA AYGGFLTTAL

51 LDRTGFSGNL KPAATLMAVL LLVAAVLLPF LPQLAAFFVA AYWLVLLLFC

101 AWLIWLDRNT DNFALLMLLA AFTVFQTAYA VSGDLNLLRA QVHLNMAAVM

151 FVSVRVSVLL GTETLKECRL KDPVFIPNVI YKNIAITLLL HAAAELWLPA

201 QTAGFTALAV GFILLAKLRE LHHHELLRKH YVRTYYLLQL FAAAGYLWTG

251 AAKLQNLPAS APLHLITLGG MTGGVMMVWL TAGLWHSGFT KLDYPKLCRI

301 AVSILFASAV SRAVLMNVNP IFFITVPEIL TAAVFMLYLLTFVPIFRANA

351 FTDDPE*
```

ORF130ng-1 and ORF130-1 show 92.4% identity in 357
aa overlap:

```
orf130-1.pep  MRPFFVGAAVLAILGALVFFINPGAIVLHRQIFLELMLPAAYGGFLTAALLDWTGFSGNL
              |||||||||||||||||||||||||||:||||||||||||||||||||:||| |||||||
orf130ng-1    MRPFFVGAAVLAILGALVFFINPGAIILHRQIFLELMLPAAYGGFLTTALLDRTGFSGNL orf130-1.pep  KPVATLMAALLLAASAILPFSPQTASFFVAAYWLVLLLFCARLIWLDRNTDNFALLMLLA
              ||:|||||:|||:|::|||  ||  | :|||||||||||||| |||||||||||||||||
orf130ng-1    KPAATLMAVLLLVAAVLLPFLPQLAAFFVAAYWLVLLLFCAWLIWLDRNTDNFALLMLLA orf130-1.pep  AFTVFQTAYAVSGDLNLLRAQVHLNMAAVMFVSVRVSILLGAEALKECRLKDPVFIPNIV
              ||||||||||||||||||||||||||||||||||||||:|||:|:||||||||||||||::
orf130ng-1    AFTVFQTAYAVSGDLNLLRAQVHLNMAAVMFVSVRVSVLLGTETLKECRLKDPVFIPNVI orf130-1.pep  YKNIAITFLLLHAAAELWLPAQTAGFTALAVGFILLAKLRELHHHELLRKHYVRTYYLLQ
              ||||||| |||||||||||||||||||||||||||||||||||||||||||||||||||
orf130ng-1    YKNIAIT-LLLHAAAELWLPAQTAGFTALAVGFILLAKLRELHHHELLRKHYVRTYYLLQ orf130-1.pep  LFAAAGYLWTGAAKLQNLPASAPLHLITLGGMMGGVMMVWLTAGLWHSGFTKLDYPKLCR
              ||||||||||||||||||||||||||||||||  ||||||||||||||||||||||||||
orf130ng-1    LFAAAGYLWTGAAKLQNLPASAPLHLITLGGMTGGVMMVWLTAGLWHSGFTKLDYPKLCR orf130-1.pep  IAVPILFAAAVSRAFLMNVNPIFFITVPAILTAAVFVLYLTFIPIFRANAFTDDPEX
              |||  |||||:|||| |||||||||||| :||:||:|:||:||||||||||||||||
orf130ng-1    IAVSILFASAVSRAVLMNVNPIFFITVPEILTAAVFMLYLLTFVPIFRANAFTDDPEX
```

Based on this analysis, it is predicted that the proteins from *N. meningitidis* and *N. gonorrhoeae*, and their epitopes, could be useful antigens for vaccines or diagnostics, or for raising antibodies.

Example 101

The following partial DNA sequence was identified in *N. meningitidis* <SEQ ID 855>:

```
  1 ATGGAAATTC GGGCAATAAA ATATACGGCA ATGGCTGCGT TGCTTGCATT

51 TACGGTTGCA GGCTGCCGGC TGGCGGGGTG GTATGAGTGT TCGTCCCTCA

101 CCGGCTGGTG TAAGCCGAGA AAACCGGCTG CCATCGATTT TTGGGATATT

151 GGCGGCGAGA GTCCGCCGTC TTTAGGGGAC TACGAGATAC CGCTTTCAGA

201 CGGCAATAGT TCCGTCAGGG CAAACGAATA TGAATCCGCA CAACAATCTT

251 ACTTTTACAG GAAAATAGGG AAGTTTGAAG C.TGCGGGCT GGATTGGCGT

301 ACGCGTGACG GCAAACCTTT GATTGAGACG TTCAAACAGG GAGGATTTGA

351 CTGCTTGGAA AAG..
```

This corresponds to the amino acid sequence <SEQ ID 856; ORF131>:

```
  1 MEIRAIKYTA MAALLAFTVA GCRLAGWYEC SSLTGWCKPR KPAAIDFWDI

51 GGESPPSLGD YEIPLSDGNS SVRANEYESA QQSYFYRKIG KFEXCGLDWR

101 TRDGKPLIET FKQGGFDCLE K..
```

Further work revealed the complete nucleotide sequence <SEQ ID 857>:

```
  1 ATGGAAATTC GGGCAATAAA ATATACGGCA ATGGCTGCGT TGCTTGCATT

51 TACGGTTGCA GGCTGCCGGC TGGCGGGGTG GTATGAGTGT TCGTCCCTCA

101 CCGGCTGGTG TAAGCCGAGA AAACCGGCTG CCATCGATTT TTGGGATATT

151 GGCGGCGAGA GTCCGCCGTC TTTAGGGGAC TACGAGATAC CGCTTTCAGA

201 CGGCAATCGT TCCGTCAGGG CAAACGAATA TGAATCCGCA CAACAATCTT

251 ACTTTTACAG GAAAATAGGG AAGTTTGAAG CCTGCGGGCT GGATTGGCGT

301 ACGCGTGACG GCAAACCTTT GATTGAGACG TTCAAACAGG GAGGATTTGA

351 CTGCTTGGAA AAGCAGGGGT TGCGGCGCAA CGGTCTGTCC GAGCGCGTCC

401 GATGGTAA
```

This corresponds to the amino acid sequence <SEQ ID 858; ORF131-1>:

```
  1 MEIRAIKYTA MAALLAFTVA GCRLAGWYEC SSLTGWCKPR KPAAIDFWDI

51 GGESPPSLGD YEIPLSDGNR SVRANEYESA QQSYFYRKIG KFEACGLDWR

101 TRDGKPLIET FKQGGFDCLE KQGLRRNGLS ERVRW*
```

Computer analysis of this amino acid sequence gave the following results:

Homology with a Predicted ORF from *N. meningitidis* (Strain A)

ORF131 shows 95.0% identity over a 121 aa overlap with an ORF (ORF131a) from strain A of *N. meningitidis*:

```
                   10        20        30        40        50        60
    orf131.pep MEIRAIKYTAMAALLAFTVAGCRLAGWYECSSLTGWCKPRKPAAIDFWDIGGESPPSLGD
               ||||||||||||||||||||||||||||||:||||||||||||||||||||||||||| |
    orf131a    MEIRAIKYTAMAALLAFTVAGCRLAGWYECSSLSGWCKPRKPAAIDFWDIGGESPPSLED
                   10        20        30        40        50        60

70        80        90       100       110       120
    orf131.pep YEIPLSDGNSSVRANEYESAQQSYFYRKIGKFEXCGLDWRTRDGKPLIETFKQGGFDCLE
               ||||||||| |||||||||||||||||||||| ||||||||||||||||||||| |||||:
    orf131a    YEIPLSDGNRSVRANEYESAQQSYFYRKIGKFEACGLDWRTRDGKPLIETFKQEGFDCLK
                   70        80        90       100       110       120 orf131.pep K
               |
    orf131a    KQGLRRNGLSERVRWX
                       130
```

The complete length ORF131a nucleotide sequence <SEQ ID 859> is:

```
  1 ATGGAAATTC GGGCAATAAA ATATACGGCA ATGGCTGCGT TGCTTGCATT

51 TACGGTTGCA GGCTGCCGGT TGGCAGGTTG GTATGAGTGT TCGTCCCTGT

101 CCGGCTGGTG TAAGCCGAGA AAACCTGCCG CCATCGATTT TTGGGATATT

151 GGCGGCGAGA GTCCTCCGTC TTTAGAGGAC TACGAGATAC CGCTTTCAGA

201 CGGCAATCGT TCCGTCAGGG CAAACGAATA TGAATCCGCA CAACAATCTT

251 ACTTTTACAG GAAAATAGGG AAGTTTGAAG CCTGCGGGTT GGATTGGCGT

301 ACGCGTGACG GCAAACCTTT GATTGAGACG TTCAAACAGG AAGGTTTTGA

351 TTGTTTGAAA AAGCAGGGGT TGCGGCGCAA CGGTCTGTCC GAGCGCGTCC

401 GATGGTAA
```

This encodes a protein having amino acid sequence <SEQ ID 860>:

```
  1 MEIRAIKYTA MAALLAFTVA GCRLAGWYEC SSLSGWCKPR KPAAIDFWDI

51 GGESPPSLED YEIPLSDGNR SVRANEYESA QQSYFYRKIG KFEACGLDWR

101 TRDGKPLIET FKQEGFDCLK KQGLRRNGLS ERVRW*
```

ORF131a and ORF131-1 show 97.0% identity in 135 aa overlap:

```
    orf131a.pep MEIRAIKYTAMAALLAFTVAGCRLAGWYECSSLSGWCKPRKPAAIDFWDIGGESPPSLED
                ||||||||||||||||||||||||||||||:|||||||||||||||||||||||||||| |
    orf131-1    MEIRAIKYTAMAALLAFTVAGCRLAGWYECSSLTGWCKPRKPAAIDFWDIGGESPPSLGD
    orf131a.pep YEIPLSDGNRSVRANEYESAQQSYFYRKIGKFEACGLDWRTRDGKPLIETFKQEGFDCLK
                |||||||||||||||||||||||||||||||||||||||||||||||||||||| ||||:
    orf131-1    YEIPLSDGNRSVRANEYESAQQSYFYRKIGKFEACGLDWRTRDGKPLIETFKQGGFDCLE
    orf131a.pep KQGLRRNGLSERVRWX
                ||||||||||||||||
    orf131-1    KQGLRRNGLSERVRWX
```

Homology with a Predicted ORF from *N. gonorrhoeae*

ORF131 shows 89.3% identity over 121 aa overlap with a predicted ORF (ORF131ng) from *N. gonorrhoeae*:

```
orf131.pep  MEIRAIKYTAMAALLAFTVAGCRLAGWYECSSLTGWCKPRKPAAIDFWDIGGESPPSLGD  60
            ||||:|||||  |||:|||||||||||||  ||:|||||||||||||||||||||||  ||  |
orf131ng    MEIRVIKYTATAALFAFTVAGCRLAGWYECLSLSGWCKPRKPAAIDFWDIGGESPLSLED  60
orf131.pep  YEIPLSDGNSSVRANEYESAQQSYFYRKIGKFEXCGLDWRTRDGKPLIETFKQGGFDCLE  120
            ||||||||| ||||||||||||:|||||||||| ||||||||||||||:| ||| ||||||
orf131ng    YEIPLSDGNRSVRANEYESAQKSYFYRKIGKFEACGLDWRTRDGKPLVERFKQEGFDCLE  120
orf131.pep  K                        121
            |
orf131ng    KQGLRRNGLSERVRW          134
```

A complete length ORF131ng nucleotide sequence <SEQ ID 861> was predicted to encode a protein having amino acid sequence <SEQ ID 862>:

```
  1 MEIRVIKYTA TAALFAFTVA GCRLAGWYEC LSLSGWCKPR KPAAIDFWDI

51 GGESPLSLED YEIPLSDGNR SVRANEYESA QKSYFYRKIG KFEACGLDWR

101 TRDGKPLVER FKQEGFDCLE KQGLRRNGLS ERVRW*
```

Further work revealed the following gonococcal DNA sequence <SEQ ID 863>:

```
  1 ATGGAAATTC GGGTAATAAA ATATACGGCA ACGGCTGCGT TGTTTGCATT

51 TACGGTTGCA GGCTGCCGGC TGGCGGGGTG GTATGAGTGT TCGTCCTTGT

101 CCGGCTGGTG TAAGCCGAGA AAACCTGCCG CCATCGATTT TTGGGATATT

151 GGCGGCGAGA GtccgctGTC TTTAGAGGAC TACGAGATAC CGCTTTCAGA

201 CGGCAATCGT TCCGTCAGGG CAAACGAATA TGAATCCGCG CAAAAATCTT

251 ACTTTTATAG GAAAATAGGG AAGTTTGAAG CCTGCGGGTT GGATTGGCGT

301 ACGCGTGACG GCAAACCTTT GGTTGAGAGG TTCAAACAGG AAGGTTTCGA

351 CTGTTTGGAA AAGCAGGGGT TGCGGCGCAA CGGCCTGTCC GAGCGCGTCC

401 GATGGTAA
```

This corresponds to the amino acid sequence <SEQ ID 864; ORF131ng-1>:

```
  1 MEIRVIKYTA TAALFAFTVA GCRLAGWYEC SSLSGWCKPR KPAAIDFWDI

51 GGESPLSLED YEIPLSDGNR SVRANEYESA QKSYFYRKIG KFEACGLDWR

101 TRDGKPLVER FKQEGFDCLE KQGLRRNGLS ERVRW*
```

ORF131ng-1 and ORF131-1 show 92.6% identity in 135 aa overlap:

```
orf131ng-1.pep MEIRVIKYTATAALFAFTVAGCRLAGWYECSSLSGWCKPRKPAAIDFWDIGGESPLSLED
               ||||:|||||  |||:|||||||||||||||||||||||||||||||||||||||  ||  |
orf131-1       MEIRAIKYTAMAALLAFTVAGCRLAGWYECSSLTGWCKPRKPAAIDFWDIGGESPPSLGD
orf131ng-1.pep YEIPLSDGNRSVRANEYESAQKSYFYRKIGKFEACGLDWRTRDGKPLVERFKQEGFDCLE
               |||||||||||||||||||||:||||||||||||||||||||||||:| ||| ||||||
orf131-1       YEIPLSDGNRSVRANEYESAQQSYFYRKIGKFEACGLDWRTRDGKPLIETFKQGGFDCLE
orf131ng-1.pep KQGLRRNGLSERVRWX
               |||||||||||||||
orf131-1       KQGLRRNGLSERVRWX
```

Based on the presence of a predicted prokaryotic membrane lipoprotein lipid attachment site, it is predicted that the proteins from N. meningitidis and N. gonorrhoeae, and their epitopes, could be useful antigens for vaccines or diagnostics, or for raising antibodies.

Example 102

The following partial DNA sequence was identified in *N. meningitidis* <SEQ ID 865>

```
  1 ATGAAACACA TCCATATTAT CGGTATCGGC GGCACGTTTA TGGGCGGGCT
 51 TGCCGCCATT GCCAAAGAAG CGGGGTTTGA AGTCAGCGGT TGCGACGCGA
101 AGATGTATCC GCCGATGAGC ACCCAGCTCG AAGCCTTGGG TATAGACGTG
151 TATGAAGGCT TCGATGCCGC TCAGTTGGAC GAATTTAAAG CCGACGTTTA
201 CGTTATCGGC AATGTCGCCA AGCGCGGGAT GGATGTGGTT GAAGCGATTT
251 TGAACCTCGG CCTGCCtTAT ATtTcCGGCC CGCAATGGCT GTCGGAAAAC
301 GTGCTGCACC ATCATTGGGT ACTCGGTGTG GCGGGGACgC ACGGCAAAAC
351 GACCACCGCC TCCATGCTCG CATGGGTCTT GGAATATgCC GGCCTCGCGC
401 CGGGCTTCCT TATtGGCGGC GTACC.GGAA AATttCGGCG TTTCCGCCCG
451 CCTGCCGCAA ACGCCGCGCC AAGACCCGAA CAGCCAATCG CCGTTTTTcG
501 TCATCGAAGC CGACGAATAC GACACCGCCT TTtTCGACAA ACGTTCTAAA
551 TtCGTGCATT ACCGTCCGCG TACCGCCGTG TTGAACAATC TGGAATTCGA
601 CCACGCCGAC ATCTTTGCCG ACTTGGGCGC GATACAGACc CAGTTCCACT
651 ACCTCGTGCG TACCGTGCCG TCTGAAGGCT TAATCGTCTG CAACGGACGG
701 CAGCAAAGCC TGCAAGATAC TTTGGACAAA GGCTGCTGGA CGCCGGTGGA
751 AAAATTCGGC ACGGAACACG GCTGGCA..
```

This corresponds to the amino acid sequence <SEQ ID 866; ORF132>:

```
  1 MKHIHIIGIG GTFMGGLAAI AKEAGFEVSG CDAKMYPPMS TQLEALGIDV
 51 YEGFDAAQLD EFKADVYVIG NVAKRGMDVV EAILNLGLPY ISGPQWLSEN
101 VLHHHWVLGV AGTHGKTTTA SMLAWVLEYA GLAPGFLIGG VXGKFRRFRP
151 PAANAAPRPE QPIAVFRHRS RRIRHRLFRQ TFXIRALPSA YRRVEQSGIR
201 PRRHLCRLGR DTDPVPLPRA YRAVXRLNRL QRTAAKPARY FGQRLLDAGG
251 KIRHGTRLA..
```

Further work revealed the complete nucleotide sequence <SEQ ID 867>:

```
  1 ATGAAACACA TCCATATTAT CGGTATCGGC GGCACGTTTA TGGGCGGGCT
 51 TGCCGCCATT GCCAAAGAAG CGGGGTTTGA AGTCAGCGGT TGCGACGCGA
101 AGATGTATCC GCCGATGAGC ACCCAGCTCG AAGCCTTGGG TATAGACGTG
151 TATGAAGGCT TCGATGCCGC TCAGTTGGAC GAATTTAAAG CCGACGTTTA
201 CGTTATCGGC AATGTCGCCA AGCGCGGGAT GGATGTGGTT GAAGCGATTT
251 TGAACCTCGG CCTGCCTTAT ATTTCCGGCC CGCAATGGCT GTCGGAAAAC
301 GTGCTGCACC ATCATTGGGT ACTCGGTGTG GCGGGGACGC ACGGCAAAAC
351 GACCACCGCC TCCATGCTCG CATGGGTCTT GGAATATGCC GGCCTCGCGC
401 CGGGCTTCCT TATTGGCGGC GTACCGGAAA ATTTCGGCGT TTCCGCCCGC
451 CTGCCGCAAA CGCCGCGCCA AGACCCGAAC AGCCAATCGC CGTTTTTCGT
501 CATCGAAGCC GACGAATACG ACACCGCCTT TTTCGACAAA CGTTCTAAAT
```

-continued

```
 551 TCGTGCATTA CCGTCCGCGT ACCGCCGTGT TGAACAATCT GGAATTCGAC

601 CACGCCGACA TCTTTGCCGA CTTGGGCGCG ATACAGACCC AGTTCCACTA

651 CCTCGTGCGT ACCGTGCCGT CTGAAGGCTT AATCGTCTGC AACGGACGGC

701 AGCAAAGCCT GCAAGATACT TTGGACAAAG GCTGCTGGAC GCCGGTGGAA

751 AAATTCGGCA CGGAACACGG CTGGCAGGCC GGCGAAGCCA ATGCCGACGG

801 CTCGTTCGAC GTGTTGCTCG ACGGCAAAAC CGCCGGACGC GTCAAATGGG

851 ATTTGATGGG CAGGCACAAC CGCATGAACG CGCTCGCCGT CATTGCCGCC

901 GCGCGTCATG TCGGTGTCGA TATTCAGACC GCCTGCGAAG CCTTGGGCGC

951 GTTTAAAAAC GTCAAACGCC GGATGGAAAT CAAAGGCACG GCAAACGGCA

1001 TCACCGTTTA CGACGACTTC GCCCACCACC CGACCGCCAT CGAAACCACG

1051 ATTCAAGGTT TGCGCCAACG CGTCGGCGGC GCGCGCATCC TCGCCGTCCT

1101 CGAACCGCGT TCCAACACGA TGAAGCTGGG CACGATGAAG TCCGCCCTGC

1151 CTGTAAGCCT CAAAGAAGCC GACCAAGTGT TCTGCTACGC CGGCGGCGTG

1201 GACTGGGACG TCGCCGAAGC CCTCGCGCCT TTGGGCGGCA GGCTGAACGT

1251 CGGCAAAGAC TTCGATGCCT TCGTTGCCGA AATCGTGAAA AACGCCGAAG

1301 TAGGCGACCA TATTTTGGTG ATGAGCAACG GCGGTTTCGG CGGAATACAC

1351 GGAAAGCTGC TGGAAGCTTT GAGATAG
```

This corresponds to the amino acid sequence <SEQ ID 30 NO: 868; ORF132-1>:

```
  1 MKHIHIIGIG GTFMGGLAAI AKEAGFEVSG CDAKMYPPMS TQLEALGIDV

51 YEGFDAAQLD EFKADVYVIG NVAKRGMDVV EAILNLGLPY ISGPQWLSEN

101 VLHHHWVLGV AGTHGKTTTA SMLAWVLEYA GLAPGFLIGG VPENFGVSAR

151 LPQTPRQDPN SQSPFFVIEA DEYDTAFFDK RSKFVHYRPR TAVLNNLEFD

201 HADIFADLGA IQTQFHYLVR TVPSEGLIVC NGRQQSLQDT LDKGCWTPVE

251 KFGTEHGWQA GEANADGSFD VLLDGKTAGR VKWDLMGRHN RMNALAVIAA

301 ARHVGVDIQT ACEALGAFKN VKRRMEIKGT ANGITVYDDF AHHPTAIETT

351 IQGLRQRVGG ARILAVLEPR SNTMKLGTMK SALPVSLKEA DQVFCYAGGV

401 DWDVAEALAP LGGRLNVGKD FDAFVAEIVK NAEVGDHILV MSNGGFGGIH

451 GKLLEALR*
```

Computer analysis of this amino acid sequence gave the following results:

Homology with the Hypothetical o457 Protein of *E. coli* (Accession Number U14003)

ORF132 and o457 show 58% aa identity in 140 aa overlap:

```
Orf132:    4 IHIIGIGGTFMGGLAAIAKEAGFEVSGCDAKMYPPMSTQLEALGIDVYEGFDAAQLDEFK   63
             IHI+GI GTFMGGLA +A++ G EV+G DA +YPPMST LE  GI++ +G+DA+QL+  +
o457:      3 IHILGICGTFMGGLAMLARQLGHEVTGSDANVYPPMSTLLEKQGIELIQGYDASQLEP-Q   61

Orf132:   64 ADVYVIGNVAKRGMDVVEAILNLGLPYISGPQWLSENVLHHHWVLGVAGTHGKTTTASML  123
             D+ +IGN   RG   VEA+L  +PY+SGPQWL + VL   WVL VAGTHGKTTTA M
o457:     62 PDLVIIGNAMTRGNPCVEAVLEKNIPYMSGPQWLHDFVLRDRWVLAVAGTHGKTTTAGMA  121

Orf132:  124 AWVLEYAGLAPGFLIGGVXG                                          143
             W+LE  G  PGF+IGGV G
o457:    122 TWILEQCGYKPGFVIGGVPG                                          141
```

Homology with a Predicted ORF from *N. meningitidis* (Strain A)

ORF132 shows 74.6% identity over a 189aa overlap with an ORF (ORF132a) from strain A of *N. meningitidis*:

```
                    10        20        30        40        50        60
    orf132.pep  MKHIHIIGIGGTFMGGLAAIAKEAGFEVSGCDAKMYPPMSTQLEALGIDVYEGFDAAQLD
                ||||||||||||||||:|||||||||||||||||||||||||||||:||||||||:||||
    orf132a     MKHIHIIGIGGTFMGGIAAIAKEAGFEXSGCDAKMYPPMSTQLEALGIGVYEGFDTAQLD
                    10        20        30        40        50        60

70        80        90       100       110       120
    orf132.pep  EFKADVYVIGNVAKRGMDVVEAILNLGLPYISGPQWLSENVLHHHWVLGVAGTHGKTTTA
                |||||||||||||||||||||||||:|||||||||||||:||||||||||||||||||||
    orf132a     EFKADVYVIGNVAKRGMDVVEAILNRGLPYISGPQWLAENXLHHHWXLGVAXTHGKTTTA
                    70        80        90       100       110       120

130       140       150       160
    orf132.pep  SMLAWVLEYAGLAPGFLIGGVXGKFR---RFRPPAANAAPRPEQPI----------AVFR
                |||||||||||||||||:||||  ::|   |:  |  :    |::|:           ||
    orf132a     SMLAWVLEYAGLAPGFXIGGVPENFSVSARL-PQTPRQDPNSQSPFFVIEADEYDTAFFD
                   130       140       150       160       170

170       180       190       200       210       220
    orf132.pep  HRSRRIRHRLFRQTFXIRALPSAYRRVEQSGIRPRRHLCRLGRDTDPVPLPRAYRAVXRL
                :|||:  :::|
    orf132a     KRSKFVHYRPRTAVLNNLEFDHADIFADLGAIQTQFHHLVRTVPSEGLIVCNGRQQSLQD
                   180       190       200       210       220       230
```

The complete length ORF132a nucleotide sequence <SEQ ID 869> is:

```
   1 ATGAAACACA TCCACATTAT CGGTATCGGC GGCACGTTTA TGGGTGGGAT
  51 TGCCGCCATT GCCAAAGAAG CAGGGTTTGA ANTCAGCGGT TGCGATGCGA
 101 AGATGTATCC GCCGATGAGC ACCCAGCTCG AAGCCTTGGG CATAGGCGTG
 151 TATGAAGGCT TCGACACCGC GCAGTTGGAC GAATTTAAAG CCGACGTTTA
 201 CGTTATCGGC AATGTCGCCA AGCGCGGGAT GGATGTGGTT GAAGCGATTT
 251 TGAACCGTGG GCTGCCTTAT ATTTCCGGCC CGCAATGGCT GGCTGAAAAC
 301 NTGCTGCACC ATCATTGGNN ACTCGGCGTG GCGGNGACGC ACGGCAAAAC
 351 GACCACCGCG TCTATGCTCG CGTGGGTTTT GGAATATGCC GGACTCGCAC
 401 CGGGCTTCNT TATCGGCGGC GTACCGGAAA ACTTCAGCGT TCCGCCCGC
 451 CTGCCGCAAA CGCCGCGCCA AGACCCGAAC AGCCAATCGC CGTTTTTCGT
 501 CATTGAAGCC GACGAATACG ACACCGCGTT TTTCGACAAA CGCTCCAAAT
 551 TCGTGCATTA CCGTCCGCGT ACCGCCGTGT TGAACAATCT GGAATTCGAC
 601 CACGCCGACA TCTTCGCCGA TTTGGGCGCG ATACAGACCC AGTTCCACCA
 651 CCTCGTGCGT ACCGTGCCGT CTGAAGGCCT CATCGTCTGC AACGGACGGC
 701 AGCAAAGCCT GCAAGACACT TTGGACAAAG CTGCTGGAC GCCGGTGGAA
 751 AAATTCGGCA CGGAACACGG CTGGCAGGCC GGCGAAGCCA ATGCCGATGG
 801 CTCGTTCGAC GTGTTGCTTG ACGGCAAAAA AGCCGGACAC GTCGCTTGGA
 851 GTTTGATGGG CGGACACAAC CGCATGAACG CGCTCGCNGT CATCGCCGCC
 901 GCGCGTCATG CCGGAGTNGA CATTCAGACG GCCTGCGAAG CCTTGAGCAC
 951 GTTTAAAAAC GTCAAACGCC GCATGGAAAT CAAAGGCACG GCAAACGGTA
1001 TCACCGTTTA CGACGACTTC GCCCACCATC CGACCGCTAT CGAAACCACG
1051 ATTCAAGGTT TGCGCCAGCG CGTCGGCGGC GCGCGCATCC TCGCCGTCCT
1101 CGAACCGCGT TCCAATACGA TGAAGCTGGG TACGATGAAA GCCGCCCTGC
1151 CCGCAAGCCT CAAAGAAGCC GACCAAGTGT TCTGNTACGC CGGCGGCGCG
```

```
1201 GACTGGGACG TTGCCGAAGC CCTCGCGCCT TTGGGCGGCA GGCTGCACGT

1251 CGGCAAAGAC TTCGATGCCT TCGTTGCCGA AATCGTGAAA AACGCCGAAG

1301 CAGGCGACCA TATTTTGGTG ATGAGCAACG GCGGTTTCGG CGGAATACAC

1351 ACCAAACTGC TGGACGCTTT GAGATAG
```

This encodes a protein having amino acid sequence <SEQ ID 870>:

```
  1  MKHIHIIGIG GTFMGGIAAI AKEAGFEXSG CDAKMYPPMS TQLEALGIGV

51  YEGFDTAQLD EFKADVYVIG NVAKRGMDVV EAILNRGLPY ISGPQWLAEN

101  XLHHHWXLGV AXTHGKTTTA SMLAWVLEYA GLAPGFXIGG VPENFSVSAR

151  LPQTPRQDPN SQSPFFVIEA DEYDTAFFDK RSKFVHYRPR TAVLNNLEFD

201  HADIFADLGA IQTQFHHLVR TVPSEGLIVC NGRQQSLQDT LDKGCWTPVE

251  KFGTEHGWQA GEANADGSFD VLLDGKKAGH VAWSLMGGHN RMNALAVIAA

301  ARHAGVDIQT ACEALSTFKN VKRRMEIKGT ANGITVYDDF AHHPTAIETT

351  IQGLRQRVGG ARILAVLEPR SNTMKLGTMK AALPASLKEA DQVFXYAGGA

401  DWDVAEALAP LGGRLHVGKD FDAFVAEIVK NAEAGDHILV MSNGGFGGIH

451  TKLLDALR*
```

ORF132a and ORF132-1 show 93.9% identity in 458 aa overlap:

```
orf132a.pep  MKHIHIIGIGGTFMGGIAAIAKEAGFEXSGCDAKMYPPMSTQLEALGIGVYEGFDTAQLD
             ||||||||||||||||||:||||||||||:|||||||||||||||||||:|||||:|||
orf132-1     MKHIHIIGIGGTFMGGLAAIAKEAGFEVSGCDAKMYPPMSTQLEALGIDVYEGFDAAQLD orf132a.pep  EFKADVYVIGNVAKRGMDVVEAILNRGLPYISGPQWLAENXLHHHWXLGVAXTHGKTTTA
             ||||||||||||||||||||||||||||||||||||||| :||  ||||| ||||||||
orf132-1     EFKADVYVIGNVAKRGMDVVEAILNLGLPYISGPQWLSENVLHHHWVLGVAGTHGKTTTA orf132a.pep  SMLAWVLEYAGLAPGFXIGGVPENFSVSARLPQTPRQDPNSQSPFFVIEADEYDTAFFDK
             ||||||||||||||||:|||||||:|||||||||||||||||||||||||||||||||
orf132-1     SMLAWVLEYAGLAPGFLIGGVPENFGVSARLPQTPRQDPNSQSPFFVIEADEYDTAFFDK orf132a.pep  RSKFVHYRPRTAVLNNLEFDHADIFADLGAIQTQFHHLVRTVPSEGLIVCNGRQQSLQDT
             |||||||||||||||||||||||||||||||||||:||||||||||||||||||||||
orf132-1     RSKFVHYRPRTAVLNNLEFDHADIFADLGAIQTQFHYLVRTVPSEGLIVCNGRQQSLQDT orf132a.pep  LDKGCWTPVEKFGTEHGWQAGEANADGSFDVLLDGKKAGHVAWSLMGGHNRMNALAVIAA
             ||||||||||||||||||||||||||||||||||||:|:|:|||||||||||||||||
orf132-1     LDKGCWTPVEKFGTEHGWQAGEANADGSFDVLLDGKTAGRVKDLMGRHNRMNALAVIAA orf132a.pep  ARHAGVDIQTACEALSTFKNVKRRMEIKGTANGITVYDDFAHHPTAIETTIQGLRQRVGG
             |||:|||||||||||:::||||||||||||||||||||||||||||||||||||||||
orf132-1     ARHVGVDIQTACEALGAFKNVKRRMEIKGTANGITVYDDFAHHPTAIETTIQGLRQRVGG orf132a.pep  ARILAVLEPRSNTMKLGTMKAALPASLKEADQVFXYAGGADWDVAEALAPLGGRLHVGKD
             ||||||||||||||||||||:|||:||||||||| |||| ||||||||||||||:||||
orf132-1     ARILAVLEPRSNTMKLGTMKSALPVSLKEADQVFCYAGGVDWDVAEALAPLGGRLNVGKD orf132a.pep  FDAFVAEIVKNAEAGDHILVMSNGGFGGIHTKLLDALRX
             |||||||||||||:|||||||||||||||| |:||||
orf132-1     FDAFVAEIVKNAEVGDHILVMSNGGFGGIHGKLLEALRX
```

Homology with a Predicted ORF from *N. gonorrhoeae*

ORF132 shows 89.6% identity over 259 aa overlap with a predicted ORF (ORF132ng) from *N. gonorrhoeae*:

```
orf132.pep  MKHIHIIGIGGTFMGGLAAIAKEAGFEVSGCDAKMYPPMSTQLEALGIDVYEGFDAAQLD   60
            ||||||||||||||||:|||||||||:|||||||||||||||||||:||||||||||:
orf132ng    MKHIHIIGIGGTFMGGIAAIAKEAGFKVSGCDAKMYPPMSTQLEALGIGVHEGFDAAQLE   60 orf132.pep  EFKADVYVIGNVAKRGMDVVEAILNLGLPYISGPQWLSENVLHHHWVLGVAGTHGKTTTA  120
            ||:||:||||||:|||||||||||||:|||||||||:|||||||||||||||||||||
orf132ng    EFQADIYVIGNVARRGMDVVEAILNRGLPYISGPQWLAENVLHHHWVLGVAGTHGKTTTA  120 orf132.pep  SMLAWVLEYAGLAPGFLIGGVXGKFRRFRPPAANAAPRPEQPIAVFRHRSRRIRHRLFRQ  180
            |||||||||||||||||||||  |||||||||:|| |||||:|||||||||||||||||
orf132ng    SMLAWVLEYAGLAPGFLIGGVPGKFRRFRPPTANAASRPEQQIAVFRHRSRRIRHRLFRQ  180
```

```
orf132.pep  TFXIRALPSAYRRVEQSGIRPRRHLCRLGRDTDPVPLPRAYRAVXRLNRLQRTAAKPARY  240
            |:||||  ||||||||||||||  ||||||||||  |||:|::  |  :||||||||||||
orf132ng    TLQIRALSPAYRRVEQSGIRPRRHLRRLGRDTDPVPPPRAHRTIRRPHRLQRTAAKPARY  240 orf132.pep  FGQRLLDAGGKIRHGTRLA                                           259
            ||||||||||||||| |||
orf132ng    FGQRLLDAGGKIRHRTRLADW                                         261
```

An ORF132ng nucleotide sequence <SEQ ID 871> was predicted to encode a protein having amino acid sequence <SEQ ID 872>:

```
  1  MKHIHIIGIG GTFMGGIAAI AKEAGFKVSG CDAKMYPPMS TQLEALGIGV

51  HEGFDAAQLE EFQADIYVIG NVARRGMDVV EAILNRGLPY ISGPQWLAEN

101  VLHHHWVLGV AGTHGKTTTA SMLAWVLEYA GLAPGFLIGG VPGKFRRFRP

151  PTANAASRPE QQIAVFRHRS RRIRHRLFRQ TLQIRALSPA YRRVEQSGIR

201  PRRHLRRLGR DTDPVPPPRA HRTIRRPHRL QRTAAKPARY FGQRLLDAGG

251  KIRHRTRLAD W*
```

Further work revealed the following gonococcal DNA sequence <SEQ ID 873>:

```
   1  ATGAAACACA TCCACATTAT CGGTATCGGC GGCACGTTTA TGGGCGGGAT

51  TGCCGCCATT GCCAAAGAAG CCGGGTTCAA AGTCAGCGGT TGCGACGCGA

101  AGATGTATCC GCCGATGAGC ACCCAGCTCG AAGCCTTGGG CATAGGCGTA

151  CACGAAGGCT TCGATGCCGC GCAGTTGGAA GAATTTCAAG CCGATATTTA

201  CGTCATCGGC AATGTCGCCA GGCGCGGGAT GGATGTGGTC GAGGCGATTT

251  TGAACCGTGG GCTGCCTTAT ATTTCCGGCC CGCAATGGCT GGCTGAAAac

301  GTGCtgcacc atcaTTGGgt ACTCGGCGTG GcagggaCGC ACGGcaaAac 351  gaccaCcGcg tCCATGCTCG CCTGGGTCTT GGAATATGCC GGACTCGCGC 401  CGGGCTTCCT CATCGGCGGt gtaccggaAA ATTTCGGCGT TCCGCCCGC

451  CTACCGCAAA CGCCGCGTCA AGACCCGAAC AGCAAATCGC CGTTTTTCGT

501  CATCGAAGCC GACGAATACG ACACCGCCTT TTTCGACAAA CGCTCCAAAT

551  TCGTGCATTA TCGCCCGCGT ACCGCCGTGT TGAACAATCT GGAATTCGAC

601  CACGCCGACA TCTTCGCCGA CTTGGGCGCG ATACAGACCC AGTTCCACCA

651  CCTCGTGCGC ACCGTACCAT CCGAAGGCCT CATCGTCTGC AACGGACAGC

701  AGCAAAGCCT GCAAGATACT TTGGACAAAG CTGCTGGAC GCCGGTGGAA

751  AAATTCGGCA CCGGACACGG CTGGCAGATT GGTGAAGTCA ATGCCGACGG

801  CTCGTTCGAC GTATTGCTTG ACGGCAAAAA AGCCGGACAC GTCGCATGGG

851  ATTTGATGGG CGGACACAAC CGCATGAACG CGCTCGCCGT CATCGCTGCC

901  GCACGCCATG CCGGAGTCGA TGTTCAGACG GCCTGCGAAG CCTTGGGTGC

951  GTTTAAAAAC GTCAAACGCC GCATGGAAAT CAAAGGCACG GCAAACGGCA

1001  TCACCGTTTA CGACGATTTC GCCCACCACC CGACCGCCAT CGAAACCACG

1051  ATTCAAGGTT TGCGCCAACG TGTCGGCGGC GCGCGCATCC TCGCCGTCCT

1101  CGAGCCGCGT TCCAACACCA TGAAACTCGG CACGATGAAG TCCGCCCTGC

1151  CCGCAAGCCT CAAAGAAGCC GACCAAGTGT TCTGCTACGC CGGCGGCGCG

1201  GACTGGGACG TTGCCGAAGC CCTCGCGCCT TTGGGCTGCA GGCTGCGCGT
```

```
1251  CGGTAAAGAT TTCGATACCT TCGTTGCCGA AATTGTGAAA AACGCCCGAA

1301  CCGGCGACCA TATTTTGGTG ATGAGCAACG GCGGTTTCGG CGGAATACAC

1351  ACCAAACTGC TGGACGCTTT GAGATAG
```

This corresponds to the amino acid sequence <SEQ ID 874; ORF132ng-1>:

```
  1  MKHIHIIGIG GTFMGGIAAI AKEAGFKVSG CDAKMYPPMS TQLEALGIGV

51  HEGFDAAQLE EFQADIYVIG NVARRGMDVV EAILNRGLPY ISGPQWLAEN

101  VLHHHWVLGV AGTHGKTTTA SMLAWVLEYA GLAPGFLIGG VPENFGVSAR

151  LPQTPRQDPN SKSPFFVIEA DEYDTAFFDK RSKFVHYRPR TAVLNNLEFD

201  HADIFADLGA IQTQFHHLVR TVPSEGLIVC NGQQQSLQDT LDKGCWTPVE

251  KFGTGHGWQI GEVNADGSFD VLLDGKKAGH VAWDLMGGHN RMNALAVIAA

301  ARHAGVDVQT ACEALGAFKN VKRRMEIKGT ANGITVYDDF AHHPTAIETT

351  IQGLRQRVGG ARILAVLEPR SNTMKLGTMK SALPASLKEA DQVFCYAGGA

401  DWDVAEALAP LGCRLRVGKD FDTFVAEIVK NARTGDHILV MSNGGFGGIH

451  TKLLDALR*
```

ORF132ng-1 and ORF132-1 show 93.2% identity in 458 aa overlap:

```
orf132ng-1.pep  MKHIHIIGIGGTFMGGIAAIAKEAGFKVSGCDAKMYPPMSTQLEALGIGVHEGFDAAQLE
                |||||||||||||||||:|||||||||:||||||||||||||||||||| :|||||||:
orf132-1        MKHIHIIGIGGTFMGGLAAIAKEAGFEVSGCDAKMYPPMSTQLEALGIDVYEGFDAAQLD orf132ng-1.pep  EFQADIYVIGNVARRGMDVVEAILNRGLPYISGPQWLAENVLHHHWVLGVAGTHGKTTTA
                ||:||:|||||||:|||||||||||:||||||||||||:|||||||||||||||||||
orf132-1        EFKADVYVIGNVAKRGMDVVEAILNLGLPYISGPQWLSENVLHHHWVLGVAGTHGKTTTA orf132ng-1.pep  SMLAWVLEYAGLAPGFLIGGVPENFGVSARLPQTPRQDPNSKSPFFVIEADEYDTAFFDK
                ||||||||||||||||||||||||||||||||||||||||:|||||||||||||||||
orf132-1        SMLAWVLEYAGLAPGFLIGGVPENFGVSARLPQTPRQDPNSQSPFFVIEADEYDTAFFDK orf132ng-1.pep  RSKFVHYRPRTAVLNNLEFDHADIFADLGAIQTQFHHLVRTVPSEGLIVCNGQQQSLQDT
                |||||||||||||||||||||||||||||||||:|||||||||||||||:||||||||
orf132-1        RSKFVHYRPRTAVLNNLEFDHADIFADLGAIQTQFHYLVRTVPSEGLIVCNGRQQSLQDT orf132ng-1.pep  LDKGCWTPVEKFGTGHGWQIGEVNADGSFDVLLDGKKAGHVAWDLMGGHNRMNALAVIAA
                ||||||||||||| |||| ||:|||||||||||||| |:| ||||||||| ||||||||
orf132-1        LDKGCWTPVEKFGTEHGWQAGEANADGSFDVLLDGKTAGRVKWDLMGRHNRMNALAVIAA orf132ng-1.pep  ARHAGVDVQTACEALGAFKNVKRRMEIKGTANGITVYDDFAHHPTAIETTIQGLRQRVGG
                |||:|||:||||||||||||||||||||||||||||||||||||||||||||||||||
orf132-1        ARHVGVDIQTACEALGAFKNVKRRMEIKGTANGITVYDDFAHHPTAIETTIQGLRQRVGG orf132ng-1.pep  ARILAVLEPRSNTMKLGTMKSALPASLKEADQVFCYAGGADWDVAEALAPLGCRLRVGKD
                ||||||||||||||||||||||||:||||||||||||| |||||||||||| || ||||
orf132-1        ARILAVLEPRSNTMKLGTMKSALPVSLKEADQVFCYAGGVDWDVAEALAPLGGRLNVGKD orf132ng-1.pep  FDTFVAEIVKNARTGDHILVMSNGGFGGIHTKLLDALRX
                ||:||||||||::|||||||||||||||||| |||:|||
orf132-1        FDAFVAEIVKNAEVGDHILVMSNGGFGGIHGKLLEALRX
```

In addition, ORF132ng-1 is homologous to a hypothetical *E. coli* protein:

```
pir||S56459 hypothetical protein o457 - Escherichia coli >gi|537075
(U14003) ORF_o457 [Escherichia coli] >gi|1790680 (AE000494),
hypothetical 48.5 kD protein in fbp-pmba intergenic region
[Escherichia coli] Length = 457 Score = 474 bits (1207), Expect = e-133
Identities = 249/439 (56%), Positives = 294/439 (66%), Gaps = 13/439 (2%)

Query:  22 KEAGFKVSGCDAKMYPPMSTQLEALGIGVHEGFDAAQLEEFQADIYVIGNVARRGMDVVE  81
            ++ G +V+G DA +YPPMST LE  GI + +G+DA+QLE  Q D+ +IGN   RG   VE
Sbjct:  21 RQLGHEVTGSDANVYPPMSTLLEKQGIELIQGYDASQLEP-QPDLVIIGNAMTRGNPCVE  79
```

-continued

```
Query:  82 AILNRGLPYISGPQWLAENVLHHHWVLGVAGTHGKTTTASMLAWVLEYAGLAPGFLIGGV 141
           A+L + +PY+SGPQWL + VL   WVL VAGTHGKTTTA M  W+LE  G  PGF+IGGV
Sbjct:  80 AVLEKNIPYMSGPQWLHDFVLADRWVLAVAGTHGKTTTAGMATWILEQCGYKPGFVIGGV 139

Query: 142 PENFGVSARLPQTPRQDPNSKSPFFVIEADEYDTAFFDKRSKFVHYRPRTAVLNNLEFDH 201
           P NF VSA L            +S FFVIEADEYD AFFDKRSKFVHY PRT +LNNLEFDH
Sbjct: 140 PGNFEVSAHL---------GESDFFVIEADEYDCAFFDKRSKFVHYCPRTLILNNLEFDH 190

Query: 202 ADIFADLGAIQTQFHHLVRTVPSEGLIVCNGQQQSLQDTLDKGCWTPVEKFGTGHGWQIG 261
           ADIF DL AIQ QFHHLVR VP +G I+       +L+ T+  GCW+   E  G    WQ
Sbjct: 191 ADIFDDLKAIQKQFHHLVRIVPGOGRIIWPENDINLKQTMANGCWSEQELVGEQGHWQAK 250

Query: 262 EVNADGS-FDVLLDGKKAGHVAWDLMGGHNRMNALAVIAAARHAGVDVQTACEALGAFKN 320
               ++   D S ++VLLDG+K G V W L+G HN  N L  IAAARH GV   A  ALG+F N
Sbjct: 251 KLTTDASEWEVLLDGEKVGEVKWSLVGEHNMHNGLMAIAAARHVGVAPADAANALGSFIN 310

Query: 321 VKRRMEIKGTANGITVYDDFAHHPTAIETTIQGLRQRVGG-ARILAVLEPRSNTMKLGTM 379
             +RR+E++G ANG+TVYDDFAHHPTAI  T+  LR +VGG ARI+AVLEPRSNTMK+G
Sbjct: 311 ARRRLELRGEANGVTVYDDFAHHPTAILATLAALRGKVGGTARIIAVLEPRSNTMKMGIC 370

Query: 380 KSALPASLKEADQVF-CYAGGADWDVAEALAPLGCRLRVGKDFDTFVAEIVKNARTGDHI 438
           K   L  SL  AD+VF       W VAE       D DT     +VK A+ GDHI
Sbjct: 371 KDDLAPSLGRADEVFLLQPAHIPWQVAEVAEACVQPAHWSGDVDTLADMVVKTAQPGDHI 430

Query: 439 LVMSNGGFGGIHTKLLDAL                                         457
           LVMSNGGFGGIH KLLD L
Sbjct: 431 LVMSNGGFGGIHQKLLDGL                                         449
```

Based on this analysis, it was predicted that these proteins from N. meningitidis and N. gonorrhoeae, and their epitopes, could be useful antigens for vaccines or diagnostics, or for raising antibodies.

ORF132-1 (26.4 kDa) was cloned in pET and pGex vectors and expressed in E. coli, as described above. The products of protein expression and purification were analyzed by SDS-PAGE. FIG. 20A shows the results of affinity purification of the His-fusion protein, and FIG. 20B shows the results of expression of the GST-fusion in E. coli. Purified His-fusion protein was used to immunise mice, whose sera were used for FACS analysis (FIG. 20C) and ELISA (positive result). These experiments confirm that ORF132 is a surface-exposed protein, and that it is a useful immunogen.

Example 103

The following partial DNA sequence was identified in N. meningitidis <SEQ ID 875>

```
  1 ..CCGGGCTATT ACGGCTCGGA TGACGAATTT AAGCGGGCAT TCGGAGAAAA
 51   CTCGCCGACA TmCAAGAAAC ATTGCAACCG GAGCTGCGGG ATTTATGAAC
101   CCGTATTGAA AAAATACGGC AAAAAGCGCG CCAACAACCA TTCGGTCAGC
151   ATTAGTGCGG ACTTCGGCGA TTATTTCATG CCGTTCGCCA GCTATTCGCG
201   CACACACCGT ATGCCCAACA TCCAAGAAAT GTATTTTTCC CAAATCGGCG
251   ACTCCGGCGT TCACACCGCC TTAAAACCAG AGCGCGCAAA CACTTGGCAA
301   TTTGGCTTCr ATACCTATAA AAAAGGATTG TTAAAACAAG ATGATACATT
351   AGGATTAAAA CTGGTCGGCT ACCGCAGCCG CATCGACAAC TACATCCACA
401   ACGTTTACGG GAAATGGTGG GATTTGAACG GGGATATTCC GAGCTGGGTC
451   AGCAGCACCG GGCTTGCCTA CACCATCCAA CATCGCrATT TCAwAGACAA
501   AGTGCATCAA nnnnnnnnnn nnnnnnnnnn nnnnTACGAT TATGGGCGTT
551   TTTTCACCAA CCTTTCTTAC GCCTATCAAA AAAGCACGCA ACCGACCAAC
601   TTCAGCGATG CGAGCGAATC GCCCAACAAT GCGTCCAAAG AAGACCAACT
651   CAAACAAGGT TATGGGTTGA GCAGGGTTTC CGCCCTGCCG CGAGATTACG
701   GACGTTTGGA AGTCGGTACG CGCTGGTTGG GCAACAAACT GACTTTGGGC
751   GGCGCGATGC GCTATTTCGG CAAGAGCATC CGCGCGACGG CTGAAGAACG
801   CTATATCGAC GGCACCAACG GGGGAAATAC CAGCAATTTC CGGCAACTGG
851   GCAAGCGTTC CATCAAACAA ACCGAAACTC TTGCCCGCCA GCCTTTGATT
901   TTwGATTTTa ACGCCGCTTA CGAGCCGAAG AAAAACCTTA TTTTCCGCGC
```

-continued

```
 951   CGAAGTCAAA AATCTGTTCG ACAGGCGTTA TATCGATCCG CTCGATGCGG
1001   GCAATGATGC GGCAAC.GAG CGTTATTACA GCTCGTTCGA CCCGAAAGAC
1051   AAGGACrrAG ACGTAACGTG TAATGCTGAT AAAACGTTGT GCaACGGCAA
1101   ATACGGCGGC ACAAGCAAAA GCGTATTGAC CAATTTTGCA CGCGGACGCA
1151   CCTTTTTgAT GACGATGAGC TACAAGTTTT AA
```

This corresponds to the amino acid sequence <SEQ ID 876; ORF133>:

```
  1 ..PGYYGSDDEF KRAFGENSPT XKKHCNRSCG IYEPVLKKYG KKRANNHSVS
 51   ISADFGDYFM PFASYSRTHR MPNIQEMYFS QIGDSGVHTA LKPERANTWQ
101   FGFXTYKKGL LKQDDTLGLK LVGYRSRIDN YIHNVYGKWW DLNGDIPSWV
151   SSTGLAYTIQ HRXFXDKVHQ XXXXXXXXYD YGRFFTNLSY AYQKSTQPTN
201   FSDASESPNN ASKEDQLKQG YGLSRVSALP RDYGRLEVGT RWLGNKLTLG
251   GAMRYFGKSI RATAEERYID GTNGGNTSNF RQLGKRSIKQ TETLARQPLI
301   XDFNAAYEPK KNLIFRAEVK NLFDRRYIDP LDAGNDAAXE RYYSSFDPKD
351   KDXDVTCNAD KTLCNGKYGG TSKSVLTNFA RGRTFLMTMS YKF*
```

Further work revealed the further partial DNA sequence <SEQ ID 877>:

```
   1 GAGGCGCAGA TACAGGTTTT GGAAGATGTG CACGTCAAGG CGAAGCGCGT
  51 ACCGAAAGAC AAAAAAGTGT TTACCGATGC GCGTGCCGTA TCGACCCGTC
 101 AGGATATATT CAAATCCAGC GAAAACCTCG ACAACATCGT ACGCAGCATC
 151 CCCGGTGCGT TTACACAGCA AGATAAAAGC TCGGGCATTG TGTCTTTGAA
 201 TATTCGCGGC GACAGCGGGT TCGGGCGGGT CAATACGATG GTGGACGGCA
 251 TCACGCAGAC CTTTTATTCG ACTTCTACCG ATGCGGGCAG GGCAGGCGGT
 301 TCATCTCAAT TCGGTGCATC TGTCGACAGC AATTTTATTG CCGGACTGGA
 351 TGTCGTCAAA GGCAGCTTCA GCGGCTCGGC AGGCATCAAC AGCCTTGCCG
 401 GTTCGGCGAA TCTGCGGACT TTAGGCGTGG ATGACGTCGT TCAGGGCAAT
 451 AATACCTACG GCCTGCTGCT AAAAGGTCTG ACCGGCACCA ATTCAACCAA
 501 AGGTAATGCG ATGGCGGCGA TAGGTGCGCG CAAATGGCTG GAAAGCGGAG
 551 CATCTGTCGG TGTGCTTTAC GGGCACAGCA GGCGCAGCGT GGCGCAAAAT
 601 TACCGCGTGG GCGGCGGCGG GCAGCACATC GGAAATTTTG GCGCGGAATA
 651 TTTGGAACGG CGCAAGCAGC GATATTTTGT ACAAGAGGGT GCTTTGAAAT
 701 TCAATTCCGA CAGCGGAAAA TGGGAGCGGG ATTTACAAAG GCAACAGTGG
 751 AAATACAAGC CGTATAAAAA TTCAACAAC CAAGAACTAC AaAAATACAT
 801 CGAAGAGCAT GACAAAAGCT GGCGGGAAAA CCTg.CaCCG CAATACGACA
 851 TTACCCCCAT CGATCCGTCC AGCCTGAAGC AGCAGTCGGC AGGCAATCTG
 901 TTTAAATTGG AATACGACGG CGTATTCAAT AAATACACGG CGCAATTTCG
 951 CGATTTAAAC ACCAAAATCG GCAGCCGCAA AATCATCAAC CGCAATTATC
1001 AGTTCAATTA CGGTTTGTCT TTGAACCCGT ATACCAACCT CAATCTGACC
1051 GCAGCCTACA ATTCGGGCAG GCAGAAATAT CCGAAAGGGT CGAAGTTTAC
```

-continued

```
1101 AGGCTGGGGG CTTTTAAAGG ATTTTGAAAC CTACAACAAC GCGAAAATCC
1151 TCGACCTCAA CAACACCGCC ACCTTCCGGC TGCCCCGCGA AACCGAGTTG
1201 CAAACCACTT TGGGCTTCAA TTATTTCCAC AACGAATACG GCAAAAACCG
1251 CTTTCCTGAA GAATTGGGGC TGTTTTTCGA CGGTCCTGAT CAGGACAACG
1301 GGCTTTATTC CTATTTGGGG CGGTTTAAGG GCGATAAAGG GCTGCTGCCC
1351 CAAAAATCAA CCATTGTCCA ACCGGCCGGC AGCCAATATT TCAACACGTT
1401 CTACTTCGAT GCCGCGCTCA AAAAGACAT TTACCGCTTA AACTACAGCA
1451 CCAATACCGT CGGCTACCGT TTCGGCGGCG AATATACGGG CTATTACGGC
1501 TCGGATGACG AATTTAAGCG GGCATTCGGA GAAAACTCGC CGACATACAA
1551 GAAACATTGC AACCGGAGCT GCGGGATTTA TGAACCCGTA TTGAAAAAAT
1601 ACGGCAAAAA GCGCGCCAAC AACCATTCGG TCAGCATTAG TGCGGACTTC
1651 GGCGATTATT TCATGCCGTT CGCCAGCTAT TCGCGCACAC ACCGTATGCC
1701 CAACATCCAA GAAATGTATT TTTCCCAAAT CGGCGACTCC GGCGTTCACA
1751 CCGCCTTAAA ACCAGAGCGC GCAAACACTT GGCAATTTGG CTTCAATACC
1801 TATAAAAAAG GATTGTTAAA ACAAGATGAT ACATTAGGAT TAAAACTGGT
1851 CGGCTACCGC AGCCGCATCG ACAACTACAT CCACAACGTT TACGGGAAAT
1901 GGTGGGATTT GAACGGGGAT ATTCCGAGCT GGGTCAGCAG CACCGGGCTT
1951 GCCTACACCA TCCAACATCG CAATTTCAAA GACAAAGTGC ACAAACACGG
2001 TTTTGAGTTG GAGCTGAATT ACGATTATGG GCGTTTTTTC ACCAACCTTT
2051 CTTACGCCTA TCAAAAAAGC ACGCAACCGA CCAACTTCAG CGATGCGAGC
2101 GAATCGCCCA ACAATGCGTC CAAAGAAGAC CAACTCAAAC AAGGTTATGG
2151 GTTGAGCAGG GTTTCCGCCC TGCCGCGAGA TTACGGACGT TTGGAAGTCG
2201 GTACGCGCTG GTTGGGCAAC AAACTGACTT TGGGCGGCGC GATGCGCTAT
2251 TTCGGCAAGA GCATCCGCGC GACGGCTGAA GAACGCTATA TCGACGGCAC
2301 CAACGGGGGA AATACCAGCA ATTTCCGGCA ACTGGGCAAG CGTTCCATCA
2351 AACAAACCGA AACTCTTGCC CGCCAGCCTT TGATTTTTGA TTTTTACGCC
2401 GCTTACGAGC CGAAGAAAAA CCTTATTTTC CGCGCCGAAG TCAAAAATCT
2451 GTTCGACAGG CGTTATATCG ATCCGCTCGA TGCGGGCAAT GATGCGGCAA
2501 CGCAGCGTTA TTACAGCTCG TTCGACCCGA AAGACAAGGA CGAAGACGTA
2551 ACGTGTAATG CTGATAAAAC GTTGTGCAAC GGCAAATACG GCGGCACAAG
2601 CAAAAGCGTA TTGACCAATT TTGCACGCGG ACGCACCTTT TTGATGACGA
2651 TGAGCTACAA GTTTTAA
```

This corresponds to the amino acid sequence <SEQ ID 878; ORF133-1>:

```
  1 EAQIQVLEDV HVKAKRVPKD KKVFTDARAV STRQDIFKSS ENLDNIVRSI
 51 PGAFTQQDKS SGIVSLNIRG DSGFGRVNTM VDGITQTFYS TSTDAGRAGG
101 SSQFGASVDS NFIAGLDVVK GSFSGSAGIN SLAGSANLRT LGVDDVVQGN
151 NTYGLLLKGL TGTNSTKGNA MAAIGARKWL ESGASVGVLY GHSRRSVAQN
201 YRVGGGGQHI GNFGAEYLER RKQRYFVQEG ALKFNSDSGK WERDLQRQQW
```

-continued

```
251 KYKPYKNYNN QELQKYIEEH DKSWRENLXP QYDITPIDPS SLKQQSAGNL

301 FKLEYDGVFN KYTAQFRDLN TKIGSRKIIN RNYQFNYGLS LNPYTNLNLT

351 AAYNSGRQKY PKGSKFTGWG LLKDFETYNN AKILDLNNTA TFRLPRETEL

401 QTTLGFNYFH NEYGKNRFPE ELGLFFDGPD QDNGLYSYLG RFKGDKGLLP

451 QKSTIVQPAG SQYFNTFYFD AALKKDIYRL NYSTNTVGYR FGGEYTGYYG

501 SDDEFKRAFG ENSPTYKKHC NRSCGIYEPV LKKYGKKRAN NHSVSISADF

551 GDYFMPFASY SRTHRMPNIQ EMYFSQIGDS GVHTALKPER ANTWQFGFNT

601 YKKGLLKQDD TLGLKLVGYR SRIDNYIHNV YGKWWDLNGD IPSWVSSTGL

651 AYTIQHRNFK DKVHKHGFEL ELNYDYGRFF TNLSYAYQKS TQPTNFSDAS

701 ESPNNASKED QLKQGYGLSR VSALPRDYGR LEVGTRWLGN KLTLGGAMRY

751 FGKSIRATAE ERYIDGTNGG NTSNFRQLGK RSIKQTETLA RQPLIFDFYA

801 AYEPKKNLIF RAEVKNLFDR RYIDPLDAGN DAATQRYYSS FDPKDKDEDV

851 TCNADKTLCN GKYGGTSKSV LTNFARGRTF LMTMSYKF*
```

Computer analysis of this amino acid sequence gave the following results:

Homology with the Probable TonB-dependent Receptor HI121 of *H. influenzae* (Accession Number U32801)

ORF133 and HI121 show 57% aa identity in 363aa overlap:

```
Orf133:   31 IYEPVLKKYGKKRANNHSVSISADFGDYFMPFASYSRTHRMPNIQEMYFSQIGDSGVHTA   90
             I EP+L K G K+A NHS ++SA+ DYFMPF +YSRTHRMPNIQEM+FSQ+ ++GV+TA
HI121:   563 INEPILHKSGHKKAFNHSATLSAELSDYFMPFFTYSRTHRMPNIQEMFFSQVSNAGVNTA  622

Orf133:   91 LKPERANTWQFGFXTYKKGLLKQDDTLGLKLVGYRSRIDNYIHNVYGKWWDLNGDIPSWV  150
             LKPE+++T+Q GF TYKKGL QDD LG+KLVGYRS I NYIHNVYG WW    +P+W
HI121:   623 LKPEQSDTYQLGFNTYKKGLFTQDDVLGVKLVGYRSFIKNYIHNVYGVWW--RDGMPTWA  680

Orf133:  151 SSTGLAYTIQHRXFXDKVHXXXXXXXXXXYDYGRFFTNLSYAYQKSTQPTNFSDASESPNN  210
               S G  YTI H+ +  V          YD GRFF N+SYAYQ++ QPTN++DAS  PNN
HI121:   681 ESNGFKYTIAHQNYKPIVKKSGVELEINYDMGRFFANVSYAYQRTNQPTNYADASPRPNN  740

Orf133:  211 ASKEDQLKQGYGLSRVSALPRDYGRLEVGTRWLGNKLTLGGAMRYFGKSIRATAEERYID  270
             AS+ED LKQGYGLSRVS LP+DYGRLE+GTRW   KLTLG A RY+GKS RAT EE YI+
HI121:   741 ASQEDILKQGYGLSRVSMLPKDYGRLELGTRWFDQKLTLGLAARYYGKSKRATIEEEYIN  800

Orf133:  271 GTNGGNTSNFRQLGKRSIKQTETLARQPLIXDFNAAYEPKKNLIFRAEVKNLFDRRYIDP  330
             G+   + R+    ++K+TE +  +QP+I D + +YEP K+LI +AEV+NL D+RY+DP
HI121:   801 GSR-FKKNTLRRENYYAVKKTEDIKKQPIILDLHVSYEPIKDLIIKAEVQNLLDKRYVDP  859

Orf133:  331 LDAGNDAAXERYYSSFDPKDKDXDVTCNADKTLCNGKYGGTSKSVLTNFARGRTFLMTMS  390
             LDAGNDAA +RYYSS     +  + C  D + C    GG+ K+VL NFARGRT++++++
HI121:   860 LDAGNDAASQRYYSSL-----NNSIECAQDSSAC----GGSDKTVLYNFARGRTYILSLN  910

Orf133:  391 YKF                                                          393
             YKF
HI121:   911 YKF                                                          913
```

Homology with a Predicted ORF from *N. meningitidis* (Strain A)

ORF133 shows 90.8% identity over a 392aa overlap with an ORF (ORF133a) from strain A of *N. meningitidis*:

```
                                             10        20        30
    orf133.pep                        PGYYGSDDEFKRAFGENSPTXKKHCNRSCGI
                                      ||| |||||||||||||| |||:|||
    orf133a      FYFDAALKKDIYRLNYSTNTVGYRFGGXYTGYYXSDDEFKRAFGENSPTXKHCNQSCGI
                     450       460       470       480       490       500
```

```
                     40          50         60          70         80         90
orf133.pep   YEPVLKKYGKKRANNHSVSISADFGDYFMPFASYSRTHRMPNIQEMYFSQIGDSGVHTAL
             ||||||||||||||||||||||||||||||||||||||||||||||||||||||||||||
orf133a      YEPVLKKYGKKRANNHSVSISADFGDYFMPFASYSRTHRMPNIQEMYFSQIGDSGVHTAL
             510         520        530        540        550        560
                     100         110        120        130        140        150
orf133.pep   KPERANTWQFGFXTYKKGLLKQDDTLGLKLVGYRSRIDNYIHNVYGKWWDLNGDIPSWVS
             |||||||||||| |||||||||||||| ||||||||||||| ||||||||||||| ||||
orf133a      KPERANTWQFGENTYKKGLLKQDDILGLKLVGYRSRIDXYIHNVYGKWWDLNGNIPSWVS
             570         580        590        600        610        620
                     160         170        180        190        200        210
orf133.pep   STGLAYTIQHRXFXDKVHQXXXXXXXXXYDYGRFFTNLSYAYQKSTQPTNFSDASESPNNA
             |||||||||||| | ||||:          ||| ||||||||||||||||||||||||||
orf133a      STGLAYTIQHRNFKDKVHKHGFELELNYDYXRFFTNLSYAYQKSTQPTNFSDASESPNNA
             630         640        650        660        670        680
                     220         230        240        250        260        270
orf133.pep   SKEDQLKQGYGLSRVSALPRDYGRLEVGTRWLGNKLTLGGAMRYFGKSIRATAEERYIDG
             ||||||||||||||||||||||||||||||||||||||||||||||||||||||||||||
orf133a      SKEDQLKQGYGLSRVSALPRDYGRLEVGTRWLGNKLTLGGAMRYFGKSIRATAEERYIDX
             690         700        710        720        730        740
                     280         290        300        310        320        330
orf133.pep   TNGGNTSNFRQLGKRSIKQTETLARQPLIXDFNAAYEPKKNLIFRAEVKNLFDRRYIDPL
             ||||  ||||||||||| |||||||||| || ||||||| | ||||||||||||||||||
orf133a      TNGXXTSNFRQLGKRSIXQTETLARQPLIFDXYAAYEPKKXLIFRAEVKNLFDRRYIDPL
             750         760        770        780        790        800
                     340         350        360        370        380        390
orf133.pep   DAGNDAAXERYYSSFDPKDKDXDVTCNADKTLCNGKYGGTSKSVLTNFARGRTFLMTMSY
             ||||||||::||||||||||| ::||| :||||||||||||||||||||||| |||:|||
orf133a      DAGMDAATQRYYSSFDPKDKDEEVTCNDDNTLCNGKYGGTSKSVLTNFARGXTFLITMSY
             810         820        830        840        850        860
orf133.pep   KFX
             |||
orf133a      KFX
             870
```

A partial ORF133a nucleotide sequence <SEQ ID 879> is:

```
   1 AAAGACAAAA AAGTGTTTAC CGATGCGCGT GCCGTATCGA CCCGTCAGGA
  51 TATATTCAAA TCCANCGAAA ACCTCGACAA CATCGTACGC ANCATCCCCG
 101 GTGCGTTTAC ACANCAANAT AAAAGCTCGG GCNTTGTGTC TTTGAATATT
 151 CGCNGCGACA GCGGGTTCGG GCGGGTCAAT ACNATGGTNG ACGGCATCAC
 201 NCANACCTTT TATTCGACTT CTACCGATGC GGGCAGGGCA GGCGGTTCAT
 251 CTCAATTCGG TGCATCTGTC GACAGCAATT TTATNGCCGG ACTGGATGTC
 301 GTCAAAGGCA GCTTCAGCGG CTCGGCAGGC ATCAACAGCC TTGCCGGTTC
 351 GGCGAATCTG CGGACTTTAN GCGTGGATGA TGTCGTTCAG GGCAATANTA
 401 CNTACGGCCT GCTGCTAAAA GGTCTGACCG GCACCAATTC AACCAAAGGT
 451 AATGCGATGG CGGCGATAGG TGCGCGCAAA TGGCTGGAAA GCGGAGCATC
 501 TGTCGGTGTG CTTTACGGGC ACAGCAGGCG CAGCGTGGCG CAAAATTACC
 551 GCGTGGGCGG CGGCGGGCAG CACATCGGAA ATTTTGGCGC GGAATATCTG
 601 GAACGACGCA AGCAACGATA TTTTGAGCAA GAAGGCGGGT TGAAATTCAA
 651 TTCCAACAGC GGAAAATGGG AGCGGGATTT CCAAAAGTCG TACTGGAAAA
 701 CCAAGTGGTA TCAAAAATAC GATGCCCCCC AAGAACTGCA AAAATACATC
 751 GAAGGTCATG ATAAAAGCTG GCGGGAAAAC CTGGCGCCGC AATACGACAT
 801 CACCCCCATC GATCCGTCCA GCCTGAAGCN GCAGTCGGCA GGCAACCTGT
 851 TTAAATTGGA ATACGACGGC GTATTCAATA AATACACGGC GCAATTTCGC
 901 GATTTAAACA CCAAAATCGG CAGCCGCAAA ATCATCAACC GCAATTATCA
 951 ATTCAATTAC GGTTTGTCTT TGAACCCGTA TACCAACCTC AATCTGACCG
1001 CAGCCTACAA TTCGGGCAGG CAGAAATATC CGAAAGGGTC GAAGTTTACA
```

```
-continued
1051 GGCTGGGGGC TTTTNAAAGA TTTTGAAACC TACAACAACG CAAAAATCCT

1101 CGACCTCANC AACACCTCCA CCTTCCGGCT GCCCCGTGAA ACCGAGTTGC

1151 AAACCACTTT GGGCTTCAAT TATTTCCACA ACGAATACGG CAAAAACCGC

1201 TTTCCTGAAG AATTGGGGCT GTTTTTCGAC GGTCCGGATC ANGACAACGG

1251 GCTTTATTCC TATTTGGGGC GGTTTAAGGG CGATAAAGGG CTGCTGCCCC

1301 AAAAATCAAC CATTGTCCAA CCGGCCGGCA GCCAATATTT CAACACGTTC

1351 TACTTCGATG CCGCGCTCAA AAAAGACATT TACCGCTTAA ACTACAGCAC

1401 CAATACCGTC GGCTACCGTT TCGGCGGCNA ATATACGGGC TATTACNGCT

1451 CGGATGACGA ATTTAAGCGG GCATTCGGAG AAAACTCGCC GACATACANG

1501 AAACATTGCA ACCAGAGCTG CGGAATTTAT GAACCCGTAT TGAAAAAATA

1551 CGGCAAAAAG CGCGCCAACA ACCATTCGGT CAGCATTAGT GCGGACTTCG

1601 GCGATTATTT CATGCCGTTC GCCAGCTATT CGCGCACACA CCGTATGCCC

1651 AACATCCAAG AAATGTATTT TTCCCAAATC GGCGACTCCG GCGTTCACAC

1701 CGCCTTAAAA CCAGAGCGCG CAAACACTTG GCAATTTGGC TTCAATACCT

1751 ATAAAAAAGG ATTGTTAAAA CAAGATGATA TATTAGGATT AAAACTGGTC

1801 GGCTACCGCA GCCGCATCGA CNACTACATC CACAACGTTT ACGGGAAATG

1851 GTGGGATTTG AACGGGAATA TTCCGAGCTG GGTCAGCAGC ACCGGGCTTG

1901 CCTACACCAT CCAACACCGC AATTTCAAAG ACAAAGTGCA CAAACACGGT

1951 TTTGAGTTGG AGCTGAATTA CGATTATNGG CGTTTTTTCA CCAACCTTTC

2001 TTACGCCTAT CAAAAAAGCA CGCAACCGAC CAACTTCAGC GATGCGAGCG

2051 AATCGCCCAA CAATGCGTCC AAAGAAGACC AACTCAAACA AGGTTATGGG

2101 TTGAGCAGGG TTTCCGCCCT GCCGCGAGAT TACGGACGTT GGAAGTCGG

2151 TACGCGCTGG TTGGGCAACA AACTGACTTT GGGCGGCGCG ATGCGCTATT

2201 TCGGCAAGAG CATCCGCGCG ACGGCTGAAG AACGCTATAT CGACGNCACC

2251 AATGGGGNAN NTACCAGCAA TTTCCGGCAA CTGGGCAAGC GTTCCATCAN

2301 ACAAACCGAA ACCCTTGCCC GCCAGCCTTT GATTTTTGAT TTNTACGCCG

2351 CTTACGAGCC GAAGAAAAAN CTTATTTTCC GCGCCGAAGT CAAAAATCTG

2401 TTCGACAGGC GTTATATCGA TCCGCTCGAT GCGGGCAATG ATGCGGCAAC

2451 GCAGCGTTAT TACAGTTCGT TCGACCCGAA AGACAAGGAC GAAGAAGTAA

2501 CGTGTAATGA TGATAACACG TTATGCAACG GCAAATACGG CGGCACAAGC

2551 AAAAGCGTAT TGACCAATTT TGCACGCGGA CNCACCTTTT TGATAACGAT

2601 GAGCTACAAG TTTTAA
```

This encodes a protein having (partial) amino acid sequence <SEQ ID 880>:

```
  1 KDKKVFTDAR AVSTRQDIFK SXENLDNIVR XIPGAFTXQX KSSGXVSLNI

51 RXDSGFGRVN TMVDGITXTF YSTSTDAGRA GGSSQFGASV DSNFXAGLDV

101 VKGSFSGSAG INSLAGSANL RTLXVDDVVQ GNXTYGLLLK GLTGTNSTKG

151 NAMAAIGARK WLESGASVGV LYGHSRRSVA QNYRVGGGGQ HIGNFGAEYL

201 ERRKQRYFEQ EGGLKFNSNS GKWERDFQKS YWKTKWYQKY DAPQELQKYI

251 EGHDKSWREN LAPQYDITPI DPSSLKXQSA GNLFKLEYDG VFNKYTAQFR
```

```
301 DLNTKIGSRK IINRNYQFNY GLSLNPYTNL NLTAAYNSGR QKYPKGSKFT

351 GWGLXKDFET YNNAKILDLX NTSTFRLPRE TELQTTLGFN YFHNEYGKNR

401 FPEELGLFFD GPDXDNGLYS YLGRFKGDKG LLPQKSTIVQ PAGSQYFNTF

451 YFDAALKKDI YRLNYSTNTV GYRFGGXYTG YYXSDDEFKR AFGENSPTYX

501 KHCNQSCGIY EPVLKKYGKK RANNHSVSIS ADFGDYFMPF ASYSRTHRMP

551 NIQEMYFSQI GDSGVHTALK PERANTWQFG FNTYKKGLLK QDDILGLKLV

601 GYRSRIDXYI HNVYGKWWDL NGNIPSWVSS TGLAYTIQHR NFKDKVHKHG

651 FELELNYDYX RFFTNLSYAY QKSTQPTNFS DASESPNNAS KEDQLKQGYG

701 LSRVSALPRD YGRLEVGTRW LGNKLTLGGA MRYFGKSIRA TAEERYIDXT

751 NGXXTSNFRQ LGKRSIXQTE TLARQPLIFD XYAAYEPKKX LIFRAEVKNL

801 FDRRYIDPLD AGNDAATQRY YSSFDPKDKD EEVTCNDDNT LCNGKYGGTS

851 KSVLTNFARG XTFLITMSYK F*
```

ORF133a and ORF133-1 show 94.3% identity in 871 aa overlap:

```
                        10         20         30         40
orf133a.pep             KDKKVFTDARAVSTRQDIFKSXENLDNIVRXIPGAFTXQXKS
                        |||||||||||||||||||| |||||||||| ||||| | ||
orf133-1    EAQIQVLEDVHVKAKRVPKDKKVFTDARAVSTRQDIFKSSENLDNIVRSIPGAFTQQDKS
            10         20         30         40         50         60

50         60         70         80         90        100
orf133a.pep     SGXVSLNIRXDSGFGRVNTMVDGITXTFYSTSTDAGRAGGSSQFGASVDSNFXAGLDVVK
                || ||||||| ||||||||||||||| |||||||||||||||||||||||||| ||||||
orf133-1        SGIVSLNIRGDSGFGRVNTMVDGITQTFYSTSTDAGRAGGSSQFGASVDSNFIAGLDVVK
                70         80         90        100        110        120

110        120        130        140        150        160
orf133a.pep     GSFSGSAGINSLAGSANLRTLXVDDVVQGNXTYGLLLKGLTGTNSTKGNAMAAIGARKWL
                |||||||||||||||||||||| ||||||||| |||||||||||||||||||||||||||
orf133-1        GSFSGSAGINSLAGSANLRTLGVDDVVQGNNTYGLLLKGLTGTNSTKGNAMAAIGARKWL
                130        140        150        160        170        180

170        180        190        200        210        220
orf133a.pep     ESGASVGVLYGHSRRSVAQNYRVGGGGQHIGNFGAEYLERRKQRYFEQEGGLKFNSNSGK
                |||||||||||||||||||||||||||||||||||||||||||||| :||||| ::|||
orf133-1        ESGASVGVLYGHSRRSVAQNYRVGGGGQHIGNFGAEYLERRKQRYFVQEGALKFNSDSGK
                190        200        210        220        230        240

230        240        250        260        270        280
orf133a.pep     WERDFQKSYWKTKWYQKYDAPQELQKYIEGHDKSWRENLAPQYDITPIDPSSLKXQSAGN
                ||||:|::||| |  |::|:   ||||||||||||||||| ||||||||||||| |||||
orf133-1        WERDLQRQQWKYKPYKNYNN-QELQKYIEEHDKSWRENLXPQYDITPIDPSSLKQQSAGN
                250        260        270        280        290

290        300        310        320        330        340
orf133a.pep     LFKLEYDGVFNKYTAQFRDLNTKIGSRKIINRNYQFNYGLSLNPYTNLNLTAAYNSGRQK
                |||||||||||||||||||||||||||||||||||||||||||||||||||||| |||||
orf133-1        LFKLEYDGVFNKYTAQFRDLNTKIGSRKIINRNYQFNYGLSLNPYTNLNLTAATNSGRQK
                300        310        320        330        340        350

350        360        370        380        390        400
orf133a.pep     YPKGSKFTGWGLXKDFETYNNAKILDLXNTSTFRLPRETELQTTLGFNYFHNEYGKNRFP
                |||||||||||| ||||||||||||||| |:||||||||||||||||||||||||||||
orf133-1        YPKGSKFTGWGLLKDFETYNNAKILDLNNTATFRLPRETELQTTLGFNYFHNEYGKNRFP
                360        370        380        390        400        410

410        420        430        440        450        460
orf133a.pep     EELGLFFDGPDXDNGLYSYLGRFKGDKGLLPQKSTIVQPAGSQYFNTFYFDAALKKDIYR
                |||||||||||| ||||||||||||||||||||||||||||||||||||||||||||| 
orf133-1        EELGLFFDGPDQDNGLYSYLGRFKGDKGLLPQKSTIVQPAGSQYFNTFYFDAALKKDITR
                420        430        440        450        460        470

470        480        490        500        510        520
orf133a.pep     LNYSTNTVGYRFGGXYTGYYXSDDEFKRAFGENSPTYXKHCNQSCGIYEPVLKKYGKKRA
                |||||||||||||| |||||| ||||||||||||||| |||| |||||||||||||||||
orf133-1        LNYSTNTVGYRFGGEYTGYYGSDDEFKRAFGENSPTYKKHCNRSCGIYEPVLKKYGKKRA
                480        490        500        510        520        530

530        540        550        560        570        580
orf133a.pep     NNHSVSISADFGDYFMPFASYSRTHRMPNIQEMYFSQIGDSGVHTALKPERANTWQFGFN
                ||||||||||||||||||||||||||||||||||||||||||||||||||||||||||||
orf133-1        NNHSVSISADFGDYFMPFASYSRTHRMPNIQEMYFSQIGDSGVHTALKPERANTWQFGFN
                540        550        560        570        580        590
```

```
                    590       600       610       620       630       640
orf133a.pep   TYKKGLLKQDDILGLKLVGYRSRIDXYIHNVYGKWWDLNGNIPSWVSSTGLAYTIQHRNF
              ||||||||||| |||||||||||| ||||||||||||:||||||||||||||||||||||
orf133-1      TYKKGLLKQDDTLGLKLVGYRSRIDNYIHNVYGKWWDLNGDIPSWVSSTGLAYTIQHRNF
              600       610       620       630       640       650

650       660       670       680       690       700
orf133a.pep   KDKVHKHGFELELNYDYXRFFTNLSYAYQKSTQPTNFSDASESPNNASKEDQLKQGYGLS
              |||||||||||||||| |||||||||||||||||||||||||||||||||||||||||||
orf133-1      KDKVHKHGFELELNYDYGRFFTNLSYAYQKSTQPTNFSDASESPNNASKEDQLKQGYGLS
              660       670       680       690       700       710

710       720       730       740       750       760
orf133a.pep   RVSALPRDYGRLEVGTRWLGNKLTLGGAMRYFGKSIRATAEERYIDXTNGXXTSNFRQLG
              |||||||||||||||||||||||||||||||||||||||||||||| ||| ||||||||
orf133-1      RVSALPRDYGRLEVGTRWLGNKLTLGGAMRYFGKSIRATAEERYIDGTNGGNTSNFRQLG
              720       730       740       750       760       770

770       780       790       800       810       820
orf133a.pep   KRSIXQTETLARQPLIFDXYAAYEPKKXLIFRAEVKNLFDRRYIDPLDAGNDAATQRYYS
              |||| |||||||||||||| |||||||| |||||||||||||||||||||||||||||||
orf133-1      KRSIKQTETLARQPLIFDFYAAYEPKKNLIFRAEVKNLFDRRYIDPLDAGNDAATQRYYS
              780       790       800       810       820       830

830       840       850       860       870
orf133a.pep   SFDPKDKDEEVTCNDDNTLCNGKYGGTSKSVLTNFARGXTFLITMSYKFX
              ||||||||:||| |:|||||||||||||||||||||| |||:||||||||
orf133-1      SFDPKDKDEDVTCNADKTLCNGKYGGTSKSVLTNFARGRTFLMTMSYKFX
              840       850       860       870       880
```

Homology with a Predicted ORF from *N. gonorrhoeae*

ORF133 shows 92.3% identity over 392 aa overlap with a predicted ORF (ORF133ng) from *N. gonorrhoeae*:

```
orf133.pep                                 PGYYGSDDEFKRAFGENSPTXKKHCNRSCGI   31
                                           |||||::|||||||||||: |:||:  |||:
orf133ng      FYFDAALKKDIYRLNYSTNAINYRFGGEYTGYYGSENEFKRAFGENSPAYKEHCDPSCGL  560
orf133.pep    YEPVLKKYGKKRANNHSVSISADFGDYFMPFASYSRTHRMPNIQEMYFSQIGDSGVHTAL   91
              |||||||||  |||||||||||||||||||||:||||||||||||||||||||||||||||
orf133ng      YEPVLKKYGDDRANNHSVSISADFGDYFMPFAGYSRTHRMPNIQEMYFSQIGDSGVHTAL  620
orf133.pep    KPERANTWQFGFXTYKKGLLKQDDTLGLKLVGYRSRIDNYIHNVYGKWWDLNGDIPSWVS  151
              ||||||||||||| ||||||||||:|||||||||||||||||| ||||||||||||||||:
orf133ng      KPERANTWQFGFNTYKKGLLKQDDILGLKLVGYRSRIDNYIGNVYGKWWDLNGDIPSWVG  680
orf133.pep    STGLAYTIQHRXFXDKVHQXXXXXXXXXYDYGRFFTNLSYAYQKSTQPTNFSDASESPNNA 211
              |||||||:|| | |||:             |||||||||||||||||||||||||||||||
orf133ng      STGLAYTIRHRNFKDKVHKHGFELELNYDYGRFFTNLSYSYQKSTQPTNFSDASESPNNA  740
orf133.pep    SKEDQLKQGYGLSRVSALPRDYGRLEVGTRWLGNKLTLGGAMRYFGKSIRATAEERYIDG  271
              ||||||||||||||||||||||||||||||||||||||||||||||||||||||||||||
orf133ng      SKEDQLKQGYGLSRVSALPRDYGRLEVGTRWLGNKLTLGGAMRYFGKSIRATAEERYIDG  800
orf133.pep    TNGGNTSNFRQLGKRSIKQTETLARQPLIXDFNAAYEPKKNLIFRAEVKNLFDRRYIDPL  331
              ||||||||:|||| ||||||||||||||| || |||||||||||||||||||||||||||
orf133ng      TNGGNTSNVRQLGKRSIKQTETLARQPLIFDFYAAYEPKKNLIFRAEVKNLFDRRYIDPL  860
orf133.pep    DAGNDAAXERYYSSFDPKDKDXDVTCNADKTLCNGKYGGTSKSVLTNFARGRTFLMTMSY  391
              |||||||::|||||||||||| ||||||||||||||||||||||||||||||||||||||
orf133ng      DAGNDAATQRYYSSFDPKDKDEDVTCNADKTLCNGKYGGTSKSVLTNFARGRTFLMTMSY  920
orf133.pep    KF  393
              ||
orf133ng      KF  922
```

The complete length ORF133ng nucleotide sequence <SEQ ID 881> is predicted to encode a protein having amino acid sequence <SEQ ID 882>:

```
  1  MRSSFRLKPI CFYLMGVMLY HHSYAEDAGR AGSEAQIQVL EDVHVKAKRV

51  PKDKKVFTDA RAVSTRQDVF KSGENLDNIV RSIPGAFTQQ DKSSGIVSLN

101  IRGDSGFGRV NTMVDGITQT FYSTSTDAGR AGGSSQFGAS VDSNFIAGLD

151  VVKGSFSGSA GINSLAGSAN LRTLGVDDVV QGNNTYGLLL KGLTGTNSTK

201  GNAMAAIGAR KWLESGASVG VLYGHSRRGV AQNYRVGGGG QHIGNFGEEY

251  LERRKQQYFV QEGGLKFNAG SGKWERDLQR QYWKTKWYKK YEDPQELQKY

301  IEEHDKSWRE NLAPQYDITP IDPSGLKQQS AGNLLNLEYD GVFNKYTAQF

351  RDLNTRIGSR KIINRNYQFN YGLSLNPYTN LNLTAAYNSG RQKYPKGAKF
```

```
401 TGWGLLKDFE TYNNAKILDL NNTATFRLPR ETELQTTLGF NYFHNEYGKN

451 RFPEELGLFF DGPDQDNGLY SYLGRFKGDK GLLPQKSTIV QPAGSQYFNT

501 FYFDAALKKD IYRLNYSTNA INYRFGGEYT GYYGSENEFK RAFGENSPAY

551 KEHCDPSCGL YEPVLKKYGK KRANNHSVSI SADFGDYFMP FAGYSRTHRM

601 PNIQEMYFSQ IGDSGVHTAL KPERANTWQF GFNTYKKGLL KQDDILGLKL

651 VGYRSRIDNY IHNVYGKWWD LNGDIPSWVG STGLAYTIRH RNFKDKVHKH

701 GFELELNYDY GRFFTNLSYA YQKSTQPTNF SDASESPNNA SKEDQLKQGY

751 GLSRVSALPR DYGRLEVGTR WLGNKLTLGG AMRYFGKSIR ATAEERYIDG

801 TNGGNTSNVR QLGKRSIKQT ETLARQPLIF DFYAAYEPKK NLIFRAEVKN

851 LFDRRYIDPL DAGNDAATQR YYSSFDPKDK DEDVTCNADK TLCNGKYGGT

901 SKSVLTNFAR GRTFLMTMSY KF*
```

A variant was also identified, being encoded by the gonococcal DNA sequence <SEQ ID 883>:

```
   1 ATGAGATCTT CTTTCCGGTT GAAGCCGATT TGTTTTTATC TTATGGGTGT

51 TATGCTATAT CATCATAGTT ATGCCGAAGA TGCAGGGCGC GCGGGCAGCG

101 AGGCGCAGAT ACAGGTTTTG GAAGATGTGC ACGTCAAGGC GAAGCGCGTA

151 CCGAAAGACA AAAAGTGTT TACCGATGCG CGTGCCGTAT CGACCCGTca 201 gGATGTGTTC AAATCCGGCG AAAACCTCGA CAACATCGTA CGCAGCATAC

251 CCGGTGCGTT TACACAGCAA GATAAAAGCT CGGGCATTGT GTCTTTGAAT

301 ATTCGCGGCG ACAGCGGGTT CGGGCGGGTC AATACGATGG TGGACGGCAT

351 CACGCAGACC TTTTATTCGA CTTCTACCGA TGCGGGCAGG GCAGGCGGTT

401 CATCTCAATT CGGTGCATCT GTCGACAGCA ATTTTATTGC CGGACTGGAT

451 GTCGTCAAAG GCAGCTTCAG CGGCTCGGCA GGCATCAACA GCCTTGCCGG

501 TTCGGCGAAT CTGCGGACTT TAGGCGTGGA TGACGTCGTT CAGGGCAATA

551 ATACCTACGG CCTGCTGCTA AAAGGTCTGA CCGGCACCAA TTCAACCAAA

601 GGTAATGCGA TGGCGGCGAT AGGTGCGCGC AAATGGCTGG AAAGCGGAGC

651 GTCTGTCGGT GTGCTTTACG GGCACAGCAG GCGCGGCGTG GCGCAAAATT

701 ACCGCGTGGG CGGCGGCGGG CAGCACATCG GAAATTTTGG TGAAGAATAT

751 CTGGAACGGC GCAAACAGCA ATATTTTGTA CAAGAGGGTG GTTTGAAATT

801 CAATGCCGGC AGCGGAAAAT GGGAACGGGA TTTGCAAAGG CAATACTGGA

851 AAACAAAGTG GTATAAAAAA TACGAAGACC CCCAAGAACT GCAAAAATAC

901 ATCGAAGAGC ATGATAAAAG CTGGCGGGAA AACCTGGCGC CGCAATACGA

951 CATCACCCCC ATCGATCCGT CCGGCCTGAA GCAGCAGTCG CAGGCAATC

1001 TGTTTAAATT GGAATACGAC GGCGTATTCA ATAAATACAC GGCGCAATTT

1051 CGCGATTTAA ACACCAGAAT CGGCAGCCGC AAAATCATCA ACCGCAATTA

1101 TCAATTCAAT TACGGTTTGT CTTTGAACCC GTATACCAAC CTCAATCTGA

1151 CCGCAGCCTA CAATTCGGGC AGGCAGAAAT ATCCGAAAGG GGCGAAGTTT

1201 ACAGGCTGGG GGCTTTTAAA AGATTTTGAA ACCTACAACA ACGCGAAAAT

1251 CCTCGACCTC AACAACACCG CCACCTTCCG GCTGCCCCGC GAAACCGAGT

1301 TGCAAACCAC TTTGGGCTTC AATTATTTCC ACAACGAATA CGGCAAAAAC
```

-continued

```
1351 CGCTTTCCTG AAGAATTGGG GCTGTTTTTC GACGGTCCTG ATCAGGACAA

1401 CGGGCTTTAT TCCTATTTGG GGCGGTTTAA GGGCGATAAA GGGCTGTTGC

1451 CTCAAAAATC AACCATTGTC CAACCGGCCG GCAGCCAATA TTTCAACACG

1501 TTCTACTTCG ATGCCGCGCT CAAAAAAGAC ATTTACCGCT TAAACTACAG

1551 CACCAATGCA ATCAACTACC GTTTCGGCGG CGAATATACG GGCTATTACG

1601 GCTCGGAAAA CGAATTTAAG CGGGCATTCG GAGAAAACTC GCCGGCATAC

1651 AAGGAACATT GCGACCCGAG CTGCGGGCTT TATGAACCCG TATTGAAAAA

1701 ATACGGCAAA AAGCGCGCCA ACAACCATTC GGTCAGCATT AGTGCGGACT

1751 TCGGCGATTA TTTCATGCCG TTCGCCGGCT ATTCGCGCAC ACACCGTATG

1801 CCCAACATCC AAGAAATGTA TTTTTCCCAA ATCGGCGACT CCGGCGTTCA

1851 CACCGCCTTA AAACCAGAGC GCGCAAACAC TTGGCAATTT GGCTTCAATA

1901 CCTATAAAAA AGGATTGTTA AAACAAGATG ATATATTAGG ATTGAAACTG

1951 GTCGGCTACC GCAGCCGCAT TGACAACTAC ATCCACAACG TTTACGGGAA

2001 ATGGTGGGAT TTGAACGGGG ATATTCCGAG CTGGGTCGGC AGCACCGGGC

2051 TTGCCTACAC CATCCGACAC CGCAATTTCA AGACAAAGT GCACAAACAC

2101 GGTTTTGAGC TGGAGCTGAA TTACGATTAT GGGCGTTTTT TCACCAACCT

2151 TTCTTACGCC TATCAAAAAA GCACGCAACC GACCAATTTC AGCGATGCGA

2201 GCGAATCGCC CAACAATGCC tccaaAGAAG ACCAACTCAA ACAAGGTTAT

2251 GGGCTGAGCA GGGTTTCCGC CCTGCCGCGA GATTACGGAC GTTTGGAAGT

2301 CGGTACGCGC TGGTTGGGCA ACAAACTGAC TTTGGGCGGC GCGAtgcGCT

2351 ATTTCGGCAA GAGCATCCGC GCGACGGCTG AAGAACGCTA TATCGACGGC

2401 ACCAACGGGG GAAATACCAG CAATGTCCGG CAACTGGGCA AGCGTTCCAT

2451 CAAACAAACC GAAACCCTTG CCCGACAGCC TTTGATTTTT GATTTTTACG

2501 CCGCTTACGA GCCGAAGAAA AACCTTATTT TCCGCGCCGA AGTCAAAAAC

2551 CTGTTCGACA GGCGTTATAT CGATCCGCTC GATGCGGGCA ATGATGCGGC

2601 AACGCAGCGT TATTACAGCT CGTTCGACCC GAAAGACAAG GACGAAGACG

2651 TAACGTGTAA TGCTGATAAA ACGTTGTGCA ACGGCAAATA CGGCGGCACA

2701 AGCAAAAGCG TATTGACCAA TTTCGCACGC GGACGCACCT TCTTGATGAC

2751 GATGAGCTAC AAGTTTTAA
```

This corresponds to the amino acid sequence <SEQ ID 884; ORF133ng-1>:

```
  1 MRSSFRLKPI CFYLMGVMLY HHSYAEDAGR AGSEAQIQVL EDVHVKAKRV

51 PKDKKVFTDA RAVSTRQDVF KSGENLDNIV RSIPGAFTQQ DKSSGIVSLN

101 IRGDSGFGRV NTMVDGITQT FYSTSTDAGR AGGSSQFGAS VDSNFIAGLD

151 VVKGSFSGSA GINSLAGSAN LRTLGVDDVV QGNNTYGLLL KGLTGTNSTK

201 GNAMAAIGAR KWLESGASVG VLYGHSRRGV AQNYRVGGGG QHIGNFGEEY

251 LERRKQQYFV QEGGLKFNAG SGKWERDLQR QYWKTKWYKK YEDPQELQKY

301 IEEHDKSWRE NLAPQYDITP IDPSGLKQQS AGNLFKLEYD GVFNKYTAQF

351 RDLNTRIGSR KIINRNYQFN YGLSLNPYTN LNLTAAYNSG RQKYPKGAKF
```

```
401 TGWGLLKDFE TYNNAKILDL NNTATFRLPR ETELQTTLGF NYFHNEYGKN

451 RFPEELGLFF DGPDQDNGLY SYLGRFKGDK GLLPQKSTIV QPAGSQYFNT

501 FYFDAALKKD IYRLNYSTNA INYRFGGEYT GYYGSENEFK RAFGENSPAY

551 KEHCDPSCGL YEPVLKKYGK KRANNHSVSI SADFGDYFMP FAGYSRTHRM

601 PNIQEMYFSQ IGDSGVHTAL KPERANTWQF GFNTYKKGLL KQDDILGLKL

651 VGYRSRIDNY IHNVYGKWWD LNGDIPSWVG STGLAYTIRH RNFKDKVHKH

701 GFELELNYDY GRFFTNLSYA YQKSTQPTNF SDASESPNNA SKEDQLKQGY

751 GLSRVSALPR DYGRLEVGTR WLGNKLTLGG AMRYFGKSIR ATAEERYIDG

801 TNGGNTSNVR QLGKRSIKQT ETLARQPLIF DFYAAYEPKK NLIFRAEVKN

851 LFDRRYIDPL DAGNDAATQR YYSSFDPKDK DEDVTCNADK TLCNGKYGGT

901 SKSVLTNFAR GRTFLMTMSY KF*
```

ORF133ng-1 and ORF133-1 show 96.2% identity in 889 aa overlap:

```
                     10         20         30         40         50         60
orf133ng-1.pep  SFRLKPICFYLMGVMLYHHSYAEDAGRAGSEAQIQVLEDVHVKAKRVPKDKKVFTDARAV
                                              ||||||||||||||||||||||||||||||
orf133-1                                    EAQIQVLEDVHVKAKRVPKDKKVFTDARAV
                                               10         20         30
                     70         80         90        100        110        120
orf133ng-1.pep  STRQDVFKSGENLDNIVRSIPGAFTQQDKSSGIVSLNIRGDSGFGRVNTMVDGITQTFYS
                |||||:|||:|||||||||||||||||||||||||||||||||||||||||||||||||
orf133-1        STRQDIFKSSENLDNIVRSIPGAFTQQDKSSGIVSLNIRGDSGFGRVNTMVDGITQTFYS
                     40         50         60         70         80         90
                    130        140        150        160        170        180
orf133ng-1.pep  TSTDAGRAGGSSQFGASVDSNFIAGLDVVKGSFSGSAGINSLAGSANLRTLGVDDVVQGN
                ||||||||||||||||||||||||||||||||||||||||||||||||||||||||||||
orf133-1        TSTDAGRAGGSSQFGASVDSNFIAGLDVVKGSFSGSAGINSLAGSANLRTLGVDDVVQGN
                    100        110        120        130        140        150
                    190        200        210        220        230        240
orf133ng-1.pep  NTYGLLLKGLTGTNSTKGNAMAAIGARKWLESGASVGVLYGHSRRGVAQNYRVGGGGQHI
                |||||||||||||||||||||||||||||||||||||||||||||:|||||||||||||
orf133-1        NTYGLLLKGLTGTNSTKGNAMAAIGARKWLESGASVGVLYGHSRRSVAQNYRVGGGGQHI
                    160        170        180        190        200        210
                    250        260        270        280        290        300
orf133ng-1.pep  GNFGEEYLERRKQQYFVQEGGLKFNAGSGKWERDLQRQYWKTKWYKKYEDPQELQKYIEE
                ||||  ||||||||:|:||:| ||| |:|||||||||||:|| |:|  :  |||||||
orf133-1        GNFGAEYLERRKQRYFVQEGALKFNSDSGKWERDLQRQQWKYKPYKNYNN-QELQKYIEE
                    220        230        240        250        260
                    310        320        330        340        350        360
orf133ng-1.pep  HDKSWRENLAPQYDITPIDPSGLKQQSAGNLFKLEYDGVFNKYTAQFRDLNTRIGSRKII
                |||||||||| ||||||||||| ||||||||||||||||||||||||||||: ||||||
orf133-1        HDKSWRENLXPQYDITPIDPSSLKQQSAGNLFKLEYDGVFNKYTAQFRDLNTKIGSRKII
                        270        280        290        300        310        320
                    370        380        390        400        410        420
orf133ng-1.pep  NRNYQFNYGLSLNPYTNLNLTAAYNSGRQKYPKGAKFTGWGLLKDFETYNNAKILDLNNT
                |||||||||||||||||||||||||||||||||||:||||||||||||||||||||||||
orf133-1        NRNYQFNYGLSLNPYTNLNLTAAYNSGRQKYPKGSKFTGWGLLKDFETYNNAKILDLNNT
                       330        340        350        360        370        380
                    430        440        450        460        470        480
orf133ng-1.pep  ATFRLPRETELQTTLGFNYFHNEYGKNRFPEELGLFFDGPDQDNGLYSYLGRFKGDKGLL
                ||||||||||||||||||||||||||||||||||||||||||||||||||||||||||||
orf133-1        ATFRLPRETELQTTLGFNYFHNEYGKNRFPEELGLFFDGPDQDNGLYSYLGRFKGDKGLL
                       390        400        410        420        430        440
                    490        500        510        520        530        540
orf133ng-1.pep  PQKSTIVQPAGSQYFNTFYFDAALKKDIYRLNTSTNAINYRFGGEYTGYYGSENEFKRAF
                |||||||||||||||||||||||||||||||:::||:| ||||||||||||:||:|||||
orf133-1        PQKSTIVQPAGSQYFNTFYFDAALKKDIYRLNYSTNTVGYRFGGEYTGYYGSDDEFKRAF
                       450        460        470        480        490        500
                    550        560        570        580        590        600
orf133ng-1.pep  GENSPAYKEHCDPSCGLYEPVLKKYGKKRANNHSVSISADFGDYFMPFAGYSRTHRMPNI
                |||||:||:||:|| ||:||||||||||||||||||||||||||||||||:|||||||||
orf133-1        GENSPTYKKHCNRSCGIYEPVLKKYGKKRANNHSVSISADFGDYFMPFASYSRTHRMPNI
                       510        520        530        540        550        560
                    610        620        630        640        650        660
orf133ng-1.pep  QEMYFSQIGDSGVHTALKPERANTWQFGFNTYKKGLLKQDDILGLKLVGYRSRIDNYIGN
                ||||||||||||||||||||||||||||||||||||||||||:|||||||||||||||:|
orf133-1        QEMYFSQIGDSGVHTALKPERANTWQFGFNTYKKGLLKQDDTLGLKLVGYRSRIDNYIHN
                       570        580        590        600        610        620
```

-continued

```
                   670        680        690        700        710        720
orf133ng-1.pep  VYGKWWDLNGDIPSWVGSTGLAYTIRHRNFKDKVHKHGFELELNYDYGRFFTNLSYAYQK
                ||||||||||||||||:|||||||||:|||||||||||||||||||||||||||||||||
orf133-1        VYGKWWDLNGDIPSWVSSTGLAYTIQHRNFKDKVHKHGFELELNYDYGRFFTNLSYAYQK
                   630        640        650        660        670        680

730        740        750        760        770        780
orf133ng-1.pep  STQPTNFSDASESPNNASKEDQLKQGYGLSRVSALPRDYGRLEVGTRWLGNKLTLGGAMR
                ||||||||||||||||||||||||||||||||||||||||||||||||||||||||||||
orf133-1        STQPTNFSDASESPNNASKEDQLKQGYGLSRVSALPRDYGRLEVGTRWLGNKLTLGGAMR
                   690        700        710        720        730        740

790        800        810        820        830        840
orf133ng-1.pep  YFGKSIRATAEERYIDGTNGGNTSNVRQLGKRSIKQTETLARQPLIFDFYAAYEPKKNLI
                |||||||||||||||||||||||||||||:||||||||||||||||||||||||||||||
orf133-1        YFGKSIRATAEERYIDGTNGGNTSNFRQLGKRSIKQTETLARQPLIFDFYAAYEPKKNLI
                   750        760        770        780        790        800

850        860        870        880        890        900
orf133ng-1.pep  FRAEVKNLFDRRYIDPLDAGNDAATQRYYSSFDPKDKDEDVTCNADKTLCNGKYGGTSKS
                ||||||||||||||||||||||||||||||||||||||||||||||||||||||||||||
orf133-1        FRAEVKNLFDRRYIDPLDAGNDAATQRYYSSFDPKDKDEDVTCNADKTLCNGKYGGTSKS
                   810        820        830        840        850        860

910        920
orf133ng-1.pep  VLTNFARGRTFLMTMSYKFX
                ||||||||||||||||||||
orf133-1        VLTNFARGRTFLMTMSYKFX
                   870        880
```

In addition, ORF133ng-1 is homologous to a TonB-dependent receptor in *H. influenzae*:

```
sp|P45114|YC17_HAEIN PROBABLE TONB-DEPENDENT RECEPTOR HI1217 PRECURSOR
>gi|1075372|pir||G64110 transferrin binding protein 1 precursor (tbp1) homolog-
Haemophilus influenzae (strain Rd KW20) >gi|1574147 (U32801) transferrin binding
protein 1 precursor (tbp1) [Haemophilus influenzae] Length = 913
  Score =  930 bits (2377), Expect = 0.0
  Identities = 476/921 (51%), Positives = 619/921 (66%), Gaps = 72/921 (7%)

Query:  38   QVLEDVHVKAKRVPKDKKVFTDARAVSTRQDVFKSGENLDNIVRSIPGAFTQQDKSSGIV    97
             + L  + +   K  + DKK FT+A+A STR++VFK   + D ++RSIPGAFTQQDK SG+V
Sbjct:  29   ETLGQIDVVEKVISNDKKPFTEAKAKSTRENVFKETQTIDQVIRSIPGAFTQQDKGSGVV    88

Query:  98   SLNIRGDSGFGRVNTMVDGITQTFYSTSTDAGRAGGSSQFGASVDSNFIAGLDVVKGSFS   157
             S+NIRG++G GRVNTMVDG+TQTFYST+ D+G++GGSSQFGA++D NFIAG+DV K +FS
Sbjct:  89   SVNIRGENGLGRVNTMVDGVTQTFYSTALDSGQSGGSSQFGAAIDPNFIAGVDVNKSNFS   148

Query: 158   GSAGINSLAGSANLRTLGVDDVVQXXXXXXXXXXXXXXXXXXXXXXXAMAAIGARKWLESGA   217
             G++GIN+LAGSAN RTLGV+DV+              M     RKWL++G
Sbjct: 149   GASGINALAGSANFRTLGVNDVITDDKPFGIILKGMTGSNATKSNFMTMAAGRKWLDNGG   208

Query: 218   SVGVLYGHSRRGVAQNYRVGGGGQHIGNFGEEYLERRKQQYFVQEGGLKFNAGSGKWERD   277
             +VGV+YG+S+R V+Q+YR+ GGG+  + G++ L + K+ YF +   G    N   G+W D
Sbjct: 209   YVGVVYGYSQREVSQDYRI-GGGERLASLGQDILAKEKEAYF-RNAGYILNP-EGQWTPD   265

Query: 278   LQRQYWK-----------TKWY--------------------KKYEDPQELQK---YIEE   303
             L +++W              +Y                 KK +D ++LQK    IEE
Sbjct: 266   LSKKHWSCNKPDYQKNGDCSYYRIGSAAKTRREILQELLTNGKKPKDIEKLQKGNDGIEE   325

Query: 304   HDKSWRENLAPQYDITPIDPSGLKQQSAGNLFKLEYDGVFNKYTAQFRDLNTRIGSRKII   363
              DKS  N   QY + PI+P  L+  +S   +L K EY     AQ R L+  +IGSRKI
Sbjct: 326   TDKSFERN-KDQYSVAPIEPGSLQSRSRSHLLKFEYGDDHQNLGAQLRTLDNKIGSRKIE   384

Query: 364   NRNYQFNYGLSLNPYTNLNLTAAYNSGRQKYPKGAKFTGWGLLKDFETYNNAKILDLNNT   423
             NRNYQ NY  + N Y +LNL AA+N G+   YPKG   F GW +    T N A I+D+NN+
Sbjct: 385   NRNYQVNYNFNNNSYLDLNLMAAHNIGKTIYPKGGFFAGWQVADKLITKNVANIVDINNS   444

Query: 424   ATFRLPRETELQTTLGFNYFPHNEYGKNRFPEELGLFFDGPDQDNGLYSY--LGRFKGDKG   481
              TF LP+E +L+TTLGFNYF NEY KNRFPEEL LFYN+   D GLYS+   GR+  G K
Sbjct: 445   HTFLLPKEIDLKTTLGFNYFTNEYSKNRFPEELSLFYNDASHDQGLYSHSKRGRYSGTKS   504

Query: 482   LLPQKSTIVQPAGSQYFNTFYFDAALKKDIYRLNYSTNAINYRFGGEYTGYYGSENEFKR   541
             LLPQ+S I+QP+G Q F T YFD AL K IY LNYS N +Y F GEY GY
Sbjct: 505   LLPQRSVILQPSGKQFKTVYFDTALSKGIYHLNYSVNFTHYAFNGEYVGY---------   555

Query: 542   AFGENSPAYKEHCDPSCGLYEPVLKKYGKKRANNHSVSISADFGDYFMPFAGYSRTHRMP   601
                 EN+       +   EP+L K G K+A NHS ++SA+ DYFMPF  YSRTHRMP
Sbjct: 556   ---ENTAGQQ--------INEPILHKSGHKKAFNHSATLSAELSDYFMPFFTYSRTHRMP   604

Query: 602   NIQEMYFSQIGDSGVHTALKPERANTWQFGFNTYKKGLLKQDDILGLKLVGYRSRIDNYI   661
             NIQEM+FSQ+ ++GV+TALKPE+++T+Q GFNTYKKGL  QDD+LG+KLVGYRS I NYI
Sbjct: 605   NIQEMFFSQVSNAGVNTALKPEQSDTYQLGFNTYKKGLFTQDDVLGVKLVGYRSFIKNYI   664

Query: 662   HNVYGKWWDLNGDIPSWVGSTGLAYTIRHRNFKDKVHKHGFELELNYDYGRFFTNLSYAY   721
             HNVYG WW   +P+W S G  YTI H+N+K V K G ELE+NYD GRFF N+SYAY
Sbjct: 665   HNVYGVWW--RDGMPTWAESNGFKYTIAHQNYKPIVKKSGVELEINYDMGRFFANVSYAY   722

Query: 722   QKSTQPTNFSDASESPNNASKEDQLKQGYGLSRVSALPRDYGRLEVGTRWLGNKLTLGGA   781
             Q++ QPTN++DAS  PNNAS+ED LKQGYGLSRVS LP+DYGRLE GTRW   KLTLG A
Sbjct: 723   QRTNQPTNYADASPRPNNASQEDILKQGYGLSRVSMLPKDYGRLELGTRWFDQKLTLGLA   782

Query: 782   MRYFGKSIRATAEERYIDGTNGGNTSNVRQLGKRSIKQTETLARQPLIFDFYAAYEPKKN   841
              RY+GKS RAT EE YI+G+     + +R+    ++K+TE + QP+I D + +YEP K+
Sbjct: 783   ARYYGKSKRATIEEEYINGSR-FKKNTLRRENYYAVKKTEDIKKQPIILDLHVSYEPIKD   841
```

-continued
```
Query: 842  LIFRAEVKNLFDRRYIDPLDAGNDAATQRYYSSFDPKDKDEDVTCNADKTLCNGKYGGTS  901
            LI +AEV+NL D+RY+DPLDAGNDAA+QRYYSS     +  + C  D + C    GG+
Sbjct: 842  LIIKAEVQNLLDKRYVDPLDAGNDAASQRYYSSL-----NNSIECAQDSSAC----GGSD  892

Query: 902  KSVLTNFARGRTFLMTMSYKF  922
            K+VL NFARGRT++++++YKF
Sbjct: 893  KTVLYNFARGRTYILSLNYKF  913
```

The underlined motif in the gonococcal protein (also present in the meningococcal protein) is predicted to be an ATP/GTP-binding site motif A (P-loop), and the analysis suggests that these proteins from *N. meningitidis* and *N. gonorrhoeae*, and their epitopes, could be useful antigens for vaccines or diagnostics, or for raising antibodies.

Example 104

The following partial DNA sequence was identified in *N. meningitidis* <SEQ ID 885>

```
  1 ATGAACCTGA TTTCACGTTA CATCATCCGT CAAATGGCGG TTATGGCGGT
 51 TTACGCGCTC CTTGCCTTCC TCGCTTTGTA CAGCTTTTTT GAAATCCTGT
101 ACGAAACCGG CAACCTCGGC AAAGGCAGTT ACGGCATATG GGAAATGCTG
151 GGCTACACCG CCCTCAAAAT GCCCGCCCGC GCCTACGAAC TGATTCCCCT
201 CGCCGTCCTT ATCGGCGGAC TGGTCTCCCT CAGCCAGCTT GCCGCCGGCA
251 GCGAACTGAC CGTCATCAAA GCCAGCGGCA TGAGCACCAA AAAGCTGCTG
301 TTGATTCTGT CGCAGTTCGG TTTTATTTTT GCTATTGCCA CCGTCGCGCT
351 CGGCGAATGG GTTGCGCCCA CACTGAGCCA AAAAGCCGAA AACATCAAAG
401 CCGCCGCCAT CAACGGCAAA ATCAGCACCG GCAATACCGG CCTTTGGCTG
451 AAAGAAAAAA ACAGCGTGAT CAATGTGCGC GAAATGTTGC CCGACCAT..
```

This corresponds to the amino acid sequence <SEQ ID 886; ORF112>:

```
  1 MNLISRYIIR QMAVMAVYAL LAFLALYSFF EILYETGNLG KGSYGIWEML
 51 GYTALKMPAR AYELIPLAVL IGGLVSLSQL AAGSELTVIK ASGMSTKKLL
101 LILSQFGFIF AIATVALGEW VAPTLSQKAE NIKAAAINGK ISTGNTGLWL
151 KEKNSVINVR EMLPDH...
```

Further work revealed further partial nucleotide sequence <SEQ ID 887>:

```
  1 ATGAACCTGA TTTCACGTTA CATCATCCGT CAAATGGCGG TTATGGCGGT
 51 TTACGCGCTC CTTGCCTTCC TCGCTTTGTA CAGCTTTTTT GAAATCCTGT
101 ACGAAACCGG CAACCTCGGC AAAGGCAGTT ACGGCATATG GGAAATGCTG
151 gGCTACACCG CCCTCAAAAT GCCCGCCCGC GCCTACGAAC TGATTCCCCT
201 CGCCGTCCTT ATCGGCGGAC TGGTCTCCCT CAGCCAGCTT GCCGCCGGCA
251 GCGAACTGAC CGTCATCAAA GCCAGCGGCA TGAGCACCAA AAAGCTGCTG
301 TTGATTCTGT CGCAGTTCGG TTTTATTTTT GCTATTGCCA CCGTCGCGCT
351 CGGCGAATGG GTTGCGCCCA CACTGAGCCA AAAAGCCGAA AACATCAAAG
```

```
401 CCGCCGCCAT CAACGGCAAA ATCAGCACCG GCAATACCGG CCTTTGGCTG

451 AAAGAAAAAA ACAGCrTkAT CAATGTGCGC GAAATGTTGC CCGACCATAC

501 GCTTTTGGGC ATCAAAATTT GGGCGCGCAA CGATAAAAAC GAATTGGCAG

551 AGGCAGTGGA AGCCGATTCC GCCGTTTTGA ACGCGACGG CAGTTGGCAG

601 TTGAAAAACA TCCGCCGCAG CACGCTTGGC GAAGACAAAG TCGAGGTCTC

651 TATTGCGGCT GAAGAAAACT GGCCGATTTC CGTCAAACGC AACCTGATGG

701 ACGTATTGCT CGTCAAACCC GACCAAATGT CCGTCGGCGA ACTGACCACC

751 TACATCCGCC ACCTCCAAAA CAACAGCCAA AACACCCGAA TCTACGCCAT

801 CGCATGGTGG CGCAAATTGG TTTACCCCGC CGCAGCCTGG GTGATGGCGC

851 TCGTCGCCTT TGCCTTTACC CCGCAAACCA CCCGCCACGG CAATATGGGC

901 TTAAAACTCT TCGGCGGCAT CTGTsTCGGA TTGCTGTTCC ACCTTGCCGG

951 ACGGCTCTTT GGGTTTACCA GCCAACTCGG...
```

This corresponds to the amino acid sequence <SEQ ID 888; ORF112-1>:

```
  1 MNLISRYIIR QMAVMAVYAL LAFLALYSFF EILYETGNLG KGSYGIWEML

51 GYTALKMPAR AYELIPLAVL IGGLVSLSQL AAGSELTVIK ASGMSTKKLL

101 LILSQFGFIF AIATVALGEW VAPTLSQKAE NIKAAAINGK ISTGNTGLWL

151 KEKNSXINVR EMLPDHTLLG IKIWARNDKN ELAEAVEADS AVLNSDGSWQ

201 LKNIRRSTLG EDKVEVSIAA EENWPISVKR NLMDVLLVKP DQMSVGELTT

251 YIRHLQNNSQ NTRIYAIAWW RKLVYPAAAW VMALVAFAFT PQTTRHGNMG

301 LKLFGGICXG LLFHLAGRLF GFTSQL...
```

Computer analysis of this amino acid sequence predicts two transmembrane domains and gave the following results:

Homology with a Predicted ORF from *N. meningitidis* (Strain A)

ORF112 shows 96.4% identity over a 166aa overlap with an ORF (ORF112a) from strain A of *N. meningitidis*:

```
                     10         20         30         40         50         60
    orf112.pep  MNLISRYIIRQMAVMAVYALLAFLALYSFFEILYETGNLGKGSYGIWEMLGYTALKMPAR
                ||||||||||||||||||||||||||||||||||||||||||||||||||| |||||| ||
    orf112a     MNLISRYIIRQMAVMAVYALLAFLALYSFFEILYETGNLGKGSYGIWEMXGYTALKMXAR
                     10         20         30         40         50         60

70         80         90        100        110        120
    orf112.pep  AYELIPLAVLIGGLVSLSQLAAGSELTVIKASGMSTKKLLLILSQFGFIFAIATVALGEW
                ||||:||||||||||| ||||||||||:||||||||||||||||||||||||||||||||
    orf112a     AYELMPLAVLIGGLVSXSQLAAGSELXVIKASGMSTKKLLLILSQFGFIFAIATVALGEW
                     70         80         90        100        110        120

130        140        150        160
    orf112.pep  VAPTLSQKAENIKAAAINGKISTGNTGLQLKEKNSVINVREMLPDH
                |||||||||||||||||||||||||||||| ||||||||||||||
    orf112a     VAPTLSQKAENIKAAAINGKISTGNTGLWLKEKNSIINVREMLPDHTLLGIKIWARNDKN
                    130        140        150        160        170        180 orf112a     ELAEAVEADSAVLNSDGSWQLKNIRRSTLGEDKVEVSIAAEEXWPISVKRNLMDVLLVKP
                    190        200        210        220        230        240
```

The ORF112a nucleotide sequence <SEQ ID 889> is:

```
  1  ATGAACCTGA TTTCACGTTA CATCATCCGT CAAATGGCGG TTATGGCGGT

51  TTACGCGCTC CTTGCCTTCC TCGCTTTGTA CAGCTTTTTT GAAATCCTGT
```

-continued

```
 101 ACGAAACCGG CAACCTCGGC AAAGGCAGTT ACGGCATATG GGAAATGNTG
 151 GGNTACACCG CCCTCAAAAT GNCCGCCCGC GCCTACGAAC TGATGCCCCT
 201 CGCCGTCCTT ATCGGCGGAC TGGTCTCTNT CAGCCAGCTT GCCGCCGGCA
 251 GCGAACTGAN CGTCATCAAA GCCAGCGGCA TGAGCACCAA AAAGCTGCTG
 301 TTGATTCTGT CGCAGTTCGG TTTTATTTTT GCTATTGCCA CCGTCGCGCT
 351 CGGCGAATGG GTTGCGCCCA CACTGAGCCA AAAAGCCGAA AACATCAAAG
 401 CCGCGGCCAT CAACGGCAAA ATCAGTACCG GCAATACCGG CCTTTGGCTG
 451 AAAGAAAAAA ACAGCATTAT CAATGTGCGC GAAATGTTGC CCGACCATAC
 501 CCTGCTGGGC ATTAAAATCT GGGCCCGCAA CGATAAAAAC GAACTGGCAG
 551 AGGCAGTGGA AGCCGATTCC GCCGTTTTGA ACAGCGACGG CAGTTGGCAG
 601 TTGAAAAACA TCCGCCGCAG CACGCTTGGC GAAGACAAAG TCGAGGTCTC
 651 TATTGCGGCT GAAGAAAANT GGCCGATTTC CGTCAAACGC AACCTGATGG
 701 ACGTATTGCT CGTCAAACCC GACCAAATGT CCGTCGGCGA ACTGACCACC
 751 TACATCCGCC ACCTCCAAAN NNACAGCCAA AACACCCGAA TCTACGCCAT
 801 CGCATGGTGG CGCAAATTGG TTTACCCCGC CGCAGCCTGG GTGATGGCGC
 851 TCGTCGCCTT TGCCTTTACC CCGCAAACCA CCCGCCACGG CAATATGGGC
 901 TTAAAANTCT TCGGCGGCAT CTGTCTCGGA TTGCTGTTCC ACCTTGCCGG
 951 NCGGCTCTTC NGGTTTACCA GCCAACTCTA CGGCATCCCG CCCTTCCTCG
1001 NCGGCGCACT ACCTACCATA GCCTTCGCCT TGCTCGCCGT TTGGCTGATA
1051 CGCAAACAGG AAAAACGCTA A
```

This encodes a protein having the amino acid sequence <SEQ ID 890>:

```
  1 MNLISRYIIR QMAVMAVYAL LAFLALYSFF EILYETGNLG KGSYGIWEMX
 51 GYTALKMXAR AYELMPLAVL IGGLVSXSQL AAGSELXVIK ASGMSTKKLL
101 LILSQFGFIF AIATVALGEW VAPTLSQKAE NIKAAAINGK ISTGNTGLWL
151 KEKNSIINVR EMLPDHTLLG IKIWARNDKN ELAEAVEADS AVLNSDGSWQ
201 LKNIRRSTLG EDKVEVSIAA EEXWPISVKR NLMDVLLVKP DQMSVGELTT
251 YIRHLQXXSQ NTRIYAIAWW RKLVYPAAAW VMALVAFAFT PQTTRHGNMG
301 LKXFGGICLG LLFHLAGRLF XFTSQLYGIP PFLXGALPTI AFALLAVWLI
351 RKQEKR*
```

ORF112a and ORF112-1 show 96.3% identity in 326 aa overlap:

```
orf112a.pep    MNLISRYIIRQMAVMAVYALLAFLALYSFFEILYETGNLGKGSYGIWEMXGYTALKMXAR
               |||||||||||||||||||||||||||||||||||||||||||||||||| ||||||| ||
orf112-1       MNLISRYIIRQMAVMAVYALLAFLALYSFFEILYETGNLGKGSYGIWEMLGYTALKMPAR orf112a.pep    AYELMPLAVLIGGLVSXSQLAAGSELXVIKASGMSTKKLLLILSQFGFIFAIATVALGEW
               ||||:|||||||||||||:|||||||:|||||||||||||||||||||||||||||||||
orf112-1       AYELIPLAVLIGGLVSLSQLAAGSELTVIKASGMSTKKLLLILSQFGFIFAIATVALGEW orf112a.pep    VAPTLSQKAENIKAAAINGKISTGNTGLWLKEKNSIINVREMLPDHTLLGIKIWARNDKN
               |||||||||||||||||||||||||||||||||||| |||||||||||||||||||||||
orf112-1       VAPTLSQKAENIKAAAINGKISTGNTGLWLKEKNSXINVREMLPDHTLLGIKIWARNDKN orf112a.pep    ELAEAVEADSAVLNSDGSWQLKNIRRSTLGEDKVEVSIAAEEXWPISVKRNLMDVLLVKP
               ||||||||||||||||||||||||||||||||||||||||| ||||||||||||||||||
orf112-1       ELAEAVEADSAVLNSDGSWQLKNIRRSTLGEDKVEVSIAAEENWPISVKRNLMDVLLVKP
```

```
orf112a.pep    DQMSVGELTTYIRHLQXXSQNTRIYAIAWWRKLVYPAAAWVMALVAFAFTPQTTRHGNMG
               ||||||||||||||   |||||||||||||||||||||||||||||||||||||||||||
orf112-1       DQMSVGELTTYIRHLQNNSQNTRIYAIAWWRKLVYPAAAWVMALVAFAFTPQTTRHGNMG orf112a.pep    LKXFGGICLGLLFHLAGRLFXFTSQLYGIPPFLXGALPTIAFALLAVWLIRKQEKRX
               || ||||| |||||||||||| |||||
orf112-1       LKLFGGICXGLLFHLAGRLFGFTSQL
```

Homology with a Predicted ORF from *N. gonorrhoeae*

ORF112 shows 95.8% identity over 166aa overlap with a predicted ORF (ORF112ng) from *N. gonorrhoeae*:

```
orf112.pep     MNLISRYIIRQMAVMAVYALLAFLALYSFFEILYETGNLGKGSYGIWEMLGYTALKMPAR    60
               ||||||||||||||||||||||||||||||||||||||||||||||||||||||||||||
orf112ng       MNLISRYIIRQMAVMAVYALLAFLALYSFFEILYETGNLGKGSYGIWEMLGYTALKMPAR    60 orf112.pep     AYELIPLAVLIGGLVSLSQLAAGSELTVIKASGMSTKKLLLILSQFGFIFAIATVALGEW   120
               ||||:|||||||||:|||||||||||:|||||||||||||||||||||||||||:|||||
orf112ng       AYELMPLAVLIGGLASLSQLAAGSELAVIKASGMSTKKLLLILSQFGFIFAIAAVALGEW   120 orf112.pep     VAPTLSQKAENIKAAAINGKISTGNTGLWLKEKNSVINVREMLPDH                166
               ||||||||||||||||||||||||||||||||||:|:||| ||||
orf112ng       VAPTLSQKAENIKAAAINGKISTGNTGLWLKEKTSIINVRGMLPDHTLLGIKIWARNDKN   180
```

The complete length ORF112ng nucleotide sequence <SEQ ID 891> is:

```
   1 ATGAACCTGA TTTCACGTTA CATCATCCGC CAAATGGCGG TTATGGCGGT

51 TTACGCGCTC CTTGCCTTCC TCGCTTTGTA CAGCTTTTTT GAAATCCTGT

101 ACGAAACCGG CAACCTCGGC AAAGGCAGTT ACGGCATATG GGAAATGCTG

151 GGCTACACCG CCCTCAAAAT GCCCGCCCGC GCCTACGAAC TCATGCCCCT

201 CGCCGTCCTC ATCGGCGGAC TGGCCTCTCT CAGCCAGCTT GCCGCCGGCA

251 GCGAACTGGC CGTCATCAAA GCCAGCGGCA TGAGCACCAA AAAGCTGCTG

301 TTGATTCTGT CTCAGTTCGG TTTTATTTTT GCTATTGCCG CCGTCGCGCT

351 CGGCGAATGG GTTGCGCCCA CGCTGAGCCA AAAAGCCGAA AACATCAAag 401 cCGCCGCCAt taacggCAAA ATCAGCAccg gcAATACCGG CCTTTggcTG 451 AAAGAAAAAa ccAGCATTAT CAATGTGcGc GGAATGTTGC CCGACCATAC

501 GCTTTTGGGC ATCAAAATTT GGGCGCGCAA CGATAAAAAC GAATTGGCAG

551 AGGCAGTGGA AGCCGATTCC GCCGTTTTGA ACAGCGACGG CAGCTGGCAG

601 TTGAAAAACA TCCGCCGCAG CATCATGGGT ACAGACAAAA TCGAAACATC 651 cgCCGCCGCC GAAGAAACTT gGCCGATTGC CGTCAGACGC AACCTGATGG

701 ACGTATTGCT CGTCAAGCCC GACCAAATGT CCGTCGGCGA GCTGACCACC

751 TACATCCGCC ACCTCCAAAA CAACAGCCAA AACACCCAAA TCTACGCCAT

801 CGCATGGTGG CGTAAACTCG TTTACCCCGT CGCCGCATGG GTCATGGCGC

851 TCGTTGCCTT CGCCTTTACG CCGCAAACCA CGCGCCACGG CAATATGGGC

901 TTAAAACTCT TCGGCGGCAT CTGTCTCGGA TTGCTGTTCC ACCTTGCCGG

951 CAGGCTCTTC GGGTTTACCA GCCAACTCTA CGGCACCCCA CCCTTCCTCG

1001 CCGGCGCACT GCCTACCATA GCCTTCGCCT TGCTCGCTGT TTGGCTGATA

1051 CGCAAACAGG AAAAACGTTG A
```

This encodes a protein having amino acid sequence <SEQ ID 892>:

```
  1 MNLISRYIIR QMAVMAVYAL LAFLALYSFF EILYETGNLG KGSYGIWEML

51 GYTALKMPAR AYELMPLAVL IGGLASLSQL AAGSELAVIK ASGMSTKKLL

101 LILSQFGFIF AIAAVALGEW VAPTLSQKAE NIKAAAINGK ISTGNTGLWL

151 KEKTSIINVR GMLPDHTLLG IKIWARNDKN ELAEAVEADS AVLNSDGSWQ

201 LKNIRRSIMG TDKIETSAAA EETWPIAVRR NLMDVLLVKP DQMSVGELTT

251 YIRHLQNNSQ NTQIYAIAWW RKLVYPVAAW VMALVAFAFT PQTTRHGNMG

301 LKLFGGICLG LLFHLAGRLF GFTSQLYGTP PFLAGALPTI AFALLAVWLI

351 RKQEKR*
```

ORF112ng and ORF112-1 show 94.2% identity in 326 aa overlap:

```
                    10         20         30         40         50         60
     orf112ng   MNLISRYIIRQMAVMAVYALLAFLALYSFFEILYETGNLGKGSYGIWEMLGYTALKMPAR
                ||||||||||||||||||||||||||||||||||||||||||||||||||||||||||||
     orf112-1   MNLISRYIIRQMAVMAVYALLAFLALYSFFEILYETGNLGKGSYGIWEMLGYTALKMPAR
                    10         20         30         40         50         60

70         80         90        100        110        120
     orf112ng   AYELMPLAVLIGGLASLSQLAAGSELAVIKASGMSTKKLLLILSQFGFIFAIAAVALGEW
                ||||:|||||||||:||||||||||||:|||||||||||||||||||||||||:||||||
     orf112-1   AYELIPLAVLIGGLVSLSQLAAGSELTVIKASGMSTKKLLLILSQFGFIFAIATVALGEW
                    70         80         90        100        110        120

130        140        150        160        170        180
     orf112ng   VAPTLSQKAENIKAAAINGKISTGNTGLWLKEKTSIINVRGMLPDHTLLGIKIWARNDKN
                |||||||||||||||||||||||||||||||||:||||||:||||||||||||||||||||
     orf112-1   VAPTLSQKAENIKAAAINGKISTGNTGLWLKEKNSXINVREMLPDHTLLGIKIWARNDKN
                   130        140        150        160        170        180

190        200        210        220        230        240
     orf112ng   ELAEAVEADSAVLNSDGSWQLKNIRRSIMGTDKIETSAAAEETWPIAVRRNLMDVLLVKP
                ||||||||||||||||||||||||||||:| ||::| |||||:||||:|:|:|||||||
     orf112-1   ELAEAVEADSAVLNSDGSWQLKNIRRSTLGEDKVEVSIAAEENWPISVKRNLMDVLLVKP
                   190        200        210        220        230        240

250        260        270        280        290        300
     orf112ng   DQMSVGELTTYIRHLQNNSQNTQIYAIAWWRKLVYPVAAWVMALVAFAFTPQTTRHGNMG
                ||||||||||||||||||||||:||||||||||||||:||||||||||||||||||||||
     orf112-1   DQMSVGELTTYIRHLQNNSQNTRIYAIAWWRKLVYPAAWVMALVAFAFTPQTTRHGNMG
                   250        260        270        280        290        300

310        320        330        340        350
     orf112ng   LKLFGGICLGLLFHLAGRLFGFTSQLYGTPPFLAGALPTIAFALLAVWLIRKQEKRX
                |||||||| |||||||||||||||||
     orf112-1   LKLFGGICXGLLFHLAGRLFGFTSQL
                   310        320
```

This analysis suggests that these proteins from *N. meningitidis* and *N. gonorrhoeae*, and their epitopes, could be useful antigens for vaccines or diagnostics, or for raising antibodies.

It will be appreciated that the invention has been described by means of example only, and that modifications may be made whilst remaining within the spirit and scope of the invention.

TABLE I

PCR primers

| ORF | Primer | Sequence | Restriction-sites | SEQ ID NO: |
|---|---|---|---|---|
| ORF 1 | Forward | CGCGGATCCGCTAGC-GGACACACTTATTTCGG | BamHI-NheI | SEQ ID NO: 924 |
|  | Reverse | CCCGCTCGAG-CCAGCGGTAGCCTAATT | XhoI | SEQ ID NO: 925 |
| ORF 2 | Forward | GCGGATCCCATATG-TTTGATTTCGGTTTGGG | BamHI-NdeI | SEQ ID NO: 926 |
|  | Reverse | CCCGCTCGAG-GACGGCATAACGGCG | XhoI | SEQ ID NO: 927 |
| ORF 2-1 | Forward | GCGGATCCCATATG-TTTGATTTCGGTTTGGG | BamHI-NdeI | SEQ ID NO: 928 |
|  | Reverse | CCCGCTCGAG-TGATTTACGGACGCGCA | XhoI | SEQ ID NO: 929 |
| ORF 4 | Forward | GCGGATCCCATATG-TGCGGAGGTCAAAAGAC | BamHI-NdeI | SEQ ID NO: 930 |
|  | Reverse | CCCGCTCGAG-TTTGGCTGCGCCTTC | XhoI | SEQ ID NO: 931 |
| ORF 5 | Forward | GGAATTCCATATGGCCATGG-TGGAAGGCGCACAACC | NdeI-NcoI | SEQ ID NO: 932 |
|  | Forward | CGGGATCC-ATGGAAGGCGCACAAC | BamHI | SEQ ID NO: 933 |
|  | Reverse | CCCGCTCGAG-GACTGTGCAAAAACGG | XhoI | SEQ ID NO: 934 |

TABLE I-continued

PCR primers

| ORF | Primer | Sequence | Restriction-sites | SEQ ID NO: |
|---|---|---|---|---|
| ORF 6 | Forward | CGC<u>GGATCCCATATG</u>-ACCCGTCAATCTCTGCA | BamHI-NdeI | SEQ ID NO: 935 |
|  | Reverse | CCCG<u>CTCGAG</u>-TGCGCCGAACACTTTC | XhoI | SEQ ID NO: 936 |
| ORF 7 | Forward | CGC<u>GGATCCGCTAGC</u>-GCGCTGCTTTTTGTTCC | BamHI-NheI | SEQ ID NO: 937 |
|  | Reverse | CCCG<u>CTCGAG</u>-TTTCAAAATATATTTGCGGA | XhoI | SEQ ID NO: 938 |
| ORF 8 | Forward | GC<u>GGATCCCATATG</u>-GCTCAACTGCTTCGTAC | BamHI-NdeI | SEQ ID NO: 939 |
|  | Reverse | CCCG<u>CTCGAG</u>-AGCAGGCTTTGGCGC | XhoI | SEQ ID NO: 940 |
| ORF 9 | Forward | CGC<u>GGATCCCATATG</u>-CCGAAGGAAGTCGGAAA | BamHI-NdeI | SEQ ID NO: 941 |
|  | Reverse | CCCG<u>CTCGAG</u>-TTTCCGAGGTTTTCGGG | XhoI | SEQ ID NO: 942 |
| ORF 10 | Forward | GC<u>GGATCCCATATG</u>-GACACAAAAGAAATCCTC | BamHI-NdeI | SEQ ID NO: 943 |
|  | Reverse | CCCG<u>CTCGAG</u>-TAATGGGAAACCTTGTTTT | XhoI | SEQ ID NO: 944 |
| ORF 11 | Forward | GC<u>GGATCCCATATG</u>-GCGGTCAACCTCTACG | BamHI-NdeI | SEQ ID NO: 945 |
|  | Reverse | CCCG<u>CTCGAG</u>-GGAAACGACTTCGCC | XhoI | SEQ ID NO: 946 |
| ORF 13 | Forward | CGC<u>GGATCCCATATG</u>-GCTCTGCTTTCCGCGC | BamHI-NdeI | SEQ ID NO: 947 |
|  | Reverse | CCCG<u>CTCGAG</u>-AGGGTGTGTGATAATAAG | XhoI | SEQ ID NO: 948 |
| ORF 15 | Forward | GGAATT<u>CCATATGGCCATGG</u>-GCGGGACACTGACAG | NdeI-NcoI | SEQ ID NO: 949 |
|  | Forward | CG<u>GGATCC</u>-TGCGGGACACTGACAGG | BamHI | SEQ ID NO: 950 |
|  | Reverse | CCCG<u>CTCGAG</u>-AGGTTGGCCTTGTCTATG | XhoI | SEQ ID NO: 951 |
| ORF 17 | Forward | GGAATT<u>CCATATGGCCATGG</u>-TTGCCGGCCTGTTCG | NdeI-NcoI | SEQ ID NO: 952 |
|  | Forward | CG<u>GGATCC</u>-ATTGCCGGCCTGTTCG | BamHI | SEQ ID NO: 953 |
|  | Reverse | CCCG<u>CTCGAG</u>-AAGCAGGTTGTACAGC | XhoI | SEQ ID NO: 954 |
| ORF 18 | Forward | GC<u>GGATCCCATATG</u>-ATTTTGCTGCATTTGGAT | BamHI-NdeI | SEQ ID NO: 955 |
|  | Reverse | CCCG<u>CTCGAG</u>-TCTTCCAATTTCTGAAAGC | XhoI | SEQ ID NO: 956 |
| ORF 19 | Forward | GGAATT<u>CCATATGGCCATGG</u>-TCGCCAGTGTTTTACC | NdeI-NcoI | SEQ ID NO: 957 |
|  | Forward | CG<u>GGATCC</u>-TTCGCCAGTGTTTTACCG | BamHI | SEQ ID NO: 958 |
|  | Reverse | CCCG<u>CTCGAG</u>-GGTGTTTTTGAAGCTGCC | XhoI | SEQ ID NO: 959 |
| ORF 20 | Forward | GGAATT<u>CCATATGGCCATGG</u>-TCGGCGCGGGTATG | NdeI-NcoI | SEQ ID NO: 960 |
|  | Forward | CG<u>GGATCC</u>-TTCGGCGCGGGTATG | BamHI | SEQ ID NO: 961 |
|  | Reverse | CCCG<u>CTCGAG</u>-CGGCGAGCGAGAGCA | XhoI | SEQ ID NO: 962 |
| ORF 22 | Forward | GGAATT<u>CCATATGGCCATGG</u>-TGATTAAAATCAAAAAGGTCT | NdeI-NcoI | SEQ ID NO: 963 |
|  | Forward | CG<u>GGATCC</u>-ATGATTAAAATCAAAAAGGTCTAAACC | BamHI | SEQ ID NO: 964 |
|  | Reverse | CCCG<u>CTCGAG</u>-ATTATGATAGCGGCCC | XhoI | SEQ ID NO: 965 |
| ORF 23 | Forward | CGC<u>GGATCCCATATG</u>-GATGTTTCTGTTTCAGAC | BamHI-NdeI | SEQ ID NO: 966 |
|  | Reverse | CCCG<u>CTCGAG</u>-TTTAAACCGATAGGTAAACG | XhoI | SEQ ID NO: 967 |
| ORF 24 | Forward | GGAATT<u>CCATATGGCCATGG</u>-TGATGCCGGAAATGGTG | NdeI-NcoI | SEQ ID NO: 968 |
|  | Forward | CG<u>GGATCC</u>-ATGATGCCGGAAATGGTG | BamHI | SEQ ID NO: 969 |
|  | Reverse | CCCG<u>CTCGAG</u>-TGTCAGCGTGGCGCA | XhoI | SEQ ID NO: 970 |
| ORF 25 | Forward | GC<u>GGATCCCATATG</u>-TATCGCAAACTGATTGC | BamHI-NdeI | SEQ ID NO: 971 |
|  | Reverse | CCCG<u>CTCGAG</u>-ATCGATGGAATAGCCG | XhoI | SEQ ID NO: 972 |
| ORF 26 | Forward | GC<u>GGATCCCATATG</u>-CAGCTGATCGACTATTC | BamHI-NdeI | SEQ ID NO: 973 |
|  | Reverse | CCCG<u>CTCGAG</u>-GACATCGGCGCGTTTT | XhoI | SEQ ID NO: 974 |
| ORF 27 | Forward | GGAATT<u>CCATATGGCCATGG</u>-AGACCTATTCTGTTTA | NdeI-NcoI | SEQ ID NO: 1168 |
|  | Forward | CG<u>GGATCC</u>-CAGACCTATTCTGTTTATTTTAATC | BamHI | SEQ ID NO: 975 |
|  | Reverse | CCCG<u>CTCGAG</u>-GGGTTCGATTAAATAACCAT | XhoI | SEQ ID NO: 976 |
| ORF 28 | Forward | GGAATT<u>CCATATGGCCATGG</u>-ACGGCGTACGTTGATGT | NdeI-NcoI | SEQ ID NO: 977 |
|  | Forward | CG<u>GGATCC</u>-AACGGCGTACGTTGATG | BamHI | SEQ ID NO: 978 |
|  | Reverse | CCCG<u>CTCGAG</u>-TTTGTCAGAGGAATTCGCG | XhoI | SEQ ID NO: 979 |
| ORF 29 | Forward | GC<u>GGATCCCATATG</u>-AACGGTTTGGATGCCCG | BamHI-NdeI | SEQ ID NO: 980 |
|  | Forward | CGC<u>GGATCCGCTAGC</u>-AACGGTTTGGATGCCCG | BamHI-NheI | SEQ ID NO: 981 |
|  | Reverse | CCCG<u>CTCGAG</u>-TTTGTCTAAGTTCCTGATATG | XhoI | SEQ ID NO: 982 |
| ORF 32 | Forward | CGC<u>GGATCCCATATG</u>-AATACTCCTCCTTTTG | BamHI-NdeI | SEQ ID NO: 983 |
|  | Reverse | CCCG<u>CTCGAG</u>-GCGTATTTTTGATGCTTTG | XhoI | SEQ ID NO: 984 |
| ORF 33 | Forward | GC<u>GGATCCCATATG</u>-ATTGATAGGGATCGTATG | BamHI-NdeI | SEQ ID NO: 985 |
|  | Reverse | CCCG<u>CTCGAG</u>-TTGATCTTTCAAACGGCC | XhoI | SEQ ID NO: 986 |
| ORF 35 | Forward | GC<u>GGATCCCATATG</u>-TTCAGAGCTCAGCTT | BamHI-NdeI | SEQ ID NO: 987 |
|  | Forward | CGC<u>GGATCCGCTAGC</u>-TTCAGAGCTCAGCTT | BamHI-NheI | SEQ ID NO: 988 |
|  | Reverse | CCCG<u>CTCGAG</u>-AAACAGCCATTTGAGCGA | XhoI | SEQ ID NO: 989 |
| ORF 37 | Forward | GC<u>GGATCCCATATG</u>-GATGACGTATCGGATTTT | BamHI-NdeI | SEQ ID NO: 990 |
|  | Reverse | CCCG<u>CTCGAG</u>-ATAGCCCGCTTTCAGG | XhoI | SEQ ID NO: 991 |
| ORF 58 | Forward | CGC<u>GGATCCGCTAGC</u>-TCCGAACGCGAGTGGAT | BamHI-NheI | SEQ ID NO: 992 |
|  | Reverse | CCCG<u>CTCGAG</u>-AGCATTGTCCAAGGGGAC | XhoI | SEQ ID NO: 993 |
| ORF 65 | Forward | GGAATT<u>CCATATGGCCATGG</u>-TGCTGTATCTGAATCAAG | NdeI-NcoI | SEQ ID NO: 994 |
|  | Forward | CG<u>GGATCC</u>-TTGCTGTATCTGAATCAAGG | BamHI | SEQ ID NO: 995 |
|  | Reverse | CCCG<u>CTCGAG</u>-CCGCATCGGCAGACA | XhoI | SEQ ID NO: 996 |
| ORF 66 | Forward | GC<u>GGATCCCATATG</u>-TACGCATTTACCGCCG | BamHI-NdeI | SEQ ID NO: 997 |
|  | Reverse | CCCG<u>CTCGAG</u>-TGGATTTTGCAGAGATGG | XhoI | SEQ ID NO: 998 |
| ORF 72 | Forward | CGC<u>GGATCCCATATG</u>-AATGCAGTAAAAATATCTGA | BamHI-NdeI | SEQ ID NO: 999 |
|  | Reverse | CCCG<u>CTCGAG</u>-GCCTGAGACCTTTGCAA | XhoI | SEQ ID NO: 1000 |
| ORF 73 | Forward | GC<u>GGATCCCATATG</u>-AGATTTTTCGGTATCGG | BamHI-NdeI | SEQ ID NO: 1001 |
|  | Reverse | CCCG<u>CTCGAG</u>-TTCATCTTTTTCATGTTCG | XhoI | SEQ ID NO: 1002 |
| ORF 75 | Forward | GC<u>GGATCCCATATG</u>-TCTGTCTTTCAAACGGC | BamHI-NdeI | SEQ ID NO: 1003 |
|  | Reverse | CCCG<u>CTCGAG</u>-TTTGTTTTTGCAAGACAG | XhoI | SEQ ID NO: 1004 |
| ORF 76 | Forward | GATCA<u>GCTAGCCATATG</u>-AAACAGAAAAAAACCGC | NheI-NdeI | SEQ ID NO: 1005 |
|  | Reverse | CG<u>GGATCC</u>-TTACGGTTTGACACCGTT | BamHI | SEQ ID NO: 1006 |
| ORF 79 | Forward | CGC<u>GGATCCCATATG</u>-GTTTCCGCCGCCG | BamHI-NdeI | SEQ ID NO: 1007 |
|  | Reverse | CCCG<u>CTCGAG</u>-GTGCTGATGCGCTTCG | XhoI | SEQ ID NO: 1008 |

TABLE I-continued

PCR primers

| ORF | Primer | Sequence | Restriction-sites | SEQ ID NO: |
|---|---|---|---|---|
| ORF 83 | Forward | GCGGATCCCATATG-AAAACCCTGCTGCTGC | BamHI-NdeI | SEQ ID NO: 1009 |
|  | Reverse | CCCGCTCGAG-GCCGCCTTTGCGGC | XhoI | SEQ ID NO: 1010 |
| ORF 84 | Forward | GCGGATCCCATATG-GCAGAGATCTGTTTG | BamHI-NdeI | SEQ ID NO: 1011 |
|  | Reverse | CCCGCTCGAG-GTTTGCCGATCCGACCA | XhoI | SEQ ID NO: 1012 |
| ORF 85 | Forward | CGCGGATCCCATATG-GCGGTTTGGGGCGGA | BamHI-NdeI | SEQ ID NO: 1013 |
|  | Reverse | CCCGCTCGAG-TCGGCGCGGCGGGC | XhoI | SEQ ID NO: 1014 |
| ORF 89 | Forward | GGAATTCCATATGGCCATGG-CCATACCTTCTTATCA | NdeI-NcoI | SEQ ID NO: 1015 |
|  | Forward | CGGGATCC-GCCATACCTTCTTATCAGAG | BamHI | SEQ ID NO: 1016 |
|  | Reverse | CCCGCTCGAG-TTTTTTGCGATTAGAAAAAGC | XhoI | SEQ ID NO: 1017 |
| ORF 97 | Forward | GCGGATCCCATATG-CATCCTGCCAGCGAAC | BamHI-NdeI | SEQ ID NO: 1018 |
|  | Reverse | CCCGCTCGAG-TTCGCCTACGGTTTTTTG | XhoI | SEQ ID NO: 1019 |
| ORF 98 | Forward | GCGGATCCCATATG-ACGGTAACTGCGG | BamHI-NdeI | SEQ ID NO: 1020 |
|  | Reverse | CCCGCTCGAG-TTGTTGTTCGGGCAAATC | XhoI | SEQ ID NO: 1021 |
| ORF 100 | Forward | GCGGATCCCATATG-TCGGGCATTTACACCG | BamHI-NdeI | SEQ ID NO: 1022 |
|  | Reverse | CCCGCTCGAG-ACGGGTTTCGGCGGAA | XhoI | SEQ ID NO: 1023 |
| ORF 101 | Forward | GCGGATCCCATATG-ATTTATCAAAGAAACCTC | BamHI-NdeI | SEQ ID NO: 1024 |
|  | Reverse | CCCGCTCGAG-TTTTCCGCCTTTCAATGT | XhoI | SEQ ID NO: 1025 |
| ORF 102 | Forward | GCGGATCCCATATG-GCAGGGCTGTTTTACC | BamHI-NdeI | SEQ ID NO: 1026 |
|  | Reverse | CCCGCTCGAG-AAACGGTTTGAACACGAC | XhoI | SEQ ID NO: 1027 |
| ORF 103 | Forward | GCGGATCCCATATG-AACCACGACATCAC | BamHI-NdeI | SEQ ID NO: 1028 |
|  | Reverse | CCCGCTCGAG-CAGCCACAGGACGGC | XhoI | SEQ ID NO: 1029 |
| ORF 104 | Forward | GCGGATCCCATATG-ACGTGGGGAACGC | BamHI-NdeI | SEQ ID NO: 1030 |
|  | Reverse | CCCGCTCGAG-GCGGCGTTTGAACGG | XhoI | SEQ ID NO: 1031 |
| ORF 105 | Forward | GCGGATCCCATATG-ACCAAATTTCAAACCCCTC | BamHI-NdeI | SEQ ID NO: 1032 |
|  | Reverse | CCCGCTCGAG-TAAACGAATGCCGTCCAG | XhoI | SEQ ID NO: 1033 |
| ORF 106 | Forward | GCGGATCCCATATG-AGGATAACGACGGCG | BamHI-NdeI | SEQ ID NO: 1034 |
|  | Reverse | CCCGCTCGAG-TTTGTTCCCGATGATGTT | XhoI | SEQ ID NO: 1035 |
| ORF 109 | Forward | GCGGATCCCATATG-GAAGATTTATATATAATACTCG | BamHI-NdeI | SEQ ID NO: 1036 |
|  | Reverse | CCCGCTCGAG-ATCAGCTTGAACCGAAG | XhoI | SEQ ID NO: 1037 |
| ORF110 | Forward | AAAGAATTC-ATGAGTAAATCCCGTAGATCTCCC | EcoRI | SEQ ID NO: 1038 |
|  | Reverse | AAACTGCAG-GGAAAACCACATCCGCACTCTGCC | PstI | SEQ ID NO: 1039 |
| ORF111 | Forward | AAAGAATTC-GCACCGCAAAAGGCAAAACCGCA | EcoRI | SEQ ID NO: 1040 |
|  | Reverse | AAACTGCAG-TCTGCGCGTTTTCGGCAGGGTGG | PstI | SEQ ID NO: 1041 |
| ORF113 | Forward | AAAGAATTC-ATGAACAAACCCTCTATCGTGTGATTTTCAACCG | EcoRI | SEQ ID NO: 1042 |
|  | Reverse | AAACTGCAG-TTACGAATGCCTGCTTGCTCGACCGTACTG | PstI | SEQ ID NO: 1043 |
| ORF115 | Forward | AAAGAATTC-TTGCTTGTGCAAACAGAAAAAGACGG | EcoRI | SEQ ID NO: 1044 |
|  | Reverse | AAAAAGTCGAC-CTATTTTTTAGGGGCTTTTGCTTGTTTGAAAAGCCTGCC | SalI | SEQ ID NO: 1045 |
| ORF119 | Forward | AAAGAATTC-TACAACATGTATCAGGAAAACCAATACCG | EcoRI | SEQ ID NO: 1046 |
|  | Reverse | AAACTGCAG-TTATGAAAACAGGCGCAGGGCGGTTTTGCC | PstI | SEQ ID NO: 1047 |
| ORF120 | Forward | AAAGAATTC-GCAAGGCTACCCCAATCCGCCGTG | EcoRI | SEQ ID NO: 1048 |
|  | Reverse | AAACTGCAG-CGGTTTGGCTGCCTGGCCGTTGAT | PstI | SEQ ID NO: 1049 |
| ORF121 | Forward | AAAGAATTC-GCCTTGGTCTGGCTGGTTTTCGC | EcoRI | SEQ ID NO: 1050 |
|  | Reverse | AAACTGCAG-TCATCCGCCACCCCACCTCGGCCATCCATC | PstI | SEQ ID NO: 1051 |
| ORF122 | Forward | AAAAAGTCGAC-ATGTCTTACCGCGCAAGCAGTTCTCC | SalI | SEQ ID NO: 1052 |
|  | Reverse | AAACTGCAG-TCAGGAACACAAACGATGACGAATATCCGTATC | PstI | SEQ ID NO: 1053 |
| ORF125 | Forward | AAAGAATTC-GCGCTGTTTTTTGCGGCGGCGTAT | EcoRI | SEQ ID NO: 1054 |
|  | Reverse | AAACTGCAG-CGCCGTTTCAAGACGAAAAAGTCG | PstI | SEQ ID NO: 1055 |
| ORF126 | Forward | AAAGAATTC-GCGGAAACGGTCGAAG | EcoRI | SEQ ID NO: 1056 |
|  | Reverse | AAACTGCAG-TTAATCTTGTCTTCCGATATAC | PstI | SEQ ID NO: 1057 |
| ORF127 | Forward | AAAGAATTC-ATGACTGATAATCGGGGGTTTACG | EcoRI | SEQ ID NO: 1058 |
|  | Reverse | AAAAAGTCGAC-CTTAAGTAACTTGCAGTCCTTATC | SalI | SEQ ID NO: 1059 |
| ORF128 | Forward | AAAGAATTC-ATGCAAGCTGTCCGCTACAGGCC | EcoRI | SEQ ID NO: 1060 |
|  | Reverse | AAACTGCAG-CTATTGCAATGCGCCGCCGCGGGAATGTTTGAGCAGGCG | PstI | SEQ ID NO: 1061 |
| ORF129 | Forward | AAAGAATTC-ATGGATTTTCGTTTTGACATTATTTACGAATACCG | EcoRI | SEQ ID NO: 1062 |
|  | Reverse | AAACTGCAG-TTATTTTTTGATGAAATTTTGGGGCGG | PstI | SEQ ID NO: 1063 |
| ORF130 | Forward | AAAGAATTC-GCAGTACTTGCCATTCTCGGTGCG | EcoRI | SEQ ID NO: 1064 |
|  | Reverse | AAACTGCAG-CTCCGGATCGTCTGTAAACGCATT | PstI | SEQ ID NO: 1065 |
| ORF 131 | Forward | GCGGATCCCATATG-GAAATTCGGGCAATAAAAT | BamHI-NdeI | SEQ ID NO: 1066 |
|  | Reverse | CCCGCTCGAG-CCAGCGGACGCGTTC | XhoI | SEQ ID NO: 1067 |
| ORF 132 | Forward | GCGGATCCCATATG-AAAGAAGCGGGGTTTG | BamHI-NdeI | SEQ ID NO: 1068 |
|  | Reverse | CCCGCTCGAG-CCAATCTGCCAGCCGT | XhoI | SEQ ID NO: 1069 |
| ORF 133 | Forward | CGCGGATCCCATATG-GAAGATGCAGGGCGCG | BamHI-NdeI | SEQ ID NO: 1070 |
|  | Reverse | CCCGCTCGAG-AAACTTGTAGCTCATCGT | XhoI | SEQ ID NO: 1071 |
| ORF 134 | Forward | GCGGATCCCATATG-TCTGTGCAAGCAGTATTG | BamHI-NdeI | SEQ ID NO: 1072 |
|  | Reverse | CCCGCTCGAG-ATCCTGTGCCAATGCG | XhoI | SEQ ID NO: 1073 |
| ORF 135 | Forward | GCGGATCCCATATG-CCGTCTGAAAAAGCTTT | BamHI-NdeI | SEQ ID NO: 1074 |
|  | Reverse | CCCGCTCGAG-AAATACCGCTGAGGATG | XhoI | SEQ ID NO: 1075 |
| ORF 136 | Forward | CGCGGATCCGCTAGC-ATGAAGCGGCGTATAGCC | BamHI-NheI | SEQ ID NO: 1076 |
|  | Reverse | CCCGCTCGAG-TTCCGAATATTTGGAACTTTT | XhoI | SEQ ID NO: 1077 |
| ORF 137 | Forward | GCGGATCCCATATG-GGCACGCGGGGAAATA | BamHI-NdeI | SEQ ID NO: 1078 |
|  | Reverse | CCCGCTCGAG-ATAACGGTATGCCGCC | XhoI | SEQ ID NO: 1079 |
| ORF 138 | Forward | GCGGATCCCATATG-TTTCGTTTACAATTCAGGC | BamHI-NdeI | SEQ ID NO: 1080 |
|  | Reverse | CCCGCTCGAG-CGGCGTTTTATAGCGG | XhoI | SEQ ID NO: 1081 |
| ORF 139 | Forward | GCGGATCCCATATG-GCTTTTTTGGCGGTAATG | BamHI-NdeI | SEQ ID NO: 1082 |
|  | Reverse | CCCGCTCGAG-TAACGTTTCCGTGCGTTT | XhoI | SEQ ID NO: 1083 |

TABLE I-continued

PCR primers

| ORF | Primer | Sequence | Restriction-sites | SEQ ID NO: |
|---|---|---|---|---|
| ORF 140 | Forward | GC<u>GGATCC</u><u>CATATG</u>-TTGCCCACAGGCAGC | BamHI-NdeI | SEQ ID NO: 1084 |
|  | Reverse | CCCG<u>CTCGAG</u>-GACGATGGCAAACAGC | XhoI | SEQ ID NO: 1085 |
| ORF 141 | Forward | GC<u>GGATCC</u><u>CATATG</u>-CCGTCTGAAGCAGTCT | BamHI-NdeI | SEQ ID NO: 1086 |
|  | Reverse | CCCG<u>CTCGAG</u>-ATCTGTTGTTTTTAAAATATT | XhoI | SEQ ID NO: 1087 |
| ORF 142 | Forward | GC<u>GGATCC</u><u>CATATG</u>-GATAATTCTGGTAGTGAAG | BamHI-NdeI | SEQ ID NO: 1088 |
|  | Reverse | CCCG<u>CTCGAG</u>-AAACGTATAGCCTACCT | XhoI | SEQ ID NO: 1089 |
| ORF 143 | Forward | GC<u>GGATCC</u><u>CATATG</u>-GATACCGCTTTGAACCT | BamHI-NdeI | SEQ ID NO: 1090 |
|  | Reverse | CCCG<u>CTCGAG</u>-AATGGCTTCCGCAATATG | XhoI | SEQ ID NO: 1091 |
| ORF 144 | Forward | GC<u>GGATCC</u><u>CATATG</u>-ACCTTTTTACAACGTTTGC | BamHI-NdeI | SEQ ID NO: 1092 |
|  | Reverse | CCCG<u>CTCGAG</u>-AGATTGTTGTTGTTTTTCG | XhoI | SEQ ID NO: 1093 |
| ORF 147 | Forward | GC<u>GGATCC</u><u>CATATG</u>-TCTGTCTTTCAAACGGC | BamHI-NdeI | SEQ ID NO: 1094 |
|  | Reverse | CCCG<u>CTCGAG</u>-TTTGTTTTTGCAAGACAG | XhoI | SEQ ID NO: 1095 |

NB:
restriction sites are underlined for ORFs 110-130, where the ORF itself carries an EcoRI site (eg. ORF122), a SalI site was used in the forward primer instead. Similarly, where the ORF carries a PstI site (eg. ORFs 115 and 127), a SalI site was used in the reverse primer.

TABLE II

Summary of cloning, expression and purification

| ORF | PCR/cloning | His-fusion expression | GST-fusion expression | Purification |
|---|---|---|---|---|
| orf 1 | + | + | + | His-fusion |
| orf 2 | + | + | + | GST-fusion |
| orf 2.1 | + | n.d. | + | GST-fusion |
| orf 4 | + | + | + | His-fusion |
| orf 5 | + | n.d. | + | GST-fusion |
| orf 6 | + | + | + | GST-fusion |
| orf 7 | + | + | + | GST-fusion |
| orf 8 | + | n.d. | n.d. |  |
| orf 9 | + | + | + | GST-fusion |
| orf 10 | + | n.d. | n.d. |  |
| orf 11 | + | n.d. | n.d. |  |
| orf 13 | + | n.d. | + | GST-fusion |
| orf 15 | + | + | + | GST-fusion |
| orf 17 | + | n.d. | n.d. |  |
| orf 18 | + | n.d. | n.d. |  |
| orf 19 | + | n.d. | n.d. |  |
| orf 20 | + | n.d. | n.d. |  |
| orf 22 | + | + | + | GST-fusion |
| orf 23 | + | + | + | His-fusion |
| orf 24 | + | n.d. | n.d. |  |
| orf 25 | + | + | + | His-fusion |
| orf 26 | + | n.d. | n.d. |  |
| orf 27 | + | + | + | GST-fusion |
| orf 28 | + | + | + | GST-fusion |
| orf 29 | + | n.d. | n.d. |  |
| orf 32 | + | + | + | His-fusion |
| orf 33 | + | n.d. | n.d. |  |
| orf 35 | + | n.d. | n.d. |  |
| orf 37 | + | + | + | GST-fusion |
| orf 58 | + | n.d. | n.d. |  |
| orf 65 | + | n.d. | n.d. |  |
| orf 66 | + | n.d. | n.d. |  |
| orf 72 | + | + | n.d. | His-fusion |
| orf 73 | + | n.d. | + | n.d. |
| orf 75 | + | n.d. | n.d. |  |
| orf 76 | + | + | n.d. | His-fusion |
| orf 79 | + | + | n.d. | His-fusion |
| orf 83 | + | n.d. | + | n.d. |
| orf 84 | + | n.d. | n.d. |  |
| orf 85 | + | n.d. | + | GST-fusion |
| orf 89 | + | n.d. | + | GST-fusion |
| orf 97 | + | + | + | GST-fusion |
| orf 98 | + | n.d. | n.d. |  |
| orf 100 | + | n.d. | n.d. |  |
| orf 101 | + | n.d. | n.d. |  |
| orf 102 | + | n.d. | n.d. |  |
| orf 103 | + | n.d. | n.d. |  |
| orf 104 | + | n.d. | n.d. |  |
| orf 105 | + | n.d. | n.d. |  |
| orf 106 | + | + | + | His-fusion |
| orf 109 | + | n.d. | n.d. |  |
| orf 110 | + | n.d. | n.d. |  |
| orf 111 | + | + | n.d. | His-fusion |
| orf 113 | + | + | n.d. | His-fusion |
| orf 115 | n.d. | n.d. | n.d. |  |
| orf 119 | + | + | n.d. | His-fusion |
| orf 120 | + | + | n.d. | His-fusion |
| orf 121 | + | n.d. | n.d. |  |
| orf 122 | + | + | n.d. | His-fusion |
| orf 125 | + | + | n.d. | His-fusion |
| orf 126 | + | + | n.d. | His-fusion |
| orf 127 | + | + | n.d. | His-fusion |
| orf 128 | + | n.d. | n.d. |  |
| orf 129 | + | + | n.d. | His-fusion |
| orf 130 | + | n.d. | n.d. |  |
| orf 131 | + | + | + | n.d. |
| orf 132 | + | + | + | His-fusion |
| orf 133 | + | n.d. | + | GST-fusion |
| orf 134 | + | n.d. | n.d. |  |
| orf 135 | + | n.d. | n.d. |  |
| orf 136 | + | n.d. | n.d. |  |
| orf 137 | + | n.d. | + | GST-fusion |
| orf 138 | + | n.d. | + | GST-fusion |
| orf 139 | + | n.d. | n.d. |  |
| orf 140 | + | n.d. | n.d. |  |
| orf 141 | + | n.d. | n.d. |  |
| orf 142 | + | n.d. | n.d. |  |
| orf 143 | + | n.d. | n.d. |  |
| orf 144 | + | n.d. | + | n.d. |
| orf 147 | + | n.d. | n.d. |  |

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US08293251B2). An electronic copy of the "Sequence Listing" will also be available from the USPTO upon request and payment of the fee set forth in 37 CFR 1.19(b)(3).

The invention claimed is:

1. An isolated protein comprising:
   (a) the amino acid sequence of SEQ ID NO: 652; or
   (b) an amino acid sequence having 95% or greater sequence identity to the amino acid sequence of SEQ ID NO: 652.

2. The isolated protein of claim 1 comprising (b).

3. The isolated protein of claim 2, wherein the amino acid sequence has 99% or greater sequence identity to the amino acid sequence of SEQ ID NO: 652.

4. A composition comprising the protein of any one of claim 1, 2, or 3 and an adjuvant.

5. The composition of claim 4 further comprising a pharmaceutically acceptable carrier.

* * * * *